United States Patent
Bartberger et al.

(10) Patent No.: US 9,296,736 B2
(45) Date of Patent: Mar. 29, 2016

(54) PIPERIDINONE DERIVATIVES AS MDM2 INHIBITORS FOR THE TREATMENT OF CANCER

(71) Applicant: AMGEN INC., Thousand Oaks, CA (US)

(72) Inventors: Michael D. Bartberger, Sherman Oaks, CA (US); Ana Gonzalez Buenrostro, San Mateo, CA (US); Hilary Plake Beck, Redwood City, CA (US); Xiaoqi Chen, Palo Alto, CA (US); Richard Victor Connors, Pacifica, CA (US); Jeffrey Deignan, San Francisco, CA (US); Jason A. Duquette, Millbrae, CA (US); John Eksterowicz, San Francisco, CA (US); Benjamin Fisher, San Mateo, CA (US); Brian M. Fox, Brisbane, CA (US); Jiasheng Fu, Foster City, CA (US); Zice Fu, Foster City, CA (US); Felix Gonzalez Lopez De Turiso, San Mateo, CA (US); Michael W. Gribble, San Francisco, CA (US); Darin J. Gustin, Half Moon Bay, CA (US); Julie A. Heath, Orinda, CA (US); Xin Huang, Wellesley, MA (US); XianYun Jiao, Belmont, CA (US); Michael G. Johnson, San Francisco, CA (US); Frank Kayser, San Francisco, CA (US); David John Kopecky, San Francisco, CA (US); SuJen Lai, Burlingame, CA (US); Yihong Li, Millbrae, CA (US); Zhihong Li, Millbrae, CA (US); Jiwen Liu, Foster City, CA (US); Jonathan D. Low, Reseda, CA (US); Brian S. Lucas, San Francisco, CA (US); Zhihua Ma, Foster City, CA (US); Lawrence R. McGee, Pacifica, CA (US); Joel McIntosh, Pacifica, CA (US); Dustin L. McMinn, Pacifica, CA (US); Julio C. Medina, San Carlos, CA (US); Jeffrey Thomas Mihalic, San Francisco, CA (US); Steven H. Olson, Millbrae, CA (US); Yosup Rew, Foster City, CA (US); Philip M. Roveto, San Francisco, CA (US); Daqing Sun, Foster City, CA (US); Xiaodong Wang, Millbrae, CA (US); Yingcai Wang, Millbrae, CA (US); Xuelei Yan, Foster City, CA (US); Ming Yu, Foster City, CA (US); Jiang Zhu, Palo Alto, CA (US)

(73) Assignee: Amgen INC., Thousand Oaks, CA (US)

(*) Notice: Subject to any disclaimer, the term of this patent is extended or adjusted under 35 U.S.C. 154(b) by 0 days.

(21) Appl. No.: 14/316,586

(22) Filed: Jun. 26, 2014

(65) Prior Publication Data

US 2014/0315895 A1 Oct. 23, 2014

Related U.S. Application Data

(60) Division of application No. 14/025,688, filed on Sep. 12, 2013, now abandoned, which is a continuation of application No. 13/153,345, filed on Jun. 3, 2011, now Pat. No. 8,569,341.

(Continued)

(51) Int. Cl.
*C07D 279/02* (2006.01)
*C07D 417/12* (2006.01)
(Continued)

(52) U.S. Cl.
CPC ............ *C07D 417/12* (2013.01); *C07D 211/76* (2013.01); *C07D 279/02* (2013.01);
(Continued)

(58) Field of Classification Search
CPC ..................................... C07D 279/02
USPC ........................................... 544/3; 514/222.2
See application file for complete search history.

(56) References Cited

U.S. PATENT DOCUMENTS

| 3,308,121 A | 3/1967 | Gannon et al. |
| 5,334,720 A | 8/1994 | Schmiesing et al. |

(Continued)

FOREIGN PATENT DOCUMENTS

| CN | 102153557 A | 8/2011 |
| CN | 102153557 A1 | 8/2011 |

(Continued)

OTHER PUBLICATIONS

N.J. Anthony, Pseudo-Allylic $A_{1,3}$ Strain as a Conformational Control Element: Stereoselective Syntheses of $\psi[CH_2O]$ Pseudodipeptides, Tetrahedron Letters, vol. 36, No. 22, pp. 3821-3824.

(Continued)

*Primary Examiner* — Kahsay Habte
(74) *Attorney, Agent, or Firm* — Todd M. Crissey; Elsa D. Lemoine; Markus Bergauer

(57) ABSTRACT

The present invention provides MDM2 inhibitor compounds of Formula I,

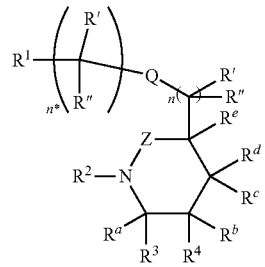

wherein the variables are defined above, which compounds are useful as therapeutic agents, particularly for the treatment of cancers. The present invention also relates to pharmaceutical compositions that contain an MDM2 inhibitor.

13 Claims, No Drawings

Related U.S. Application Data

(60) Provisional application No. 61/452,578, filed on Mar. 14, 2011, provisional application No. 61/352,322, filed on Jun. 7, 2010, provisional application No. 61/351,827, filed on Jun. 4, 2010.

(51) Int. Cl.

| | | |
|---|---|---|
| *C07D 211/76* | (2006.01) | |
| *C07D 401/04* | (2006.01) | |
| *C07D 401/06* | (2006.01) | |
| *C07D 401/12* | (2006.01) | |
| *C07D 407/04* | (2006.01) | |
| *C07D 407/06* | (2006.01) | |
| *C07D 409/04* | (2006.01) | |
| *C07D 413/06* | (2006.01) | |
| *C07D 417/06* | (2006.01) | |
| *C07D 471/10* | (2006.01) | |
| *C07D 498/08* | (2006.01) | |
| *C07D 498/20* | (2006.01) | |
| *C07D 405/04* | (2006.01) | |
| *C07D 417/14* | (2006.01) | |
| *C07D 491/08* | (2006.01) | |
| *C07D 491/153* | (2006.01) | |

(52) U.S. Cl.
CPC ............ *C07D401/04* (2013.01); *C07D 401/06* (2013.01); *C07D 401/12* (2013.01); *C07D 405/04* (2013.01); *C07D 407/04* (2013.01); *C07D 407/06* (2013.01); *C07D 409/04* (2013.01); *C07D 413/06* (2013.01); *C07D 417/06* (2013.01); *C07D 417/14* (2013.01); *C07D 471/10* (2013.01); *C07D 491/08* (2013.01); *C07D 491/153* (2013.01); *C07D 498/08* (2013.01); *C07D 498/20* (2013.01)

(56) References Cited

U.S. PATENT DOCUMENTS

| | | |
|---|---|---|
| 6,620,815 B1 | 9/2003 | Lagu et al. |
| 6,860,940 B2 | 3/2005 | Segelke et al. |
| 7,015,041 B2 | 3/2006 | Santarsiero et al. |
| 7,052,545 B2 | 5/2006 | Quake et al. |
| 7,195,670 B2 | 3/2007 | Hansen et al. |
| 7,214,540 B2 | 5/2007 | DeLucas et al. |
| 7,229,500 B2 | 6/2007 | Haushalter et al. |
| 7,425,638 B2 | 9/2008 | Haley et al. |
| 8,569,341 B2 | 10/2013 | Gribble, Jr. et al. |
| 8,952,036 B2 | 2/2015 | Rew |
| 2004/0186134 A1 | 9/2004 | O'Connor et al. |
| 2007/0129416 A1 | 6/2007 | Ding et al. |
| 2008/0280769 A1 | 11/2008 | Doemling |
| 2009/0143364 A1 | 6/2009 | Fotouhi et al. |
| 2009/0163512 A1 | 6/2009 | Chen et al. |
| 2011/0319378 A1 | 12/2011 | Bartberger et al. |
| 2014/0235629 A1 | 8/2014 | Bartberger et al. |
| 2014/0364455 A1 | 12/2014 | Bio et al. |

FOREIGN PATENT DOCUMENTS

| | | |
|---|---|---|
| DE | 3246148 A1 | 6/1984 |
| TW | 200801000 A | 1/2008 |
| TW | 200808781 A | 2/2008 |
| WO | WO95/23135 A1 | 8/1995 |
| WO | WO96/06095 A1 | 2/1996 |
| WO | WO97/30045 A1 | 8/1997 |
| WO | WO99/06397 A2 | 2/1999 |
| WO | WO99/31507 A1 | 6/1999 |
| WO | WO02/17912 A1 | 3/2002 |
| WO | WO02/089738 A2 | 11/2002 |
| WO | WO02/094787 A1 | 11/2002 |
| WO | WO03/051359 A1 | 6/2003 |
| WO | WO2004/031149 A1 | 4/2004 |
| WO | WO2005/110996 A1 | 11/2005 |
| WO | WO2005/123691 A1 | 12/2005 |
| WO | WO2006/097261 A1 | 9/2006 |
| WO | WO2006/107859 A2 | 10/2006 |
| WO | WO2006/107860 A2 | 10/2006 |
| WO | WO2007/063013 A1 | 6/2007 |
| WO | WO2007/104664 A1 | 9/2007 |
| WO | WO2008/005268 A1 | 1/2008 |
| WO | WO2008/010953 A2 | 1/2008 |
| WO | WO2008/021338 A2 | 2/2008 |
| WO | WO2008/021339 A2 | 2/2008 |
| WO | WO2008/076754 A2 | 6/2008 |
| WO | WO2008/110793 A1 | 9/2008 |
| WO | WO2008/125487 A1 | 10/2008 |
| WO | WO2008/141975 A1 | 11/2008 |
| WO | WO2009/004430 A1 | 1/2009 |
| WO | WO2009/007750 A1 | 1/2009 |
| WO | WO2009/047161 A1 | 4/2009 |
| WO | WO2009/082038 A2 | 7/2009 |
| WO | WO2009/114950 A1 | 9/2009 |
| WO | WO2009/156735 A2 | 12/2009 |
| WO | WO2010/028862 A1 | 3/2010 |
| WO | WO2010/031713 A1 | 3/2010 |
| WO | WO2010/121995 A1 | 10/2010 |
| WO | WO2010/028862 A1 | 3/2011 |
| WO | WO2011/023677 A1 | 3/2011 |
| WO | WO2011/067185 A1 | 6/2011 |
| WO | WO2011/076786 A1 | 6/2011 |
| WO | WO2011/153509 A1 | 12/2011 |
| WO | WO2013/049250 A1 | 4/2013 |
| WO | WO2014/130470 A1 | 8/2014 |
| WO | WO2014/134201 A1 | 9/2014 |
| WO | WO2014/151863 A1 | 9/2014 |
| WO | WO2014/200937 A1 | 12/2014 |

OTHER PUBLICATIONS

Uli Rothweiler, Isoquinolin-1-one Inhibitors of the MDM2-p53 Interaction, ChemMedChem 2008, vol. 3, pp. 1118-1128.
International Search Report, PCT/US2011/039184, Issued Sep. 9, 2011, pp. 1-3.
Written Opinion of the international Searching Authority, PCT/US2011/039814, Issued Sep. 9, 2011, pp. 1-5.
Rew, Yosup, Structure-Based Design of Novel Inhibitors of the MDM-p53 Interaction, Journal of Medicinal Chemistry, Jun. 14, 2012;55(11); pp. 4936-4954, E-published May 9, 2012.
Michelsen, Klaus, Ordering of the N-Terminus of Human MDM2 by Small Molecule Inhibitors, Journal American Chemical Society, Oct. 17, 2012;134(41): pp. 17059-17067, Epublished Oct. 5, 2012.
Allen, John G., Discovery and Optimization of Chromenotriazolopyrimidines as Potent Inhibitors of the Mouse Double Minute 2-Tumor Protein 53 Protein-Protein interaction, Journal of Medicinal Chemistry, Nov. 26, 2009;52(22): pp. 7044-7053.
Haruo Nakayama et al: "Hydrates of Organic Compounds, X. The Formation of Clathrate Hydrates of Tetrabutylammonium Alkanesulfonates", Bulletin of the Chemical Society of Japan, Jan. 1, 1986, pp. 833-837, XP055133190, DOI: 10.1246/bcsj.59.833 Retrieved from the Internet: URL:https://www.jstage.jst.go.jp/article/bcsjl926/59/3/59.
Daqing Sun et al: "Discovery of AMG 232, a Potent, Selective, and Orally Bioavailable MDM2-p53 Inhibitor in Clinical Development", Journal of Medicinal Chemistry, vol. 57, No. 4, Feb. 27, 2014, pp. 1454-1472, XP05516592, ISSN: 0022-2623, DOI: 10.1021/jm401753e scheme 7; compound 2.
International Search Report, PCT/US2014/041594, Issued Aug. 18, 2014, pp. 1-7.
Written Opinion of the International Searching Authority, PCT/US2014/041594, Issued Aug. 18, 2014, pp. 1-12.
International Search Report, PCT/US2014/016971, Issued May 15, 2014, pp. 1-5.
Written Opinion of the International Searching Authority, PCT/US2014/016971, Issued May 15, 2014, pp. 1-3.
Qiuxia He et al: "Novel morpholin-3-one derivatives induced apoptosis and elevated the level of P53 and Fas in A549 lung cancer cells", Bigoorganic & Medicinal Chemistry, Pergamon, GB, vol. 15,

(56) References Cited

OTHER PUBLICATIONS

No. 11, Apr. 26, 2007, pp. 3889-3895, XP022047574, ISSN: 0968-0896, DOI: 10.1016/J.BMC.2007.03.008
International Search Report, PCT/US2014/026584, Issued Jun. 26, 2014, pp. 1-5.
Written Opinion of the International Searching Authority, PCT/US2014/026584, Issued Jun. 26, 2014, pp. 1-6.
Patani Ga etal: "Bioisosterism: A Rational Approach in Drug Design", Chemical Reviews, American Chemical Society, US, vol. 96, No. 8, Dec. 16, 1996, pp. 3147-3176, XP000652176, ISSN: 0009-2665, DOI: 10.1021/CR950066Q.
Ana Z. Gonzalez et al: "Novel Inhibitors of the MDM2-p53 Interaction Featuring Hydrogen Bond Acceptors as Carboxylic Acid Isosteres", Journal of Medicinal Chemistry, vol. 57, No. 7, Mar. 6, 2014, pp. 2963-2988, XP055116598, ISSN: 0022-2623, DOI: 10.1021/jm401911v.
International Search Report, PCT/US2014/018759, Issued Jun. 12, 2014, pp. 1-5.
Written Opinion of the International Searching Authority, PCT/US2014/018759, Issued Jun. 12, 2014, pp. 1-7.
J.L. Garcia Ruana et al: "Synthesis of 2-phenyl-, 3-phenyl-, cis-2,3-diphenyl-, and trans-2,3-diphenyl-1,4-thiazanes and derivatives (N-methyl, N-alkoxycarbonyl, S-oxides, and S,S-dioxides)", The Journal of Organic Chemistry, vol. 57, No. 15, Jul. 1, 1992, pp. 4215-4224, XP55047606, ISSN: 0022-3263, DOI: 10.1021/jo000041a029.
U.S. Appl. No. 14/768,529, filed Aug. 18, 2015, Amgen Inc.
U.S. Appl. No. 14/774,645, filed Sep. 10, 2015, Amgen Inc.
International Search Report, PCT/US2012/057389, Issued Jan. 18, 2013, pp. 1-4.
"Guidance for Industry ANDAs: Pharmaceutical Solid Polymorphism Chemistry Manufacturing, and Controls Information,"U.S. Department of Health and Human Services, Food and Drug Administration, Center for Drug Evaluation and Research (CDER), Jul. 2007, pp. 1-13.
Gattermann, L. "The Practical Methods of Organic Chemistry" 1896, MacMillan: New York, pp. 1-14.
Lawrence, H. R. et al., "Identification of a disruptor of the MDM2-p53 protein—protein interaction facilitated by high-throughput in silico docking," Bioorganic & Medicinal Chemistry Letters 19, 3756-3759 (2009).
Morissette, S. L. et. al. "High-throughput crystallization: polymorphs, salts, co-crystals and solvates of pharmaceutical solids," Advanced Drug Delivery Reviews 56, 275-300 (2004).
Stefanovsky, J. N. et al., "Ueber die Verhaeltnisse bei Ringschlussreaktionen epimerer 2-Amino-1,2-diphenyl-aethanole," Chem. Ber. 102, 717-727 (1969), cited on p. 19 of in Office Action mailed Dec. 24, 2014 for U.S. Appl. No. 14/347,628, pp. 1-21 (attached).
Written Opinion of the International Searching Authority, PCT/US2012/057389, Issued Jan. 18, 2013, pp. 1-6.
Zeitler, J. A. et al. "Characterization of Temperature-Induced Phase Transitions in Five Polymorphic Forms of Sulfathiazole by Terahertz Pulsed Spectroscopy and Differential Scanning Calorimetry," Journal of Pharmaceutical Sciences 95(11), 2486-2498 (2006).

PIPERIDINONE DERIVATIVES AS MDM2 INHIBITORS FOR THE TREATMENT OF CANCER

CROSS REFERENCE TO RELATED APPLICATIONS

This application is a divisional application of U.S. patent application Ser. No. 14/025,688, filed Sep. 12, 2013, now abandoned which is a continuation of U.S. patent application Ser. No. 13/153,345, filed Jun. 3, 2011, now issued U.S. Pat. No. 8,569,341, which claims the benefit of U.S. Provisional Patent Application Nos. 61/452,578, filed Mar. 14, 2011, 61/352,322, filed Jun. 7, 2010, and 61/351,827, filed Jun. 4, 2010.

FIELD OF THE INVENTION

The present invention relates to compounds that are MDM2 inhibitors that are useful as therapeutic agents, particularly for the treatment of cancers. The invention also relates to pharmaceutical compositions that contain an MDM2 inhibitor.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in p53$^{WT}$ tumors (p53 wildtype). In support of this concept, some p53$^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are p53$^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to compounds capable of inhibiting the interaction between p53 and MDM2 and activating p53 downstream effector genes. As such, compounds of the present invention would be useful in the treatment of cancers, bacterial infections, viral infections, ulcers and inflammation. In particular, the compounds of the present invention are useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

SUMMARY OF THE INVENTION

The present invention relates to piperidinone derivatives of Formula I.

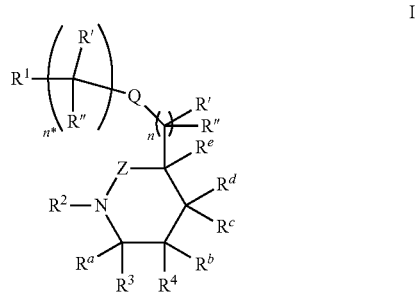

I enantiomers, diastereomers and pharmaceutically acceptable salts thereof, wherein Q is a bond or optionally can be selected from O, NR$^7$ and S(O)$_v$, when n* is an integer from 1 to 6, Z is C=O or S(=O)$_2$ R$^a$ is at each occurrence independently selected from H, (C$_1$-C$_3$)alkyl, (halo)(C$_1$-C$_3$)alkyl, (hydroxy)(C$_1$-C$_3$)alkyl, (alkoxy)(C$_1$-C$_3$)alkyl, or cyano;

R$^b$ is H, halo, (C$_1$-C$_3$)alkyl, (halo)(C$_1$-C$_3$)alkyl, (hydroxy)(C$_1$-C$_3$)alkyl, (alkoxy)(C$_1$-C$_3$)alkyl, or cyano;

R$^c$ and R$^d$ are independently H, halo, (C$_1$-C$_3$)alkyl, (C$_1$-C$_3$)alkoxy, (halo)(C$_1$-C$_3$)alkyl, (halo)(C$_1$-C$_3$)alkoxy, (alkoxy)(C$_1$-C$_3$)alkyl, (hydroxy)(C$_1$-C$_3$)alkyl;

or R$^c$ and R$^d$ may optionally combine to form a spiro-cycloalkyl or heterocyclo ring system;

R$^e$ is (a) H, or halo; or
    (b) (C$_1$-C$_8$)alkyl, (C$_3$-C$_8$)cycloalkyl, (C$_3$-C$_8$)heterocyclo, cyano, halogen, hydroxyl, —OR$^5$, NR$^7$R$^8$, heterocloalkyl, any of which may be optionally substituted with 1 or more R$^x$ groups as allowed by valence.

or R$^e$ and any one of the R' or R" groups may optionally combine to form a spiro-cycloalkyl or heterocyclo ring system;

or R$^d$ and any one of the R' or R" groups may optionally combine to form a fused cycloalkyl or heterocyclo ring system;

or R$^d$ and R$^e$ may optionally combine to form a fused cycloalkyl or heterocyclo ring system;

R' and R" at each occurrence, respectively, are independently H, halo, (C$_1$-C$_3$)alkyl, (C$_1$-C$_3$)alkoxy, (halo)(C$_1$-C$_3$)alkyl, (halo)(C$_1$-C$_3$)alkoxy, (alkoxy)(C$_1$-C$_3$)alkyl, (hydroxy)(C$_1$-C$_3$)alkyl, —S—(C$_1$-C$_3$)alkyl, C(O)(C$_1$-C$_3$)alkyl, —NR$^7$R$^8$, or hydroxyl or R' and R" bound to the same carbon atom may optionally combine to form =O;

or R' and R" bound to the same carbon atom may optionally combine to form a spiro-fused cycloalkyl or heterocyclo ring system $R^1$ is
(a) —COOH, —C(O)OR$^{10}$, —C(O)NHOH, —C(O)NH—NH$_2$, —C(O)NHS(O)$_2$R$^{10}$, —S(O)$_2$NHC(O)R$^{10}$, —S(O)$_2$NR$^7$R$^8$, —NR$^7$C(O)R$^{10}$, —NR$^7$C(O)OR$^5$, —C(O)NR$^7$R$^8$, —NR$^7$S(O)$_2$R$^{10}$, or —NR$^7$C(O)NR$^7$R$^8$, —S(O)$_x$R$^{10}$, or CN;
(b) heteroaryl or heterocyclo either of which may be optionally independently substituted with one or more $R^x$ groups as allowed by valence;

$R^2$ is
(a) —NR$^7$R$^8$, NR$^7$C(O)OR$^{10}$, NR$^7$C(O)NR$^7$R$^{10}$, or —C(R$^a$)R$^5$R$^6$;
(b) aryl, heteroaryl, cycloalkyl, or heterocyclo any of which may be optionally independently substituted with one or more $R^x$ groups as allowed by valence;

$R^3$ and $R^4$ are independently aryl or heteroaryl, either of which may be optionally independently substituted with one or more $R^x$ groups as allowed by valence;

or either $R^3$ and $R^a$ together with the ring carbon atom to which they are both bonded, or $R^4$ and $R^b$ together with the ring carbon atom to which they are both bonded may optionally combine to form a spiro-fused bicyclic ring system selected from

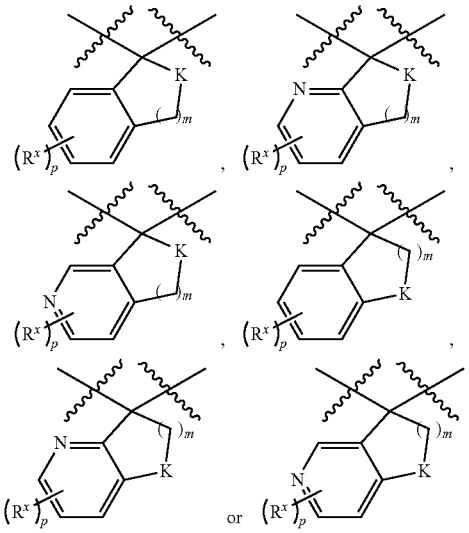

wherein K is —O—, —NR$^7$—, or —C(=O)NR$^7$—, $R^5$, and $R^6$ at each occurrence, respectively, are independently selected from
(a) H and CN; or
(b) -(alkylene)$_t$-OH, -(alkylene)$_t$-OR$^9$, -(alkylene)$_t$-SR$^9$, -(alkylene)$_t$-NR$^{10}$R$^{11}$, -(alkylene)$_t$-C(O)R$^9$, -(alkylene)$_t$- C(O)OR$^9$, -(alkylene)$_t$-OC(O)R$^9$, -(alkylene)$_t$-S(O)$_v$R$^9$, -(alkylene)$_t$-NHS(O)$_2$R$^{10}$, -(alkylene)$_t$-N(R$^{11}$)S(O)$_2$R$^{10}$, -(alkylene)$_t$- —NR$^{10}$C(O)R$^9$, C(O)NR$^{10}$R$^{11}$, NR$^{10}$S(O)$_2$R$^9$, S(O)$_2$NR$^{10}$, and NR$^{10}$C(O)NR$^{10}$R$^{11}$; or
(a) haloalkyl, haloalkoxy, C$_{1-6}$-alkyl, C$_{2-6}$alkenyl, C$_{2-6}$-alkynyl, C$_{3-8}$-cycloalkyl, (C$_{3-8}$-cycloalkyl)(C$_{1-3}$alkyl), C$_{4-8}$-cycloalkenyl, aryl, aryl(C$_{1-3}$-alkyl) heteroaryl, heteroaryl(C$_{1-3}$-alkyl), heterocyclo and heterocyclo(C$_{1-3}$-alkyl) m any of which may be optionally independently substituted with one or more $R^x$ groups as allowed by valence;

$R^7$, and $R^8$ at each occurrence, respectively, are independently selected from H, C$_{1-6}$-alkyl, halo(C$_{1-6}$)-alkyl, cycloalkyl, C$_{2-6}$-alkenyl, C$_{2-6}$-alkynyl, aryl, heteroaryl, heterocyclo, arylalkyl, heteroarylalkyl, heterocyclo(C$_{1-10}$alkyl), and (C$_{3-8}$-cycloalkyl)(C$_{1-3}$alkyl), any of which may be optionally substituted as allowed by valence with one or more $R^x$;

or $R^7$ and $R^8$ may combine to form a C$_4$-C$_8$-heterocyclo ring optionally substituted with one or more $R^x$;

$R^9$ is
haloalkyl, haloalkoxy, C$_{1-6}$-alkyl, C$_{2-6}$alkenyl, C$_{2-6}$-alkynyl, C$_{3-8}$-cycloalkyl, (C$_{3-8}$-cycloalkyl)(C$_{1-3}$alkyl), C$_{4-8}$-cycloalkenyl, aryl, heteroaryl, and heterocyclo any of which may be optionally independently substituted with one or more $R^x$ groups as allowed by valence;

$R^{10}$ and $R^{11}$ at each occurrence, respectively, are independently selected from alkyl, haloalkyl, cycloalkyl, alkenyl, alkynyl, aryl, heteroaryl, heterocyclo, arylalkyl, heteroarylalkyl, heterocycloalkyl, and cycloalkylalkyl, any of which may be optionally substituted as allowed by valence with one or more $R^x$;

or $R^{10}$ and $R^{11}$ may combine to form a heterocyclo ring optionally substituted with one or more $R^x$;

$R^x$ at each occurrence is independently, deuterium, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more halo, cyano, oxo, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*;

R* is
haloalkyl, haloalkoxy, C$_{1-6}$-alkyl, C$_{2-6}$alkenyl, C$_{2-6}$-alkynyl, C$_{3-8}$-cycloalkyl, C$_{4-8}$-cycloalkenyl, aryl, heteroaryl, and heterocyclo $R^+$ and $R^{++}$ are independently H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl, or $R^+$ and $R^{++}$ bound to the same nitrogen atom may optionally combine to form a heterocyclo ring system;

m is 1, 2 or 3 n and n* are each independently selected from 0 and integers from 1 to 6;

p is 0, 1, 2 or 3;

t at each occurrence is independently 0 or an integer from 1 to 6;

v at each occurrence is independently 0, 1 or 2;

Preferred compounds within the scope of Formula I include compounds wherein $R^2$ is —C(H)$R^5R^6$ or —N$R^7R^8$, phenyl or pyridine, the phenyl or the pyridyl may be optionally substituted with one or more $R^x$ as allowed by valence.

Preferred compounds within the scope of Formula I include compounds wherein $R^2$ is $R^2$ is selected from

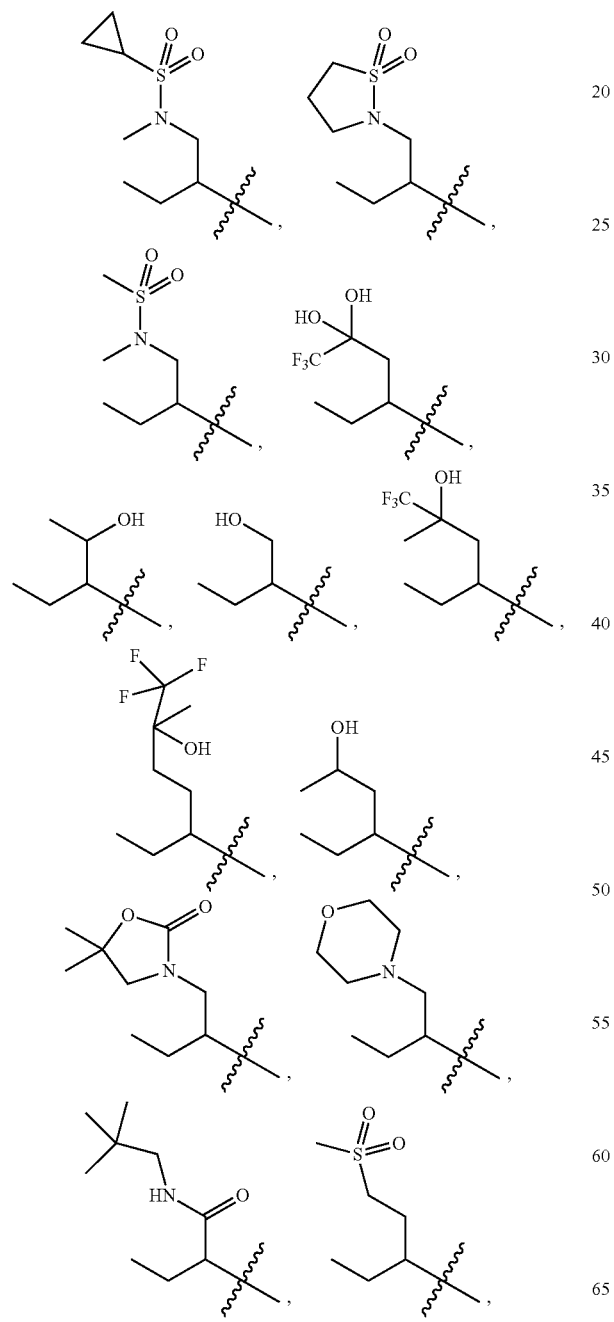

-continued

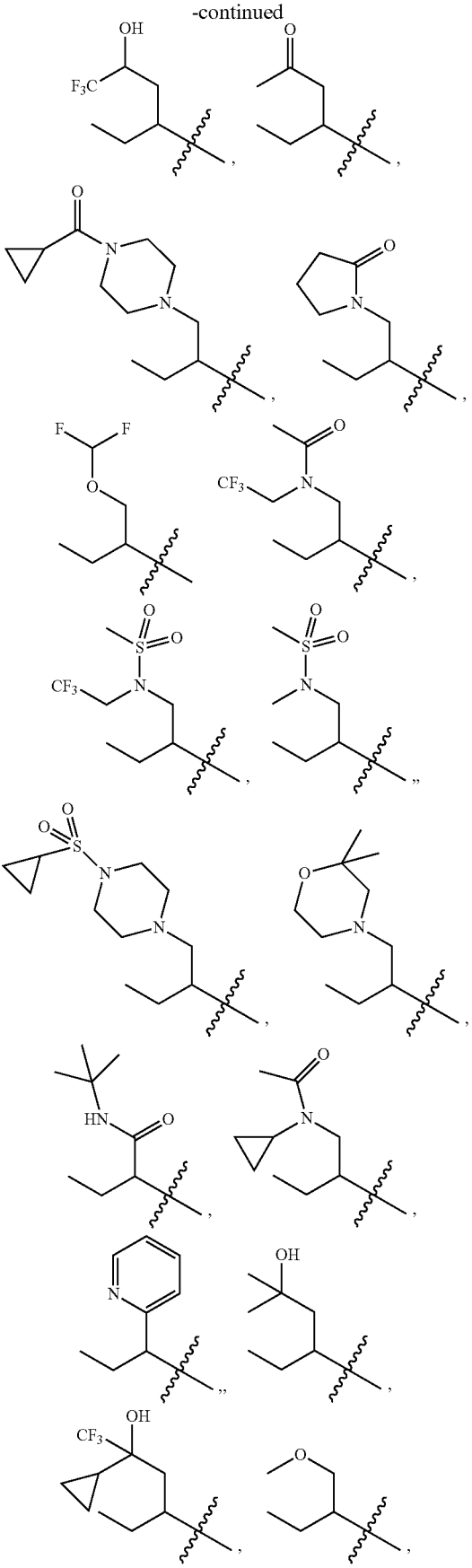

-continued
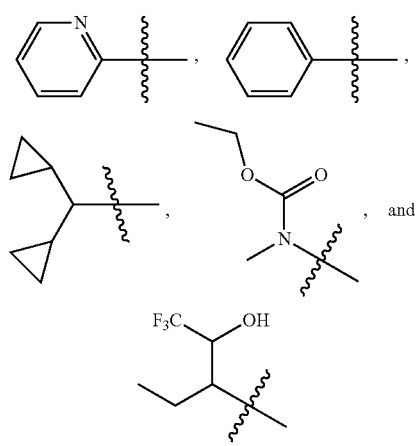
any of which may be optionally substituted with one or more $R^x$ groups as allowed by valence.
Preferred compounds within the scope of Formula I include compounds wherein $R^1$ is
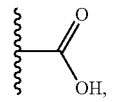
or a heterocycle selected from
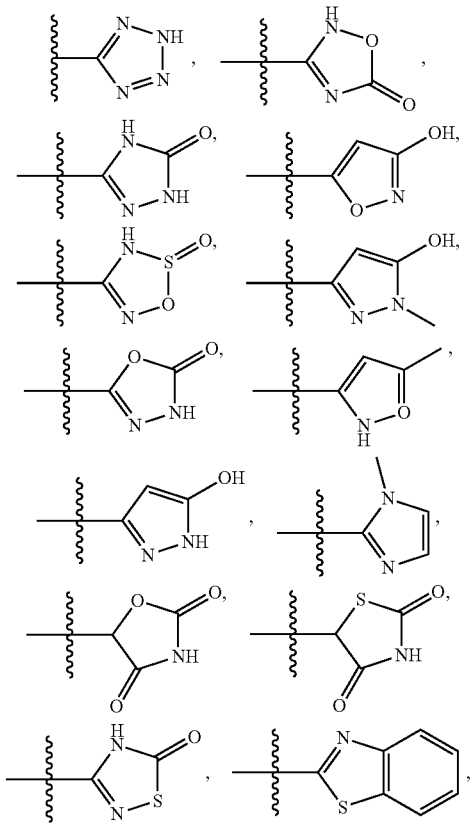
-continued
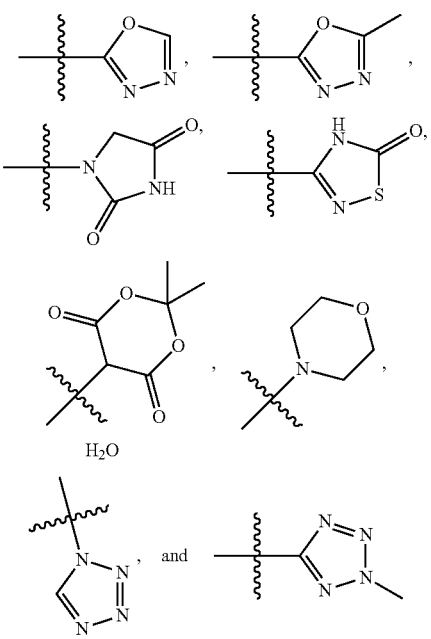
(most preferentially
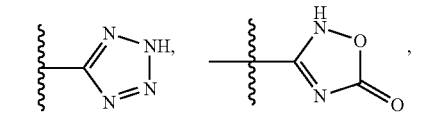
or a heterocycle selected from
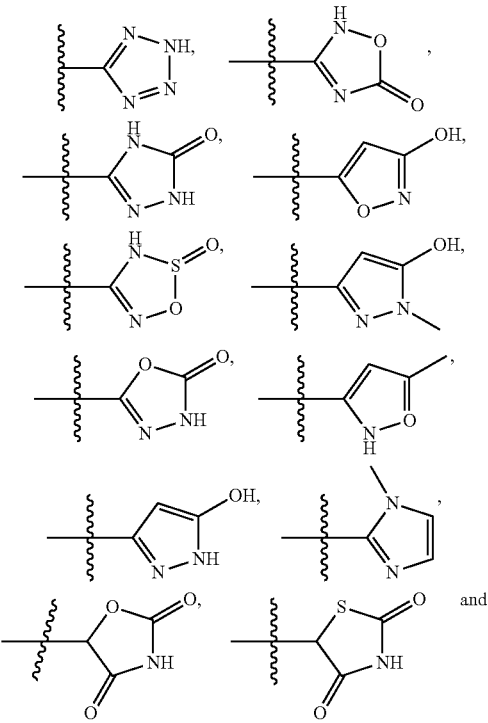

-continued

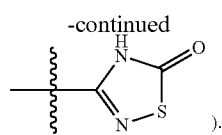).

Preferred compounds within the scope of Formula I include compounds of Formula IA:

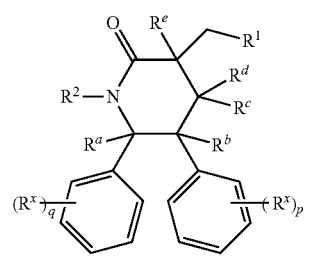

IA enantiomers, diastereomers and pharmaceutically acceptable salts thereof
wherein q and p are each independently 0, 1, 2 or 3. Preferred compounds of Formula IA include compounds containing preferred $R^1$ and $R^2$ groups previously mentioned.

Preferred compounds within the scope of Formula I include compounds of Formula IB:

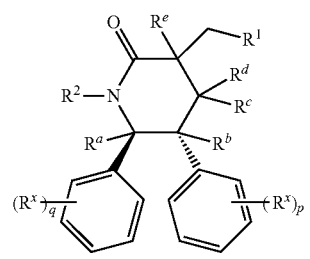

IB enantiomers, diastereomers and pharmaceutically acceptable salts thereof
wherein q and p are each independently 0, 1, 2 or 3. Preferred compounds of Formula IB include compounds containing preferred $R^1$ and $R^2$ groups previously mentioned Preferred compounds within the scope of formula I include compounds of Formula IC:

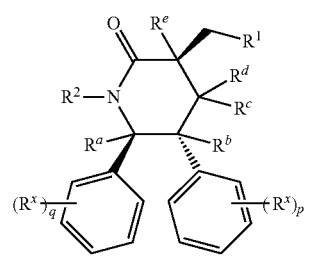

IC enantiomers, diastereomers and pharmaceutically acceptable salts thereof
wherein q and p are each independently 0, 1, 2 or 3. Preferred compounds of Formula IC include compounds containing preferred $R^1$ and $R^2$ groups mentioned herein.

Preferred compounds within the scope of Formulae IA, IB and IC further include compounds wherein $R^2$ is selected from

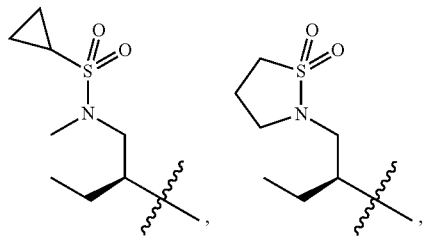

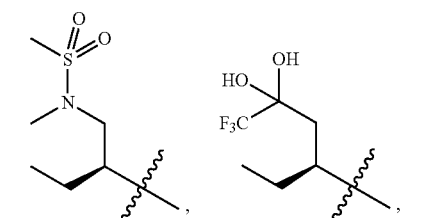

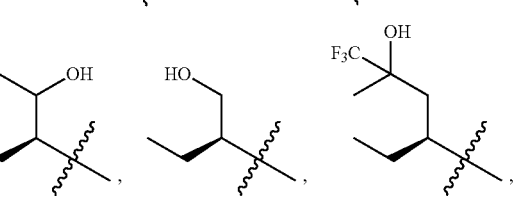

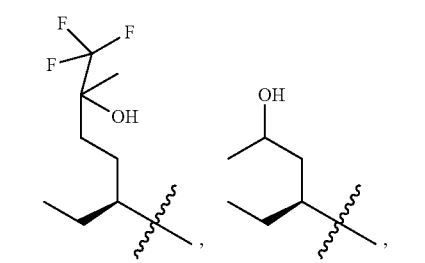

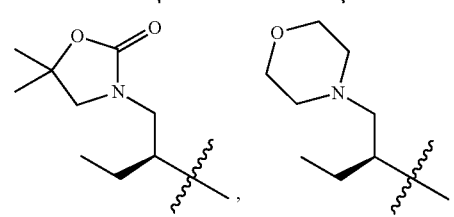

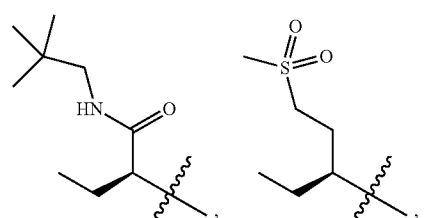

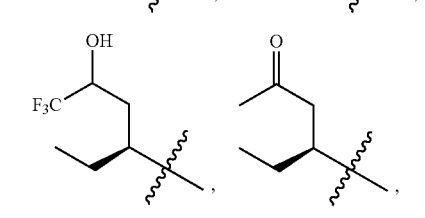

-continued

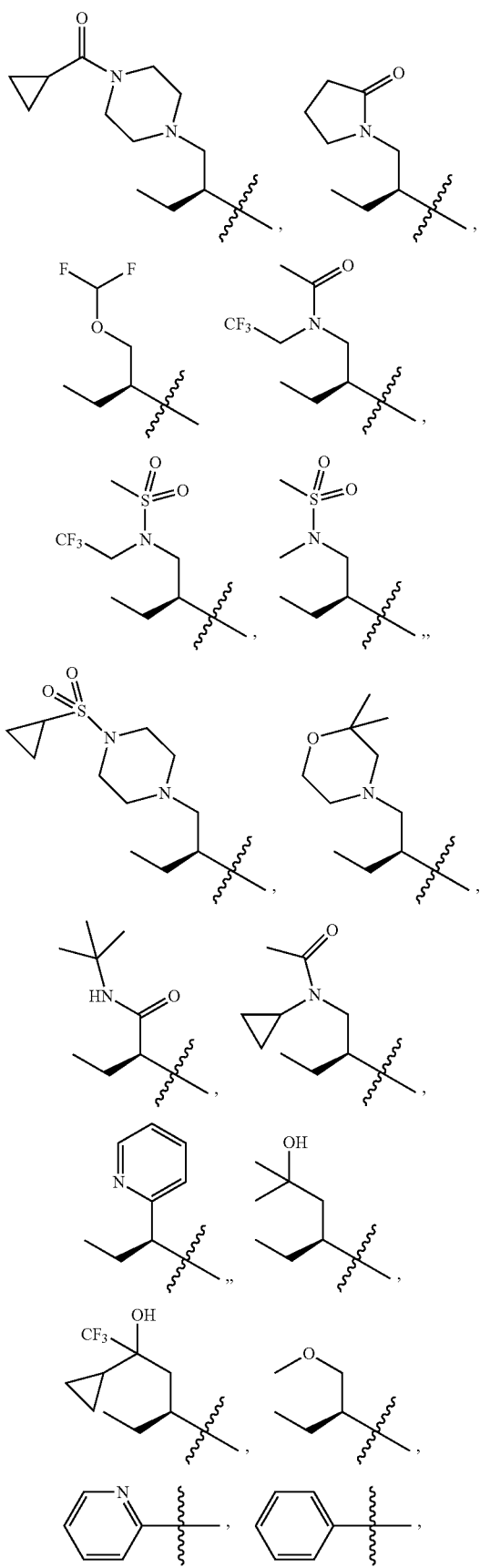

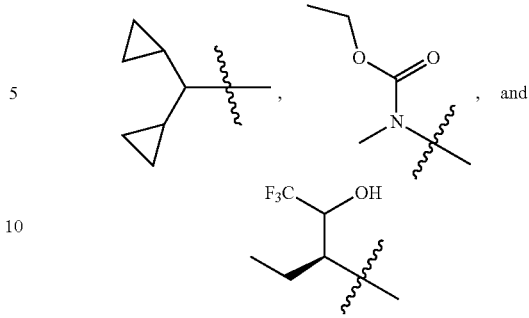

any of which may be optionally substituted with one or more $R^x$ groups as allowed by valence.

In another aspect, aspect A, the present invention provides compounds of Formula I:

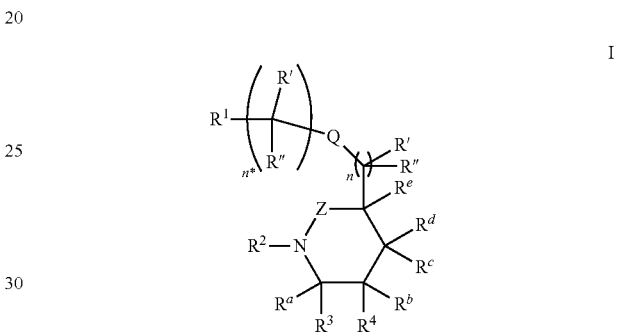

I or a pharmaceutically acceptable salt thereof, wherein:
Q is a bond or optionally can be selected from O, $NR^7$ or $S(O)_v$, when n* is an integer from 1 to 6;
Z is C=O or $S(=O)_2$;
$R^a$ at each occurrence is independently selected from H, $(C_1-C_3)$alkyl, (halo)$(C_1-C_3)$alkyl, (hydroxy)$(C_1-C_3)$alkyl, (alkoxy)$(C_1-C_3)$alkyl, or cyano;
$R^b$ is H, halo, $(C_1-C_3)$alkyl, (halo)$(C_1-C_3)$alkyl, (hydroxy)$(C_1-C_3)$alkyl, (alkoxy)$(C_1-C_3)$alkyl, or cyano;
$R^c$ and $R^d$ are independently selected from H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, or (hydroxy)$(C_1-C_3)$alkyl, or $R^c$ and $R^d$ may optionally combine to form a spiro-cycloalkyl or heterocyclo ring system;
$R^e$ is
(a) H or halo; or
(b) $(C_1-C_8)$alkyl, $(C_3-C_8)$cycloalkyl, $(C_3-C_8)$heterocyclo, cyano, halogen, hydroxyl, —$OR^5$, $NR^7R^8$, or heterocycloalkyl, any of which may be optionally substituted with 1 or more $R^x$ groups as allowed by valence, or $R^e$ and any one of the R' or R" groups may optionally combine to form a spiro-cycloalkyl or heterocyclo ring system, or $R^d$ and any one of the R' or R" groups may optionally combine to form a fused cycloalkyl or heterocyclo ring system, or $R^d$ and $R^e$ may optionally combine to form a fused cycloalkyl or heterocyclo ring system;
R' and R" at each occurrence, respectively, are independently H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, (hydroxy)$(C_1-C_3)$alkyl, —S—$(C_1-C_3)$alkyl, $C(O)(C_1-C_3)$alkyl, —$NR^7R^8$, or hydroxyl, or R' and R" bound to the same carbon atom may optionally combine to form =O, or R' and R" bound to the same carbon atom may optionally combine to form a spiro-fused cycloalkyl or heterocyclo ring system;

$R^1$ is (a) —COOH, —C(O)OR$^{10}$, —C(O)NHOH, —C(O)NH—NH$_2$, —C(O)NHS(O)$_2$R$^{10}$, —S(O)$_2$NHC(O)R$^{10}$, —S(O)$_2$NR$^7$R$^8$, —NR$^7$C(O)R$^{10}$, —NR$^7$C(O)OR$^5$, —C(O)NR$^7$R$^8$, —NR$^7$S(O)$_2$R$^{10}$, '—NR$^7$C(O)NR$^7$R$^8$, —S(O)$_v$R$^{10}$, hydroxylalkyl, -cyclopropyl-COOH, or CN; or (b) heteroaryl or heterocyclo, either of which may be optionally independently substituted with one or more $R^x$ groups as allowed by valence;

$R^2$ is (a) —NR$^7$R$^8$, NR$^7$C(O)OR$^{10}$, NR$^7$C(O)NR$^7$R$^{10}$, or —C(R$^a$)R$^5$R$^6$; or (b) aryl, heteroaryl, cycloalkyl, or heterocyclo, any of which may be optionally independently substituted with one or more $R^x$ groups as allowed by valence;

$R^3$ and $R^4$ are independently aryl or heteroaryl, either of which may be optionally independently substituted with one or more $R^x$ groups as allowed by valence, or either $R^3$ and $R^a$ together with the ring carbon atom to which they are both bonded, or $R^4$ and $R^b$ together with the ring carbon atom to which they are both bonded may optionally combine to form a spiro-fused bicyclic ring system selected from

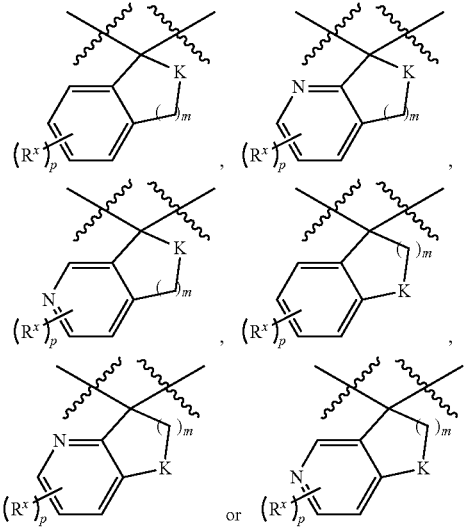

wherein K is —O—, —NR$^7$—, or —C(=O)NR$^7$—;

$R^5$ and $R^6$ at each occurrence, respectively, are independently selected from (a) H or CN;

(b) -(alkylene)$_t$-OH, -(alkylene)$_t$-OR$^9$, -(alkylene)$_t$-SR$^9$, -(alkylene)$_t$-NR$^{10}$R$^{11}$, -(alkylene)$_t$-C(O)R$^9$, -(alkylene)$_t$-C(O)OR$^9$, -(alkylene)$_t$-OC(O)R$^9$, -(alkylene)$_t$-S(O)$_v$R$^9$, -(alkylene)$_t$-NHS(O)$_2$R$^{10}$, -(alkylene)$_t$-N(R$^{11}$)S(O)$_2$R$^{10}$, -(alkylene)$_t$-S(O)$_2$NR$^{10}$R$^{11}$, —NR$^{10}$C(O)R$^9$, —C(O)NR$^{10}$R$^{11}$, —NR$^{10}$S(O)$_2$R$^9$, S(O)$_2$NR$^{10}$, or NR$^{10}$C(O)NR$^{10}$R$^{11}$; or (c) haloalkyl, haloalkoxy, C$_{1-6}$-alkyl, C$_{2-6}$alkenyl, C$_{2-6}$-alkynyl, C$_{3-8}$-cycloalkyl, (C$_{3-8}$-cycloalkyl)(C$_{1-3}$alkyl), C$_{4-8}$-cycloalkenyl, aryl, aryl(C$_{1-3}$-alkyl), heteroaryl, heteroaryl(C$_{1-3}$-alkyl), heterocyclo or heterocyclo(C$_{1-3}$-alkyl), any of which may be optionally independently substituted with one or more $R^x$ groups as allowed by valence;

$R^7$ and $R^8$ at each occurrence, respectively, are independently selected from H, cyano, —OC$_{1-6}$-alkyl, C$_{1-6}$-alkyl, halo(C$_{1-6}$)-alkyl, cycloalkyl, C$_{2-6}$-alkenyl, C$_{2-6}$-alkynyl, aryl, heteroaryl, heterocyclo, arylalkyl, heteroarylalkyl, heterocyclo(C$_{1-10}$alkyl), or (C$_{3-8}$-cycloalkyl)(C$_{1-3}$alkyl), any of which may be optionally substituted as allowed by valence with one or more $R^x$, or $R^7$ and $R^8$ may combine to form a C$_4$-C$_8$-heterocyclo ring optionally substituted with one or more $R^x$;

$R^9$ is haloalkyl, haloalkoxy, C$_{1-6}$-alkyl, C$_{2-6}$alkenyl, C$_{2-6}$-alkynyl, C$_{3-8}$-cycloalkyl, (C$_{3-8}$-cycloalkyl)(C$_{1-3}$alkyl), C$_{4-8}$-cycloalkenyl, aryl, heteroaryl, or heterocyclo, any of which may be optionally independently substituted with one or more $R^x$ groups as allowed by valence;

$R^{10}$ and $R^{11}$ at each occurrence, respectively, are independently selected from H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, any of which may be optionally substituted as allowed by valence with one or more $R^x$, or $R^{10}$ and $R^{11}$ may combine to form a heterocyclo ring optionally substituted with one or more $R^x$;

$R^x$ at each occurrence is independently, deuterium, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more halo, cyano, oxo, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*;

R* is H, haloalkyl, haloalkoxy, C$_{1-6}$-alkyl, C$_{2-6}$alkenyl, C$_{2-6}$-alkynyl, C$_{3-8}$-cycloalkyl, C$_{4-8}$-cycloalkenyl, aryl, heteroaryl, or heterocyclo;

R$^+$ and R$^{++}$ are independently H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, or R$^+$ and R$^{++}$ bound to the same nitrogen atom may optionally combine to form a heterocyclo ring system;

m is 1, 2 or 3;

n and n* are each independently selected from 0 or an integer from 1 to 6;

p is 0, 1, 2 or 3;

t at each occurrence is independently 0 or an integer from 1 to 6; and v at each occurrence is independently 0, 1 or 2.

In another aspect, aspect AA, the present invention provides compounds of Formula I:

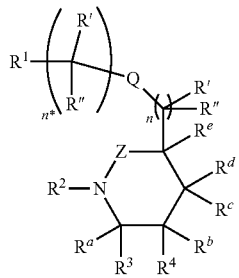

or a pharmaceutically acceptable salt thereof, wherein:

Q is a bond or optionally can be selected from O, $NR^7$ or $S(O)_v$, when n* is an integer from 1 to 6;

Z is C=O or $S(=O)_2$;

$R^a$ at each occurrence is independently selected from H, $(C_1-C_3)$alkyl, (halo)$(C_1-C_3)$alkyl, (hydroxy)$(C_1-C_3)$alkyl, (alkoxy)$(C_1-C_3)$alkyl, or cyano;

$R^b$ is H, halo, $(C_1-C_3)$alkyl, (halo)$(C_1-C_3)$alkyl, (hydroxy)$(C_1-C_3)$alkyl, (alkoxy)$(C_1-C_3)$alkyl, or cyano;

$R^c$ and $R^d$ are independently selected from H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, or (hydroxy)$(C_1-C_3)$alkyl, or $R^c$ and $R^d$ may optionally combine to form a spiro-cycloalkyl or heterocyclo ring system;

$R^e$ is (a) H or halo; or (b) $(C_1-C_8)$alkyl, $(C_3-C_8)$cycloalkyl, $(C_3-C_8)$heterocyclo, cyano, halogen, hydroxyl, $—OR^5$, $NR^7R^8$, or heterocloalkyl, any of which may be optionally substituted with 1 or more $R^x$ groups as allowed by valence, or $R^e$ and any one of the R' or R'' groups may optionally combine to form a spiro-cycloalkyl or heterocyclo ring system, or $R^d$ and any one of the R' or R'' groups may optionally combine to form a fused cycloalkyl or heterocyclo ring system, or $R^d$ and $R^e$ may optionally combine to form a fused cycloalkyl or heterocyclo ring system;

R' and R'' at each occurrence, respectively, are independently H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, (hydroxy)$(C_1-C_3)$alkyl, $—S—(C_1-C_3)$alkyl, $C(O)(C_1-C_3)$alkyl, $—NR^7R^8$, or hydroxyl, or R' and R'' bound to the same carbon atom may optionally combine to form =O, or R' and R'' bound to the same carbon atom may optionally combine to form a spiro-fused cycloalkyl or heterocyclo ring system;

$R^1$ is (a) —COOH, —$C(O)OR^{10}$, —C(O)NHOH, —C(O)NH—$NH_2$, —$C(O)NHS(O)_2R^{10}$, —$S(O)_2NHC(O)R^{10}$, —$S(O)_2NR^7R^8$, —$NR^7C(O)R^{10}$, —$NR^7C(O)OR^5$, —$C(O)NR^7R^8$, —$NR^7S(O)_2R^{10}$, —$NR^7C(O)NR^7R^8$, —$S(O)_vR^{10}$, hydroxylalkyl, -cyclopropyl-COOH, or CN; or (b) heteroaryl or heterocyclo, either of which may be optionally independently substituted with one or more $R^x$ groups as allowed by valence;

$R^2$ is (a) —$NR^7R^8$, $NR^7C(O)OR^{10}$, $NR^7C(O)NR^7R^{10}$, or —$C(R^a)R^5R^6$; or (b) aryl, heteroaryl, cycloalkyl, or heterocyclo, any of which may be optionally independently substituted with one or more $R^x$ groups as allowed by valence;

$R^3$ and $R^4$ are independently aryl or heteroaryl, either of which may be optionally independently substituted with one or more $R^x$ groups as allowed by valence, or either $R^3$ and $R^a$ together with the ring carbon atom to which they are both bonded, or $R^4$ and $R^b$ together with the ring carbon atom to which they are both bonded may optionally combine to form a spiro-fused bicyclic ring system selected from

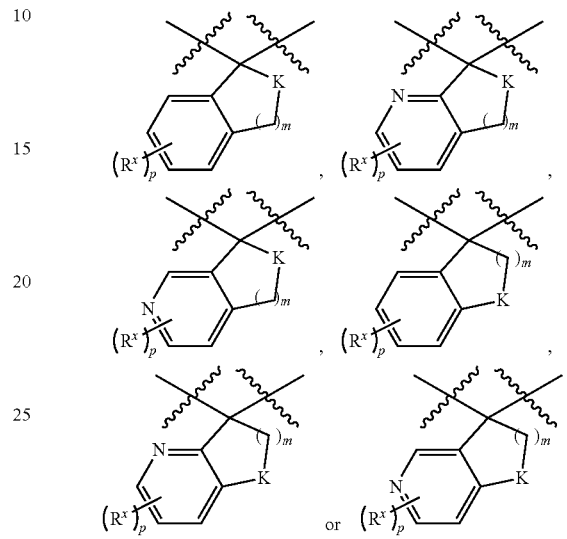

wherein K is —O—, —$NR^7$—, or —$C(=O)NR^7$—;

$R^5$ and $R^6$ at each occurrence, respectively, are independently selected from (a) H or CN;

(b) -(alkylene)$_t$-OH, -(alkylene)$_t$-$OR^9$, -(alkylene)$_t$-$SR^9$, -(alkylene)$_t$-$NR^{10}R^{11}$, -(alkylene)$_t$-$C(O)R^9$, -(alkylene)$_t$-$C(O)OR^9$, -(alkylene)$_t$-$OC(O)R^9$, -(alkylene)$_t$-$S(O)_vR^9$, -(alkylene)$_t$-$NHS(O)_2R^{10}$, -(alkylene)$_t$-$N(R^{11})S(O)_2R^{10}$, -(alkylene)$_t$-$S(O)_2NR^{10}R^{11}$, -(alkylene)$_t$-$N(R^{11})S(O)_2NR^{10}R^{11}$, —$NR^{10}C(O)R^9$, —$C(O)NR^{10}R^{11}$, —$NR^{10}S(O)_2R^9$, $S(O)_2NR^{10}$, or $NR^{10}C(O)NR^{10}R^{11}$; or (c) haloalkyl, haloalkoxy, $C_{1-6}$-alkyl, $C_{2-6}$alkenyl, $C_{2-6}$-alkynyl, $C_{3-8}$-cycloalkyl, $(C_{3-8}$-cycloalkyl)$(C_{1-3}$alkyl), $C_{4-8}$-cycloalkenyl, aryl, aryl$(C_{1-3}$-alkyl), heteroaryl, heteroaryl$(C_{1-3}$-alkyl), heterocyclo or heterocyclo$(C_{1-3}$-alkyl), any of which may be optionally independently substituted with one or more $R^x$ groups as allowed by valence;

$R^7$ and $R^8$ at each occurrence, respectively, are independently selected from H, cyano, —$OC_{1-6}$-alkyl, $C_{1-6}$-alkyl, halo$(C_{1-6})$-alkyl, cycloalkyl, $C_{2-6}$-alkenyl, $C_{2-6}$-alkynyl, aryl, heteroaryl, heterocyclo, arylalkyl, heteroarylalkyl, heterocyclo$(C_{1-10}$alkyl), or $(C_{3-8}$-cycloalkyl)$(C_{1-3}$alkyl), any of which may be optionally substituted as allowed by valence with one or more $R^x$, or $R^7$ and $R^8$ may combine to form a $C_4-C_8$-heterocyclo ring optionally substituted with one or more $R^x$;

$R^9$ is haloalkyl, haloalkoxy, $C_{1-6}$-alkyl, $C_{2-6}$alkenyl, $C_{2-6}$-alkynyl, $C_{3-8}$-cycloalkyl, $(C_{3-8}$-cycloalkyl)$(C_{1-3}$alkyl), $C_{4-8}$-cycloalkenyl, aryl, heteroaryl, heterocyclo, or heterocloalkyl, any of which may be optionally independently substituted with one or more $R^x$ groups as allowed by valence;

$R^{10}$ and $R^{11}$ at each occurrence, respectively, are independently selected from H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, any of which may be optionally substituted as allowed by valence with one or more $R^x$, or $R^{10}$ and $R^{11}$ may combine to form a heterocyclo ring optionally substituted with one or more $R^x$;

$R^x$ at each occurrence is independently, deuterium, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more halo, cyano, oxo, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*;

R* is H, haloalkyl, haloalkoxy, $C_{1-6}$-alkyl, $C_{2-6}$-alkenyl, $C_{2-6}$-alkynyl, $C_{3-8}$-cycloalkyl, $C_{4-8}$-cycloalkenyl, aryl, heteroaryl, or heterocyclo;

R$^+$ and R$^{++}$ are independently H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, or R$^+$ and R$^{++}$ bound to the same nitrogen atom may optionally combine to form a heterocyclo ring system;

m is 1, 2 or 3;

n and n* are each independently selected from 0 or an integer from 1 to 6;

p is 0, 1, 2 or 3;

t at each occurrence is independently 0 or an integer from 1 to 6; and v at each occurrence is independently 0, 1 or 2.

In another embodiment, embodiment 2, of the compounds of Aspect A or AA, or the pharmaceutically acceptable salts thereof, $R^2$ is —C(H)$R^5R^6$, —NR$^7R^8$, phenyl or pyridine, wherein the phenyl or the pyridyl may be optionally substituted with one or more $R^x$ as allowed by valence.

In another embodiment, embodiment 3, of the compounds of Aspect A or AA, or the pharmaceutically acceptable salts thereof, $R^2$ is selected from

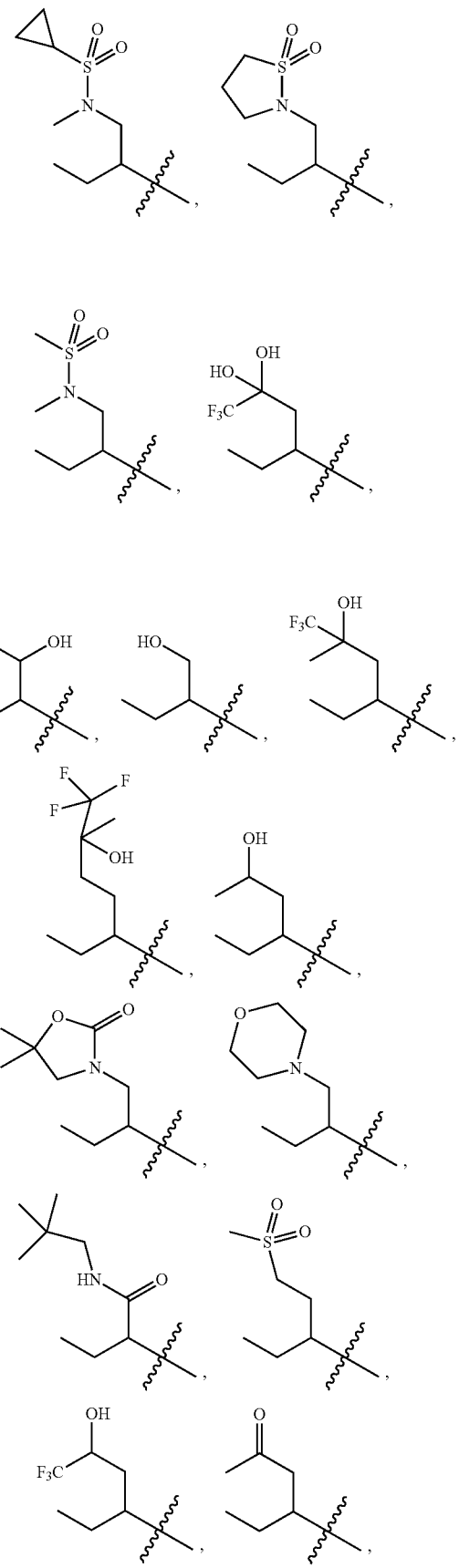

-continued

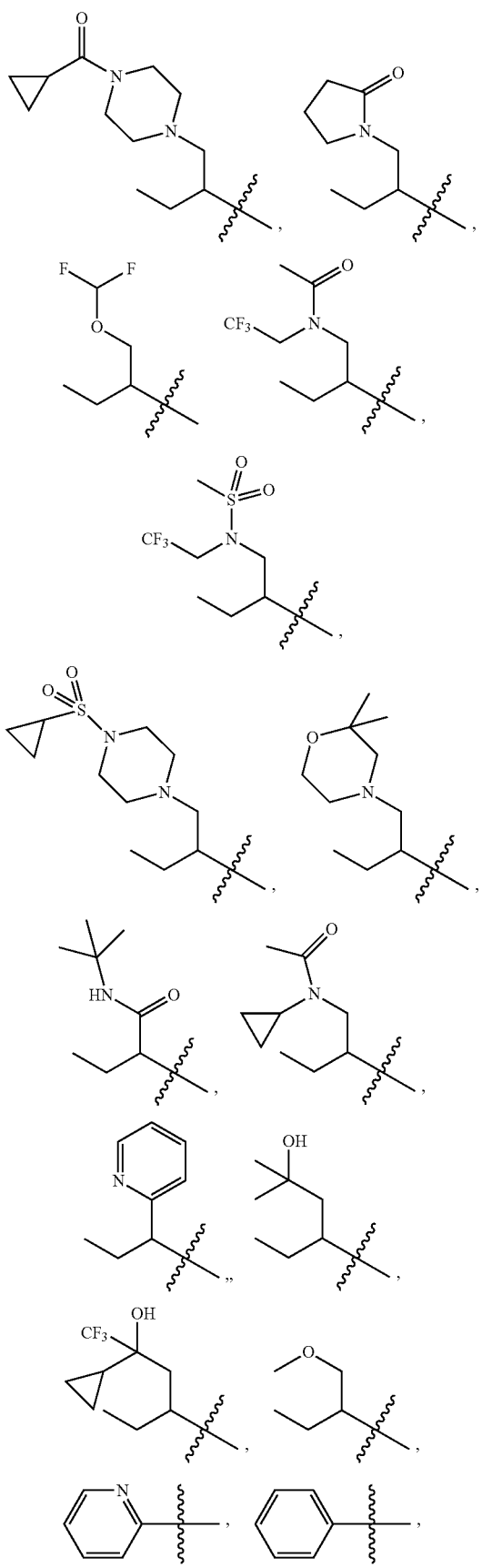

-continued

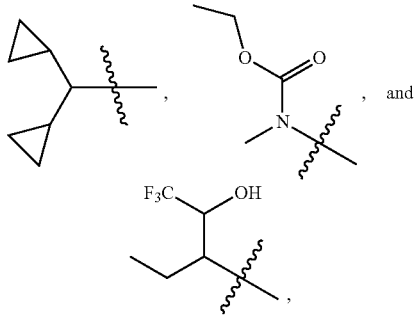

any of which may be optionally substituted with one or more $R^x$ groups as allowed by valence.

In another embodiment, embodiment 4, the compounds of Aspect A or AA have the structure of Formula IA

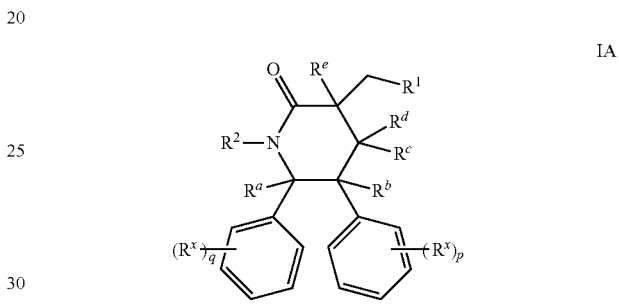

or the pharmaceutically acceptable salts thereof, wherein q and p are each independently 0, 1, 2 or 3.

In another embodiment, embodiment 5, the compounds of Aspect A or AA have the structure of Formula IB

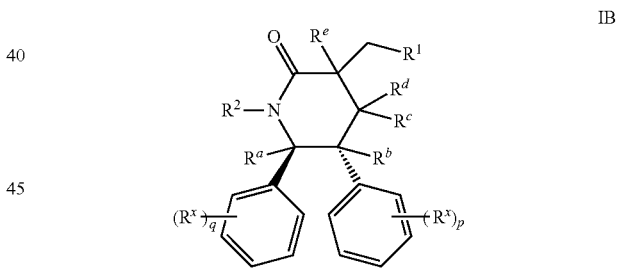

or the pharmaceutically acceptable salts thereof, wherein q and p are each independently 0, 1, 2 or 3.

In another embodiment, embodiment 6, the compounds of Aspect A or AA have the structure of Formula IC

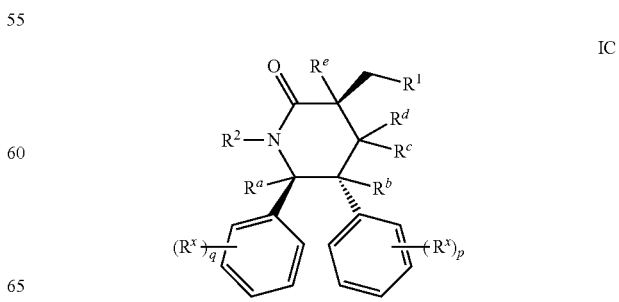

or the pharmaceutically acceptable salts thereof, wherein q and p are each independently 0, 1, 2 or 3.
In another aspect of embodiment 6 (embodiment 7), or the pharmaceutically acceptable salts thereof, R² is selected from
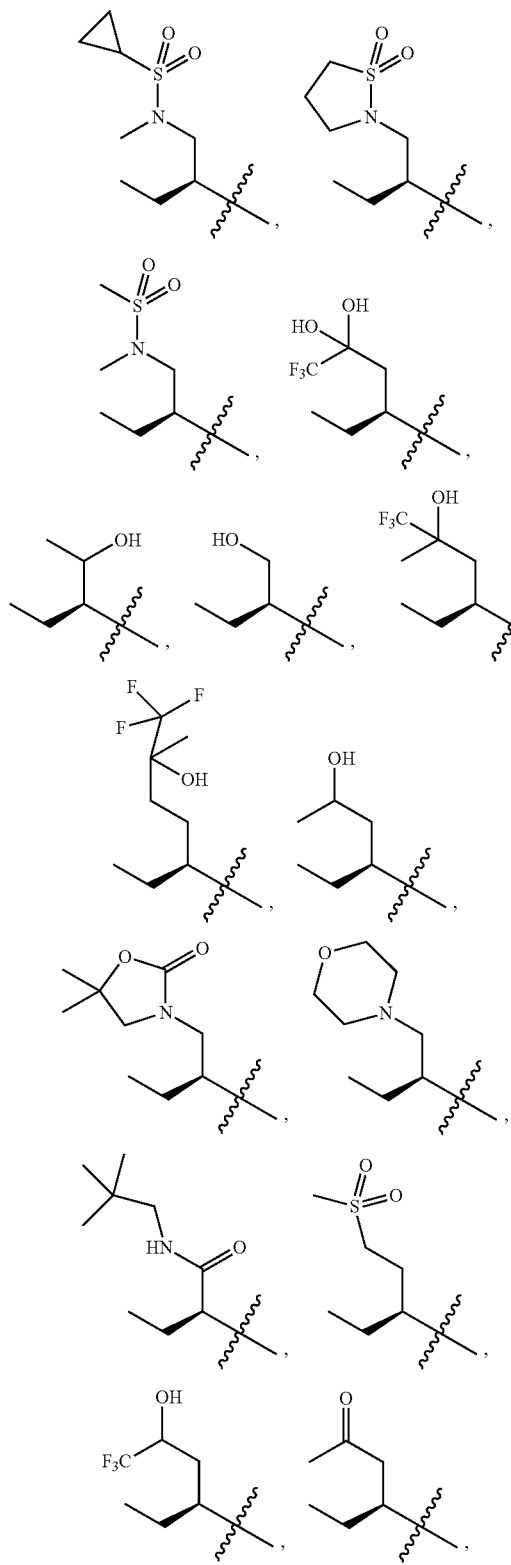
-continued
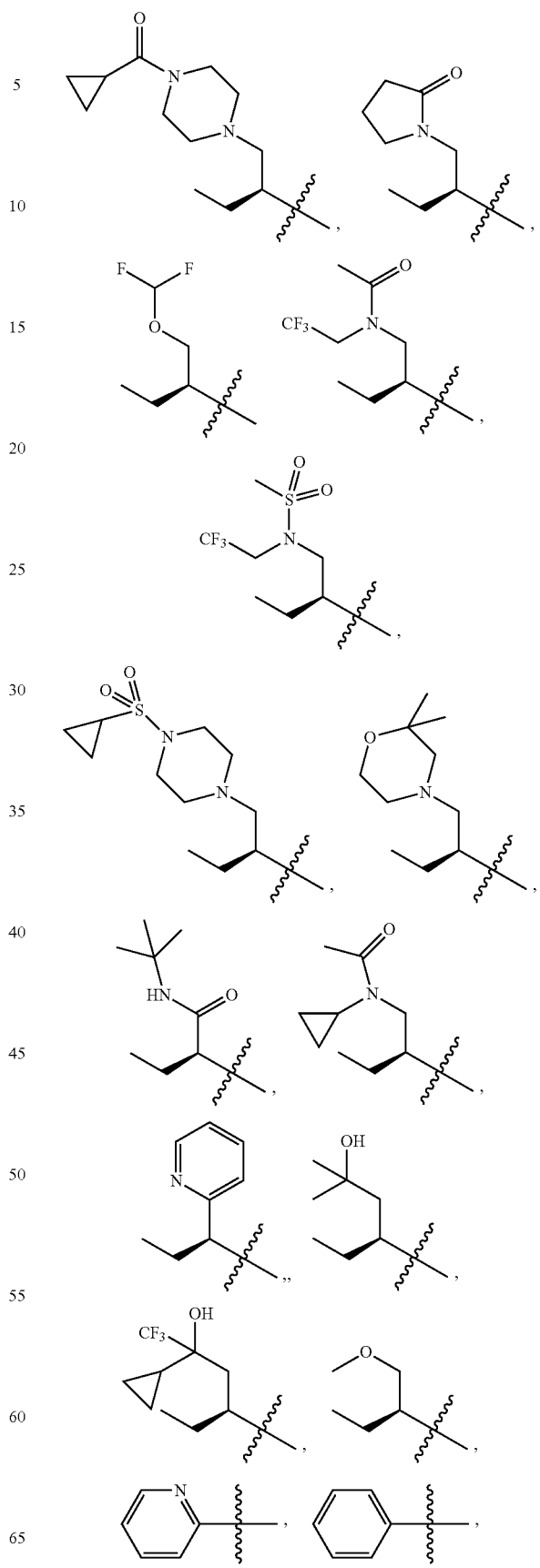

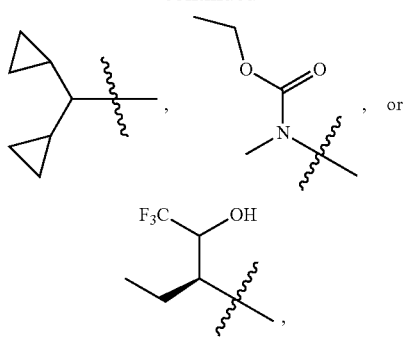
any of which may be optionally substituted with one or more $R^x$ groups as allowed by valence.
In another aspect of embodiment 6 (embodiment 8) or the pharmaceutically acceptable salts thereof,
$R^2$ is selected from
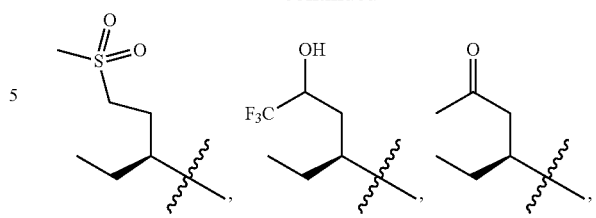
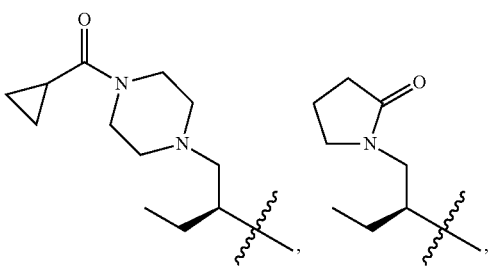
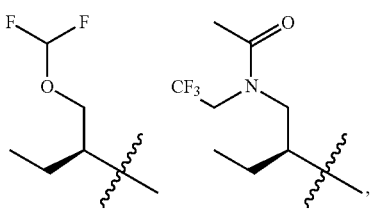
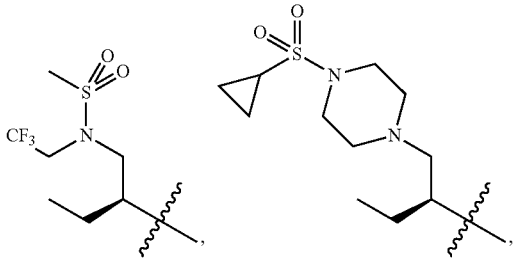
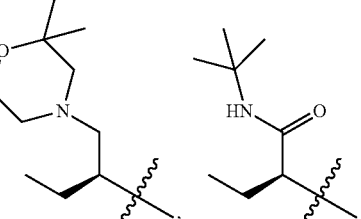
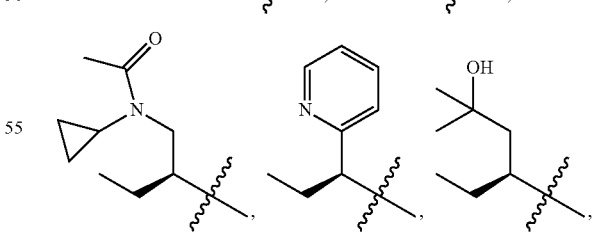
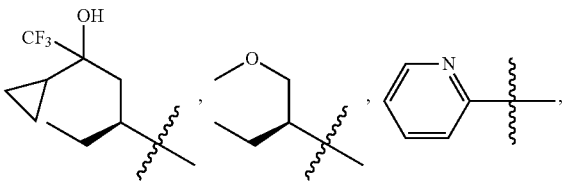

-continued
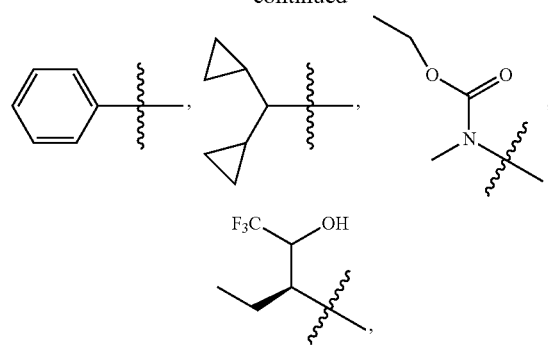, or
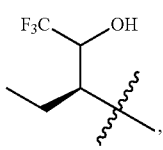,
any of which may be optionally substituted with one or more $R^x$ groups as allowed by valence;
and $R^1$ is
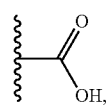
or a heteroaryl or heterocycle selected from
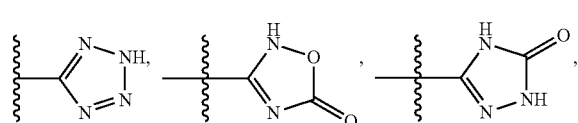
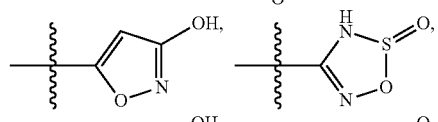
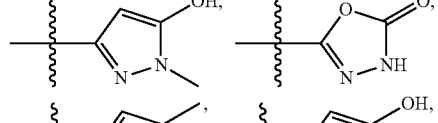
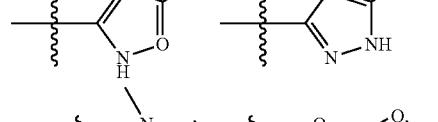
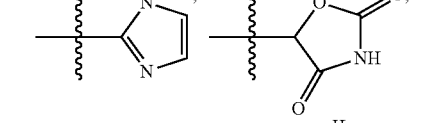
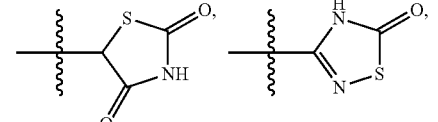
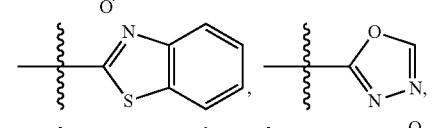
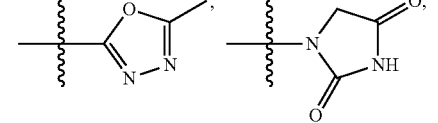
-continued
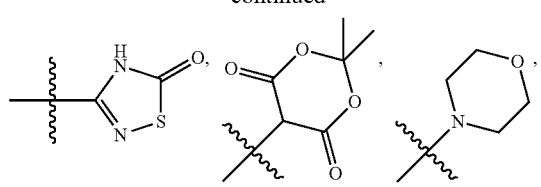
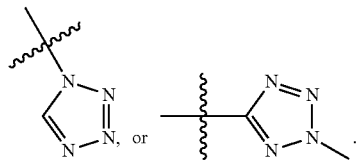, or
In another aspect of embodiment 6 (embodiment 9), or the pharmaceutically acceptable salts thereof,
$R^2$ is selected from
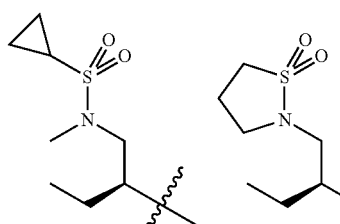
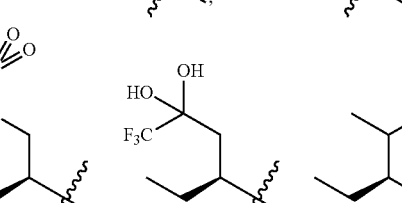
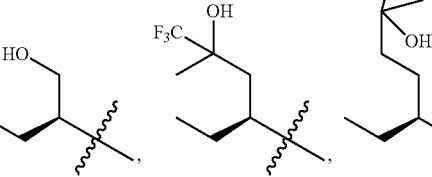
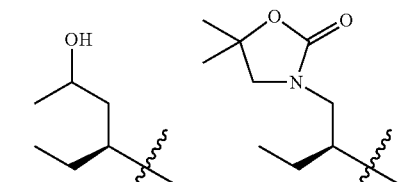
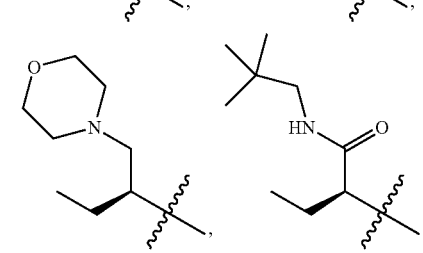

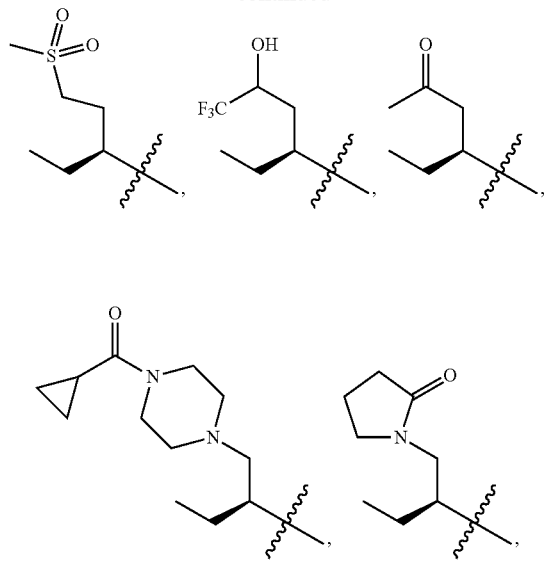
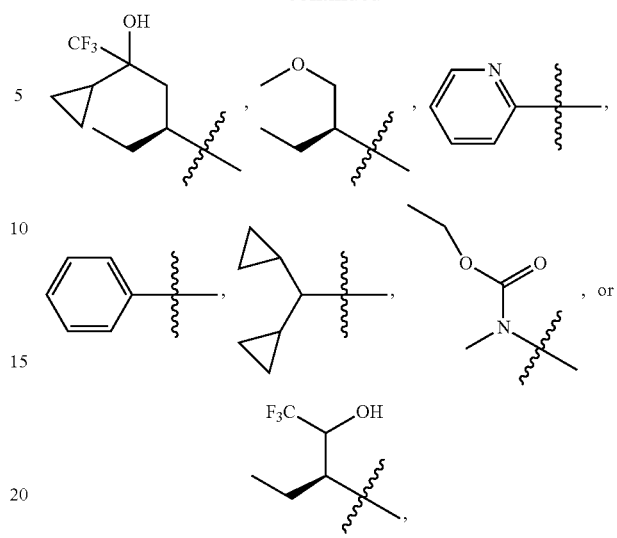
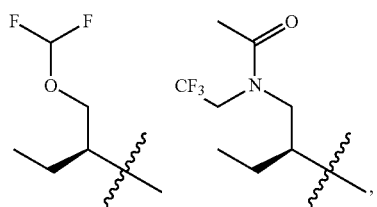
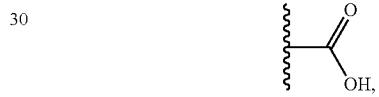
any of which may be optionally substituted with one or more R$^x$ groups as allowed by valence; and
R$^1$ is
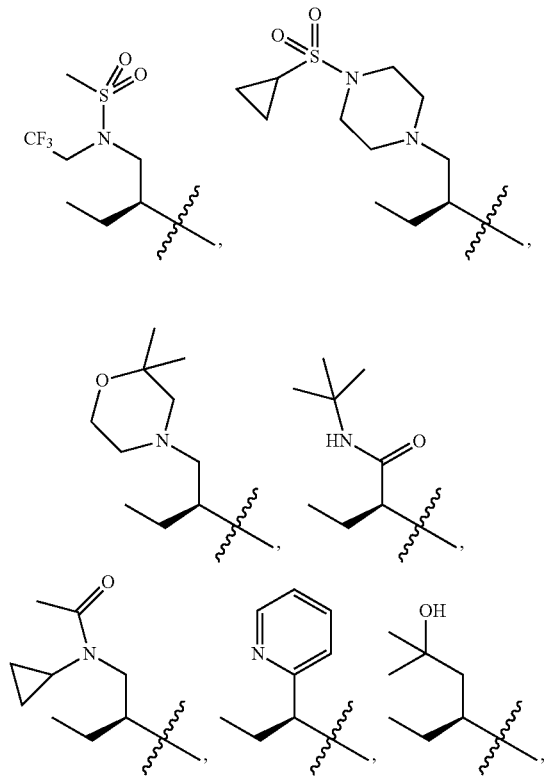
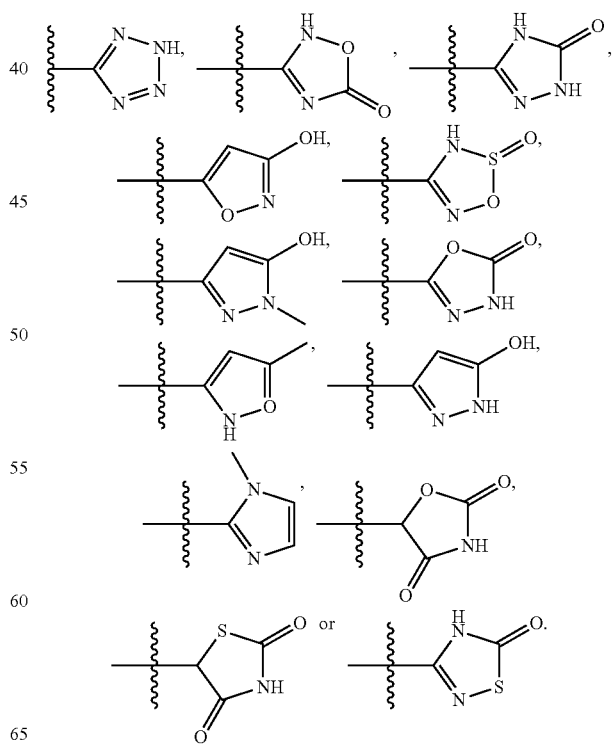
or a heteroaryl or heterocycle selected from In another aspect of embodiment 6 (embodiment 10), or the pharmaceutically acceptable salts thereof,
R² is selected from
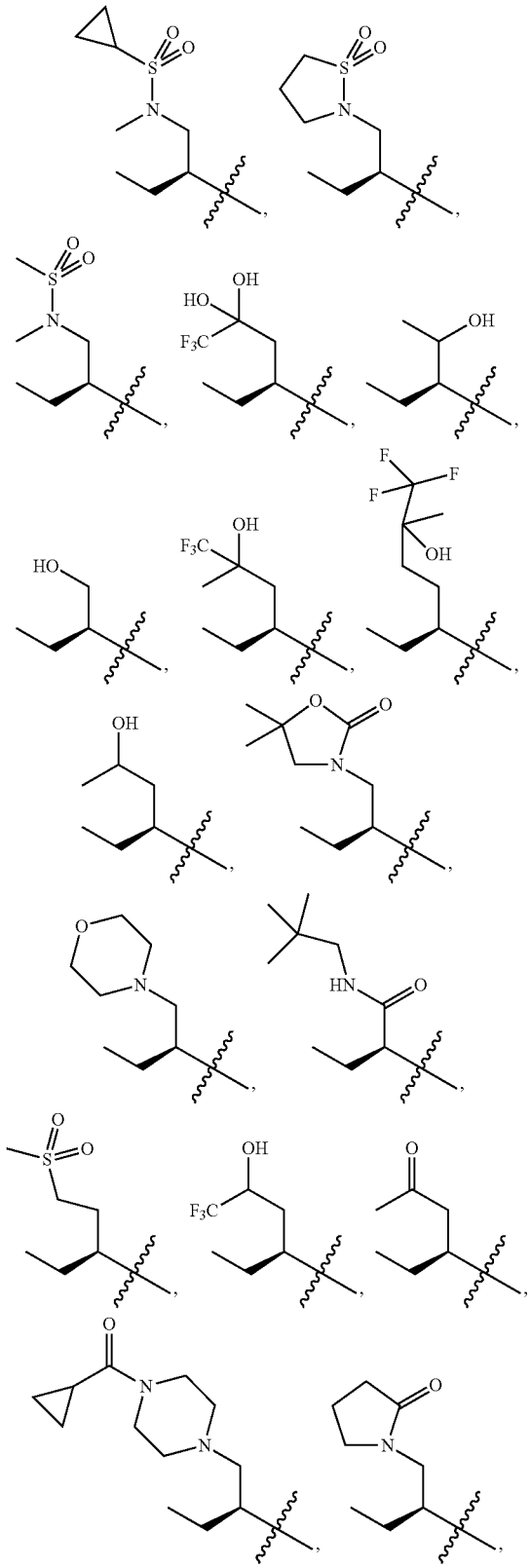
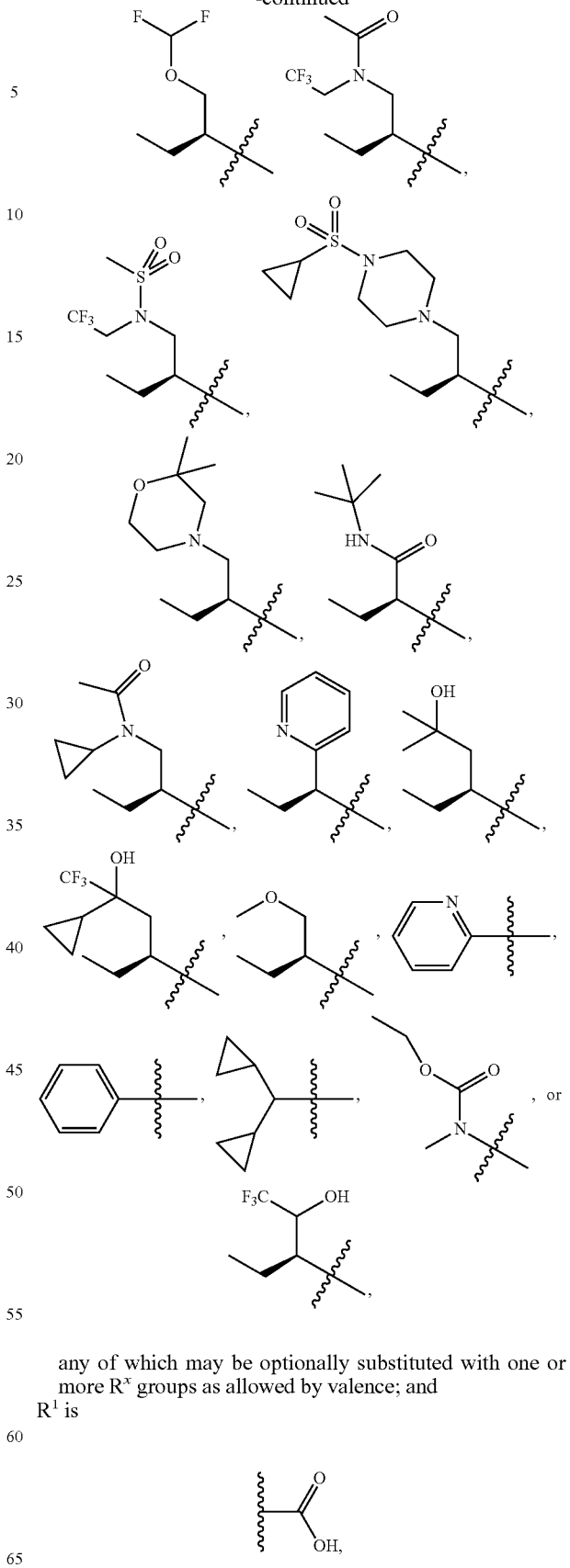
any of which may be optionally substituted with one or more R^x groups as allowed by valence; and
R¹ is
or a heteroaryl or heterocycle selected from

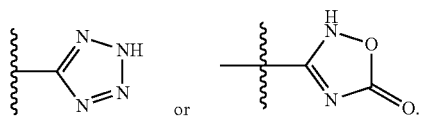 [SMILES: *c1nn[nH]n1 ; *c1nc(=O)o[nH]1]

In another embodiment, embodiment 11, the compounds of Aspect A have the structure of Formula ID

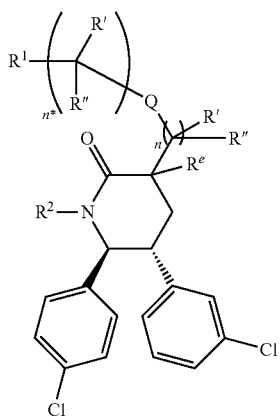

ID or a pharmaceutically acceptable salt thereof.

In another aspect of embodiment 11 (embodiment 12), or the pharmaceutically acceptable salts thereof, Re is H or methyl or ethyl.

In another embodiment, embodiment 13, the compounds of Aspect A have the structure of Formula IE

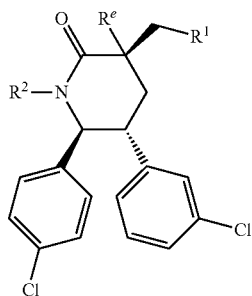

IE or the pharmaceutically acceptable salts thereof.

In another aspect of embodiment 13 (embodiment 14), or the pharmaceutically acceptable salts thereof, Re is H or methyl or ethyl.

In another aspect of embodiment 13 (embodiment 15), or the pharmaceutically acceptable salts thereof, wherein $R^2$ is selected from

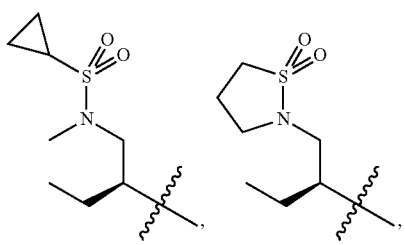

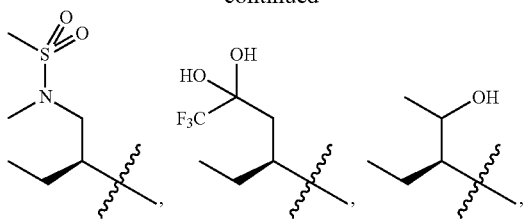

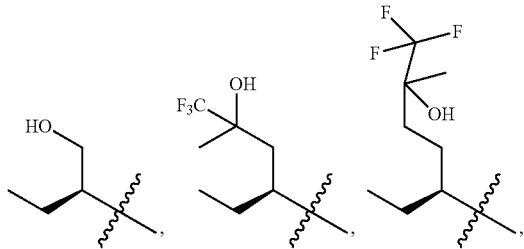

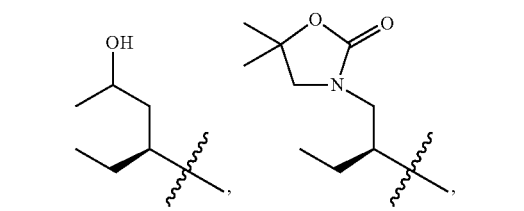

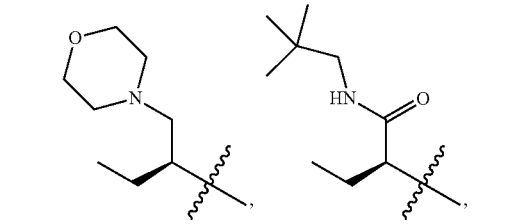

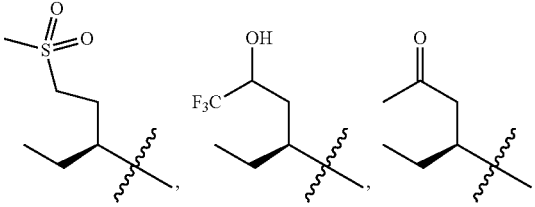

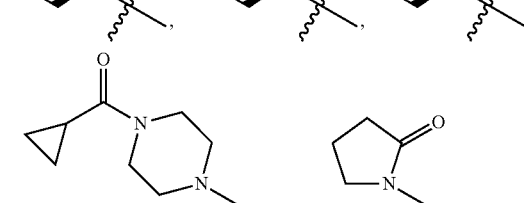

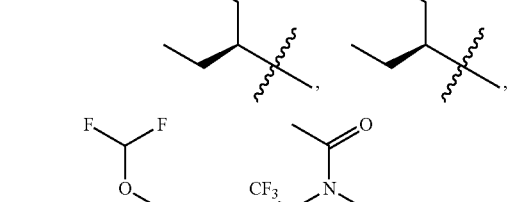

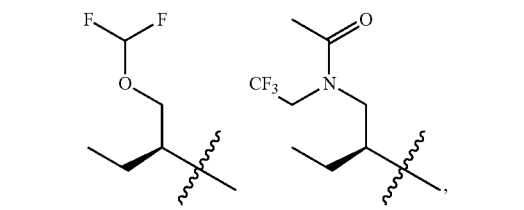

-continued

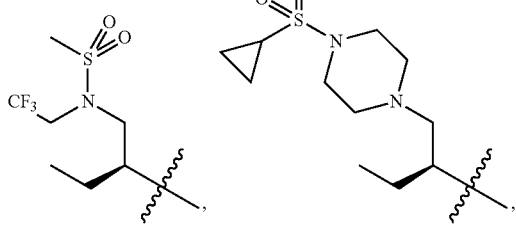

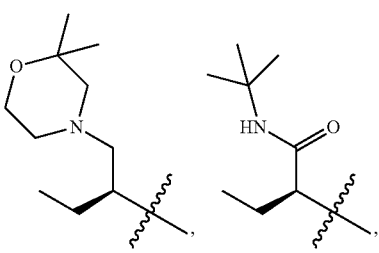

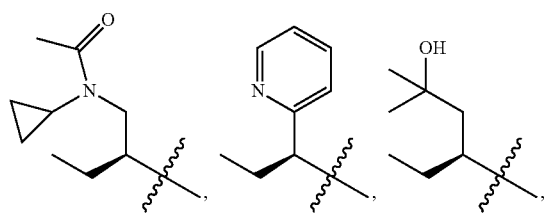

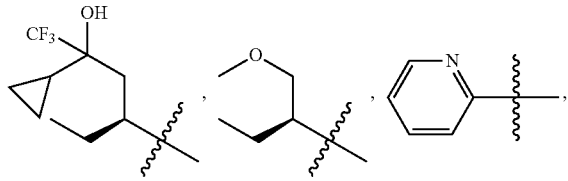

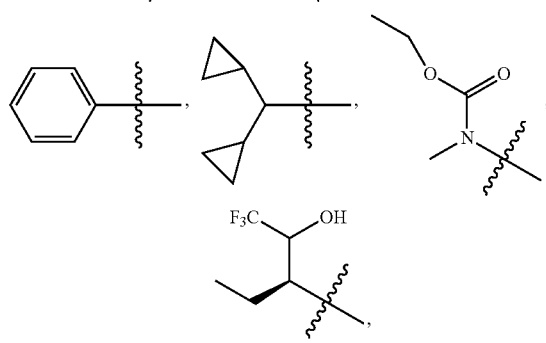

any of which may be optionally substituted with one or more R[x] groups as allowed by valence; and
R[1] is

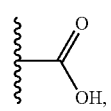

or a heteroaryl or heterocycle selected from

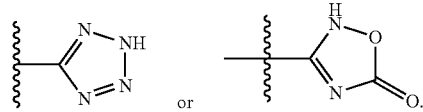 [SMILES: *c1nn[nH]n1 ; *c1nc(=O)o[nH]1]

In another aspect of embodiment 13 (embodiment 16), or a pharmaceutically acceptable salt thereof,
R[1] is

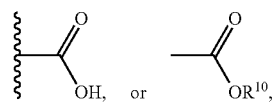

or a heteroaryl or heterocycle selected from

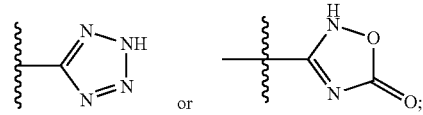 [SMILES: *c1nn[nH]n1 ; *c1nc(=O)o[nH]1]

R[2] is

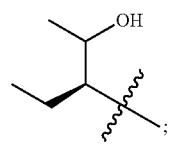 [SMILES: *[C@@H](CC)C(C)O]

and
R[e] is methyl.

In another aspect of embodiment 13 (embodiment 17), or a pharmaceutically acceptable salt thereof:
R[2] is

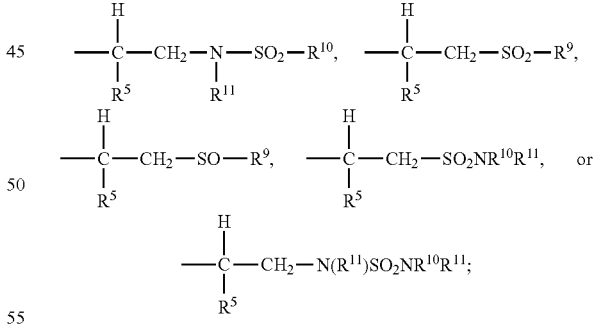

R[5] is cyclopropyl, or $C_{1-6}$alkyl;
R[9] is haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, heteroaryl, or heterocycloalkyl, or
R[9] is haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, heteroaryl, or heterocyclo, any of which may be optionally independently substituted with one or more R[x] groups as allowed by valence; and
R[10] and R[11] at each occurrence, respectively, are independently selected from H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, any of which may be optionally substituted as allowed by valence with one or more $R^x$, or $R^{10}$ and $R^{11}$ may combine to form a heterocyclo ring optionally substituted with one or more $R^x$.

In another aspect of embodiment 13 (embodiment 18), or a pharmaceutically acceptable salt thereof,
$R^1$ is

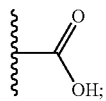

$R^2$ is

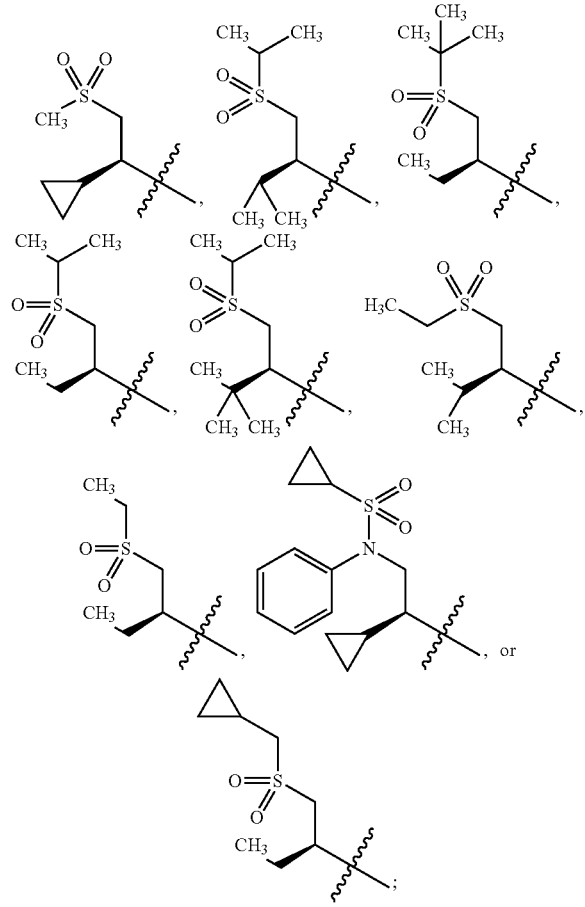

and $R^e$ is methyl.

In another aspect, the present invention provides a compound, or a pharmaceutically acceptable salt thereof, selected from:

2-((3R,5R,6S)-1-((S)-1-tert-butoxy-1-oxobutan-2-yl)-5-(3-chlorophenyl)-6-(4-chlorophenyl)-2-oxopiperidin-3-yl)acetic acid;

2-((3S,5R,6S)-1-((S)-1-tert-butoxy-1-oxobutan-2-yl)-5-(3-chlorophenyl)-6-(4-chlorophenyl)-2-oxopiperidin-3-yl)acetic acid;

2-((3R,5R,6S)-5-(3-Chlorophenyl)-6-(4-chlorophenyl)-1-((S)-1-ethoxy-1-oxobutan-2-yl)-2-oxopiperidin-3-yl)acetic acid;

2-((3R,5R,6S)-5-(3-Chlorophenyl)-6-(4-chlorophenyl)-1-((S)-1-ethoxy-4-methyl-1-oxopentan-2-yl)-2-oxopiperidin-3-yl)acetic acid;

2-((3R,5R,6S)-5-(3-Chlorophenyl)-6-(4-chlorophenyl)-1-((S)-1-ethoxy-1-oxopentan-2-yl)-2-oxopiperidin-3-yl)acetic acid;

2-((3S,5S,6R)-5-(3-Chlorophenyl)-6-(4-chlorophenyl)-1-((R)-1-ethoxy-1-oxopentan-2-yl)-2-oxopiperidin-3-yl)acetic acid;

2-((3R,5R,6S)-1-((S)-2-tert-Butoxy-1-cyclopropyl-2-oxoethyl)-5-(3-chlorophenyl)-6-(4-chlorophenyl)-2-oxopiperidin-3-yl)acetic acid;

2-((3R,5R,6S)-5-(3-Chlorophenyl)-6-(4-chlorophenyl)-1-((S)-1-hydroxybutan-2-yl)-2-oxopiperidin-3-yl)acetic acid;

2-((3R,5R,6S)-5-(3-chlorophenyl)-6-(4-chlorophenyl)-1-((S)-1-cyclopropyl-2-hydroxyethyl)-2-oxopiperidin-3-yl)acetic acid;

2-((3R,5R,6S)-5-(3-chlorophenyl)-6-(4-chlorophenyl)-1-((S)-1-(cyclopropylmethoxy)butan-2-yl)-2-oxopiperidin-3-yl)acetic acid;

2-((3R,5R,6S)-5-(3-Chlorophenyl)-6-(4-chlorophenyl)-1-((S)-1-methoxybutan-2-yl)-2-oxopiperidin-3-yl)acetic acid;

2-((3R,5R,6S)-5-(3-Chlorophenyl)-6-(4-chlorophenyl)-1-((S)-1-(2-methoxyethoxy)butan-2-yl)-2-oxopiperidin-3-yl)acetic acid;

2-((3R,5R,6S)-5-(3-Chlorophenyl)-6-(4-chlorophenyl)-1-((S)-1-((1-cyanocyclopropyl)methoxy)butan-2-yl)-2-oxopiperidin-3-yl)acetic acid;

2-((3S,5R,6S)-5-(3-Chlorophenyl)-6-(4-chlorophenyl)-1-((S)-1-(cyclopropylmethoxy)butan-2-yl)-2-oxopiperidin-3-yl)acetic acid;

2-((3S,5R,6S)-5-(3-Chlorophenyl)-6-(4-chlorophenyl)-1-((S)-1-methoxybutan-2-yl)-2-oxopiperidin-3-yl)acetic acid;

2-((3S,5R,6S)-5-(3-Chlorophenyl)-6-(4-chlorophenyl)-1-((S)-1-(2-methoxyethoxy)butan-2-yl)-2-oxopiperidin-3-yl)acetic acid;

2-((3R,5R,6S)-1-((S)-1-((1-carbamoylcyclopropyl)methoxy)butan-2-yl)-5-(3-chlorophenyl)-6-(4-chlorophenyl)-2-oxopiperidin-3-yl)acetic acid (isomer 1);

2-((3S,5R,6S)-1-((S)-1-((1-carbamoylcyclopropyl)methoxy)butan-2-yl)-5-(3-chlorophenyl)-6-(4-chlorophenyl)-2-oxopiperidin-3-yl)acetic acid (isomer 2);

2-((3R,5R,6S)-5-(3-chlorophenyl)-6-(4-chlorophenyl)-1-((S)-1-(2-hydroxy-2-methylpropoxy)butan-2-yl)-2-oxopiperidin-3-yl)acetic acid;

2-((3R,5R,6S)-5-(3-Chlorophenyl)-6-(4-chlorophenyl)-2-oxo-1-((3S)-1,1,1-trifluoro-2-hydroxypentan-3-yl)piperidin-3-yl)acetic acid (isomer 1);

2-((3R,5R,6S)-5-(3-Chlorophenyl)-6-(4-chlorophenyl)-2-oxo-1-((3S)-1,1,1-trifluoro-2-hydroxypentan-3-yl)piperidin-3-yl)acetic acid (isomer 2);

2-((3R,5R,6S)-5-(3-chlorophenyl)-6-(4-chlorophenyl)-1-((S)-1-morpholinobutan-2-yl)-2-oxopiperidin-3-yl)acetic acid;

2-((3R,5R,6S)-5-(3-chlorophenyl)-6-(4-chlorophenyl)-1-((S)-1-(ethylamino)butan-2-yl)-2-oxopiperidin-3-yl)acetic acid;

2-((3R,5R,6S)-5-(3-chlorophenyl)-6-(4-chlorophenyl)-2-oxo-1-((S)-1-(2,2,2-trifluoroethylamino)butan-2-yl)piperidin-3-yl)acetic acid;

2-((3R,5R,6S)-5-(3-chlorophenyl)-6-(4-chlorophenyl)-2-oxo-1-((S)-1-(pyrrolidin-1-yl)butan-2-yl)piperidin-3-yl)acetic acid;

2-((3R,5R,6S)-5-(3-chlorophenyl)-6-(4-chlorophenyl)-2-oxo-1-((S)-1-(2-oxopyrrolidin-1-yl)butan-2-yl)piperidin-3-yl)acetic acid;

2-((3R,5R,6S)-5-(3-Chlorophenyl)-6-(4-chlorophenyl)-1-((S)-1-(1,1-dioxidothiomorpholino)butan-2-yl)-2-oxopiperidin-3-yl)acetic acid;

2-((3R,5R,6S)-5-(3-chlorophenyl)-6-(4-chlorophenyl)-2-oxo-1-((S)-1-(thiazol-2-ylamino)butan-2-yl)piperidin-3-yl)acetic acid;

2-((3R,5R,6S)-1-((S)-1-acetamidobutan-2-yl)-5-(3-chlorophenyl)-6-(4-chlorophenyl)-2-oxopiperidin-3-yl)acetic acid;

2-((3R,5R,6S)-5-(3-chlorophenyl)-6-(4-chlorophenyl)-1-((S)-1-(methylsulfonamido) butan-2-yl)-2-oxopiperidin-3-yl)acetic acid;

2-((3R,5R,6S)-5-(3-chlorophenyl)-6-(4-chlorophenyl)-1-((S)-1-cyanopentan-3-yl)-2-oxopiperidin-3-yl)acetic acid;

2-((3R,5R,6S)-5-(3-chlorophenyl)-6-(4-chlorophenyl)-1-((S)-1-(methylsulfonyl)pentan-3-yl)-2-oxopiperidin-3-yl)acetic acid;

2-((3R,5R,6S)-5-(3-chlorophenyl)-6-(4-chlorophenyl)-2-oxo-1-((S)-1-(pyridin-2-yl)pentan-3-yl)piperidin-3-yl)acetic acid;

2-((3R,5R,6S)-5-(3-Chlorophenyl)-6-(4-chlorophenyl)-1-((S)-1-(ethylamino)-1-oxobutan-2-yl)-2-oxopiperidin-3-yl)acetic acid;

2-((3R,5R,6S)-5-(3-Chlorophenyl)-6-(4-chlorophenyl)-1-((R)-1-(ethylamino)-1-oxobutan-2-yl)-2-oxopiperidin-3-yl)acetic acid;

2-((3R,5R,6S)-5-(3-Chlorophenyl)-6-(4-chlorophenyl)-1-((S)-1-(5-methyl-1,3,4-oxadiazol-2-yl)propyl)-2-oxopiperidin-3-yl)acetic;

2-((3R,5R,6S)-5-(3-Chlorophenyl)-6-(4-chlorophenyl)-1-((R)-1-(5-methyl-1,3,4-oxadiazol-2-yl)propyl)-2-oxopiperidin-3-yl)acetic acid;

2-((3R,5R,6S)-5-(3-chlorophenyl)-6-(4-chlorophenyl)-1-(cyclopropylmethyl)-2-oxopiperidin-3-yl)acetic acid;

2-((3R,5R,6S)-5-(3-chlorophenyl)-6-(4-chlorophenyl)-1-(cyclobutylmethyl)-2-oxopiperidin-3-yl)acetic acid;

2-((3R,5R,6S)-5-(3-chlorophenyl)-6-(4-chlorophenyl)-1-(2-ethylbutyl)-2-oxopiperidin-3-yl)acetic acid;

2-((3R,5R,6S)-5-(3-chlorophenyl)-6-(4-chlorophenyl)-1-(cyclopentylmethyl)-2-oxopiperidin-3-yl)acetic acid;

2-((3R,5R,6S)-5-(3-chlorophenyl)-6-(4-chlorophenyl)-1-((2,2-dimethylcyclopentyl)methyl)-2-oxopiperidin-3-yl)acetic acid;

2-((3R,5R,6S)-5-(3-chlorophenyl)-6-(4-chlorophenyl)-1-(cyclohexylmethyl)-2-oxopiperidin-3-yl)acetic acid;

2-((3S,5R,6S)-5-(3-chlorophenyl)-6-(4-chlorophenyl)-1-(cyclopropylmethyl)-2-oxopiperidin-3-yl)acetic acid;

2-((3S,5R,6S)-5-(3-chlorophenyl)-6-(4-chlorophenyl)-2-oxo-1-propylpiperidin-3-yl)acetic acid;

2-((3S,5R,6S)-5-(3-chlorophenyl)-6-(4-chlorophenyl)-1-(cyclobutylmethyl)-2-oxopiperidin-3-yl)acetic acid;

2-((3S,5R,6S)-5-(3-chlorophenyl)-6-(4-chlorophenyl)-1-isobutyl-2-oxopiperidin-3-yl)acetic acid;

2-((3S,5R,6S)-5-(3-chlorophenyl)-6-(4-chlorophenyl)-1-(cyclopentylmethyl)-2-oxopiperidin-3-yl)acetic acid;

2-((3S,5R,6S)-5-(3-chlorophenyl)-6-(4-chlorophenyl)-2-oxo-1-(pentan-3-yl)piperidin-3-yl)acetic acid;

Methyl 2-((3R,5R,6S)-5-(3-chlorophenyl)-6-(4-chlorophenyl)-1-(cyclopropylmethyl)-2-oxopiperidin-3-yl)acetate;

2-((3R,5R,6S)-5-(3-chlorophenyl)-6-(4-chlorophenyl)-1-(cyclopropylmethyl)-2-oxopiperidin-3-yl)acetamide;

Ethyl 2-(2-((3R,5R,6S)-5-(3-chlorophenyl)-6-(4-chlorophenyl)-1-(cyclopropylmethyl)-2-oxopiperidin-3-yl)acetamido)acetate;

2-(2-((3R,5R,6S)-5-(3-Chlorophenyl)-6-(4-chlorophenyl)-1-(cyclopropylmethyl)-2-oxopiperidin-3-yl)acetamido) acetic acid;

2-((3R,5R,6S)-5-(3-Chlorophenyl)-6-(4-chlorophenyl)-1-(cyclopropylmethyl)-2-oxopiperidin-3-yl)acetohydrazide;

2-((3R,5R,6S)-5-(3-chlorophenyl)-6-(4-chlorophenyl)-1-(cyclopropylmethyl)-2-oxopiperidin-3-yl)-N-hydroxyacetamide;

(S)-Ethyl 2-((2S,3R,5R)-3-(3-chlorophenyl)-2-(4-chlorophenyl)-5-(2-(methylsulfonamido)-2-oxoethyl)-6-oxopiperidin-1-yl)butanoate;

(S)-Ethyl 2-((2S,3R,5R)-3-(3-chlorophenyl)-2-(4-chlorophenyl)-5-(2-((3-morpholinopropyl)amino)-2-oxoethyl)-6-oxopiperidin-1-yl)butanoate;

(3R,5R,6S)-3-((1H-Tetrazol-5-yl)methyl)-5-(3-chlorophenyl)-6-(4-chlorophenyl)-1-(cyclopropylmethyl)piperidin-2-one;

(3R,5R,6S)-3-((1,3,4-oxadiazol-2-yl)methyl)-5-(3-chlorophenyl)-6-(4-chlorophenyl)-1-(cyclopropylmethyl)piperidin-2-one;

(3R,5R,6S)-5-(3-chlorophenyl)-6-(4-chlorophenyl)-1-(cyclopropylmethyl)-3-((5-methyl-1,3,4-oxadiazol-2-yl)methyl)piperidin-2-one;

2-((3S,5R,6S)-5-(3-chlorophenyl)-6-(4-chlorophenyl)-1-(cyclopropylmethyl)-2-oxopiperidin-3-yl)-N-(methylsulfonyl)acetamide;

2-((3S,5R,6S)-5-(3-chlorophenyl)-6-(4-chlorophenyl)-1-(cyclopropylmethyl)-2-oxopiperidin-3-yl)acetamide;

(3S,5R,6S)-3-((1H-tetrazol-5-yl)methyl)-5-(3-chlorophenyl)-6-(4-chlorophenyl)-1-(cyclopropylmethyl)piperidin-2-one;

(3S,5R,6S)-5-(3-chlorophenyl)-6-(4-chlorophenyl)-1-(cyclopropylmethyl)-3-((5-methylisoxazol-3-yl)methyl)piperidin-2-one;

2-((2'S,3'R,5'R)-6-chloro-3'-(3-chlorophenyl)-1'-(cyclopropylmethyl)-2,6'-dioxospiro[indoline-3,2'-piperidine]-5'-yl)acetic acid;

2-((2'R,3'S,5'S)-6-chloro-3'-(3-chlorophenyl)-1'-(cyclopropylmethyl)-2,6'-dioxospiro[indoline-3,2'-piperidine]-5'-yl)acetic acid;

2-((3R,5R,6S)-5-(3-chlorophenyl)-6-(5-chlorothiophen-2-yl)-1-(cyclopropylmethyl)-2-oxopiperidin-3-yl)acetic acid;

2-((3S,5R,6S)-5-(3-chlorophenyl)-6-(5-chlorothiophen-2-yl)-1-(cyclopropylmethyl)-2-oxopiperidin-3-yl)acetic acid;

2-((3R,5R,6S)-5-(3-chlorophenyl)-6-(4-chlorophenyl)-1-((S)-1-ethoxy-1-oxobutan-2-yl)-3-methyl-2-oxopiperidin-3-yl)acetic acid;

2-((3R,5R,6S)-1-((S)-1-tert-butoxy-1-oxobutan-2-yl)-5-(3-chlorophenyl)-6-(4-chlorophenyl)-3-methyl-2-oxopiperidin-3-yl)acetic acid;

2-((3R,5R,6S)-1-((R)-1-tert-butoxy-1-oxobutan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-1-((S)-1-(cyclopropylmethoxy)butan-2-yl)-3-methyl-2-oxopiperidin-3-yl)acetic acid;

2-((3S,5R,6S)-5-(3-chlorophenyl)-6-(4-chlorophenyl)-1-(cyclopropylmethyl)-2-oxo-3-(2-(pyrrolidin-1-yl)ethyl)piperidin-3-yl)acetic acid;

2-((3S,5R,6S)-5-(3-chlorophenyl)-6-(4-chlorophenyl)-1-(cyclopropylmethyl)-3-(2-morpholinoethyl)-2-oxopiperidin-3-yl)acetic acid;

2-((3R,5R,6S)-5-(3-chlorophenyl)-6-(4-chlorophenyl)-3-methyl-2-oxo-1-(pentan-3-yl)piperidin-3-yl)acetic acid;

2-((3R,5R,6S)-5-(3-chlorophenyl)-6-(4-chlorophenyl)-1-(cyclopropylmethyl)-3-methyl-2-oxopiperidin-3-yl)acetic acid;

2-((3R,5R,6S)-5-(3-chlorophenyl)-6-(4-chlorophenyl)-1-isopropyl-3-methyl-2-oxopiperidin-3-yl)acetic acid;

2-((3R,5R,6S)-5-(3-chlorophenyl)-6-(4-chlorophenyl)-1-cyclobutyl-3-methyl-2-oxopiperidin-3-yl)acetic acid;

2-((3R,5R,6S)-5-(3-chlorophenyl)-6-(4-chlorophenyl)-1-cyclopentyl-3-methyl-2-oxopiperidin-3-yl)acetic acid;

(3R,5R,6S)-5-(3-chlorophenyl)-6-(4-chlorophenyl)-3-methyl-3-((5-oxo-4,5-dihydro-1H-1,2,4-triazol-3-yl)methyl)-1-(pentan-3-yl)piperidin-2-one;

5-(((3R,5R,6S)-5-(3-chlorophenyl)-6-(4-chlorophenyl)-3-methyl-2-oxo-1-(pentan-3-yl)piperidin-3-yl)methyl)-1,3,4-oxadiazol-2(3H)-one;

2-((3R,5R,6S)-5-(3-chlorophenyl)-6-(4-chlorophenyl)-3-methyl-2-oxo-1-(pentan-3-yl)piperidin-3-yl)-N-(trifluoromethylsulfonyl)acetamide;

(3R,5R,6S)-5-(3-chlorophenyl)-6-(4-chlorophenyl)-3-((3-hydroxy-1H-pyrazol-5-yl)methyl)-3-methyl-1-(pentan-3-yl)piperidin-2-one;

(3R,5R,6S)-5-(3-chlorophenyl)-6-(4-chlorophenyl)-3-((3-hydroxyisoxazol-5-yl)methyl)-3-methyl-1-(pentan-3-yl)piperidin-2-one;

5-(((3R,5R,6S)-5-(3-chlorophenyl)-6-(4-chlorophenyl)-3-methyl-2-oxo-1-(pentan-3-yl)piperidin-3-yl)methyl)oxazolidine-2,4-dione;

3-(((3R,5R,6S)-5-(3-chlorophenyl)-6-(4-chlorophenyl)-3-methyl-2-oxo-1-(pentan-3-yl)piperidin-3-yl)methyl)-1,2,4-oxadiazol-5(4H)-one;

3-(((3R,5R,6S)-5-(3-chlorophenyl)-6-(4-chlorophenyl)-1-isopropyl-3-methyl-2-oxopiperidin-3-yl)methyl)-1,2,4-oxadiazol-5(4H)-one;

3-(((3R,5R,6S)-5-(3-chlorophenyl)-6-(4-chlorophenyl)-3-methyl-2-oxo-1-(pentan-3-yl)piperidin-3-yl)methyl)-1,2,4-thiadiazol-5(4H)-one;

3-(((3R,5R,6S)-5-(3-chlorophenyl)-6-(4-chlorophenyl)-1-isopropyl-3-methyl-2-oxopiperidin-3-yl)methyl)-1,2,4-thiadiazol-5(4H)-one;

(3R,5R,6S)-3-((1H-Tetrazol-5-yl)methyl)-5-(3-chlorophenyl)-6-(4-chlorophenyl)-1-isopropyl-3-methylpiperidin-2-one;

2-((3R,5R,6S)-5-(3-chlorophenyl)-6-(4-chlorophenyl)-3-ethyl-2-oxo-1-(pentan-3-yl)piperidin-3-yl)acetic acid;

(3S,5R,6S)-5-(3-chlorophenyl)-6-(4-chlorophenyl)-3-methyl-3-(methylsulfonylmethyl)-1-(pentan-3-yl)piperidin-2-one;

2-((3R,5R,6S)-5-(3-chlorophenyl)-6-(4-chlorophenyl)-1-((S)-1-(3-cyclopropyl-1,2,4-oxadiazol-5-yl)propyl)-3-methyl-2-oxopiperidin-3-yl)acetic acid;

2-((3R,5R,6S)-5-(3-chlorophenyl)-6-(4-chlorophenyl)-1-((R)-1-(3-cyclopropyl-1,2,4-oxadiazol-5-yl)propyl)-3-methyl-2-oxopiperidin-3-yl)acetic acid;

2-((3R,5R,6S)-5-(3-Chlorophenyl)-6-(4-chlorophenyl)-3-methyl-1-((S)-1-morpholinobutan-2-yl)-2-oxopiperidin-3-yl)acetic acid;

2-((3R,5R,6S)-5-(3-chlorophenyl)-6-(4-chlorophenyl)-3-methyl-2-oxo-1-((S)-1-(2,2,2-trifluoroethylamino)butan-2-yl)piperidin-3-yl)acetic acid;

2-((3R,5R,6S)-5-(3-chlorophenyl)-6-(4-chlorophenyl)-1-((S)-1-(2,2-dimethylmorpholino)butan-2-yl)-3-methyl-2-oxopiperidin-3-yl)acetic acid;

2-((3R,5R,6S)-5-(3-chlorophenyl)-6-(4-chlorophenyl)-1-((2S)-1-(2,6-dimethylmorpholino)butan-2-yl)-3-methyl-2-oxopiperidin-3-yl)acetic acid;

2-((3R,5R,6S)-5-(3-chlorophenyl)-6-(4-chlorophenyl)-1-((S)-1-(4-(cyclopropylsulfonyl)piperazin-1-yl)butan-2-yl)-3-methyl-2-oxopiperidin-3-yl)acetic acid;

2-((3R,5R,6S)-5-(3-chlorophenyl)-6-(4-chlorophenyl)-3-methyl-1-((S)-1-(4-(methylsulfonyl)piperazin-1-yl)butan-2-yl)-2-oxopiperidin-3-yl)acetic acid;

2-((3R,5R,6S)-1-((S)-1-(4-acetylpiperazin-1-yl)butan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-1-((S)-1-(4-(cyclopropanecarbonyl)piperazin-1-yl)butan-2-yl)-3-methyl-2-oxopiperidin-3-yl)acetic acid;

3-(((3R,5R,6S)-5-(3-chlorophenyl)-6-(4-chlorophenyl)-3-methyl-1-((S)-1-morpholinobutan-2-yl)-2-oxopiperidin-3-yl)methyl)-1,2,4-oxadiazol-5(4H)-one;

2-((3R,5R,6S)-5-(3-chlorophenyl)-6-(4-chlorophenyl)-1-((S)-1-(5,5-dimethyl-2-oxooxazolidin-3-yl)butan-2-yl)-3-methyl-2-oxopiperidin-3-yl)acetic acid;

2-((3R,5R,6S)-1-((S)-1-(tert-butylamino)-1-oxobutan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-1-((1S,2R,3S)-2,3-dihydroxycyclopentyl)-3-methyl-2-oxopiperidin-3-yl)acetic acid;

2-((3R,5R,6S)-5-(3-chlorophenyl)-6-(4-chlorophenyl)-1-((1R,2R,3S)-2,3-dihydroxycyclopentyl)-3-methyl-2-oxopiperidin-3-yl)acetic acid;

2-((3R,3'S,5R,6S)-5-(3-chlorophenyl)-6-(4-chlorophenyl)-3-methyl-2-oxo-1'-(2,2,2-trifluoroethyl)-1,3'-bipiperidin-3-yl)acetic acid;

2-((3R,3'R,5R,6S)-5-(3-chlorophenyl)-6-(4-chlorophenyl)-3-methyl-2-oxo-1'-(2,2,2-trifluoroethyl)-1,3'-bipiperidin-3-yl)acetic acid;

2-((3R,5R,6S)-5-(3-chlorophenyl)-6-(4-chlorophenyl)-1-((1S,3S)-3-hydroxycyclopentyl)-3-methyl-2-oxopiperidin-3-yl)acetic acid;

2-((3R,5R,6S)-5-(3-chlorophenyl)-6-(4-chlorophenyl)-1-((1S,3R)-3-hydroxycyclopentyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-tetrahydro-2H-pyran-3-yl)piperidin-3-yl)acetic acid;

2-((3R,5R,6S)-5-(3-chlorophenyl)-6-(4-chlorophenyl)-3-methyl-2-oxo-1-((R)-tetrahydro-2H-pyran-3-yl)piperidin-3-yl)acetic acid;

2-((3R,5R,6S)-5-(3-chlorophenyl)-6-(4-chlorophenyl)-3-methyl-2-oxo-1-(pyrazin-2-yl)piperidin-3-yl)acetic acid;

2-((3R,5R,6S)-5-(3-chlorophenyl)-6-(4-chlorophenyl)-3-methyl-1-(1-methyl-1H-pyrazol-4-yl)-2-oxopiperidin-3-yl)acetic acid;

2-((3R,5R,6S)-5-(3-chlorophenyl)-6-(4-chlorophenyl)-3-methyl-2-oxo-1-(pyrimidin-4-yl)piperidin-3-yl)acetic acid;

2-((3R,5R,6S)-5-(3-chlorophenyl)-6-(4-chlorophenyl)-1-(2-chloropyrimidin-4-yl)-3-methyl-2-oxopiperidin-3-yl)acetic acid;

2-((3R,5R,6S)-5-(3-chlorophenyl)-6-(4-chlorophenyl)-3-methyl-2-oxo-1-(pyrimidin-2-yl)piperidin-3-yl)acetic acid;

2-((3R,5R,6S)-5-(3-chlorophenyl)-6-(4-chlorophenyl)-3-methyl-1-(3-methylpyridin-2-yl)-2-oxopiperidin-3-yl)acetic acid;

2-((3R,5R,6S)-5-(3-chlorophenyl)-6-(4-chlorophenyl)-3-methyl-1-(4-methylpyridin-2-yl)-2-oxopiperidin-3-yl)acetic acid;
2-((3R,5R,6S)-5-(3-chlorophenyl)-6-(4-chlorophenyl)-1-(dicyclopropylmethyl)-3-methyl-2-oxopiperidin-3-yl)acetic acid;
2-((3S,5R,6S)-5-(3-chlorophenyl)-6-(4-chlorophenyl)-1-(dicyclopropylmethyl)-3-methyl-2-oxopiperidin-3-yl)acetic acid;
((3S,4R,6R)-4-(3-chlorophenyl)-3-(4-chlorophenyl)-1,1-dioxido-2-(2-propanyl)-1,2-thiazinan-6-yl)acetic acid;
((3S,4R,6S)-4-(3-chlorophenyl)-3-(4-chlorophenyl)-1,1-dioxido-2-(2-propanyl)-1,2-thiazinan-6-yl)acetic acid;
((3S,4R,6R)-4-(3-chlorophenyl)-3-(4-chlorophenyl)-6-methyl-1,1-dioxido-2-(2-propanyl)-1,2-thiazinan-6-yl)acetic acid;
((3S,4R,6S)-4-(3-chlorophenyl)-3-(4-chlorophenyl)-6-methyl-1,1-dioxido-2-(2-propanyl)-1,2-thiazinan-6-yl)acetic acid;
2-((3R,5R,6S)-5-(3-chlorophenyl)-6-(5-chloropyridin-2-yl)-3-methyl-1-((S)-1-morpholinobutan-2-yl)-2-oxopiperidin-3-yl)acetic acid;
2-((3S,5R,6S)-5-(3-Chlorophenyl)-6-(5-chloropyridin-2-yl)-3-methyl-2-oxo-1-(pentan-3-yl)piperidin-3-yl)acetic acid;
2-((3R,5R,6S)-5-(3-Chlorophenyl)-6-(5-chloropyridin-2-yl)-3-methyl-2-oxo-1-(pentan-3-yl)piperidin-3-yl)acetic acid;
2-((3S,5R,6S)-5-(3-Chlorophenyl)-6-(5-chloropyridin-2-yl)-3-methyl-2-oxo-1-(pentan-3-yl)piperidin-3-yl)acetic acid;
2-((3R,5R,6S)-1-((S)-1-tert-butoxy-1-oxobutan-2-yl)-5-(3-chlorophenyl)-6-(5-chloropyridin-2-yl)-3-methyl-2-oxopiperidin-3-yl)acetic acid; or
2-((3R,5S,6S)-1-((S)-1-tert-butoxy-1-oxobutan-2-yl)-6-(4-chlorophenyl)-5-(4-chloropyridin-2-yl)-3-methyl-2-oxopiperidin-3-yl)acetic acid.

In another aspect, the present invention provides a compound, or a pharmaceutically acceptable salt thereof, selected from:
2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)acetic acid;
2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)propanoic acid;
(S)-tert-butyl 2-((3R,5R,6S)-3-((1H-tetrazol-5-yl)methyl)-5-(3-chlorophenyl)-6-(4-chlorophenyl)-3-methyl-2-oxopiperidin-1-yl)butanoate;
2-((3R,5R,6S)-5-(3-chlorophenyl)-6-(4-chlorophenyl)-3-methyl-1-((S)-1-(methylsulfonamido)butan-2-yl)-2-oxopiperidin-3-yl)acetic acid;
2-((3R,5R,6S)-5-(3-Chlorophenyl)-6-(4-chlorophenyl)-3-methyl-2-oxo-1-((S)-5-oxohexan-3-yl)piperidin-3-yl)acetic acid;
2-((3R,5R,6S)-5-(3-chlorophenyl)-6-(4-chlorophenyl)-1-((S)-5-hydroxy-5-methylhexan-3-yl)-3-methyl-2-oxopiperidin-3-yl)acetic acid;
2-((3R,5R,6S)-5-(3-chlorophenyl)-6-(4-chlorophenyl)-3-methyl-2-oxo-1-((3S,5S)-6,6,6-trifluoro-5-hydroxy-5-methylhexan-3-yl)piperidin-3-yl)acetic acid (isomer 1);
2-((3R,5R,6S)-5-(3-chlorophenyl)-6-(4-chlorophenyl)-3-methyl-2-oxo-1-((3S,5R)-6,6,6-trifluoro-5-hydroxy-5-methylhexan-3-yl)piperidin-3-yl)acetic acid (isomer 2);
2-((3R,5R,6S)-5-(3-chlorophenyl)-6-(4-chlorophenyl)-3-methyl-1-((S)-1-(N-methylmethylsulfonamido)butan-2-yl)-2-oxopiperidin-3-yl)acetic acid;
2-((3R,5R,6S)-5-(3-chlorophenyl)-6-(4-chlorophenyl)-1-((3S)-5-cyclopropyl-6,6,6-trifluoro-5-hydroxyhexan-3-yl)-3-methyl-2-oxopiperidin-3-yl)acetic acid;
2-((3R,5R,6S)-5-(3-chlorophenyl)-6-(4-chlorophenyl)-1-((S)-6-hydroxy-6-methylheptan-3-yl)-3-methyl-2-oxopiperidin-3-yl)acetic acid;
2-((3R,5R,6S)-5-(3-chlorophenyl)-6-(4-chlorophenyl)-3-methyl-2-oxo-1-((S)-6,6,6-trifluoro-5,5-dihydroxyhexan-3-yl)piperidin-3-yl)acetic acid;
2-((3R,5R,6S)-5-(3-chlorophenyl)-6-(4-chlorophenyl)-3-methyl-2-oxo-1-((3S)-7,7,7-trifluoro-6-hydroxy-6-methylheptan-3-yl)piperidin-3-yl)acetic acid (isomer 1);
2-((3R,5R,6S)-5-(3-chlorophenyl)-6-(4-chlorophenyl)-3-methyl-2-oxo-1-((3S)-7,7,7-trifluoro-6-hydroxy-6-methylheptan-3-yl)piperidin-3-yl)acetic acid (isomer 2);
2-((3R,5R,6S)-5-(3-chlorophenyl)-6-(4-chlorophenyl)-1-((S)-7-hydroxy-7-methyloctan-3-yl)-3-methyl-2-oxopiperidin-3-yl)acetic acid;
2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid;
2-((3R,5R,6S)-5-(3-chlorophenyl)-6-(4-chlorophenyl)-1-((S)-1-(N-cyclopropylmethylsulfonamido)butan-2-yl)-3-methyl-2-oxopiperidin-3-yl)acetic acid;
2-((3R,5R,6S)-5-(3-chlorophenyl)-6-(4-chlorophenyl)-3-methyl-2-oxo-1-((3S)-6,6,6-trifluoro-5-hydroxyhexan-3-yl)piperidin-3-yl)acetic acid (isomer 1);
2-((3R,5R,6S)-5-(3-chlorophenyl)-6-(4-chlorophenyl)-3-methyl-2-oxo-1-((3S)-6,6,6-trifluoro-5-hydroxyhexan-3-yl)piperidin-3-yl)acetic acid (isomer 2);
2-((3R,5R,6S)-5-(3-chlorophenyl)-6-(4-chlorophenyl)-1-((3S)-5-hydroxyhexan-3-yl)-3-methyl-2-oxopiperidin-3-yl)acetic acid (isomer 1);
2-((3R,5R,6S)-5-(3-chlorophenyl)-6-(4-chlorophenyl)-1-((3S)-5-hydroxyhexan-3-yl)-3-methyl-2-oxopiperidin-3-yl)acetic acid (isomer 2);
2-((3R,5R,6S)-5-(3-chlorophenyl)-6-(4-chlorophenyl)-3-methyl-2-oxo-1-((S)-1-(N-(2,2,2-trifluoroethyl)methylsulfonamido)butan-2-yl)piperidin-3-yl)acetic acid;
2-((3R,5R,6S)-5-(3-chlorophenyl)-6-(4-chlorophenyl)-1-((S)-1-(1,1-dioxidoisothiazolidin-2-yl)butan-2-yl)-3-methyl-2-oxopiperidin-3-yl)acetic acid;
2-((3R,5R,6S)-5-(3-Chlorophenyl)-6-(4-chlorophenyl)-1-((3S,4R)-5-hydroxy-4,5-dimethylhexan-3-yl)-3-methyl-2-oxopiperidin-3-yl)acetic acid;
2-((3R,5R,6S)-5-(3-Chlorophenyl)-6-(4-chlorophenyl)-1-((3S,4S)-5-hydroxy-4,5-dimethylhexan-3-yl)-3-methyl-2-oxopiperidin-3-yl)acetic acid;
2-((3R,5R,6S)-5-(3-chlorophenyl)-6-(4-chlorophenyl)-1-((S)-5-cyano-5-methylhexan-3-yl)-3-methyl-2-oxopiperidin-3-yl)acetic acid;
2-((3R,5R,6S)-5-(3-Chlorophenyl)-6-(4-chlorophenyl)-3-methyl-2-oxo-1-((S)-2-oxopentan-3-yl)piperidin-3-yl)acetic acid;
2-((3R,5R,6S)-5-(3-Chlorophenyl)-6-(4-chlorophenyl)-1-((2S,3S)-2-hydroxypentan-3-yl)-3-methyl-2-oxopiperidin-3-yl)acetic acid;
2-((3R,5R,6S)-5-(3-Chlorophenyl)-6-(4-chlorophenyl)-1-((2S,3S)-2-methoxypentan-3-yl)-3-methyl-2-oxopiperidin-3-yl)acetic acid;
2-((3R,5R,6S)-5-(3-Chlorophenyl)-6-(4-chlorophenyl)-1-((2R,3S)-2-hydroxypentan-3-yl)-3-methyl-2-oxopiperidin-3-yl)acetic acid;
2-((3R,5R,6S)-5-(3-Chlorophenyl)-6-(4-chlorophenyl)-1-((2S,3R)-2-hydroxypentan-3-yl)-3-methyl-2-oxopiperidin-3-yl)acetic acid;

2-((3R,5R,6S)-5-(3-chlorophenyl)-6-(4-chlorophenyl)-1-((2R,3R)-2-hydroxypentan-3-yl)-3-methyl-2-oxopiperidin-3-yl)acetic acid;

2-((3R,5R,6S)-5-(3-Chlorophenyl)-6-(4-chlorophenyl)-1-((S)-2-hydroxy-2-methylpentan-3-yl)-3-methyl-2-oxopiperidin-3-yl)acetic acid;

2-((3R,5R,6S)-5-(3-Chlorophenyl)-6-(4-chlorophenyl)-1-((3S,4S)-4-hydroxyhexan-3-yl)-3-methyl-2-oxopiperidin-3-yl)acetic acid;

2-((3R,5R,6S)-5-(3-Chlorophenyl)-6-(4-chlorophenyl)-1-((3S,4R)-4-hydroxyhexan-3-yl)-3-methyl-2-oxopiperidin-3-yl)acetic acid;

2-((3R,5R,6S)-5-(3-Chlorophenyl)-6-(4-chlorophenyl)-1-((S)-1-methoxybutan-2-yl)-3-methyl-2-oxopiperidin-3-yl)acetic acid;

2-((3R,5R,6S)-5-(3-Chlorophenyl)-6-(4-chlorophenyl)-3-methyl-2-oxo-1-(3S)-1,1,1-trifluoro-2-hydroxy-2-methylpentan-3-yl)piperidin-3-yl)acetic acid;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(methylsulfonyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(3-hydroxypropyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(2-hydroxyethyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-hydroxyacetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-methoxyacetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N—((R)-2,3-dihydroxypropyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-((S)-2,3-dihydroxypropyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-cyanoacetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(2-(dimethylamino)ethyl)acetamide;

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(3,4-dihydroxybutyl)acetamide;

2-((3R,5R,6S)-5-(3-chlorophenyl)-6-(4-chlorophenyl)-1-((S)-1-(cyclopropanesulfonamido)butan-2-yl)-3-methyl-2-oxopiperidin-3-yl)acetic acid;

(S)-2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)propanoic acid;

2-((3R,5R,6S)-5-(3-Chlorophenyl)-6-(4-chlorophenyl)-1-(3S)-2-(cyclopropanesulfonamido)pentan-3-yl)-3-methyl-2-oxopiperidin-3-yl)acetic acid (isomer 1);

2-((3R,5R,6S)-5-(3-chlorophenyl)-6-(4-chlorophenyl)-1-(3S)-2-(cyclopropanesulfonamido)pentan-3-yl)-3-methyl-2-oxopiperidin-3-yl)acetic acid (isomer 2);

2-((3R,5R,6S)-5-(3-chlorophenyl)-6-(4-chlorophenyl)-3-methyl-1-((2R,3S)-2-(1-methylethylsulfonamido)pentan-3-yl)-2-oxopiperidin-3-yl)acetic acid;

2-((3R,5R,6S)-5-(3-chlorophenyl)-6-(4-chlorophenyl)-3-methyl-1-((S)-1-(N-methylcyclopropanesulfonamido)-1-oxobutan-2-yl)-2-oxopiperidin-3-yl)acetic acid;

2-((3R,5R,6S)-5-(3-Chlorophenyl)-6-(4-chlorophenyl)-3-methyl-1-((S)-1-(neopentylamino)-1-oxobutan-2-yl)-2-oxopiperidin-3-yl)acetic acid;

2-((3R,5R,6S)-5-(3-chlorophenyl)-6-(4-chlorophenyl)-1-((S)-1-(4,4-dimethyl-4,5-dihydrooxazol-2-yl)propyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(N-(2,2,2-trifluoroethyl)acetamido)butan-2-yl)piperidin-3-yl)acetic acid;

2-((3R,5R,6S)-5-(3-chlorophenyl)-6-(4-chlorophenyl)-1-((S)-1-(1,1-dimethylethylsulfonamido)butan-2-yl)-3-methyl-2-oxopiperidin-3-yl)acetic acid 2-((3R,5R,6S)-5-(3-chlorophenyl)-6-(4-chlorophenyl)-1-((S)-1-(N,2-dimethylpropan-2-ylsulfonamido)butan-2-yl)-3-methyl-2-oxopiperidin-3-yl)acetic acid;

2-((3R,5R,6S)-5-(3-chlorophenyl)-6-(4-chlorophenyl)-3-methyl-1-((S)-1-(1-methylethylsulfonamido)butan-2-yl)-2-oxopiperidin-3-yl)acetic acid;

2-((3R,5R,6S)-5-(3-chlorophenyl)-6-(4-chlorophenyl)-1-((S)-1-(N-ethylpropan-2-ylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-hydroxybutan-2-yl)-3-methyl-2-oxopiperidin-3-yl)acetic acid;

2-((3R,5R,6S)-5-(3-Chlorophenyl)-6-(4-chlorophenyl)-3-methyl-2-oxo-1-((S)-1-(trifluoromethylsulfonamido)butan-2-yl)piperidin-3-yl)acetic acid;

2-((3R,5R,6S)-5-(3-Chlorophenyl)-6-(4-chlorophenyl)-1-((S)-1-(4-chlorophenylsulfonamido)butan-2-yl)-3-methyl-2-oxopiperidin-3-yl)acetic acid;

2-((3R,5R,6S)-5-(3-Chlorophenyl)-6-(4-chlorophenyl)-3-methyl-1-((S)-1-(4-methylphenylsulfonamido)butan-2-yl)-2-oxopiperidin-3-yl)acetic acid;

2-((3R,5R,6S)-5-(3-Chlorophenyl)-6-(4-chlorophenyl)-1-((S)-1-(2-chlorophenylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(2-methylphenylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(4-methoxyphenylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(phenylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(1-methylcyclopropanesulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(1,1-dioxidobenzo[d]isothiazol-2(3H)-yl)butan-2-yl)-3-methyl-2-oxopiperidin-3-yl)acetic acid;

2-((3R,5R,6S)-5-(3-Chlorophenyl)-6-(4-chlorophenyl)-1-((S)-1-(3,3-dimethyl-1,1-dioxidobenzo[d]isothiazol-2(3H)-yl)butan-2-yl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(pyridine-3-sulfonamido)butan-2-yl)piperidin-3-yl)acetic acid;

2-((3R,5R,6S)-5-(3-Chlorophenyl)-6-(4-chlorophenyl)-1-((S)-1-(4-cyanophenylsulfonamido)butan-2-yl)-3-methyl-2-oxopiperidin-3-yl)acetic acid;

2-((3R,5R,6S)-5-(3-Chlorophenyl)-6-(4-chlorophenyl)-1-((S)-1-(3-cyanophenylsulfonamido)butan-2-yl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(pyridine-2-sulfonamido)butan-2-yl)piperidin-3-yl)acetic acid.

2-((3R,5R,6S)-5-(3-Chlorophenyl)-6-(4-chlorophenyl)-1-((S)-1-(N,1-dimethylcyclopropanesulfonamido)butan-2-yl)-3-methyl-2-oxopiperidin-3-yl)acetic acid;

3-((3S,5R,6S)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid;

3-((3R,5S,6R)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid;

2-((3R,5R,6S)-5-(3-chlorophenyl)-6-(4-chlorophenyl)-3-ethyl-1-((S)-1-(N-methylcyclopropanesulfonamido)butan-2-yl)-2-oxopiperidin-3-yl)acetic acid;

2-((3S,5R,6S)-5-(3-chlorophenyl)-6-(4-chlorophenyl)-3-methoxy-1-((S)-1-(N-methylcyclopropanesulfonamido)butan-2-yl)-2-oxopiperidin-3-yl)acetic acid;

2-((3R,5R,6S)-5-(3-chlorophenyl)-6-(4-chlorophenyl)-3-methyl-1-((S)-6-methyl-4-oxoheptan-3-yl)-2-oxopiperidin-3-yl)acetic acid;

2-((3R,5R,6S)-5-(3-chlorophenyl)-6-(4-chlorophenyl)-1-((S)-1-(ethylsulfonyl)pentan-3-yl)-3-methyl-2-oxopiperidin-3-yl)acetic acid;

2-((3R,5R,6S)-5-(3-chlorophenyl)-6-(4-chlorophenyl)-1-((S)-1-(isopropylsulfonyl)pentan-3-yl)-3-methyl-2-oxopiperidin-3-yl)acetic acid;

2-((3R,5R,6S)-5-(3-chlorophenyl)-6-(4-chlorophenyl)-1-((S)-1-(cyclopropylmethylsulfonyl)pentan-3-yl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(2-oxopyrrolidin-1-yl)butan-2-yl)piperidin-3-yl)acetic acid;

2-((3R,5R,6S)-1-((S)-1-((1R,4R)-2-oxa-5-azabicyclo[2.2.1]heptan-5-yl)butan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-3-methyl-1-((S)-1-((S)-3-methylmorpholino)butan-2-yl)-2-oxopiperidin-3-yl)acetic acid;

2-((3R,5R,6S)-5-(3-chlorophenyl)-6-(4-chlorophenyl)-3-methyl-1-((S)-1-((R)-3-methylmorpholino)butan-2-yl)-2-oxopiperidin-3-yl)acetic acid;

2-((3R,5R,6S)-5-(3-chlorophenyl)-6-(4-chlorophenyl)-1-((S)-1-(thiomorpholino-1,1-dioxide)butan-2-yl)-3-methyl-2-oxopiperidin-3-yl)acetic acid;

2-((3R,5R,6S)-5-(3-chlorophenyl)-6-(4-chlorophenyl)-1-((S)-1-(3,3-difluoroazetidin-1-yl)butan-2-yl)-3-methyl-2-oxopiperidin-3-yl)acetic acid;

2-((3R,5R,6S)-1-((2S)-1-(8-oxa-3-azabicyclo[3.2.1]octan-3-yl)butan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-1-((S)-1-(3,3-dimethylmorpholino)butan-2-yl)-3-methyl-2-oxopiperidin-3-yl)acetic acid;

2-((3R,5R,6S)-5-(3-chlorophenyl)-6-(4-chlorophenyl)-1-((S)-1-(3-hydroxy-3-(trifluoromethyl)azetidin-1-yl)butan-2-yl)-3-methyl-2-oxopiperidin-3-yl)acetic acid;

2-((3R,5R,6S)-5-(3-chlorophenyl)-6-(4-chlorophenyl)-3-methyl-1-((S)-1-(methyl(oxetan-3-yl)amino)butan-2-yl)-2-oxopiperidin-3-yl)acetic acid;

2-((3R,5R,6S)-5-(3-Chlorophenyl)-6-(4-chlorophenyl)-3-methyl-2-oxo-1-((S)-1-(2-oxooxazolidin-3-yl)butan-2-yl)piperidin-3-yl)acetic acid;

2-((3R,5R,6S)-5-(3-chlorophenyl)-6-(4-chlorophenyl)-3-methyl-2-oxo-1-((S)-1-(2-oxopyridin-1(2H)-yl)butan-2-yl)piperidin-3-yl)acetic acid;

2-((3R,5R,6S)-5-(3-Chlorophenyl)-6-(4-chlorophenyl)-3-methyl-2-oxo-1-((S)-1-(2-oxo-5-(trifluoromethyl)pyridin-1(2H)-yl)butan-2-yl)piperidin-3-yl)acetic acid;

(3S,5R,6S)-3-allyl-5-(3-chlorophenyl)-6-(4-chlorophenyl)-3-methyl-1-((S)-1-(pyridin-3-yloxy)butan-2-yl)piperidin-2-one;

2-((3R,5R,6S)-5-(3-chlorophenyl)-6-(4-chlorophenyl)-3-methyl-2-oxo-1-((1S)-1-(tetrahydrofuran-2-yl)propyl)piperidin-3-yl)acetic acid (isomer 1);

2-((3R,5R,6S)-5-(3-chlorophenyl)-6-(4-chlorophenyl)-3-methyl-2-oxo-1-((1S)-1-(tetrahydrofuran-2-yl)propyl)piperidin-3-yl)acetic acid (isomer 2);

2-((3R,5R,6S)-5-(3-chlorophenyl)-6-(4-chlorophenyl)-3-methyl-2-oxo-1-((1S)-1-5-oxotetrahydrofuran-2-yl)propyl)piperidin-3-yl)acetic acid;

2-((3R,5R,6S)-5-(3-chlorophenyl)-6-(4-chlorophenyl)-3-methyl-2-oxo-1-((1S)-1-(tetrahydro-2H-pyran-2-yl)propyl)piperidin-3-yl)acetic acid (isomer 1);

2-((3R,5R,6S)-5-(3-chlorophenyl)-6-(4-chlorophenyl)-3-methyl-2-oxo-1-((1S)-1-(tetrahydro-2H-pyran-2-yl)propyl)piperidin-3-yl)acetic acid (isomer 2);

2-((3R,5R,6S)-1-((R)-1-(benzo[d]thiazol-2-yl)propyl)-5-(3-chlorophenyl)-6-(4-chlorophenyl)-3-methyl-2-oxopiperidin-3-yl)acetic acid;

2-((3R,5R,6S)-1-((S)-1-(benzo[d]thiazol-2-yl)propyl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-3-methyl-1-((S)-1-(3-methylisoxazol-5-yl)propyl)-2-oxopiperidin-3-yl)acetic acid;

2-((3R,5R,6S)-5-(3-chlorophenyl)-6-(4-chlorophenyl)-3-methyl-1-((R)-1-(3-methylisoxazol-5-yl)propyl)-2-oxopiperidin-3-yl)acetic acid;

2-((3R,5R,6S)-5-(3-chlorophenyl)-6-(4-chlorophenyl)-1-((S)-1-(6-chloropyridin-2-yl)propyl)-3-methyl-2-oxopiperidin-3-yl)acetic acid;

2-((3R,5R,6S)-5-(3-chlorophenyl)-6-(4-chlorophenyl)-1-((R)-1-(6-chloropyridin-2-yl)propyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(pyridin-2-yl)propyl)piperidin-3-yl)acetic acid;

2-((3R,5R,6S)-5-(3-chlorophenyl)-6-(4-chlorophenyl)-3-methyl-2-oxo-1-((R)-1-(pyridin-2-yl)propyl)piperidin-3-yl)acetic acid;

2-((3R,5R,6S)-5-(3-chlorophenyl)-6-(4-chlorophenyl)-3-methyl-2-oxo-1-((S)-1-(pyridin-2-yl)butyl)piperidin-3-yl)acetic acid;

2-((3R,5R,6S)-5-(3-chlorophenyl)-6-(4-chlorophenyl)-3-methyl-2-oxo-1-((R)-1-(pyridin-2-yl)butyl)piperidin-3-yl)acetic acid;

2-((3R,5R,6S)-5-(3-chlorophenyl)-6-(4-chlorophenyl)-1-((S)-2-cyclopropyl-1-(pyridin-2-yl)ethyl)-3-methyl-2-oxopiperidin-3-yl)acetic acid;

2-((3R,5R,6S)-5-(3-chlorophenyl)-6-(4-chlorophenyl)-1-((R)-2-cyclopropyl-1-(pyridin-2-yl)ethyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(pyridin-3-yl)propyl)piperidin-3-yl)acetic acid;

2-((3R,5R,6S)-5-(3-chlorophenyl)-6-(4-chlorophenyl)-3-methyl-2-oxo-1-((R)-1-(pyridin-3-yl)propyl)piperidin-3-yl)acetic acid;

2-((3R,5R,6S)-5-(3-chlorophenyl)-6-(4-chlorophenyl)-3-methyl-2-oxo-1-((S)-1-(pyrazin-2-yl)propyl)piperidin-3-yl)acetic acid;

2-((3R,5R,6S)-5-(3-chlorophenyl)-6-(4-chlorophenyl)-3-methyl-2-oxo-1-((R)-1-(pyrazin-2-yl)propyl)piperidin-3-yl)acetic acid;

2-((3R,5R,6S)-5-(3-chlorophenyl)-6-(4-chlorophenyl)-3-methyl-2-oxo-1-((S)-1-(pyrimidin-2-yl)propyl)piperidin-3-yl)acetic acid;

2-((3R,5R,6S)-5-(3-chlorophenyl)-6-(4-chlorophenyl)-3-methyl-2-oxo-1-((R)-1-(pyrimidin-2-yl)propyl)piperidin-3-yl)acetic acid;

2-((3R,5R,6S)-5-(3-chlorophenyl)-6-(4-chlorophenyl)-3-methyl-1-((S)-1-(6-methylpyridin-2-yl)propyl)-2-oxopiperidin-3-yl)acetic acid;

2-((3R,5R,6S)-5-(3-chlorophenyl)-6-(4-chlorophenyl)-3-methyl-1-((R)-1-(6-methylpyridin-2-yl)propyl)-2-oxopiperidin-3-yl)acetic acid;

2-((3R,5R,6S)-5-(3-chlorophenyl)-6-(4-chlorophenyl)-3-methyl-2-oxo-1-((S)-1-(pyridin-4-yl)propyl)piperidin-3-yl)acetic acid;

2-((3R,5R,6S)-5-(3-chlorophenyl)-6-(4-chlorophenyl)-3-methyl-2-oxo-1-((R)-1-(pyridin-4-yl)propyl)piperidin-3-yl)acetic acid;

2-((3R,5R,6S)-5-(3-chlorophenyl)-6-(4-chlorophenyl)-3-methyl-2-oxo-1-((S)-1-(6-(trifluoromethyl)pyridin-2-yl)propyl)piperidin-3-yl)acetic acid;

2-((3R,5R,6S)-5-(3-chlorophenyl)-6-(4-chlorophenyl)-3-methyl-2-oxo-1-((R)-1-(6-(trifluoromethyl)pyridin-2-yl)propyl)piperidin-3-yl)acetic acid;

2-((3R,5R,6S)-1-((S)-1-(6-bromopyridin-2-yl)propyl)-5-(3-chlorophenyl)-6-(4-chlorophenyl)-3-methyl-2-oxopiperidin-3-yl)acetic acid;

2-((3R,5R,6S)-1-((R)-1-(6-bromopyridin-2-yl)propyl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-1-(thiazol-2-yl)propyl)piperidin-3-yl)acetic acid;

2-((3R,5R,6S)-5-(3-chlorophenyl)-6-(4-chlorophenyl)-3-methyl-2-oxo-1-((R)-1-(thiazol-2-yl)propyl)piperidin-3-yl)acetic acid;

2-((3R,5R,6S)-5-(3-chlorophenyl)-6-(4-chlorophenyl)-1-((S)-1-(6-(2-hydroxypropan-2-yl)pyridin-2-yl)propyl)-3-methyl-2-oxopiperidin-3-yl)acetic acid;

2-((3R,5R,6S)-5-(3-chlorophenyl)-6-(4-chlorophenyl)-1-((R)-1-(6-(2-hydroxypropan-2-yl)pyridin-2-yl)propyl)-3-methyl-2-oxopiperidin-3-yl)acetic acid;

2-((3R,5R,6S)-5-(3-chlorophenyl)-6-(4-chlorophenyl)-1-((S)-1-(6-cyclopropylpyridin-2-yl)propyl)-3-methyl-2-oxopiperidin-3-yl)acetic acid;

2-((3R,5R,6S)-5-(3-chlorophenyl)-6-(4-chlorophenyl)-1-((R)-1-(6-cyclopropylpyridin-2-yl)propyl)-3-methyl-2-oxopiperidin-3-yl)acetic acid;

2-((3R,5R,6S)-5-(3-chlorophenyl)-6-(4-chlorophenyl)-3-methyl-2-oxo-1-((S)-3,3,3-trifluoro-1-(pyridin-2-yl)propyl)piperidin-3-yl)acetic acid;

2-((3R,5R,6S)-5-(3-chlorophenyl)-6-(4-chlorophenyl)-3-methyl-2-oxo-1-((R)-3,3,3-trifluoro-1-(pyridin-2-yl)propyl)piperidin-3-yl)acetic acid;

2-((3R,5R,6S)-5-(3-chlorophenyl)-6-(4-chlorophenyl)-3-methyl-1-((S)-2-methyl-1-(pyridin-2-yl)propyl)-2-oxopiperidin-3-yl)acetic acid;

2-((3R,5R,6S)-5-(3-chlorophenyl)-6-(4-chlorophenyl)-3-methyl-1-((R)-2-methyl-1-(pyridin-2-yl)propyl)-2-oxopiperidin-3-yl)acetic acid;

(3R,5R,6S)-3-((1H-tetrazol-5-yl)methyl)-5-(3-chlorophenyl)-6-(4-chlorophenyl)-3-methyl-1-(pentan-3-yl)piperidin-2-one;

(3R,5R,6S)-5-(3-chlorophenyl)-6-(4-chlorophenyl)-3-((R)-2,3-dihydroxypropyl)-1-((2S,3S)-2-hydroxypentan-3-yl)-3-methylpiperidin-2-one;

(3R,5R,6S)-5-(3-chlorophenyl)-6-(4-chlorophenyl)-3-((S)-2,3-dihydroxypropyl)-1-((2S,3S)-2-hydroxypentan-3-yl)-3-methylpiperidin-2-one;

2-((3R,5R,6S)-5-(3-Chlorophenyl)-6-(4-chlorophenyl)-1-((S)-1-hydroxybutan-2-yl)-3-methyl-2-oxopiperidin-3-yl)cyclopropanecarboxylic acid;

2-((3R,5R,6S)-1-((S)-2-(tert-Butoxy)-1-cyclopropyl-2-oxoethyl)-5-(3-chlorophenyl)-6-(4-chlorophenyl)-2-oxopiperidin-3-yl)acetic acid;

2-((3R,5R,6S)-5-(3-Chlorophenyl)-6-(4-chlorophenyl)-1-((S)-1-cyclopropyl-2-ethoxy-2-oxoethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetic acid;

2-((3R,5R,6S)-5-(3-Chlorophenyl)-6-(4-chlorophenyl)-1-((1S,2S)-1-cyclopropyl-2-hydroxybutyl)-3-methyl-2-oxopiperidin-3-yl)acetic acid;

2-((3R,5R,6S)-5-(3-Chlorophenyl)-6-(4-chlorophenyl)-1-((1S,2R)-1-cyclopropyl-2-hydroxybutyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(N-methylcyclopropanesulfonamido)ethyl)-3-ethyl-2-oxopiperidin-3-yl)acetic acid;

2-((3R,5R,6S)-5-(3-Chlorophenyl)-6-(4-chlorophenyl)-1-((S)-2-(cyclopropanesulfonamido)-1-cyclopropylethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-(ethylsulfonamido)ethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-(N-methylcyclopropanesulfonamido)ethyl)-3-methyl-2-oxopiperidin-3-yl)acetic acid;

2-((3R,5R,6S)-5-(3-Chlorophenyl)-6-(4-chlorophenyl)-1-((1S,2R)-1-cyclopropyl-2-hydroxypropyl)-3-methyl-2-oxopiperidin-3-yl)acetic acid;

2-((3R,5R,6S)-5-(3-Chlorophenyl)-6-(4-chlorophenyl)-1-((1S,2S)-1-cyclopropyl-2-hydroxypropyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(1-methylethylsulfonamido)ethyl)-3-methyl-2-oxopiperidin-3-yl)acetic acid;

2-((3R,5R,6S)-5-(3-Chlorophenyl)-6-(4-chlorophenyl)-1-((R)-1-cyclopropyl-2-(N-methylcyclopropanesulfonamido)ethyl)-3-methyl-2-oxopiperidin-3-yl)acetic acid;

2-((3R,5R,6S)-5-(3-Chlorophenyl)-6-(4-chlorophenyl)-1-((2S,3S)-2-hydroxy-4-methylpentan-3-yl)-3-methyl-2-oxopiperidin-3-yl)acetic acid;

2-((3R,5R,6S)-5-(3-Chlorophenyl)-6-(4-chlorophenyl)-1-((S)-cyclopropyl(pyridin-2-yl)methyl)-3-methyl-2-oxopiperidin-3-yl)acetic acid; or 2-((3R,5R,6S)-5-(3-Chlorophenyl)-6-(4-chlorophenyl)-1-((R)-cyclopropyl(pyridin-2-yl)methyl)-3-methyl-2-oxopiperidin-3-yl)acetic acid.

In another aspect, the present invention provides a compound, or a pharmaceutically acceptable salt thereof, selected from:

2-(1-(1-tert-butoxy-1-oxobutan-2-yl)-5-(3-chlorophenyl)-6-(4-chlorophenyl)-2-oxopiperidin-3-yl)acetic acid;
2-(5-(3-Chlorophenyl)-6-(4-chlorophenyl)-1-(1-ethoxy-1-oxobutan-2-yl)-2-oxopiperidin-3-yl)acetic acid;
2-(5-(3-Chlorophenyl)-6-(4-chlorophenyl)-1-(1-ethoxy-4-methyl-1-oxopentan-2-yl)-2-oxopiperidin-3-yl)acetic acid;
2-(5-(3-Chlorophenyl)-6-(4-chlorophenyl)-1-(1-ethoxy-1-oxopentan-2-yl)-2-oxopiperidin-3-yl)acetic acid;
2-(1-(2-tert-Butoxy-1-cyclopropyl-2-oxoethyl)-5-(3-chlorophenyl)-6-(4-chlorophenyl)-2-oxopiperidin-3-yl)acetic acid;
2-(5-(3-Chlorophenyl)-6-(4-chlorophenyl)-1-(1-hydroxybutan-2-yl)-2-oxopiperidin-3-yl)acetic acid;
2-(5-(3-chlorophenyl)-6-(4-chlorophenyl)-1-(1-cyclopropyl-2-hydroxyethyl)-2-oxopiperidin-3-yl)acetic acid;
2-(5-(3-chlorophenyl)-6-(4-chlorophenyl)-1-(1-(cyclopropylmethoxy)butan-2-yl)-2-oxopiperidin-3-yl)acetic acid;
2-(5-(3-Chlorophenyl)-6-(4-chlorophenyl)-1-(1-methoxybutan-2-yl)-2-oxopiperidin-3-yl)acetic acid;
2-(5-(3-Chlorophenyl)-6-(4-chlorophenyl)-1-(1-(2-methoxyethoxy)butan-2-yl)-2-oxopiperidin-3-yl)acetic acid;
2-(5-(3-Chlorophenyl)-6-(4-chlorophenyl)-1-(1-((1-cyanocyclopropyl)methoxy)butan-2-yl)-2-oxopiperidin-3-yl)acetic acid;
2-(5-(3-Chlorophenyl)-6-(4-chlorophenyl)-1-(1-(cyclopropylmethoxy)butan-2-yl)-2-oxopiperidin-3-yl)acetic acid;
2-(5-(3-Chlorophenyl)-6-(4-chlorophenyl)-1-(1-methoxybutan-2-yl)-2-oxopiperidin-3-yl)acetic acid;
2-(5-(3-Chlorophenyl)-6-(4-chlorophenyl)-1-(1-(2-methoxyethoxy)butan-2-yl)-2-oxopiperidin-3-yl)acetic acid;
2-(1-(1-((1-carbamoylcyclopropyl)methoxy)butan-2-yl)-5-(3-chlorophenyl)-6-(4-chlorophenyl)-2-oxopiperidin-3-yl)acetic acid;
2-(5-(3-chlorophenyl)-6-(4-chlorophenyl)-1-(1-(2-hydroxy-2-methylpropoxy)butan-2-yl)-2-oxopiperidin-3-yl)acetic acid;
2-(5-(3-chlorophenyl)-6-(4-chlorophenyl)-2-oxo-1-(1,1,1-trifluoro-2-hydroxypentan-3-yl)piperidin-3-yl)acetic acid;
2-(5-(3-chlorophenyl)-6-(4-chlorophenyl)-1-(1-morpholinobutan-2-yl)-2-oxopiperidin-3-yl)acetic acid;
2-(5-(3-chlorophenyl)-6-(4-chlorophenyl)-1-(1-(ethylamino)butan-2-yl)-2-oxopiperidin-3-yl)acetic acid;
2-(5-(3-chlorophenyl)-6-(4-chlorophenyl)-2-oxo-1-(1-(2,2,2-trifluoroethylamino)butan-2-yl)piperidin-3-yl)acetic acid;
2-(5-(3-chlorophenyl)-6-(4-chlorophenyl)-2-oxo-1-(1-(pyrrolidin-1-yl)butan-2-yl)piperidin-3-yl)acetic acid;
2-(5-(3-chlorophenyl)-6-(4-chlorophenyl)-2-oxo-1-(1-(2-oxopyrrolidin-1-yl)butan-2-yl)piperidin-3-yl)acetic acid;
2-(5-(3-Chlorophenyl)-6-(4-chlorophenyl)-1-(1-(1,1-dioxidothiomorpholino)butan-2-yl)-2-oxopiperidin-3-yl)acetic acid;
2-(5-(3-chlorophenyl)-6-(4-chlorophenyl)-2-oxo-1-(1-(thiazol-2-ylamino)butan-2-yl)piperidin-3-yl)acetic acid;
2-(1-(1-acetamidobutan-2-yl)-5-(3-chlorophenyl)-6-(4-chlorophenyl)-2-oxopiperidin-3-yl)acetic acid;
2-(5-(3-chlorophenyl)-6-(4-chlorophenyl)-1-(1-(methylsulfonamido) butan-2-yl)-2-oxopiperidin-3-yl)acetic acid;
2-(5-(3-chlorophenyl)-6-(4-chlorophenyl)-1-(1-cyanopentan-3-yl)-2-oxopiperidin-3-yl)acetic acid;
2-(5-(3-chlorophenyl)-6-(4-chlorophenyl)-1-(1-(methylsulfonyl)pentan-3-yl)-2-oxopiperidin-3-yl)acetic acid;
2-(5-(3-chlorophenyl)-6-(4-chlorophenyl)-2-oxo-1-(1-(pyridin-2-yl)pentan-3-yl)piperidin-3-yl)acetic acid;
2-(5-(3-Chlorophenyl)-6-(4-chlorophenyl)-1-(1-(ethylamino)-1-oxobutan-2-yl)-2-oxopiperidin-3-yl)acetic acid;
2-(5-(3-Chlorophenyl)-6-(4-chlorophenyl)-1-(1-(5-methyl-1,3,4-oxadiazol-2-yl)propyl)-2-oxopiperidin-3-yl)acetic;
2-(5-(3-chlorophenyl)-6-(4-chlorophenyl)-1-(cyclopropylmethyl)-2-oxopiperidin-3-yl)acetic acid;
2-(5-(3-chlorophenyl)-6-(4-chlorophenyl)-1-(cyclobutylmethyl)-2-oxopiperidin-3-yl)acetic acid;
2-(5-(3-chlorophenyl)-6-(4-chlorophenyl)-1-(2-ethylbutyl)-2-oxopiperidin-3-yl)acetic acid;
2-(5-(3-chlorophenyl)-6-(4-chlorophenyl)-1-(cyclopentylmethyl)-2-oxopiperidin-3-yl)acetic acid;
2-(5-(3-chlorophenyl)-6-(4-chlorophenyl)-1-((2,2-dimethylcyclopentyl)methyl)-2-oxopiperidin-3-yl)acetic acid;
2-(5-(3-chlorophenyl)-6-(4-chlorophenyl)-1-(cyclohexylmethyl)-2-oxopiperidin-3-yl)acetic acid;
2-(5-(3-chlorophenyl)-6-(4-chlorophenyl)-1-(cyclopropylmethyl)-2-oxopiperidin-3-yl)acetic acid;
2-(5-(3-chlorophenyl)-6-(4-chlorophenyl)-2-oxo-1-propylpiperidin-3-yl)acetic acid;
2-(5-(3-chlorophenyl)-6-(4-chlorophenyl)-1-(cyclobutylmethyl)-2-oxopiperidin-3-yl)acetic acid;
2-(5-(3-chlorophenyl)-6-(4-chlorophenyl)-1-isobutyl-2-oxopiperidin-3-yl)acetic acid;
2-(5-(3-chlorophenyl)-6-(4-chlorophenyl)-1-(cyclopentylmethyl)-2-oxopiperidin-3-yl)acetic acid;
2-(5-(3-chlorophenyl)-6-(4-chlorophenyl)-2-oxo-1-(pentan-3-yl)piperidin-3-yl)acetic acid;
Methyl 2-(5-(3-chlorophenyl)-6-(4-chlorophenyl)-1-(cyclopropylmethyl)-2-oxopiperidin-3-yl)acetate;
2-(5-(3-chlorophenyl)-6-(4-chlorophenyl)-1-(cyclopropylmethyl)-2-oxopiperidin-3-yl)acetamide;
Ethyl 2-(2-(5-(3-chlorophenyl)-6-(4-chlorophenyl)-1-(cyclopropylmethyl)-2-oxopiperidin-3-yl)acetamido)acetate;
2-(2-(5-(3-Chlorophenyl)-6-(4-chlorophenyl)-1-(cyclopropylmethyl)-2-oxopiperidin-3-yl)acetamido)acetic acid;
2-(5-(3-Chlorophenyl)-6-(4-chlorophenyl)-1-(cyclopropylmethyl)-2-oxopiperidin-3-yl)acetohydrazide;
2-(5-(3-chlorophenyl)-6-(4-chlorophenyl)-1-(cyclopropylmethyl)-2-oxopiperidin-3-yl)-N-hydroxyacetamide;
Ethyl 2-(3-(3-chlorophenyl)-2-(4-chlorophenyl)-5-(2-(methylsulfonamido)-2-oxoethyl)-6-oxopiperidin-1-yl)butanoate;
Ethyl 2-(3-(3-chlorophenyl)-2-(4-chlorophenyl)-5-(2-((3-morpholinopropyl)amino)-2-oxoethyl)-6-oxopiperidin-1-yl)butanoate;
3-((1H-Tetrazol-5-yl)methyl)-5-(3-chlorophenyl)-6-(4-chlorophenyl)-1-(cyclopropylmethyl)piperidin-2-one;
3-((1,3,4-oxadiazol-2-yl)methyl)-5-(3-chlorophenyl)-6-(4-chlorophenyl)-1-(cyclopropylmethyl)piperidin-2-one;
5-(3-chlorophenyl)-6-(4-chlorophenyl)-1-(cyclopropylmethyl)-3-((5-methyl-1,3,4-oxadiazol-2-yl)methyl)piperidin-2-one;
2-(5-(3-chlorophenyl)-6-(4-chlorophenyl)-1-(cyclopropylmethyl)-2-oxopiperidin-3-yl)-N-(methylsulfonyl)acetamide;
2-(5-(3-chlorophenyl)-6-(4-chlorophenyl)-1-(cyclopropylmethyl)-2-oxopiperidin-3-yl)acetamide.
3-((1H-tetrazol-5-yl)methyl)-5-(3-chlorophenyl)-6-(4-chlorophenyl)-1-(cyclopropylmethyl)piperidin-2-one;
5-(3-chlorophenyl)-6-(4-chlorophenyl)-1-(cyclopropylmethyl)-3-((5-methylisoxazol-3-yl)methyl)piperidin-2-one;
2-(6-chloro-3'-(3-chlorophenyl)-1'-(cyclopropylmethyl)-2,6'-dioxospiro[indoline-3,2'-piperidine]-5'-yl)acetic acid;
2-(5-(3-chlorophenyl)-6-(5-chlorothiophen-2-yl)-1-(cyclopropylmethyl)-2-oxopiperidin-3-yl)acetic acid;

2-(5-(3-chlorophenyl)-6-(5-chlorothiophen-2-yl)-1-(cyclopropylmethyl)-2-oxopiperidin-3-yl)acetic acid;
2-(5-(3-chlorophenyl)-6-(4-chlorophenyl)-1-(1-ethoxy-1-oxobutan-2-yl)-3-methyl-2-oxopiperidin-3-yl)acetic acid;
2-(1-(1-tert-butoxy-1-oxobutan-2-yl)-5-(3-chlorophenyl)-6-(4-chlorophenyl)-3-methyl-2-oxopiperidin-3-yl)acetic acid;
2-(5-(3-chlorophenyl)-6-(4-chlorophenyl)-1-(1-(cyclopropylmethoxy)butan-2-yl)-3-methyl-2-oxopiperidin-3-yl)acetic acid;
2-(5-(3-chlorophenyl)-6-(4-chlorophenyl)-1-(cyclopropylmethyl)-2-oxo-3-(2-(pyrrolidin-1-yl)ethyl)piperidin-3-yl)acetic acid;
2-(5-(3-chlorophenyl)-6-(4-chlorophenyl)-1-(cyclopropylmethyl)-3-(2-morpholinoethyl)-2-oxopiperidin-3-yl)acetic acid;
2-(5-(3-chlorophenyl)-6-(4-chlorophenyl)-3-methyl-2-oxo-1-(pentan-3-yl)piperidin-3-yl)acetic acid;
2-(5-(3-chlorophenyl)-6-(4-chlorophenyl)-1-(cyclopropylmethyl)-3-methyl-2-oxopiperidin-3-yl)acetic acid;
2-(5-(3-chlorophenyl)-6-(4-chlorophenyl)-1-isopropyl-3-methyl-2-oxopiperidin-3-yl)acetic acid;
2-(5-(3-chlorophenyl)-6-(4-chlorophenyl)-1-cyclobutyl-3-methyl-2-oxopiperidin-3-yl)acetic acid;
2-(5-(3-chlorophenyl)-6-(4-chlorophenyl)-1-cyclopentyl-3-methyl-2-oxopiperidin-3-yl)acetic acid;
5-(3-chlorophenyl)-6-(4-chlorophenyl)-3-methyl-3-((5-oxo-4,5-dihydro-1H-1,2,4-triazol-3-yl)methyl)-1-(pentan-3-yl)piperidin-2-one;
5-((5-(3-chlorophenyl)-6-(4-chlorophenyl)-3-methyl-2-oxo-1-(pentan-3-yl)piperidin-3-yl)methyl)-1,3,4-oxadiazol-2(3H)-one;
2-(5-(3-chlorophenyl)-6-(4-chlorophenyl)-3-methyl-2-oxo-1-(pentan-3-yl)piperidin-3-yl)-N-(trifluoromethylsulfonyl)acetamide;
5-(3-chlorophenyl)-6-(4-chlorophenyl)-3-((3-hydroxy-1H-pyrazol-5-yl)methyl)-3-methyl-1-(pentan-3-yl)piperidin-2-one;
5-(3-chlorophenyl)-6-(4-chlorophenyl)-3-((3-hydroxyisoxazol-5-yl)methyl)-3-methyl-1-(pentan-3-yl)piperidin-2-one;
5-((5-(3-chlorophenyl)-6-(4-chlorophenyl)-3-methyl-2-oxo-1-(pentan-3-yl)piperidin-3-yl)methyl)oxazolidine-2,4-dione;
3-((5-(3-chlorophenyl)-6-(4-chlorophenyl)-3-methyl-2-oxo-1-(pentan-3-yl)piperidin-3-yl)methyl)-1,2,4-oxadiazol-5(4H)-one;
3-((5-(3-chlorophenyl)-6-(4-chlorophenyl)-1-isopropyl-3-methyl-2-oxopiperidin-3-yl)methyl)-1,2,4-oxadiazol-5(4H)-one;
3-((5-(3-chlorophenyl)-6-(4-chlorophenyl)-3-methyl-2-oxo-1-(pentan-3-yl)piperidin-3-yl)methyl)-1,2,4-thiadiazol-5(4H)-one;
3-((5-(3-chlorophenyl)-6-(4-chlorophenyl)-1-isopropyl-3-methyl-2-oxopiperidin-3-yl)methyl)-1,2,4-thiadiazol-5(4H)-one;
3-((1H-Tetrazol-5-yl)methyl)-5-(3-chlorophenyl)-6-(4-chlorophenyl)-1-isopropyl-3-methylpiperidin-2-one;
2-(5-(3-chlorophenyl)-6-(4-chlorophenyl)-3-ethyl-2-oxo-1-(pentan-3-yl)piperidin-3-yl)acetic acid;
5-(3-chlorophenyl)-6-(4-chlorophenyl)-3-methyl-3-(methylsulfonylmethyl)-1-(pentan-3-yl)piperidin-2-one;
2-(5-(3-chlorophenyl)-6-(4-chlorophenyl)-1-(1-(3-cyclopropyl-1,2,4-oxadiazol-5-yl)propyl)-3-methyl-2-oxopiperidin-3-yl)acetic acid;
2-(5-(3-Chlorophenyl)-6-(4-chlorophenyl)-3-methyl-1-(1-morpholinobutan-2-yl)-2-oxopiperidin-3-yl)acetic acid;
2-(5-(3-chlorophenyl)-6-(4-chlorophenyl)-3-methyl-2-oxo-1-(1-(2,2,2-trifluoroethylamino)butan-2-yl)piperidin-3-yl)acetic acid;
2-(5-(3-chlorophenyl)-6-(4-chlorophenyl)-1-(1-(2,2-dimethylmorpholino)butan-2-yl)-3-methyl-2-oxopiperidin-3-yl)acetic acid;
2-(5-(3-chlorophenyl)-6-(4-chlorophenyl)-1-(1-(2,6-dimethylmorpholino)butan-2-yl)-3-methyl-2-oxopiperidin-3-yl)acetic acid;
2-(5-(3-chlorophenyl)-6-(4-chlorophenyl)-1-(1-(4-(cyclopropylsulfonyl)piperazin-1-yl)butan-2-yl)-3-methyl-2-oxopiperidin-3-yl)acetic acid;
2-(5-(3-chlorophenyl)-6-(4-chlorophenyl)-3-methyl-1-(1-(4-(methylsulfonyl)piperazin-1-yl)butan-2-yl)-2-oxopiperidin-3-yl)acetic acid;
2-(1-(1-(4-acetylpiperazin-1-yl)butan-2-yl)-5-(3-chlorophenyl)-6-(4-chlorophenyl)-3-methyl-2-oxopiperidin-3-yl)acetic acid;
2-(5-(3-chlorophenyl)-6-(4-chlorophenyl)-1-(1-(4-(cyclopropanecarbonyl)piperazin-1-yl)butan-2-yl)-3-methyl-2-oxopiperidin-3-yl)acetic acid;
3-((5-(3-chlorophenyl)-6-(4-chlorophenyl)-3-methyl-1-(1-morpholinobutan-2-yl)-2-oxopiperidin-3-yl)methyl)-1,2,4-oxadiazol-5(4H)-one;
2-(5-(3-chlorophenyl)-6-(4-chlorophenyl)-1-(1-(5,5-dimethyl-2-oxooxazolidin-3-yl)butan-2-yl)-3-methyl-2-oxopiperidin-3-yl)acetic acid;
2-(1-(1-(tert-butylamino)-1-oxobutan-2-yl)-5-(3-chlorophenyl)-6-(4-chlorophenyl)-3-methyl-2-oxopiperidin-3-yl)acetic acid;
2-(5-(3-chlorophenyl)-6-(4-chlorophenyl)-1-(2,3-dihydroxycyclopentyl)-3-methyl-2-oxopiperidin-3-yl)acetic acid;
2-(5-(3-chlorophenyl)-6-(4-chlorophenyl)-3-methyl-2-oxo-1'-(2,2,2-trifluoroethyl)-1,3'-bipiperidin-3-yl)acetic acid;
2-(5-(3-chlorophenyl)-6-(4-chlorophenyl)-1-(3-hydroxycyclopentyl)-3-methyl-2-oxopiperidin-3-yl)acetic acid;
2-(5-(3-chlorophenyl)-6-(4-chlorophenyl)-3-methyl-2-oxo-1-(tetrahydro-2H-pyran-3-yl)piperidin-3-yl)acetic acid;
2-(5-(3-chlorophenyl)-6-(4-chlorophenyl)-3-methyl-2-oxo-1-(pyrazin-2-yl)piperidin-3-yl)acetic acid;
2-(5-(3-chlorophenyl)-6-(4-chlorophenyl)-3-methyl-1-(1-methyl-1H-pyrazol-4-yl)-2-oxopiperidin-3-yl)acetic acid;
2-(5-(3-chlorophenyl)-6-(4-chlorophenyl)-3-methyl-2-oxo-1-(pyrimidin-4-yl)piperidin-3-yl)acetic acid;
2-(5-(3-chlorophenyl)-6-(4-chlorophenyl)-1-(2-chloropyrimidin-4-yl)-3-methyl-2-oxopiperidin-3-yl)acetic acid;
2-(5-(3-chlorophenyl)-6-(4-chlorophenyl)-3-methyl-2-oxo-1-(pyrimidin-2-yl)piperidin-3-yl)acetic acid;
2-(5-(3-chlorophenyl)-6-(4-chlorophenyl)-3-methyl-1-(3-methylpyridin-2-yl)-2-oxopiperidin-3-yl)acetic acid;
2-(5-(3-chlorophenyl)-6-(4-chlorophenyl)-3-methyl-1-(4-methylpyridin-2-yl)-2-oxopiperidin-3-yl)acetic acid;
2-(5-(3-chlorophenyl)-6-(4-chlorophenyl)-1-(dicyclopropylmethyl)-3-methyl-2-oxopiperidin-3-yl)acetic acid;
(4-(3-chlorophenyl)-3-(4-chlorophenyl)-1,1-dioxido-2-(2-propanyl)-1,2-thiazinan-6-yl)acetic acid;
(4-(3-chlorophenyl)-3-(4-chlorophenyl)-6-methyl-1,1-dioxido-2-(2-propanyl)-1,2-thiazinan-6-yl)acetic acid;
2-(5-(3-chlorophenyl)-6-(5-chloropyridin-2-yl)-3-methyl-1-(1-morpholinobutan-2-yl)-2-oxopiperidin-3-yl)acetic acid;
2-(5-(3-Chlorophenyl)-6-(5-chloropyridin-2-yl)-3-methyl-2-oxo-1-(pentan-3-yl)piperidin-3-yl)acetic acid;
2-(1-(1-tert-butoxy-1-oxobutan-2-yl)-5-(3-chlorophenyl)-6-(5-chloropyridin-2-yl)-3-methyl-2-oxopiperidin-3-yl)acetic acid; or 2-(1-(1-tert-butoxy-1-oxobutan-2-yl)-6-(4-chlorophenyl)-5-(4-chloropyridin-2-yl)-3-methyl-2-oxopiperidin-3-yl) acetic acid.

In another aspect, the present invention provides a compound, or a pharmaceutically acceptable salt thereof, selected from:

2-(5-(3-chlorophenyl)-6-(4-chlorophenyl)-1-(1-(N-methylcyclopropanesulfonamido)butan-2-yl)-2-oxopiperidin-3-yl)acetic acid;

5-(3-chlorophenyl)-6-(4-chlorophenyl)-1-(1-(N-methylcyclopropanesulfonamido)butan-2-yl)-2-oxopiperidin-3-yl) propanoic acid;

tert-butyl 2-(3-((1H-tetrazol-5-yl)methyl)-5-(3-chlorophenyl)-6-(4-chlorophenyl)-3-methyl-2-oxopiperidin-1-yl) butanoate;

2-(5-(3-chlorophenyl)-6-(4-chlorophenyl)-3-methyl-1-(1-(methylsulfonamido)butan-2-yl)-2-oxopiperidin-3-yl) acetic acid;

2-(5-(3-Chlorophenyl)-6-(4-chlorophenyl)-3-methyl-2-oxo-1-(5-oxohexan-3-yl)piperidin-3-yl)acetic acid;

2-(5-(3-chlorophenyl)-6-(4-chlorophenyl)-1-(5-hydroxy-5-methylhexan-3-yl)-3-methyl-2-oxopiperidin-3-yl)acetic acid;

2-(5-(3-chlorophenyl)-6-(4-chlorophenyl)-3-methyl-2-oxo-1-(6,6,6-trifluoro-5-hydroxy-5-methylhexan-3-yl)piperidin-3-yl)acetic acid;

2-(5-(3-chlorophenyl)-6-(4-chlorophenyl)-3-methyl-1-(1-(N-methylmethylsulfonamido)butan-2-yl)-2-oxopiperidin-3-yl)acetic acid;

2-(5-(3-chlorophenyl)-6-(4-chlorophenyl)-1-(5-cyclopropyl-6,6,6-trifluoro-5-hydroxyhexan-3-yl)-3-methyl-2-oxopiperidin-3-yl)acetic acid;

2-(5-(3-chlorophenyl)-6-(4-chlorophenyl)-1-(6-hydroxy-6-methylheptan-3-yl)-3-methyl-2-oxopiperidin-3-yl)acetic acid;

2-(5-(3-chlorophenyl)-6-(4-chlorophenyl)-3-methyl-2-oxo-1-(6,6,6-trifluoro-5,5-dihydroxyhexan-3-yl)piperidin-3-yl)acetic acid;

2-(5-(3-chlorophenyl)-6-(4-chlorophenyl)-3-methyl-2-oxo-1-(7,7,7-trifluoro-6-hydroxy-6-methylheptan-3-yl)piperidin-3-yl)acetic acid;

2-(5-(3-chlorophenyl)-6-(4-chlorophenyl)-1-(7-hydroxy-7-methyloctan-3-yl)-3-methyl-2-oxopiperidin-3-yl)acetic acid;

2-(5-(3-chlorophenyl)-6-(4-chlorophenyl)-3-methyl-1-(1-(N-methylcyclopropanesulfonamido)butan-2-yl)-2-oxopiperidin-3-yl)acetic acid;

2-(5-(3-chlorophenyl)-6-(4-chlorophenyl)-1-(1-(N-cyclopropylmethylsulfonamido)butan-2-yl)-3-methyl-2-oxopiperidin-3-yl)acetic acid;

2-(5-(3-chlorophenyl)-6-(4-chlorophenyl)-3-methyl-2-oxo-1-(6,6,6-trifluoro-5-hydroxyhexan-3-yl)piperidin-3-yl) acetic acid;

2-(5-(3-chlorophenyl)-6-(4-chlorophenyl)-1-(5-hydroxyhexan-3-yl)-3-methyl-2-oxopiperidin-3-yl)acetic acid;

2-(5-(3-chlorophenyl)-6-(4-chlorophenyl)-3-methyl-2-oxo-1-(1-(N-(2,2,2-trifluoroethyl)methylsulfonamido)butan-2-yl)piperidin-3-yl)acetic acid;

2-(5-(3-chlorophenyl)-6-(4-chlorophenyl)-1-(1-(1,1-dioxidoisothiazolidin-2-yl)butan-2-yl)-3-methyl-2-oxopiperidin-3-yl)acetic acid;

2-(5-(3-chlorophenyl)-6-(4-chlorophenyl)-1-(5-hydroxy-4,5-dimethylhexan-3-yl)-3-methyl-2-oxopiperidin-3-yl) acetic acid;

2-(5-(3-chlorophenyl)-6-(4-chlorophenyl)-1-(5-cyano-5-methylhexan-3-yl)-3-methyl-2-oxopiperidin-3-yl)acetic acid;

2-(5-(3-Chlorophenyl)-6-(4-chlorophenyl)-3-methyl-2-oxo-1-(2-oxopentan-3-yl)piperidin-3-yl)acetic acid;

2-(5-(3-Chlorophenyl)-6-(4-chlorophenyl)-1-(2-hydroxypentan-3-yl)-3-methyl-2-oxopiperidin-3-yl)acetic acid;

2-(5-(3-Chlorophenyl)-6-(4-chlorophenyl)-1-(2-methoxypentan-3-yl)-3-methyl-2-oxopiperidin-3-yl)acetic acid;

2-(5-(3-Chlorophenyl)-6-(4-chlorophenyl)-1-(2-hydroxypentan-3-yl)-3-methyl-2-oxopiperidin-3-yl)acetic acid;

2-(5-(3-Chlorophenyl)-6-(4-chlorophenyl)-1-(2-hydroxy-2-methylpentan-3-yl)-3-methyl-2-oxopiperidin-3-yl)acetic acid;

2-(5-(3-Chlorophenyl)-6-(4-chlorophenyl)-1-(4-hydroxyhexan-3-yl)-3-methyl-2-oxopiperidin-3-yl)acetic acid;

2-(5-(3-Chlorophenyl)-6-(4-chlorophenyl)-1-(1-methoxybutan-2-yl)-3-methyl-2-oxopiperidin-3-yl)acetic acid;

2-(5-(3-Chlorophenyl)-6-(4-chlorophenyl)-3-methyl-2-oxo-1-(1,1,1-trifluoro-2-hydroxy-2-methylpentan-3-yl)piperidin-3-yl)acetic acid;

2-(5-(3-chlorophenyl)-6-(4-chlorophenyl)-3-methyl-1-(1-(N-methylcyclopropanesulfonamido)butan-2-yl)-2-oxopiperidin-3-yl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(methylsulfonyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(3-hydroxypropyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(2-hydroxyethyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-hydroxyacetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-methoxyacetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(2,3-dihydroxypropyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(2,3-dihydroxypropyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-cyanoacetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(2-(dimethylamino)ethyl)acetamide;

2-(5-(3-chlorophenyl)-6-(4-chlorophenyl)-3-methyl-1-(1-(N-methylcyclopropanesulfonamido)butan-2-yl)-2-oxopiperidin-3-yl)-N-(3,4-dihydroxybutyl)acetamide;

2-(5-(3-chlorophenyl)-6-(4-chlorophenyl)-1-(1-(cyclopropanesulfonamido)butan-2-yl)-3-methyl-2-oxopiperidin-3-yl)acetic acid;

2-(5-(3-chlorophenyl)-6-(4-chlorophenyl)-3-methyl-1-(1-(N-methylcyclopropanesulfonamido)butan-2-yl)-2-oxopiperidin-3-yl)propanoic acid;

2-(5-(3-Chlorophenyl)-6-(4-chlorophenyl)-1-(2-(cyclopropanesulfonamido)pentan-3-yl)-3-methyl-2-oxopiperidin-3-yl)acetic acid;

2-(5-(3-chlorophenyl)-6-(4-chlorophenyl)-3-methyl-1-(2-(1-methylethylsulfonamido)pentan-3-yl)-2-oxopiperidin-3-yl)acetic acid;

2-(5-(3-chlorophenyl)-6-(4-chlorophenyl)-3-methyl-1-(1-(N-methylcyclopropanesulfonamido)-1-oxobutan-2-yl)-2-oxopiperidin-3-yl)acetic acid;

2-(5-(3-Chlorophenyl)-6-(4-chlorophenyl)-3-methyl-1-(1-(neopentylamino)-1-oxobutan-2-yl)-2-oxopiperidin-3-yl)acetic acid;

2-(5-(3-chlorophenyl)-6-(4-chlorophenyl)-1-(1-(4,4-dimethyl-4,5-dihydrooxazol-2-yl)propyl)-3-methyl-2-oxopiperidin-3-yl)acetic acid;

2-(5-(3-chlorophenyl)-6-(4-chlorophenyl)-3-methyl-2-oxo-1-(1-(N-(2,2,2-trifluoroethyl)acetamido)butan-2-yl)piperidin-3-yl)acetic acid;

2-(5-(3-chlorophenyl)-6-(4-chlorophenyl)-1-(1-(1,1-dimethylethylsulfonamido)butan-2-yl)-3-methyl-2-oxopiperidin-3-yl)acetic acid 2-(5-(3-chlorophenyl)-6-(4-chlorophenyl)-1-(1-(N,2-dimethylpropan-2-ylsulfonamido)butan-2-yl)-3-methyl-2-oxopiperidin-3-yl)acetic acid;

2-(5-(3-chlorophenyl)-6-(4-chlorophenyl)-3-methyl-1-(1-(1-methylethylsulfonamido)butan-2-yl)-2-oxopiperidin-3-yl)acetic acid;

2-(5-(3-chlorophenyl)-6-(4-chlorophenyl)-1-(1-(N-ethylpropan-2-ylsulfonamido)butan-2-yl)-3-methyl-2-oxopiperidin-3-yl)acetic acid;

2-(5-(3-Chlorophenyl)-6-(4-chlorophenyl)-1-(1-hydroxybutan-2-yl)-3-methyl-2-oxopiperidin-3-yl)acetic acid;

2-(5-(3-Chlorophenyl)-6-(4-chlorophenyl)-3-methyl-2-oxo-1-(1-(trifluoromethylsulfonamido)butan-2-yl)piperidin-3-yl)acetic acid;

2-(5-(3-Chlorophenyl)-6-(4-chlorophenyl)-1-(1-(4-chlorophenylsulfonamido)butan-2-yl)-3-methyl-2-oxopiperidin-3-yl)acetic acid;

2-(5-(3-Chlorophenyl)-6-(4-chlorophenyl)-3-methyl-1-(1-(4-methylphenylsulfonamido)butan-2-yl)-2-oxopiperidin-3-yl)acetic acid;

2-(5-(3-Chlorophenyl)-6-(4-chlorophenyl)-1-(1-(2-chlorophenylsulfonamido)butan-2-yl)-3-methyl-2-oxopiperidin-3-yl)acetic acid;

2-(5-(3-Chlorophenyl)-6-(4-chlorophenyl)-1-(1-(2-methylphenylsulfonamido)butan-2-yl)-3-methyl-2-oxopiperidin-3-yl)acetic acid;

2-(5-(3-Chlorophenyl)-6-(4-chlorophenyl)-1-(1-(4-methoxyphenylsulfonamido)butan-2-yl)-3-methyl-2-oxopiperidin-3-yl)acetic acid;

2-(5-(3-Chlorophenyl)-6-(4-chlorophenyl)-1-(1-(phenylsulfonamido)butan-2-yl)-3-methyl-2-oxopiperidin-3-yl)acetic acid;

2-(5-(3-Chlorophenyl)-6-(4-chlorophenyl)-1-(1-(1-methylcyclopropanesulfonamido)butan-2-yl)-3-methyl-2-oxopiperidin-3-yl)acetic acid;

2-(5-(3-Chlorophenyl)-6-(4-chlorophenyl)-1-(1-(1,1-dioxidobenzo[d]isothiazol-2(3H)-yl)butan-2-yl)-3-methyl-2-oxopiperidin-3-yl)acetic acid;

2-(5-(3-Chlorophenyl)-6-(4-chlorophenyl)-1-(1-(3,3-dimethyl-1,1-dioxidobenzo[d]isothiazol-2(3H)-yl)butan-2-yl)-3-methyl-2-oxopiperidin-3-yl)acetic acid;

2-(5-(3-chlorophenyl)-6-(4-chlorophenyl)-3-methyl-2-oxo-1-(1-(pyridine-3-sulfonamido)butan-2-yl)piperidin-3-yl)acetic acid;

2-(5-(3-Chlorophenyl)-6-(4-chlorophenyl)-1-(1-(4-cyanophenylsulfonamido)butan-2-yl)-3-methyl-2-oxopiperidin-3-yl)acetic acid;

2-(5-(3-Chlorophenyl)-6-(4-chlorophenyl)-1-(1-(3-cyanophenylsulfonamido)butan-2-yl)-3-methyl-2-oxopiperidin-3-yl)acetic acid;

2-(5-(3-chlorophenyl)-6-(4-chlorophenyl)-3-methyl-2-oxo-1-(1-(pyridine-2-sulfonamido)butan-2-yl)piperidin-3-yl)acetic acid;

2-(5-(3-Chlorophenyl)-6-(4-chlorophenyl)-1-(1-(N,1-dimethylcyclopropanesulfonamido)butan-2-yl)-3-methyl-2-oxopiperidin-3-yl)acetic acid;

3-(5-(3-Chlorophenyl)-6-(4-chlorophenyl)-3-methyl-1-(1-(N-methylcyclopropanesulfonamido)butan-2-yl)-2-oxopiperidin-3-yl)propanoic acid;

2-(5-(3-chlorophenyl)-6-(4-chlorophenyl)-3-methyl-1-(1-(N-methylcyclopropanesulfonamido)butan-2-yl)-2-oxopiperidin-3-yl)acetic acid;

2-(5-(3-Chlorophenyl)-6-(4-chlorophenyl)-3-methoxy-1-(1-(N-methylcyclopropanesulfonamido)butan-2-yl)-2-oxopiperidin-3-yl)acetic acid;

2-(5-(3-chlorophenyl)-6-(4-chlorophenyl)-3-methyl-1-(6-methyl-4-oxoheptan-3-yl)-2-oxopiperidin-3-yl)acetic acid;

2-(5-(3-chlorophenyl)-6-(4-chlorophenyl)-1-(1-(ethylsulfonyl)pentan-3-yl)-3-methyl-2-oxopiperidin-3-yl)acetic acid;

2-(5-(3-chlorophenyl)-6-(4-chlorophenyl)-1-(1-(isopropylsulfonyl)pentan-3-yl)-3-methyl-2-oxopiperidin-3-yl)acetic acid;

2-(5-(3-chlorophenyl)-6-(4-chlorophenyl)-1-(1-(cyclopropylmethylsulfonyl)pentan-3-yl)-3-methyl-2-oxopiperidin-3-yl)acetic acid;

2-(5-(3-chlorophenyl)-6-(4-chlorophenyl)-3-methyl-2-oxo-1-(1-(2-oxopyrrolidin-1-yl)butan-2-yl)piperidin-3-yl)acetic acid;

2-(1-(1-(2-oxa-5-azabicyclo[2.2.1]heptan-5-yl)butan-2-yl)-5-(3-chlorophenyl)-6-(4-chlorophenyl)-3-methyl-2-oxopiperidin-3-yl)acetic acid;

2-(5-(3-chlorophenyl)-6-(4-chlorophenyl)-3-methyl-1-(1-(3-methylmorpholino)butan-2-yl)-2-oxopiperidin-3-yl)acetic acid;

2-(5-(3-chlorophenyl)-6-(4-chlorophenyl)-1-(1-(thiomorpholino-1,1-dioxide)butan-2-yl)-3-methyl-2-oxopiperidin-3-yl)acetic acid;

2-(5-(3-chlorophenyl)-6-(4-chlorophenyl)-1-(1-(3,3-difluoroazetidin-1-yl)butan-2-yl)-3-methyl-2-oxopiperidin-3-yl)acetic acid;

2-(1-(1-(8-oxa-3-azabicyclo[3.2.1]octan-3-yl)butan-2-yl)-5-(3-chlorophenyl)-6-(4-chlorophenyl)-3-methyl-2-oxopiperidin-3-yl)acetic acid;

2-(5-(3-chlorophenyl)-6-(4-chlorophenyl)-1-(1-(3,3-dimethylmorpholino)butan-2-yl)-3-methyl-2-oxopiperidin-3-yl)acetic acid;

2-(5-(3-chlorophenyl)-6-(4-chlorophenyl)-1-(1-(3-hydroxy-3-(trifluoromethyl)azetidin-1-yl)butan-2-yl)-3-methyl-2-oxopiperidin-3-yl)acetic acid;

2-(5-(3-chlorophenyl)-6-(4-chlorophenyl)-3-methyl-1-(1-(methyl(oxetan-3-yl)amino)butan-2-yl)-2-oxopiperidin-3-yl)acetic acid;

2-(5-(3-Chlorophenyl)-6-(4-chlorophenyl)-3-methyl-2-oxo-1-(1-(2-oxooxazolidin-3-yl)butan-2-yl)piperidin-3-yl)acetic acid;

2-(5-(3-chlorophenyl)-6-(4-chlorophenyl)-3-methyl-2-oxo-1-(1-(2-oxopyridin-1(2H)-yl)butan-2-yl)piperidin-3-yl)acetic acid;

2-(5-(3-Chlorophenyl)-6-(4-chlorophenyl)-3-methyl-2-oxo-1-(1-(2-oxo-5-(trifluoromethyl)pyridin-1(2H)-yl)butan-2-yl)piperidin-3-yl)acetic acid;

3-allyl-5-(3-chlorophenyl)-6-(4-chlorophenyl)-3-methyl-1-(1-(pyridin-3-yloxy)butan-2-yl)piperidin-2-one;

2-(5-(3-chlorophenyl)-6-(4-chlorophenyl)-3-methyl-2-oxo-1-(1-(tetrahydrofuran-2-yl)propyl)piperidin-3-yl)acetic acid;

2-(5-(3-chlorophenyl)-6-(4-chlorophenyl)-3-methyl-2-oxo-1-(1-(5-oxotetrahydrofuran-2-yl)propyl)piperidin-3-yl)acetic acid;
2-(5-(3-chlorophenyl)-6-(4-chlorophenyl)-3-methyl-2-oxo-1-(1-(tetrahydro-2H-pyran-2-yl)propyl)piperidin-3-yl)acetic acid;
2-(1-(1-(benzo[d]thiazol-2-yl)propyl)-5-(3-chlorophenyl)-6-(4-chlorophenyl)-3-methyl-2-oxopiperidin-3-yl)acetic acid;
2-(5-(3-chlorophenyl)-6-(4-chlorophenyl)-3-methyl-1-(1-(3-methylisoxazol-5-yl)propyl)-2-oxopiperidin-3-yl)acetic acid;
2-(5-(3-chlorophenyl)-6-(4-chlorophenyl)-1-(1-(6-chloropyridin-2-yl)propyl)-3-methyl-2-oxopiperidin-3-yl)acetic acid;
2-(5-(3-chlorophenyl)-6-(4-chlorophenyl)-3-methyl-2-oxo-1-(1-(pyridin-2-yl)propyl)piperidin-3-yl)acetic acid;
2-(5-(3-chlorophenyl)-6-(4-chlorophenyl)-3-methyl-2-oxo-1-(1-(pyridin-2-yl)butyl)piperidin-3-yl)acetic acid;
2-(5-(3-chlorophenyl)-6-(4-chlorophenyl)-1-(2-cyclopropyl-1-(pyridin-2-yl)ethyl)-3-methyl-2-oxopiperidin-3-yl)acetic acid;
2-(5-(3-chlorophenyl)-6-(4-chlorophenyl)-3-methyl-2-oxo-1-(1-(pyridin-3-yl)propyl)piperidin-3-yl)acetic acid;
2-(5-(3-chlorophenyl)-6-(4-chlorophenyl)-3-methyl-2-oxo-1-(1-(pyrazin-2-yl)propyl)piperidin-3-yl)acetic acid;
2-(5-(3-chlorophenyl)-6-(4-chlorophenyl)-3-methyl-2-oxo-1-(1-(pyrimidin-2-yl)propyl)piperidin-3-yl)acetic acid;
2-(5-(3-chlorophenyl)-6-(4-chlorophenyl)-3-methyl-1-(1-(6-methylpyridin-2-yl)propyl)-2-oxopiperidin-3-yl)acetic acid;
2-(5-(3-chlorophenyl)-6-(4-chlorophenyl)-3-methyl-2-oxo-1-(1-(pyridin-4-yl)propyl)piperidin-3-yl)acetic acid;
2-(5-(3-chlorophenyl)-6-(4-chlorophenyl)-3-methyl-2-oxo-1-(1-(6-(trifluoromethyl)pyridin-2-yl)propyl)piperidin-3-yl)acetic acid;
2-(1-(1-(6-bromopyridin-2-yl)propyl)-5-(3-chlorophenyl)-6-(4-chlorophenyl)-3-methyl-2-oxopiperidin-3-yl)acetic acid;
2-(5-(3-chlorophenyl)-6-(4-chlorophenyl)-3-methyl-2-oxo-1-(1-(thiazol-2-yl)propyl)piperidin-3-yl)acetic acid;
2-(5-(3-chlorophenyl)-6-(4-chlorophenyl)-1-(1-(6-(2-hydroxypropan-2-yl)pyridin-2-yl)propyl)-3-methyl-2-oxopiperidin-3-yl)acetic acid;
2-(5-(3-chlorophenyl)-6-(4-chlorophenyl)-1-(1-(6-cyclopropylpyridin-2-yl)propyl)-3-methyl-2-oxopiperidin-3-yl)acetic acid;
2-(5-(3-chlorophenyl)-6-(4-chlorophenyl)-3-methyl-2-oxo-1-(3,3,3-trifluoro-1-(pyridin-2-yl)propyl)piperidin-3-yl)acetic acid;
2-(5-(3-chlorophenyl)-6-(4-chlorophenyl)-3-methyl-1-(2-methyl-1-(pyridin-2-yl)propyl)-2-oxopiperidin-3-yl)acetic acid;
3-((1H-tetrazol-5-yl)methyl)-5-(3-chlorophenyl)-6-(4-chlorophenyl)-3-methyl-1-(pentan-3-yl)piperidin-2-one;
5-(3-chlorophenyl)-6-(4-chlorophenyl)-3-(2,3-dihydroxypropyl)-1-(2-hydroxypentan-3-yl)-3-methylpiperidin-2-one;
2-(5-(3-Chlorophenyl)-6-(4-chlorophenyl)-1-(1-hydroxybutan-2-yl)-3-methyl-2-oxopiperidin-3-yl)cyclopropanecarboxylic acid;
2-(1-(2-(tert-Butoxy)-1-cyclopropyl-2-oxoethyl)-5-(3-chlorophenyl)-6-(4-chlorophenyl)-2-oxopiperidin-3-yl)acetic acid;
2-(5-(3-Chlorophenyl)-6-(4-chlorophenyl)-1-(1-cyclopropyl-2-ethoxy-2-oxoethyl)-3-methyl-2-oxopiperidin-3-yl)acetic acid;
2-(5-(3-chlorophenyl)-6-(4-chlorophenyl)-1-(1-cyclopropyl-2-hydroxyethyl)-3-methyl-2-oxopiperidin-3-yl)acetic acid;
2-(5-(3-Chlorophenyl)-6-(4-chlorophenyl)-1-(1-cyclopropyl-2-hydroxybutyl)-3-methyl-2-oxopiperidin-3-yl)acetic acid;
2-(5-(3-Chlorophenyl)-6-(4-chlorophenyl)-1-(1-cyclopropyl-2-(N-methylcyclopropanesulfonamido)ethyl)-3-ethyl-2-oxopiperidin-3-yl)acetic acid;
2-(5-(3-Chlorophenyl)-6-(4-chlorophenyl)-1-(2-(cyclopropanesulfonamido)-1-cyclopropylethyl)-3-ethyl-2-oxopiperidin-3-yl)acetic acid;
2-(5-(3-Chlorophenyl)-6-(4-chlorophenyl)-1-(1-cyclopropyl-2-(ethylsulfonamido)ethyl)-3-ethyl-2-oxopiperidin-3-yl)acetic acid;
2-(5-(3-Chlorophenyl)-6-(4-chlorophenyl)-1-(1-cyclopropyl-2-(N-methylcyclopropanesulfonamido)ethyl)-3-methyl-2-oxopiperidin-3-yl)acetic acid;
2-(5-(3-Chlorophenyl)-6-(4-chlorophenyl)-1-(1-cyclopropyl-2-hydroxypropyl)-3-methyl-2-oxopiperidin-3-yl)acetic acid;
2-(5-(3-Chlorophenyl)-6-(4-chlorophenyl)-1-(1-cyclopropyl-2-(1-methylethylsulfonamido)ethyl)-3-methyl-2-oxopiperidin-3-yl)acetic acid;
2-(5-(3-Chlorophenyl)-6-(4-chlorophenyl)-1-(1-cyclopropyl-2-(N-methylcyclopropanesulfonamido)ethyl)-3-methyl-2-oxopiperidin-3-yl)acetic acid;
2-(5-(3-Chlorophenyl)-6-(4-chlorophenyl)-1-(2-hydroxy-4-methylpentan-3-yl)-3-methyl-2-oxopiperidin-3-yl)acetic acid; or
2-(5-(3-Chlorophenyl)-6-(4-chlorophenyl)-1-(cyclopropyl(pyridin-2-yl)methyl)-3-methyl-2-oxopiperidin-3-yl)acetic acid.

In another aspect, the present invention provides a compound, or a pharmaceutically acceptable salt thereof, selected from:
2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)acetic acid;
2-((3R,5R,6S)-5-(3-chlorophenyl)-6-(4-chlorophenyl)-1-((S)-1-(1,1-dioxidoisothiazolidin-2-yl)butan-2-yl)-3-methyl-2-oxopiperidin-3-yl)acetic acid;
2-((3R,5R,6S)-5-(3-Chlorophenyl)-6-(4-chlorophenyl)-1-((2S,3S)-2-hydroxypentan-3-yl)-3-methyl-2-oxopiperidin-3-yl)acetic acid;
2-((3R,5R,6S)-5-(3-Chlorophenyl)-6-(4-chlorophenyl)-1-((2R,3S)-2-hydroxypentan-3-yl)-3-methyl-2-oxopiperidin-3-yl)acetic acid;
2-((3R,5R,6S)-5-(3-chlorophenyl)-6-(4-chlorophenyl)-1-((S)-1-(1,1-dimethylethylsulfonamido)butan-2-yl)-3-methyl-2-oxopiperidin-3-yl)acetic acid
2-((3R,5R,6S)-5-(3-chlorophenyl)-6-(4-chlorophenyl)-1-((S)-1-(N,2-dimethylpropan-2-ylsulfonamido)butan-2-yl)-3-methyl-2-oxopiperidin-3-yl)acetic acid;
2-((3R,5R,6S)-5-(3-Chlorophenyl)-6-(4-chlorophenyl)-1-((S)-1-(N,1-dimethylcyclopropanesulfonamido)butan-2-yl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(N-methylcyclopropanesulfonamido)ethyl)-3-methyl-2-oxopiperidin-3-yl)acetic acid;
2-((3R,5R,6S)-5-(3-Chlorophenyl)-6-(4-chlorophenyl)-1-((1S,2R)-1-cyclopropyl-2-hydroxypropyl)-3-methyl-2-oxopiperidin-3-yl)acetic acid; or
2-((3R,5R,6S)-5-(3-Chlorophenyl)-6-(4-chlorophenyl)-1-((1S,2S)-1-cyclopropyl-2-hydroxypropyl)-3-methyl-2-oxopiperidin-3-yl)acetic acid.

In another aspect, the present invention provides a compound, or a pharmaceutically acceptable salt thereof, selected from:

2-(5-(3-Chlorophenyl)-6-(4-chlorophenyl)-1-(1-(N-methylcyclopropanesulfonamido)butan-2-yl)-2-oxopiperidin-3-yl)acetic acid;

2-(5-(3-Chlorophenyl)-6-(4-chlorophenyl)-1-(1-(1,1-dioxidoisothiazolidin-2-yl)butan-2-yl)-3-methyl-2-oxopiperidin-3-yl)acetic acid;

2-(5-(3-Chlorophenyl)-6-(4-chlorophenyl)-1-(2-hydroxypentan-3-yl)-3-methyl-2-oxopiperidin-3-yl)acetic acid;

2-(5-(3-Chlorophenyl)-6-(4-chlorophenyl)-1-(2-hydroxypentan-3-yl)-3-methyl-2-oxopiperidin-3-yl)acetic acid;

2-(5-(3-Chlorophenyl)-6-(4-chlorophenyl)-1-(1-(1,1-dimethylethylsulfonamido)butan-2-yl)-3-methyl-2-oxopiperidin-3-yl)acetic acid 2-(5-(3-Chlorophenyl)-6-(4-chlorophenyl)-1-(1-(N,2-dimethylpropan-2-ylsulfonamido)butan-2-yl)-3-methyl-2-oxopiperidin-3-yl)acetic acid;

2-(5-(3-Chlorophenyl)-6-(4-chlorophenyl)-1-(1-(N,1-dimethylcyclopropanesulfonamido)butan-2-yl)-3-methyl-2-oxopiperidin-3-yl)acetic acid;

2-(5-(3-Chlorophenyl)-6-(4-chlorophenyl)-1-(1-cyclopropyl-2-(N-methylcyclopropanesulfonamido)ethyl)-3-methyl-2-oxopiperidin-3-yl)acetic acid; or 2-(5-(3-Chlorophenyl)-6-(4-chlorophenyl)-1-(1-cyclopropyl-2-hydroxypropyl)-3-methyl-2-oxopiperidin-3-yl)acetic acid.

In another aspect, the present invention provides a compound, or a pharmaceutically acceptable salt thereof, selected from:

2-((3R,5R,6S)-5-(3-Chlorophenyl)-6-(4-chlorophenyl)-1-((S)-1-cyclopropyl-2-(thiophene-2-sulfonamido)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(N-methylthiophene-2-sulfonamido)ethyl)-3-methyl-2-oxopiperidin-3-yl)acetic acid;

2-((3R,5R,6S)-5-(3-Chlorophenyl)-6-(4-chlorophenyl)-1-((S)-2-(5-chlorothiophene-2-sulfonamido)-1-cyclopropylethyl)-3-methyl-2-oxopiperidin-3-yl)acetic acid;

2-((3R,5R,6S)-1-((S)-2-(5-Chloro-N-methylthiophene-2-sulfonamido)-1-cyclopropylethyl)-5-(3-chlorophenyl)-6-(4-chlorophenyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(N-(difluoromethyl)-2-methylpropan-2-ylsulfonamido)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(N-(difluoromethyl)ethylsulfonamido)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(N-(difluoromethyl)cyclopropanesulfonamido)ethyl)-3-methyl-2-oxopiperidin-3-yl)acetic acid;

1-((3R,5R,6S)-5-(3-Chlorophenyl)-6-(4-chlorophenyl)-1-((S)-2-(cyclopropanesulfonamido)-1-cyclopropylethyl)-3-methyl-2-oxopiperidin-3-yl)cyclopropanecarboxylic acid;

2-((3R,5R,6S)-5-(3-chlorophenyl)-6-(4-chlorophenyl)-1-((S)-1-cyclopropyl-2-(N-(2-fluorophenyl)ethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(2-fluorophenyl)methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-phenylcyclopropanesulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-phenylethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(ethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(3-fluorophenyl)ethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-2-(N-(2-cyanophenyl)methylsulfonamido)-1-cyclopropylethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(propylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-phenylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-2-(N-(3-cyanophenyl)methylsulfonamido)-1-cyclopropylethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(pyridin-3-yl)methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(thiophen-2-ylmethyl)methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(3-methoxybenzyl)methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(phenylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(pyridin-2-ylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(pyridin-3-ylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-(pyridin-2-yl)methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(methylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-ethylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-isopropylmethylsulfonamido)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(1-methylethylsulfonamido)ethyl)-3-ethyl-2-oxopiperidin-3-yl)acetic acid;

2-((3R,5R,6S)-5-(3-chlorophenyl)-6-(4-chlorophenyl)-1-((S)-2-(cyclobutanesulfonamido)-1-cyclopropylethyl)-3-ethyl-2-oxopiperidin-3-yl)acetic acid;

2-((3R,5R,6S)-5-(3-chlorophenyl)-6-(4-chlorophenyl)-1-((S)-2-(cyclopentanesulfonamido)-1-cyclopropylethyl)-3-ethyl-2-oxopiperidin-3-yl)acetic acid;

2-((3R,5R,6S)-5-(3-chlorophenyl)-6-(4-chlorophenyl)-3-methyl-1-((S)-3-methyl-1-(N-methylcyclopropanesulfonamido)butan-2-yl)-2-oxopiperidin-3-yl)acetic acid;

2-((3R,5R,6S)-5-(3-chlorophenyl)-6-(4-chlorophenyl)-1-((S)-1-(cyclopropanesulfonamido)-3-methylbutan-2-yl)-3-methyl-2-oxopiperidin-3-yl)acetic acid;

2-((3R,5R,6S)-5-(3-chlorophenyl)-6-(4-chlorophenyl)-1-((S)-1-(ethylsulfonamido)-3-methylbutan-2-yl)-3-methyl-2-oxopiperidin-3-yl)acetic acid;

2-((3R,5R,6S)-5-(3-chlorophenyl)-6-(4-chlorophenyl)-1-((S)-1-(cyclobutanesulfonamido)butan-2-yl)-3-methyl-2-oxopiperidin-3-yl)acetic acid;

2-((3R,5R,6S)-5-(3-chlorophenyl)-6-(4-chlorophenyl)-1-((S)-1-(N-ethylcyclobutanesulfonamido)butan-2-yl)-3-methyl-2-oxopiperidin-3-yl)acetic acid;

2-((3R,5R,6S)-5-(3-Chlorophenyl)-6-(4-chlorophenyl)-3-methyl-2-oxo-1-((S)-1-(phenylsulfonyl)butan-2-yl)piperidin-3-yl)acetic acid;

2-((3R,5R,6S)-5-(3-Chlorophenyl)-6-(4-chlorophenyl)-3-methyl-1-((S)-1-(methylsulfonyl)butan-2-yl)-2-oxopiperidin-3-yl)acetic acid;

2-((3R,5R,6S)-5-(3-Chlorophenyl)-6-(4-chlorophenyl)-3-methyl-2-oxo-1-((S)-1-(propylsulfonyl)butan-2-yl)piperidin-3-yl)acetic acid;

2-((3R,5R,6S)-5-(3-Chlorophenyl)-6-(4-chlorophenyl)-1-((S)-1-(isobutylsulfonyl)butan-2-yl)-3-methyl-2-oxopiperidin-3-yl)acetic acid;

2-((3R,5R,6S)-5-(3-Chlorophenyl)-6-(4-chlorophenyl)-1-((S)-1-((cyclopropylmethyl)sulfonyl)butan-2-yl)-3-methyl-2-oxopiperidin-3-yl)acetic acid;

2-((3R,5R,6S)-5-(3-Chlorophenyl)-6-(4-chlorophenyl)-1-((S)-1-((cyclobutylmethyl)sulfonyl)butan-2-yl)-3-methyl-2-oxopiperidin-3-yl)acetic acid;

2-((3R,5R,6S)-5-(3-Chlorophenyl)-6-(4-chlorophenyl)-1-((S)-1-(cyclopentylsulfonyl)butan-2-yl)-3-methyl-2-oxopiperidin-3-yl)acetic acid;

2-((3R,5R,6S)-5-(3-Chlorophenyl)-6-(4-chlorophenyl)-3-methyl-1-((S)-1-(oxetan-3-ylsulfonyl)butan-2-yl)-2-oxopiperidin-3-yl)acetic acid;

2-((3R,5R,6S)-5-(3-Chlorophenyl)-6-(4-chlorophenyl)-3-methyl-1-((S)-1-(((3-methyloxetan-3-yl)methyl)sulfonyl)butan-2-yl)-2-oxopiperidin-3-yl)acetic acid;

2-((3R,5R,6S)-5-(3-Chlorophenyl)-6-(4-chlorophenyl)-3-methyl-2-oxo-1-((S)-1-((tetrahydro-2H-pyran-4-yl)sulfonyl)butan-2-yl)piperidin-3-yl)acetic acid;

2-((3R,5R,6S)-5-(3-Chlorophenyl)-6-(4-chlorophenyl)-1-((S)-1-((2-hydroxy-2-methylpropyl)sulfonyl)butan-2-yl)-3-methyl-2-oxopiperidin-3-yl)acetic acid;

2-((3R,5R,6S)-1-((S)-1-((R)-sec-butylsulfonyl)butan-2-yl)-5-(3-chlorophenyl)-6-(4-chlorophenyl)-3-methyl-2-oxopiperidin-3-yl)acetic acid;

2-((3R,5R,6S)-1-((S)-1-((S)-sec-butylsulfonyl)butan-2-yl)-5-(3-chlorophenyl)-6-(4-chlorophenyl)-3-methyl-2-oxopiperidin-3-yl)acetic acid;

2-((3R,5R,6S)-5-(3-Chlorophenyl)-6-(4-chlorophenyl)-1-((S)-2-(cyclopentylsulfonyl)-1-cyclopropylethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(((3-methyloxetan-3-yl)methyl)sulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(phenylsulfonyl)ethyl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(o-tolylsulfonyl)ethyl)-3-methyl-2-oxopiperidin-3-yl)acetic acid;

2-((3R,5R,6S)-5-(3-Chlorophenyl)-6-(4-chlorophenyl)-1-((S)-2-((2-chlorophenyl)sulfonyl)-1-cyclopropylethyl)-3-methyl-2-oxopiperidin-3-yl)acetic acid;

2-((3R,5R,6S)-5-(3-Chlorophenyl)-6-(4-chlorophenyl)-1-((S)-2-((4-chlorophenyl)sulfonyl)-1-cyclopropylethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-((4-fluorophenyl)sulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(pyridin-4-ylsulfonyl)ethyl)-3-methyl-2-oxopiperidin-3-yl)acetic acid;

2-((3R,5R,6S)-1-((S)-2-((2-Chloro-4-fluorophenyl)sulfonyl)-1-cyclopropylethyl)-5-(3-chlorophenyl)-6-(4-chlorophenyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-((cyclopropylmethyl)sulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-((2,2,2-trifluoroethyl)sulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(((trifluoromethyl)sulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(phenylsulfonyl)ethyl)-3-ethyl-2-oxopiperidin-3-yl)acetic acid;

2-((3R,5R,6S)-5-(3-Chlorophenyl)-6-(4-chlorophenyl)-1-((S)-2-((2-chlorophenyl)sulfonyl)-1-cyclopropylethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-((2-fluorophenyl)sulfonyl)ethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-((3-fluorophenyl)sulfonyl)ethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-((4-fluorophenyl)sulfonyl)ethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-(propylsulfonyl)ethyl)-3-ethyl-2-oxopiperidin-3-yl)acetic acid;

2-((3R,5R,6S)-1-((S)-2-(Butylsulfonyl)-1-cyclopropylethyl)-5-(3-chlorophenyl)-6-(4-chlorophenyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-(isopentylsulfonyl)ethyl)-3-ethyl-2-oxopiperidin-3-yl)acetic acid;

2-((3R,5R,6S)-5-(3-Chlorophenyl)-6-(4-chlorophenyl)-1-((S)-2-(cyclopentylsulfonyl)-1-cyclopropylethyl)-3-ethyl-2-oxopiperidin-3-yl)acetic acid;

2-((3R,5R,6S)-5-(3-Chlorophenyl)-6-(4-chlorophenyl)-1-((S)-2-(cyclohexylsulfonyl)-1-cyclopropylethyl)-3-ethyl-2-oxopiperidin-3-yl)acetic acid;

2-((3R,5R,6S)-5-(3-Chlorophenyl)-6-(4-chlorophenyl)-1-((S)-1-cyclopropyl-2-(methylsulfonyl)ethyl)-3-ethyl-2-oxopiperidin-3-yl)acetic acid;

2-((3R,5R,6S)-5-(3-Chlorophenyl)-6-(4-chlorophenyl)-3-methyl-1-((S)-3-methyl-1-((2,2,2-trifluoroethyl)sulfonyl)butan-2-yl)-2-oxopiperidin-3-yl)acetic acid;

2-((3R,5R,6S)-1-((S)-1-(tert-Butylsulfonyl)-3-methylbutan-2-yl)-5-(3-chlorophenyl)-6-(4-chlorophenyl)-3-methyl-2-oxopiperidin-3-yl)acetic acid;

2-((3R,5R,6S)-5-(3-Chlorophenyl)-6-(4-chlorophenyl)-3-methyl-1-((S)-3-methyl-1-(methylsulfonyl)butan-2-yl)-2-oxopiperidin-3-yl)acetic acid;

2-((3R,5R,6S)-5-(3-Chlorophenyl)-6-(4-chlorophenyl)-1-((S)-1-(ethylsulfonyl)butan-2-yl)-3-methyl-2-oxopiperidin-3-yl)acetic acid;
2-((3R,5R,6S)-5-(3-Chlorophenyl)-6-(4-chlorophenyl)-1-((S)-1-(cyclopropylsulfonyl)butan-2-yl)-3-methyl-2-oxopiperidin-3-yl)acetic acid;
2-((3R,5R,6S)-5-(3-chlorophenyl)-6-(4-chlorophenyl)-1-((S)-1-(isopropylsulfonyl)butan-2-yl)-3-methyl-2-oxopiperidin-3-yl)acetic acid;
2-((3R,5R,6S)-1-((S)-1-(tert-butylsulfonyl)butan-2-yl)-5-(3-chlorophenyl)-6-(4-chlorophenyl)-3-methyl-2-oxopiperidin-3-yl)acetic acid;
2-((3R,5R,6S)-5-(3-Chlorophenyl)-6-(4-chlorophenyl)-1-((S)-1-(cyclobutylsulfonyl)butan-2-yl)-3-methyl-2-oxopiperidin-3-yl)acetic acid;
2-((3R,5R,6S)-5-(3-Chlorophenyl)-6-(4-chlorophenyl)-3-ethyl-1-((S)-1-(ethylsulfonyl)butan-2-yl)-2-oxopiperidin-3-yl)acetic acid;
2-((3R,5R,6S)-5-(3-Chlorophenyl)-6-(4-chlorophenyl)-3-ethyl-1-((S)-1-(isopropylsulfonyl)butan-2-yl)-2-oxopiperidin-3-yl)acetic acid;
2-((3R,5R,6S)-1-((S)-1-(tert-butylsulfonyl)butan-2-yl)-5-(3-chlorophenyl)-6-(4-chlorophenyl)-3-ethyl-2-oxopiperidin-3-yl)acetic acid;
2-((3R,5R,6S)-5-(3-Chlorophenyl)-6-(4-chlorophenyl)-1-((S)-1-(cyclobutylsulfonyl)butan-2-yl)-3-ethyl-2-oxopiperidin-3-yl)acetic acid;
2-((3R,5R,6S)-5-(3-Chlorophenyl)-6-(4-chlorophenyl)-1-((S)-1-(cyclopropylsulfonyl)butan-2-yl)-3-ethyl-2-oxopiperidin-3-yl)acetic acid;
2-((3R,5R,6S)-5-(3-chlorophenyl)-6-(4-chlorophenyl)-1-((S)-1-cyclopropyl-2-(ethylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(isopropylsulfonyl)ethyl)-3-methyl-2-oxopiperidin-3-yl)acetic acid;
2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetic acid;
2-((3R,5R,6S)-5-(3-Chlorophenyl)-6-(4-chlorophenyl)-1-((S)-2-(cyclobutylsulfonyl)-1-cyclopropylethyl)-3-methyl-2-oxopiperidin-3-yl)acetic acid;
2-((3R,5R,6S)-5-(3-chlorophenyl)-6-(4-chlorophenyl)-1-((S)-1-cyclopropyl-2-(cyclopropylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(methylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(tert-pentylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-((2,4-difluorophenyl)sulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(ethylsulfonyl)ethyl)-3-ethyl-2-oxopiperidin-3-yl)acetic acid;
2-((3R,5R,6S)-5-(3-Chlorophenyl)-6-(4-chlorophenyl)-1-((S)-1-cyclopropyl-2-(isopropylsulfonyl)ethyl)-3-ethyl-2-oxopiperidin-3-yl)acetic acid;
2-((3R,5R,6S)-1-((S)-2-(tert-Butylsulfonyl)-1-cyclopropylethyl)-5-(3-chlorophenyl)-6-(4-chlorophenyl)-3-ethyl-2-oxopiperidin-3-yl)acetic acid;
2-((3R,5R,6S)-5-(3-Chlorophenyl)-6-(4-chlorophenyl)-1-((S)-1-cyclopropyl-2-(cyclopropylsulfonyl)ethyl)-3-ethyl-2-oxopiperidin-3-yl)acetic acid;
2-((3R,5R,6S)-5-(3-Chlorophenyl)-6-(4-chlorophenyl)-1-((S)-1-(ethylsulfonyl)-3-methylbutan-2-yl)-3-methyl-2-oxopiperidin-3-yl)acetic acid;
2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid;
2-((3R,5R,6S)-5-(3-Chlorophenyl)-6-(4-chlorophenyl)-1-((S)-3,3-dimethyl-1-(methylsulfonyl)butan-2-yl)-3-methyl-2-oxopiperidin-3-yl)acetic acid;
2-((3R,5R,6S)-5-(3-Chlorophenyl)-6-(4-chlorophenyl)-1-((S)-1-(ethylsulfonyl)-3,3-dimethylbutan-2-yl)-3-methyl-2-oxopiperidin-3-yl)acetic acid;
2-((3R,5R,6S)-5-(3-Chlorophenyl)-6-(4-chlorophenyl)-1-((S)-1-(isopropylsulfonyl)-3,3-dimethylbutan-2-yl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(pentan-3-ylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-((S)-isopropylsulfinyl)butan-2-yl)-3-methyl-2-oxopiperidin-3-yl)acetic acid;
2-((3R,5R,6S)-5-(3-Chlorophenyl)-6-(4-chlorophenyl)-1-((S)-1-((R)-isopropylsulfinyl)butan-2-yl)-3-methyl-2-oxopiperidin-3-yl)acetic acid; more polar isomer;
2-((3R,5R,6S)-5-(3-Chlorophenyl)-6-(4-chlorophenyl)-3-methyl-1-((2S,3S)-2-(methylsulfonyl)pentan-3-yl)-2-oxopiperidin-3-yl)acetic acid;
2-((3R,5R,6S)-5-(3-Chlorophenyl)-6-(4-chlorophenyl)-3-methyl-1-((2R,3S)-2-(methylsulfonyl)pentan-3-yl)-2-oxopiperidin-3-yl)acetic acid;
2-((3R,5R,6S)-5-(3-Chlorophenyl)-6-(4-chlorophenyl)-1-((2S,3S)-2-(ethylsulfonyl)pentan-3-yl)-3-methyl-2-oxopiperidin-3-yl)acetic acid;
2-((3R,5R,6S)-5-(3-Chlorophenyl)-6-(4-chlorophenyl)-1-((2R,3S)-2-(ethylsulfonyl)pentan-3-yl)-3-methyl-2-oxopiperidin-3-yl)acetic acid;
2-((3R,5R,6S)-5-(3-Chlorophenyl)-6-(4-chlorophenyl)-3-methyl-1-((S)-1-(N-(oxetan-3-yl)sulfamoyl)butan-2-yl)-2-oxopiperidin-3-yl)acetic acid;
2-((3R,5R,6S)-5-(3-Chlorophenyl)-6-(4-chlorophenyl)-3-methyl-1-((S)-1-(N-((3-methyloxetan-3-yl)methyl)sulfamoyl)butan-2-yl)-2-oxopiperidin-3-yl)acetic acid;
2-((3R,5R,6S)-5-(3-chlorophenyl)-6-(4-chlorophenyl)-3-methyl-1-((S)-1-(N-(oxetan-3-ylmethyl)sulfamoyl)butan-2-yl)-2-oxopiperidin-3-yl)acetic acid;
2-((3R,5R,6S)-1-((S)-2-(N-(tert-Butyl)sulfamoyl)-1-cyclopropylethyl)-5-(3-chlorophenyl)-6-(4-chlorophenyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(N-methylsulfamoyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(N,N-dimethylsulfamoyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(N-isopropylsulfamoyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(morpholinosulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(piperidin-1-ylsulfonyl)ethyl)-3-methyl-2-oxopiperidin-3-yl)acetic acid;
2-((3R,5R,6S)-5-(3-Chlorophenyl)-6-(4-chlorophenyl)-1-((S)-1-cyclopropyl-2-(pyrrolidin-1-ylsulfonyl)ethyl)-3-methyl-2-oxopiperidin-3-yl)acetic acid;

2-((3R,5R,6S)-1-((S)-2-(Azetidin-1-ylsulfonyl)-1-cyclopropylethyl)-5-(3-chlorophenyl)-6-(4-chlorophenyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-((N,N-dimethylsulfamoyl)amino)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-((N,N-dimethylsulfamoyl)(methyl)amino)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(3-methyl-2,5-dioxoimidazolidin-1-yl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(3,4,4-trimethyl-2,5-dioxoimidazolidin-1-yl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(4,4-dimethyl-2,5-dioxoimidazolidin-1-yl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(3-isopropyl-2,2-dioxido-4-oxo-3,4-dihydro-1H-benzo[c][1,2,6]thiadiazin-1-yl)ethyl)-3-methyl-2-oxopiperidin-3-yl)acetic acid;

2-((3R,5R,6S)-5-(3-Chlorophenyl)-6-(4-chlorophenyl)-1-((S)-1-cyclopropyl-2-(2-oxo-2,3-dihydro-1H-benzo[d]imidazol-1-yl)ethyl)-3-methyl-2-oxopiperidin-3-yl)acetic acid;

2-((3R,5R,6S)-5-(3-Chloro-4-fluorophenyl)-6-(4-chlorophenyl)-1-isopropyl-3-methyl-2-oxopiperidin-3-yl)acetic acid;

2-((3R,5R,6S)-5-(3-Chloro-5-fluorophenyl)-6-(4-chlorophenyl)-1-isopropyl-3-methyl-2-oxopiperidin-3-yl)acetic acid;

2-((3S,5R,6S)-5-(3-Chloro-5-fluorophenyl)-6-(4-chlorophenyl)-1-isopropyl-3-methyl-2-oxopiperidin-3-yl)acetic acid;

2-((3R,5R,6S)-5-(3-Chloro-5-fluorophenyl)-6-(4-chlorophenyl)-1-((S)-1-(ethylsulfonamido)butan-2-yl)-3-methyl-2-oxopiperidin-3-yl)acetic acid;

2-((3R,5R,6S)-5-(3-Chloro-5-fluorophenyl)-6-(4-chlorophenyl)-3-methyl-1-((S)-1-(N-methylethylsulfonamido)butan-2-yl)-2-oxopiperidin-3-yl)acetic acid;

2-((3R,5R,6S)-5-(3-Chloro-5-fluorophenyl)-6-(4-chlorophenyl)-3-methyl-1-((S)-1-(methylsulfonyl)butan-2-yl)-2-oxopiperidin-3-yl)acetic acid;

2-((3R,5R,6S)-5-(3-Chloro-5-fluorophenyl)-6-(4-chlorophenyl)-1-((S)-1-(ethylsulfonyl)butan-2-yl)-3-methyl-2-oxopiperidin-3-yl)acetic acid;

2-((3R,5R,6S)-5-(3-Chloro-5-fluorophenyl)-6-(4-chlorophenyl)-1-((S)-1-(cyclopropylsulfonyl)butan-2-yl)-3-methyl-2-oxopiperidin-3-yl)acetic acid;

2-((3R,5R,6S)-1-((S)-1-(tert-Butylsulfonyl)butan-2-yl)-5-(3-chloro-5-fluorophenyl)-6-(4-chlorophenyl)-3-methyl-2-oxopiperidin-3-yl)acetic acid;

2-((3R,5R,6S)-5-(3-Chloro-5-fluorophenyl)-6-(4-chlorophenyl)-1-((S)-1-(isopropylsulfonyl)butan-2-yl)-3-methyl-2-oxopiperidin-3-yl)acetic acid;

2-((3R,5R,6S)-6-(4-Chlorophenyl)-5-(5-chloropyridin-3-yl)-1-((S)-1-(cyclopropylsulfonyl)butan-2-yl)-3-methyl-2-oxopiperidin-3-yl)acetic acid;

2-((3R,5R,6S)-1-((S)-1-(tert-Butylsulfonyl)butan-2-yl)-6-(4-chlorophenyl)-5-(5-chloropyridin-3-yl)-3-methyl-2-oxopiperidin-3-yl)acetic acid;

2-((3R,5R,6S)-6-(4-Chlorophenyl)-5-(5-chloropyridin-3-yl)-1-((S)-1-(cyclopropanesulfonamido)butan-2-yl)-3-methyl-2-oxopiperidin-3-yl)acetic acid;

2-((3R,5R,6S)-6-(4-Chlorophenyl)-5-(5-chloropyridin-3-yl)-3-methyl-1-((S)-1-(N-methylcyclopropanesulfonamido)butan-2-yl)-2-oxopiperidin-3-yl)acetic acid;

2-((3R,5R,6S)-5-(3-Chlorophenyl)-6-(4-chlorophenyl)-5-(5-chloropyridin-2-yl)-1-((S)-1-(ethylsulfonyl)butan-2-yl)-3-methyl-2-oxopiperidin-3-yl)acetic acid;

2-((3R,5R,6S)-5-(3-Chlorophenyl)-6-(4-chlorophenyl)-3-methyl-1-((S)-1-((S)-morpholin-2-yl)propyl)-2-oxopiperidin-3-yl)acetic acid;

2-((3R,5R,6S)-5-(3-chlorophenyl)-6-(4-chlorophenyl)-3-methyl-1-((S)-1-((R)-morpholin-2-yl)propyl)-2-oxopiperidin-3-yl)acetic acid;

2-((3R,5R,6S)-5-(3-chlorophenyl)-6-(4-chlorophenyl)-3-methyl-1-((R)-1-((S)-morpholin-2-yl)propyl)-2-oxopiperidin-3-yl)acetic acid;

2-((3R,5R,6S)-5-(3-chlorophenyl)-6-(4-chlorophenyl)-3-methyl-1-((R)-1-((R)-morpholin-2-yl)propyl)-2-oxopiperidin-3-yl)acetic acid;

2-((3R,5R,6S)-5-(3-chlorophenyl)-6-(4-chlorophenyl)-3-methyl-1-((R)-1-((R)-morpholin-2-yl)propyl)-2-oxopiperidin-3-yl)acetic acid;

or 2-((3R,5R,6S)-5-(3-chlorophenyl)-6-(4-chlorophenyl)-3-methyl-1-((R)-1-((S)-morpholin-2-yl)propyl)-2-oxopiperidin-3-yl)acetic acid;

2-((3S,5R,6S)-5-(3-Chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetic acid;

2-((3S,5R,6S)-5-(3-Chlorophenyl)-6-(4-chlorophenyl)-3-(2-(1,1(-dioxidothiomorpholino)ethyl)-1-((S)-1-(N-methylcyclopropanesulfonamido)butan-2-yl)-2-oxopiperidin-3-yl)acetic acid;

2-((3S,5R,6S)-5-(3-Chlorophenyl)-6-(4-chlorophenyl)-1-((S)-1-(N-methylcyclopropanesulfonamido)butan-2-yl)-2-oxo-3-(2-(pyrrolidin-1-yl)ethyl)piperidin-3-yl)acetic acid;

2-((3S,5R,6S)-5-(3-Chlorophenyl)-6-(4-chlorophenyl)-3-(2-(dimethylamino)ethyl)-1-((S)-1-(N-methylcyclopropanesulfonamido)butan-2-yl)-2-oxopiperidin-3-yl)acetic acid;

2-((3S,5R,6S)-5-(3-Chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetamide;

2-((3S,5R,6S)-5-(3-chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetamide;

(1R,3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid;

(3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid;

2-((3R,5R,6S)-5-(3-Chlorophenyl)-6-(4-chlorophenyl)-1-((2S,3S)-1,2-dihydroxypentan-3-yl)-3-methyl-2-oxopiperidin-3-yl)acetic acid;

2-((3R,5R,6S)-5-(3-Chlorophenyl)-6-(4-chlorophenyl)-1-((2R,3S)-1,2-dihydroxypentan-3-yl)-3-methyl-2-oxopiperidin-3-yl)acetic acid;

2-((3R,5R,6S)-5-(3-Chlorophenyl)-6-(4-chlorophenyl)-1-((2R,3S)-1,2-dihydroxypentan-3-yl)-3-methyl-2-oxopiperidin-3-yl)acetic acid;

2-((3R,5R,6S)-5-(3-Chlorophenyl)-6-(4-chlorophenyl)-1-((2S,3S)-1,2-dihydroxypentan-3-yl)-3-methyl-2-oxopiperidin-3-yl)acetic acid;

2-((3R,5R,6S)-5-(3-Chlorophenyl)-6-(4-chlorophenyl)-1-((1S,2S)-1-cyclopropyl-1-hydroxybutan-2-yl)-3-methyl-2-oxopiperidin-3-yl)acetic acid;

2-((3R,5R,6S)-5-(3-Chlorophenyl)-6-(4-chlorophenyl)-1-((1R,2S)-1-cyclopropyl-1-hydroxybutan-2-yl)-3-methyl-2-oxopiperidin-3-yl)acetic acid;
2-((3S,5R,6S)-5-(3-Chlorophenyl)-6-(4-chlorophenyl)-1-isopropyl-6-methyl-2-oxopiperidin-3-yl)acetic acid;
2-((3R,5R,6S)-5-(3-Chlorophenyl)-6-(4-chlorophenyl)-1-isopropyl-6-methyl-2-oxopiperidin-3-yl)acetic acid;
(3S,5R,6S)-5-(3-chlorophenyl)-6-(4-chlorophenyl)-1-((S)-1-(1,1-dioxidoisothiazolidin-2-yl)butan-2-yl)-3-((6-methoxypyridin-2-yl)methyl)piperidin-2-one;
(3R,5R,6S)-5-(3-Chlorophenyl)-6-(4-chlorophenyl)-1-((S)-1-((1,1-dioxidoisothiazolidin-2-yl)butan-2-yl)-3-((6-methoxypyridin-2-yl)methyl)piperidin-2-one;
(3S,5R,6S)-5-(3-Chlorophenyl)-6-(4-chlorophenyl)-1-((S)-1-((1,1-dioxidoisothiazolidin-2-yl)butan-2-yl)-3-((6-hydroxypyridin-2-yl)methyl)piperidin-2-one;
(3R,5R,6S)-5-(3-Chlorophenyl)-6-(4-chlorophenyl)-1-((S)-1-(1,1-dioxidoisothiazolidin-2-yl)butan-2-yl)-3-((6-hydroxypyridin-2-yl)methyl)piperidin-2-one;
(3S,5R,6S)-5-(3-Chlorophenyl)-6-(4-chlorophenyl)-1-((S)-1-((1,1-dioxidoisothiazolidin-2-yl)butan-2-yl)-3-((6-methoxypyridin-2-yl)methyl)-3-methylpiperidin-2-one;
(3R,5R,6S)-5-(3-Chlorophenyl)-6-(4-chlorophenyl)-1-((S)-1-((1,1-dioxidoisothiazolidin-2-yl)butan-2-yl)-3-((6-methoxypyridin-2-yl)methyl)-3-methylpiperidin-2-one;
(3S,5R,6S)-5-(3-Chlorophenyl)-6-(4-chlorophenyl)-1-((S)-1-((1,1-dioxidoisothiazolidin-2-yl)butan-2-yl)-3-((6-hydroxypyridin-2-yl)methyl)-3-methylpiperidin-2-one;
(3R,5R,6S)-5-(3-Chlorophenyl)-6-(4-chlorophenyl)-1-((S)-1-((1,1-dioxidoisothiazolidin-2-yl)butan-2-yl)-3-((6-hydroxypyridin-2-yl)methyl)-3-methylpiperidin-2-one;
(3R,5R,6S)-5-(3-chlorophenyl)-6-(4-chlorophenyl)-1-((S)-1-cyclopropyl-2-(ethylsulfonyl)ethyl)-3-(3-hydroxy-2-oxopropyl)-3-methylpiperidin-2-one;
2-((3R,5R,6S)-5-(3-Chlorophenyl)-6-(4-chlorophenyl)-1-(diethylamino)-3-methyl-2-oxopiperidin-3-yl)acetic acid;
2-((3R,5R,6S)-5-(3-Chlorophenyl)-6-(4-chlorophenyl)-1-(dimethylamino)-3-methyl-2-oxopiperidin-3-yl)acetic acid; or
(2S,3S,5S,6R,7aR,10aS)-6-(3-chlorophenyl)-5-(4-chlorophenyl)-3-ethyl-2,7a-dimethylhexahydrofuro[2,3-b]oxazolo[3,2-a]pyridin-9(5H)-one.

In another aspect, the present invention provides a compound, or a pharmaceutically acceptable salt thereof, selected from:
2-(5-(3-Chlorophenyl)-6-(4-chlorophenyl)-1-(1-cyclopropyl-2-(thiophene-2-sulfonamido)ethyl)-3-methyl-2-oxopiperidin-3-yl)acetic acid;
2-(5-(3-Chlorophenyl)-6-(4-chlorophenyl)-1-(1-cyclopropyl-2-(N-methylthiophene-2-sulfonamido)ethyl)-3-methyl-2-oxopiperidin-3-yl)acetic acid;
2-(5-(3-Chlorophenyl)-6-(4-chlorophenyl)-1-(2-(5-chlorothiophene-2-sulfonamido)-1-cyclopropylethyl)-3-methyl-2-oxopiperidin-3-yl)acetic acid;
2-(1-(2-(5-Chloro-N-methylthiophene-2-sulfonamido)-1-cyclopropylethyl)-5-(3-chlorophenyl)-6-(4-chlorophenyl)-3-methyl-2-oxopiperidin-3-yl)acetic acid;
2-(5-(3-Chlorophenyl)-6-(4-chlorophenyl)-1-(1-cyclopropyl-2-(N-(difluoromethyl)-2-methylpropan-2-ylsulfonamido)ethyl)-3-methyl-2-oxopiperidin-3-yl)acetic acid;
2-(5-(3-Chlorophenyl)-6-(4-chlorophenyl)-1-(1-cyclopropyl-2-(N-(difluoromethyl)ethylsulfonamido)ethyl)-3-methyl-2-oxopiperidin-3-yl)acetic acid;
2-(5-(3-Chlorophenyl)-6-(4-chlorophenyl)-1-(1-cyclopropyl-2-(N-(difluoromethyl)cyclopropanesulfonamido)ethyl)-3-methyl-2-oxopiperidin-3-yl)acetic acid;
1-(5-(3-Chlorophenyl)-6-(4-chlorophenyl)-1-(2-(cyclopropanesulfonamido)-1-cyclopropylethyl)-3-methyl-2-oxopiperidin-3-yl)cyclopropanecarboxylic acid;
2-(5-(3-chlorophenyl)-6-(4-chlorophenyl)-1-(1-cyclopropyl-2-(N-(2-fluorophenyl)ethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-(2-fluorophenyl)methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-phenylcyclopropanesulfonamido)ethyl)-3-methyl-2-oxopiperidin-3-yl)acetic acid;
2-(5-(3-chlorophenyl)-6-(4-chlorophenyl)-1-(1-cyclopropyl-2-(N-phenylethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(ethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-(3-fluorophenyl)ethylsulfonamido)ethyl)-3-methyl-2-oxopiperidin-3-yl)acetic acid;
2-(5-(3-chlorophenyl)-6-(4-chlorophenyl)-1-(2-(N-(2-cyanophenyl)methylsulfonamido)-1-cyclopropylethyl)-3-methyl-2-oxopiperidin-3-yl)acetic acid;
2-(5-(3-chlorophenyl)-6-(4-chlorophenyl)-1-(1-cyclopropyl-2-(propylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-phenylmethylsulfonamido)ethyl)-3-methyl-2-oxopiperidin-3-yl)acetic acid;
2-(5-(3-chlorophenyl)-6-(4-chlorophenyl)-1-(2-(N-(3-cyanophenyl)methylsulfonamido)-1-cyclopropylethyl)-3-methyl-2-oxopiperidin-3-yl)acetic acid;
2-(5-(3-chlorophenyl)-6-(4-chlorophenyl)-1-(1-cyclopropyl-2-(N-(pyridin-3-yl)methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-(thiophen-2-ylmethyl)methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-(3-methoxybenzyl)methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(phenylmethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(pyridin-2-ylmethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(pyridin-3-ylmethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-(pyridin-2-yl)methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(methylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-ethylmethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(N-isopropylmethylsulfonamido)ethyl)-3-methyl-2-oxopiperidin-3-yl)acetic acid;
2-(5-(3-chlorophenyl)-6-(4-chlorophenyl)-1-(1-cyclopropyl-2-(1-methylethylsulfonamido)ethyl)-3-ethyl-2-oxopiperidin-3-yl)acetic acid;

2-(5-(3-chlorophenyl)-6-(4-chlorophenyl)-1-(2-(cyclobutanesulfonamido)-1-cyclopropylethyl)-3-ethyl-2-oxopiperidin-3-yl)acetic acid;

2-(5-(3-chlorophenyl)-6-(4-chlorophenyl)-1-(2-(cyclopentanesulfonamido)-1-cyclopropylethyl)-3-ethyl-2-oxopiperidin-3-yl)acetic acid;

2-(5-(3-chlorophenyl)-6-(4-chlorophenyl)-3-methyl-1-(3-methyl-1-(N-methylcyclopropanesulfonamido)butan-2-yl)-2-oxopiperidin-3-yl)acetic acid;

2-(5-(3-chlorophenyl)-6-(4-chlorophenyl)-1-(1-(cyclopropanesulfonamido)-3-methylbutan-2-yl)-3-methyl-2-oxopiperidin-3-yl)acetic acid;

2-(5-(3-chlorophenyl)-6-(4-chlorophenyl)-1-(1-(ethylsulfonamido)-3-methylbutan-2-yl)-3-methyl-2-oxopiperidin-3-yl)acetic acid;

2-(5-(3-chlorophenyl)-6-(4-chlorophenyl)-1-(1-(cyclobutanesulfonamido)butan-2-yl)-3-methyl-2-oxopiperidin-3-yl)acetic acid;

2-(5-(3-chlorophenyl)-6-(4-chlorophenyl)-1-(1-(N-ethylcyclobutanesulfonamido)butan-2-yl)-3-methyl-2-oxopiperidin-3-yl)acetic acid;

2-(5-(3-Chlorophenyl)-6-(4-chlorophenyl)-3-methyl-2-oxo-1-(1-(phenylsulfonyl)butan-2-yl)piperidin-3-yl)acetic acid;

2-(5-(3-Chlorophenyl)-6-(4-chlorophenyl)-3-methyl-1-(1-(methylsulfonyl)butan-2-yl)-2-oxopiperidin-3-yl)acetic acid;

2-(5-(3-Chlorophenyl)-6-(4-chlorophenyl)-3-methyl-2-oxo-1-(1-(propylsulfonyl)butan-2-yl)piperidin-3-yl)acetic acid;

2-(5-(3-Chlorophenyl)-6-(4-chlorophenyl)-1-(1-(isobutylsulfonyl)butan-2-yl)-3-methyl-2-oxopiperidin-3-yl)acetic acid;

2-(5-(3-Chlorophenyl)-6-(4-chlorophenyl)-1-(1-((cyclopropylmethyl)sulfonyl)butan-2-yl)-3-methyl-2-oxopiperidin-3-yl)acetic acid;

2-(5-(3-Chlorophenyl)-6-(4-chlorophenyl)-1-(1-((cyclobutylmethyl)sulfonyl)butan-2-yl)-3-methyl-2-oxopiperidin-3-yl)acetic acid;

2-(5-(3-Chlorophenyl)-6-(4-chlorophenyl)-1-(1-(cyclopentylsulfonyl)butan-2-yl)-3-methyl-2-oxopiperidin-3-yl)acetic acid;

2-(5-(3-Chlorophenyl)-6-(4-chlorophenyl)-3-methyl-1-(1-(oxetan-3-ylsulfonyl)butan-2-yl)-2-oxopiperidin-3-yl)acetic acid;

2-(5-(3-Chlorophenyl)-6-(4-chlorophenyl)-3-methyl-1-(1-(((3-methyloxetan-3-yl)methyl)sulfonyl)butan-2-yl)-2-oxopiperidin-3-yl)acetic acid;

2-(5-(3-Chlorophenyl)-6-(4-chlorophenyl)-3-methyl-2-oxo-1-(1-(((tetrahydro-2H-pyran-4-yl)sulfonyl)butan-2-yl)piperidin-3-yl)acetic acid;

2-(5-(3-Chlorophenyl)-6-(4-chlorophenyl)-1-(1-((2-hydroxy-2-methylpropyl)sulfonyl)butan-2-yl)-3-methyl-2-oxopiperidin-3-yl)acetic acid;

2-(1-(1-(-sec-butylsulfonyl)butan-2-yl)-5-(3-chlorophenyl)-6-(4-chlorophenyl)-3-methyl-2-oxopiperidin-3-yl)acetic acid 2-(5-(3-Chlorophenyl)-6-(4-chlorophenyl)-1-(2-(cyclopentylsulfonyl)-1-cyclopropylethyl)-3-methyl-2-oxopiperidin-3-yl)acetic acid;

2-(5-(3-Chlorophenyl)-6-(4-chlorophenyl)-1-(1-cyclopropyl-2-(((3-methyloxetan-3-yl)methyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-(phenylsulfonyl)ethyl)-3-methyl-2-oxopiperidin-3-yl)acetic acid;

2-(5-(3-chlorophenyl)-6-(4-chlorophenyl)-1-(1-cyclopropyl-2-(o-tolylsulfonyl)ethyl)-3-methyl-2-oxopiperidin-3-yl)acetic acid;

2-(5-(3-Chlorophenyl)-6-(4-chlorophenyl)-1-(2-((2-chlorophenyl)sulfonyl)-1-cyclopropylethyl)-3-methyl-2-oxopiperidin-3-yl)acetic acid;

2-(5-(3-Chlorophenyl)-6-(4-chlorophenyl)-1-(2-((4-chlorophenyl)sulfonyl)-1-cyclopropylethyl)-3-methyl-2-oxopiperidin-3-yl)acetic acid;

2-(5-(3-Chlorophenyl)-6-(4-chlorophenyl)-1-(1-cyclopropyl-2-((4-fluorophenyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-(pyridin-4-ylsulfonyl)ethyl)-3-methyl-2-oxopiperidin-3-yl)acetic acid;

2-(1-(2-((2-Chloro-4-fluorophenyl)sulfonyl)-1-cyclopropylethyl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-1-(1-cyclopropyl-2-((cyclopropylmethyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-((2,2,2-trifluoroethyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-((trifluoromethyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-(phenylsulfonyl)ethyl)-3-ethyl-2-oxopiperidin-3-yl)acetic acid;

2-(5-(3-Chlorophenyl)-6-(4-chlorophenyl)-1-(2-((2-chlorophenyl)sulfonyl)-1-cyclopropylethyl)-3-ethyl-2-oxopiperidin-3-yl)acetic acid;

2-(5-(3-Chlorophenyl)-6-(4-chlorophenyl)-1-(1-cyclopropyl-2-((2-fluorophenyl)sulfonyl)ethyl)-3-ethyl-2-oxopiperidin-3-yl)acetic acid;

2-(5-(3-Chlorophenyl)-6-(4-chlorophenyl)-1-(1-cyclopropyl-2-((3-fluorophenyl)sulfonyl)ethyl)-3-ethyl-2-oxopiperidin-3-yl)acetic acid;

2-(5-(3-Chlorophenyl)-6-(4-chlorophenyl)-1-(1-cyclopropyl-2-((4-fluorophenyl)sulfonyl)ethyl)-3-ethyl-2-oxopiperidin-3-yl)acetic acid;

2-(5-(3-Chlorophenyl)-6-(4-chlorophenyl)-1-(1-cyclopropyl-2-(propylsulfonyl)ethyl)-3-ethyl-2-oxopiperidin-3-yl)acetic acid;

2-(1-(2-(Butylsulfonyl)-1-cyclopropylethyl)-5-(3-chlorophenyl)-6-(4-chlorophenyl)-3-ethyl-2-oxopiperidin-3-yl)acetic acid;

2-(5-(3-Chlorophenyl)-6-(4-chlorophenyl)-1-(1-cyclopropyl-2-(isopentylsulfonyl)ethyl)-3-ethyl-2-oxopiperidin-3-yl)acetic acid;

2-(5-(3-Chlorophenyl)-6-(4-chlorophenyl)-1-(2-(cyclopentylsulfonyl)-1-cyclopropylethyl)-3-ethyl-2-oxopiperidin-3-yl)acetic acid;

2-(5-(3-Chlorophenyl)-6-(4-chlorophenyl)-1-(2-(cyclohexylsulfonyl)-1-cyclopropylethyl)-3-ethyl-2-oxopiperidin-3-yl)acetic acid;

2-(5-(3-Chlorophenyl)-6-(4-chlorophenyl)-1-(1-cyclopropyl-2-(methylsulfonyl)ethyl)-3-ethyl-2-oxopiperidin-3-yl)acetic acid;

2-(5-(3-Chlorophenyl)-6-(4-chlorophenyl)-3-methyl-1-(3-methyl-1-((2,2,2-trifluoroethyl)sulfonyl)butan-2-yl)-2-oxopiperidin-3-yl)acetic acid;

2-(1-(1-(tert-Butylsulfonyl)-3-methylbutan-2-yl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-3-methyl-1-(3-methyl-1-(methylsulfonyl)butan-2-yl)-2-oxopiperidin-3-yl)acetic acid;

2-(5-(3-Chlorophenyl)-6-(4-chlorophenyl)-1-(1-(ethylsulfonyl)butan-2-yl)-3-methyl-2-oxopiperidin-3-yl)acetic acid;

2-(5-(3-Chlorophenyl)-6-(4-chlorophenyl)-1-(1-(cyclopropylsulfonyl)butan-2-yl)-3-methyl-2-oxopiperidin-3-yl)acetic acid;

2-(5-(3-chlorophenyl)-6-(4-chlorophenyl)-1-(1-(isopropylsulfonyl)butan-2-yl)-3-methyl-2-oxopiperidin-3-yl)acetic acid;

2-(1-(1-(tert-butylsulfonyl)butan-2-yl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-1-(1-(cyclobutylsulfonyl)butan-2-yl)-3-methyl-2-oxopiperidin-3-yl)acetic acid;

2-(5-(3-Chlorophenyl)-6-(4-chlorophenyl)-3-ethyl-1-(1-(ethylsulfonyl)butan-2-yl)-2-oxopiperidin-3-yl)acetic acid;

2-(5-(3-Chlorophenyl)-6-(4-chlorophenyl)-3-ethyl-1-(1-(isopropylsulfonyl)butan-2-yl)-2-oxopiperidin-3-yl)acetic acid;

2-(1-(1-(tert-butylsulfonyl)butan-2-yl)-5-(3-chlorophenyl)-6-(4-chlorophenyl)-3-ethyl-2-oxopiperidin-3-yl)acetic acid;

2-(5-(3-Chlorophenyl)-6-(4-chlorophenyl)-1-(1-(cyclobutylsulfonyl)butan-2-yl)-3-ethyl-2-oxopiperidin-3-yl)acetic acid;

2-(5-(3-Chlorophenyl)-6-(4-chlorophenyl)-1-(1-(cyclopropylsulfonyl)butan-2-yl)-3-ethyl-2-oxopiperidin-3-yl)acetic acid;

2-(5-(3-chlorophenyl)-6-(4-chlorophenyl)-1-(1-cyclopropyl-2-(ethylsulfonyl)ethyl)-3-methyl-2-oxopiperidin-3-yl)acetic acid;

2-(5-(3-Chlorophenyl)-6-(4-chlorophenyl)-1-(1-cyclopropyl-2-(isopropylsulfonyl)ethyl)-3-methyl-2-oxopiperidin-3-yl)acetic acid;

2-(1-(2-(tert-Butylsulfonyl)-1-cyclopropylethyl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-1-(2-(cyclobutylsulfonyl)-1-cyclopropylethyl)-3-methyl-2-oxopiperidin-3-yl)acetic acid;

2-(5-(3-chlorophenyl)-6-(4-chlorophenyl)-1-(1-cyclopropyl-2-(cyclopropylsulfonyl)ethyl)-3-methyl-2-oxopiperidin-3-yl)acetic acid;

2-(5-(3-Chlorophenyl)-6-(4-chlorophenyl)-1-(1-cyclopropyl-2-(methylsulfonyl)ethyl)-3-methyl-2-oxopiperidin-3-yl)acetic acid;

2-(5-(3-Chlorophenyl)-6-(4-chlorophenyl)-1-(1-cyclopropyl-2-(tert-pentylsulfonyl)ethyl)-3-methyl-2-oxopiperidin-3-yl)acetic acid;

2-(5-(3-Chlorophenyl)-6-(4-chlorophenyl)-1-(1-cyclopropyl-2-((2,4-difluorophenyl)sulfonyl)ethyl)-3-methyl-2-oxopiperidin-3-yl)acetic acid;

2-(5-(3-Chlorophenyl)-6-(4-chlorophenyl)-1-(1-cyclopropyl-2-(ethylsulfonyl)ethyl)-3-ethyl-2-oxopiperidin-3-yl)acetic acid;

2-(5-(3-Chlorophenyl)-6-(4-chlorophenyl)-1-(1-cyclopropyl-2-(isopropylsulfonyl)ethyl)-3-ethyl-2-oxopiperidin-3-yl)acetic acid;

2-(1-((2-(tert-Butylsulfonyl)-1-cyclopropylethyl)-5-(3-chlorophenyl)-6-(4-chlorophenyl)-3-ethyl-2-oxopiperidin-3-yl)acetic acid;

2-(5-(3-Chlorophenyl)-6-(4-chlorophenyl)-1-(1-cyclopropyl-2-(cyclopropylsulfonyl)ethyl)-3-ethyl-2-oxopiperidin-3-yl)acetic acid;

2-(5-(3-Chlorophenyl)-6-(4-chlorophenyl)-1-(1-(ethylsulfonyl)-3-methylbutan-2-yl)-3-methyl-2-oxopiperidin-3-yl)acetic acid;

2-(5-(3-Chlorophenyl)-6-(4-chlorophenyl)-1-(1-(isopropylsulfonyl)-3-methylbutan-2-yl)-3-methyl-2-oxopiperidin-3-yl)acetic acid;

2-(5-(3-Chlorophenyl)-6-(4-chlorophenyl)-1-(3,3-dimethyl-1-(methylsulfonyl)butan-2-yl)-3-methyl-2-oxopiperidin-3-yl)acetic acid;

2-(5-(3-Chlorophenyl)-6-(4-chlorophenyl)-1-(1-(ethylsulfonyl)-3,3-dimethylbutan-2-yl)-3-methyl-2-oxopiperidin-3-yl)acetic acid;

2-(5-(3-Chlorophenyl)-6-(4-chlorophenyl)-1-(1-(isopropylsulfonyl)-3,3-dimethylbutan-2-yl)-3-methyl-2-oxopiperidin-3-yl)acetic acid;

2-(5-(3-Chlorophenyl)-6-(4-chlorophenyl)-1-(1-cyclopropyl-2-(pentan-3-ylsulfonyl)ethyl)-3-methyl-2-oxopiperidin-3-yl)acetic acid;

2-(5-(3-Chlorophenyl)-6-(4-chlorophenyl)-1-(1-(isopropylsulfinyl)butan-2-yl)-3-methyl-2-oxopiperidin-3-yl)acetic acid;

2-(5-(3-Chlorophenyl)-6-(4-chlorophenyl)-3-methyl-1-(2-(methylsulfonyl)pentan-3-yl)-2-oxopiperidin-3-yl)acetic acid;

2-(5-(3-Chlorophenyl)-6-(4-chlorophenyl)-1-(2-(ethylsulfonyl)pentan-3-yl)-3-methyl-2-oxopiperidin-3-yl)acetic acid;

2-(5-(3-Chlorophenyl)-6-(4-chlorophenyl)-3-methyl-1-(1-(N-(oxetan-3-yl)sulfamoyl)butan-2-yl)-2-oxopiperidin-3-yl)acetic acid;

2-(5-(3-Chlorophenyl)-6-(4-chlorophenyl)-3-methyl-1-(1-(N-((3-methyloxetan-3-yl)methyl)sulfamoyl)butan-2-yl)-2-oxopiperidin-3-yl)acetic acid;

2-(5-(3-Chlorophenyl)-6-(4-chlorophenyl)-3-methyl-1-(1-(N-(oxetan-3-ylmethyl)sulfamoyl)butan-2-yl)-2-oxopiperidin-3-yl)acetic acid;

2-(1-(2-(N-(tert-Butyl)sulfamoyl)-1-cyclopropylethyl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-1-(1-cyclopropyl-2-(N-methylsulfamoyl)ethyl)-3-methyl-2-oxopiperidin-3-yl)acetic acid;

2-(5-(3-Chlorophenyl)-6-(4-chlorophenyl)-1-(1-cyclopropyl-2-(N,N-dimethylsulfamoyl)ethyl)-3-methyl-2-oxopiperidin-3-yl)acetic acid;

2-(5-(3-Chlorophenyl)-6-(4-chlorophenyl)-1-(1-cyclopropyl-2-(N-isopropylsulfamoyl)ethyl)-3-methyl-2-oxopiperidin-3-yl)acetic acid;

2-(5-(3-Chlorophenyl)-6-(4-chlorophenyl)-1-(1-cyclopropyl-2-(morpholinosulfonyl)ethyl)-3-methyl-2-oxopiperidin-3-yl)acetic acid;

2-(5-(3-Chlorophenyl)-6-(4-chlorophenyl)-1-(1-cyclopropyl-2-(piperidin-1-ylsulfonyl)ethyl)-3-methyl-2-oxopiperidin-3-yl)acetic acid;

2-(5-(3-Chlorophenyl)-6-(4-chlorophenyl)-1-(1-cyclopropyl-2-(pyrrolidin-1-ylsulfonyl)ethyl)-3-methyl-2-oxopiperidin-3-yl)acetic acid;

2-(1-(2-(Azetidin-1-ylsulfonyl)-1-cyclopropylethyl)-5-(3-chlorophenyl)-6-(4-chlorophenyl)-3-methyl-2-oxopiperidin-3-yl)acetic acid;

2-(5-(3-Chlorophenyl)-6-(4-chlorophenyl)-1-(1-cyclopropyl-2-((N,N-dimethylsulfamoyl)amino)ethyl)-3-methyl-2-oxopiperidin-3-yl)acetic acid;

2-(5-(3-Chlorophenyl)-6-(4-chlorophenyl)-1-(1-cyclopropyl-2-((N,N-dimethylsulfamoyl)(methyl)amino)ethyl)-3-methyl-2-oxopiperidin-3-yl)acetic acid;

2-(5-(3-Chlorophenyl)-6-(4-chlorophenyl)-1-(1-cyclopropyl-2-(3-methyl-2,5-dioxoimidazolidin-1-yl)ethyl)-3-methyl-2-oxopiperidin-3-yl)acetic acid;

2-(5-(3-Chlorophenyl)-6-(4-chlorophenyl)-1-(1-cyclopropyl-2-(3,4,4-trimethyl-2,5-dioxoimidazolidin-1-yl)ethyl)-3-methyl-2-oxopiperidin-3-yl)acetic acid;

2-(5-(3-Chlorophenyl)-6-(4-chlorophenyl)-1-(1-cyclopropyl-2-(4,4-dimethyl-2,5-dioxoimidazolidin-1-yl)ethyl)-3-methyl-2-oxopiperidin-3-yl)acetic acid;

2-(5-(3-Chlorophenyl)-6-(4-chlorophenyl)-1-(1-cyclopropyl-2-(3-isopropyl-2,2-dioxido-4-oxo-3,4-dihydro-1H-benzo[c][1,2,6]thiadiazin-1-yl)ethyl)-3-methyl-2-oxopiperidin-3-yl)acetic acid;

2-(5-(3-Chlorophenyl)-6-(4-chlorophenyl)-1-(1-cyclopropyl-2-(2-oxo-2,3-dihydro-1H-benzo[d]imidazol-1-yl)ethyl)-3-methyl-2-oxopiperidin-3-yl)acetic acid;

2-(5-(3-Chloro-4-fluorophenyl)-6-(4-chlorophenyl)-1-isopropyl-3-methyl-2-oxopiperidin-3-yl)acetic acid;

2-(5-(3-Chloro-5-fluorophenyl)-6-(4-chlorophenyl)-1-isopropyl-3-methyl-2-oxopiperidin-3-yl)acetic acid;

2-(5-(3-Chloro-5-fluorophenyl)-6-(4-chlorophenyl)-1-(1-(ethylsulfonamido)butan-2-yl)-3-methyl-2-oxopiperidin-3-yl)acetic acid;

2-(5-(3-Chloro-5-fluorophenyl)-6-(4-chlorophenyl)-3-methyl-1-(1-(N-methylethylsulfonamido)butan-2-yl)-2-oxopiperidin-3-yl)acetic acid;

2-(5-(3-Chloro-5-fluorophenyl)-6-(4-chlorophenyl)-3-methyl-1-(1-(methylsulfonyl)butan-2-yl)-2-oxopiperidin-3-yl)acetic acid;

2-(5-(3-Chloro-5-fluorophenyl)-6-(4-chlorophenyl)-1-(1-(ethylsulfonyl)butan-2-yl)-3-methyl-2-oxopiperidin-3-yl)acetic acid;

2-(5-(3-Chloro-5-fluorophenyl)-6-(4-chlorophenyl)-1-(1-(cyclopropylsulfonyl)butan-2-yl)-3-methyl-2-oxopiperidin-3-yl)acetic acid;

2-(1-(1-(tert-Butylsulfonyl)butan-2-yl)-5-(3-chloro-5-fluorophenyl)-6-(4-chlorophenyl)-3-methyl-2-oxopiperidin-3-yl)acetic acid;

2-(5-(3-Chloro-5-fluorophenyl)-6-(4-chlorophenyl)-1-(1-(isopropylsulfonyl)butan-2-yl)-3-methyl-2-oxopiperidin-3-yl)acetic acid;

2-(6-(4-Chlorophenyl)-5-(5-chloropyridin-3-yl)-1-(1-(cyclopropylsulfonyl)butan-2-yl)-3-methyl-2-oxopiperidin-3-yl)acetic acid;

2-(1-(1-(tert-Butylsulfonyl)butan-2-yl)-6-(4-chlorophenyl)-5-(5-chloropyridin-3-yl)-3-methyl-2-oxopiperidin-3-yl)acetic acid;

2-(6-(4-Chlorophenyl)-5-(5-chloropyridin-3-yl)-1-(1-(cyclopropanesulfonamido)butan-2-yl)-3-methyl-2-oxopiperidin-3-yl)acetic acid;

2-(6-(4-Chlorophenyl)-5-(5-chloropyridin-3-yl)-3-methyl-1-(1-(N-methylcyclopropanesulfonamido)butan-2-yl)-2-oxopiperidin-3-yl)acetic acid;

2-(5-(3-Chlorophenyl)-6-(5-chloropyridin-2-yl)-1-(1-(ethylsulfonyl)butan-2-yl)-3-methyl-2-oxopiperidin-3-yl)acetic acid;

2-(5-(3-Chlorophenyl)-6-(4-chlorophenyl)-3-methyl-1-(1-(morpholin-2-yl)propyl)-2-oxopiperidin-3-yl)acetic acid;

2-(5-(3-Chlorophenyl)-6-(4-chlorophenyl)-1-(1-(N-methylcyclopropanesulfonamido)butan-2-yl)-3-(2-morpholinoethyl)-2-oxopiperidin-3-yl)acetic acid;

2-(5-(3-Chlorophenyl)-6-(4-chlorophenyl)-3-(2-(1,1-dioxidothiomorpholino)ethyl)-1-(1-(N-methylcyclopropanesulfonamido)butan-2-yl)-2-oxopiperidin-3-yl)acetic acid;

2-(5-(3-Chlorophenyl)-6-(4-chlorophenyl)-1-(1-(N-methylcyclopropanesulfonamido)butan-2-yl)-2-oxo-3-(2-(pyrrolidin-1-yl)ethyl)piperidin-3-yl)acetic acid;

2-(5-(3-Chlorophenyl)-6-(4-chlorophenyl)-3-(2-(dimethylamino)ethyl)-1-(1-(N-methylcyclopropanesulfonamido)butan-2-yl)-2-oxopiperidin-3-yl)acetic acid;

2-(5-(3-Chlorophenyl)-6-(4-chlorophenyl)-1-(1-(N-methylcyclopropanesulfonamido)butan-2-yl)-3-(2-morpholinoethyl)-2-oxopiperidin-3-yl)acetamide;

7-(3-Chlorophenyl)-6-(4-chlorophenyl)-5-(1-(N-methylcyclopropanesulfonamido)butan-2-yl)-4-oxo-5-azaspiro[2.5]octane-1-carboxylic acid;

2-(5-(3-Chlorophenyl)-6-(4-chlorophenyl)-1-(1,2-dihydroxypentan-3-yl)-3-methyl-2-oxopiperidin-3-yl)acetic acid;

2-(5-(3-Chlorophenyl)-6-(4-chlorophenyl)-1-(1-cyclopropyl-1-hydroxybutan-2-yl)-3-methyl-2-oxopiperidin-3-yl)acetic acid;

2-(5-(3-Chlorophenyl)-6-(4-chlorophenyl)-1-isopropyl-6-methyl-2-oxopiperidin-3-yl)acetic acid;

5-(3-chlorophenyl)-6-(4-chlorophenyl)-1-(1-(1,1-dioxidoisothiazolidin-2-yl)butan-2-yl)-3-((6-methoxypyridin-2-yl)methyl)piperidin-2-one;

5-(3-Chlorophenyl)-6-(4-chlorophenyl)-1-(1-(1,1-dioxidoisothiazolidin-2-yl)butan-2-yl)-3-((6-hydroxypyridin-2-yl)methyl)piperidin-2-one;

5-(3-Chlorophenyl)-6-(4-chlorophenyl)-1-(1-(1,1-dioxidoisothiazolidin-2-yl)butan-2-yl)-3-((6-methoxypyridin-2-yl)methyl)-3-methylpiperidin-2-one;

5-(3-Chlorophenyl)-6-(4-chlorophenyl)-1-(1-(1,1-dioxidoisothiazolidin-2-yl)butan-2-yl)-3-((6-hydroxypyridin-2-yl)methyl)-3-methylpiperidin-2-one;

(5-(3-chlorophenyl)-6-(4-chlorophenyl)-1-(1-cyclopropyl-2-(ethylsulfonyl)ethyl)-3-(3-hydroxy-2-oxopropyl)-3-methylpiperidin-2-one;

2-(5-(3-Chlorophenyl)-6-(4-chlorophenyl)-1-(diethylamino)-3-methyl-2-oxopiperidin-3-yl)acetic acid;

2-(5-(3-Chlorophenyl)-6-(4-chlorophenyl)-1-(dimethylamino)-3-methyl-2-oxopiperidin-3-yl)acetic acid; or 6-(3-chlorophenyl)-5-(4-chlorophenyl)-3-ethyl-2,7a-dimethylhexahydrofuro[2,3-b]oxazolo[3,2-a]pyridin-9(5H)-one.

In another aspect, the present invention provides a compound, or a pharmaceutically acceptable salt thereof, selected from:

2-((3R,5R,6S)-5-(3-Chlorophenyl)-6-(4-chlorophenyl)-1-((S)-1-cyclopropyl-2-(methylsulfonyl)ethyl)-3-methyl-2-oxopiperidin-3-yl)acetic acid;

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid;

2-((3R,5R,6S)-1-((S)-1-(tert-butylsulfonyl)butan-2-yl)-5-(3-chlorophenyl)-6-(4-chlorophenyl)-3-methyl-2-oxopiperidin-3-yl)acetic acid;

2-((3R,5R,6S)-5-(3-chlorophenyl)-6-(4-chlorophenyl)-1-((S)-1-(isopropylsulfonyl)butan-2-yl)-3-methyl-2-oxopiperidin-3-yl)acetic acid;

2-((3R,5R,6S)-5-(3-Chlorophenyl)-6-(4-chlorophenyl)-1-((S)-1-(isopropylsulfonyl)-3,3-dimethylbutan-2-yl)-3-methyl-2-oxopiperidin-3-yl)acetic acid;

2-((3R,5R,6S)-5-(3-Chlorophenyl)-6-(4-chlorophenyl)-1-((S)-1-(ethylsulfonyl)-3-methylbutan-2-yl)-3-methyl-2-oxopiperidin-3-yl)acetic acid;

2-((3R,5R,6S)-5-(3-Chlorophenyl)-6-(4-chlorophenyl)-1-((S)-1-(ethylsulfonyl)butan-2-yl)-3-methyl-2-oxopiperidin-3-yl)acetic acid;

2-((3R,5R,6S)-5-(3-chlorophenyl)-6-(4-chlorophenyl)-1-((S)-1-cyclopropyl-2-(N-phenylcyclopropanesulfonamido)ethyl)-3-methyl-2-oxopiperidin-3-yl)acetic acid; or 2-((3R,5R,6S)-5-(3-Chlorophenyl)-6-(4-chlorophenyl)-1-((S)-1-((cyclopropylmethyl)sulfonyl)butan-2-yl)-3-methyl-2-oxopiperidin-3-yl)acetic acid.

In another aspect, the present invention provides a compound, or a pharmaceutically acceptable salt thereof, selected from:

2-(-5-(3-Chlorophenyl)-6-(4-chlorophenyl)-1-(-1-cyclopropyl-2-(methylsulfonyl)ethyl)-3-methyl-2-oxopiperidin-3-yl)acetic acid;

2-(-5-(3-Chlorophenyl)-6-(4-chlorophenyl)-1-(-1-(isopropylsulfonyl)-3-methylbutan-2-yl)-3-methyl-2-oxopiperidin-3-yl)acetic acid;

2-(-1-(-1-(tert-butylsulfonyl)butan-2-yl)-5-(3-chlorophenyl)-6-(4-chlorophenyl)-3-methyl-2-oxopiperidin-3-yl)acetic acid;

2-(-5-(3-chlorophenyl)-6-(4-chlorophenyl)-1-(-1-(isopropylsulfonyl)butan-2-yl)-3-methyl-2-oxopiperidin-3-yl)acetic acid;

2-(-5-(3-Chlorophenyl)-6-(4-chlorophenyl)-1-(-1-(isopropylsulfonyl)-3,3-dimethylbutan-2-yl)-3-methyl-2-oxopiperidin-3-yl)acetic acid;

2-(-5-(3-Chlorophenyl)-6-(4-chlorophenyl)-1-(-1-(ethylsulfonyl)-3-methylbutan-2-yl)-3-methyl-2-oxopiperidin-3-yl)acetic acid;

2-(-5-(3-Chlorophenyl)-6-(4-chlorophenyl)-1-(-1-(ethylsulfonyl)butan-2-yl)-3-methyl-2-oxopiperidin-3-yl)acetic acid;

2-(-5-(3-chlorophenyl)-6-(4-chlorophenyl)-1-(-1-cyclopropyl-2-(N-phenylcyclopropanesulfonamido)ethyl)-3-methyl-2-oxopiperidin-3-yl)acetic acid;

2-(-5-(3-Chlorophenyl)-6-(4-chlorophenyl)-1-(-1-((cyclopropylmethyl)sulfonyl)butan-2-yl)-3-methyl-2-oxopiperidin-3-yl)acetic acid;

2-(-5-(3-Chlorophenyl)-6-(4-chlorophenyl)-1-(-1-cyclopropyl-2-(methylsulfonyl)ethyl)-3-methyl-2-oxopiperidin-3-yl)acetic acid;

2-(-5-(3-Chlorophenyl)-6-(4-chlorophenyl)-1-(-1-(isopropylsulfonyl)-3-methylbutan-2-yl)-3-methyl-2-oxopiperidin-3-yl)acetic acid; or 2-(-1-(-1-(tert-butylsulfonyl)butan-2-yl)-5-(3-chlorophenyl)-6-(4-chlorophenyl)-3-methyl-2-oxopiperidin-3-yl) acetic acid.

The present invention provides pharmaceutical compositions comprising a compound of any one of the above aspects or embodiments, or a pharmaceutically acceptable salt thereof, together with a pharmaceutically acceptable excipient, diluent or carrier.

The present invention also provides method of treating cancer in a subject in need of said treatment, the method comprising administering to the subject an effective dosage amount of a compound according to any one of the above aspects or embodiments, or a pharmaceutically acceptable salt thereof.

DETAILED DESCRIPTION OF THE INVENTION

The term "H" denotes a single hydrogen atom. This radical may be attached, for example, to an oxygen atom to form a hydroxyl radical.

Where the term "alkyl" is used, either alone or within other terms such as "haloalkyl" or "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" or "alkylene" embraces bridging divalent alkyl radicals such as methylenyl or ethylenyl. The term "lower alkyl substituted with $R^2$" does not include an acetal moiety. The term "alkyl" further includes alkyl radicals wherein one or more carbon atoms in the chain is substituted with a heteroatom selected from oxygen, nitrogen, or sulfur.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, and butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, and heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1 to 6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings, wherein such rings may be attached together in a fused manner. The term "aryl" embraces aromatic radicals such as phenyl, naphthyl, indenyl, tetrahydronaphthyl, and indanyl. More preferred aryl is phenyl. An "aryl" group may have 1 or more substituents such as lower alkyl, hydroxyl, halo, haloalkyl, nitro, cyano, alkoxy, and lower alkylamino, and the like. Phenyl substituted with —O—CH$_2$—O— forms the aryl benzodioxolyl substituent.

The term "heterocyclyl" (or "heterocyclo") embraces saturated, partially saturated and unsaturated heteroatom-containing ring radicals, where the heteroatoms may be selected from nitrogen, sulfur and oxygen. It does not include rings containing —O—O—, —O—S— or —S—S— portions. The "heterocyclyl" group may have 1 to 4 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, and benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "heterocyclo" thus encompasses the following ring systems:

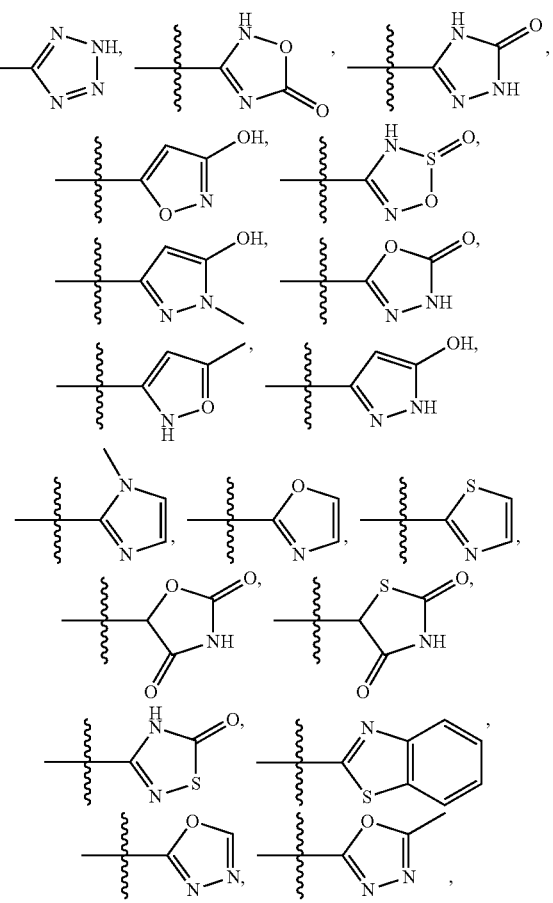

-continued
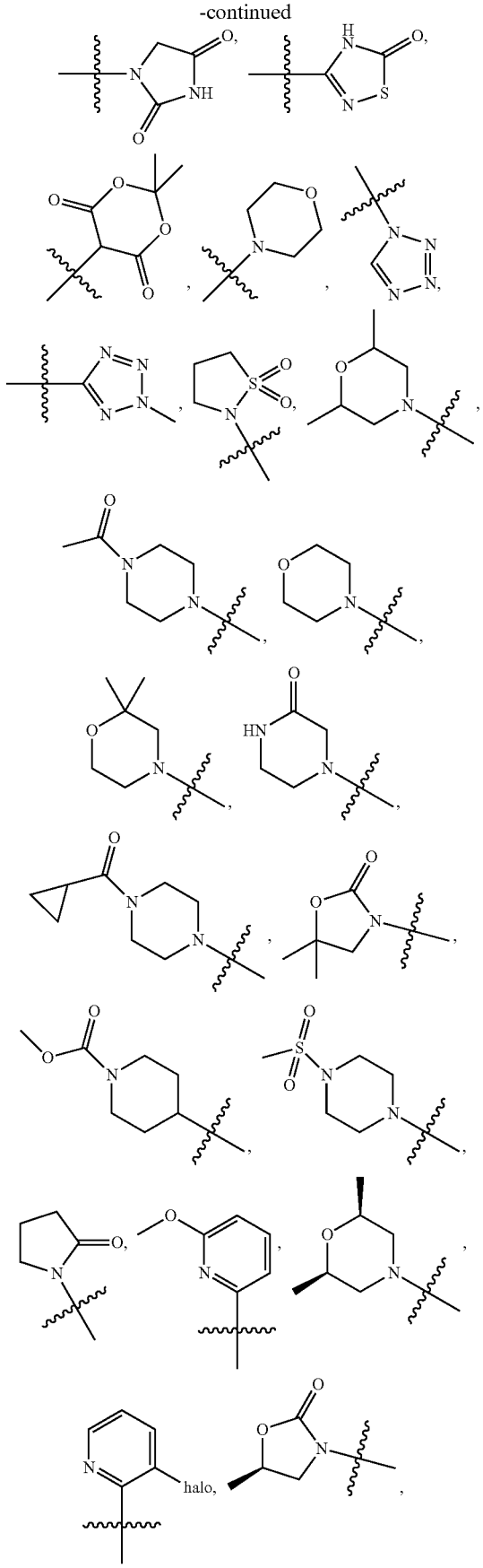
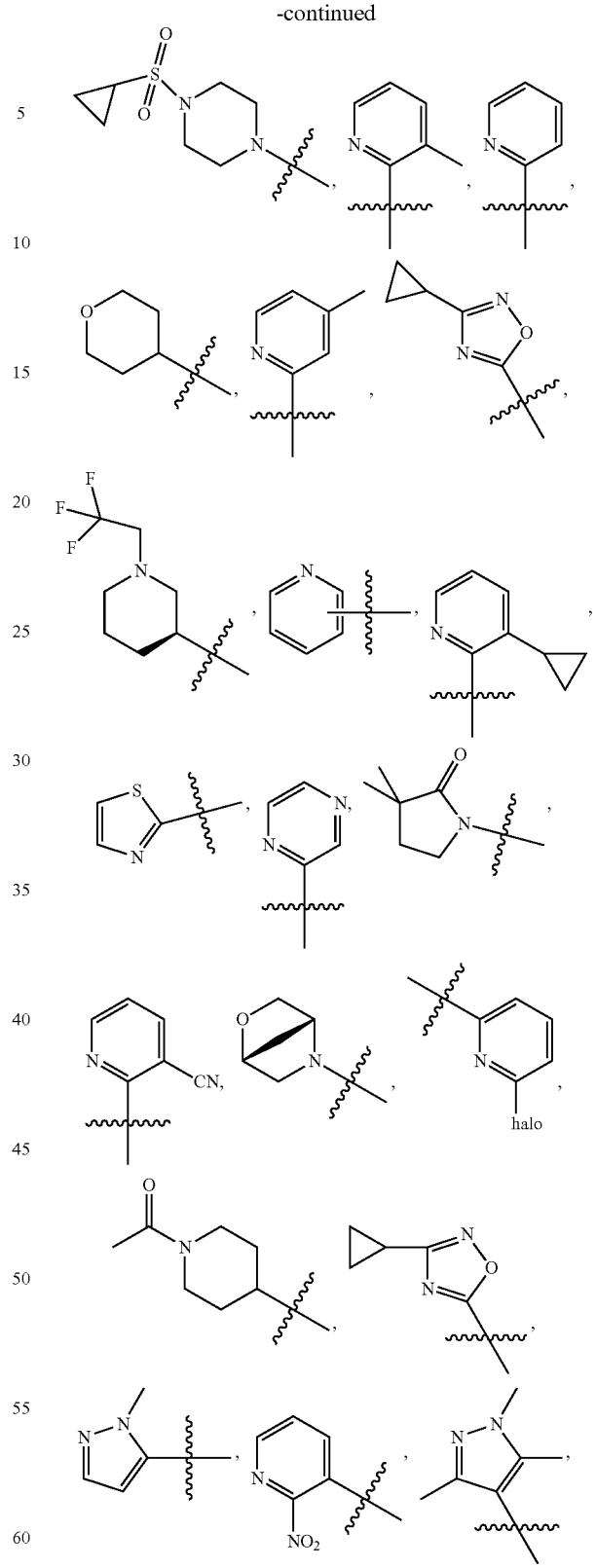
and the like.
The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl," whether used alone or with other terms, such as "carboxyalkyl," denotes —CO$_2$H.

The term "carbonyl," whether used alone or with other terms, such as "aminocarbonyl," denotes —(C=O)—.

The term "aminocarbonyl" denotes an amide group of the formula C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, and N,N-diethylamino, and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethylaminoethyl, and N,N-diethylaminomethyl, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, and N,N-diethylaminoethoxy, and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, and N,N-diethylaminomethoxymethoxy, and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, and carboxypropyl, and the like. Even more preferred are lower carboxyalkyl radicals having one to three CH$_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5 to 6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I, IA, IB, IC, ID or IE, or a pharmaceutically acceptable salt thereof.

The compounds of the present invention can be used to treat tumors. The methods of treating a tumor comprise administering to a patient in need thereof a therapeutically effective amount of a compound of Formula I, IA, IB, IC, ID or IE, or a pharmaceutically acceptable salt thereof.

The invention also concerns the use of a compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "$p53^{WT}$" means a protein encoded by genomic DNA sequence no. NC_000017 version 9 (7512445.7531642)(GenBank); a protein encoded by cDNA sequence no. NM_000546 (GenBank); or a protein having the GenBank sequence no. NP_000537.3. The term "CDNK2A mutant" means a CDNK2A protein that in not wildtype. The term "CDKN2A wildtype" means a protein encoded by genomic DNA sequence no. 9:21957751-21984490 (Ensembl ID); a protein encoded by cDNA sequence no. NM_000077 (GenBank) or NM_058195 9GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis and Huntington's disease.

The compounds of the present invention can also be used to treat inflammatory diseases, hypoxia, ulcers, viral infections, bacterial infections, and bacterial sepsis.

The compounds of Formula I, IA, IB, IC, ID or IE, or the pharmaceutically acceptable salts thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: vascular endothelial growth factor (VEGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand (TRAIL), insulin-like growth factor 1 receptor (IGFR-1) inhibitors, cFMS inhibitors, HER 2 inhibitors, c-met inhibitors, aurora kinase inhibitors, CDK 4 and/or 6 inhibitors, and B-raf inhibitors.

Further additional pharmaceutically active agents that can be used in the treatment of cancers and that can be used in combination with one or more compound of the present invention include antibody drug conjugates (ADCs) whereby an antibody that binds to a protein, preferably on a cancer cell, is conjugated using a linker with a chemical compound that is detrimental to the cancer cell. Examples of chemical compounds that are detrimental to a cancer cell include maytansinoids derivatives and auristatin derivatives.

Still further additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 319; AMG 386; AMG 479 (Ganitumab); AMG 511, AMG 900, AMG 655 (Conatumumab); AMG 745; AMG 951; and AMG 706 (Motesanib), or a pharmaceutically acceptable salt thereof.

In another aspect, the present invention relates to the use of the compounds of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compounds inhibit one or more isoform more that other isoforms. Selectivity is a concept well known to those is the art and can be measured with well known activity in vitro or cell-based assays. Preferred selectivity includes greater than 2 fold, preferably 10 fold, or more preferably 100 fold greater selectivity for one or more isoform over the other isoforms. In one aspect, the PI3K inhibitors that can be used in combination with compounds of the present invention is a PI3K α selective inhibitor. In another aspect the compound is a PI3K δ selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with compounds of the present invention include:

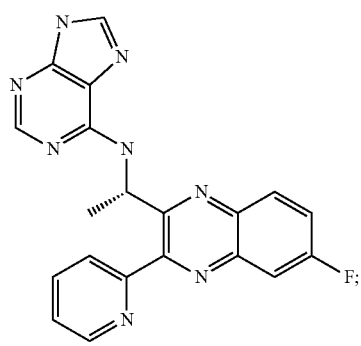

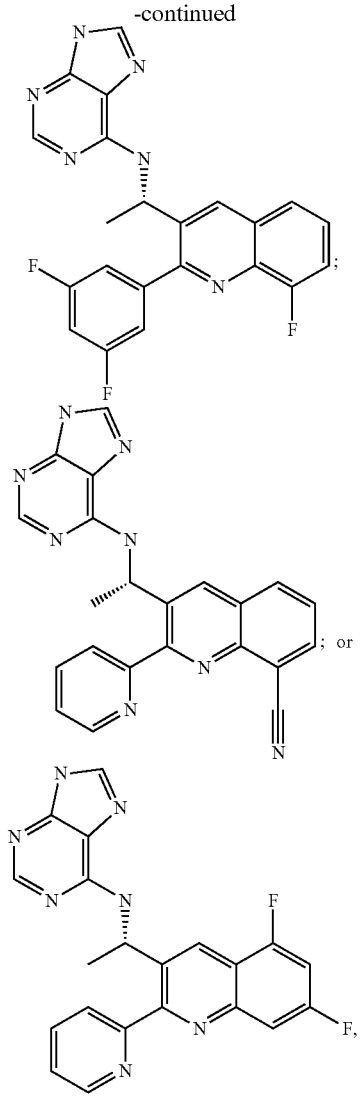

or a pharmaceutically acceptable salt thereof.

Also preferred is a compound of Formula IIa below, or a pharmaceutically acceptable salt thereof,

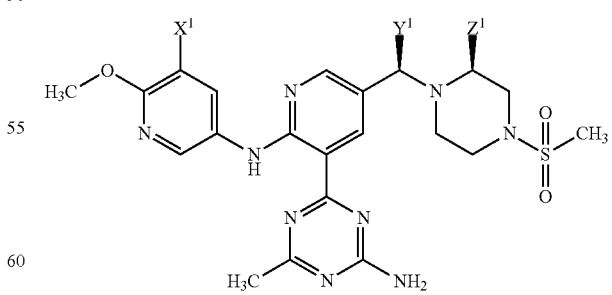

IIa wherein $X^1$ is fluorine or hydrogen; $Y^1$ is hydrogen or methyl; and $Z^1$ is hydrogen or methyl.

Compounds that inhibit both PI3K and mTOR (dual inhibitors) are known. In still another aspect, the present invention provides the use of dual PI3K and mTOR inhibitors for use in combination with a compound of the present invention.

mTOR is a protein in the PI3K pathway. It is another aspect of the present invention to use an mTOR inhibitor in combination with one or more compounds of the present invention. mTOR inhibitors that can be used in combination with compounds of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with one or more compounds of the present invention. PKB inhibitors that can be used in combination with compounds of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1.

The compounds of the present invention can be used in combination with CDK4 and/or 6 inhibitors. CDK 4 and/or 6 inhibitors that can be used in combination with compounds of the present invention include those disclosed in the following documents: PCT published application no. WO 2009/085185 or U.S. patent application publication no. US2011/0097305.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aetema); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody(MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N $^{16}$O, $^{17}$O, $^{18}$O, $^{31}$P, $^{32}$P, $^{35}$S, $^{18}$F, and $^{36}$Cl. In one aspect, the present invention relates to compounds wherein one or more hydrogen atom is replaced with deuterium ($^2$H) atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition. When a percent is used herein with respect to a liquid, the percent is by volume with respect to the referenced solution.

$^1$H-NMR spectra were typically acquired on a Bruker Avance III 500 spectrometer system (Bruker, Bilerica, Mass.) operating at a $^1$H frequency of 500.13 MHz, equipped with a Bruker 5 mm PABBI probe with a z-axis gradient; or on a Bruker Avance II 400 spectrometer operating at a $^1$H frequency of 400.23 MHz, equipped with a Bruker 5 mm PABBO probe with a z-axis gradient. Samples were typically dissolved in 500 µL of either DMSO-d$_6$ or CD$_3$OD for NMR analysis. $^1$H chemical shifts are referenced to the residual solvent signals from DMSO-d$_6$ at δ 2.50 and CD$_3$OD at δ 3.30.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

The following abbreviations may be used herein:
~ about
+ve or pos. ion positive ion
Δ heat
Ac acetyl
Ac$_2$O acetic anhydride
aq aqueous
AcOH acetic acid
Bn benzyl
Boc tert-butyloxycarbonyl
BSA bovine serum albumin
Bu butyl
Bz benzoyl
Calcd or Calc'd calculated
Conc. concentrated
CSA camphor-10-sulfonic acid
d day(s)
DBU 1,8-diazabicyclo[5.4.0]undec-7-ene
DCE dichloroethane
DCM dichloromethane
DEA diethylamine
Dess-Martin periodinane;
    1,1,1-triacetoxy-1,1-dihydro-1,2-benziodoxol-3-(1H)-one
Dess-Martin reagent
DIEA or DIPEA diisopropylethylamine
DMAP 4-dimethylaminopyridine
DME 1,2-dimethoxyethane
DMF N,N-dimethylformamide
DMSO dimethyl sulfoxide
dr diastereomeric ratio
DTT dithiothreitol
DVB divinylbenzene
EDC N-Ethyl-N'-(3-dimethylaminopropyl)carbodiimide
eq equivalent
ESI or ES electrospray ionization
Et ethyl
Et$_2$O diethyl ether
Et$_3$N triethylamine EtOAc ethyl acetate
EtOH ethyl alcohol
g gram(s)
h hour(s)
HATU O-(7-azabenzotriazol-1-yl)-N,N,N',N'-tetramethyl-uronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HPLC high pressure liquid chromatography
IPA or iPrOH isopropyl alcohol
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol L$^{-1}$)
m/z mass divided by charge
mCPBA m-chloroperoxybenzoic acid
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB parametoxybenzyl
Pr propyl
ppm parts per million
rac racemic
RP-HPLC or RPHPLC reversed phase high pressure liquid chromatography
RT or rt room temperature
sat. or sat'd or satd saturated
SFC supercritical fluid chromatography
TBAF tetrabutylammonium fluoride
TBDMS tert-butyldinmethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA trifluoroacetic acid
THF tetrahydrofuran
TIPS triisopropylsilyl
TLC thin layer chromatography
TMS trimethylsilyl or trimethylsilane
TPAP tetrapropylammonium perruthenate
$t_R$ retention time
tBuOH tert-butyl alcohol
v/v volume per volume

EXAMPLES

General Synthetic Schemes

Compounds of the present invention generally can be prepared beginning with commercially available starting materials and using synthetic techniques known to those of skill in the art. Outlined below are some reaction schemes suitable for preparing compounds of the present invention. Further exemplification is found in the specific examples provided.

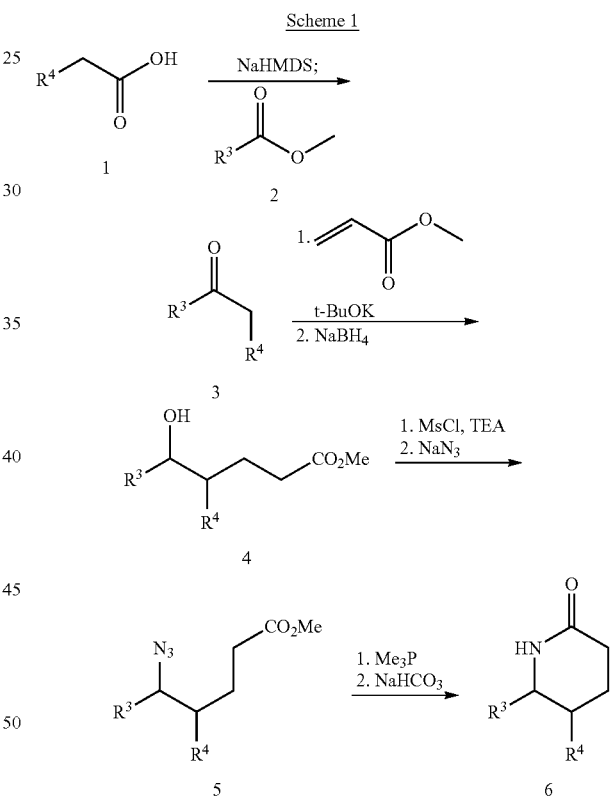

As shown in Scheme 1, compounds of the present invention wherein $R^a$ and $R^b$ are both H, can be prepared by reacting a suitably substituted aryl acetic acid 1 and an aryl carboxylic acid 2 in an organic solvent or mixture of solvents (including aqueous mixtures) in the presence of a base, such as LHMDs or KHMDS to provide, after workup, a compound of formula 3. Treatment of 3 with methyl acrylate in the presence of a base, such as tBuOK results in the formation of a 4,5-substituted 5-oxopentanoate, which can be reduced with a reducing reagent such as NaBH$_4$ or LiBEt$_3$H in a suitable solvent such as THF, diethylether or dimethoxyethane to produce racemic compound 4. 5 can in turn be obtained from 4 by converting the alcohol into a toluenesulfonate, methanesulfonate, or trifluoromethanesulfonate, followed by reaction with sodium azide in a suitable solvent such as, for example, DMF, DME or acetone. The azide can be reduced to a primary amine by a number of reducing agents including NaBH$_4$, H$_2$ and a catalyst, triphenylphosphine and trimethylphoshine, which in turn, upon treatment with a base, such as LiOH, K$_2$CO$_3$ or NaHCO$_3$ in an aqueous mixture with a suitable organic solvent, such as THF will cyclize to the piperidin-2-one 6. Individual enantiomers of racemic 6 can be separated by chiral HPLC using, for example, a Chiralcel® OD-H 20 mm I.D.×250 mm column (Daicel Chemical Industries LTD, Fort Lee, N.J.) using 40% isopropyl alcohol/hexane as the eluent.

Scheme 2

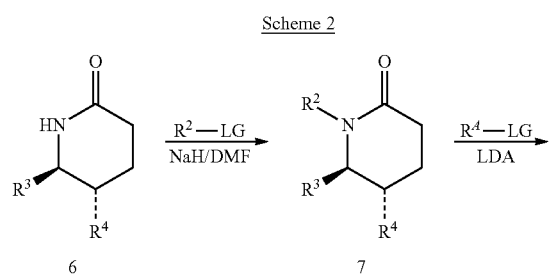

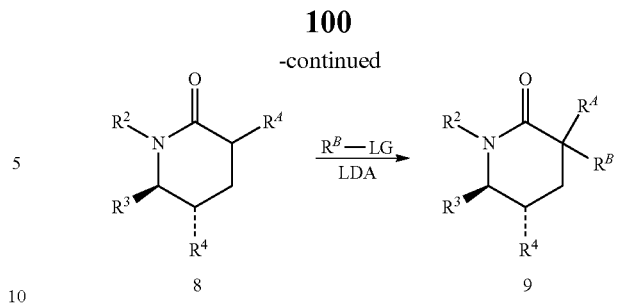

As shown in Scheme 2, the piperidin-2-one 6 can be further modified, for example by arylating or alkylating the nitrogen by methods well known to those of ordinary skill in the art. For example, reacting 6 with an alkyl halide in the presence of a base such as sodium hydride in a solvent such as DME, DMF or THF will accomplish this transformation. 7 may be further alkylated by treatment with a base such as lithium diisopropylamide or lithium hexamethyldisilazide in a suitable solvent such as THF, followed by reaction with an alkylating agent, such as an alkyl halide, alkyl methanesulfonate, alkyl trifluoromethanesulfonate, or alkyl toluenesulfonate to give intermediate 8. If desired, the sequence may be repeated to give compounds of the general formula 9. LG is a leaving group.

As shown in Scheme 3, the group attached to the nitrogen can potentially be removed to give intermediate 16. For example treating a 2,4-dimethoxybenzyl derivative with TFA accomplishes such a transformation. Similar transformations are well documented (see e.g. P. G. M. Wuts and T. W. Greene, "Greene's protective groups in organic synthesis", 4$^{th}$ ed., John Wiley & Sons, New York, (2007)). Resubjecting compound 16 to alkylation conditions similar to the ones described above will give 17.

Scheme 3

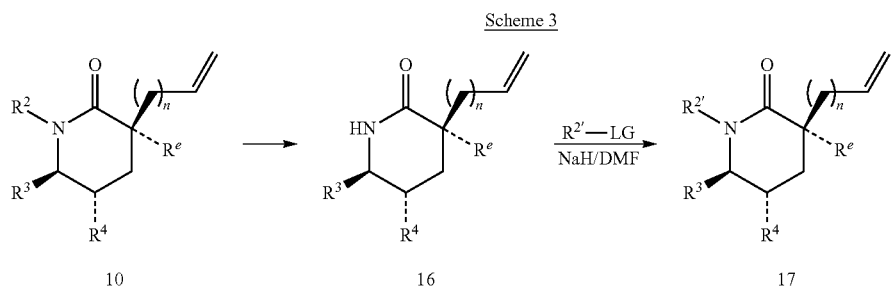

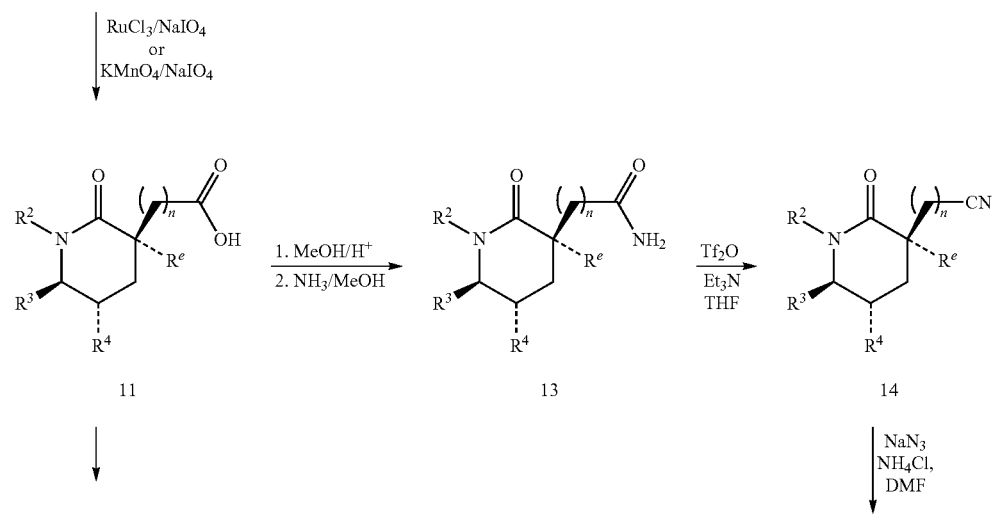

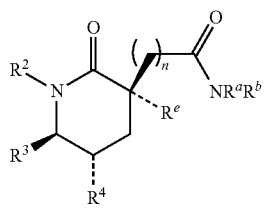

12

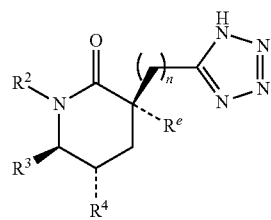

15

As further shown in Scheme 3, if one of the alkyl groups contains a double bond, this double bond can be converted into a carboxylic acid 11 by a number of methods known to those of ordinary skill in the art. For example, reacting 10 with a solution of periodate containing $KMnO_4$ or $RuCl_3$ (see e.g. R. U. Lemieux, E. von Rudloff, Can. J. Chem., 38, 1703, (1955)) will accomplish this transformation. The carboxylic acid 11 can, in turn, be converted into other groups such as an amide or hydrazide by methods well known to those of ordinary skill in the art. For example, the carboxylic acid 11 can be activated by condensation with a variety of coupling reagents, including hydroxybenzotriazole (HOBt) and N-hydroxysuccinimide (HOSu), for example, using dicyclohexylcarbodiimide (DCC) or a similar carbodiimide reagent or a wide variety of reagents such as those developed for formation of peptide bonds. Conditions for such reactions are well known to those of ordinary skill in the art. The activated intermediate, an ester of HOBt or HOSu, for example, can then be condensed with a wide variety of nucleophiles such as amines or alcohols.

Scheme 3 shows the conversion of a compound of formula 11 into an amide 12 by this sequence. Using ammonia as the nucleophile, compound 13 is obtained. Dehydration of the amide 13 to a nitrile 14 can be accomplished by a variety of methods. Phosphorous pentoxide is a common dehydrating reagent for this reaction, but many others are known to those skilled in the art (see e.g. R. C. Larock; Comprehensive Organic Transformations, $2^{nd}$ ed., John Wiley & Sons, New York, pp. 1983, (1999)). The nitrile can, in turn, be converted into other groups such as a tetrazole by reacting the nitrile with an azide, such as sodium azide, lithium azide or hydrazoic acid in a solvent such as DMF or water.

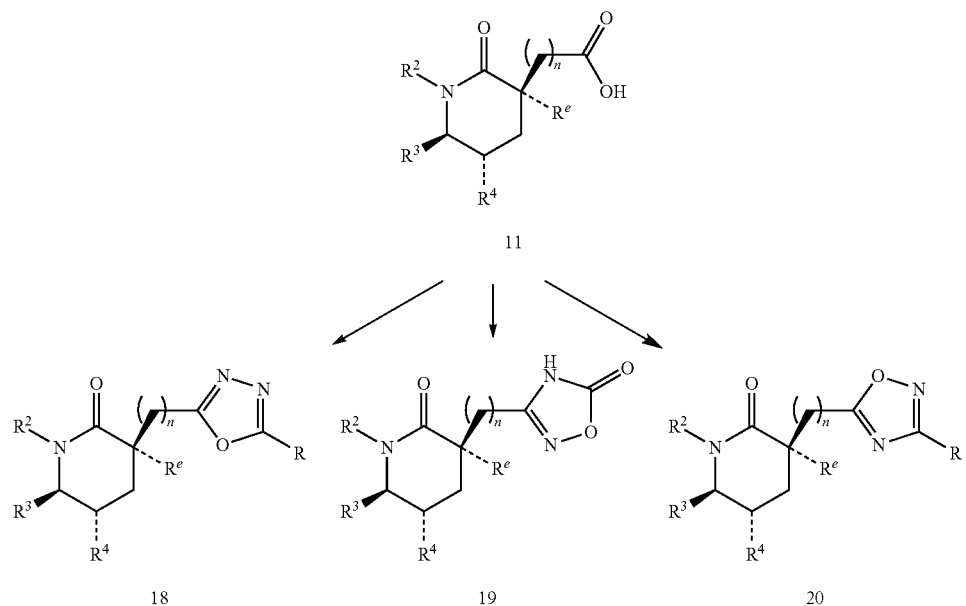

As shown in Scheme 4, the acid 11 can also be used to produce heterocyclic derivatives, such as, for example, [1,3,4]-oxadiazoles 18, [1,2,4]-oxadiazol-5(4H)-ones 19, and [1,2,4]-oxadiazoles 20 by methods well known to those of ordinary skill in the art. For example, converting the acid 11 into an diacylhydrazide, followed by treatment with a base at elevated temperature will provide 18. In another example 11 is converted into a nitrile as described in Scheme 3, which is treated with hydroxylamine. Reaction with 1,1'-carbonyldiimidazole in the presence of a base, such as DBU, generates 19 In yet another example, 11 reacts with a N-hydroxycarboxamidine derivative in the presence of 1,1'-carbonyldiimidazole, followed by treatment with tetrabutylammonium fluoride to give 20.

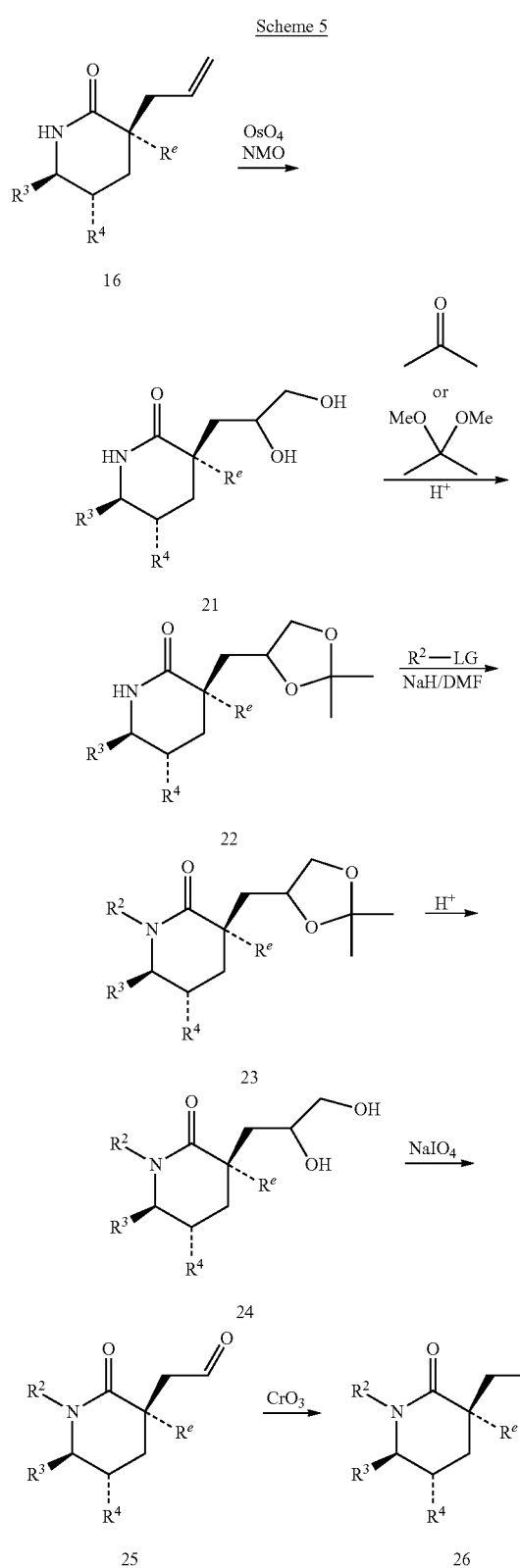

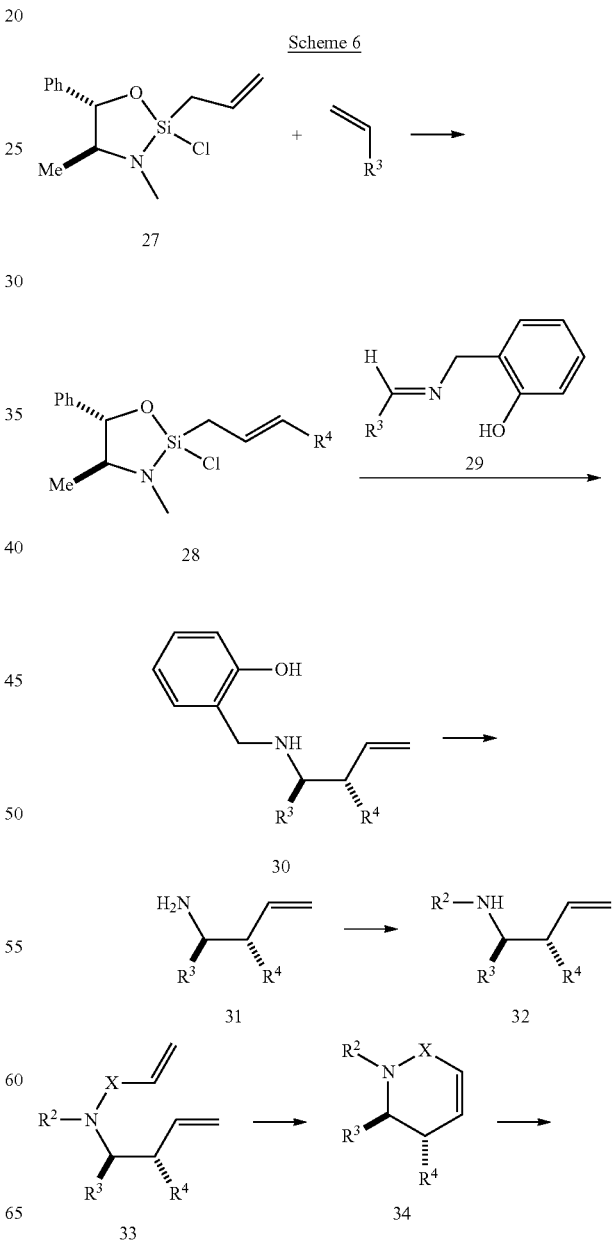

transformation. 21 can be converted into 22 by reaction with acetone or 2,2-dimethoxypropane in the presence of an acid, such as methanesulfonic acid, p-toluenesulfonic acid or camphorsulfonic acid. Compound 22 can then be N-arylated or N-alkylated by a variety of methods well known to those of ordinary skill in the art, such as treating 22 with an alkylhalide, alkylmethanesulfonate or alkyltoluenesulfonate in the presence of a base such as butyllithium or sodium hydride in a solvent such as DME, DMF or THF. Treating 23 with an acid such as HCl or $H_2SO_4$ in the presence of water will give the diol 24, which can be cleaved to the aldehyde 25 by a variety of oxidizing agents, such as periodic acid or lead tetraacetate (see e.g. Haines, A. H. *Methods for the Oxidation of Organic Compounds*, Vol 2.; p 277, Academic Press, NY, (1988)). The aldehyde 25 can be converted into the acid 26 by strong oxidizing agents including $CrO_3$ or a solution of periodate containing $RuCl_3$.

As shown in Scheme 5, a compound of formula 16 can also be dihydroxylated to give 21. Osmiumtetroxide in the presence of a second oxidizing agent such as 4-methylmorpholine-4-oxide in a suitable solvent will accomplish such a

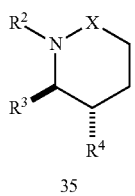

X = —C(O)—, SO₂—

Scheme 6 illustrates an alternative method for the preparation of intermediate compounds of general structure 35. This intermiate can be used to make additional compounds in this invention. Here, a (4S,5S)-2-allyl-2-chloro-3,4-dimethyl-5-phenyl-1,3,2-oxazasilolidine of the general formula 28 is formed by the reaction of 27 (prepared as described in J. Am. Chem. Soc. 124, 7920, (2002) with an alkene in the presence of Grubb's catalyst. Reaction with imine 29, which is prepared by the reaction of 2-(aminomethyl)phenol with an aldehyde using conditions well known to those skilled in the art, will yield compound 30 (See also J. Am. Chem. Soc. 129, 14552, (2007)). Intermediate 30 can in turn be converted into compound 31, by reacting consecutively with acetic anhydride in the presence of a base such as triethylamine, toluenesulfonic acid and oxalyl chloride in the presence of propylene glycol as described in Org. Letters, 11, 433, (2009), for example. Homoallyl amine 31 can optionally be further modified, for example by arylating or alkylating the nitrogen by methods well known to those of ordinary skill in the art. For example, the reaction of 31 with a ketone or aldehyde in the presence of a reducing agent such as sodium borohydride, sodium cyanoborohydride or sodium triacetoxyborohydride in a solvent such as DME, DMF or THF will accomplish this transformation. 32 can be acylated or sulfonylated by conditions well known to those of ordinary skill in the art to yield 33. 33 can be cyclized to 34 by a Ring Closing Metathesis (RCM) reaction. Catalysts suitable for such transformations are known to those of skill in the art (see e.g. (a) Grubbs, R. H. Handbook of Metathesis; Wiley-VCH: Weinheim, (2003); (b) Angew. Chem., Int. Ed., 42, 1900, (2003)) and include Grubbs $1^{st}$ generation and Grubbs $2^{nd}$ generation catalysts. Catalytic hydrogenation of 34 using, for example, a palladium, platinum or iridium catalyst in a solvent such as DCM, THF, methanol, or an aqueous mixture containing an alcohol or THF as a co-solvent, for example, is used to reduce the double bond, producing compound 35.

Scheme 7

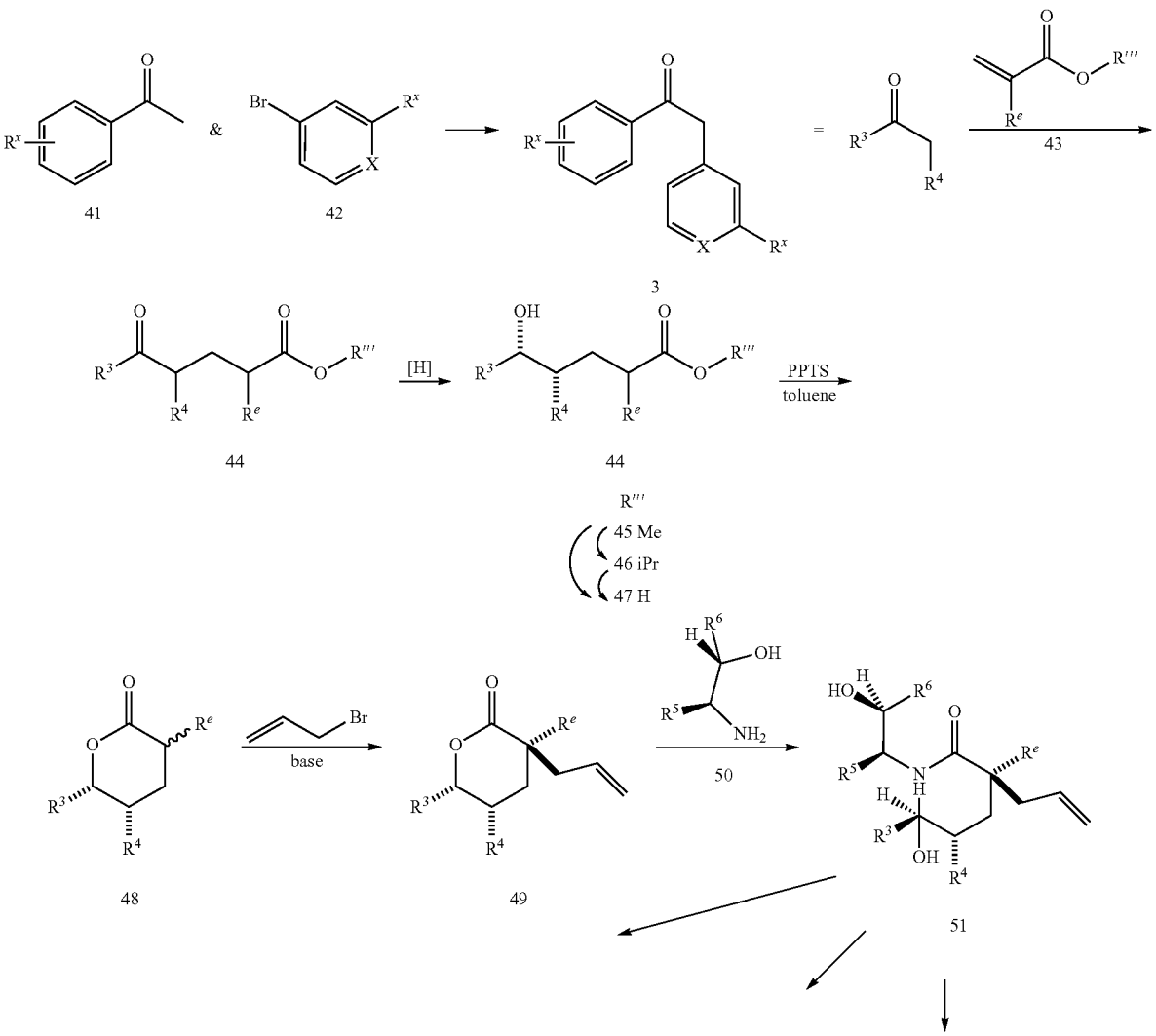

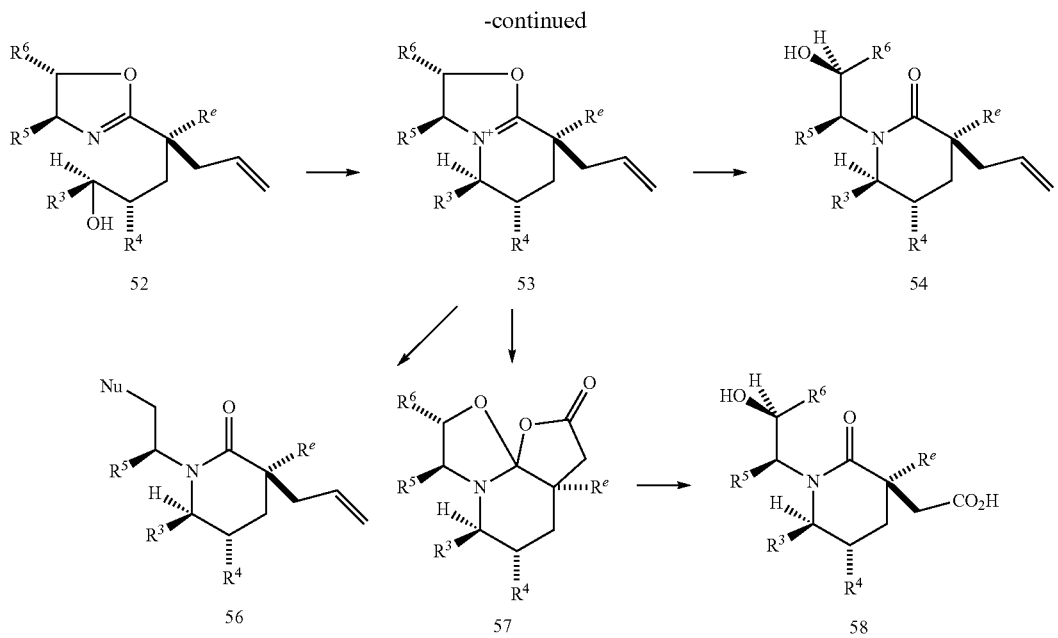

Compounds of the present invention may also be prepared via the lactone route illustrated in Scheme 7. Aryl benzyl ketones 3, commercially available or prepared by Dieckmann condensation or by coupling an aryl methyl ketone 41 with a bromoaryl compound 42, can be condensed with acrylate esters 43 including methacrylate, ethacrylate, etc., to form the keto ester 44. Stereoselective reduction occurs with sodium borohydride in methanol to form racemic 45 as a mixture of epimers at the $R^e$ position. Alternatively, this reduction can be carried out via dynamic kinetic resolution (see, Chen, et. al., *Organic Process Research & Development*, 2007, 11, 616-623 and references contained therein) to give enantioenriched 46, also as a mixture of epimers at the R" position. In this process, isopropyl esters are produced by transesterification. Hydrolysis to the carboxylic acid 47 followed by lactonization affords the racemic or enantioenriched lactone 48 as a mixture of diastereomers at the $R^e$ position. The diastereomers as a mixture can be enolized with strong base such as LiHMDS or LDA to give a common enolate which is alkylated with allyl bromide to afford lactone 49 as a single diastereomer. (see Example 261 Step E). Condensation of racemic lactone 49 with enantiopure aminoalcohols 50 results in diastereomeric hydroxylamides 51 which can be converted into oxazolines 52, oxazolinium salts 53 or hydroxylactams 54. Separation of the diastereomers can generally be done on any of these intermediates by normal phase silica chromatography. Alternatively, condensation of enantioenriched lactone 49 with enantioenriched amino alcohols 50 leads to enhanced enantiopurity of the resulting 51, 52, 53 or 54. For example 94% ee lactone combined with 98% ee amino alcohol results in the major diastereomer of 99.94% ee.

Hydroxylactam 54 ($R^5$=Et, cPr) has been prepared by alternate procedures (see Example 91 Step B; and Example 252 Step A) and used as an intermediate for many of the compounds of the present invention (equivalent to lactam 10 of Scheme 3). Using the lactone procedure, additional examples ($R^5$=iPr [Example 261, Step H], tBu, etc.) can be prepared. Additionally, aminoalcohols containing two adjacent stereocenters (i.e., $R^6$ not H) can be incorporated into this route. The oxazolinium salt 53 is also a versatile intermediate. It can be intercepted with various nucleophiles such as azide, thiols or sulfinate salts to form lactams 56, leading to amines, amides, sulfonamides and sulfones. The allyl group of oxazolinium salt 53 can be oxidized to the carboxylic acid oxidation state with minimal complication from the primary or secondary alcohol center which is tied up in the oxazoline ring. The resulting orthoamide 57 releases the lactam carboxylate 58 under mild hydrolysis conditions. Thus lactone 49 [$R^3$=pClPh, $R^4$=mClPh, $R^e$=Me] and (2S,3S)-3-aminopentan-2-ol [WO2007/110649A2] were combined. The corresponding oxazoline 52 [$R^3$=pClPh, $R^4$=mClPh, $R^e$=Me R=Et, $R^6$=Me] was formed by dehydration under Dean-Stark conditions in toluene with ammonium molybdate as a catalyst. Treatment with triflic anhydride in dichloromethane with lutidine at –50° C. gave oxazolinium salt 53 [$R^3$=pClPh, $R^4$=mClPh, $R^e$=Me $R^5$=Et, $R^6$=Me]. Oxidation with KMnO$_4$ in dichloromethane/water facilitated by tetrabutylammonium chloride gave after workup and hydrolysis with sodium bicarbonate solution in isopropyl acetate at 70° C., compound 58 [$R^3$=pClPh, $R^4$=mClPh, $R^e$=Me $R^5$=Et, $R^6$=Me] identical to material prepared in Example 152.

Example 1

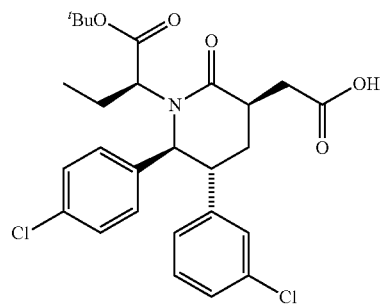

2-((3R,5R,6S)-1-((S)-1-tert-butoxy-1-oxobutan-2-yl)-5-(3-chlorophenyl)-6-(4-chlorophenyl)-2-oxopiperidin-3-yl)acetic acid

Step A.
2-(3-Chlorophenyl)-1-(4-chlorophenyl)ethanone

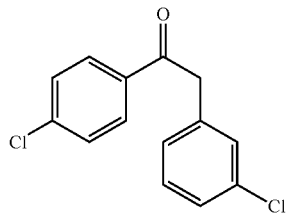 [SMILES: O=C(Cc1cccc(Cl)c1)c1ccc(Cl)cc1]

To a solution of 2-(3-chlorophenyl)acetic acid (10 g, 58.6 mmol) in THF (58 ml) was added 117 mL of a 1M solution of sodium bis-(trimethylsilyl) amide in THF slowly over 1 h at −78° C. After being stirred at −78° C. for 40 min, a solution of methyl 4-chlorobenzoate (10 g, 58.6 mmol) in THF (35 ml) was added over a period of 10 min. The reaction was stirred at −78° C. for 3 h, then allowed to warm to 25° C., and stirred an additional 2 h until completion. The reaction was quenched with saturated aqueous $NH_4Cl$ solution and most of the THF was removed under reduced pressure. The residue was extracted with ethyl acetate (2×100 ml). The combined organic layers were washed with sat. NaCl solution, dried over $Na_2SO_4$, filtered and the filtrate was concentrated. The product was recrystallized from ether/pentane to provide the title compound as a white solid.

Step B. Methyl 4-(3-chlorophenyl)-5-(4-chlorophenyl)-5-oxopentanoate

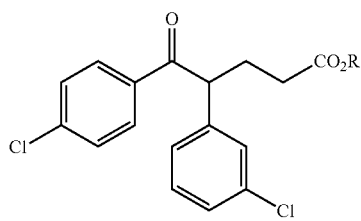

To a solution of 52.1 g (197 mmol) of 2-(3-chlorophenyl)-1-(4-chlorophenyl)ethanone (Example 1, Step A) and methyl acrylate (19.5 ml, 216 mmol) in 360 mL of THF was added 20 mL of a 1M solution of potassium tert-butoxide in THF slowly at 0° C. over a period of 20 min (reaction solution temp kept <10° C.). The reaction was allowed to warm to ambient temperature. After being stirred at rt for 1 h, the reaction was concentrated under reduced pressure, diluted with water and extracted with ethyl acetate. The combined organic layers were washed with sat. NaCl solution, dried over $Na_2SO_4$, filtered and the filtrate was concentrated. Purification of the residue by flash chromatography on silica gel (eluent: 15% EtOAc/hexanes) provided the title compound as a colorless liquid. R is $CH_3$.

Step C. (4S,5S)-Methyl 4-(3-chlorophenyl)-5-(4-chlorophenyl)-5-hydroxy pentanoate and (4R,5R)-Methyl 4-(3-chlorophenyl)-5-(4-chlorophenyl)-5-hydroxy pentanoate

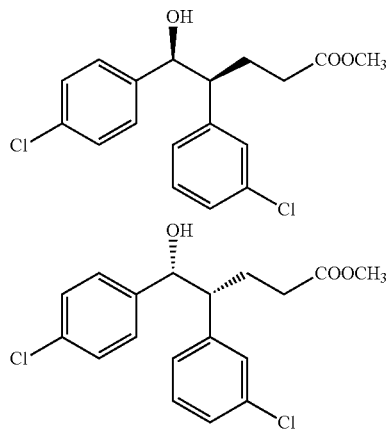

To a solution of 75.1 g (213 mmol) of methyl 4-(3-chlorophenyl)-5-(4-chlorophenyl)-5-oxopentanoate (Example 1, Step B) in MeOH (0.71 L, c=0.3 M) at 0° C. was added sodium borohydride (8058 mg, 213 mmol) in several small portions. After being stirred at 0° C. for 30 min, the reaction mixture was quenched with ice-cold $H_2O$, concentrated under reduced pressure, and extracted with EtOAc. The combined organic layers were washed (sat. aq. NaCl solution), dried over $Na_2SO_4$, filtered and the filtrate was concentrated. Purification of the residue by flash chromatography on silica gel (eluent: 20 to 30% EtOAc/hexanes, gradient elution) provided a racemic mixture of the title compounds as a colorless liquid.

Step D. (4S,5R)-Methyl 5-azido-4-(3-chlorophenyl)-5-(4-chlorophenyl)pentanoate and (4R,5S)-Methyl 5-azido-4-(3-chlorophenyl)-5-(4-chlorophenyl)pentanoate

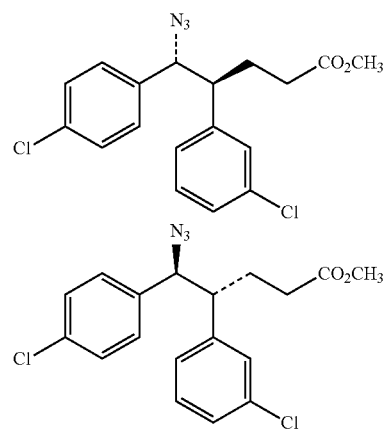

To a solution of 63.1 g (179 mmol) of (4S,5S)-methyl 4-(3-chlorophenyl)-5-(4-chlorophenyl)-5-hydroxy pentanoate and (4R,5R)-methyl 4-(3-chlorophenyl)-5-(4-chlorophenyl)-5-hydroxy pentanoate (Example 1, Step C) and triethylamine (49.8 ml, 357 mmol) in DCM (600 mL, 0.3 M) was added methanesulfonyl chloride (18 ml, 232 mmol) at 0° C. dropwise over a period of 10 min. The reaction was stirred at 0° C. for 40 min and monitored by TLC for completion. Then the reaction was quenched with ice-cold water, extracted (3×DCM), and washed with sat aq. NaCl solution. The combined organic layers were dried ($Na_2SO_4$), and concentrated under the reduced pressure.

The crude mesylate synthesized above was dissolved in DMF (350 mL, 0.5 M) and sodium azide (58 g, 893 mmol) was added in several portions. The mixture was heated to 100° C. and after being stirred at 100° C. for 30 min, the reaction mixture was cooled to room temperature, diluted with water and extracted with EtOAc. The combined organic layers were washed (sat. aq. NaCl solution), dried over $Na_2SO_4$, filtered and the filtrate was concentrated. Purification of the residue by flash chromatography on silica gel (eluent: 5 to 20% EtOAc/hexanes, gradient elution) provided the title compound as a colorless liquid.

Step E. (5R,6S)-5-(3-Chlorophenyl)-6-(4-chlorophenyl)piperidin-2-one

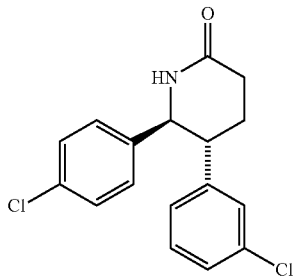 [SMILES: O=C1CC[C@H](c2cccc(Cl)c2)[C@@H](c2ccc(Cl)cc2)N1]

To a solution of 45.9 g (121 mmol) of methyl 5-azido-4-(3-chlorophenyl)-5-(4-chlorophenyl)pentanoate (Example 1, Step D) in THF/$H_2O$ (4:1, 375 mL) was added 152 mL of a 1M solution of trimethylphosphine in THF (152 mmol). After being stirred for 1 h at 25° C., most of the THF was removed under reduced pressure. The residue was basified (ice-cold 2 M LiOH) and the product was extracted with methylene chloride. The combined organic layers were washed with sat. NaCl solution, dried over $Na_2SO_4$, filtered and the filtrate was concentrated under reduced pressure to provide a white solid.

This solid was dissolved in MeOH/saturated aq. $NaHCO_3$ (4:1, 2.4 L, c=0.05 M) and the reaction was heated to reflux for 3 h. Excess organic solvent was removed under reduced pressure, the residue was diluted with water and extracted (2×10% MeOH/DCM). The combined organic layers were washed with sat. NaCl solution, dried over $Na_2SO_4$, filtered and the filtrate was concentrated under reduced pressure to provide trans-5-(3-chlorophenyl)-6-(4-chlorophenyl)piperidin-2-one as a mixture of stereoisomers. Individual stereoisomers were separated by chiral HPLC (flowrate: 18 ml/min on a Chiralcel® OD-H 20 mm I.D.×250 mm, 5 mic column (Daicel Inc., Fort Lee, N.J.), using 40% isopropyl alcohol/hexane as the eluent) to to give the title compound ($t_R$=8.2 min) as a white solid.

$[\alpha]_D$=+158 (T=23.4° C., c=1.12, MeOH); $^1$H NMR (400 MHz, CHLOROFORM-d) δ ppm 7.21 (2 H, d, J=8.2 Hz), 7.09-7.19 (3 H, m), 7.04-7.01 (1 H, m), 6.97 (2 H, d, J=8.2 Hz), 6.80-6.77 (1 H, m), 5.83 (1 H, s, br), 4.51 (1 H, d, J=9.8 Hz), 2.94-2.77 (1 H, m), 2.74-2.60 (2 H, m), 2.34-2.20 (1 H, m), 2.17-2.08 (1 H, m); MS (ESI) 320.0 [M+H]$^+$.

Also obtained by the above method was the enantiomer of the title compound, (5S,6R)-5-(3-chlorophenyl)-6-(4-chlorophenyl)piperidin-2-one: $t_R$=12.4 min; $[\alpha]_D$=−156 (T=23.4° C., c=1.13, MeOH).

Step F. tert-butyl (2S)-2-((2S,3R)-3-(3-chlorophenyl)-2-(4-chlorophenyl)-6-oxo-1-piperidinyl)butanoate and tert-butyl (2R)-2-((2S,3R)-3-(3-chlorophenyl)-2-(4-chlorophenyl)-6-oxo-1-piperidinyl) butanoate

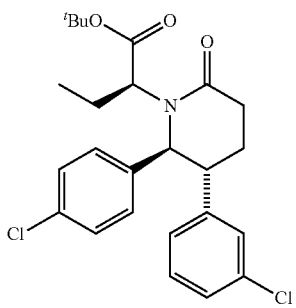

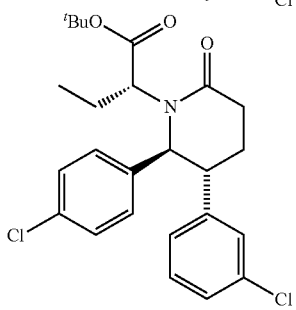

To a solution of 13.5 g (42.2 mmol) of (5R,6S)-5,6-bis(4-chlorophenyl)piperidin-2-one (Example 1, Step E) in 140 mL of DMF was added 4.22 g (105 mmol) of a dispersion of 60% sodium hydride in mineral oil at 0° C. After being stirred for 20 min, tert-butyl 2-bromobutanoate (28.2 g, 126 mmol) was added at 0° C. and the resulting solution was stirred at 25° C. for 1.5 h until completion of the reaction. Then sat. aq. $NH_4Cl$ solution was added and the mixture was extracted with ethylacetate. The combined organic layers were washed with water and sat. NaCl solution, dried over $Na_2SO_4$, filtered and the filtrate was concentrated under reduced pressure. Purification of the residue by flash chromatography on silica gel (eluent: 20 to 50% EtOAc/hexanes, gradient elution) provided tert-butyl (2S)-2-((2S,3R)-3-(3-chlorophenyl)-2-(4-chlorophenyl)-6-oxo-1-piperidinyl)butanoate as the faster eluting minor isomer:

$^1$H NMR (400 MHz, CHLOROFORM-d) δ ppm 7.22 (2 H, d, J=8.2 Hz), 7.20-7.10 (2 H, m), 7.08 (2 H, t, J=8.2 Hz) 6.99-6.96 (1 H, m), 6.77-6.73 (1 H, m), 4.48 (1 H, d, J=9.4 Hz), 3.24 (1 H, t, J=7.0 Hz), 3.04-2.94 (1 H, m), 2.72-2.58 (2 H, m), 2.25-2.00 (3 H, m), 1.93-1.82 (1 H, m), 1.45 (9 H, s), 0.98 (3 H, t, J=7.4 Hz); MS (ESI) 462.1 [M+H]$^+$.

Further elution provided tert-butyl (2R)-2-((2S,3R)-3-(3-chlorophenyl)-2-(4-chlorophenyl)-6-oxo-1-piperidinyl)butanoate as the slower eluting major isomer ¹H NMR (400 MHz, CHLOROFORM-d) δ ppm 7.24 (2 H, d, J=8.2 Hz), 7.18-7.10 (2 H, m), 7.01 (2 H, d, J=8.2 Hz), 7.02-6.98 (1 H, m), 6.82-6.78 (1 H, m), 5.83 (1 H, s), 4.54 (1 H, d, J=9.8 Hz), 3.09 (1 H, dd, J=8.2, 4.3 Hz), 3.05-2.99 (1 H, m), 2.70-2.64 (2 H, m), 2.28-2.18 (2 H, m), 2.08-2.02 (1 H, m), 1.48 (9 H, s), 0.57 (3 H, t, J=7.4 Hz); MS (ESI) 462.1 [M+H]⁺.

Step G. tert-Butyl (2S)-2-((3S,5R,6S)-3-allyl-5-(3-chlorophenyl)-6-(4-chlorophenyl)-2-oxopiperidin-1-yl)butanoate and. tert-Butyl (2S)-2-((3R,5R,6S)-3-allyl-5-(3-chlorophenyl)-6-(4-chlorophenyl)-2-oxopiperidin-1-yl)butanoate

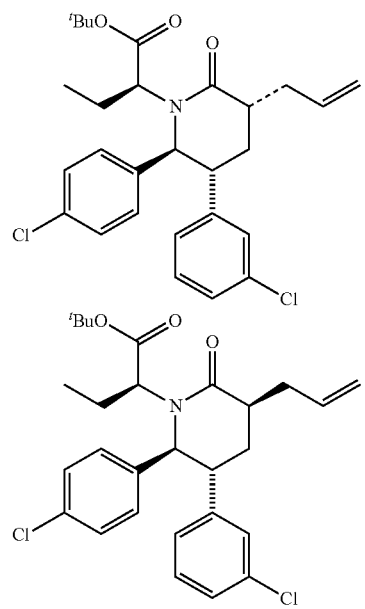

To a solution of 1.45 g (3.14 mmol) of tert-butyl (2S)-2-((2S,3R)-3-(3-chlorophenyl)-2-(4-chlorophenyl)-6-oxo-1-piperidinyl)butanoate (Example 1, Step F) and allyl bromide (0.326 mL, 3.76 mmol) in 12.5 mL of THF was added dropwise at −78° C. 3.3 mL of a 1 M solution of lithium bis(trimethylsilyl)-amide in THF (3.3 mmol). After being stirred at −78° C. for 3 h, the reaction was quenched with sat. aqueous NH₄Cl solution, extracted with ethyl acetate. The combined organic layers were washed with sat. NaCl solution, dried over Na₂SO₄, filtered and the filtrate was concentrated under reduced pressure. Purification of the residue by flash chromatography on silica gel (50 g SiO₂, eluent: 5 to 20% EtOAc/hexanes, gradient elution) provided tert-butyl (2S)-2-((3R,5R,6S)-3-allyl-5-(3-chlorophenyl)-6-(4-chlorophenyl)-2-oxopiperidin-1-yl)butanoate as the faster eluting major isomer.

¹H NMR (400 MHz, CHLOROFORM-d) δ ppm 7.27-7.24 (2 H, m), 7.21-7.12 (2 H, m), 7.11-7.00 (3 H, m), 6.93-6.87 (1 H, m), 5.90-5.77 (1 H, m), 5.19-5.09 (2 H, m), 4.64 (1 H, d, J=8.6 Hz), 3.21-3.10 (2 H, m), 2.80-2.71 (1 H, m), 2.70-2.63 (1 H, m), 2.56-2.48 (1 H, m), 2.30-2.15 (2 H, m), 2.07-1.99 (1 H, m), 1.60-1.48 (1 H, m), 1.47 (9 H, s), 0.61 (3 H, t, J=7.6 Hz); MS (ESI) 446.0 [M+H]⁺.

Further elution provided tert-butyl (2S)-2-((3S,5R,6S)-3-allyl-5-(3-chlorophenyl)-6-(4-chlorophenyl)-2-oxopiperidin-1-yl)butanoate as the slower eluting, minor isomer ¹H NMR (400 MHz, CHLOROFORM-d) δ ppm 7.23 (2 H, d, J=8.2 Hz), 7.19-7.07 (2 H, m), 7.01-6.95 (3 H, m), 6.77-6.72 (1 H, m), 5.95-5.77 (1 H, m), 5.16-4.99 (2 H, m), 4.51 (1 H, d, J=10.6 Hz), 3.13-3.04 (1 H, m), 2.94 (1 H, dd, J=7.8, 4.3 Hz), 2.87-2.77 (1 H, m), 2.68-2.58 (1 H, m), 2.39-2.27 (2 H, m), 2.16-1.95 (2 H, m), 1.54-1.50 (1 H, m), 1.51 (9 H, s), 0.55 (3 H, t, J=7.4 Hz); MS (ESI) 446.0 [M+H]⁺.

Step H. 2-((3R,5R,6S)-1-((S)-1-tert-Butoxy-1-oxobutan-2-yl)-5-(3-chlorophenyl)-6-(4-chlorophenyl)-2-oxopiperidin-3-yl)acetic acid

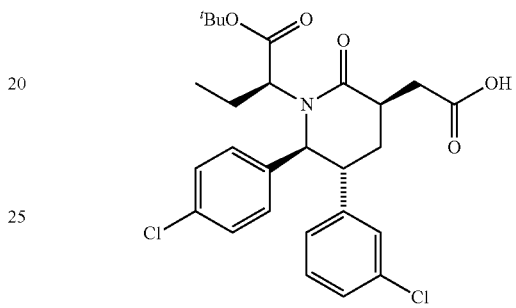

To a rapidly stirring solution of 842 mg (1.67 mmol) of tert-butyl (2S)-2-((3S,5R,6S)-3-allyl-5-(3-chlorophenyl)-6-(4-chlorophenyl)-2-oxopiperidin-1-yl) butanoate (Example 1, Step G) in a mixture of 7 mL of water, 5 mL of acetonitrile and 5 mL of CCl₄ was added sodium periodate (1.43 g, 6.70 mmol), followed by ruthenium(III) chloride hydrate (37.8 mg, 0.168 mmol). After being stirred vigorously for 18 h, the reaction was acidified (10% citric acid) and diluted with EtOAc. The reaction mixture was filtered through celite and the filtrate was extracted with EtOAc. The combined organic layers were washed with sat. NaCl solution, dried over Na₂SO₄, filtered and the filtrate was concentrated under reduced pressure. The residue was purified by reversed phase preparatory HPLC (Gemini™ Prep C18 5 μm column, Phenomenex, Torrance, Calif.; eluent: 60 to 80% acetonitrile +0.1% TFA in water +0.1% TFA, gradient elution) to give the title compound as a white solid.

¹H NMR (400 MHz, CHLOROFORM-d) δ ppm 7.35 (2 H, d, J=8.6 Hz), 7.27-7.24 (3 H, m), 7.22-7.16 (1 H, m), 7.18 (2 H, d, J=8.6 Hz), 4.85 (1 H, d, J=5.1 Hz), 3.36 (1 H, dd, J=8.6, 3.5 Hz), 3.18-3.14 (1 H, m), 2.92-2.80 (2 H, m), 2.79-2.72 (1 H, m), 2.32-2.18 (2 H, m), 2.15-2.06 (1 H, m), 1.63-1.50 (1 H, m), 1.44 (9 H, s), 0.67 (3 H, t, J=7.4 Hz); MS (ESI) 520.2 [M+H]⁺, 518.0 [M−H]⁻.

Example 2

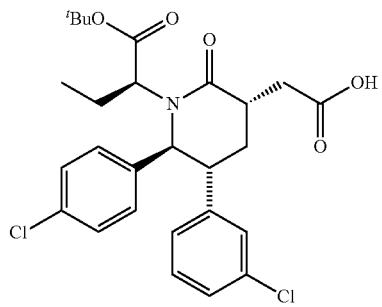 [SMILES: CC[C@@H](C(=O)OC(C)(C)C)N1C(=O)[C@H](CC(=O)O)C[C@H](c2cccc(Cl)c2)[C@H]1c1ccc(Cl)cc1]

2-((3S,5R,6S)-1-((S)-1-tert-Butoxy-1-oxobutan-2-yl)-5-(3-chlorophenyl)-6-(4-chlorophenyl)-2-oxopiperidin-3-yl)acetic acid The title compound was prepared from (S)-tert-butyl 2-((3R,5R,6S)-3-allyl-5-(3-chlorophenyl)-6-(4-chlorophenyl)-2-oxopiperidin-1-yl) butanoate (Example 1, Step G) by the procedure described in Example 1, Step H.

$^1$H NMR (500 MHz, CHLOROFORM-d) δ ppm 7.27-7.26 (2 H, m), 7.12-7.16 (1 H, m), 7.13-7.10 (1 H, m), 7.02-6.94 (3 H, m), 6.74-6.71 (1 H, m), 4.51 (1 H, d, J=10.8 Hz), 3.18-3.08 (2 H, m), 3.06-2.96 (2 H, m), 2.47 (1 H, dd, J=15.4, 3.2 Hz), 2.35-2.25 (1 H, m), 2.24-2.12 (2 H, m), 1.52-1.57 (1 H, m), 1.51 (9 H, s), 0.56 (3 H, t, J=7.5 Hz); MS (ESI) 520.2 [M+H]$^+$, 518.0 [M−H]$^-$.

The following examples 3 to 6 were prepared as described in Example 1, substituting tert-butyl 2-bromobutanoate in step F, with the appropriate amount of ethyl 2-bromobutanoate, ethyl 2-bromo-3-methylpentanoate, ethyl 2-bromopentanoate, and ethyl 2-bromo-2-cyclopropylacetate, respectively.

Example 3

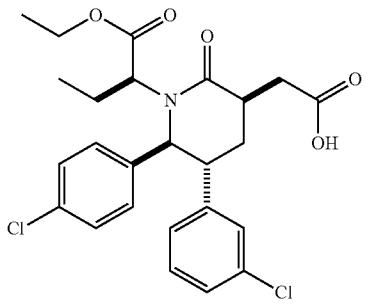

2-((3R,5R,6S)-5-(3-Chlorophenyl)-6-(4-chlorophenyl)-1-((S)-1-ethoxy-1-oxobutan-2-yl)-2-oxopiperidin-3-yl)acetic acid $^1$H NMR (400 MHz, CHLOROFORM-d) δ ppm 7.42-7.33 (3 H, m), 7.32-7.28 (3 H, m), 7.27-7.24 (2 H, m), 4.91 (1 H, d, J=3.5 Hz), 4.23-4.10 (2 H, m), 3.54 (1 H, dd, J=8.6, 3.5 Hz), 3.22-3.16 (1 H, m), 2.84-2.73 (3 H, m), 2.38-2.30 (2 H, m), 2.05-1.97 (1 H, m), 1.60-1.50 (1 H, m), 1.27 (3 H, t, J=7.4 Hz), 0.70 (3 H, t, J=7.4 Hz); MS (ESI) 491.8 [M+H]$^+$, 489.9 [M−H]$^-$.

Example 4

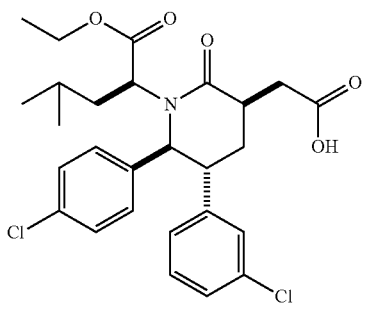

2-((3R,5R,6S)-5-(3-Chlorophenyl)-6-(4-chlorophenyl)-1-((S)-1-ethoxy-4-methyl-1-oxopentan-2-yl)-2-oxopiperidin-3-yl)acetic acid $^1$H NMR (400 MHz, CHLOROFORM-d) δppm 0.34 (d, J=6.7 Hz, 3 H), 0.77 (d, J=6.7 Hz, 3 H), 1.13 (m, 1 H), 1.28 (t, J=7.1 Hz, 3 H), 1.30-1.44 (m, 1 H), 1.98 (m, 1 H), 2.32-2.47 (m, 2 H), 2.75 (m, 1 H), 2.79-2.86 (m, 2 H), 3.14-3.19 (m, 1 H), 3.66 (dd, J=9.2, 2.4 Hz, 1 H), 4.11-4.24 (m, 2H), 4.95 (m, 1H), 7.23-7.34 (m, 5 H), 7.36-7.41 (m, 3 H), MS (ESI) 520.2 [M+H]$^+$, 518.0 [M−H]$^-$.

Example 5

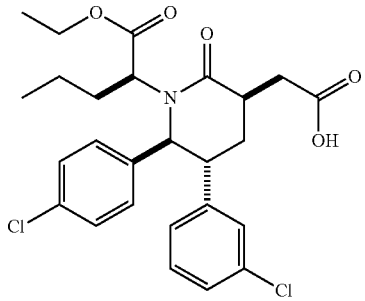

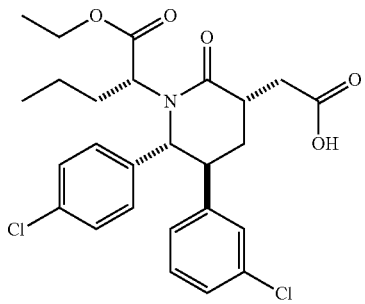

2-((3R,5R,6S)-5-(3-Chlorophenyl)-6-(4-chlorophenyl)-1-((S)-1-ethoxy-1-oxopentan-2-yl)-2-oxopiperidin-3-yl)acetic acid and 2-((3S,5S,6R)-5-(3-Chlorophenyl)-6-(4-chlorophenyl)-1-((R)-1-ethoxy-1-oxopentan-2-yl)-2-oxopiperidin-3-yl)acetic acid The compounds described in Example 5 were derived from racemic piperidinone which was prepared in Example 1, Step E.

$^1$H NMR (400 MHz, CHLOROFORM-d) δ ppm 7.40-7.37 (3 H, m), 7.31-7.27 (3 H, m), 7.27-7.24 (2 H, m), 4.92 (1 H, d, J=3.5 Hz), 4.20-4.10 (2 H, m), 3.60 (1 H, dd, J=8.6, 3.5 Hz), 3.20-3.15 (1 H, m), 2.83-2.72 (3 H, m), 2.40-2.30 (2 H, m), 2.03-1.97 (1 H, m), 1.44-1.37 (1 H, m), 1.27 (3 H, t, J=7.2 Hz), 1.26-1.17 (1 H, m), 0.92-0.80 (1 H, m), 0.54-0.78 (3 H, t, J=7.4 Hz); MS (ESI) 506.0 [M+H]$^+$, 504.0 [M−H]$^-$.

Example 6

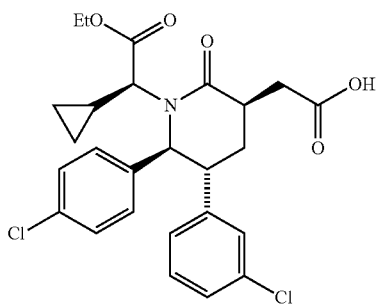 [SMILES: CCOC(=O)[C@H](C1CC1)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-1-((S)-1-cyclopropyl-2-ethoxy-2-oxoethyl)-2-oxopiperidin-3-yl)acetic acid $^1$H NMR (400 MHz, CHLOROFORM-d) δ ppm 0.08 (1 H, m), 0.34 (1 H, m), 0.47 (1 H, m), 0.58 (1 H, m), 1.06 (1 H, m), 1.13 (3 H, t, J=7.1 Hz), 1.83 (1 H, m), 2.19 (1 H, m), 2.50-2.63 (2 H, m), 2.74 (1 H, dd, J=16, 6.8 Hz), 3.08 (1 H, m), 3.42 (1 H, d, J=10.8 Hz), 3.97 (2 H, m), 5.20 (1 H, s), 7.08 (1 H, m), 7.15-7.25 (7 H, m); MS (ESI) 504.1 [M+H]$^+$.

Example 7

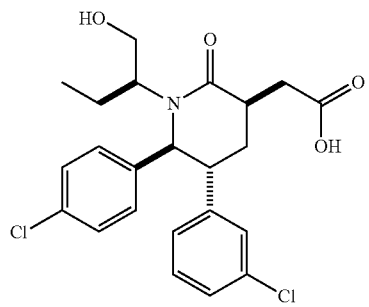

2-((3R,5R,6S)-5-(3-Chlorophenyl)-6-(4-chlorophenyl)-1-((S)-1-hydroxybutan-2-yl)-2-oxopiperidin-3-yl)acetic acid To a solution of 300 mg (0.61 mmol) of 2-((3R,5R,6S)-5-(3-chlorophenyl)-6-(4-chlorophenyl)-1-((S)-1-ethoxy-1-oxobutan-2-yl)-2-oxopiperidin-3-yl)acetic acid (Example 3) in 12 mL of Et$_2$O was added lithium tetrahydroborate (39.8 mg, 1.83 mmol) at 0° C. After being stirred for 20 min, methanol (37.0 μl, 914 μmol) was added at 0° C. and the resulting solution was stirred at 25° C. for 2 h. The reaction was quenched (10% citric acid), extracted (2×EtOAc) and washed (1×sat. aq. NaCl solution). The combined organic layers were washed with sat. NaCl solution, dried over Na$_2$SO$_4$, filtered and the filtrate was concentrated under reduced pressure. Purification by reversed phase preparatory HPLC (Gemini™ Prep C18 5 μm column, Phenomenex, Torrance, Calif.; eluent: 35 to 75% acetonitrile +0.1% TFA in water +0.1% TFA, gradient elution) provided the title compound as a white foam.

$^1$H NMR (400 MHz, CHLOROFORM-d) δppm 7.42-7.37 (3 H, m), 7.34-7.27 (4 H, m), 7.18-7.13 (1 H, m), 4.89 (1 H, d, J=2.7 Hz), 3.99-3.90 (1 H, m), 3.78 (1 H, dd, J=11.5, 3.3 Hz), 3.32-3.23 (1 H, m), 3.13-3.07 (1 H, m), 2.88-2.65 (3 H, m), 2.35-2.25 (1 H, m), 2.12-2.03 (1 H, m), 1.95-1.84 (1 H, m), 1.58-1.46 (1 H, m), 0.71 (3 H, t, J=7.4 Hz); MS (ESI) 450.1 [M+H]$^+$, 448.0 [M−H]$^−$.

Example 8

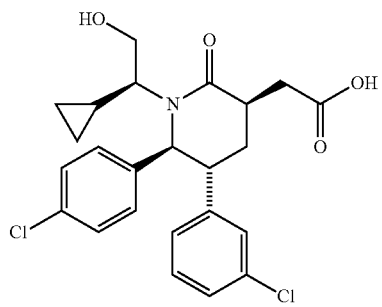 [SMILES: O=C(O)C[C@H]1C[C@H](c2cccc(Cl)c2)[C@@H](c2ccc(Cl)cc2)N([C@H](CO)C2CC2)C1=O]

2-((3R,5R,6S)-5-(3-chlorophenyl)-6-(4-chlorophenyl)-1-((S)-1-cyclopropyl-2-hydroxyethyl)-2-oxopiperidin-3-yl)acetic acid The title compound was prepared from 2-((3R,5R,6S)-5-(3-chlorophenyl)-6-(4-chlorophenyl)-1-((S)-1-cyclopropyl-2-ethoxy-2-oxoethyl)-2-oxopiperidin-3-yl)acetic acid (Example 6) as described in Example 7.

$^1$H NMR (400 MHz, CHLOROFORM-d) δ ppm 0.23 (m, 1 H), 0.36 (m, 1 H), 0.65-0.69 (m, 2 H), 0.95 (m, 1 H), 1.90 (m, 1 H), 2.40 (m, 1 H), 2.68 (m, 1 H), 2.80 (2 H, d, J=5.3 Hz), 3.13 (1 H, m), 3.48 (m, 1 H), 3.60-3.85 (m, 2 H), 5.32 (s, 1 H), 7.20 (m, 1 H), 7.27-7.40 (m, 3 H), 7.40-7.43 (m, 4 H); MS (ESI) 462.1 [M+H]$^+$.

Example 9

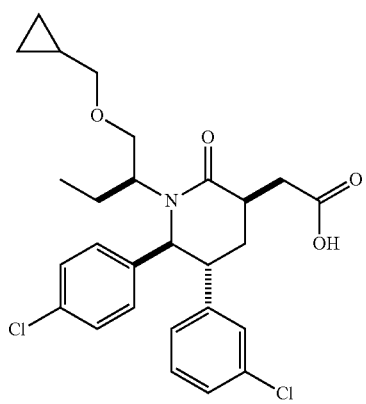

2-((3R,5R,6S)-5-(3-chlorophenyl)-6-(4-chlorophenyl)-1-((S)-1-(cyclopropylmethoxy)butan-2-yl)-2-oxopiperidin-3-yl)acetic acid Step A. (S)-Ethyl 2-((2S,3R)-3-(3-chlorophenyl)-2-(4-chlorophenyl)-6-oxopiperidin-1-yl)butanoate

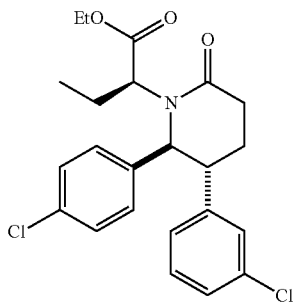

To a solution of 15 g (46.8 mmol) of ((5R,6S)-5-(3-Chlorophenyl)-6-(4-chlorophenyl)piperidin-2-one (Example 1, Step E) in 140 mL of DMF was added 3.75 g (94 mmol) of a dispersion of 60% sodium hydride in mineral oil at 0° C. After being stirred for 20 min, ethyl 2-bromobutanoate (17.2 mL, 117 mmol) was added at 0° C. and the resulting solution was stirred at 25° C. for 12 h until completion of the reaction. Then sat. aq. NH$_4$Cl solution was added and the mixture was extracted with ethyl acetate. The combined organic layers were washed with water and sat. NaCl solution, dried over Na$_2$SO$_4$, filtered and the filtrate was concentrated under reduced pressure. Purification of the residue by flash chromatography on silica gel (eluent: 30% EtOAc/hexanes, gradient elution) provided the title compound as the faster eluting isomer.

Step B. (S)-Ethyl 2-((3S,5R,6S)-3-allyl-5-(3-chlorophenyl)-6-(4-chlorophenyl)-2-oxopiperidin-1-yl)butanoate

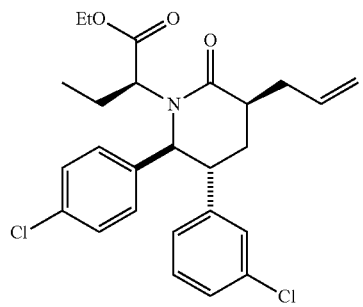

To a solution of 0.62 g (1.4 mmol) of (S)-ethyl 2-((2S,3R)-3-(3-chlorophenyl)-2-(4-chlorophenyl)-6-oxopiperidin-1-yl)butanoate (Example 9, Step A) and allyl bromide (0.14 ml, 1.7 mmol) in THF (6.0 mL, 0.25 M) was added lithium bis(trimethylsilyl)-amide (1M solution in THF, 1.5 ml, 1.5 mmol) at −78° C. The reaction was allowed to warm to R.T., then was quenched (sat. aqueous NH$_4$Cl) and extracted with EtOAc. The combined organic layers were washed with water and sat. NaCl solution, dried over Na$_2$SO$_4$, filtered and the filtrate was concentrated under reduced pressure. Purification of the residue by flash chromatography on silica gel (15 to 20% EtOAc/Hex, gradient elution) provided the title compound as the slower eluting isomer as a colorless oil.

Step C. (3S,5R,6S)-3-allyl-5-(3-chlorophenyl)-6-(4-chlorophenyl)-1-((S)-1-hydroxybutan-2-yl)piperidin-2-one

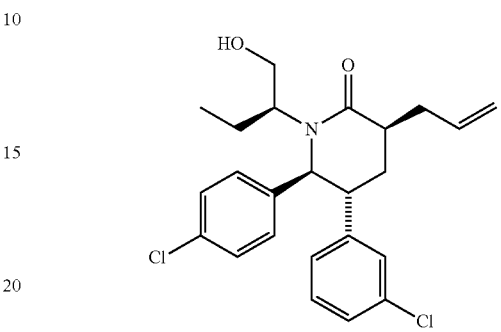

To a solution of 256 mg (0.54 mmol) of (S)-ethyl 2-((3S,5R,6S)-3-allyl-5-(3-chlorophenyl)-6-(4-chlorophenyl)-2-oxopiperidin-1-yl)butanoate (Example 9, Step B) in Et$_2$O (5.5 mL) was added lithium borohydride of 90% purity (17.6 mg, 0.809 mmol) at 0° C. After being stirred at 0° C. for 10 min, the reaction was quenched (ice cold 10% citric acid), extracted (2×EtOAc) and washed (sat. aq. NaCl solution). The combined organic layers were washed with sat. NaCl solution, dried over Na$_2$SO$_4$, filtered and the filtrate was concentrated under reduced pressure. Purification by chromatography on silica gel (eluent 30% to 50% EtOAc/Hexanes, a gradient elution) provided the title compound.

Step D. (3S,5R,6S)-3-allyl-5-(3-chlorophenyl)-6-(4-chlorophenyl)-1-((S)-1-(cyclopropylmethoxy)butan-2-yl)piperidin-2-one

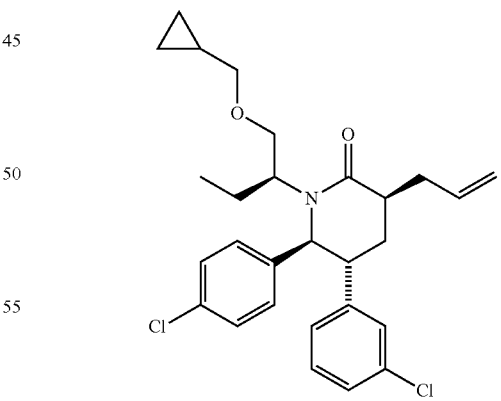

To a solution of (3S,5R,6S)-3-Allyl-5-(3-chlorophenyl)-6-(4-chlorophenyl)-1-((S)-1-hydroxybutan-2-yl)piperidin-2-one (98 mg, 0.227 mmol) in DMF (1.10 mL) was added 60% sodium hydride in mineral oil (27.2 mg, 0.680 mmol) at 0° C. After being stirred at 0° C. for 2 min, (bromomethyl)cyclopropane (47.3 μL, 0.680 mmol) was added. The mixture was stirred at 0° C. for 2 h and then warmed to rt. Then the reaction was stirred at rt overnight. The reaction was quenched (sat aq. NH₄Cl), extracted (2×EtOAc) and washed (sat. aq. NaCl solution). The combined organic layer was dried (Na₂SO₄) and concentrated under reduced pressure. Purification by chromatography on silica gel (10% to 20% EtOAc/Hexanes gradient) provided (3S,5R,6S)-3-allyl-5-(3-chlorophenyl)-6-(4-chlorophenyl)-1-((R)-1-(cyclopropylmethoxy)butan-2-yl)piperidin-2-one as the less polar isomer and the title compound as the more polar stereoisomer.

Step E. 2-((3R,5R,6S)-5-(3-Chlorophenyl)-6-(4-chlorophenyl)-1-((S)-1-(cyclopropylmethoxy)butan-2-yl)-2-oxopiperidin-3-yl)acetic acid

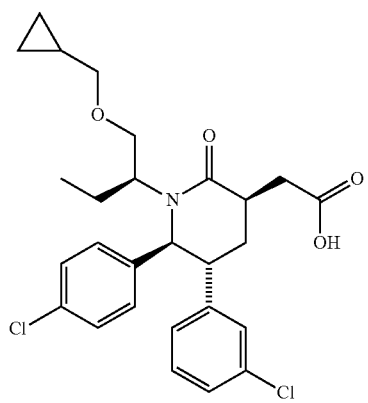 [SMILES: CC[C@@H](COCC1CC1)N1C(=O)[C@@H](CC(=O)O)C[C@H](c2cccc(Cl)c2)[C@H]1c1ccc(Cl)cc1]

(3S,5R,6S)-3-allyl-5-(3-chlorophenyl)-6-(4-chlorophenyl)-1-((S)-1-(cyclopropylmethoxy)butan-2-yl)piperidin-2-one was converted into the carboxylic acid by a procedure similar to the one described in Example 1, Step H. Purification by reversed phase preparatory HPLC (Gemini™ Prep C18 5 µm column, Phenomenex, Torrance, Calif.; eluent: 50 to 80% acetonitrile +0.1% TFA in water +0.1% TFA, gradient elution) provided the title compound as a white solid.

¹H NMR (400 MHz, CHLOROFORM-d) δ ppm 7.39 (2 H, d, J=8.2 Hz), 7.38-7.36 (1 H, m), 7.33-7.28 (3 H, m), 7.23 (2 H, d, J=8.2 Hz), 5.09 (1 H, d, J=2.0 Hz), 4.17-4.07 (1 H, m), 3.47-3.40 (2 H, m), 3.23-3.15 (m, 2 H), 3.12-3.08 (1 H, m), 2.85 (1 H, dd, J=15.8, 8.8 Hz), 2.66-2.55 (2 H, m), 2.22-2.12 (1 H, m), 2.07-1.99 (1 H, m), 1.95-1.85 (1 H, m), 1.62-1.54 (1 H, m), 1.07-1.00 (1 H, m), 0.65 (3 H, t, J=7.4 Hz), 0.60-0.52 (2 H, m), 0.24-0.18 (2 H, m);

MS (ESI) 504.1 [M+H]⁺, 502.1 [M−H]⁻.

The following Examples 10 to 12 were prepared from (3R,5R,6S)-3-allyl-5-(3-chlorophenyl)-6-(4-chlorophenyl)-1-((S)-1-hydroxybutan-2-yl)piperidin-2-one (Example 9, Step C) by procedures similar to those described in Example 9, Steps D and E, substituting (bromomethyl)cyclopropane in step D for the appropriate amount of methyliodide, 2-methoxyethylbromide, and 1-(bromomethyl)cyclopropanecarbonitrile, respectively.

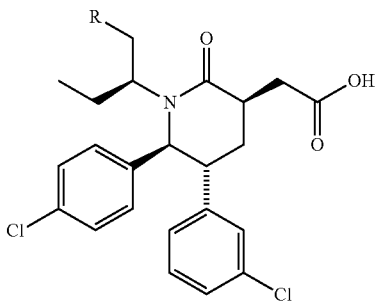

| Example | R |
|---------|---|
| 10 | 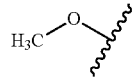 |
| 11 | 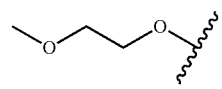 [SMILES: *OCCOC] |
| 12 | 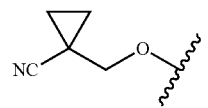 |

Example 10

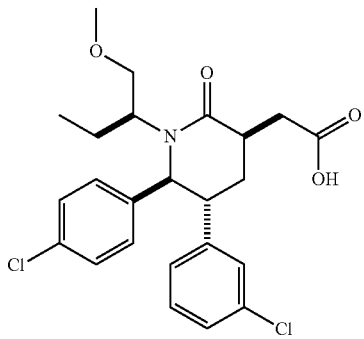

2-((3R,5R,6S)-5-(3-Chlorophenyl)-6-(4-chlorophenyl)-1-((S)-1-methoxybutan-2-yl)-2-oxopiperidin-3-yl)acetic acid ¹H NMR (400 MHz, CHLOROFORM-d) δ ppm 7.52-7.48 (1 H, m), 7.40 (2 H, d, J=8.2 Hz), 7.31-7.28 (2 H, m), 7.27-7.24 (1 H, m), 7.24-7.27 (2 H, m), 5.05 (1 H, s), 4.08 (1 H, t, J=9.6 Hz), 3.39 (3 H, s), 3.34 (1 H, dd, J=9.8, 3.1 Hz), 3.20-3.10 (2 H, m), 2.88-2.78 (1 H, m), 2.64-2.55 (2 H, m), 2.25-2.16 (1 H, m), 2.10-2.00 (1 H, m), 1.90-1.81 (1 H, m), 1.56-1.50 (1 H, m), 0.65 (3 H, t, J=7.4 Hz); MS (ESI) 464.0 [M+H]⁺, 462.1 [M−H]⁻.

Example 11

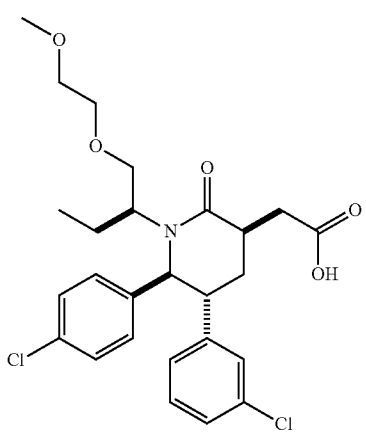

2-((3R,5R,6S)-5-(3-Chlorophenyl)-6-(4-chlorophenyl)-1-((S)-1-(2-methoxyethoxy)butan-2-yl)-2-oxopiperidin-3-yl)acetic acid ¹H NMR (400 MHz, CHLOROFORM-d) δ ppm 7.41-7.35 (3 H, m), 7.28-7.26 (2 H, m), 7.25-7.21 (3 H, m), 5.09 (1 H, d, J=2.7 Hz), 4.17-4.10 (1 H, m), 3.74-3.65 (1 H, m), 3.60-3.52 (3 H, m), 3.44 (1 H, dd, J=10.4, 3.3 Hz), 3.35 (3 H, s), 3.25-3.15 (1 H, m), 3.12-3.07 (1 H, m), 2.91-2.80 (1 H, m), 2.71-2.58 (2 H, m), 2.21-2.12 (1 H, m), 2.05-1.89 (2 H, m), 1.61-1.52 (1 H, m), 0.64 (3 H, t, J=7.6 Hz); MS (ESI) 508.1 [M+H]⁺, 506.0 [M−H]⁻.

Example 12

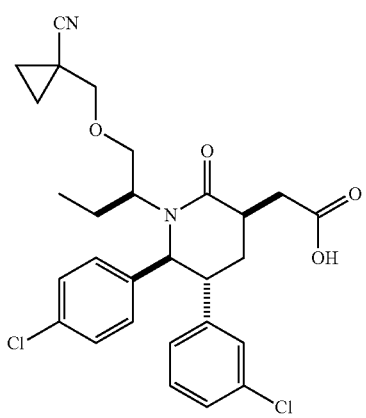

2-((3R,5R,6S)-5-(3-Chlorophenyl)-6-(4-chlorophenyl)-1-((S)-1-((1-cyanocyclopropyl)methoxy)butan-2-yl)-2-oxopiperidin-3-yl)acetic acid ¹H NMR (400 MHz, CHLOROFORM-d) δ ppm 7.43-7.30 (3 H, m), 7.28-7.20 (4 H, m), 7.18-7.10 (1 H, m), 5.04 (1 H, d, J=3.9 Hz), 4.13 (1 H, t, J=9.4 Hz), 3.52-3.43 (2 H, m), 3.42-3.33 (1 H, m), 3.32-3.24 (1 H, m), 3.13-3.05 (1 H, m), 2.92-2.75 (2 H, m), 2.72-2.60 (1 H, m), 2.20-2.10 (1 H, m), 2.10-1.90 (1 H, m), 1.64-1.49 (1 H, m), 1.35-1.25 (2 H, m), 1.00-0.90 (2 H, m), 0.71-0.57 (3 H, m); MS (ESI) 529.2 [M+H]⁺, 527.0 [M−H]⁻.

Examples 13-15 were prepared from (3R,5R,6S)-3-allyl-5-(3-chlorophenyl)-6-(4-chlorophenyl)-1-((S)-1-cyclopropyl-2-hydroxyethyl)piperidin-2-one in a process similar to that described for Example 9, Step D and E.

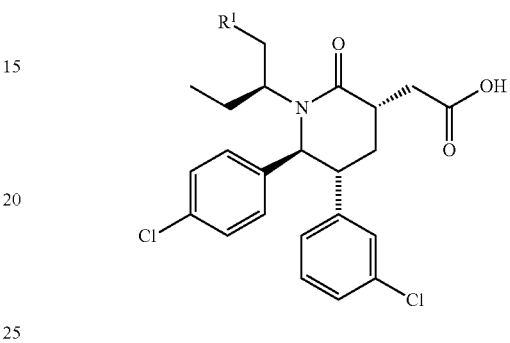

| Example | R¹ |
|---------|----|
| 13 | cyclopropylmethyl-O- |
| 14 | H₃C-O- |
| 15 | methoxyethoxy-O- |

Example 13

2-((3S,5R,6S)-5-(3-Chlorophenyl)-6-(4-chlorophenyl)-1-((S)-1-(cyclopropylmethoxy)butan-2-yl)-2-oxopiperidin-3-yl)acetic acid ¹H NMR (400 MHz, CHLOROFORM-d) δ ppm 7.25 (2 H, d, J=8.6 Hz), 7.22-7.18 (1 H, m), 7.15-7.11 (1 H, m), 7.08-7.04 (1 H, m), 6.96 (2 H, d, J=8.6 Hz), 6.77-6.73 (1 H, m), 4.69 (1 H, d, J=10.2 Hz), 4.03 (1 H, t, J=9.8 Hz), 3.42-3.33 (2 H, m), 3.28-3.22 (1 H, m), 3.10-2.90 (4 H, m), 2.50 (1 H, dd, J=15.3, 3.1 Hz), 2.20-2.10 (1 H, m), 2.01-2.01 (1 H, m), 1.92-1.80 (1 H, m), 1.65-1.53 (1 H, m), 1.16-1.08 (1 H, m), 0.66-0.60 (2 H, m), 0.53 (3 H, t, J=7.6 Hz), 0.28-0.24 (2 H, m); MS (ESI) 504.1 [M+H]⁺, 502.1 [M−H]⁻.

Example 14

2-((3S,5R,6S)-5-(3-Chlorophenyl)-6-(4-chlorophenyl)-1-((S)-1-methoxybutan-2-yl)-2-oxopiperidin-3-yl)acetic acid ¹H NMR (400 MHz, CHLOROFORM-d) δ ppm 0.55 (t, J=7.53 Hz, 3 H), 1.49-1.60 (m, 1 H), 1.77-1.91 (m, 1 H), 2.02-2.15 (m, 2 H), 2.51 (dd, J=15.26, 3.33 Hz, 1 H), 2.89-2.99 (m, 1 H), 2.99-3.09 (m, 2 H), 3.09-3.17 (m, 1 H), 3.29 (dd, J=9.68, 4.21 Hz, 1 H), 3.34 (s, 3 H), 3.90 (t, J=9.49 Hz, 1 H), 4.57 (d, J=9.98 Hz, 1 H), 6.75 (d, J=7.43 Hz, 1 H), 6.97 (d, J=8.41 Hz, 2 H), 7.00 (t, J=1.76 Hz, 1 H), 7.14 (t, J=7.73 Hz, 1 H), 7.17-7.22 (m, 1 H), 7.25 (d, J=8.41 Hz, 2 H).

Example 15

2-((3S,5R,6S)-5-(3-Chlorophenyl)-6-(4-chlorophenyl)-1-((S)-1-(2-methoxyethoxy)butan-2-yl)-2-oxopiperidin-3-yl)acetic acid $^1$H NMR (400 MHz, CHLOROFORM-d) δ ppm 7.24 (2 H, d, J=8.2 Hz), 7.21-7.16 (1 H, m), 7.14-7.09 (1 H, m), 7.05-7.03 (1 H, m), 6.97 (2 H, d, J=8.2 Hz), 6.75-6.71 (1 H, m), 4.66 (1 H, d, J=10.6 Hz), 4.09 (1 H, t, J=9.8 Hz), 3.70-3.55 (4 H, m), 3.47 (3 H, s), 3.44 (1 H, dd, J=9.8, 4.3 Hz), 3.05-2.90 (4 H, m), 2.53 (1 H, dd, J=15.1, 2.5 Hz), 2.28-2.15 (1 H, m), 2.05-1.97 (1 H, m), 1.92-1.82 (1 H, m), 1.65-1.55 (1 H, m), 0.50 (3 H, t, J=7.6 Hz); MS (ESI) 508.1 [M+H]$^+$, 506.0 [M−H]$^-$.

Example 16

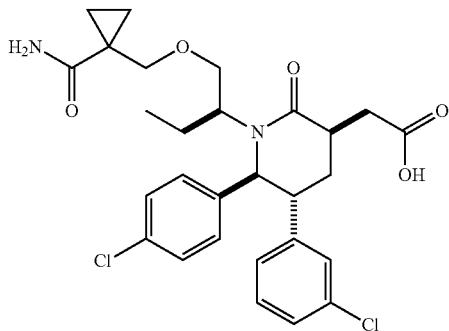

2-((3R,5R,6S)-1-((S)-1-((1-carbamoylcyclopropyl)methoxy)butan-2-yl)-5-(3-chlorophenyl)-6-(4-chlorophenyl)-2-oxopiperidin-3-yl)acetic acid A solution of 10 mg (0.02 mmol) 2-((3R,5R,6S)-5-(3-chlorophenyl)-6-(4-chlorophenyl)-1-((S)-1-((1-cyanocyclopropyl)methoxy)butan-2-yl)-2-oxopiperidin-3-yl)acetic acid (Example 11) and potassium hydroxide (3.2 mg, 0.06 mmol) in t-BuOH (189 μL) was stirred at 85° C. for 24 h. The reaction was acidified (10% citric acid) and extracted (2×EtOAc). The combined organic layers were washed with sat. NaCl solution, dried over Na$_2$SO$_4$, filtered and the filtrate was concentrated under reduced pressure. Purification by reversed phase preparatory HPLC (Gemini™ Prep C18 5 μm column, Phenomenex, Torrance, Calif.; eluent: 35 to 75% acetonitrile +0.1% TFA in water +0.1% TFA, gradient elution) provided the title compound.

$^1$H NMR (400 MHz, CHLOROFORM-d) δppm 0.67 (m, 5 H), 1.34 (m., 2 H), 1.54 (m., 1 H), 1.87-2.18 (m, 4 H), 2.65 (m, 1 H), 2.71-2.90 (m, 2 H), 3.08 (m, 1 H), 3.38-3.64 (m, 4 H), 3.94 (m, 1 H), 4.84 (m, 1 H), 6.35 (br. s., 1 H), 6.91 (br. s., 1 H) 7.13 (m, 1 H) 7.21-7.38 (m, 7 H). MS (ESI) 547.2 [M+H]$^+$, 545.0 [M−H]$^-$.

Further elution provided Example 17.

Example 17

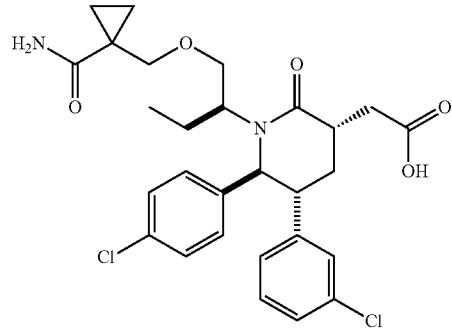

2-((3S,5R,6S)-1-((S)-1-((1-carbamoylcyclopropyl)methoxy)butan-2-yl)-5-(3-chlorophenyl)-6-(4-chlorophenyl)-2-oxopiperidin-3-yl)acetic acid $^1$H NMR (400 MHz, CHLOROFORM-d) δ ppm 7.26-7.21 (2 H, m), 7.17-7.12 (2 H, m), 7.06 (1 H, br, s), 6.95-6.90 (2 H, m), 6.88-6.80 (1 H, s), 6.79-6.76 (1 H, m), 6.74 (1 H, br, s), 4.63 (1 H, d, J=10.2 Hz), 4.10-4.00 (1 H, m), 3.33-3.10 (3 H, m), 3.02-2.92 (2 H, m), 2.90-2.78 (1 H, m), 2.70-2.60 (1 H, m), 2.44-2.34 (1 H, m), 2.00-1.90 (1 H, m), 1.85-1.75 (1 H, m), 1.65-1.55 (1 H, m), 1.43-1.35 (2 H, m), 0.85-0.73 (2 H, m), 0.63-0.52 (3 H, m); MS (ESI) 547.2 [M+H]$^+$, 545.0 [M−H]$^-$.

Example 18

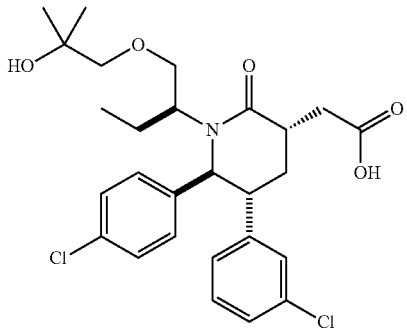

2-((3R,5R,6S)-5-(3-chlorophenyl)-6-(4-chlorophenyl)-1-((S)-1-(2-hydroxy-2-methylpropoxy)butan-2-yl)-2-oxopiperidin-3-yl)acetic acid Step A. Ethyl 2-((S)-2-((3S,5R,6S)-3-allyl-5-(3-chlorophenyl)-6-(4-chlorophenyl)-2-oxopiperidin-1-yl)butoxy)acetate

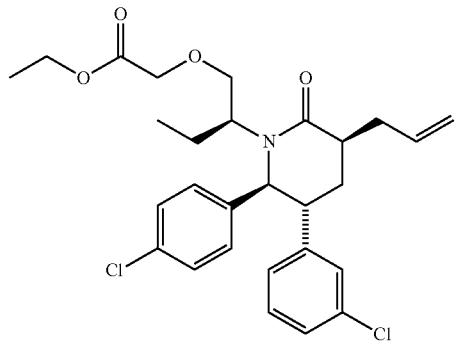 [SMILES: C=CC[C@H]1C[C@H](c2cccc(Cl)c2)[C@@H](c2ccc(Cl)cc2)N([C@@H](CC)COCC(=O)OCC)C1=O]

To a solution of 203 mg (0.47 mmol) of (3S,5R,6S)-3-allyl-5-(3-chlorophenyl)-6-(4-chlorophenyl)-1-((S)-1-hydroxybutan-2-yl)piperidin-2-one (Example 9, Step B) and rhodium(II)acetate dimmer (10.4 mg, 0.047 mmol) in CH$_2$Cl$_2$ (1.90 mL) was added dropwise ethyl diazoacetate (286 μL, 2.35 mmol) at 25° C. After being stirred at 25° C. for 14h, the reaction was concentrated under reduced pressure and purified by chromatography on silica gel (20% to 30% EtOAc/Hexanes, gradient elution) to provide the title compound as a colorless liquid:

Step B. (3S,5R,6S)-3-allyl-5-(3-chlorophenyl)-6-(4-chlorophenyl)-1-((S)-1-(2-hydroxy-2-methylpropoxy)butan-2-yl)piperidin-2-one

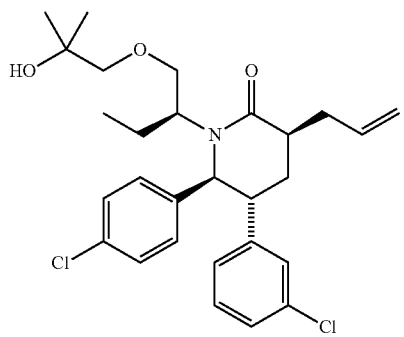 [SMILES: C=CC[C@H]1C[C@H](c2cccc(Cl)c2)[C@@H](c2ccc(Cl)cc2)N([C@@H](CC)COCC(C)(C)O)C1=O]

To a solution of ethyl 2-((S)-2-((3S,5R,6S)-3-allyl-5-(3-chlorophenyl)-6-(4-chlorophenyl)-2-oxopiperidin-1-yl)butoxy)acetate (69.0 mg, 0.133 mmol) in THF (2.22 mL) was added methylmagnesium bromide, 1.4M in Toluene/THF, (0.38 mL, 0.532 mmol) at 0° C. After being stirred at 25° C. for 3 h, the reaction was quenched (sat. aq. NH$_4$Cl), and extracted with EtOAc. The combined organic layers were washed with sat. NaCl solution, dried over Na$_2$SO$_4$, filtered and the filtrate was concentrated under reduced pressure. Purification by chromatography on silica gel (20% to 50% EtOAc/Hexanes, gradient elution) provided the title compound as a colorless liquid.

Step C. 2-((3R,5R,6S)-5-(3-chlorophenyl)-6-(4-chlorophenyl)-1-((S)-1-(2-hydroxy-2-methylpropoxy)butan-2-yl)-2-oxopiperidin-3-yl)acetic acid To a rapidly stirring solution of (3S,5R,6S)-3-allyl-5-(3-chlorophenyl)-6-(4-chlorophenyl)-1-((S)-1-(2-hydroxy-2-methylpropoxy)butan-2-yl)piperidin-2-one (51.0 mg, 0.101 mmol) in a mixture of water (361 μL), acetonitrile (241 μL), and CCl$_4$ (241 μL) was added sodium periodate (86 mg, 0.404 mmol), followed by ruthenium(III) chloride hydrate (2.28 mg, 10.1 μmol). After being stirred vigorously for 18 h, the reaction was acidified (10% citric acid) and diluted (EtOAc). The mixture was filtered through Celite® (J. T. Baker, Phillipsberg, N.J., J. T. Baker, Phillipsberg, N.J., diatomaceous earth) and the filtrate was extracted with EtOAc. The combined organic layers were washed with sat. NaCl solution, dried over Na$_2$SO$_4$, filtered and the filtrate was concentrated under reduced pressure. Purification by reversed phase preparatory HPLC (Gemini™ Prep C18 5 μm column, Phenomenex, Torrance, Calif.; eluent: 50 to 76% acetonitrile +0.1% TFA in water +0.1% TFA, gradient elution) provided the title compound as a white solid.

$^1$H NMR (400 MHz, CHLOROFORM-d) δ ppm 0.64-0.74 (t, J=7.6 Hz, 3 H), 1.21 (d, J=3.7 Hz, 6 H), 1.58 (ddd, J=14.0, 7.6, 4.4 Hz, 1 H), 1.84-1.99 (m, 2 H), 2.21 (m, 1 H), 2.64-2.83 (m, 3 H), 3.04-3.15 (m, 1 H), 3.19 (d, J=9.2 Hz, 1 H), 3.29 (d, J=9.2 Hz, 1 H), 3.38 (m, 1 H), 3.41-3.55 (m, 1 H), 3.98 (t, J=8.6 Hz, 1 H), 4.98 (d, J=2.9 Hz, 1 H) 7.12-7.20 (m, 1 H), 7.21-7.34 (m, 5 H), 7.34-7.41 (m, 2 H); MS (ESI) 522.1 [M+H]$^+$, 520.2 [M−H]$^-$.

Example 19

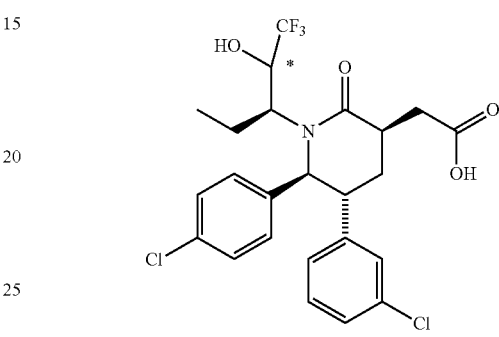

* absolute stereochemistry unknown 2-((3R,5R,6S)-5-(3-Chlorophenyl)-6-(4-chlorophenyl)-2-oxo-1-((3S)-1,1,1-trifluoro-2-hydroxypentan-3-yl)piperidin-3-yl)acetic acid (Isomer 1)

Step A. (S)-2-((3S,5R,6S)-3-allyl-5-(3-chlorophenyl)-6-(4-chlorophenyl)-2-oxopiperidin-1-yl) butanal

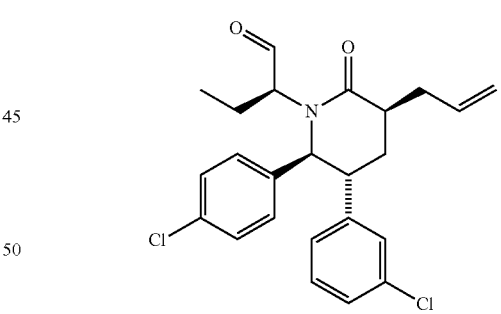

To a solution of oxalyl dichloride (166 μL, 1.87 mmol) in DCM (4.16 mL) at −60° C. was added a solution of DMSO (222 μL, 3.12 mmol) in DCM (4.16 mL) under N$_2$. After about 20 min, a solution of 540 mg (1.25 mmol) of (3S,5R,6S)-3-allyl-5-(3-chlorophenyl)-6-(4-chlorophenyl)-1-((S)-1-hydroxybutan-2-yl)piperidin-2-one (Example 9, Step B) in 4.2 mL of DCM was added, and the resulting solution was stirred for 15 min. Triethylamine (872 μL, 6.24 mmol) was then added. After being stirred at −60° C. for 5 min, the reaction was allowed to warm to rt, and 5 mL of water was added. The solution was extracted (2×DCM), washed (sat. aq.

NaCl solution), dried (MgSO₄) and concentrated under the reduced pressure to give the crude title compound containing 20% starting material (SM).

Step B. (3S,5R,6S)-3-allyl-5-(3-chlorophenyl)-6-(4-chlorophenyl)-1-((3S)-1,1,1-trifluoro-2-hydroxypentan-3-yl)piperidin-2-one

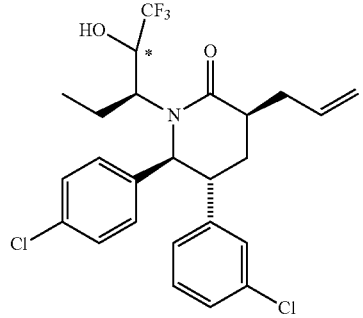

*absolute stereochemistry unknown

A solution of (S)-2-((3S,5R,6S)-3-allyl-5-(3-chlorophenyl)-6-(4-chlorophenyl)-2-oxopiperidin-1-yl)butanal (80 mg, 0.186 mmol) and trimethyl(trifluoromethyl)silane (82 µL, 0.558 mmol) in THF (929 µL) was treated at 0° C. with 1 M tetrabutylammonium fluoride in THF (93 µL, 0.093 mmol). After being stirred for 1 h, three additional equivalents of trimethyl(trifluoromethyl)silane (82 µL, 0.558 mmol) and 1 M tetrabutylammonium fluoride in THF (93 µL, 0.093 mmol) were added to the reaction at 0° C. and the reaction was stirred for 14 h. The reaction mixture was diluted (EtOAc), washed (1×H₂O and 1×sat. aq. NaCl solution), dried (Na₂SO₄), and concentrated under reduced pressure. Purification by reverse phase preparatory HPLC (Gemini™ Prep C18 5 µm column, Phenomenex, Torrance, Calif.; eluent: 60 to 90% acetonitrile +0.1% TFA in water +0.1% TFA, gradient elution) provided two compounds which are diastereomers at the secondary alcohol.

Step C. 2-((3R,5R,6S)-5-(3-Chlorophenyl)-6-(4-chlorophenyl)-2-oxo-1-((3S)-1,1,1-trifluoro-2-hydroxypentan-3-yl)piperidin-3-yl)acetic acid The title compound was prepared from a single diastereomer of (3S,5R,6S)-3-allyl-5-(3-chlorophenyl)-6-(4-chlorophenyl)-1-((3S)-1,1,1-trifluoro-2-hydroxypentan-3-yl)piperidin-2-one by a procedure similar to the one described in Example 18, Step C.

¹H NMR (400 MHz, CHLOROFORM-d) δ ppm 0.53 (t, J=7.5 Hz, 3 H), 1.66 (m, 1 H), 1.97-2.05 (m, 1 H), 2.18 (m, 1 H), 2.32-2.45 (m, 1 H), 2.68-2.83 (m, 2 H), 2.94-3.05 (m, 1 H), 3.15-3.25 (m, 1 H), 4.42 (m, 1 H), 4.69 (d, J=3.9 Hz, 1 H), 6.95-7.02 (m, 1 H), 7.12 (m, 1 H), 7.22-7.37 (m, 5 H), 7.37-7.46 (m, 2 H); MS (ESI) 518.0 [M+H]⁺. 516.0 [M−H]⁻.

Example 20

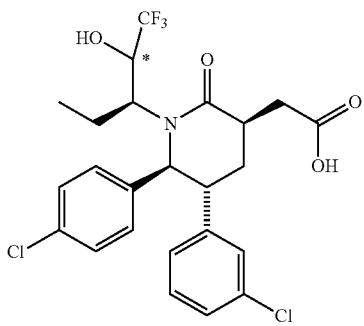

*absolute stereochemistry unknown 2-((3R,5R,6S)-5-(3-Chlorophenyl)-6-(4-chlorophenyl)-2-oxo-1-((3S)-1,1,1-trifluoro-2-hydroxypentan-3-yl)piperidin-3-yl)acetic acid (Isomer 2)

To a rapidly stirring solution of 6.3 mg (0.013 mmol) of (3S,5R,6S)-3-allyl-5-(3-chlorophenyl)-6-(4-chlorophenyl)-1-((3S)-1,1,1-trifluoro-2-hydroxypentan-3-yl)piperidin-2-one (Example 19, Step B, the diastereomer not used for Example 19 Step B)) (6.30 mg, 0.013 mmol) in a mixture of water (108 µL), acetonitrile (71.9 µL), and CCl₄ (71.9 µL) was added sodium periodate (10.7 mg, 0.050 mmol), followed by ruthenium(III) chloride hydrate (0.284 mg, 1.26 µmol). After being stirred vigorously for 18 h, the reaction was acidified (10% citric acid) and diluted (EtOAc). The reaction mixture was filtered through Celite® (J. T. Baker, Phillipsberg, N.J., J. T. Baker, Phillipsberg, N.J., diatomaceous earth). The filtrate was extracted (2×EtOAc). The combined organic layers were washed with sat. NaCl solution, dried over Na₂SO₄, filtered and the filtrate was concentrated under reduced pressure. Purification by reversed phase preparatory HPLC (Gemini™ Prep C18 5 µm column, Phenomenex, Torrance, Calif.; eluent: 45 to 70% acetonitrile +0.1% TFA in water +0.1% TFA, gradient elution) provided the title compound as a white solid.

¹H NMR (400 MHz, CHLOROFORM-d) δ ppm 0.44-0.72 (m, 3 H); 1.28-1.46 (m, 1 H), 2.15-2.28 (m, 2 H), 2.45-2.55 (m, 1 H), 2.89-3.05 (m, 3 H), 3.10-3.18 (m, 2 H), 4.02-4.16 (m, 1 H), 4.56 (d, J=7.8 Hz, 1 H), 6.84-6.93 (m, 1 H), 7.01-7.04 (m, 1 H), 7.08-7.14 (m, 2 H), 7.17-7.20 (m, 2 H), 7.32-7.38 (m, 2 H); MS (ESI) 518.0 [M+H]⁺. 516.0 [M−H]⁻.

Example 21

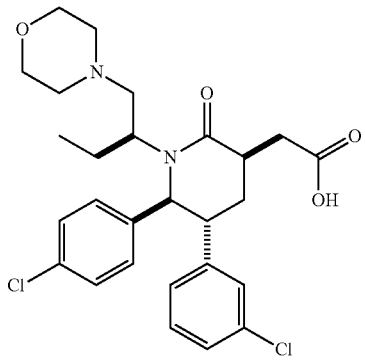 [SMILES: CC[C@@H](CN1CCOCC1)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-1-((S)-1-morpholinobutan-2-yl)-2-oxopiperidin-3-yl)acetic acid Step A. (S)-ethyl 2-((3R,5R,6S)-3-(2-tert-butoxy-2-oxoethyl)-5-(3-chlorophenyl)-6-(4-chlorophenyl)-2-oxopiperidin-1-yl)butanoate

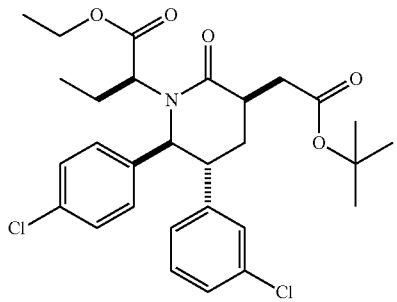 [SMILES: CCOC(=O)[C@H](CC)N1C(=O)[C@@H](CC(=O)OC(C)(C)C)C[C@H](c2cccc(Cl)c2)[C@H]1c1ccc(Cl)cc1]

To a stirred solution of 1.14 g (2.3 mmol) of 2-((3R,5R,6S)-5-(3-chlorophenyl)-6-(4-chlorophenyl)-1-((S)-1-ethoxy-1-oxobutan-2-yl)-2-oxopiperidin-3-yl)acetic acid (Example 3) in DCM (21.0 mL) was added sulfuric acid (0.247 mL, 4.63 mmol) followed by isobutylene (4.42 mL, 46.3 mmol) at −78° C. The reaction vessel was sealed and the mixture was slowly warmed to rt and vigorously stirred for 3 days. After cooling to −78° C., the tube was opened and the reaction was quenched with aqueous saturated NaHCO$_3$ to pH 8. The organic solvent was removed under reduced pressure, and the remaining mixture was extracted (2×EtOAc). The combined organic layers were washed with sat. NaCl solution, dried over Na$_2$SO$_4$, filtered and the filtrate was concentrated under reduced pressure. The residue was purified by chromatography on silica gel (eluent: 20 to 35% EtOAc/hexanes) to provide the title compound as a foam.

Step B. tert-butyl 2-((3R,5R,6S)-5-(3-chlorophenyl)-6-(4-chlorophenyl)-1-((S)-1-hydroxybutan-2-yl)-2-oxopiperidin-3-yl)acetate

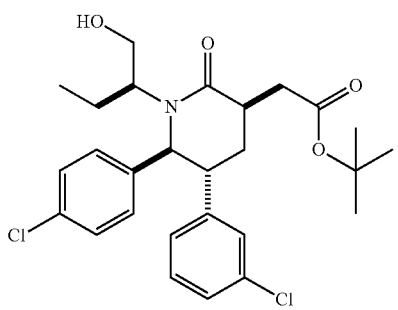 [SMILES: CC[C@@H](CO)N1C(=O)[C@@H](CC(=O)OC(C)(C)C)C[C@H](c2cccc(Cl)c2)[C@H]1c1ccc(Cl)cc1]

To a solution of (S)-ethyl 2-((3R,5R,6S)-3-(2-tert-butoxy-2-oxoethyl)-5-(3-chlorophenyl)-6-(4-chlorophenyl)-2-oxopiperidin-1-yl)butanoate (1.94 g, 3.54 mmol, Example 21, Step A) in Et$_2$O (35.4 mL) was added 90% lithium borohydride (0.154 g, 7.07 mmol) at 0° C. After being stirred at 0° C. for 30 min, the reaction was quenched (ice cold 10% citric acid), extracted (2×EtOAc) and washed (sat. aq. NaCl solution). The combined organic layers were washed with sat. NaCl solution, dried over Na$_2$SO$_4$, filtered and the filtrate was concentrated under reduced pressure. Purification by chromatography on silica gel (50% to 100% EtOAc/Hexanes, gradient elution) provided the title compound.

Step C. tert-butyl 2-((3R,5R,6S)-5-(3-chlorophenyl)-6-(4-chlorophenyl)-2-oxo-1-((S)-1-oxobutan-2-yl)piperidin-3-yl)acetate To a solution of oxalyl chloride (0.261 mL, 2.99 mmol) in DCM (5.87 mL) at −60° C. was added a solution of DMSO (0.512 mL, 5.98 mmol) in DCM (5.87 mL) under N$_2$. After being stirred for 20 min, a solution of tert-butyl 2-((3R,5R,6S)-5-(3-chlorophenyl)-6-(4-chlorophenyl)-1-((S)-1-hydroxybutan-2-yl)-2-oxopiperidin-3-yl)acetate (1.01 g, 1.99 mmol, Example 21, Step B) in DCM (5.87 mL) was added, and the resulting solution was stirred for 15 min. To this solution was added triethylamine (1.39 mL, 9.97 mmol). After being stirred at −60° C. for 5 min, the reaction was allowed to warm to rt, and quenched (H$_2$O). The solution was extracted (3×DCM) and washed (H$_2$O and sat. aq. NaCl solution). The combined organic layers were washed with sat. NaCl solution, dried over Na$_2$SO$_4$, filtered and the filtrate was concentrated under reduced pressure to give the title compound.

Step D. tert-butyl 2-((3R,5R,6S)-5-(3-chlorophenyl)-6-(4-chlorophenyl)-1-((S)-1-morpholinobutan-2-yl)-2-oxopiperidin-3-yl)acetate

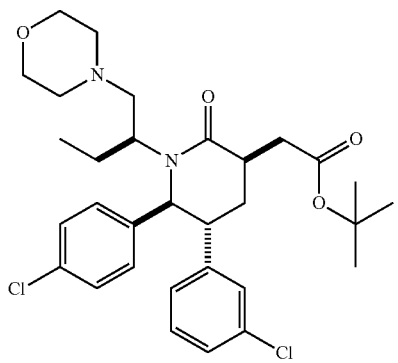 [SMILES: CC[C@@H](CN1CCOCC1)N1C(=O)[C@@H](CC(=O)OC(C)(C)C)C[C@H](c2cccc(Cl)c2)[C@H]1c1ccc(Cl)cc1]

To a solution of tert-butyl 2-((3R,5R,6S)-5-(3-chlorophenyl)-6-(4-chlorophenyl)-2-oxo-1-((S)-1-oxobutan-2-yl)piperidin-3-yl)acetate (0.050 g, 0.099 mmol, Example 21, Step C) and morpholine (0.013 mL, 0.149 mmol) in DCE (1.0 mL) was added sodium triacetoxyhydroborate (0.063 g, 0.297 mmol) at 0° C. After being stirred at 25° C. for 18 h, the reaction was quenched by adding ice-cold saturated aqueous NaHCO$_3$ and extracted (2×DCM) and the combined organic layers were washed (1×sat. aq. NaCl solution) and concentrated under the reduced pressure. This was used in next step without further purification.

Step E. 2-((3R,5R,6S)-5-(3-chlorophenyl)-6-(4-chlorophenyl)-1-((S)-1-morpholinobutan-2-yl)-2-oxopiperidin-3-yl)acetic acid To a round-bottomed flask with tert-butyl 2-((3R,5R,6S)-5-(3-chlorophenyl)-6-(4-chlorophenyl)-1-((S)-1-morpholinobutan-2-yl)-2-oxopiperidin-3-yl)acetate (0.057 g, 0.099 mmol; Example 21, Step D) in DCM (1 mL) was added TFA (1.129 g, 9.90 mmol) at 0° C. The ice-bath was removed and the mixture was stirred at rt for 3h. The solvent was removed. Purification by reversed phase preparatory HPLC (Gemini™ Prep C18 5 µm column, Phenomenex, Torrance, Calif.; eluent: 10 to 90% acetonitrile +0.1% TFA in water +0.1% TFA, gradient elution) provided the title compound as a white powder.

$^1$H NMR (400 MHz, CHLOROFORM-d) δ ppm 0.99 (m, 3 H), 1.60-2.43 (m., 4 H), 2.60-2.86 (m, 5 H), 3.11-3.40 (m, 2 H), 3.83-4.04 (m, 5 H), 4.43 (m, 2 H), 4.90 (m, 1 H), 7.01 (m, 1 H) 7.12 (m, 1 H) 7.20-7.36 (m, 2 H) 7.46 (m., 4 H); MS (ESI) 519.1 [M+H]$^+$. 517.2 [M−H]$^-$ Examples 22 to 27 were prepared in a process similar to that described for Example 21, substituting morpholine in step D for the appropriate amine.

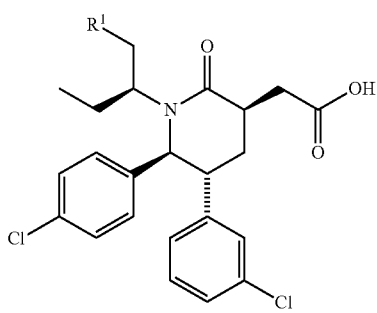

| Example | R¹ |
|---------|-----|
| 22 | ethylamino-CH₂- group (H-N-CH₂-CH₃ attached) |
| 23 | F₃C-CH₂-NH- group |
| 24 | pyrrolidin-1-yl |
| 25 | 2-oxopyrrolidin-1-yl |
| 26 | 1,1-dioxidothiomorpholino |
| 27 | thiazol-2-ylamino |

Example 22

2-((3RS,5RS,6SR)-5-(3-chlorophenyl)-6-(4-chlorophenyl)-1-((SR)-1-(ethylamino)butan-2-yl)-2-oxopiperidin-3-yl)acetic acid (prepared from racemic intermediate)

$^1$H NMR (400 MHz, CHLOROFORM-d) δ ppm 0.91-1.13 (t, J=7.8 Hz, 3 H), 1.28 (t, J=7.14 Hz, 3 H), 1.55-1.65 (m, 1 H), 1.76-1.86 (m, 1 H), 1.95-2.05 (m, 1 H), 2.31-2.59 (m, 2 H), 2.73-2.85 (m, 2 H), 2.90-3.09 (m, 5 H), 4.78-4.82 (m, 1 H), 4.88-5.02 (m, 1 H), 6.90-6.98 (m, 1 H), 7.04-7.12 (m, 1 H), 7.20-7.30 (m, 3 H), 7.36-7.42 (m, 2 H), 7.45-7.56 (m, 1H); MS (ESI) 477.1 [M+H]$^+$, 475.1 [M−H]$^-$.

Example 23

2-((3R,5R,6S)-5-(3-chlorophenyl)-6-(4-chlorophenyl)-2-oxo-1-((S)-1-(2,2,2-trifluoroethylamino)butan-2-yl)piperidin-3-yl)acetic acid $^1$H NMR (400 MHz, CHLOROFORM-d) δ ppm 0.96 (t, J=7.3 Hz, 3 H), 1.62-1.74 (m, 1 H), 1.79-1.98 (m, 2 H), 2.41-2.51 (m, 1 H), 2.61-2.75 (m, 2 H), 3.01-3.21 (m, 4 H), 3.74-3.91 (m, 2 H), 4.57 (m, 1 H), 4.89 (d, J=2.9 Hz, 1 H), 6.96-7.02 (m, 1 H), 7.12 (m, 1 H), 7.24-7.31 (m, 2 H), 7.36-7.49 (m, 4 H); MS (ESI) 531.1 [M+H]$^+$, 529.0 [M−H]$^-$.

Example 24

2-((3R,5R,6S)-5-(3-chlorophenyl)-6-(4-chlorophenyl)-2-oxo-1-((S)-1-(pyrrolidin-1-yl)butan-2-yl)piperidin-3-yl)acetic acid $^1$H NMR (400 MHz, CHLOROFORM-d) δ ppm 0.93 (m., 3 H), 1.67-1.75 (m, 2 H), 2.03-2.39 (m., 7 H), 2.74-2.91 (m, 6 H), 3.09-3.17 (m, 2 H), 3.86 (m, 1 H), 4.05 (m, 1 H), 4.86 (m, 1 H), 6.82-7.04 (m, 1 H) 7.09 (m, 1 H) 7.25 (m, 2 H) 7.44 (m, 4 H); MS (ESI) 503.2 [M+H]$^+$, 501.1 [M−H]$^-$.

Example 25

2-((3RS,5RS,6SR)-5-(3-chlorophenyl)-6-(4-chlorophenyl)-2-oxo-1-((SR)-1-(2-oxopyrrolidin-1-yl)butan-2-yl)piperidin-3-yl)acetic acid (prepared from racemic intermediate.)

Ethyl 4-aminobutanoate hydrochloride was used at the amine. After reductive amination the intermediate was cyclized by heating to 120° C. in acetic acid and toluent to provide the title compound.

$^1$H NMR (400 MHz, CHLOROFORM-d) δ ppm 0.93 (m., 3 H), 1.67 (m, 1 H), 1.82 (m, 1 H), 2.07-2.20 (m., 5 H), 2.44-2.46 (m, 3 H), 2.71-3.06 (m, 3 H), 3.20-3.30 (m, 2 H), 3.40-3.55 (m, 3 H), 3.69 (m, 1 H), 4.70 (m, 1 H), 6.99-7.04 (m, 1 H) 7.12-7.16 (m, 3 H) 7.24-7.27 (m, 2 H) 7.35 (m, 2 H); MS (ESI) 517.2 [M+H]$^+$.

Example 26

2-((3R,5R,6S)-5-(3-Chlorophenyl)-6-(4-chlorophenyl)-1-((S)-1-(1,1-dioxidothiomorpholino)butan-2-yl)-2-oxopiperidin-3-yl)acetic acid $^1$H NMR (400 MHz, CHLOROFORM-d) δ ppm 0.85 (m., 3 H) 1.71 (m, 2 H) 1.83-1.98 (m, 1 H) 2.37 (m, 1 H) 2.58 (m, 1 H) 2.63-2.83 (m, 2 H) 3.04-3.15 (m, 3 H), 3.25-3.35 (m., 6 H) 3.43-3.64 (m, 2 H) 4.88 (m, 1 H) 7.09 (m., 1 H) 7.19 (m, 1 H) 7.29 (m, 2 H) 7.34-7.50 (m, 4 H); MS (ESI) 567.1 [M+H]$^+$, 565.2 [M−H]$^-$.

Example 27

2-((3R,5R,6S)-5-(3-chlorophenyl)-6-(4-chlorophenyl)-2-oxo-1-((S)-1-(thiazol-2-ylamino)butan-2-yl)piperidin-3-yl)acetic acid $^1$H NMR (500 MHz, ACETONITRILE-d$_3$) δ ppm 0.58 (t, J=7.2 Hz, 3 H), 1.52-1.64 (m, 1 H), 1.73-1.89 (m, 1 H), 1.98-2.05 (m, 1 H), 2.05-2.16 (m, 1 H), 2.67-2.81 (m, 1 H), 2.81-2.92 (m, 2 H), 3.11-3.32 (m, 2 H), 3.50 (m, 1 H), 3.68 (m, 1 H), 4.81 (d, J=6.8 Hz, 1 H), 6.72-6.79 (m, 1 H), 7.04-7.12

(m, 1 H), 7.14 (s, 1 H), 7.17-7.23 (m, 2 H), 7.25 (d, J=4.4 Hz, 1 H), 7.29-7.41 (m, 4 H); MS (ESI) 530.0 [M–H]⁻.

Example 28

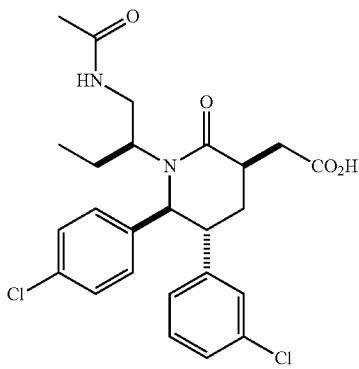 [SMILES: CC[C@@H](CNC(C)=O)N1C(=O)[C@@H](CC(=O)O)C[C@H](c2cccc(Cl)c2)[C@H]1c1ccc(Cl)cc1]

2-((3RS,5RS,6SR)-1-((SR)-1-acetamidobutan-2-yl)-5-(3-chlorophenyl)-6-(4-chlorophenyl)-2-oxopiperidin-3-yl)acetic acid (racemic)

Step A. (3SR,5RS,6SR)-3-allyl-5-(3-chlorophenyl)-6-(4-chlorophenyl)-1-((SR)-1-(4-methoxybenzylamino)butan-2-yl)piperidin-2-one To a solution of 79 mg (0.184 mmol) of (SR)-2-((3SR,5RS,6SR)-3-allyl-5-(3-chlorophenyl)-6-(4-chlorophenyl)-2-oxopiperidin-1-yl)butanal (racemate of Example 19, Step A) and 4-methoxybenzylamine (35.7 µL, 0.275 mmol) in 1.8 mL of dichloroethane was added sodium triacetoxyborohydride (117 mg, 0.551 mmol) at 0° C. in several portions. After being stirred at 25° C. for 18 h, the reaction was quenched by adding ice-cold saturated aqueous NaHCO₃ and extracted (2×DCM) and the combined organic layers were washed with sat. NaCl solution, dried over Na₂SO₄, filtered and the filtrate was concentrated under reduced pressure. Purification by flash chromatography on silica (0% to 3% MeOH/DCM with 1% aq. NH₄OH) provided the title compound as a yellow film.

Step B. (3SR,5RS,6SR)-3-allyl-1-((SR)-1-aminobutan-2-yl)-5-(3-chlorophenyl)-6-(4-chlorophenyl)piperidin-2-one To a solution of (3SR,5RS,6SR)-3-allyl-5-(3-chlorophenyl)-6-(4-chlorophenyl)-1-((SR)-1-(4-methoxybenzylamino)butan-2-yl)piperidin-2-one (88 mg, 0.160 mmol) in acetonitrile (1899 µL) and water (380 µL) was added ceric ammonium nitrate (350 mg, 0.638 mmol) at 25° C. The reaction was monitored by LCMS and HPLC and on completion was diluted with 0.5 M aq. NaOH and EtOAc and the resulting emulsion was filtered through a pad of Celite® (J. T. Baker, Phillipsberg, N.J., J. T. Baker, Phillipsberg, N.J., diatomaceous earth). The filtrate was extracted with ethyl acetate and the combined organic layers were washed with sat. NaCl solution, dried over Na₂SO₄, filtered and the filtrate was concentrated under reduced pressure to provide the crude product which was used n subsequent steps without further purification.

Step C. N-((SR)-2-((3SR,5RS,6SR)-3-allyl-5-(3-chlorophenyl)-6-(4-chlorophenyl)-2-oxopiperidin-1-yl)butyl)acetamide To a solution of 53 mg (0.123 mmol) of (3SR,5RS,6SR)-3-allyl-1-((RS)-1-aminobutan-2-yl)-5-(3-chlorophenyl)-6-(4-chlorophenyl)piperidin-2-one (Step B) in DMF (307 µL) was added acetic anhydride (116 µL, 1.229 mmol) at 25° C. After being stirred at 25° C. for 14h the reaction was quenched (H₂O) and extracted (2×EtOAc). The combined organic layers were washed with sat. NaCl solution, dried over Na₂SO₄, filtered and the filtrate was concentrated under reduced pressure. Separation by reversed phase HPLC (50 to 80% AcCN/H₂O in 25 min, 2 injections, $t_R$=15.683 min) provided the title compound as a yellow solid.

Step D. 2-((3RS,5RS,6SR)-1-((SR)-1-acetamidobutan-2-yl)-5-(3-chlorophenyl)-6-(4-chlorophenyl)-2-oxopiperidin-3-yl)acetic acid The oxidation of N-((SRR)-2-((3SR,5RS,6SR)-3-allyl-5-(3-chlorophenyl)-6-(4-chlorophenyl)-2-oxopiperidin-1-yl)butyl)acetamide to the title compound was carried out as described in Example 1, Step H to give the title compound as white solid.

¹H NMR (500 MHz, CHLOROFORM-d) δ ppm 0.80 (t, J=7.4 Hz, 3 H,) 1.62-1.75 (m, 1 H), 1.84-1.97 (m, 2 H), 2.07 (s, 3 H), 2.36-2.49 (m, 1 H), 2.64-2.80 (m, 2 H), 3.02-3.16 (m, 2 H), 3.16-3.31 (m, 1 H), 3.32-3.40 (m, 1 H), 3.74-3.90 (m, 1H), 4.76-4.82 (m, 1 H), 7.04-7.08 (m, 1 H), 7.16-7.19 (m, 1 H), 7.22-7.30 (m, 2 H), 7.32-7.38 (m, 4 H); MS (ESI) 491.0 [M+H]⁺, 489.1 [M–H]⁻.

Example 29

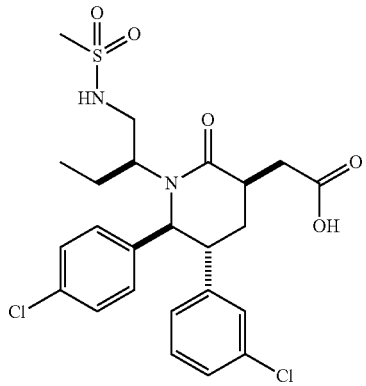 [SMILES: CC[C@@H](CNS(C)(=O)=O)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-1-((S)-1-(methylsulfonamido) butan-2-yl)-2-oxopiperidin-3-yl)acetic acid Step A. N-((S)-2-((3S,5R,6S)-3-allyl-5-(3-chlorophenyl)-6-(4-chlorophenyl)-2-oxopiperidin-1-yl)butyl)methanesulfonamide To a solution of 69 mg (0.16 mmol) of (3S,5R,6S)-3-allyl-1-((S)-1-aminobutan-2-yl)-5-(3-chlorophenyl)-6-(4-chlorophenyl)piperidin-2-one (Example 28, Step B from the non-racemic precursor described in Example 19, Step A) in 1.6 mL of DCM was added methanesulfonyl chloride (13.7 µL, 0.175 mmol) and pyridine (38.7 µL, 0.478 mmol) successively at 0° C. After being stirred at rt for 14 h the reaction mixture was acidified with 10% aq. citric acid and extracted (2×DCM). The combined organic layers were washed with sat. NaCl solution, dried over Na₂SO₄, filtered and the filtrate was concentrated under reduced pressure. Purification by Step B. 2-((3R,5R,6S)-5-(3-chlorophenyl)-6-(4-chlorophenyl)-1-((S)-1-(methylsulfonamido) butan-2-yl)-2-oxopiperidin-3-yl)acetic acid The title compound was prepared as described in Example 28, Step D, using N-((S)-2-((3S,5R,6S)-3-allyl-5-(3-chlorophenyl)-6-(4-chlorophenyl)-2-oxopiperidin-1-yl)butyl) methanesulfonamide (Step A).

$^1$H NMR (500 MHz, CHLOROFORM-d) δ ppm 0.67 (t, J=7.6 Hz, 3 H), 1.51-1.61 (m, 1 H), 1.88-1.92 (m, 1 H), 2.13-2.26 (m, 2 H), 2.79-2.89 (m, 2 H), 2.89-2.95 (m, 1 H), 2.98 (s, 3 H), 3.02-3.10 (m, 1 H), 3.17-3.21 (m, 1 H), 3.42-3.52 (m, 1 H), 4.85 (d, J=5.4 Hz, 1 H), 5.27 (br. s., 1 H), 7.02-7.10 (m, 1 H), 7.10-7.15 (m, 1 H), 7.18-7.30 (m, 4 H), 7.34 (d, J=8.6 Hz, 2 H);

MS (ESI) 527.0 [M+H]$^+$, 525.1 [M-H]$^-$.

Example 30

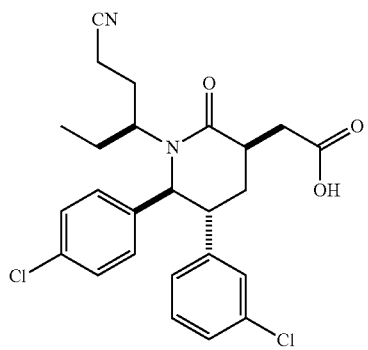 [SMILES: CC[C@@H](CCC#N)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-1-((S)-1-cyanopentan-3-yl)-2-oxopiperidin-3-yl)acetic acid Step A. tert-butyl 2-((3R,5R,6S)-5-(3-chlorophenyl)-6-(4-chlorophenyl)-1-((S)-1-cyanopent-1-en-3-yl)-2-oxopiperidin-3-yl)acetate To a solution of diethyl cyanomethylphosphonate (62.4 µL, 0.396 mmol) and DMPU (239 µL, 1.98 mmol) in THF (661 µL) was added 60% sodium hydride a s asuspension in mineral oil (11.89 mg, 0.297 mmol) at 0° C. The mixture was stirred for 30 min, and then treated with a solution of 100 mg (0.2 mmol) of tert-butyl 2-((3R,5R,6S)-5-(3-chlorophenyl)-6-(4-chlorophenyl)-2-oxo-1-((R)-1-oxobutan-2-yl)piperidin-3-yl)acetate (Example 21, Step C) in THF (661 µL). After being stirred for 12 h, the reaction was quenched with water, extracted (2×EtOAc) and the combined organic layers were washed with sat. NaCl solution, dried over Na$_2$SO$_4$, filtered and the filtrate was concentrated under reduced pressure. Purification of the residue by flash chromatography on silica gel (10 to 20% EtOAc/Hex, a gradient elution) provided the of the title compound as a mixture of E- and Z-isomers.

MS (ESI) 527.2 [M+H]$^+$.

Step B. tert-butyl 2-((3R,5R,6S)-5-(3-chlorophenyl)-6-(4-chlorophenyl)-1-((S)-1-cyanopentan-3-yl)-2-oxopiperidin-3-yl)acetate To a solution of 56 mg (0.106 mmol) of tert-butyl 2-((3R,5R,6S)-5-(3-chlorophenyl)-6-(4-chlorophenyl)-1-((S)-1-cyanopent-1-en-3-yl)-2-oxopiperidin-3-yl)acetate (Example 30, Step A) in 3.5 mL of EtOH was added 10% palladium on activated carbon (11.30 mg, 10.62 µmol). Then the reaction mixture was subjected to regular hydrogenation with hydrogen. After being stirred under a hydrogen atmosphere at rt for 2 h, the catalyst was filtered using a short plug of silica gel. The plug was washed several times with EtOAc. The combined filtrates were concentrated under reduced pressure to provide the crude title compound as a colorless film which was used in the subsequent reaction without further purification. MS (ESI) 529.2 [M+H]$^+$.

Step C. 2-((3R,5R,6S)-5-(3-chlorophenyl)-6-(4-chlorophenyl)-1-((S)-1-cyanopentan-3-yl)-2-oxopiperidin-3-yl)acetic acid To a solution of 57 mg (0.11 mmol) of tert-butyl 2-((3R,5R,6S)-5-(3-chlorophenyl)-6-(4-chlorophenyl)-1-((S)-1-cyanopentan-3-yl)-2-oxopiperidin-3-yl)acetate (Example 30, Step B) in DCM (359 µL) was added trifluoroacetic acid (415 µL, 5.38 mmol) at 0° C. After being stirred at 25 C. for 2 h, solvents were removed under reduced pressure and the residual TFA was removed by azeotroping with toluene under reduced pressure three times. Separation of the crude product by reversed phase HPLC (45 to 70% AcCN/H$_2$O in 30 min, 3 time runs, t$_R$=18.52 min) provided the title compound as a white solid.

$^1$H NMR (400 MHz, CHLOROFORM-d) δ ppm 7.37 (2 H, d, J=8.6 Hz), 7.27-7.25 (2 H, m), 7.21 (2 H, d, J=8.6 Hz), 7.15-7.12 (1 H, m), 7.04-6.98 (1 H, m), 4.74 (1 H, d, J=5.3 Hz), 3.42-3.32 (1 H, m), 3.13-3.08 (1 H, m), 3.08-3.00 (1 H, m), 2.99-2.92 (1 H, m), 2.85-2.77 (1 H, m), 2.43-2.33 (2 H, m), 2.23-2.15 (2 H, m), 2.13-2.03 (1 H, m), 1.94-1.77 (2 H, m), 1.64-1.54 (1 H, m), 0.64 (3 H, t, J=7.4 Hz); MS (ESI) 473.0 [M+H]$^+$, 471.1 [M-H]$^-$.

Examples 31 and 32 were prepared in a process similar to that described for Example 30, using the appropriately substituted phosphonates in Step A:

Example 31

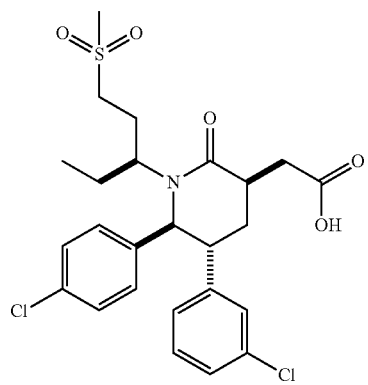 [SMILES: CC[C@@H](CCS(C)(=O)=O)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-1-((S)-1-(methylsulfonyl)pentan-3-yl)-2-oxopiperidin-3-yl)acetic acid $^1$H NMR (400 MHz, CHLOROFORM-d) δ ppm 0.71 (t, J=8.0 Hz, 3 H), 1.58-1.69 (m, 1 H), 1.82 (m, 1 H), 1.98-2.17 (m, 3 H), 2.20-2.34 (m, 1 H), 2.83-3.13 (m, 10 H), 4.80-4.84 (m, 1 H), 7.00-7.07 (m, 1 H), 7.13-7.18 (m, 1 H), 7.23-7.32 (m, 4 H), 7.34-7.41 (m, 2 H); MS (ESI) 526.2 [M+H]$^+$.

Example 32

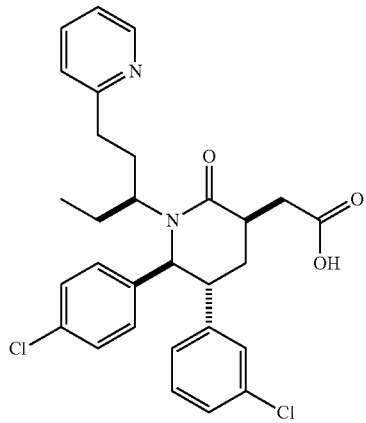 [SMILES: CC[C@@H](CCc1ccccn1)N1C(=O)[C@@H](CC(=O)O)C[C@H](c2cccc(Cl)c2)[C@H]1c1ccc(Cl)cc1]

2-((3R,5R,6S)-5-(3-chlorophenyl)-6-(4-chlorophenyl)-2-oxo-1-((S)-1-(pyridin-2-yl)pentan-3-yl)piperidin-3-yl)acetic acid $^1$H NMR (400 MHz, CHLOROFORM-d) δ ppm 0.89 (t, J=7.5 Hz, 3 H), 1.60-1.79 (m, 4 H), 1.90-1.98 (m, 1 H), 2.53 (m, 1 H), 2.61-2.69 (m, 1 H), 2.72-2.79 (m, 1 H), 2.90-3.03 (m, 2 H), 3.07-3.12 (m, 1 H), 3.19-3.28 (m, 1 H), 4.15 (m, 1 H), 4.80-4.81 (m, 1 H), 7.01-7.07 (m, 1 H), 7.15 (s, 1 H), 7.22-7.35 (m, 4 H), 7.40-7.47 (m, 1 H), 7.59 (d, J=7.82 Hz, 1 H), 7.75 (t, J=6.75 Hz, 1 H), 8.28 (t, J=7.92 Hz, 1 H), 8.85-8.89 (m, 1 H); MS (ESI) 525.1 [M+H]$^+$

Example 33

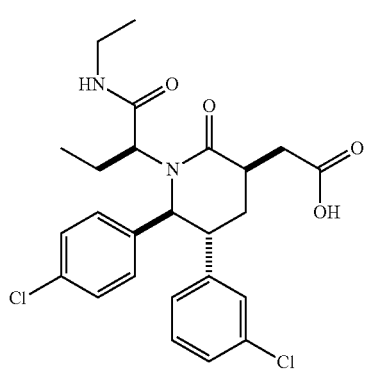

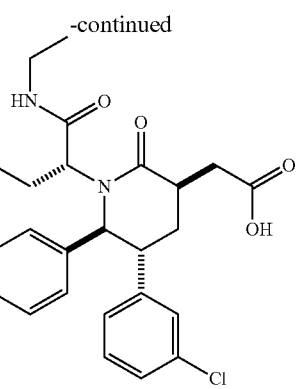

2-((3R,5R,6S)-5-(3-Chlorophenyl)-6-(4-chlorophenyl)-1-((S)-1-(ethylamino)-1-oxobutan-2-yl)-2-oxopiperidin-3-yl)acetic acid and 2-((3R,5R,6S)-5-(3-Chlorophenyl)-6-(4-chlorophenyl)-1-((R)-1-(ethylamino)-1-oxobutan-2-yl)-2-oxopiperidin-3-yl)acetic acid

Step A. (R)-2-((3S,5R,6S)-3-allyl-5-(3-chlorophenyl)-6-(4-chlorophenyl)-2-oxopiperidin-1-yl)butanoic acid To a solution of 320 mg (0.64 mmol) of tert-butyl (2S)-2-((3S,5R,6S)-3-allyl-5-(3-chlorophenyl)-6-(4-chlorophenyl)-2-oxopiperidin-1-yl)butanoate (Example 1, Step G) in DCM (3184 µL) was added trifluoroacetic acid (2453 µL, 31.8 mmol) at 0° C. After being stirred at 25 C. for 3 h, solvents were removed under reduced pressure and the residual TFA was removed by azeotroping with toluene under reduced pressure 3-times to provide the title compound as a pale yellow foam which was used in the subsequent reaction without further purification.

Step B. (S)-2-((3S,5R,6S)-3-allyl-5-(3-chlorophenyl)-6-(4-chlorophenyl)-2-oxopiperidin-1-yl)-N-ethylbutanamide A solution of 107 mg (0.24 mmol) of (S)-2-((3S,5R,6S)-3-allyl-5-(3-chlorophenyl)-6-(4-chlorophenyl)-2-oxopiperidin-1-yl)butanoic acid (Example 33, Step A) and ethylamine (31.4 µL, 0.479 mmol) in DCM (539 µL) and DMF (59.9 µL) was treated at 0° C. with N1-((ethylimino)methylene)-N3,N3-dimethylpropane-1,3-diamine hydrochloride (138 mg, 0.719 mmol), 3H-[1,2,3]triazolo[4,5-b]pyridin-3-ol (98 mg, 0.719 mmol), and sodium bicarbonate (60.4 mg, 0.719 mmol), successively. Then the reaction was stirred at 25° C. for 12 h. The reaction was diluted (1 N aq. HCl), extracted (2×EtOAc), the combined organic layers were washed with sat. aq. NaCl and NaHCO$_3$-solutions, dried over Na$_2$SO$_4$, filtered and the filtrate was concentrated under reduced pressure. Purification by chromatography on silica gel (30% to 40% EtOAc/Hexanes, a gradient elution) provided the title compound as a mixture of diastereomers (dr=5:1) as a white solid: MS (ESI) 473.2 [M+H]$^+$.

Step C. 2-((3R,5R,6S)-5-(3-chlorophenyl)-6-(4-chlorophenyl)-1-((S)-1-(ethylamino)-1-oxobutan-2-yl)-2-oxopiperidin-3-yl)acetic acid and 2-((3R,5R,6S)-5-(3-Chlorophenyl)-6-(4-chlorophenyl)-1-((R)-1-(ethylamino)-1-oxobutan-2-yl)-2-oxopiperidin-3-yl)acetic acid 2-((3S,5R,6S)-3-allyl-5-(3-chlorophenyl)-6-(4-chlorophenyl)-2-oxopiperidin-1-yl)-N-ethylbutanamide (Example 33, Step B) was converted to the acid as described in Example 1, Step H to give the title compounds as a mixture of diastereomers (dr=5:1).

$^1$H NMR (400 MHz, CHLOROFORM-d) δ ppm 0.81 (t, J=7.8 Hz, 3 H), 1.10 (t, J=7.2 Hz, 3 H), 1.65-1.75 (m, 1 H), 1.87 (m, 1 H), 2.24-2.41 (m, 2 H), 2.57-2.66 (m, 1 H), 2.70 (dd, J=16.8, 5.09 Hz, 1 H), 2.98 (dd, J=16.9, 5.58 Hz, 1 H), 3.04-3.26 (m, 3 H), 3.97 (dd, J=10.37, 4.89 Hz, 1 H), 5.05-5.10 (m, 1 H), 7.06-7.19 (m, 2 H), 7.19-7.24 (m, 1 H) 7.24-7.38 (m, 5 H); MS (ESI) 491.0 [M+H]$^+$. 489.1 [M−H]$^-$.

Example 34

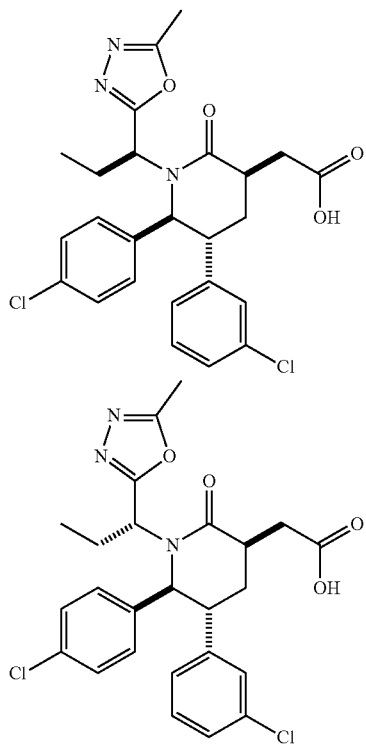

2-((3R,5R,6S)-5-(3-Chlorophenyl)-6-(4-chlorophenyl)-1-((S)-1-(5-methyl-1,3,4-oxadiazol-2-yl)propyl)-2-oxopiperidin-3-yl)acetic acid and 2-((3R,5R,6S)-5-(3-Chlorophenyl)-6-(4-chlorophenyl)-1-((R)-1-(5-methyl-1,3,4-oxadiazol-2-yl)propyl)-2-oxopiperidin-3-yl)acetic acid Step A. (S)-N'-acetyl-2-((3S,5R,6S)-3-allyl-5-(3-chlorophenyl)-6-(4-chlorophenyl)-2-oxopiperidin-1-yl)butanehydrazide A solution of 95 mg (0.213 mmol) of (S)-2-((3S,5R,6S)-3-allyl-5-(3-chlorophenyl)-6-(4-chlorophenyl)-2-oxopiperidin-1-yl)butanoic acid (Example 33, Step A) and acetic hydrazide (23.65 mg, 0.319 mmol) in DCM (479 μL) and DMF (53.2 μL) was treated at 0° C. with N1-((ethylimino)methylene)-N3,N3-dimethylpropane-1,3-diamine hydrochloride (122 mg, 0.638 mmol), 3H-[1,2,3]triazolo[4,5-b]pyridin-3-ol (87 mg, 0.638 mmol), and sodium bicarbonate (53.6 mg, 0.638 mmol) at 0° C., successively. Then the reaction was stirred at 25° C. for 12 h. The reaction was diluted with 1 N aq. HCl and extracted (2×EtOAc). The combined organic layers were washed with sat. aq. NaCl and NaHCO$_3$-solutions, dried over Na$_2$SO$_4$, filtered and the filtrate was concentrated under reduced pressure. Purification by chromatography on silica gel (60% to 80% EtOAc/Hexanes, gradient elution) provided the title compound as a colorless film. MS (ESI) 502.1 [M+H]$^+$.

Step B. (3S,5R,6S)-3-allyl-5-(3-chlorophenyl)-6-(4-chlorophenyl)-1-((S)-1-(5-methyl-1,3,4-oxadiazol-2-yl)propyl)piperidin-2-one A solution of 58 mg (0.115 mmol) of (S)-N'-acetyl-2-((3S,5R,6S)-3-allyl-5-(3-chlorophenyl)-6-(4-chlorophenyl)-2-oxopiperidin-1-yl)butanehydrazide (Example 34, Step A) and Burgess' reagent (110 mg, 0.462 mmol) in dichloroethane (1154 μL) was heated in the microwave at 120° C. for 30 min. Then the reaction mixture was diluted with water and extracted with DCM. The combined organic layers were washed with sat. aq. NaCl and NaHCO$_3$-solutions, dried over Na$_2$SO$_4$, filtered and the filtrate was concentrated under reduced pressure. Separation by reversed phase HPLC (55 to 90% MeCN/H$_2$O in 35 min, 29 mg injection each time) provided the title compound as a colorless film. MS (ESI) 484.1 [M+H]$^+$.

Step C. 2-((3R,5R,6S)-5-(3-chlorophenyl)-6-(4-chlorophenyl)-1-((S)-1-(5-methyl-1,3,4-oxadiazol-2-yl)propyl)-2-oxopiperidin-3-yl)acetic acid (3S,5R,6S)-3-allyl-5-(3-chlorophenyl)-6-(4-chlorophenyl)-1-((S)-1-(5-methyl-1,3,4-oxadiazol-2-yl)propyl)piperidin-2-one (Example 34, Step B) was converted to the acid as described in Example 1, Step H to give the title compound as a mixture of diastereomers (dr=10:1).

$^1$H NMR (400 MHz, CHLOROFORM-d) δppm 0.81 (t, J=7.8 Hz, 3 H), 1.93-2.04 (m, 2 H), 2.25 (m, 1 H), 2.26 (s, 3 H), 2.33-2.44 (m, 1 H), 2.83-2.94 (m, 3 H), 3.12 (d, J=2.3 Hz, 1 H), 5.08-5.18 (m, 1 H), 5.60 (br. s., 1 H), 7.07 (d, J=8.2 Hz, 2 H), 7.18-7.23 (m, 1 H), 7.26 (m, 1 H), 7.28 (m, 1 H), 7.30-7.35 (m, 3 H); MS (ESI) 502.1 [M+H]$^+$, 500.0 [M−H]$^-$.

Example 35

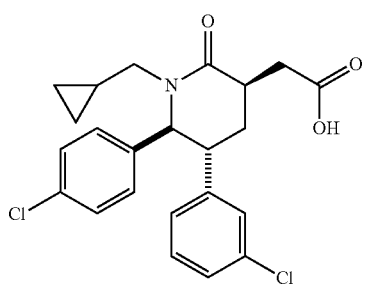

2-((3R,5R,6S)-5-(3-chlorophenyl)-6-(4-chlorophenyl)-1-(cyclopropylmethyl)-2-oxopiperidin-3-yl)acetic acid Step A. (5R,6S)-5-(3-chlorophenyl)-6-(4-chlorophenyl)-1-(cyclopropylmethyl)piperidin-2-one

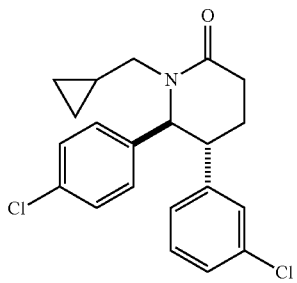

To a solution of 1.5 g (4.7 mmol) of (5R,6S)-5-(3-chlorophenyl)-6-(4-chlorophenyl)piperidin-2-one (Example 1, Step E) in 9.4 mL of DMF was added sodium hydride (60% suspension in mineral oil, 244 mg, 6.1 mmol) at 0° C. The reaction was stirred at 0° C. for 20 min and then treated with cyclopropylmethyl bromide (759 µl, 5621 µmol). After being stirred at 25° C. for 5 h, the reaction was quenched (sat. aqueous NH$_4$Cl), extracted (2×EtOAc). The combined organic layers were washed with sat. aq. NaCl and NaHCO$_3$— solutions, dried over Na$_2$SO$_4$, filtered and the filtrate was concentrated under reduced pressure. Purification of the residue by flash chromatography on silica gel (30 to 50% EtOAc/hexanes, gradient elution) provided the title compound as a colorless foam.

Step B. (3S,5R,6S)-3-allyl-5-(3-chlorophenyl)-6-(4-chlorophenyl)-1-(cyclopropylmethyl)piperidin-2-one

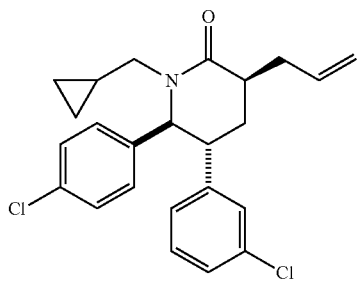

To a solution of (5R,6S)-5-(3-chlorophenyl)-6-(4-chlorophenyl)-1-(cyclopropylmethyl)piperidin-2-one (1481 mg, 3957 µmol; Example 35, Step A) and allyl bromide (360 µl, 4155 µmol) in THF (16 mL, 0.25 M) was added dropwise lithium bis(trimethylsilyl) amide (1M solution in THF, 4352 µl, 4352 µmol) at −78° C.
After being stirred at −78° C. for 3 h, the reaction was quenched (sat. aqueous NH$_4$Cl), extracted (2×EtOAc). The combined organic layers were washed with sat. aq. NaCl solution, dried over Na$_2$SO$_4$, filtered and the filtrate was concentrated under reduced pressure. Purification of the residue by flash chromatography (SiO$_2$, 20 to 30% EtOAc/Hex, gradient elution) provided the title compound as a mixture of stereoisomers.

Individual stereoisomers were separated by HPLC on a Chiralcel OD column (eluent: 25% iPA/hexanes).

Step C. 2-((3R,5R,6S)-5-(3-chlorophenyl)-6-(4-chlorophenyl)-1-(cyclopropylmethyl)-2-oxopiperidin-3-yl)acetic acid (3S,5R,6S)-3-allyl-5-(3-chlorophenyl)-6-(4-chlorophenyl)-1-(cyclopropylmethyl)piperidin-2-one (Example 35, Step B) was converted to the acid as described in Example 1, Step H to give the title compound as a white solid.

$^1$H NMR (400 MHz, CHLOROFORM-d) δ ppm 7.48-7.46 (1 H, m), 7.40 (2 H, d, J=8.6 Hz), 7.31-7.35 (2 H, m), 7.22-7.26 (1 H, m), 7.13 (2 H, d, J=8.6 Hz), 5.17 (1 H, s), 4.24 (1 H, dd, J=14.1, 6.7 Hz), 3.23-3.19 (1 H, m), 2.96-2.78 (1 H, m), 2.64-2.50 (2 H, m), 2.36 (1 H, dd, J=14.1, 7.8 Hz), 2.17-2.08 (1 H, m), 1.93-1.83 (1 H, m), 1.29-1.17 (1 H, m), 0.77-0.69 (1 H, m), 0.67-0.58 (1 H, m), 0.37-0.25 (2 H, m); MS (ESI) 432.1 [M+H]$^+$, 429.9 [M−H]$^−$.

Examples 36 to 40 were prepared in a process similar to that described for Example 35, substituting (bromomethyl)cyclopropane in Step A for the appropriate amount of alkylbromide or alkyliodide.

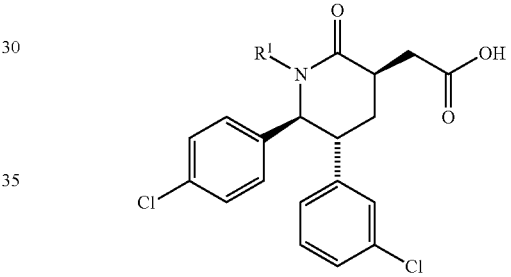

| Example | R$^1$ |
|---|---|
| 36 | cyclobutylmethyl |
| 37 | pentan-3-yl |
| 38 | cyclopentylmethyl |
| 39 | (2,2-dimethylcyclopentyl)methyl |

145

-continued

| Example | R¹ |
|---------|-----|
| 40 | 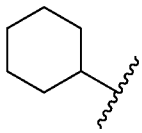 [SMILES: *C1CCCCC1] |

Example 36

2-((3R,5R,6S)-5-(3-chlorophenyl)-6-(4-chlorophenyl)-1-(cyclobutylmethyl)-2-oxopiperidin-3-yl)acetic acid $^1$H NMR (400 MHz, CDCl$_3$) δ ppm 1.62-1.74 (m, 1 H), 1.75-1.84 (m, 2 H), 1.84-2.01 (m, 2 H), 2.03-2.17 (m, 2 H), 2.18-2.29 (m, 1 H), 2.53 (dd, J=13.69 and 7.24 Hz, 1 H), 2.57-2.63 (m, 1 H), 2.63-2.70 (m, 1 H), 2.69-2.76 (m, 1 H), 2.76-2.85 (m, 1 H), 3.04-3.17 (m, 1 H), 4.25 (dd, J=13.69 and 7.63 Hz, 1 H), 4.76-4.89 (m, 1 H), 7.07-7.17 (m, 1 H), 7.22 (d, J=8.61 Hz, 2 H), 7.27-7.31 (m, 3 H), 7.39 (d, J=8.61 Hz, 2 H). MS (ESI) 446.2 [M+H]$^+$.

Example 37

2-((3R,5R,6S)-5-(3-chlorophenyl)-6-(4-chlorophenyl)-1-(2-ethylbutyl)-2-oxopiperidin-3-yl)acetic acid $^1$H NMR (400 MHz, CHLOROFORM-d) δ ppm 7.37 (2 H, d, J=8.4 Hz), 7.27 (2 H, m), 7.18 (1 H, s), 7.15 (2 H, d, J=8.4 Hz), 7.03 (1 H, m), 4.67 (1 H, d, J=7.5 Hz), 3.29 (1 H, m), 3.09-2.97 (3 H, m), 2.72 (1 H, dd, J=15.4, 3.7 Hz), 2.20-2.00 (2 H, m), 1.83 (1 H, m), 1.68 (1 H, m), 1.55-1.40 (2 H, m), 0.89 (3 H, t, J=8.0 Hz), 0.55 (3 H, t, J=8 Hz); MS (ESI) 448.1 [M–H]$^-$.

Example 38

2-((3R,5R,6S)-5-(3-chlorophenyl)-6-(4-chlorophenyl)-1-(cyclopentylmethyl)-2-oxopiperidin-3-yl)acetic acid $^1$H NMR (400 MHz, CHLOROFORM-d) δ ppm 7.42 (2 H, d, J=8.4 Hz), 7.31 (2 H, m), 7.24 (1 H, s), 7.20 (2 H, d, J=8.4 Hz), 7.11 (1 H, m), 4.93 (1 H, s), 3.87 (1 H, m), 3.16 (1 H, m), 2.81 (1 H, dd, J=16.4, 7.8 Hz), 2.68 (1 H, dd, J=16.4, 3.9 Hz), 2.57 (1 H, m), 2.12 (1 H, m), 2.00 (1 H, m), 1.90-1.65 (6 H, m), 1.55-1.40 (2 H, m); MS (ESI) 446.0 [M–H]$^-$.

Example 39

2-((3R,5R,6S)-5-(3-chlorophenyl)-6-(4-chlorophenyl)-1-((2,2-dimethylcyclopentyl)methyl)-2-oxopiperidin-3-yl)acetic acid $^1$H NMR (400 MHz, CHLOROFORM-d) δ ppm 7.41 (2 H, d, J=8.2 Hz), 7.39 (1 H, m), 7.35-7.27 (3 H, m), 7.13 (2 H, d, J=8.2 Hz), 4.93 (1 H, s), 4.45 (1 H, m), 3.20 (2 H, m), 3.00 (1 H, dd, J=16.8, 8.0 Hz), 2.51 (1 H, dd, J=16.8, 3.3 Hz), 2.10 (1H, m), 1.90 (1 H, m), 1.65-1.35 (5 H, m), 0.88 (3 H, s), 0.53 (3 H, s); MS (ESI) 474.1 [M–H]$^-$.

146

Example 40

2-((3R,5R,6S)-5-(3-chlorophenyl)-6-(4-chlorophenyl)-1-(cyclohexylmethyl)-2-oxopiperidin-3-yl)acetic acid $^1$H NMR (400 MHz, CHLOROFORM-d) δ ppm 7.41 (2 H, d, J=8.6 Hz), 7.35-7.27 (3 H, m), 7.18 (2 H, d, J=8.6 Hz), 7.14 (1 H, m), 4.95 (1 H, s), 3.08 (1 H, m), 2.90 (1 H, dd, J=15.8, 9.2 Hz), 2.65 (1 H, m), 2.51 (1 H, dd, J=15.8, 2.7 Hz), 2.10 (1 H, m), 1.90-1.55 (4 H, m), 1.35-1.20 (8 H, m); MS (ESI) 460.4 [M–H]$^-$.

Example 41

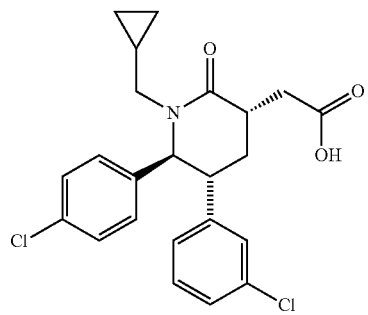

2-((3S,5R,6S)-5-(3-chlorophenyl)-6-(4-chlorophenyl)-1-(cyclopropylmethyl)-2-oxopiperidin-3-yl)acetic acid (3R,5R,6S)-3-allyl-5-(3-chlorophenyl)-6-(4-chlorophenyl)-1-(cyclopropylmethyl)piperidin-2-one (Example 35, Step B) was converted to the acid as described in Example 1, Step H to give the title compound as a white solid.

$^1$H NMR (400 MHz, CHLOROFORM-d) δ ppm 7.24 (2 H, d, J=8.2 Hz), 7.23-7.19 (1 H, m), 7.17-7.12 (1 H, t, J=7.4 Hz), 7.01 (1 H, s), 6.86 (2 H, d, J=8.2 Hz), 6.74 (1 H, d, J=7.4 Hz), 4.63 (1 H, d, J=10.2 Hz), 3.92 (1 H, dd, J=14.1, 6.3 Hz), 3.12-2.92 (3 H, m), 2.60 (1 H, dd, J=15.5, 3.3 Hz), 2.34 (1 H, dd, J=14.1, 7.4 Hz), 2.29-2.08 (2 H, m), 0.95-0.85 (1 H, m), 0.55-0.47 (1 H, m), 0.46-0.39 (1 H, m), 0.15-(-)0.02 (2 H, m); MS (ESI) 432.0 [M+H]$^+$, 429.9 [M–H]$^-$.

Example 42

2-((3S,5R,6S)-5-(3-chlorophenyl)-6-(4-chlorophenyl)-2-oxo-1-propylpiperidin-3-yl)acetic acid

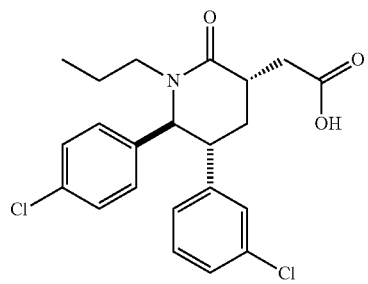

Step A. (3R,5R,6S)-3-allyl-5-(3-chlorophenyl)-6-(4-chlorophenyl)piperidin-2-one

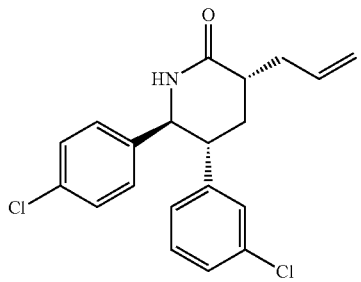 [SMILES: C=CC[C@@H]1C[C@H](c2cccc(Cl)c2)[C@@H](c2ccc(Cl)cc2)NC1=O]

A 100 mL flame-dried round-bottomed flask equipped with a magnetic stir bar was charged with (5R,6S)-5-(3-chlorophenyl)-6-(4-chlorophenyl)piperidin-2-one (1.32 g, 4.12 mmol) (Example 1, Step E) and anhydrous THF (41.2 mL). This solution was cooled to 0° C. under argon and BuLi (3.30 mL, 8.24 mmol) was added. After 10 minutes allyl bromide (0.357 mL, 4.12 mmol) was added. After an additional 45 minutes the reaction was quenched by the addition of sat. aq. NH$_4$Cl and the layers were separated. The aqueous layer was extracted with EtOAc twice and the organics were pooled, washed with sat. aq. NaCl solution, dried (MgSO$_4$), filtered and concentrated in vacuo to provide a colorless oil. Purification using a Combiflash Companion (flash column chromatography, Teledyne Isco, Lincoln, Nebr.) with a 120 g SiO$_2$ column and eluting with 10 to 100% EtOAc/hexanes provided the title compound.

$^1$H NMR (400 MHz, CDCl$_3$) δ ppm 2.07 (m, 1H), 2.15 (m, 1H), 2.45 (m, 1H), 2.69 (m, 1H), 2.80 (m, 1H), 2.88 (m, 1H), 4.49 (d, J=10.3 Hz, 1H), 5.13 (m, 2H), 5.82 (br s, 1H), 5.84 (m, 1H), 6.77 (m, 1H), 6.95 (d, J=8.4 Hz, 2H), 7.01 (m, 1H), 7.12 (t, J=7.7 Hz, 1H), 7.18 (m, 1H), 7.21 (d, J=8.6 Hz, 2H).

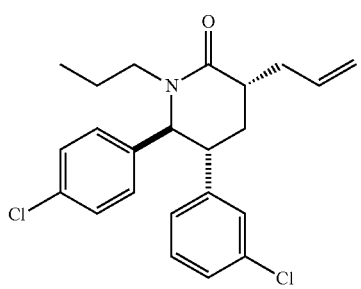

Step B. (3R,5R,6S)-3-allyl-5-(3-chlorophenyl)-6-(4-chlorophenyl)-1-propylpiperidin-2-one To a solution of (3R,5R,6S)-3-allyl-5-(3-chlorophenyl)-6-(4-chlorophenyl)piperidin-2-one (Example 42, Step A) (70 mg, 0.19 mmol) in 430 μL of DMF was added sodium hydride (60% suspension in mineral oil, 20 mg, 0.51 mmol) at 0° C. The reaction was stirred at 0° C. for 15 min and then treated with 1-bromopropane (53 μL, 0.58 mmol). After being stirred at 25° C. for 4 h, the reaction was quenched with sat. aqueous NaHCO$_3$ and extracted (2×EtOAc). The combined organic layers were washed with sat. aq. NaCl and NaHCO$_3$-solutions, dried over Na$_2$SO$_4$, filtered and the filtrate was concentrated under reduced pressure. Purification of the residue by silica gel prep plate (25% EtOAc/hexanes) provided the title compound as a colorless solid.

Step C. 2-((3S,5R,6S)-5-(3-chlorophenyl)-6-(4-chlorophenyl)-2-oxo-1-propylpiperidin-3-yl)acetic acid The title compound was obtained from (3R,5R,6S)-3-allyl-5-(3-chlorophenyl)-6-(4-chlorophenyl)-1-propylpiperidin-2-one (Example 42, Step B) by a procedure similar to the one described in Example 1, Step H. Purification by silica gel prep plate (5% MeOH/DCM) provided the title compound as a white solid.

$^1$H NMR (400 MHz, CDCl$_3$) δ ppm 0.78 (t, J=7.34 Hz, 3 H) 1.33-1.45 (m, 1 H) 1.45-1.57 (m, 1 H) 2.05-2.21 (m, 2 H) 2.48 (ddd, J=13.89, 9.39 and 5.09 Hz, 1 H) 2.60 (dd, J=15.94 and 4.79 Hz, 1 H) 2.96 (dd, J=16.04 and 7.43 Hz, 1 H) 2.97-3.02 (m, 1 H) 3.02-3.12 (m, 1 H) 3.75 (ddd, J=13.69, 9.68 and 6.36 Hz, 1 H) 4.41 (d, J=10.17 Hz, 1 H) 6.66-6.76 (m, 1 H) 6.87 (d, J=8.41 Hz, 2 H) 6.97 (t, J=1.66 Hz, 1 H) 7.12 (t, J=7.83 Hz, 1 H) 7.16-7.20 (m, 1 H) 7.23 (d, J=8.41 Hz, 2 H). MS (ESI) 420.2 [M+H]$^+$.

Example 43

2-((3S,5R,6S)-5-(3-chlorophenyl)-6-(4-chlorophenyl)-1-(cyclobutylmethyl)-2-oxopiperidin-3-yl)acetic acid

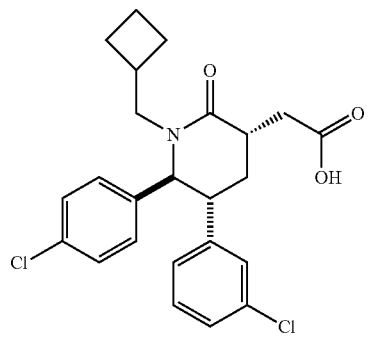

Step A. (5R,6S)-3-allyl-5-(3-chlorophenyl)-6-(4-chlorophenyl)-1-(cyclobutylmethyl)piperidin-2-one

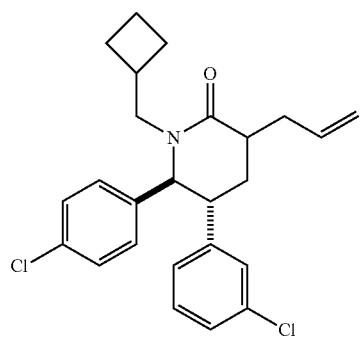

To a solution of (3R,5R,6S)-3-allyl-5-(3-chlorophenyl)-6-(4-chlorophenyl)piperidin-2-one (Example 42, Step A) (70 mg, 0.19 mmol) in 430 μL of DMF was added sodium hydride (60% suspension in mineral oil, 20 mg, 0.51 mmol) at 0° C. The reaction mixture was stirred at 0° C. for 15 min and after treatment with (bromomethyl)cyclobutane (66 μL, 0.58 mmol) the reaction mixture was heated to 70° C. for 15 h. The reaction mixture was cooled to room temperature, quenched with sat. aqueous NaHCO$_3$ and extracted (2×EtOAc). The combined organic layers were washed with sat. aq. NaCl and NaHCO$_3$-solutions, dried over Na$_2$SO$_4$, filtered and the filtrate was concentrated under reduced pressure. Purification of the residue by silica gel prep plate (25% EtOAc/hexanes) provided the title compound as a colorless solid.

Step B. 2-((3S,5R,6S)-5-(3-chlorophenyl)-6-(4-chlorophenyl)-1-(cyclobutylmethyl)-2-oxopiperidin-3-yl)acetic acid The title compounds were prepared from (5R,6S)-3-allyl-5-(3-chlorophenyl)-6-(4-chlorophenyl)-1-(cyclobutylmethyl)piperidin-2-one (Example 43, Step A) as described in Example 1 Step H and purified by reversed phase HPLC on an Eclipse column (45-60% acetonitrile/water, gradient elution) to provide the title compound as a white solid.
$^1$H NMR (400 MHz, CDCl$_3$) δ ppm 1.52-1.69 (m, 2 H), 1.72-1.90 (m, 2 H), 1.91-2.09 (m, 3 H), 2.14 (t, J=12.52 Hz, 1 H), 2.42 (dd, J=13.50 and 7.43 Hz, 1 H), 2.46-2.57 (m, 1 H), 2.62 (dd, J=16.43 and 6.85 Hz, 1 H), 2.86-3.01 (m, 2 H), 3.01-3.12 (m, 1 H), 4.05 (dd, J=13.50 and 7.24 Hz, 1 H), 4.38 (d, J=9.98 Hz, 1 H), 6.70 (d, J=7.43 Hz, 1 H), 6.84 (d, J=8.22 Hz, 2 H), 6.97 (s, 1 H), 7.12 (t, J=7.83 Hz, 1 H), 7.16-7.20 (m, 1 H), 7.22 (d, J=8.22 Hz, 2 H). MS (ESI) 446.2 [M+H]$^+$.

Example 44

2-((3S,5R,6S)-5-(3-chlorophenyl)-6-(4-chlorophenyl)-1-isobutyl-2-oxopiperidin-3-yl)acetic acid

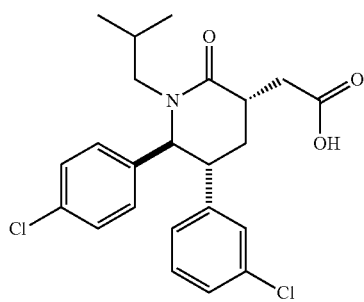

Step A. (3R,5R,6S)-3-allyl-5-(3-chlorophenyl)-6-(4-chlorophenyl)-1-isobutylpiperidin-2-one

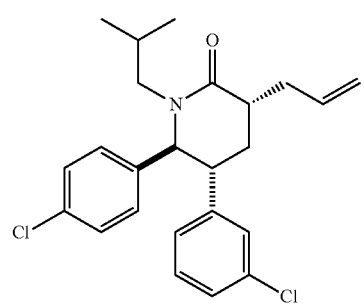

To a solution of (3R,5R,6S)-3-allyl-5-(3-chlorophenyl)-6-(4-chlorophenyl)piperidin-2-one (Example 42, Step A) (78 mg, 0.22 mmol) in 480 μL of DMF was added potassium tert-butoxide (40 mg, 0.54 mmol) at 0° C. The reaction mixture was stirred at 0° C. for 15 min and then treated with 1-bromo-2-methylpropane (82 μL, 0.76 mmol). After being stirred at 25° C. for 4 h, the reaction was quenched with sat. aqueous NaHCO$_3$ and extracted (2×EtOAc). The combined organic layers were washed with sat. aq. NaCl and NaHCO$_3$-solutions, dried over Na$_2$SO$_4$, filtered and the filtrate was concentrated under reduced pressure. Purification of the residue by silica gel prep plate (25% EtOAc/hexanes) provided the title compound as a colorless solid.

Step B. 2-((3S,5R,6S)-5-(3-chlorophenyl)-6-(4-chlorophenyl)-1-isobutyl-2-oxopiperidin-3-yl)acetic acid The title compound was prepared from (3R,5R,6S)-3-allyl-5-(3-chlorophenyl)-6-(4-chlorophenyl)-1-isobutylpiperidin-2-one (Example 44, Step A) as described in Example 1, Step H to provide a white solid.
$^1$H NMR (400 MHz, CDCl$_3$) δ ppm 0.83 (d, J=6.65 Hz, 3 H), 0.85 (d, J=6.85 Hz, 3 H), 1.93 (dq, J=8.39 and 6.66 Hz, 1 H), 2.06-2.16 (m, 2 H), 2.17-2.24 (m, 1 H), 2.60 (dd, J=15.85 and 4.30 Hz, 1 H), 2.90-2.97 (m, 1 H), 2.97-3.03 (m, 1 H), 3.04-3.13 (m, 1 H), 3.86 (dd, J=13.69 and 8.80 Hz, 1 H), 4.41 (d, J=10.17 Hz, 1 H), 6.68-6.76 (m, 1 H), 6.84 (d, J=8.41 Hz, 2 H), 6.96 (t, J=1.76 Hz, 1 H), 7.14 (t, J=7.82 Hz, 1 H), 7.18-7.22 (m, 1 H), 7.24 (m, 2 H). MS (ESI) 434.2 [M+H]$^+$.

Example 45

2-((3S,5R,6S)-5-(3-chlorophenyl)-6-(4-chlorophenyl)-1-(cyclopentylmethyl)-2-oxopiperidin-3-yl)acetic acid

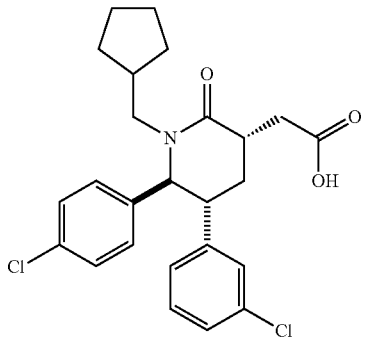

Step A. (3R,5R,6S)-3-allyl-5-(3-chlorophenyl)-6-(4-chlorophenyl)-1-(cyclopentylmethyl)piperidin-2-one

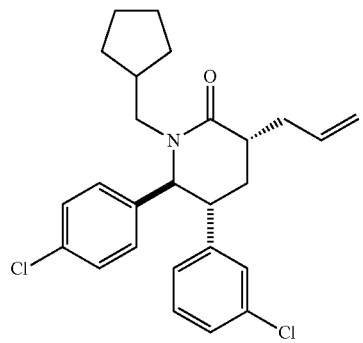

The title compound was prepared from (3R,5R,6S)-3-allyl-5-(3-chlorophenyl)-6-(4-chlorophenyl)piperidin-2-one (Example 42, Step A) and (bromomethyl)cyclopentane as described in Example 44, Step A. Purification of the residue by silica gel prep plate (25% EtOAc/hexanes) provided the title compound as a colorless solid.

Step B. 2-((3S,5R,6S)-5-(3-chlorophenyl)-6-(4-chlorophenyl)-1-(cyclopentylmethyl)-2-oxopiperidin-3-yl)acetic acid The title compound was prepared from (3R,5R,6S)-3-allyl-5-(3-chlorophenyl)-6-(4-chlorophenyl)-1-(cyclopentylmethyl)piperidin-2-one (Example 45, Step A) as described in Example 1, Step H to provide a white solid.

$^1$H NMR (500 MHz, CDCl$_3$) δ ppm 1.02-1.10 (m, 1 H), 1.12-1.19 (m, 1 H), 1.46-1.57 (m, 2 H), 1.59-1.71 (m, 4 H), 2.04-2.21 (m, 3 H), 2.32 (dd, J=13.69 and 6.85 Hz, 1 H), 2.60 (dd, J=15.77 and 4.03 Hz, 1 H), 2.92-3.01 (m, 2 H), 3.06 (dd, J=11.98 and 7.09 Hz, 1 H), 4.02 (dd, J=13.69 and 8.56 Hz, 1 H), 4.48 (d, J=10.03 Hz, 1 H), 6.72 (d, J=7.82 Hz, 1 H), 6.84 (d, J=8.31 Hz, 2 H), 6.93-7.00 (m, 1 H), 7.14 (t, J=7.70 Hz, 1 H), 7.18-7.22 (m, 1 H), 7.24 (m, 2 H). MS (ESI) 460.2 [M+H]$^+$.

Example 46

2-((3S,5R,6S)-5-(3-chlorophenyl)-6-(4-chlorophenyl)-2-oxo-1-(pentan-3-yl)piperidin-3-yl)acetic acid

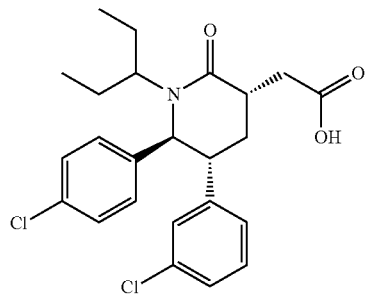 [SMILES: CCC(CC)N1C(=O)[C@H](CC(=O)O)C[C@H](c2cccc(Cl)c2)[C@H]1c1ccc(Cl)cc1]

Step A. (3R,5R,6S)-3-allyl-5-(3-chlorophenyl)-6-(4-chlorophenyl)-1-(pentan-3-yl)piperidin-2-one

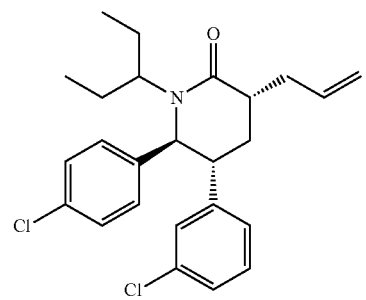 [SMILES: C=CC[C@@H]1C[C@H](c2cccc(Cl)c2)[C@@H](c2ccc(Cl)cc2)N(C(CC)CC)C1=O]

To a solution of (3R,5R,6S)-3-allyl-5-(3-chlorophenyl)-6-(4-chlorophenyl)piperidin-2-one (Example 42, Step A) (440 mg, 1.221 mmol) in 3-bromopentane (3196 μL, 25.6 mmol) under nitrogen at rt was added a dispersion of 60% sodium hydride in mineral oil (244 mg, 6.11 mmol). Evolution of gas was observed. The reaction was stirred at room temperature for 10 min and then heated to 120° C. under N$_2$ for 19 h. The reaction mixture was cooled to room temperature and quenched with sat. NH$_4$Cl. The layers were separated and the organic layer was dried over Na$_2$SO$_4$ and concentrated under reduced pressure. The residue was purified by flash chromatography on silica gel (eluent: 0 to 25% EtOAc in hexanes) to give the title compound (375 mg, 71% yield) as a mixture of diastereomers.

Step B. 2-((3S,5R,6S)-5-(3-chlorophenyl)-6-(4-chlorophenyl)-2-oxo-1-(pentan-3-yl)piperidin-3-yl)acetic acid The title compound was prepared from (5R,6S)-3-allyl-5-(3-chlorophenyl)-6-(4-chlorophenyl)-3-ethyl-1-(pentan-3-yl)piperidin-2-one (Example 46, Step A) as described in Example 1 Step H. Purification by reversed phase preparatory HPLC (eluent: 0 to 100% MeCN +0.1% TFA in water +0.1% TFA, over 20 minutes) provided the title compound.

$^1$H NMR (400 MHz, CHLOROFORM-d) δ ppm 0.55 (t, J=7.53 Hz, 3 H) 0.94 (t, J=7.34 Hz, 3 H) 1.32-1.54 (m, 2 H) 1.85 (tt, J=14.38 and 7.24 Hz, 2 H) 2.04-2.12 (m, 1 H) 2.18 (q, J=12.72 Hz, 1 H) 2.66 (dd, J=16.14 and 4.40 Hz, 1 H) 2.85-3.01 (m, 2 H) 3.01-3.17 (m, 2 H) 4.33 (d, J=9.98 Hz, 1 H) 6.71 (d, J=7.63 Hz, 1 H) 6.90-7.01 (m, 3 H) 7.09-7.22 (m, 2 H) 7.23-7.26 (m, 1 H) 10.11 (br. s., 1 H). Mass spectrum (ESI) m/z=448 [M+H]$^+$.

Example 47

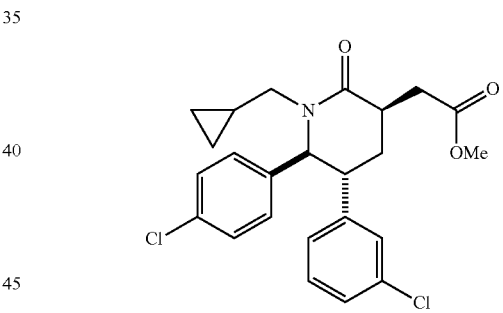

Methyl 2-((3R,5R,6S)-5-(3-chlorophenyl)-6-(4-chlorophenyl)-1-(cyclopropylmethyl)-2-oxopiperidin-3-yl)acetate To a suspension of 250 mg (0.578 mmol) of 2-((3R,5R,6S)-5-(3-chlorophenyl)-6-(4-chlorophenyl)-1-(cyclopropylmethyl)-2-oxopiperidin-3-yl)acetic acid (Example 35) in MeOH (3 mL) was added thionyl chloride (78.0 μl, 1070 μmol) dropwise at 0° C. After being stirred at 25° C. for 14h, the reaction was diluted (EtOAc), basified (sat NaHCO$_3$), extracted (2×EtOAc). The combined organic layers were washed with sat. aq. NaCl solution, dried over Na$_2$SO$_4$, filtered and the filtrate was concentrated under reduced pressure to provide the title compound as a colorless liquid.

$^1$H NMR (400 MHz, CHLOROFORM-d) δ ppm 7.53-7.49 (1 H, m), 7.39 (2 H, d, J=8.6 Hz), 7.31-7.28 (2 H, m), 7.27-7.22 (3 H, m), 5.12 (1 H, s), 4.25-4.18 (1 H, m), 3.69 (3 H, s), 3.20-3.14 (1 H, m), 2.85-2.82 (1 H, m), 2.69-2.63 (1 H, m), 2.60-2.53 (1 H, m), 2.33-2.20 (2 H, m), 1.85-1.77 (1 H, m), 1.20-1.15 (1 H, m), 0.70-0.63 (1 H, m), 0.61-0.53 (1 H, m), 0.30-0.20 (2 H, m); MS (ESI) 445.9 [M+H]$^+$.

Example 48

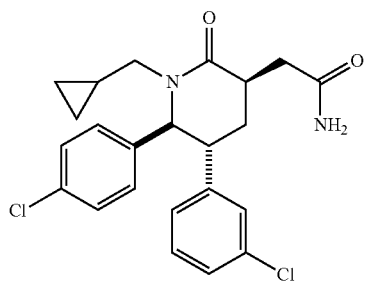 [SMILES: NC(=O)C[C@H]1C[C@H](c2cccc(Cl)c2)[C@@H](c2ccc(Cl)cc2)N(CC2CC2)C1=O]

2-((3R,5R,6S)-5-(3-chlorophenyl)-6-(4-chlorophenyl)-1-(cyclopropylmethyl)-2-oxopiperidin-3-yl)acetamide In a sealed tube, 60 mg (134 μmol) of methyl 2-((3R,5R,6S)-5-(3-chlorophenyl)-6-(4-chlorophenyl)-1-(cyclopropylmethyl)-2-oxopiperidin-3-yl)acetate (Example 47) and 4.8 mL of a solution of ammonia in methanol (7N, 3.4 mmol) were stirred at 25° C. for 5 days. Then NaCN (3 mg) was added and the resulting solution was stirred at 50° C. for 3 days. Excess NH$_3$ and MeOH were removed under reduced pressure. Separation by reversed phase HPLC (10 to 90% AcCN/H$_2$O in 45 min) provided the title compound as a a white solid.

$^1$H NMR (400 MHz, CHLOROFORM-d) δ ppm 7.52-7.45 (1 H, m), 7.37 (2 H, d, J=8.2 Hz), 7.33-7.29 (2 H, m), 7.26-7.22 (1 H, m), 7.17 (2 H, d, J=8.6 Hz), 6.40 (1 H, br. s.), 5.42 (1 H, br. s.), 5.11 (1 H, br. s.), 4.21 (1 H, dd, J=14.1, 6.3 Hz), 3.20-3.16 (1 H, m), 2.77-2.70 (1 H, m), 2.60-2.48 (2 H, m), 2.33-2.25 (2 H, m), 1.92-1.85 (1 H, m), 1.22-1.15 (1 H, m), 0.72-0.64 (1 H, m), 0.62-0.54 (1 H, m), 0.32-0.20 (2 H, m); MS (ESI) 430.9 [M+H]$^+$.

Example 49

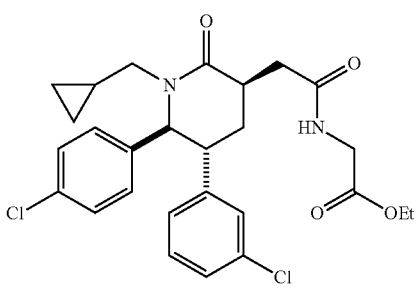 [SMILES: CCOC(=O)CNC(=O)C[C@H]1C[C@H](c2cccc(Cl)c2)[C@@H](c2ccc(Cl)cc2)N(CC2CC2)C1=O]

Ethyl 2-(2-((3R,5R,6S)-5-(3-chlorophenyl)-6-(4-chlorophenyl)-1-(cyclopropylmethyl)-2-oxopiperidin-3-yl)acetamido)acetate A solution of 40 mg (93 μmol) of 2-((3R,5R,6S)-5-(3-chlorophenyl)-6-(4-chlorophenyl)-1-(cyclopropylmethyl)-2-oxopiperidin-3-yl)acetic acid (Example 35) and ethyl 2-aminoacetate hydrochloride (14 mg, 102 μmol) in DMF (0.31 mL) was treated at 0° C. with N1-((ethylimino)methylene)-N3,N3-dimethylpropane-1,3-diamine hydrochloride (27 mg, 139 μmol), 3H-[1,2,3]triazolo[4,5-b]pyridin-3-ol (19 mg, 139 μmol), and sodium hydrogencarbonate (23 mg, 278 μmol), successively. After being stirred at 25° C. for 12 h, the reaction was diluted with water and extracted with EtOAc. The combined organic layers were successively washed with 10% aq. citric acid solution, sat. aq. NaHCO$_3$ solution and sat. aq. NaCl solution, dried over Na$_2$SO$_4$, filtered and the filtrate was concentrated under reduced pressure. Purification of the residue by flash chromatography (SiO$_2$, 40% to 60% EtOAc/Hexanes, gradient elution) provided the title compound as a colorless film.

$^1$H NMR (400 MHz, CHLOROFORM-d) δ ppm 7.51-7.47 (1 H, m), 7.35 (2 H, d, J=8.6 Hz), 7.32-7.28 (2 H, m), 7.26-7.24 (1 H, m), 7.16 (2 H, d, J=8.2 Hz), 6.89 (1 H, br, s), 5.11 (1 H, s), 4.27-4.18 (3 H, m), 4.11-3.98 (2 H, m), 3.20-3.15 (1 H, d, J=1.6 Hz), 2.83-2.72 (1 H, m), 2.63-2.55 (2 H, m), 2.32-2.16 (2 H, m), 1.95-1.87 (1 H, m), 1.29 (3 H, t, J=7.0 Hz), 1.22-1.12 (1 H, m), 0.72-0.62 (1 H, m), 0.60-0.52 (1 H, m), 0.30-0.18 (2 H, m); MS (ESI) 516.8 [M+H]$^+$.

Example 50

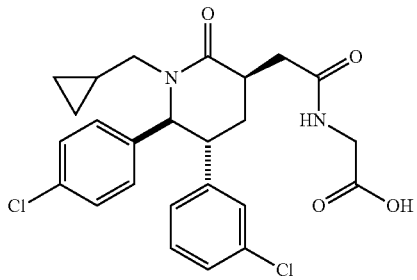 [SMILES: O=C(O)CNC(=O)C[C@H]1C[C@H](c2cccc(Cl)c2)[C@@H](c2ccc(Cl)cc2)N(CC2CC2)C1=O]

2-(2-((3R,5R,6S)-5-(3-Chlorophenyl)-6-(4-chlorophenyl)-1-(cyclopropylmethyl)-2-oxopiperidin-3-yl)acetamido)acetic acid To a solution of 38 mg (73 μmol) of ethyl 2-(2-((3R,5R,6S)-5-(3-chlorophenyl)-6-(4-chlorophenyl)-1-(cyclopropylmethyl)-2-oxopiperidin-3-yl)acetamido)acetate (Example 49) in 0.75 mL of MeOH/THF/H$_2$O (2/2/1) was added a 2M solution of lithium hydroxide in water (70 μl, 141 μmol) at 25° C. and the mixture was stirred for 10 h. The reaction was acidified (1N aq. HCl) and extracted with DCM (2×). The combined organic layers were successively washed with 10% aq. citric acid solution and sat. aq. NaCl solution, dried over Na$_2$SO$_4$, filtered and the filtrate was concentrated under reduced pressure. Purification of the residue by reversed phase HPLC (10 to 90% AcCN/H$_2$O with 0.1% TFA in 45 min) provided the title compound as a white solid.

$^1$H NMR (400 MHz, CHLOROFORM-d) δ ppm 7.37-7.34 (1 H, m), 7.35 (2 H, d, J=8.2 Hz), 7.27-7.25 (1 H, m), 7.23-7.19 (1 H, m), 7.17-7.14 (1 H, m), 7.08 (2 H, d, J=8.2 Hz), 5.00 (1 H, d, J=3.9 Hz), 4.18-4.08 (2 H, m), 4.07-3.99 (1 H, m), 3.23-3.18 (1 H, m), 2.83-2.75 (1 H, m), 2.72-2.64 (1 H, m), 2.35-2.23 (2 H, m), 2.05-1.95 (1 H, m), 1.16-1.05 (1 H, d, J=1.2 Hz), 0.68-0.60 (1 H, m), 0.58-0.50 (1 H, m), 0.27-0.13 (2 H, m); MS (ESI) 488.8 [M+H]⁺, 486.9 [M−H]⁻.

Example 51

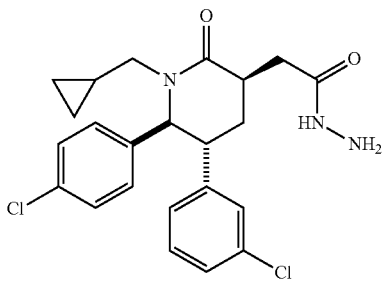 [SMILES: NNC(=O)C[C@H]1C[C@H](c2cccc(Cl)c2)[C@@H](c2ccc(Cl)cc2)N(CC2CC2)C1=O]

2-((3R,5R,6S)-5-(3-Chlorophenyl)-6-(4-chlorophenyl)-1-(cyclopropylmethyl)-2-oxopiperidin-3-yl)acetohydrazide To a solution of 120 mg (0.27 mmol) of methyl 2-((3R,5R,6S)-5-(3-chlorophenyl)-6-(4-chlorophenyl)-1-(cyclopropylmethyl)-2-oxopiperidin-3-yl)acetate (Example 47) in EtOH was added hydrazine, monohydrate (135 µl, 2688 µmol). After being refluxed for 14 h, the reaction was concentrated, diluted (H₂O) and extracted (2×EtOAc). The combined organic layers were washed with sat. aq. NaCl solution, dried over Na₂SO₄, filtered and the filtrate was concentrated under reduced pressure. Purification of the residue by flash chromatography on silica gel (5% MeOH/CH₂Cl₂, gradient elution) provided the title compound as a white solid.

$^1$H NMR (400 MHz, CHLOROFORM-d) δ ppm 7.52-7.46 (1 H, m), 7.37 (2 H, d, J=8.6 Hz), 7.33-7.28 (2 H, m), 7.26-7.22 (1 H, m), 7.15 (2 H, d, J=8.6 Hz), 5.10 (1 H, s), 4.20 (1 H, dd, J=14.1, 6.7 Hz), 3.20-3.15 (1 H, m), 2.71-2.63 (1 H, m), 2.60-2.48 (2 H, m), 2.31-2.18 (1 H, m), 1.92-1.82 (1 H, m), 1.20-1.10 (1 H, dt, J=7.9, 3.3 Hz), 0.70-0.63 (1 H, m), 0.59-0.52 (1 H, m), 0.30-0.18 (2 H, m); MS (ESI) 445.9 [M+H]⁺.

Example 52

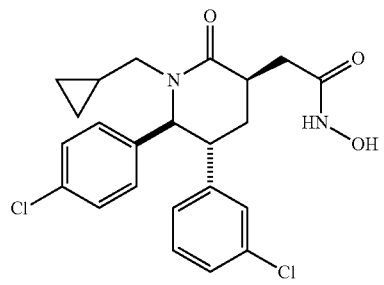 [SMILES: O=C(C[C@H]1C[C@H](c2cccc(Cl)c2)[C@@H](c2ccc(Cl)cc2)N(CC2CC2)C1=O)NO]

2-((3R,5R,6S)-5-(3-chlorophenyl)-6-(4-chlorophenyl)-1-(cyclopropylmethyl)-2-oxopiperidin-3-yl)-N-hydroxyacetamide A solution of 30 mg (0.07 mmol) of 2-((3R,5R,6S)-5-(3-chlorophenyl)-6-(4-chlorophenyl)-1-(cyclopropylmethyl)-2-oxopiperidin-3-yl)acetic acid (Example 35) in DMF (0.5 mL, c=0.14 M) was treated with N1-((ethylimino)methylene)-N3,N3-dimethylpropane-1,3-diamine hydrochloride (0.03 g, 0.1 mmol), 3H-[1,2,3]triazolo[4,5-b]pyridin-3-ol (0.02 g, 0.1 mmol), hydroxylamine hydrochloride (0.006 ml, 0.1 mmol) and sodium hydrogencarbonate (0.02 g, 0.2 mmol) successively. After being stirred at 25° C. for 12 h, the reaction was diluted with water and extracted with EtOAc. The combined organic layers were successively washed with sat. aq. NaHCO₃ solution and sat. aq. NaCl solution, dried over Na₂SO₄, filtered and the filtrate was concentrated under reduced pressure. The residue was purified by reversed phase HPLC (10 to 90% AcCN/H₂O with 0.1% TFA in 45 min) to give the title compound as a white solid.

$^1$H NMR (400 MHz, CHLOROFORM-d) δ ppm 7.45 (1 H, s), 7.41-7.16 (5 H, m), 7.16-6.98 (2 H, m), 5.10 (1 H, br. s.), 4.26-4.13 (1 H, m), 3.25-3.17 (1 H, m), 2.65 (3 H, br. s.), 2.30 (2 H, dd, J=14.1, 7.8 Hz), 1.91 (1 H, br. s.), 1.15 (1 H, d, J=2.0 Hz), 0.77-0.65 (1 H, m), 0.65-0.51 (1 H, m), 0.37-0.14 (2 H, m).

Example 53

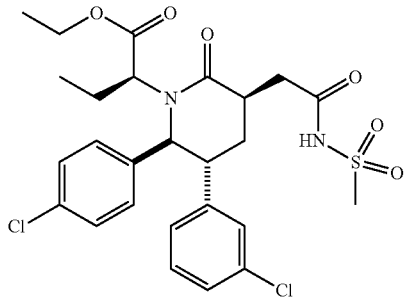 [SMILES: CCOC(=O)[C@H](CC)N1C(=O)[C@@H](CC(=O)NS(C)(=O)=O)C[C@H](c2cccc(Cl)c2)[C@H]1c1ccc(Cl)cc1]

(S)-Ethyl 2-((2S,3R,5R)-3-(3-chlorophenyl)-2-(4-chlorophenyl)-5-(2-(methylsulfonamido)-2-oxoethyl)-6-oxopiperidin-1-yl)butanoate Methanesulfonamide (0.02 g, 0.2 mmol), N-ethyl-N-isopropylpropan-2-amine (0.05 ml, 0.3 mmol), di(1H-imidazol-1-yl)methanone (0.04 g, 0.2 mmol) and 2-((3R,5R,6S)-5-(3-chlorophenyl)-6-(4-chlorophenyl)-1-((R)-1-ethoxy-1-oxobutan-2-yl)-2-oxopiperidin-3-yl)acetic acid (Example 3, 0.030 g, 0.06 mmol) were combined in 2 mL of THF. After being stirred at 25° C. for 12 h, sat. NH₄Cl solution was added and the reaction mixture was extracted with EtOAc. The combined organic layers were successively washed with sat. aq. NaHCO₃ solution and sat. aq. NaCl solution, dried over Na₂SO₄, filtered and the filtrate was concentrated under reduced pressure. The residue was purified by reversed phase HPLC (10 to 90% AcCN/H₂O with 0.1% TFA in 45 min) to give the title compound as a white solid.

$^1$H NMR (400 MHz, CHLOROFORM-d) δ ppm 7.45-7.33 (3 H, m), 7.33-7.21 (5 H, m), 4.88 (1 H, d, J=3.9 Hz), 4.27-4.10 (2 H, m), 3.48 (1 H, dd, J=8.8, 3.3 Hz), 3.30 (3 H, s), 3.20 (1 H, dd, J=4.7, 0.8 Hz), 3.04-2.74 (2 H, m), 2.72-2.59 (1 H, m), 2.48-2.28 (2 H, m), 2.03 (1 H, s), 1.63-1.46 (1 H, m), 1.28 (3 H, t, J=7.2 Hz), 0.69 (3 H, t, J=7.4 Hz).

Example 54

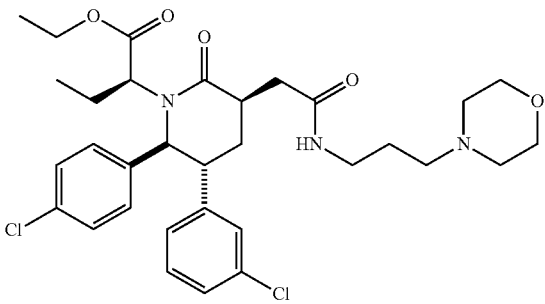 [SMILES: CCOC(=O)[C@H](CC)N1C(=O)[C@@H](CC(=O)NCCCN2CCOCC2)C[C@H](c2cccc(Cl)c2)[C@H]1c1ccc(Cl)cc1]

(S)-Ethyl 2-((2S,3R,5R)-3-(3-chlorophenyl)-2-(4-chlorophenyl)-5-(2-((3-morpholinopropyl)amino)-2-oxoethyl)-6-oxopiperidin-1-yl)butanoate The title compound was prepared as described in Example 49, using 2-((3R,5R,6S)-5-(3-chlorophenyl)-6-(4-chlorophenyl)-1-((R)-1-ethoxy-1-oxobutan-2-yl)-2-oxopiperidin-3-yl)acetic acid (Example 3) as starting material.

¹H NMR (400 MHz, CHLOROFORM-d) δ ppm 7.34 (2 H, d, J=8.6 Hz), 7.30-7.16 (5 H, m), 7.11-7.03 (1 H, m), 4.73 (1 H, d, J=5.5 Hz), 4.14 (2 H, q, J=7.3 Hz), 4.09-3.92 (4 H, m), 3.67-3.51 (2 H, m), 3.50-3.40 (1 H, m), 3.39-3.30 (2 H, m), 3.25 (1 H, dd, J=8.8, 3.3 Hz), 3.22-3.12 (2 H, m), 2.98-2.50 (5 H, m), 2.33-2.03 (5 H, m), 1.52-1.37 (0 H, m), 1.26 (3 H, t, J=7.2 Hz), 0.60 (3 H, t, J=7.4 Hz).

Example 55

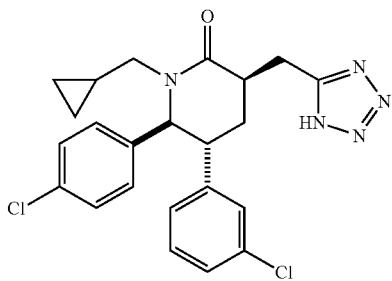 [SMILES: O=C1[C@@H](Cc2nnn[nH]2)C[C@H](c2cccc(Cl)c2)[C@@H](c2ccc(Cl)cc2)N1CC1CC1]

(3R,5R,6S)-3-((1H-Tetrazol-5-yl)methyl)-5-(3-chlorophenyl)-6-(4-chlorophenyl)-1-(cyclopropylmethyl)piperidin-2-one Step A. 2-((3R,5R,6S)-5-(3-chlorophenyl)-6-(4-chlorophenyl)-1-(cyclopropylmethyl)-2-oxopiperidin-3-yl)acetonitrile

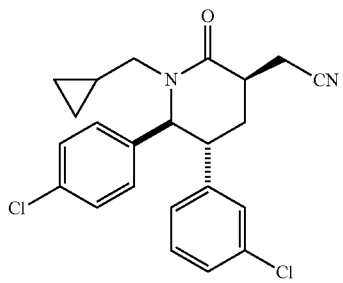 [SMILES: N#CC[C@H]1C[C@H](c2cccc(Cl)c2)[C@@H](c2ccc(Cl)cc2)N(CC2CC2)C1=O]

A solution of 136 mg (0.315 mmol) of 2-((3R,5R,6S)-5-(3-chlorophenyl)-6-(4-chlorophenyl)-1-(cyclopropylmethyl)-2-oxopiperidin-3-yl)acetamide (Example 48) and triethylamine (220 µl, 1576 µmol) in 5 mL of THF was treated with trifluoroacetic anhydride (111 µl, 788 µmol) at 0° C. After being stirred at 0° C. for 2 h, the reaction was quenched (sat. NH₄Cl), extracted (2×EtOAc) and washed (sat. aq. NaCl solution). The combined organic layer were dried (Na₂SO₄) and concentrated under the reduced pressure.

After being stirred at 0° C. for 2 h, sat. NH₄Cl solution was added and the reaction mixture was extracted with EtOAc. The combined organic layers were washed with sat. aq. NaCl solution, dried over Na₂SO₄, filtered and the filtrate was concentrated under reduced pressure. Purification of the residue by flash chromatography (SiO₂, 20-25% EtOAc/Hexanes) provided the title compound which was used without further purification.

Step B. (3R,5R,6S)-3-((1H-Tetrazol-5-yl)methyl)-5-(3-chlorophenyl)-6-(4-chlorophenyl)-1-(cyclopropylmethyl)piperidin-2-one To a solution of 136 mg (0.33 mmol) of 2-((3R,5R,6S)-5-(3-chlorophenyl)-6-(4-chlorophenyl)-1-(cyclopropylmethyl)-2-oxopiperidin-3-yl)acetonitrile (Example 55, Step A) in 1.8 mL of DMF was added ammonium chloride (176 mg, 3290 µmol) and sodium azide (214 mg, 3290 µmol). The resulting mixture was stirred at 90° C. for 4 days. Then, the reaction was acidified (aq. 10% citric acid) and extracted (2×EtOAc). The combined organic layers were washed with sat. aq. NaCl solution, dried over Na₂SO₄, filtered and the filtrate was concentrated under reduced pressure. Separation by reversed phase HPLC (60-90% AcCN/H₂O in 30 min) provided the title compound as a white solid.

¹H NMR (400 MHz, CHLOROFORM-d) δ ppm 7.51-7.48 (1 H, s), 7.35 (2 H, d, J=8.2 Hz), 7.32-7.28 (2 H, m), 7.25-7.21 (1 H, m), 6.86 (2 H, d, J=8.2 Hz), 5.14 (1 H, s), 4.23 (1 H, dd, J=14.1, 6.7 Hz), 3.40 (1 H, dd, J=15.3, 3.1 Hz), 3.28-3.20 (1 H, m), 3.15 (1 H, dd, J=15.1, 8.0 Hz), 2.60-2.52 (1 H, m), 2.33 (1 H, dd, J=14.1, 8.2 Hz), 2.26-2.18 (2 H, br. s.), 2.04-1.93 (1 H, m), 1.25-1.15 (1 H, m), 0.77-0.70 (1 H, m), 0.68-0.59 (1 H, m), 0.36-0.24 (2 H, m); MS (ESI) 456.0[M+H]⁺, 453.9[M−H]⁻.

Example 56

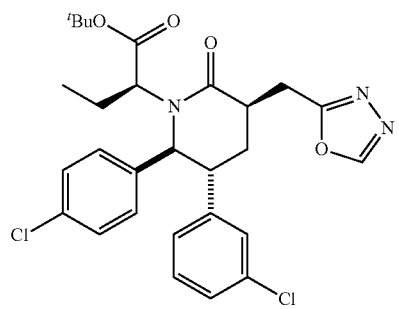 [SMILES: CC[C@@H](C(=O)OC(C)(C)C)N1C(=O)[C@@H](Cc2nnco2)C[C@H](c2cccc(Cl)c2)[C@H]1c1ccc(Cl)cc1]

(3R,5R,6S)-3-((1,3,4-oxadiazol-2-yl)methyl)-5-(3-chlorophenyl)-6-(4-chlorophenyl)-1-(cyclopropylmethyl)piperidin-2-one To a solution of 20 mg (45 µmol) of 2-((3R,5R,6S)-5-(3-chlorophenyl)-6-(4-chlorophenyl)-1-(cyclopropylmethyl)-2-oxopiperidin-3-yl)acetohydrazide (Example 51) in 0.2 mL of toluene was added ethyl formimidate hydrochloride (6.4 mg, 58 µmol). The reaction mixture was heated to reflux for 14 h and then the reaction was concentrated under reduced pressure. Separation by reversed phase HPLC (10 to 90% AcCN/H$_2$O in 40 min) provided the title compound as a colorless film.

$^1$H NMR (400 MHz, CHLOROFORM-d) δ ppm 8.35 (1 H, s), 7.50-7.45 (1 H, m), 7.37 (2 H, d, J=8.6 Hz), 7.34-7.28 (2 H, m), 7.26-7.22 (1 H, m), 7.13 (2 H, d, J=8.6 Hz), 5.13 (1 H, s), 4.22-4.17 (1 H, m), 3.38-3.35 (2 H, m), 3.24-3.18 (1 H, m), 2.80-2.72 (1 H, m), 2.35-2.28 (1 H, m), 2.25-2.18 (1 H, m), 1.96-1.86 (1 H, m), 1.21-1.12 (1 H, m), 0.70-0.62 (1 H, m), 0.61-0.54 (1 H, m), 0.30-0.20 (2 H, m); MS (ESI) 456.0[M+H]$^+$.

Example 57

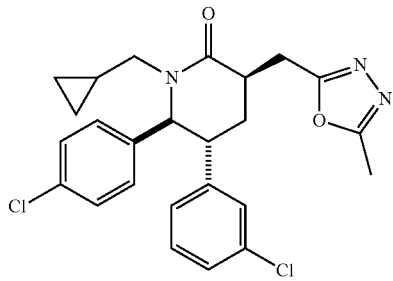 [SMILES: Cc1nnc(C[C@H]2C[C@H](c3cccc(Cl)c3)[C@@H](c3ccc(Cl)cc3)N(CC3CC3)C2=O)o1]

(3R,5R,6S)-5-(3-chlorophenyl)-6-(4-chlorophenyl)-1-(cyclopropylmethyl)-3-((5-methyl-1,3,4-oxadiazol-2-yl)methyl)piperidin-2-one To a solution of 40 mg (90 µmol) of 2-((3R,5R,6S)-5-(3-chlorophenyl)-6-(4-chlorophenyl)-1-(cyclopropylmethyl)-2-oxopiperidin-3-yl)acetohydrazide (Example 51) in 0.2 mL of toluene was added methyl acetimidate hydrochloride (13 mg, 116 µmol). The reaction mixture was heated to reflux for 14 h and then the reaction was concentrated under reduced pressure. Separation by reversed phase HPLC (10 to 90% AcCN/H$_2$O in 45 min) provided the title compound as a colorless film.

$^1$H NMR (400 MHz, CHLOROFORM-d) δ ppm 7.47-7.45 (1 H, s), 7.38 (2 H, d, J=8.6 Hz), 7.33-7.29 (2 H, m), 7.24-7.19 (1 H, m), 7.15 (2 H, d, J=8.6 Hz), 5.12-5.10 (1 H, m), 4.18 (1 H, dd, J=14.1, 6.7 Hz), 3.38-3.23 (2 H, m), 3.22-3.18 (1 H, m), 2.80-2.72 (1 H, m), 2.54 (3 H, s), 2.36-2.22 (2 H, m), 1.94-1.88 (1 H, m), 1.20-1.10 (1 H, m), 0.70-0.63 (1 H, m), 0.60-0.52 (1 H, m), 0.30-0.20 (2 H, m); MS (ESI) 469.9 [M+H]$^+$.

Example 58

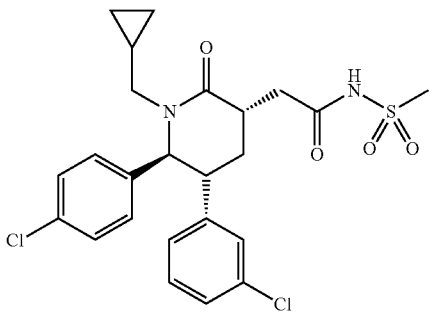

2-((3S,5R,6S)-5-(3-chlorophenyl)-6-(4-chlorophenyl)-1-(cyclopropylmethyl)-2-oxopiperidin-3-yl)-N-(methylsulfonyl)acetamide To a solution of 2-((3S,5R,6S)-5-(3-chlorophenyl)-6-(4-chlorophenyl)-1-(cyclopropylmethyl)-2-oxopiperidin-3-yl) acetic acid (Example 41) (83 mg, 0.192 mmol), methanesulfonamide (22.59 mg, 0.230 mmol) and 4-dimethylaminopyridine (1.057 mg, 0.00865 mmol) in DCM (2 mL) was added diisopropylethylamine (80 µL, 0.461 mmol). The reaction mixture was stirred at room temperature for one minute before adding bromo-tris-pyrrolidino-phosphonium hexafluorophosphate (125 mg, 0.269 mmol). The reaction mixture was stirred at room temperature for 3 hours. The reaction was quenched with 1N HCl and the aqueous layer was extracted with DCM (10 mL). The combined organic layers were washed with 1N HCl, 1N NaOH, sat. aq. NaCl solution and concentrated under reduced pressure. The residue was purified by reversed phase preparatory HPLC (column: Gemini-NX C$_{18}$ 5 um column; Phenomonex, Torrance, Calif.; eluent: 0 to 100% MeCN +0.1% TFA in water +0.1% TFA, over 20 minutes) to afford the title compound.

$^1$H NMR (400 MHz, CHLOROFORM-d) δ ppm −0.06-0.04 (m, 1 H) 0.06-0.16 (m, 1 H) 0.43 (dd, J=8.51 and 4.60 Hz, 1 H) 0.47-0.60 (m, 1 H) 0.88 (d, J=6.26 Hz, 1 H) 2.09-2.18 (m, 1 H) 2.29 (dt, J=14.04 and 6.77 Hz, 2 H) 2.62 (dd, J=15.26 and 3.52 Hz, 1 H) 2.90 (dd, J=15.26 and 7.63 Hz, 1 H) 3.02 (t, J=2.64 Hz, 1 H) 3.14 (d, J=3.72 Hz, 1 H) 3.32 (s, 3 H) 3.93 (dd, J=14.28 and 6.26 Hz, 2 H) 4.64 (d, J=10.17 Hz, 1 H) 6.74 (d, J=7.63 Hz, 1 H) 6.85-6.91 (m, 2 H) 7.00 (d, J=1.76 Hz, 1 H) 7.10-7.26 (m, 4 H). Mass Spectrum (ESI) m/z=509 [M+H]$^+$.

Example 59

2-((3S,5R,6S)-5-(3-chlorophenyl)-6-(4-chlorophenyl)-1-(cyclopropylmethyl)-2-oxopiperidin-3-yl)acetamide

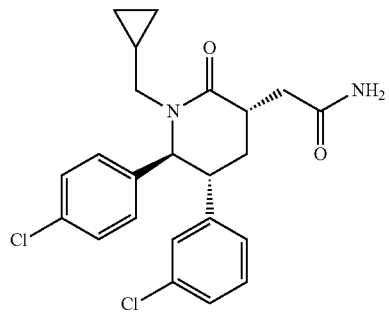 [SMILES: NC(=O)C[C@@H]1C[C@H](c2cccc(Cl)c2)[C@@H](c2ccc(Cl)cc2)N(CC2CC2)C1=O]

Step A. Methyl 2-((3S,5R,6S)-5-(3-chlorophenyl)-6-(4-chlorophenyl)-1-(cyclopropylmethyl)-2-oxopiperidin-3-yl)acetate

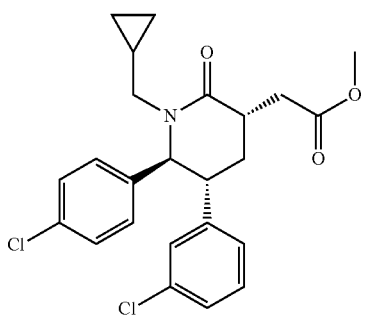 [SMILES: COC(=O)C[C@@H]1C[C@H](c2cccc(Cl)c2)[C@@H](c2ccc(Cl)cc2)N(CC2CC2)C1=O]

To a solution of 2-((3S,5R,6S)-5-(3-chlorophenyl)-6-(4-chlorophenyl)-1-(cyclopropylmethyl)-2-oxopiperidin-3-yl) acetic acid (Example 41) (500 mg, 1.156 mmol) in 10% MeOH in DCM (10 mL) was added (trimethylsilyl)diazomethane (2.0 M in diethyl ether) (1 mL). The yellow colored reaction mixture was stirred at room temperature for 30 min. The reaction was concentrated under reduced pressure and was purified by flash chromatography on silica gel (eluent: 0 to 50% EtOAc in hexanes) to give the title compound as a clear oil.

Step B. 2-((3S,5R,6S)-5-(3-chlorophenyl)-6-(4-chlorophenyl)-1-(cyclopropylmethyl)-2-oxopiperidin-3-yl)acetamide

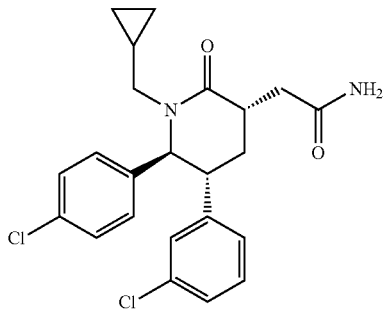 [SMILES: NC(=O)C[C@@H]1C[C@H](c2cccc(Cl)c2)[C@@H](c2ccc(Cl)cc2)N(CC2CC2)C1=O]

A sealed tube was charged with methyl 2-((3S,5R,6S)-5-(3-chlorophenyl)-6-(4-chlorophenyl)-1-(cyclopropylmethyl)-2-oxopiperidin-3-yl)acetate (Example 59, Step A) (109 mg, 0.244 mmol), ammonia, 7N solution in methanol (2 ml, 14.00 mmol) and sodium cyanide (1.197 mg, 0.024 mmol). The tube was sealed and heated to 50° C. The pressure reached 35 kilopascals after 1 hour. The reaction was stirred at 50° C. for 18 h. The reaction was cooled to rt and anhydrous ammonia (gas) was bubbled through the solution for ten minutes at room temperature. The reaction mixture was capped and heated to 50° C. for 18 h. The reaction was cooled to rt and anhydrous ammonia (gas) was bubbled through the solution for twenty minutes at room temperature. The reaction mixture was capped and heated to 50° C. for 2 days. The crude reaction was concentrated under reduced pressure and purified by reversed phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes) to afford the title compound.
$^1$H NMR (400 MHz, CHLOROFORM-d) δ ppm −0.05-0.04 (m, 1 H) 0.06-0.15 (m, 1 H) 0.36-0.45 (m, 1 H) 0.46-0.56 (m, 1 H) 0.79-0.93 (m, 1 H) 2.11-2.20 (m, 1 H) 2.29 (dt, J=13.99, 6.90 Hz, 1 H) 2.64-2.73 (m, 1 H) 2.75-2.83 (m, 1 H) 2.96-3.13 (m, 2 H) 3.91 (dd, J=14.09, 6.46 Hz, 1 H) 4.63 (d, J=9.98 Hz, 1 H) 6.41 (br. s., 1 H) 6.75 (dt, J=7.58, 1.59 Hz, 2 H) 6.83-6.90 (m, 2 H) 7.01 (t, J=1.96 Hz, 1 H) 7.10-7.26 (m, 4 H). Mass Spectrum (ESI) m/z=431 [M+H]$^+$.

Example 60

(3S,5R,6S)-3-((1H-tetrazol-5-yl)methyl)-5-(3-chlorophenyl)-6-(4-chlorophenyl)-1-(cyclopropylmethyl) piperidin-2-one

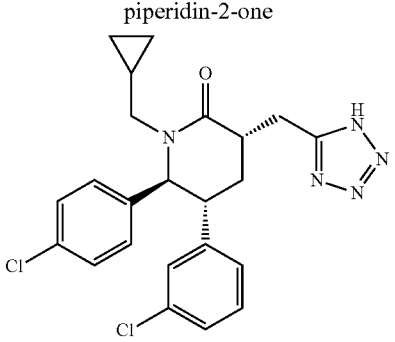

Step A. (3S,5R,6S)-3-((1H-tetrazol-5-yl)methyl)-5-(3-chlorophenyl)-6-(4-chlorophenyl)piperidin-2-one

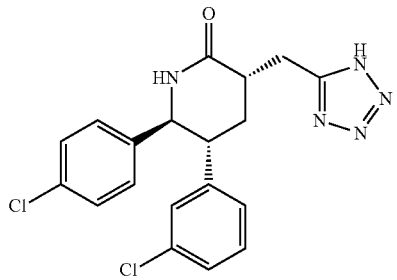 [SMILES: O=C1N[C@H](c2ccc(Cl)cc2)[C@@H](c2cccc(Cl)c2)C[C@H]1Cc1nnn[nH]1]

A 100 mL round-bottomed flask was placed under vacuum and heated with a heat gun to ensure dryness. The flask was allowed to cool to room temperature and a solution of 500 mg (1.56 mmol) of (5R,6S)-5-(3-chlorophenyl)-6-(4-chlorophenyl)piperidin-2-one (Example 1, Step E) in THF (12 mL) under argon was added and cooled to 0° C. Butyllithium (1.6M in hexanes, 2440 μL, 3.90 mmol) was added followed by 5-chloromethyl-1H-tetrazole (185 mg, 1.561 mmol) and the reaction mixture was stirred for 15 minutes at 0° C. The reaction was quenched with saturated ammonium chloride solution and extracted with ethyl acetate. The aqueous layer was acidified with 1M HCl. The aqueous layer was extracted with ethyl acetate (2×30 mL) and the combined organic layers were washed with sat. aq. NaCl solution, dried over sodium sulfate, and concentrated under reduced pressure. The residue was purified by reversed phase preparatory HPLC (column: Gemini-NX $C_{18}$ 5 um column; Phenomonex, Torrance, Calif.; eluent: 0 to 100% MeCN +0.1% TFA in water +0.1% TFA, over 25 minutes) to afford the title compound.

Step B. (3S,5R,6S)-3-((1H-tetrazol-5-yl)methyl)-5-(3-chlorophenyl)-6-(4-chlorophenyl)-1-(cyclopropylmethyl)piperidin-2-one A solution of (3S,5R,6S)-3-((1H-tetrazol-5-yl)methyl)-5-(3-chlorophenyl)-6-(4-chlorophenyl)piperidin-2-one (Example 60, Step A) (65 mg, 0.162 mmol) in DMF (1.6 mL) was cooled to 0° C. and sodium tert-butoxide (31.1 mg, 0.323 mmol) was added. The reaction mixture was stirred at 0° C. for ten minutes before adding (bromomethyl)cyclopropane (78 μL, 0.808 mmol). The reaction mixture was warmed to room temperature and stirred for 16 hours, quenched with saturated ammonium chloride and diluted with water and ethyl acetate. The aqueous layer was extracted with ethyl acetate and the organic layers were combined, washed with 1M LiCl, sat. aq. NaCl solution, dried over sodium sulfate, and concentrated under reduced pressure. The residue was purified by reversed phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes) to afford the title compound.

Example 61

(3S,5R,6S)-5-(3-chlorophenyl)-6-(4-chlorophenyl)-1-(cyclopropylmethyl)-3-((5-methylisoxazol-3-yl)methyl)piperidin-2-one

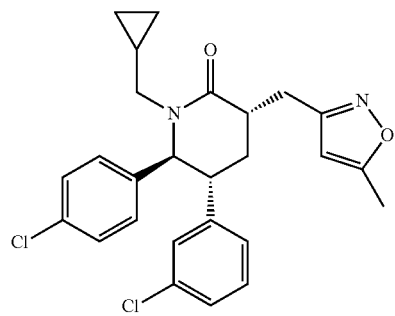 [SMILES: Cc1cc(C[C@@H]2C[C@H](c3cccc(Cl)c3)[C@@H](c3ccc(Cl)cc3)N(CC3CC3)C2=O)no1]

The title compound was prepared from (5R,6S)-5-(3-chlorophenyl)-6-(4-chlorophenyl)piperidin-2-one (Example 1, Step E), 3-(bromomethyl)-5-methylisoxazole, and (bromomethyl)cylopropane as described in Example 60.

¹H NMR (400 MHz, CHLOROFORM-d) δ ppm −0.05-0.04 (m, 1 H) 0.05-0.14 (m, 1 H) 0.32-0.41 (m, 1 H) 0.42-0.51 (m, 1 H) 0.79-0.94 (m, 1 H) 2.04-2.09 (m, 2 H) 2.28 (dd, J=14.28 and 7.24 Hz, 1 H) 2.37 (d, J=0.59 Hz, 3 H) 2.86-3.04 (m, 3 H) 3.33-3.41 (m, 1 H) 3.93 (dd, J=14.18 and 6.55 Hz, 1 H) 4.56 (d, J=9.98 Hz, 1 H) 5.92 (d, J=0.78 Hz, 1 H) 6.70 (dt, J=7.58 and 1.30 Hz, 1 H) 6.80-6.86 (m, 2 H) 6.95 (t, J=1.76 Hz, 1 H) 7.06-7.11 (m, 1 H) 7.13-7.17 (m, 1 H) 7.17-7.23 (m, 2 H). Mass Spectrum (ESI) m/z=469 [M+H]⁺.

Example 62

(rac) 2-((2'S,3'R,5'R)-6-chloro-3'-(3-chlorophenyl)-1'-(cyclopropylmethyl)-2,6'-dioxospiro[indoline-3,2'-piperidine]-5'-yl)acetic acid

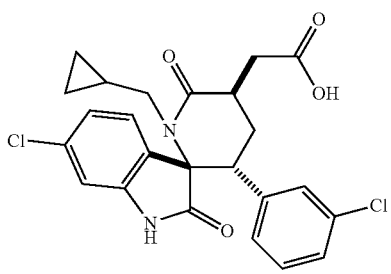

¹H NMR (400 MHz, CHLOROFORM-d) δ ppm −0.08-0.02 (m, 1 H) 0.11 (dt, J=9.44 and 4.77 Hz, 1 H) 0.38-0.46 (m, 1 H) 0.50 (td, J=8.31 and 4.50 Hz, 1 H) 0.78-0.89 (m, 1 H) 2.18-2.28 (m, 2 H) 2.31-2.41 (m, 1 H) 2.96-3.07 (m, 2 H) 3.29 (dd, J=14.87 and 7.82 Hz, 1 H) 3.47-3.56 (m, 1 H) 3.89 (dd, J=14.09 and 6.46 Hz, 1 H) 4.58 (d, J=9.98 Hz, 1 H) 6.71-6.76 (m, 1 H) 6.80-6.87 (m, 2 H) 6.98 (d, J=1.76 Hz, 1 H) 7.12-7.18 (m, 1 H) 7.19-7.25 (m, 3 H). Mass Spectrum (ESI) m/z=456 [M+H]⁺.

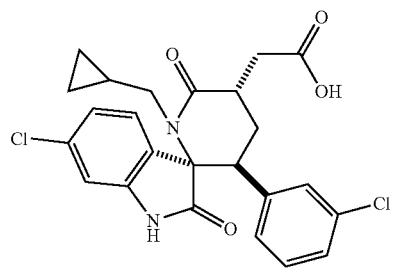

Step A. 1-(3-chlorophenyl)pent-4-en-1-one

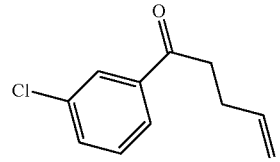

To a solution of 3-chlorobenzoyl chloride (7 ml, 54.7 mmol) in THF (60 mL) was added copper (I) iodide (0.521 g, 2.73 mmol). The slurry was cooled to −10° C. and 3-butenylmagnesium bromide (0.5M in THF) (112 ml, 55.8 mmol) was added dropwise via cannula over 30 min. The reaction mixture was stirred at −10° C. for 1 h and then warmed to room temperature. The reaction mixture was concentrated to 25 mL and diluted with 100 mL DCM and 100 mL 1M HCl. The layers were separated and the organic layer was filtered. The filtrate was washed with sat. NaHCO₃, dried over Na₂SO₄ and concentrated under reduced pressure. The residue was purified by flash chromatography on silica gel (eluent: 0 to 50% DCM in hexanes) to give the title compound.

Step B. 6-chloro-3-(1-(3-chlorophenyl)pent-4-enylidene)indolin-2-one

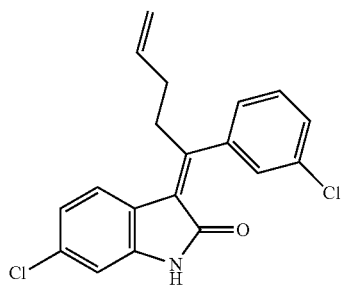 [SMILES: C=CCC/C(=C1/C(=O)Nc2cc(Cl)ccc21)c1cccc(Cl)c1]

To a mixture of 1-(3-chlorophenyl)pent-4-en-1-one (Example 62, Step A) (14.86 g, 76 mmol) and 6-chloroindolin-2-one (12.79 g, 76 mmol) in toluene (50 mL) at room temperature was added pyrrolidine (6.31 mL, 76 mmol). The slurry was heated at reflux with a Dean Stark trap for 6 h. The reaction mixture was cooled to room temperature and concentrated under reduced pressure. The residue was purified by flash chromatography on silica gel (eluent: 10 to 20% EtOAc in hexanes) to give the title compound.

Step C. 6-chloro-3-(1-(3-chlorophenyl)pent-4-enyl)indolin-2-one

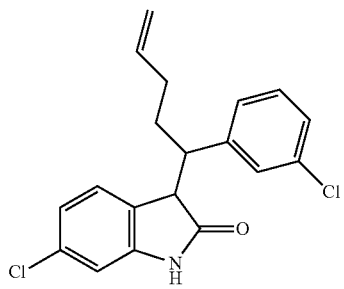 [SMILES: C=CCCC(c1cccc(Cl)c1)C1C(=O)Nc2cc(Cl)ccc21]

To a yellow slurry of 6-chloro-3-(1-(3-chlorophenyl)pent-4-enylidene)indolin-2-one (Example 62, Step B) (12.81 g, 37.2 mmol) in MeOH (200 mL) at room temperature was slowly added sodium borohydride (1.689 g, 44.7 mmol). Evolution of gas was observed. The yellow reaction mixture was stirred at room temperature for 30 min. Additional sodium borohydride (1.689 g, 44.7 mmol) was slowly added and the reaction mixture was stirred at room temperature for 1 h. The reaction mixture was poured into water (200 mL). A precipitate formed and the mixture was sonicated for 15 min then filtered. The filtrate was concentrated under reduced pressure to 36 mL and then extracted with EtOAc twice. The organic layers were combined, dried over Na$_2$SO$_4$ and concentrated under reduced pressure to provide the title compound.

Step D. 3-bromo-6-chloro-3-(1-(3-chlorophenyl)pent-4-enyl)indolin-2-one

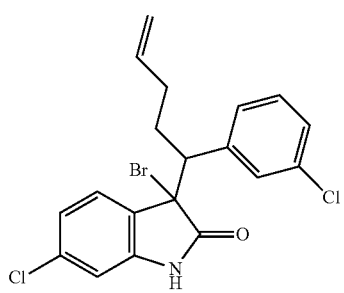 [SMILES: C=CCCC(c1cccc(Cl)c1)C1(Br)C(=O)Nc2cc(Cl)ccc21]

To a solution of 6-chloro-3-(1-(3-chlorophenyl)pent-4-enyl)indolin-2-one (Example 62, Step C (13.0 g, 37.5 mmol) in THF (200 mL) (previously degassed with Ar) at −78° C. under Ar was added N1,N1,N2,N2-tetramethylethane-1,2-diamine (11.79 mL, 79 mmol) (previously degassed with Ar) and butyllithium (1.6 M in hexanes) (49.3 mL, 79 mmol) (previously degassed with Ar) via addition funnel. The light brown reaction mixture was stirred at −78° C. for 30 min., wrapped in foil and recrystallized 1-bromopyrrolidine-2,5-dione (6.68 g, 37.5 mmol) in THF (50 mL) (previously degassed with Ar) was added via cannula. After the addition the reaction was quenched immediately with sat. potassium phosphate mono basic and warmed to room temperature. The mixture was extracted with EtOAc twice. The organic layers were combined, dried over Na$_2$SO$_4$ and concentrated under reduced pressure. The residue was purified by flash chromatography on silica gel (eluent: 0 to 10% EtOAc in hexanes) to give the title compound as a 1:1.7 ratio of diastereomers.

Step E. 4-(3-bromo-6-chloro-2-oxoindolin-3-yl)-4-(3-chlorophenyl)butanoic acid

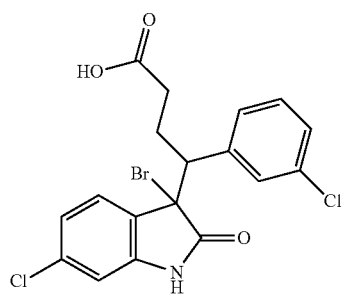 [SMILES: O=C(O)CCC(c1cccc(Cl)c1)C1(Br)C(=O)Nc2cc(Cl)ccc21]

To a rapidly stirred solution of 3-bromo-6-chloro-3-(1-(3-chlorophenyl)pent-4-enyl)indolin-2-one (Example 62, Step D) (7.74 g, 18.21 mmol) in H$_2$O/CCl$_4$/MeCN (1.5/1/1) (80 mL/50 mL/50 mL) was added sodium periodate (15.58 g, 72.8 mmol) and ruthenium(III) chloride hydrate (0.205 g, 0.910 mmol). The reaction mixture was stirred vigorously for 30 min and the reaction monitored by TLC. The reaction mixture was acidified (10% citric acid) and extracted with EtOAc. The organic layer was washed with sat. aq. NaCl solution, dried over Na$_2$SO$_4$ and concentrated under reduced pressure. The residue was purified by flash chromatography on silica gel (eluent: 30 to 70% EtOAc in hexanes) to give the title compound.

Step F. methyl 4-(3-bromo-6-chloro-2-oxoindolin-3-yl)-4-(3-chlorophenyl)butanoate

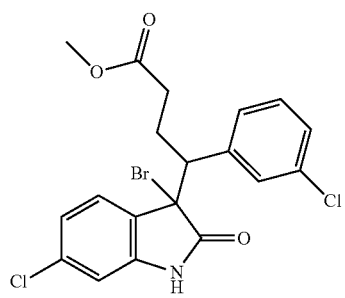 [SMILES: COC(=O)CCC(c1cccc(Cl)c1)C1(Br)C(=O)Nc2cc(Cl)ccc21]

To a solution of 4-(3-bromo-6-chloro-2-oxoindolin-3-yl)-4-(3-chlorophenyl)butanoic acid (Example 62, Step E) (5.38 g, 12.14 mmol) in MeOH (120 mL) at room temperature was added one drop of concentrated sulfuric acid. The reaction mixture was stirred at room temperature for 18 h and then concentrated under reduced pressure. The residue was purified by flash chromatography on silica gel (eluent: 0 to 50% EtOAc in hexanes) to give the title compound.

Step G. (rac) (S)-methyl 4-((S)-6-chloro-3-(cyclopropylmethylamino)-2-oxoindolin-3-yl)-4-(3-chlorophenyl)butanoate and (rac) (R)-methyl 4-((S)-6-chloro-3-(cyclopropylmethylamino)-2-oxoindolin-3-yl)-4-(3-chlorophenyl)butanoate

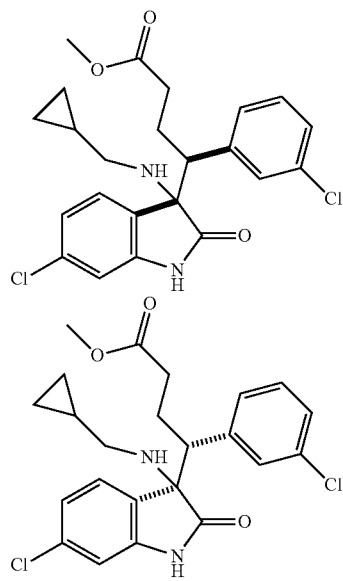

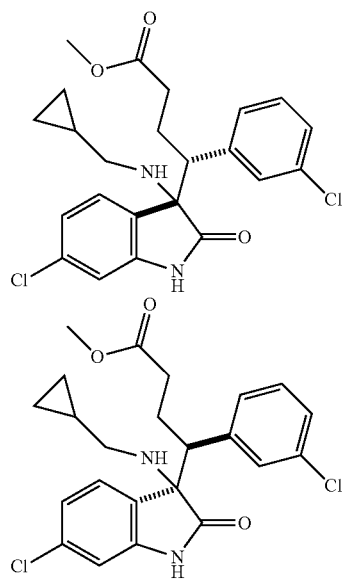

A solution of methyl 4-(3-bromo-6-chloro-2-oxoindolin-3-yl)-4-(3-chlorophenyl) butanoate (Example 62, Step F) (110 mg, 0.241 mmol) in DCE (4 mL) was heated at reflux. Cesium carbonate (157 mg, 0.481 mmol) and cyclopropylmethylamine hydrochloride (25.9 mg, 0.241 mmol) in DCE (1 mL) were added in one portion. The reaction mixture was heated at reflux for 5 h and then cooled to room temperature. The reaction mixture was filtered through celite and washed with DCM. The filtrate was concentrated and the diastereomeric pairs were separated by flash chromatography on silica gel (eluent: 20 to 60% EtOAc in hexanes) to give the title compounds. The more polar isomer is used in Example 62, Step H.

Step H. (rac) (2'S,3'R)-6-chloro-3'-(3-chlorophenyl)-1'-(cyclopropylmethyl)spiro[indoline-3,2'-piperidine]-2,6'-dione

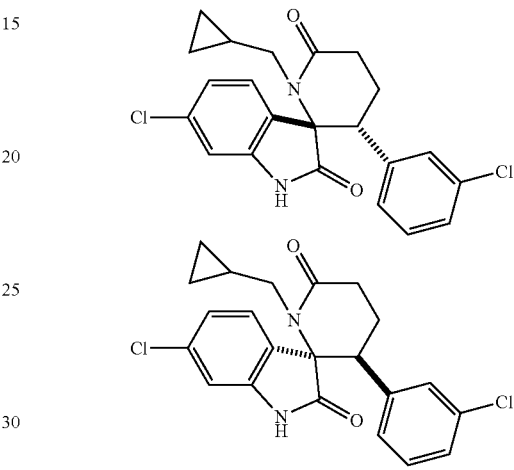

A solution of (rac) (R)-methyl 4-((S)-6-chloro-3-(cyclopropylmethylamino)-2-oxoindolin-3-yl)-4-(3-chlorophenyl)butanoate (Example 62, Step G, more polar isomer) in DCM was washed with sat NaHCO$_3$, dried over Na$_2$SO$_4$ and concentrated under reduced pressure. The residue was dissolved in distilled xylene (5 mL) and the reaction mixture was heated to 135° C. for 24 h. The reaction mixture was cooled to room temperature and concentrated under reduced pressure. The residue was purified by flash chromatography on silica gel (eluent: 20 to 60% EtOAc in hexanes) to give the title compound.

Step I. (rac) (2'S,3'R)-6-chloro-3'-(3-chlorophenyl)-1'-(cyclopropylmethyl)-1-((2-(trimethylsilyl)ethoxy)methyl)spiro[indoline-3,2'-piperidine]-2,6'-dione

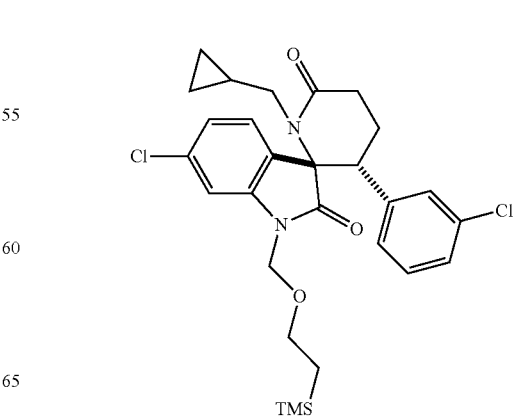

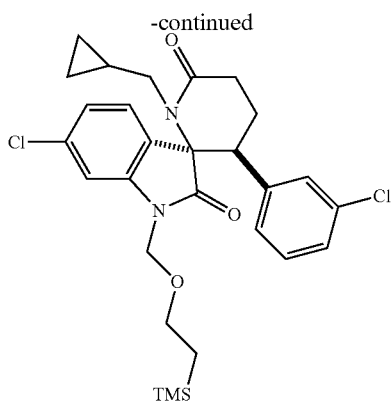

To a solution of (rac) (2'S,3'R)-6-chloro-3'-(3-chlorophenyl)-1'-(cyclopropylmethyl)spiro[indoline-3,2'-piperidine]-2,6'-dione (Example 62, Step H) (114 mg, 0.274 mmol) in DMF (2 mL) at 0° C. was added a dispersion of 60% sodium hydride in mineral oil (10.98 mg, 0.274 mmol) followed by (2-(chloromethoxy)ethyl)trimethylsilane (48.4 µL, 0.274 mmol). The reaction mixture was stirred at 0° C. for 30 min and then warmed to room temperature and stirred at room temperature for 24 h. The reaction mixture was poured into ice water and extracted with EtOAc. The organic layer was washed with 1M LiCl, sat. aq. NaCl solution, dried over Na$_2$SO$_4$ and concentrated under reduced pressure. The residue was purified by flash chromatography on silica gel (eluent: 0 to 50% EtOAc in hexanes) to give the title compound.

Step J. (rac) (2'S,3'R,5'S)-5'-allyl-6-chloro-3'-(3-chlorophenyl)-1'-(cyclopropylmethyl)-1-((2-(trimethylsilyl)ethoxy)methyl)spiro[indoline-3,2'-piperidine]-2,6'-dione

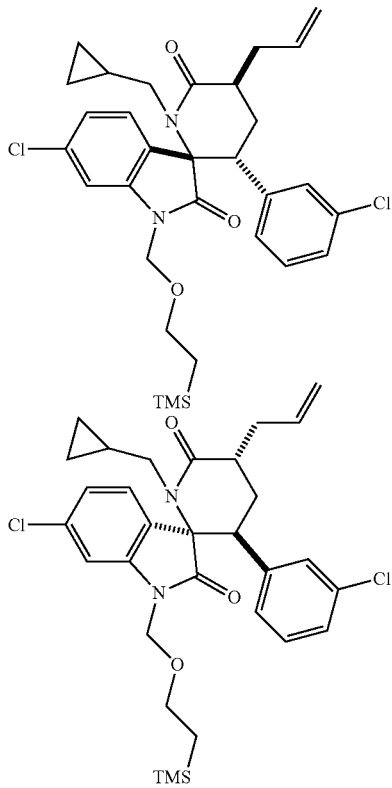

To a solution of (rac) (2'S,3'R)-6-chloro-3'-(3-chlorophenyl)-1'-(cyclopropylmethyl)-1-((2-(trimethylsilyl)ethoxy)methyl)spiro[indoline-3,2'-piperidine]-2,6'-dione (Example 62, Step I) (97 mg, 0.178 mmol) in THF (1 mL) at −78° C. under Ar was added freshly prepared LDA (1.0 M in THF) (178 µL, 0.178 mmol). The reaction color turned yellowish orange. The reaction was stirred at −78° C. for 30 min then distilled allyl bromide (15.39 µL, 0.178 mmol) was added. The reaction was stirred at −78° C. for 10 min then warmed to 0° C. The reaction was quenched with sat. NH$_4$Cl and warmed to room temperature. The mixture was diluted with EtOAc and the layers were separated. The organic layer was dried over Na$_2$SO$_4$ and concentrated under reduced pressure. The residue was purified by flash chromatography on silica gel (eluent: 0 to 25% EtOAc in hexanes) to give the title compound.

Step K. (rac) 2-((2'S,3'R,5'R)-6-chloro-3'-(3-chlorophenyl)-1'-(cyclopropylmethyl)-2,6'-dioxo-1-((2-(trimethylsilyl)ethoxy)methyl)spiro[indoline-3,2'-piperidine]-5'-yl)acetic acid To a rapidly stirred solution of (rac) (2'S,3'R,5'S)-5'-allyl-6-chloro-3'-(3-chlorophenyl)-1'-(cyclopropylmethyl)-1-((2-(trimethylsilyl)ethoxy)methyl)spiro[indoline-3,2'-piperidine]-2,6'-dione (Example 62, Step J) (46 mg, 0.079 mmol) in H$_2$O/CCl$_4$/MeCN (0.75 ml/0.5 mL/0.5 mL) was added sodium periodate (67.2 mg, 0.314 mmol) and ruthenium(III) chloride hydrate (1.771 mg, 7.85 µmol). The reaction mixture was stirred vigorously for 19 h and then acidified (10% citric acid) and filtered through a plug of celite and washed with EtOAc. The filtrate was transferred to a separatory funnel and extracted with EtOAc. The organic layer was dried over Na₂SO₄ and concentrated under reduced pressure to provide the title compound.

Step L. (rac) 2-((2'S,3'R,5'R)-6-chloro-3'-(3-chlorophenyl)-1'-(cyclopropylmethyl)-1-(hydroxymethyl)-2,6'-dioxospiro[indoline-3,2'-piperidine]-5'-yl)acetic acid

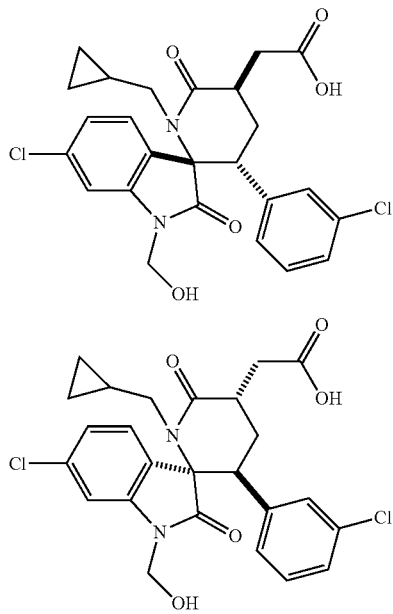

To a solution of (rac) 2-((2'S,3'R,5'R)-6-chloro-3'-(3-chlorophenyl)-1'-(cyclopropylmethyl)-2,6'-dioxo-1-((2-(trimethylsilyl)ethoxy)methyl)spiro[indoline-3,2'-piperidine]-5'-yl) acetic acid (Example 62, Step K) (47 mg, 0.078 mmol) in DCM (0.8 mL) at room temperature was added 0.2 mL TFA. The reaction mixture was stirred at room temperature for 19 h before concentrating under reduced pressure. The residue was purified by flash chromatography on silica gel (eluent: 50 to 100% EtOAc in hexanes) to give the title compound.

Step M. (rac) 2-((2'S,3'R,5'R)-6-chloro-3'-(3-chlorophenyl)-1'-(cyclopropylmethyl)-2,6'-dioxospiro[indoline-3,2'-piperidine]-5'-yl)acetic acid

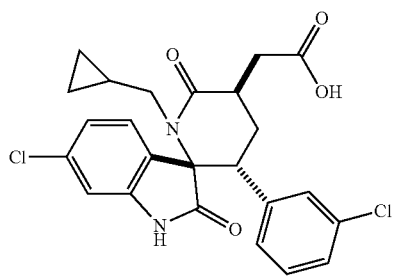

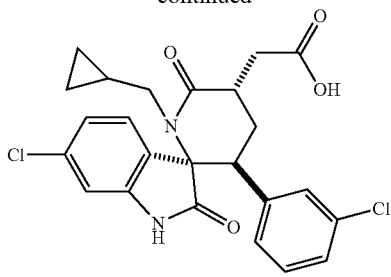

To a solution of (rac) 2-((2'S,3'R,5'R)-6-chloro-3'-(3-chlorophenyl)-1'-(cyclopropylmethyl)-1-(hydroxymethyl)-2,6'-dioxospiro[indoline-3,2'-piperidine]-5'-yl)acetic acid (Example 62, Step L) (12.6 mg, 0.025 mmol) in MeOH (1 mL) at room temperature was added DIEA (8.74 µL, 0.050 mmol). The reaction mixture was stirred at room temperature for 1 h. The reaction was quenched with 10% citric acid and concentrated under reduced pressure. The residue was purified by reversed phase preparatory HPLC (column: Gemini-NX C₁₈ 5 um column; Phenomonex, Torrance, Calif.; eluent: 0 to 100% MeCN +0.1% TFA in water +0.1% TFA) to give the title compound.

¹H NMR (400 MHz, ACETONITRILE-d₃) δ ppm −0.25-−0.18 (1 H, m) −0.12-−0.04 (1 H, m) 0.20-0.34 (2 H, m) 0.66-0.77 (1 H, m) 1.64-1.73 (1 H, m) 2.68 (1 H, dd, J=14.3 and 7.0 Hz) 2.73-2.81 (1 H, m) 2.86-3.02 (1 H, m) 3.12-3.33 (3 H, m) 3.53-3.65 (1 H, m) 6.61 (1 H, d, J=1.8 Hz) 6.79-6.91 (2 H, m) 7.08 (1 H, t, J=7.8 Hz) 7.11-7.20 (2 H, m) 7.49 (1 H, d, J=8.2 Hz) 8.29 (1 H, br s). Mass Spectrum (ESI) m/z=473 [M+H]⁺.

Example 63

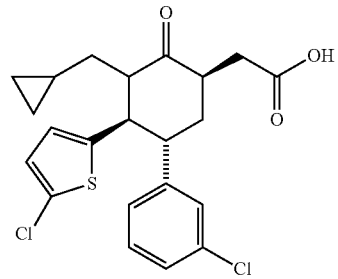 [SMILES: O=C(O)C[C@H]1C[C@H](c2cccc(Cl)c2)[C@@H](c2ccc(Cl)s2)C(CC2CC2)C1=O]

2-((3R,5R,6S)-5-(3-chlorophenyl)-6-(5-chlorothiophen-2-yl)-1-(cyclopropylmethyl)-2-oxopiperidin-3-yl)acetic acid Step A. 2-(3-Chlorophenyl)-1-(5-chlorothiophen-2-yl)ethanone

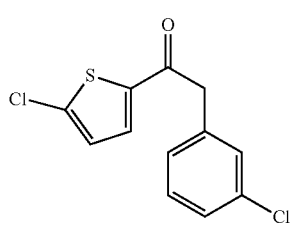 [SMILES: O=C(Cc1cccc(Cl)c1)c1ccc(Cl)s1]

173

To a 500-mL round-bottomed flask was added silica gel 60 (21 g, 350 mmol) and the flask was heated with a heat gun under high vacuum for 30 min. The system was cooled to room temperature and phosphorus pentoxide (8.75 mL, 148 mmol) was added. The mixture was stirred at 110° C. (oil bath) under high vacuum for 120 min. The mixture was allowed to cool to room temperature. 3-chlorophenylacetic acid (15.6 g, 91 mmol), 2-chlorothiophene (33.8 mL, 366 mmol) and DCE (50 mL) were added. The reaction mixture was stirred at reflux for 4 hours. LCMS analysis showed the reaction was complete. The reaction mixture was allowed to cool to room temperature. The reaction mixture was diluted with ether (300 mL) and filtered. The organic solution was concentrated under reduced pressure. The residue was triturated with hexane to afford the title compound as an off-white solid. The hexane mother liquid was concentrated and purified by flash chromatography (SiO$_2$, 0 to 30% EtOAc/Hex, a gradient elution) provided another batch of the title compounde as a light yellow solid. Mass Spectrum (ESI) m/z=271 (M+1).

Step B. rac. Methyl 4-(3-chlorophenyl)-5-(5-chlorothiophen-2-yl)-5-oxopentanoate

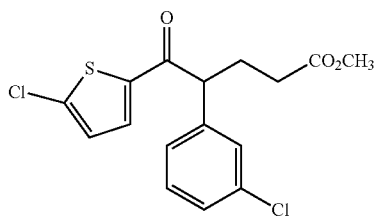 [SMILES: COC(=O)CCC(C(=O)c1ccc(Cl)s1)c1cccc(Cl)c1]

To a solution of 7.35 g (27.1 mmol) of 2-(3-chlorophenyl)-1-(5-chlorothiophen-2-yl)ethanone (Example 63, Step A) and acrylic acid methyl ester (2.81 mL, 31.2 mmol) in DCM (60 mL) was added 1,8-diazabicyclo[5.4.0]undec-7-ene (4.05 mL, 27.1 mmol) in DCM (10 mL) slowly at 0° C. over 20 min. Then the reaction was allowed to warm to ambient temperature. After being stirred at 25° C. for two days, the reaction mixture was diluted with DCM and washed with 2N HCl, water and sat. aq. NaCl solution. The organic extract was dried over Na$_2$SO$_4$. The solution was filtered and concentrated in vacuo to give the crude material as light yellow oil. The crude material was absorbed onto a plug of silica gel and purified by chromatography through a pre-packed silica gel column (220 g), eluting with a gradient of 0% to 30% EtOAc in hexane, to provided the title compound as a light-yellow oil.

Mass Spectrum (ESI) m/z=357 (M+1).

Step C. rac (4S,5S)(4R,5R) methyl 4-(3-chlorophenyl)-5-(5-chlorothiophen-2-yl)-5-hydroxypentanoate

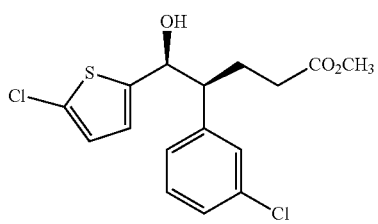 [SMILES: COC(=O)CC[C@@H](c1cccc(Cl)c1)[C@H](O)c1ccc(Cl)s1]

174

To a solution of 8.20 g (22.95 mmol) of methyl 4-(3-chlorophenyl)-5-(5-chlorothiophen-2-yl)-5-oxopentanoate (Example 63, Step B) in MeOH (100 mL) was added sodium borohydrate (0.809 mL, 22.95 mmol) portion-wise at 0° C. Then the reaction was stirred at 0° C. for 30 min. LCMS analysis showed the reaction went to completion. Ice-water was added to quench the reaction. The reaction mixture was concentrated under reduced pressure to remove most of MeOH. The residue was extracted with DCM (3×100 mL). The combined organic layers were washed with sat. aq. NaCl solution, dried over Na$_2$SO$_4$, and concentrated under reduced pressure. Purification of the residue by flash chromatography (TLC, SiO$_2$, 20 to 30% EtOAc/hexanes, gradient elution) provided the title compound as a colorless oil.

Step D. rac. (4S,5R)(4R,5S)-methyl-5-azido-4-(3-chlorophenyl)-5-(5-chlorothiophen-2-yl)pentanoate

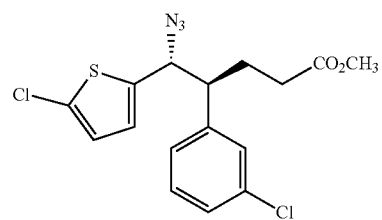 [SMILES: COC(=O)CC[C@@H](c1cccc(Cl)c1)[C@@H](N=[N+]=[N-])c1ccc(Cl)s1]

To a solution of 1.18 g (3.28 mmol) of racemic (4S,5S)(4R,5R)-methyl 4-(3-chlorophenyl)-5-(5-chlorothiophen-2-yl)-5-hydroxypentanoate (Example 63, Step C) in toluene (10 mL) was added 1,8-diazabicyclo[5.4.0]undec-7-ene (0.639 mL, 4.27 mmol) over 5 min at 0° C. with stirring. To the above solution, diphenylphosphoryl azide (0.852 mL, 3.94 mmol) was added dropwise over a period of 8 min. The reaction mixture was stirred at 0° C. to rt for 14 hours and monitored by LCMS analysis. The reaction mixture was diluted (sat. aq. NH$_4$Cl), extracted (3×EtOAc), and washed (2×sat. aq. NaCl solution). The combined organic layers were dried (Na$_2$SO$_4$) and concentrated under reduced pressure. The crude material was dissolved in small amount of DCM for chromatography. The insoluble material was removed by filtration and the solution was absorbed onto a plug of silica gel and purified by chromatography through a Redi-Sep pre-packed silica gel column (40 g), eluting with a gradient of 0% to 60% EtOAc in hexane, to provide the racemic title compound as a colorless oil.

Mass Spectrum (ESI) m/z=406 (M+23).

Step E. (5R,6S)-5-(3-chlorophenyl)-6-(5-chlorothiophen-2-yl)piperidin-2-one

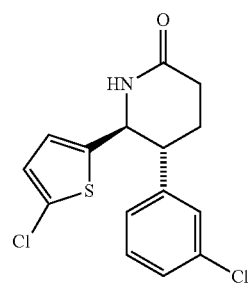 [SMILES: O=C1CC[C@H](c2cccc(Cl)c2)[C@@H](c2ccc(Cl)s2)N1]

To a solution of 7.8 g (20.3 mmol) of racemic (4S,5R)(4R,5S)-methyl 5-azido-4-(3-chlorophenyl)-5-(5-chlorothiophen-2-yl)pentanoate (Example 63, Step D) in THF/H$_2$O (4/1, 75 mL) was added trimethylphosphine, 1.0M solution in tetrahydrofuran (24.36 mL, 24.36 mmol). After being stirred for 1 h at 23° C., LCMS analysis showed reaction was complete. Most of THF was removed under reduced pressure and the residue was basified (ice-cold 2 M LiOH) and the product was extracted (3×DCM) and washed (2×sat. aq. NaCl solution). The combined organic layers were dried (Na$_2$SO$_4$) and concentrated under reduced pressure to provide a crude mixture of amines as a yellow solid.

The crude amine from above was dissolved in MeOH/saturated aq. NaHCO$_3$(4/1, 60 mL, c=0.04 M) and the reaction was refluxed for 3 h. After LCMS analysis showed the reaction to be complete, excess solvent was removed under reduced pressure, the residue was diluted (water), extracted (2×10% MeOH/DCM), and washed (1×sat. aq. NaCl solution). The combined organic layers were dried (Na$_2$SO$_4$) and concentrated under reduced pressure to provide the crude title compound.

The crude material was absorbed onto a plug of silica gel and purified by chromatography through a pre-packed silica gel column (220 g), eluting with a gradient of 20% to 100% EtOAc in CH$_2$Cl$_2$, to provide the racemic title compound as a white solid.

Individual enantiomers of the racemic (5R,6S)(5S,6R)-5-(3-chlorophenyl)-6-(5-chlorothiophen-2-yl)piperidin-2-one were separated by chiral SFC on a 250×30 mm Chiralcel AS-H column with 50 g/min MeOH(+20 mM NH$_3$)+50 g/min CO$_2$ on Thar 350 SFC (Thar Technologies, Inc., Pittsburg, Pa.). Outlet pressure=100 bar; Temp.=46° C.; Wavelength=245 nm. Run time=20 min.; cycle time=17 min. The title compound (5R,6S)-5-(3-chlorophenyl)-6-(5-chlorothiophen-2-yl)piperidin-2-one was obtained as the faster eluting isomer.

$^1$H NMR (400 MHz, CHLOROFORM-d) δ ppm 7.18-7.24 (2 H, m), 7.10 (1 H, m), 6.93-6.95 (1 H, m) 6.23 (1 H, d, J=4 Hz), 6.42 (1 H, d, J=4 Hz), 6.09 (1 H, s), 4.73 (1 H, d, J=8 Hz), 2.87-2.94 (1 H, m), 2.60-2.65 (2 H, m), 2.05-2.25 (2 H, m); Mass Spectrum (ESI) m/z=326 (M+1 ); [α]$_D$=+165.8 (T=24.7° C., c=0.104, CHCl$_3$)

Also obtained by the above method was the enantiomer of the title compound, (5S,6R)-5-(3-chlorophenyl)-6-(5-chlorothiophen-2-yl)piperidin-2-one as the slower eluting isomer.

[α]$_D$=−158 (T=24.8° C., c=0.104, CHCl$_3$)

Step F. rac. (5R,6S)(5S,6R)-5-(3-chlorophenyl)-6-(5-chlorothiophen-2-yl)-1-(cyclopropylmethyl)piperidin-2-one

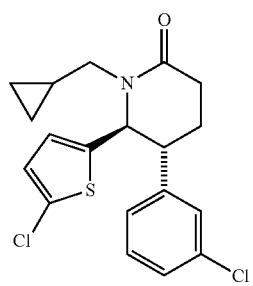 [SMILES: O=C1CC[C@H](c2cccc(Cl)c2)[C@@H](c2ccc(Cl)s2)N1CC1CC1]

The title compound was prepared from racemic (5R,6S),(5S,6R)-5-(3-chlorophenyl)-6-(5-chlorothiophen-2-yl)piperidin-2-one (Example 63, Step E) as described in Example 35, Step A.

$^1$H NMR (400 MHz, CHLOROFORM-d) α ppm 7.34 (1H, br s), 7.25-7.30 (2 H, m), 7.13-7.17 (1 H, m), 6.74 (1 H, d, J=4 Hz), 6.56 (1 H, d, J=4 Hz), 5.06 (1 H, d, J=4 Hz), 4.13-4.19 (1H, m), 3.19-3.23 (1 H, m), 2.46-2.60 (3H, m), 2.23-2.29 (1 H, m), 2.01-2.10 (1H, m), 1.05-1.13 (1 H, m), 0.59-0.66 (1 H, m), 0.49-0.56 (1 H, m), 0.27-0.33 (1 H, m), 0.18-0.24 (1 H, m). Mass Spectrum (ESI) m/z=380 (M+1).

Step G. (3R,5R,6S) (3S,5S,6R)-3-Allyl-5-(3-chlorophenyl)-6-(4-chlorophenyl)-1-(cyclopropylmethyl)piperidin-2-one and (3S,5R,6S) (3R,5S,6R)-3-allyl-5-(3-chlorophenyl)-6-(4-chlorophenyl)-1-(cyclopropylmethyl)piperidin-2-one

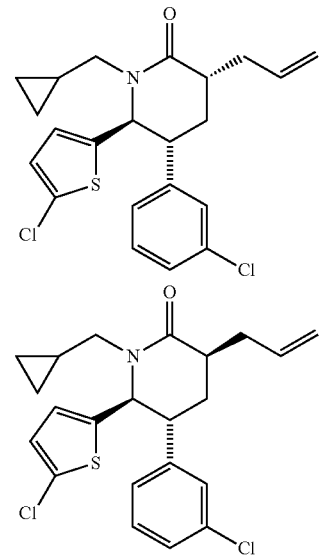

The title compounds were prepared from racemic ((5R,6S) (5S,6R)-5-(3-chlorophenyl)-6-(5-chlorothiophen-2-yl)-1-(cyclopropylmethyl)piperidin-2-one (Example 63, Step F) as described in Example 1, Step G and were obtained as a mixture of stereoisomers. The individual racemic stereoisomers were separated by silica gel chromatography.

The title compound (3R,5R,6S) (3S,5S,6R)-3-allyl-5-(3-chlorophenyl)-6-(4-chlorophenyl)-1-(cyclopropylmethyl)piperidin-2-one was obtained as the faster eluting isomer (less polar isomer) by silica gel chromatography.

$^1$H NMR (400 MHz, CHLOROFORM-d) δ ppm 7.16-7.23 (2 H, m), 7.10-7.12 (1 H, m), 6.60 (1 H, d, J=4 Hz), 6.32 (1 H, d, J=4 Hz), 5.75-5.84 (1H, m), 5.05-5.12 (2 H, m), 4.76 (1 h, d, J=8 Hz), 3.98-4.03 (1 H, m), 3.04-3.10 (1 H, m), 2.75-2.81 (1 H, m), 2.51-2.63 (2H, m), 2.35-2.42 (1 H, m), 2.05-2.11 (1 H, m), 1.89-1.99 (1 H, m), 0.88-0.98 (1 H, m), 0.49-0.56 (1 H, m), 0.39-0.46 (1 H, m), 0.19-0.25 (1 H, m), 0.07-0.13 (1 H, m). Mass Spectrum (ESI) m/z=420 (M+1).

The title compound (3S,5R,6S) (3R,5S,6R)-3-allyl-5-(3-chlorophenyl)-6-(4-chlorophenyl)-1-(cyclopropylmethyl)piperidin-2-one was obtained as the slower eluting isomer on silica gel chromatography.

$^1$H NMR (400 MHz, CHLOROFORM-d) δ ppm 7.42 (1 H, br s) 726-7.31 (1 H, m), 7.19-7.23 (1 H, m),6.79 (1 H, d, J=4

Hz), 6.60 (1 H, d, J=4 Hz), 5.70-5.80 (1H, m), 5.06-5.15 (3 H, m), 4.18-4.23 (1 H, m), 3.26-3.29 (1 H, m), 2.62-2.68 (1 H, m), 2.41-2.51 (2H, m), 2.31-2.38 (1 H, m), 2.15-2.22 (1 H, m), 1.92-1.98 (1 H, m), 1.11-1.21 (1 H, m), 0.63-0.69 (1 H, m), 0.54-0.60 (1 H, m), 0.24-0.34 (2 H, m). Mass Spectrum (ESI) m/z=420 (M+1).

Step H. 2-((3R,5R,6S)-5-(3-chlorophenyl)-6-(5-chlorothiophen-2-yl)-1-(cyclopropylmethyl)-2-oxopiperidin-3-yl)acetic acid

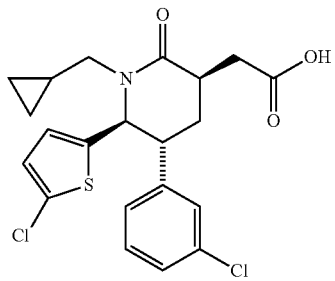 [SMILES: O=C(O)C[C@H]1C[C@H](c2cccc(Cl)c2)[C@@H](c2ccc(Cl)s2)N(CC2CC2)C1=O]

The title compound was prepared from racemic (3R,5R,6S)(3S,5S,6R)-3-allyl-5-(3-chlorophenyl)-6-(4-chlorophenyl)-1-(cyclopropylmethyl)piperidin-2-one (Example 63, Step G) as described in Example 1, Step H and resolved by chiral SFC on a CHRALCEL® OJ column (Daicel, Fort Lee, N.J.). It was obtained as the slower eluting isomer.
$^1$H NMR (400 MHz, CHLOROFORM-d) δ ppm 7.45 (1 H, br s) 7.31-7.34 (2 H, m), 7.23-7.35 (1 H, m), 6.84 (1 H, d, J=4 Hz), 6.74 (1 H, d, J=4 Hz), 5.27 (1 H, br s), 4.22-4.27 (1 H, m), 3.33 (1 H, br s), 2.76-2.84 (1 H, m), 2.52-2.63 (3H, m), 2.31-2.36 (1 H, m), 1.96-2.02 (1 H, m), 1.15-1.24 (1 H, m), 0.71-0.77 (1 H, m), 0.60-0.67 (1 H, m), 0.34-0.40 (1 H, m), 0.27-0.33 (1 H, m). Mass Spectrum (ESI) m/z=438 (M+1).

Example 64

2-((3S,5R,6S)-5-(3-chlorophenyl)-6-(5-chlorothiophen-2-yl)-1-(cyclopropylmethyl)-2-oxopiperidin-3-yl)acetic acid

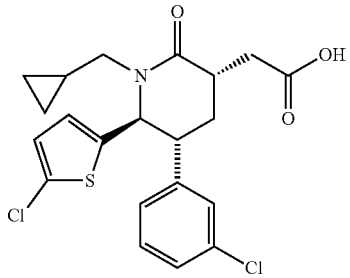

The title compound was prepared from racemic (3R,5R,6S)(3S,5S,6R)-3-allyl-5-(3-chlorophenyl)-6-(4-chlorophenyl)-1-(cyclopropylmethyl)piperidin-2-one (Example 63, Step G) as described in Example 1, Step H and resolved by chiral SFC on an AD column. It was obtained as the slower eluting isomer on a CHIRALCEL® (Daicel, Fort Lee, N.J.) AD column.
$^1$H NMR (400 MHz, CHLOROFORM-d) δ ppm 7.17-7.24 (2 H, m), 7.09-7.10 (1 H, m), 6.90-6.92 (1H, m), 6.62 (1 H, d, J=4 Hz), 6.35 (1 H, d, J=4 Hz), 4.80 (1 H, d, J=12 Hz), 3.94-3.99 (1 H, m), 3.11-3.18 (1 H, m), 2.99-3.16 (1 H, m), 2.54-2.66 (2H, m), 2.09-2.22 (2 H, m), 0.87-0.98 (1 H, m), 0.50-0.57 (1 H, m), 0.40-0.47 (1 H, m), 0.18-0.24 (1 H, m), 0.07-0.13 (1 H, m). Mass Spectrum (ESI) m/z=438 (M+1).

Example 65

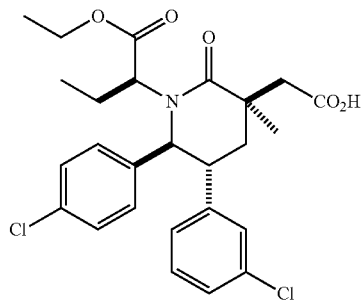

2-((3R,5R,6S)-5-(3-chlorophenyl)-6-(4-chlorophenyl)-1-((S)-1-ethoxy-1-oxobutan-2-yl)-3-methyl-2-oxopiperidin-3-yl)acetic acid Step A. (S)-Ethyl 2-((3R,5R,6S)-3-allyl-5-(3-chlorophenyl)-6-(4-chlorophenyl)-2-oxopiperidin-1-yl)butanoate and (S)-Ethyl 2-((3S,5R,6S)-3-allyl-5-(3-chlorophenyl)-6-(4-chlorophenyl)-2-oxopiperidin-1-yl)butanoate

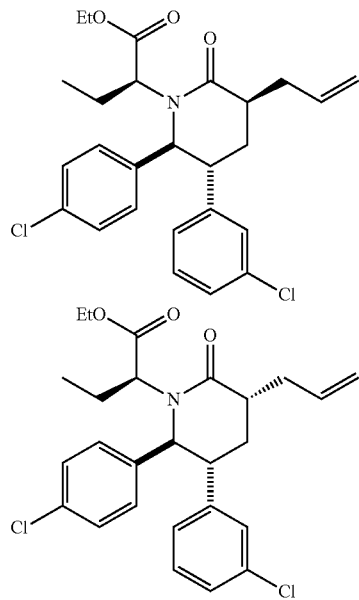

To a solution of 362 mg (833 μmol) of (S)-Ethyl 2-((2S, 3R)-3-(3-chlorophenyl)-2-(4-chlorophenyl)-6-oxopiperidin-1-yl)butanoate (Example 9, Step A) and allyl bromide (87 μl, 1000 μmol) in THF (3.30 mL, 0.25 M) was added dropwise lithium bis(trimethylsilyl) amide (1M solution in THF; 875

μl, 875 μmol) at −78° C. After being stirred at −78° C. for 3 h, the reaction was quenched (sat. aqueous NH₄Cl), extracted (2×EtOAc). The combined organic layers were washed with water and sat. aq. NaCl solution, dried over Na₂SO₄, filtered and the filtrate was concentrated under reduced pressure. Purification of the residue by chromatography (12 g SiO₂, 15 to 20% EtOAc/Hex, a gradient elution) provided the title compounds as a mixture of stereoisomers.

Step B. (2S)-Ethyl 2-((3S,5R,6S)-3-allyl-5-(3-chlorophenyl)-6-(4-chlorophenyl)-3-methyl-2-oxopiperidin-1-yl)butanoate and (2S)-Ethyl 2-((3R,5R,6S)-3-allyl-5-(3-chlorophenyl)-6-(4-chlorophenyl)-3-methyl-2-oxopiperidin-1-yl)butanoate

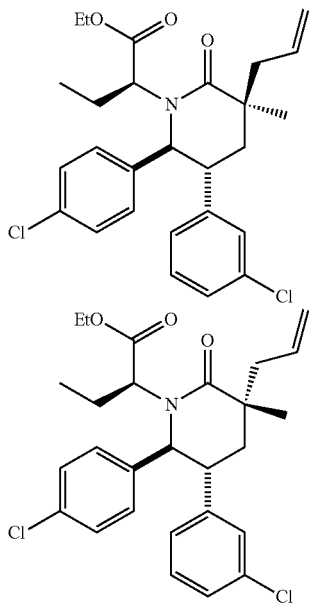

To a solution of 0.66 g (1.39 mmol) of (S)-ethyl 2-((5R,6S)-3-allyl-5-(3-chlorophenyl)-6-(4-chlorophenyl)-2-oxopiperidin-1-yl)butanoate (Example 65, Step A; mixture of diastereomers) and iodomethane (0.592 g, 4.17 mmol) in 15 mL of THF was added LHMDS (1.0M solution in THF; 4.17 mL, 4.17 mmol) at RT. After being stirred for 12 h, the reaction was quenched (sat. aqueous NH₄Cl), extracted (2×EtOAc). The combined organic layers were washed with water and sat. aq. NaCl solution, dried over Na₂SO₄, filtered and the filtrate was concentrated under reduced pressure. Purification of the residue by reversed phase preparatory HPLC (Gemini™ Prep C18 5 μm column, Phenomenex, Torrance, Calif.; eluent: 10 to 90% acetonitrile +0.1% TFA in water +0.1% TFA, gradient elution) gave the title compound as a mixture of stereoisomers.

Step D. 2-((3R,5R,6S)-5-(3-chlorophenyl)-6-(4-chlorophenyl)-1-((S)-1-ethoxy-1-oxobutan-2-yl)-3-methyl-2-oxopiperidin-3-yl)acetic acid

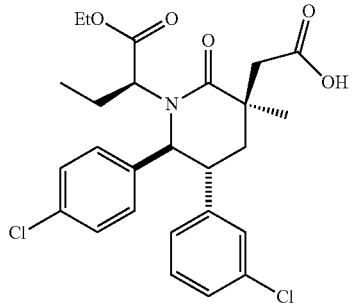

To a rapidly stirring solution of 0.28 g (0.573 mmol) of (2S)-ethyl 2-((5R,6S)-3-allyl-5-(3-chlorophenyl)-6-(4-chlorophenyl)-3-methyl-2-oxopiperidin-1-yl) butanoate (Example 65, Step B; mixt. of diastereomers) in H₂O/CCl₄/MeCN (4.0/2.0/2.0, 8.0 mL) was added sodium periodate (0.490 g, 2.29 mmol), followed by ruthenium(III) chloride hydrate (0.013 g, 0.057 mmol). After being stirred vigorously for 12 h, the reaction was acidified (10% citric acid) and diluted with EtOAc. The insoluble material was removed by filtration through a pad of Celite® (J. T. Baker, Phillipsberg, N.J., diatomaceous earth). The filtrate was extracted (2×EtOAc).

The combined organic layers were washed with water and sat. aq. NaCl solution, dried over Na₂SO₄, filtered and the filtrate was concentrated under reduced pressure. The residue was purified by reversed phase preparatory HPLC (Gemini™ Prep C18 5 μm column, Phenomenex, Torrance, Calif.; eluent: 10 to 90% acetonitrile +0.1% TFA in water +0.1% TFA, gradient elution) to give the title compound as the first eluting isomer as a white powder.

¹H NMR (400 MHz, CHLOROFORM-d) δ ppm 0.59 (t, J=7.6 Hz, 3 H), 1.28 (t, J=7.2 Hz, 3 H), 1.44 (s, 3 H), 1.50-1.64 (m, 1 H), 2.10-2.19 (m, 1 H), 2.19-2.37 (m, 2 H), 2.86 (q, J=14.5 Hz, 2 H), 3.19-3.35 (m, 2 H), 4.11-4.27 (m, 2 H), 4.58 (d, J=10.5 Hz, 1 H), 6.77 (m, 1 H) 6.93-7.05 (m, 3 H) 7.05-7.17 (m, 2 H) 7.20-7.33 (m, 2 H); MS (ESI) 506.2 [M+H]⁺. 504.1 [M−H]⁻.

Example 66

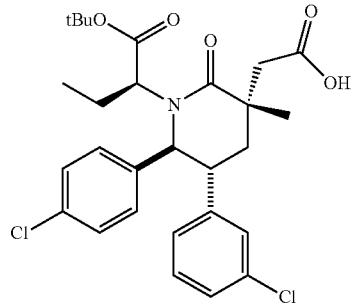

2-((3S,5R,6S)-1-((S)-1-tert-butoxy-1-oxobutan-2-yl)-5-(3-chlorophenyl)-6-(4-chlorophenyl)-3-methyl-2-oxopiperidin-3-yl)acetic acid Step A. (S)-tert-butyl 2-((2S,3R)-3-(3-chlorophenyl)-2-(4-chlorophenyl)-6-oxopiperidin-1-yl)butanoate

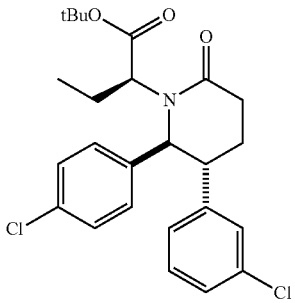

The title compound was synthesized as described in Example 9, Step A, substituting ethyl 2-bromobutanoate for t-butyl 2-bromobutanoate. Purification by flash chromatography on silica gel (30% EtOAc/Hexanes) provided the title compound as the faster eluting component as a white foam.

Step B. (2S)-tert-butyl 2-((2S,3R)-3-(3-chlorophenyl)-2-(4-chlorophenyl)-5-methyl-6-oxopiperidin-1-yl)butanoate

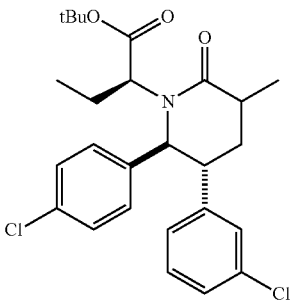

To a solution of 11.2 g (24.2 mmol) of (S)-tert-butyl 2-((2S, 3R)-3-(3-chlorophenyl)-2-(4-chlorophenyl)-6-oxopiperidin-1-yl)butanoate (Example 66, Step A) and iodomethane (1.813 mL, 29.1 mmol) in THF (120.0 mL) was added a lithium bis(trimethylsilyl)amide, (1M solution in THF; 26.6 mL, 26.6 mmol) at −78° C. The reaction was allowed to warm to R.T., then was quenched (sat. aqueous NH$_4$Cl) and extracted (2×EtOAc). The combined organic layers were washed with water and sat. aq. NaCl solution, dried over Na$_2$SO$_4$, filtered and the filtrate was concentrated under reduced pressure. The residue was absorbed onto a plug of silica gel and purified by chromatography on silica gel, eluting with a gradient of 10% to 30% EtOAc in hexane, to provide the title compound as a mixture of stereoisomers.

Step C. (2S)-tert-butyl 2-((5R,6S)-3-allyl-5-(3-chlorophenyl)-6-(4-chlorophenyl)-3-methyl-2-oxopiperidin-1-yl)butanoate

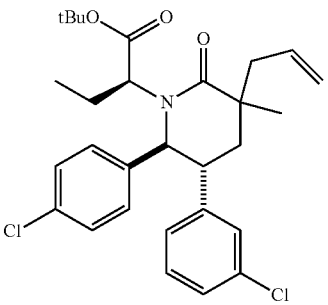

To a solution of 10.2 g (21.4 mmol) of (2S)-tert-butyl 2-((2S, 3R)-3-(3-chlorophenyl)-2-(4-chlorophenyl)-5-methyl-6-oxopiperidin-1-yl)butanoate (Example 66, Step B, mixture of diastereomers) and allyl bromide (7.24 mL, 86 mmol) in THF (210 mL) was added LHMDS, (1.0M solution in THF; 64.2 mL, 64.2 mmol) at R.T. Let it stir at R.T. for 5 min. Then the reaction mixture was heated at 50° C. for 3 h. Sat. aq. NH$_4$Cl solution was added and the mixture was extracted with CH$_2$Cl$_2$. The combined organic layers were washed with water and sat. aq. NaCl solution, dried over MgSO$_4$, filtered and the filtrate was concentrated under reduced pressure. The residue was purified by chromatography, eluting with a gradient of 0% to 20% EtOAc in hexane, to provide the title compound as a mixture of stereoisomers at C-3.

Step D. 2-((3S,5R,6S)-1-((S)-1-tert-butoxy-1-oxobutan-2-yl)-5-(3-chlorophenyl)-6-(4-chlorophenyl)-3-methyl-2-oxopiperidin-3-yl)acetic acid

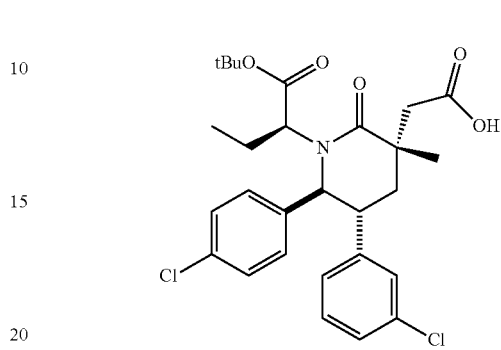

(2S)-tert-butyl 2-((5R,6S)-3-allyl-5-(3-chlorophenyl)-6-(4-chlorophenyl)-3-methyl-2-oxopiperidin-1-yl)butanoate (Example 66, Step C, mixture of diastereomers) was converted to the acid by a procedure similar to the one described in Example 65, Step D. The crude product was purified by reversed phase preparatory HPLC (Gemini™ Prep C18 5 µm column, Phenomenex, Torrance, Calif.; eluent: 10 to 90% acetonitrile +0.1% TFA in water +0.1% TFA, gradient elution) to give, the title compound as the first eluting isomer.

$^1$H NMR (400 MHz, CHLOROFORM-d) δ ppm 0.54 (t, J=7.5 Hz, 3 H), 1.41-1.55 (m, 14 H), 2.07-2.17 (m, 1 H), 2.25 (d, J=13.5 Hz, 1 H), 2.28-2.42 (m, 1 H), 2.81 (d, J=15.4 Hz, 1 H), 2.93-3.03 (m, 2 H), 3.24 (ddd, J=13.3, 10.5, 3.1 Hz, 1 H), 4.58 (d, J=10.5 Hz, 1 H), 6.76 (m, 1 H) 6.97-7.06 (m, 3 H) 7.08-7.20 (m, 2 H) 7.25 (s, 2 H); MS (ESI) 534.1 [M+H]$^+$. 532.0 [M−H]$^-$.

Further elution provided Example 67.

Example 67

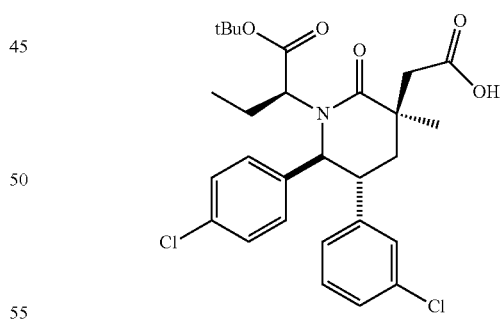

2-((3R,5R,6S)-1-((S)-1-tert-butoxy-1-oxobutan-2-yl)-5-(3-chlorophenyl)-6-(4-chlorophenyl)-3-methyl-2-oxopiperidin-3-yl)acetic acid $^1$H NMR (400 MHz, CHLOROFORM-d) δ ppm 1.00 (t, J=7.5 Hz, 3 H), 1.43 (s, 9 H), 1.50 (s, 3 H), 1.93-2.27 (m, 4 H), 2.79 (d, J=15.3 Hz, 1 H), 3.04 (d, J=15.5 Hz, 1 H), 3.15-3.29 (m, 2 H), 4.52 (d, J=10.4 Hz, 1 H), 6.68-6.78 (m, 1 H), 6.90-6.98 (m, 1 H), 7.05-7.29 (m, 6 H);

MS (ESI) 534.1 [M+H]$^+$. 532.0 [M−H]$^-$.

Example 68

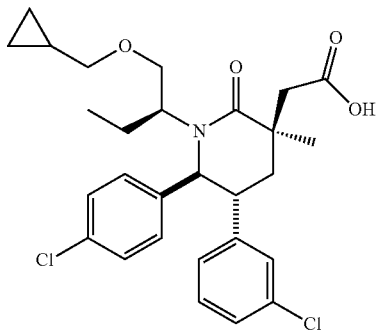

2-((3R,5R,6S)-5-(3-chlorophenyl)-6-(4-chlorophenyl)-1-((S)-1-(cyclopropylmethoxy)butan-2-yl)-3-methyl-2-oxopiperidin-3-yl)acetic acid Step A. (5R,6S)-5-(3-chlorophenyl)-6-(4-chlorophenyl)-1-((S)-1-hydroxybutan-2-yl)piperidin-2-one

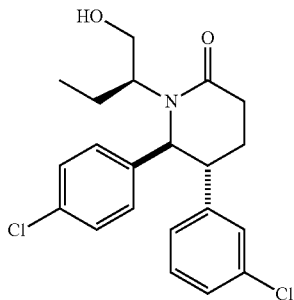

To a solution of 3 g (6.9 mmol) of (S)-ethyl 2-((2S,3R)-3-(3-chlorophenyl)-2-(4-chlorophenyl)-6-oxopiperidin-1-yl)butanoate (Example 9, Step A) in 45 mL of Et₂O was added lithium tetrahydroborate (0.334 g, 13.81 mmol) at 0° C. After being stirred at 0° C. for 50 min, the reaction was quenched (ice cold 10% citric acid) and extracted (2×EtOAc). The combined organic layers were washed with water and sat. aq. NaCl solution, dried over MgSO₄, filtered and the filtrate was concentrated under reduced pressure. Purification by flash chromatography on silica gel (eluent: 30% to 60% EtOAc/Hexanes, gradient elution) provided the title compound.

Step B. (5R,6S)-5-(3-chlorophenyl)-6-(4-chlorophenyl)-1-((S)-1-(cyclopropylmethoxy)butan-2-yl)piperidin-2-one

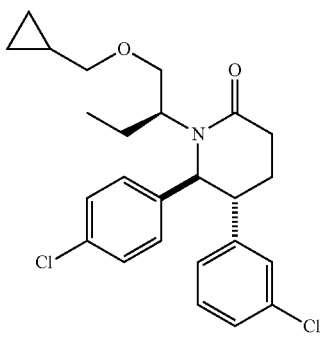

To a solution of 1.48 g (3.77 mmol) of (5R,6S)-5-(3-chlorophenyl)-6-(4-chlorophenyl)-1-((S)-1-hydroxybutan-2-yl)piperidin-2-one (Example 68, Step A) and bromomethylcyclopropane (0.828 mL, 7.54 mmol) in DMF (20 mL) was added sodium t-butoxide (0.544 g, 5.66 mmol) at 0° C. The mixture was stirred at 0° C. for 2 h and then warmed to rt. Then the reaction was stirred at rt for 14 h. The reaction was quenched with sat. aqueous NH₄Cl solution and extracted with EtOAc. The combined organic layers were washed with water and sat. aq. NaCl solution, dried over MgSO₄, filtered and the filtrate was concentrated under reduced pressure. Purification by flash chromatography on silica gel (eluent: 20%-40% EtOAc/Hexanes, gradient elution) provided the title compound as a colorless oil.

Step C. (5R,6S)-5-(3-chlorophenyl)-6-(4-chlorophenyl)-1-((S)-1-(cyclopropylmethoxy)butan-2-yl)-3-methylpiperidin-2-one

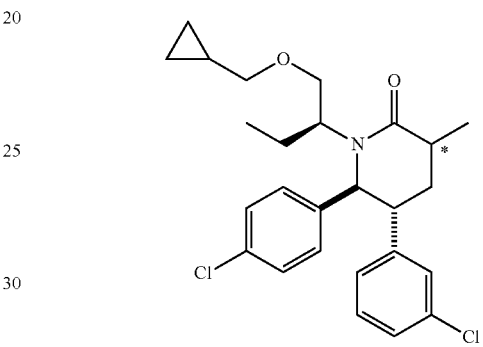

To a solution of 0.325 g (0.73 mmol) of (5R,6S)-5-(3-chlorophenyl)-6-(4-chlorophenyl)-1-((S)-1-(cyclopropylmethoxy)butan-2-yl)piperidin-2-one (Example 68, Step B) and iodomethane (0.055 mL, 0.874 mmol) in THF (7.0 mL) was added lithium bis(trimethylsilyl) amide (1M solution in THF, 0.8 mL, 0.8 mmol) at −78° C. The reaction was allowed to warm to R.T., then was quenched with sat. aqueous NH₄Cl solution and extracted with EtOAc. The combined organic layers were washed with water and sat. aq. NaCl solution, dried over MgSO₄, filtered and the filtrate was concentrated under reduced pressure. The crude material was absorbed onto a plug of silica gel and purified by chromatography on silica gel, eluting with a gradient of 10% to 30% EtOAc in hexane, to provide the title compound as a mixture of C-3 stereoisomers, as indicated by *.

Step D. (3S,5R,6S)-3-allyl-5-(3-chlorophenyl)-6-(4-chlorophenyl)-1-((S)-1-(cyclopropylmethoxy)butan-2-yl)-3-methylpiperidin-2-one

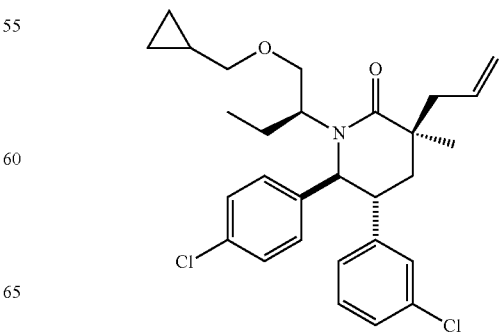

To a solution of 0.2 g (0.434 mmol) of (5R,6S)-5-(3-chlorophenyl)-6-(4-chlorophenyl)-1-((S)-1-(cyclopropylmethoxy)butan-2-yl)-3-methylpiperidin-2-one (Example 68, Step C, mixture of diastereomers) and allyl bromide (0.147 mL, 1.737 mmol) in THF (5 mL) was added LHMDS, (1.0 M solution in THF, 1.3 mL, 1.3 mmol) at RT. Let it stir at RT for 5 min. Then the reaction mixture was heated at 50° C. for 3 h. The reaction mixture was diluted with satd. NH₄Cl. and extracted with CH₂Cl₂. The combined organic layers were washed with water and sat. aq. NaCl solution, dried over MgSO₄, filtered and the filtrate was concentrated under reduced pressure. The crude material was purified by chromatography, eluting with a gradient of 0% to 20% EtOAc in hexane, to provide the title compound as a colorless oil.

Step E. 2-((3R,5R,6S)-5-(3-chlorophenyl)-6-(4-chlorophenyl)-1-((S)-1-(cyclopropylmethoxy)butan-2-yl)-3-methyl-2-oxopiperidin-3-yl)acetic acid (3S,5R,6S)-3-Allyl-5-(3-chlorophenyl)-6-(4-chlorophenyl)-1-((S)-1-(cyclopropylmethoxy)butan-2-yl)-3-methylpiperidin-2-one (Example 68, Step E) was converted to the acid by a procedure similar to the one described in Example 1, Step H, to provide the title compound.

$^1$H NMR (400 MHz, CHLOROFORM-d) δ ppm 0.20-0.33 (m, 2 H), 0.51 (t, J=7.5 Hz, 3 H), 0.57-0.70 (m, 2 H), 1.05-1.17 (m, 1 H), 1.44 (s, 3 H), 1.48-1.62 (m, 1 H), 1.82-1.95 (m, 1 H), 2.01 (dd, J=13.9, 3.3 Hz, 1 H), 2.20 (t, J=13.5 Hz, 1 H), 2.72 (d, J=15.1 Hz, 1 H), 2.95-3.12 (m, 3 H), 3.24-3.40 (m, 3 H), 3.95 (t, J=9.8 Hz, 1 H), 4.69 (d, J=10.0 Hz, 1 H), 6.72-6.80 (m, 1 H), 6.94-7.07 (m, 3 H), 7.07-7.21 (m, 2 H), 7.25 (d, J=8.61 Hz, 2 H);

Example 69

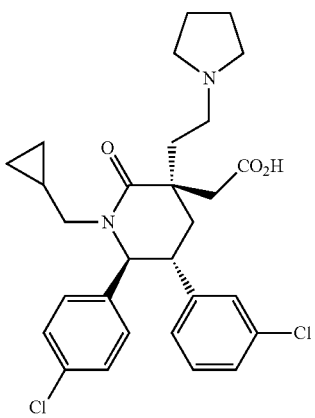 [SMILES: O=C(O)C[C@@]1(CCN2CCCC2)C[C@H](c2cccc(Cl)c2)[C@@H](c2ccc(Cl)cc2)N(CC2CC2)C1=O]

2-((3S,5R,6S)-5-(3-chlorophenyl)-6-(4-chlorophenyl)-1-(cyclopropylmethyl)-2-oxo-3-(2-(pyrrolidin-1-yl)ethyl)piperidin-3-yl)acetic acid Step A. (5R,6S)-3-Allyl-5-(3-chlorophenyl)-6-(4-chlorophenyl)-1-(cyclopropylmethyl)-3-(2-(triisopropylsilyloxy)ethyl)piperidin-2-one

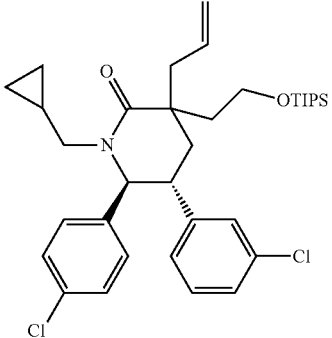

To a solution of 3.70 g (8.9 mmol) of a mixture of C-3 diastereomers of (5R,6S)-3-allyl-5-(3-chlorophenyl)-6-(4-chlorophenyl)-1-(cyclopropylmethyl)piperidin-2-oneoxopentanoate (Example 35, Step B) and 20.7 g (63 mmol) of (2-iodoethoxy)triisopropylsilane in dry, degassed THF (60 mL) was added 54.5 mL (54.5 mmol) of a 1 M solution of lithium bis(trimethylsilyl)amide in THF slowly via syringe over 6 min. After 10 min, the orange solution was warmed to 40° C. and stirred for an additional 2.25 h. The reaction was cooled to room temperature, quenched with saturated aqueous ammonium chloride, and extracted with EtOAc (3×). The combined organic layers were dried over Na₂SO₄, filtered and the filtrate was concentrated. Purification of the residue by flash chromatography on silica gel (2-25% EtOAc/hexanes, gradient elution) provided the title compound (mixture of C-3 epimers) as a light yellow oil.

Step B. 2-((5R,6S)-5-(3-chlorophenyl)-6-(4-chlorophenyl)-1-(cyclopropylmethyl)-2-oxo-3-(2-(triisopropylsilyloxy)ethyl)piperidin-3-yl)acetaldehyde

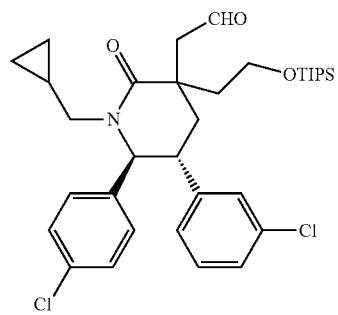

To a solution of 1.28 g (2.08 mmol) of (5R,6S)-3-allyl-5-(3-chlorophenyl)-6-(4-chlorophenyl)-1-(cyclopropylmethyl)-3-(2-(triisopropylsilyloxy)ethyl)piperidin-2-one (Example 69, Step A, mixture of diastereomers) in THF (50 mL) and water (17.5 mL) was added a catalytic amount of osmium tetroxide. After 25 min, 1.34 g (6.25 mmol) of sodium periodate was added. The resulting light brown slurry was stirred for 19 h and then was filtered through a fritted funnel. The filtrate was partially concentrated under reduced pressure, then was diluted with water and extracted with ethyl acetate (2×). The combined organic layers were washed with saturated aqueous sodium thiosulfate and then saturated aqueous sodium chloride. The organic layer was dried over Na₂SO₄, filtered and the filtrate was concentrated. The crude title compound (mixture of C-3 epimers) was used directly in the next step.

Step C. Synthesis of (5R,6S)-5-(3-chlorophenyl)-6-(4-chlorophenyl)-1-(cyclopropylmethyl)-3-(2-(pyrrolidin-1-yl)ethyl)-3-(2-(triisopropylsilyloxy)ethyl)piperidin-2-one

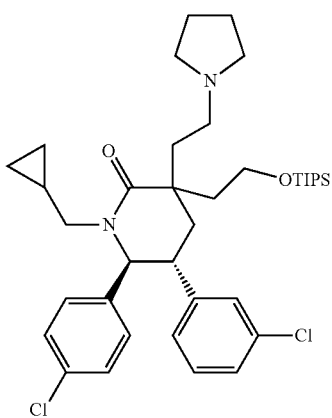

A mixture of 1.02 g (1.66 mmol) of crude 2-((5R,6S)-5-(3-chlorophenyl)-6-(4-chlorophenyl)-1-(cyclopropylmethyl)-2-oxo-3-(2-(triisopropylsilyloxy)ethyl)piperidin-3-yl)acetaldehyde (Example 69, Step B, mixture of diastereomers), 0.55 mL (6.6 mmol) of pyrrolidine, 880 mg (4.15 mmol) of sodium triacetoxyborohydride and 285 μL (4.98 mmol) of acetic acid was suspended in a mixture of 1,2-dichloroethane (36 mL) and DMF (12 mL). After being stirred at room temperature for 20 h, the reaction mixture was quenched with saturated aqueous sodium bicarbonate and extracted with DCM (3×). The combined organic layers were dried over $Na_2SO_4$, filtered and the filtrate was concentrated. The crude title compound (mixture of C-3 epimers) was used directly in the next step.

Step D. (5R,6S)-5-(3-chlorophenyl)-6-(4-chlorophenyl)-1-(cyclopropylmethyl)-3-(2-hydroxyethyl)-3-(2-(pyrrolidin-1-yl)ethyl)piperidin-2-one

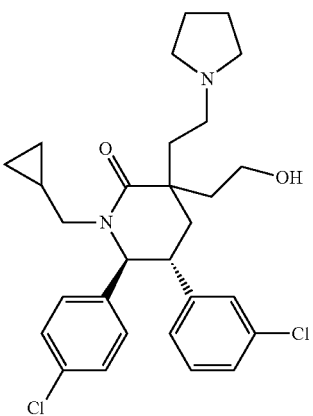 [SMILES: O=C1N(CC2CC2)[C@H](c2ccc(Cl)cc2)[C@@H](c2cccc(Cl)c2)CC1(CCO)CCN1CCCC1]

To an ice-cooled solution of 1.12 g (1.66 mmol) of crude (5R,6S)-5-(3-chlorophenyl)-6-(4-chlorophenyl)-1-(cyclopropylmethyl)-3-(2-(pyrrolidin-1-yl)ethyl)-3-(2-(triisopropylsilyloxy)ethyl)piperidin-2-one (Example 69, Step C, mixture of diastereomers) in THF (55 mL) added 8.3 mL (8.3 mmol) of a 1M solution of TBAF in THF. After being stirred at room temperature for 1.5 h, the reaction mixture was quenched with water and extracted with EtOAc (3×). The combined organic layers were dried ($Na_2SO_4$), and concentrated under the reduced pressure. Purification of the residue by flash chromatography on silica gel (3-30% MeOH/DCM, gradient elution) provided the title compound (mixture of C-3 epimers) as a light yellow oil.

Step E. 2-((3S,5R,6S)-5-(3-chlorophenyl)-6-(4-chlorophenyl)-1-(cyclopropylmethyl)-2-oxo-3-(2-(pyrrolidin-1-yl)ethyl)piperidin-3-yl)acetic acid An ice-cooled solution of 2.05 g (20.5 mmol) of chromium (VI) oxide in water (4 mL) was treated with 1.75 mL (32.7 mmol) of sulfuric acid via syringe. The mixture was diluted with additional water (4 mL) and stored at 0° C. at prior to use. In a separate flask, 105 mg (0.21 mmol) of (5R,6S)-5-(3-chlorophenyl)-6-(4-chlorophenyl)-1-(cyclopropylmethyl)-3-(2-hydroxyethyl)-3-(2-(pyrrolidin-1-yl)ethyl)piperidin-2-one (Example 69, Step D, mixture of diastereomers) was dissolved in acetone (20 mL) and then treated with Jones reagent (see above) slowly via pipette at room temperature. After 30 min, the resulting dark red solution was heated at 55° C. for an additional 17.5 h. The reaction was concentrated under reduced pressure, then was diluted with water and extracted with ethyl acetate (4×). The organic layers were over $Na_2SO_4$, filtered and the filtrate was concentrated. Purification of the residue by reversed phase prep. HPLC (Sunfire Prep $C_{18}$ OBD 10 μm column (Waters, Milford, Mass.), gradient elution of 40% MeCN in water to 55% MeCN in water over a 35 min period, where both solvents contain 0.1% TFA) provided the title compound (single enantiomer) as a white solid. [Note that the desired C-3 (3S) epimer is the less polar epimer and elutes off second].

$^1$H NMR (400 MHz, $CDCl_3$) δ ppm 11.11 (1 H, br s), 7.18-7.24 (2 H, m), 7.08-7.18 (2 H, m), 6.99 (1 H, br s), 6.77-6.87 (3 H, m), 4.61 (1 H, dd, J=10.1 Hz, 4.7 Hz), 3.72-3.86 (3 H, m), 3.61 (1 H, br s), 3.36 (1 H, br s), 3.13 (1 H, br s), 2.75-2.97 (4 H, m), 2.20-2.35 (2 H, m), 1.99-2.22 (7 H, m), 0.84 (1 H, br s), 0.36-0.54 (2 H, m), −0.05-0.13 (2 H, m). Mass Spectrum (ESI) m/z=529 (M+1).

Example 70

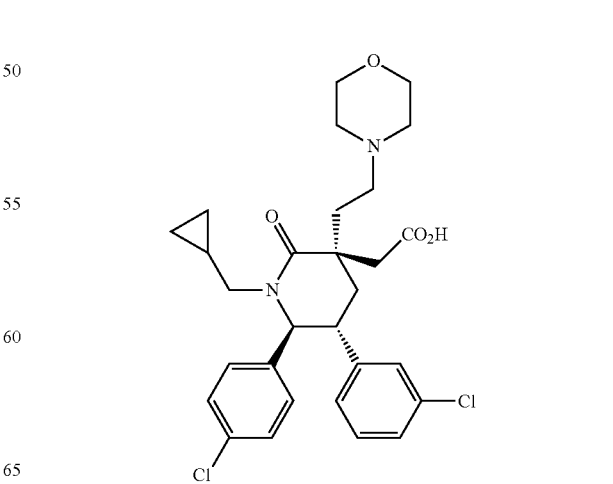

2-((3S,5R,6S)-5-(3-chlorophenyl)-6-(4-chlorophenyl)-1-(cyclopropylmethyl)-3-(2-morpholinoethyl)-2-oxopiperidin-3-yl)acetic acid Step A. (5R,6S)-5-(3-chlorophenyl)-6-(4-chlorophenyl)-1-(cyclopropylmethyl)-3-(2-hydroxyethyl)-3-(2-morpholinoethyl)piperidin-2-one

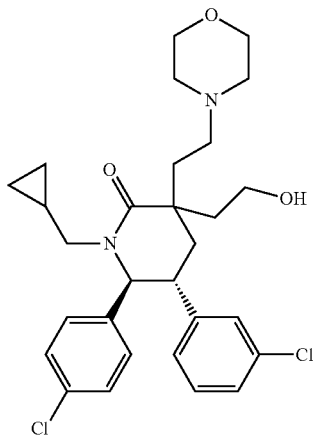 [SMILES: O=C1N(CC2CC2)[C@H](c2ccc(Cl)cc2)[C@@H](c2cccc(Cl)c2)CC1(CCO)CCN1CCOCC1]

A mixture of 94 mg (0.15 mmol) of crude 2-((5R,6S)-5-(3-chlorophenyl)-6-(4-chlorophenyl)-1-(cyclopropylmethyl)-2-oxo-3-(2-(triisopropylsilyloxy)ethyl)piperidin-3-yl)acetaldehyde (Example 69, Step B, mixture of diastereomers), 66 µL (0.76 mmol) of morpholine, 97 mg (0.46 mmol) of sodium triacetoxyborohydride and 30 µL (0.53 mmol) of acetic acid was suspended in a mixture of 1,2-dichloroethane (6 mL) and DMF (2 mL). After being stirred at room temperature for 20 h, the reaction mixture was quenched with saturated aqueous sodium bicarbonate and extracted with DCM (3×). The combined organic layers were dried over Na$_2$SO$_4$, filtered and the filtrate was concentrated. Purification of the residue by reversed phase preparatory HPLC (SunFire™ Prep C$_{18}$ OBD 10 µm column (Waters, Milford, Mass.), gradient elution of 50% MeCN in water to 90% MeCN in water over a 30 min period, where both solvents contain 0.1% TFA) provided the title compound (mixture of C-3 epimers) along with the corresponding TIPS ether (mixture of C-3 epimers) and the corresponding trifluoroacetate (mixture of C-3 epimers) as a colorless oil.

This mixture was dissolved in THF (5 mL) and treated with 0.76 mL (0.76 mmol) of a 1M solution of TBAF in THF. After being stirred at room temperature for 3.5 h, the reaction mixture was quenched with water and extracted with EtOAc (3×). The combined organic layers were dried (Na$_2$SO$_4$), and concentrated under the reduced pressure. Purification of the residue by flash chromatography on silica gel (8-35% MeOH/DCM, gradient elution) provided the title compound (mixture of C-3 epimers) as a white solid.

Step B. 2-((3S,5R,6S)-5-(3-chlorophenyl)-6-(4-chlorophenyl)-1-(cyclopropylmethyl)-3-(2-morpholinoethyl)-2-oxopiperidin-3-yl)acetic acid An ice-cooled solution of 403 mg (4.03 mmol) of chromium(VI) oxide in water (1 mL) was treated with 343 µL (6.44 mmol) of sulfuric acid via syringe. The solution was diluted with additional water (1 mL) and stored at 0° C. at prior to use. In a separate flask, (5R,6S)-5-(3-chlorophenyl)-6-(4-chlorophenyl)-1-(cyclopropylmethyl)-3-(2-hydroxyethyl)-3-(2-morpholinoethyl)piperidin-2-one (Example 70, Step A, mixture of diastereomers) was dissolved in acetone (5 mL) and then treated with Jones reagent (see above) slowly via pipette at room temperature. After 30 min, the resulting dark red solution was heated at 55° C. for an additional 17 h. The reaction was concentrated under reduced pressure, then was diluted with water and extracted with ethyl acetate (3×). The organic layers were over Na$_2$SO$_4$, filtered and the filtrate was concentrated. Purification of the residue by reversed phase prep. HPLC (SunFire™ Prep C$_{18}$ OBD 10 µm column (Waters, Milford, Mass.), gradient elution of 40% MeCN in water to 60% MeCN in water over a 35 min period, where both solvents contain 0.1% TFA) provided the title compound (single enantiomer) as a white solid. [Note that the desired (3S)C-3 epimer is the less polar epimer and elutes off second].

$^1$H NMR (400 MHz, CDCl$_3$) δ ppm 12.05 (1 H, br s), 6.95-7.26 (5 H, m), 6.76-6.88 (3 H, m), 4.64 (1 H, d, J=10.0 Hz), 4.23 (1 H, br s), 3.76-4.10 (5 H, m), 3.43-3.65 (2 H, m), 3.08-3.34 (2 H, m), 2.78-3.01 (3 H, m), 2.41-2.76 (2 H, m), 2.26-2.39 (2 H, m), 2.08-2.24 (2 H, m), 0.85 (1 H, br s), 0.33-0.55 (2 H, m), −0.10-0.15 (2 H, m). Mass Spectrum (ESI) m/z=545 (M+1).

Example 71

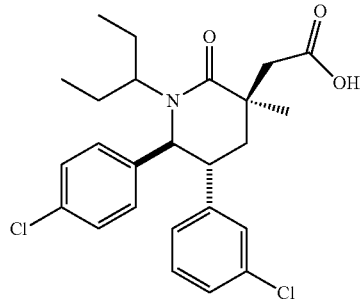

2-((3R,5R,6S)-5-(3-chlorophenyl)-6-(4-chlorophenyl)-3-methyl-2-oxo-1-(pentan-3-yl)piperidin-3-yl)acetic acid Step A. (5R,6S)-5-(3-chlorophenyl)-6-(4-chlorophenyl)-1-(2,4-dimethoxybenzyl)piperidin-2-one

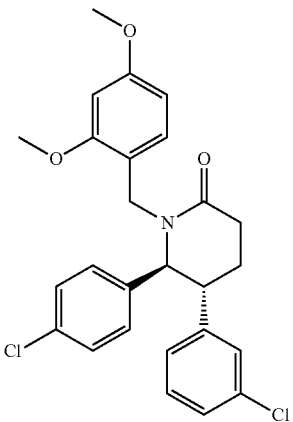 [SMILES: COc1ccc(CN2C(=O)CC[C@H](c3cccc(Cl)c3)[C@H]2c2ccc(Cl)cc2)c(OC)c1]

Thionyl chloride (116 mL, 1586 mmol) was added dropwise over 1 hour to a turbid solution of (2,4-dimethoxyphenyl)methanol (97.00 g, 577 mmol) and pyridine (93 mL, 1153 mmol) in anhydrous Et₂O (1153 mL) at 0° C. under nitrogen with mechanical stirring. After 1 hour the reaction mixture was poured into 2 L of ice water and the layers were separated. The aqueous layer was extracted with Et₂O (2×1 L) and the organics were pooled, washed with ice water (1.2 L), cold 5:1 sat. aq. NaCl solution/sat. aq. NaHCO₃ (1.2 L), dried (MgSO₄), filtered and most of the ether was removed in vacuo at 12° C. Benzene (300 mL) was added and the mixture was concentrated at 12° C. until 100 mL of benzene remained to provide a solution of 1-(chloromethyl)-2,4-dimethoxybenzene.

80 g (250 mmol) of (5R,6S)-5-(3-chlorophenyl)-6-(4-chlorophenyl)piperidin-2-one (Example 1, Step E) was added in portions over 20 minutes to a mixture of NaH (19.98 g, 500 mmol) in anhydrous DMF (400 mL) at 0° C. under nitrogen. After the addition was complete the ice bath was removed and the mixture was stirred at rt for 1 hour before cooling the solution to 0° C. To the cooled solution was added a solution of 1-(chloromethyl)-2,4-dimethoxybenzene (107 g, 575 mmol) in benzene and the reaction mixture was allowed to warm to rt. After 16 hours the reaction mixture was poured into ice water (2 L) and extracted with EtOAc (3×1 L). The organics were pooled, washed with water (3×1 L), sat. aq. NaCl solution (1 L), dried (MgSO₄), filtered and concentrated in vacuo to provide a thick yellow oil. Purification on the Combiflash XL (flash column chromatography, Teledyne Isco, Lincoln, Nebr.) using four stacked 330 g columns and one 1.5 kg column and eluting with 35-40-45-50-55% EtOAc/hexanes provided a very pale yellow oil. This was dissolved in benzene and the solvent removed in vacuo and dried under vacuum for 2 days to provide the title compound as a white foam (105.8 g, 90%).

Step B. (5R,6S)-5-(3-chlorophenyl)-6-(4-chlorophenyl)-1-(2,4-dimethoxybenzyl)-3-methylpiperidin-2-one

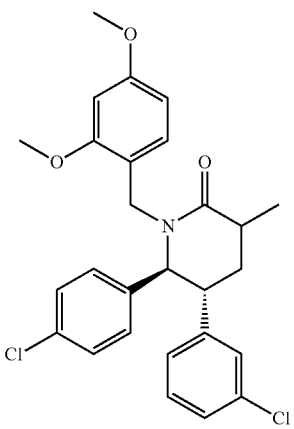 [SMILES: COc1ccc(CN2C(=O)C(C)C[C@H](c3cccc(Cl)c3)[C@H]2c2ccc(Cl)cc2)c(OC)c1]

A solution of (5R,6S)-5-(3-chlorophenyl)-6-(4-chlorophenyl)-1-(2,4-dimethoxybenzyl)piperidin-2-one (Example 71, Step A) (140.34 g, 298 mmol) in anhydrous THF (994 mL) was degassed by bubbling argon through the solution for 20 minutes while it cooled to −78° C. Iodomethane (23.32 mL, 373 mmol) was added followed by the addition of LHMDS (328 mL, 328 mmol) over 15 minutes. The reaction mixture was stirred for 15 minutes at −78° C. and then the reaction was removed from the cold bath and stirred at rt for 12 hours. The reaction was quenched by the addition of sat. aq. NH₄Cl and the layers were separated. The aqueous layer was extracted with EtOAc (2×500 mL) and the organics were pooled, washed with sat. aq. NaCl solution, dried (MgSO₄), filtered and concentrated in vacuo to provide an orange oil. Purification (wet loaded with small amount of DCM) using the Combiflash Companion XL (flash column chromatography, Teledyne Isco, Lincoln, Nebr.) with a 1.5 kg SiO₂ column and eluting with 4 L each of 15-20-25-30-35% EtOAc/hexanes provided the title compound as a thick very pale yellow oil and a 3.7:1 mixture of C-3 diastereomers.

Step C. (5R,6S)-3-allyl-5-(3-chlorophenyl)-6-(4-chlorophenyl)-1-(2,4-dimethoxybenzyl)-3-methylpiperidin-2-one

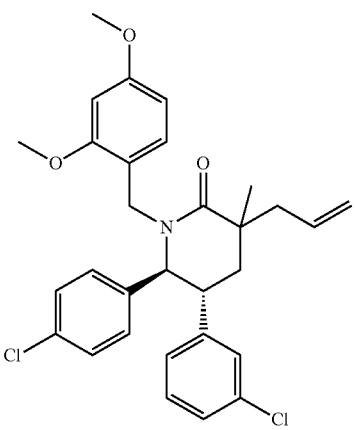 [SMILES: C=CCC1(C)C[C@H](c2cccc(Cl)c2)[C@@H](c2ccc(Cl)cc2)N(Cc2ccc(OC)cc2OC)C1=O]

A solution of (5R,6S)-5-(3-chlorophenyl)-6-(4-chlorophenyl)-1-(2,4-dimethoxybenzyl)-3-methylpiperidin-2-one (Example 71, Step B, mixture of C-3 diastereomers) (117.0 g, 242 mmol) in anhydrous THF (966 mL) was degassed by bubbling argon through the solution for 20 minutes. Allyl bromide (105 mL, 1208 mmol) was added followed by the addition of LHMDS (725 mL, 725 mmol) over 20 minutes. The reaction mixture was heated at 40° C. under argon for 5 hours. The reaction mixture was cooled to rt. and the reaction was quenched by the addition of sat. aqueous NH₄Cl (500 mL) and the layers were separated. The aqueous layer was extracted with EtOAc (2×1 L) and the organics were pooled, washed with sat. aq. NaCl solution (1 L), dried (MgSO₄), filtered and concentrated in vacuo to provide a red oil (180 g). Purification using the Biotage system (Charlotte, N.C.) with a 1.5 kg SiO₂ column and eluting with 10-30% EtOAc/hexanes provided the title compound as a very pale yellow oil as a 3.7:1 mixture of (3S):(3R) diastereomers.

Step D. (3S,5R,6S)-3-allyl-5-(3-chlorophenyl)-6-(4-chlorophenyl)-3-methylpiperidin-2-one

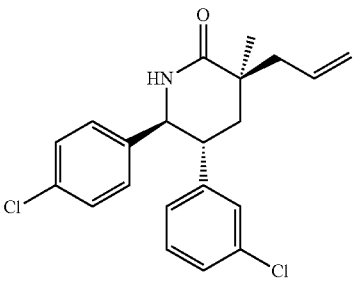 [SMILES: C=CC[C@@]1(C)C[C@H](c2cccc(Cl)c2)[C@@H](c2ccc(Cl)cc2)NC1=O]

A solution of (5R,6S)-3-allyl-5-(3-chlorophenyl)-6-(4-chlorophenyl)-1-(2,4-dimethoxybenzyl)-3-methylpiperidin-2-one (Example 71, Step C, mixture of diastereomers) (105.87 g, 202 mmol) in TFA (778 mL, 1.01E+04 mmol) was heated at 50° C. for 2 hours before concentrating the reaction mixture in vacuo. The residue was azeotroped with hexanes to remove all of the TFA. The deep purple oil containing some residue was taken up in a minimum amount of DCM, filtered and washed liberally with DCM. The filtrate was concentrated in vacuo to provide a dark purple oil. Purification (wet packed with a minimum amount of DCM) using the Biotage Isolera (Biotage, Charlotte, N.C.) with a 1.5 kg column and eluting with 25-40% EtOAc/hexanes provided the title compound as a white solid.

$^1$H NMR (500 MHz, CDCl$_3$) δ ppm 1.30 (s, 3H), 2.06 (m, 2H), 2.52 (dd, J=13.7 and 7.1 Hz, 1H), 2.60 (dd, J=13.7 and 7.8 Hz, 1H), 3.06 (m, 1H), 4.50 (d, J=10.7 Hz, 1H), 5.17 (m, 2H), 5.81 (br s, 1H), 5.86 (m, 1H), 6.77 (d, J=7.6 Hz, 1H), 6.96 (d, J=8.3 Hz, 2H), 7.00 (s, 1H), 7.12 (t, J=7.7 Hz, 1H), 7.17 (m, 1H), 7.20 (d, J=8.3 Hz, 2H). [ ]$^{22}$D+182.2° (c 1.55, CHCl$_3$).

Step E. (3S,5R,6S)-3-allyl-5-(3-chlorophenyl)-6-(4-chlorophenyl)-3-methyl-1-(pentan-3-yl)piperidin-2-one

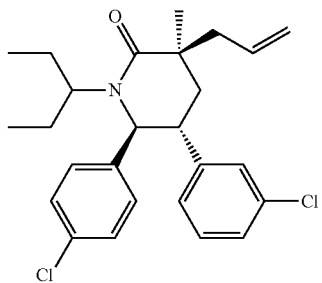 [SMILES: C=CC[C@@]1(C)C[C@H](c2cccc(Cl)c2)[C@@H](c2ccc(Cl)cc2)N(C(CC)CC)C1=O]

To a suspension of 1.81 g (4.8 mmol) of (3S,5R,6S)-3-allyl-5-(3-chlorophenyl)-6-(4-chlorophenyl)-3-methylpiperidin-2-one (Example 71, Step D) in 3-bromopentane (17.6 mL) added 967 mg (60 wt. % in mineral oil, 24.2 mmol) of sodium hydride. The resulting milky white slurry was heated at 120° C. for 20 h, and then more 3-bromopentane (5.1 mL) was added. After an additional 24 h at 120° C., the reaction was cooled to room temperature and quenched with saturated aqueous ammonium chloride. The mixture was extracted with ethyl acetate (3×) and the combined organic layers were dried over Na$_2$SO$_4$, filtered and the filtrate was concentrated. Purification of the residue by flash chromatography on silica gel (2 to 26% EtOAc/hexanes, gradient elution) provided the title compound as a white solid.

Step F. Synthesis of 2-((3R,5R,6S)-5-(3-chlorophenyl)-6-(4-chlorophenyl)-3-methyl-2-oxo-1-(pentan-3-yl)piperidin-3-yl)acetic acid To a solution of 725 mg (1.63 mmol) of (3S,5R,6S)-3-allyl-5-(3-chlorophenyl)-6-(4-chlorophenyl)-3-methyl-1-(pentan-3-yl)piperidin-2-one (Example 3, Step A) in a mixture of acetonitrile (4 mL), carbon tetrachloride (4 mL) and water (5.9 mL) added 1.40 g (6.53 mmol) of sodium periodate followed by 44 mg (0.20 mmol) of ruthenium(III) chloride hydrate. The dark brown biphasic mixture was stirred vigorously at room temperature for 21 h, and then was acidified with 1 N HCl. The mixture was diluted with EtOAc and filtered through a pad of Celite® (J. T. Baker, Phillipsberg, N.J., diatomaceous earth). After filtration, the layers were separated and the aqueous layer was extracted with EtOAc (1×). The combined organic layers were washed with saturated aqueous sodium chloride (1×), then were dried over Na$_2$SO$_4$, filtered and the filtrate was concentrated. Purification of the residue by flash chromatography on silica gel (0 to 25% MeOH/DCM, gradient elution) provided the title compound as a white solid.

$^1$H NMR (400 MHz, CDCl$_3$) δ ppm 7.06-7.27 (5 H, m), 6.90-7.01 (2 H, m), 6.68 (d, 1 H, J=7.8 Hz), 4.34 (1 H, d, J=10.4 Hz), 3.00-3.15 (2 H, m), 2.63-2.79 (2 H, m), 2.15-2.27 (1 H, m), 1.85-2.03 (3 H, m), 1.51 (s, 3 H), 1.38-1.51 (2 H, m), 0.95 (3 H, t, J=7.4 Hz), 0.50 (3 H, t, J=7.4 Hz). Mass Spectrum (ESI) m/z=462 (M+1).

Examples 72-75 were prepared in a process similar to that described for Example 71, substituting 3-bromopentane in Step E for the appropriate amount of alkylhalide.

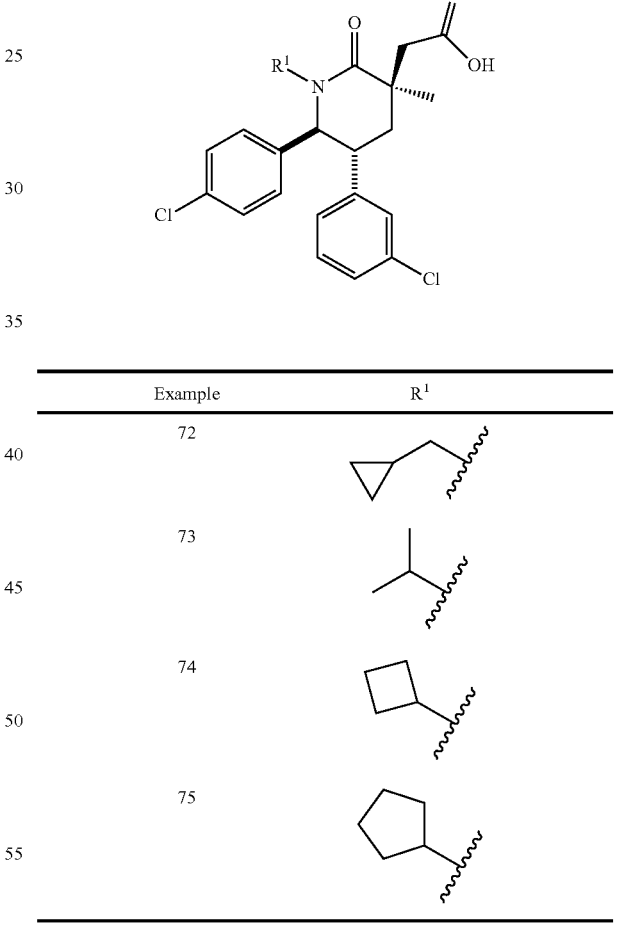

Example 72

2-((3R,5R,6S)-5-(3-chlorophenyl)-6-(4-chlorophenyl)-1-(cyclopropylmethyl)-3-methyl-2-oxopiperidin-3-yl)acetic acid $^1$H NMR (400 MHz, CHLOROFORM-d) δ ppm 7.29 (2 H, d, J=8.6 Hz), 7.12-7.24 (3 H, m), 6.90 (2 H, d, J=8.6 Hz), 6.88-6.82 (1 H, m), 4.80 (1 H, d, J=8.4 Hz), 4.02 (1 H, dd, J=14.1, 6.8 Hz), 3.11-3.03 (1 H, m), 2.98 (1 H, d, J=15.5 Hz), 2.68 (1 H, d, J=15.5 Hz), 2.37 (1 H, dd, J=14.1, 7.4 Hz), 2.23-2.14 (1 H, m), 2.13-2.05 (1 H, m), 1.39 (3 H, s), 1.03-0.94 (1 H, m), 0.62-0.46 (2 H, m), 0.23-0.08 (1 H, m); MS (ESI) 446.0 [M+H]⁺, 444.1 [M–H]⁻.

Example 73

2-((3R,5R,6S)-5-(3-chlorophenyl)-6-(4-chlorophenyl)-1-isopropyl-3-methyl-2-oxopiperidin-3-yl)acetic acid 1H NMR (400 MHz, CHLOROFORM-d) δ ppm 7.27 (2 H, d, J=7.8 Hz), 7.14-7.20 (2 H, m), 7.02 (1 H, s), 6.97 (2 H, d, J=7.8 Hz), 6.75 (1 H, d, J=7.6 Hz), 4.49 (1 H, d, J=9.0 Hz), 3.45 (1 H, m), 3.08 (1 H, m), 2.98 (1 H, d, J=15.2 Hz), 2.77 (1 H, d, J=15.2 Hz), 2.08 (2 H, m), 1.38 (3 H, s), 1.24 (6 H, t, J=6.7 Hz); MS (ESI) 434.0 [M+H]⁺.

Example 74

2-((3R,5R,6S)-5-(3-chlorophenyl)-6-(4-chlorophenyl)-1-cyclobutyl-3-methyl-2-oxopiperidin-3-yl)acetic acid 1H NMR (400 MHz, CHLOROFORM-d) δ ppm 7.15-7.26 (3 H, m), 7.17 (1 H, m), 7.04 (1 H, s), 6.65-6.79 (3 H, m), 4.65 (1 H, d, J=8.8 Hz), 3.85 (1 H, m), 3.05 (1 H, d, J=15.8 Hz), 2.85 (1 H, m), 2.60 (1 H, d, J=15.8 Hz), 2.45 (1 H, m), 2.20 (1 H, m), 1.90-2.2.20 (2 H, m), 1.65 (1 H, m), 1.42-1.55 (3 H, m), 1.42 (3 H, s); MS (ESI) 446.0 [M+H]⁺.

Example 75

2-((3R,5R,6S)-5-(3-chlorophenyl)-6-(4-chlorophenyl)-1-cyclopentyl-3-methyl-2-oxopiperidin-3-yl)acetic acid 1H NMR (400 MHz, CHLOROFORM-d) δ ppm 7.28 (2 H, d, J=8.3 Hz), 7.14-7.25 (2 H, m), 7.06 (1 H, s), 6.93 (2 H, d, J=8.3 Hz), 6.80 (1 H, d, J=7.6 Hz), 4.63 (1 H, d, J=8.1 Hz), 3.40 (1 H, m), 3.03 (1 H, d, J=15.7 Hz), 3.02 (1 H, m), 2.62 (1 H, d, J=15.7 Hz), 1.75-2.13 (7 H, m), 1.26-1.45 (3 H, m), 1.33 (3 H, s); MS (ESI) 460.1 [M+H]⁺.

Example 76

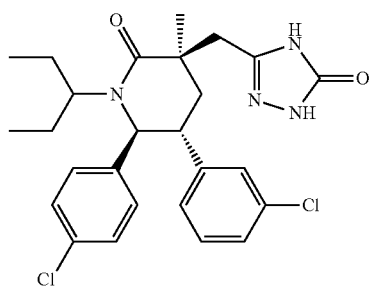 [SMILES: CCC(CC)N1C(=O)[C@@](C)(Cc2n[nH]c(=O)[nH]2)C[C@H](c2cccc(Cl)c2)[C@H]1c1ccc(Cl)cc1]

(3R,5R,6S)-5-(3-chlorophenyl)-6-(4-chlorophenyl)-3-methyl-3-((5-oxo-4,5-dihydro-1H-1,2,4-triazol-3-yl)methyl)-1-(pentan-3-yl)piperidin-2-one Step A. 2-(2-((3R,5R,6S)-5-(3-chlorophenyl)-6-(4-chlorophenyl)-3-methyl-2-oxo-1-(pentan-3-yl)piperidin-3-yl)acetyl)hydrazinecarboxamide

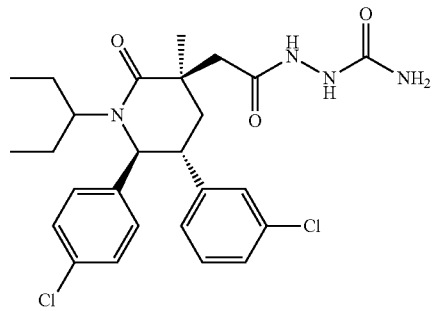 [SMILES: CCC(CC)N1C(=O)[C@@](C)(CC(=O)NNC(N)=O)C[C@H](c2cccc(Cl)c2)[C@H]1c1ccc(Cl)cc1]

To a solution of 320 mg (0.69 mmol) of 2-((3R,5R,6S)-5-(3-chlorophenyl)-6-(4-chlorophenyl)-3-methyl-2-oxo-1-(pentan-3-yl)piperidin-3-yl)acetic acid (Example 71, Step F) and 921 mg (2.42 mmol) of HOBt in DMF (13 mL) was added 0.58 mL (4.15 mmol) of triethylamine. After stirring at room temperature for 40 min, added 270 mg (2.42 mmol) of semicarbazide hydrochloride. The resulting dark red solution was stirred at room temperature for 2.5 h, and then was concentrated under reduced pressure. Purification of the residue by reversed phase prep. HPLC (Sunfire™ Prep C₁₈ OBD 10 μm column (Waters, Milford, Mass.), gradient elution of 40% MeCN in water to 90% MeCN in water over a 30 min period, where both solvents contain 0.1% TFA) provided the title compound as a light yellow solid.

Step B. (3R,5R,6S)-5-(3-chlorophenyl)-6-(4-chlorophenyl)-3-methyl-3-((5-oxo-4,5-dihydro-1H-1,2,4-triazol-3-yl)methyl)-1-(pentan-3-yl)piperidin-2-one 259 mg (0.50 mmol) of 2-(2-((3R,5R,6S)-5-(3-Chlorophenyl)-6-(4-chlorophenyl)-3-methyl-2-oxo-1-(pentan-3-yl)piperidin-3-yl)acetyl)hydrazinecarboxamide (Example 76, Step A) was suspended in 2 N aqueous sodium hydroxide (16 mL) and heated at reflux for 3.25 h. Upon cooling to room temperature, the mixture was acidified with conc. HCl until strongly acidic and then extracted with EtOAc (3×). The combined organic layers were dried over Na₂SO₄, filtered and the filtrate was concentrated. Purification of the residue by reversed phase prep. HPLC (Sunfire™ Prep C₁₈ OBD 10 μm column (Waters, Milford, Mass.), gradient elution of 40% MeCN in water to 75% MeCN in water over a 30 min period, where both solvents contain 0.1% TFA) provided the title compound as a white solid.

¹H NMR (400 MHz, CDCl₃) δ ppm 10.36 (1 H, br s), 9.35 (1 H, br s), 7.20-7.27 (3 H, m), 7.05-7.17 (2 H, m), 6.86-6.95 (2 H, m), 6.68 (1 H, d, J=7.8 Hz), 4.34 (1 H, d, J=10.5 Hz), 2.90-3.09 (3 H, m), 2.68-2.76 (1 H, m), 2.21 (1 H, t, J=13.8 Hz), 2.05 (1 H, dd, J=13.9 Hz, 2.9 Hz) 1.85-1.99 (2 H, m), 1.37-1.52 (2 H, m), 1.36 (3 H, s), 0.94 (3 H, t, J=7.4 Hz), 0.50 (3 H, t, J=7.5 Hz). Mass Spectrum (ESI) m/z=501 (M+1), 523 (M+23).

Example 77

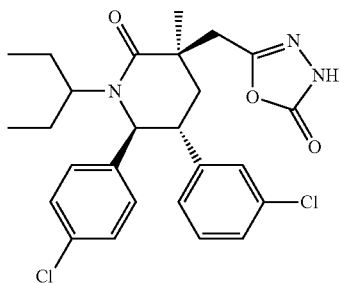 [SMILES: CCC(CC)N1C(=O)[C@@](C)(Cc2n[nH]c(=O)o2)C[C@H](c2cccc(Cl)c2)[C@H]1c1ccc(Cl)cc1]

5-(((3R,5R,6S)-5-(3-chlorophenyl)-6-(4-chlorophenyl)-3-methyl-2-oxo-1-(pentan-3-yl)piperidin-3-yl)methyl)-1,3,4-oxadiazol-2(3H)-one A solution of 56 mg (0.19 mmol) of triphosgene in DCM (1 mL) was added dropwise to a solution of 62 mg (0.13 mmol) of 2-((3R,5R,6S)-5-(3-chlorophenyl)-6-(4-chlorophenyl)-3-methyl-2-oxo-1-(pentan-3-yl)piperidin-3-yl)acetohydrazide (obtained as a byproduct in Example 76, Step B) and 170 μL (0.98 mmol) of diisopropylethylamine in DCM (4 mL). The resulting light yellow solution was stirred at room temperature for 18 h, then was quenched with saturated aqueous sodium bicarbonate and extracted with EtOAc (3×). The combined organic layers were dried over $Na_2SO_4$, filtered and the filtrate was concentrated. Purification of the residue by reversed phase preparative HPLC (Sunfire™ Prep $C_{18}$ OBD 10 μm column, (Waters, Milford, Mass.) gradient elution of 40% MeCN in water to 75% MeCN in water over a 30 min period, where both solvents contain 0.1% TFA) provided the title compound as a white solid.

$^1$H NMR (400 MHz, $CDCl_3$) δ ppm 9.68 (1 H, br s), 7.08-7.27 (4 H, m), 6.90-7.01 (3 H, m), 6.70 (1 H, d, J=7.4 Hz), 4.35 (1 H, d, J=10.4 Hz), 3.01-3.15 (3 H, m), 2.70-2.79 (1 H, m), 2.15 (1 H, t, J=13.8 Hz), 2.01 (1 H, dd, J=13.8 Hz, 3.1 Hz) 1.82-1.95 (2 H, m), 1.35-1.57 (2 H, m), 1.43 (3 H, s), 0.93 (3 H, t, J=7.4 Hz), 0.51 (3 H, t, J=7.4 Hz). Mass Spectrum (ESI) m/z=502 (M+1).

Example 78

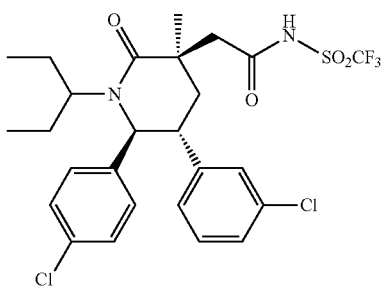

2-((3R,5R,6S)-5-(3-chlorophenyl)-6-(4-chlorophenyl)-3-methyl-2-oxo-1-(pentan-3-yl)piperidin-3-yl)-N-(trifluoromethylsulfonyl)acetamide To a solution of 47 mg (0.10 mmol) of 2-((3R,5R,6S)-5-(3-chlorophenyl)-6-(4-chlorophenyl)-3-methyl-2-oxo-1-(pentan-3-yl)piperidin-3-yl)acetic acid (Example 71, Step F) in DMF (4 mL) was added 64 mg (0.34 mmol) of EDC, 48 mg (0.36 mmol) of HOBt, and a catalytic amount of DMAP. After 30 min, 45.5 mg (0.30 mmol) of trifluoromethanesulfonamide was added. The resulting light yellow solution was stirred at room temperature for 3 h, and then was concentrated under reduced pressure. Purification of the residue by reversed phase prep. HPLC (Sunfire™ Prep $C_{18}$ OBD 10 μm column (Waters, Milford, Mass.), gradient elution of 50% MeCN in water to 90% MeCN in water over a 30 min period, where both solvents contain 0.1% TFA) provided the title compound as a white solid.

$^1$H NMR (400 MHz, $CDCl_3$) δ ppm 7.25-7.32 (3 H, m), 7.16-7.20 (1 H, m), 7.11 (t, 1 H, J=7.8 Hz), 6.92-7.00 (2 H, m), 6.67 (d, 1 H, J=7.6 Hz), 4.35 (1 H, d, J=10.4 Hz), 3.19 (d, 1 H, J=15.7 Hz), 2.97-3.06 (1 H, m), 2.73-2.83 (1 H, m), 2.68 (1 H, d, J=15.7 Hz), 2.26 (1 H, t, J=13.8 Hz), 1.86-2.08 (3 H, m), 1.52 (3 H, s), 1.39-1.52 (2 H, m), 0.95 (3 H, t, J=7.4 Hz), 0.50 (3 H, t, J=7.4 Hz). Mass Spectrum (ESI) m/z=593 (M+1), 615 (M+23).

Example 79

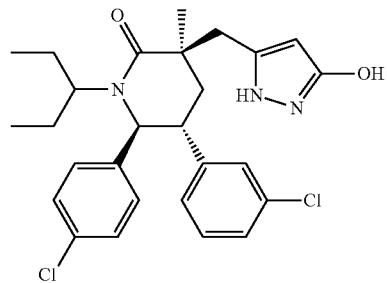 [SMILES: CCC(CC)N1C(=O)[C@@](C)(Cc2cc(O)n[nH]2)C[C@H](c2cccc(Cl)c2)[C@H]1c1ccc(Cl)cc1]

(3R,5R,6S)-5-(3-chlorophenyl)-6-(4-chlorophenyl)-3-((3-hydroxy-1H-pyrazol-5-yl)methyl)-3-methyl-1-(pentan-3-yl)piperidin-2-one Step A. 2-((3R,5R,6S)-5-(3-chlorophenyl)-6-(4-chlorophenyl)-3-methyl-2-oxo-1-(pentan-3-yl)piperidin-3-yl)acetaldehyde

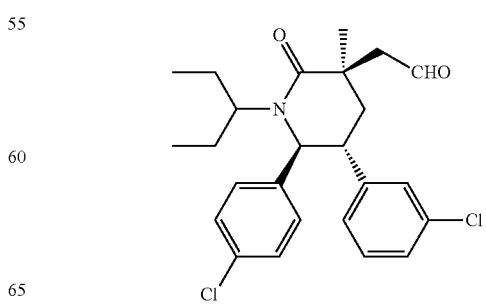

To a solution of 240 mg (0.54 mmol) of (3S,5R,6S)-3-allyl-5-(3-chlorophenyl)-6-(4-chlorophenyl)-3-methyl-1-(pentan-3-yl)piperidin-2-one (Example 71, Step E) in THF (8 mL) and water (2.8 mL) added a catalytic amount of osmium tetroxide. After 1.25 h, 323 mg (1.51 mmol) of sodium periodate were added. The resulting light brown slurry was stirred at room temperature for 18.5 h, and then filtered through a fritted funnel. The filtrate was partially concentrated under reduced pressure, then was diluted with water and extracted with ethyl acetate (2×). The combined organic layers were washed with saturated aqueous sodium thiosulfate and then saturated aqueous sodium chloride. The organic layer was dried over $Na_2SO_4$, filtered and the filtrate was concentrated. The crude title compound was used directly in the next step.

Step B. Ethyl 4-((3R,5R,6S)-5-(3-chlorophenyl)-6-(4-chlorophenyl)-3-methyl-2-oxo-1-(pentan-3-yl)piperidin-3-yl)-3-oxobutanoate

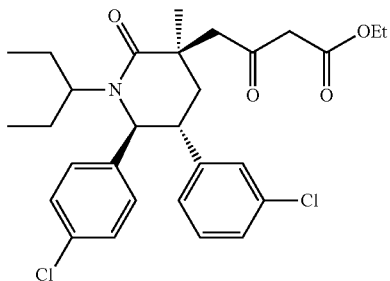 [SMILES: CCOC(=O)CC(=O)C[C@@]1(C)C[C@H](c2cccc(Cl)c2)[C@@H](c2ccc(Cl)cc2)N(C(CC)CC)C1=O]

To a suspension of 160 mg (0.36 mmol) of 2-((3R,5R,6S)-5-(3-chlorophenyl)-6-(4-chlorophenyl)-3-methyl-2-oxo-1-(pentan-3-yl)piperidin-3-yl)acetaldehyde (Example 79, Step A) and 20.4 mg (0.11 mmol) of tin(II) chloride in DCM (6 mL) was added 104 μL (1.00 mmol) of ethyl diazoacetate via syringe over 3 min. The resulting yellow slurry was stirred at room temperature for 14.25 h, then was quenched with 1 N HCl and extracted with EtOAc (2×). The combined organic layers were washed with 1 N HCl (1×), then were dried over $Na_2SO_4$, filtered and the filtrate was concentrated. Purification of the residue by reversed phase prep. HPLC (Sunfire™ Prep $C_{18}$ OBD 10 μm column (Waters, Milford, Mass.), gradient elution of 55% MeCN in water to 85% MeCN in water over a 30 min period, where both solvents contain 0.1% TFA) provided the title compound as a light yellow oil.

Step C. (3R,5R,6S)-5-(3-chlorophenyl)-6-(4-chlorophenyl)-3-((3-hydroxy-1H-pyrazol-5-yl)methyl)-3-methyl-1-(pentan-3-yl)piperidin-2-one To a solution of 42 mg (0.08 mmol) of ethyl 4-((3R,5R,6S)-5-(3-chlorophenyl)-6-(4-chlorophenyl)-3-methyl-2-oxo-1-(pentan-3-yl)piperidin-3-yl)-3-oxobutanoate (Example 79, Step B) in ethanol (4 mL) was added 36 μL (0.48 mmol) hydrazine monohydrate (64-65% weight percent hydrazine). The resulting colorless solution was heated at 65° C. for 3.5 h, and then was concentrated under reduced pressure. Purification of the residue by reversed phase prep. HPLC (Sunfire Prep $C_{18}$ OBD 10 μm column, gradient elution of 45% MeCN in water to 80% MeCN in water over a 30 min period, where both solvents contain 0.1% TFA) provided the title compound as a white solid.

$^1$H NMR (400 MHz, $CDCl_3$) δ ppm 7.23-7.30 (3 H, m), 7.18-7.22 (1 H, m), 7.12 (1 H, t, J=7.7 Hz), 6.90-6.96 (2 H, m), 6.67 (1 H, d, J=7.8 Hz), 5.66 (1 H, s), 4.34 (1 H, d, J=10.6 Hz), 3.42 (1 H, d, J=15.9 Hz), 3.02-3.11 (1 H, m), 2.82 (1 H, d, J=15.9 Hz), 2.68-2.77 (1 H, m), 2.36 (1 H, t, J=13.9 Hz), 1.87-2.03 (3 H, m), 1.40-1.51 (2 H, m), 1.36 (3 H, s), 0.96 (3 H, t, J=7.4 Hz), 0.50 (3 H, t, J=7.5 Hz). Mass Spectrum (ESI) m/z=500 (M+1), 522 (M+23).

Example 80

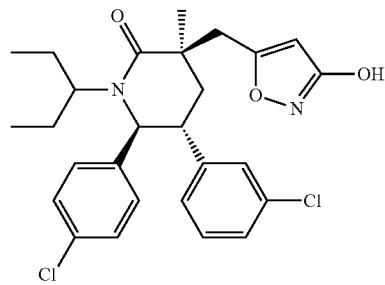 [SMILES: CCC(CC)N1C(=O)[C@@](C)(Cc2cc(O)no2)C[C@H](c2cccc(Cl)c2)[C@H]1c1ccc(Cl)cc1]

(3R,5R,6S)-5-(3-chlorophenyl)-6-(4-chlorophenyl)-3-((3-hydroxyisoxazol-5-yl)methyl)-3-methyl-1-(pentan-3-yl)piperidin-2-one To an ice-cooled slurry of 65 mg (0.12 mmol) of ethyl 4-((3R,5R,6S)-5-(3-chlorophenyl)-6-(4-chlorophenyl)-3-methyl-2-oxo-1-(pentan-3-yl)piperidin-3-yl)-3-oxobutanoate (Example 79, Step B) in water (2 mL) was added 53.5 mg (0.77 mmol) of hydroxylamine hydrochloride and 62 mg (1.55 mmol) of sodium hydroxide. After 5 min, THF (1 mL) and MeOH (1 mL) were added. The resulting cloudy light yellow solution was stirred at 0° C. for 20 min, then was warmed to room temperature and stirred for an additional 6 h. The reaction was acidified by dropwise addition of conc. HCl until strongly acidic, then was diluted with water and extracted with EtOAc (4×). The combined organic layers were dried over $Na_2SO_4$, filtered and the filtrate was concentrated. Purification of the residue by reversed phase prep. HPLC (Sunfire™ Prep $C_{18}$ OBD 10 μm column (Waters, Milford, Mass.), gradient elution of 55% MeCN in water to 85% MeCN in water over a 30 min period, where both solvents contain 0.1% TFA) provided the title compound as a white solid.

$^1$H NMR (400 MHz, $CDCl_3$) δ ppm 7.20-7.27 (3 H, m), 7.14-7.20 (1 H, m), 7.11 (1 H, dt, J=7.8 Hz, 3.8 Hz), 6.89-7.01 (3 H, m), 6.70 (1 H, d, J=7.4 Hz), 4.33 (1 H, dd, J=10.5 Hz, 3.4 Hz), 3.59-3.78 (2 H, m), 3.13-3.23 (1 H, m), 3.07 (1 H, dd, J=14.1 Hz, 3.1 Hz), 2.66-2.77 (2 H, m), 2.15-2.26 (1 H, m), 1.96-2.04 (1 H, m), 1.78-1.94 (2 H, m), 1.40-1.51 (1 H, m), 1.41 (3 H, s), 0.93 (3 H, dt, J=7.4 Hz, 3.5 Hz), 0.51 (3 H, dt, J=7.5 Hz, 3.6 Hz). Mass Spectrum (ESI) m/z=501 (M+1).

Example 81

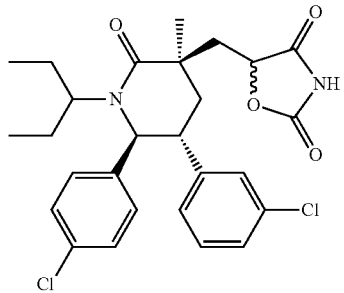 [SMILES: CCC(CC)N1C(=O)[C@@](C)(CC2OC(=O)NC2=O)C[C@H](c2cccc(Cl)c2)[C@H]1c1ccc(Cl)cc1]

5-(((3R,5R,6S)-5-(3-chlorophenyl)-6-(4-chlorophenyl)-3-methyl-2-oxo-1-(pentan-3-yl)piperidin-3-yl)methyl)oxazolidine-2,4-dione Step A. (3R,5R,6S)-5-(3-chlorophenyl)-6-(4-chlorophenyl)-3-(2,3-dihydroxypropyl)-3-methyl-1-(pentan-3-yl)piperidin-2-one

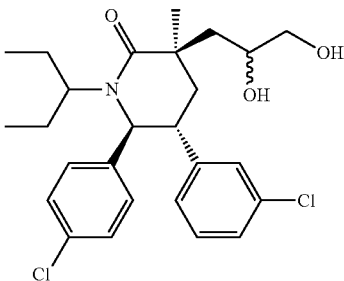 [SMILES: CCC(CC)N1C(=O)[C@@](C)(CC(O)CO)C[C@H](c2cccc(Cl)c2)[C@H]1c1ccc(Cl)cc1]

To a solution of 298 mg (0.67 mmol) of (3S,5R,6S)-3-allyl-5-(3-chlorophenyl)-6-(4-chlorophenyl)-3-methyl-1-(pentan-3-yl)piperidin-2-one (Example 71, Step E) in a mixture of acetone (11.5 mL) and water (4 mL) added a catalytic amount of osmium tetroxide. After 4 min, 275 mg (2.35 mmol) of N-methylmorpholine-N-oxide was added. The resulting brown solution was stirred at room temperature for 3.5 h, and then was partitioned between water and DCM (3×). The combined organic layers were dried over Na₂SO₄, filtered and the filtrate was concentrated. Purification of the residue by flash chromatography on silica gel (1 to 20% MeOH/DCM, gradient elution) provided the title compound (mixture of alcohol epimers) as a yellow oil.

Step B. 3-((3R,5R,6S)-5-(3-chlorophenyl)-6-(4-chlorophenyl)-3-methyl-2-oxo-1-(pentan-3-yl)piperidin-3-yl)-2-hydroxypropanoic acid

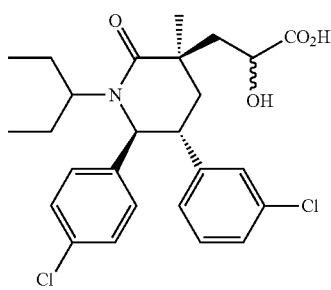 [SMILES: CCC(CC)N1C(=O)[C@@](C)(CC(O)C(=O)O)C[C@H](c2cccc(Cl)c2)[C@H]1c1ccc(Cl)cc1]

A mixture of 142 mg (0.30 mmol) of (3R,5R,6S)-5-(3-chlorophenyl)-6-(4-chlorophenyl)-3-(2,3-dihydroxypropyl)-3-methyl-1-(pentan-3-yl)piperidin-2-one (Example 81, Step A) and 28 mg (0.18 mmol) of TEMPO in a mixture of acetonitrile (6 mL) and sodium phosphate-sodium hydroxide buffer (pH 6.7, 4.5 mL) at 35° C. was treated simultaneously with a solution of 105 mg (1.16 mmol) of sodium chlorite in water (1.2 mL) and a solution of 106 µL (0.07 mmol) of bleach solution (ca. 0.7 N) in water (0.6 mL) over 10 min. The resulting dark orange solution was stirred at 35° C. for 1.75 h, and then was partitioned between 1 N HCl and EtOAc (3×). The combined organic layers were dried over Na₂SO₄, filtered and the filtrate was concentrated. Purification of the residue by reversed phase prep. HPLC (Sunfire™ Prep C₁₈ OBD 10 µm column (Waters, Milford, Mass.), gradient elution of 60% MeCN in water to 80% MeCN in water over a 30 min period, where both solvents contain 0.1% TFA) provided the title compound (mixture of alcohol epimers) as a white solid.

Step C. 3-((3R,5R,6S)-5-(3-chlorophenyl)-6-(4-chlorophenyl)-3-methyl-2-oxo-1-(pentan-3-yl)piperidin-3-yl)-N-(2,4-dimethoxybenzyl)-2-hydroxypropanamide

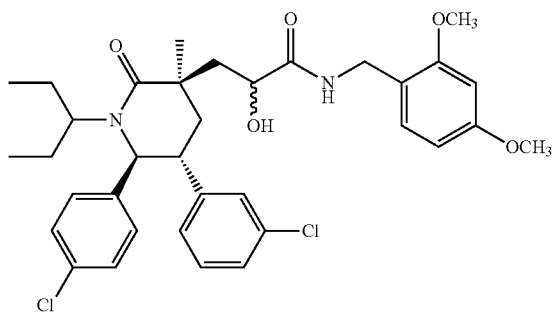 [SMILES: CCC(CC)N1C(=O)[C@@](C)(CC(O)C(=O)NCc2ccc(OC)cc2OC)C[C@H](c2cccc(Cl)c2)[C@H]1c1ccc(Cl)cc1]

To a solution of 43 mg (0.09 mmol) of 3-((3R,5R,6S)-5-(3-chlorophenyl)-6-(4-chlorophenyl)-3-methyl-2-oxo-1-(pentan-3-yl)piperidin-3-yl)-2-hydroxypropanoic acid (Example 81, Step B) in DMF (5 mL) was added 67 mg (0.18 mmol) of HATU, 58.5 mg (0.35 mmol) of 2,4-dimethoxybenzylamine and 36 µL (0.26 mmol) of triethylamine. The resulting yellow solution was stirred at room temperature for 1.1 h, and then was partitioned between saturated aqueous sodium bicarbonate and EtOAc (2×). The combined organic layers were dried over Na₂SO₄, filtered and the filtrate was concentrated. The crude title compound (mixture of alcohol epimers) was used directly in the next step.

Step D. (S)-3-((3R,5R,6S)-5-(3-chlorophenyl)-6-(4-chlorophenyl)-3-methyl-2-oxo-1-(pentan-3-yl)piperidin-3-yl)-2-hydroxypropanamide and (R)-3-((3R,5R,6S)-5-(3-chlorophenyl)-6-(4-chlorophenyl)-3-methyl-2-oxo-1-(pentan-3-yl)piperidin-3-yl)-2-hydroxypropanamide

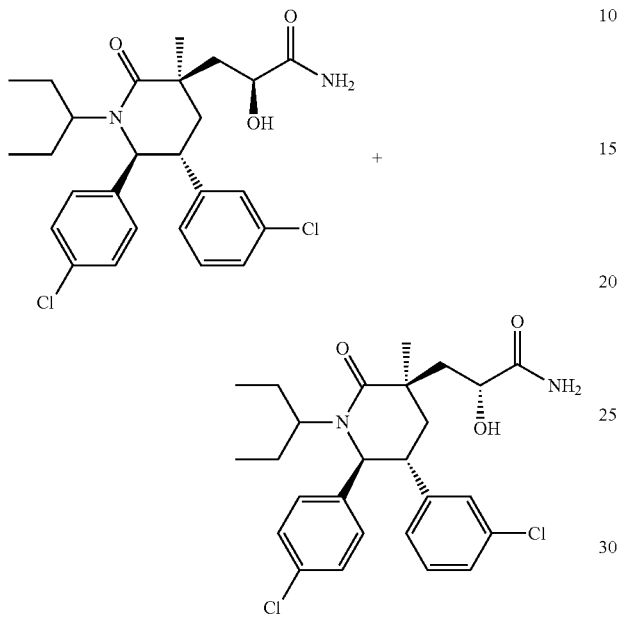

A solution of 56 mg (0.09 mmol) of 3-((3R,5R,6S)-5-(3-chlorophenyl)-6-(4-chlorophenyl)-3-methyl-2-oxo-1-(pentan-3-yl)piperidin-3-yl)-N-(2,4-dimethoxybenzyl)-2-hydroxypropanamide (Example 81, Step C) in trifluoroacetic acid (2.3 mL) was heated at 50° C. for 2.5 h, and then was concentrated under reduced pressure. Purification of the residue by reversed phase prep. HPLC (Sunfire™ Prep $C_{18}$ OBD 10 µm column (Waters, Milford, Mass.), gradient elution of 50% MeCN in water to 75% MeCN in water over a 30 min period, where both solvents contain 0.1% TFA) provided the two title compounds (in each case the stereochemistry at alcohol stereocenter is arbitrarily assigned) each as a light green solid.

Step E. 5-(((3R,5R,6S)-5-(3-chlorophenyl)-6-(4-chlorophenyl)-3-methyl-2-oxo-1-(pentan-3-yl)piperidin-3-yl)methyl)oxazolidine-2,4-dione To a solution of 10.3 mg (0.02 mmol) of (S)-3-((3R,5R,6S)-5-(3-chlorophenyl)-6-(4-chlorophenyl)-3-methyl-2-oxo-1-(pentan-3-yl)piperidin-3-yl)-2-hydroxypropanamide (Example 81, Step D) in MeOH (2.5 mL) was added 0.50 mL (1.22 mmol) of sodium ethoxide (21 wt. % solution in ethanol) and 1.20 mL (9.90 mmol) of diethyl carbonate. The resulting mixture was heated at reflux for 15 min, and then was concentrated under reduced pressure. The residue was partitioned between 0.5 M HCl and EtOAc (3×). The combined organic layers were dried over $Na_2SO_4$, filtered and the filtrate was concentrated. Purification of the residue by reversed phase prep. HPLC (Sunfire™ Prep $C_{18}$ OBD 10 µm column (Waters, Milford, Mass.), gradient elution of 60 MeCN in water to 80 MeCN in water over a 30 min period, where both solvents contain 0.1% TFA) provided the title compound (mixture of ether epimers) as a white solid.

$^1$H NMR (400 MHz, $CDCl_3$, mixture of epimers) δ ppm 8.90 (1 H, br s, major epimer), 8.83 (1 H, br s, minor epimer), 7.20-7.27 (3 H, m), 7.15-7.20 (1 H, m), 7.11 (1 H, dt, J=7.7 Hz, 1.9 Hz), 6.94-7.02 (2 H, m), 6.71 (1 H, d, J=7.6 Hz), 5.37 (1 H, t, J=10.0 Hz), 4.33 (1 H, d, J=10.4 Hz), 2.67-2.79 (1 H, m), 2.67-2.79 (1 H, m, major epimer) 2.41 (1 H, dd, J=15.2 Hz, 8.6 Hz, minor epimer), 1.82-2.31 (6 H, m), 1.48-1.61 (1 H, m), 1.35-1.45 (1 H, m), 1.45 (3 H, s, minor epimer), 1.44 (s, 3 H, major epimer), 0.94 (3 H, t, J=7.4 Hz), 0.52 (3 H, t, J=7.5 Hz). Mass Spectrum (ESI) m/z=517 (M+1), 539 (M+23).

Example 82

3-(((3R,5R,6S)-5-(3-chlorophenyl)-6-(4-chlorophenyl)-3-methyl-2-oxo-1-(pentan-3-yl)piperidin-3-yl)methyl)-1,2,4-oxadiazol-5(4H)-one

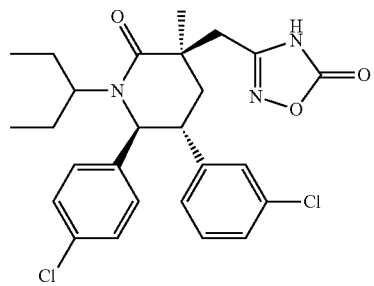

Step A. 2-((3R,5R,6S)-5-(3-chlorophenyl)-6-(4-chlorophenyl)-3-methyl-2-oxo-1-(pentan-3-yl)piperidin-3-yl)acetamide

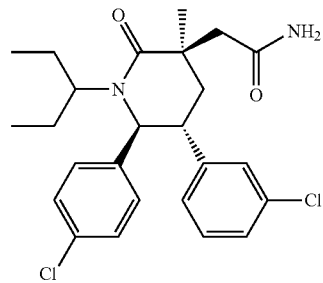 [SMILES: CCC(CC)N1C(=O)[C@@](C)(CC(N)=O)C[C@H](c2cccc(Cl)c2)[C@H]1c1ccc(Cl)cc1]

To an ice-cooled solution of 1.15 g (2.49 mmol) of 2-((3R,5R,6S)-5-(3-chlorophenyl)-6-(4-chlorophenyl)-3-methyl-2-oxo-1-(pentan-3-yl)piperidin-3-yl)acetic acid (Example 71, Step F) in THF (12.5 mL) was added 383 µL (3.48 mmol) of N-methylmorpholine and 392 µL (2.98 mmol) of isobutyl chloroformate. The resulting off-white slurry was stirred at 0° C. for 2 h, and then 336 µL (28% ammonia in water, 4.97 mmol) of ammonium hydroxide was added. After an additional 3 h at 0° C., the reaction was quenched with saturated aqueous ammonium chloride and extracted with EtOAc (3×).

Step B. 2-((3R,5R,6S)-5-(3-chlorophenyl)-6-(4-chlorophenyl)-3-methyl-2-oxo-1-(pentan-3-yl)piperidin-3-yl)acetonitrile

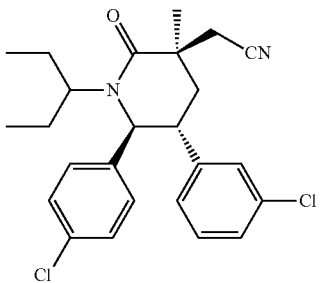 [SMILES: CCC(CC)N1C(=O)[C@@](C)(CC#N)C[C@H](c2cccc(Cl)c2)[C@H]1c1ccc(Cl)cc1]

To an ice-cooled solution of 1.15 g (2.49 mmol) of 2-((3R,5R,6S)-5-(3-chlorophenyl)-6-(4-chlorophenyl)-3-methyl-2-oxo-1-(pentan-3-yl)piperidin-3-yl)acetamide (Example 82, Step A) in THF (21 mL) was added 1.73 mL (12.4 mmol) of triethylamine and 865 µL (6.22 mmol) of TFA. The resulting tan solution was stirred at 0° C. for 2.75 h, then was warmed to room temperature and stirred for an additional 2 h. The reaction was recooled to 0° C., quenched with 1 N citric acid, and then extracted with EtOAc (3×). The combined organic layers were dried over Na$_2$SO$_4$, filtered and the filtrate was concentrated. The combined organic layers were washed with saturated aqueous sodium chloride (1×), then were dried over Na$_2$SO$_4$, filtered and the filtrate was concentrated. Purification of the residue by flash chromatography on silica gel (5 to 35% EtOAc/hexanes, gradient elution) provided the title compound as a white solid.

Step C. 2-((3R,5R,6S)-5-(3-chlorophenyl)-6-(4-chlorophenyl)-3-methyl-2-oxo-1-(pentan-3-yl)piperidin-3-yl)-N'-hydroxyacetimidamide

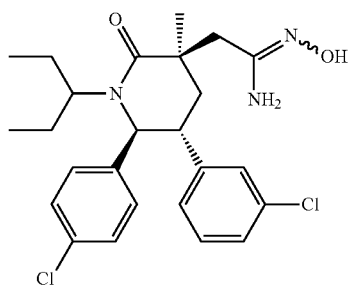 [SMILES: CCC(CC)N1C(=O)[C@@](C)(CC(N)=NO)C[C@H](c2cccc(Cl)c2)[C@H]1c1ccc(Cl)cc1]

To a suspension of 1.49 g (20.6 mmol) of hydroxylamine hydrochloride in DMSO (10 mL) was added 2.88 mL (20.6 mmol) of triethylamine. The slurry was stirred for 5 min and then filtered twice through cotton, rinsing with THF, to remove the solids. The filtrate was partially concentrated under reduced pressure to remove THF, and then was added to a flask containing 915 mg (2.06 mmol) of 2-((3R,5R,6S)-5-(3-chlorophenyl)-6-(4-chlorophenyl)-3-methyl-2-oxo-1-(pentan-3-yl)piperidin-3-yl)acetonitrile (Example 82, Step B). The resulting yellow solution was heated at 75° C. for 22 h, and then was partitioned between water and EtOAc. The organic layer was dried over Na$_2$SO$_4$, filtered and the filtrate was concentrated. Purification of the residue by flash chromatography on silica gel (1 to 7% MeOH/DCM, gradient elution) provided the title compound as a white solid.

Step D. 3-(((3R,5R,6S)-5-(3-chlorophenyl)-6-(4-chlorophenyl)-3-methyl-2-oxo-1-(pentan-3-yl)piperidin-3-yl)methyl)-1,2,4-oxadiazol-5(4H)-one

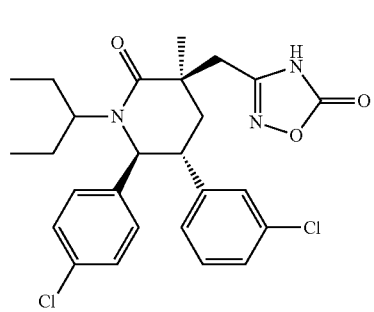

To a solution of 385 mg (0.81 mmol) of 2-((3R,5R,6S)-5-(3-chlorophenyl)-6-(4-chlorophenyl)-3-methyl-2-oxo-1-(pentan-3-yl)piperidin-3-yl)-N'-hydroxyacetimidamide (Example 82, Step C) in dioxane (12.5 mL) was added 211 µL (1.41 mmol) of DBU and 262 mg (1.62 mmol) of 1,1'-carbonyldiimidazole. The resulting colorless solution was heated at 100° C. for 25 min, and then was quenched with water and extracted with EtOAc. The organic layer was washed with saturated aqueous sodium chloride, and then was dried over Na$_2$SO$_4$, filtered and the filtrate was concentrated. Purification of the residue by reversed phase prep. HPLC (Sunfire™ Prep C$_{18}$ OBD 10 µm column (Waters, Milford, Mass.), gradient elution of 55% MeCN in water to 80% MeCN in water over a 35 min period, where both solvents contain 0.1% TFA) provided the title compound as a white solid.

$^1$H NMR (400 MHz, CDCl$_3$) δ ppm 10.39 (1 H, br s), 7.22-7.27 (3 H, m), 7.18 (1 H, d, J=8.1 Hz), 7.12 (1 H, t, J=7.8 Hz), 6.87-6.98 (2 H, m), 6.68 (1 H, d, J=7.6 Hz), 4.35 (1 H, d, J=10.3 Hz), 3.19 (1 H, d, J=15.4 Hz), 3.05 (1 H, ddd, J=13.3 Hz, 10.5 Hz, 2.6 Hz), 2.82 (1 H, d, J=15.4 Hz), 2.69-2.78 (1 H, m), 2.31 (1 H, t, J=13.8 Hz), 2.06 (1 H, dd, J=13.9 Hz, 2.7 Hz), 1.84-2.00 (2 H, m), 1.39-1.51 (2 H, m), 1.38 (3 H, s), 0.95 (3 H, t, J=7.5 Hz), 0.50 (3 H, t, J=7.5 Hz). Mass Spectrum (ESI) m/z=502 (M+1), 524 (M+23).

Example 83

3-(((3R,5R,6S)-5-(3-chlorophenyl)-6-(4-chlorophenyl)-1-isopropyl-3-methyl-2-oxopiperidin-3-yl)methyl)-1,2,4-oxadiazol-5(4H)-one

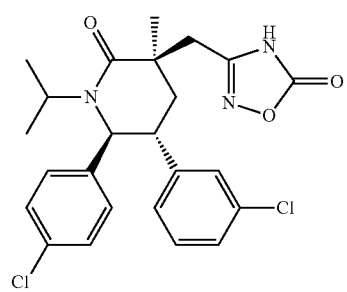 [SMILES: CC(C)N1C(=O)[C@@](C)(Cc2noc(=O)[nH]2)C[C@H](c2cccc(Cl)c2)[C@H]1c1ccc(Cl)cc1]

The title compound was prepared by methods similar to those described in Example 82.

$^1$H NMR (400 MHz, CDCl$_3$) δ ppm 10.38 (1 H, br s), 7.24-7.32 (2 H, m), 7.18-7.23 (m, 1 H), 7.15 (1 H, dt, J=7.8 Hz, 3.6 Hz), 7.04 (1 H, br s), 6.90 (2 H, d, J=5.4 Hz), 6.76 (1 H, d, J=7.1 Hz), 4.52 (1 H, dd, J=8.6 Hz, 3.2 Hz), 3.40-3.50 (1 H, m), 3.09 (1 H, dd, J=15.3 Hz, 2.8 Hz), 2.99-3.06 (1 H, m), 2.78 (1 H, dd, J=15.3 Hz, 3.1 Hz), 2.18 (1 H, dt, J=11.9 Hz, 3.2 Hz), 2.05-2.13 (1 H, m), 1.22-1.27 (m, 9 H). Mass Spectrum (ESI) m/z=474 (M+1).

Example 84

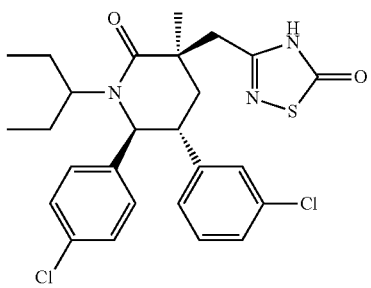

3-(((3R,5R,6S)-5-(3-chlorophenyl)-6-(4-chlorophenyl)-3-methyl-2-oxo-1-(pentan-3-yl)piperidin-3-yl)methyl)-1,2,4-thiadiazol-5(4H)-one To a solution of 83 mg (0.17 mmol) of 2-((3R,5R,6S)-5-(3-chlorophenyl)-6-(4-chlorophenyl)-3-methyl-2-oxo-1-(pentan-3-yl)piperidin-3-yl)-N'-hydroxyacetimidamide (Example 82, Step C) in THF (4 mL) was added 50 mg (0.28 mmol) of 1,1'-thiocarbonyldiimidazole. The resulting yellow solution was stirred at room temperature for 1 h, and then was quenched with water and extracted with EtOAc. The organic layer was dried over Na$_2$SO$_4$, filtered and the filtrate was concentrated. The residue was dissolved in THF (4.5 mL), and 69 µL (0.56 mmol) of boron trifluoride etherate was added via syringe. The resulting light yellow solution was stirred at room temperature for 2.5 h, and then was quenched with water and extracted with EtOAc. The organic layer was dried over Na$_2$SO$_4$, filtered and the filtrate was concentrated. Purification of the residue by reversed phase prep. HPLC (Sunfire Prep C$_{18}$ OBD 10 µm column, gradient elution of 55% MeCN in water to 85% MeCN in water over a 35 min period, where both solvents contain 0.1% TFA) provided the title compound as a white solid.

$^1$H NMR (400 MHz, CDCl$_3$) δ ppm 10.94 (1 H, br s), 7.20-7.27 (3 H, m), 7.13-7.18 (1 H, m), 7.09 (1 H, t, J=7.7 Hz), 6.85-6.95 (2 H, m), 6.66 (1 H, d, J=7.6 Hz), 4.34 (1 H, d, J=10.2 Hz), 3.09 (1 H, d, J=14.8 Hz), 2.87-3.01 (2 H, m), 2.68-2.77 (1 H, m), 2.25 (1 H, t, J=13.5 Hz), 2.04-2.13 (1 H, m), 1.87-2.04 (2 H, m), 1.39-1.51 (2 H, m), 1.38 (3 H, s), 0.95 (3 H, t, J=7.4 Hz), 0.50 (3 H, t, J=7.4 Hz). Mass Spectrum (ESI) m/z=518 (M+1), 540 (M+23).

Example 85

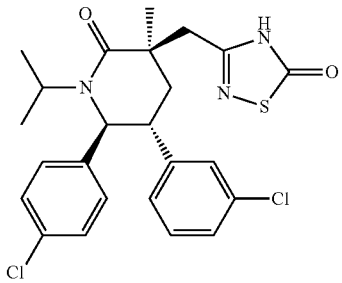 [SMILES: CC(C)N1C(=O)[C@@](C)(Cc2nsc(=O)[nH]2)C[C@H](c2cccc(Cl)c2)[C@H]1c1ccc(Cl)cc1]

3-(((3R,5R,6S)-5-(3-chlorophenyl)-6-(4-chlorophenyl)-1-isopropyl-3-methyl-2-oxopiperidin-3-yl)methyl)-1,2,4-thiadiazol-5(4H)-one The title compound was prepared by methods similar to those described in Example 84.

$^1$H NMR (400 MHz, CDCl$_3$) δ ppm 10.89 (1 H, br s), 7.24-7.30 (2 H, m), 7.18-7.22 (m, 1 H), 7.15 (1 H, t, J=7.8 Hz), 7.04 (1 H, br s), 6.86 (2 H, d, J=8.3 Hz), 6.77 (1 H, d, J=7.8 Hz), 4.53 (1 H, d, J=8.3 Hz), 3.41-3.50 (1 H, m), 2.90-3.04 (3 H, m), 2.05-2.19 (2 H, m), 1.27 (6 H, dd, J=6.6 Hz, 6.6 Hz), 1.23 (s, 3 H). Mass Spectrum (ESI) m/z=490 (M+1), 512 (M+23).

Example 86

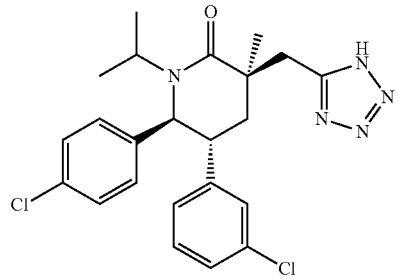 [SMILES: CC(C)N1C(=O)[C@@](C)(Cc2nnn[nH]2)C[C@H](c2cccc(Cl)c2)[C@H]1c1ccc(Cl)cc1]

(3R,5R,6S)-3-((1H-Tetrazol-5-yl)methyl)-5-(3-chlorophenyl)-6-(4-chlorophenyl)-1-isopropyl-3-methylpiperidin-2-one The title compound was prepared from 2-((3R,5R,6S)-5-(3-chlorophenyl)-6-(4-chlorophenyl)-1-isopropyl-3-methyl-2-oxopiperidin-3-yl)acetic acid (Example 73) as described in Example 51.

$^1$H NMR (400 MHz, CDCl$_3$) δ ppm 1.20 (s, 3H), 1.27 (d, J=6.9 Hz, 3H), 1.29 (d, J=6.8 Hz, 3H), 2.20 (m, 2H), 3.08 (m, 1H), 3.41 (d, J=15.7 Hz, 1H), 3.47 (m, 1H), 3.50 (d, J=15.6

Hz, 1H), 4.52 (d, J=8.8 Hz, 1H), 6.78 (m, 3H), 7.06 (m, 1H), 7.16 (m, 1H), 7.23 (m, 3H). Mass spectrum (ESI) m/z 458.0 [M+H]⁺.

Example 87

2-((3R,5R,6S)-5-(3-chlorophenyl)-6-(4-chlorophenyl)-3-ethyl-2-oxo-1-(pentan-3-yl)piperidin-3-yl)acetic acid

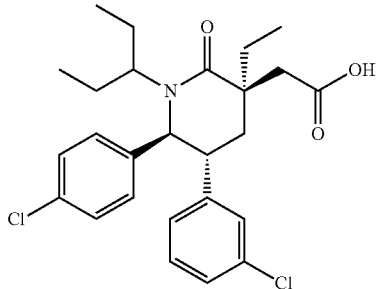 [SMILES: CCC(CC)N1C(=O)[C@@](CC)(CC(=O)O)C[C@H](c2cccc(Cl)c2)[C@H]1c1ccc(Cl)cc1]

Step A. (5R,6S)-3-allyl-5-(3-chlorophenyl)-6-(4-chlorophenyl)-3-ethyl-1-(pentan-3-yl)piperidin-2-one

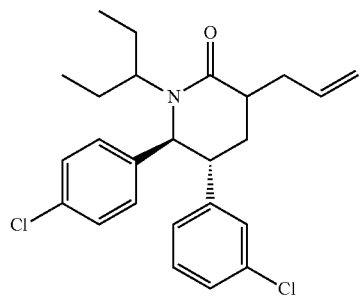 [SMILES: C=CCC1C[C@H](c2cccc(Cl)c2)[C@@H](c2ccc(Cl)cc2)N(C(CC)CC)C1=O]

To a solution of (3R,5R,6S)-3-allyl-5-(3-chlorophenyl)-6-(4-chlorophenyl)piperidin-2-one (Example 42, Step A) (440 mg, 1.221 mmol) in 3-bromopentane (3196 μL, 25.6 mmol) under nitrogen at rt was added a dispersion of 60% sodium hydride in mineral oil (244 mg, 6.11 mmol). Evolution of gas was observed. The reaction was stirred at room temperature for 10 min and then heated to 120° C. under N₂ for 19 h. The reaction mixture was cooled to room temperature and quenched with sat. NH₄Cl. The layers were separated and the organic layer was dried over Na₂SO₄ and concentrated under reduced pressure. The residue was purified by flash chromatography on silica gel (eluent: 0 to 25% EtOAc in hexanes) to give the title compound as a mixture of diastereomers.

Step B. (5R,6S)-3-allyl-5-(3-chlorophenyl)-6-(4-chlorophenyl)-3-ethyl-1-(pentan-3-yl)piperidin-2-one

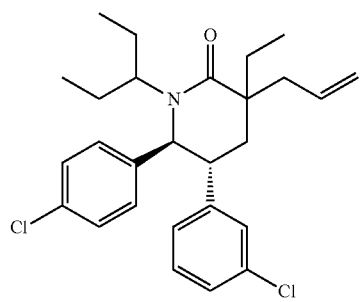 [SMILES: C=CCC1(CC)C[C@H](c2cccc(Cl)c2)[C@@H](c2ccc(Cl)cc2)N(C(CC)CC)C1=O]

To (5R,6S)-3-allyl-5-(3-chlorophenyl)-6-(4-chlorophenyl)-1-(pentan-3-yl)piperidin-2-one (Example 87, Step A) (125 mg, 0.290 mmol) was added toluene (15 mL) and the mixture was concentrated under reduced pressure. This step was repeated three times. Inhibitor free THF (1 mL) was added and the mixture was cooled to −78° C. Freshly prepared LDA (1.0M in THF) (290 μL, 0.290 mmol) was added and the reaction turned a golden-yellow color. The reaction was warmed to 0° C. for 30 min and the reaction color turned orange. The reaction was cooled to −78° C. and ethyl iodide (281 μL, 3.49 mmol) was added. The reaction mixture was warmed to 0° C. and stirred for 30 min. The reaction was quenched with sat. NH₄Cl, warmed to room temperature, diluted with EtOAc and the layers were separated. The organic layer was dried over Na₂SO₄ and concentrated under reduced pressure. The residue was purified by flash chromatography on silica gel (eluent: 0 to 10% EtOAc in hexanes) to give the title compound as a 1:1 mixture of diastereomers.

Step C. 2-((3R,5R,6S)-5-(3-chlorophenyl)-6-(4-chlorophenyl)-3-ethyl-2-oxo-1-(pentan-3-yl)piperidin-3-yl)acetic acid The title compound was prepared from (5R,6S)-3-allyl-5-(3-chlorophenyl)-6-(4-chlorophenyl)-3-ethyl-1-(pentan-3-yl)piperidin-2-one (Example 87, Step B) as described in Example 42, Step C. Purification by reversed phase preparatory HPLC (eluent: 0 to 100% MeCN +0.1% TFA in water +0.1% TFA) provided the title compound as the first eluting diastereomer.

¹H NMR (500 MHz, CHLOROFORM-d) δ ppm 0.50 (3 H, t, J=7.5 Hz) 0.95 (3 H, t, J=7.5 Hz) 1.00 (3 H, t, J=7.5 Hz) 1.29-1.45 (2 H, m) 1.45-1.53 (1 H, m) 1.84-2.01 (4 H, m) 2.30 (1 H, t, J=13.8 Hz) 2.72-2.80 (2 H, m) 3.03-3.11 (2 H, m) 4.34 (1 H, d, J=10.3 Hz) 6.69 (1 H, d, J=7.6 Hz) 6.95 (2 H, br s) 7.05-7.20 (2 H, m) 7.08-7.17 (2 H, m) 7.22-7.25 (1 H, m). Mass Spectrum (ESI) m/z=476 [M+H]⁺.

Example 88

(3S,5R,6S)-5-(3-chlorophenyl)-6-(4-chlorophenyl)-3-methyl-3-(methylsulfonylmethyl)-1-(pentan-3-yl)piperidin-2-one

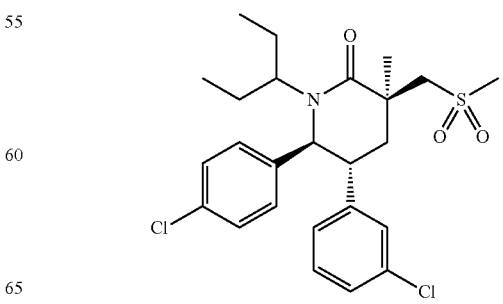

Step A. (5R,6S)-methyl 5-(3-chlorophenyl)-6-(4-chlorophenyl)-1-(2,4-dimethoxybenzyl)-3-methyl-2-oxopiperidine-3-carboxylate

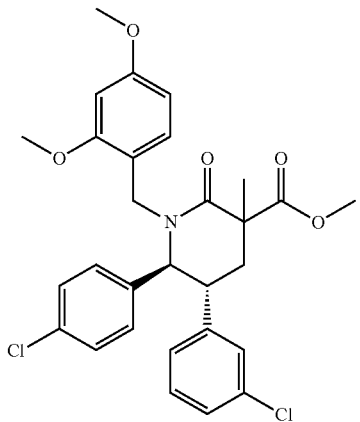 [SMILES: COC(=O)C1(C)C[C@H](c2cccc(Cl)c2)[C@@H](c2ccc(Cl)cc2)N(Cc2ccc(OC)cc2OC)C1=O]

LHMDS (5.42 mL, 5.42 mmol) was added to a solution of (5R,6S)-5-(3-chlorophenyl)-6-(4-chlorophenyl)-1-(2,4-dimethoxybenzyl)-3-methylpiperidin-2-one (Example 71, Step B) (1.75 g, 3.61 mmol) in anhydrous THF (14.45 mL) at rt under argon. After 5 minutes dimethyl dicarbonate (1.159 mL, 10.84 mmol) was added. After 4 hours TLC indicated that a significant amount of product had formed but some starting material remained. Additional LHMDS (5.42 mL, 5.42 mmol) was added followed by dimethyl dicarbonate (1.159 mL, 10.84 mmol). After 2.5 hours the reaction was quenched by the addition of sat. aq. NH$_4$Cl and the layers were separated. The aqueous layer was extracted with EtOAc twice and the organics were pooled, washed with sat. aq. NaCl solution, dried (MgSO$_4$), filtered and concentrated in vacuo to provide a yellow oil. Purification using a 120 g SiO$_2$ column and eluting with 25 to 40% EtOAc/hexanes provided the title compound as a colorless oil as a mixture of isomers.

Step B. (5R,6S)-5-(3-chlorophenyl)-6-(4-chlorophenyl)-1-(2,4-dimethoxybenzyl)-3-(hydroxymethyl)-3-methylpiperidin-2-one

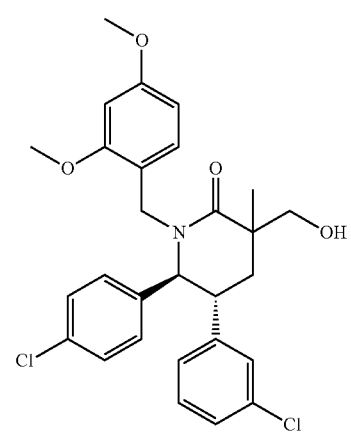 [SMILES: COc1ccc(CN2C(=O)C(C)(CO)C[C@H](c3cccc(Cl)c3)[C@H]2c2ccc(Cl)cc2)c(OC)c1]

2M lithium borohydride (1.078 mL, 2.157 mmol) was added to a solution of (5R,6S)-methyl 5-(3-chlorophenyl)-6-(4-chlorophenyl)-1-(2,4-dimethoxybenzyl)-3-methyl-2-oxopiperidine-3-carboxylate (Example 88, Step A) (1.17 g, 2.157 mmol) in anhydrous THF (21.57 mL) and anhydrous ether (20 mL) at 0° C. under nitrogen. The reaction was quenched after 58 hours with the addition of sat. aq. NH$_4$Cl and the layers were separated. The aqueous layer was extracted with EtOAc twice and the organics were pooled, washed with sat. aq. NaCl solution, dried (MgSO$_4$), filtered and concentrated in vacuo to provide a colorless oil. Purification using a 80 g SiO$_2$ column and eluting with 35 to 65% EtOAc/hexanes provided the title compound as a ~30:1 mixture of isomers.

Step C. ((5R,6S)-5-(3-chlorophenyl)-6-(4-chlorophenyl)-1-(2,4-dimethoxybenzyl)-3-methyl-2-oxopiperidin-3-yl)methyl 4-methylbenzenesulfonate

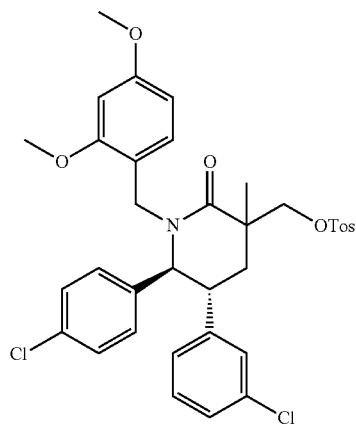

DMAP (0.015 g, 0.120 mmol) was added to a solution of (5R,6S)-5-(3-chlorophenyl)-6-(4-chlorophenyl)-1-(2,4-dimethoxybenzyl)-3-(hydroxymethyl)-3-methylpiperidin-2-one (Example 88, Step B) (0.616 g, 1.197 mmol) and tosyl-Cl (0.457 g, 2.395 mmol) in pyridine (5.99 mL) at rt. The reaction mixture was heated at 100° C. for 5 hours before removing the solvent in vacuo to provide a beige oil. Purification using a 80 g SiO$_2$ column and eluting with 25 to 55% EtOAc/hexanes provided the title compound as a colorless oil as a 33:1 mixture of isomers.

Step D. (3S,5R,6S)-5-(3-chlorophenyl)-6-(4-chlorophenyl)-1-(2,4-dimethoxybenzyl)-3-methyl-3-(methylthiomethyl)piperidin-2-one

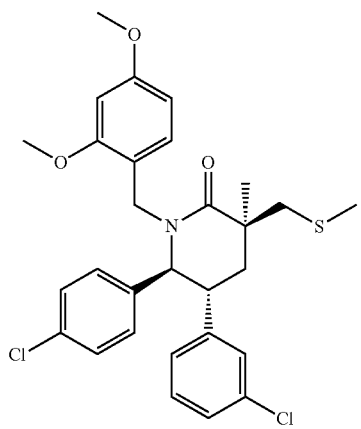 [SMILES: COc1ccc(CN2C(=O)[C@@](C)(CSC)C[C@H](c3cccc(Cl)c3)[C@H]2c2ccc(Cl)cc2)c(OC)c1]

Sodium thiomethoxide (0.193 g, 2.76 mmol) was added to a solution of ((5R,6S)-5-(3-chlorophenyl)-6-(4-chlorophenyl)-1-(2,4-dimethoxybenzyl)-3-methyl-2-oxopiperidin-3-yl)methyl 4-methylbenzenesulfonate (Example 88, Step C) (0.738 g, 1.104 mmol) in anhydrous DMF (5.52 mL) at rt under nitrogen. The reaction mixture was heated at 50° C. for 8 hours before being cooled to rt, diluted with water and extracted with ether three times. The organics were pooled, washed with water three times, sat. aq. NaCl solution, dried (MgSO₄), filtered and concentrated in vacuo to provide a colorless oil. Purification using a 40 g SiO₂ column and eluting with 15 to 40% EtOAc/hexanes provided the title compound as a colorless foam.

Step E. (3S,5R,6S)-5-(3-chlorophenyl)-6-(4-chlorophenyl)-3-methyl-3-(methylthiomethyl)piperidin-2-one

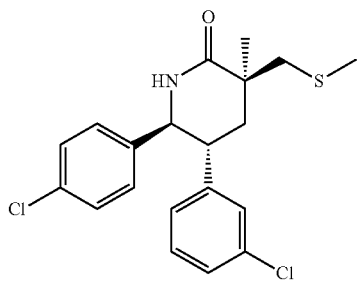 [SMILES: CSC[C@@]1(C)C[C@H](c2cccc(Cl)c2)[C@@H](c2ccc(Cl)cc2)NC1=O]

A solution of (3S,5R,6S)-5-(3-chlorophenyl)-6-(4-chlorophenyl)-1-(2,4-dimethoxybenzyl)-3-methyl-3-(methylthiomethyl)piperidin-2-one (Example 88, Step D) (0.406 g, 0.746 mmol) in TFA (6.00 mL) was heated at 50° C. under nitrogen for 2 hours. The reaction mixture was concentrated in vacuo to provide a purple oil. Purification using a 40 g SiO₂ column and eluting with 35 to 60% EtOAc/hexanes provided the title compound as a white solid.

Step F. (3S,5R,6S)-5-(3-chlorophenyl)-6-(4-chlorophenyl)-3-methyl-3-(methylthiomethyl)-1-(pentan-3-yl)piperidin-2-one

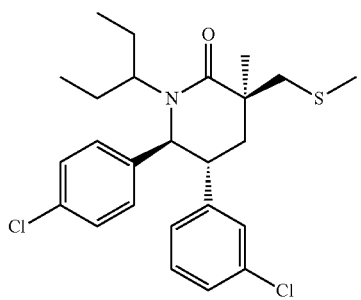 [SMILES: CCC(CC)N1C(=O)[C@@](C)(CSC)C[C@H](c2cccc(Cl)c2)[C@H]1c1ccc(Cl)cc1]

NaH (0.076 g, 1.900 mmol) was added to a solution of (3S,5R,6S)-5-(3-chlorophenyl)-6-(4-chlorophenyl)-3-methyl-3-(methylthiomethyl)piperidin-2-one (Example 88, step E) (0.150 g, 0.380 mmol) in 3-bromopentane (1.42 mL, 11.41 mmol) at rt under nitrogen. The reaction mixture was heated at 120° C. for 24 hours, cooled to rt, diluted with water and extracted with DCM three times. The organics were pooled, washed with sat. aq. NaCl solution, dried (MgSO₄), filtered and concentrated in vacuo to provide a yellow oil. Purification using a 24 g SiO₂ column and eluting with 15% EtOAc/hexanes provided the title compound as a colorless syrup.

Step G. (3S,5R,6S)-5-(3-chlorophenyl)-6-(4-chlorophenyl)-3-methyl-3-(methylsulfonylmethyl)-1-(pentan-3-yl)piperidin-2-one

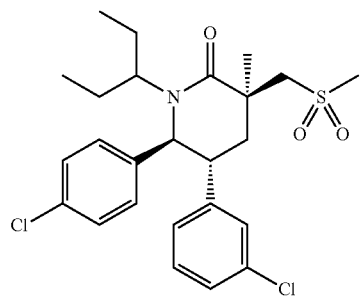 [SMILES: CCC(CC)N1C(=O)[C@@](C)(CS(C)(=O)=O)C[C@H](c2cccc(Cl)c2)[C@H]1c1ccc(Cl)cc1]

3-Chloroperbenzoic acid (0.054 g, 0.242 mmol) was added to a solution of (3S,5R,6S)-5-(3-chlorophenyl)-6-(4-chlorophenyl)-3-methyl-3-(methylthiomethyl)-1-(pentan-3-yl)piperidin-2-one (Example 88, Step F) (0.045 g, 0.097 mmol) in DCM (0.969 mL) at 0° C. The reaction mixture was stirred at rt for 1 hour, washed with sat. NaHCO₃, sat. aq. NaCl solution, dried (MgSO₄), filtered and concentrated in vacuo to provide a colorless oil. Purification using a 4 g SiO₂ ISCO column and eluting with 25 to 75% EtOAc/hexanes provided the title compound as a colorless glass.

$^1$H NMR (500 MHz, CDCl₃) δ ppm 0.49 (t, J=7.6 Hz, 3H), 0.95 (t, J=7.5 Hz, 3H), 1.39 (m, 1H), 1.54 (s, 3H), 1.56 (m, 1H), 1.89 (m, 2H), 2.10 (m, 1H), 2.57 (dd, J=14.4 and 3.1 Hz, 1H), 2.72 (m, 1H), 3.05 (s, 3H), 3.24 (d, J=13.9 Hz, 1H), 3.63 (m, 1H), 3.82 (d, J=13.9 Hz, 1H), 4.40 (d, J=10.7 Hz, 1H), 6.78 (m, 1H), 7.02 (br s, 1H), 7.06 (m, 2H), 7.10 (m, 2H), 7.20 (m, 2H). Mass spectrum (ESI) m/z 496.2 [M+H]⁺.

Example 89

2-((3R,5R,6S)-5-(3-chlorophenyl)-6-(4-chlorophenyl)-1-((S)-1-(3-cyclopropyl-1,2,4-oxadiazol-5-yl)propyl)-3-methyl-2-oxopiperidin-3-yl)acetic acid

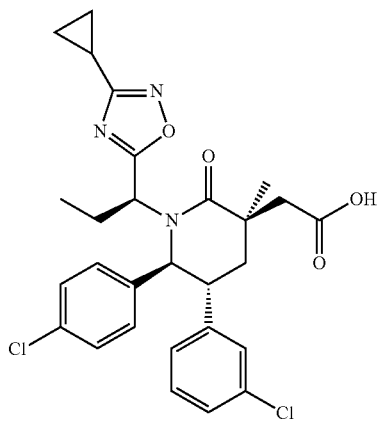 [SMILES: CC[C@@H](c1nc(C2CC2)no1)N1C(=O)[C@@](C)(CC(=O)O)C[C@H](c2cccc(Cl)c2)[C@H]1c1ccc(Cl)cc1]

Step A. 2-((3S,5R,6S)-3-allyl-5-(3-chlorophenyl)-6-(4-chlorophenyl)-3-methyl-2-oxopiperidin-1-yl)butanoic acid

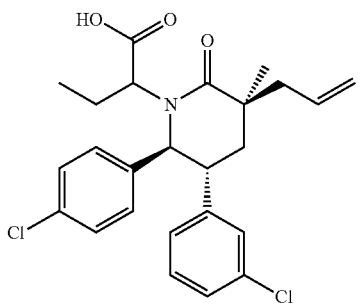 [SMILES: C=CC[C@@]1(C)C[C@H](c2cccc(Cl)c2)[C@@H](c2ccc(Cl)cc2)N(C(CC)C(=O)O)C1=O]

LiOH (0.267 g, 11.13 mmol) in water (2.6 mL) was added to a solution of methyl 2-((3S,5R,6S)-3-allyl-5-(3-chlorophenyl)-6-(4-chlorophenyl)-3-methyl-2-oxopiperidin-1-yl)butanoate (Example 65, Step B) (0.528 g, 1.113 mmol) in MeOH (7.5 mL) at rt. The reaction mixture was heated at 80° C. for 14 hours, cooled to rt and acidified to pH=1 with 3M HCl. The mixture was extracted with EtOAc three times and the organics were pooled, washed with sat. aq. NaCl solution, dried (MgSO$_4$), filtered and concentrated in vacuo to provide a white solid. Purification using a 40 g SiO$_2$ column and eluting with 35-60% EtOAc/hexanes provided the title compound as a mixture of isomers.

Step B. N'-(2-((3S,5R,6S)-3-allyl-5-(3-chlorophenyl)-6-(4-chlorophenyl)-3-methyl-2-oxopiperidin-1-yl)butanoyloxy)cyclopropanecarboximidamide

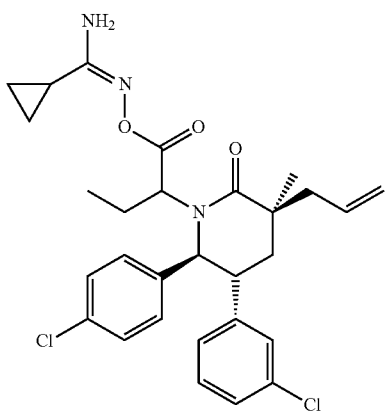

1,1'-Carbonyldiimidazole (0.104 g, 0.639 mmol) was added to a solution of 2-((3S,5R,6S)-3-allyl-5-(3-chlorophenyl)-6-(4-chlorophenyl)-3-methyl-2-oxopiperidin-1-yl)butanoic acid (Example 89, Step A) (0.196 g, 0.426 mmol) in dichloromethane (1.703 mL) at rt and stirred for 22 hours before adding n-hydroxycyclopropanecarboxamidine (0.064 g, 0.639 mmol). After 6 hours the reaction mixture was adsorbed onto silica and purified using a 12 g SiO$_2$ ISCO column and eluting with 35 to 60% EtOAc/hexanes to provide a 2:1 mixture of isomers.

Step C. (3S,5R,6S)-3-allyl-5-(3-chlorophenyl)-6-(4-chlorophenyl)-1-((S)-1-(3-cyclopropyl-1,2,4-oxadiazol-5-yl)propyl)-3-methylpiperidin-2-one and (3S,5R,6S)-3-allyl-5-(3-chlorophenyl)-6-(4-chlorophenyl)-1-((R)-1-(3-cyclopropyl-1,2,4-oxadiazol-5-yl)propyl)-3-methylpiperidin-2-one

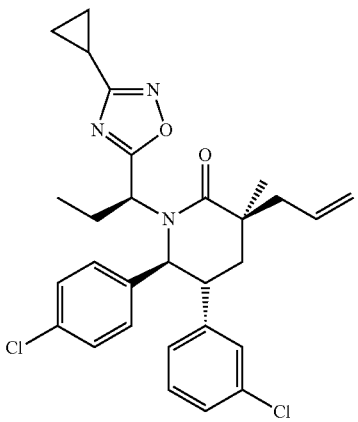

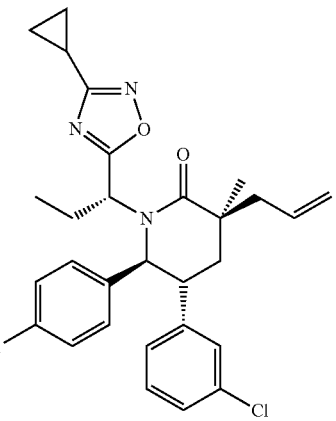

A solution of tetrabutylammonium fluoride (1.0M in THF, 1.880 mL, 1.880 mmol) was added to a solution of N'-(2-((3S,5R,6S)-3-allyl-5-(3-chlorophenyl)-6-(4-chlorophenyl)-3-methyl-2-oxopiperidin-1-yl)butanoyloxy)cyclopropanecarboximidamide (Example 89, Step B) (0.204 g, 0.376 mmol) in THF (3.76 mL) at rt. After 2 hours the reaction mixture was concentrated in vacuo and purified using a 24 g SiO$_2$ column eluting with 25% Et$_2$O/hexames to provide (3S,5R,6S)-3-allyl-5-(3-chlorophenyl)-6-(4-chlorophenyl)-1-((S)-1-(3-cyclopropyl-1,2,4-oxadiazol-5-yl)propyl)-3-methylpiperidin-2-one.

Further elution provided (3S,5R,6S)-3-allyl-5-(3-chlorophenyl)-6-(4-chlorophenyl)-1-((R)-1-(3-cyclopropyl-1,2,4-oxadiazol-5-yl)propyl)-3-methylpiperidin-2-one.

Step D. 2-((3R,5R,6S)-5-(3-chlorophenyl)-6-(4-chlorophenyl)-1-((S)-1-(3-cyclopropyl-1,2,4-oxadiazol-5-yl)propyl)-3-methyl-2-oxopiperidin-3-yl)acetic acid

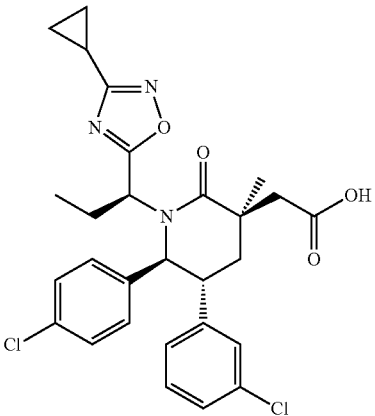 [SMILES: CC[C@@H](c1nc(C2CC2)no1)N1C(=O)[C@@](C)(CC(=O)O)C[C@H](c2cccc(Cl)c2)[C@H]1c1ccc(Cl)cc1]

The title compound was prepared from (3S,5R,6S)-3-allyl-5-(3-chlorophenyl)-6-(4-chlorophenyl)-1-((S)-1-(3-cyclopropyl-1,2,4-oxadiazol-5-yl)propyl)-3-methylpiperidin-2-one (Example 89, Step C), as described in Example 42 Step C. Purification using a 4 g SiO$_2$ column and eluting with 35 to 100% EtOAc/hexanes provided the title compound as a colorless film.

$^1$H NMR (500 MHz, CDCl$_3$) δ ppm 0.84 (t, J=7.5 Hz, 3H), 0.89 (m, 2 H), 1.01 (m, 2H), 1.25 (m, 1H), 1.43 (s, 3H), 1.95 (m, 1H), 1.98 (m, 1H), 2.20 (m, 2H), 2.37 (m, 1H), 2.90 (m, 2H), 3.26 (m, 1H), 4.60 (t, J=6.9 Hz, 1H), 4.63 (d, J=10.3 Hz, 1H), 6.76 (m, 1H), 6.90 (m, 2H), 7.00 (br s, 1H), 7.10 (t, J=7.9 Hz, 1H), 7.16 (m, 3H). Mass spectrum (ESI) m/z 542.2 [M+H]$^+$.

Example 90

2-((3R,5R,6S)-5-(3-chlorophenyl)-6-(4-chlorophenyl)-1-((R)-1-(3-cyclopropyl-1,2,4-oxadiazol-5-yl)propyl)-3-methyl-2-oxopiperidin-3-yl)acetic acid

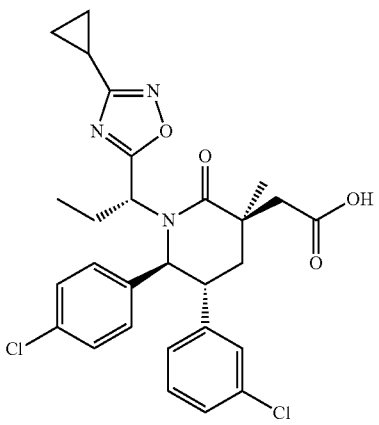 [SMILES: CC[C@H](c1nc(C2CC2)no1)N1C(=O)[C@@](C)(CC(=O)O)C[C@H](c2cccc(Cl)c2)[C@H]1c1ccc(Cl)cc1]

The title compound was prepared from (3S,5R,6S)-3-allyl-5-(3-chlorophenyl)-6-(4-chlorophenyl)-1-((R)-1-(3-cyclopropyl-1,2,4-oxadiazol-5-yl)propyl)-3-methylpiperidin-2-one (Example 89, Step C) as described in Example 42, Step C.

$^1$H NMR (400 MHz, CDCl$_3$) δ ppm 0.85-1.05 (m, 3H) 1.09 (t, J=7.6 Hz, 3H), 1.44 (s, 3H), 2.01 (m, 1H), 2.19 (m, 1H), 2.26 (m, 3H), 2.83 (d, J=14.7 Hz, 1H), 2.91 (d, J=14.7 Hz, 2H), 3.32 (m, 1H), 3.95 (t, J=7.2 Hz, 1H), 4.57 (d, J=10.4 Hz, 1H), 6.73 (m, 1H), 6.98 (m, 1H), 7.09 (t, J=7.8 Hz, 1H), 7.16 (m, 2H), 7.20 (m, 3H). Mass spectrum (ESI) m/z 542.2 [M+H]$^+$.

Example 91

2-((3R,5R,6S)-5-(3-Chlorophenyl)-6-(4-chlorophenyl)-3-methyl-1-((S)-1-morpholinobutan-2-yl)-2-oxopiperidin-3-yl)acetic acid

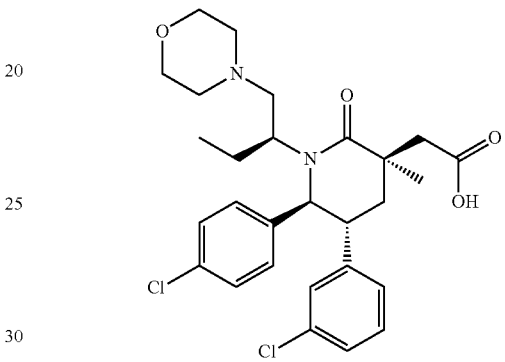

Step A. (S)-Methyl 2-((3S,5R,6S)-3-allyl-5-(3-chlorophenyl)-6-(4-chlorophenyl)-3-methyl-2-oxopiperidin-1-yl)butanoate

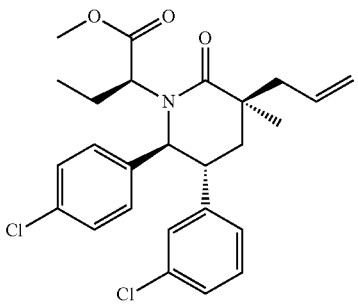 [SMILES: C=CC[C@@]1(C)C[C@H](c2cccc(Cl)c2)[C@@H](c2ccc(Cl)cc2)N([C@@H](CC)C(=O)OC)C1=O]

To a solution of (3S,5R,6S)-3-allyl-5-(3-chlorophenyl)-6-(4-chlorophenyl)-3-methylpiperidin-2-one (Example 71, Step D) (4.00 g, 10.7 mmol) in 45 mL of DMF was added a dispersion of 60% sodium hydride in mineral oil (1.71 g, 42.7 mmol) at 0° C. After being stirred for 20 min, methyl 2-bromobutanoate (6.15 mL, 53.4 mmol) was added at 0° C. and the resulting solution was stirred at 25° C. for 12 h until completion of the reaction. Then sat. aq. NH$_4$Cl solution was added and the mixture was extracted with ethyl acetate. The combined organic layers were washed with water and sat. aq. NaCl solution, dried over Na$_2$SO$_4$, filtered and the filtrate was concentrated under reduced pressure. Purification of the residue by flash chromatography on silica gel (eluent: 0 to 100% MTBE/hexanes, gradient elution), followed by separation of individual stereoisomers by chiral SFC (flowrate: 65 mL/min on a ChiralPak® AD-H column (Diacel Inc., Fort Lee, N.J.) using 3:1 heptanes/IPA (0.1% DEA)/CO$_2$ as the eluent) provided the title compound as the faster eluting isomer.

¹H NMR (400 MHz, CHLOROFORM-d) δ ppm 7.23 (2 H, d, J=8.4 Hz), 7.06-7.17 (2 H, m), 7.00 (3 H, t, J=1.8 Hz), 6.77 (1 H, d, J=7.6 Hz), 5.79-5.94 (1 H, m), 5.20 (1 H, d, J=4.7 Hz), 5.17 (1 H, s), 4.56 (1 H, d, J=10.8 Hz), 3.73 (3 H, s), 3.25-3.37 (1 H, m), 3.18 (1 H, dd, J=7.6 Hz, 4.9 Hz), 2.61 (2 H, d, J=7.4 Hz), 2.20-2.34 (1 H, m), 2.09-2.19 (1 H, m), 1.99 (1 H, d, J=3.1 Hz), 1.57-1.72 (1 H, m), 1.24 (3 H, s), 0.61 (3 H, t, J=7.5 Hz); Mass Spectrum (ESI) m/z=474.1 [M+H]⁺.

Further elution provided:
(R)-Methyl 2-((3S,5R,6S)-3-allyl-5-(3-chlorophenyl)-6-(4-chlorophenyl)-3-methyl-2-oxopiperidin-1-yl)butanoate

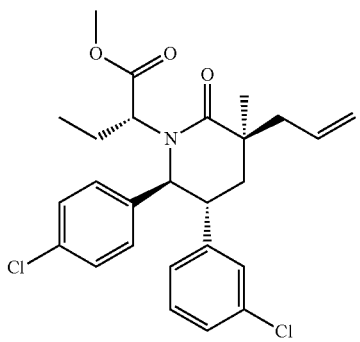 [SMILES: C=CC[C@@]1(C)C[C@H](c2cccc(Cl)c2)[C@@H](c2ccc(Cl)cc2)N([C@H](CC)C(=O)OC)C1=O]

as the slower eluting isomer.
¹H NMR (400 MHz, CHLOROFORM-d) δ ppm 7.22 (2 H, d, J=8.0 Hz), 6.99-7.19 (4 H, m), 6.95 (1 H, t, J=1.8 Hz), 6.71 (1 H, d, J=7.6 Hz), 5.81-5.95 (1 H, m), 5.19 (1 H, d, J=2.7 Hz), 5.16 (1 H, d, J=1.0 Hz), 4.48 (1 H, d, J=10.6 Hz), 3.67 (3 H, s), 3.24-3.32 (1 H, m), 3.20 (1 H, dd, J=7.8 Hz, 6.1 Hz), 2.61-2.72 (1 H, m), 2.49-2.60 (1 H, m), 1.91-2.21 (4 H, m), 1.27 (3 H, s), 1.00 (3 H, t, J=7.5 Hz); MS (ESI) m/z=474.1 [M+H]⁺.

Step B. (3S,5R,6S)-3-Allyl-5-(3-chlorophenyl)-6-(4-chlorophenyl)-1-((R)-1-hydroxybutan-2-yl)-3-methylpiperidin-2-one

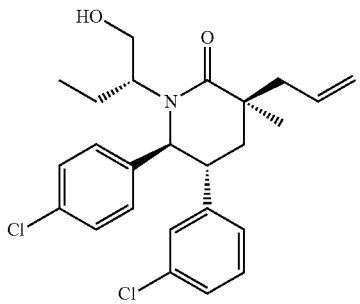 [SMILES: C=CC[C@@]1(C)C[C@H](c2cccc(Cl)c2)[C@@H](c2ccc(Cl)cc2)N([C@H](CC)CO)C1=O]

To a solution of (S)-methyl 2-((3S,5R,6S)-3-allyl-5-(3-chlorophenyl)-6-(4-chlorophenyl)-3-methyl-2-oxopiperidin-1-yl)butanoate and (R)-methyl 2-((3S,5R,6S)-3-allyl-5-(3-chlorophenyl)-6-(4-chlorophenyl)-3-methyl-2-oxopiperidin-1-yl)butanoate (1.73 g, 3.64 mmol) (mixture of stereoisomers from Example 91, Step A) in 27 mL of Et₂O and 9 mL of THF was added a solution of lithium tetrahydroborate in THF (0.238 mL, 7.28 mmol) at 0° C. The resulting solution was stirred at 25° C. for 2 h. The reaction was quenched (10% citric acid), extracted (2×EtOAc) and washed (1×Sat. aq. NaCl solution). The combined organic layers were washed with sat. aq. NaCl solution, dried over Na₂SO₄, filtered and the filtrate was concentrated under reduced pressure. The residue was purified by flash chromatography on silica gel (eluent: 0-60% EtOAc in hexanes) to give the title compound as the faster eluting isomer.
¹H NMR (400 MHz, CHLOROFORM-d) δ ppm 0.99 (t, J=7.4 Hz, 3 H), 1.29 (s, 3 H), 1.79-2.03 (m, 4 H), 2.62 (d, J=7.4 Hz, 2 H), 2.80-2.85 (m, 1 H), 3.05-3.16 (m, 1 H), 3.40-3.49 (m, 2 H), 4.33 (d, J=10.4 Hz, 1 H), 5.13-5.22 (m, 2 H), 5.79-5.95 (m, 1 H), 6.7 (d, J=7.6 Hz, 1 H), 6.85-6.97 (m, 3 H), 7.08-7.15 (m, 1 H), 7.17-7.19 (m, 1 H), 7.23 (d, J=8.6 Hz, 2 H); Mass Spectrum (ESI) m/z=446 (M+1).

Further elution provided:
(3S,5R,6S)-3-Allyl-5-(3-chlorophenyl)-6-(4-chlorophenyl)-1-((S)-1-hydroxybutan-2-yl)-3-methylpiperidin-2-one

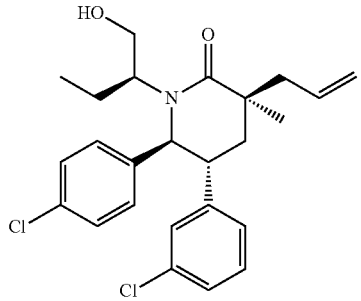 [SMILES: C=CC[C@@]1(C)C[C@H](c2cccc(Cl)c2)[C@@H](c2ccc(Cl)cc2)N([C@@H](CC)CO)C1=O]

as the slower eluting isomer.
¹H NMR (400 MHz, CHLOROFORM-d) δ ppm 0.68 (t, J=7.5 Hz, 3 H), 1.27 (s, 3 H), 1.38-1.52 (m, 1 H), 1.90-2.08 (m, 4 H), 2.61 (d, J=7.4 Hz, 2 H), 3.10-3.25 (m, 2 H), 3.59-3.68 (m, 2 H), 4.46 (d, J=10.2 Hz, 1 H), 5.18 (dd, J=13.7, 1.8 Hz, 2 H), 5.79-5.93 (m, 1 H), 6.72 (d, J=7.6 Hz, 1 H), 6.93-7.04 (m, 2 H), 7.09-7.13 (m, 1 H), 7.15-7.20 (m, 1 H), 7.24 (d, J=8.6 Hz, 2 H); Mass Spectrum (ESI) m/z=446 (M+1).

Step C. (S)-2-((3S,5R,6S)-3-Allyl-5-(3-chlorophenyl)-6-(4-chlorophenyl)-3-methyl-2-oxopiperidin-1-yl)butanal

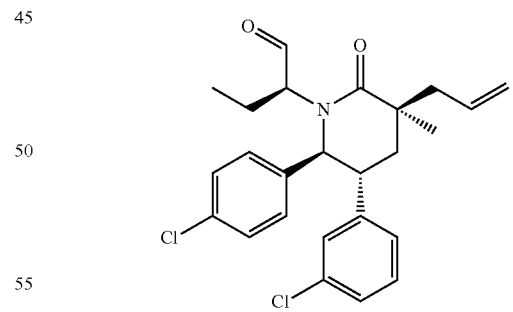

To a solution of 218 mg (0.49 mmol) of (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) in a mixture of water (13.20 μL, 0.733 mmol) and DCM (4883 μL) was added 1,1,1,-tris(acetoxy)-1,1-dihydro-1,2-benziodoxol-3-(1H)one ("Dess Martin periodinane") (311 mg, 0.733 mmol) at ambient temperature. The reaction was monitored by LCMS, and several small portions of additional periodinane were added until the reaction was complete. The reaction was quenched (2 mL, 1 M Na₂S₂O₃), extracted (2×DCM), and the combined organic layers were washed with sat. NaHCO₃ solution (2×), sat NaCl solution, dried over Na₂SO₄, filtered and the filtrate was concentrated under reduced pressure. Purification of the residue by flash chromatography on silica gel (eluent: 20 to 35% EtOAc/hexanes, gradient elution) provided the title compound.

Step D. (3S,5R,6S)-3Allyl-5-(3-chlorophenyl)-6-(4-chlorophenyl)-3-methyl-1-((S)-1-morpholinobutan-2-yl)piperidin-2-one

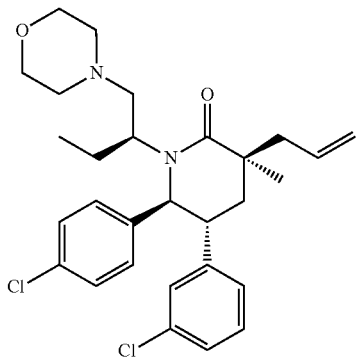 [SMILES: C=CC[C@@]1(C)C[C@H](c2cccc(Cl)c2)[C@@H](c2ccc(Cl)cc2)N([C@@H](CC)CN2CCOCC2)C1=O]

To a solution of 100 mg (0.225 mmol) of (S)-2-((3S,5R,6S)-3-allyl-5-(3-chlorophenyl)-6-(4-chlorophenyl)-3-methyl-2-oxopiperidin-1-yl)butanal (Example 91, Step C) in DCE (2420 μL) was added morpholine (200 μL, 2.297 mmol), acetic acid (1.288 μL, 0.023 mmol) and sodium triacetoxyborohydride (95 mg, 0.450 mmol). The reaction mixture was stirred at room temperature for 18 hours. The reaction was quenched with sat. sodium bicarbonate solution and extracted with DCM (2×10 mL). The combined organic layers were washed with sat NaCl solution, dried over Na₂SO₄, filtered and the filtrate was concentrated under reduced pressure to afford the crude title compound as an oil.

Step E. 2-((3R,5R,6S)-5-(3-Chlorophenyl)-6-(4-chlorophenyl)-3-methyl-1-((S)-1-morpholinobutan-2-yl)-2-oxopiperidin-3-yl)acetaldehyde

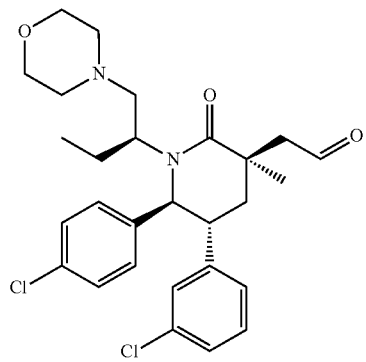 [SMILES: CC[C@@H](CN1CCOCC1)N1C(=O)[C@@](C)(CC=O)C[C@H](c2cccc(Cl)c2)[C@H]1c1ccc(Cl)cc1]

To a round-bottomed flask charged with (3S,5R,6S)-3-allyl-5-(3-chlorophenyl)-6-(4-chlorophenyl)-3-methyl-1-((S)-1-morpholinobutan-2-yl)piperidin-2-one (Example 91, Step D) (125 mg, 0.242 mmol) was added THF (2 mL). Approximately 1 mL water was added dropwise until the solution became and remained cloudy with gentle stirring. t-BuOH (0.350 mL) was added dropwise until the solution became homogeneous. NMO (42.6 mg, 0.364 mmol) was added followed by osmium tetroxide, 4 wt. %, in water (1 drop from glass Pasteur pipette). The reaction mixture was stirred at room temperature for 16 hours. An additional drop of osmium tetroxide, 4 wt. %, in water was added. After 5 hours, two additional drops of osmium tetroxide, 4 wt. %, in water were added and the reaction mixture was stirred at room temperature for an additional 16 hours. Sodium periodate (145 mg, 0.679 mmol) was added and the reaction mixture was stirred at room temperature for 2 hours. The reaction mixture was diluted with ethyl acetate (10 mL) and water (10 mL) and filtered. The aqueous layer of the filtrate was extracted with additional ethyl acetate (10 mL) and the combined organic layers were washed with sat. aq. NaCl solution, dried over sodium sulfate, filtered and the filtrate was concentrated under reduced pressure to provide the title compound.

Step F. 2-((3R,5R,6S)-5-(3-Chlorophenyl)-6-(4-chlorophenyl)-3-methyl-1-((S)-1-morpholinobutan-2-yl)-2-oxopiperidin-3-yl)acetic acid

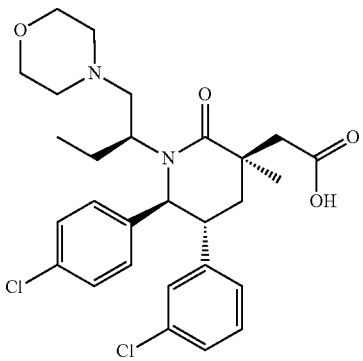 [SMILES: CC[C@@H](CN1CCOCC1)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-1-((S)-1-morpholinobutan-2-yl)-2-oxopiperidin-3-yl)acetaldehyde (Example 91, Step E) (125 mg, 0.242 mmol) in acetone (2 mL) was added 3 mL of a mixture of CrO₃ in water (2 mL) and concentrated H₂SO₄ (1 ml). The reaction mixture was stirred at room temperature for 2 hours and then diluted with water (10 mL) and ethyl acetate (10 mL) and the layers were separated. The aqueous layer was extracted with additional ethyl acetate (10 mL). The combined organic layers were concentrated under reduced pressure. The residue was purified by reversed phase preparatory HPLC (column: Gemini-NX C₁₈ 5 um column; Phenomonex, Torrance, Calif.; eluent: 0 to 100% MeCN +0.1% TFA in water +0.1% TFA) to provide the title compound.

¹H NMR (400 MHz, CHLOROFORM-d) δ ppm 0.57 (t, J=7.53 Hz, 1 H) 1.26 (s, 1 H) 1.39 (s, 3 H) 1.54-1.70 (m, 1 H) 1.72-1.89 (m, 1 H) 2.02-2.27 (m, 3 H) 2.49 (br. s., 2 H) 2.69 (br. s., 2 H) 2.82 (m, 2 H) 3.02 (br. s., 2 H) 3.13-3.30 (m, 2 H) 3.74-3.93 (m, 4 H) 4.47-4.72 (m, 1 H) 6.75 (d, J=7.82 Hz, 1 H) 6.96 (t, J=1.86 Hz, 1 H) 7.01 (br. s., 1 H) 7.04-7.17 (m, 3 H) 7.22 (d, J=8.41 Hz, 2 H). Mass Spectrum (ESI) m/z=533 [M+H]⁺.

Examples 92-94 were prepared from (3S,5R,6S)-3-allyl-5-(3-chlorophenyl)-6-(4-chlorophenyl)-1-((S)-1-cyclopropyl-2-hydroxyethyl)piperidin-2-one by procedures similar to those described in Example 91, substituting morpholine in step D for the appropriate amount of amine

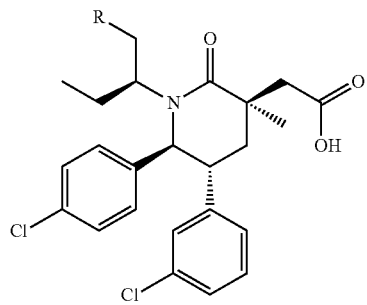

| Example | R = |
|---------|-----|
| 92 | ![F3C-CH2-NH-] |
| 93 | ![2,2-dimethylmorpholino] |
| 94 | ![2,6-dimethylmorpholino with *] |

Example 92

2-((3R,5R,6S)-5-(3-chlorophenyl)-6-(4-chlorophenyl)-3-methyl-2-oxo-1-((S)-1-(2,2,2-trifluoroethylamino)butan-2-yl)piperidin-3-yl)acetic acid $^1$H NMR (400 MHz, CHLOROFORM-d) δ ppm 0.56 (t, J=7.43 Hz, 3 H) 1.23-1.35 (m, 1 H) 1.44 (s, 3 H) 1.48-1.65 (m, 2 H) 1.77-1.91 (m, 1 H) 2.02-2.11 (m, 1 H) 2.13-2.25 (m, 1 H) 2.59-2.71 (m, 1 H) 2.73-2.84 (m, 1 H) 2.90-3.24 (m, 5 H) 4.60 (d, J=10.17 Hz, 1 H) 6.69-6.77 (m, 1 H) 6.91-7.05 (m, 3 H) 7.06-7.13 (m, 1 H) 7.13-7.18 (m, 1 H) 7.23 (d, J=8.22 Hz, 2 H). Mass Spectrum (ESI) m/z=545 [M+H]$^+$.

Example 93

2-((3R,5R,6S)-5-(3-chlorophenyl)-6-(4-chlorophenyl)-1-((S)-1-(2,2-dimethylmorpholino)butan-2-yl)-3-methyl-2-oxopiperidin-3-yl)acetic acid $^1$H NMR (400 MHz, CHLOROFORM-d) δ ppm 0.49 (t, J=7.34 Hz, 3 H) 1.21-1.30 (m, 4 H) 1.34 (s, 3 H) 1.37 (s, 3 H) 1.42 (s, 3 H) 1.51-1.68 (m, 1 H) 1.86 (dd, J=14.48 and 7.24 Hz, 1 H) 2.08-2.22 (m, 2 H) 2.30 (br. s., 1 H) 2.35-2.48 (m, 2 H) 2.74-2.84 (m, 1 H) 2.86-2.94 (m, 1 H) 3.00-3.22 (m, 2 H) 3.68-3.91 (m, 2 H) 4.57 (d, J=10.37 Hz, 1 H) 6.68 (d, J=7.63 Hz, 1 H) 6.91-7.00 (m, 2 H) 7.03-7.11 (m, 1 H) 7.14 (d, J=7.24 Hz, 2 H) 7.23 (d, J=7.43 Hz, 2 H). Mass Spectrum (ESI) m/z=561 [M+H]$^+$.

Example 94

2-((3R,5R,6S)-5-(3-chlorophenyl)-6-(4-chlorophenyl)-1-((2S)-1-(2,6-dimethylmorpholino)butan-2-yl)-3-methyl-2-oxopiperidin-3-yl)acetic acid The crude product was purified by reversed phase preparatory HPLC (column: Gemini-NX C$_{18}$ 5 um column; Phenomonex, Torrance, Calif.; eluent: 0 to 100% MeCN +0.1% TFA in Water +0.1% TFA) to provide a 4:1 ratio of diastereomers of undetermined configuration at the positions indicated by *.

$^1$H NMR (400 MHz, CHLOROFORM-d) δ ppm 1.02 (br. s., 1 H) 1.24 (d, J=6.06 Hz, 6 H) 1.35-1.49 (m, 4 H) 2.02-2.44 (m, 4 H) 2.68 (s, 1 H) 2.79-2.89 (m, 2 H) 3.20-3.32 (m, 2 H) 3.37-3.49 (m, 1 H) 3.80-4.00 (m, 2 H) 4.10 (br. s., 3 H) 4.23-4.34 (m, 1 H) 4.41-4.58 (m, 1 H) 4.91-5.10 (m, 1 H) 6.89-6.98 (m, 2 H) 6.99-7.15 (m, 4 H) 7.20-7.30 (m, 2 H). Mass Spectrum (ESI) m/z=561 [M+H]$^+$.

Example 95

2-((3R,5R,6S)-5-(3-chlorophenyl)-6-(4-chlorophenyl)-1-((S)-1-(4-(cyclopropylsulfonyl)piperazin-1-yl)butan-2-yl)-3-methyl-2-oxopiperidin-3-yl)acetic acid

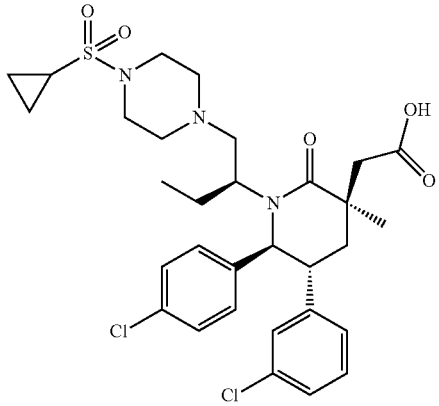 [SMILES: CC[C@@H](CN1CCN(S(=O)(=O)C2CC2)CC1)N1C(=O)[C@@](C)(CC(=O)O)C[C@H](c2cccc(Cl)c2)[C@H]1c1ccc(Cl)cc1]

Step A. tert-butyl 4-((S)-2-((3S,5R,6S)-3-allyl-5-(3-chlorophenyl)-6-(4-chlorophenyl)-3-methyl-2-oxopiperidin-1-yl)butyl)piperazine-1-carboxylate

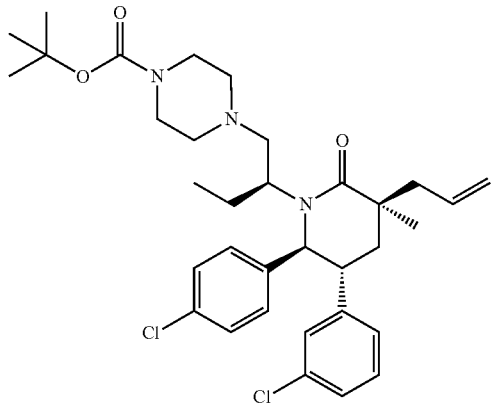 [SMILES: C=CC[C@@]1(C)C[C@H](c2cccc(Cl)c2)[C@@H](c2ccc(Cl)cc2)N([C@@H](CC)CN2CCN(C(=O)OC(C)(C)C)CC2)C1=O]

The title compound was prepared from (S)-2-((3S,5R,6S)-3-allyl-5-(3-chlorophenyl)-6-(4-chlorophenyl)-3-methyl-2-oxopiperidin-1-yl)butanal (Example 91, Step C) and tert-butyl piperazine-1-carboxylate according to the procedure described in Example 91 Step D.

Step B. (3S,5R,6S)-3-allyl-5-(3-chlorophenyl)-6-(4-chlorophenyl)-3-methyl-1-((S)-1-(piperazin-1-yl)butan-2-yl)piperidin-2-one

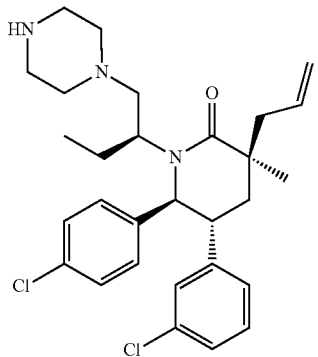 [SMILES: C=CC[C@@]1(C)C[C@H](c2cccc(Cl)c2)[C@@H](c2ccc(Cl)cc2)N([C@@H](CC)CN2CCNCC2)C1=O]

To a solution of tert-butyl 4-((S)-2-((3S,5R,6S)-3-allyl-5-(3-chlorophenyl)-6-(4-chlorophenyl)-3-methyl-2-oxopiperidin-1-yl)butyl)piperazine-1-carboxylate (Example 95, Step A) (187 mg, 0.304 mmol in DCM (2.4 mL) was added TFA (600 µL, 7.79 mmol). The reaction mixture was stirred at room temperature for 16 hours before concentrating under reduced pressure. The residue was taken up in DCM (15 mL) and washed with sat. sodium bicarbonate solution (10 mL) and saturated sodium chloride solution (10 mL). The organic layer was dried over sodium sulfate, filtered and the filtrate concentrated under reduced pressure to afford the title compound as a white foam.

Step C. (3S,5R,6S)-3-allyl-5-(3-chlorophenyl)-6-(4-chlorophenyl)-1-((S)-1-(4-(cyclopropylsulfonyl)piperazin-1-yl)butan-2-yl)-3-methylpiperidin-2-one

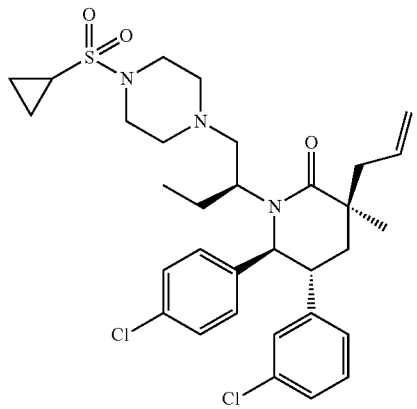 [SMILES: C=CC[C@@]1(C)C[C@H](c2cccc(Cl)c2)[C@@H](c2ccc(Cl)cc2)N([C@@H](CC)CN2CCN(S(=O)(=O)C3CC3)CC2)C1=O]

To a solution of (3S,5R,6S)-3-allyl-5-(3-chlorophenyl)-6-(4-chlorophenyl)-3-methyl-1-((S)-1-(piperazin-1-yl)butan-2-yl)piperidin-2-one (Example 95, Step B) (60 mg, 0.117 mmol) in DCE (1.2 mL) was added cyclopropanesulfonyl chloride (23.76 µL, 0.233 mmol) followed by diisopropylethylamine (40.6 µL, 0.233 mmol). The reaction mixture was stirred at room temperature for 16 hours, diluted with water (10 mL) and the layers were separated. The aqueous layer was extracted with DCM (2×10 mL). The combined organic layers were washed with saturated NaCl solution (10 mL), dried over sodium sulfate, filtered, and the filtrate concentrated under reduced pressure to afford the title compound as a solid.

Step D. 2-((3R,5R,6S)-5-(3-chlorophenyl)-6-(4-chlorophenyl)-1-((S)-1-(4-(cyclopropylsulfonyl)piperazin-1-yl)butan-2-yl)-3-methyl-2-oxopiperidin-3-yl)acetic acid To a 10 mL round-bottomed flask charged with (3S,5R,6S)-3-allyl-5-(3-chlorophenyl)-6-(4-chlorophenyl)-1-((S)-1-(4-(cyclopropylsulfonyl)piperazin-1-yl)butan-2-yl)-3-methylpiperidin-2-one (Example 23, Step C) (85.1 mg, 0.138 mmol) was added THF (~800 uL) followed by water (~600 uL, until the reaction remains cloudy with gentle stirring) followed by tBuOH (~200 uL, untril the reaction becomes translucent). NMO (24.17 mg, 0.206 mmol) was added followed by 5 drops of osmium tetroxide, 4 wt. %, in water (33.6 µL, 0.138 mmol) via pasteur pipette. The reaction was stirred at rt over night before adding Jones reagent (0.154 mL). The reaction was stirred at room temperature for 2 hours, diluted with water (15 mL) and extracted with ethyl acetate (3×15 mL). The combined organic layers are washed with water (3×20 mL), saturated sodium chloride solution (20 mL), dried over sodium sulfate, filtered and the filtrate concentrated under reduced pressure. The residue was purified by reversed phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes) to give the title compound.

$^1$H NMR (400 MHz, CHLOROFORM-d) δ ppm 0.92-1.25 (m, 10 H) 1.43 (s, 3 H) 1.85 (br. s., 1 H) 2.08 (d, J=13.50 Hz, 1 H) 2.16-2.30 (m, 1 H) 2.40 (d, J=5.87 Hz, 2 H) 2.52 (br. s., 2 H) 2.69-2.79 (m, 2 H) 2.79-2.92 (m, 2 H) 3.21-3.34 (m, 2 H) 3.83 (br. s., 3 H) 4.51 (br. s., 1 H) 6.67 (br. s., 1 H) 6.91-7.01 (m, 2 H) 7.03-7.09 (m, 2 H) 7.11-7.18 (m, 3 H). Mass Spectrum (ESI) m/z=636 [M+H]$^+$.

Example 96

2-((3R,5R,6S)-5-(3-chlorophenyl)-6-(4-chlorophenyl)-3-methyl-1-((S)-1-(4-(methylsulfonyl)piperazin-1-yl)butan-2-yl)-2-oxopiperidin-3-yl)acetic acid

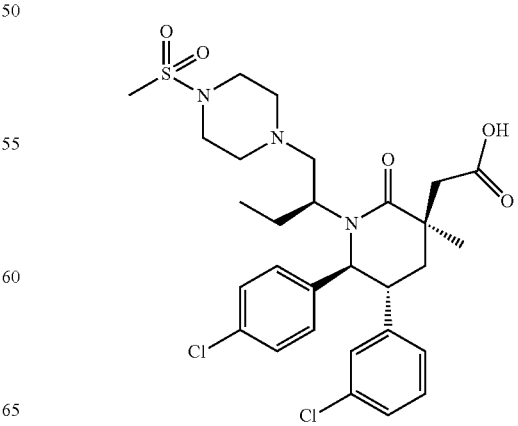

The title compound was prepared from (3S,5R,6S)-3-allyl-5-(3-chlorophenyl)-6-(4-chlorophenyl)-3-methyl-1-((S)-1-(piperazin-1-yl)butan-2-yl)piperidin-2-one (Example 95, Step B) and methanesulfonyl chloride as described in Example 95, Steps C and D.

¹H NMR (400 MHz, CHLOROFORM-d) δ ppm 1.04 (br. s., 3 H) 1.42 (s, 3 H) 1.85 (br. s., 2 H) 2.00-2.13 (m, 1 H) 2.14-2.28 (m, 1 H) 2.56 (br. s., 3 H) 2.66-2.77 (m, 3 H) 2.85 (d, J=14.48 Hz, 2 H) 2.90-2.99 (m, 3 H) 3.27 (t, J=10.27 Hz, 3 H) 3.80 (br. s., 3 H) 4.51 (br. s., 1 H) 6.63-6.71 (m, 1 H) 6.97 (s, 2 H) 7.03-7.10 (m, 2 H) 7.11-7.17 (m, 3 H). Mass Spectrum (ESI) m/z=610 [M+H]⁺.

Example 97

2-((3R,5R,6S)-1-((S)-1-(4-acetylpiperazin-1-yl)butan-2-yl)-5-(3-chlorophenyl)-6-(4-chlorophenyl)-3-methyl-2-oxopiperidin-3-yl)acetic acid

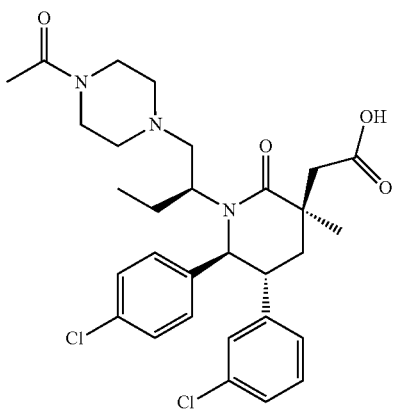 [SMILES: CC[C@@H](CN1CCN(C(C)=O)CC1)N1C(=O)[C@@](C)(CC(=O)O)C[C@H](c2cccc(Cl)c2)[C@H]1c1ccc(Cl)cc1]

Step A. (3S,5R,6S)-1-((S)-1-(4-acetylpiperazin-1-yl)butan-2-yl)-3-allyl-5-(3-chlorophenyl)-6-(4-chlorophenyl)-3-methylpiperidin-2-one

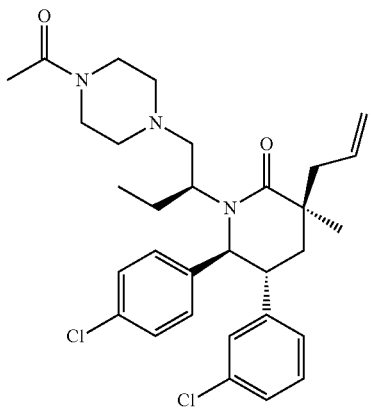 [SMILES: C=CC[C@@]1(C)C[C@H](c2cccc(Cl)c2)[C@@H](c2ccc(Cl)cc2)N([C@@H](CC)CN2CCN(C(C)=O)CC2)C1=O]

To a solution of (3S,5R,6S)-3-allyl-5-(3-chlorophenyl)-6-(4-chlorophenyl)-3-methyl-1-((S)-1-(piperazin-1-yl)butan-2-yl)piperidin-2-one (Example 95, Step B) (80 mg, 0.155 mmol) in DCE (1.5 mL) was added acetyl chloride (22.1 μL, 0.31 mmol) followed by diisopropylethylamine (54.1 μL, 0.311 mmol). The reaction mixture was stirred at room temperature for 16 hours and then concentrated under reduced pressure to provide the title compound.

Step B. 2-((3R,5R,6S)-1-((S)-1-(4-acetylpiperazin-1-yl)butan-2-yl)-5-(3-chlorophenyl)-6-(4-chlorophenyl)-3-methyl-2-oxopiperidin-3-yl)acetic acid The title compound was prepared from (3S,5R,6S)-1-((S)-1-(4-acetylpiperazin-1-yl)butan-2-yl)-3-allyl-5-(3-chlorophenyl)-6-(4-chlorophenyl)-3-methylpiperidin-2-one (Example 97, Step A) as described in Example 95, Step D. The residue was purified by reversed phase preparatory HPLC (column: Gemini-NX C₁₈ 5 um column; Phenomonex, Torrance, Calif.; eluent: 0 to 100% MeCN +0.1% TFA in water +0.1% TFA, over 20 minutes) to give the title compound.

¹H NMR (400 MHz, CHLOROFORM-d) δ ppm 0.94-1.18 (m, 3 H) 1.42 (s, 3 H) 1.77-1.98 (m, 1 H) 2.12 (s, 4 H) 2.23 (s, 2 H) 2.48-2.63 (m, 3 H) 2.67 (s, 3 H) 2.84 (br. s., 3 H) 3.16-3.35 (m, 2 H) 3.83-4.05 (m, 3 H) 4.43-4.61 (m, 1 H) 6.62-6.75 (m, 1 H) 6.97 (s, 2 H) 7.07 (d, J=7.83 Hz, 2 H) 7.10-7.17 (m, 3 H). Mass Spectrum (ESI) m/z=574 [M+H]⁺.

Example 98

2-((3R,5R,6S)-5-(3-chlorophenyl)-6-(4-chlorophenyl)-1-((S)-1-(4-(cyclopropanecarbonyl)piperazin-1-yl)butan-2-yl)-3-methyl-2-oxopiperidin-3-yl)acetic acid

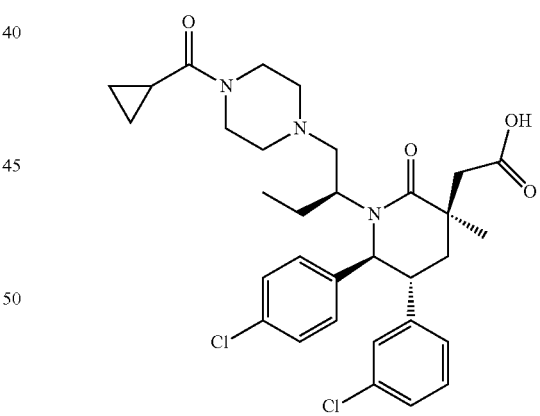

The title compound was prepared from (3S,5R,6S)-3-allyl-5-(3-chlorophenyl)-6-(4-chlorophenyl)-3-methyl-1-((S)-1-(piperazin-1-yl)butan-2-yl)piperidin-2-one (Example 95, Step B) and cyclopropanecarbonyl chloride as described in Example 97.

¹H NMR (400 MHz, CHLOROFORM-d) δ ppm 0.79-0.91 (m, 6 H) 1.02 (br. s., 6 H) 1.43 (s, 3 H) 1.65-1.75 (m, 2 H) 2.11 (br. s., 2 H) 2.17-2.30 (m, 2 H) 2.51 (br. s., 3 H) 2.65 (s, 2 H)

2.80-2.88 (m, 2 H) 3.29 (t, J=11.44 Hz, 2 H) 6.98 (s, 2 H) 7.06 (t, J=7.83 Hz, 2 H) 7.10-7.16 (m, 2 H) 7.19-7.26 (m, 2 H). Mass Spectrum (ESI) m/z=600 [M+H]⁺.

Example 99

3-(((3R,5R,6S)-5-(3-chlorophenyl)-6-(4-chlorophenyl)-3-methyl-1-((S)-1-morpholinobutan-2-yl)-2-oxopiperidin-3-yl)methyl)-1,2,4-oxadiazol-5(4H)-one

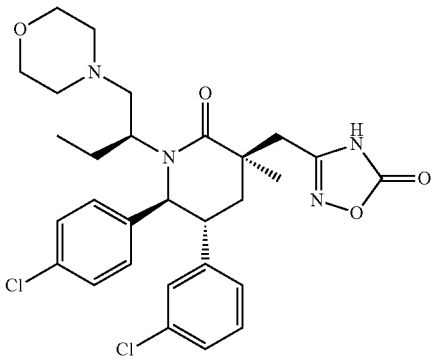 [SMILES: CC[C@@H](CN1CCOCC1)N1C(=O)[C@@](C)(Cc2noc(=O)[nH]2)C[C@H](c2cccc(Cl)c2)[C@H]1c1ccc(Cl)cc1]

The title compound was prepared from 2-((3R,5R,6S)-5-(3-chlorophenyl)-6-(4-chlorophenyl)-3-methyl-1-((S)-1-morpholinobutan-2-yl)-2-oxopiperidin-3-yl)acetic acid (Example 91) using a similar procedure as the one described for Example 82. The crude product was purified by flash chromatography on silica gel (eluent: 0 to 10% MeOH in DCM) to give the title compound.
¹H NMR (400 MHz, CHLOROFORM-d) δ ppm 0.56 (t, J=7.34 Hz, 3 H) 1.29 (br. s., 1 H) 1.30-1.38 (m, 3 H) 1.57 (ddd, J=13.99, 7.53 and 3.91 Hz, 1 H) 1.81 (dt, J=14.48 and 7.43 Hz, 1 H) 2.09 (dd, J=13.99 and 3.03 Hz, 1 H) 2.18 (d, J=9.98 Hz, 1 H) 2.22-2.32 (m, 1 H) 2.46 (d, J=3.72 Hz, 2 H) 2.66 (br. s., 2 H) 2.90 (d, J=15.06 Hz, 1 H) 2.95-3.21 (m, 4 H) 3.74-3.89 (m, 4 H) 4.59 (d, J=10.17 Hz, 1 H) 6.72 (d, J=7.63 Hz, 1 H) 6.84-6.99 (m, 3 H) 7.08-7.13 (m, 1 H) 7.14-7.18 (m, 1 H) 7.23 (d, J=8.22 Hz, 2 H). Mass Spectrum (ESI) m/z=573 [M+H]⁺.

Example 100

2-((3R,5R,6S)-5-(3-chlorophenyl)-6-(4-chlorophenyl)-1-((S)-1-(5,5-dimethyl-2-oxooxazolidin-3-yl)butan-2-yl)-3-methyl-2-oxopiperidin-3-yl)acetic acid

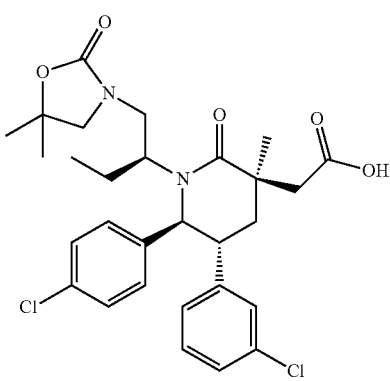 [SMILES: CC[C@@H](CN1CC(C)(C)OC1=O)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-1-((S)-1-(2-hydroxy-2-methylpropylamino)butan-2-yl)-3-methylpiperidin-2-one

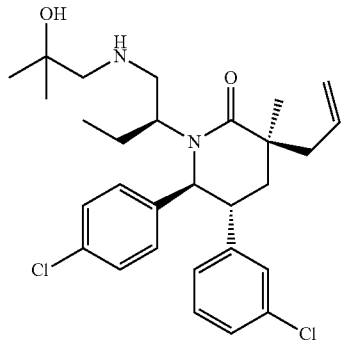 [SMILES: C=CC[C@@]1(C)C[C@H](c2cccc(Cl)c2)[C@@H](c2ccc(Cl)cc2)N([C@@H](CC)CNCC(C)(C)O)C1=O]

The title compound was prepared as described in Example 91, Step D and using and using 1-amino-2-methylpropan-2-ol (Tyger Scientific, Inc., Ewing, N.J.).

Step B. 3-((S)-2-((3S,5R,6S)-3-allyl-5-(3-chlorophenyl)-6-(4-chlorophenyl)-3-methyl-2-oxopiperidin-1-yl)butyl)-5,5-dimethyloxazolidin-2-one

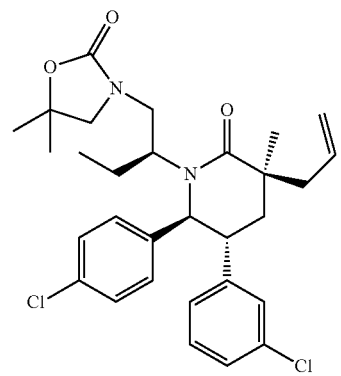 [SMILES: C=CC[C@@]1(C)C[C@H](c2cccc(Cl)c2)[C@@H](c2ccc(Cl)cc2)N([C@@H](CC)CN2CC(C)(C)OC2=O)C1=O]

To a solution of 42 mg (0.081 mmol) of (3S,5R,6S)-3-allyl-5-(3-chlorophenyl)-6-(4-chlorophenyl)-1-((S)-1-(2-hydroxy-2-methylpropylamino)butan-2-yl)-3-methylpiperidin-2-one (Example 100, Step A) in dioxane (2705 µL) was added carbonyldiimidazole (132 mg, 0.812 mmol). The reaction was heated to 100° for 6 h. Purification of the residue by reversed phase HPLC (Sunfire™ Prep C₁₈ OBD 10 µm column (Waters, Milford, Mass.) (eluent: 60 to 85% MeCN/water (0.1% TFA), gradient elution) provided the title compound.

Step C. 2-((3R,5R,6S)-5-(3-chlorophenyl)-6-(4-chlorophenyl)-1-((S)-1-(5,5-dimethyl-2-oxooxazolidin-3-yl)butan-2-yl)-3-methyl-2-oxopiperidin-3-yl)acetic acid To a rapidly stirring solution of 20 mg (0.037 mmol) of 3-((S)-2-((3S,5R,6S)-3-allyl-5-(3-chlorophenyl)-6-(4-chlorophenyl)-3-methyl-2-oxopiperidin-1-yl)butyl)-5,5-dimethyloxazolidin-2-one (Example 100, Step B) in a mixture of CCl4 (210 μL), MeCN (210 μL), and water (315 μL) was added sodium periodate (31.5 mg, 0.147 mmol), followed by catalytic ruthenium(III) chloride hydrate (4.15 mg, 0.018 mmol). When complete by LCMS monitoring, acidified the reaction with citric acid and diluted with chloroform. Insoluble material was removed by filtration through celite. Extracted to ethyl acetate and the combined organic layer was washed with sat. NaCl, dried over Na$_2$SO$_4$, filtered and the filtrate was concentrated in vacuo. Purification of the residue by reversed phase HPLC (Sunfire™ Prep C$_{18}$ OBD 10 μm column (Waters, Milford, Mass.) (eluent: 60 to 80% MeCN/water (0.1% TFA), gradient elution) provided the title compound as a white powder.

$^1$H NMR (500 MHz, CHLOROFORM-d) δ ppm 0.55 (t, J=7.21 Hz, 2 H) 0.94 (br. s., 2 H) 1.27 (d, J=2.93 Hz, 1 H) 1.33 (d, J=2.69 Hz, 1 H) 1.52 (t, 7 H) 1.88-1.99 (m, 2 H) 2.34 (t, J=13.82 Hz, 1 H) 2.71 (d, J=14.92 Hz, 2 H) 2.95-3.12 (m, 4 H) 3.29-3.39 (m, 2 H) 4.44 (d, J=10.27 Hz, 1 H) 6.73 (d, J=7.58 Hz, 1 H) 6.95 (s, 2 H) 7.11 (t, J=7.70 Hz, 1 H) 7.13-7.20 (m, 1 H). Mass Spectrum (ESI) m/z=561 (M+1).

Example 101

2-((3R,5R,6S)-1-((S)-1-(tert-butylamino)-1-oxobutan-2-yl)-5-(3-chlorophenyl)-6-(4-chlorophenyl)-3-methyl-2-oxopiperidin-3-yl)acetic acid

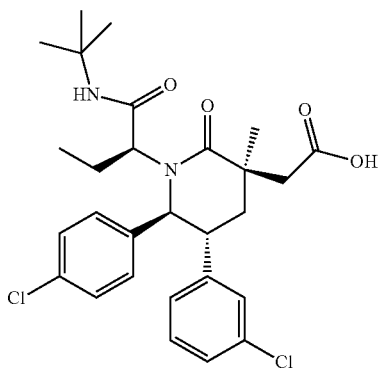 [SMILES: CC[C@@H](C(=O)NC(C)(C)C)N1C(=O)[C@@](C)(CC(=O)O)C[C@H](c2cccc(Cl)c2)[C@H]1c1ccc(Cl)cc1]

Step A. 2-((3S,5R,6S)-3-allyl-5-(3-chlorophenyl)-6-(4-chlorophenyl)-3-methyl-2-oxopiperidin-1-yl)butanoic acid

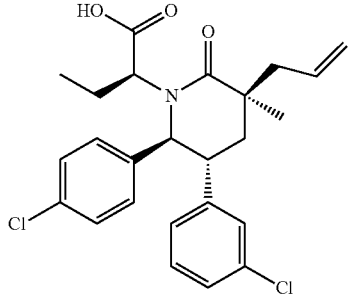 [SMILES: C=CC[C@@]1(C)C[C@H](c2cccc(Cl)c2)[C@@H](c2ccc(Cl)cc2)N([C@@H](CC)C(=O)O)C1=O]

To a 15-mL round-bottomed flask was added (S)-tert-butyl 2-((3S,5R,6S)-3-allyl-5-(3-chlorophenyl)-6-(4-chlorophenyl)-3-methyl-2-oxopiperidin-1-yl)butanoate (420 mg, 0.813 mmol) (Example 1, Step F) and anisole (444 μL, 4.07 mmol), followed by TFA (4066 μL) which had been pre-cooled to 0° C. The reaction mixture was stirred at 0° C. for 1 h, diluted with 50 ml of ether, and the combined organics were washed with 20 ml water, NaHCO$_3$/sat NaCl solution until neutral, then dried over Na$_2$SO$_4$, filtered and the filtrate was concentrated. Purification of the residue by flash chromatography on silica gel (eluent: 0 to 20% EtOAc/hexanes, gradient elution) provided the title compound.

1H NMR (400 MHz, CHLOROFORM-d) δ ppm 7.25 (1 H, s), 7.07-7.19 (2 H, m), 7.00 (3 H, br. s.), 6.76 (1 H, d, J=7.4 Hz), 5.77-5.93 (1 H, m), 5.15-5.25 (2 H, m), 4.58 (1 H, d, J=10.8 Hz), 3.35 (1 H, br. s.), 3.23-3.33 (1 H, m), 2.62 (2 H, d, J=7.2 Hz), 2.27 (1 H, dquin, J=14.6, 7.5, 7.5, 7.5, 7.5 Hz), 2.14 (1 H, t, J=13.5 Hz), 1.99 (1 H, dd, J=13.7, 2.9 Hz), 1.50-1.64 (1 H, m), 1.29 (3 H, s), 0.66 (3 H, t, J=7.4 Hz).

Step B. 2-((5R,6S)-3-allyl-5-(3-chlorophenyl)-6-(4-chlorophenyl)-3-methyl-2-oxopiperidin-1-yl)-N-tert-butylbutanamide

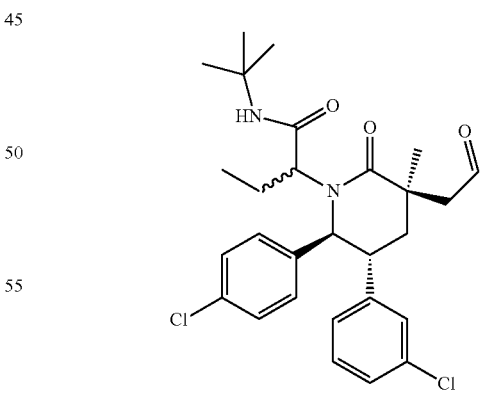

To a solution of 2-((3S,5R,6S)-3-allyl-5-(3-chlorophenyl)-6-(4-chlorophenyl)-3-methyl-2-oxopiperidin-1-yl)butanoic acid (81 mg, 0.176 mmol) (Example 101, Step A) in dry DMF (880 μL) with 3 eq TEA (73.6 μL, 0.528 mmol) at 0° was added 2 eq HATU (134 mg, 0.352 mmol). The reaction was stirred at 0° for 5 min, followed by addition of t-butyl amine (25.7 mg, 0.352 mmol). It was stirred for 30 min at 0°, quenched with sat. NaHCO₃ and extracted to EtOAc. The combined organic layers were washed with sat. NaCl solution, dried over Na₂SO₄, filtered and the filtrate was concentrated. Purification of the residue by flash chromatography on silica gel (eluent: 0-30% EtOAc/hexanes, gradient elution) provided the title compound as a mixture of stereoisomers.

Step C. 2-((3R,5R,6S)-1-((S)-1-(tert-butylamino)-1-oxobutan-2-yl)-5-(3-chlorophenyl)-6-(4-chlorophenyl)-3-methyl-2-oxopiperidin-3-yl)acetic acid The title compound was prepared from (5R,6S)-5-(3-chlorophenyl)-6-(5-chloropyridin-2-yl)piperidin-2-one (Example 101, Step B) as described in Example 1, Step H. The crude product was purified by reversed phase preparatory HPLC (Sunfire™ Prep C₁₈ OBD 10 μm column (Waters, Milford, Mass.) (eluent: 55% acetonitrile, water, 0.1% TFA, gradient elution).
¹H NMR (500 MHz, CHLOROFORM-d) δ ppm 0.71 (t, J=7.46 Hz, 3 H), 1.32 (s, 9 H), 1.40 (s, 3 H), 1.60-1.71 (m, 1 H), 2.07-2.25 (m, 3 H), 2.86 (d, J=2.20 Hz, 2 H), 3.16 (ddd, J=12.65, 9.60, 3.42 Hz, 1 H), 3.67 (dd, J=8.80, 5.62 Hz, 1 H), 4.70 (d, J=9.78 Hz, 1 H), 6.78 (d, J=7.58 Hz, 1 H), 6.97 (s, 1 H), 6.98-7.05 (m, 3 H), 7.11 (t, J=7.83 Hz, 1 H), 7.14-7.19 (m, 1 H), 7.21 (d, J=8.56 Hz, 2 H). Mass Spectrum (ESI) m/z=533 (M+1).

Example 102

2-((3R,5R,6S)-5-(3-Chlorophenyl)-6-(4-chlorophenyl)-1-((1S,2S,3R)-2,3-dihydroxycyclopentyl)-3-methyl-2-oxopiperidin-3-yl)acetic acid

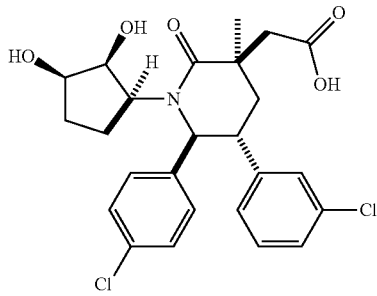

Step A. (3R,5R,6S)-5-(3-chlorophenyl)-6-(4-chlorophenyl)-3-(2,3-dihydroxypropyl)-3-methylpiperidin-2-one

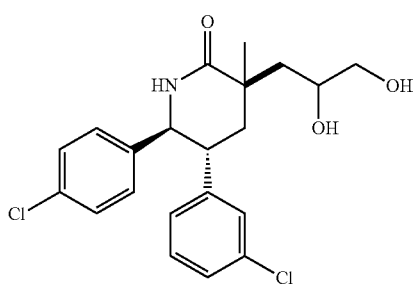 [SMILES: C[C@]1(CC(O)CO)C[C@H](c2cccc(Cl)c2)[C@@H](c2ccc(Cl)cc2)NC1=O]

To a solution of 4 g (10.69 mmol) of (3S,5R,6S)-3-allyl-5-(3-chlorophenyl)-6-(4-chlorophenyl)-3-methylpiperidin-2-one (Example 71, Step D) in 100 mL of THF was added water (60 mL) followed by 4-methylmorpholine 4-oxide (1.878 g, 16.03 mmol). The cloudy reaction mixture became clear within 5 min and osmium(VIII) oxide (4% aq) (0.340 mL, 0.053 mmol) was added and the reaction mixture remained clear. The reaction mixture was stirred at room temperature for 18 h. Osmium(VIII) oxide (4% aq) (0.1 mL) was added and the reaction mixture was stirred at room temperature for 24 h. Sat NaCl solution was added and the mixture was extracted with EtOAc. The organic layers were combined, dried over Na₂SO₄, filtered and the filtrate was concentrated to give the title compound as a 1:1 ratio of diastereomers.

Step B. (3R,5R,6S)-5-(3-chlorophenyl)-6-(4-chlorophenyl)-3-((2,2-dimethyl-1,3-dioxolan-4-yl)methyl)-3-methylpiperidin-2-one

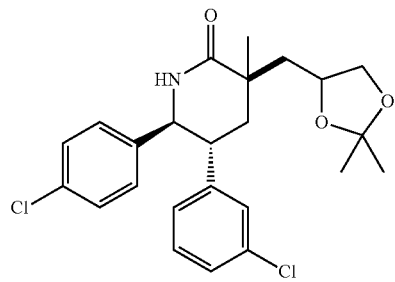 [SMILES: CC1(C)OCC(C[C@@]2(C)C[C@H](c3cccc(Cl)c3)[C@@H](c3ccc(Cl)cc3)NC2=O)O1]

To a solution of (3R,5R,6S)-5-(3-chlorophenyl)-6-(4-chlorophenyl)-3-(2,3-dihydroxypropyl)-3-methylpiperidin-2-one (Example 102, Step A) (4.900 g, 12.00 mmol) and 2,2-dimethoxypropane (14.76 mL, 120 mmol) in N,N-dimethylformamide (34 mL) at room temperature was added CSA (0.279 g, 1.200 mmol) and the reaction mixture was allowed to stir for 1 hr at room temperature. The reaction was quenched with sodium bicarbonate (100 mL) and EtOAc (100 mL). The layers were separated and the organic layer was washed three times with sat. sodium carbonate (100 mL). The aqueous layers were combined and were extracted with EtOAc (200 mL). The organic layers were combined, washed with sat. aq. NaCl solution, dried with sodium sulfate, filtered, and concentrated under reduced pressure to provide the title compound.

Step C. (3R,5R,6S)-5-(3-chlorophenyl)-6-(4-chlorophenyl)-1-(cyclopent-2-enyl)-3-((2,2-dimethyl-1,3-dioxolan-4-yl)methyl)-3-methylpiperidin-2-one

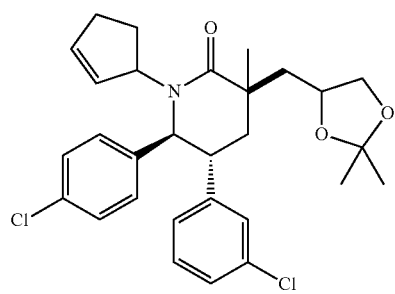 [SMILES: CC1(C)OCC(C[C@@]2(C)C[C@H](c3cccc(Cl)c3)[C@@H](c3ccc(Cl)cc3)N(C3C=CCC3)C2=O)O1]

To (3R,5R,6S)-5-(3-chlorophenyl)-6-(4-chlorophenyl)-3-((2,2-dimethyl-1,3-dioxolan-4-yl)methyl)-3-methylpiperidin-2-one (Example 102, Step B) (0.909 g, 2.027 mmol) was added toluene (15 mL) and the mixture was concentrated under reduced pressure. This step was repeated three times. Inhibitor free THF (20 mL) was added and the solution was cooled to −78° C. Butyllithium in pentane (2.0M) (1.014 mL, 2.027 mmol) was added dropwise and the reaction mixture remained colorless. The reaction mixture warmed to 0° C. and the reaction color turned very light yellow. nBuLi in pentane (2.0M) was added dropwise until the reaction mixture remained bright yellow. The reaction mixture was cooled to −78° C. and freshly prepared 3-bromocyclopent-1-ene (0.4 g, 2.72 mmol) in THF (2 mL) was added dropwise. The reaction mixture was wrapped in foil and warmed to 0° C. The reaction mixture was stirred at 0° C. for 1 h and then at rt for 2 days. The reaction was quenched with sat. NH$_4$Cl and extracted with EtOAc. The organic layer was dried over Na$_2$SO$_4$ and concentrated under reduced pressure. The residue was purified by flash chromatography on silica gel (eluent: 0 to 100% EtOAc in hexanes) to give the title compound as a colorless film.

Step D. (3R,5R,6S)-5-(3-chlorophenyl)-6-(4-chlorophenyl)-1-(cyclopent-2-enyl)-3-(2,3-dihydroxypropyl)-3-methylpiperidin-2-one

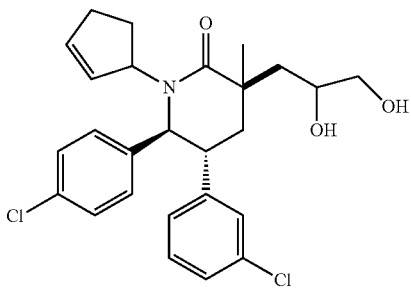 [SMILES: C[C@]1(CC(O)CO)C[C@H](c2cccc(Cl)c2)[C@@H](c2ccc(Cl)cc2)N(C2C=CCC2)C1=O]

To a solution of (3R,5R,6S)-5-(3-chlorophenyl)-6-(4-chlorophenyl)-1-(cyclopent-2-enyl)-3-((2,2-dimethyl-1,3-dioxolan-4-yl)methyl)-3-methylpiperidin-2-one (Example 28, Step C) (310 mg, 0.603 mmol) in THF (3 mL) at room temperature was added aq. HCl (1 M) (3013 μL, 3.01 mmol). The reaction mixture was stirred at room temperature for 19 h. The reaction mixture was diluted with EtOAc and the layers were separated. The organic layer was washed with sat. NaHCO$_3$, sat. aq. NaCl solution and dried over Na$_2$SO$_4$ and concentrated under reduced pressure to provide the title compound.

Step E. 2-((3R,5R,6S)-5-(3-chlorophenyl)-6-(4-chlorophenyl)-1-(cyclopent-2-enyl)-3-methyl-2-oxopiperidin-3-yl)acetaldehyde

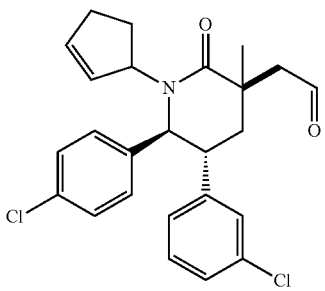 [SMILES: C[C@]1(CC=O)C[C@H](c2cccc(Cl)c2)[C@@H](c2ccc(Cl)cc2)N(C2C=CCC2)C1=O]

To a solution of (3R,5R,6S)-5-(3-chlorophenyl)-6-(4-chlorophenyl)-1-(cyclopent-2-enyl)-3-(2,3-dihydroxypropyl)-3-methylpiperidin-2-one (Example 102, Step D) (286 mg, 0.603 mmol) in THF (3 mL) and water (3 mL) was added sodium periodate (258 mg, 1.206 mmol) at room temperature. The slurry was stirred at room temperature for 1 h and then diluted with EtOAc and the layers were separated. The organic layer was washed with sat. Na$_2$S$_2$O$_3$ and sat. aq. NaCl solution and dried over Na$_2$SO$_4$ and concentrated under reduced pressure to provide the title compound.

Step F. 2-((3R,5R,6S)-5-(3-chlorophenyl)-6-(4-chlorophenyl)-1-(cyclopent-2-enyl)-3-methyl-2-oxopiperidin-3-yl)acetic acid

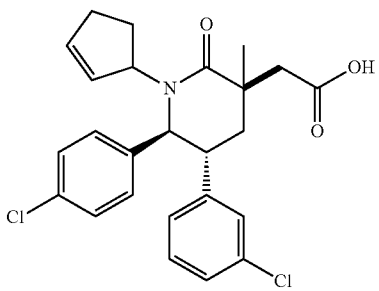 [SMILES: C[C@]1(CC(=O)O)C[C@H](c2cccc(Cl)c2)[C@@H](c2ccc(Cl)cc2)N(C2C=CCC2)C1=O]

To 2-((3R,5R,6S)-5-(3-chlorophenyl)-6-(4-chlorophenyl)-1-(cyclopent-2-enyl)-3-methyl-2-oxopiperidin-3-yl)acetaldehyde (Example 102, Step E) (267 mg, 0.604 mmol) in acetone (4 mL) was added freshly prepared Jones reagent (0.5 mL) at rt. The reaction mixture was stirred at room temperature for 15 min. before it was diluted with EtOAc and washed with water and sat. aq. NaCl solution. The organic layer was dried over Na$_2$SO$_4$ and concentrated under reduced pressure. The residue was purified by flash chromatography on silica gel (eluent: 50 to 100% EtOAc in hexanes) to give the title compound as a colorless film as a 3.6:1 mixture of diastereomers.

Step G. 2-((3R,5R,6S)-5-(3-Chlorophenyl)-6-(4-chlorophenyl)-1-((1S,2S,3R)-2,3-dihydroxycyclopentyl)-3-methyl-2-oxopiperidin-3-yl)acetic acid To a solution of 2-((3R,5R,6S)-5-(3-chlorophenyl)-6-(4-chlorophenyl)-1-(cyclopent-2-enyl)-3-methyl-2-oxopiperidin-3-yl)acetic acid (Example 102, Step F) (94 mg, 0.205 mmol) in THF (1.0 mL) was added water (0.25 mL) and tBuOH (0.2 mL) at room temperature. NMO (36.0 mg, 0.308 mmol) was added followed by osmium tetroxide (4% aq) (1.303 μL, 0.205 μmol). The reaction mixture was stirred at room temperature for 24 h. Water (10 mL) was added and the mixture was extracted with DCM twice. The organic layers were combined and dried over Na$_2$SO$_4$ and concentrated under reduced pressure. The residue, containing a mixture of three stereoisomers, was purified by reversed phase preparatory HPLC (column: Gemini-NX C$_{18}$ 5 um column; Phenomonex, Torrance, Calif.; eluent: 30 to 50% MeCN +0.1% TFA in water +0.1% TFA, over 20 minutes) to provide the title compound as the first eluting isomer.

237

¹H NMR (400 MHz, CHLOROFORM-d) δ ppm 1.21-1.36 (3 H, m), 1.38 (3 H, s), 1.53-1.56 (2 H, m), 2.20-2.02 (3 H, m), 2.22 (1 H, t, J=13.2 Hz), 2.62-2.78 (1 H, m), 2.85-3.00 (1 H, m), 3.00-3.13 (1 H, m), 4.06-4.17 (1 H, m), 4.35 (1 H, br s), 4.70 (1 H, d, J=8.8 Hz), 6.76-6.88 (1 H, m), 6.93-7.12 (4 H, m), 7.12-7.25 (3 H, m). Mass Spectrum (ESI) m/z=492 [M+H]⁺.

Further elution provided as the last eluting isomer Example 103.

Example 103

2-((3R,5R,6S)-5-(3-Chlorophenyl)-6-(4-chlorophenyl)-1-((1R,2R,3S)-2,3-dihydroxycyclopentyl)-3-methyl-2-oxopiperidin-3-yl)acetic acid

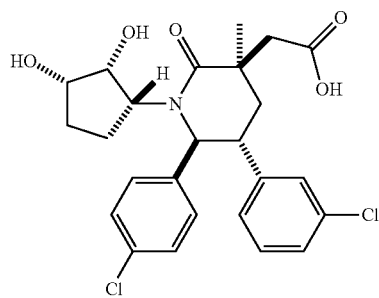

¹H NMR (400 MHz, CHLOROFORM-d) δ ppm 1.19-1.38 (1 H, m) 1.38-1.50 (3 H, m) 1.38-1.50 (1 H, m) 1.71-1.98 (2 H, m) 2.06-2.27 (3 H, m) 2.33 (1 H, d, J=8.2 Hz) 2.70-2.79 (1 H, m) 2.79-2.90 (1 H, m) 3.20-3.37 (2 H, m) 3.40 (1 H, d, J=5.1 Hz) 3.86 (1 H, br. s.) 4.50 (1 H, d, J=10.2 Hz) 6.67-6.77 (1 H, m) 6.93-7.07 (1 H, m) 7.06-7.19 (3 H, m) 7.23 (3 H, d, J=8.6 Hz). Mass Spectrum (ESI) m/z=492 [M+H]⁺.

Example 104

2-((3R,3'S,5R,6S)-5-(3-Chlorophenyl)-6-(4-chlorophenyl)-3-methyl-2-oxo-1'-(2,2,2-trifluoroethyl)-1,3'-bipiperidin-3-yl)acetic acid or 2-((3R,3'R,5R,6S)-5-(3-Chlorophenyl)-6-(4-chlorophenyl)-3-methyl-2-oxo-1'-(2,2,2-trifluoroethyl)-1,3'-bipiperidin-3-yl)acetic acid

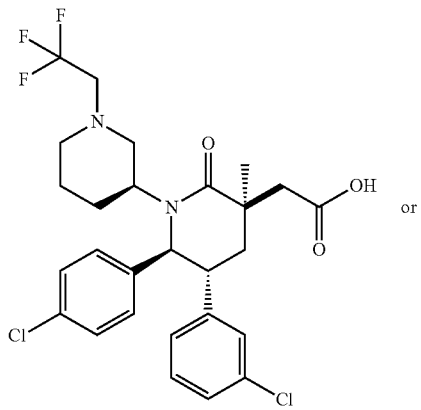

or

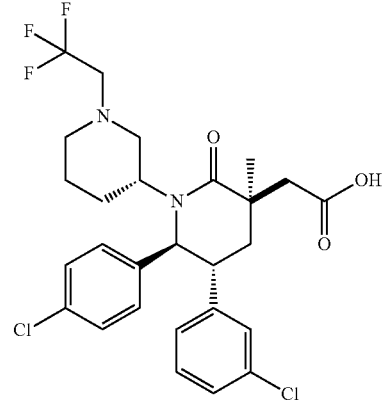

Step A. 2-((3R,5R,6S)-5-(3-chlorophenyl)-6-(4-chlorophenyl)-1-(1,5-dioxopentan-2-yl)-3-methyl-2-oxopiperidin-3-yl)acetic acid

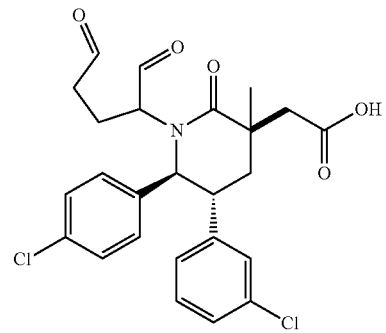 [SMILES: C[C@]1(CC(=O)O)C[C@H](c2cccc(Cl)c2)[C@@H](c2ccc(Cl)cc2)N(C(C=O)CCC=O)C1=O]

To a solution of 2-((3R,5R,6S)-5-(3-chlorophenyl)-6-(4-chlorophenyl)-1-(2,3-dihydroxycyclopentyl)-3-methyl-2-oxopiperidin-3-yl)acetic acid (Example 102, Step F) (110 mg, 0.223 mmol) in THF (3 mL) and water (3 mL) was added sodium periodate (134 mg, 0.626 mmol) at room temperature. The reaction mixture was stirred at room temperature for 45 min and was diluted with EtOAc and the layers were separated. The organic layer was washed with sat. aq. Na₂S₂O₃ solution, sat. aq. NaCl solution, dried over Na₂SO₄ and concentrated under reduced pressure to provide the title compound.

Step B 2-((3R,3'S,5R,6S)-5-(3-Chlorophenyl)-6-(4-chlorophenyl)-3-methyl-2-oxo-1'-(2,2,2-trifluoroethyl)-1,3'-bipiperidin-3-yl)acetic acid or 2-((3R,3'R,5R,6S)-5-(3-Chlorophenyl)-6-(4-chlorophenyl)-3-methyl-2-oxo-1'-(2,2,2-trifluoroethyl)-1,3'-bipiperidin-3-yl) acetic acid (Isomer 1)

To a solution of 2-((3R,5R,6S)-5-(3-chlorophenyl)-6-(4-chlorophenyl)-1-(1,5-dioxopentan-2-yl)-3-methyl-2-oxopiperidin-3-yl)acetic acid (Example 104, Step A) (55 mg, 0.112 mmol) in DCE (1 mL) was added 2,2,2-trifluoroethanamine (9.24 μL, 0.118 mmol) and sodium triacetoxyborohydride (76 mg, 0.359 mmol) at room temperature. The cloudy reaction mixture was stirred at room temperature for 2 h. The reaction mixture was concentrated under reduced pressure, diluted with DCM and washed with sat. aq. NaHCO₃ solution and sat. aq. NaCl solution. The layers were separated and the aqueous layer was extracted three times with DCM. The organic layers were combined, dried over Na₂SO₄ and concentrated under reduced pressure. The residue was purified by reversed phase preparatory HPLC (column: Gemini-NX C$_{18}$ 5 um column; Phenomonex, Torrance, Calif.; eluent: 40% MeCN +0.1% TFA in water +0.1% TFA, over 20 minutes) and concentrated in vacuo to provide the first eluting diastereomer. The residue was dissolved in DCM (1 mL) and HCl in ether (1M) (1 mL) was added and the solvent was removed under reduced pressure to provide the hydrochloride salt of one of the title compounds as the first eluting isomer.

$^1$H NMR (400 MHz, CHLOROFORM-d) δ ppm 0.73-1.00 (4 H, m), 1.13-1.53 (6 H, m), 1.58-1.84 (2 H, m), 1.98-2.13 (1 H, m), 2.24-2.44 (1 H, m), 2.67-2.99 (3 H, m), 3.17-3.32 (1 H, m), 4.22 (2 H, t, J=6.0 Hz), 6.65-6.91 (1 H, m), 7.00 (1 H, d, J=0.6 Hz), 7.05-7.24 (4 H, m), 7.48-7.59 (1 H, m), 7.63-7.79 (1 H, m). Mass Spectrum (ESI) m/z=557 [M+H]⁺.

Further elution and concentration in vacuo provided example 105.

Example 105

2-((3R,3'S,5R,6S)-5-(3-Chlorophenyl)-6-(4-chlorophenyl)-3-methyl-2-oxo-1'-(2,2,2-trifluoroethyl)-1,3'-bipiperidin-3-yl)acetic acid or 2-((3R,3'R,5R,6S)-5-(3-Chlorophenyl)-6-(4-chlorophenyl)-3-methyl-2-oxo-1'-(2,2,2-trifluoroethyl)-1,3'-bipiperidin-3-yl) acetic acid (Isomer 2)

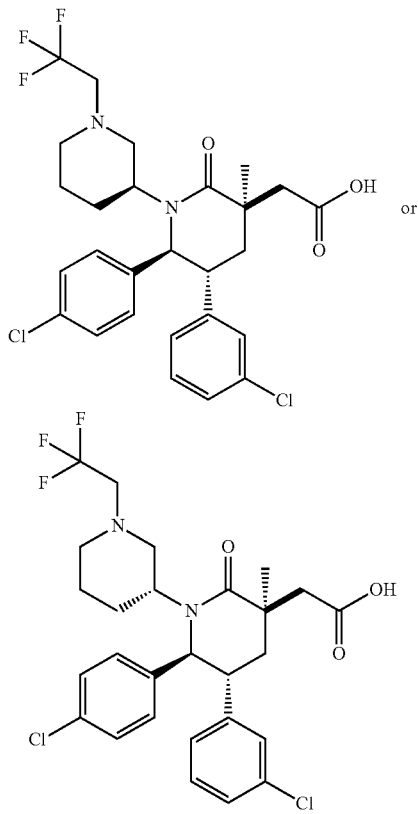

The residue was dissolved in DCM (1 mL) and HCl in ether (1M) (1 mL) was added and the solvent was removed under reduced pressure to provide the hydrochloride salt of one of the title compounds as the second eluting isomer.

$^1$H NMR (400 MHz, CHLOROFORM-d) δ ppm 0.73-1.08 (7 H, m), 1.13-1.50 (7 H, m), 1.69 (6 H, d, J=6.1 Hz), 7.54 (4 H, dd, J=5.7 and 3.3 Hz), 7.72 (4 H, dd, J=5.7 and 3.3 Hz). Mass Spectrum (ESI) m/z=557 [M+H]⁺.

Example 106

2-((3R,5R,6S)-5-(3-Chlorophenyl)-6-(4-chlorophenyl)-1-((1S,3S)-3-hydroxycyclopentyl)-3-methyl-2-oxopiperidin-3-yl)acetic acid or 2-((3R,5R,6S)-5-(3-Chlorophenyl)-6-(4-chlorophenyl)-1-((1S,3R)-3-hydroxycyclopentyl)-3-methyl-2-oxopiperidin-3-yl) acetic acid

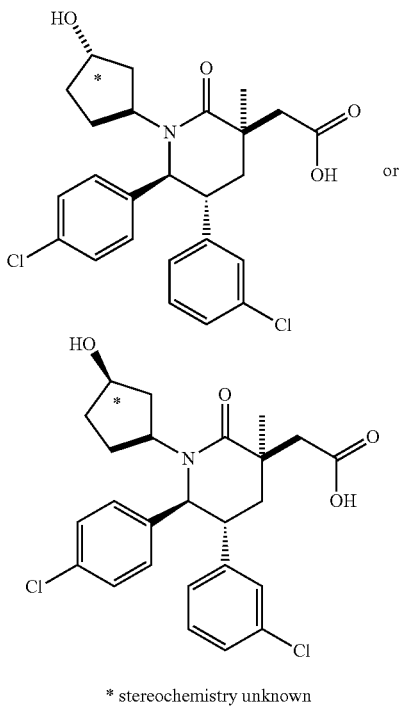

* stereochemistry unknown

Step A. (5R,6S)-5-(3-chlorophenyl)-6-(4-chlorophenyl)-1-(cyclopent-2-enyl)piperidin-2-one

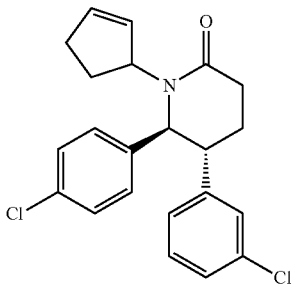 [SMILES: O=C1CC[C@H](c2cccc(Cl)c2)[C@@H](c2ccc(Cl)cc2)N1C1C=CCC1]

To a solution of 3.25 g (10.16 mmol) of (5R,6S)-5-(3-chlorophenyl)-6-(4-chlorophenyl)piperidin-2-one (Example 1, Step E) in DMF (150 mL) at 0° C. was added a dispersion of 60% sodium hydride in mineral oil (1.016 g, 25.4 mmol). Evolution of gas was observed. The cloudy reaction mixture was stirred at 0° C. for 20 min before adding 3-bromocyclopent-1-ene (4.48 g, 30.5 mmol). The cloudy reaction mixture warmed to room temperature and stirred at room temperature for 18 h. The reaction was quenched with sat. aq. NH₄Cl solution, diluted with EtOAc and the layers were separated. The organic layer was washed with 1M LiCl, sat. aq. NaCl solution, dried over Na₂SO₄ and concentrated under reduced pressure. The residue was purified by flash chromatography on silica gel (eluent: 25 to 100% EtOAc in hexanes) to give the title compound as a 5:2 mixture of diastereomers.

Step B. (5R,6S)-5-(3-chlorophenyl)-6-(4-chlorophenyl)-1-(3-hydroxycyclopentyl)piperidin-2-one

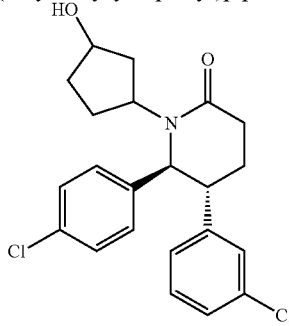

To a solution of (5R,6S)-5-(3-chlorophenyl)-6-(4-chlorophenyl)-1-(cyclopent-2-enyl)piperidin-2-one (Example 106, Step A) (394 mg, 1.020 mmol) in THF (10 mL) was added borane tetrahydrofuran complex (1.0 m in THF) (1020 µL, 1.020 mmol). Evolution of gas was observed. The reaction was stirred at room temperature for 30 min. before adding aq. NaOH (6 M) (1.25 mL) and 30% H₂O₂ (1.25 mL). The reaction mixture became cloudy and was stirred at room temperature for 1 h. The reaction mixture was extracted with EtOAc. The organic layers were washed with sat. aq. NaCl solution and dried over Na₂SO₄. The residue was purified by flash chromatography on silica gel (eluent: 40 to 100% EtOAc in hexanes) to give the title compound as a mixture of diastereomers.

Step C. (5R,6S)-1-((1S,3S)-3-((tert-Butyldimethylsilyl)oxy)cyclopentyl)-5-(3-chlorophenyl)-6-(4-chlorophenyl)piperidin-2-one or (2S,3R)-1-((1S,3R)-3-((tert-Butyldimethylsilyl)oxy)cyclopentyl)-3-(3-chlorophenyl)-2-(4-chlorophenyl)piperidine

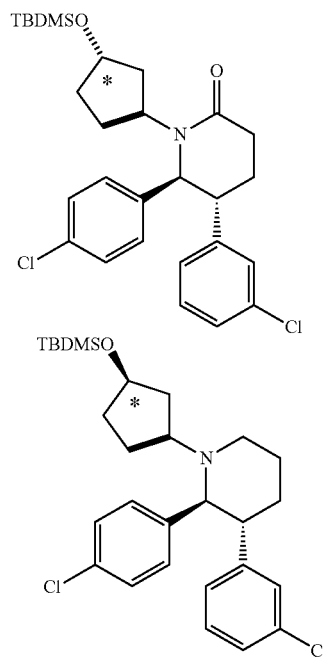

* stereochemistry unknown

To a solution of (5R,6S)-5-(3-chlorophenyl)-6-(4-chlorophenyl)-1-(3-hydroxycyclopentyl)piperidin-2-one (Example 106, Step B) (175 mg, 0.433 mmol) in DMF (4 mL) at room temperature was added TBDMS-Cl (71.8 mg, 0.476 mmol) and imidazole (29.5 mg, 0.433 mmol). The reaction mixture was stirred at room temperature for 18 h. Additional imidazole (29.5 mg, 0.433 mmol) and TBDMS-Cl (71.8 mg, 0.476 mmol) were added. The reaction mixture was stirred at room temperature for 18 h and was then diluted with EtOAc, washed with aq. 1M LiCl solution, 1M HCl and sat. aq. Na₂CO.solution. The organic layer was dried over Na₂SO₄ and concentrated under reduced pressure. The residue was purified by flash chromatography on silica gel (eluent: 0 to 100% EtOAc in hexanes) to give the title compound as the major single isomer.

Step D. (5R,6S)-1-((1S,3S)-3-(tert-Butyldimethylsilyloxy)cyclopentyl)-5-(3-chlorophenyl)-6-(4-chlorophenyl)-3-methylpiperidin-2-one or (2S,3R)-1-((1S,3R)-3-((tert-Butyldimethylsilyl)oxy)cyclopentyl)-3-(3-chlorophenyl)-2-(4-chlorophenyl)-5-methylpiperidine

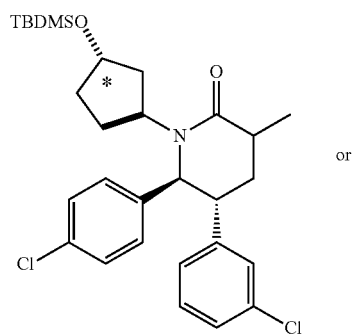

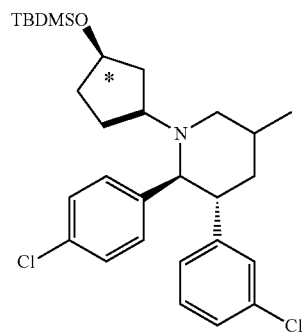

* stereochemistry unknown

To (5R,6S)-1-((1S,3S)-3-((tert-Butyldimethylsilyl)oxy)cyclopentyl)-5-(3-chlorophenyl)-6-(4-chlorophenyl)piperidin-2-one or (2S,3R)-1-((1S,3R)-3-((tert-Butyldimethylsilyl)oxy)cyclopentyl)-3-(3-chlorophenyl)-2-(4-chlorophenyl)piperidine from above (Example 106, Step C) (104 mg, 0.201 mmol) was added toluene (15 mL) and the mixture was concentrated under reduced pressure. This step was repeated three times. The residue was dissolved in inhibitor free THF (2 mL) that was previously degassed with Ar and the mixture was cooled to 0° C. under Ar. Methyliodide (13.79 µL, 0.221 mmol) was added followed by LHMDS (previously degassed with Ar) (1.0M in THF) (221 µL, 0.221 mmol). The reaction mixture was warmed to room temperature and stirred under Ar for 24 h. Additional LHMDS (1.0 M in THF) (221 µL, 0.221 mmol) was added and the reaction mixture was stirred at room temperature for 1 h. The reaction was quenched with sat. aq. NH$_4$Cl solution and extracted with EtOAc. The organic layers were dried over Na$_2$SO$_4$, filtered and the filtrate was concentrated in vacuo to provide the title compound.

Step E. (5R,6S)-3-Allyl-1-((1S,3S)-3-((tert-butyldimethylsilyl)oxy)cyclopentyl)-5-(3-chlorophenyl)-6-(4-chlorophenyl)-3-methylpiperidin-2-one or (2S,3R)-5-Allyl-1-((1S,3R)-3-((tert-butyldimethylsilyl)oxy)cyclopentyl)-3-(3-chlorophenyl)-2-(4-chlorophenyl)-5-methylpiperidine

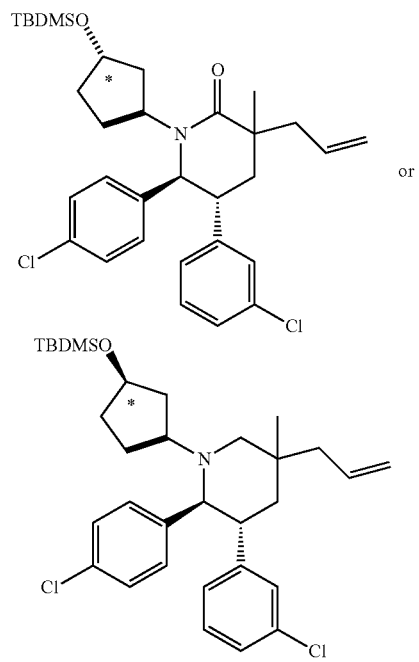

* stereochemistry unknown

To (5R,6S)-1-((1S,3S)-3-(tert-Butyldimethylsilyloxy)cyclopentyl)-5-(3-chlorophenyl)-6-(4-chlorophenyl)-3-methylpiperidin-2-one or (2S,3R)-1-((1S,3R)-3-((tert-Butyldimethylsilyl)oxy)cyclopentyl)-3-(3-chlorophenyl)-2-(4-chlorophenyl)-5-methylpiperidine from above (Example 106, Step D) (107 mg, 0.201 mmol) was added toluene (15 mL) and the mixture was concentrated under reduced pressure. This step was repeated three times. The residue was dissolved in inhibitor free THF (2 mL) that was previously degassed with Ar and the mixture was cooled to 0° C. under Ar. Distilled allyl bromide (87 µL, 1.004 mmol) and LHMDS (1M in THF) (502 µL, 0.502 mmol) were added and the reaction mixture was warmed to room temperature and stirred at room temperature for 1 h before heating the reaction mixture at 50° C. under Ar overnight. The reaction mixture was cooled to room temperature and additional allyl bromide (87 µL, 1.004 mmol) and LHMDS (1.0 M in THF) (502 µL, 0.502 mmol) were added and the reaction mixture was heated to 60° C. for 6 h under Ar. The reaction mixture was cooled to room temperature and the reaction was quenched with sat. NH$_4$Cl solution and extracted with EtOAc. The organic layers were dried over Na$_2$SO$_4$ and concentrated under reduced pressure. The residue was purified by flash chromatography on silica gel (eluent: 0 to 20% MTBE in hexanes) to give the title compound as a mixture of diastereomers.

Step F. 2-((5R,6S)-1-((1S,3S)-3-(tert-Butyldimethylsilyloxy)cyclopentyl)-5-(3-chlorophenyl)-6-(4-chlorophenyl)-3-methyl-2-oxopiperidin-3-yl)acetic acid or 2-((5R,6S)-1-((1S,3R)-3-((tert-Butyldimethylsilyl)oxy)cyclopentyl)-5-(3-chlorophenyl)-6-(4-chlorophenyl)-3-methylpiperidin-3-yl)acetic acid

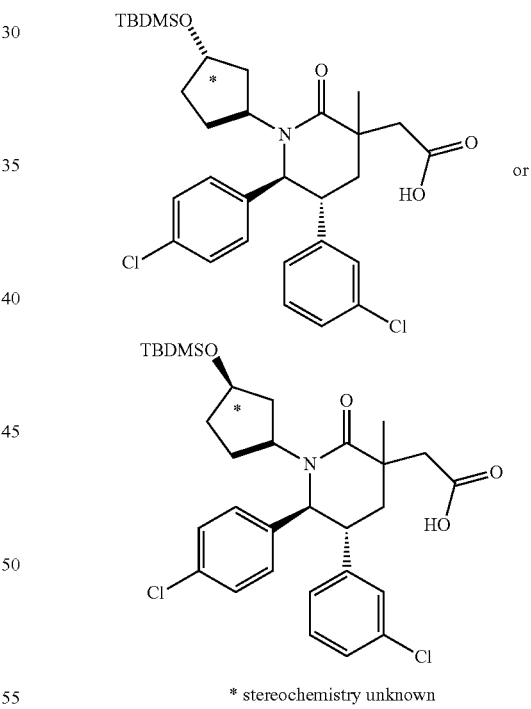

* stereochemistry unknown

The title compound was prepared from (5R,6S)-3-Allyl-1-((1S,3S)-3-((tert-butyldimethylsilyl)oxy)cyclopentyl)-5-(3-chlorophenyl)-6-(4-chlorophenyl)-3-methylpiperidin-2-one or (2S,3R)-5-Allyl-1-((1S,3R)-3-((tert-butyldimethylsilyl)oxy)cyclopentyl)-3-(3-chlorophenyl)-2-(4-chlorophenyl)-5-methylpiperidine from above (Example 106, Step E) as described in Example 95, Step D.

Step G. 2-((3R,5R,6S)-5-(3-Chlorophenyl)-6-(4-chlorophenyl)-1-((1S,3S)-3-hydroxycyclopentyl)-3-methyl-2-oxopiperidin-3-yl)acetic acid or 2-((3R,5R,6S)-5-(3-Chlorophenyl)-6-(4-chlorophenyl)-1-((1S,3R)-3-hydroxycyclopentyl)-3-methyl-2-oxopiperidin-3-yl)acetic acid To a solution of 2-((5R,6S)-1-((1S,3S)-3-(tert-Butyldimethylsilyloxy)cyclopentyl)-5-(3-chlorophenyl)-6-(4-chlorophenyl)-3-methyl-2-oxopiperidin-3-yl)acetic acid or 2-((5R,6S)-1-((1S,3R)-3-((tert-Butyldimethylsilyl)oxy)cyclopentyl)-5-(3-chlorophenyl)-6-(4-chlorophenyl)-3-methylpiperidin-3-yl)acetic acid from above (Example 106, Step F) (31 mg, 0.052 mmol) in THF (1.0 mL) was added 1.0M TBAF in THF (262 μL, 0.262 mmol) at room temperature. The reaction mixture was stirred at room temperature for 19 h before being concentrated under reduced pressure. The residue was purified by reversed phase preparatory HPLC (column: Gemini-NX C$_{18}$ 5 um column; Phenomonex, Torrance, Calif.; eluent: 45 to 75% MeCN +0.1% TFA in water +0.1% TFA) to give the title compound.

$^1$H NMR (400 MHz, CHLOROFORM-d) δ ppm 1.31 (3 H, s), 1.49-1.65 (3 H, m), 1.65-1.90 (3 H, m), 2.06-2.19 (3 H, m), 2.68-2.78 (1 H, m), 3.05-3.18 (1 H, m), 2.88 (1 H, d, J=15.1 Hz), 3.35-3.54 (1 H, m), 4.41-4.49 (1 H, m), 4.68 (1 H, d, J=8.0 Hz), 6.85 (1 H, dt, J=7.4 and 1.7 Hz), 6.95-7.00 (2 H, m), 7.09 (1 H, t, J=1.9 Hz), 7.15-7.26 (2 H, m), 7.30 (2 H, d, J=8.6 Hz).

Mass Spectrum (ESI) m/z=476 [M+H]$^+$.

Example 107

2-((3R,5R,6S)-5-(3-Chlorophenyl)-6-(4-chlorophenyl)-3-methyl-2-oxo-1-((S)-tetrahydro-2H-pyran-3-yl)piperidin-3-yl)acetic acid or 2-((3R,5R,6S)-5-(3-Chlorophenyl)-6-(4-chlorophenyl)-3-methyl-2-oxo-1-((R)-tetrahydro-2H-pyran-3-yl)piperidin-3-yl) acetic acid

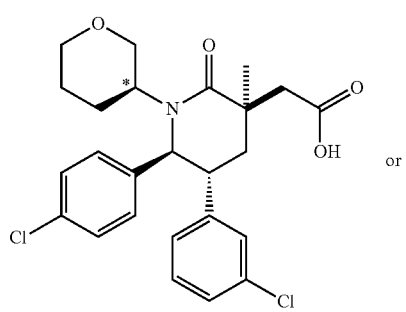

or

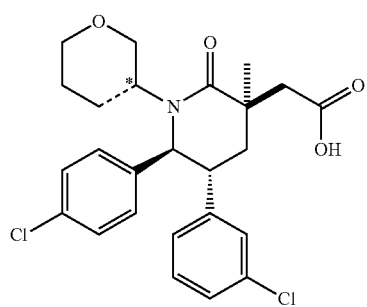

* stereochemistry not assigned

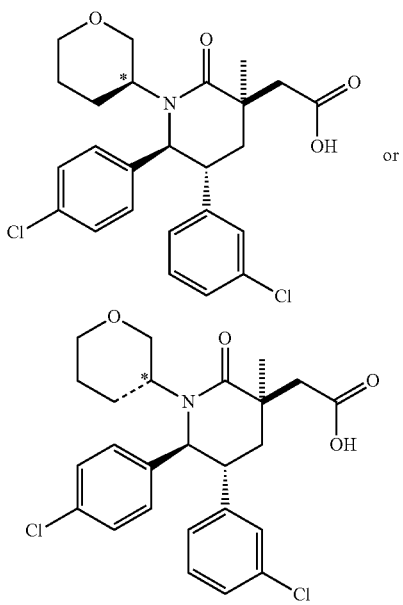

* stereochemistry not assigned

Step A. 2-((2S,3R)-3-(3-chlorophenyl)-2-(4-chlorophenyl)-6-oxopiperidin-1-yl)pentanedial

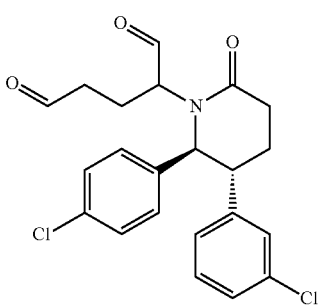 [SMILES: O=CCCC(C=O)N1C(=O)CC[C@H](c2cccc(Cl)c2)[C@H]1c1ccc(Cl)cc1]

To a solution of 454 mg (1.175 mmol) of (5R,6S)-5-(3-chlorophenyl)-6-(4-chlorophenyl)-1-(cyclopent-2-enyl)piperidin-2-one (Example 104, Step A) in THF (6 mL) was added water dropwise (3.5 mL) and tBuOH (0.2 mL). 4-methylmorpholine 4-oxide (207 mg, 1.763 mmol) was added followed by 4% aq. osmium(VIII) oxide (37.3 μL, 5.88 μmol). The reaction mixture was stirred at room temperature for 18 h. Sodium periodate (704 mg, 3.29 mmol) was added and the cloudy reaction mixture was stirred at room temperature for 90 min. Water (4 mL) was added and the mixture was filtered and washed with EtOAc. The filtrate was diluted with EtOAc and the layers were separated. The combined organic layers were washed with sat. Na₂S₂O₃, sat. aq. NaCl solution, dried over Na₂SO₄ and concentrated in vacuo to provide the title compound.

Step B. (5R,6S)-5-(3-chlorophenyl)-6-(4-chlorophenyl)-1-(1,5-dihydroxypentan-2-yl)piperidin-2-one

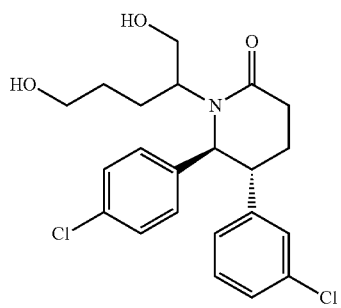 [SMILES: O=C1CC[C@H](c2cccc(Cl)c2)[C@@H](c2ccc(Cl)cc2)N1C(CO)CCCO]

To a solution of 2-((2S,3R)-3-(3-chlorophenyl)-2-(4-chlorophenyl)-6-oxopiperidin-1-yl)pentanedial (Example 107, Step A) (492 mg, 1.176 mmol) in MeOH (11 mL) was added sodium borohydride (89 mg, 2.352 mmol) at room temperature. Evolution of gas was observed. The reaction mixture was stirred at room temperature for 15 min and then concentrated under reduced pressure. The residue was purified by flash chromatography on silica gel (eluent: 50 to 100% EtOAc in hexanes and then 10% MeOH in DCM) to give the title compound.

Step C. (5R,6S)-5-(3-chlorophenyl)-6-(4-chlorophenyl)-1-(tetrahydro-2H-pyran-3-yl)piperidin-2-one

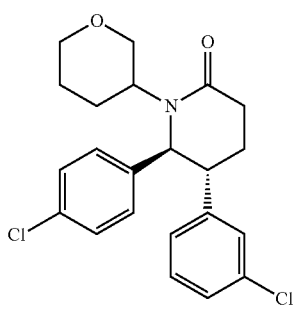 [SMILES: O=C1CC[C@H](c2cccc(Cl)c2)[C@@H](c2ccc(Cl)cc2)N1C1CCCOC1]

To a solution of (5R,6S)-5-(3-chlorophenyl)-6-(4-chlorophenyl)-1-(1,5-dihydroxypentan-2-yl)piperidin-2-one (Example 107, Step B) (192 mg, 0.455 mmol) in THF (5 mL) at room temperature was added triphenylphosphine (119 mg, 0.455 mmol) followed by the dropwise addition of diisopropyl azodicarboxylate (89 µL, 0.455 mmol). The reaction mixture turned light yellow during the addition and then became colorless within 5 min. The reaction mixture was stirred at room temperature for 1 h. The reaction mixture was diluted with EtOAc and washed with sat. aq. NaCl solution. The organic layer was dried over Na₂SO₄ and concentrated in vacuo. The residue was purified by flash chromatography on silica gel (eluent: 0 to 100% EtOAc in hexanes) to give the title compound as a mixture of diastereomers.

Step D. (5R,6S)-5-(3-chlorophenyl)-6-(4-chlorophenyl)-3-methyl-1-(tetrahydro-2H-pyran-3-yl)piperidin-2-one

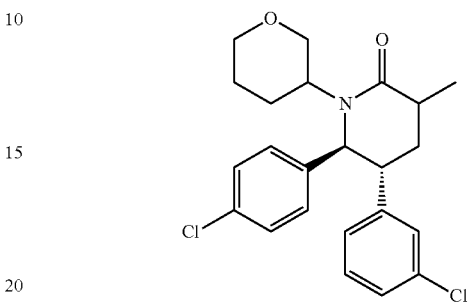

The title compound was prepared from (5R,6S)-5-(3-chlorophenyl)-6-(4-chlorophenyl)-1-(tetrahydro-2H-pyran-3-yl)piperidin-2-one (Example 107, Step C) as described in Example 71, Step B.

Step E. (5R,6S)-3-allyl-5-(3-chlorophenyl)-6-(4-chlorophenyl)-3-methyl-1-(tetrahydro-2H-pyran-3-yl)piperidin-2-one

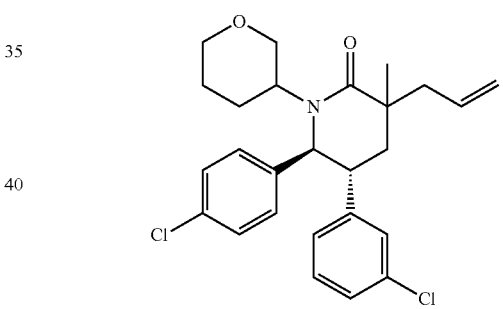

The title compound was prepared as a mixture of stereoisomers from (5R,6S)-5-(3-chlorophenyl)-6-(4-chlorophenyl)-3-methyl-1-(tetrahydro-2H-pyran-3-yl)piperidin-2-one (Example 107, Step D) as described in Example 71 Step C.

Step F. 2-((3R,5R,6S)-5-(3-Chlorophenyl)-6-(4-chlorophenyl)-3-methyl-2-oxo-1-((S)-tetrahydro-2H-pyran-3-yl)piperidin-3-yl)acetic acid Or 2-((3R,5R,6S)-5-(3-Chlorophenyl)-6-(4-chlorophenyl)-3-methyl-2-oxo-1-((R)-tetrahydro-2H-pyran-3-yl)piperidin-3-yl)acetic acid The title compound was prepared from (5R,6S)-3-allyl-5-(3-chlorophenyl)-6-(4-chlorophenyl)-3-methyl-1-(tetrahydro-2H-pyran-3-yl)piperidin-2-one (Example 107, Step E) as described previously in Example 42, Step C. The residue was purified by reversed phase preparatory HPLC (column: Gemini-NX C₁₈ 5 um column; Phenomonex, Torrance, Calif.; eluent: 0 to 100% MeCN +0.1% TFA in water +0.1% TFA) to give the title compound as a single, but unassigned stereoisomer.

¹H NMR (400 MHz, CHLOROFORM-d) δ ppm 1.40 (3 H, s), 1.49-1.84 (3 H, m), 2.01-2.16 (3 H, m), 2.39 (1 H, dd, J=12.3 and 4.3 Hz), 2.66-2.77 (1 H, m), 2.90-3.10 (2 H, m), 3.22-3.33 (1 H, m), 3.48 (1 H, br. s.), 3.69-3.79 (1 H, m), 4.24 (1 H, t, J=10.5 Hz), 4.42 (1 H, d, J=9.4 Hz), 6.72 (1 H, d, J=7.6 Hz), 6.89-7.04 (3 H, m), 7.06-7.26 (4 H, m). Mass Spectrum (ESI) m/z=476 [M+H]⁺.

Example 108

2-((3R,5R,6S)-5-(3-chlorophenyl)-6-(4-chlorophenyl)-3-methyl-2-oxo-1-(pyrazin-2-yl)piperidin-3-yl)acetic acid

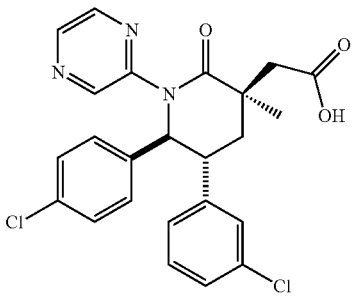

Step A. (3S,5R,6S)-3-allyl-5-(3-chlorophenyl)-6-(4-chlorophenyl)-3-methyl-1-(pyrazin-2-yl)piperidin-2-one

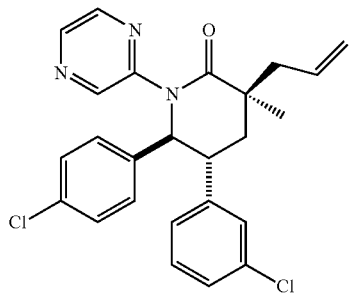

(3S,5R,6S)-3-allyl-5-(3-chlorophenyl)-6-(4-chlorophenyl)-3-methylpiperidin-2-one (Example 71, Step D) (100 mg, 0.27 mmol), 2-iodopyrazine (170 μL, 0.80 mmol) and cesium carbonate (220 mg, 0.67 mmol) were dissolved in 2.7 mL of 1,4-dioxane. The reaction vessel was flushed with argon, copper (I) iodide (5.1 mg, 27 μmol) and TMEDA (11 μL, 80 μmol) were added, and the reaction mixture was allowed to stir at 110° C. for 15 hours. The reaction mixture was cooled to room temperature, quenched with water and extracted (2×EtOAc). The combined organic layers were washed with sat. aq. NaCl solution, dried over Na₂SO₄, filtered and the filtrate was concentrated under reduced pressure. Purification of the residue by flash chromatography on silica gel (0 to 50% EtOAc/hexanes) provided the title compound as a colorless solid.

Step B. 2-((3R,5R,6S)-5-(3-chlorophenyl)-6-(4-chlorophenyl)-3-methyl-2-oxo-1-(pyrazin-2-yl)piperidin-3-yl)acetic acid The title compound was prepared from (3S,5R,6S)-3-allyl-5-(3-chlorophenyl)-6-(4-chlorophenyl)-3-methyl-1-(pyrazin-2-yl)piperidin-2-one (Example 108, Step A) as described in Example 42 Step C to provide a white solid.

¹H NMR (400 MHz, MeOD) δ ppm 1.42 (s, 3 H), 2.30-2.39 (m, 1 H), 2.39-2.49 (m, 1 H), 2.60 (d, J=14.67 Hz, 1 H), 3.07 (d, J=12.52 Hz, 1 H), 3.71-3.81 (m, 1 H), 5.50 (d, J=10.76 Hz, 1 H), 6.96-7.03 (m, 2 H), 7.04-7.11 (m, 3 H), 7.12-7.17 (m, 2 H), 7.19 (br. s., 1 H), 8.16 (br. s., 1 H), 8.30 (s, 1 H), 8.62 (br. s., 1 H). MS (ESI) 470.2 [M+H]⁺.

Example 109

2-((3R,5R,6S)-5-(3-chlorophenyl)-6-(4-chlorophenyl)-3-methyl-1-(1-methyl-1H-pyrazol-4-yl)-2-oxopiperidin-3-yl)acetic acid

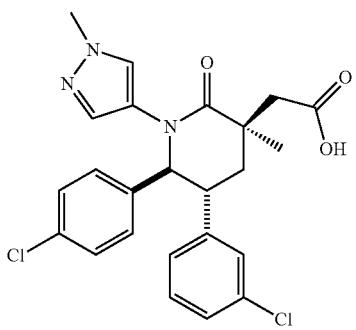 [SMILES: Cn1cc(N2C(=O)[C@@](C)(CC(=O)O)C[C@H](c3cccc(Cl)c3)[C@H]2c2ccc(Cl)cc2)cn1]

Step A. (3S,5R,6S)-3-allyl-5-(3-chlorophenyl)-6-(4-chlorophenyl)-3-methyl-1-(1-methyl-1H-pyrazol-4-yl)piperidin-2-one

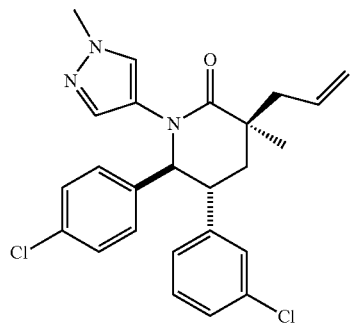 [SMILES: C=CC[C@@]1(C)C[C@H](c2cccc(Cl)c2)[C@@H](c2ccc(Cl)cc2)N(c2cnn(C)c2)C1=O]

(3S,5R,6S)-3-allyl-5-(3-chlorophenyl)-6-(4-chlorophenyl)-3-methylpiperidin-2-one (Example 71, Step D) (90 mg, 0.24 mmol), 1-methyl-4-(4,4,5,5-tetramethyl-1,3,2-dioxaborolan-2-yl)-1H-pyrazole (125 mg, 0.60 mmol), diacetoxycopper (44 mg, 0.24 mmol) and N,N-dimethylpyridin-4-amine (88 mg, 0.72 mmol) were dissolved in 1.2 mL of toluene. Sodium bis(trimethylsilyl)amide (480 μL, 0.48 mmol) was added and the reaction apparatus was outfitted with a reflux condenser and was allowed to stir at 115° C. for 13 hours. The reaction mixture was cooled to room temperature, quenched with water and extracted (2×EtOAc). The combined organic layers were washed with sat. aq. NaCl solution, dried over Na₂SO₄, filtered and the filtrate was concentrated under reduced pressure. Purification of the residue by flash chromatography (0 to 60% EtOAc/hexanes) provided the title compound as a colorless solid.

Step B. 2-((3R,5R,6S)-5-(3-chlorophenyl)-6-(4-chlorophenyl)-3-methyl-1-(1-methyl-1H-pyrazol-4-yl)-2-oxopiperidin-3-yl)acetic acid The title compound was prepared from (3S,5R,6S)-3-allyl-5-(3-chlorophenyl)-6-(4-chlorophenyl)-3-methyl-1-(1-methyl-1H-pyrazol-4-yl)piperidin-2-one (Example 108, Step A) as described in Example 42, Step C to provide a white solid.

$^1$H NMR (400 MHz, MeOD) δ ppm 1.42 (s, 3 H), 2.25-2.33 (m, 1 H), 2.31-2.44 (m, 1 H), 2.60 (d, J=12.91 Hz, 1 H), 3.01 (d, J=13.30 Hz, 1 H), 3.47-3.59 (m, 1 H), 3.68 (s, 3 H), 5.06 (d, J=10.37 Hz, 1 H), 6.95-7.05 (m, 3 H), 7.09 (d, J=8.41 Hz, 2 H), 7.12-7.20 (m, 3 H), 7.24 (s, 1 H), 7.49 (s, 1 H). MS (ESI) 472.2 [M+H]$^+$.

Example 110
2-((3R,5R,6S)-5-(3-chlorophenyl)-6-(4-chlorophenyl)-3-methyl-2-oxo-1-(pyrimidin-4-yl)piperidin-3-yl)acetic acid

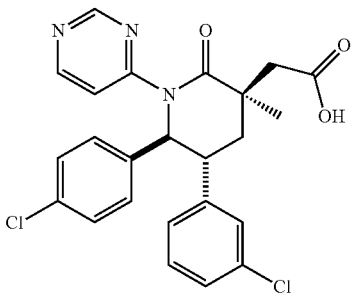 [SMILES: C[C@]1(CC(=O)O)C[C@H](c2cccc(Cl)c2)[C@@H](c2ccc(Cl)cc2)N(c2ccncn2)C1=O]

Step A.
1-(Pyrimidin-4-yloxy)-1H-benzo[d][1,2,3]triazole

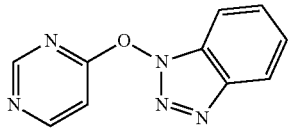 [SMILES: c1ccc2c(c1)nnn2Oc1ccncn1]

To a solution of pyrimidin-4-ol (350 mg, 3.6 mmol) and (1H-benzo[d][1,2,3]triazol-1-yloxy)tris(dimethylamino)phosphonium hexafluorophosphate(V) (1.9 g, 4.4 mmol) in 24 mL of acetonitrile was added 2,3,4,6,7,8,9,10-octahydropyrimido[1,2-a]azepine (820 μL, 5.5 mmol) dropwise at room temperature. After the reaction mixture was stirred for 1 hour, the reaction solvent was removed under reduced pressure. Purification of the residue by flash chromatography (0 to 70% EtOAc/hexanes) provided the title compound as a light yellow solid.

Step B. (3S,5R,6S)-3-allyl-5-(3-chlorophenyl)-6-(4-chlorophenyl)-3-methyl-1-(pyrimidin-4-yl)piperidin-2-one

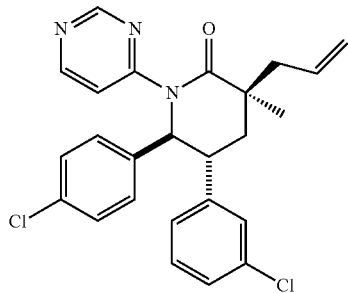 [SMILES: C=CC[C@@]1(C)C[C@H](c2cccc(Cl)c2)[C@@H](c2ccc(Cl)cc2)N(c2ccncn2)C1=O]

To a solution of (3S,5R,6S)-3-allyl-5-(3-chlorophenyl)-6-(4-chlorophenyl)-3-methylpiperidin-2-one (Example 71, Step D) (100 mg, 0.27 mmol) in 1.3 mL of DMSO was added sodium hydride (60% suspension in mineral oil, 13 mg, 0.32 mmol) at room temperature. The reaction mixture was stirred for 5 minutes, and was treated with 1-(pyrimidin-4-yloxy)-1H-benzo[d][1,2,3]triazole (Example 110, Step A) (170 mg, 0.80 mmol). The reaction mixture was stirred at 110° C. for 13 hours. The reaction mixture was cooled to room temperature, quenched with water and extracted (2×EtOAc). The combined organic layers were washed with sat. aq. NaCl solution, dried over Na$_2$SO$_4$, filtered and the filtrate was concentrated under reduced pressure. Purification of the residue by flash chromatography (0 to 45% EtOAc/hexanes) provided the title compound as a colorless solid.

Step C. 2-((3R,5R,6S)-5-(3-chlorophenyl)-6-(4-chlorophenyl)-3-methyl-2-oxo-1-(pyrimidin-4-yl)piperidin-3-yl)acetaldehyde

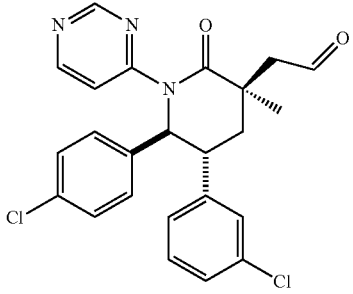 [SMILES: C[C@]1(CC=O)C[C@H](c2cccc(Cl)c2)[C@@H](c2ccc(Cl)cc2)N(c2ccncn2)C1=O]

To a solution of (3S,5R,6S)-3-allyl-5-(3-chlorophenyl)-6-(4-chlorophenyl)-3-methyl-1-(pyrimidin-4-yl)piperidin-2-one (Example 110, Step B) (60 mg, 0.13 mmol) in a mixture of tetrahydrofuran (2.7 mL) and water (880 μL) was added osmium tetroxide (1.7 mg, 6.6 μmol). After 5 minutes, sodium periodate (89 mg, 0.46 mmol) was added and the reaction mixture was stirred for 14 hours. The reaction mixture was filtered through Celite® (J. T. Baker, Phillipsberg, N.J., diatomaceous earth) and washed with EtOAc and water. The organic layer was washed with sat. aq. NaCl solution, dried over Na$_2$SO$_4$, filtered and the filtrate was concentrated under reduced pressure. Purification of the residue by flash chromatography (0 to 75% EtOAc/hexanes, gradient elution) provided the title compound as a colorless solid.

Step D. 2-((3R,5R,6S)-5-(3-chlorophenyl)-6-(4-chlorophenyl)-3-methyl-2-oxo-1-(pyrimidin-4-yl)piperidin-3-yl)acetic acid To a solution of 2-((3R,5R,6S)-5-(3-chlorophenyl)-6-(4-chlorophenyl)-3-methyl-2-oxo-1-(pyrimidin-4-yl)piperidin-3-yl)acetaldehyde (Example 110, Step C) (25 mg, 55 μmol) in a mixture of 2-methylpropan-2-ol (1.0 mL) and 2-methyl-2-butene (55 μL, 2.0 M soln in THF, 0.11 mmol) was added a solution of sodium chlorite (37 mg, 0.55 mmol) and sodium dihydrogen phosphate (4.8 mg, 50 μmol) in 550 μL of water at room temperature. The reaction mixture was stirred for 1 hour before it was quenched with water and extracted (2×EtOAc). The combined organic layers were washed with sat. aq. NaCl solution, dried over Na$_2$SO$_4$, filtered and the filtrate was concentrated under reduced pressure. Purification of the residue by silica gel prep plate (10% MeOH/DCM) provided the title compound as a colorless solid.

$^1$H NMR (500 MHz, CDCl$_3$) δ ppm 1.43 (s, 3 H), 2.21-2.27 (m, 1 H), 2.29-2.36 (m, 1 H), 2.84-2.95 (m, 2 H), 3.34-3.42 (m, 1 H), 5.71 (d, J=9.78 Hz, 1 H), 6.85-6.92 (m, 3 H), 7.01 (d, J=8.31 Hz, 2 H), 7.10-7.16 (m, 2 H), 7.18-7.22 (m, 1 H), 7.63 (d, J=5.38 Hz, 1 H), 8.49 (d, J=5.38 Hz, 1 H), 8.82 (s, 1 H). MS (ESI) 470.2 [M+H]$^+$.

Example 111

2-((3R,5R,6S)-5-(3-chlorophenyl)-6-(4-chlorophenyl)-1-(2-chloropyrimidin-4-yl)-3-methyl-2-oxopiperidin-3-yl)acetic acid

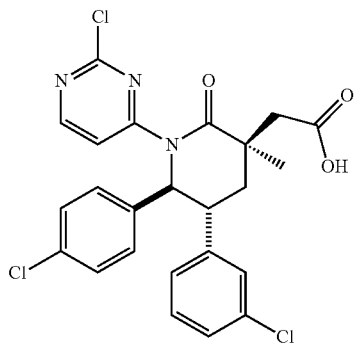 [SMILES: C[C@]1(CC(=O)O)C[C@H](c2cccc(Cl)c2)[C@@H](c2ccc(Cl)cc2)N(c2ccnc(Cl)n2)C1=O]

Step A. (3S,5R,6S)-3-allyl-5-(3-chlorophenyl)-6-(4-chlorophenyl)-1-(2-chloropyrimidin-4-yl)-3-methylpiperidin-2-one

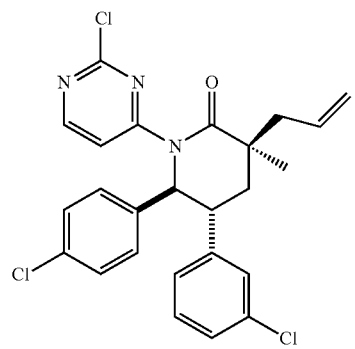 [SMILES: C=CC[C@@]1(C)C[C@H](c2cccc(Cl)c2)[C@@H](c2ccc(Cl)cc2)N(c2ccnc(Cl)n2)C1=O]

To a solution of (3S,5R,6S)-3-allyl-5-(3-chlorophenyl)-6-(4-chlorophenyl)-3-methylpiperidin-2-one (Example 71, Step D) (100 mg, 0.27 mmol) in 1.1 mL of DMSO was added sodium hydride (60% suspension in mineral oil, 32 mg, 0.80 mmol) at room temperature. The reaction mixture was stirred for 15 minutes, and was treated with 2,4-dichloropyrimidine (200 mg, 1.3 mmol). The reaction mixture was stirred at 60° C. for 5 hours. The reaction mixture was cooled to room temperature and quenched with water and extracted (2×EtOAc). The combined organic layers were washed with sat. aq. NaCl solution, dried over Na$_2$SO$_4$, filtered and the filtrate was concentrated under reduced pressure. Purification of the residue by silica gel prep plate (50% EtOAc/hexanes) provided the title compound as a colorless solid.

Step B. 2-((3R,5R,6S)-5-(3-chlorophenyl)-6-(4-chlorophenyl)-1-(2-chloropyrimidin-4-yl)-3-methyl-2-oxopiperidin-3-yl)acetaldehyde

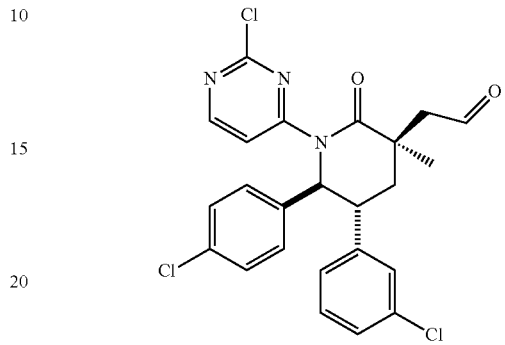

The title compound was prepared from (3S,5R,6S)-3-allyl-5-(3-chlorophenyl)-6-(4-chlorophenyl)-1-(2-chloropyrimidin-4-yl)-3-methylpiperidin-2-one (Example 111, Step A) as described in Example 110, Step C to provide a white solid.

Step C. 2-((3R,5R,6S)-5-(3-chlorophenyl)-6-(4-chlorophenyl)-1-(2-chloropyrimidin-4-yl)-3-methyl-2-oxopiperidin-3-yl)acetic acid The title compound was prepared from 2-((3R,5R,6S)-5-(3-chlorophenyl)-6-(4-chlorophenyl)-1-(2-chloropyrimidin-4-yl)-3-methyl-2-oxopiperidin-3-yl)acetaldehyde (Example 111, Step B) as described in Example 110 Step D to provide a white foam.

$^1$H NMR (400 MHz, CDCl$_3$) δ ppm 1.48 (s, 3 H), 2.29 (d, J=3.91 Hz, 1 H), 2.33 (d, J=12.52 Hz, 1 H), 2.86 (d, J=14.87 Hz, 1 H), 3.06 (d, J=14.67 Hz, 1 H), 3.31-3.41 (m, 1 H), 5.65 (d, J=10.37 Hz, 1 H), 6.83-6.87 (m, 1 H), 6.88-6.93 (m, 2 H), 7.04-7.07 (m, 1 H), 7.07-7.10 (m, 2 H), 7.15 (m, 1 H), 7.18-7.23 (m, 1 H), 7.70 (d, J=5.67 Hz, 1 H), 8.39 (d, J=5.7 Hz, 1 H). MS (ESI) 504.0 [M+H]$^+$.

Example 112

2-((3R,5R,6S)-5-(3-chlorophenyl)-6-(4-chlorophenyl)-3-methyl-2-oxo-1-(pyrimidin-2-yl)piperidin-3-yl)acetic acid

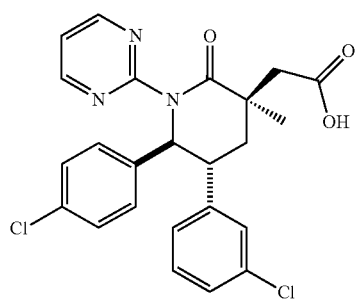 [SMILES: C[C@]1(CC(=O)O)C[C@H](c2cccc(Cl)c2)[C@@H](c2ccc(Cl)cc2)N(c2ncccn2)C1=O]

The title compound was prepared from (3S,5R,6S)-3-allyl-5-(3-chlorophenyl)-6-(4-chlorophenyl)-3-methylpiperidin-2-one (Example 71, Step D) and 2-chloropyrimidine as described in Example 111, followed by conversion to the acid as described in Example 71, Step F.

$^1$H NMR (500 MHz, CDCl$_3$) δ ppm 1.49 (s, 3 H), 2.34-2.40 (m, 2 H), 2.94 (d, J=14.18 Hz, 1 H), 3.10 (d, J=13.45 Hz, 1 H), 3.50 (td, J=10.88 and 3.91 Hz, 1 H), 5.46 (d, J=10.27 Hz, 1 H), 6.89 (d, J=7.34 Hz, 1 H), 6.93-7.01 (m, 5 H), 7.11 (t, J=8.19 Hz, 1 H), 7.14-7.18 (m, 2 H), 8.56 (d, J=4.9 Hz, 2 H). MS (ESI) 470.2 [M+H]$^+$.

Example 113

2-((3R,5R,6S)-5-(3-chlorophenyl)-6-(4-chlorophenyl)-3-methyl-1-(3-methylpyridin-2-yl)-2-oxopiperidin-3-yl)acetic acid

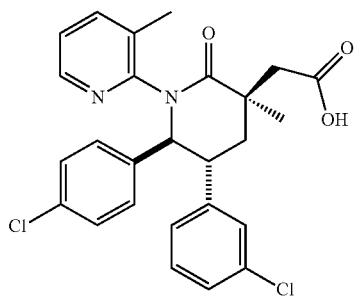 [SMILES: Cc1cccnc1N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-3-methyl-1-(3-methyl-5-nitropyridin-2-yl)piperidin-2-one

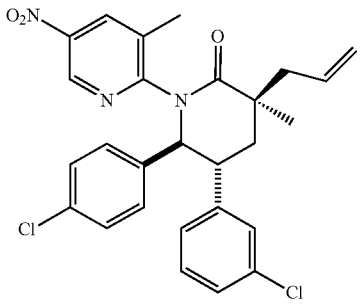 [SMILES: C=CC[C@@]1(C)C[C@H](c2cccc(Cl)c2)[C@@H](c2ccc(Cl)cc2)N(c2ncc([N+](=O)[O-])cc2C)C1=O]

The title compound was prepared from (3S,5R,6S)-3-allyl-5-(3-chlorophenyl)-6-(4-chlorophenyl)-3-methylpiperidin-2-one (Example 71, Step D) and 2-chloro-3-methyl-5-nitropyridine as described in Example 111, Step A to provide a light-yellow solid.

Step B. (3S,5R,6S)-3-allyl-1-(5-amino-3-methylpyridin-2-yl)-5-(3-chlorophenyl)-6-(4-chlorophenyl)-3-methylpiperidin-2-one

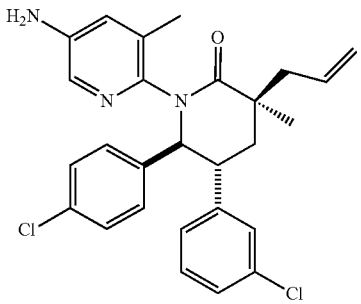

(3S,5R,6S)-3-allyl-5-(3-chlorophenyl)-6-(4-chlorophenyl)-3-methyl-(3-methyl-5-nitropyridin-2-yl)piperidin-2-one (Example 113, Step A) (120 mg, 0.23 mmol) and tin(II) chloride dihydrate (260 mg, 1.1 mmol) were dissolved in 2.3 mL of ethyl acetate. The reaction apparatus was outfitted with a reflux condenser and was stirred at 90° C. for 4 hours. The reaction mixture was cooled to room temperature, quenched with 1M NaOH and extracted (2×EtOAc). The combined organic layers were washed with sat. aq. NaCl solution, dried over Na$_2$SO$_4$, filtered and the filtrate was concentrated under reduced pressure. Purification of the residue by flash chromatography (0 to 90% EtOAc/Hex, gradient elution) provided the title compound as a colorless solid.

Step C. (3S,5R,6S)-3-allyl-5-(3-chlorophenyl)-6-(4-chlorophenyl)-3-methyl-1-(3-methylpyridin-2-yl)piperidin-2-one

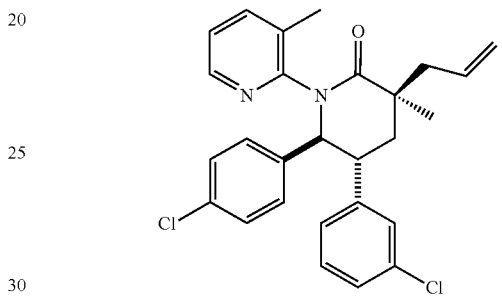

To a solution of (3S,5R,6S)-3-allyl-1-(5-amino-3-methylpyridin-2-yl)-5-(3-chlorophenyl)-6-(4-chlorophenyl)-3-methylpiperidin-2-one (Example 113, Step B) (89 mg, 0.185 mmol) in 1,4-dioxane (4.0 mL) and acetic acid (0.50 mL) was added 3.0M HCl (730 µL, 2.2 mmol) at 0° C. After the reaction was stirred for 5 minutes, hydrogen peroxide (6% wt aq., 95 µL, 0.185 mmol) was added dropwise, followed by sodium nitrite (46 mg, 0.74 mmol). The reaction mixture was stirred for 2 hours at 0° C. The reaction mixture was warmed to room temperature, quenched with 1M NaOH and extracted (2×EtOAc). The combined organic layers were washed with sat. aq. NaCl solution, dried over Na$_2$SO$_4$, filtered and the filtrate was concentrated under reduced pressure. Purification of the residue by flash chromatography (0 to 55% EtOAc/Hex, gradient elution) provided the title compound as a colorless solid.

Step D. 2-((3R,5R,6S)-5-(3-chlorophenyl)-6-(4-chlorophenyl)-3-methyl-1-(3-methylpyridin-2-yl)-2-oxopiperidin-3-yl)acetaldehyde

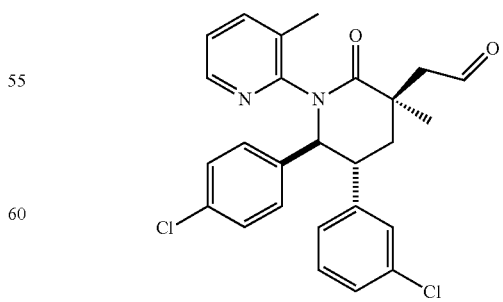

The title compound was prepared from (3S,5R,6S)-3-allyl-5-(3-chlorophenyl)-6-(4-chlorophenyl)-3-methyl-1-(3-methylpyridin-2-yl)piperidin-2-one (Example 113, Step C) as described in Example 110, Step C to provide a white solid.

Step E. 2-((3R,5R,6S)-5-(3-chlorophenyl)-6-(4-chlorophenyl)-3-methyl-1-(3-methylpyridin-2-yl)-2-oxopiperidin-3-yl)acetic acid The title compound was prepared from 2-((3R,5R,6S)-5-(3-chlorophenyl)-6-(4-chlorophenyl)-3-methyl-1-(3-methylpyridin-2-yl)-2-oxopiperidin-3-yl)acetaldehyde (Example 113, Step D) as described in Example 110 Step D to provide a white foam.

$^{1}$H NMR (500 MHz, CDCl$_3$) δ ppm 1.54 (s, 3 H), 2.12 (s, 3 H), 2.29 (dd, J=14.31 and 3.06 Hz, 1 H), 2.50 (t, J=13.82 Hz, 1 H), 2.92-3.01 (m, 1 H), 3.07-3.17 (m, 1 H), 3.56-3.67 (m, 1 H), 5.51 (d, J=11.00 Hz, 1 H), 6.90-7.02 (m, 5 H), 7.05-7.15 (m, 4 H), 7.45 (d, J=7.09 Hz, 1 H), 8.30 (d, J=3.67 Hz, 1 H). MS (ESI) 483.2 [M+H]$^+$.

Example 114

2-((3R,5R,6S)-5-(3-chlorophenyl)-6-(4-chlorophenyl)-3-methyl-1-(4-methylpyridin-2-yl)-2-oxopiperidin-3-yl)acetic acid

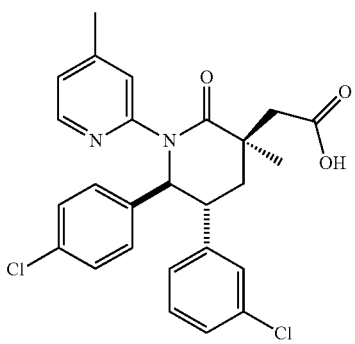 [SMILES: Cc1ccnc(N2C(=O)[C@@](C)(CC(=O)O)C[C@H](c3cccc(Cl)c3)[C@H]2c2ccc(Cl)cc2)c1]

Step A. (3S,5R,6S)-3-allyl-5-(3-chlorophenyl)-6-(4-chlorophenyl)-3-methyl-1-(4-methylpyridin-2-yl)piperidin-2-one

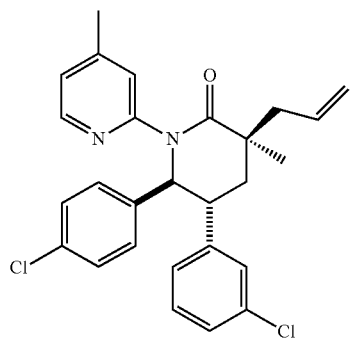 [SMILES: C=CC[C@@]1(C)C[C@H](c2cccc(Cl)c2)[C@@H](c2ccc(Cl)cc2)N(c2cc(C)ccn2)C1=O]

The title compound was prepared from (3S,5R,6S)-3-allyl-5-(3-chlorophenyl)-6-(4-chlorophenyl)-3-methylpiperidin-2-one (Example 71, Step D) and 2-chloro-4-methyl-5-nitropyridine as described in Example 113 Steps A-C to provide a white solid.

Step B. 2-((3R,5R,6S)-5-(3-chlorophenyl)-6-(4-chlorophenyl)-3-methyl-1-(4-methylpyridin-2-yl)-2-oxopiperidin-3-yl)acetic acid To a solution of (3S,5R,6S)-3-allyl-5-(3-chlorophenyl)-6-(4-chlorophenyl)-3-methyl-1-(4-methylpyridin-2-yl)piperidin-2-one (Example 114, Step A) (73 mg, 0.16 mmol) in 780 µL of tetrahydrofuran was added water (1.0 mL), followed by 2-methylpropan-2-ol (100 µL) at room temperature. The reaction mixture was treated with 4-methylmorpholine 4-oxide (28 mg, 0.24 mmol), followed by osmium tetroxide (2.0 mg, 7.8 µmol) and was stirred at room temperature for 2 hours. The reaction mixture was treated with a 1.25 M solution of Jones reagent (190 µL, 0.24 mmol) at room temperature and was stirred at room temperature for 1 hour. The reaction was quenched with water and extracted (3×EtOAc). The combined organic layers were washed with sat. aq. NaCl solution, dried over Na$_2$SO$_4$, filtered and the filtrate was concentrated under reduced pressure. Purification of the residue by HPLC on an Eclipse column (Agilent Technologies, Santa, Clara, Calif.) (20 to 80% acetonitrile/water, gradient elution) provided the title compound as a colorless solid.

$^{1}$H NMR (500 MHz, CDCl$_3$) δ ppm 1.49 (s, 3 H), 2.23 (s, 3 H), 2.28 (dd, J=14.2 and 3.2 Hz, 1 H), 2.42 (t, J=13.45 Hz, 1 H), 2.96 (m, 1 H), 3.04 (m, 1 H), 3.39 (ddd, J=12.9, 10.2 and 3.1 Hz, 1 H), 5.57 (d, J=10.3 Hz, 1 H), 6.81 (d, J=5.1 Hz, 1 H), 6.86-6.92 (m, 3 H), 6.99 (d, J=8.1 Hz, 2 H), 7.08-7.13 (m, 2 H), 7.13-7.18 (m, 2 H), 8.13 (d, J=5.1 Hz, 1 H). MS (ESI) 483.2 [M+H]$^+$.

Example 115

2-((3R,5R,6S)-5-(3-chlorophenyl)-6-(4-chlorophenyl)-1-(dicyclopropylmethyl)-3-methyl-2-oxopiperidin-3-yl)acetic acid

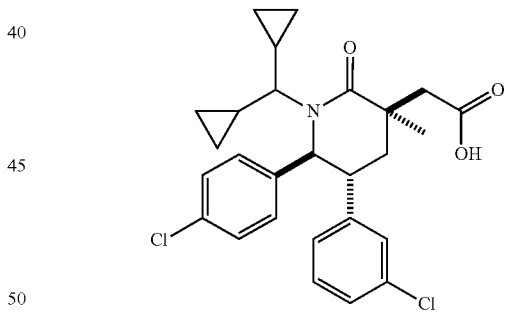

Step A. (Z)-2-(((4-chlorobenzylideneamino)methyl)phenol

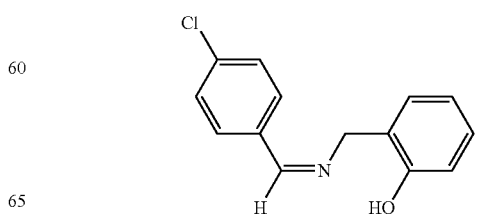

To a stirred suspension of 2-(aminomethyl)phenol, (4.0 g, 32.5 mmol) in ethanol (65 mL) was added 4-chlorobenzaldehyde (3.86 mL, 32.8 mmol). The resulting reaction mixture was stirred at rt for 3 h. The solvent was removed and 100 ml of toluene was added and concentrated in vacuum twice. The resulting imine was dried under vacuum overnight and used in the next step without further purification.

$^1$H NMR (500 MHz, DMSO-d6) δ ppm 9.47 (1 H, br. s.), 8.44 (1 H, s), 7.79 (2 H, d, J=8.6 Hz), 7.51 (2 H, d, J=8.6 Hz), 7.16 (1 H, dd, J=7.3, 1.6 Hz), 7.08 (1 H, td, J=7.6, 1.6 Hz), 6.72-6.87 (2 H, m), 4.71 (2 H, s).

Step B. 2-(((1S,2R)-2-(3-chlorophenyl)-1-(4-chlorophenyl)but-3-enylamino)methyl)phenol

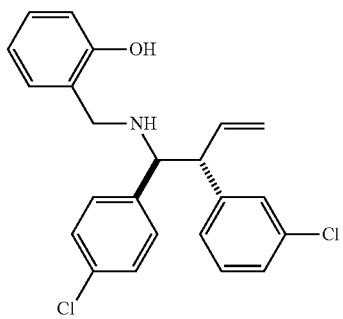

To a solution of 1.42 g (5.3 mmol) (4S,5S)-2-allyl-2-chloro-3,4-dimethyl-5-phenyl-[1,3,2]-oxazasilolidine (prepared according to J. Am. Chem. Soc. 124, 7920, 2002) and 1-chloro-3-vinylbenzene (1.69 g, 12.21 mmol) in DCM (12 mL) and DCE (12 mL) was added 0.173 g (0.2 mmol) of 1,3-bis-(2,4,6-trimethylphenyl)-2-(imidazolidinylidene) (dichlorophenylmethylene)(tricyclohexylphosphine)ruthenium ("Grubb's 2nd Generation Catalyst"). The resulting mixture was degassed two times and then heated to reflux for 8 h. The reaction mixture was cooled to room temperature. The imine, from above (Step A) (1.0 g, 4.07 mmol) was added. The reaction mixture was heated to reflux for 14 h, and then cooled to rt and quenched by adding 8 ml of ethanol. The reaction mixture was diluted with ethyl acetate (120 ml) and washed with water (30 ml) and sat. NaCl solution (30 ml). The combined organic layers were dried over MgSO$_4$, filtered and the filtrate was concentrated. The residue was purified by chromatography on silica gel, (eluent: hexane/ethyl acetate 90/10-65/35) to give the title compound.

$^1$H NMR (500 MHz, ACETONITRILE-d3) δ ppm 7.52 (2 H, d, J=8.3 Hz), 7.23-7.37 (3 H, m), 7.10-7.17 (3 H, m), 7.06 (1 H, d, J=8.1 Hz), 6.92-7.03 (2 H, m), 6.88 (1 H, td, J=7.5, 1.0 Hz), 6.14 (1 H, dt, J=16.4, 9.8 Hz), 5.72 (1 H, d, J=16.4 Hz), 5.47 (1 H, dd, J=9.8, 1.2 Hz), 4.35-4.47 (1 H, m), 4.25-4.35 (1 H, m), 4.05 (1 H, d, J=13.4 Hz), 3.78 (1 H, d, J=13.4 Hz). MS (ESI) [M+H]$^+$, 398.0.

Step C. 2-((N-((1S,2R)-2-(3-chlorophenyl)-1-(4-chlorophenyl)but-3-enyl)acetamido)methyl)phenyl acetate

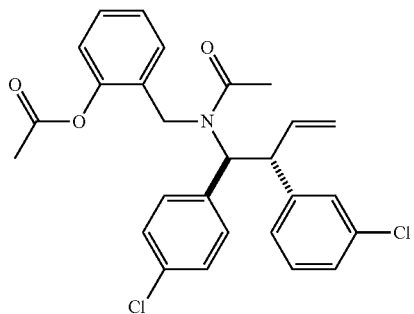

To a solution of 1.1 g (2.76 mmol) of 2-(((1S,2R)-2-(3-chlorophenyl)-1-(4-chlorophenyl)but-3-enylamino)methyl) phenol (Example 115, Step B) and triethylamine (0.85 mL, 6.08 mmol) in a mixture of THF (5.0 mL) and DCM (5.0 mL) was added acetic anhydride (0.55 mL, 5.80 mmol) at 0° C. The temperature of the reaction was slowly allowed to rise to room temperature and the mixture was stirred at ambient temperature overnight. When LCMS indicated completion of the reaction, 100 ml of ethyl acetate was added and the combined organics were washed consecutively with water (30 ml), citric acid (30 ml, 1M), NaHCO$_3$ solution (30 ml) and sat. NaCl solution (30 ml), dried over MgSO$_4$, filtered and the filtrate was concentrated to give the title compound. The crude product was used without further purification.

$^1$H NMR (400 MHz, CHLOROFORM-d) δ ppm 7.05-7.14 (4 H, m), 6.91-7.05 (6 H, m), 6.88 (1 H, d, J=7.4, Hz), 6.81 (1 H, t, J=7.5 Hz), 6.42 (1H, m), 5.95 (1 H, dt, J=16.8, 9.6 Hz), 4.97-5.18 (2 H, m), 4.24-4.45 (2H, m), 4.05 (1 H, q, J=7.0 Hz), 2.31 (3 H, s), 1.91 (3 H, s). MS (ESI) [M+H]$^+$, 482.0.

Step D. N-((1S,2R)-2-(3-chlorophenyl)-1-(4-chlorophenyl)but-3-enyl)acetamide

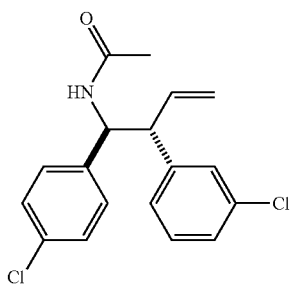

A solution of 1.05 g (2.18 mmol) of 2-((N-((1S,2R)-2-(3-chlorophenyl)-1-(4-chlorophenyl)but-3-enyl)acetamido)methyl)phenyl acetate (Example 115, Step C) and toluenesulfonic acid monohydrate (1.66 g, 8.71 mmol) in toluene (15.0 mL) was heated to reflux for about 2 h. 120 ml of ethyl acetate was added, and the combined organics were washed consecutively with NaHCO$_3$ solution and sat. NaCl solution, dried over MgSO$_4$, filtered and the filtrate was concentrated. The crude mixture was purified by preparative HPLC to give the title compound.

$^1$H NMR (500 MHz, CHLOROFORM-d) δ ppm 7.08-7.15 (2 H, m), 7.02-7.08 (2 H, m), 6.92 (3 H, t, J=8.6, Hz), 6.81 (1 H, dd, J=3.5, 2.1 Hz), 5.83-6.07 (2 H, m), 5.04-5.21 (3 H, m), 3.48 (1 H, t, J=9.3 Hz), 1.97 (3 H, s). MS (ESI) [M+H]$^+$, 334.0.

Step E. (1S,2R)-2-(3-chlorophenyl)-1-(4-chlorophenyl)but-3-en-1-amine

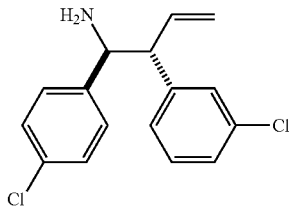

To a mixture of 4.1 g (12.27 mmol) of N-((1S,2R)-2-(3-chlorophenyl)-1-(4-chlorophenyl)but-3-enyl)acetamide (Example 115, Step D) and pyridine (1.20 mL, 14.72 mmol) in THF (35.0 mL) was added 1.2 mL (13.5 mmol) of oxalyl chloride at 0° C. The resulting light yellow slurry was stirred at 0° C. for 1.5 h. 1,2-dihydroxypropane (1.80 mL, 24.53 mmol) was added in one portion and the reaction was warmed to rt. The mixture was treated with ethanol (16.0 ml) followed by 6 N HCl (16.0 ml). The reaction mixture was heated at 55° C. for 10 min and then cooled down to rt. When LCMS indicated that most SM was consumed, 200 ml of ethyl acetate was added, and the organic layer was washed consecutively with NaHCO$_3$ solution and sat. NaCl solution, dried over MgSO$_4$, filtered and the filtrate was concentrated. The crude mixture was purified by flash chromatography on silica gel to give the title compound.

$^1$H NMR (400 MHz, CHLOROFORM-d) δ ppm 7.21 (3 H, d, J=8.4 Hz), 7.03-7.17 (3 H, m), 6.96 (1 H, s), 6.79 (1 H, ddd, J=6.2, 2.2, 2.0 Hz), 5.98 (1 H, dt, J=16.8, 9.8 Hz), 5.39 (1 H, d, J=16.8 Hz), 5.24 (1 H, d, J=10.2 Hz), 4.14 (1 H, d, J=11.2 Hz), 3.76 (1 H, t, J=10.2 Hz). MS (ESI) [M+H]$^+$, 292.1.

Step F. (1S,2R)-2-(3-chlorophenyl)-1-(4-chlorophenyl)-N-(dicyclopropylmethyl)but-3-en-1-amine

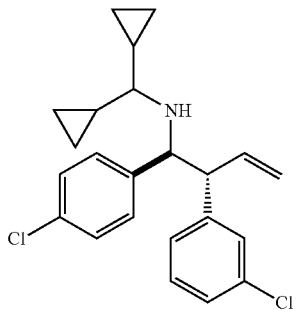

To a solution of 2.0 g (6.84 mmol) of (1S,2R)-2-(3-chlorophenyl)-1-(4-chlorophenyl)but-3-en-1-amine (Example 115, Step E), dicyclopropyl ketone (7.54 mL, 68.4 mmol), and acetic acid (1.96 mL, 34.2 mmol) in methanol (25.0 mL) was added sodium cyanoborohydride (1.44 mL, 27.4 mmol) at rt. The resulting mixture was stirred at 50° C. for 2 days. Acetic acid (1.5 ml) and sodium cyanoborohydride (0.6 g) were added again and heating was continued overnight. 200 ml of ethyl acetate was added, and the organic layer was washed consecutively with K$_2$CO$_3$ solution and sat. NaCl solution, dried over K$_2$CO$_3$, filtered and the filtrate was concentrated under reduced pressure at 60° C. The mixture was purified by flash chromatography on silica gel (eluent: DCM/MeOH, 95/5) to give the title compound.

$^1$H NMR (400 MHz, CHLOROFORM-d) δ ppm 7.20-7.41 (4 H, m), 7.04-7.20 (2 H, m), 6.92-7.04 (1 H, m), 6.80 (1 H, dt, J=7.0, 1.6 Hz), 6.11 (1 H, ddd, J=16.8, 10.0, 9.8 Hz), 5.63 (1 H, d, J=16.8 Hz), 5.52 (1 H, d, J=10.0 Hz), 4.47 (1 H, d, J=10.8 Hz), 4.06 (1 H, t, J=10.0 Hz), 1.79 (1 H, t, J=9.4 Hz), 1.08-1.24 (1 H, m), 0.91-1.08 (2 H, m), 0.50-0.78 (3 H, m), 0.29-0.50 (2 H, m), 0.24 (1 H, dq, J=9.9, 5.0 Hz), 0.09 (1 H, ddd, J=9.9, 5.2, 5.0 Hz). MS (ESI) [M+H]$^+$, 386.0.

Step G. N-((1S,2R)-2-(3-chlorophenyl)-1-(4-chlorophenyl)but-3-enyl)-N-(dicyclopropylmethyl)acrylamide

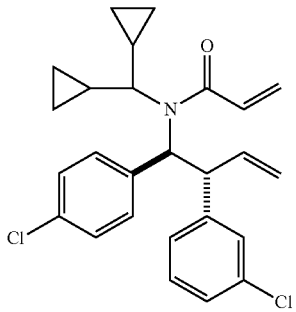

To a solution of 2.1 g (5.44 mmol) of (1S,2R)-2-(3-chlorophenyl)-1-(4-chlorophenyl)-N-(dicyclopropylmethyl)but-3-en-1-amine (Example 115, Step F) and triethylamine (1.89 mL, 13.59 mmol) in THF (30.0 mL) was added acryloyl chloride (0.66 mL, 8.15 mmol) at 0° C. The resulting reaction mixture was stirred at rt for 2 h. When LCMS indicated completion of the reaction, 100 ml of ethyl acetate was added and the combined organics were washed consecutively with water (10 ml), citric acid (10 ml, 1M), NaHCO$_3$ solution (10 ml) and sat. NaCl solution (30 ml), dried over MgSO$_4$, filtered and the filtrate was concentrated. The crude product was purified by flash chromatography on silica gel (eluent: hexane/ethyl acetate, 90/10 to 20/80) to give the title compound.

$^1$H NMR (500 MHz, CHLOROFORM-d) δ ppm 7.28 (3 H, br. s.), 6.94-7.17 (5 H, m), 6.87 (1 H, br. s.), 6.42 (1 H, m.), 6.20 (2 H, ddd, J=16.9, 9.8, 9.5 Hz), 5.58 (1 H, d, J=10.3 Hz), 5.18 (1 H, d, J=16.9 Hz), 5.06 (2 H, dd, J=10.3, 1.3 Hz), 2.72 (1 H, br. s.), 1.19-1.41 (1 H, m), 0.77-1.00 (2 H, m), 0.63 (3 H, d, J=5.6 Hz), 0.50 (1 H, br. s.), 0.43 (1 H, d, J=4.6 Hz), 0.20 (1 H, br. s.), −0.28 (1 H, br. s.). MS (ESI) [M+H]$^+$, 440.0.

Step H. (5R,6S)-5-(3-chlorophenyl)-6-(4-chlorophenyl)-1-(dicyclopropylmethyl)-5,6-dihydropyridin-2(1H)-one

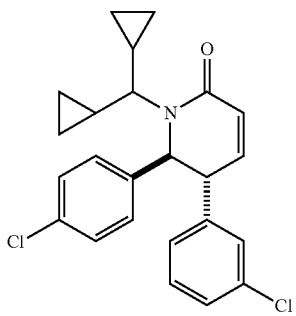

To a solution of 2.1 g (4.77 mmol) of N-((1S,2R)-2-(3-chlorophenyl)-1-(4-chlorophenyl)but-3-enyl)-N-(dicyclopropylmethyl)acrylamide (Example 115, Step G) in 50 mL of DCE was added 160 mg of 1,3-bis-(2,4,6-trimethylphenyl)-2-(imidazolidinylidene)(dichlorophenylmethylene)(tricyclohexylphosphine)ruthenium ("Grubb's 2nd Generation Catalyst"). The resulting mixture was degassed two times and then heated to 70° C. for 18 h. Another 160 mg of Grubb's 2nd Generation Catalyst was added at that time and heating was continued for another 18 h. The reaction mixture was cooled to room temperature. The solvent was removed and the residue was purified by chromatography on silica gel (eluent: hexane/ethyl acetate, 90/10 to 20/80) to give the title compound.

$^1$H NMR (500 MHz, CHLOROFORM-d) δ ppm 7.13-7.36 (8 H, m), 6.42 (1 H, d, J=9.8 Hz), 6.27 (1 H, ddd, J=9.8, 6.1, 1.3 Hz), 4.91 (1 H, s), 3.67 (1 H, d, J=6.1 Hz), 3.28-3.44 (1 H, m), 0.42 (1 H, ddd, J=8.9, 4.6, 4.5 Hz), 0.26-0.37 (3 H, m), 0.12-0.26 (3 H, m), −0.07-0.02 (1 H, m), −0.24−−0.12 (1 H, m), −0.34−−0.24 (1 H, m). MS (ESI) [M+H]$^+$, 412.1.

Step I. (5R,6S)-5-(3-chlorophenyl)-6-(4-chlorophenyl)-1-(dicyclopropylmethyl)piperidin-2-one

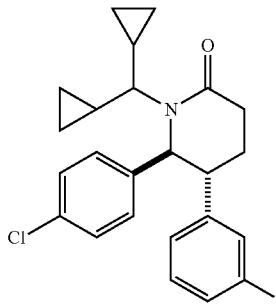

A solution of (5R,6S)-5-(3-chlorophenyl)-6-(4-chlorophenyl)-1-(dicyclopropylmethyl)-5,6-dihydropyridin-2(1H)-one (Example 115, Step H, 0.826 g, 2.003 mmol) and (1,5-cyclooctadiene)(pyridine) (tricyclohexylphosphine)iridium (i) hexafluorophosphate (0.129 g, 0.160 mmol) in DCM (60.0 ml) was saturated with hydrogen. The resulting mixture was stirred at rt under a hydrogen atmosphere for 2 h, then another 66.0 mg of (1,5-cyclooctadiene)(pyridine) (tricyclohexylphosphine)iridium (i) hexafluorophosphate were added. Stirring under hydrogen atmosphere was continued until LCMS indicated complete saturation of the double bond. The solvent was removed and the crude mixture was purified by chromatography on silica gel (eluting with ethyl acetate:hexane, 10:90) to give the title compound.

$^1$H NMR (400 MHz, CHLOROFORM-d) δ ppm 7.11-7.32 (7 H, m), 6.98-7.11 (1 H, m), 4.96 (1 H, d, J=4.7 Hz), 3.26 (1 H, m.), 2.92-3.15 (1 H, m), 2.60 (2 H, t, J=6.9 Hz), 2.09 (1 H, dddd, J=14.1, 7.3, 7.1, 4.9 Hz), 1.83-2.01 (1 H, m), 0.80-0.94 (1 H, m), 0.45-0.61 (1 H, m), 0.12-0.41 (6 H, m), 0.05 (1 H, dt, J=9.7, 4.8, Hz), −0.19−−0.04 (1 H, m). MS (ESI) [M+H]$^+$, 414.0.

Step J. (5R,6S)-5-(3-chlorophenyl)-6-(4-chlorophenyl)-1-(dicyclopropylmethyl)-3 (R,S)-methylpiperidin-2-one

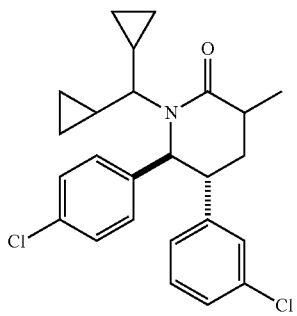

The title compound was prepared form (5R,6S)-5-(3-chlorophenyl)-6-(4-chlorophenyl)-1-(dicyclopropylmethyl)piperidin-2-one (Example 115, Step I) as described in Example 68, Step C. The crude product was purified by chromatography on silica gel (eluent: ethyl acetate:hexane, 10:90) to give the title compound as colorless oil.

$^1$H NMR (500 MHz, CHLOROFORM-d) δ ppm 7.16 (2 H, d, J=8.6 Hz), 7.00-7.14 (6 H, m), 4.95 (1 H, d, J=2.2 Hz), 3.21 (1 H, br. s.), 2.85-2.99 (1 H, m), 2.40 (1 H, dt, J=10.3, 7.1 Hz), 1.68-1.87 (2 H, m), 1.21 (3 H, s), 1.04-1.17 (1 H, m), 0.86 (1 H, d, J=4.2 Hz), 0.35-0.51 (1 H, m), 0.12-0.28 (4 H, m), −0.04-0.12 (2 H, m), −0.34−−0.15 (1 H, m).

Step K. (3S/3R,5R,6S)-3-allyl-5-(3-chlorophenyl)-6-(4-chlorophenyl)-1-(dicyclopropylmethyl)-3-methylpiperidin-2-one

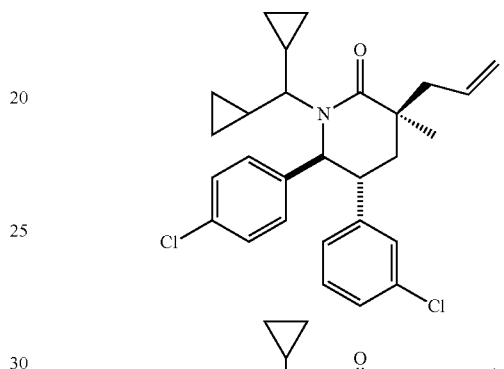

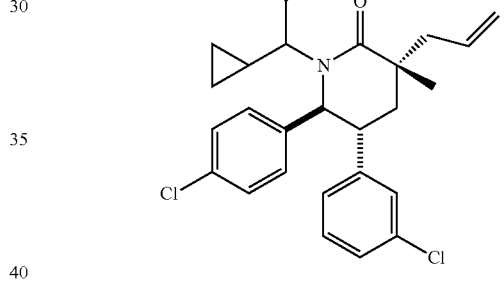

The title compound was obtained as a mixture of stereoisomers by using a procedure similar to the one described in Example 68, Step D.

$^1$H NMR (400 MHz, CHLOROFORM-d) δ ppm 7.06-7.23 (4 H, m), 6.91-7.06 (3 H, m), 6.69-6.86 (1 H, m), 5.79-5.98 (1 H, m), 5.03-5.26 (2 H, m), 4.81 (1 H, d, J=9.6 Hz), 3.03-3.22 (1 H, m), 2.49-2.78 (2 H, m), 1.88-2.01 (2 H, m), 1.46 (1 H, s), 1.21 (2 H, s), 0.98-1.16 (1 H, m), 0.44-0.71 (3 H, m), 0.19-0.44 (3 H, m), −0.11-0.19 (3 H, m). MS (ESI) [M+H]$^+$, 468.2.

Step L. 2-((3R,5R,6S)-5-(3-chlorophenyl)-6-(4-chlorophenyl)-1-(dicyclopropylmethyl)-3-methyl-2-oxopiperidin-3-yl)acetic acid

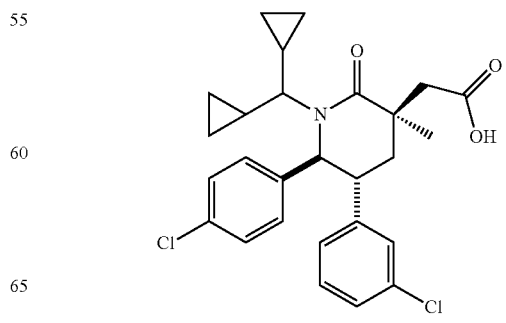

A mixture of diastereomers of (3S/3R,5R,6S)-3-allyl-5-(3-chlorophenyl)-6-(4-chlorophenyl)-1-(dicyclopropylmethyl)-3-methylpiperidin-2-one (Example 115, Step K) was converted to a distereomeric mixture of the acids by a procedure similar to the one described in Example 71, Step F. Individual steroisomers were separated by reverse phase prep. HPLC (Sunfire™ Prep C$_{18}$ OBD 10 μm column (Waters, Milford, Mass.), gradient elution of 40% MeCN in water to 80% MeCN in water over a 30 min period, where both solvents contain 0.1% TFA) to give the title compound as the faster eluting isomer.

$^1$H NMR (400 MHz, CHLOROFORM-d) δ ppm 7.98 (1 H, dd, J=7.6, 6.5 Hz), 7.00-7.29 (7 H, m), 6.86 (1 H, d, J=7.4 Hz), 4.93 (1 H, d, J=8.2 Hz), 4.33 (1 H, d, J=5.1 Hz), 3.09-3.15 (1 H, m), 3.03 (1 H, d, J=15.1 Hz), 2.69-2.80 (1 H, m), 2.08-2.17 (2 H, m), 1.35 (3 H, s), 1.14-1.21 (1 H, m), 0.53-0.73 (2 H, m), 0.41-0.51 (2 H, m), 0.27-0.40 (2 H, m), 0.02-0.21 (3 H, m). MS (ESI) [M+H]$^+$, 486.2.

Further elution and concentration in vacuo provided Example 116.

Example 116

2-((3S,5R,6S)-5-(3-chlorophenyl)-6-(4-chlorophenyl)-1-(dicyclopropylmethyl)-3-methyl-2-oxopiperidin-3-yl)acetic acid

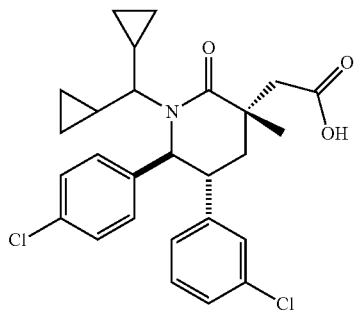

The title compound was obtained from procedure 115 as the slower eluting isomer.

$^1$H NMR (500 MHz, CHLOROFORM-d) δ ppm 7.10-7.33 (6 H, m), 6.95-7.03 (2 H, m), 6.73-6.83 (1 H, m), 4.80 (1 H, d, J=9.8 Hz), 3.18-3.23 (1 H, m), 2.84 (1 H, t, J=13.4 Hz), 2.72-2.79 (1 H, m), 2.63-2.72 (1 H, m), 2.32-2.39 (1 H, m), 1.77 (1 H, dd, J=13.2, 3.4 Hz), 1.64-1.68 (3 H, m), 1.14 (1 H, m), 0.64-0.70 (1 H, m), 0.52-0.58 (1 H, m), 0.44-0.49 (2 H, m), 0.27-0.33 (2 H, m), 0.13-0.18 (2 H, m), -0.01 (1 H, m). MS (ESI) [M–H], 484.0.

Example 117

((3S,4R,6R)-4-(3-chlorophenyl)-3-(4-chlorophenyl)-1,1-dioxido-2-(2-propanyl)-1,2-thiazinan-6-yl)acetic acid

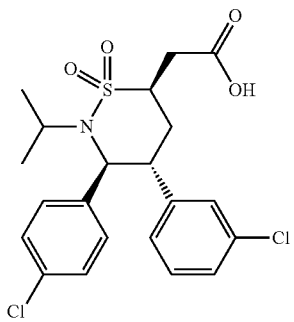 [SMILES: CC(C)N1[C@H](c2ccc(Cl)cc2)[C@@H](c2cccc(Cl)c2)C[C@H](CC(=O)O)S1(=O)=O]

Step A. (E)-N-((1S,2R)-2-(3-chlorophenyl)-1-(4-chlorophenyl)but-3-enyl)-2-phenylethenesulfonamide

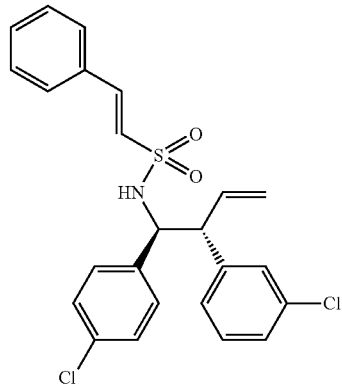 [SMILES: C=C[C@H](c1cccc(Cl)c1)[C@H](NS(=O)(=O)/C=C/c1ccccc1)c1ccc(Cl)cc1]

To a solution of 5.33 g (18.24 mmol) of (1S,2R)-2-(3-chlorophenyl)-1-(4-chlorophenyl)but-3-en-1-amine (Example 115, Step E) in DCM (45.0 mL) was added N,N-diisopropylethylamine (4.8 mL, 27.5 mmol), followed by trans-beta-styrenesulfonyl chloride (4.17 g, 20.58 mmol). The resulting solution was stirred at ambient temperature under an N$_2$ atmosphere. After being stirred for 3.25 hours, the reaction was diluted with water and extracted with DCM. The combined organic layers were washed with sat. aq. NaCl solution, dried over Na$_2$SO$_4$, filtered and the filtrate was concentrated. Purification by flash chromatography on silica gel (0 to 40% EtOAc in hexanes gradient) provided the title compound as a yellow solid.

$^1$H NMR (500 MHz, CHLOROFORM-d) δ 7.30-7.41 (m, 3H), 7.12-7.17 (m, 2H), 7.05-7.11 (m, 5H), 6.97-7.03 (m, 3H), 6.82-6.89 (m, 1H), 6.17 (d, J=15.41 Hz, 1H), 6.06-6.15 (m, 1H), 5.21-5.40 (m, 2H), 5.13 (d, J=5.62 Hz, 1H), 4.60 (dd, J=5.87, 9.29 Hz, 1H), 3.54 (t, J=9.17 Hz, 1H). MS (ESI) 480.0 [M+Na]$^+$.

Step B. (3S,4R)-4-(3-chlorophenyl)-3-(4-chlorophenyl)-3,4-dihydro-2H-1,2-thiazin

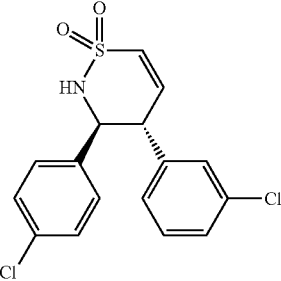 [SMILES: O=S1(=O)C=C[C@H](c2cccc(Cl)c2)[C@@H](c2ccc(Cl)cc2)N1]

To a degassed solution of 7.29 g (15.90 mmol) of (E)-N-((1S,2R)-2-(3-chlorophenyl)-1-(4-chlorophenyl)but-3-enyl)-2-phenylethenesulfonamide (Example 117, Step A) in a 1:1 mixture of DCM (350 mL) and DCE (350 mL) was added Grubbs First Generation (1.20 g, 1.434 mmol). The resulting solution was stirred at 70° C. for 20 hours. After cooling to room temperature, the reaction was concentrated under reduced pressure. Purification by flash chromatography on silica gel (0 to 2% MeOH in DCM gradient) provided the title compound.

$^1$H NMR (500 MHz, CHLOROFORM-d) δ 7.20-7.29 (m, J=8.80 Hz, 3H), 7.11-7.19 (m, 1H), 7.02 (d, J=8.31 Hz, 2H), 6.99 (t, J=/0.71 Hz, 1H), 6.86 (dd, J=2.69, 10.76 Hz, 1H), 6.79 (d, J=7.58 Hz, 1H), 6.44 (dd, J=2.20, 11.00 Hz, 1H), 5.14 (d, J=11.00 Hz, 1H), 4.86 (t, J=10.76 Hz, 1H), 3.76 (td, J=2.35, 10.70 Hz, 1H). MS (ESI) 376.0 [M+Na]$^+$.

Step C. (3S,4R)-4-(3-chlorophenyl)-3-(4-chlorophenyl)-1,2-thiazinan

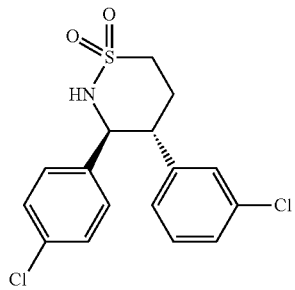 [SMILES: O=S1(=O)CC[C@H](c2cccc(Cl)c2)[C@@H](c2ccc(Cl)cc2)N1]

A solution of 4.14 g (11.69 mmol) of (3S,4R)-4-(3-chlorophenyl)-3-(4-chlorophenyl)-3,4-dihydro-2H-1,2-thiazin (Example 117, Step B) in dichloromethane (63.0 mL) was purged with argon three times, and then Crabtree's catalyst (835.2 mg, 1.027 mmol) was added to the reaction mixture. The reaction was purged again with argon, and then a hydrogen atmosphere was placed over the reaction. The solution was stirred at ambient temperature for 15 hours, at which point the reaction was concentrated down to an oil. Purification by flash chromatography on silica gel (0 to 4% MeOH in DCM gradient) provided the title compound as a tan solid.

$^1$H NMR (500 MHz, CHLOROFORM-d) δ 7.16-7.22 (m, 2H), 7.08-7.14 (m, 2H), 6.99-7.07 (m, 3H), 6.82-6.88 (m, 1H), 4.67 (dd, J=5.01, 10.88 Hz, 1H), 4.55 (d, J=4.65 Hz, 1H), 3.25-3.39 (m, 2H), 2.89-3.04 (m, 1H), 2.67 (dddd, J=6.60, 10.39, 12.50, 14.52 Hz, 1H), 2.39 (qd, J=3.67, 14.43 Hz, 1H). MS (ESI) 378.0 [M+Na]$^+$.

Step D. (3S,4R)-4-(3-chlorophenyl)-3-(4-chlorophenyl)-2-(2-propanyl)-1,2-thiazinan

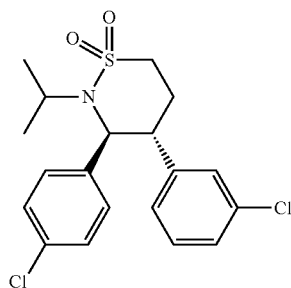 [SMILES: CC(C)N1[C@H](c2ccc(Cl)cc2)[C@@H](c2cccc(Cl)c2)CCS1(=O)=O]

To a solution of 1.21 g (3.40 mmol) of (3S,4R)-4-(3-chlorophenyl)-3-(4-chlorophenyl)-1,2-thiazinan (Example 117, Step C) in DMF (8.5 mL) was added cesium carbonate (4.31 g, 13.23 mmol), followed by 2-iodopropane (2.9 mL, 29.0 mmol). The resulting mixture was heated at 85° C. for 23 hours. After cooling to room temperature, the reaction mixture was diluted with water and extracted with ethyl acetate. The combined organic layers were washed with sat. NaCl solution, dried over Na$_2$SO$_4$, filtered and the filtrate was concentrated. Purification by flash chromatography on silica gel (0 to 2% MeOH in DCM gradient) provided the title compound as a white solid.

$^1$H NMR (500 MHz, CHLOROFORM-d) δ 7.13-7.19 (m, 3H), 7.04-7.12 (m, 3H), 7.00 (t, J=1.83 Hz, 1H), 6.75 (d, J=7.58 Hz, 1H), 4.51 (d, J=10.76 Hz, 1H), 3.81 (td, J=6.94, 13.75 Hz, 1H), 3.40-3.49 (m, 1H), 3.25-3.39 (m, 2H), 2.53 (ddt, J=6.85, 11.49, 13.45 Hz, 1H), 2.23 (tdd, J=2.96, 6.54, 13.94 Hz, 1H), 1.36 (d, J=6.85 Hz, 3H), 1.07 (d, J=7.09 Hz, 3H). MS (ESI) 420.0 [M+Na]$^+$.

Step E. (3S,4R,6R/6S)-4-(3-chlorophenyl)-3-(4-chlorophenyl)-2-(2-propanyl)-6-(2-propen-1-yl)-1,2-thiazinan

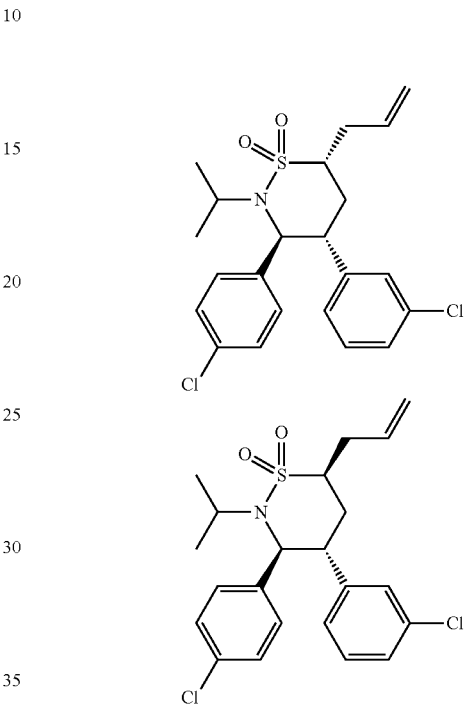

To a degassed solution of 211.7 mg (0.531 mmol) of (3S,4R)-4-(3-chlorophenyl)-3-(4-chlorophenyl)-2-(2-propanyl)-1,2-thiazinan (Example 117, Step D) in THF (2.5 mL) was added allyl iodide (0.25 mL, 2.74 mmol). The resulting solution was heated to 50° C. After 10 minutes, a 1 M solution of lithium bis(trimethylsilyl)-amide in THF (0.86 mL, 0.860 mmol) was added dropwise, over one minute. After heating at 50° C. for 20 hours, the reaction was cooled to room temperature, quenched with water (2 mL), and then concentrated under reduced pressure. Purification by flash chromatography on silica gel (0 to 100% DCM in hexanes gradient) provided the title compounds as a white solid. The $^1$H NMR showed a 91:9 mixture of R/S allyl epimers.

A degassed solution of 98.6 mg (0.225 mmol) of the epimeric mixture in THF (5 mL) was heated to 60° C. After 10 minutes, a 1 M solution of lithium bis(trimethylsilyl)-amide in THF (1.0 mL, 1.00 mmol) was added. The resulting solution was then stirred at 60° C. for 45 minutes, at which point methanol (275.0 µL, 6.80 mmol) was then added. The solution was heated for another 45 minutes at 60° C. Upon cooling to room temperature, the reaction was quenched with methanol (5 mL), then concentrated under reduced pressure. The material was purified by reverse-phase preparative HPLC using an Agilent Eclipse Plus C18 column (Agilent Technologies, Santa, Clara, Calif.), 0.1% TFA in MeN/H$_2$O, gradient 30% to 95% over 25 minutes to provide the title compounds, as a white solid. The $^1$H NMR showed ~2:1 mixture of epimers. Individual stereoisomers were separated by SFC (Chiralcel® AD-H column (Diacel, Fort Lee N.J.), 30 mm I.D.×250 mm, using 12 g/min of a 20 mM solution of NH$_3$ in isopropyl alcohol and 68 g/min of $CO_2$ as the eluent) to give (3S,4R,6S)-4-(3-chlorophenyl)-3-(4-chlorophenyl)-2-(2-propanyl)-6-(2-propen-1-yl)-1,2-thiazinan ($t_R$=1.62 min) as a white solid.

$^1$H NMR (500 MHz, CHLOROFORM-d) δ ppm 7.16-7.21 (m, 1 H), 7.06-7.15 (m, 5 H), 7.00 (t, J=1.59 Hz, 1 H), 6.72 (d, J=7.58 Hz, 1 H), 5.71-5.88 (m, 1 H), 5.11-5.24 (m, 2 H), 4.34 (d, J=11.00 Hz, 1 H), 3.99-4.11 (m, 1 H), 3.46 (ddd, J=13.33, 10.76, 3.06 Hz, 1 H), 3.32-3.43 (m, 1 H), 2.85-2.96 (m, 1 H), 2.43-2.61 (m, 2 H), 2.00 (dt, J=13.94, 2.45 Hz, 1 H), 1.35 (d, J=6.85 Hz, 3 H), 1.00 (d, J=7.09 Hz, 3 H). MS (ESI) 460.0 [M+Na]$^+$.

Also obtained was (3S,4R,6R)-4-(3-chlorophenyl)-3-(4-chlorophenyl)-2-(2-propanyl)-6-(2-propen-1-yl)-1,2-thiazinan ($t_R$=1.87 min) as a white solid.

$^1$H NMR (500 MHz, CHLOROFORM-d) δ ppm 7.16 (d, J=8.31 Hz, 2 H), 7.10-7.14 (m, 1 H), 7.04-7.10 (m, 3 H), 6.99 (t, J=1.59 Hz, 1 H), 6.74 (d, J=7.58 Hz, 1 H), 5.76 (dddd, J=16.84, 10.24, 8.13, 6.11 Hz, 1 H), 5.10-5.22 (m, 2 H), 4.57 (d, J=11.00 Hz, 1 H), 3.59 (dt, J=13.94, 6.97 Hz, 1 H), 3.30-3.41 (m, J=11.49, 9.66, 4.71, 4.71 Hz, 1 H), 3.26 (ddd, J=12.65, 10.82, 3.42 Hz, 1 H), 2.84-2.98 (m, 1 H), 2.21-2.33 (m, 2 H), 2.04-2.19 (m, 1 H), 1.36 (d, J=6.85 Hz, 3 H), 1.13 (d, J=6.85 Hz, 3 H). MS (ESI) 460.0 [M+Na]$^+$.

Step F. ((3S,4R,6R)-4-(3-chlorophenyl)-3-(4-chlorophenyl)-1,1-dioxido-2-(2-propanyl)-1,2-thiazinan-6-yl)acetic acid

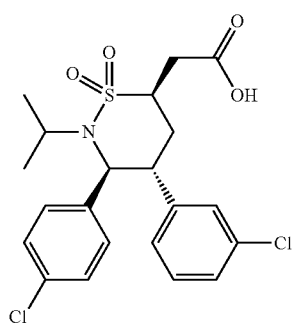 [SMILES: CC(C)N1[C@H](c2ccc(Cl)cc2)[C@@H](c2cccc(Cl)c2)C[C@H](CC(=O)O)S1(=O)=O]

The title compound was obtained from (3S,4R,6S)-4-(3-chlorophenyl)-3-(4-chlorophenyl)-2-(2-propanyl)-6-(2-propen-1-yl)-1,2-thiazinan (Example 117, Step E) by a procedure similar to the one described in Example 71, Step F. Purification by reversed phase preparative HPLC using an Agilent Eclipse Plus C18 column (Agilent Technologies, Santa, Clara, Calif.), 0.1% TFA in MeCN/$H_2O$, gradient 30% to 95% over 25 minutes, provided the title compound as a white solid.

$^1$H NMR (500 MHz, CHLOROFORM-d) δ ppm 7.12-7.19 (m, 3 H), 7.04-7.12 (m, 3 H), 6.99 (br. s., 1 H), 6.73 (d, J=7.58 Hz, 1 H), 4.38 (d, J=11.00 Hz, 1 H), 3.91-4.05 (m, 1 H), 3.84 (br. s., 1 H), 3.39-3.49 (m, 1 H), 3.24 (d, J=17.12 Hz, 1 H), 2.88 (dd, J=17.12, 10.27 Hz, 1 H), 2.66-2.79 (m, 1 H), 2.02 (d, J=12.72 Hz, 1 H), 1.32-1.40 (m, 3 H), 1.03 (d, J=6.85 Hz, 3 H). MS (ESI) 478.0 [M+Na]$^+$.

Example 118

((3S,4R,6S)-4-(3-chlorophenyl)-3-(4-chlorophenyl)-1,1-dioxido-2-(2-propanyl)-1,2-thiazinan-6-yl)acetic acid

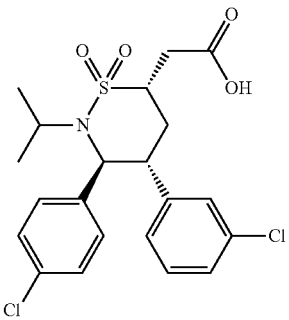 [SMILES: CC(C)N1[C@H](c2ccc(Cl)cc2)[C@@H](c2cccc(Cl)c2)C[C@@H](CC(=O)O)S1(=O)=O]

The title compound was prepared from (3S,4R,6R)-4-(3-chlorophenyl)-3-(4-chlorophenyl)-2-(2-propanyl)-6-(2-propen-1-yl)-1,2-thiazinan (Example 117, Step E) as described in Example 117, Step F.

$^1$H NMR (500 MHz, CHLOROFORM-d) δ ppm 7.07 (d, J=6.85 Hz, 2 H), 6.94-7.05 (m, 4 H), 6.90 (br. s., 1 H), 6.65 (d, J=7.34 Hz, 1 H), 4.48 (d, J=11.00 Hz, 1 H), 3.70-3.79 (m, 1 H), 3.48-3.57 (m, 1 H), 3.22-3.32 (m, 1 H), 3.10 (dd, J=17.12, 4.65 Hz, 1 H), 2.46 (dd, J=17.12, 8.80 Hz, 1 H), 2.22-2.34 (m, 1 H), 2.07 (d, J=12.47 Hz, 1 H), 1.25 (d, J=6.60 Hz, 3 H), 1.01 (d, J=6.60 Hz, 3 H). MS (ESI) 478.0 [M+Na]$^+$.

Example 119

((3S,4R,6R)-4-(3-chlorophenyl)-3-(4-chlorophenyl)-6-methyl-1,1-dioxido-2-(2-propanyl)-1,2-thiazinan-6-yl)acetic acid

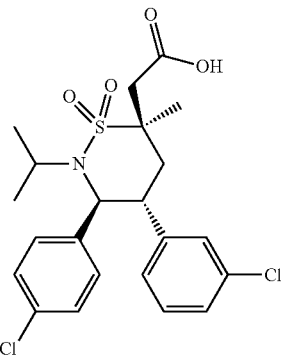 [SMILES: CC(C)N1[C@H](c2ccc(Cl)cc2)[C@@H](c2cccc(Cl)c2)C[C@](C)(CC(=O)O)S1(=O)=O]

Step A. Synthesis of (3S,4R,6S)-4-(3-chlorophenyl)-3-(4-chlorophenyl)-6-methyl-2-(2-propanyl)-6-(2-propen-1-yl)-1,2-thiazinan

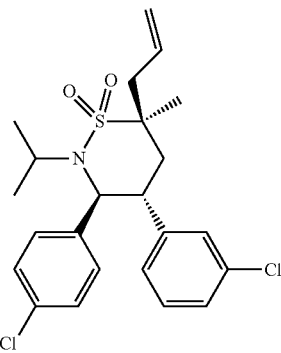 [SMILES: C=CC[C@@]1(C)C[C@H](c2cccc(Cl)c2)[C@@H](c2ccc(Cl)cc2)N(C(C)C)S1(=O)=O]

To a degassed solution of diisopropylamine (300 μL, 2.123 mmol) in THF (1.0 ml) was added dropwise at −78° C. n-butyllithium, 2.5 M in hexanes (800 μL, 2.000 mmol). After stirring the solution at −78° C. for 10 min, the reaction was warmed to room temperature. In a separate flask, a degassed solution of 111.9 mg (0.255 mmol) of (3S,4R,6R)-4-(3-chlorophenyl)-3-(4-chlorophenyl)-2-(2-propanyl)-6-(2-propen-1-yl)-1,2-thiazinan (Example 117, Step E) and methyl iodide (0.6 ml, 9.62 mmol) in THF (1.0 ml) was heated to 50° C. After five minutes, the LDA solution was added dropwise to the other flask, and stirring continued for 14 hours at 50° C. Upon cooling to room temperature, the reaction was quenched with water (3 mL), then concentrated under reduced pressure. Purification by reverse-phase preparative HPLC using an Agilent Eclipse Plus C18 column (Agilent Technologies, Santa, Clara, Calif.), 0.1% TFA in CH$_3$CN/H$_2$O, gradient 60% to 80% over 25 minutes provided the title compound as a white solid.

$^1$H NMR (500 MHz, CHLOROFORM-d) δ ppm 7.18 (br. s., 2 H), 7.03-7.14 (m, 4 H), 6.96 (d, J=1.71 Hz, 1 H), 6.72 (d, J=7.34 Hz, 1 H), 5.64-5.93 (m, 1 H), 5.18-5.28 (m, 2 H), 4.45 (d, J=10.76 Hz, 1 H), 3.61-3.75 (m, 1 H), 3.30-3.44 (m, 1 H), 2.82-2.90 (m, 1 H), 2.74-2.82 (m, 1 H), 2.17-2.32 (m, 1 H), 2.02 (dd, J=13.94, 3.18 Hz, 1 H), 1.42 (s, 3 H), 1.34 (d, J=6.85 Hz, 3 H), 1.11 (d, J=6.85 Hz, 3 H). MS (ESI) 474.1 [M+Na]$^+$.

Step B. ((3S,4R,6R)-4-(3-chlorophenyl)-3-(4-chlorophenyl)-6-methyl-1,1-dioxido-2-(2-propanyl)-1,2-thiazinan-6-yl)acetic acid

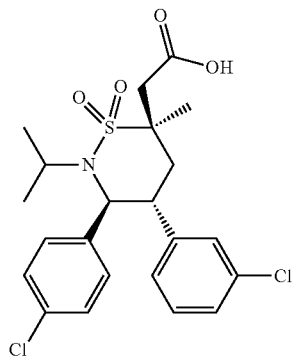 [SMILES: CC(C)N1[C@H](c2ccc(Cl)cc2)[C@@H](c2cccc(Cl)c2)C[C@](C)(CC(=O)O)S1(=O)=O]

The title compound was prepared from (3S,4R,6S)-4-(3-chlorophenyl)-3-(4-chlorophenyl)-6-methyl-2-(2-propanyl)-6-(2-propen-1-yl)-1,2-thiazinan (Example 119, Step A) as described in Example 1, Step F.

$^1$H NMR (500 MHz, CHLOROFORM-d) δ ppm 7.08 (d, J=7.34 Hz, 2 H), 6.92-7.03 (m, 4 H), 6.87 (br. s., 1 H), 6.63 (d, J=7.34 Hz, 1 H), 4.41 (d, J=11.00 Hz, 1 H), 3.41-3.52 (m, 1 H), 3.29-3.36 (m, 1 H), 3.25 (d, J=14.92 Hz, 1 H), 2.93 (d, J=15.16 Hz, 1 H), 2.21-2.36 (m, 2 H), 1.51 (s, 3 H), 1.23 (d, J=6.60 Hz, 3 H), 1.05 (d, J=6.60 Hz, 3 H). MS (ESI) 492.1 [M+Na]$^+$.

Example 120

((3S,4R,6S)-4-(3-chlorophenyl)-3-(4-chlorophenyl)-6-methyl-1,1-dioxido-2-(2-propanyl)-1,2-thiazinan-6-yl)acetic acid

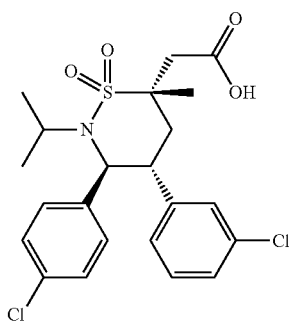 [SMILES: CC(C)N1[C@H](c2ccc(Cl)cc2)[C@@H](c2cccc(Cl)c2)C[C@@](C)(CC(=O)O)S1(=O)=O]

Step A. (3S,4R,6R)-4-(3-chlorophenyl)-3-(4-chlorophenyl)-6-methyl-2-(2-propanyl)-1,2-thiazinan

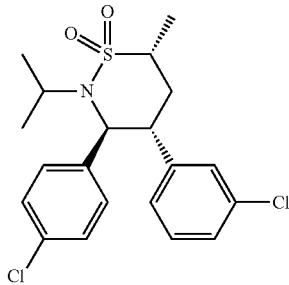 [SMILES: CC(C)N1[C@H](c2ccc(Cl)cc2)[C@@H](c2cccc(Cl)c2)C[C@@H](C)S1(=O)=O]

To a degassed solution of 239.9 mg (0.602 mmol) of (3S,4R)-4-(3-chlorophenyl)-3-(4-chlorophenyl)-2-(2-propanyl)-1,2-thiazinan (Example 117, Step D) in THF (2.0 mL) was added iodomethane (60.0 μl, 0.960 mmol), followed by dropwise addition of a 1 M solution of lithium bis(trimethylsilyl)amide in THF (640.0 μl, 0.640 mmol). After stirring at room temperature for 17 hours, the reaction was quenched with MeOH (3 mL), then concentrated under reduced pressure. Purification by flash chromatography on silica gel (0 to 70% DCM in hexanes gradient) provided the title compound as a white solid. The $^1$H NMR showed 6% of the 6S epimer was also isolated.

$^1$H NMR (500 MHz, CHLOROFORM-d) δ ppm 7.14-7.18 (m, 2 H), 7.04-7.13 (m, 4 H), 6.95-7.01 (m, 1 H), 6.71-6.77 (m, 1 H), 4.57 (d, J=10.76 Hz, 1 H), 3.54-3.63 (m, 1 H), 3.39-3.51 (m, 1 H), 3.23-3.39 (m, 1 H), 2.14-2.27 (m, 2 H), 1.42 (d, J=6.85 Hz, 3 H), 1.34-1.38 (m, 3 H), 1.13 (d, J=6.85 Hz, 3 H). MS (ESI) 434.0 [M+Na]⁺.

Step B. (3S,4R,6R)-4-(3-chlorophenyl)-3-(4-chlorophenyl)-6-methyl-2-(2-propanyl)-6-(2-propen-1-yl)-1,2-thiazinan

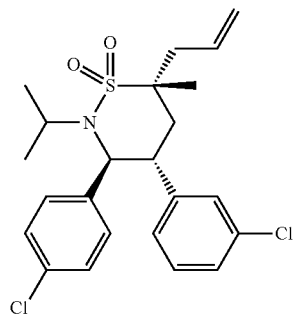 [SMILES: C=CC[C@]1(C)C[C@H](c2cccc(Cl)c2)[C@@H](c2ccc(Cl)cc2)N(C(C)C)S1(=O)=O]

To a degassed solution of 174.7 mg (0.424 mmol) of (3S,4R,6R)-4-(3-chlorophenyl)-3-(4-chlorophenyl)-6-methyl-2-(2-propanyl)-1,2-thiazinan (Example 120, Step A) in THF (1.5 mL) was added allyl iodide (0.55 mL, 6.02 mmol). The resulting solution was heated to 60° C. for 10 minutes, then a 1 M solution of lithium bis(trimethylsilyl)-amide in THF (2.0 mL, 2.00 mmol) was added dropwise, over one minute. After heating at 60° C. for 17 hours, the reaction was cooled to room temperature, quenched with water (2 mL), and then concentrated under reduced pressure. Purification by reverse-phase preparative HPLC using an Agilent Eclipse Plus C18 column (Agilent Technologies, Santa, Clara, Calif.), 0.1% TFA in MeCN/H₂O, gradient 40% to 95% over 25 minutes, provided the title compound as a white solid.

¹H NMR (500 MHz, CHLOROFORM-d) δ ppm 7.15-7.20 (m, 2 H), 7.03-7.13 (m, 4 H), 6.97 (s, 1 H), 6.73 (d, J=7.34 Hz, 1 H), 5.72-5.89 (m, 1 H), 5.22 (d, J=4.65 Hz, 1 H), 5.19 (s, 1 H), 4.47 (d, J=10.76 Hz, 1 H), 3.56-3.69 (m, 1 H), 3.31-3.42 (m, 1 H), 2.69 (dd, J=13.82, 7.21 Hz, 1 H), 2.55 (dd, J=13.82, 7.70 Hz, 1 H), 2.38 (t, J=13.45 Hz, 1 H), 1.87 (dd, J=13.94, 3.18 Hz, 1 H), 1.61 (s, 3 H), 1.33 (d, J=6.85 Hz, 3 H), 1.12 (d, J=6.85 Hz, 3 H). MS (ESI) 474.1 [M+Na]⁺.

Step C. ((3S,4R,6S)-4-(3-chlorophenyl)-3-(4-chlorophenyl)-6-methyl-1,1-dioxido-2-(2-propanyl)-1,2-thiazinan-6-yl)acetic acid

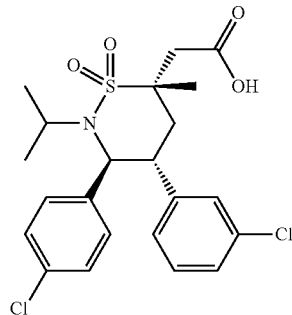 [SMILES: CC(C)N1[C@H](c2ccc(Cl)cc2)[C@@H](c2cccc(Cl)c2)C[C@@](C)(CC(=O)O)S1(=O)=O]

The title compound was prepared from (3S,4R,6R)-4-(3-chlorophenyl)-3-(4-chlorophenyl)-6-methyl-2-(2-propanyl)-6-(2-propen-1-yl)-1,2-thiazinan (Example 120, Step B) as described in Example 1, Step F.

¹H NMR (500 MHz, CHLOROFORM-d) δ ppm 7.15-7.23 (m, 2 H), 7.03-7.14 (m, 4 H), 6.97 (br. s., 1 H), 6.73 (d, J=6.60 Hz, 1 H), 4.47 (d, J=10.52 Hz, 1 H), 3.59-3.73 (m, 1 H), 3.42 (t, J=11.74 Hz, 1 H), 2.95-3.03 (m, 1 H), 2.84-2.93 (m, 1 H), 2.47 (t, J=13.08 Hz, 1 H), 2.28 (d, J=13.94 Hz, 1 H), 1.79 (br. s., 3 H), 1.30-1.39 (m, 3 H), 1.02-1.14 (m, 3 H). MS (ESI) 492.1 [M+Na]⁺.

Example 121

2-((3R,5R,6S)-5-(3-chlorophenyl)-6-(5-chloropyridin-2-yl)-3-methyl-1-((S)-1-morpholinobutan-2-yl)-2-oxopiperidin-3-yl)acetic acid

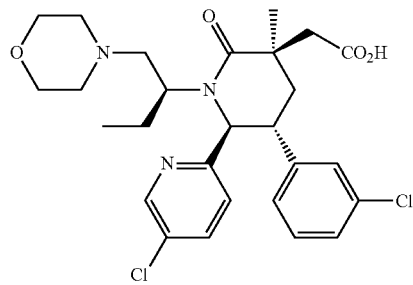 [SMILES: CC[C@@H](CN1CCOCC1)N1C(=O)[C@@](C)(CC(=O)O)C[C@H](c2cccc(Cl)c2)[C@H]1c1ccc(Cl)cn1]

Step A. Methyl 5-chloropicolinate

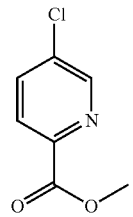

To a solution of 5-chloropyridin-2-carboxylic acid (309 g, 1.96 mol) in anhydrous MeOH (2 L) was slowly added thionyl chloride (299.7 mL, 4.12 mol, 2.1 eq) at room temperature (cloudy solution became clear brown solution during the addition of thionyl chloride). After the addition was complete, the reaction mixture was heated to 50° C. and stirred at this temperature overnight. The solvent and excess thionyl chloride were removed under reduced pressure and the crude product was azeotroped with toluene twice. The resulting solid was transferred to a filter funnel and washed with saturated aqueous NaHCO₃ until the filtrate was basic. The resulting solid was dissolved in dichloromethane (2 L) and washed with saturated aqueous NaHCO₃. The organics were dried over sodium sulfate, filtered and the filtrate was concentrated to provide the title compound as an off-white solid.

Step B. 2-(3-Chlorophenyl)-1-(5-chloropyridin-2-yl)ethanone

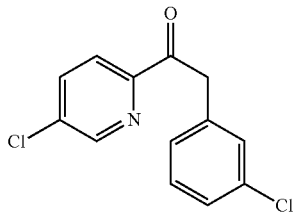 [SMILES: O=C(Cc1cccc(Cl)c1)c1ccc(Cl)cn1]

To a solution of 3-chlorophenylacetic acid (326.5 g, 1.91 mol, 0.95 eq) in THF (1.82 L) at −78° C. was slowly added NaHMDS (1M solution in THF, 3.82 L, 3.82 mol, 2 eq) over 2 h 45 min while keeping the temperature below −65° C. After the addition was complete, the reaction mixture was stirred for 30 min at −78° C. A solution of methyl 5-chloropicolinate (326.5 g, 1.91 mol, Example 121, Step A) in THF (0.9 L) was added to the above solution at −78° C. over 30 min. The reaction was stirred for another 1 h and then allowed to warm to ambient temperature overnight. The reaction mixture was slowly transferred into a sat. aq. ammonium chloride solution (4 L), extracted with ethyl acetate (2×8 L), and then the combined organic layers were dried over $Na_2SO_4$, filtered and the filtrate was concentrated. Purification of the residue by flash chromatography on silica gel (eluent: DCM) provided the title compound as a white solid.

Step C. methyl 4-(3-chlorophenyl)-5-(5-chloropyridin-2-yl)-5-oxopentanoate

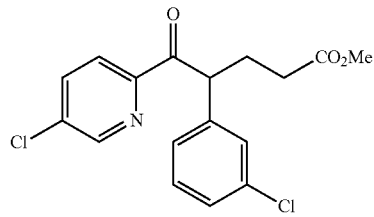 [SMILES: COC(=O)CCC(C(=O)c1ccc(Cl)cn1)c1cccc(Cl)c1]

To a solution of 368.5 g (1.39 mol) of 2-(3-chlorophenyl)-1-(5-chloropyridin-2-yl)ethanone (Example 121, Step B) in dioxane (1.5 L) at 80° C. was added DBU (207 mL, 1.39 mole, 1 eq), followed by dropwise addition of methyl acrylate (124.7 mL, 1.39 mol, 1 eq) at 80° C. The reaction was stirred at 80° C. for 1 h 30 min and then allowed to cool to ambient temperature. It was quenched with 2 M aqueous HCl solution (56.5 eq) and then basified to pH 7 with saturated aqueous $NaHCO_3$. The aqueous layer was extracted with EtOAc (2×4 L). The combined organic layers were dried over $Na_2SO_4$, filtered and the filtrate was evaporated. Purification by flash chromatography on silica gel (eluent: 40 to 100% DCM/hexanes) provided the title compound as a yellow liquid.

Step D. (4R,5R) Methyl 4-(3-chlorophenyl)-5-(5-chloropyridin-2-yl)-5-hydroxy pentanoate and (4S,5S)-methyl 4-(3-chlorophenyl)-5-(5-chloropyridin-2-yl)-5-hydroxypentanoate

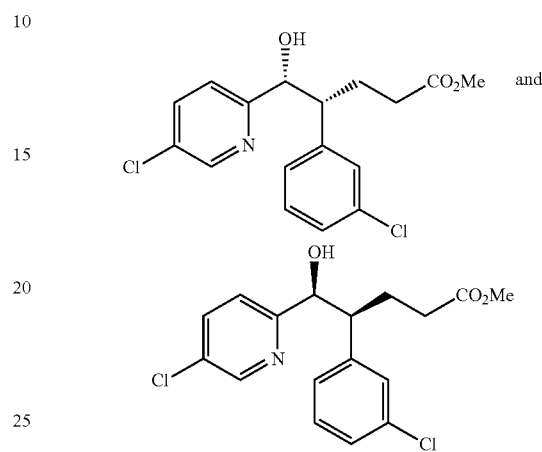

To a solution of 2-(3-chlorophenyl)-1-(5-chloropyridin-2-yl)ethanone (459.5 g, 1.3 mol, Example 121, Step C) in anhydrous MeOH (1.5 L) was portionwise added sodium borohydride (14.8 g, 0.392 mol, 0.3 eq) at 0-5° C. The reaction was stirred at same temperature for 30 min then quenched with ice-water. The methanol was removed under reduced pressure. The residue was dissolved in ethyl acetate and washed with water. The aqueous layer was extracted with ethyl acetate (3×2 L). The combined organic layers were washed with sat. NaCl solution, dried over $Na_2SO_4$, filtered and the filtrate was concentrated under reduced pressure. Purification of the residue by flash chromatography on silica gel (eluent: 10 to 70% EtOAc/hexanes, gradient elution) provided the title compound as a yellow liquid.

Step E. (4R,5S) Methyl 5-azido-4-(3-chlorophenyl)-5-(5-chloropyridin-2-yl)pentanoate and (4S,5R)-methyl 5-azido-4-(3-chlorophenyl)-5-(5-chloropyridin-2-yl)pentanoate

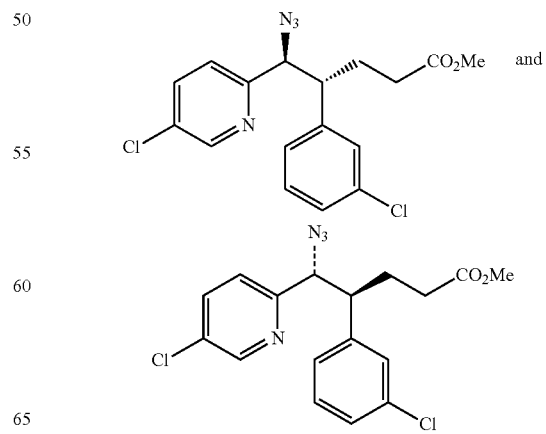

To a solution of (4R,5R)-methyl 4-(3-chlorophenyl)-5-(5-chloropyridin-2-yl)-5-hydroxypentanoate (432 g, 1.22 mol, Example 121, Step D) and triethylamine (340 mL, 2.4 mol, 2 eq) in DCM (2.4 L) was added dropwise methanesulfonyl chloride (123.21 mL, 1.59 mol, 1.3 eq) at 0-5° C. The reaction was stirred at 0-5° C. for 30 min, then quenched slowly with ice water and extracted with DCM (2×2 L). The combined organic layers were washed with sat. aq. NaCl solution, dried over MgSO₄, filtered and the filtrate was concentrated under reduced pressure.

The crude mesylate thus obtained was dissolved in DMF (1.5 L) and to it was added sodium azide (300 g, 4.6 mol, 3.8 eq). The reaction mixture was heated to 90° C. (internal temperature) for 2 h. It was allowed to cool to ambient temperature. The reaction mixture was diluted with water (2 L) and extracted with ethyl acetate (2×4 L). The combined organic layers were washed with sat. NaCl solution (2 L), dried over Na₂SO₄, filtered and the filtrate was concentrated under reduced pressure. The crude azide was carried directly to the next step without further purification.

Step F. (5R,6S)-5-(3-Chlorophenyl)-6-(5-chloropyridin-2-yl)piperidin-2-one

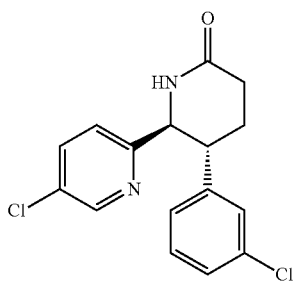 [SMILES: O=C1CC[C@H](c2cccc(Cl)c2)[C@@H](c2ccc(Cl)cn2)N1]

Crude (4R,5S)-methyl 5-azido-4-(3-chlorophenyl)-5-(5-chloropyridin-2-yl)pentanoate (463 g, 1.22 mol, Example 121, Step E) was dissolved in 2.5 L THF/water (4:1). Trimethyl phosphine (1 M in THF, 1.46 L, 1.46 mol, 1.2 eq) was added slowly at 0-5° C. The reaction was stirred for 30 min and then basified with 2.0 M aqueous LiOH solution to pH 12. The reaction mixture was stirred for another 30 min, and extracted to ethyl acetate (2×5 L). The combined organic layers were washed with sat. NaCl solution, dried over Na₂SO₄, filtered and the filtrate was concentrated under reduced pressure.

Purification of the residue by flash chromatography on silica gel (eluent: 20-90% EtOAc/hexanes, gradient elution) followed by recrystallization from EtOAc/hexanes provided trans 5-(3-chlorophenyl)-6-(5-chloropyridin-2-yl)piperidin-2-one as a mixture of stereoisomers. Individual stereoisomers were separated by chiral HPLC (flowrate: 100 ml/min on a Chiralcel® OD-H 10 cm I.D.×50 cm, 20 mic column (Daicel Chemical Industries LTD), using 25% isopropyl alcohol/hexane as the eluent) to give the title compound ($t_R$=17-25 min, earlier eluting peak) as a white solid.

¹H NMR (300 MHz, CDCl₃) δ 8.49 (d, J=2.34 Hz, 1H), 7.52 (dd, J=2.35 and 8.21 Hz, 1H), 7.20-7.17 (m, 2H), 7.07 (s, 1H), 6.93-6.88 (m, 2H), 6.11 (s, 1H), 4.70 (d, J=9.37 Hz, 1H), 3.20-3.13 (m, 1H), 2.61 (q, J=5.27 and 8.2 Hz, 2H), 2.26-2.04 (m, 2H). Mass Spectrum (ESI) m/z=321 (M+1).

Step G. (S)-Ethyl 2-((2S,3R)-3-(3-chlorophenyl)-2-(5-chloropyridin-2-yl)-6-oxopiperidin-1-yl)butanoate

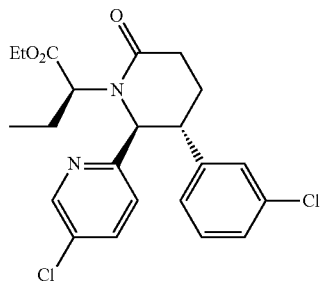 [SMILES: CCOC(=O)[C@H](CC)N1C(=O)CC[C@H](c2cccc(Cl)c2)[C@H]1c1ccc(Cl)cn1]

To an ice-cooled solution of 9.93 g (30.9 mmol) of (5R,6S)-5-(3-chlorophenyl)-6-(5-chloropyridin-2-yl)piperidin-2-one (Example 121, Step F) in DMF (65 mL) was added 2.47 g (60 wt. % in mineral oil, 61.8 mmol) of sodium hydride. The resulting yellow slurry was stirred at 0° C. for 5 min, then was warmed to room temperature and stirred for an additional 12 min. The reaction was re-cooled to 0° C. and 11.4 mL (77 mmol) of ethyl 2-bromobutyrate was added slowly via syringe over 10 min. The resulting orange slurry was warmed to room temperature and stirred for 4.75 h, and then was quenched with saturated aqueous ammonium chloride. The mixture was extracted with ethyl acetate (3×), and the combined organic layers were washed with water (2×) and sat. aq. NaCl solution (1×). The organic layer was dried over Na₂SO₄, filtered and the filtrate was concentrated. Purification of the residue by flash chromatography on silica gel (38 to 40% EtOAc/hexanes, gradient elution) provided the title compound as a light yellow solid.

Step H. (5R,6S)-5-(3-chlorophenyl)-6-(5-chloropyridin-2-yl)-1-((S)-1-hydroxybutan-2-yl)piperidin-2-one

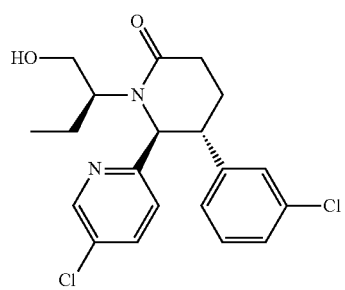 [SMILES: CC[C@@H](CO)N1C(=O)CC[C@H](c2cccc(Cl)c2)[C@H]1c1ccc(Cl)cn1]

To an ice-cooled solution of 3.95 g (10.0 mmol) of (S)-ethyl 2-((2S,3R)-3-(3-chlorophenyl)-2-(5-chloropyridin-2-yl)-6-oxopiperidin-1-yl)butanoate (Example 121, Step G) in ether (100 mL) was added 486 mg (90%, 20.1 mmol) of lithium borohydride. The resulting light yellow slurry was stirred at 0° C. for 3 h, and then was warmed to room temperature and stirred for an additional 3 h. The reaction was re-cooled to 0° C. and quenched by cautious addition of 1 N HCl until bubbling subsided. The mixture was extracted with EtOAc (3×), and the combined organic layers were washed Step I. (5R,6S)-1-((S)-1-(tert-butyldiphenylsilyloxy)butan-2-yl)-5-(3-chlorophenyl)-6-(5-chloropyridin-2-yl)piperidin-2-one

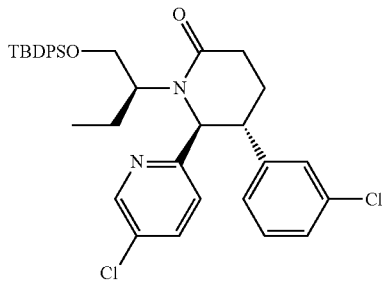

To a solution of 2.03 g (5.2 mmol) of (5R,6S)-5-(3-chlorophenyl)-6-(5-chloropyridin-2-yl)-1-((S)-1-hydroxybutan-2-yl)piperidin-2-one (Example 121, Step H) and 877 mg (12.9 mmol) of imidazole in DMF (32 mL) was added 1.9 mL (7.3 mmol) of tert-butyldiphenylsilyl chloride. The resulting light yellow solution was stirred at room temperature for 4.5 h. The reaction was partitioned between water and EtOAc (2×), and then the combined organic layers were dried over Na$_2$SO$_4$, filtered and the filtrate was concentrated. Purification of the residue by flash chromatography on silica gel (0 to 4% MeOH/DCM, gradient elution) provided the title compound as a white solid.

Step J. (5R,6S)-1-((S)-1-(tert-butyldiphenylsilyloxy)butan-2-yl)-5-(3-chlorophenyl)-6-(5-chloropyridin-2-yl)-3-methylpiperidin-2-one

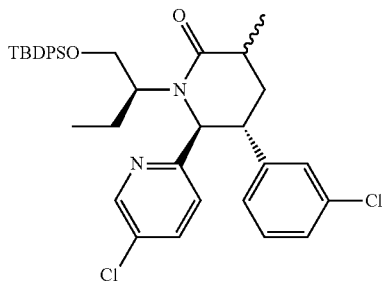

To a −78° C. solution of 3.19 g (5.05 mmol) of (5R,6S)-1-((S)-1-(tert-butyldiphenylsilyloxy)butan-2-yl)-5-(3-chlorophenyl)-6-(5-chloropyridin-2-yl)piperidin-2-one (Example 121, Step I) and 347 μL (5.55 mmol) of methyl iodide in dry, degassed THF (40 mL) was added 6.82 mL (6.82 mmol) of a 1 M solution of lithium bis(trimethylsilyl)amide in THF slowly via syringe over 2 min. The yellow solution was warmed to 0° C. and stirred for 1.5 h, and then was warmed to room temperature and stirred for an additional 15 min. The reaction was quenched with saturated aqueous ammonium chloride, and extracted with EtOAc (3×). The combined organic layers were dried over Na$_2$SO$_4$, filtered and the filtrate was concentrated. Purification of the residue by flash chromatography on silica gel (0-15% MeOH/DCM, gradient elution) provided the title compound (mixture of C-3 epimers) as a white solid.

Step K. (5R,6S)-3-allyl-1-((S)-1-((tert-butyldiphenylsilyl)oxy)butan-2-yl)-5-(3-chlorophenyl)-6-(5-chloropyridin-2-yl)-3-methylpiperidin-2-one

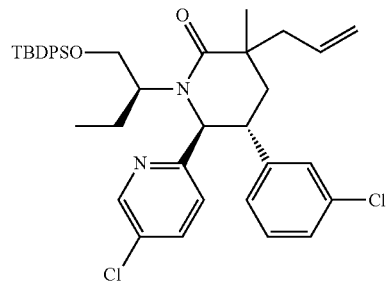

To a solution of 2.95 g (4.57 mmol) of (5R,6S)-1-((S)-1-(tert-butyldiphenylsilyloxy)butan-2-yl)-5-(3-chlorophenyl)-6-(5-chloropyridin-2-yl)-3-methylpiperidin-2-one (Example 121, Step J) and 7.91 mL (91.0 mmol) of allyl bromide in dry, degassed THF (22 mL) was added 68.6 mL (68.6 mmol) of a 1 M solution of lithium bis(trimethylsilyl)amide in THF slowly via syringe over 6 min at room temperature. After 10 min, the orange solution was warmed to 50° C. and stirred for 24 h. At this time, 11.4 mL (11.4 mmol) of a 1 M solution of lithium bis(trimethylsilyl)amide in THF and 790 μL (0.79 mmol) of allyl bromide were added. The reaction was stirred for an additional 6.25 h at 50° C., and then was cooled to room temperature and quenched with saturated aqueous ammonium chloride. The mixture was extracted with EtOAc (3×), and the combined organic layers were dried over Na$_2$SO$_4$, filtered and the filtrate was concentrated. Purification of the residue by flash chromatography on silica gel (2 to 25% EtOAc/hexanes, gradient elution) provided the title compound (mixture of C-3 epimers) as a light yellow solid.

Step L. (5R,6S)-3-Allyl-5-(3-chlorophenyl)-6-(5-chloropyridin-2-yl)-1-((S)-1-hydroxybutan-2-yl)-3-methylpiperidin-2-one

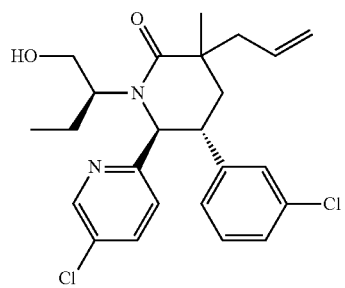 [SMILES: C=CCC1(C)C[C@H](c2cccc(Cl)c2)[C@@H](c2ccc(Cl)cn2)N([C@@H](CC)CO)C1=O]

To an ice-cooled solution of 1.30 g (1.90 mmol) of (5R,6S)-3-allyl-1-((S)-1-(tert-butyldiphenylsilyloxy)butan-2-yl)-5-(3-chlorophenyl)-6-(5-chloropyridin-2-yl)-3-methylpiperidin-2-one (Example 121, Step K) in THF (55 mL) was added 11.37 mL (11.37 mmol) of a 1 M solution of TBAF in THF.

The orange solution was warmed to room temperature and stirred for 3.75 h. The reaction was partitioned between 1 M HCl and EtOAc (2×), and then the combined organic layers were washed with water (2×). The organic layer was dried over Na$_2$SO$_4$, filtered and the filtrate was concentrated. Purification of the residue by flash chromatography on silica gel (0 to 10% MeOH/DCM, gradient elution) provided the title compound as a light yellow solid.

Step M. (S)-2-((5R,6S)-3-Allyl-5-(3-chlorophenyl)-6-(5-chloropyridin-2-yl)-3-methyl-2-oxopiperidin-1-yl)butanal

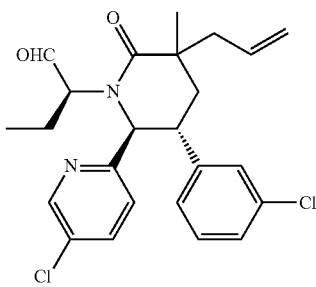 [SMILES: C=CCC1(C)C[C@H](c2cccc(Cl)c2)[C@@H](c2ccc(Cl)cn2)N([C@H](C=O)CC)C1=O]

To a solution of 197 mg (0.44 mmol) of (5R,6S)-3-allyl-5-(3-chlorophenyl)-6-(5-chloropyridin-2-yl)-1-((S)-1-hydroxybutan-2-yl)-3-methylpiperidin-2-one (Example 121, Step L) in DCM (6 mL) was added 12 µL (0.66 mmol) of water and 280 mg (0.66 mmol) of Dess-Martin periodinane. The resulting light yellow slurry was warmed to room temperature and stirred for 50 min. The reaction was quenched with saturated aqueous sodium thiosulfate, diluted with water, and extracted with DCM (2×). The combined organic layers were washed with saturated aqueous sodium bicarbonate (1×) and saturated aqueous sodium chloride (1×), and then were dried over Na$_2$SO$_4$, filtered and the filtrate was concentrated. Purification of the residue by flash chromatography on silica gel (0 to 7% MeOH/DCM, gradient elution) provided the title compound as a light yellow solid.

Step N. (3S,5R,6S)-3-Allyl-5-(3-chlorophenyl)-6-(5-chloropyridin-2-yl)-3-methyl-1-((S)-1-morpholinobutan-2-yl)piperidin-2-one

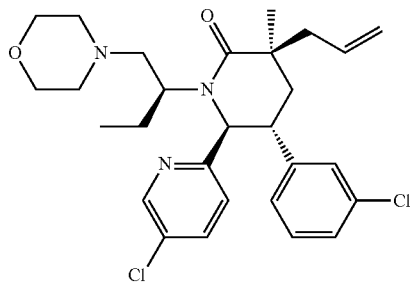 [SMILES: C=CC[C@@]1(C)C[C@H](c2cccc(Cl)c2)[C@@H](c2ccc(Cl)cn2)N([C@@H](CC)CN2CCOCC2)C1=O]

The title compound was prepared from (S)-2-((3S,5R,6S)-3-allyl-5-(3-chlorophenyl)-6-(5-chloropyridin-2-yl)-3-methyl-2-oxopiperidin-1-yl)butanal (Example 121, Step M) as described in Example 91, Step A. Purification of the crude product by flash chromatography on silica gel (3 to 10% MeOH/DCM, gradient elution) provided the title compound as a white solid.

Step O. 2-((3R,5R,6S)-5-(3-chlorophenyl)-6-(5-chloropyridin-2-yl)-3-methyl-1-((S)-1-morpholinobutan-2-yl)-2-oxopiperidin-3-yl)acetaldehyde

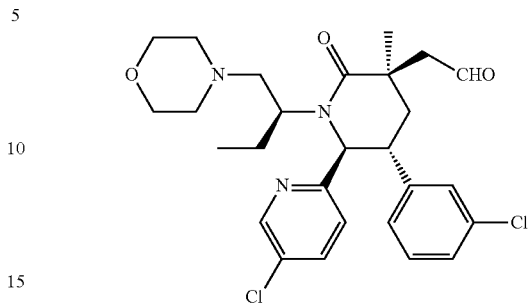

To a solution of 42 mg (0.08 mmol) of (3S,5R,6S)-3-allyl-5-(3-chlorophenyl)-6-(5-chloropyridin-2-yl)-3-methyl-1-((S)-1-morpholinobutan-2-yl)piperidin-2-one (Example 121, Step N) in THF (6 mL) and water (2 mL) added a catalytic amount of osmium tetroxide. After 3 min, 87 mg (0.41 mmol) of sodium periodate was added. The resulting white slurry was stirred at room temperature for 4.25 h, and then filtered through a fritted funnel. The filtrate was partially concentrated under reduced pressure, and then was diluted with a mixture of water and saturated aqueous sodium chloride and extracted with ethyl acetate (2×). The combined organic layers were washed with saturated aqueous sodium thiosulfate and then saturated aqueous sodium chloride. The organic layer was dried over Na$_2$SO$_4$, filtered and the filtrate was concentrated. Purification of the residue by reversed phase prep. HPLC (Sunfire™ Prep C$_{18}$ OBD 10 µm column (Waters, Milford, Mass.), gradient elution of 35% MeCN in water to 75% MeCN in water over a 35 min period, where both solvents contain 0.1% TFA provided the title compound as a white solid.

Step P. 2-((3R,5R,6S)-5-(3-chlorophenyl)-6-(5-chloropyridin-2-yl)-3-methyl-1-((S)-1-morpholinobutan-2-yl)-2-oxopiperidin-3-yl)acetic acid

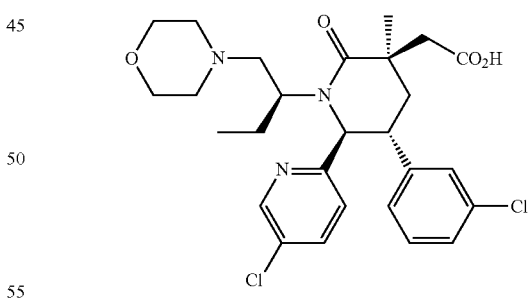

To a solution of 16 mg (0.03 mmol) of 2-((3R,5R,6S)-5-(3-chlorophenyl)-6-(5-chloropyridin-2-yl)-3-methyl-1-((S)-1-morpholinobutan-2-yl)-2-oxopiperidin-3-yl)acetaldehyde (Example 121, Step O) and 1.0 mL (9.4 mmol) of 2-methyl-2-butene in t-BuOH (3 mL) was added a solution of 28 mg (0.31 mmol) of sodium chlorite and 4.6 mg (0.03 mmol) of sodium dihydrogenphosphate dihydrate in water (1.6 mL). The resulting mixture was stirred at room temperature for 2 h, and then was quenched with 1 M HCl and extracted with EtOAc (3×). The combined organic layers were dried over Na$_2$SO$_4$, filtered and the filtrate was concentrated. Purification of the residue by reversed phase prep. HPLC (Sunfire™ Prep C$_{18}$ OBD 10 μm column (Waters, Milford, Mass.), gradient elution of 35% MeCN in water to 60% MeCN in water over a 35 min period, where both solvents contain 0.1% TFA provided the title compound as a white solid.

$^1$H NMR (400 MHz, CD$_3$OD) δ ppm 8.69 (1 H, d, J=2.4 Hz), 7.65 (1 H, dd, J=8.3 Hz, 2.5 Hz), 7.14-7.22 (2 H, m), 7.01-7.08 (2 H, m), 6.88-6.95 (1 H, m), 4.85-4.90 (1 H, buried d), 3.94-4.09 (4 H, m), 3.42-3.53 (1 H, m), 3.07-3.24 (2 H, m), 2.88-3.01 (2 H, m), 2.73 (1 H, d, J=13.7 Hz), 2.38 (1 H, t, J=13.9 Hz), 2.10 (1 H, dd, J=13.9 Hz. 3.5 Hz), 1.80-1.92 (1 H, m), 1.41 (3 H, s), 1.39-1.47 (2 H, m), 1.13 (3 H, dd, J=6.5 Hz, 4.9 Hz), 0.93-1.05 (3 H, br s). Mass Spectrum (ESI) m/z=534 (M+1).

Example 122

2-((3R,5R,6S)-5-(3-chlorophenyl)-6-(5-chloropyridin-2-yl)-3-methyl-2-oxo-1-(pentan-3-yl)piperidin-3-yl)acetic acid

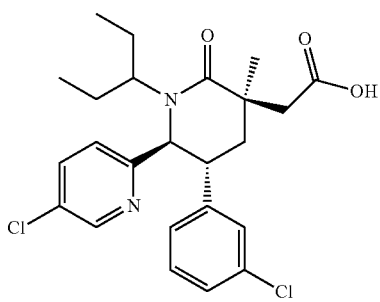 [SMILES: CCC(CC)N1C(=O)[C@@](C)(CC(=O)O)C[C@H](c2cccc(Cl)c2)[C@H]1c1ccc(Cl)cn1]

Step A. (5R,6S)-5-(3-Chlorophenyl)-6-(5-chloropyridin-2-yl)-1-(pentan-3-yl)piperidin-2-one

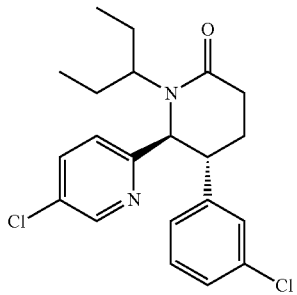 [SMILES: CCC(CC)N1C(=O)CC[C@H](c2cccc(Cl)c2)[C@H]1c1ccc(Cl)cn1]

To a degassed solution of (5R,6S)-5-(3-chlorophenyl)-6-(5-chloropyridin-2-yl)piperidin-2-one (1.00 g, 3.11 mmol, Example 121, Step F), 3-bromopentane (6.0 ml, 48.1 mmol) and tetrabutylammonium iodide (3.45 g, 9.34 mmol) in dry DMF (5.2 ml) was added 1.25 g (31 mmol) of a dispersion of 60% sodium hydride in mineral oil at 0° C. The reaction was heated to 90° for 8 h. Sat. aq. NaHCO$_3$/NaCl solution was added and the mixture was extracted with ethyl acetate. The organic layers were washed with water and sat. NaCl solution, dried over Na$_2$SO$_4$, filtered and the filtrate was concentrated under reduced pressure. Purification of the residue by flash chromatography on silica gel (eluent: 25 to 50% EtOAc/hexanes which had been sparged with NH$_3$ gas, gradient elution) provided the title compound.

Step B. (5R,6S)-3-Allyl-5-(3-chlorophenyl)-6-(5-chloropyridin-2-yl)-3-methyl-1-(pentan-3-yl)piperidin-2-one

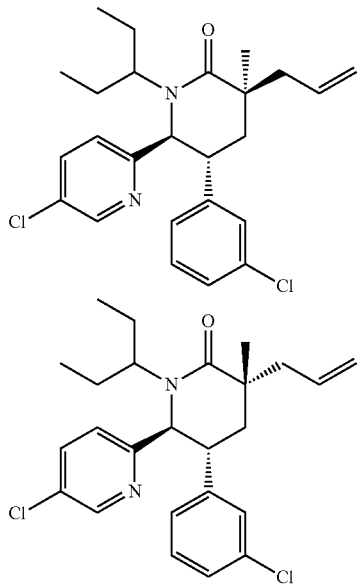

The title compound was prepared from (5R,6S)-5-(3-chlorophenyl)-6-(5-chloropyridin-2-yl)-1-(pentan-3-yl)piperidin-2-one (Example 122, Step A) by a procedure similar to the one described in Example 121, Steps J and K and was obtained as a mixture of epimers at C-3.

Step C. 2-((3R,5R,6S)-5-(3-Chlorophenyl)-6-(5-chloropyridin-2-yl)-3-methyl-2-oxo-1-(pentan-3-yl)piperidin-3-yl)acetic acid

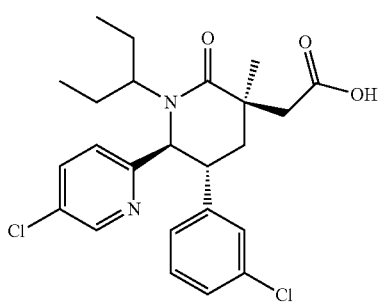 [SMILES: CCC(CC)N1C(=O)[C@@](C)(CC(=O)O)C[C@H](c2cccc(Cl)c2)[C@H]1c1ccc(Cl)cn1]

The title compound was obtained from (5R,6S)-3-allyl-5-(3-chlorophenyl)-6-(5-chloropyridin-2-yl)-3-methyl-1-(pentan-3-yl)piperidin-2-one (149 mg, 0.335 mmol, mixture of stereoisomers at C-3, Example 122, Step B) by a procedure similar to the one described in Example 71, Step F. Purification by reversed phase preparatory HPLC (eluent: 50% MeCN/water (0.1% TFA), isocratic elution) using a Sunfire™ C18 OBD column, 10 uM, (30×150 mm), Waters Corp (Milford, Mass.) provided the title compound as the more polar, major isomer.

1H NMR (500 MHz, CHLOROFORM-d) δ ppm 0.53 (t, J=7.46 Hz, 3 H), 0.93 (t, J=7.46 Hz, 3 H), 1.20-1.34 (m, 1 H), 1.34-1.46 (m, 1 H), 1.49 (s, 3 H), 1.62-1.78 (m, 1 H), 1.83 (ddd, J=14.61, 7.58, 7.40 Hz, 1 H), 1.99 (dd, J=13.69, 3.18 Hz, 1 H), 2.22 (t, J=13.57 Hz, 1 H), 2.72 (d, J=15.89 Hz, 1 H), 2.88-2.99 (m, 1 H), 3.35 (d, J=15.89 Hz, 1 H), 3.43 (ddd, J=13.14, 9.72, 3.06 Hz, 1 H), 4.50 (d, J=9.78 Hz, 1 H), 6.76 (dt, J=7.58, 1.22 Hz, 1 H), 6.84 (d, J=8.07 Hz, 1 H), 6.98 (t, J=1.83 Hz, 1 H), 7.14 (t, J=7.70 Hz, 1 H), 7.53 (dd, J=8.07, 2.45 Hz, 1 H), 8.60 (d, J=2.20 Hz, 1 H). Mass Spectrum (ESI) m/z=463 (M+1).

Example 123

2-((3S,5R,6S)-5-(3-Chlorophenyl)-6-(5-chloropyridin-2-yl)-3-methyl-2-oxo-1-(pentan-3-yl)piperidin-3-yl)acetic acid

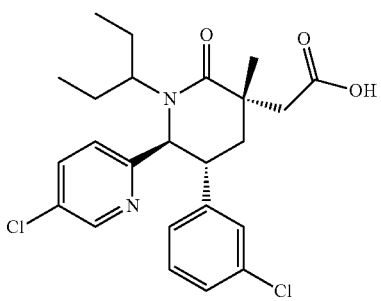 [SMILES: CCC(CC)N1C(=O)[C@](C)(CC(=O)O)C[C@H](c2cccc(Cl)c2)[C@H]1c1ccc(Cl)cn1]

The title compound was obtained in Example 122, Step C as the less polar, minor isomer.

1H NMR (500 MHz, CHLOROFORM-d) δ ppm 0.51 (t, J=7.46 Hz, 3 H), 0.94 (t, J=7.46 Hz, 3 H), 1.33-1.55 (m, 3 H), 1.73 (s, 3 H), 1.73-1.82 (m, 3 H), 2.24 (t, J=13.69 Hz, 1 H), 2.49 (d, J=15.16 Hz, 1 H), 2.88 (d, J=14.92 Hz, 1 H), 3.62 (ddd, J=13.88, 10.21, 3.55 Hz, 1 H), 4.42 (d, J=10.03 Hz, 1 H), 6.70-6.82 (m, 2 H), 6.96 (t, J=1.83 Hz, 1 H), 7.09-7.24 (m, 2 H), 7.52 (dd, J=8.07, 2.45 Hz, 1 H), 8.62 (d, J=2.45 Hz, 1 H). Mass Spectrum (ESI) m/z=463 (M+1).

Example 124

2-((3R,5R,6S)-1-((S)-1-tert-butoxy-1-oxobutan-2-yl)-5-(3-chlorophenyl)-6-(5-chloropyridin-2-yl)-3-methyl-2-oxopiperidin-3-yl)acetic acid

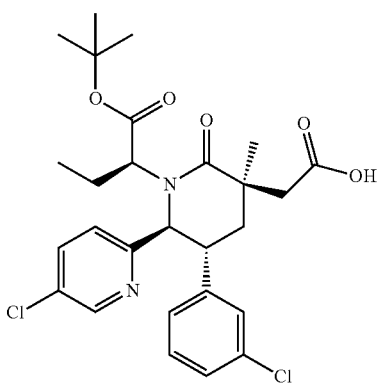 [SMILES: CC[C@@H](C(=O)OC(C)(C)C)N1C(=O)[C@@](C)(CC(=O)O)C[C@H](c2cccc(Cl)c2)[C@H]1c1ccc(Cl)cn1]

Step A. (5R,6S)-5-(3-chlorophenyl)-6-(5-chloropyridin-2-yl)-1-(2,4-dimethoxybenzyl)piperidin-2-one

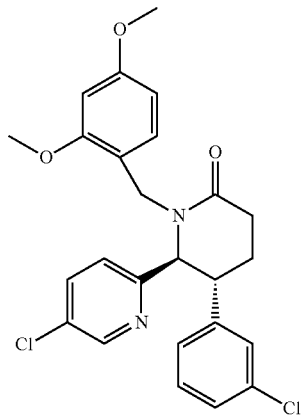 [SMILES: COc1ccc(CN2C(=O)CC[C@H](c3cccc(Cl)c3)[C@H]2c2ccc(Cl)cn2)c(OC)c1]

To a solution of 6.72 g (20.92 mmol) of (5R,6S)-5-(3-chlorophenyl)-6-(5-chloropyridin-2-yl)piperidin-2-one (Example 121, Step F) in DMF (~0.5M) at 0° C. was slowly added a dispersion of 60% sodium hydride in mineral oil (2.51 g, 62.8 mmol). The reaction was stirred 0° C. for 30 min, followed by addition of 1-(chloromethyl)-2,4-dimethoxybenzene (7.81 g, 41.8 mmol). Upon completion, the reaction was quenched at 0° C. with a small excess of acetic acid (4.79 mL, 84 mmol). It was neutralized with sat. aq. NaHCO$_3$ solution and extracted with ethyl acetate. The organic layer was dried over Na$_2$SO$_4$, filtered and the filtrate as concentrated under reduced pressure to yield a reddish oil. Purification by flash chromatography on silica gel (eluent: 0 to 30% ethyl acetate/DCM, gradient elution) provided the title compound as a pale yellow oil.

1H NMR (500 MHz, CHLOROFORM-d) δ ppm 1.81-1.93 (m, 1 H), 2.00-2.11 (m, 1 H), 2.38-2.50 (m, 1 H), 2.50-2.61 (m, 1 H), 3.30 (dt, J=6.60, 4.16 Hz, 1 H), 3.63 (s, 3 H), 3.74 (d, J=14.43 Hz, 1 H), 3.80 (s, 3 H), 4.86 (d, J=4.40 Hz, 1 H), 5.23 (d, J=14.43 Hz, 1 H), 6.37 (d, J=2.20 Hz, 1 H), 6.44 (dd, J=8.31, 2.45 Hz, 1 H), 6.84 (d, J=7.58 Hz, 1 H), 6.90-7.00 (m, 2 H), 7.08 (t, J=7.83 Hz, 1 H), 7.11-7.16 (m, 1 H), 7.18 (d, J=8.31 Hz, 1 H), 7.61 (dd, J=8.31, 2.45 Hz, 1 H), 8.56 (d, J=2.45 Hz, 1 H). Mass Spectrum (ESI) m/z=471 (M+1).

Step B. (3S,5R,6S)-3-allyl-5-(3-chlorophenyl)-6-(5-chloropyridin-2-yl)-1-(2,4-dimethoxybenzyl)-3-methylpiperidin-2-one and (3R,5R,6S)-3-allyl-5-(3-chlorophenyl)-6-(5-chloropyridin-2-yl)-1-(2,4-dimethoxybenzyl)-3-methylpiperidin-2-one

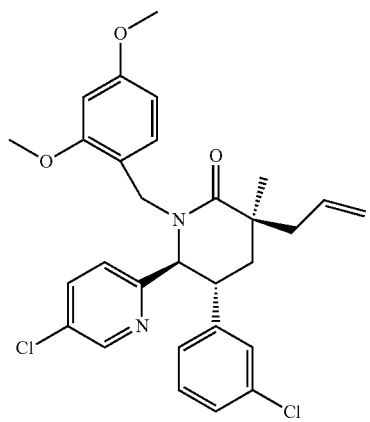

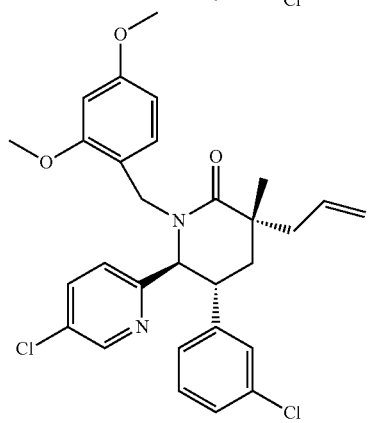

The title compound was prepared from (5R,6S)-5-(3-chlorophenyl)-6-(5-chloropyridin-2-yl)-1-(2,4-dimethoxybenzyl)piperidin-2-one (Example 124, Step A) by a procedure similar to the ones described in Example 121, Steps J and K and was obtained as a mixture of epimers at C-3.

Step C. (3S,5R,6S)-3-allyl-5-(3-chlorophenyl)-6-(5-chloropyridin-2-yl)-3-methylpiperidin-2-one (5R,6S)-3-allyl-5-(3-chlorophenyl)-6-(5-chloropyridin-2-yl)-1-(2,4-dimethoxybenzyl)-3-methylpiperidin-2-one (3.6 g, 6.85 mmol, mixture of C-3 epimers, Example 124, Step B) was dissolved in TFA (26.4 mL, 343 mmol) and the reaction was heated to 70° for 1.5 h. It was then cooled to ambient temperature and the TFA was removed by concentration under reduced pressure. The product was azeotroped with heptanes, dissolved in DCM and the organic layer was washed with sat. aq. NaHCO$_3$ solution and sat. NaCl solution. Purification by flash chromatography on silica gel (eluent: 35 to 45% EtOAc/hexanes which had been NH$_3$ sparged, gradient elution) provided the title compound as the more polar isomer as a white solid: (R$_f$ in 75% EtOAc/Hexanes=0.44).
1H NMR (500 MHz, CHLOROFORM-d) δ ppm 0.67-0.84 (m, 1 H), 1.10-1.25 (m, 3 H), 1.60 (br. s., 1 H), 1.85-2.04 (m, 2 H), 2.32-2.50 (m, 1 H), 2.56 (d, J=8.31 Hz, 1 H), 3.19-3.33 (m, 1 H), 4.56-4.66 (m, 1 H), 4.99-5.14 (m, 2 H), 5.68-5.84 (m, 1 H), 5.89 (br. s., 1 H), 6.72-6.84 (m, 2 H), 6.92-7.01 (m, 1 H), 7.01-7.12 (m, 2 H), 7.12-7.23 (m, 1 H), 7.35-7.48 (m, 1 H), 8.31-8.48 (m, 1 H). Mass Spectrum (ESI) m/z=375 (M+1).

Step D. (S) tert-Butyl 2-((3S,5R,6S)-3-allyl-5-(3-chlorophenyl)-6-(5-chloropyridin-2-yl)-3-methyl-2-oxopiperidin-1-yl)butanoate

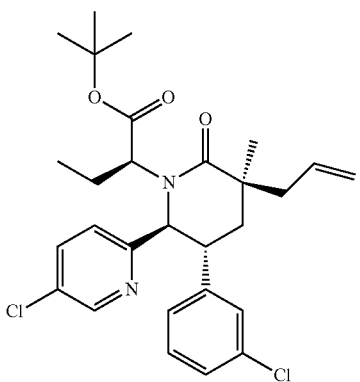 [SMILES: C=CC[C@@]1(C)C[C@H](c2cccc(Cl)c2)[C@@H](c2ccc(Cl)cn2)N([C@@H](CC)C(=O)OC(C)(C)C)C1=O]

To a solution of (3S,5R,6S)-3-allyl-5-(3-chlorophenyl)-6-(5-chloropyridin-2-yl)-3-methylpiperidin-2-one (77 mg, 0.205 mmol, Example 124, Step C) in DMF (0.3 mL) was added slowly 9.5 mg (0.24 mmol) of a dispersion of 60% sodium hydride in mineral oil followed by tert-butyl 2-bromobutanoate (92 mg, 0.410 mmol). The reaction was stirred at ambient temperature overnight, quenched with MeOH/HOAc, was diluted with EtOAc and water and extracted to EtOAc. The organics were dried over Na$_2$SO$_4$, filtered and the filtrate was concentrated. Purification by reversed phase preparatory HPLC (Sunfire™ Prep C18 OBD 10 µm column (Waters, Milford, Mass.) (eluent: 70% acetonitrile, water, 0.1% TFA) provided the title compound, as well as its stereoisomer, (R)-tert-butyl 2-((3S,5R,6S)-3-allyl-5-(3-chlorophenyl)-6-(5-chloropyridin-2-yl)-3-methyl-2-oxopiperidin-1-yl)butanoate.

Step E. (S)-tert-butyl 2-((3R,5R,6S)-5-(3-chlorophenyl)-6-(5-chloropyridin-2-yl)-3-methyl-2-oxo-3-(2-oxoethyl)piperidin-1-yl)butanoate

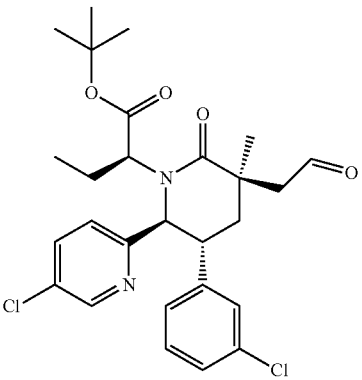 [SMILES: CC[C@@H](C(=O)OC(C)(C)C)N1C(=O)[C@@](C)(CC=O)C[C@H](c2cccc(Cl)c2)[C@H]1c1ccc(Cl)cn1]

The example was prepared from (S)-tert-butyl 2-((3S,5R,6S)-3-allyl-5-(3-chlorophenyl)-6-(5-chloropyridin-2-yl)-3- methyl-2-oxopiperidin-1-yl)butanoate (Example 124, Step D) as described in Example 121, Step O. Purification of the residue by reversed phase preparatory HPLC(Sunfire™ Prep C18 OBD 10 μm column (Waters, Milford, Mass.) (eluent: 55 to 75% acetonitrile, water, 0.1% TFA, gradient elution) provided the title compound as a white solid after lyophilization.

Step F. 2-((3R,5R,6S)-1-((S)-1-tert-butoxy-1-oxobutan-2-yl)-5-(3-chlorophenyl)-6-(5-chloropyridin-2-yl)-3-methyl-2-oxopiperidin-3-yl)acetic acid

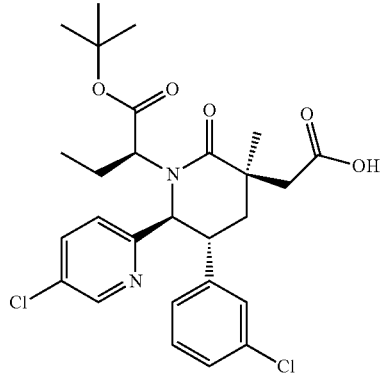 [SMILES: CC[C@@H](C(=O)OC(C)(C)C)N1C(=O)[C@@](C)(CC(=O)O)C[C@H](c2cccc(Cl)c2)[C@H]1c1ccc(Cl)cn1]

The title compound was prepared from (S)-tert-butyl 2-((3R,5R,6S)-5-(3-chlorophenyl)-6-(5-chloropyridin-2-yl)-3-methyl-2-oxo-3-(2-oxoethyl)piperidin-1-yl)butanoate (Example 124, Step E) as described in Example 121, Step P.
$^1$H NMR (500 MHz, CHLOROFORM-d) δ ppm 0.46 (t, J=7.46 Hz, 2 H), 1.09-1.28 (m, 2 H), 1.28-1.42 (m, 2 H), 1.42-1.46 (m, 2 H), 1.49 (s, 7 H), 1.71-1.90 (m, 3 H), 1.93-2.04 (m, 1 H), 2.12-2.29 (m, 2 H), 2.89-2.97 (m, 1 H), 2.99 (dd, J=7.70, 4.28 Hz, 1 H), 3.01-3.09 (m, 1 H), 3.61 (ddd, J=13.02, 9.84, 3.55 Hz, 1 H), 4.73 (d, J=10.27 Hz, 1 H), 6.83 (d, J=7.58 Hz, 1 H), 6.94 (d, J=8.31 Hz, 1 H), 7.03 (s, 1 H), 7.11 (t, J=7.70 Hz, 1 H), 7.14-7.18 (m, 1 H), 7.56 (dd, J=8.31, 2.45 Hz, 1 H), 8.61 (d, J=2.45 Hz, 1 H). Mass Spectrum (ESI) m/z=535 (M+1).

Example 125

2-((3R,5S,6S)-1-((S)-1-tert-butoxy-1-oxobutan-2-yl)-6-(4-chlorophenyl)-5-(4-chloropyridin-2-yl)-3-methyl-2-oxopiperidin-3-yl)acetic acid

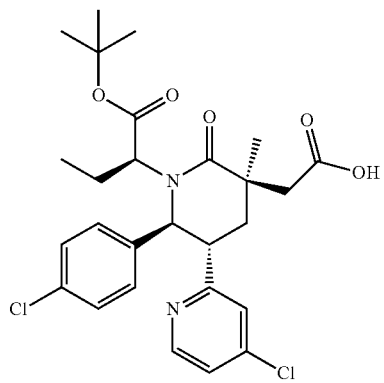 [SMILES: CC[C@@H](C(=O)OC(C)(C)C)N1C(=O)[C@@](C)(CC(=O)O)C[C@H](c2cc(Cl)ccn2)[C@H]1c1ccc(Cl)cc1]

Step A. 1-(4-Chlorophenyl)-2-(4-chloropyridin-2-yl)ethanone

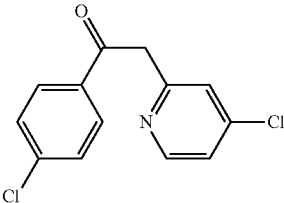 [SMILES: O=C(Cc1cc(Cl)ccn1)c1ccc(Cl)cc1]

To a solution of 4-chloro-2-methylpyridine (23.07 g, 181 mmol) and methyl 4-chlorobenzoate (30.8 g, 181 mmol) in dry THF (500 mL) at 0° C. was added 1 M LiHMDS in THF (63.5 g, 380 mmol) slowly via a dropping funnel. When complete, the reaction was quenched with NaHCO$_3$ solution, concentrated under reduced pressure, and extracted with ethyl acetate. The combined organics were dried over Na$_2$SO$_4$, filtered and the filtrate was concentrated under reduced pressure to provide the title compound.

Step B. (4R,5R)-methyl 5-(4-chlorophenyl)-4-(4-chloropyridin-2-yl)-5-hydroxypentanoate and (4S,5S)-methyl 5-(4-chlorophenyl)-4-(4-chloropyridin-2-yl)-5-hydroxypentanoate

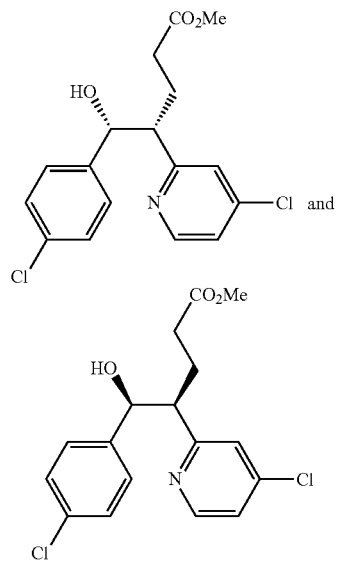

To a solution of 1-(4-chlorophenyl)-2-(4-chloropyridin-2-yl)ethanone (42.0 g, 158 mmol) and DBU (28.5 mL, 189 mmol, Example 125, Step A) in dioxane (316 mL) at 80° C. was added methyl acrylate (15.73 mL, 174 mmol), dropwise. The reaction was stirred at 80° C. for 30 min, at which time more methyl acrylate (2.86 mL, 31 mmol) was added. When the reaction was complete, it was cooled to 0° C. Methanol (500 mL) was added slowly, the reaction was cooled to 0° C. and NaBH$_4$ (5.97 g, 158 mmol) was slowly added. The solution was concentrated under reduced pressure, and partitioned between ethyl acetate and 1 N NaOH. The organic layer was concentrated under reduced pressure. Purification by flash chromatography on silica gel (eluent: EtOAc/hexanes which had been NH$_3$ sparged, gradient elution) provided the title compound.

Step C. (4S,5S)-methyl 5-azido-5-(4-chlorophenyl)-4-(4-chloropyridin-2-yl)pentanoate and (4R,5R)-methyl 5-azido-5-(4-chlorophenyl)-4-(4-chloropyridin-2-yl)

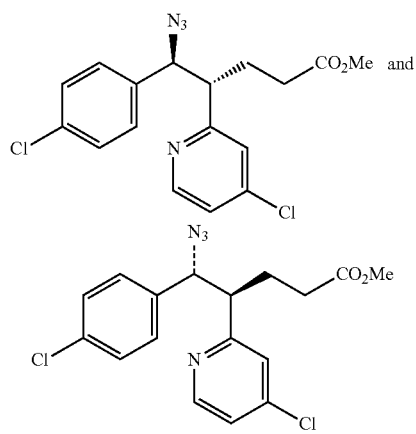

The title compound mixture was prepared from methyl 5-(4-chlorophenyl)-4-(4-chloropyridin-2-yl)-5-hydroxypentanoate (Example 125, Step B) as described in Example 121, Step E, using 2.0 eq of NaN₃ at 100° C. The residue was purified by flash chromatography on silica gel (eluent: 15 to 45% ethyl acetate/hexanes, gradient elution).

Step D. (5S,6S)-6-(4-chlorophenyl)-5-(4-chloropyridin-2-yl)piperidin-2-one

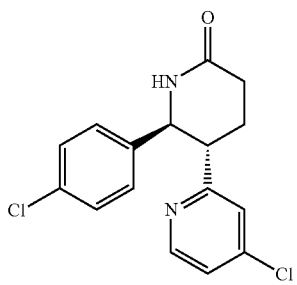 [SMILES: O=C1CC[C@H](c2cc(Cl)ccn2)[C@@H](c2ccc(Cl)cc2)N1]

The title compound mixture was prepared from (4S,5S)-methyl 5-azido-5-(4-chlorophenyl)-4-(4-chloropyridin-2-yl)pentanoate (racemic compound mixture) (Example 125, Step C) as described in Example 121, Step F. The crude product was first purified by flash chromatography on silica gel (eluent: 5 to 40% ethyl acetate/DCM, gradient elution), then individual stereoisomers were separated by chiral HPLC (250×30 mm AS-H column with 50 g/min IPA (0.2% DEA)+50 g/min CO₂ on Thar 350 SFC (Thar Technologies, Pittsburg, Pa.)) to give the title compound as the faster eluting stereoisomer.

1H NMR (500 MHz, CHLOROFORM-d) δ ppm 1.60 (br. s., 3 H), 2.07 (dddd, J=13.60, 5.84, 2.93, 2.81 Hz, 2 H), 2.30-2.46 (m, 2 H), 2.54-2.72 (m, 4 H), 2.96 (ddd, J=12.10, 9.54, 2.81 Hz, 2 H), 3.50 (s, 1 H), 4.98 (d, J=10.03 Hz, 2 H), 5.78 (br. s., 2 H), 6.81 (d, J=1.71 Hz, 2 H), 7.03 (d, J=8.31 Hz, 4 H), 7.09-7.17 (m, 2 H), 7.21 (d, J=8.07 Hz, 4 H), 8.46 (d, J=5.38 Hz, 2 H), Mass Spectrum (ESI) m/z=321 (M+1), (t$_R$=7.1 min on 40% iPrOH/Hexanes on Chiracel OD analytical column)

Step E. (5S,6S)-6-(4-chlorophenyl)-5-(4-chloropyridin-2-yl)-1-(2,4-dimethoxybenzyl)piperidin-2-one or (5R,6R)-6-(4-chlorophenyl)-5-(4-chloropyridin-2-yl)-1-(2,4-dimethoxybenzyl)piperidin-2-one

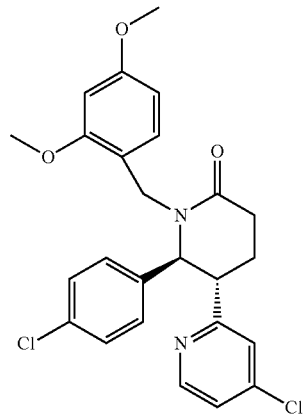 [SMILES: COc1ccc(CN2C(=O)CC[C@H](c3cc(Cl)ccn3)[C@H]2c2ccc(Cl)cc2)c(OC)c1]

The title compound mixture was prepared from (5S,6S)-6-(4-chlorophenyl)-5-(4-chloropyridin-2-yl)piperidin-2-one or (5R,6R)-6-(4-chlorophenyl)-5-(4-chloropyridin-2-yl)piperidin-2-one (Example 125, Step D and 1-(chloromethyl)-2,4-dimethoxybenzene using a similar procedure to that described in Example 124, Step A.

Step F. (3S,5S,6S)-3-allyl-6-(4-chlorophenyl)-5-(4-chloropyridin-2-yl)-1-(2,4-dimethoxybenzyl)-3-methylpiperidin-2-one and (3R,5S,6S)-3-allyl-6-(4-chlorophenyl)-5-(4-chloropyridin-2-yl)-1-(2,4-dimethoxybenzyl)-3-methylpiperidin-2-one

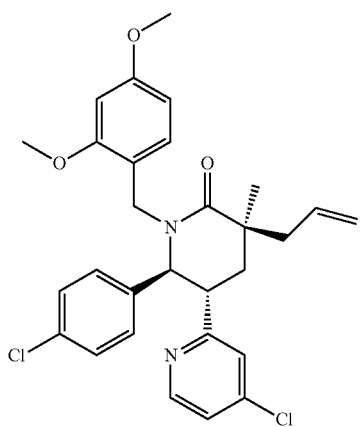

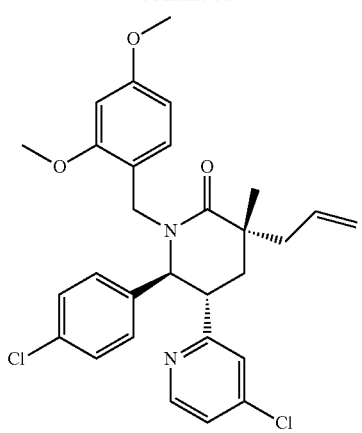

The title compound was prepared as a mixture of stereoisomers from (5S,6S)-6-(4-chlorophenyl)-5-(4-chloropyridin-2-yl)-1-(2,4-dimethoxybenzyl)-3-methylpiperidin-2-one (Example 125, Step E) using a similar procedure to that described in Example 121, Steps J and K.

Step G. (5R,6S)-5-(3-chlorophenyl)-6-(5-chloropyridin-2-yl)piperidin-2-one

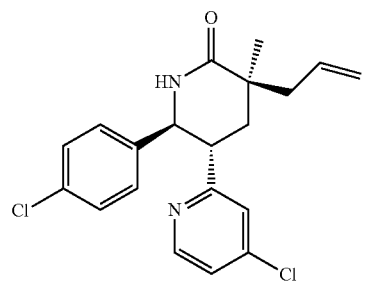

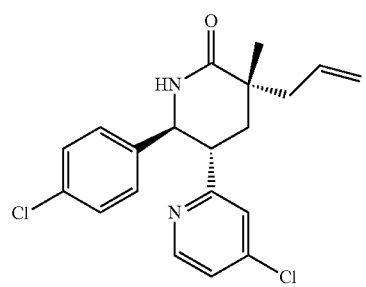

The title compound was prepared as a mixture of stereoisomers at the C3 position from (5S,6S)-6-(4-chlorophenyl)-5-(4-chloropyridin-2-yl)-1-(2,4-dimethoxybenzyl)-3-methylpiperidin-2-one (Example 125, Step F) in a similar procedure to that described in Example 124, Step C, followed by purification on silica gel, except that the reaction was warmed to ambient temperature rather than 70° and the eluents were 0 to 3% MeOH/DCM.

Step H. tert-butyl 2-((3S,5S,6S)-3-allyl-6-(4-chlorophenyl)-5-(4-chloropyridin-2-yl)-3-methyl-2-oxopiperidin-1-yl)butanoate and tert-butyl 2-((3R,5S,6S)-3-allyl-6-(4-chlorophenyl)-5-(4-chloropyridin-2-yl)-3-methyl-2-oxopiperidin-1-yl)butanoate

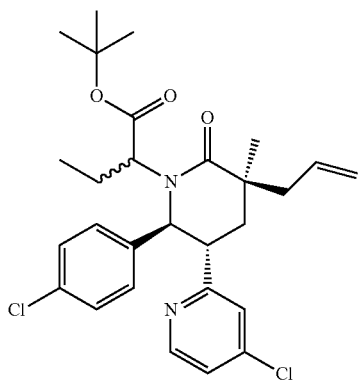

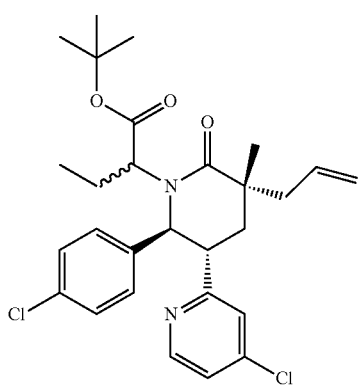

To a solution of 100 mg, (0.266 mmol) of (5S,6S)-3-allyl-6-(4-chlorophenyl)-5-(4-chloropyridin-2-yl)-3-methylpiperidin-2-one (Example 125, Step G; mixture of stereoisomers) in dry DMF (533 µL) at ambient temperature was added a dispersion of 60% sodium hydride in mineral oil (15.99 mg, 0.400 mmol). The mixture was sonicated at 40° C. for 10 min, followed by addition of tert-butyl 2-bromobutanoate (119 mg, 0.533 mmol). Stirred at ambient temperature for 24 h, then added 2 eq more NaH, and stirred overnight. The reaction was quenched with a small amount of 10% HOAc in MeOH, diluted with EtOAc and water and extracted to EtOAc×3. The combined organics were dried over $Na_2SO_4$, filtered and the filtrate was concentrated under reduced pressure. Purification of the residue by preparatory RP-HPLC (Sunfire™ Prep C18 OBD 10 µm column (Waters, Milford, Mass., gradient elution of 55% MeCN in water to 75% MeCN in water over a 35 min period, where both solvents contain 0.1% TFA) yielded a mixture of 4 epimers including the title compound and the other 3 epimers. After HPLC, the product containing fractions were concentrated under reduced pres- Step I. 2-((3R,5S,6S)-1-((S)-1-tert-butoxy-1-oxobutan-2-yl)-6-(4-chlorophenyl)-5-(4-chloropyridin-2-yl)-3-methyl-2-oxopiperidin-3-yl)acetic acid

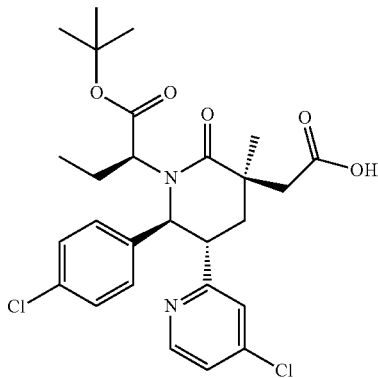 [SMILES: CC[C@@H](C(=O)OC(C)(C)C)N1C(=O)[C@@](C)(CC(=O)O)C[C@H](c2cc(Cl)ccn2)[C@H]1c1ccc(Cl)cc1]

The title compound was prepared from (5R,6S)-5-(3-chlorophenyl)-6-(5-chloropyridin-2-yl)piperidin-2-one (Example 125, Step H) as described in Example 121, Steps O and P. Purification of the residue by reversed phase HPLC (Sunfire™ Prep C18 OBD 10 μm column (Waters, Milford, Mass.) (eluent: 55% MeCN/water (0.1% TFA) provided the title compound as a white solid.

1H NMR (500 MHz, CHLOROFORM-d) δ ppm 0.56 (t, J=7.46 Hz, 3 H), 1.43 (s, 3 H), 1.45-1.57 (m, 11 H), 2.17-2.35 (m, 3 H), 2.78-2.92 (m, 2 H), 3.09 (dd, J=7.70, 3.79 Hz, 1 H), 3.57-3.66 (m, 1 H), 5.00 (d, J=10.51 Hz, 1 H), 7.02 (d, J=1.71 Hz, 1 H), 7.11 (d, J=7.34 Hz, 2 H), 7.20 (dd, J=5.50, 1.83 Hz, 1 H), 7.24 (d, J=8.56 Hz, 2 H), 8.41 (d, J=5.38 Hz, 1 H). Mass Spectrum (ESI) m/z=535 (M+1).

Example 126

2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)acetic acid

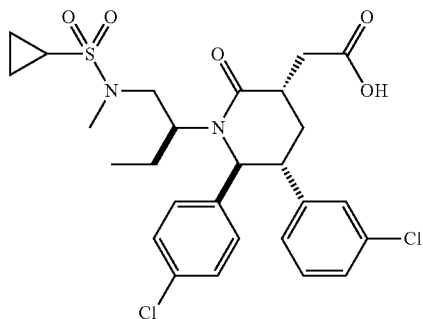

Step A. (S)-Methyl 2-((3R,5R,6S)-3-allyl-5-(3-chlorophenyl)-6-(4-chlorophenyl)-2-oxopiperidin-1-yl)butanoate

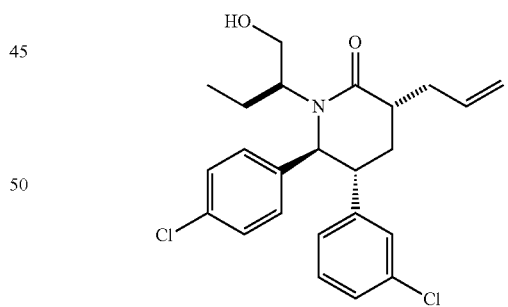

To a solution of 1.3 g (3.61 mmol) of (3R,5R,6S)-3-allyl-5-(3-chlorophenyl)-6-(4-chlorophenyl)piperidin-2-one (Example 42, Step A) in DMF (14.43 mL) at 0° C. was added a dispersion of 60% sodium hydride in mineral oil (0.361 g, 9.02 mmol). The grey slurry was stirred at 0° C. for 30 minutes. Then methyl 2-bromobutanoate (1.246 mL, 10.83 mmol) was added. The mixture was warmed to room temperature and stirred at room temperature for 1 h. The mixture was quenched with sat. NH₄Cl. The mixture was extracted with ethyl acetate. The organic layer was washed with water, 1 M LiCl (2×), and sat. aq. NaCl solution. The organic layer was dried over Na₂SO₄ filtered and the filtrate was concentrated under reduced pressure. The residue was purified by flash chromatography on silica gel (80 g column; eluent: 10 to 35% EtOAc in hexanes) to give the title compound as the less polar, major diastereomer.

Step B. (3R,5R,6S)-3-allyl-5-(3-chlorophenyl)-6-(4-chlorophenyl)-1-((S)-1-hydroxybutan-2-yl)piperidin-2-one To a solution of 710 mg (1.542 mmol) (S)-methyl 2-((3R,5R,6S)-3-allyl-5-(3-chlorophenyl)-6-(4-chlorophenyl)-2-oxopiperidin-1-yl)butanoate (Example 126, Step A) in Et₂O (15 mL) was added lithium borohydride (67.2 mg, 3.08 mmol) at 0° C. Evolution of gas was observed. The resulting white slurry was stirred at 0° C. for 60 min. The mixture was quenched with ice cold 1 M HCl. Evolution of gas was observed. The mixture was warmed to room temperature and extracted with EtOAc. The organic layer was washed with sat. aq. NaCl solution, dried over Na₂SO₄, filtered, and the filtrate was concentrated under reduced pressure. The residue was purified by flash chromatography on silica gel (24 g column; eluent: 20 to 40% EtOAc in hexanes) to give the title compound.

Step C. (S)-2-((3R,5R,6S)-3-allyl-5-(3-chlorophenyl)-6-(4-chlorophenyl)-2-oxopiperidin-1-yl)butanal

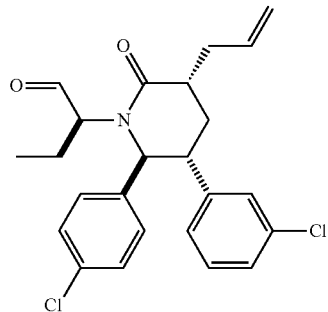

To a mixture of 2.00 g (4.63 mmol) (3R,5R,6S)-3-allyl-5-(3-chlorophenyl)-6-(4-chlorophenyl)-1-((S)-1-hydroxybutan-2-yl)piperidin-2-one (Example 126, Step B) in water (0.125 g, 6.94 mmol) and DCM (50 mL) was added Dess-Martin periodinane (2.94 g, 6.94 mmol) at ambient temperature. After being stirred for 1 h (no SM detected by TLC), the reaction was quenched by addition of 10 mL of 0.5 M Na$_2$S$_2$O$_3$, extracted with DCM, and washed with sat. aq. NaHCO$_3$ solution and sat. aq. NaCl solution. The combined organic layers were dried over Na$_2$SO$_4$, filtered and the filtrate was concentrated under reduced pressure. Purification of the residue by chromatography on silica gel (80 g SiO$_2$, 5 to 20% EtOAc/hexanes) provided the title compound as a white foam.

Step D. (3R,5R,6S)-3-allyl-5-(3-chlorophenyl)-6-(4-chlorophenyl)-1-(1-(methylamino)butan-2-yl)piperidin-2-one

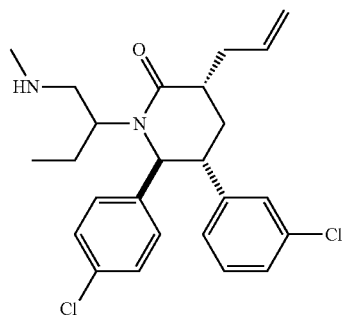 [SMILES: C=CC[C@@H]1C[C@H](c2cccc(Cl)c2)[C@@H](c2ccc(Cl)cc2)N(C(CC)CNC)C1=O]

To a solution of 1.67 g (3.88 mmol) of (S)-2-((3R,5R,6S)-3-allyl-5-(3-chlorophenyl)-6-(4-chlorophenyl)-2-oxopiperidin-1-yl)butanal (Example 126, Step C) and acetic acid (6.60 mL, 116 mmol) in DCE (40 mL) was added 2 M methylamine in THF (19.40 mL, 38.8 mmol) and sodium triacetoxy hydroborate (3.29 g, 15.52 mmol) at room temperature. The reaction was stirred for 2 days. The reaction was quenched with sat aq. NaHCO$_3$, extracted with EtOAc, and the combined organic layers were washed with 1N NaOH and sat. aq. NaCl solution, dried over Na$_2$SO$_4$ and concentrated under reduced pressure to provide the title compound as a pale yellow oil, which was used without further purification in the next step.

Step E. N-(2-((3R,5R,6S)-3-allyl-5-(3-chlorophenyl)-6-(4-chlorophenyl)-2-oxopiperidin-1-yl)butyl)-N-methylcyclopropanesulfonamide

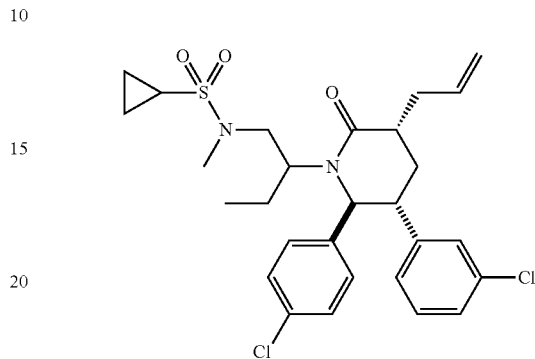

To a solution of the free amine made in Example 126, step D (1.67 g, 3.75 mmol) in DCE (15 mL) was added pyridine (6.06 mL, 75.0 mmol) and cyclopropanesulfonyl chloride (3.85 mL, 37.5 mmol) successively at 40° C. The reaction was stirred at 40° C. for 14 h. After that time additional 10 eq. pyridine and 10 eq. cyclopropanesulfonyl chloride were added. The reaction was stirred at 40° C. for 14 h. The reaction was acidified with 10% citric acid and extracted with EtOAc. The combined organic layers were washed with saturated aq. NaHCO$_3$ solution and sat. aq. NaCl solution, dried over Na$_2$SO$_4$, and concentrated under reduced pressure. Purification by chromatography on silica gel (SiO$_2$, 25 g; eluent: 20% to 40% EtOAc/Hexanes) provided the title compound as a white foam.

Step F. 2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)acetic acid N-(2-((3R,5R,6S)-3-allyl-5-(3-chlorophenyl)-6-(4-chlorophenyl)-2-oxopiperidin-1-yl)butyl)-N-methylcyclopropanesulfonamide (Example 126, Step D) was converted to the acid by a procedure similar to the one described in Example 1, Step H, to provide the crude title compound. The crude material was absorbed onto a plug of silica gel and purified by chromatography, eluting with 60% to 80% EtOAc in hexane, to provide a colorless oil. This was purified by reverse phase preparatory HPLC (eluent: 10 to 90% acetonitrile, water, 0.1% TFA, gradient elution) to provide the title compound as the second eluting peak from reverse-phase-HPLC) as a white solid after lyophilization.

$^1$H NMR (400 MHz, CHLOROFORM-d) δ ppm 0.51 (t, J=7.53 Hz, 3 H), 0.96-1.11 (m, 2 H), 1.17-1.32 (m, 2 H), 1.61 (ddd, J=14.28, 7.83, 3.91 Hz, 1 H), 1.88-2.02 (m, 2 H), 2.31-2.47 (m, 3 H), 2.68-2.77 (m, 1 H), 2.81 (br. s., 1 H), 2.86-3.10 (m, 2 H), 2.92 (s, 3 H), 3.23 (dd, J=15.45, 10.17 Hz, 1 H), 4.67 (d, J=10.56 Hz, 1 H), 6.86 (m, 1 H), 6.94 (m, 3 H), 7.11-7.20 (m, 2 H), 7.23-7.32 (m, 2 H); Mass Spectrum (ESI) m/z=567.2 (M+1).

Example 127

2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)propanoic acid

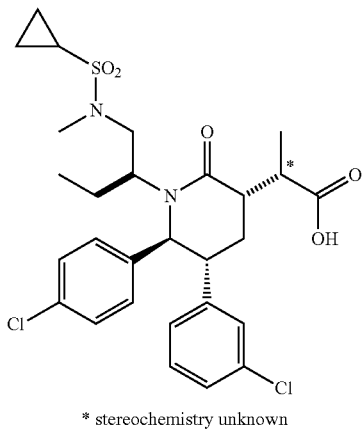 [SMILES: CC[C@@H](CN(C)S(=O)(=O)C1CC1)N1C(=O)[C@H](C(C)C(=O)O)C[C@H](c2cccc(Cl)c2)[C@H]1c1ccc(Cl)cc1]

* stereochemistry unknown

Step A. (3R,5R,6S)-3-allyl-1-((S)-1-((tert-butyl-diphenylsilyl)oxy)butan-2-yl)-5-(3-chlorophenyl)-6-(4-chlorophenyl)piperidin-2-one

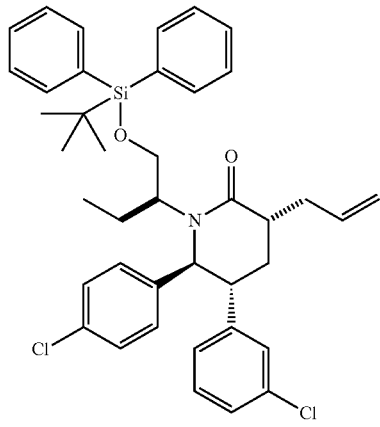 [SMILES: C=CC[C@@H]1C[C@H](c2cccc(Cl)c2)[C@@H](c2ccc(Cl)cc2)N([C@@H](CC)CO[Si](c2ccccc2)(c2ccccc2)C(C)(C)C)C1=O]

To a solution of 615 mg (1.422 mmol) (3R,5R,6S)-3-allyl-5-(3-chlorophenyl)-6-(4-chlorophenyl)-1-((S)-1-hydroxybutan-2-yl)piperidin-2-one (Example 126, Step B) in DMF (4741 µL) at 0° C. was added 1H-imidazole (97 mg, 1.422 mmol) followed by tert-butylchlorodiphenylsilane (473 µL, 1.849 mmol). The mixture was stirred at 0° C. for 15 min and then warmed to room temperature. The mixture was stirred at room temperature for 30 min and then quenched with sat. NH₄Cl. The mixture was extracted with EtOAc and the organic layer was washed with water, 1 M LiCl, and sat. aq. NaCl solution. The mixture was dried over Na₂SO₄ and concentrated under reduced pressure. The residue was purified by flash chromatography on silica gel (24 g column; eluent: 0 to 30% EtOAc in hexanes) to give the title compound.

Step B. 2-((3S,5R,6S)-1-((S)-1-((tert-butyldiphenyl-silyl)oxy)butan-2-yl)-5-(3-chlorophenyl)-6-(4-chlorophenyl)-2-oxopiperidin-3-yl)acetic acid

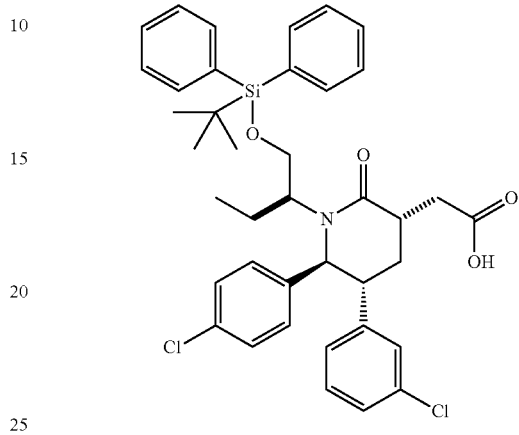

To a solution of (3R,5R,6S)-3-allyl-1-((S)-1-(tert-butyl-diphenylsilyloxy)butan-2-yl)-5-(3-chlorophenyl)-6-(4-chlorophenyl)piperidin-2-one (816 mg, 1.216 mmol; Example 127, Step A) in water/acetonitrile/CCl₄ (7 mL/5 mL/5 mL) at room temperature was added sodium periodate (1041 mg, 4.87 mmol) and ruthenium chloride hydrate (27.4 mg, 0.122 mmol). The mixture was stirred vigorously at room temperature for 3 h. The mixture was diluted with EtOAc and acidified with 1 M HCl. Sat. aq. NaCl solution was added and the mixture was filtered to remove the emulsion. The layers of the filtrate were separated. The organic layer was dried over Na₂SO₄ and concentrated under reduced pressure. The residue was purified by flash chromatography on silica gel (24 g column; eluent: 0 to 50% EtOAc in hexanes) to give the title compound.

Step C. Methyl 2-((3S,5R,6S)-1-((S)-1-((tert-butyl-diphenylsilyl)oxy)butan-2-yl)-5-(3-chlorophenyl)-6-(4-chlorophenyl)-2-oxopiperidin-3-yl)acetate

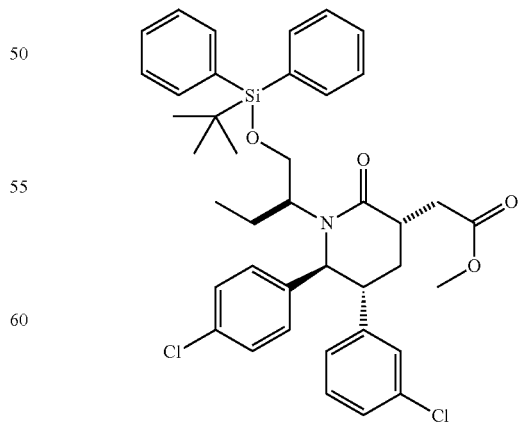

To a solution of 2-((3S,5R,6S)-1-((S)-1-(tert-butyldiphenylsilyloxy)butan-2-yl)-5-(3-chlorophenyl)-6-(4-chlorophenyl)-2-oxopiperidin-3-yl)acetic acid (741 mg, 1.076 mmol; Example 127, Step B) in 10 mL of a 10% solution of MeOH in DCM at room temperature was added TMS-diazomethane (2.0M in ether) (807 μL, 1.614 mmol). Evolution of gas was observed and the yellow mixture was stirred at room temperature for 45 min. More TMS-diazomethane (2.0M in ether) (807 μL, 1.614 mmol) was added and the reaction was stirred at room temperature for 45 min. The mixture was concentrated under reduced pressure. The residue was purified by flash chromatography on silica gel (24 g column; eluent: 0 to 30% EtOAc in hexanes) to give the title compound.

Step D. Methyl 2-((3S,5R,6S)-1-((S)-1-((tert-butyl-diphenylsilyl)oxy)butan-2-yl)-5-(3-chlorophenyl)-6-(4-chlorophenyl)-2-oxopiperidin-3-yl)propanoate

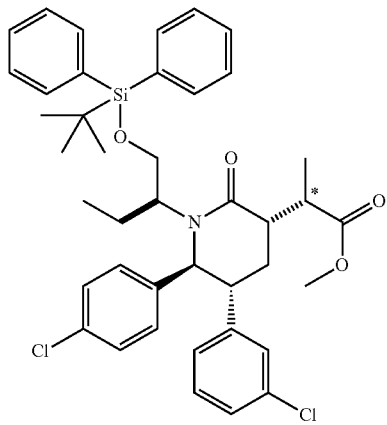 [SMILES: CC[C@@H](CO[Si](c1ccccc1)(c1ccccc1)C(C)(C)C)N1C(=O)[C@H](CC(=O)OC)C[C@H](c2cccc(Cl)c2)[C@H]1c1ccc(Cl)cc1]

* stereochemistry unknown

Methyl 2-((3S,5R,6S)-1-((S)-1-((tert-butyldiphenylsilyl) oxy)butan-2-yl)-5-(3-chlorophenyl)-6-(4-chlorophenyl)-2-oxopiperidin-3-yl)acetate (Example 127, Step C) was azetroped with toluene 3× and then dissolved in THF (14 mL) under Ar and the mixture was cooled to −78° C. HMPA (236 μL, 1.356 mmol) and LHMDS (1.0M in THF) (1356 μL, 1.356 mmol) were added under Ar at −78° C. The mixture was stirred at −78° C. for 30 min. The mixture color turned light yellow. Then iodomethane (110 μL, 1.763 mmol) was added and the reaction mixture was allowed to slowly warm to room temperature. The mixture was quenched with sat. NH₄Cl and the layers were separated. The combined organic layers were dried over Na₂SO₄ and concentrated under reduced pressure. The residue was purified by flash chromatography on silica gel (2×50 g stacked VersaPak I-style, Spherical, Supelco, Bellenfonte, Pa.; eluent: 20 to 30% MtBE in hexanes) to give the title compound as the less polar, major diastereomer. The retention time of the less polar diastereomer is 0.871 min (80-100% MeCN +0.1% TFA in water +0.1% TFA, over 1 minute). The retention time of the more polar diastereomer is 0.841 min (80 to 100% MeCN +0.1% TFA in water +0.1% TFA, over 1 minute).

Step E. Methyl 2-((3S,5R,6S)-5-(3-chlorophenyl)-6-(4-chlorophenyl)-1-((S)-1-hydroxybutan-2-yl)-2-oxopiperidin-3-yl)propanoate

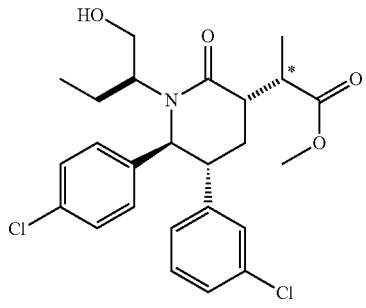

* stereochemistry unknown

To a solution of methyl 2-((3S,5R,6S)-1-((S)-1-((tert-butyldiphenylsilyl)oxy)butan-2-yl)-5-(3-chlorophenyl)-6-(4-chlorophenyl)-2-oxopiperidin-3-yl)propanoate (285 mg, 0.398 mmol) (the less polar isomer from step D) in THF (1988 μL) was added TBAF (1.0M in THF) (1590 μL, 1.590 mmol). The mixture was stirred at room temperature for 16 h. The mixture was quenched with 1 M HCl and diluted with EtOAc. The organic layer was washed with sat. aq. NaCl solution, dried over Na₂SO₄ and concentrated under reduced pressure. The residue was purified by flash chromatography on silica gel (11 g VersaPak I-style, Spherical, Supelco, Bellenfonte, Pa.; eluent: 50 to 75% MtBE in hexanes) to give the title compound.

Step F. Methyl 2-((3S,5R,6S)-5-(3-chlorophenyl)-6-(4-chlorophenyl)-1-((S)-1-(N-methylcyclopropane-sulfonamido)butan-2-yl)-2-oxopiperidin-3-yl)propanoate

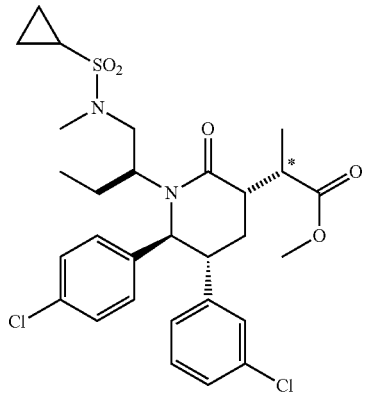

* stereochemistry unknown

A flask, containing a solution of methyl 2-((3S,5R,6S)-5-(3-chlorophenyl)-6-(4-chlorophenyl)-1-((S)-1-hydroxybutan-2-yl)-2-oxopiperidin-3-yl)propanoate (195 mg, 0.408 mmol; Example 127, Step E) and N-methylcyclopropanesulfonamide (165 mg, 1.223 mmol) in toluene (2038 μL) was evacuated and backfilled with Ar (5×). Then cyanomethylenetributylphosphorane (321 μL, 1.223 mmol) was added. The light brownish orange mixture was heated to 70° C. for 2 h. More N-methylcyclopropanesulfonamide (134 mg, 0.991 mmol) was added and the mixture was heated to 70° C. for 2 h. The mixture was heated to reflux overnight and then cooled to room temperature. The mixture was diluted with EtOAc and sat. aq. NaCl solution. The layers were separated. The organic layer was dried over $Na_2SO_4$ and concentrated under reduced pressure. The residue was purified by flash chromatography on silica gel (4 g column eluent: 0 to 100% EtOAc in hexanes) to give the title compound.

Step G. 2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)propanoic acid To a solution of methyl 2-((3S,5R,6S)-5-(3-chlorophenyl)-6-(4-chlorophenyl)-1-((S)-1-(N-methylcyclopropanesulfonamido)butan-2-yl)-2-oxopiperidin-3-yl)propanoate (56 mg, 0.094 mmol; Example 127, Step F) in MeOH/THF/$H_2O$ (1 mL/1 mL/2 mL) was added LiOH (3 M in water) (157 μL, 0.470 mmol) at room temperature. The slurry was heated to ~100° C. for 3 h. The mixture was cooled to room temperature, acidified with 1 M HCl and extracted with EtOAc (2×). The organic layers were combined, dried over $Na_2SO_4$, filtered and the filtrate was concentrated under reduced pressure. The colorless film was purified by reverse phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes) to give the title compound.
$^1$H NMR (400 MHz, CHLOROFORM-d) δ ppm 0.50 (t, J=6.65 Hz, 3 H), 0.95-1.07 (m, 2 H), 1.20-1.26 (m, 5 H), 1.40 (dd, J=10.96, 7.24 Hz, 1 H), 1.52-1.66 (m, 1 H), 1.85-1.93 (m, 1 H), 1.96-2.00 (m, 1 H), 2.22-2.36 (m, 2 H), 2.70-2.79 (m, 1 H), 2.88-3.07 (m, 6 H), 3.13 (quin, J=7.19 Hz, 1 H), 4.67 (d, J=10.56 Hz, 1 H), 6.89-6.92 (m, 1 H), 6.94-7.01 (m, 3 H), 7.14-7.18 (m, 2 H), 7.25 (d, J=8.41 Hz, 2 H); Mass Spectrum (ESI) m/z=603 (M+23), 581 (M+1).

Example 128

(S)-tert-butyl 2-((3R,5R,6S)-3-((1H-tetrazol-5-yl)methyl)-5-(3-chlorophenyl)-6-(4-chlorophenyl)-3-methyl-2-oxopiperidin-1-yl)butanoate

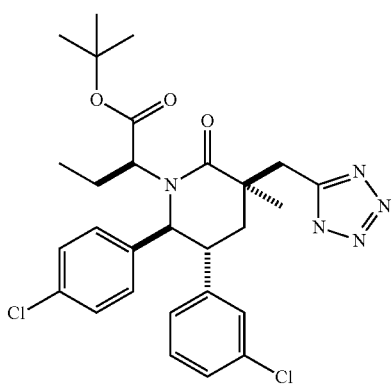 [SMILES: CC[C@@H](C(=O)OC(C)(C)C)N1C(=O)[C@@](C)(Cc2nnn[nH]2)C[C@H](c2cccc(Cl)c2)[C@H]1c1ccc(Cl)cc1]

Step A. (S)-tert-butyl 2-((3R,5R,6S)-3-(2-amino-2-oxoethyl)-5-(3-chlorophenyl)-6-(4-chlorophenyl)-3-methyl-2-oxopiperidin-1-yl)butanoate

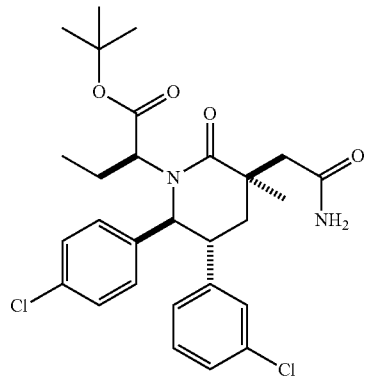 [SMILES: CC[C@@H](C(=O)OC(C)(C)C)N1C(=O)[C@@](C)(CC(N)=O)C[C@H](c2cccc(Cl)c2)[C@H]1c1ccc(Cl)cc1]

A solution of 2-((3R,5R,6S)-1-((S)-1-tert-butoxy-1-oxobutan-2-yl)-5-(3-chlorophenyl)-6-(4-chlorophenyl)-3-methyl-2-oxopiperidin-3-yl)acetic acid (230 mg, 0.430 mmol; Example 67) in DMF (4.3 mL) was treated with N-(3-dimethylaminopropyl)-N'-ethylcarbodiimide hydrochloride (165 mg, 0.86 mmol), 1-hydroxy-7-azabenzotriazole (117 mg, 0.86 mmol) and $NaHCO_3$ (72.3 mg, 0.861 mmol) successively. After being stirred at rt for 0.5 h, 7 M ammonia in methanol (6.2 mL, 4.30 mmol) was added dropwise and the reaction was stirred overnight. Then, the reaction was diluted (water), extracted (2×EtOAc), and washed (1× saturated $NaHCO_3$, and 2×sat. aq. NaCl solution). The combined organic layers were dried ($Na_2SO_4$) and concentrated under reduced pressure. Purification by RP-HPLC (45 to 70% MeCN/$H_2O$ (0.1% TFA), a gradient elution) provided the title compound as a white solid.

Step B. (S)-tert-butyl 2-((3R,5R,6S)-5-(3-chlorophenyl)-6-(4-chlorophenyl)-3-(cyanomethyl)-3-methyl-2-oxopiperidin-1-yl)butanoate

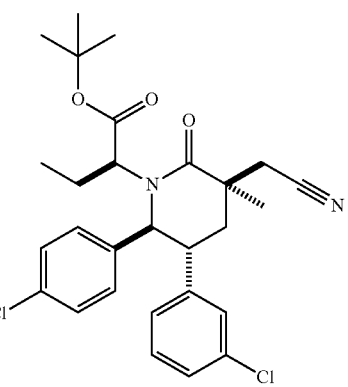

A solution of (S)-tert-butyl 2-((3R,5R,6S)-3-(2-amino-2-oxoethyl)-5-(3-chlorophenyl)-6-(4-chlorophenyl)-3-methyl-2-oxopiperidin-1-yl)butanoate (105 mg, 0.197 mmol; Example 128, Step A) and triethylamine (137 μL, 0.984 mmol) in THF (3.3 mL) was treated with 2,2,2-trifluoroacetic anhydride (69.8 μL, 0.492 mmol) at 0° C. After being stirred at 0° C. for 3 h, the reaction was quenched (10% citric acid), extracted (2×EtOAc) and washed (sat. aq. NaCl solution).

The combined organic layers were dried (Na$_2$SO$_4$) and concentrated under reduced pressure. Purification of the residue by chromatography on silica gel (12 g SiO$_2$, 20 to 50% EtOAc/Hex, a gradient elution) provided the title compound as a colorless foam.

Step C. (S)-tert-butyl 2-((3R,5R,6S)-3-((1H-tetrazol-5-yl)methyl)-5-(3-chlorophenyl)-6-(4-chlorophenyl)-3-methyl-2-oxopiperidin-1-yl)butanoate To a solution of (S)-tert-butyl 2-((3R,5R,6S)-5-(3-chlorophenyl)-6-(4-chlorophenyl)-3-(cyanomethyl)-3-methyl-2-oxopiperidin-1-yl)butanoate (101 mg, 0.196 mmol; Example 128, Step B) in DMF (0.50 mL) was added sodium azide (127 mg, 1.96 mmol) and NH$_4$Cl (105 mg, 1.96 mmol). The resulting mixture was stirred at 90° C. for 5 days. Then, the reaction was quenched (aq. 10% citric acid), extracted (2×EtOAc), and washed (3×sat. aq. NaCl solution). The combined organic layer was dried (Na$_2$SO$_4$) and concentrated under reduced pressure. Purification by RP-HPLC (60 to 85% AcCN/H$_2$O, gradient elution) provided the title compound as a white solid.
$^1$H NMR (400 MHz, CHLOROFORM-d) δ ppm 7.23-7.26 (2 H, m), 7.09-7.19 (2 H, m), 7.01 (1 H, t, J=1.9 Hz), 6.92 (2 H, d, J=8.6 Hz), 6.75-6.80 (1 H, m), 4.60 (1 H, d, J=10.8 Hz), 3.44-3.63 (2 H, m), 3.27 (1 H, br. s.), 3.15 (1 H, dd, J=8.3, 3.4 Hz), 2.29-2.42 (2 H, m), 2.24 (1 H, d, J=3.3 Hz), 1.49-1.52 (8 H, m), 1.34-1.40 (1 H, m), 1.32 (3 H, s), 0.55 (3 H, t, J=7.4 Hz); MS (ESI) 558.1 [M+H]$^+$, 556.2 [M−H]$^-$.

Example 129

2-((3R,5R,6S)-5-(3-chlorophenyl)-6-(4-chlorophenyl)-3-methyl-1-((S)-1-(methylsulfonamido)butan-2-yl)-2-oxopiperidin-3-yl)acetic acid

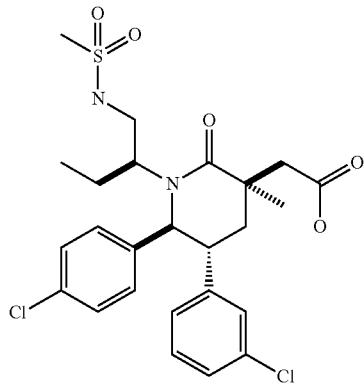 [SMILES: CC[C@@H](CNS(C)(=O)=O)N1C(=O)[C@@](C)(CC(=O)O)C[C@H](c2cccc(Cl)c2)[C@H]1c1ccc(Cl)cc1]

Step A. (3R,5R,6S)-3-allyl-5-(3-chlorophenyl)-6-(4-chlorophenyl)-1-((S)-1-((4-methoxybenzyl)amino)butan-2-yl)-3-methylpiperidin-2-one

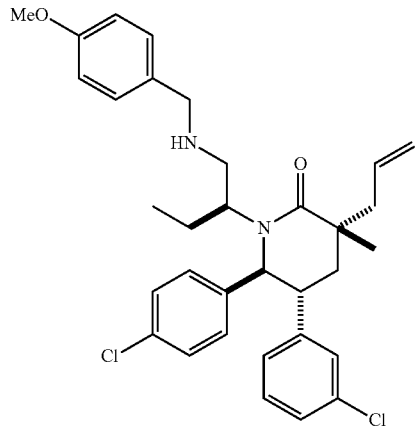 [SMILES: C=CC[C@]1(C)C[C@H](c2cccc(Cl)c2)[C@@H](c2ccc(Cl)cc2)N([C@@H](CC)CNCc2ccc(OC)cc2)C1=O]

To a solution of (S)-2-((3R,5R,6S)-3-allyl-5-(3-chlorophenyl)-6-(4-chlorophenyl)-3-methyl-2-oxopiperidin-1-yl)butanal (300 mg, 0.675 mmol; Example 91, Step C) and (4-methoxyphenyl)methanamine (131 µL, 1.01 mmol) in DCE (4.5 mL) was added sodium triacetoxyborohydride (429 mg, 2.03 mmol) at 0° C. in several portions. After being stirred at 25° C. for 18 h, the reaction was quenched by adding ice-cold saturated aqueous NaHCO$_3$ and extracted (2×DCM). The combined organic layers were washed (1×sat. aq. NaCl solution) and concentrated under reduced pressure to provide the title compound as a yellow film. The product was used in the next step without further purification.

Step B. (S)-2-((3S,5R,6S)-3-Allyl-5-(3-chlorophenyl)-6-(4-chlorophenyl)-3-methyl-2-oxopiperidin-1-yl)butan-1-ammonium 2,2,2-trifluoroacetate

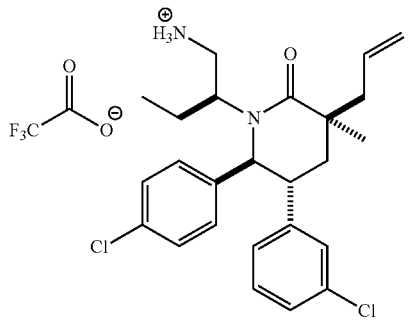 [SMILES: O=C([O-])C(F)(F)F ; C=CC[C@@]1(C)C[C@H](c2cccc(Cl)c2)[C@@H](c2ccc(Cl)cc2)N([C@@H](CC)C[NH3+])C1=O]

To a solution of (3S,5R,6S)-3-allyl-5-(3-chlorophenyl)-6-(4-chlorophenyl)-1-((S)-1-(4-methoxybenzylamino)butan-2-yl)-3-methylpiperidin-2-one (370 mg, 0.654 mmol; Example 129, Step A) in acetonitrile (8.0 mL) and water (1.6 mL) was added ceric ammonium nitrate (2.87 g, 5.23 mmol) at 25° C. After being stirred at rt for 2 days, the reaction was quenched (sat. aq. NaCl solution), extracted (3×EtOAc), and washed (1×sat. aq. NaCl solution). The combined organic layers were dried (Na$_2$SO$_4$) and concentrated under reduced pressure. Purification by RP-HPLC (35 to 70% MeCN/H$_2$O (0.1% TFA), a gradient elution) provided the title compound as a pale yellow powder.

Step C. N-((S)-2-((3S,5R,6S)-3-Allyl-5-(3-chlorophenyl)-6-(4-chlorophenyl)-3-methyl-2-oxopiperidin-1-yl)butyl)methanesulfonamide

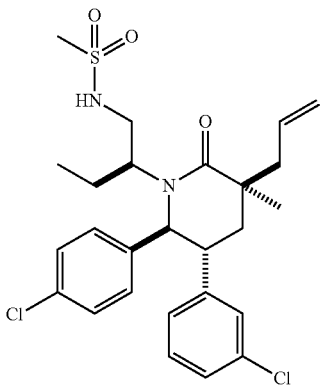 [SMILES: C=CC[C@@]1(C)C[C@H](c2cccc(Cl)c2)[C@@H](c2ccc(Cl)cc2)N([C@@H](CC)CNS(C)(=O)=O)C1=O]

(S)-2-((3S,5R,6S)-3-allyl-5-(3-chlorophenyl)-6-(4-chlorophenyl)-3-methyl-2-oxopiperidin-1-yl)butan-1-aminium 2,2,2-trifluoroacetate (74 mg, 0.14 mmol; Example 129, Step B) was dissolved in DCM at 0° C. and 2 N lithium hydroxide (0.34 mL, 0.68 mmol) was added and the resulting solution was stirred for 5 min at 0° C. The solution was extracted (2×DCM), washed (sat. aq. NaCl solution), dried (Na$_2$SO$_4$), and concentrated under reduced pressure to give the free amine. To a solution of the free amine from above in DMF (0.34 mL) was added methanesulfonyl chloride (53 μL, 0.68 mmol) and pyridine (66 μL, 0.820 mmol) successively at 0° C. After being stirred at 25° C. for overnight, the reaction was acidified (10% citric acid) and extracted (2×EtOAc) and washed (sat. aq. NaCl solution). The combined organic layers were dried (Na$_2$SO$_4$), and concentrated under reduced pressure. Purification by RP-HPLC (45 to 80% MeCN/H$_2$O (0.1% TFA), a gradient elution) provided the title compound as a white powder.

Step D. 2-((3R,5R,6S)-5-(3-Chlorophenyl)-6-(4-chlorophenyl)-3-methyl-1-((S)-1-(methylsulfonamido)butan-2-yl)-2-oxopiperidin-3-yl)acetic acid To a rapidly stirring solution of N-((S)-2-((3S,5R,6S)-3-allyl-5-(3-chlorophenyl)-6-(4-chlorophenyl)-3-methyl-2-oxopiperidin-1-yl)butyl)methanesulfonamide (34 mg, 0.064 mmol; Example 91, Step C) in a mixture of water (0.55 mL), acetonitrile (0.37 mL), and CCl$_4$ (0.37 mL) was added sodium periodate (55 mg, 0.26 mmol) and ruthenium(III) chloride hydrate (1.5 mg, 6.5 μmol). After being stirred vigorously for 20 h, the reaction was acidified (10% citric acid) and diluted with EtOAc. The insoluble material was removed by filtering through a pad of Celite® (J. T. Baker, Phillipsberg, N.J., diatomaceous earth). The filtrate was extracted (2×EtOAc) and washed (sat. aq. NaCl solution). The combined organic layers were dried (Na$_2$SO$_4$) and concentrated under reduced pressure. Purification by RP-HPLC (40 to 70% MeCN/H$_2$O (0.1% TFA), a gradient elution) provided the title compound as a white foam.

$^1$H NMR (400 MHz, CHLOROFORM-d) δ ppm 7.25 (2 H, d, J=8.2 Hz), 7.10-7.18 (2 H, m), 7.00-7.10 (2 H, m), 6.97 (1 H, s), 6.83 (1 H, d, J=7.2 Hz), 4.99-5.20 (1 H, m), 4.87-4.97 (1 H, m), 4.74 (1 H, d, J=10.4 Hz), 3.44-3.65 (1 H, m), 3.10-3.33 (2 H, m), 3.02-3.09 (1 H, m), 2.99 (3 H, s), 2.96 (1 H, s), 2.77 (1 H, s), 2.36 (1 H, s), 1.94-2.05 (1 H, m), 1.77-1.92 (1 H, m), 1.52-1.59 (1 H, m), 1.50 (3 H, s), 0.58 (3 H, t, J=7.3 Hz); MS (ESI) 541.0 [M+H]$^+$, 539.0 [M−H]$^−$.

Example 130

2-((3R,5R,6S)-5-(3-Chlorophenyl)-6-(4-chlorophenyl)-3-methyl-2-oxo-1-((S)-5-oxohexan-3-yl)piperidin-3-yl)acetic acid

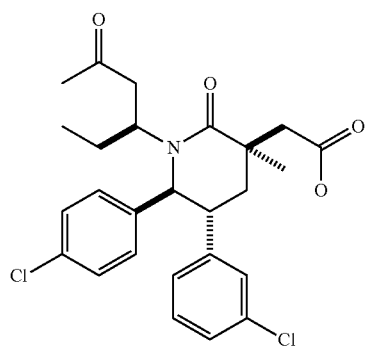 [SMILES: CC[C@@H](CC(C)=O)N1C(=O)[C@@](C)(CC(=O)O)C[C@H](c2cccc(Cl)c2)[C@H]1c1ccc(Cl)cc1]

Step A. (S)-3-((3S,5R,6S)-3-allyl-5-(3-chlorophenyl)-6-(4-chlorophenyl)-3-methyl-2-oxopiperidin-1-yl)pentanal

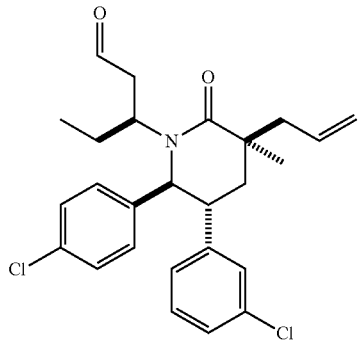 [SMILES: C=CC[C@@]1(C)C[C@H](c2cccc(Cl)c2)[C@@H](c2ccc(Cl)cc2)N([C@@H](CC)CC=O)C1=O]

(Methoxymethyl)triphenylphosphonium chloride was dried at 80° C. under vacuum for 3 h. To a solution of the dried (methoxymethyl)triphenylphosphonium chloride (1.96 g, 5.71 mmol) in THF (10 mL) was added 0.5 M KHMDS in toluene (10.2 mL, 5.08 mmol) at −78° C. The color of the solution turned blood red in color. After stirring at 0° C. for 30 min., a solution of (S)-2-((3S,5R,6S)-3-allyl-5-(3-chlorophenyl)-6-(4-chlorophenyl)-3-methyl-2-oxopiperidin-1-yl)butanal (Example 91, Step C; 564 mg, 1.27 mmol) in THF (10.1 mL) was added at 0° C. dropwise. After being stirred at rt for overnight, the reaction was quenched (sat NH$_4$Cl solution), extracted (2×EtOAc), and washed (sat. aq. NaCl solution). The combined organic layers were dried (Na$_2$SO$_4$) and concentrated under reduced pressure. Purification by chromatography on silica gel (SiO$_2$, 40 g, 15% and 20% EtOAc/Hexanes) provided the vinyl ether (3S,5R,6S)-3-allyl-5-(3-chlorophenyl)-6-(4-chlorophenyl)-1-((S,E)-1-methoxypent-1-en-3-yl)-3-methylpiperidin-2-one. To a solution of (3S,5R,6S)-3-allyl-5-(3-chlorophenyl)-6-(4-chlorophenyl)-1-((S,E)-1-methoxypent-1-en-3-yl)-3-methylpiperidin-2-one prepared above in acetonitrile (7.8 mL) was added 3 N hydrochloric acid (4.4 mL, 13 mmol) and the resulting solution was stirred at rt for 1.5 h. Then, the reaction was extracted (2×EtOAc), and washed (sat. aq. NaCl solution). The combined organic layers were dried (Na$_2$SO$_4$) and concentrated under reduced pressure to provide the title compound as a pale yellow film.

Step B. (3S,5R,6S)-3-allyl-5-(3-chlorophenyl)-6-(4-chlorophenyl)-1-((3S)-5-hydroxyhexan-3-yl)-3-methylpiperidin-2-one

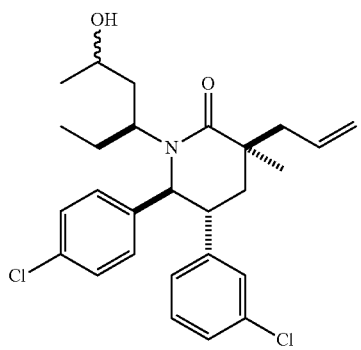 [SMILES: C=CC[C@@]1(C)C[C@H](c2cccc(Cl)c2)[C@@H](c2ccc(Cl)cc2)N([C@@H](CC)CC(C)O)C1=O]

309

To a solution of (S)-3-((3S,5R,6S)-3-allyl-5-(3-chlorophenyl)-6-(4-chlorophenyl)-3-methyl-2-oxopiperidin-1-yl)pentanal (540 mg, 1.18 mmol; Example 130, Step A) in THF (12 mL) was added 1.4 M methylmagnesium bromide in toluene and THF (75:25) (2.52 mL, 3.53 mmol) at 0° C. Then the reaction was allowed to warm to rt and stirred for 3 h. The reaction was quenched (sat NH₄Cl solution), extracted (2×EtOAc), and washed (sat. aq. NaCl solution). The combined organic layers were dried (Na₂SO₄) and concentrated under reduced pressure to provide the crude title compound as a mixture of diastereomers.

Step C. 2-((3R,5R,6S)-5-(3-chlorophenyl)-6-(4-chlorophenyl)-3-methyl-2-oxo-1-((S)-5-oxohexan-3-yl)piperidin-3-yl)acetic acid The title compound was obtained from (3S,5R,6S)-3-allyl-5-(3-chlorophenyl)-6-(4-chlorophenyl)-1-((S)-5-hydroxyhexan-3-yl)-3-methylpiperidin-2-one (90 mg, 0.19 mmol; Example 130 Step B) as described in Example 71, Step F as a white foam.

¹H NMR (400 MHz, CHLOROFORM-d) δ ppm 7.23-7.27 (2 H, m), 7.06-7.17 (4 H, m), 7.00 (1 H, t, J=1.8 Hz), 6.81 (1 H, s), 4.92 (1 H, d, J=10.8 Hz), 3.54-3.63 (1 H, m), 3.07 (3 H, d, J=15.7 Hz), 2.67 (1 H, d, J=15.8 Hz), 2.50-2.60 (1 H, m), 2.19 (3 H, s), 2.12 (1 H, s), 1.97-2.07 (1 H, m), 1.88-1.96 (1 H, m), 1.39 (3 H, s), 1.21-1.32 (1 H, m), 0.37 (3 H, t, J=7.5 Hz);

MS (ESI) 490.0 [M+H]⁺, 488.0 [M−H]⁻.

Example 131

2-((3R,5R,6S)-5-(3-chlorophenyl)-6-(4-chlorophenyl)-1-((S)-5-hydroxy-5-methylhexan-3-yl)-3-methyl-2-oxopiperidin-3-yl)acetic acid

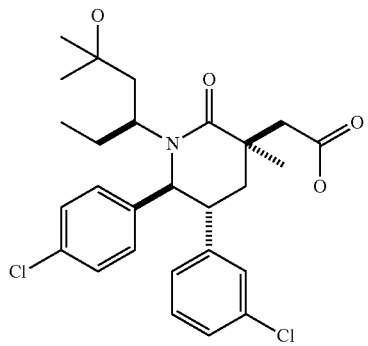 [SMILES: CC[C@@H](CC(C)(C)O)N1C(=O)[C@@](C)(CC(=O)O)C[C@H](c2cccc(Cl)c2)[C@H]1c1ccc(Cl)cc1]

310

Step A. (3S,5R,6S)-3-allyl-5-(3-chlorophenyl)-6-(4-chlorophenyl)-3-methyl-1-((S)-5-oxohexan-3-yl)piperidin-2-one

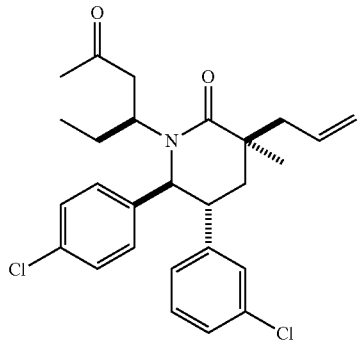 [SMILES: C=CC[C@@]1(C)C[C@H](c2cccc(Cl)c2)[C@@H](c2ccc(Cl)cc2)N([C@@H](CC)CC(C)=O)C1=O]

The title compound was prepared from (3S,5R,6S)-3-allyl-5-(3-chlorophenyl)-6-(4-chlorophenyl)-1-((S)-5-hydroxyhexan-3-yl)-3-methylpiperidin-2-one (100 mg, 0.21 mmol; Example 130, Step B) by a procedure similar to the one described in Example 129, Step C.

Step B. (3S,5R,6S)-3-allyl-5-(3-chlorophenyl)-6-(4-chlorophenyl)-1-((S)-5-hydroxy-5-methylhexan-3-yl)-3-methylpiperidin-2-one

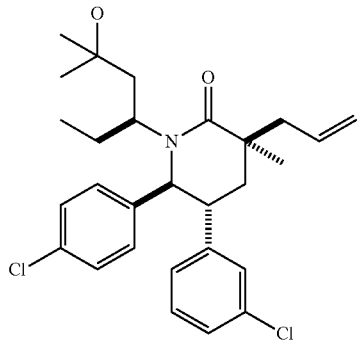 [SMILES: C=CC[C@@]1(C)C[C@H](c2cccc(Cl)c2)[C@@H](c2ccc(Cl)cc2)N([C@@H](CC)CC(C)(C)O)C1=O]

To a solution of (3S,5R,6S)-3-allyl-5-(3-chlorophenyl)-6-(4-chlorophenyl)-3-methyl-1-((S)-5-oxohexan-3-yl)piperidin-2-one (90 mg, 0.19 mmol; Example 131, Step A) in THF (1.9 mL) was added 1.4 M methylmagnesium bromide in toluene and THF (75:25) (408 µL, 0.571 mmol) at 0° C. Then the reaction was allowed to warm to rt and stirred for 4 h. The reaction was quenched (sat NH₄Cl solution), extracted (2×EtOAc), and washed (sat. aq. NaCl solution). The combined organic layer was dried (Na₂SO₄) and concentrated under reduced pressure and purification of the residue by chromatography on silica gel (12 g SiO₂, 30% and 35% EtOAc/Hex) provided the title compound as a colorless foam.

Step C. 2-((3R,5R,6S)-5-(3-chlorophenyl)-6-(4-chlorophenyl)-1-((S)-5-hydroxy-5-methylhexan-3-yl)-3-methyl-2-oxopiperidin-3-yl)acetic acid The title compound was obtained from (3S,5R,6S)-3-allyl-5-(3-chlorophenyl)-6-(4-chlorophenyl)-1-((S)-5-hydroxy-5-methylhexan-3-yl)-3-methylpiperidin-2-one (73 mg, 0.15 mmol; Example 131, Step B) by a procedure similar to the one described in Example 71, Step F as a white foam.

¹H NMR (400 MHz, CHLOROFORM-d) δ ppm 7.25 (2 H, d, J=7.8 Hz), 6.98-7.18 (4 H, m), 6.95 (1 H, t, J=1.8 Hz), 6.70 (1 H, d, J=7.6 Hz), 4.90-5.38 (2 H, m), 4.67-4.81 (1 H, m), 3.51 (1 H, s), 2.98-3.13 (2 H, m), 2.70 (1 H, d, J=15.1 Hz), 2.19 (1 H, t, J=13.8 Hz), 1.93 (2 H, d, J=13.3 Hz), 1.48 (4 H, s), 1.16-1.28 (7 H, m), 0.53 (3 H, br. s.); MS (ESI) 506.0 [M+H]⁺, 504.0 [M−H]⁻.

Example 132

2-((3R,5R,6S)-5-(3-chlorophenyl)-6-(4-chlorophenyl)-3-methyl-2-oxo-1-((3S)-6,6,6-trifluoro-5-hydroxy-5-methylhexan-3-yl)piperidin-3-yl)acetic acid (Isomer 1)

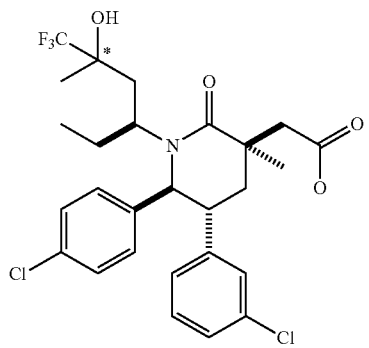

* stereochemistry unknown

Step A. (3S,5R,6S)-3-allyl-5-(3-chlorophenyl)-6-(4-chlorophenyl)-3-methyl-1-((3S,5S)-6,6,6-trifluoro-5-hydroxy-5-methylhexan-3-yl)piperidin-2-one and (3S,5R,6S)-3-allyl-5-(3-chlorophenyl)-6-(4-chlorophenyl)-3-methyl-1-((3S,5R)-6,6,6-trifluoro-5-hydroxy-5-methylhexan-3-yl)piperidin-2-one

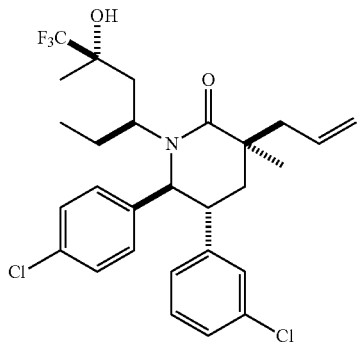

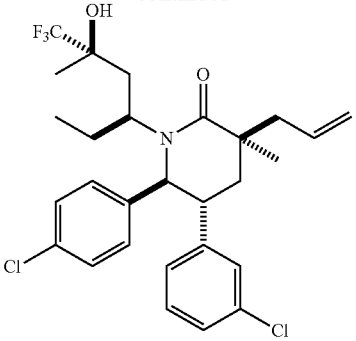

To a solution of (3S,5R,6S)-3-allyl-5-(3-chlorophenyl)-6-(4-chlorophenyl)-3-methyl-1-((S)-5-oxohexan-3-yl)piperidin-2-one (120 mg, 0.254 mmol; Example 131, Step A) in THF (2.5 mL) was added trimethyl(trifluoromethyl)silane (113 μL, 0.762 mmol) at 0° C. and the reaction was stirred for 5 min. Then 1 M TBAF in THF (381 μL, 0.381 mmol) was added slowly at 0° C. After being stirred at 0° C. for 20 min, the reaction was allowed to warm to rt. After being stirred at rt for 40 min the reaction was quenched (sat aq. NH₄Cl), extracted (2×DCM), and washed (2×sat. NaHCO₃ and 1×sat. aq. NaCl solution). The combined organic layers were dried (Na₂SO₄) and concentrated under reduced pressure. Purification of the residue by chromatography on silica gel (12 g SiO₂, 13% and 24% EtOAc/Hex) provided a less polar isomer and a more polar isomer.

(3S,5R,6S)-3-Allyl-5-(3-chlorophenyl)-6-(4-chlorophenyl)-3-methyl-1-((3S)-6,6,6-trifluoro-5-hydroxy-5-methylhexan-3-yl)piperidin-2-one (less polar isomer)

¹H NMR (400 MHz, CHLOROFORM-d) δ ppm 7.24 (2 H, d, J=8.2 Hz), 7.15-7.20 (1 H, m), 7.07-7.14 (1 H, m), 6.88-7.06 (3 H, m), 6.69 (1 H, d, J=7.4 Hz), 5.77-5.92 (1 H, m), 5.09-5.23 (2 H, m), 4.44-4.59 (1 H, m), 3.13 (1 H, br. s.), 2.62 (2 H, d, J=7.4 Hz), 1.84-2.05 (3 H, m), 1.64-1.82 (2 H, m), 1.33 (3 H, s), 1.25-1.31 (5 H, m), 0.72-0.94 (3 H, m); MS (ESI) 542.0 [M+H]⁺.

(3S,5R,6S)-3-Allyl-5-(3-chlorophenyl)-6-(4-chlorophenyl)-3-methyl-1-((3S)-6,6,6-trifluoro-5-hydroxy-5-methylhexan-3-yl)piperidin-2-one (more polar isomer)

¹H NMR (400 MHz, CHLOROFORM-d) δ ppm 7.22-7.27 (2 H, m), 7.14-7.20 (1 H, m), 7.09-7.14 (1 H, m), 6.90-7.08 (3 H, m), 6.70 (1 H, d, J=7.4 Hz), 5.86 (1 H, dd, J=17.4, 9.6 Hz), 5.12-5.22 (2 H, m), 4.44-4.56 (1 H, m), 3.06-3.21 (1 H, m), 1.83-2.03 (2 H, m), 1.53-1.82 (3 H, m), 1.37-1.49 (1 H, m), 1.29 (3 H, s), 1.23 (3 H, d, J=14.5 Hz), 0.62-0.94 (3 H, m); MS (ESI) 542.0 [M+H]⁺.

Step B. 2-((3R,5R,6S)-5-(3-chlorophenyl)-6-(4-chlorophenyl)-3-methyl-2-oxo-1-((3S)-6,6,6-trifluoro-5-hydroxy-5-methylhexan-3-yl)piperidin-3-yl)acetic acid (isomer 1)

The title compound was obtained from the less polar isomer of (3S,5R,6S)-3-allyl-5-(3-chlorophenyl)-6-(4-chlorophenyl)-3-methyl-1-((3S)-6,6,6-trifluoro-5-hydroxy-5- methylhexan-3-yl)piperidin-2-one prepared in Step A by a procedure similar to the one described in Example 71, Step F as a white foam.

¹H NMR (400 MHz, CHLOROFORM-d) δ ppm 7.24-7.27 (2 H, m), 7.14-7.19 (1 H, m), 6.96-7.12 (3 H, m), 6.93 (1 H, t, J=1.7 Hz), 6.68 (1 H, d, J=7.6 Hz), 4.58-4.67 (1 H, m), 2.98-3.14 (2 H, m), 2.71-2.81 (1 H, m), 2.17 (1 H, s), 2.02 (2 H, s), 1.52-1.70 (1 H, m), 1.48 (3 H, s), 1.34 (5 H, s), 0.19-0.93 (3 H, m); MS (ESI) 558.0 [M+H]⁺, 560.0 [M−H]⁻.

Example 133

2-((3R,5R,6S)-5-(3-chlorophenyl)-6-(4-chlorophenyl)-3-methyl-2-oxo-1-((3S)-6,6,6-trifluoro-5-hydroxy-5-methylhexan-3-yl)piperidin-3-yl)acetic acid (Isomer 2)

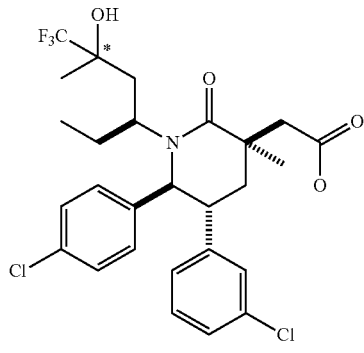

* stereochemistry unknown

The title compound was obtained from the more polar isomer of (3S,5R,6S)-3-allyl-5-(3-chlorophenyl)-6-(4-chlorophenyl)-3-methyl-1-((3S)-6,6,6-trifluoro-5-hydroxy-5-methylhexan-3-yl)piperidin-2-one (48 mg, 0.088 mmol; Example 132, Step A) by a procedure similar to the one described in Example 71, Step F as a white foam.

¹H NMR (400 MHz, CHLOROFORM-d) δ ppm 7.25 (2 H, br. s.), 6.96-7.19 (4 H, m), 6.93 (1 H, t, J=1.8 Hz), 6.69 (1 H, d, J=7.6 Hz), 4.60-4.70 (1 H, m), 3.01 (2 H, s), 2.75 (1 H, d, J=15.1 Hz), 2.11-2.21 (1 H, m), 2.02 (2 H, s), 1.77-1.93 (1 H, m), 1.48 (6 H, s), 1.35 (3 H, br. s.), 0.39-0.71 (3 H, m); MS (ESI) 560.0 [M+H]⁺, 558.0 [M−H]⁻.

Example 134

2-((3R,5R,6S)-5-(3-chlorophenyl)-6-(4-chlorophenyl)-3-methyl-1-((S)-1-(N-methylmethylsulfonamido)butan-2-yl)-2-oxopiperidin-3-yl)acetic acid

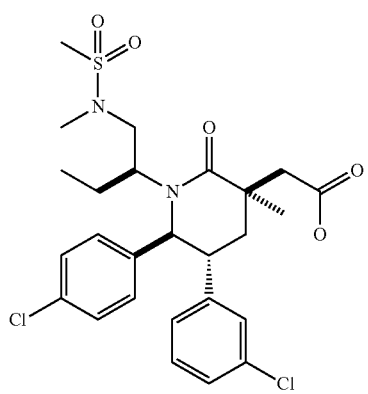 [SMILES: CC[C@@H](CN(C)S(C)(=O)=O)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-3-methyl-1-((S)-1-(methylamino)butan-2-yl)piperidin-2-one

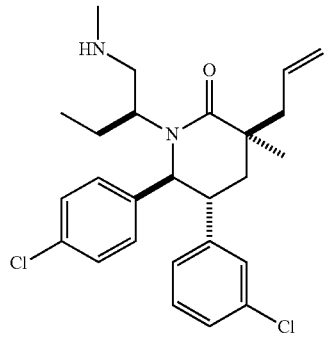 [SMILES: C=CC[C@@]1(C)C[C@H](c2cccc(Cl)c2)[C@@H](c2ccc(Cl)cc2)N([C@@H](CC)CNC)C1=O]

To a solution of (S)-2-((3S,5R,6S)-3-allyl-5-(3-chlorophenyl)-6-(4-chlorophenyl)-3-methyl-2-oxopiperidin-1-yl)butanal (70 mg, 0.16 mmol; Example 91, Step C) and acetic acid (271 μL, 4.73 mmol) in ClCH₂CH₂Cl (2.6 mL) was added 2 M methylamine in THF (788 μL, 1.58 mmol) and sodium triacetoxyborohydride (100 mg, 0.47 mmol) at rt. After being stirred at rt for 3 h, the reaction was quenched (sat aq. NaHCO₃), extracted (2×EtOAc), and washed (sat. aq. NaCl solution). The combined organic layers were dried (Na₂SO₄) and concentrated under reduced pressure to provide the crude title compound as a pale yellow film. The product was used in the next step without further purification.

Step B. N-((S)-2-((3S,5R,6S)-3-allyl-5-(3-chlorophenyl)-6-(4-chlorophenyl)-3-methyl-2-oxopiperidin-1-yl)butyl)-N-methylmethanesulfonamide

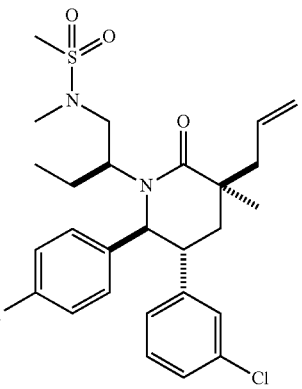

To a solution of (3S,5R,6S)-3-allyl-5-(3-chlorophenyl)-6-(4-chlorophenyl)-3-methyl-1-((S)-1-(methylamino)butan-2-yl)piperidin-2-one (72 mg, 0.16 mmol; Example 134 Step A) in DMF (0.40 mL) was added methanesulfonyl chloride (61 μL, 0.79 mmol) and pyridine (76 μL, 0.95 mmol) successively at 0° C. After being stirred at 25° C. for overnight, the reaction was acidified (10% citric acid) and extracted (2×EtOAc). The combined organic layers were washed (sat. aq. NaCl solution), dried (Na₂SO₄), and concentrated under reduced pressure. Separation by RP-HPLC (50 to 85% MeCN/H₂O (0.1% TFA) a gradient elution) provided the title compound as a pale yellow film.

Step C. 2-((3R,5R,6S)-5-(3-chlorophenyl)-6-(4-chlorophenyl)-3-methyl-1-((S)-1-(N-methylmethylsulfonamido)butan-2-yl)-2-oxopiperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)butyl)-N-methylmethanesulfonamide (Example 134, Step B) described in Example AB, Step G.

$^1$H NMR (400 MHz, CHLOROFORM-d) δ ppm 7.21-7.27 (2 H, m), 7.10-7.17 (2 H, m), 6.92-7.07 (3 H, m), 6.87 (1 H, dd, J=6.5, 1.8 Hz), 4.78 (1 H, d, J=10.6 Hz), 4.12-4.27 (1 H, m), 2.97-3.15 (2 H, m), 2.84-2.90 (1 H, m), 2.85 (3 H, s), 2.84 (3 H, s), 2.63-2.77 (2 H, m), 2.43 (1 H, t, J=13.9 Hz), 1.88-1.97 (2 H, m), 1.55-1.68 (1 H, m), 1.51 (3 H, s), 0.50 (3 H, t, J=7.5 Hz); MS (ESI) 555.1 [M+H]$^+$, 553.0 [M−H]$^−$.

Example 135

2-((3R,5R,6S)-5-(3-chlorophenyl)-6-(4-chlorophenyl)-1-((3S)-5-cyclopropyl-6,6,6-trifluoro-5-hydroxyhexan-3-yl)-3-methyl-2-oxopiperidin-3-yl)acetic acid

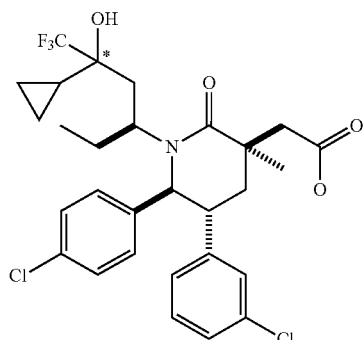

* stereochemistry unknown

Step A. (3S,5R,6S)-3-allyl-5-(3-chlorophenyl)-6-(4-chlorophenyl)-1-((3S)-1-cyclopropyl-1-hydroxypentan-3-yl)-3-methylpiperidin-2-one

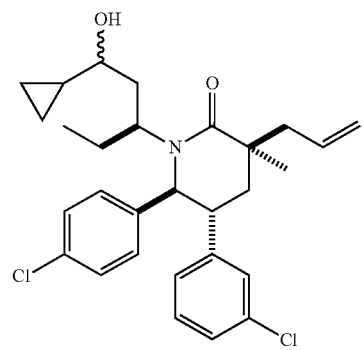 [SMILES: C=CC[C@@]1(C)C[C@H](c2cccc(Cl)c2)[C@@H](c2ccc(Cl)cc2)N([C@@H](CC)CC(O)C2CC2)C1=O]

To a solution of (S)-3-((3S,5R,6S)-3-allyl-5-(3-chlorophenyl)-6-(4-chlorophenyl)-3-methyl-2-oxopiperidin-1-yl)pentanal (160 mg, 0.349 mmol; Example 130, Step A) in THF (3.5 mL) was added 0.5 M cyclopropylmagnesium bromide in THF (2.09 mL, 1.05 mmol) at 0° C. Then the reaction was allowed to warm to rt and stirred for 3.5 h. The reaction was quenched (sat NH$_4$Cl solution), extracted (2×EtOAc), and washed (sat. aq. NaCl solution). The combined organic layers were dried (Na$_2$SO$_4$) and concentrated under reduced pressure to provide the title compound as a mixture of two diastereomers. The crude product was used in the next step without further purification.

Step B. (3S,5R,6S)-3-allyl-5-(3-chlorophenyl)-6-(4-chlorophenyl)-1-((S)-1-cyclopropyl-1-oxopentan-3-yl)-3-methylpiperidin-2-one

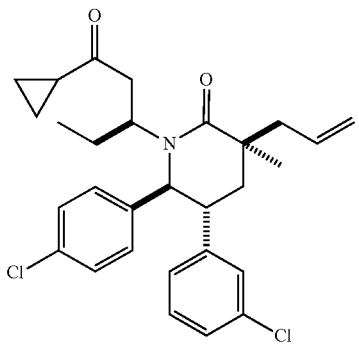 [SMILES: C=CC[C@@]1(C)C[C@H](c2cccc(Cl)c2)[C@@H](c2ccc(Cl)cc2)N([C@@H](CC)CC(=O)C2CC2)C1=O]

To a solution of (3S,5R,6S)-3-allyl-5-(3-chlorophenyl)-6-(4-chlorophenyl)-1-((S)-1-cyclopropyl-1-hydroxypentan-3-yl)-3-methylpiperidin-2-one prepared above in Step A (175 mg, 0.350 mmol) and water (9.5 μL, 0.52 mmol) in DCM (3.9 mL) was added Dess-Martin periodinane (222 mg, 0.524 mmol) at rt. After being stirred at rt for 40 min, the reaction was quenched (1 M aq. Na$_2$S$_2$O$_3$), extracted (2×DCM), and washed (2×sat. NaHCO$_3$ and 1×sat. aq. NaCl solution). The combined organic layers were dried (Na$_2$SO$_4$) and concentrated under reduced pressure. Purification of the residue by chromatography on silica gel (12 g SiO$_2$, 15% and 25% EtOAc/Hex) provided the title compound as a colorless film.

Step C. (3S,5R,6S)-3-allyl-5-(3-chlorophenyl)-6-(4-chlorophenyl)-1-((3S,5S)-5-cyclopropyl-6,6,6-trifluoro-5-hydroxyhexan-3-yl)-3-methylpiperidin-2-one and (3S,5R,6S)-3-allyl-5-(3-chlorophenyl)-6-(4-chlorophenyl)-1-((3S,5R)-5-cyclopropyl-6,6,6-trifluoro-5-hydroxyhexan-3-yl)-3-methylpiperidin-2-one

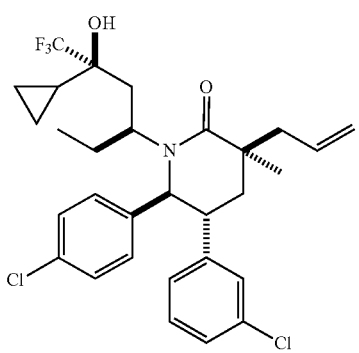

-continued

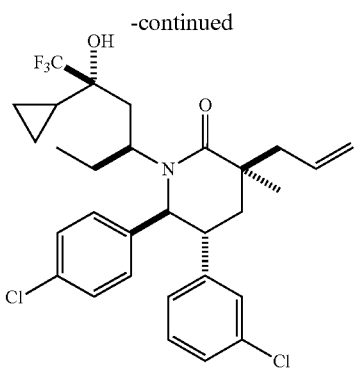

To a solution of (3S,5R,6S)-3-allyl-5-(3-chlorophenyl)-6-(4-chlorophenyl)-1-((S)-1-cyclopropyl-1-oxopentan-3-yl)-3-methylpiperidin-2-one prepared above in Step B (132 mg, 0.265 mmol) in THF (2.6 mL) was added trimethyl(trifluoromethyl)silane (117 μL, 0.794 mmol) at 0° C. and the reaction was stirred for 5 min. Then 1 M tetrabutylammonium fluoride in THF (397 μL, 0.397 mmol) was added slowly at 0° C. Then the reaction was allowed to warm to rt. After being stirred for 3 h, additional trimethyl(trifluoromethyl)silane (234 μL, 1.59 mmol) and 1 M tetrabutylammonium fluoride in THF (794 μL, 0.794 mmol) were added at 0° C. and the reaction was allowed to warm to rt. After being stirred at rt for 15 h, the reaction was quenched (sat. aq. NaCl solution), extracted (2×EtOAc), and washed (sat. aq. NaCl solution). The combined organic layers were dried ($Na_2SO_4$) and concentrated under reduced pressure. Purification of the residue by chromatography on silica gel (12 g SiO2, 6% and 13% EtOAc/Hex) provided one of the title compounds as the less polar isomer and another one of the title compounds as the more polar isomer, successively.

(3S,5R,6S)-3-allyl-5-(3-chlorophenyl)-6-(4-chlorophenyl)-1-((3S)-5-cyclopropyl-6,6,6-trifluoro-5-hydroxyhexan-3-yl)-3-methylpiperidin-2-one (less polar isomer)

$^1$H NMR (400 MHz, CHLOROFORM-d) δ ppm 7.24 (2 H, d, J=8.2 Hz), 7.15-7.20 (1 H, m), 7.07-7.14 (1 H, m), 6.88-7.06 (3 H, m), 6.69 (1 H, d, J=7.4 Hz), 5.77-5.92 (1 H, m), 5.09-5.23 (2 H, m), 4.44-4.59 (1 H, m), 3.13 (1 H, br. s.), 2.62 (2 H, d, J=7.4 Hz), 1.84-2.05 (3 H, m), 1.64-1.82 (2 H, m), 1.33 (3 H, s), 1.25-1.31 (5 H, m), 0.72-0.94 (3 H, m); MS (ESI) 568.2 [M+H]$^+$.

(3S,5R,6S)-3-allyl-5-(3-chlorophenyl)-6-(4-chlorophenyl)-1-((3S)-5-cyclopropyl-6,6,6-trifluoro-5-hydroxyhexan-3-yl)-3-methylpiperidin-2-one (more polar isomer)

$^1$H NMR (400 MHz, CHLOROFORM-d) δ ppm 7.22-7.27 (2 H, m), 7.14-7.20 (1 H, m), 7.09-7.14 (1 H, m), 6.90-7.08 (3 H, m), 6.70 (1 H, d, J=7.4 Hz), 5.86 (1 H, dd, J=17.4, 9.6 Hz), 5.12-5.22 (2 H, m), 4.44-4.56 (1 H, m), 3.06-3.21 (1 H, m), 1.83-2.03 (2 H, m), 1.53-1.82 (3 H, m), 1.37-1.49 (1 H, m), 1.29 (3 H, s), 1.23 (3 H, d, J=14.5 Hz), 0.62-0.94 (3 H, m); MS (ESI) 568.2 [M+H]$^+$.

Step D. 2-((3R,5R,6S)-5-(3-chlorophenyl)-6-(4-chlorophenyl)-1-((3S)-5-cyclopropyl-6,6,6-trifluoro-5-hydroxyhexan-3-yl)-3-methyl-2-oxopiperidin-3-yl) acetic acid The title compound was prepared from (3S,5R,6S)-3-allyl-5-(3-chlorophenyl)-6-(4-chlorophenyl)-1-((3S)-5-cyclopropyl-6,6,6-trifluoro-5-hydroxyhexan-3-yl)-3-methylpiperidin-2-one (Example 135, Step C, more polar product) by a procedure similar to the one described in Example 71, Step F.

$^1$H NMR (400 MHz, CHLOROFORM-d) δ ppm 7.00-7.04 (2 H, m), 6.91-6.96 (1 H, m), 6.84-6.90 (1 H, m), 6.67-6.84 (3 H, m), 6.46 (1 H, d, J=7.6 Hz), 4.29-4.45 (1 H, m), 2.76-2.91 (2 H, m), 2.51 (1 H, d, J=15.1 Hz), 1.84-1.96 (1 H, m), 1.69-1.79 (1 H, m), 1.48-1.67 (1 H, m), 1.12-1.35 (6 H, m), 0.62-0.81 (1 H, m), 0.01-0.51 (8 H, m); MS (ESI) 586.2 [M+H]$^+$, 584.0 [M−H]$^-$.

Example 136

2-((3R,5R,6S)-5-(3-chlorophenyl)-6-(4-chlorophenyl)-1-((S)-6-hydroxy-6-methylheptan-3-yl)-3-methyl-2-oxopiperidin-3-yl)acetic acid

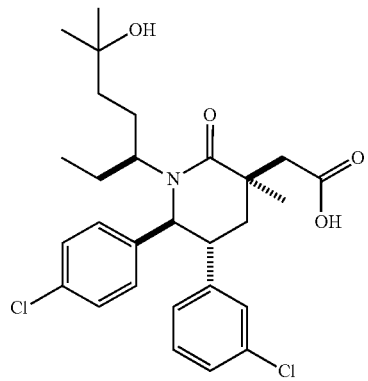 [SMILES: CC[C@@H](CCC(C)(C)O)N1C(=O)[C@@](C)(CC(=O)O)C[C@H](c2cccc(Cl)c2)[C@H]1c1ccc(Cl)cc1]

Step A. (S)-4-((3S,5R,6S)-3-allyl-5-(3-chlorophenyl)-6-(4-chlorophenyl)-3-methyl-2-oxopiperidin-1-yl)hexanal

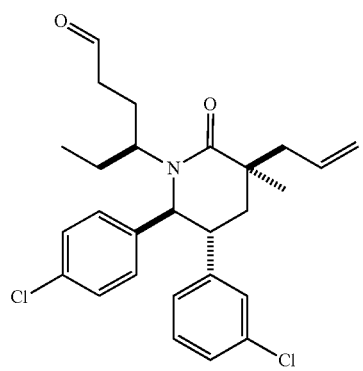 [SMILES: C=CC[C@@]1(C)C[C@H](c2cccc(Cl)c2)[C@@H](c2ccc(Cl)cc2)N([C@@H](CC)CCC=O)C1=O]

The title compound was prepared form (S)-3-((3S,5R,6S)-3-allyl-5-(3-chlorophenyl)-6-(4-chlorophenyl)-3-methyl-2-oxopiperidin-1-yl)pentanal (106 mg, 0.231 mmol; Example 130, Step A) by a procedure similar to the one described in Example 130, Step A.

Step B. (3S,5R,6S)-3-allyl-5-(3-chlorophenyl)-6-(4-chlorophenyl)-1-((3S)-6-hydroxyheptan-3-yl)-3-methylpiperidin-2-one

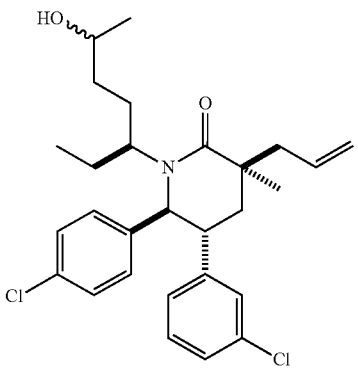 [SMILES: C=CC[C@@]1(C)C[C@H](c2cccc(Cl)c2)[C@@H](c2ccc(Cl)cc2)N([C@@H](CC)CCC(C)O)C1=O]

The title compound was prepared from (S)-4-((3S,5R,6S)-3-allyl-5-(3-chlorophenyl)-6-(4-chlorophenyl)-3-methyl-2-oxopiperidin-1-yl)hexanal (84 mg, 0.18 mmol; Example 136, Step A) by a procedure similar to the one described in Example 130, Step B as a colorless film. The crude product was used in the next step without further purification Step C. (3S,5R,6S)-3-allyl-5-(3-chlorophenyl)-6-(4-chlorophenyl)-3-methyl-1-((S)-6-oxoheptan-3-yl)piperidin-2-one

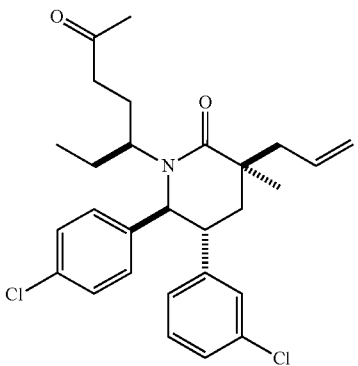 [SMILES: C=CC[C@@]1(C)C[C@H](c2cccc(Cl)c2)[C@@H](c2ccc(Cl)cc2)N([C@@H](CC)CCC(C)=O)C1=O]

The title compound was prepared from a mixture of (3S,5R,6S)-3-allyl-5-(3-chlorophenyl)-6-(4-chlorophenyl)-1-((S)-6-hydroxyheptan-3-yl)-3-methylpiperidin-2-one prepared above in Step B by a procedure similar to the one described in Example 129, Step C.

Step D. (3S,5R,6S)-3-allyl-5-(3-chlorophenyl)-6-(4-chlorophenyl)-1-((S)-6-hydroxy-6-methylheptan-3-yl)-3-methylpiperidin-2-one

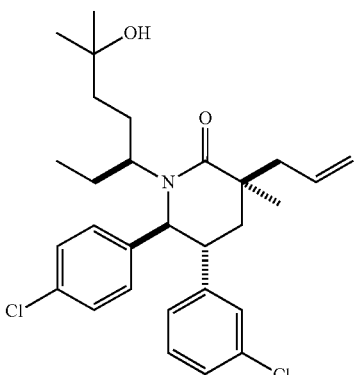

To a solution of (3S,5R,6S)-3-allyl-5-(3-chlorophenyl)-6-(4-chlorophenyl)-3-methyl-1-((S)-6-oxoheptan-3-yl)piperidin-2-one prepared above in Step C (78 mg, 0.16 mmol) in THF (1.6 mL) was added 1.4 M methylmagnesium bromide in toluene and THF (75:25) (344 µL, 0.481 mmol) at 0° C. Then the reaction was allowed to warm to rt and stirred for 2 h. The reaction was quenched (sat NH$_4$Cl solution), extracted (2×EtOAc), and washed (sat. aq. NaCl solution). The combined organic layer was dried (Na$_2$SO$_4$) and concentrated under reduced pressure. Purification of the residue by chromatography on silica gel (12 g SiO$_2$, 33% and 43% EtOAc/Hex) provided the title compound as a colorless foam.

Step E. 2-((3R,5R,6S)-5-(3-chlorophenyl)-6-(4-chlorophenyl)-1-((S)-6-hydroxy-6-methylheptan-3-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-6-hydroxy-6-methylheptan-3-yl)-3-methylpiperidin-2-one (Example 136, Step D) by a procedure similar to the one described in Example 71, Step F.

$^1$H NMR (400 MHz, CHLOROFORM-d) δ ppm 7.25 (2 H, d, J=8.4 Hz), 7.16 (1 H, dd, J=1.9, 1.1 Hz), 7.11 (1 H, d, J=7.6 Hz), 6.94 (3 H, t, J=1.8 Hz), 6.70 (1 H, d, J=7.6 Hz), 5.01-5.25 (2 H, m), 4.37 (1 H, d, J=10.4 Hz), 3.06 (2 H, d, J=15.3 Hz), 2.93-3.03 (1 H, m), 2.71 (1 H, d, J=15.3 Hz), 2.20 (1 H, s), 2.02 (1 H, s), 1.78-1.97 (2 H, m), 1.37-1.56 (7 H, m), 1.22 (6 H, d, J=5.5 Hz), 0.55 (3 H, t, J=7.5 Hz); MS (ESI) 520.2 [M+H]$^+$, 518.0 [M−H]$^-$.

Example 137

2-((3R,5R,6S)-5-(3-chlorophenyl)-6-(4-chlorophenyl)-3-methyl-2-oxo-1-((S)-6,6,6-trifluoro-5,5-dihydroxyhexan-3-yl)piperidin-3-yl)acetic acid

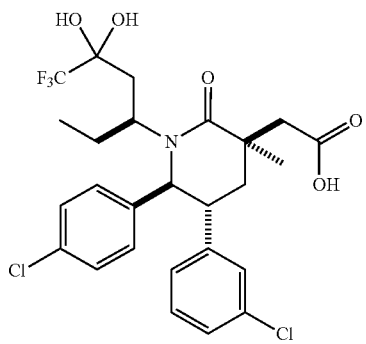 [SMILES: CC[C@@H](CC(O)(O)C(F)(F)F)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-3-methyl-1-((3S)-6,6,6-trifluoro-5-hydroxyhexan-3-yl)piperidin-2-one

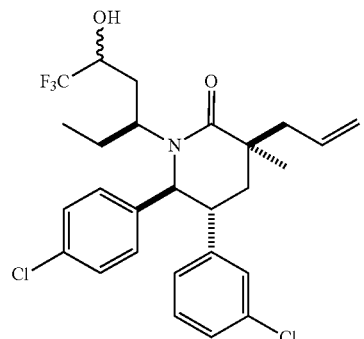

321

To a solution of (S)-3-((3S,5R,6S)-3-allyl-5-(3-chlorophenyl)-6-(4-chlorophenyl)-3-methyl-2-oxopiperidin-1-yl)pentanal (100 mg, 0.218 mmol; Example 130, Step A) in THF (2.2 mL) was added trimethyl(trifluoromethyl)silane (97 µL, 0.66 mmol) at 0° C. and the reaction was stirred for 5 min. Then 1 M TBAF in THF (327 µL, 0.327 mmol) was added slowly at 0° C. After being stirred at 0° C. for 40 min, the reaction was quenched (sat. aq. NaCl solution), extracted (2×EtOAc), and washed (sat. aq. NaCl solution). The combined organic layers were dried (Na₂SO₄) and concentrated under reduced pressure. Purification of the residue by chromatography on silica gel (12 g SiO₂, 13% and 23% EtOAc/Hex) provided the title compound as a mixture of two diastereomers.

Step B. (3S,5R,6S)-3-allyl-5-(3-chlorophenyl)-6-(4-chlorophenyl)-3-methyl-1-((S)-6,6,6-trifluoro-5,5-dihydroxyhexan-3-yl)piperidin-2-one

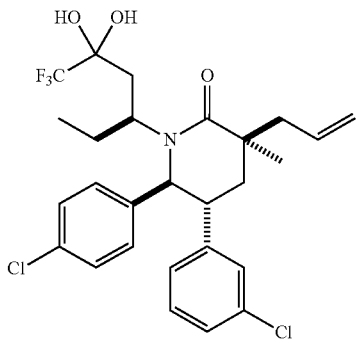 [SMILES: C=CC[C@@]1(C)C[C@H](c2cccc(Cl)c2)[C@@H](c2ccc(Cl)cc2)N([C@@H](CC)CC(O)(O)C(F)(F)F)C1=O]

To a solution of (3S,5R,6S)-3-allyl-5-(3-chlorophenyl)-6-(4-chlorophenyl)-3-methyl-1-((S)-6,6,6-trifluoro-5-hydroxyhexan-3-yl)piperidin-2-one prepared above in Step A (100 mg, 0.189 mmol) in DCM (2.1 mL) was added water (17 µL, 0.95 mmol) and Dess-Martin periodinane (161 mg, 0.378 mmol) at rt and the resulting solution was stirred overnight. The reaction was quenched (1 M aq. Na₂S₂O₃), extracted (2×DCM), and washed (2×sat. NaHCO₃ and 1×sat. aq. NaCl solution). The combined organic layers were dried (Na₂SO₄) and concentrated under reduced pressure to provide the title compound as a colorless film. The product was used in the next step without further purification.

Step C. 2-((3R,5R,6S)-5-(3-chlorophenyl)-6-(4-chlorophenyl)-3-methyl-2-oxo-1-((S)-6,6,6-trifluoro-5,5-dihydroxyhexan-3-yl)piperidin-3-yl)acetic acid The title compound was prepared from (3S,5R,6S)-3-allyl-5-(3-chlorophenyl)-6-(4-chlorophenyl)-3-methyl-1-((S)-6,6,6-trifluoro-5,5-dihydroxyhexan-3-yl)piperidin-2-one (Example 137, Step B) by a procedure similar to the one described in Example 71, Step F.

¹H NMR (400 MHz, CHLOROFORM-d) δ ppm 7.29 (2 H, br. s.), 7.06-7.20 (4 H, m), 6.97 (1 H, s), 6.76-6.82 (1 H, m), 4.74 (1 H, d, J=10.6 Hz), 3.88-3.98 (1 H, m), 3.09-3.19 (2 H, m), 2.96 (1 H, s), 2.78 (2 H, s), 2.08 (3 H, s), 1.38 (4 H, s), 0.42 (3 H, t, J=7.5 Hz); MS (ESI) 562.1 [M+H]⁺, 560.0 [M−H]⁻.

Example 138

2-((3R,5R,6S)-5-(3-Chlorophenyl)-6-(4-chlorophenyl)-3-methyl-2-oxo-1-((3S)-7,7,7-trifluoro-6-hydroxy-6-methylheptan-3-yl)piperidin-3-yl)acetic acid (Isomer 1)

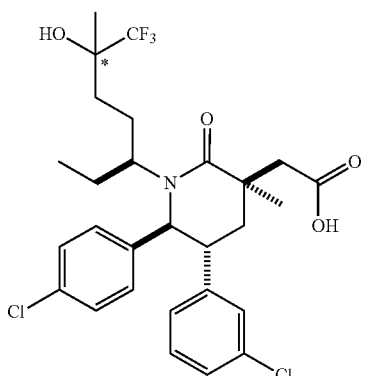

* stereochemistry unknown

Step A. (3S,5R,6S)-3-allyl-5-(3-chlorophenyl)-6-(4-chlorophenyl)-3-methyl-1-((3S,6R)-7,7,7-trifluoro-6-hydroxy-6-methylheptan-3-yl)piperidin-2-one and (3S,5R,6S)-3-allyl-5-(3-chlorophenyl)-6-(4-chlorophenyl)-3-methyl-1-((3S,6S)-7,7,7-trifluoro-6-hydroxy-6-methylheptan-3-yl)piperidin-2-one

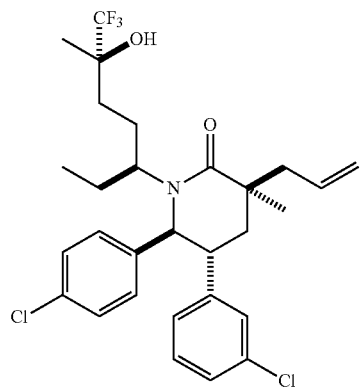

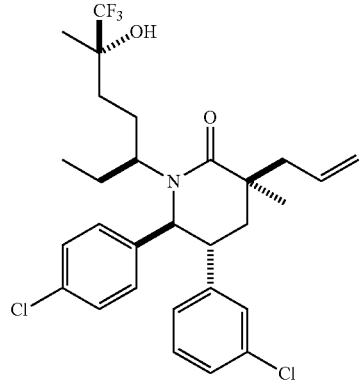

To a solution of (3S,5R,6S)-3-allyl-5-(3-chlorophenyl)-6-(4-chlorophenyl)-3-methyl-1-((S)-6-oxoheptan-3-yl)piperidin-2-one (169 mg, 0.347 mmol; Example 136, Step C) in THF (3.5 mL) was added trimethyl(trifluoromethyl)silane (154 μL, 1.04 mmol) at 0° C. and the reaction was stirred for 5 min. Then 1 M TBAF in THF (521 μL, 0.521 mmol) was added slowly at 0° C. Then the reaction was allowed to warm to rt. After being stirred at rt for 1.5 h, the reaction was quenched (water), extracted (2×EtOAc), and washed (water and sat. aq. NaCl solution). The combined organic layers were dried ($Na_2SO_4$) and concentrated under reduced pressure. Purification of the residue by chromatography on silica gel (40 g $SiO_2$, 13%, 23% and 33% EtOAc/Hex) provided one of the title compounds as the less polar isomer and another one of the title compounds as the more polar isomer, successively (3S,5R,6S)-3-allyl-5-(3-chlorophenyl)-6-(4-chlorophenyl)-3-methyl-1-((3S)-7,7,7-trifluoro-6-hydroxy-6-methylheptan-3-yl)piperidin-2-one (less polar isomer)

$^1$H NMR (400 MHz, CHLOROFORM-d) δ ppm 7.22 (2 H, d, J=8.2 Hz), 7.07-7.20 (2 H, m), 6.91 (3 H, t, J=1.8 Hz), 6.65-6.74 (1 H, m), 5.82-5.97 (1 H, m), 5.13-5.24 (2 H, m), 4.33 (1 H, d, J=10.6 Hz), 3.78-3.99 (1 H, m), 3.10-3.26 (1 H, m), 2.64 (2 H, dd, J=7.4, 4.5 Hz), 1.91-2.04 (2 H, m), 1.68-1.78 (1 H, m), 1.62 (3 H, t, J=7.3 Hz), 1.33-1.46 (1 H, m), 1.29 (4 H, s), 1.25 (3 H, s), 0.94-1.13 (1 H, m), 0.84 (3 H, t, J=7.3 Hz); MS (ESI) 556.2 [M+H]$^+$.

(3S,5R,6S)-3-allyl-5-(3-chlorophenyl)-6-(4-chlorophenyl)-3-methyl-1-((3S)-7,7,7-trifluoro-6-hydroxy-6-methylheptan-3-yl)piperidin-2-one (more polar isomer)

$^1$H NMR (400 MHz, CHLOROFORM-d) δ ppm 7.23 (2 H, d, J=8.4 Hz), 7.08-7.20 (2 H, m), 6.89-7.01 (3 H, m), 6.68-6.75 (1 H, m), 5.84 (1 H, s), 5.13-5.23 (2 H, m), 4.28 (1 H, d, J=10.4 Hz), 3.09-3.22 (2 H, m), 2.62 (2 H, d, J=7.2 Hz), 1.90-2.05 (2 H, m), 1.73-1.84 (2 H, m), 1.53-1.66 (3 H, m), 1.35-1.48 (1 H, m), 1.31 (3 H, s), 1.24-1.29 (4 H, m), 0.66 (3 H, t, J=7.4 Hz); MS (ESI) 556.2 [M+H]$^+$.

Step B. 2-((3R,5R,6S)-5-(3-chlorophenyl)-6-(4-chlorophenyl)-3-methyl-2-oxo-1-((3S)-7,7,7-trifluoro-6-hydroxy-6-methylheptan-3-yl)piperidin-3-yl)acetic acid (Isomer 1)

The title compound was prepared from (3S,5R,6S)-3-allyl-5-(3-chlorophenyl)-6-(4-chlorophenyl)-3-methyl-1-((3S)-7,7,7-trifluoro-6-hydroxy-6-methylheptan-3-yl)piperidin-2-one (Example 138, Step A, less polar product) by a procedure similar to the one described in Example 71, Step F.

$^1$H NMR (400 MHz, CHLOROFORM-d) δ ppm 7.23 (2 H, d, J=8.0 Hz), 7.14-7.19 (1 H, m), 7.07-7.13 (1 H, m), 7.01 (2 H, br. s.), 6.92 (1 H, t, J=1.7 Hz), 6.69 (1 H, d, J=7.6 Hz), 5.57-5.68 (1 H, m), 4.38 (1 H, d, J=10.4 Hz), 3.52 (1 H, s), 3.17 (1 H, br. s.), 2.77-3.02 (2 H, m), 2.05-2.24 (2 H, m), 1.75 (2 H, dd, J=11.8, 6.6 Hz), 1.53-1.65 (1 H, m), 1.48 (3 H, s), 1.34-1.45 (3 H, m), 1.29 (3 H, s), 0.71 (3 H, t, J=7.3 Hz); MS (ESI) 574.2 [M+H]$^+$, 572.0 [M−H]$^−$.

Example 139

2-((3R,5R,6S)-5-(3-chlorophenyl)-6-(4-chlorophenyl)-3-methyl-2-oxo-1-((3S)-7,7,7-trifluoro-6-hydroxy-6-methylheptan-3-yl)piperidin-3-yl)acetic acid (Isomer 2)

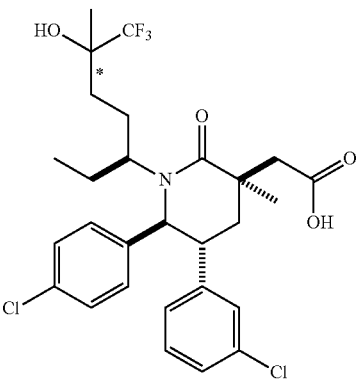

*sterochemistry unknown

The title compound was prepared from (3S,5R,6S)-3-allyl-5-(3-chlorophenyl)-6-(4-chlorophenyl)-3-methyl-1-((3S)-7,7,7-trifluoro-6-hydroxy-6-methylheptan-3-yl)piperidin-2-one (Example 138, Step A, more polar product) by a procedure similar to the one described in Example 71, Step F.

$^1$H NMR (400 MHz, CHLOROFORM-d) δ ppm 7.25 (2 H, s), 7.16-7.21 (1 H, m), 7.09-7.15 (1 H, m), 7.01 (2 H, d, J=4.1 Hz), 6.93 (1 H, t, J=1.7 Hz), 6.72 (1 H, d, J=7.6 Hz), 5.66-5.74 (1 H, m), 4.34 (1 H, d, J=10.2 Hz), 3.09-3.27 (2 H, m), 2.98 (1 H, d, J=14.5 Hz), 2.74 (1 H, d, J=14.5 Hz), 2.14-2.24 (1 H, m), 2.02-2.08 (1 H, m), 1.81 (2 H, dd, J=14.3, 7.2 Hz), 1.52-1.70 (3 H, m), 1.50 (3 H, s), 1.29-1.38 (1 H, m), 1.27 (3 H, s), 0.64 (3 H, t, J=7.3 Hz); MS (ESI) 574.2 [M+H]$^+$, 572.0 [M−H]$^−$.

Example 140

2-((3R,5R,6S)-5-(3-chlorophenyl)-6-(4-chlorophenyl)-1-((S)-7-hydroxy-7-methyloctan-3-yl)-3-methyl-2-oxopiperidin-3-yl)acetic acid

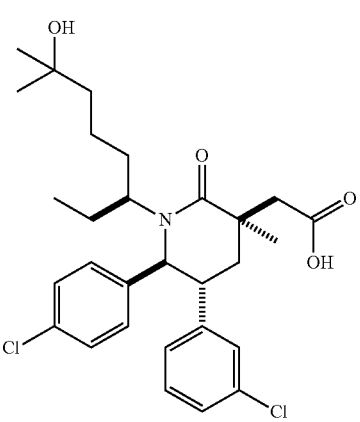

Step A. (S)-5-((3S,5R,6S)-3-allyl-5-(3-chlorophenyl)-6-(4-chlorophenyl)-3-methyl-2-oxopiperidin-1-yl)heptanal

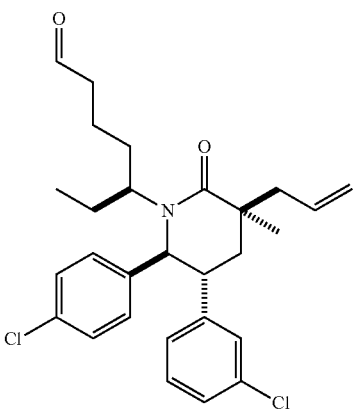

The title compound was prepared from (S)-4-((3S,5R,6S)-3-allyl-5-(3-chlorophenyl)-6-(4-chlorophenyl)-3-methyl-2-oxopiperidin-1-yl)hexanal (147 mg, 0.311 mmol; Example 136, Step A) by a procedure similar to the one described in Example 130, Step A.

Step B. (3S,5R,6S)-3-allyl-5-(3-chlorophenyl)-6-(4-chlorophenyl)-1-((3S)-7-hydroxyoctan-3-yl)-3-methylpiperidin-2-one

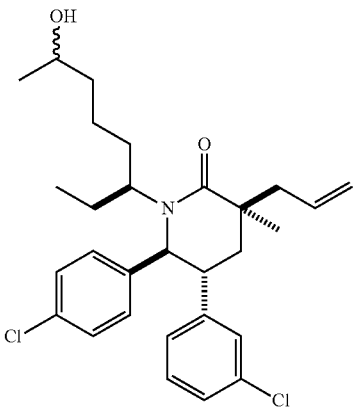

To a solution of (S)-5-((3S,5R,6S)-3-allyl-5-(3-chlorophenyl)-6-(4-chlorophenyl)-3-methyl-2-oxopiperidin-1-yl)heptanal prepared above in Step A (138 mg, 0.284 mmol) in THF (2.8 mL) was added 1.4 M methylmagnesium bromide in toluene and THF (75:25) (608 µL, 0.851 mmol) at 0° C. Then the reaction was allowed to warm to rt and stirred for 2 h. The reaction was quenched (sat NH₄Cl solution), extracted (2×EtOAc), and washed (sat. aq. NaCl solution). The combined organic layer was dried (Na₂SO₄) and concentrated under reduced pressure to provide the title compound as a colorless film.

Step C. (3S,5R,6S)-3-allyl-5-(3-chlorophenyl)-6-(4-chlorophenyl)-3-methyl-1-((S)-7-oxooctan-3-yl)piperidin-2-one

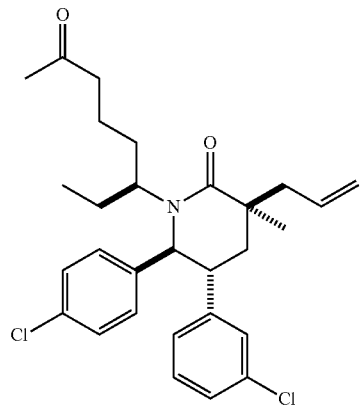

The title compound was prepared from (3S,5R,6S)-3-allyl-5-(3-chlorophenyl)-6-(4-chlorophenyl)-1-((S)-7-hydroxyoctan-3-yl)-3-methylpiperidin-2-one prepared above in Step B (143 mg, 0.285 mmol) by a procedure similar to the one described in Example 131, Step A as a white solid.

Step D. (3S,5R,6S)-3-allyl-5-(3-chlorophenyl)-6-(4-chlorophenyl)-1-((S)-7-hydroxy-7-methyloctan-3-yl)-3-methylpiperidin-2-one

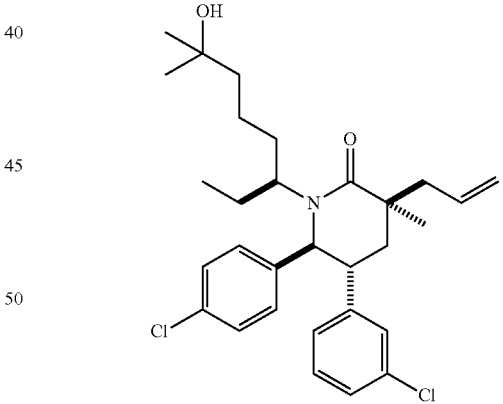

To a solution of (3S,5R,6S)-3-allyl-5-(3-chlorophenyl)-6-(4-chlorophenyl)-3-methyl-1-((S)-7-oxooctan-3-yl)piperidin-2-one prepared above in Step C (122 mg, 0.244 mmol) in THF (2.4 mL) was added 1.4 M methylmagnesium bromide in toluene and THF (75:25) (522 µL, 0.731 mmol) at 0° C. Then the reaction was allowed to warm to rt and stirred for 2 h. The reaction was quenched (sat NH₄Cl solution), extracted (2×EtOAc), and washed (sat. aq. NaCl solution). The combined organic layers were dried (Na₂SO₄) and concentrated under reduced pressure and purification of the residue by chromatography on silica gel (12 g SiO₂, 30% and 40% EtOAc/Hex) provided the title compound as a colorless foam.

Step E. 2-((3R,5R,6S)-5-(3-chlorophenyl)-6-(4-chlorophenyl)-1-((S)-7-hydroxy-7-methyloctan-3-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-7-hydroxy-7-methyloctan-3-yl)-3-methylpiperidin-2-one (Example 140, Step D) by a procedure similar to the one described in Example 71, Step F.

$^1$H NMR (400 MHz, CHLOROFORM-d) δ ppm 7.23 (2 H, d, J=8.0 Hz), 7.05-7.18 (2 H, m), 6.92-7.05 (3 H, m), 6.70 (1 H, d, J=7.6 Hz), 4.42 (1 H, d, J=10.4 Hz), 3.05-3.18 (2 H, m), 3.00 (1 H, d, J=15.1 Hz), 2.72 (1 H, d, J=15.1 Hz), 2.11-2.26 (1 H, m), 1.97-2.08 (1 H, m), 1.79-1.92 (1 H, m), 1.64-1.79 (1 H, m), 1.50-1.59 (2 H, m), 1.48 (3 H, s), 1.34-1.45 (3 H, m), 1.28-1.33 (1 H, m), 1.27 (3 H, s), 1.25 (3 H, s), 0.56 (3 H, t, J=7.4 Hz); MS (ESI) 534.1 [M+H]$^+$, 532.2 [M–H]$^-$.

Example 141

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid

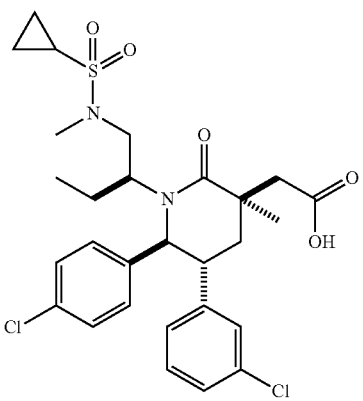

The title compound was prepared from (3S,5R,6S)-3-allyl-5-(3-chlorophenyl)-6-(4-chlorophenyl)-3-methyl-1-((S)-1-(methylamino)butan-2-yl)piperidin-2-one (Example 134, Step A) by procedures similar to those described in Example 134, Steps B and C, substituting methanesuflonylchloride in Step B for the appropriate amount of cyclopropylsulfonyl chloride.

$^1$H NMR (400 MHz, CHLOROFORM-d) δ ppm 7.24 (2 H, br. s.), 7.10-7.17 (2 H, m), 6.80-7.09 (4 H, m), 4.79 (1 H, d, J=10.8 Hz), 4.13-4.30 (1 H, m), 2.99-3.12 (2 H, m), 2.89 (4 H, s), 2.64-2.81 (2 H, m), 2.45 (1 H, t, J=13.8 Hz), 2.33 (1 H, s), 1.88 (2 H, dd, J=13.9, 2.7 Hz), 1.54-1.66 (1 H, m), 1.50-1.54 (3 H, m), 1.22 (2 H, d, J=4.5 Hz), 1.02 (2 H, dd, J=8.0, 3.9 Hz), 0.51 (3 H, t, J=7.4 Hz); MS (ESI) 581.0 [M+H]$^+$, 579.0 [M–H]$^-$.

Example 142

2-((3R,5R,6S)-5-(3-chlorophenyl)-6-(4-chlorophenyl)-1-((S)-1-(N-cyclopropylmethylsulfonamido)butan-2-yl)-3-methyl-2-oxopiperidin-3-yl)acetic acid

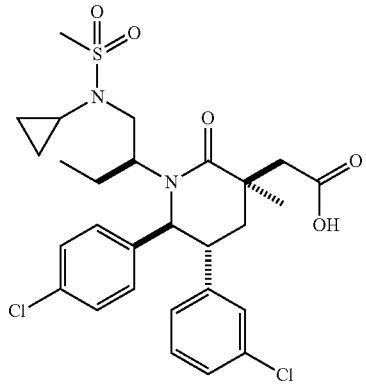

The title compound was prepared from (S)-2-((3S,5R,6S)-3-allyl-5-(3-chlorophenyl)-6-(4-chlorophenyl)-3-methyl-2-oxopiperidin-1-yl)butanal (Example 91, Step C) by procedures similar to those described in Example 134, Step A-C, substituting methylamine in Step A for the appropriate amount of cyclopropylamine.

$^1$H NMR (400 MHz, CHLOROFORM-d) δ ppm 7.22-7.27 (2 H, m), 7.11-7.18 (2 H, m), 6.81-7.06 (4 H, m), 4.81 (1 H, d, J=10.6 Hz), 4.25-4.41 (1 H, m), 3.08 (2 H, d, J=15.5 Hz), 2.95 (3 H, s), 2.81-2.90 (1 H, m), 2.73-2.80 (1 H, m), 2.67 (1 H, d, J=15.5 Hz), 2.52 (2 H, s), 1.95-2.14 (1 H, m), 1.77-1.88 (1 H, m), 1.53 (4 H, s), 0.70-0.92 (3 H, m), 0.59-0.69 (1 H, m), 0.50 (3 H, t, J=7.5 Hz); MS (ESI) 581.0 [M+H]$^+$, 579.0 [M–H]$^-$.

Example 143

2-((3R,5R,6S)-5-(3-chlorophenyl)-6-(4-chlorophenyl)-3-methyl-2-oxo-1-((3S)-6,6,6-trifluoro-5-hydroxyhexan-3-yl)piperidin-3-yl)acetic acid (Isomer 1)

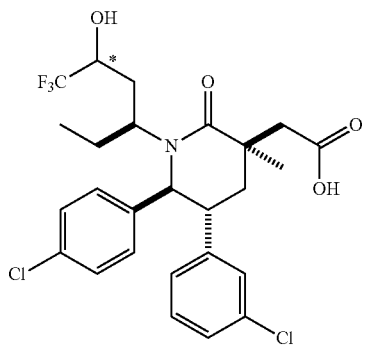

*stereochemistry unknown

Step A. (3S,5R,6S)-3-allyl-5-(3-chlorophenyl)-6-(4-chlorophenyl)-3-methyl-1-((3S,5S)-6,6,6-trifluoro-5-hydroxyhexan-3-yl)piperidin-2-one and (3S,5R,6S)-3-allyl-5-(3-chlorophenyl)-6-(4-chlorophenyl)-3-methyl-1-((3S,5R)-6,6,6-trifluoro-5-hydroxyhexan-3-yl)piperidin-2-one

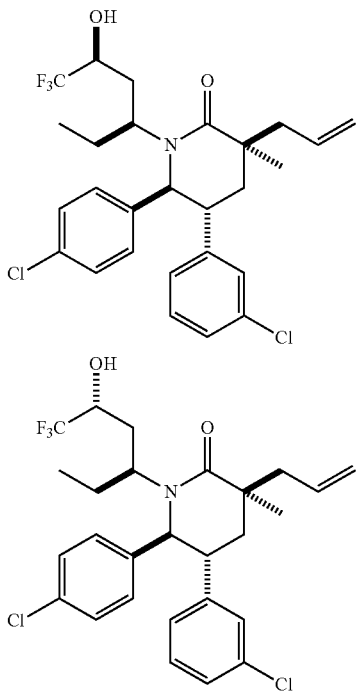

To a solution of (S)-3-((3S,5R,6S)-3-allyl-5-(3-chlorophenyl)-6-(4-chlorophenyl)-3-methyl-2-oxopiperidin-1-yl)pentanal (139 mg, 0.303 mmol; Example 130, Step A) in THF (3.0 mL) was added trimethyl(trifluoromethyl)silane (134 µL, 0.910 mmol) at 0° C. and the reaction was stirred for 5 min. Then 1 M TBAF in THF (455 µL, 0.455 mmol) was added slowly at 0° C. Then, the reaction was allowed to warm to rt. After being stirred at rt for 1.5 h, the reaction was quenched (sat. aq. NaCl solution), extracted (2×EtOAc), and washed (sat. aq. NaCl solution). The combined organic layers were dried (Na$_2$SO$_4$) and concentrated under reduced pressure. Purification of the residue by chromatography on silica gel (24 g SiO$_2$, 6% and 16% EtOAc/Hex) provided one of the title compounds as the less polar isomer and another one of the title compounds as the more polar isomer, successively.

(3S,5R,6S)-3-allyl-5-(3-chlorophenyl)-6-(4-chlorophenyl)-3-methyl-1-((3S)-6,6,6-trifluoro-5-hydroxyhexan-3-yl)piperidin-2-one (less polar isomer)

$^1$H NMR (400 MHz, CHLOROFORM-d) δ ppm 7.15-7.26 (3 H, m), 7.11 (1 H, t, J=7.7 Hz), 6.93 (3 H, t, J=1.9 Hz), 6.68 (1 H, dt, J=7.6, 1.5 Hz), 5.83-5.95 (1 H, m), 5.17-5.26 (2 H, m), 4.38 (1 H, d, J=10.4 Hz), 3.69-3.81 (1 H, m), 3.11-3.22 (1 H, m), 2.66 (2 H, d, J=7.6 Hz), 1.92-2.12 (3 H, m), 1.72-1.89 (1 H, m), 1.49-1.60 (1 H, m), 1.25-1.37 (5 H, m), 1.00 (1 H, none), 0.92-1.07 (3 H, m); MS (ESI) 528.1 [M+H]$^+$.

(3S,5R,6S)-3-allyl-5-(3-chlorophenyl)-6-(4-chlorophenyl)-3-methyl-1-((3S)-6,6,6-trifluoro-5-hydroxyhexan-3-yl)piperidin-2-one (more polar isomer)

$^1$H NMR (400 MHz, CHLOROFORM-d) δ ppm 7.24 (2 H, dd, J=7.4, 1.4 Hz), 7.15-7.20 (1 H, m), 7.11 (1 H, t, J=7.8 Hz), 6.90-7.05 (3 H, m), 6.70 (1 H, dt, J=7.5, 1.5 Hz), 5.79-5.92 (1 H, m), 5.13-5.22 (2 H, m), 4.43 (1 H, d, J=10.4 Hz), 3.90 (1 H, ddd, J=11.1, 6.6, 2.2 Hz), 3.09-3.22 (1 H, m), 2.53-2.71 (2 H, m), 1.90-2.05 (2 H, m), 1.56-1.86 (4 H, m), 1.22-1.32 (4 H, m), 0.79 (3 H, t, J=7.4 Hz); MS (ESI) 528.1 [M+H]$^+$.

Step B. 2-((3R,5R,6S)-5-(3-chlorophenyl)-6-(4-chlorophenyl)-3-methyl-2-oxo-1-((3S,5S)-6,6,6-trifluoro-5-hydroxyhexan-3-yl)piperidin-3-yl)acetic acid (Isomer 1)

The title compound was prepared from (3S,5R,6S)-3-allyl-5-(3-chlorophenyl)-6-(4-chlorophenyl)-3-methyl-1-((3S)-6,6,6-trifluoro-5-hydroxyhexan-3-yl)piperidin-2-one (Step A, less polar product) by a procedure similar to the one described in Example 71, Step F.

$^1$H NMR (400 MHz, CHLOROFORM-d) δ ppm 7.06-7.27 (6 H, m), 6.94 (1 H, t, J=1.7 Hz), 6.68 (1 H, d, J=7.6 Hz), 4.58-5.15 (3 H, m), 4.42 (2 H, d, J=10.4 Hz), 3.88-4.01 (1 H, m), 3.19-3.28 (1 H, m), 2.86 (2 H, d, J=12.7 Hz), 2.03-2.24 (2 H, m), 1.71-1.89 (1 H, m), 1.54-1.66 (1 H, m), 1.50 (3 H, s), 1.26-1.40 (1 H, m), 0.97 (3 H, br. s.); MS (ESI) 546.0 [M+H]$^+$, 544.0 [M–H]$^-$.

Example 144

2-((3R,5R,6S)-5-(3-chlorophenyl)-6-(4-chlorophenyl)-3-methyl-2-oxo-1-((3S)-6,6,6-trifluoro-5-hydroxyhexan-3-yl)piperidin-3-yl)acetic acid (Isomer 2)

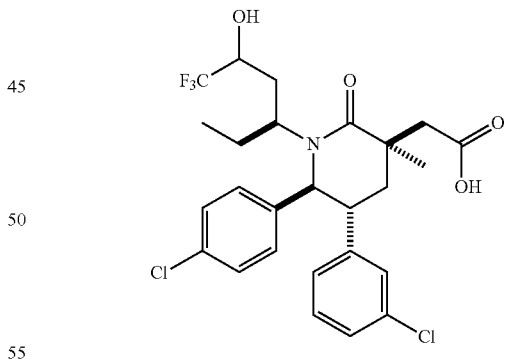

The title compound was prepared from (3S,5R,6S)-3-allyl-5-(3-chlorophenyl)-6-(4-chlorophenyl)-3-methyl-1-((3S)-6,6,6-trifluoro-5-hydroxyhexan-3-yl)piperidin-2-one (Example 143, Step A; more polar product) by a procedure similar to the one described in Example 71, Step F.

$^1$H NMR (400 MHz, CHLOROFORM-d) δ ppm 7.23-7.27 (2 H, m), 7.08-7.20 (2 H, m), 6.93-7.08 (3 H, m), 6.70 (1 H, dt, J=7.7, 1.4 Hz), 4.49 (1 H, d, J=10.4 Hz), 3.88-4.01 (1 H, m), 3.51 (1 H, s), 3.10-3.22 (1 H, m), 2.95 (1 H, d, J=14.5 Hz), 2.75 (1 H, d, J=14.5 Hz), 2.20 (1 H, t, J=13.8 Hz), 1.99-2.08 (1 H, m), 1.95 (1 H, d, J=2.3 Hz), 1.77 (1 H, dd, J=14.3, 7.2

Hz), 1.52-1.70 (2 H, m), 1.48 (3 H, s), 0.72 (3 H, t, J=7.5 Hz); MS (ESI) 546.0 [M+H]⁺, 544.0 [M−H]⁻.

Example 145

2-((3R,5R,6S)-5-(3-chlorophenyl)-6-(4-chlorophenyl)-1-((3S)-5-hydroxyhexan-3-yl)-3-methyl-2-oxopiperidin-3-yl)acetic acid (Isomer 1)

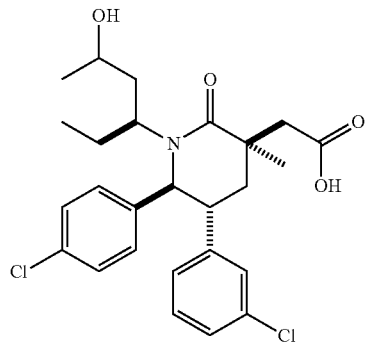

To a solution of 2-((3R,5R,6S)-5-(3-chlorophenyl)-6-(4-chlorophenyl)-3-methyl-2-oxo-1-((S)-5-oxohexan-3-yl)piperidin-3-yl)acetic acid (24 mg, 0.049 mmol; Example 130) in ether (0.40 mL) and MeOH (0.10 mL) was added sodium borohydride (9.26 mg, 0.245 mmol) at 0° C. Then the reaction was allowed to warm to rt. After being stirred at rt for 1 h, the reaction was quenched (10% citric acid) and extracted (2×EtOAc). The combined organic layer was washed (sat. aq. NaCl solution), dried (Na₂SO₄), and concentrated under reduced pressure. Purification by RP-HPLC (30 to 70% MeCN/H₂O (0.1% TFA), a gradient elution) provided the title compound as the more polar isomer.

¹H NMR (400 MHz, CHLOROFORM-d) δ ppm 7.22-7.27 (2 H, m), 7.07-7.19 (2 H, m), 6.95-7.06 (3 H, m), 6.71 (1 H, dt, J=7.6, 1.6 Hz), 4.57 (1 H, d, J=10.2 Hz), 3.77-3.89 (1 H, m), 2.99-3.15 (2 H, m), 2.69 (1 H, d, J=14.9 Hz), 2.23 (1 H, t, J=13.6 Hz), 1.81-1.99 (2 H, m), 1.52-1.64 (1 H, m), 1.47 (3 H, s), 1.39 (1 H, d, J=2.0 Hz), 1.19 (3 H, d, J=6.3 Hz), 0.60 (3 H, t, J=7.4 Hz); MS (ESI) 492.1 [M+H]⁺, 490.0 [M−H]⁻.

Example 146

2-((3R,5R,6S)-5-(3-chlorophenyl)-6-(4-chlorophenyl)-1-((3S)-5-hydroxyhexan-3-yl)-3-methyl-2-oxopiperidin-3-yl)acetic acid (Isomer 2)

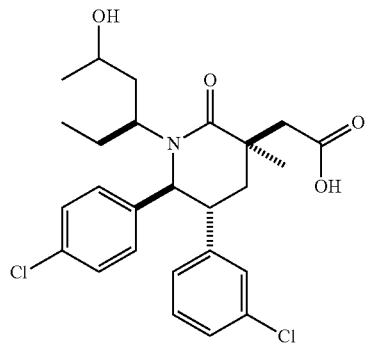

Further elution from Example 145 provided the title compound as the less polar isomer.

¹H NMR (400 MHz, CHLOROFORM-d) δ ppm 7.04-7.27 (5 H, m), 6.91-7.04 (2 H, m), 6.70 (1 H, dt, J=7.7, 1.5 Hz), 4.47 (1 H, d, J=10.4 Hz), 3.75 (1 H, ddd, J=12.4, 6.1, 0.7 Hz), 3.15-3.27 (1 H, m), 2.96 (1 H, d, J=14.5 Hz), 2.76 (1 H, d, J=14.7 Hz), 2.18 (1 H, t, J=13.8 Hz), 2.02-2.09 (1 H, m), 1.59-1.71 (2 H, m), 1.50 (3 H, s), 1.26 (1 H, dd, J=16.8, 6.8 Hz), 1.08-1.21 (2 H, m), 0.99-1.07 (3 H, m), 0.89 (3 H, br. s.); MS (ESI) 492.1 [M+H]⁺, 490.0 [M−H]⁻.

Example 147

2-((3R,5R,6S)-5-(3-chlorophenyl)-6-(4-chlorophenyl)-3-methyl-2-oxo-1-((S)-1-(N-(2,2,2-trifluoroethyl)methylsulfonamido)butan-2-yl)piperidin-3-yl)acetic acid

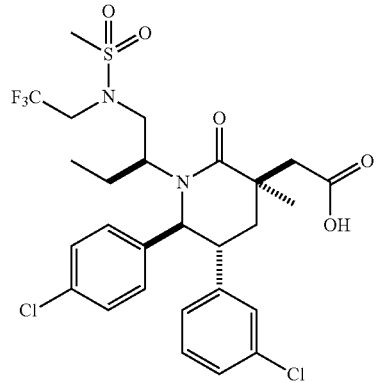

Step A. (3S,5R,6S)-3-allyl-5-(3-chlorophenyl)-6-(4-chlorophenyl)-3-methyl-1-((S)-1-((2,2,2-trifluoroethyl)amino)butan-2-yl)piperidin-2-one

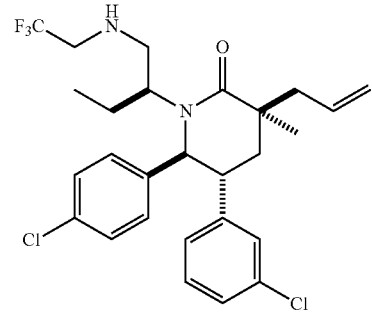

To a solution of (S)-2-((3S,5R,6S)-3-allyl-5-(3-chlorophenyl)-6-(4-chlorophenyl)-3-methyl-2-oxopiperidin-1-yl)butanal (104 mg, 0.234 mmol; Example 130, Step A) in ClCH₂CH₂Cl (3.9 mL) was added 2,2,2-trifluoroethylamine (74 μL, 0.94 mmol) and sodium triacetoxyborohydride (248 mg, 1.17 mmol) at rt. After being stirred at rt overnight, the reaction was quenched (sat aq. NaHCO₃), extracted (2×EtOAc), and washed (sat. aq. NaCl solution). The combined organic layers were dried (Na₂SO₄) and concentrated under reduced pressure to provide the title compound as a white solid. The product was used in the next step without further purification.

Step B. N-((S)-2-((3S,5R,6S)-3-allyl-5-(3-chlorophenyl)-6-(4-chlorophenyl)-3-methyl-2-oxopiperidin-1-yl)butyl)-N-(2,2,2-trifluoroethyl)methanesulfonamide

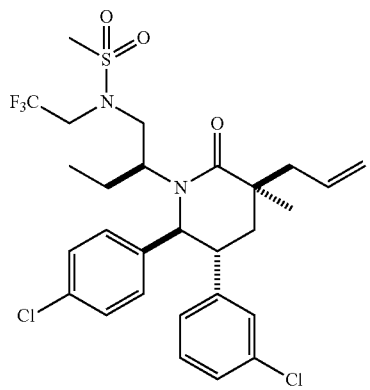

To a solution of (3S,5R,6S)-3-allyl-5-(3-chlorophenyl)-6-(4-chlorophenyl)-3-methyl-1-((S)-1-(2,2,2-trifluoroethylamino)butan-2-yl)piperidin-2-one prepared above in Step A (60.9 mg, 0.115 mmol) in DCE (770 μL) was added DMAP (70.5 mg, 0.577 mmol) and methanesulfonyl chloride (35.9 μL, 0.462 mmol) successively at rt. After being stirred at rt for 3 h, pyridine (46.7 μL, 0.577 mmol), methanesulfonyl chloride (35.9 μL, 0.462 mmol), and DCE (0.77 mL) were added and the resulting solution was stirred for 15 h.

The reaction was quenched (sat. NH$_4$Cl), and extracted (3×DCM). The combined organic layers were washed (water and sat. aq. NaCl solution), dried (Na$_2$SO$_4$), and concentrated under reduced pressure. Separation by RP-HPLC (10 to 90% MeCN/H$_2$O (0.1% TFA), a gradient elution) provided the title compound as a yellow solid.

Step C. 2-((3R,5R,6S)-5-(3-chlorophenyl)-6-(4-chlorophenyl)-3-methyl-2-oxo-1-((S)-1-(N-(2,2,2-trifluoroethyl)methylsulfonamido)butan-2-yl)piperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)butyl)-N-(2,2,2-trifluoroethyl)methanesulfonamide (Step B) by a procedure similar to the one described in Example 71, Step F.

$^1$H NMR (400 MHz, CHLOROFORM-d) δ ppm 7.21-7.28 (2 H, m), 7.11-7.20 (2 H, m), 6.74-7.10 (4 H, m), 4.65 (1 H, d, J=10.8 Hz), 4.32-4.50 (1 H, m), 4.11 (1 H, d, J=7.8 Hz), 3.48-3.65 (1 H, m), 2.94-3.19 (6 H, m), 2.79-2.92 (1 H, m), 2.75 (1 H, d, J=14.7 Hz), 2.42 (1 H, t, J=13.9 Hz), 1.85-2.12 (2 H, m), 1.50 (4 H, s), 0.48 (3 H, t, J=7.4 Hz); MS (ESI) 623.0 [M+H]$^+$, 621.0 [M−H]$^−$.

Example 148

2-((3R,5R,6S)-5-(3-chlorophenyl)-6-(4-chlorophenyl)-1-((S)-(1,1-dioxidoisothiazolidin-2-yl)butan-2-yl)-3-methyl-2-oxopiperidin-3-yl)acetic acid

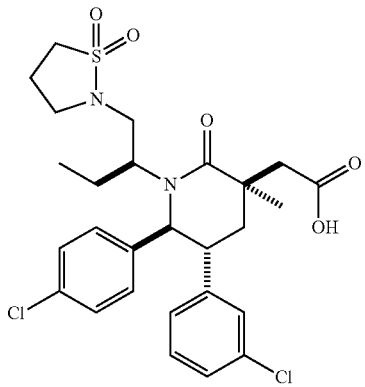

Step A. N-((S)-2-((3S,5R,6S)-3-allyl-5-(3-chlorophenyl)-6-(4-chlorophenyl)-3-methyl-2-oxopiperidin-1-yl)butyl)-3-chloropropane-1-sulfonamide

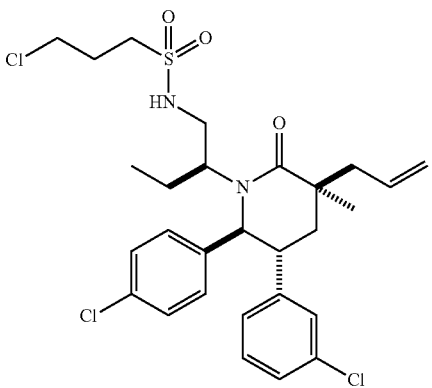

(3S,5R,6S)-3-Allyl-1-((S)-1-aminobutan-2-yl)-5-(3-chlorophenyl)-6-(4-chlorophenyl)-3-methylpiperidin-2-one 2,2,2-trifluoroacetate (76 mg, 0.14 mmol; Example 129, Step B) was dissolved in DCM, basified (1 N LiOH), extracted (3×DCM), and washed (sat. aq. NaCl solution). The combined organic layers were dried (Na$_2$SO$_4$) and concentrated under reduced pressure to provide the free amine. To a solution of the free amine in DCE (0.68 mL) was added pyridine (55 μL, 0.68 mmol) and 3-chloropropane-1-sulfonyl chloride (96 mg, 0.54 mmol) successively at rt. The reaction was stirred at rt for 5 h. Then additional pyridine (55 μL, 0.68 mmol) and 3-chloropropane-1-sulfonyl chloride (96 mg, 0.54 mmol) was added. After being stirred overnight, the reaction was quenched (10% citric acid), extracted (3×EtOAc), and washed (saturated aq. NaHCO$_3$ and sat. aq. NaCl solution).

Step B. (3S,5R,6S)-3-allyl-5-(3-chlorophenyl)-6-(4-chlorophenyl)-1-((S)-1-(1,1-dioxidoisothiazolidin-2-yl)butan-2-yl)-3-methylpiperidin-2-one

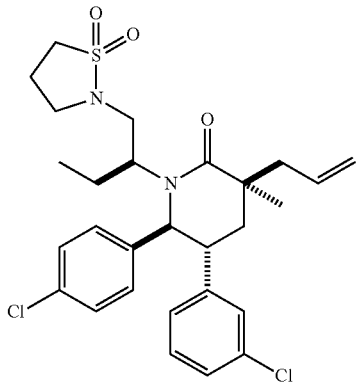

To a solution of N-((S)-2-((3S,5R,6S)-3-allyl-5-(3-chlorophenyl)-6-(4-chlorophenyl)-3-methyl-2-oxopiperidin-1-yl)butyl)-3-chloropropane-1-sulfonamide prepared above in Step A (36.1 mg, 0.062 mmol) in DMF (1.2 mL) was added DBU (46.4 µL, 0.308 mmol) at rt. After being stirred at rt overnight, the reaction was quenched (10% citric acid), extracted (3×EtOAc), and washed (saturated aq. NaHCO₃ and sat. aq. NaCl solution). The combined organic layers were dried (Na₂SO₄) and concentrated under reduced pressure to provide the title compound as a pale brown film.

Step C. 2-((3R,5R,6S)-5-(3-chlorophenyl)-6-(4-chlorophenyl)-1-((S)-1-(1,1-dioxidoisothiazolidin-2-yl)butan-2-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-(1,1-dioxidoisothiazolidin-2-yl)butan-2-yl)-3-methylpiperidin-2-one (Step B)) by a procedure similar to the one described in Example 71, Step F.

¹H NMR (400 MHz, CHLOROFORM-d) δ ppm 7.27 (2 H, d, J=8.0 Hz), 7.10-7.19 (2 H, m), 6.97-7.10 (3 H, m), 6.83 (1 H, d, J=7.4 Hz), 4.87 (1 H, d, J=0.6 Hz), 3.33 (2 H, t, J=6.6 Hz), 3.24 (2 H, t, J=7.5 Hz), 3.09 (2 H, d, J=15.3 Hz), 2.96 (2 H, d, J=2.3 Hz), 2.74 (1 H, d, J=15.3 Hz), 2.37-2.51 (3 H, m), 1.90-2.02 (2 H, m), 1.53 (4 H, s), 0.49 (3 H, t, J=7.5 Hz); MS (ESI) 567.1 [M+H]⁺, 565.0 [M−H]⁻.

Example 149

2-((3R,5R,6S)-5-(3-Chlorophenyl)-6-(4-chlorophenyl)-1-((3S,4R)-5-hydroxy-4,5-dimethylhexan-3-yl)-3-methyl-2-oxopiperidin-3-yl)acetic acid or 2-((3R,5R,6S)-5-(3-Chlorophenyl)-6-(4-chlorophenyl)-1-((3S,4S)-5-hydroxy-4,5-dimethylhexan-3-yl)-3-methyl-2-oxopiperidin-3-yl)acetic acid

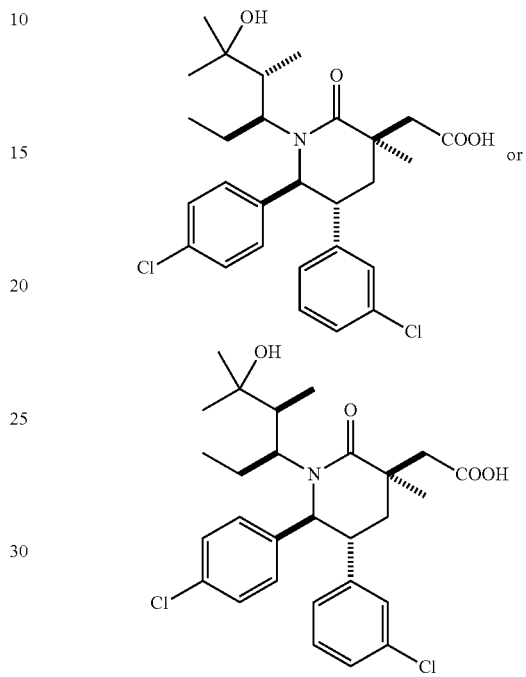

Step A. (3S,5R,6S)-3-Allyl-5-(3-chlorophenyl)-6-(4-chlorophenyl)-3-methyl-1-((S)-2-oxopentan-3-yl)piperidin-2-one

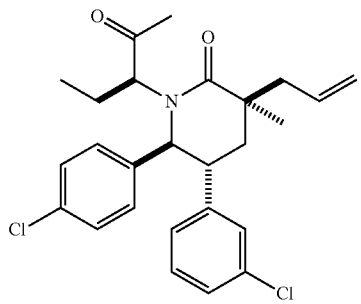

To a solution of oxalyl dichloride (78 µL, 0.87 mmol) in DCM (1.5 mL) at −60° C. was added a solution of DMSO (93 µL, 1.30 mmol) in DCM (1.5 mL) under N₂. After being stirred for 2 min, a solution of (3S,5R,6S)-3-allyl-5-(3-chlorophenyl)-6-(4-chlorophenyl)-1-((3S)-2-hydroxypentan-3-yl)-3-methylpiperidin-2-one prepared in example 151, Step C (200 mg, 0.434 mmol) in DCM (1.5 mL) was added and the resulting solution was stirred for 15 min. at −60° C. Then, triethylamine (305 µL, 2.17 mmol) was added to the reaction solution. After being stirred at rt for 20 min, the reaction was quenched (water), extracted (2×EtOAc), and washed (2×sat. aq. NaCl solution). The combined organic layers were dried (Na₂SO₄) and concentrated under reduced pressure. Purification by combi flash (SiO₂, 24 g, 20% and 30% EtOAc/Hexanes) provided the title compound as a colorless foam.

Step B. ((3S,5R,6S)-3-Allyl-5-(3-chlorophenyl)-6-(4-chlorophenyl)-1-((S)-1-methoxy-2-methylpent-1-en-3-yl)-3-methylpiperidin-2-one

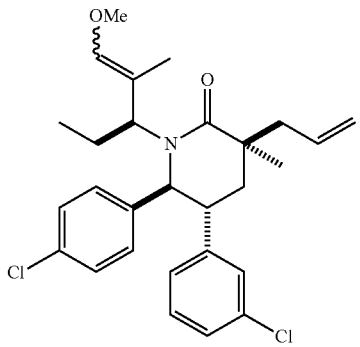

(Methoxymethyl)triphenylphosphonium chloride was dried at 80° C. under vacuum for 2 h. To a solution of the dried (methoxymethyl)triphenylphosphonium chloride (673 mg, 1.96 mmol) in THF (3.5 mL) was added 0.5 M KHMDS in toluene (3.49 mL, 1.75 mmol) at −78° C. The solution resulted in a blood red color. After addition, the reaction was stirred at 0° C. for 30 min and a solution of (3S,5R,6S)-3-allyl-5-(3-chlorophenyl)-6-(4-chlorophenyl)-3-methyl-1-((S)-2-oxopentan-3-yl)piperidin-2-one prepared above in Step B (200 mg, 0.436 mmol) in THF (3.5 mL) was added dropwisely at 0° C. The reaction was allowed to warm to rt and stirred for 1.5 h. Then the reaction was quenched (sat NH$_4$Cl solution), extracted (2×EtOAc), and washed (brine). The combined organic layers were dried (Na$_2$SO$_4$) and concentrated under reduced pressure. Purification by combi flash (SiO$_2$, 24 g, 15% and 20% EtOAc/Hexanes) provided the title compound as a colorless film.

Step C. (2S,3S)-3-((3S,5R,6S)-3-Allyl-5-(3-chlorophenyl)-6-(4-chlorophenyl)-3-methyl-2-oxopiperidin-1-yl)-2-methylpentanal and (2R,3S)-3-((3S,5R,6S)-3-Allyl-5-(3-chlorophenyl)-6-(4-chlorophenyl)-3-methyl-2-oxopiperidin-1-yl)-2-methylpentanal

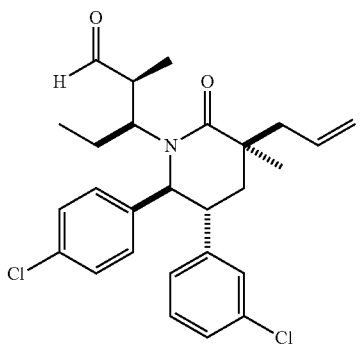

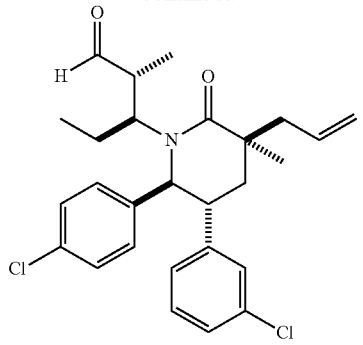

To a solution of (3S,5R,6S)-3-allyl-5-(3-chlorophenyl)-6-(4-chlorophenyl)-1-((S)-1-methoxy-2-methylpent-1-en-3-yl)-3-methylpiperidin-2-one prepared above in Step B (179 mg, 0.368 mmol) in acetonitrile (3.7 mL) was added 3 N hydrochloric acid (1.5 mL, 4.5 mmol) at rt. After being stirred at rt for 1.5 h, the reaction was extracted (2×EtOAc), and washed (2×brine). The combined organic layers were dried (Na$_2$SO$_4$) and concentrated under reduced pressure provided the title compounds as a mixture of stereoisomers (dr=7:3) as a pale yellow film.

Step D. (3S,5R,6S)-3-allyl-5-(3-chlorophenyl)-6-(4-chlorophenyl)-3-methyl-1-((3S,4R)-4-methyl-5-oxohexan-3-yl)piperidin-2-one and (3S,5R,6S)-3-allyl-5-(3-chlorophenyl)-6-(4-chlorophenyl)-3-methyl-1-((3S,4S)-4-methyl-5-oxohexan-3-yl)piperidin-2-one

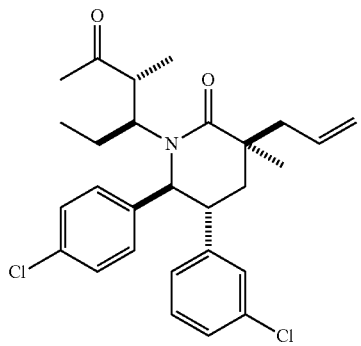

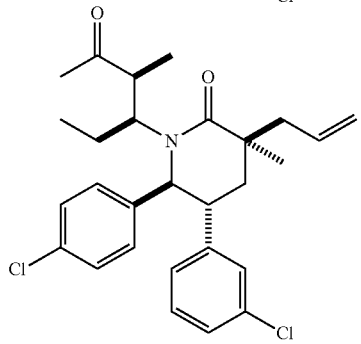

To a solution of (2S,3S)-3-((3S,5R,6S)-3-allyl-5-(3-chlorophenyl)-6-(4-chlorophenyl)-3-methyl-2-oxopiperidin-1-yl)-2-methylpentanal and (2R,3S)-3-((3S,5R,6S)-3-allyl-5-(3-chlorophenyl)-6-(4-chlorophenyl)-3-methyl-2-oxopiperidin-1-yl)-2-methylpentanal prepared above in Step C (177 mg, 0.375 mmol) in THF (3.076 ml) was added 1.4 M methylmagnesium bromide in toluene and THF (75:25) (0.803 ml, 1.12 mmol) at 0° C. Then the reaction was allowed to warm to rt and stirred for 2 h. The reaction was quenched (sat NH₄Cl solution), extracted (2×EtOAc), and washed (brine). The combined organic layer was dried (Na₂SO₄) and concentrated under the reduced pressure to provide a crude secondary alcohol product.

To a solution of the crude secondary alcohol product (183 mg, 0.375 mmol) in DCM (4.2 mL) was added water (14 μL, 0.75 mmol) and dess-martinperiodinane (196 mg, 0.462 mmol) successively. After being stirred ar rt for overnight, the reaction was quenched (1 M aq. Na₂S₂O₃), extracted (2×DCM), and washed (2×sat. NaHCO₃ and 1×brine). The combined organic layers were dried (Na₂SO₄) and concentrated under reduced pressure. Purification of the residue by chromatography on silica gel (24 g SiO₂, 13%, 27% and 37% EtOAc/Hex) provided a less polar and more polar isomer, successively.

Less polar isomer: ¹H NMR (400 MHz, CHLOROFORM-d) δ ppm 7.25 (2 H, d, J=8.0 Hz), 7.03-7.17 (4 H, m), 6.94-6.99 (1 H, m), 6.81-6.87 (1 H, m), 5.12-5.23 (2 H, m), 4.58 (1 H, d, J=10.8 Hz), 3.14 (1 H, s), 2.66 (1 H, s), 2.58 (2 H, d, J=7.4 Hz), 2.22 (3 H, s), 1.81 (1 H, d, J=4.3 Hz), 1.75 (1 H, d, J=7.2 Hz), 1.51-1.65 (2 H, m), 1.19 (3 H, s), 1.00 (3 H, d, J=7.2 Hz), 0.30 (3 H, t, J=7.7 Hz); MS (ESI) 486.1 [M+H]⁺.

More polar isomer: ¹H NMR (400 MHz, CHLOROFORM-d) δ ppm 7.22-7.27 (2 H, m), 7.01-7.17 (4 H, m), 6.89-6.95 (1 H, m), 6.71 (1 H, dt, J=7.5, 1.3 Hz), 5.81-5.93 (1 H, m), 5.17-5.25 (2 H, m), 4.32 (1 H, d, J=10.8 Hz), 3.50 (1 H, br. s.), 3.23-3.32 (1 H, m), 3.06 (1 H, br. s.), 2.60-2.66 (2 H, m), 2.13-2.20 (3 H, m), 1.91-2.01 (2 H, m), 1.64-1.70 (2 H, m), 1.28-1.32 (3 H, m), 1.13 (3 H, d, J=7.0 Hz), 0.34 (3 H, t, J=7.5 Hz); MS (ESI) 486.1 [M+H]⁺.

Step E. (3S,5R,6S)-3-Allyl-5-(3-chlorophenyl)-6-(4-chlorophenyl)-1-((3S,4R)-5-hydroxy-4,5-dimethylhexan-3-yl)-3-methylpiperidin-2-one or (3S,5R,6S)-3-Allyl-5-(3-chlorophenyl)-6-(4-chlorophenyl)-1-((3S,4S)-5-hydroxy-4,5-dimethylhexan-3-yl)-3-methylpiperidin-2-one

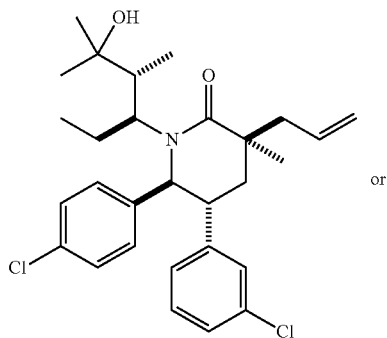

or

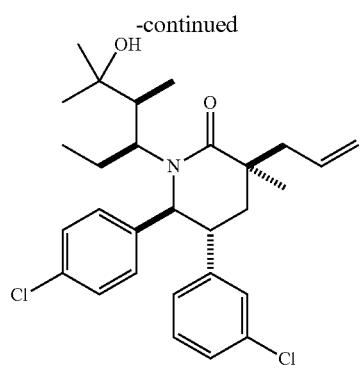

To a solution of the less polar isomer prepared above in example 149, step D (96 mg, 0.20 mmol) in THF (2.0 mL) was added 1.4 M methylmagnesium bromide in toluene and THF (75:25) (423 μL, 0.592 mmol) at 0° C. Then the reaction was allowed to warm to rt and stirred for overnight. The reaction was quenched (sat NH₄Cl solution), extracted (2×EtOAc), and washed (brine). The combined organic layers were dried (Na₂SO₄) and concentrated under reduced pressure. Purification of the residue by combi-flash (12 g SiO₂, 30% EtOAc/Hex) provided the title compound as a single isomer.

Step F. 2-((3R,5R,6S)-5-(3-Chlorophenyl)-6-(4-chlorophenyl)-1-((3S,4R)-5-hydroxy-4,5-dimethylhexan-3-yl)-3-methyl-2-oxopiperidin-3-yl)acetic acid or 2-((3R,5R,6S)-5-(3-Chlorophenyl)-6-(4-chlorophenyl)-1-((3S,4S)-5-hydroxy-4,5-dimethylhexan-3-yl)-3-methyl-2-oxopiperidin-3-yl)acetic acid

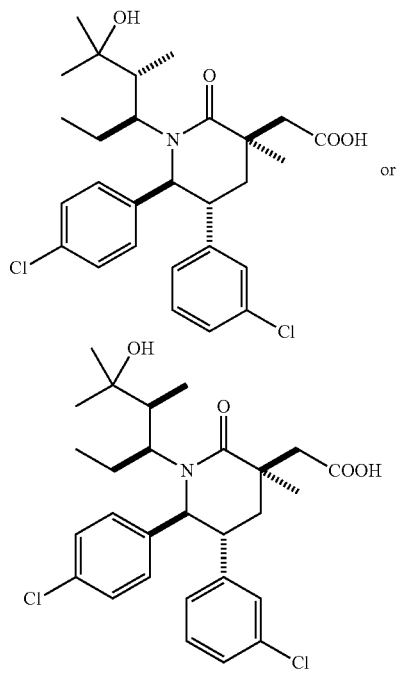

The title compound was prepared from (3S,5R,6S)-3-allyl-5-(3-chlorophenyl)-6-(4-chlorophenyl)-1-((3S,4R)-5-hydroxy-4,5-dimethylhexan-3-yl)-3-methylpiperidin-2-one or (3S,5R,6S)-3-allyl-5-(3-chlorophenyl)-6-(4-chlorophenyl)-

1-((3S,4S)-5-hydroxy-4,5-dimethylhexan-3-yl)-3-methylpiperidin-2-one (Example 149, Step E) by a procedure similar to the one described in example 129, Step D.

$^1$H NMR (400 MHz, CHLOROFORM-d) δ ppm 7.01-7.27 (6 H, m), 6.96 (1 H, t, J=1.7 Hz), 6.70 (3 H, d, J=7.6 Hz), 4.59 (1 H, d, J=9.8 Hz), 3.63-3.91 (1 H, m), 3.14 (1 H, s), 2.98 (1 H, d, J=14.5 Hz), 2.72 (1 H, d, J=14.5 Hz), 1.98-2.21 (2 H, m), 1.84-1.96 (1 H, m), 1.56-1.69 (2 H, m), 1.48 (3 H, s), 1.15 (3 H, s), 1.06 (3 H, s), 0.75 (3 H, br. s.), 0.28 (3 H, br. s.); MS (ESI) 520.2 [M+H]$^+$, 518.2 [M−H]$^-$.

Example 150

2-((3R,5R,6S)-5-(3-chlorophenyl)-6-(4-chlorophenyl)-1-((S)-5-cyano-5-methylhexan-3-yl)-3-methyl-2-oxopiperidin-3-yl)acetic acid

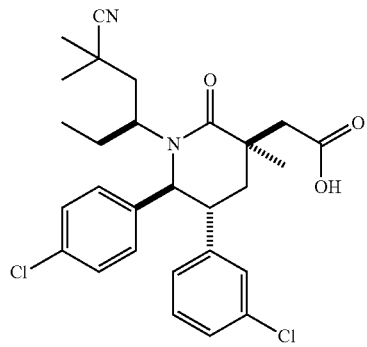

Step A. (2S)-methyl 2-((3R,5R,6S)-5-(3-chlorophenyl)-6-(4-chlorophenyl)-3-(2,3-dihydroxypropyl)-3-methyl-2-oxopiperidin-1-yl)butanoate

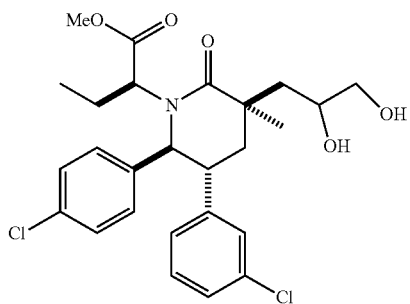

To a solution of (S)-methyl 2-((3S,5R,6S)-3-allyl-5-(3-chlorophenyl)-6-(4-chlorophenyl)-3-methyl-2-oxopiperidin-1-yl)butanoate (1.06 g, 2.23 mmol; Example 91, Step A) and 4-methylmorpholine 4-oxide (393 mg, 3.35 mmol) in DCM (15.800 mL) was added osmium(VIII) oxide polymer-bound, 1% DVB (56.8 mg, 2.234 μmol). After being vigorously stirred at rt for 2 days, additional osmium(VIII) oxide polymer-bound, 1% DVB (56.8 mg, 2.23 μmol) was added and the resulting solution was vigorously stirred at rt for 2 days. The resin was filtered and washed (DCM). The combined organic layers were washed (sat. aq. NaCl solution), dried (Na$_2$SO$_4$), and concentrated under reduced pressure. Purification by chromatography on silica gel (SiO$_2$, 40 g, 53% and 63% EtOAc/Hexanes) provided the title compound.

Step B. (2S)-methyl 2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanoate

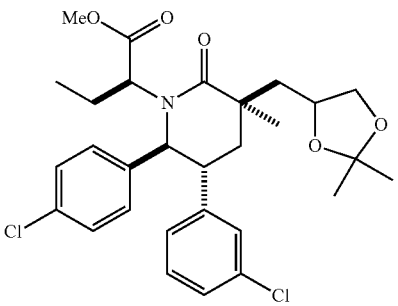

To a solution of (S)-methyl 2-((3R,5R,6S)-5-(3-chlorophenyl)-6-(4-chlorophenyl)-3-(2,3-dihydroxypropyl)-3-methyl-2-oxopiperidin-1-yl)butanoate prepared above in Step A (749 mg, 1.47 mmol) in DCM (8.2 mL) was added p-toluenesulfonic acid monohydrate (14.0 mg, 0.074 mmol) and 2,2-dimethoxypropane (8.15 mL, 66.3 mmol). After being stirred at rt for 3 h, the reaction mixture was concentrated under reduced pressure and the residue was dissolved (EtOAc and sat. aq. NaHCO$_3$) and extracted (3×EtOAc). The combined organic layers were washed (sat. aq. NaCl solution), dried (Na$_2$SO$_4$), and concentrated under reduced pressure. Purification by chromatography on silica gel (SiO$_2$, 40 g, 27% and 37% EtOAc/Hexanes) provided the title compound as a colorless film.

Step C. (3R,5R,6S)-5-(3-chlorophenyl)-6-(4-chlorophenyl)-3-((2,2-dimethyl-1,3-dioxolan-4-yl)methyl)-1-((S)-1-hydroxybutan-2-yl)-3-methylpiperidin-2-one

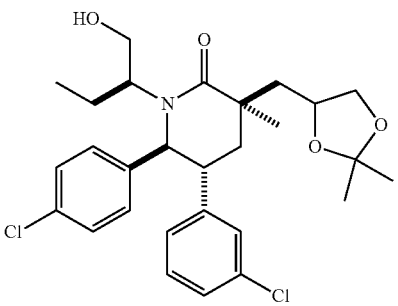 [SMILES: CC[C@@H](CO)N1C(=O)[C@@](C)(CC2COC(C)(C)O2)C[C@H](c2cccc(Cl)c2)[C@H]1c1ccc(Cl)cc1]

To a solution of (2S)-methyl 2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanoate prepared above in Step B (734 mg, 1.34 mmol) in ether (12.2 mL) was added lithium borohydride (58.3 mg, 2.68 mmol) at 0° C. After being stirred at 0° C. for 30 min, the reaction was quenched (ice cold 10% citric acid), extracted (2×EtOAc) and washed (sat. aq. NaCl solution). The combined organic layers were dried (Na$_2$SO$_4$) and concentrated under reduced pres- Step D. (2S)-2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanal

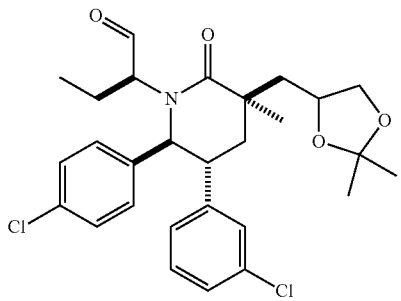 [SMILES: CC[C@@H](C=O)N1C(=O)[C@@](C)(CC2COC(C)(C)O2)C[C@H](c2cccc(Cl)c2)[C@H]1c1ccc(Cl)cc1]

The title compound was prepared form (3R,5R,6S)-5-(3-chlorophenyl)-6-(4-chlorophenyl)-3-((2,2-dimethyl-1,3-dioxolan-4-yl)methyl)-1-((S)-1-hydroxybutan-2-yl)-3-methylpiperidin-2-one (Example 150, Step C) by a procedure similar to the one described in Example 91, Step C.

Step E. (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)hex-2-ene nitrile

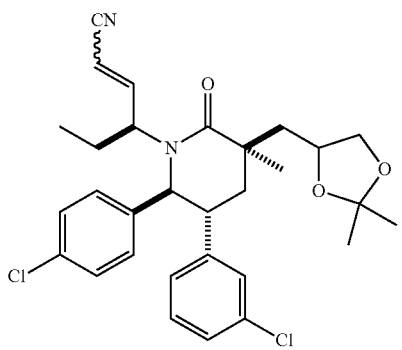 [SMILES: CC[C@@H](C=CC#N)N1C(=O)[C@@](C)(CC2COC(C)(C)O2)C[C@H](c2cccc(Cl)c2)[C@H]1c1ccc(Cl)cc1]

To a solution of diethyl cyanomethylphosphonate (126 µL, 0.799 mmol) and DMPU (481 µL, 3.99 mmol) in THF (1.33 mL) was added 60% sodium hydride in mineral oil (24.0 mg, 0.599 mmol) at 0° C. The mixture was stirred for 30 min, and then treated with a solution of (2S)-2-((3R,5R,6S)-5-(3-chlorophenyl)-6-(4-chlorophenyl)-3-((2,2-dimethyl-1-1,3-dioxolan-4-yl)methyl)-3-methyl-2-oxopiperidin-1-yl)butanal prepared above in Step D (207 mg, 0.399 mmol) in THF (1.33 mL). After being stirred for 4 h, the reaction was quenched (water), extracted (2×EtOAc), and washed (sat. aq. NaCl solution). The combined organic layers were dried (Na$_2$SO$_4$) and concentrated under reduced pressure. Purification of the residue by chromatography on silica gel (24 g SiO$_2$, 30 to 40% EtOAc/Hex, gradient elution) provided the title compound as a colorless liquid.

Step F. (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)hexanenitrile

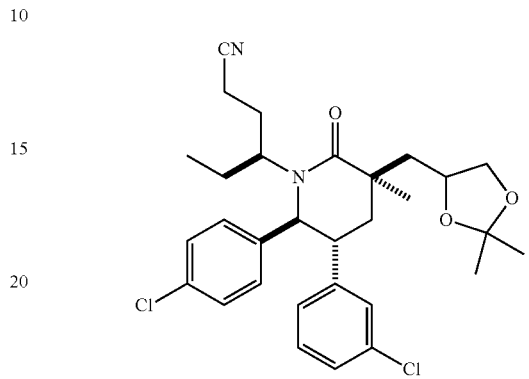

To a solution of (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)hex-2-enenitrile prepared above in Step E (208 mg, 0.384 mmol) in EtOH (12.8 mL) was added 10% palladium on activated carbon (40.9 mg, 0.038 mmol). Then the reaction mixture was subjected to regular hydrogenation with hydrogen (0.774 mg, 0.384 mmol). After being stirred at rt for 1.5 h, the catalyst was filtered using a short plug of silica-gel and washed (EtOAc). The combined organic solutions were concentrated under reduced pressure. Purification by combi flash (flash column chromatography, Teledyne Isco, Lincoln, Nebr.) (SiO$_2$, 24 g, 35% and 40% EtOAc/Hexanes) provided the title compound as a colorless film.

Step G. (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)-2,2-dimethylhexanenitrile

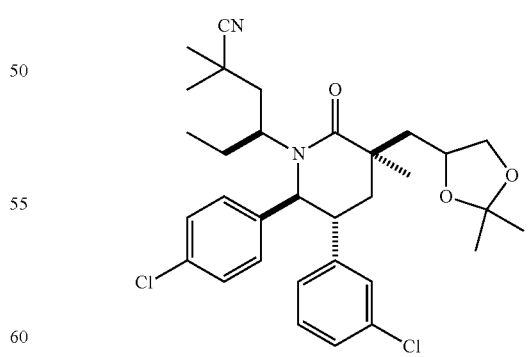

To a solution of (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)hexanenitrile prepared in Step F (120 mg, 0.221 mmol) in THF (1.10 mL) was added 2 M lithium diisopropylamide (552 µL, 1.10 mmol) at −78° C.

After being stirred for 5 min at −78° C., iodomethane (94 μL, 1.51 mmol) was added and the resulting solution was stirred at −78° C. for 30 min. Then the reaction was allowed to warm to rt and stirred for overnight. The reaction was quenched (aq. sat. NH₄Cl) and extracted (2×EtOAc) and the combined organic layers were washed (sat. aq. NaCl solution), dried (Na₂SO₄), and concentrated under reduced pressure. Purification by chromatography on silica gel (SiO₂, 30% and 40% EtOAc/hex) provided a mixture of dimethylated product and monomethylated product, which was resubecjected to the methylation conditions described below.

To a solution of the crude product from the previous reaction in THF (1.10 mL) was added 2 M lithium diisopropylamide in heptane/THF/ethylbenzene (552 μL, 1.10 mmol) at −78° C. After being stirred for 5 min at −78° C., iodomethane (94 μL, 1.51 mmol) was added and the resulting solution was stirred at −78° C. for 30 min. Then the reaction was allowed to warm to rt and stirred for overnight. The reaction was quenched (aq. sat. NH₄Cl) and extracted (2×EtOAc) and the combined organic layers were washed (sat. aq. NaCl solution), dried (Na₂SO₄), and concentrated under reduced pressure. Purification by RP-HPLC purification (60 to 90% MeCN/H₂O (0.1% TFA), gradient elution) provided the title compound.

Step H. (4S)-4-((3R,5R,6S)-5-(3-chlorophenyl)-6-(4-chlorophenyl)-3-(2,3-dihydroxypropyl)-3-methyl-2-oxopiperidin-1-yl)-2,2-dimethylhexanenitrile

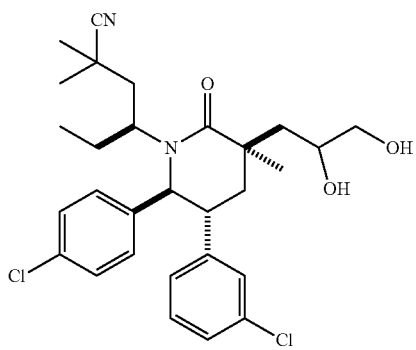 [SMILES: CC[C@@H](CC(C)(C)C#N)N1C(=O)[C@@](C)(CC(O)CO)C[C@H](c2cccc(Cl)c2)[C@H]1c1ccc(Cl)cc1]

To a solution of (4S)-4-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)-2,2-dimethylhexanenitrile prepared above in Step G (77 mg, 0.135 mmol) in THF (2.69 mL) was added 3 N hydrochloric acid in water (1.35 μL, 4.04 mmol) at rt. After being stirred at rt for 4 h, the reaction was diluted (sat. aq. NaCl) and extracted (2×EtOAc). The combined organic layers were washed (sat. aq. NaCl solution), dried (Na₂SO₄), and concentrated under reduced pressure to provide the title compound as a colorless foam.

Step I. 2-((3R,5R,6S)-5-(3-chlorophenyl)-6-(4-chlorophenyl)-1-((S)-5-cyano-5-methylhexan-3-yl)-3-methyl-2-oxopiperidin-3-yl)acetic acid The title compound was prepared from (4S)-4-((3R,5R,6S)-5-(3-chlorophenyl)-6-(4-chlorophenyl)-3-(2,3-dihydroxypropyl)-3-methyl-2-oxopiperidin-1-yl)-2,2-dimethylhexanenitrile prepared above in Step H by a procedure similar to the one described in Example 71, Step F.

¹H NMR (400 MHz, CHLOROFORM-d) δ ppm 7.27 (2 H, s), 7.00-7.20 (4 H, m), 6.97 (1 H, t, J=1.7 Hz), 6.82 (1 H, dt, J=7.4, 1.4 Hz), 4.82 (1 H, d, J=10.6 Hz), 3.12 (1 H, s), 3.01 (1 H, d, J=15.1 Hz), 2.75 (3 H, d, J=15.1 Hz), 2.54 (1 H, s), 2.03-2.12 (1 H, m), 2.01 (1 H, s), 1.90 (1 H, dd, J=14.0, 2.6 Hz), 1.52 (3 H, s), 1.43 (3 H, s), 1.35-1.41 (1 H, m), 1.31 (3 H, s), 1.23 (1 H, d, J=13.9 Hz), 0.33 (3 H, t, J=7.3 Hz); MS (ESI) 515.0 [M+H]⁺, 513.0 [M−H]⁻.

Example 151

2-((3R,5R,6S)-5-(3-Chlorophenyl)-6-(4-chlorophenyl)-3-methyl-2-oxo-1-((S)-2-oxopentan-3-yl)piperidin-3-yl)acetic acid

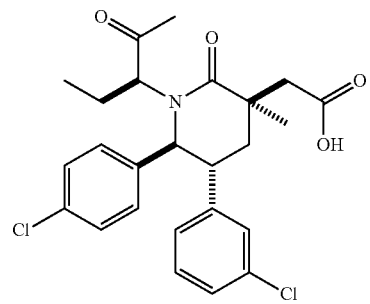 [SMILES: CC[C@@H](C(C)=O)N1C(=O)[C@@](C)(CC(=O)O)C[C@H](c2cccc(Cl)c2)[C@H]1c1ccc(Cl)cc1]

Step A. (3S,5R,6S)-3-Allyl-5-(3-chlorophenyl)-6-(4-chlorophenyl)-1-((S)-1-hydroxybutan-2-yl)-3-methylpiperidin-2-one

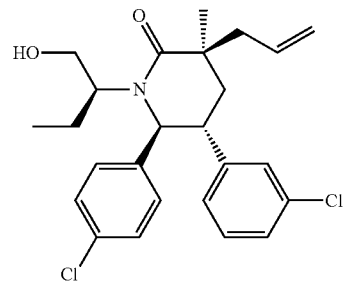

To a solution of 1004 g (1.47 mol) of (3S,5R,6S)-3-allyl-1-((S)-1-((tert-butyldiphenylsilyl)oxy)butan-2-yl)-5-(3-chlorophenyl)-6-(4-chlorophenyl)-3-methylpiperidin-2-one (Example 185, Step E) in THF (3.0 L) was added 2.50 L (2.50 mol) of a 1 M solution of TBAF in THF over a 10 min period. The orange solution was stirred at room temperature for 4 h. The reaction was quenched with 1 N HCl (3 L) and extracted with EtOAc (3×). The combined organic layers were washed with a 3:1 mixture of water and saturated aqueous sodium chloride (4×) and then saturated aqueous sodium chloride (1×). The organic layer was dried over Na₂SO₄, filtered and the filtrate was concentrated. Purification of the residue by chromatography (Biotage® Snap™ column; Biotage, LLC, Charlotte, N.C.), 10 to 50% EtOAc/hexanes, where the EtOAc contains 2% MeCN, gradient elution) provided the title compound as a white foam.

Step B. (S)-2-((3S,5R,6S)-3-Allyl-5-(3-chlorophenyl)-6-(4-chlorophenyl)-3-methyl-2-oxopiperidin-1-yl)butanal

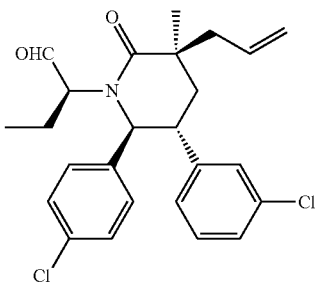 [SMILES: C=CC[C@@]1(C)C[C@H](c2cccc(Cl)c2)[C@@H](c2ccc(Cl)cc2)N([C@H](C=O)CC)C1=O]

To a solution of 428 g (959 mmol) of (3S,5R,6S)-3-allyl-5-(3-chlorophenyl)-6-(4-chlorophenyl)-1-((S)-1-hydroxybutan-2-yl)-3-methylpiperidin-2-one (Example 151, Step A) in dichloromethane (4.55 L) was added 25.9 mL (1.44 mol) of water. A solution of 610 g (1.44 mol) of Dess-Martin periodinane in dichloromethane (4.55 L) was added slowly over a 25 min period so as to maintain an internal reaction temperature not exceeding 25° C. The white slurry was stirred for 2.5 h and then was quenched by cautious, slow addition of saturated aqueous sodium thiosulfate (5.2 L) so as to maintain an internal reaction temperature below 30° C. Water was added and the mixture was extracted with dichloromethane (3×). The combined organic layers were washed with saturated aqueous sodium bicarbonate solution (4×) and then saturated aqueous sodium chloride (1×), dried over $Na_2SO_4$, filtered and the filtrate was concentrated to afford a yellow oily solid. A mixture of ethyl ether and DCM were added, and precipitated solids were filtered off. The precipitation/filtration process was repeated. The filtrate was concentrated to provide the title compound as a white solid. The crude product was used directly in the next step.

Step C. (3S,5R,6S)-3-Allyl-5-(3-chlorophenyl)-6-(4-chlorophenyl)-1-((3S)-2-hydroxypentan-3-yl)-3-methylpiperidin-2-one

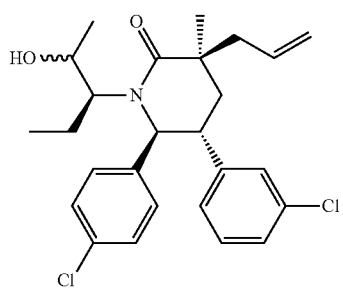 [SMILES: C=CC[C@@]1(C)C[C@H](c2cccc(Cl)c2)[C@@H](c2ccc(Cl)cc2)N([C@@H](CC)C(C)O)C1=O]

To a 0° C. solution of 399 g (899 mmol) of (S)-2-((3S,5R,6S)-3-allyl-5-(3-chlorophenyl)-6-(4-chlorophenyl)-3-methyl-2-oxopiperidin-1-yl)butanal (Example 151, Step B) in THF (9 L) was added 1.93 L (2.70 mol) of a 1.4 M solution of methylmagnesium bromide 75:25 in toluene/tetrahydrofuran slowly over a 30 min period so as to maintain an internal reaction temperature below 6° C. The yellow solution was warmed to room temperature and stirred for 1.5 h. At this time the reaction was cooled to 0° C. and quenched by cautious, slow addition of saturated aqueous ammonium chloride (4.6 L) so as to maintain an internal reaction temperature below 15° C. The mixture was warmed to room temperature, ethyl acetate was added, and the layers were separated. The aqueous layer was extracted with EtOAc (2×). The combined organic layers were washed with water (1×) and then saturated aqueous sodium chloride (1×), dried over $Na_2SO_4$, filtered and the filtrate was concentrated to afford a yellow oil. Purification of the residue by chromatography on silica (Biotage® Snap™ column; Biotage, LLC, Charlotte, N.C.), 5% acetone/5% EtOAc/90% hexanes grading to 5% acetone/29% EtOAc/66% hexanes) provided the title compound as a white solid.

Step D. 2-((3R,5R,6S)-5-(3-Chlorophenyl)-6-(4-chlorophenyl)-3-methyl-2-oxo-1-((S)-2-oxopentan-3-yl)piperidin-3-yl)acetic acid Ruthenium(III) chloride hydrate (1.404 g, 6.23 mmol) was added to a solution of (3S,5R,6S)-3-allyl-5-(3-chlorophenyl)-6-(4-chlorophenyl)-1-((3S)-2-hydroxypentan-3-yl)-3-methylpiperidin-2-one (Example 151, Step C) (130.30 g, 283 mmol) and $NaIO_4$ (61.5 g) in EtOAc (630 mL), $CH_3CN$ (630 mL) and water (935 mL) at 18° C. The remaining $NaIO_4$ (307.5 g) was added in five portions over 2.5 hours while maintaining the temperature below 26° C. 15 minutes after the final addition of $NaIO_4$ the cooling bath was removed and the reaction mixture was stirred at ambient temperature for 50 minutes. The tan reaction mixture was filtered using a Büchner funnel and washed with EtOAc (500 mL) and $CH_3CN$ (500 mL). The layers were separated and the aqueous layer was extracted with EtOAc twice. The organics were pooled, washed with 10% aq. $NaHSO_3$ (3×1 L), brine (1 L), dried ($Na_2SO_4$), decanted and concentrated in vacuo to provide a green oil. The material was dissolved in a minimum amount of DCM and purified using two 1.5 kg Biotage® Snap™ columns (Biotage, LLC, Charlotte, N.C.) and eluting with 10-50% (15% MeOH/acetone)/hexanes to provide a light pink foam (109.67 g).

$^1$H NMR (400 MHz, CHLOROFORM-d) δ ppm 7.25 (2 H, d, J=8.2 Hz), 6.93-7.18 (5 H, m), 6.73-6.80 (1 H, m), 4.47 (1 H, d, J=10.6 Hz), 3.28 (1 H, ddd, J=13.4, 10.5, 3.0 Hz), 3.16 (1 H, dd, J=7.0, 5.5 Hz), 2.73-3.00 (2 H, m), 2.28-2.40 (1 H, m), 2.18-2.25 (1 H, m), 2.16 (3 H, s), 2.11-2.15 (1 H, m), 1.83 (1 H, ddd, J=14.3, 7.8, 5.7 Hz), 1.47 (3 H, s), 0.64 (3 H, t, J=7.5 Hz); MS (ESI) 476.2 [M+H]$^+$.

Example 152

2-((3R,5R,6S)-5-(3-Chlorophenyl)-6-(4-chlorophenyl)-1-((2S,3S)-2-hydroxypentan-3-yl)-3-methyl-2-oxopiperidin-3-yl)acetic acid

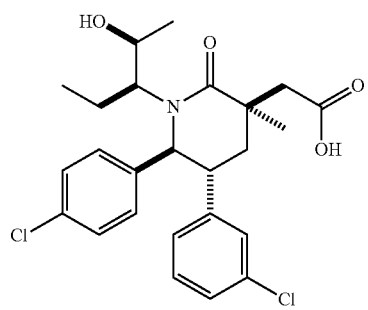 [SMILES: CC[C@@H]([C@H](C)O)N1C(=O)[C@@](C)(CC(=O)O)C[C@H](c2cccc(Cl)c2)[C@H]1c1ccc(Cl)cc1]

To a solution of 3.86 g (8.13 mmol) of 2-((3R,5R,6S)-5-(3-chlorophenyl)-6-(4-chlorophenyl)-3-methyl-2-oxo-1-((S)-2-oxopentan-3-yl)piperidin-3-yl)acetic acid (Example 151) in THF (102 mL) was added a 1 M solution of sodium tri-sec-butylborohydride (N-Selectride®, Aldrich, St. Louis, Mo.) in THF (16.26 mL, 16.26 mmol) at −78° C. dropwise over a period of 5 min. After being stirred at −78° C. for 30 min, the reaction was allowed to warm to rt. The reaction was stirred at rt for 2 h, the reaction was quenched (sat. $NH_4Cl$ solution), extracted (3×EtOAc) and washed (3×ice-cold 1 N aq. HCl and 3×saturated aqueous sodium chloride). The combined organic layers were dried over $Na_2SO_4$, filtered and the filtrate was concentrated under reduced pressure. The crude material was purified by chromatography on a Biotage Isolera flash purification system (Biotage, Charlotte, N.C.) (2×1500 g columns, using a gradient from 10-30% (15% MeOH/acetone) in hexanes. The purified material was then recrystallized from 3:1 hexane/acetone (8 mL/g) to provide the title compound.

$^1$H NMR (500 MHz, DMSO-$d_6$) δ ppm 0.30 (t, J=7.6 Hz, 3 H), 1.00 (d, J=6.3 Hz, 3 H), 1.26 (s, 3 H), 1.41-1.49 (m, 1 H), 1.55-1.64 (m, 1 H), 2.04-2.15 (m, 2 H), 2.29-2.33 (m, 1 H), 2.48 (d, J=13.7 Hz, 1 H), 2.87 (d, J=13.7 Hz, 1 H), 3.35-3.40 (m, 1 H), 4.01-4.06 (m, 1 H), 4.77 (d, J=10.9 Hz, 1 H), 4.80 (br. s, 1 H), 6.93-6.95 (m, 1 H), 7.08-7.10 (m, 1 H), 7.17-7.27 (m, 4 H), 7.33 (d, J=8.4 Hz, 2 H), 12.42 (br s, 1 H); MS (ESI) 478.2 $[M+H]^+$, 476.2 $[M-H]^-$. $[α]_D$=+110° (T=23° C., MeOH, c=0.51).

Alternatively the title compound can be prepared from (3S,5R,6R)-3-allyl-5-(3-chlorophenyl)-6-(4-chlorophenyl)-3-methyltetrahydro-2H-pyran-2-one as prepared in Example 261 step F.

To a 10 mL round-bottom reaction flask was added (3S, 5R,6R)-3-allyl-5-(3-chlorophenyl)-6-(4-chlorophenyl)-3-methyltetrahydro-2H-pyran-2-one (750 mg, 1.998 mmol), (2S,3S)-3-aminopentan-2-ol hydrochloride (837 mg, 6.00 mmol, reference: *J. Org. Chem.*, 2003, 68 (26), 9948), and triethylamine (1966 μl, 13.99 mmol). The vessel was fitted with a reflux condensor and heated to 85 to 95° C. for 2d. The reaction was cooled to RT and diluted with ethyl acetate and washed with 1N HCl (2×20 mL) and brine. The organic layer was dried over $MgSO_4$, filtered, and concentrated. Purification by column chromatography using 40 to 50% ethyl acetate in hexanes afforded (S)-2-((2R,3R)-2-(3-chlorophenyl)-3-(4-chlorophenyl)-3-hydroxypropyl)-N-((2S,3S)-2-hydroxypentan-3-yl)-2-methylpent-4-enamide.

$^1$H NMR (500 MHz, DMSO-d6) δ 7.17 (m, 2H), 7.16 (m, 1H), 7.14-7.08 (series of m, 2H), 6.97 (m, 2H), 6.88 (br d, J=6.9 Hz, 1H), 5.96 (d, J=8.3 Hz, 1H), 5.65 (ddt, J=17.4, 10.2, 7.2 Hz, 1H), 5.07 (dd J=10.3, 1.0 Hz, 1H), 5.02 (d, J=17.6, 1H), 4.75 (t, J=4.2 Hz, 1H), 3.79 (m, 1H), 3.66 (ddd, J=8.8, 5.9, 4.2 Hz, 1H), 3.30 (d, J=3.4 Hz, 1H), 3.03 (dt, J=6.9, 5.4 Hz, 1H), 2.37 (dd, J=13.9, 7.3 Hz, 1H), 2.32 (dd, J=14.7, 5.6 Hz, 1H), 2.12 (dd, J=13.7, 7.1 Hz, 1H), 2.01 (d, J=4.7 Hz, 1H), 1.83 (dd, J=14.7, 7.3 Hz, 1H), 1.58 (m, 1H), 1.42 (ddq, J=14.9, 8.6, 7.3 Hz), 1.14 (s, 3H), 1.14 (d, J=6.4 Hz, 3H), 0.90 (t, J=7.3 Hz, 3H) ppm. LC/MS (M+H)=478.2.

To a solution of (S)-2-((2R,3R)-2-(3-chlorophenyl)-3-(4-chlorophenyl)-3-hydroxypropyl)-N-((2S,3S)-2-hydroxypentan-3-yl)-2-methylpent-4-enamide (127 mg, 0.265 mmol) in toluene (5309 μl) was added ammonium molybdate $((NH_4)_2MoO_4)$ (5.20 mg, 0.027 mmol) and heated to reflux under Dean-Stark conditions overnight. The reaction was cooled to room temperature, diluted with ethyl acetate and washed with sat. $NaHCO_3$ and brine. The organics were dried over $MgSO_4$, filtered and concentrated. Purification by column chromatography using 20 to 40% ethyl acetate in hexanes afforded (1R,2R,4S)-2-(3-chlorophenyl)-1-(4-chlorophenyl)-4-((4S,5S)-4-ethyl-5-methyl-4,5-dihydrooxazol-2-yl)-4-methylhept-6-en-1-ol $^1$H NMR (500 MHz, DMSO-d6) δ 7.25 (m, 2H), 7.12 (m, 2H), 7.07 (br s, 1H), 7.05 (m, 2H), 6.96 (br d, J=6.8 Hz, 1H), 5.53 (ddt, J=17.4, 10.3, 7.4 Hz, 1H), 5.42 (d, J=4.2 Hz, 1H), 4.95 (m, 2H), 4.66 (t, J=4.9 Hz, 1H), 3.56 (dq, J=7.6, 6.1 Hz, 1H), 3.12 (q, J=7.1 Hz, 1H), 2.90 (ddd, (9.5, 5.1, 2.3 Hz, 1H), 2.20 (m, 2H), 1.93 (dd, J=13.7, 7.8 Hz, 1H), 1.75 (dd, J=14.3, 2.2 Hz, 1H), 1.11 (m, 1H), 1.10 (d, J=6.4 Hz, 3H), 0.98 (m, 1H), 0.97 (s, 3H), 0.75 (t, J=7.6 Hz, 3H) ppm. LC/MS (M+H)=460.2.

To a solution of (1R,2R,4S)-2-(3-chlorophenyl)-1-(4-chlorophenyl)-4-((4S,5S)-4-ethyl-5-methyl-4,5-dihydrooxazol-2-yl)-4-methylhept-6-en-1-ol (80 mg, 0.174 mmol) in $CH_2Cl_2$ (1737 μl) at −50° C. was added 2,6-lutidine (46.4 μl, 0.400 mmol) followed by trifluoromethanesulfonic anhydride solution, 1 M in methylene chloride (191 μl, 0.191 mmol). The reaction was stirred at −50° C. for 30 min and then treated with an additional 25 uL of trifluoromethanesulfonic anhydride solution, 1 M in methylene chloride, then 2 mL of sat. $CuSO_4$. The reaction was warmed to rt and extracted with dichloromethane. The organic phase was dried over $MgSO_4$, filtered and concentrated. Purification by column chromatography using 40 to 80% acetone in hexanes afforded (2S,3S,5S,6R,8S)-8-allyl-6-(3-chlorophenyl)-5-(4-chlorophenyl)-3-ethyl-2,8-dimethyl-2,3,5,6,7,8-hexahydrooxazolo[3,2-a]pyridin-4-ium triflate.

$^1$H NMR (500 MHz, DMSO-d6) δ 7.55-7.05 (series of m, 8H), 5.88 (ddt, J=17.3, 10.0, 7.8 Hz, 1H), 5.36 (dd, J=17.1, 2.0 Hz, 1H), 5.31 (d, J=10.8 Hz, 1H), 5.28 (dd, J=10.0, 2.0 Hz, 1H), 5.18 (quintet, J=6.1 Hz, 1H), 4.10 (td, J=6.6, 2.7 Hz, 1H), 3.98 (ddd, J=13.7, 11.2, 3.4 Hz, 1H), 2.80 (A_BX, J_{AB}=13.7 Hz, J_{AX}=7.3 Hz, 1H), 2.73 (AB_X J_{AB}=13.7 Hz, J_{BX}=7.8 Hz, 1H), 2.49 (m, 1H), 2.41 (t, J=13.7 Hz, 1H), 2.00 (dd, J=13.9, 3.7 Hz, 1H), 1.55 (d, J=6.1 Hz, 1H), 1.31 (s, 3H), 0.95 (dqd, J=14.2, 7.8, 3.0 Hz, 1H), 0.58 (t, J=7.3 Hz, 1H), 0.47 (ddq, J=13.7, 6.3, 6.3 Hz, 1H) ppm. LC/MS (M+=442.2).

To a solution of (2S,3S,5S,6R,8S)-8-allyl-6-(3-chlorophenyl)-5-(4-chlorophenyl)-3-ethyl-2,8-dimethyl-2,3,5,6,7,8-hexahydrooxazolo[3,2-a]pyridin-4-ium triflate (60 mg, 0.101 mmol) in 1 mL dichloromethane at 0° C. was added tetra-n-butylammonium chloride (2.81 mg, 10.13 μmol) and acetic acid (116 μl, 2.025 mmol). To this was added $KMnO_4$ (32.0 mg, 0.203 mmol) in 1 mL water followed by a 1 mL water rinse. An additional 10 eq. acetic acid were added followed by an additional 16 mg $KMnO_4$ in 1 mL water. This was repeated once more. A total of 4 eq $KMnO_4$ and 40 eq. acetic acid were added.

The reaction was quenched with 1 mL of sat. $Na_2S_2O_3$ solution and diluted with ethyl acetate. The layers were separated and the organic phase was washed once with brine, dried over $MgSO_4$, filtered and concentrated to afford crude (2S, 3S,5S,6R,7aR)-6-(3-chlorophenyl)-5-(4-chlorophenyl)-3-ethyl-2,7a-dimethylhexahydrofuro [2,3-b]oxazolo[3,2-a]pyridin-9(5H)-one. This crude residue was redissolved in 2 mL isopropyl acetate and treated with 2 mL sat. $NaHCO_3$ and heated to 70° C. After 2 h, the reaction was cooled to 0° C. and treated with 10% acetic acid to a pH of about 3. The reaction was diluted with ethyl acetate and washed once with 10% acetic acid solution, dried over $MgSO_4$, filtered, and concentrated. Purification by column chromatography using 10 to 50% of (15% MeOH/acetone) in hexanes afforded 2-((3R, 5R,6S)-5-(3-chlorophenyl)-6-(4-chlorophenyl)-1-((2S,3S)-2-hydroxypentan-3-yl)-3-methyl-2-oxopiperidin-3-yl)acetic acid.

Example 153

2-((3R,5R,6S)-5-(3-Chlorophenyl)-6-(4-chlorophenyl)-1-((2S,3S)-2-methoxypentan-3-yl)-3-methyl-2-oxopiperidin-3-yl)acetic acid

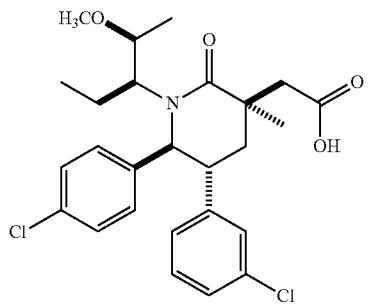 [SMILES: CC[C@@H]([C@H](C)OC)N1C(=O)[C@@](C)(CC(=O)O)C[C@H](c2cccc(Cl)c2)[C@H]1c1ccc(Cl)cc1]

Step A. Methyl 2-((3R,5R,6S)-5-(3-chlorophenyl)-6-(4-chlorophenyl)-1-((2S,3S)-2-hydroxypentan-3-yl)-3-methyl-2-oxopiperidin-3-yl)acetate

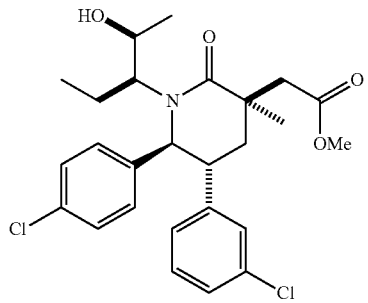 [SMILES: CC[C@@H]([C@H](C)O)N1C(=O)[C@@](C)(CC(=O)OC)C[C@H](c2cccc(Cl)c2)[C@H]1c1ccc(Cl)cc1]

To a solution of 260 mg (0.543 mmol) of 2-((3R,5R,6S)-5-(3-chlorophenyl)-6-(4-chlorophenyl)-1-((2S,3S)-2-hydroxypentan-3-yl)-3-methyl-2-oxopiperidin-3-yl)acetic acid (Example 152) in 5 mL of THF was added 60% sodium hydride (217 mg, 5.43 mmol) at 0° C. After being stirred at 0° C. for 20 min, iodomethane (271 uL, 4.35 mmol) was added. The reaction was allowed to warm to ambient temperature, and stirred for an additional 3 h until completion. The reaction was quenched with saturated aqueous NH$_4$Cl solution, extracted with EtOAc (2×25 mL). The combined organic layers were washed with saturated NaCl, dried over MgSO$_4$, filtered and the filtrate was concentrated to provide the title compound.

Step B. Methyl 2-((3R,5R,6S)-5-(3-chlorophenyl)-6-(4-chlorophenyl)-1-((2S,3S)-2-methoxypentan-3-yl)-3-methyl-2-oxopiperidin-3-yl)acetate

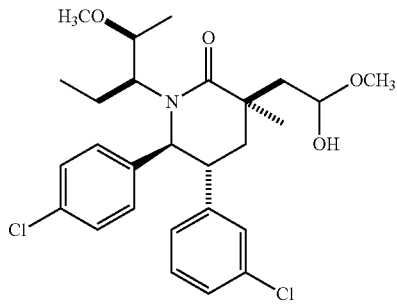 [SMILES: CC[C@@H]([C@H](C)OC)N1C(=O)[C@@](C)(CC(O)OC)C[C@H](c2cccc(Cl)c2)[C@H]1c1ccc(Cl)cc1]

To a solution of 50 mg (0.102 mmol) of methyl 2-((3R,5R,6S)-5-(3-chlorophenyl)-6-(4-chlorophenyl)-1-((2S,3S)-2-hydroxypentan-3-yl)-3-methyl-2-oxopiperidin-3-yl)acetate (Example 153, Step A) in 0.3 mL of DMF was added 60% sodium hydride (20.31 mg, 0.508 mmol) at 25° C. After being stirred at 25° C. for 20 min, iodomethane (25.4 uL, 0.406 mmol) was added. The reaction was stirred for an additional 30 min and was quenched with saturated aqueous NH$_4$Cl solution, extracted with EtOAc (2×25 mL). The combined organic layers were washed with saturated NaCl, dried over MgSO$_4$, filtered and the filtrate was concentrated. Purification of the residue by flash chromatography on silica gel (eluent: 20 to 60% EtOAc/hexanes) provided the title compound.

Step C. 2-((3R,5R,6S)-5-(3-Chlorophenyl)-6-(4-chlorophenyl)-1-((2S,3S)-2-methoxypentan-3-yl)-3-methyl-2-oxopiperidin-3-yl)acetic acid To a solution of methyl 2-((3R,5R,6S)-5-(3-chlorophenyl)-6-(4-chlorophenyl)-1-((2S,3S)-2-methoxypentan-3-yl)-3-methyl-2-oxopiperidin-3-yl)acetate (34 mg, 0.067 mmol; Example 153, Step B) in THF/MeOH/H$_2$O (1/1/1, 0.48 mL) was added 2 M lithium hydroxide (67 uL, 0.134 mmol) at rt. After being stirred at rt for 4 h, the reaction was quenched saturated aqueous NH$_4$Cl and extracted (2×DCM) and the combined organic layers were washed (1×sat. aq. NaCl solution) and concentrated under the reduced pressure. Purification of the residue by flash chromatography on silica gel (eluent: 70 to 100% EtOAc/hexanes) provided the title compound.

$^1$H NMR (400 MHz, CHLOROFORM-d) δ ppm 0.38 (t, J=8.0 Hz, 3 H), 1.05 (d, J=4.0 Hz, 1 H), 1.48 (s, 3 H), 1.65 (m, 1 H), 1.75 (m, 1 H), 2.00 (dd, J=12.0, 4 Hz, 1 H), 2.21 (m, 1 H), 2.48 (m, 1 H), 2.70 (d, J=16.0 Hz, 1 H), 3.06-3.15 (m, 2 H), 3.41 (s, 3 H), 3.94 (m, 1 H), 4.63 (d, J=12.0 Hz, 1 H), 6.75 (d, J=8.0 Hz, 1 H), 6.90-7.05 (m, 3 H), 7.05-7.15 (m, 2 H), 7.25 (d, J=8.0 Hz, 2 H); MS (ESI) 492.1 [M+H]$^+$.

Example 154

2-((3R,5R,6S)-5-(3-Chlorophenyl)-6-(4-chlorophenyl)-1-((2R,3S)-2-hydroxypentan-3-yl)-3-methyl-2-oxopiperidin-3-yl)acetic acid

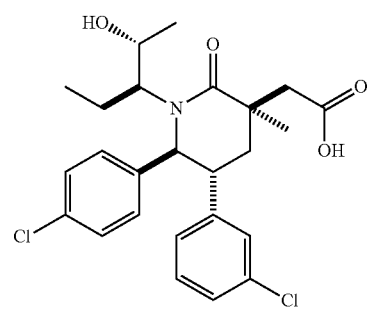 [SMILES: CC[C@@H]([C@@H](C)O)N1C(=O)[C@@](C)(CC(=O)O)C[C@H](c2cccc(Cl)c2)[C@H]1c1ccc(Cl)cc1]

A solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (71 mg, 0.154 mmol)(Example 210, Step A) in THF (2 mL) was sparged with argon for 5 minutes. The mixture was cooled to 0° C. and methylmagnesium chloride, 3.0 M solution in tetrahydrofuran (0.113 ml, 0.339 mmol) was added at such a rate that the internal temperature did not get above 4° C. The mixture was stirred at 0° C. for 45 minutes. The mixture was quenched with sat. aq. NH₄Cl solution and extracted with EtOAc. The combined organic layers were dried over Na₂SO₄, filtered and the filtrate was concentrated. The residue was purified by flash chromatography on silica gel (2×4 g stacked columns, eluent: 5 to 15% isopropanol/hexanes) to give the title compound as the more polar diastereomer.

¹H NMR (400 MHz, CHLOROFORM-d) δ ppm 0.55 (t, J=7.63 Hz, 3 H), 1.18 (d, J=6.65 Hz, 3 H), 1.44 (s, 3 H), 1.63-1.77 (m, 1 H), 1.99-2.18 (m, 3 H), 2.61-2.71 (m, 1 H), 2.81 (d, J=14.28 Hz, 1 H), 2.92 (d, J=14.48 Hz, 1 H), 3.24 (td, J=10.22, 5.77 Hz, 1 H), 4.11-4.22 (m, 1 H), 4.45 (d, J=10.17 Hz, 1 H), 6.74 (dt, J=7.53, 1.61 Hz, 1 H), 6.93-7.05 (m, 3 H), 7.07-7.14 (m, 1 H), 7.15-7.20 (m, 1 H), 7.24-7.31 (m, 2 H). Mass Spectrum (ESI) m/e=478.1 (M+1).

Example 155

2-((3R,5R,6S)-5-(3-Chlorophenyl)-6-(4-chlorophenyl)-1-((2S,3R)-2-hydroxypentan-3-yl)-3-methyl-2-oxopiperidin-3-yl)acetic acid (isomer 1)

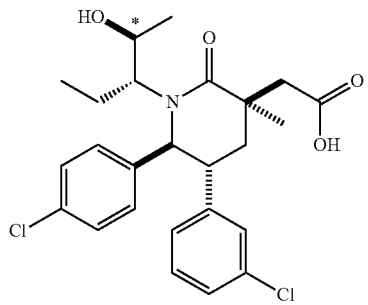

\* stereochemistry was not confirmed

Step A. (R)-2-((3S,5R,6S)-3-Allyl-5-(3-chlorophenyl)-6-(4-chlorophenyl)-3-methyl-2-oxopiperidin-1-yl)butanal

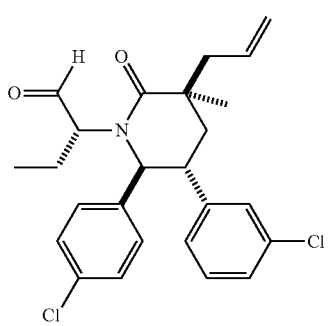

The title compound was prepared from (3S,5R,6S)-3-allyl-5-(3-chlorophenyl)-6-(4-chlorophenyl)-1-((R)-1-hydroxybutan-2-yl)-3-methylpiperidin-2-one by a procedure similar to the one described in Example 91, Step B. The product was used in the next step without further purification.

Step B. (3S,5R,6S)-3-allyl-5-(3-chlorophenyl)-6-(4-chlorophenyl)-1-((3R)-2-hydroxypentan-3-yl)-3-methylpiperidin-2-one

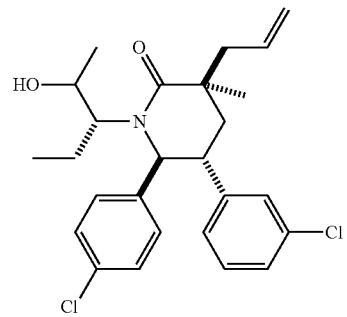

The title compound was prepared from (R)-2-((3S,5R,6S)-3-allyl-5-(3-chlorophenyl)-6-(4-chlorophenyl)-3-methyl-2-oxopiperidin-1-yl)butanal (Example 155, Step A) as described in Example 149, Step A. Purification by flash chromatography (SiO₂, 40 g, 10% to 25% EtOAc/hexanes) provided the title compound as a mixture of two diastereomers at the newly formed stereocenter.

Step C. 2-((3R,5R,6S)-5-(3-Chlorophenyl)-6-(4-chlorophenyl)-3-methyl-2-oxo-1-((R)-2-oxopentan-3-yl)piperidin-3-yl)acetic acid

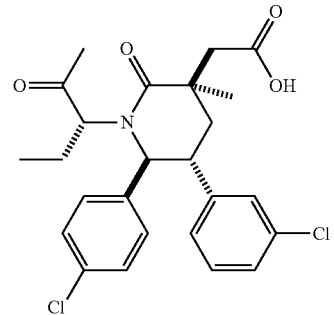

The title compound was prepared from (3S,5R,6S)-3-allyl-5-(3-chlorophenyl)-6-(4-chlorophenyl)-1-((3R)-2-hydroxypentan-3-yl)-3-methylpiperidin-2-one (0.210 g, 0.456 mmol; Example 155, Step B) by a procedure similar to the one described in Example 71, Step F.

Step D. 2-((3R,5R,6S)-5-(3-Chlorophenyl)-6-(4-chlorophenyl)-1-((2S,3R)-2-hydroxypentan-3-yl)-3-methyl-2-oxopiperidin-3-yl)acetic acid To a solution of 2-((3R,5R,6S)-5-(3-chlorophenyl)-6-(4-chlorophenyl)-3-methyl-2-oxo-1-((R)-2-oxopentan-3-yl)piperidin-3-yl)acetic acid (0.150 g, 0.315 mmol, Example 155, Step C) in THF/MeOH (3/1, 4 mL) was added sodium borohydride (0.060 g, 1.574 mmol) at room temperature. After being stirred at room temperature for 1 h, the reaction was acidified with sat. aq. NH₄Cl solution and extracted with EtOAc. The combined organic layers were washed with sat. aq. NaCl solution, dried over MgSO₄, filtered and the filtrate was concentrated under reduced pressure. The crude material was purified by reversed phase preparatory HPLC (eluent: 10-90% acetonitrile, water, 0.1% TFA, gradient elution) to give a mixture of two isomers (dr=93:7). Individual stereoisomers were separated by chiral HPLC (250×30 mm CHIRALPAK® IC column (CHIRAL TECHNOLOGIES, INC., West Chester, Pa., USA) with 46 g/min ispropylamine+ (20 μM NH₃)+84 g/min $CO_2$ on Thar 350 SFC (Thar Technologies, Inc., Pittsburg, Pa.)) to give the title compound as the faster eluting stereoisomer.

¹H NMR (400 MHz, CHLOROFORM-d) δppm 0.61 (d, J=6.65 Hz, 3 H), 0.99-1.08 (t, J=7.34 Hz, 3 H), 1.18-1.37 (m, 1 H), 1.45-1.60 (m, 4 H), 1.99-2.21 (m, 3 H), 2.69 (dd, J=11.15, 3.72 Hz, 1 H), 2.82-2.90 (m, 1 H), 3.18-3.30 (m, 1 H), 3.69-3.79 (m, 1 H), 4.34 (d, J=10.56 Hz, 1 H), 6.71 (d, J=7.63 Hz, 1 H), 6.88-7.04 (m, 2 H), 7.04-7.20 (m, 3 H), 7.20-7.32 (m, 2 H). MS (ESI) 478.0 [M+H]⁺.

Further elution provided Example 156.

Example 156

2-((3R,5R,6S)-5-(3-chlorophenyl)-6-(4-chlorophenyl)-1-((2R,3R)-2-hydroxypentan-3-yl)-3-methyl-2-oxopiperidin-3-yl)acetic acid

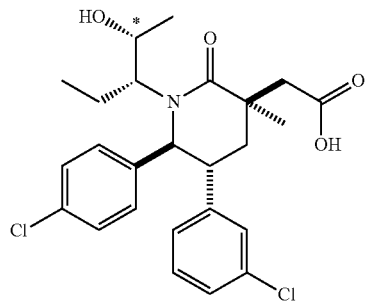

* stereochemistry was not confirmed

Example 155, Step D; slower eluting isomer from chiral HPLC.

¹H NMR (400 MHz, CHLOROFORM-d) δppm 0.81 (d, J=6.46 Hz, 3 H), 1.01 (t, J=7.43 Hz, 3 H), 1.47 (s, 3 H), 1.64 (m, 1 H), 1.82-1.95 (m, 1 H), 2.13-2.25 (m, 2 H), 2.73-2.84 (m, 2 H), 2.93 (d, J=14.87 Hz, 1 H), 3.37 (m, 1 H), 3.93 (m, 1 H), 4.45 (d, J=10.56 Hz, 1 H), 6.72 (d, J=7.43 Hz, 1 H), 6.96 (m, 1 H), 7.02-7.17 (m, 4 H), 7.21 (m, 2 H); Mass Spectrum (ESI) m/z=478.0 (M+1).

Example 157

2-((3R,5R,6S)-5-(3-Chlorophenyl)-6-(4-chlorophenyl)-1-((S)-2-hydroxy-2-methylpentan-3-yl)-3-methyl-2-oxopiperidin-3-yl)acetic acid

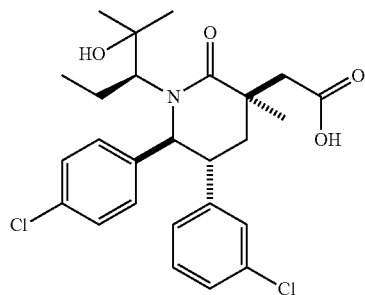 [SMILES: CC[C@H](N1C(=O)[C@@](C)(CC(=O)O)C[C@H](c2cccc(Cl)c2)[C@H]1c1ccc(Cl)cc1)C(C)(C)O]

Step A. (3S,5R,6S)-3-allyl-5-(3-chlorophenyl)-6-(4-chlorophenyl)-1-((S)-2-hydroxy-2-methylpentan-3-yl)-3-methylpiperidin-2-one

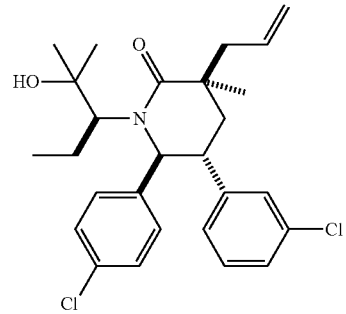

To a solution of (3S,5R,6S)-3-allyl-5-(3-chlorophenyl)-6-(4-chlorophenyl)-3-methyl-1-((S)-2-oxopentan-3-yl)piperidin-2-one (0.100 g, 0.218 mmol; Example 149, Step B) in THF (4 mL) was added a solution of methylmagnesium bromide, 1.4M in toluene (0.104 g, 0.873 mmol) at 0° C. The reaction was allowed to warm to room temperature. After being stirred at room temperature for 4 h, another 1 eq. of MeMgBr was added and stirred for another 2 h. The reaction was quenched w/sat NH₄Cl solution, and extracted with EtOAc. The combined organic layers were washed with sat. aq. NaCl solution, dried over MgSO₄, filtered and the filtrate was concentrated under reduced pressure. The crude material was absorbed onto a plug of silica gel and purified by chromatography on silica gel, eluting with 40% EtOAc/hexanes, to provide the title compound as a light-yellow oil.

Step B. 2-((3R,5R,6S)-5-(3-chlorophenyl)-6-(4-chlorophenyl)-1-((S)-2-hydroxy-2-methylpentan-3-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-2-hydroxy-2-methylpentan-3-yl)-3-methylpiperidin-2-one (Example 157, Step A) by a procedure similar to the one described in Example 71, Step F.

¹H NMR (400 MHz, CHLOROFORM-d) δ ppm 0.37 (t, J=7.63 Hz, 3 H) 1.10 (s, 3 H) 1.35 (s, 3 H) 1.50 (s, 3 H) 1.68 (ddd, J=15.21, 7.78, 4.01 Hz, 1 H) 2.10-2.31 (m, 3 H) 2.44-2.55 (m, 1 H) 2.78-2.95 (m, 2 H) 3.24-3.37 (m, 1 H) 4.40 (d, J=10.56 Hz, 1 H) 6.73 (dt, J=7.53, 1.52 Hz, 1 H) 6.95 (m, 1 H) 7.01-7.21 (m, 4 H) 7.21-7.38 (m, 2 H). MS (ESI) 492.2 [M+H]⁺.

Example 158

2-((3R,5R,6S)-5-(3-Chlorophenyl)-6-(4-chlorophenyl)-1-((3S,4S)-4-hydroxyhexan-3-yl)-3-methyl-2-oxopiperidin-3-yl)acetic acid or 2-((3R,5R,6S)-5-(3-Chlorophenyl)-6-(4-chlorophenyl)-1-((3S,4R)-4-hydroxyhexan-3-yl)-3-methyl-2-oxopiperidin-3-yl)acetic acid

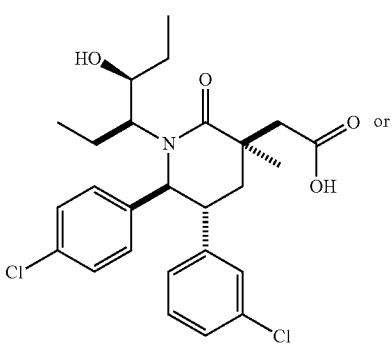

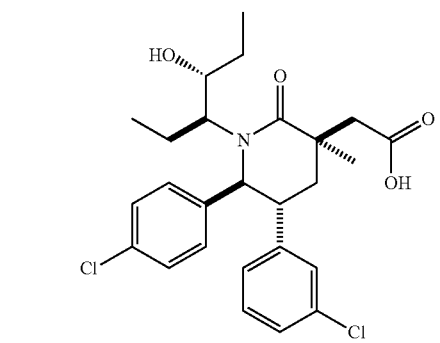

Step A. (3S,5R,6S)-3-Allyl-5-(3-chlorophenyl)-6-(4-chlorophenyl)-1-((S)-4-hydroxyhexan-3-yl)-3-methylpiperidin-2-one

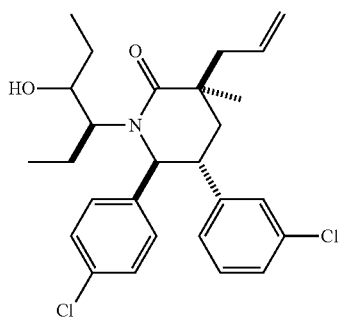

The title compound was prepared from (S)-2-((3S,5R,6S)-3-allyl-5-(3-chlorophenyl)-6-(4-chlorophenyl)-3-methyl-2-oxopiperidin-1-yl)butanal (Example 91, Step C) and ethylmagnesium bromide as described in Example 149, Step A. The crude material was used in the next step without further purification

Step B. 2-((3R,5R,6S)-5-(3-chlorophenyl)-6-(4-chlorophenyl)-3-methyl-2-oxo-1-((S)-4-oxohexan-3-yl)piperidin-3-yl)acetic acid

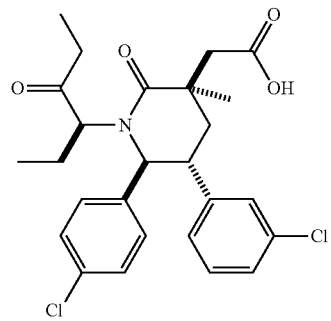

The title compound was prepared from (3S,5R,6S)-3-allyl-5-(3-chlorophenyl)-6-(4-chlorophenyl)-1-((S)-4-hydroxyhexan-3-yl)-3-methylpiperidin-2-one (Example 158, Step A) as described in Example 71, Step F.

Step C. 2-((3R,5R,6S)-5-(3-Chlorophenyl)-6-(4-chlorophenyl)-1-((3S)-4-hydroxyhexan-3-yl)-3-methyl-2-oxopiperidin-3-yl)acetic acid To a solution of 2-((3R,5R,6S)-5-(3-chlorophenyl)-6-(4-chlorophenyl)-3-methyl-2-oxo-1-((S)-4-oxohexan-3-yl)piperidin-3-yl)acetic acid (0.038 g, 0.077 mmol; Example 158, Step B) in a mixture of THF and methanol (4:1, 5 mL) was added sodium borohydride (9 mg, 0.24 mmol) at 0° C. Then the reaction was allowed to warm to room temperature. After being stirred at room temperature for 1.5 h, another 2 eq. of sodium borohydride were added and stirred for another 0.5 h. The reaction was acidified (10% citric acid) and extracted (2×EtOAc). The combined organic layers were washed (sat. aq. NaCl solution), dried (MgSO$_4$), and concentrated under reduced pressure. The crude material was purified by reverse phase preparatory HPLC (eluent: 10 to 90% acetonitrile, water, 0.1% TFA, gradient elution) to give the title compound as the first eluting fraction as a white solid after lyophilization.
$^1$H NMR (400 MHz, CHLOROFORM-d) δ ppm 0.55 (t, J=7.53 Hz, 3 H) 0.91 (t, J=7.34 Hz, 3 H) 1.38 (m, 1 H) 1.44 (s, 3 H) 1.54 (m, 1 H) 1.72 (m, 1H) 2.00-2.25 (m, 3 H) 2.73-2.79 (m, 1 H) 2.82 (d, J=14.48 Hz, 1H) 2.92 (d, J=14.48 Hz, 1 H) 3.26 (m, 1 H) 3.87-3.93 (m, 1 H) 4.43 (d, J=10.17 Hz, 1 H) 6.75 (dt, J=7.53, 1.52 Hz, 1 H) 6.95-7.07 (m, 3 H) 7.12 (t, J=7.73 Hz, 1 H) 7.17 (m, 1 H) 7.25-7.35 (m, 2 H). MS (ESI) 492.2 [M+H]$^+$.

Example 159

2-((3R,5R,6S)-5-(3-Chlorophenyl)-6-(4-chlorophenyl)-1-((S)-1-methoxybutan-2-yl)-3-methyl-2-oxopiperidin-3-yl)acetic acid

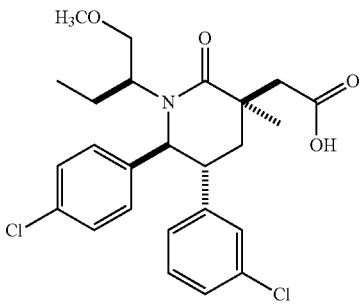 [SMILES: CC[C@@H](COC)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-1-((S)-1-methoxybutan-2-yl)-3-methylpiperidin-2-one

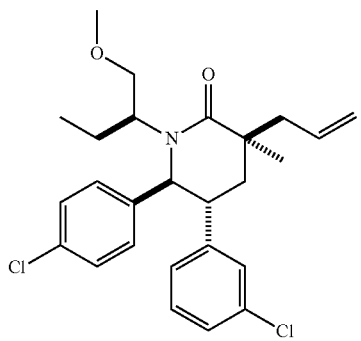 [SMILES: C=CC[C@@]1(C)C[C@H](c2cccc(Cl)c2)[C@@H](c2ccc(Cl)cc2)N([C@@H](CC)COC)C1=O]

To a solution of 50 mg (0.112 mmol) of (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) in 0.5 mL of THF was added 60% sodium hydride (8.96 mg, 0.244 mmol) at 0° C. After being stirred at 0° C. for 30 min, iodomethane (14.01 uL, 0.244 mmol) was added. The reaction was allowed to warm to 25° C., and stirred for an additional 2 h until completion. The reaction was quenched with saturated aqueous NH$_4$Cl solution, extracted with EtOAc (2×25 mL). The combined organic layers were washed with saturated NaCl solution, dried over MgSO$_4$, filtered and the filtrate was concentrated to provide the title compound.

Step B. 2-((3R,5R,6S)-5-(3-chlorophenyl)-6-(4-chlorophenyl)-1-((S)-1-methoxybutan-2-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-methoxybutan-2-yl)-3-methylpiperidin-2-one (Example 159, Step A) by a procedure similar to the one described in Example 71, Step F. The residue was purified by reverse phase preparatory HPLC (MeCN in water with 0.1% TFA, gradient elution) to give the title compound as a white solid.

$^1$H NMR (400 MHz, CHLOROFORM-d) δ ppm 0.50 (t, J=8.0 Hz, 3 H), 1.42 (s, 3 H), 1.50 (m, 1 H), 1.93 (m, 1 H), 2.02 (dd, J=12.0, 4.0 Hz, 1 H), 2.18 (dd, J=12.0, 12.0 Hz, 1 H), 2.71 (d, J=16.0 Hz, 1 H), 3.05 (d, J=12.0 Hz, 1 H), 2.90-3.10 (m, 2 H), 3.31 (dd, J=8.0, 4.0 Hz, 1 H), 3.38 (s, 3 H), 3.93 (t, J=12.0 Hz, 1 H), 4.61 (d, J=8.0 Hz, 1 H), 6.78 (d, J=8.0 Hz, 1 H), 7.01 (d, J=8.0 Hz, 2 H), 7.05 (s, 1 H), 7.12 (t, J=8.0 Hz, 1 H), 7.17 (d, J=8.0 Hz, 1 H), 7.26 (d, J=8.0 Hz, 2 H); MS (ESI) 478.0 [M+H]$^+$.

Example 160

2-((3R,5R,6S)-5-(3-Chlorophenyl)-6-(4-chlorophenyl)-3-methyl-2-oxo-1-((3S)-1,1,1-trifluoro-2-hydroxy-2-methylpentan-3-yl)piperidin-3-yl)acetic acid

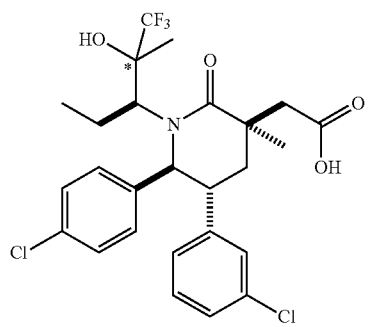

* stereochemistry unknown

Step A. (3S,5R,6S)-3-Allyl-5-(3-chlorophenyl)-6-(4-chlorophenyl)-3-methyl-1-((3S)-1,1,1-trifluoro-2-hydroxy-2-methylpentan-3-yl)piperidin-2-one

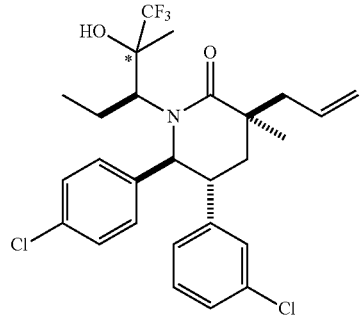

* stereochemistry unknown

A solution of (3S,5R,6S)-3-allyl-5-(3-chlorophenyl)-6-(4-chlorophenyl)-3-methyl-1-((S)-2-oxopentan-3-yl)piperidin-2-one (30 mg, 0.065 mmo; Example 149, Step B) and trimethyl(trifluoromethyl)silane (48.5 μL, 0.327 mmol) in THF (0.5 mL) was treated with 1 M tetrabutylammonium fluoride solution in THF (196 μL, 0.196 mmol) at 0° C. After being stirred for 2 h, the reaction mixture was extracted with EtOAc. The combined organic layers were washed with water and saturated NaCl solution, dried over Na$_2$SO$_4$, filtered and the filtrate was concentrated. The residue was purified by the flash chromatography on silica gel (eluent: 10 to 20% EtOAc/Hexane, gradient elution) to provide the title compound as the major product.

Step B. 2-((3R,5R,6S)-5-(3-chlorophenyl)-6-(4-chlorophenyl)-3-methyl-2-oxo-1-((3S)-1,1,1-trifluoro-2-hydroxy-2-methylpentan-3-yl)piperidin-3-yl)acetic acid The title compound was prepared from (3S,5R,6S)-3-allyl-5-(3-chlorophenyl)-6-(4-chlorophenyl)-3-methyl-1-((3S)-1,1,1-trifluoro-2-hydroxy-2-methylpentan-3-yl)piperidin-2-one (Example 160, Step A) by a procedure similar to the one described in Example 71, Step F.

$^1$H NMR (400 MHz, CHLOROFORM-d) δ ppm 0.33 (t, J=8.0 Hz, 3 H), 1.47 (s, 3 H), 1.52 (s, 3 H), 1.70 (m, 1 H), 2.10-2.25 (m, 3 H), 2.89 (d, J=8.0 Hz, 2 H), 2.95 (t, J=8.0, 1 H), 3.43 (m, 1H), 4.40 (d, J=12.0 Hz, 1 H), 6.75 (d, J=8.0 Hz, 1 H), 6.95 (m, 1 H), 7.08-7.20 (m, 3 H), 7.26-7.40 (m, 3 H); MS (ESI) 545.2 [M+H]$^+$.

Example 161

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetamide

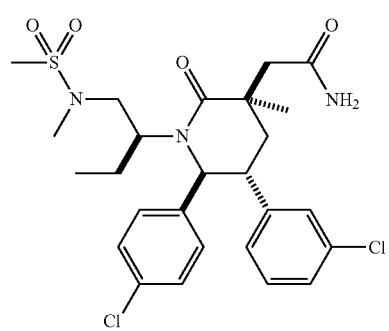

A solution of 2-((3R,5R,6S)-5-(3-chlorophenyl)-6-(4-chlorophenyl)-3-methyl-1-((S)-1-(N-methylcyclopropane-sulfonamido)butan-2-yl)-2-oxopiperidin-3-yl)acetic acid (0.055 g, 0.095 mmol; Example 141) in DMF (2.0 mL) was treated with HBTU (0.072 g, 0.189 mmol), $N^1$-((ethylimino)methylene)-$N^3$,$N^3$-dimethylpropane-1,3-diamine hydrochloride (0.036 g, 0.189 mmol) and sodium hydrogencarbonate (0.016 g, 0.189 mmol) successively. Let it stir for 0.5 h. 7.0M ammonia in methanol (0.135 mL, 0.946 mmol) was added dropwise. After being stirred at room temperature for 18 h, the reaction was diluted with water, extracted (2×EtOAc), and washed (1×saturated NaHCO$_3$, and 2×sat. aq. NaCl solution). The combined organic layers were dried over Na$_2$SO$_4$, filtered and the filtrate was concentrated under reduced pressure. The residue was purified by reverse phase preparatory HPLC (eluent: 10 to 90% acetonitrile, water, 0.1% TFA, gradient elution) to give the title compound as a white solid after lyophilization.

$^1$H NMR (400 MHz, CHLOROFORM-d) δ ppm 0.52 (t, J=7.53 Hz, 3 H) 0.97-1.07 (m, 2 H) 1.18-1.25 (m, 2 H) 1.47 (s, 3 H) 1.59-1.62 (m, 1 H) 1.84-2.06 (m, 2 H) 2.33 (ddd, J=8.02, 4.79, 3.23 Hz, 1 H) 2.43 (t, J=13.8 Hz, 1 H) 2.65-2.80 (m, 2 H) 2.81-2.95 (m, 5 H) 3.17 (ddd, J=13.74, 10.91, 2.93 Hz, 1 H) 4.80 (d, J=10.76 Hz, 1 H) 6.78 (br. s., 1 H) 6.86-6.90 (m, 1 H) 6.97-7.01 (m, 1 H) 7.10-7.15 (m, 2 H) 7.24 (d, J=7.82 Hz, 4 H) 7.42 (br. s., 1 H); Mass Spectrum (ESI) m/z=580.2 (M+1).

Example 162

2-((3R,5R,6S)-5-(3-chlorophenyl)-6-(4-chlorophenyl)-3-methyl-1-((S)-1-(N-methylcyclopropane-sulfonamido)butan-2-yl)-2-oxopiperidin-3-yl)-N-(methylsulfonyl)acetamide A solution of 2-((3R,5R,6S)-5-(3-chlorophenyl)-6-(4-chlorophenyl)-3-methyl-1-((S)-1-(N-methylcyclopropane-sulfonamido)butan-2-yl)-2-oxopiperidin-3-yl)acetic acid (0.045 g, 0.077 mmol) (Example 141) in THF (2.0 mL) was treated with methanesulfonamide (0.029 g, 0.310 mmol), N-ethyl-N-isopropylpropan-2-amine (0.050 g, 0.387 mmol) and 1,1'-carbonyldiimidazole (0.050 g, 0.310 mmol), successively. The mixture was heated to reflux for 48 h, quenched with sat. NH$_4$Cl solution and extracted with EtOAc. The combined organic layers were dried over MgSO$_4$, filtered and the filtrate was concentrated under reduced pressure. The residue was purified by reverse phase preparatory HPLC (eluent: 10 to 90% acetonitrile, water, 0.1% TFA, gradient elution) to give the title compound as a white solid after lyophilization.

$^1$H NMR (400 MHz, CHLOROFORM-d) δ ppm 0.52 (t, J=7.53 Hz, 3 H) 0.96-1.08 (m, 2 H) 1.15-1.28 (m, 2 H) 1.50 (s, 3 H) 1.61 (ddd, J=14.33, 7.68, 3.62 Hz, 1 H) 1.92 (dd, J=13.69, 2.93 Hz, 1 H) 1.96-2.10 (m, 1 H) 2.34 (tt, J=8.02, 4.79 Hz, 1 H) 2.49 (t, J=13.89 Hz, 1 H) 2.65 (d, J=14.87 Hz, 1 H) 2.73 (dd, J=14.48, 2.35 Hz, 1 H) 2.87 (s, 3 H) 2.98-3.08 (m, 2 H) 3.32 (s, 3 H) 4.79 (d, J=10.56 Hz, 1 H) 6.84-6.90 (m, 1 H) 6.94-7.07 (m, 1 H) 7.08-7.16 (m, 2 H) 7.19-7.32 (m, 4 H)

Examples 163-170 were prepared from 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid (Example 141) by using the following general procedure using the appropriate amine, unless noted otherwise.

A mixture of 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid (0.020 g, 0.034 mmol; Example 141), corresponding amine (1.2 eq.), N-ethyl-N-isopropylpropan-2-amine (3.3 eq.) and (1H-benzo[d][1,2,3]triazol-1-yloxy)tripyrrolidin-1-ylphosphonium hexafluorophosphate (V) (1.05 eq.) in 2 ml of DCM was stirred at room temperature for 5 h. The solvent was removed under reduced pressure, and the residue was purified by reverse phase HPLC (40-90% water/acetonitrile gradient with 0.1% TFA). Desired fractions were then collected and concentrated to give pure product.

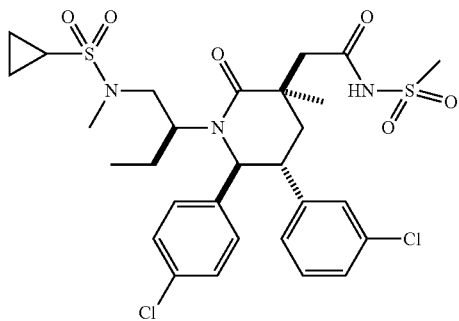

| Example | R | Amine used |
|---|---|---|
| 163 | ~~~~OH | 3-Aminopropan-1-ol |
| 164 | ~~~OH | 2-Aminoethanol |
| 165 | ~OH | Hydroxylamine |
| 166 | ~O~ | O-Methylhydroxylamine |
| 167 | ~~(OH)~OH | (R)-3-Aminopropane-1,2-diol |

-continued

| Example | R | Amine used |
|---|---|---|
| 168 | (structure: CH with OH and CH2OH, stereochemistry shown) | (S)-3-Aminopropane-1,2-diol |
| 169 | CN | Monosodium cyanamide |
| 170 | (structure: CH2CH2N(CH3)2) | N¹,N¹-Dimethylethane-1,2-diamine |

Example 163

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(3-hydroxypropyl)acetamide $^1$H NMR (400 MHz, MeOH-d$_4$) δppm 0.54 (t, J=7.63 Hz, 3 H), 1.00-1.19 (m, 4 H), 1.39 (s, 3 H), 1.65-2.13 (m, 5 H), 2.25-2.36 (m, 1H), 2.48-2.61 (m, 2 H), 2.81-2.95 (m, 6 H), 3.25-3.43 (m, 3 H), 3.61 (t, J=6.26 Hz, 1 H), 4.13-4.26 (br, 1H), 4.44 (s, 1 H), 4.82 (d, J=10.76 Hz, 1 H), 6.97-7.07 (m, 2 H), 7.11-7.22 (m, 4 H), 7.27-7.347 (m, 2 H). Mass Spectrum (ESI) m/z=638.2 (M+1).

Example 164

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(2-hydroxyethyl)acetamide $^1$H NMR (400 MHz, MeOH-d$_4$) δppm 0.51 (t, J=7.53 Hz, 3 H), 0.95-1.15 (m, 4H), 1.38 (s, 3H), 1.60-1.74 (m, 1 H), 1.79-1.92 (m, 1 H), 2.02-2.11 (m, 1 H), 2.22-2.33 (m, 1 H), 2.49-2.58 (m, 2H), 2.78-2.93 (m, 6 H), 3.37-3.39 (m, 2 H), 3.53-3.64 (m, 2 H), 4.10-4.24 (m, 1 H), 4.39-4.49 (m, 1 H), 4.79 (d, J=10.76 Hz, 1H), 6.95-7.05 (m, 2 H), 7.10-7.21 (m, 4 H), 7.24-7.32 (m, 2 H).
Mass Spectrum (ESI) m/z=624.4 (M+1).

Example 165

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-hydroxyacetamide $^1$H NMR (400 MHz, MeOH-d$_4$) δppm 0.53 (t, J=7.53 Hz, 3 H), 1.00-1.16 (m, 4 H), 1.38 (s, 3 H), 1.70 (ddd, J=14.23, 7.78, 4.21 Hz, 1 H), 1.88 (ddd, J=14.28, 8.51, 7.34 Hz, 1 H), 2.09-2.16 (m, 1 H), 2.17-2.22 (m, 1H), 2.24-2.39 (m, 2 H), 2.52-2.60 (m, 1 H), 2.77-2.88 (m, 2 H), 2.92 (s, 3 H), 3.37-3.44 (m, 1 H), 4.20 (br 1 H), 4.82 (d, J=10.76 Hz, 1 H), 7.01-7.09 (m, 2 H), 7.13-7.22 (m, 4 H), 7.30 (d, J=8.02 Hz, 2 H). Mass Spectrum (ESI) m/z=618 (M+1).

Example 166

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-methoxyacetamide $^1$H NMR (400 MHz, CHLOROFORM-d) δ ppm 0.50 (t, J=7.53 Hz, 3 H), 0.96-1.07 (m, 2 H), 1.17-1.28 (m, 2 H), 1.43 (s, 3 H), 1.55-1.65 (m, 1 H), 1.87-2.00 (m, 1H), 2.07-2.13 (dd, J=13.79, 2.64 Hz, 1 H), 2.28-2.42 (m, 2 H), 2.63-2.77 (m, 3 H), 2.88 (br, 4 H), 3.26 (ddd, J=13.89, 10.66, 3.03 Hz, 1 H), 3.82 (s, 3 H), 4.25 (br, 1 H), 4.77 (d, J=10.76 Hz, 1 H), 6.88-6.92 (m, 1 H), 6.99-7.05 (m, 2 H), 7.10-7.14 (m, 2 H), 7.18-7.30 (m, 3 H). Mass Spectrum (ESI) m/z=632 (M+1).

Example 167

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N—((R)-2,3-dihydroxypropyl)acetamide $^1$H NMR (500 MHz, CHLOROFORM-d) δ ppm 0.51 (t, J=6.6 Hz, 3 H), 1.01 (t, J=8.3 Hz, 2H), 1.21 (br. s., 2H), 1.40-1.48 (m, 3 H), 1.58 (dd, J=7.8, 3.9 Hz, 1 H), 1.81-1.99 (m, 2 H), 2.28-2.36 (m, 1 H), 2.37-2.49 (m, 1 H), 2.52-2.64 (m, 1 H,), 2.67-2.77 (m, 1 H), 2.84 (br. s., 2 H), 2.88 (s, 4 H), 2.90-3.05 (m, 7 H), 3.11-3.23 (m, 2 H), 3.47 (br. s., 2 H), 3.55-3.72 (m, 2 H), 3.89 (br. s., 1H), 4.25 (br. s., 1 H), 4.76 (d, J=10.3 Hz, 1 H), 6.85-6.92 (m, 1 H) 6.98 (br. s., 2 H), 7.00-7.06 (m, 1 H), 7.13 (br. s., 3 H), 7.20-7.26 (m, 2 H).

Example 168

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-((S)-2,3-dihydroxypropyl)acetamide $^1$H NMR (500 MHz, CHLOROFORM-d) δ ppm 0.43-0.58 (m, 3 H), 1.01 (t, J=7.6 Hz, 2 H), 1.16-1.24 (m, 2 H), 1.41-1.45 (m, 1 H), 1.45-1.49 (m, 2 H), 1.49 (s, 1 H), 1.54-1.66 (m, 1 H), 1.79-1.95 (m, 2 H), 2.28-2.36 (m, 1 H), 2.38-2.49 (m, 1 H), 2.55 (d, J=13.7 Hz, 1 H), 2.72 (s, 5 H), 2.74 (s, 4 H,), 2.84 (d, J=13.2 Hz, 2 H), 2.88 (s, 3 H), 3.11-3.25 (m, 2 H), 3.28-3.39 (m, 1 H), 3.51-3.59 (m, 1 H), 3.59-3.76 (m, 2 H), 3.92 (br. s., 1 H), 4.18-4.31 (m, 1 H), 4.70-4.81 (m, 1 H), 6.90 (d, J=5.1 Hz, 1 H) 6.92-7.01 (m, 2 H,), 7.10-7.16 (m, 2 H), 7.20-7.26 (m, 2 H).

Example 169

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-cyanoacetamide A mixture of 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid (0.030 g, 0.052 mmol; Example 141), N,N'-dicyclohexylcarbodiimide (10.64 mg, 0.052 mmol) and N-hydroxysuccinimide (5.94 mg, 0.052 mmol) in 3 mL of THF was stirred while cooling with an ice bath for 3 h. The reaction mixture was filtered and the filtrate was added dropwise to a solution of monosodium cyanamide (10.90 mg, 0.170 mmol) in 2 mL of water at an ice bath temperature. The reaction mixture was stirred at room temperature for 12 h. Solvents were removed and the residue was purified by reverse phase HPLC (40 to 90% water/acetonitrile gradient with 0.1% TFA). Desired fractions were then collected and concentrated to give the title compound.

¹H NMR (500 MHz, CHLOROFORM-d) δ ppm 0.52 (t, J=7.6 Hz, 3 H), 0.98-1.10 (m, 2 H), 1.17-1.30 (m, 2 H), 1.49-1.53 (m, 3 H), 1.54-1.61 (m, 1 H), 1.91-2.03 (m, 1 H), 2.35 (tt, J=8.0, 4.7 Hz, 1 H), 2.56 (t, J=13.8 Hz, 1 H), 2.60-2.66 (m, 1 H), 2.71-2.77 (m, 1 H), 2.80-2.87 (m, 1 H), 2.87-2.91 (m, 3 H), 2.91-3.01 (m, 1 H), 3.18 (d, J=16.1 Hz, 1 H), 4.19-4.32 (m, 1 H), 4.79 (d, J=10.8 Hz, 1 H), 6.84 (dt, J=7.1, 1.6 Hz, 1 H), 6.92-6.96 (m, 1 H), 7.11-7.18 (m, 2 H), 11.77 (br. s., 1 H).

Example 170

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(2-(dimethylamino)ethyl)acetamide ¹H NMR (400 MHz, MeOH-d₄) δ ppm 0.52 (t, J=7.53 Hz, 3 H), 1.01-1.21 (m, 4 H), 1.47 (s, 3 H) 1.62-1.85 (m, 2 H), 1.90 (dd, J=13.50, 3.13 Hz, 1H), 2.42 (t, J=13.69 Hz, 1 H), 2.51-2.62 (m, 2 H), 2.80-2.91 (m, 3 H, 2.93 (s, 3 H), 3.03 (s, 6 H), 3.38-3.50 (m, 2 H), 3.29-3.39 (m, 2 H), 3.84 (ddd, J=15.01, 7.38, 4.79 Hz, 1 H), 4.21 (dd, J=13.89, 10.56 Hz, 1 H), 4.80 (d, J=10.76 Hz, 1 H), 7.00-7.12 (m, 2 H) 7.15-7.25 (m, 4 H) 7.33 (d, J=6.85 Hz, 2 H). Mass Spectrum (ESI) m/z=651.2 (M+1).

Example 171

2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)-N-(3,4-dihydroxybutyl)acetamide

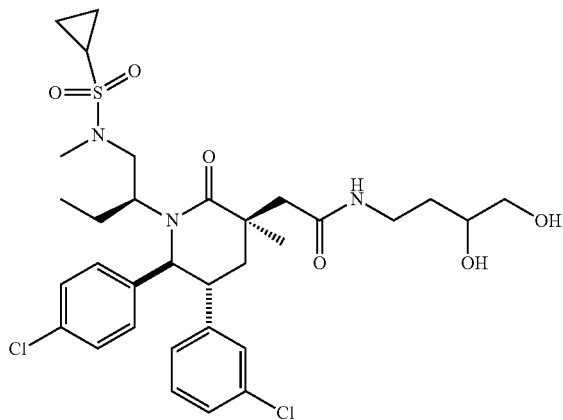

To a solution of N-(but-3-enyl)-2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetamide (0.030 g, 0.047 mmol; Example 170) in 1 mL of THF/H₂O (4:1) was added osmium(VIII) oxide (0.030 mL, 2.363 μmol), followed by 4-methylmorpholine-4-oxide (8.31 mg, 0.071 mmol). The reaction mixture was stirred at room temperature for 12 h. Solvents were removed and the residue was purified by reverse phase HPLC (40 to 90% water/acetonitrile gradient with 0.1% TFA). Desired fractions were then collected and concentrated to give the title compound.

¹H NMR (400 MHz, CHLOROFORM-d) δppm 0.51 (t, 3 H), 1.00 (t, J=7.24 Hz, 2 H), 1.21 (d, J=4.11 Hz, 2 H), 1.42 (br. s., 3 H), 1.61 (br. s., 2 H), 1.75-2.10 (m, 2 H) 2.26-2.44 (m, 2 H) 2.52-2.80 (m, 7 H) 2.88 (s, 3 H), 3.21 (br. s., 2 H), 3.45-3.85 (m, 4 H), 4.23 (br. s., 1 H), 4.76 (d, J=10.56 Hz, 1 H), 6.90 (br. s., 1 H), 6.95-7.04 (m, 2 H), 7.07-7.15 (m, 3 H) 7.23 (d, J=7.04 Hz, 2 H). Mass Spectrum (ESI) m/z=668 (M+1).

Example 172

2-((3R,5R,6S)-5-(3-chlorophenyl)-6-(4-chlorophenyl)-1-((S)-1-(cyclopropanesulfonamido)butan-2-yl)-3-methyl-2-oxopiperidin-3-yl)acetic acid

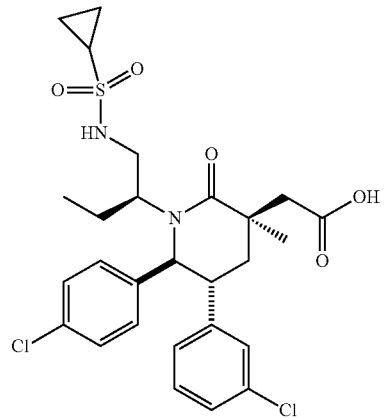

The title compound was prepared by a procedure similar to the one described in Example 129, using the equivalent amount of cyclopropanesulfonyl chloride instead of methanesulfonyl chloride in Step C. Purification of the residue by reverse phase preparatory HPLC (eluent: 10 to 90% acetonitrile, water, 0.1% TFA, gradient elution) provided the title compound as a white solid after lyophilization of the collected fractions.

¹H NMR (400 MHz, CHLOROFORM-d) δ ppm 0.54 (t, J=7.53 Hz, 3 H) 0.92-1.08 (m, 2 H) 1.08-1.23 (m, 2 H) 1.39-1.64 (m, 4 H) 1.77-1.92 (m, 1 H) 1.96-2.07 (m, 1 H) 2.28-2.49 (m, 2 H) 2.77 (d, J=14.28 Hz, 1 H) 2.92 (d, J=14.09 Hz, 1 H) 3.01-3.28 (m, 3 H) 3.61 (m, 1 H) 4.76 (d, J=10.56 Hz, 1 H) 6.78-6.90 (m, 1 H) 6.90-7.18 (m, 5 H) 7.23 (m, 2 H).

Example 173

(S)-2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)propanoic acid

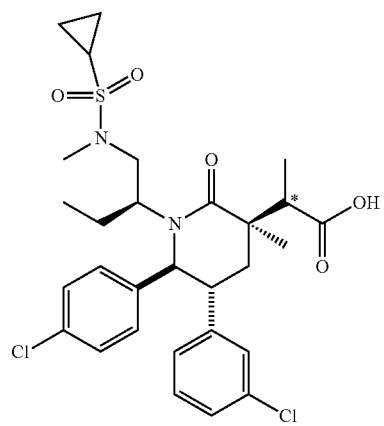

* stereochemistry not established

Step A. Methyl 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetate

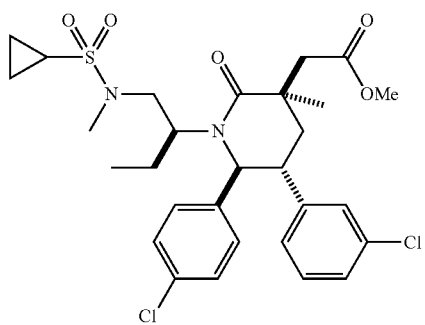

To a solution of 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetic acid (0.055 g, 0.095 mmol; Example 141) in 1 mL of MeOH and 4 mL of benzene was added a 2.0 M solution of (trimethylsilyl)diazomethane in diethyl ether (0.095 mL, 0.189 mmol) at 0° C. The reaction mixture was stirred at 0° C. for 0.5 h and was then concentrated. The crude material was purified by reverse phase preparatory HPLC (eluent: 10 to 90% acetonitrile, water, 0.1% TFA, gradient elution) to provide the title compound as a white powder after lyophilization of the pooled collected fractions.

Step B. (S)-Methyl 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)propanoate

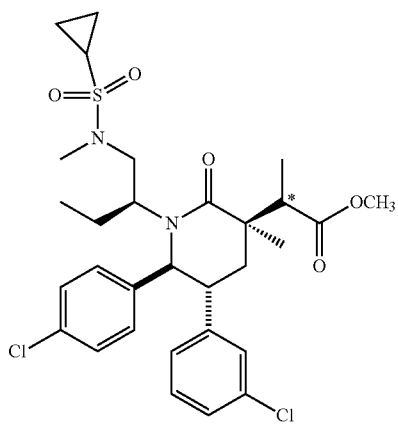

* stereochemistry not established

To a solution of methyl 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)acetate (0.040 g, 0.067 mmol) from Step A above and HMPA (0.012 mL, 0.067 mmol) in anhydrous THF (1 mL) was added LDA, 2.0M in THF (0.037 mL, 0.074 mmol) at −78° C. Let it stir for 0.5 h at −78° C. Then iodomethane (0.057 mL, 0.913 mmol) was added. After stirring for 1 h, the reaction was quenched with sat. aq. NH$_4$Cl solution and extracted with EtOAc. The organics were pooled, washed with sat. aq. NaCl solution, dried (MgSO$_4$), filtered and the filtrate was concentrated under the reduced pressure to provide a yellow oil. This was used in the next step without further purification.

Step C. S)-2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)propanoic acid To a solution of (S)-methyl 2-((3R,5R,6S)-5-(3-chlorophenyl)-6-(4-chlorophenyl)-3-methyl-1-((S)-1-(N-methylcyclopropanesulfonamido)butan-2-yl)-2-oxopiperidin-3-yl)propanoate (0.041 g, 0.067 mmol) from Step B above in MeOH/THF/H$_2$O (1 mL/1 mL/2 mL) was added lithium hydroxide (8.02 mg, 0.335 mmol). The mixture was heated to 60° C. for 14 h. The reaction mixture was acidified with 1N HCl and extracted with EtOAc (×2). The organics were pooled, washed with sat. aq. NaCl solution, dried (MgSO$_4$), filtered and the filtrate was concentrated under reduced pressure to provide a colorless film. The crude material was purified by reverse phase preparatory HPLC (eluent: 10 to 90% acetonitrile, water, 0.1% TFA, gradient elution) to provide the title compound as the first eluting peak.

$^1$H NMR (400 MHz, CHLOROFORM-d) δ ppm 0.52 (t, J=7.53 Hz, 3 H) 0.97-1.06 (m, 2 H) 1.20-1.26 (m, 2 H) 1.41 (s, 3 H) 1.43-1.51 (m, 3 H) 1.57-1.70 (m, 1 H) 1.88-2.04 (m, 2 H) 2.26-2.38 (m, 2 H) 2.78-2.97 (m, 5 H) 3.13 (q, J=7.11 Hz, 1 H) 3.32 (ddd, J=13.55, 10.51, 3.13 Hz, 1 H) 4.86 (d, J=10.56 Hz, 1 H) 6.88-7.03 (m, 3 H) 7.10-7.16 (m, 2 H) 7.24 (m, 3 H).

Example 174

2-((3R,5R,6S)-5-(3-chlorophenyl)-6-(4-chlorophenyl)-1-((3S)-2-(cyclopropanesulfonamido)pentan-3-yl)-3-methyl-2-oxopiperidin-3-yl)acetic acid (Isomer 1)

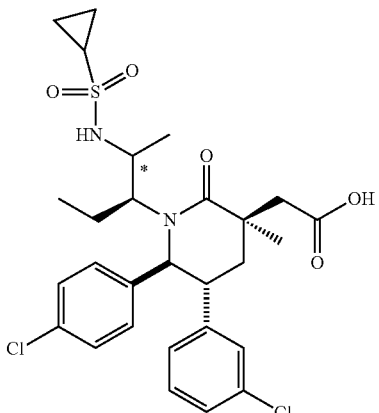

* stereochemistry not established

Step A. N-((2S,3S)-3-((3S,5R,6S)-3-allyl-5-(3-chlorophenyl)-6-(4-chlorophenyl)-3-methyl-2-oxopiperidin-1-yl)pentan-2-yl)cyclopropanesulfonamide and N-((2R,3S)-3-((3S,5R,6S)-3-allyl-5-(3-chlorophenyl)-6-(4-chlorophenyl)-3-methyl-2-oxopiperidin-1-yl)pentan-2-yl)cyclopropanesulfonamide

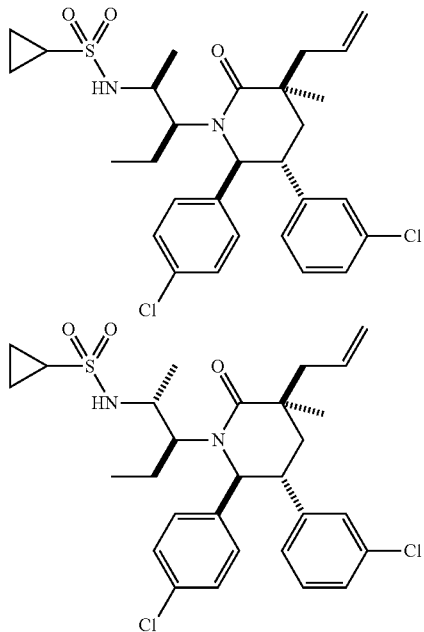

To a solution of (3S,5R,6S)-3-allyl-5-(3-chlorophenyl)-6-(4-chlorophenyl)-1-((3S)-2-hydroxypentan-3-yl)-3-methylpiperidin-2-one (0.053 g, 0.115 mmol; mixture of stereoisomers; Example 149, Step A) and cyclopropanesulfonamide (0.042 g, 0.345 mmol) in toluene (2 mL) was added cyanomethylenetri-n-butylphosphorane (0.093 mL, 0.345 mmol) at room temperature under an argon atmosphere, which solution was then stirred at 110° C. for 2 days. Then the reaction was quenched (sat NH₄Cl), extracted (3×EtOAc) and the combined extracts were washed (2×water and 1×sat. aq. NaCl solution). The combined organic layer was dried (Na₂SO₄) and concentrated under reduced pressure. The crude material was purified by reversed phase preparatory HPLC (eluent: 10 to 90% acetonitrile, water, 0.1% TFA, gradient elution) to provide the title compounds as two separate fractions.

Step B. 2-((3R,5R,6S)-5-(3-chlorophenyl)-6-(4-chlorophenyl)-1-((2S,3S)-2-(cyclopropanesulfonamido)pentan-3-yl)-3-methyl-2-oxopiperidin-3-yl)acetic acid The title compound was prepared from N-((S)-3-((3S,5R,6S)-3-allyl-5-(3-chlorophenyl)-6-(4-chlorophenyl)-3-methyl-2-oxopiperidin-1-yl)pentan-2-yl)cyclopropanesulfonamide (Example 174, Step A, faster eluting isomer) by a procedure similar to the one described in Example 71, Step F.

¹H NMR (400 MHz, CHLOROFORM-d) δ ppm 0.67 (t, J=7.43 Hz, 3 H) 0.92-1.04 (m, 2 H) 1.04-1.19 (m, 2 H) 1.22 (d, J=6.85 Hz, 3 H) 1.50 (s, 3 H) 1.79-1.93 (m, 1 H) 1.96-2.09 (m, 2 H) 2.28-2.42 (m, 2 H) 2.77 (d, J=13.89 Hz, 1 H) 2.92-2.96 (m, 2 H) 3.14-3.31 (m, 1 H) 4.54 (d, J=10.37 Hz, 1 H) 6.80 (m, 1 H) 6.91-7.19 (m, 5 H) 7.21-7.27 (m, 2 H)

Example 175

2-((3R,5R,6S)-5-(3-chlorophenyl)-6-(4-chlorophenyl)-1-((3S)-2-(cyclopropanesulfonamido)pentan-3-yl)-3-methyl-2-oxopiperidin-3-yl)acetic acid (isomer 2)

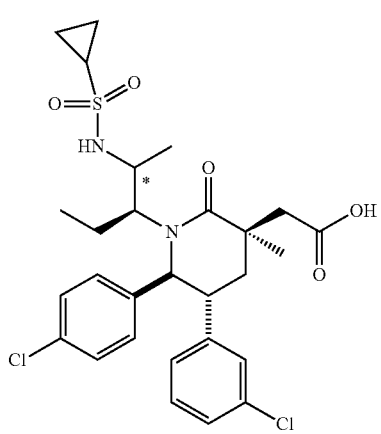

* stereochemistry not established

The title compound was prepared from N-((3S)-3-((3S,5R,6S)-3-allyl-5-(3-chlorophenyl)-6-(4-chlorophenyl)-3-methyl-2-oxopiperidin-1-yl)pentan-2-yl)cyclopropanesulfonamide (Example 174, Step A, slower eluting isomer) by a procedure similar to the one described in Example 71, Step F.

¹H NMR (400 MHz, CHLOROFORM-d) δ ppm 0.45-0.53 (m, 3 H) 0.97-1.12 (m, 2 H) 1.18 (m, 1 H) 1.23-1.32 (m, 5 H) 1.52 (s, 3 H) 1.70 (m, 1H) 1.92 (m, 2 H) 2.40-2.54 (m, 2 H) 2.74 (d, J=15.06 Hz, 1 H) 3.02 (d, J=15.06 Hz, 1 H) 3.14 (m, 1 H) 4.85 (d, J=10.56 Hz, 1 H) 6.84 (m, 1 H) 6.99 (m, 1 H) 7.08-7.17 (m, 2 H) 7.25 (m, 4 H)

Example 176

2-((3R,5R,6S)-5-(3-chlorophenyl)-6-(4-chlorophenyl)-3-methyl-1-((3S)-2-(1-methylethylsulfonamido)pentan-3-yl)-2-oxopiperidin-3-yl)acetic acid

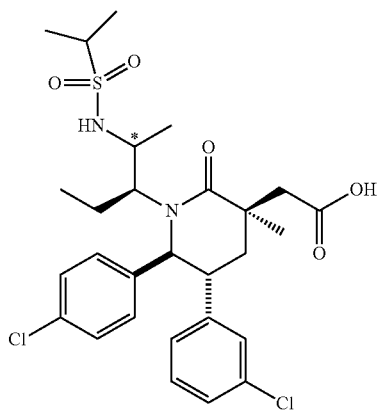

* stereochemistry not established

The title compound was prepared from (3S,5R,6S)-3-allyl-5-(3-chlorophenyl)-6-(4-chlorophenyl)-1-((3S)-2-hydroxypentan-3-yl)-3-methylpiperidin-2-one (mixture of stereoisomers; Example 149, Step A) and propane-2-sulfonamide by a procedure similar to the one described in Example 174.

¹H NMR (400 MHz, CHLOROFORM-d) δ ppm 0.47 (t, J=7.83 Hz, 3 H) 1.20 (d, J=6.85 Hz, 3 H) 1.41 (dd, J=14.87, 6.85 Hz, 6 H) 1.51-1.60 (s, 3 H) 1.60-1.73 (m, 1 H) 1.80-2.00 (m, 2 H) 2.50 (t, J=13.89 Hz, 1 H) 2.72-2.81 (d, J=14.67 Hz, 1 H) 2.97 (d, J=14.67 Hz, 1 H) 3.07-3.23 (m, 2 H) 4.85 (d, J=10.96 Hz, 1 H) 6.87 (m, 1 H) 6.97-7.07 (m, 1 H) 7.07-7.19 (m, 2 H) 7.19-7.33 (m, 4 H).

Example 177

2-((3R,5R,6S)-5-(3-chlorophenyl)-6-(4-chlorophenyl)-3-methyl-1-((S)-1-(N-methylcyclopropanesulfonamido)-1-oxobutan-2-yl)-2-oxopiperidin-3-yl)acetic acid

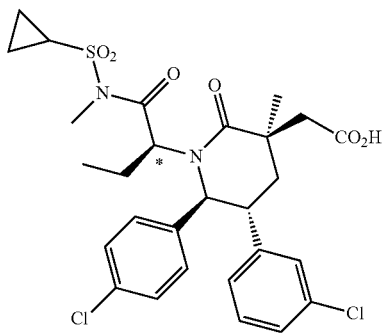

* stereochemistry was not confirmed

Step A. 2-((3S,5R,6S)-3-Allyl-5-(3-chlorophenyl)-6-(4-chlorophenyl)-3-methyl-2-oxopiperidin-1-yl)butanoic acid

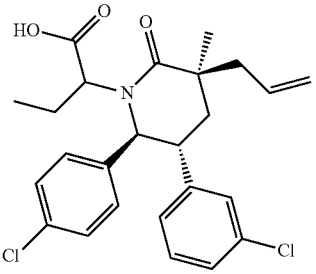 [SMILES: C=CC[C@@]1(C)C[C@H](c2cccc(Cl)c2)[C@@H](c2ccc(Cl)cc2)N(C(CC)C(=O)O)C1=O]

To a stirred solution of methyl 2-((3S,5R,6S)-3-allyl-5-(3-chlorophenyl)-6-(4-chlorophenyl)-3-methyl-2-oxopiperidin-1-yl)butanoate (200 mg, 0.42 mmol; Example 91, Step A) in THF (5 mL) was added sodium hydroxide (506 mg, 12.65 mmol) in water (5 mL) and the reaction was heated at reflux for about 12 h. After this time the reaction was cooled to rt and partitioned between EtOAc (80 mL) and 1.0 M HCl (20 mL). The separated aqueous layer was extracted with EtOAc (30 mL) and the combined organic layers were dried over MgSO₄, filtered and the filtrate was evaporated in vacuo to give the title compound as a white solid.

Mass Spectrum (ESI) m/z=460.0 (M+1).

Step B. (S)-2-((3S,5R,6S)-3-allyl-5-(3-chlorophenyl)-6-(4-chlorophenyl)-3-methyl-2-oxopiperidin-1-yl)-N-(cyclopropylsulfonyl)butanamide

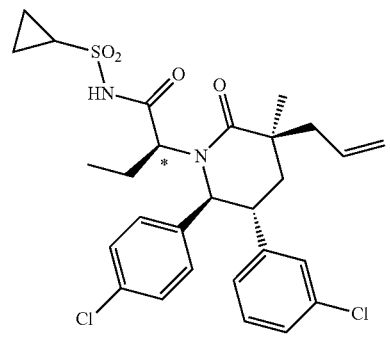

* stereochemistry was not confirmed

To a stirred solution of 2-((3S,5R,6S)-3-allyl-5-(3-chlorophenyl)-6-(4-chlorophenyl)-3-methyl-2-oxopiperidin-1-yl)butanoic acid (140 mg, 0.304 mmol; Example 177, Step A) in DMF (2 mL) was added bromotripyrrolidin-1-ylphosphonium hexafluorophosphate (V) (354 mg, 0.76 mmol) and N,N-diisopropylethylamine (0.11 mL, 0.61 mmol) and the reaction was stirred at rt for 3 hours. After this time the reaction was partitioned between EtOAc (60 mL) and 1.0 M aq. LiCl solution (20 mL). The separated organic layer was dried over MgSO₄, filtered and evaporated in vacuo. Column chromatography (SiO₂, hexanes:EtOAc, 1:0 to 1:1) gave the title compound. Mass Spectrum (ESI) m/z=563.0 (M+1).

Step C. (S)-2-((3S,5R,6S)-3-allyl-5-(3-chlorophenyl)-6-(4-chlorophenyl)-3-methyl-2-oxopiperidin-1-yl)-N-(cyclopropylsulfonyl)-N-methylbutanamide

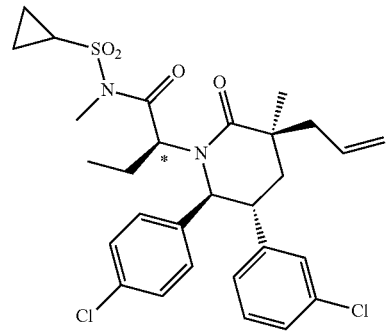

* stereochemistry was not confirmed

To a stirred solution of (S)-2-((3S,5R,6S)-3-allyl-5-(3-chlorophenyl)-6-(4-chlorophenyl)-3-methyl-2-oxopiperidin-1-yl)-N-(cyclopropylsulfonyl)butanamide (8 mg, 0.014 mmol; Example 177, Step B) in DMF (1.0 mL) was added potassium carbonate (2.9 mg, 0.021 mmol) and iodomethane (1.1 µL, 0.017 mmol) at rt. The reaction was stirred for 1 hour. After this time more iodomethane (1.1 µL, 0.017 mmol) and potassium carbonate (2.9 mg, 0.021 mmol) was added and the reaction was stirred at rt for 60 hours. After this time the reaction was partitioned between EtOAc (20 mL) and 1.0 M LiCl (5 mL). The separated organic layer was washed with 1.0 M LiCl (5 mL), dried over MgSO$_4$, filtered and evaporated in vacuo to give the title compound.

Mass Spectrum (ESI) m/z=577.0 (M+1).

Step D. 2-((3R,5R,6S)-5-(3-chlorophenyl)-6-(4-chlorophenyl)-3-methyl-1-((S)-1-(N-methylcyclopropanesulfonamido)-1-oxobutan-2-yl)-2-oxopiperidin-3-yl)acetic acid The title compound was prepared from 2-((3S,5R,6S)-3-allyl-5-(3-chlorophenyl)-6-(4-chlorophenyl)-3-methyl-2-oxopiperidin-1-yl)-N-(cyclopropylsulfonyl)-N-methylbutanamide (Example 177, Step C) by a procedure similar to the one described in Example 71, Step F.

$^1$H NMR (400 MHz, CHLOROFORM-d) δ ppm 7.30 (2 H, d, J=8.4 Hz), 7.15-7.25 (4 H, m), 6.94 (2 H, d, J=7.6 Hz), 4.79-4.93 (2 H, m), 3.31 (3 H, s), 3.08-3.17 (1 H, m), 2.92 (1 H, d, J=15.1 Hz), 2.70 (1 H, d, J=14.7 Hz), 2.08-2.19 (2 H, m), 1.72 (2 H, t, J=7.5 Hz), 0.92-1.39 (8 H, m), 0.84-0.91 (3 H, m). Mass Spectrum (ESI) m/z=595.0 (M+1).

Example 178

2-((3R,5R,6S)-5-(3-Chlorophenyl)-6-(4-chlorophenyl)-3-methyl-1-((S)-1-(neopentylamino)-1-oxobutan-2-yl)-2-oxopiperidin-3-yl)acetic acid

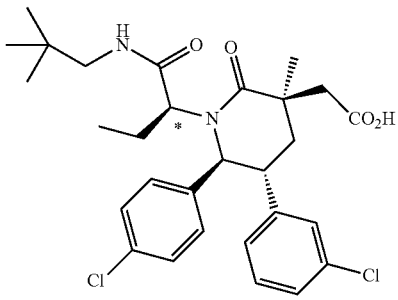

*stereochemistry was not confirmed

Step A. 2-((3S,5R,6S)-3-Allyl-5-(3-chlorophenyl)-6-(4-chlorophenyl)-3-methyl-2-oxopiperidin-1-yl)butanoic acid

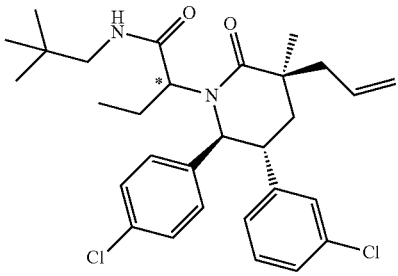

* Mixture of stereoisomers

To a stirred solution of 2-((3S,5R,6S)-3-allyl-5-(3-chlorophenyl)-6-(4-chlorophenyl)-3-methyl-2-oxopiperidin-1-yl)butanoic acid (110 mg, 0.24 mmol; Example 177, Step A or Example 1, Step F) and DIEA (0.050 ml, 0.287 mmol) in dry DMF (1195 μL) at 0° C. was added HATU (109 mg, 0.287 mmol). The reaction was stirred at 0° 5 min, followed by addition of 2 eq. of neopentyl amine (55.9 μL, 0.478 mmol; TCI America). The reaction solution was stirred at 0° C. for 10 min until complete by LCMS, then filtered. Purification of the solution by reverse phase preparatory HPLC (Sunfire™ Prep C18 OBD 10 μm column (Waters, Milford, Mass.), gradient elution of 70 to 100% MeCN in water over a 35 min period, where both solvents contain 0.1% TFA) provided the title compounds as an epimeric mixture.

Step B. 2-((3R,5R,6S)-5-(3-chlorophenyl)-6-(4-chlorophenyl)-3-methyl-1-((S)-1-(neopentylamino)-1-oxobutan-2-yl)-2-oxopiperidin-3-yl)acetic acid The title compound was obtained from 2-((3S,5R,6S)-3-allyl-5-(3-chlorophenyl)-6-(4-chlorophenyl)-3-methyl-2-oxopiperidin-1-yl)-N-neopentylbutanamide (88 mg, 0.166 mmol) (Example 178, Step A) by a procedure similar to the one described in Example 71, Step F, followed by purification of the residue by reverse phase HPLC (eluens: 55% MeCN/water (0.1% TFA), isocratic elution) using a Sunfire C18 OBD column, 10 uM, (30×150 mm), Waters Corp (Milford, Mass.).

$^1$H NMR (500 MHz, CHLOROFORM-d) δ ppm 0.79 (t, J=7.46 Hz, 3 H), 0.93 (s, 9 H), 1.26 (s, 2 H), 1.43 (s, 3 H), 1.78 (dquin, J=14.38, 7.29, 7.29, 7.29, 7.29 Hz, 1 H), 2.08-2.23 (m, 3 H), 2.81 (dd, J=13.20, 5.14 Hz, 1 H), 2.88 (s, 2 H), 3.09 (dd, J=13.20, 6.60 Hz, 1 H), 3.17 (ddd, J=12.78, 9.72, 3.67 Hz, 1 H), 3.92 (t, J=7.34 Hz, 1 H), 4.63 (d, J=9.78 Hz, 1 H), 6.75 (d, J=7.58 Hz, 1 H), 6.94-7.00 (m, 3 H), 7.10 (t, J=7.70 Hz, 2 H), 7.13-7.24 (m, 3 H). Mass Spectrum (ESI) m/z=547 (M+1).

Example 179

2-((3R,5R,6S)-5-(3-chlorophenyl)-6-(4-chlorophenyl)-1-((S)-1-(4,4-dimethyl-4,5-dihydrooxazol-2-yl)propyl)-3-methyl-2-oxopiperidin-3-yl)acetic acid

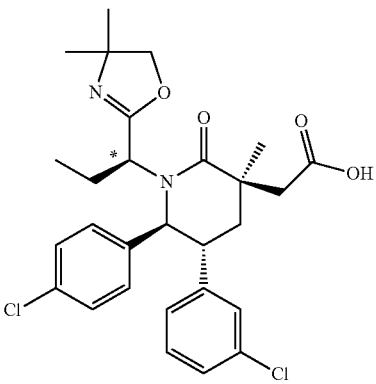

*stereochemistry was not confirmed

Step A. 2-((3S,5R,6S)-3-allyl-5-(3-chlorophenyl)-6-(4-chlorophenyl)-3-methyl-2-oxopiperidin-1-yl)-N-(1-hydroxy-2-methylpropan-2-yl)butanamide

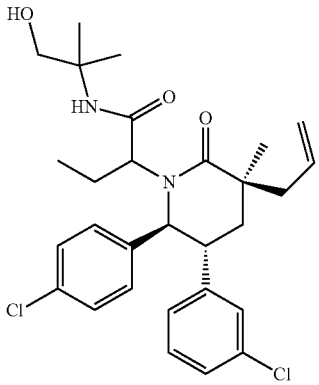

*Mixture of stereoisomers

To a solution of 2-((3S,5R,6S)-3-allyl-5-(3-chlorophenyl)-6-(4-chlorophenyl)-3-methyl-2-oxopiperidin-1-yl)-N-(1-hydroxy-2-methylpropan-2-yl)butanamide (Example 177, Step A) and 5 eq. of 2-amino-2-methylpropan-1-ol (80 μL, 0.836 mmol; Sigma-Aldrich) in DMF (1672 μL) at 0° C. was added 1.2 eq HATU (76 mg, 0.201 mmol). The reaction solution was stirred for 1 hour, at which time the reaction was judged to be complete by LCMS. The reaction mixture was diluted with EtOAc (50 mL) and washed with NaHCO$_3$ (20 mL), 1N HCl, and water. The combined organic layers were dried over Na$_2$SO$_4$, filtered and the filtrate was concentrated to give the crude material as a clear solution (residual DMF present). The product was used in the next step without further purification.

Step B. (3S,5R,6S)-3-allyl-5-(3-chlorophenyl)-6-(4-chlorophenyl)-1-((S)-1-(4,4-dimethyl-4,5-dihydrooxazol-2-yl)propyl)-3-methylpiperidin-2-one

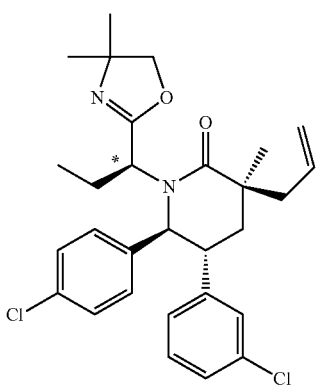

*stereochemistry was not confirmed

To a cold (-78° C.) solution of 2-((3S,5R,6S)-3-allyl-5-(3-chlorophenyl)-6-(4-chlorophenyl)-3-methyl-2-oxopiperidin-1-yl)-N-(1-hydroxy-2-methylpropan-2-yl)butanamide (89 mg, 0.167 mmol; Example 179, Step A: epimeric mixture) in DCM (1674 μL) was added 3 eq. of diethylaminosulfur trifluoride (26.5 μL, 0.201 mmol) dropwise. The reaction mixture was stirred at -78° C. for 20 min. Anhydrous K$_2$CO$_3$ (1.5 equiv) was then added in one portion and the mixture was allowed to warm to ambient temperature. The reaction was poured into saturated aqueous NaHCO$_3$, and the biphasic mixture was extracted with EtOAc×2. The combined organic extracts were dried over MgSO$_4$, filtered, and the filtrate was concentrated under reduced pressure. Purification of the residue by flash chromatography on silica gel (eluent: 0 to 20% ethyl acetate/hexane) provided the title compound.

$^1$H NMR (500 MHz, CHLOROFORM-d) δ ppm 0.76 (t, J=7.46 Hz, 3 H), 1.08 (s, 3 H), 1.15 (s, 3 H), 1.24 (s, 3 H), 1.67 (s, 1 H), 1.82 (dt, J=14.43, 7.21 Hz, 1 H), 1.89-1.96 (m, 1 H), 2.00-2.11 (m, 1 H), 2.21 (dt, J=14.31, 7.27 Hz, 1 H), 2.61 (d, J=7.58 Hz, 2 H), 3.21 (ddd, J=13.14, 10.09, 3.18 Hz, 1 H), 3.64 (d, J=7.83 Hz, 1 H), 3.90 (d, J=7.83 Hz, 1 H), 4.12 (t, J=6.85 Hz, 1 H), 4.54 (d, J=10.27 Hz, 1 H), 5.16 (s, 1 H), 5.18 (d, J=3.18 Hz, 1 H), 5.81-5.93 (m, 1 H), 6.75 (d, J=7.58 Hz, 1 H), 7.00 (s, 3 H), 7.10 (t, J=7.70 Hz, 1 H), 7.15 (d, J=8.07 Hz, 1 H), 7.20 (d, J=8.31 Hz, 2 H). Mass Spectrum (ESI) m/z=513 (M+1).

Further elution provided the other epimer: (3S,5R,6S)-3-allyl-5-(3-chlorophenyl)-6-(4-chlorophenyl)-1-((R)-1-(4,4-dimethyl-4,5-dihydrooxazol-2-yl)propyl)-3-methylpiperidin-2-one.

$^1$H NMR (500 MHz, CHLOROFORM-d) δ ppm 0.96 (t, J=7.46 Hz, 3 H), 1.19 (s, 3 H), 1.27 (s, 3 H), 1.30 (s, 3 H), 1.65 (br. s., 1 H), 1.86-2.06 (m, 4 H), 2.60 (qd, J=14.06, 7.70 Hz, 2 H), 3.20 (ddd, J=13.27, 10.09, 3.30 Hz, 1 H), 3.79-3.89 (m, 2 H), 3.89-3.95 (m, 1 H), 4.49 (d, J=10.03 Hz, 1 H), 5.15 (s, 1 H), 5.18 (d, J=3.91 Hz, 1 H), 5.82-5.95 (m, 1 H), 6.72 (d, J=7.58 Hz, 1 H), 6.97 (t, J=1.83 Hz, 1 H), 7.08-7.13 (m, 1 H), 7.13-7.23 (m, 3 H). Mass Spectrum (ESI) m/z=513 (M+1).

Step C. 2-((3R,5R,6S)-5-(3-chlorophenyl)-6-(4-chlorophenyl)-1-((S)-1-(4,4-dimethyl-4,5-dihydrooxazol-2-yl)propyl)-3-methyl-2-oxopiperidin-3-yl)acetic acid The title compound was obtained from (3S,5R,6S)-3-allyl-5-(3-chlorophenyl)-6-(4-chlorophenyl)-1-((S)-1-(4,4-dimethyl-4,5-dihydrooxazol-2-yl)propyl)-3-methylpiperidin-2-one (53 mg, 0.103 mmol; Example 179, Step B) by a procedure similar to the one described in Example 71, Step F.

$^1$H NMR (500 MHz, CHLOROFORM-d) δ ppm 0.74 (t, J=7.46 Hz, 3 H) 1.08 (s, 3 H) 1.14 (s, 3 H) 1.41 (s, 3 H) 1.74 (dt, J=14.31, 7.03 Hz, 1 H) 2.04-2.12 (m, 1 H) 2.12-2.30 (m, 2 H) 2.76 (d, J=14.43 Hz, 1 H) 2.88 (d, J=14.18 Hz, 1 H) 3.24 (ddd, J=12.59, 9.66, 3.18 Hz, 1 H) 3.66 (d, J=8.07 Hz, 1 H) 3.88 (d, J=8.07 Hz, 1 H) 4.16 (t, J=6.72 Hz, 1 H) 4.60 (d, J=9.78 Hz, 1 H) 6.78 (d, J=7.58 Hz, 1 H) 6.99-7.06 (m, 2 H) 7.10 (t, J=7.82 Hz, 2 H) 7.14-7.18 (m, 1 H) 7.22 (d, J=8.31 Hz, 2 H). Mass Spectrum (ESI) m/z=531 (M+1).

Example 180

2-((3R,5R,6S)-5-(3-chlorophenyl)-6-(4-chlorophenyl)-3-methyl-2-oxo-1-((S)-1-(N-(2,2,2-trifluoroethyl)acetamido)butan-2-yl)piperidin-3-yl)acetic acid

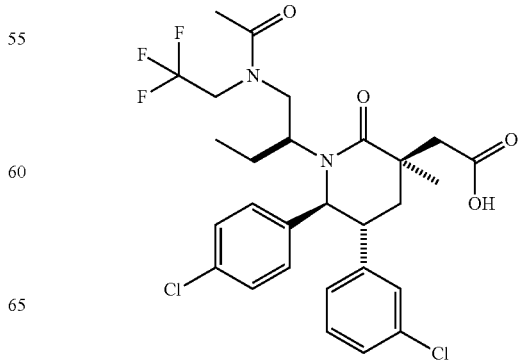

377

Step A. N-((S)-2-((3S,5R,6S)-3-allyl-5-(3-chlorophenyl)-6-(4-chlorophenyl)-3-methyl-2-oxopiperidin-1-yl)butyl)-N-(2,2,2-trifluoroethyl)acetamide

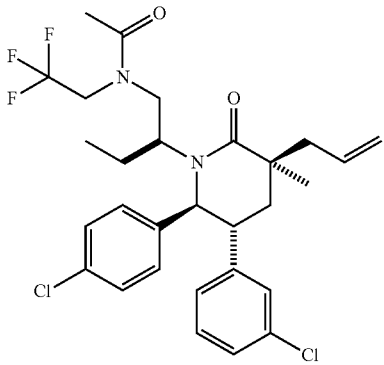 [SMILES: C=CC[C@@]1(C)C[C@H](c2cccc(Cl)c2)[C@@H](c2ccc(Cl)cc2)N([C@@H](CC)CN(CC(F)(F)F)C(C)=O)C1=O]

The title compound was obtained by acetylating (3S,5R,6S)-3-allyl-5-(3-chlorophenyl)-6-(4-chlorophenyl)-3-methyl-1-((S)-1-((2,2,2-trifluoroethyl)amino)butan-2-yl)piperidin-2-one (Example 147, Step A) by a procedure similar to the one described in Example 28, Step C.

Step B. 2-((3R,5R,6S)-5-(3-chlorophenyl)-6-(4-chlorophenyl)-3-methyl-2-oxo-1-((S)-1-(N-(2,2,2-trifluoroethyl)acetamido)butan-2-yl)piperidin-3-yl)acetic acid The title compound was obtained from N-((S)-2-((3S,5R,6S)-3-allyl-5-(3-chlorophenyl)-6-(4-chlorophenyl)-3-methyl-2-oxopiperidin-1-yl)butyl)-N-(2,2,2-trifluoroethyl)acetamide (Example 180, Step A) by a procedure similar to the one described in Example 71, Step F.

$^1$H NMR (400 MHz, CHLOROFORM-d) δ ppm 0.52 (t, J=8.0 Hz, 3 H), 1.50 (s, 3 H), 1.61 (m, 1 H), 1.87 (m, 1 H), 1.90-2.40 (m, 3 H), 2.27 (s, 3 H), 2.77 (d, J=16.0 Hz, 1 H), 3.00 (d, J=16.0 Hz, 1 H), 3.10-3.30 (m, 2 H), 3.43 (m, 1H), 3.85-4.05 (m, 3 H), 4.40 (d, J=8.0 Hz, 1 H), 6.71 (d, J=8.0 Hz, 1 H), 6.92 (s, 1 H), 7.01 (m, 2 H), 7.05-7.20 (m, 2 H), 7.25 (d, J=8.0 Hz, 2 H).

Example 181

2-((3R,5R,6S)-5-(3-chlorophenyl)-6-(4-chlorophenyl)-1-((S)-1-(1,1-dimethylethylsulfonamido)butan-2-yl)-3-methyl-2-oxopiperidin-3-yl)acetic acid

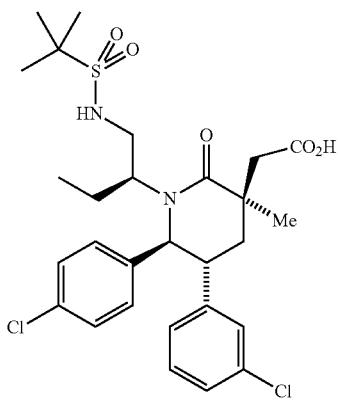 [SMILES: CC[C@@H](CNS(=O)(=O)C(C)(C)C)N1C(=O)[C@@](C)(CC(=O)O)C[C@H](c2cccc(Cl)c2)[C@H]1c1ccc(Cl)cc1]

378

Step A. N-((S)-2-((3S,5R,6S)-3-allyl-5-(3-chlorophenyl)-6-(4-chlorophenyl)-3-methyl-2-oxopiperidin-1-yl)butyl)-2-methylpropane-2-sulfonamide

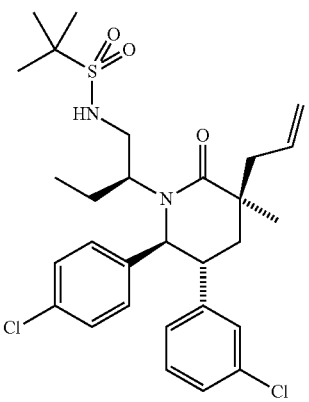 [SMILES: C=CC[C@@]1(C)C[C@H](c2cccc(Cl)c2)[C@@H](c2ccc(Cl)cc2)N([C@@H](CC)CNS(=O)(=O)C(C)(C)C)C1=O]

202.6 mg (0.454 mmol) (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) and 2-methylpropane-2-sulfonamide (130 mg, 0.948 mmol, Oakwood) were dissolved in anhydrous toluene (4.5 mL). Cyanomethylenetributylphosphorane, 421 mg, was transferred to the reaction vessel via syringe. An additional ca. 30 mg of the phosphorane reagent was added 2 minutes after the first addition. The reaction mixture was stirred between 34-41° C. in a pre-heated oil bath. The reaction was monitored by LCMS. An additional 133 mg of t-butyl sulfonamide was added after 2 h 15 min the reaction mixture was heated at 35° C. overnight.

On the following day, after 26 h, 15 min total reaction time, additional 133 mg of t-butyl sulfonamide was added. 30 minutes later, an additional 421 mg of cyanomethylenetributylphosphorane was added. Heating between 35 to 40° C. was continued overnight.

On the third day, the reaction appeared complete by LCMS. After 53 h total reaction time, the mixture was partitioned between ethyl acetate and saturated ammonium chloride. The aqueous phase was back extracted 2× with EtOAc, washed with sat. aq. NaCl solution, dried over sodium sulfate, filtered, and the filtrate was concentrated in vacuo to a residue that was chromatographed on a 24 g silica column, eluting with a gradient of 0 to 30% EtOAc in hexanes. Fractions containing the desired product by were combined and concentrated to give the title compound as an off-white solid that was dried under high vacuum. MS (ESI) m/z=565 [M+H]$^+$.

Step B. 2-((3R,5R,6S)-5-(3-chlorophenyl)-6-(4-chlorophenyl)-1-((S)-1-(1,1-dimethylethylsulfonamido)butan-2-yl)-3-methyl-2-oxopiperidin-3-yl)acetic acid N-((S)-2-((3S,5R,6S)-3-allyl-5-(3-chlorophenyl)-6-(4-chlorophenyl)-3-methyl-2-oxopiperidin-1-yl)butyl)-2-methylpropane-2-sulfonamide (100 mg, 0.177 mmol; Example 181, Step A) was transferred to a round bottom flask containing a stir bar, followed by carbon tetrachloride (1.100 mL), acetonitrile (1.1 mL), and water (1.6 mL). The flask was then charged with sodium periodate (190 mg, 0.888 mmol) and ruthenium(III) chloride hydrate (6 mg, 0.023 mmol), and the resulting reddish-brown suspension was stirred vigorously at ambient temperature. After 18 h reaction time, an additional 200 mg of sodium periodate were added, along with another 2 mg of ruthenium(III) chloride hydrate. Stirring at ambient temperature was continued. After 4 h, the reaction was quenched by addition of 1.3 M aq. HCl and diluted with ethyl acetate. The resulting mixture was filtered. Sat. aq. NaCl solution was added to the aqueous phase to promote phase separation. Combined organics were washed with sat. aq. NaCl solution, dried over sodium sulfate, filtered, and the filtrate was concentrated in vacuo. The resulting residue was chromatographed on a Sunfire™ reverse-phase prep HPLC column (Waters, Milford, Mass.), eluting with a gradient of 50 to 95% MeCN in water (0.1% TFA in both solvents) over the course of 35 minutes. Fractions containing the desired product in high purity by HPLC were combined, stripped of volatiles on the rotary evaporator, and lyophilized to provide the title compound as an off-white solid.

$^1$H NMR (500 MHz, CD$_3$OD) δ 0.46 (t, J=7.58 Hz, 3 H), 1.30-1.42 (m, 9 H), 1.45 (s, 3 H), 1.52-1.66 (m, 1 H), 1.75-1.89 (m, 1 H), 1.96-2.10 (m, 1 H), 2.33-2.49 (m, 1 H), 2.64 (d, J=13.45 Hz, 1 H), 2.72-2.83 (m, 1 H), 2.88-2.97 (m, 1 H), 2.97-3.07 (m, 1 H), 3.32-3.40 (m, 1 H), 3.86-4.05 (m, 1 H), 4.94-5.05 (m, 1 H), 6.79-7.45 (m, 8 H). MS (ESI) m/z=583 [M+H]$^+$.

Example 182

2-((3R,5R,6S)-5-(3-chlorophenyl)-6-(4-chlorophenyl)-1-((S)-1-(N,2-dimethylpropan-2-ylsulfonamido)butan-2-yl)-3-methyl-2-oxopiperidin-3-yl)acetic acid

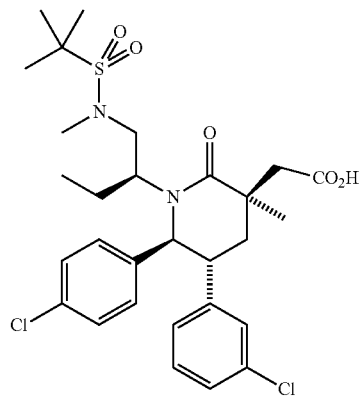 [SMILES: CC[C@@H](CN(C)S(=O)(=O)C(C)(C)C)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)butyl)-N,2-dimethylpropane-2-sulfonamide

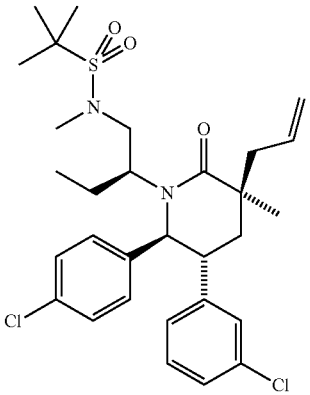 [SMILES: C=CC[C@@]1(C)C[C@H](c2cccc(Cl)c2)[C@@H](c2ccc(Cl)cc2)N([C@@H](CC)CN(C)S(=O)(=O)C(C)(C)C)C1=O]

N-((S)-2-((3S,5R,6S)-3-allyl-5-(3-chlorophenyl)-6-(4-chlorophenyl)-3-methyl-2-oxopiperidin-1-yl)butyl)-2-methylpropane-2-sulfonamide (100 mg, 0.177 mmol; Example 181, Step A) was dissolved in DMF (2.5 mL), and sodium hydride (60% dispersion in mineral oil, 19 mg, 0.45 mmol) was added in a single portion. After 25 minutes, this mixture was cooled to 0° C. in an ice-water bath, and iodomethane (0.04 mL, 0.643 mmol) was added dropwise by syringe. The mixture was allowed to gradually warm to ambient temperature, gradually becoming a pale yellow suspension. After 2 h water (2 mL) was added very carefully. The resulting mixture was partitioned between ethyl acetate and saturated aq. NH$_4$Cl solution. The aqueous phase was back-extracted (2×) and the combined organics were washed with sat. aq. NaCl solution (2×), dried over sodium sulfate, filtered, and the filtrate was concentrated in vacuo to an oily residue that was chromatographed on a 12 g silica column, eluting with a gradient of 0 to 35% EtOAc in hexanes. Fractions containing the sulfonamide product were pooled and concentrated to give the title compound. MS (ESI) m/z=579 [M+H]$^+$.

Step B. 2-((3R,5R,6S)-5-(3-chlorophenyl)-6-(4-chlorophenyl)-1-((S)-1-(N,2-dimethylpropan-2-ylsulfonamido)butan-2-yl)-3-methyl-2-oxopiperidin-3-yl)acetic acid The compound was prepared from N-((S)-2-((3S,5R,6S)-3-allyl-5-(3-chlorophenyl)-6-(4-chlorophenyl)-3-methyl-2-oxopiperidin-1-yl)butyl)-N,2-dimethylpropane-2-sulfonamide (Example 182, Step A) by a procedure similar to the one described in Example 181, Step B. The crude material obtained was taken up in methanol, filtered, and purified by reversed phase HPLC on a Sunfire™ reverse phase prep HPLC column (Waters, Milford, Mass.), eluting with a gradient of 50 to 100% MeCN in water (0.1% TFA in both solvents). Volatiles were removed and the suspension was re-dissolved with minimal MeCN, frozen, and lyophilized to give the title compound as an off-white solid.

$^1$H NMR (500 MHz, CD$_3$OD) δ 0.51 (t, J=7.21 Hz, 3 H), 1.32-1.48 (m, 12 H), 1.58-1.71 (m, 1 H), 1.78-1.92 (m, 1 H), 1.94-2.06 (m, 1 H), 2.43 (t, J=13.69 Hz, 1 H), 2.63 (d, J=13.20 Hz, 1 H), 2.71-2.88 (m, 2 H), 2.88-3.01 (m, 4 H), 3.28 (d,

J=2.93 Hz, 0 H), 3.32-3.35 (m, 1 H), 4.40 (br. s., 1 H), 4.79 (d, J=10.76 Hz, 1 H), 6.96-7.09 (m, 3 H), 7.10-7.40 (m, 5 H). MS (ESI) m/z=597 [M+H]⁺.

Example 183

2-((3R,5R,6S)-5-(3-chlorophenyl)-6-(4-chlorophenyl)-3-methyl-1-((S)-1-(1-methylethylsulfonamido)butan-2-yl)-2-oxopiperidin-3-yl)acetic acid

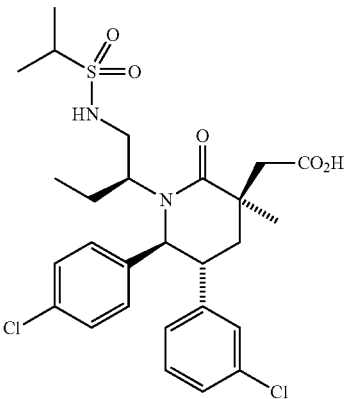 [SMILES: CC[C@@H](CNS(=O)(=O)C(C)C)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)butyl)propane-2-sulfonamide

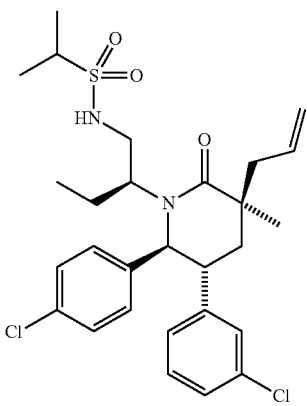 [SMILES: C=CC[C@@]1(C)C[C@H](c2cccc(Cl)c2)[C@@H](c2ccc(Cl)cc2)N([C@@H](CC)CNS(=O)(=O)C(C)C)C1=O]

The title compound was prepared from (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) and propane-2-sulfonamide as described in Example 181, Step A. MS (ESI) m/z=551 [M+H]⁺.

Step B. 2-((3R,5R,6S)-5-(3-chlorophenyl)-6-(4-chlorophenyl)-3-methyl-1-((S)-1-(1-methylethylsulfonamido)butan-2-yl)-2-oxopiperidin-3-yl)acetic acid The title compound was obtained from N-((S)-2-((3S,5R,6S)-3-allyl-5-(3-chlorophenyl)-6-(4-chlorophenyl)-3-methyl-2-oxopiperidin-1-yl)butyl)propane-2-sulfonamide (Example 183, Step A) by a procedure similar to the one described in Example 181, Step B. The residue was purified by reversed phase HPLC on a Sunfire™ reverse phase prep HPLC column (Waters, Milford, Mass.), eluting with a gradient of 50 to 100% MeCN in water (0.1% TFA in both solvents). Chromatography fractions were combined and concentrated in vacuo. The resulting suspension was made homogeneous by addition of minimal MeCN, frozen, and lyophilized to give the title compound.

¹H NMR (500 MHz, CD₃OD) δ 0.45 (t, J=7.58 Hz, 3 H), 1.35 (dd, J=8.56, 6.85 Hz, 6 H), 1.41 (br. s., 3 H), 1.51-1.64 (m, 1 H), 1.83 (ddd, J=14.43, 8.56, 7.34 Hz, 1 H), 2.05 (dd, J=13.69, 2.93 Hz, 1 H), 2.39 (t, J=13.69 Hz, 1 H), 2.64 (d, J=13.45 Hz, 1 H), 2.80 (t, J=9.29 Hz, 1 H), 2.87-3.04 (m, 2 H), 3.23 (dt, J=13.51, 6.82 Hz, 1 H), 3.33-3.40 (m, 1 H), 3.85 (dd, J=14.06, 10.15 Hz, 1 H), 4.96 (d, J=11.00 Hz, 1 H), 6.36-7.71 (m, 8 H). MS (ESI) m/z=569 [M+H]⁺.

Example 184

2-((3R,5R,6S)-5-(3-chlorophenyl)-6-(4-chlorophenyl)-1-((S)-1-(N-ethylpropan-2-ylsulfonamido)butan-2-yl)-3-methyl-2-oxopiperidin-3-yl)acetic acid

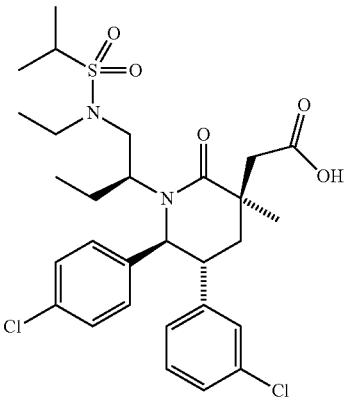 [SMILES: CC[C@@H](CN(CC)S(=O)(=O)C(C)C)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)butyl)-N-ethylpropane-2-sulfonamide

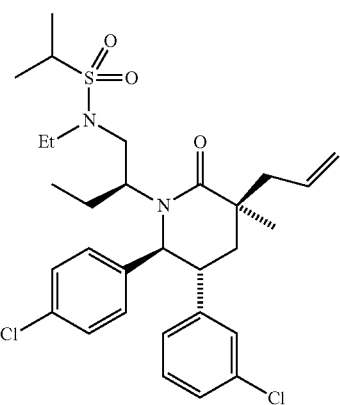 [SMILES: C=CC[C@@]1(C)C[C@H](c2cccc(Cl)c2)[C@@H](c2ccc(Cl)cc2)N([C@@H](CC)CN(CC)S(=O)(=O)C(C)C)C1=O]

The title compound was prepared from N-((S)-2-((3S,5R,6S)-3-allyl-5-(3-chlorophenyl)-6-(4-chlorophenyl)-3-methyl-2-oxopiperidin-1-yl)butyl)propane-2-sulfonamide (Example 183, Step A) by a procedure similar to the one described in Example 182, Step A, replacing iodomethane with iodoethane. MS (ESI) m/z=579 [M+H]+.

Step B. 2-((3R,5R,6S)-5-(3-chlorophenyl)-6-(4-chlorophenyl)-1-((S)-1-(N-ethylpropan-2-ylsulfonamido)butan-2-yl)-3-methyl-2-oxopiperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)butyl)-N-ethylpropane-2-sulfonamide (Example 184, Step A) by a procedure similar to the one described in Example 71, Step F. The residue was chromatographed on a Sunfire™ C18 reverse phase prep HPLC column (Waters, Milford, Mass.), eluting with a gradient of 50 to 100% MeCN in water (0.1% TFA in both solvents). Fractions containing the product in high purity by HPLC were combined and stripped of volatiles on the rotary evaporator. The suspension was re-dissolved in minimal MeCN, frozen, and lyophilized overnight to give the title compound as a white foam.
$^1$H NMR (500 MHz, CD$_3$OD) δ 0.52 (t, J=7.21 Hz, 3 H), 1.09-1.20 (m, 3 H), 1.30 (d, J=6.85 Hz, 3 H), 1.38 (d, J=6.85 Hz, 3 H), 1.43 (s, 3 H), 1.56-1.69 (m, 1 H), 1.82-1.97 (m, 1 H), 2.01 (dd, J=13.69, 2.93 Hz, 1 H), 2.41 (t, J=13.69 Hz, 1 H), 2.64 (d, J=13.20 Hz, 1 H), 2.82 (br. s., 1 H), 2.88-3.02 (m, 2 H), 3.15-3.25 (m, 1 H), 3.28 (d, J=3.18 Hz, 1 H), 3.33-3.36 (m, 1 H), 3.40-3.55 (m, 1 H), 4.29 (d, J=6.36 Hz, 1 H), 4.84 (br. d, J=1.00 Hz, 1 H), 6.81-7.55 (m, 8 H). MS (ESI) m/z=597 [M+H]+.

Example 185

2-((3R,5R,6S)-5-(3-Chlorophenyl)-6-(4-chlorophenyl)-1-((S)-1-hydroxybutan-2-yl)-3-methyl-2-oxopiperidin-3-yl)acetic acid

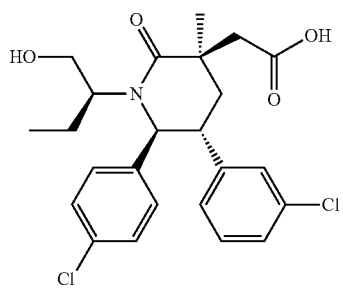 [SMILES: CC[C@@H](CO)N1C(=O)[C@@](C)(CC(=O)O)C[C@H](c2cccc(Cl)c2)[C@H]1c1ccc(Cl)cc1]

Step A. (S)-Methyl 2-((2S,3R)-3-(3-chlorophenyl)-2-(4-chlorophenyl)-6-oxopiperidin-1-yl)butanoate

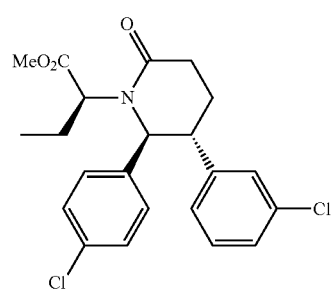 [SMILES: CC[C@@H](C(=O)OC)N1C(=O)CC[C@H](c2cccc(Cl)c2)[C@H]1c1ccc(Cl)cc1]

To a 50° C. solution of 33.8 g (60% in mineral oil, 845 mmol) of sodium hydride in 2-methyltetrahydrofuran (550 mL) was added a solution of 240 g (750 mmol) of (5R,6S)-5-(3-chlorophenyl)-6-(4-chlorophenyl)piperidin-2-one (Example 1, Step E) in 2-methyltetrahydrofuran (550 mL) over a period of 45 min. After an additional 1.25 h at 50° C., 105 mL (912 mmol) of methyl 2-bromobutyrate was added over a 20 min period. The resulting slurry was stirred at 50° C. for 3.5 h, and then was cooled to room temperature and quenched with saturated aq. NH$_4$Cl solution. Water was added to dissolve the precipitate and the resulting mixture was extracted with ethyl acetate (4×). The combined organic layers were washed with sat. aq. NaCl solution (1×), dried over Na$_2$SO$_4$, filtered and the filtrate was concentrated. Purification of the residue by chromatography on silica gel (Biotage® Snap™ column (Biotage, LLC, Charlotte, N.C.), 0 to 35% EtOAc/DCM, gradient elution) provided the title compound as a white oily solid.

Step B. (5R,6S)-5-(3-chlorophenyl)-6-(4-chlorophenyl)-1-((S)-1-hydroxybutan-2-yl)piperidin-2-one

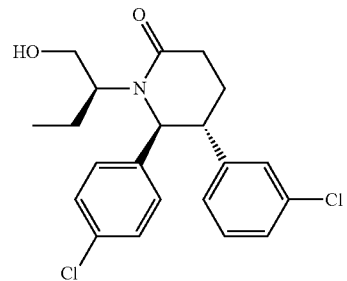 [SMILES: CC[C@@H](CO)N1C(=O)CC[C@H](c2cccc(Cl)c2)[C@H]1c1ccc(Cl)cc1]

To an ice-cooled solution of 48.5 g (115 mmol) of (S)-methyl 2-((2S,3R)-3-(3-chlorophenyl)-2-(4-chlorophenyl)-6-oxopiperidin-1-yl)butanoate (Example 185, Step A) in ethyl ether (850 mL) was added 5.96 g (90%, 246 mmol) of lithium borohydride. The resulting light yellow solution was stirred at 0° C. for 3 h, and then MeOH (2.5 mL) and more ethyl ether (100 mL) were added. Gas evolution was observed upon the addition of MeOH. After 40 min, the reaction was quenched by cautious addition of 1 N HCl until bubbling subsided. The mixture was extracted with EtOAc (2×), and the combined organic layers were washed with saturated aqueous sodium chloride (1×). The organic layer was dried over Na$_2$SO$_4$, filtered and the filtrate was concentrated to afford the title compound as a white foam. The crude product was used directly in the next step without further purification.

Step C. (5R,6S)-1-((S)-1-(tert-butyldiphenylsilyloxy)butan-2-yl)-5-(3-chlorophenyl)-6-(4-chlorophenyl)piperidin-2-one

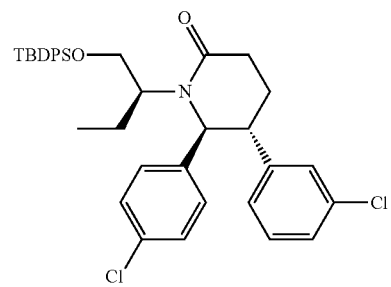

To a solution of 44.7 g (114 mmol) of (5R,6S)-5-(3-chlorophenyl)-6-(4-chlorophenyl)-1-((S)-1-hydroxybutan-2-yl)piperidin-2-one (Example 185, Step B) and 19.4 g (285 mmol) of imidazole in DMF (350 mL) was added 39.4 mL (154 mmol) of tert-butyldiphenylsilyl chloride. The colorless solution was stirred at room temperature for 17 h. The reaction was partitioned between water and ethyl ether (3×), and then the combined organic layers were washed with saturated aqueous sodium chloride (1×), dried over $Na_2SO_4$, filtered and the filtrate was concentrated. Purification of the residue by chromatography on silica gel (Biotage® Snap™ column (Biotage, LLC, Charlotte, N.C.), 0 to 60% EtOAc/hexanes, gradient elution) provided the title compound as a white foam.

Step D. (5R,6S)-1-((S)-1-(tert-Butyldiphenylsilyloxy)butan-2-yl)-5-(3-chlorophenyl)-6-(4-chlorophenyl)-3-methylpiperidin-2-one

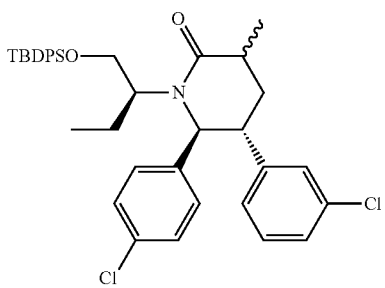

To a −78° C. solution of 98.2 g (156 mmol) of (5R,6S)-1-((S)-1-(tert-butyldiphenylsilyloxy)butan-2-yl)-5-(3-chlorophenyl)-6-(4-chlorophenyl)piperidin-2-one (Example 185, Step C) and 10.0 mL (160 mmol) of methyl iodide in dry, degassed THF (400 mL) was added 200 mL (200 mmol) of a degassed 1 M solution of lithium bis(trimethylsilyl)amide in THF slowly over 20 min. The orange solution was stirred at −78° C. for 1.5 h and then warmed to 0° C. and stirred for an additional 1.5 h. The reaction was quenched with saturated aqueous ammonium chloride, and extracted with EtOAc (3×). The combined organic layers were dried over $Na_2SO_4$, filtered and the filtrate was concentrated. Purification of the residue by chromatography on silica gel (Biotage® Snap™ column; Biotage, LLC, Charlotte, N.C.), 5-55% EtOAc/hexanes, gradient elution) provided the title compound as a light yellow foam.

Step E. (3S,5R,6S)-3-allyl-1-((S)-1-(tert-butyldiphenylsilyloxy)butan-2-yl)-5-(3-chlorophenyl)-6-(4-chlorophenyl)-3-methylpiperidin-2-one

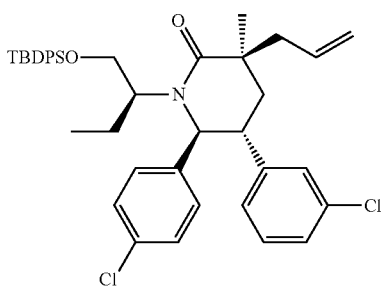

To a −78° C. solution of 37.3 mL (266 mmol) of diisopropylamine in dry, degassed THF (150 mL) was added 100 mL (250 mmol) of a degassed 2.5 M solution of n-butyllithium in hexanes slowly via cannula. The light yellow solution was stirred at −78° C. for 15 min, then was warmed to 0° C. and stirred for an additional 5 min. To the ice-cooled LDA solution was added a solution of 85.7 g (133 mmol) of (5R,6S)-1-((S)-1-(tert-butyldiphenylsilyloxy)butan-2-yl)-5-(3-chlorophenyl)-6-(4-chlorophenyl)-3-methylpiperidin-2-one (Example 185, Step D) in dry, degassed THF (210 mL) via cannula over a 15 min period. The dark orange solution was stirred at 0° C. for 30 min and then 34.5 mL (399 mmol) of allyl bromide was added quickly via syringe. After 20 sec, the ice bath was removed and the reaction was placed in a room temperature water bath and stirred for an additional 15 min. The reaction was quenched with saturated aq. ammonium chloride, and extracted with EtOAc (3×). The combined organic layers were dried over $Na_2SO_4$, filtered and the filtrate was concentrated. Purification of the residue by chromatography on silica gel (Biotage® Snap™ column; Biotage, LLC, Charlotte, N.C.), 6-14% EtOAc/hexanes, gradient elution) provided the title compound as a white foam.

Step F. 2-((3R,5R,6S)-1-((S)-1-(tert-butyldiphenylsilyloxy)butan-2-yl)-5-(3-chlorophenyl)-6-(4-chlorophenyl)-3-methyl-2-oxopiperidin-3-yl)acetic acid

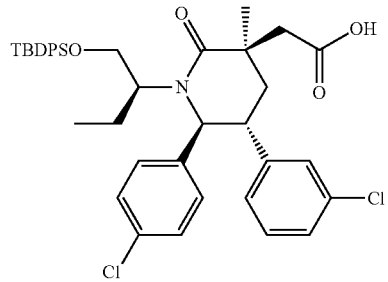

The title compound was prepared from (3S,5R,6S)-3-allyl-1-((S)-1-(tert-butyldiphenylsilyloxy)butan-2-yl)-5-(3-chlorophenyl)-6-(4-chlorophenyl)-3-methylpiperidin-2-one (Example 185, Step E) by a procedure similar to the one described in Example 71, Step F.

$^1$H NMR (400 MHz, CHLOROFORM-d) δ ppm 0.30 (t, J=7.53 Hz, 3 H) 1.17 (s, 9 H) 1.34-1.48 (m, 1 H) 1.53 (s, 3H) 1.74-1.88 (m, 1 H) 1.93-2.03 (m, 1 H) 2.29 (t, J=13.69 Hz, 1 H) 2.69 (d, J=15.85 Hz, 1 H) 2.81-2.93 (m, 1 H) 2.98-3.08 (m, 1 H) 3.12 (d, J=15.65 Hz, 1 H) 3.52 (dd, J=10.66, 4.21 Hz, 1 H) 4.32 (t, J=10.27 Hz, 1 H) 4.71 (d, J=10.76 Hz, 1 H) 6.56-6.66 (m, 1 H) 6.91-6.97 (m, 1 H) 7.02-7.09 (m, 1 H) 7.12-7.18 (m, 1 H) 7.20-7.30 (m, 4 H) 7.33-7.51 (m, 6 H) 7.64 (td, J=7.83, 1.57 Hz, 4 H).

Step G. 2-((3R,5R,6S)-5-(3-chlorophenyl)-6-(4-chlorophenyl)-1-((S)-1-hydroxybutan-2-yl)-3-methyl-2-oxopiperidin-3-yl)acetic acid To an ice-cooled solution of 370 g (0.53 mmol) of 2-((3R,5R,6S)-1-((S)-1-(tert-butyldiphenylsilyloxy)butan-2-yl)-5-(3-chlorophenyl)-6-(4-chlorophenyl)-3-methyl-2-oxopiperidin-3-yl)acetic acid (Example 185, Step F) in THF (15 mL) was added 2.60 mL (2.60 mmol) of a 1 M solution of TBAF in THF. The yellow solution was warmed to rt and stirred for 5 h. At this time 2.60 mL (2.60 mmol) of a 1 M solution of TBAF in THF was added and the reaction was stirred for an additional 20 h. The reaction was partitioned between 1 N HCl and EtOAc (4×). The combined organic layers were dried over $Na_2SO_4$, filtered and the filtrate was concentrated. The residue was purified by reverse phase prep. HPLC (Sunfire™ Prep $C_{18}$ OBD 10 µm column (Waters, Milford, Mass.), gradient elution of 40% MeCN in water to 80% MeCN in water over a 30 min period, where both solvents contain 0.1% TFA) provided the title compound as a white solid.

$^1$H NMR (400 MHz, $CDCl_3$) δ ppm 7.23-7.28 (2 H, m), 7.15-7.20 (1 H, m), 7.07-7.14 (1 H, m), 6.98-7.06 (3 H, m), 6.74 (1H, d, J=7.1 Hz), 4.55 (1 H, dd J=9.8 Hz, 2.9 Hz), 3.71-3.79 (1 H, m), 3.58-3.66 (1 H, m), 3.19-3.28 (1 H, m), 3.07-3.16 (1 H, m), 2.96-3.03 (1 H, m), 2.75 (1 H, dd, J=14.9 Hz, 2.9 Hz), 2.16-2.25 (1 H, m), 2.03-2.10 (1 H, m), 1.87-1.98 (1 H, m), 1.46 (3 H, s), 1.41-1.54 (m, 1 H), 0.63 (3 H, dd, J=7.3 Hz, 3.3 Hz). Mass Spectrum (ESI) m/z=464.1 (M+1).

Example 186

2-((3R,5R,6S)-5-(3-Chlorophenyl)-6-(4-chlorophenyl)-3-methyl-2-oxo-1-((S)-1-(trifluoromethylsulfonamido)butan-2-yl)piperidin-3-yl)acetic acid

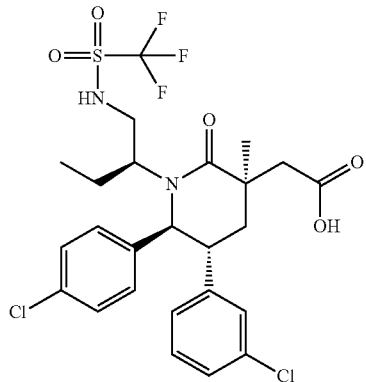 [SMILES: CC[C@@H](CNS(=O)(=O)C(F)(F)F)N1C(=O)[C@@](C)(CC(=O)O)C[C@H](c2cccc(Cl)c2)[C@H]1c1ccc(Cl)cc1]

Step A. Methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate

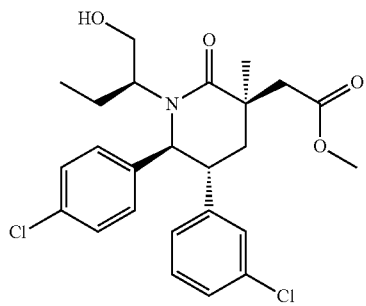 [SMILES: CC[C@@H](CO)N1C(=O)[C@@](C)(CC(=O)OC)C[C@H](c2cccc(Cl)c2)[C@H]1c1ccc(Cl)cc1]

A solution of 2-((3R,5R,6S)-1-((S)-1-(tert-butyldiphenylsilyloxy)butan-2-yl)-5-(3-chlorophenyl)-6-(4-chlorophenyl)-3-methyl-2-oxopiperidin-3-yl)acetic acid (Example 185) in MeOH (2 mL) and benzene (8 mL) was stirred with (trimethylsilyl)diazomethane, 2.0 M in diethyl ether (2.02 mL, 4.04 mmol) at rt for 0.5 h. After that time the mixture was concentrated to give the crude methyl ester, which was treated with TBAF in THF at rt for 30 h. The mixture was concentrated and purified by chromatography on silica gel (0 to 100% EtOAc in hexanes) to give the title compound. Mass Spectrum (ESI) m/z=478 (M+1).

Step B. 2-((3R,5R,6S)-5-(3-Chlorophenyl)-6-(4-chlorophenyl)-3-methyl-2-oxo-1-((S)-1-(trifluoromethylsulfonamido)butan-2-yl)piperidin-3-yl)acetic acid A reaction vial under argon was charged with methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (0.048 g, 0.1 mmol; Example 186, Step A), 2-(tributylphosphoranylidene) acetonitrile (0.036 g, 0.15 mmol) and trifluoromethanesulfonamide (0.022 g, 0.15 mmol) in toluene (0.5 mL). The reaction mixture in the reaction vial was sealed and stirred at 110° C. for 1 h. Column chromatography on silica gel gave a mixture of methyl 2-((3R,5R,6S)-5-(3-chlorophenyl)-6-(4-chlorophenyl)-3-methyl-2-oxo-1-((S)-1-(trifluoromethylsulfonamido)butan-2-yl)piperidin-3-yl)acetate with an unknown impurity. This mixture was hydrolyzed with LiOH (1N solution in water, 0.3 mL) in ethanol (0.5 mL) for 3 h at rt. HPLC purification (C18 column, eluted with 10 to 95% $CH_3CN$ in water, with 0.1% TFA) gave the title compound.

$^1$H NMR (500 MHz, CHLOROFORM-d) δ ppm 7.26 (2 H, br. s.), 7.15-7.20 (1 H, m), 7.12 (1 H, t, J=7.8 Hz), 7.05 (1 H, d, J=9.3 Hz), 6.95 (1 H, t, J=1.7 Hz), 6.75 (1 H, d, J=7.6 Hz), 6.49 (1 H, br. s.), 4.53 (1 H, d, J=10.3 Hz), 3.13-3.27 (3 H, m), 2.80-2.93 (3 H, m), 2.24 (1 H, t, J=13.8 Hz), 2.10 (1 H, dd, J=14.1, 3.1 Hz), 1.83 (1 H, br. s.), 1.55-1.66 (1 H, m), 1.49 (3 H, s), 0.71 (3 H, br. s.). Mass Spectrum (ESI) m/z=595 (M+1).

EXAMPLES 187-195 were, unless noted otherwise, prepared from methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (Example 186, Step A) by procedures similar to the one described in Example 186, Step B, replacing trifluoromethanesulfonamide with the appropriate reagent.

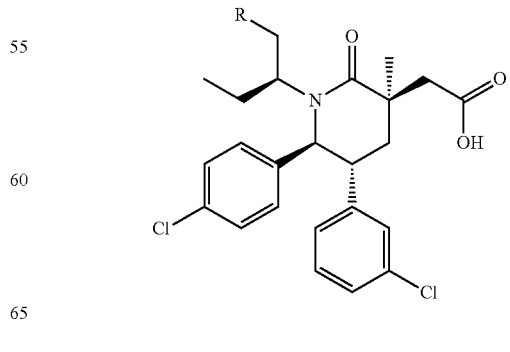

| Example | R | Reagent used |
|---|---|---|
| 187 | 4-chlorophenylsulfonamide group (Cl-C6H4-SO2-NH-) | 4-Chlorobenzene-sulfonamide |
| 188 | 4-methylphenylsulfonamide group | 4-Methylbenzene-sulfonamide |
| 189 | 2-chlorophenylsulfonamide group | 2-Chlorobenzene-sulfonamide |
| 190 | 2-methylphenylsulfonamide group | 2-Methylbenzene-sulfonamide |
| 191 | 4-methoxyphenylsulfonamide group | 4-Methoxybenzene-sulfonamide |
| 192 | phenylsulfonamide group | Benzenesulfonamide |
| 193 | 1-methylcyclopropanesulfonamide group | 1-Methylcyclopropane-1-sulfonamide |
| 194 | 2,3-dihydro-1,1-dioxo-1,2-benzisothiazol-2-yl | 2,3-Dihydro-1,1-dioxo-1,2-benzisothiazole |
| 195 | 2,3-dihydro-3,3-dimethyl-1,2-benzisothiazole 1,1-dioxide-2-yl | 2,3-Dihydro-3,3-dimethyl-1,2-benzisothiazole 1,1-dioxide |

Example 187

2-((3R,5R,6S)-5-(3-Chlorophenyl)-6-(4-chlorophenyl)-1-((S)-1-(4-chlorophenylsulfonamido)butan-2-yl)-3-methyl-2-oxopiperidin-3-yl)acetic acid $^1$H NMR (500 MHz, CHLOROFORM-d) δ ppm 7.77 (2 H, m, J=8.6 Hz), 7.48-7.54 (2 H, m), 7.23 (2 H, d, J=8.1 Hz), 7.11-7.19 (2 H, m), 7.05 (2 H, d, J=5.9 Hz), 6.98 (1 H, s), 6.86 (1 H, d, J=7.3 Hz), 5.31 (2 H, br. s.), 5.26 (3 H, br. s.), 4.78 (1 H, d, J=10.3 Hz), 3.43 (1 H, br. s.), 3.17 (2 H, ddd, J=13.5, 10.7, 2.9 Hz), 2.97 (1 H, d, J=14.4 Hz), 2.79 (1 H, d, J=14.4 Hz), 2.74 (1 H, d, J=13.7 Hz), 2.38 (1 H, t, J=13.8 Hz), 2.05 (1 H, dd, J=13.9, 2.9 Hz), 1.80 (1 H, dt, J=14.6, 7.5 Hz), 1.52 (3 H, s), 1.43-1.50 (1 H, m), 0.51 (3 H, t, J=7.1 Hz). Mass Spectrum (ESI) m/z=637 (M+1).

Example 188

2-((3R,5R,6S)-5-(3-Chlorophenyl)-6-(4-chlorophenyl)-3-methyl-1-((S)-1-(4-methylphenylsulfonamido)butan-2-yl)-2-oxopiperidin-3-yl)acetic acid $^1$H NMR (500 MHz, CHLOROFORM-d) δ ppm 7.72 (2 H, m, J=8.3 Hz), 7.33 (2 H, m, J=8.1 Hz), 7.23 (2 H, d, J=8.1 Hz), 7.11-7.19 (2 H, m), 7.05 (2 H, d, J=6.6 Hz), 6.96-6.99 (1 H, m), 6.85-6.91 (1 H, m), 4.95 (1 H, br. s.), 4.83 (1 H, d, J=10.5 Hz), 3.49 (1 H, br. s.), 3.14 (2 H, ddd, J=13.4, 10.6, 2.8 Hz), 3.02 (1 H, d, J=14.9 Hz), 2.70-2.81 (2 H, m), 2.45 (3 H, s), 2.36-2.44 (1 H, m), 2.01 (1 H, dd, J=13.9, 2.9 Hz), 1.81 (1 H, dd, J=15.3, 7.5 Hz), 1.53 (3 H, s), 1.47 (1 H, ddd, J=14.2, 7.6, 4.3 Hz), 0.47 (3 H, t, J=7.5 Hz). Mass Spectrum (ESI) m/z=617 (M+1).

Example 189

2-((3R,5R,6S)-5-(3-Chlorophenyl)-6-(4-chlorophenyl)-1-((S)-1-(2-chlorophenylsulfonamido)butan-2-yl)-3-methyl-2-oxopiperidin-3-yl)acetic acid $^1$H NMR (500 MHz, CHLOROFORM-d) δ ppm 7.77 (2 H, m, J=8.6 Hz), 7.48-7.54 (2 H, m), 7.23 (2 H, d, J=8.1 Hz), 7.11-7.19 (2 H, m), 7.05 (2 H, d, J=5.9 Hz), 6.98 (1 H, s), 6.86 (1 H, d, J=7.3 Hz), 5.31 (2 H, br. s.), 5.26 (3 H, br. s.), 4.78 (1 H, d, J=10.3 Hz), 3.43 (1 H, br. s.), 3.17 (2 H, ddd, J=13.5, 10.7, 2.9 Hz), 2.97 (1 H, d, J=14.4 Hz), 2.79 (1 H, d, J=14.4 Hz), 2.74 (1 H, d, J=13.7 Hz), 2.38 (1 H, t, J=13.8 Hz), 2.05 (1 H, dd, J=13.9, 2.9 Hz), 1.80 (1 H, dt, J=14.6, 7.5 Hz), 1.52 (3 H, s), 1.43-1.50 (1 H, m), 0.51 (3 H, t, J=7.1 Hz). Mass Spectrum (ESI) m/z=651 (M+1).

Example 190

2-((3R,5R,6S)-5-(3-Chlorophenyl)-6-(4-chlorophenyl)-1-((S)-1-(2-methylphenylsulfonamido)butan-2-yl)-3-methyl-2-oxopiperidin-3-yl)acetic acid $^1$H NMR (500 MHz, CHLOROFORM-d) δ ppm 7.89 (1 H, d, J=7.8 Hz), 7.46-7.52 (1 H, m), 7.31-7.38 (2 H, m), 7.23 (2 H, d, J=7.8 Hz), 7.12-7.18 (2H, m), 7.06 (2 H, br. s.), 6.99 (1 H, s), 6.88 (1 H, d, J=7.1 Hz), 5.16 (1 H, br. s.), 4.85 (1 H, d, J=10.5 Hz), 4.46 (3 H, br. s.), 3.44 (1 H, br. s.), 3.11-3.22 (2 H, m), 2.99 (1 H, d, J=14.9 Hz), 2.73-2.84 (2 H, m), 2.67 (3 H, s), 2.36-2.47 (1 H, m), 2.04 (1 H, dd, J=13.9, 2.9 Hz), 1.80 (1 H, dt, J=14.7, 7.7 Hz), 1.53 (3 H, s), 1.45 (1 H, ddd, J=14.1, 7.6, 4.4 Hz), 0.46 (3 H, t, J=7.5 Hz). Mass Spectrum (ESI) m/z=617 (M+1).

Example 191

2-((3R,5R,6S)-5-(3-Chlorophenyl)-6-(4-chlorophenyl)-1-((S)-1-(4-methoxyphenylsulfonamido)butan-2-yl)-3-methyl-2-oxopiperidin-3-yl)acetic acid $^1$H NMR (500 MHz, CHLOROFORM-d) δ ppm 7.76 (2 H, d, J=8.8 Hz), 7.24 (2 H, d, J=7.8 Hz), 7.11-7.19 (2 H, m), 7.04 (1 H, br. s.), 7.01 (1 H, s), 6.98 (2 H, d, J=4.4 Hz), 6.88 (1 H, d, J=6.8 Hz), 4.92 (1 H, br. s.), 4.83 (1 H, d, J=10.5 Hz), 4.03 (3H, br. s.), 3.89 (3 H, s), 3.49 (1 H, br. s.), 3.14 (2 H, t, J=10.8 Hz), 3.02 (1 H, d, J=14.9 Hz), 2.69-2.80 (2 H, m), 2.42 (1 H, t, J=13.8 Hz), 1.97-2.05 (1 H, m), 1.82 (1 H, dt, J=14.6, 7.5 Hz), 1.53 (3 H, s), 1.41-1.50 (1 H, m), 0.47 (3 H, t, J=7.3 Hz). Mass Spectrum (ESI) m/z=633 (M+1).

Example 192

2-((3R,5R,6S)-5-(3-Chlorophenyl)-6-(4-chlorophenyl)-1-((S)-1-(phenylsulfonamido)butan-2-yl)-3-methyl-2-oxopiperidin-3-yl)acetic acid $^1$H NMR (500 MHz, CHLOROFORM-d) δ ppm 7.84 (2 H, d, J=7.3 Hz), 7.62 (1 H, t, J=7.3 Hz), 7.55 (2 H, t, J=7.7 Hz), 7.24 (2 H, d, J=8.1 Hz), 7.12-7.19 (2 H, m), 7.05 (2 H, d, J=6.6 Hz), 6.98 (1 H, s), 6.87 (1 H, d, J=6.8 Hz), 5.03 (1 H, br. s.), 4.82 (1 H, d, J=10.5 Hz), 4.01 (2 H, br. s.), 3.49 (1 H, br. s.), 3.09-3.21 (2 H, m), 3.02 (1 H, d, J=14.9 Hz), 2.77 (2 H, d, J=14.7 Hz), 2.41 (1 H, t, J=13.8 Hz), 2.02 (1 H, dd, J=13.9, 2.7 Hz), 1.82 (1 H, dt, J=14.9, 7.6 Hz), 1.53 (3 H, s), 1.48 (1 H, ddd, J=14.2, 7.7, 4.5 Hz), 0.49 (3 H, t, J=7.5 Hz). Mass Spectrum (ESI) m/z=603 (M+1).

Example 193

2-((3R,5R,6S)-5-(3-Chlorophenyl)-6-(4-chlorophenyl)-1-((S)-1-(1-methylcyclopropanesulfonamido)butan-2-yl)-3-methyl-2-oxopiperidin-3-yl)acetic acid $^1$H NMR (500 MHz, CHLOROFORM-d) δ ppm 7.24 (2 H, d, J=7.8 Hz), 7.10-7.17 (2 H, m), 7.03 (1 H, s), 7.06 (1 H, s), 6.95-6.97 (1 H, m), 6.84-6.89 (1 H, m), 4.88 (2 H, br. s.), 4.81 (2 H, d, J=10.5 Hz), 4.71 (1 H, br. s.), 3.71 (1 H, br. s.), 3.03-3.18 (3 H, m), 2.96-3.02 (1 H, m), 2.76 (1 H, d, J=14.7 Hz), 2.40 (1 H, t, J=13.8 Hz), 1.98 (1 H, dd, J=13.9, 2.9 Hz), 1.88 (1 H, dt, J=15.0, 7.5 Hz), 1.52 (3 H, s), 1.50 (3 H, s), 1.45-1.49 (1 H, m), 1.33-1.43 (2 H, m), 0.77-0.86 (2 H, m), 0.52 (3 H, t, J=7.5 Hz). Mass Spectrum (ESI) m/z=581 (M+1).

Example 194

2-((3R,5R,6S)-5-(3-Chlorophenyl)-6-(4-chlorophenyl)-1-((S)-1-(1,1-dioxidobenzo[d]isothiazol-2(3H)-yl)butan-2-yl)-3-methyl-2-oxopiperidin-3-yl)acetic acid $^1$H NMR (500 MHz, CHLOROFORM-d) δ ppm 7.91 (1 H, d, J=7.6 Hz), 7.66-7.72 (1 H, m), 7.60-7.65 (1 H, m), 7.43 (1 H, d, J=7.6 Hz), 7.25 (1 H, br. s.), 7.06-7.11 (1 H, m), 6.95-7.06 (3 H, m), 6.87 (1 H, s), 6.71 (1 H, d, J=7.6 Hz), 4.86 (1 H, d, J=10.3 Hz), 4.36-4.47 (2 H, m), 4.20 (1 H, dd, J=14.2, 10.5 Hz), 4.03 (5 H, br. s.), 3.24 (1 H, dd, J=14.7, 3.4 Hz), 3.01-3.15 (3 H, m), 2.74 (1 H, d, J=14.9 Hz), 2.32 (1 H, t, J=13.8 Hz), 1.95-2.07 (1 H, m), 1.90 (1 H, dd, J=13.8, 2.8 Hz), 1.53 (1 H, ddd, J=10.7, 7.4, 3.9 Hz), 1.49 (3 H, s), 0.53 (3 H, t, J=7.5 Hz). Mass Spectrum (ESI) m/z=615 (M+1).

Example 195

2-((3R,5R,6S)-5-(3-Chlorophenyl)-6-(4-chlorophenyl)-1-((S)-1-(3,3-dimethyl-1,1-dioxidobenzo[d]isothiazol-2(3H)-yl)butan-2-yl)-3-methyl-2-oxopiperidin-3-yl)acetic acid $^1$H NMR (500 MHz, CHLOROFORM-d) δ ppm 7.88 (1 H, d, J=7.6 Hz), 7.68-7.74 (1 H, m), 7.58-7.64 (1 H, m), 7.45 (1 H, d, J=7.8 Hz), 7.25 (1 H, br. s.), 7.02-7.12 (3 H, m), 6.99 (1 H, t, J=7.8 Hz), 6.94 (1 H, s), 6.75 (1 H, d, J=7.6 Hz), 5.02 (1 H, d, J=10.0 Hz), 4.24 (1 H, dd, J=14.8, 10.6 Hz), 3.15 (2 H, d, J=13.0 Hz), 3.03-3.13 (3 H, m), 2.92 (8 H, br. s.), 2.71 (1 H, d, J=15.4 Hz), 2.36 (1 H, t, J=13.6 Hz), 2.06-2.19 (1 H, m), 1.90 (1 H, dd, J=13.8, 3.1 Hz), 1.57 (3 H, s), 1.48-1.52 (4 H, m), 1.47 (3 H, s), 0.51 (3 H, t, J=7.5 Hz). Mass Spectrum (ESI) m/z=643 (M+1).

Example 196

2-((3R,5R,6S)-5-(3-chlorophenyl)-6-(4-chlorophenyl)-3-methyl-2-oxo-1-((S)-1-(pyridine-3-sulfonamido)butan-2-yl)piperidin-3-yl)acetic acid, as the 2,2,2-trifluoroacetic acid salt

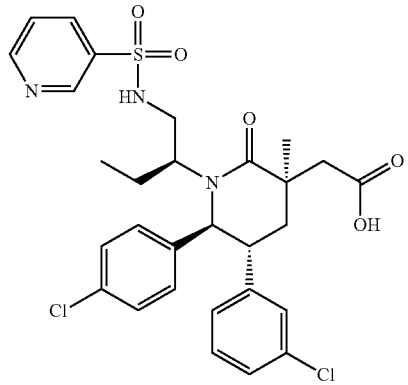 [SMILES: CC[C@@H](CNS(=O)(=O)c1cccnc1)N1C(=O)[C@@](C)(CC(=O)O)C[C@H](c2cccc(Cl)c2)[C@H]1c1ccc(Cl)cc1]

Step A. Methyl 2-((3R,5R,6S)-1-((S)-1-(bis(tert-butoxycarbonyl)amino)butan-2-yl)-5-(3-chlorophenyl)-6-(4-chlorophenyl)-3-methyl-2-oxopiperidin-3-yl)acetate

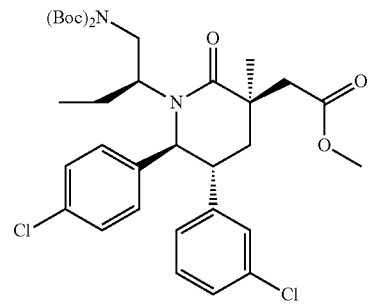

A solution of methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (282 mg, 0.589 mmol; Example 186, Step A), 2-(tributylphosphoranylidene)acetonitrile (171 mg, 0.707 mmol) and di-tert-butyl iminodicarbonate (256 mg, 1.179 mmol) in toluene (3 mL) under argon was stirred at 110° C. for 2 h. Flash column purification on silica gel (0 to 60% EtOAc in hexanes) gave the title compound.

Mass Spectrum (ESI) m/z=677 (M+1).

Step B. Methyl 2-((3R,5R,6S)-1-((S)-1-aminobutan-2-yl)-5-(3-chlorophenyl)-6-(4-chlorophenyl)-3-methyl-2-oxopiperidin-3-yl)acetate

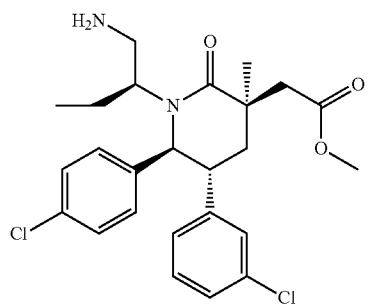 [SMILES: CC[C@@H](CN)N1C(=O)[C@@](C)(CC(=O)OC)C[C@H](c2cccc(Cl)c2)[C@H]1c1ccc(Cl)cc1]

A solution of methyl 2-((3R,5R,6S)-1-((S)-1-(bis(tert-butoxycarbonyl)amino)butan-2-yl)-5-(3-chlorophenyl)-6-(4-chlorophenyl)-3-methyl-2-oxopiperidin-3-yl)acetate (167 mg, 0.246 mmol) prepared in Step A above in dioxane was stirred with HCl (4M, 0.6 mL) at rt for 2 h. Chromatography on silica gel (0 to 20% MeOH/DCM) gave the title compound. Mass Spectrum (ESI) m/z=477 (M+1).

Step C. 2-((3R,5R,6S)-5-(3-chlorophenyl)-6-(4-chlorophenyl)-3-methyl-2-oxo-1-((S)-1-(pyridine-3-sulfonamido)butan-2-yl)piperidin-3-yl)acetic acid A solution of methyl 2-((3R,5R,6S)-1-((S)-1-aminobutan-2-yl)-5-(3-chlorophenyl)-6-(4-chlorophenyl)-3-methyl-2-oxopiperidin-3-yl)acetate (13 mg, 0.027 mmol; Example 196, Step A) and pyridine-3-sulfonyl chloride (4.84 mg, 0.027 mmol) in pyridine (0.3 mL) was stirred at 110° C. for 4 h. Chromatography on silica gel (0 to 60% EtOAc in hexanes) gave methyl 2-((3R,5R,6S)-5-(3-chlorophenyl)-6-(4-chlorophenyl)-3-methyl-2-oxo-1-((S)-1-(pyridine-3-sulfonamido)butan-2-yl)piperidin-3-yl)acetate. This was hydrolyzed with LiOH (1N solution in water, 0.3 mL) in ethanol (0.5 mL) for 3 h at rt. HPLC purification (C18 column, eluted with 10 to 95% CH₃CN in water, with 0.1% TFA) gave the title compound as a 1:1 complex with 2,2,2-trifluoroacetic acid.

¹H NMR (500 MHz, CHLOROFORM-d) δ ppm 9.29 (1 H, br. s.), 8.90 (1 H, d, J=4.4 Hz), 8.32 (1 H, d, J=8.1 Hz), 7.66-7.76 (1 H, m), 7.15 (1 H, d, J=8.1 Hz), 7.10 (1 H, t, J=7.8 Hz), 7.02 (2 H, s), 7.06 (1 H, s), 6.94 (1 H, s), 6.74 (1 H, d, J=7.3 Hz), 4.60 (1 H, d, J=9.0 Hz), 3.18 (1 H, ddd, J=13.4, 10.4, 2.8 Hz), 2.86 (4 H, br. s.), 2.27-2.35 (3 H, m), 2.03 (2 H, dd, J=14.1, 3.1 Hz), 1.66 (1 H, br. s.), 1.54-1.64 (1 H, m), 1.48 (3 H, s), 0.72 (3 H, br. s.). Mass Spectrum (ESI) m/z=604 (M+1).

EXAMPLES 197-199 were also prepared from methyl 2-((3R,5R,6S)-1-((S)-1-aminobutan-2-yl)-5-(3-chlorophenyl)-6-(4-chlorophenyl)-3-methyl-2-oxopiperidin-3-yl)acetate (Example 196, Step B) by procedures similar to the one described in Example 196, Step C, replacing pyridine-3-sulfonyl chloride with the appropriate reagent.

| Example | R | Reagent used |
|---------|---|--------------|
| 197 | NC-C₆H₄-SO₂-NH- | 4-Cyanobenzene-1-sulfonyl chloride |
| 198 | 3-NC-C₆H₄-SO₂-NH- | 3-Cyanobenzene-1-sulfonyl chloride |
| 199 | 2-Pyridyl-SO₂-NH- | Pyridine-2-sulfonyl chloride |

Example 197

2-((3R,5R,6S)-5-(3-Chlorophenyl)-6-(4-chlorophenyl)-1-((S)-1-(4-cyanophenylsulfonamido)butan-2-yl)-3-methyl-2-oxopiperidin-3-yl)acetic acid ¹H NMR (500 MHz, CHLOROFORM-d) δ ppm 7.95 (2 H, m, J=8.6 Hz), 7.81-7.87 (2 H, m), 7.22 (2 H, d, J=8.1 Hz), 7.16-7.20 (1 H, m), 7.11-7.16 (1 H, m), 7.06 (1 H, s), 6.98 (1 H, t, J=1.7 Hz), 6.80 (1 H, d, J=7.6 Hz), 5.41 (1 H, br. s.), 4.68 (1 H, d, J=10.0 Hz), 3.38 (1 H, br. s.), 3.17 (1 H, ddd, J=13.5, 10.5, 2.7 Hz), 2.98 (1 H, d, J=14.7 Hz), 2.78 (1 H, d, J=14.7 Hz), 2.69-2.76 (1 H, m), 2.35 (1 H, t, J=13.8 Hz), 2.00-2.08 (2 H, m), 1.55 (1 H, d, J=7.6 Hz), 1.52 (4 H, s), 0.59 (3 H, br. s.). Mass Spectrum (ESI) m/z=628 (M+1).

Example 198

2-((3R,5R,6S)-5-(3-Chlorophenyl)-6-(4-chlorophenyl)-1-((S)-1-(3-cyanophenylsulfonamido)butan-2-yl)-3-methyl-2-oxopiperidin-3-yl)acetic acid ¹H NMR (500 MHz, CHLOROFORM-d) δ ppm 8.15 (1 H, t, J=1.5 Hz), 8.07 (1 H, d, J=7.8 Hz), 7.89 (1 H, dt, J=7.8, 1.2

Hz), 7.70 (1 H, t, J=7.9 Hz), 7.20 (2 H, d, J=7.8 Hz), 7.17 (1 H, dt, J=8.3, 1.5 Hz), 7.13 (1 H, t, J=7.7 Hz), 7.06 (1 H, s), 6.97 (1 H, s), 6.80 (1 H, d, J=7.3 Hz), 5.49 (1 H, br. s.), 4.68 (1 H, d, J=10.0 Hz), 3.40 (1 H, br. s.), 3.27 (1 H, br. s.), 3.17 (1 H, ddd, J=13.4, 10.5, 2.9 Hz), 2.97 (1 H, d, J=14.9 Hz), 2.80 (1 H, d, J=14.7 Hz), 2.76 (1 H, br. s.), 2.35 (1 H, t, J=13.7 Hz), 2.04 (1 H, dd, J=13.9, 2.9 Hz), 1.56 (1 H, d, J=7.1 Hz), 1.52 (3 H, s), 0.61 (3 H, br. s.). Mass Spectrum (ESI) m/z=628 (M+1).

Example 199

2-((3R,5R,6S)-5-(3-chlorophenyl)-6-(4-chlorophenyl)-3-methyl-2-oxo-1-((S)-1-(pyridine-2-sulfonamido)butan-2-yl)piperidin-3-yl)acetic acid. Compound obtained as 2,2,2-trifluoroacetic acid salt $^1$H NMR (500 MHz, CHLOROFORM-d) δ ppm 8.73 (1 H, d, J=4.2 Hz), 7.93-8.04 (2 H, m), 7.53-7.60 (1 H, m), 7.18-7.24 (2 H, m), 7.11-7.18 (2 H, m), 7.00-7.09 (2 H, m), 6.98 (1 H, s), 6.87 (1 H, d, J=6.8 Hz), 5.54 (1 H, br. s.), 4.82 (1 H, d, J=10.5 Hz), 3.51 (1 H, br. s.), 3.22 (1 H, br. s.), 3.10-3.18 (1 H, m), 3.03 (1 H, d, J=14.9 Hz), 2.94 (1 H, dt, J=14.0, 4.1 Hz), 2.75 (1 H, d, J=14.9 Hz), 2.44 (1 H, t, J=13.7 Hz), 1.99 (4 H, dd, J=14.1, 2.8 Hz), 1.78-1.83 (3 H, m), 1.54 (3 H, s), 1.43-1.53 (2 H, m), 0.51 (3 H, t, J=7.3 Hz). Mass Spectrum (ESI) m/z=604 (M+1).

Example 200

2-((3R,5R,6S)-5-(3-Chlorophenyl)-6-(4-chlorophenyl)-1-((S)-1-(N,1-dimethylcyclopropanesulfonamido)butan-2-yl)-3-methyl-2-oxopiperidin-3-yl)acetic acid

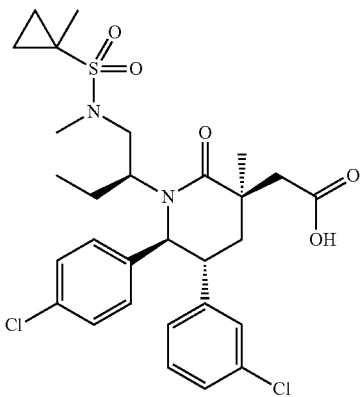 [SMILES: CC[C@@H](CN(C)S(=O)(=O)C1(C)CC1)N1C(=O)[C@@](C)(CC(=O)O)C[C@H](c2cccc(Cl)c2)[C@H]1c1ccc(Cl)cc1]

A solution of methyl 2-((3R,5R,6S)-5-(3-chlorophenyl)-6-(4-chlorophenyl)-3-methyl-1-((S)-1-(1-methylcyclopropanesulfonamido)butan-2-yl)-2-oxopiperidin-3-yl)acetate (21.7 mg, 0.036 mmol; Example 193), 2-(tributylphosphoranylidene)acetonitrile (8.8 mg, 0.036 mmol) and one drop of MeOH in toluene (0.5 mL) was stirred at 110° C. for 1 h. Flash column purification on silica gel (0 to 60% EtOAc in hexanes) gave methyl 2-((3R,5R,6S)-5-(3-chlorophenyl)-6-(4-chlorophenyl)-1-((S)-1-(N,1-dimethylcyclopropanesulfonamido)butan-2-yl)-3-methyl-2-oxopiperidin-3-yl)acetate. This was hydrolyzed with LiOH (1N solution in water, 0.3 mL) in ethanol (0.5 mL) for 3 h at rt. HPLC purification (C18 column, eluted with 10 to 95% CH$_3$CN in water, with 0.1% TFA) gave the title compound.

$^1$H 1H NMR (500 MHz, CHLOROFORM-d) δ ppm 7.26 (2 H, br. s.), 7.13 (2 H, d, J=3.7 Hz), 6.94 (2 H, br. s.), 6.88 (1 H, br. s.), 4.80 (1 H, d, J=9.5 Hz), 4.36 (1 H, br. s.), 2.96-3.12 (3 H, m), 2.86-2.93 (4 H, m), 2.79 (3 H, d, J=14.2 Hz), 2.69 (3 H, d, J=15.4 Hz), 2.41-2.64 (15 H, m), 1.96 (1 H, dd, J=14.4, 7.3 Hz), 1.84 (1 H, d, J=13.7 Hz), 1.55-1.64 (2 H, m), 1.53 (3 H, br. s.), 1.38-1.48 (6 H, m), 0.81 (2 H, br. s.), 0.51 (3 H, t, J=6.2 Hz). Mass Spectrum (ESI) m/z=595 (M+1).

Example 201

3-((3S,5R,6S)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid or 3-((3R,5R,6S)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid

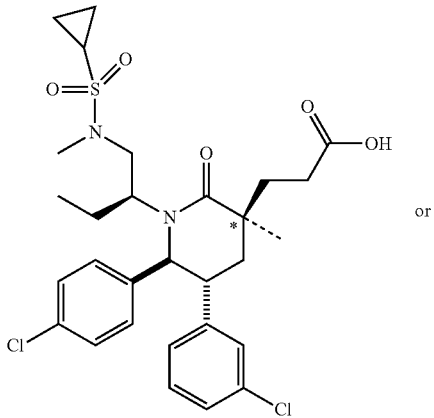

or

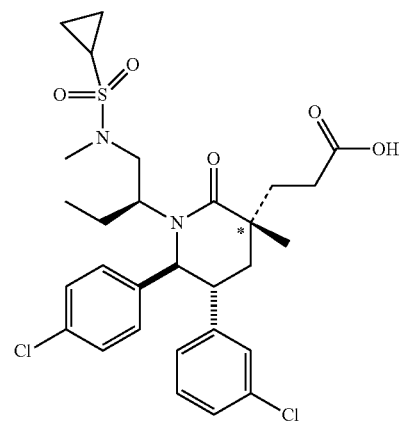

* stereochemistry not determined

Step A. (5R,6S)-5-(3-Chlorophenyl)-6-(4-chlorophenyl)-1-((S)-1-hydroxybutan-2-yl)piperidin-2-one

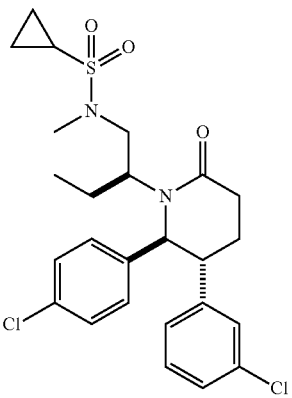

To a mixture of (5R,6S)-5-(3-chlorophenyl)-6-(4-chlorophenyl)-1-((S)-1-hydroxybutan-2-yl)piperidin-2-one (20.00 g, 51.0 mmol; Example 185, Step B) and N-methylcyclopropanesulfonamide (10.34 g, 76 mmol) in 100 mL of toluene at room temperature was added cyanomethylenetributylphosphorane (20.51 mL, 76 mmol). The resulting mixture was heated to 130° C. for 12 h, then cooled to room temperature and directly loaded onto a silica gel column for purification, eluting with 0 to 10% MeOH in DCM to provide the title compound.

Mass Spectrum (ESI) m/z=509 (M+1).

Step B. N-((2S)-2-((2S,3R)-3-(3-Chlorophenyl)-2-(4-chlorophenyl)-5-methyl-6-oxopiperidin-1-yl)butyl)-N-methylcyclopropanesulfonamide

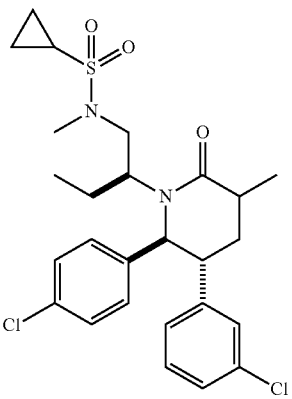

The title compound was obtained as a mixture of diastereomers from N-((S)-2-((2S,3R)-3-(3-chlorophenyl)-2-(4-chlorophenyl)-6-oxopiperidin-1-yl)butyl)-N-methylcyclopropanesulfonamide (Example 201, Step A) using a procedure similar to one described in Example 185, Step D. Mass Spectrum (ESI) m/z=523 (M+1).

Step C. N-((S)-2-((5R,6S)-3-(But-3-enyl)-5-(3-chlorophenyl)-6-(4-chlorophenyl)-3-methyl-2-oxopiperidin-1-yl)butyl)-N-methylcyclopropanesulfonamide (Isomer 1)

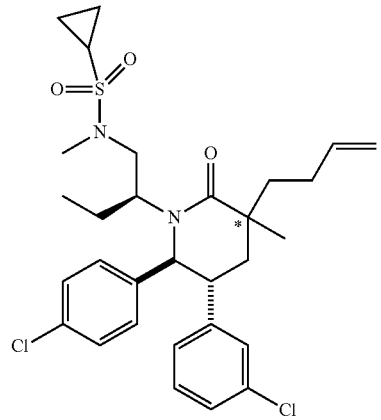

\* stereochemistry not determined

To a solution of N-((2S)-2-((2S,3R)-3-(3-chlorophenyl)-2-(4-chlorophenyl)-5-methyl-6-oxopiperidin-1-yl)butyl)-N-methylcyclopropanesulfonamide (2618 mg, 5.0 mmol; Example 201, Step B) in degassed THF (10 mL) was added lithium diisopropylamide (5.00 mL, 10.00 mmol) at −15° C. After stirring at −15° C. for 30 min, the reaction mixture was cooled to −74° C. 4-Bromobut-1-ene (1.066 mL, 10.50 mmol) was added slowly. The reaction mixture was stirred at −74° C. for 3 h before warming up to rt and then stirred at rt for 66 h. Filtered and purified by HPLC (C18 column, eluted with 10 to 95% $CH_3CN$ in water, with 0.1% TFA) to give the title compound as the first eluting isomer Its stereoisomer is obtained as the later eluting isomer.

$^1$H NMR (500 MHz, CHLOROFORM-d) δ ppm 7.22 (2 H, d, J=7.6 Hz), 7.10-7.17 (2 H, m), 6.96 (2 H, s), 6.90-6.95 (1 H, m), 5.90 (1 H, ddt, J=17.0, 10.3, 6.4, 6.4 Hz), 5.10 (1 H, dd, J=17.1, 1.5 Hz), 5.03 (1 H, dd, J=10.0, 1.5 Hz), 4.77 (1 H, d, J=10.5 Hz), 4.24 (1 H, br. s.), 3.07 (1 H, ddd, J=13.7, 10.6, 3.1 Hz), 2.90 (3 H, s), 2.74-2.87 (2 H, m), 2.24-2.37 (2 H, m), 2.11-2.21 (2 H, m), 2.00 (1 H, ddd, J=13.6, 10.1, 6.6 Hz), 1.78-1.93 (3 H, m), 1.60-1.70 (1 H, m), 1.58 (2 H, br. 15s.), 1.28-1.32 (3 H, m), 1.22 (2 H, d, J=3.2 Hz), 0.95-1.04 (2 H, m), 0.53 (3 H, t, J=7.5 Hz).

Mass Spectrum (ESI) m/z=577 (M+1).

Step D. 3-((3S,5R,6S)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid or 3-((3R,5R,6S)-5-(3-Chlorophenyl)-6-(4-chlorophenyl)-3-methyl-1-((S)-1-(N-methylcyclopropanesulfonamido)butan-2-yl)-2-oxopiperidin-3-yl)propanoic acid The title compound was obtained from N-((S)-2-((5R,6S)-3-(but-3-enyl)-5-(3-chlorophenyl)-6-(4-chlorophenyl)-3-methyl-2-oxopiperidin-1-yl)butyl)-N-methylcyclopropanesulfonamide (Isomer1, 604 mg, 1.046 mmol; Example 201, Step C) by a procedure similar to the one described in Example 71, Step F.

¹H NMR (400 MHz, CHLOROFORM-d) δ ppm 7.23 (2 H, d, J=7.4 Hz), 7.11-7.17 (3 H, m), 6.98 (2 H, m), 6.89-6.94 (1 H, m), 4.75 (1 H, d, J=11.3 Hz), 4.24 (1 H, br. s.), 3.17 (1 H, ddd, J=13.8, 10.8, 3.1 Hz), 2.89 (3 H, s), 2.63-2.82 (3 H, m), 2.55 (1 H, dd, J=8.5, 6.2 Hz), 2.39-2.52 (2 H, m), 2.27-2.39 (2 H, m), 1.82-1.94 (2 H, m), 1.73 (1 H, dd, J=13.7, 3.1 Hz), 1.48-1.65 (2 H, m), 1.28-1.33 (4 H, m), 1.17-1.25 (2 H, m), 0.95-1.04 (2H, m), 0.46-0.55 (3 H, m). Mass Spectrum (ESI) m/z=595 (M+1).

Example 202

2-((3R,5R,6S)-5-(3-chlorophenyl)-6-(4-chlorophenyl)-3-ethyl-1-((S)-1-(N-methylcyclopropanesulfonamido)butan-2-yl)-2-oxopiperidin-3-yl)acetic acid

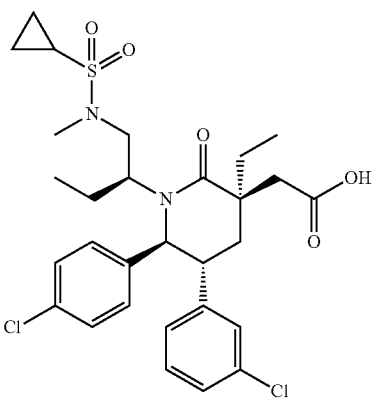 [SMILES: CC[C@@H](CN(C)S(=O)(=O)C1CC1)N1C(=O)[C@@](CC)(CC(=O)O)C[C@H](c2cccc(Cl)c2)[C@H]1c1ccc(Cl)cc1]

Step A. (5R,6S)-1-((S)-1-(tert-butyldiphenylsilyloxy)butan-2-yl)-5-(3-chlorophenyl)-6-(4-chlorophenyl)-3-ethylpiperidin-2-one

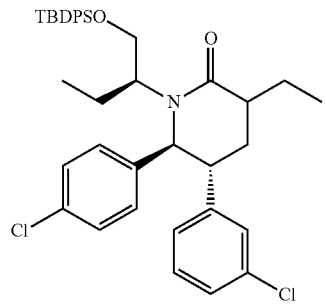

To a −78° C. solution of (5R,6S)-1-((S)-1-(tert-butyldiphenylsilyloxy)butan-2-yl)-5-(3-chlorophenyl)-6-(4-chlorophenyl)piperidin-2-one (764 mg, 1.211 mmol; Example 185, Step C) in THF (6 mL) under argon was added 1.0M lithium diisopropyl amide solution in THF (1.211 mL, 1.211 mmol). The mixture was warmed to 0° C. for 30 minutes. The mixture was cooled to −78° C. and iodoethane (0.117 mL, 1.454 mmol) was added. The resulting solution stirred at 0° C. for 1 hour. The mixture was quenched with sat. aq. NH₄Cl solution. The mixture was extracted with ethyl acetate. The combined organic layers were washed with sat. aq. NaCl solution, dried over Na₂SO₄ and concentrated. The residue was purified by flash chromatography on silica gel (eluent: 5 to 25% ethyl acetate/hexanes) to afford the title compound as a mixture of diastereomers.

Step B. (5R,6S)-3-allyl-5-(3-chlorophenyl)-6-(4-chlorophenyl)-3-ethyl-1-((S)-1-hydroxybutan-2-yl)piperidin-2-one

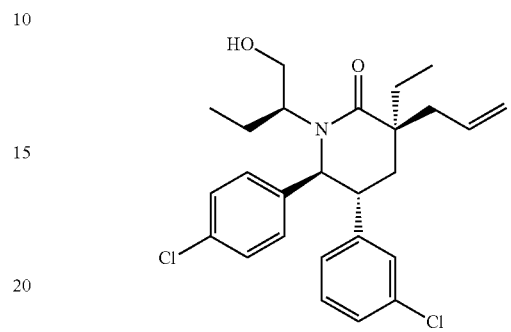

(5R,6S)-1-((S)-1-(Tert-butyldiphenylsilyloxy)butan-2-yl)-5-(3-chlorophenyl)-6-(4-chlorophenyl)-3-ethylpiperidin-2-one (421 mg, 0.639 mmol; Example 202, Step A) was azeotroped with toluene (3×). THF (1.6 mL) was added. The mixture was sparged with argon for 5 minutes and then cooled to 0° C. 1.0 M lithium diisopropylamide solution in THF (1.246 mL, 1.246 mmol) was added dropwise. After 25 minutes, allyl bromide (0.166 mL, 1.917 mmol) was added dropwise. After 20 minutes, the mixture was quenched with sat. aq. NH₄Cl solution. The mixture was extracted with ethyl acetate. The organic layer was washed with sat. aq. NaCl solution, dried over Na₂SO₄, and concentrated. The residue was dissolved in THF (3 mL) and 1.0M tetrabutylammonium fluoride solution in THF (2.335 mL, 2.335 mmol) was added. After stirring overnight, the mixture was partitioned between 5% aq. HCl and ethyl acetate. The organic layer was washed with sat. aq. NaCl solution, dried over Na₂SO₄, and concentrated. The residue was purified by flash chromatography on silica gel (eluent: 20 to 50% ethyl acetate/hexanes) to afford the title compound as the more polar major diastereomer.

Step C. N-((2S)-2-((5R,6S)-3-allyl-5-(3-chlorophenyl)-6-(4-chlorophenyl)-3-ethyl-2-oxopiperidin-1-yl)butyl)-N-methylcyclopropanesulfonamide

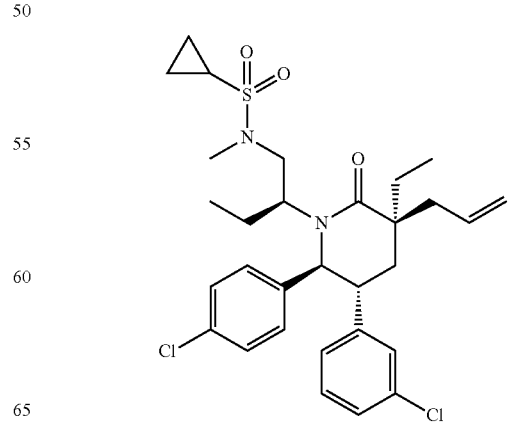

(5R,6S)-3-Allyl-5-(3-chlorophenyl)-6-(4-chlorophenyl)-3-ethyl-1-((S)-1-hydroxybutan-2-yl)piperidin-2-one (147 mg, 0.319 mmol; Example 202, Step B) and N-methylcyclopropanesulfonamide (129 mg, 0.958 mmol) were dissolved in toluene (2 mL). The mixture was evacuated and backfilled with argon (5×). Cyanomethylenetributylphosphorane (0.251 mL, 0.958 mmol) was added. The mixture was evacuated and backfilled with argon (5×). The mixture was heated at 70° C. for 2 hours. The mixture was loaded onto silica gel and the product was eluted with 5 to 75% ethyl acetate/hexanes to afford the title compound.

Step D. 2-((3R,5R,6S)-5-(3-chlorophenyl)-6-(4-chlorophenyl)-3-ethyl-1-((S)-1-(N-methylcyclopropanesulfonamido)butan-2-yl)-2-oxopiperidin-3-yl)acetic acid The title compound was obtained from N-((2S)-2-((5R,6S)-3-allyl-5-(3-chlorophenyl)-6-(4-chlorophenyl)-3-ethyl-2-oxopiperidin-1-yl)butyl)-N-methylcyclopropanesulfonamide (Example 202, Step C) by a procedure similar to the one described in Example 71, Step F.

¹H NMR (400 MHz, CHLOROFORM-d) δ ppm 0.54 (t, J=7.53 Hz, 3 H) 0.85-1.10 (m, 7 H) 1.15-1.23 (m, 2 H) 1.51-1.65 (m, 1 H) 1.84-2.04 (m, 4 H) 2.15-2.25 (m, 1 H) 2.25-2.38 (m, 2 H) 2.69-2.82 (m, 1 H) 2.87 (s, 3 H) 2.93-3.10 (m, 2 H) 4.76 (d, J=10.37 Hz, 1 H) 6.84 (d, J=6.65 Hz, 1 H) 6.91-6.97 (m, 1 H) 7.08-7.17 (m, 2 H) 7.20-7.29 (m, 4 H). Mass Spectrum (ESI) m/z=595.2 (M+1).

Example 203

2-((3S,5R,6S)-5-(3-chlorophenyl)-6-(4-chlorophenyl)-3-methoxy-1-((S)-1-(N-methylcyclopropanesulfonamido)butan-2-yl)-2-oxopiperidin-3-yl)acetic acid

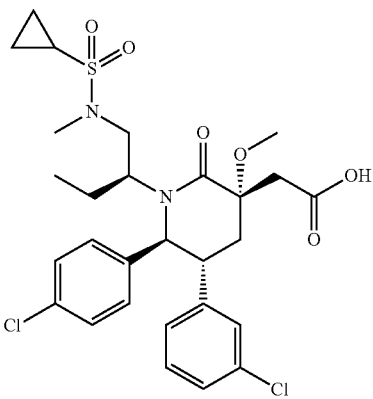 [SMILES: CC[C@@H](CN(C)S(=O)(=O)C1CC1)N1C(=O)[C@](CC(=O)O)(OC)C[C@H](c2cccc(Cl)c2)[C@H]1c1ccc(Cl)cc1]

Step A. (5R,6S)-1-((S)-1-(tert-butyldiphenylsilyloxy)butan-2-yl)-5-(3-chlorophenyl)-6-(4-chlorophenyl)-3-hydroxypiperidin-2-one

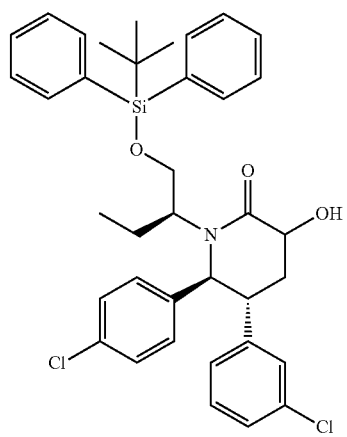 [SMILES: CC[C@@H](CO[Si](c1ccccc1)(c1ccccc1)C(C)(C)C)N1C(=O)C(O)C[C@H](c2cccc(Cl)c2)[C@H]1c1ccc(Cl)cc1]

(5R,6S)-1-((S)-1-(Tert-butyldiphenylsilyloxy)butan-2-yl)-5-(3-chlorophenyl)-6-(4-chlorophenyl)piperidin-2-one (1.100 g, 1.744 mmol; Example 185, Step C) was dissolved in THF (8.72 mL) and sparged with argon for 5 minutes. The mixture was cooled to −78° C. and 1.0 M lithium bis(trimethylsilyl)amide solution in THF (2.093 mL, 2.093 mmol) was added dropwise. After 30 minutes, peroxybis(trimethylsilane) (0.413 mL, 1.918 mmol) was added dropwise. After 1 hour, the cooling bath was removed. After stirring overnight, the mixture was quenched with sat. aq. NH₄Cl solution and extracted with ethyl acetate. The organic layer was washed with sat. aq. NaCl solution, dried over Na₂SO₄, and concentrated. The residue was dissolved in EtOH (14 mL) and pyridine p-toluenesulfonate (131 mg, 0.523 mmol) was added. After 1 hour, the mixture was basified with sat. aq. NaHCO₃ solution. The mixture was partitioned between ethyl acetate and water. The organic layer was washed with sat. aq. NaCl solution, dried over Na₂SO₄, and concentrated. The residue was purified by flash chromatography on silica gel (40 g column, eluent: 5 to 50% ethylacetate/hexanes) to afford the title compound.

Step B. (5R,6S)-1-((S)-1-(tert-butyldiphenylsilyloxy)butan-2-yl)-5-(3-chlorophenyl)-6-(4-chlorophenyl)-3-methoxypiperidin-2-one

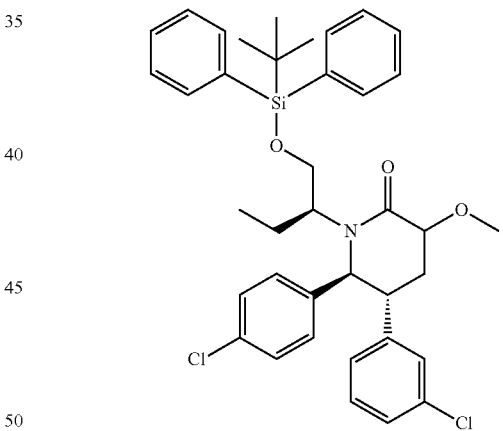

To a 0° C. solution of (5R,6S)-1-((S)-1-(tert-butyldiphenylsilyloxy)butan-2-yl)-5-(3-chlorophenyl)-6-(4-chlorophenyl)-3-hydroxypiperidin-2-one (476 mg, 0.736 mmol; Example 203, Step A) in THF (7.360 mL) was added sodium hydride (58.9 mg, 1.472 mmol). After 30 minutes, iodomethane (0.092 mL, 1.472 mmol) was added. After 5 minutes, the cooling bath was removed. After 2 hours, the mixture was quenched with sat. aq. NH₄Cl solution. The mixture was partitioned between ethyl acetate and water. The organic layer was washed with sat. aq. NaCl solution, dried over Na₂SO₄, and concentrated to afford the title compound.

Step C. (3R,5R,6S)-3-allyl-1-((S)-1-((tert-butyl-diphenylsilyl)oxy)butan-2-yl)-5-(3-chlorophenyl)-6-(4-chlorophenyl)-3-methoxypiperidin-2-one

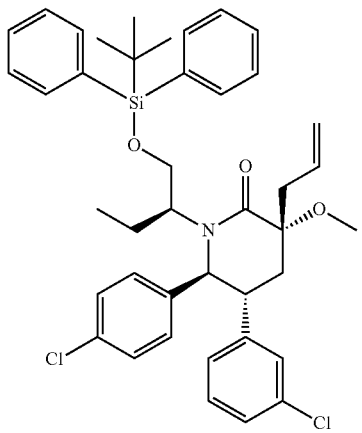 [SMILES: C=CC[C@@]1(OC)C[C@H](c2cccc(Cl)c2)[C@@H](c2ccc(Cl)cc2)N([C@@H](CC)CO[Si](c2ccccc2)(c2ccccc2)C(C)(C)C)C1=O]

A solution of (5R,6S)-1-((S)-1-((tert-butyldiphenylsilyl)oxy)butan-2-yl)-5-(3-chlorophenyl)-6-(4-chlorophenyl)-3-methoxypiperidin-2-one (495 mg, 0.749 mmol; Example 203, Step B) in THF (7.49 mL) was sparged with argon for 5 minutes and cooled to 0° C. 1.0 M lithiumdiisopropylamide solution in THF (1.461 mL, 1.461 mmol) was added dropwise. The internal temperature did not rise above 2° C. After 30 minutes, allyl bromide (0.194 mL, 2.247 mmol) was added. The cooling bath was replaced with a room temperature water bath. After 70 minutes, the mixture was quenched with sat. aq. NH$_4$Cl solution and extracted with ethyl acetate. The organic layer was washed with sat. aq. NaCl solution, dried over Na$_2$SO$_4$ and concentrated. The residue was purified by flash chromatography on silica gel (40 g column, eluent: 5 to 30% ethyl acetate/hexanes) to afford the title compound as the more polar diastereomer.

Step D. (3R,5R,6S)-3-allyl-5-(3-chlorophenyl)-6-(4-chlorophenyl)-1-((S)-1-hydroxybutan-2-yl)-3-methoxypiperidin-2-one

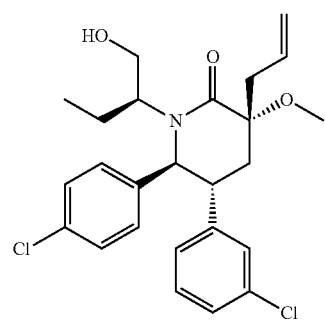 [SMILES: C=CC[C@@]1(OC)C[C@H](c2cccc(Cl)c2)[C@@H](c2ccc(Cl)cc2)N([C@@H](CC)CO)C1=O]

To a solution of (3R,5R,6S)-3-allyl-1-((S)-1-((tert-butyl-diphenylsilyl)oxy)butan-2-yl)-5-(3-chlorophenyl)-6-(4-chlorophenyl)-3-methoxypiperidin-2-one (260 mg, 0.371 mmol; Example 203, Step C) in THF (1 mL) was added 1.0 M tetrabutylammonium fluoride solution in THF (1.484 mL, 1.484 mmol). After stirring overnight, the mixture was partitioned between water and ethyl acetate. Sat. aq. NH$_4$Cl solution was added to break up the emulsion. The organic layer was washed with sat. aq. NaCl solution, dried over Na$_2$SO$_4$, and concentrated. The residue was purified by flash chromatography on silica gel (12 g column, eluent: 35 to 100% ethyl acetate/hexanes) to afford the title compound.

Step E. N-((SR)-2-((3R,5R,6S)-3-allyl-5-(3-chlorophenyl)-6-(4-chlorophenyl)-3-methoxy-2-oxopiperidin-1-yl)butyl)-N-methylcyclopropanesulfonamide

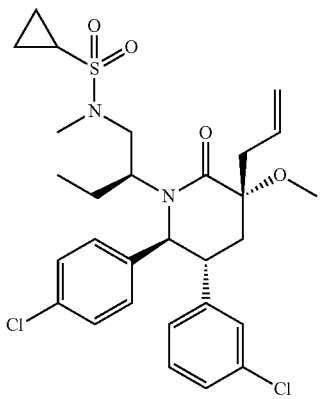 [SMILES: C=CC[C@@]1(OC)C[C@H](c2cccc(Cl)c2)[C@@H](c2ccc(Cl)cc2)N([C@@H](CC)CN(C)S(=O)(=O)C2CC2)C1=O]

To a solution of (3R,5R,6S)-3-allyl-5-(3-chlorophenyl)-6-(4-chlorophenyl)-1-((S)-1-hydroxybutan-2-yl)-3-methoxypiperidin-2-one (124 mg, 0.268 mmol; Example 203, Step D) in toluene (1.3 mL) was added N-methylcyclopropanesulfonamide (109 mg, 0.804 mmol). The mixture was evacuated and backfilled with argon (5×). Cyanomethylenetributylphosphorane (0.211 mL, 0.804 mmol) was added. The mixture was evacuated and backfilled with argon (5×). The mixture was heated in a 70° C. oil bath for 12 hours then cooled to room temperature and stirred for 2 days at room temperature. The mixture was loaded onto silica gel and the product was eluted with 20-60% ethyl acetate/hexanes. The residue was one more time purified by flash chromatography on silica gel (12 g column, eluent: 10 to 60% ethylacetate/hexanes) to afford the title compound.

Step F. 2-((3S,5R,6S)-5-(3-chlorophenyl)-6-(4-chlorophenyl)-3-methoxy-1-((S)-1-(N-methylcyclopropanesulfonamido)butan-2-yl)-2-oxopiperidin-3-yl) acetic acid The title compound was obtained from N-((S)-2-((3R,5R,6S)-3-allyl-5-(3-chlorophenyl)-6-(4-chlorophenyl)-3-methoxy-2-oxopiperidin-1-yl)butyl)-N-methylcyclopropanesulfonamide (Example 203, Step E) by a procedure similar to the one described in Example 71, Step F.

$^1$H NMR (400 MHz, CHLOROFORM-d) δ ppm 0.59 (t, J=7.53 Hz, 3 H) 1.02-1.05 (m, 2 H) 1.16-1.27 (m, 2 H) 1.59-1.77 (m, 1 H) 1.85-1.99 (m, 2 H) 2.22-2.40 (m, 1 H) 2.75 (d, J=13.30 Hz, 1 H) 2.84-2.98 (m, 6 H) 3.03-3.16 (m, 2 H) 3.26 (d, J=15.65 Hz, 1 H) 3.52 (s, 3 H) 4.99 (d, J=10.76 Hz, 1 H) 6.91-6.97 (m, 2 H) 7.02 (s, 1 H) 7.10-7.20 (m, 2 H) 7.22-7.31 (m, 3 H).

Mass Spectrum (ESI) m/z=597.1 (M+1).

Example 204

2-((3R,5R,6S)-5-(3-chlorophenyl)-6-(4-chlorophenyl)-3-methyl-1-((S)-6-methyl-4-oxoheptan-3-yl)-2-oxopiperidin-3-yl)acetic acid

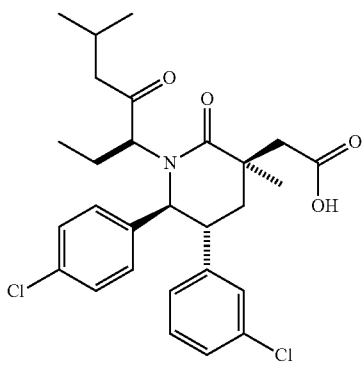

Step A. (3S,5R,6S)-3-allyl-5-(3-chlorophenyl)-6-(4-chlorophenyl)-1-((3S)-4-hydroxy-6-methylheptan-3-yl)-3-methylpiperidin-2-one

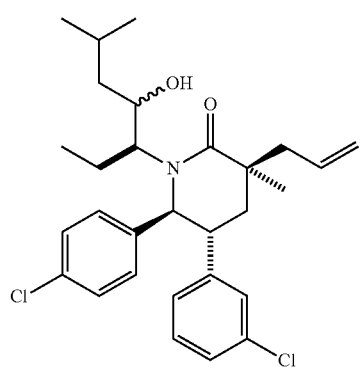

To a solution of (S)-2-((3S,5R,6S)-3-allyl-5-(3-chlorophenyl)-6-(4-chlorophenyl)-3-methyl-2-oxopiperidin-1-yl)butanal (1.755 mmol) (Example 91, Step C) in THF (5 mL) at 0° C. was added 2 M isobutylmagnesium bromide (878 µL, 1.742 mmol) under $N_2$. The reaction was allowed to warm to rt. After being stirred for 2 h at rt, the reaction was quenched with saturated $NH_4Cl$ solution and extracted with EtOAc. The combined organic layers were washed (sat. aq. NaCl solution), dried over $MgSO_4$, filtered and the filtrate was concentrated under reduced pressure. The residue was purified by the flash chromatography on silica gel (eluent: 15 to 35% EtOAc/Hexane, gradient elution) to provide the title compound as a mixture of two diastereomers.

Step B. 2-((3R,5R,6S)-5-(3-chlorophenyl)-6-(4-chlorophenyl)-3-methyl-1-((S)-6-methyl-4-oxoheptan-3-yl)-2-oxopiperidin-3-yl)acetic acid To a rapidly stirring solution of 120 mg (0.239 mmol) of (3S,5R,6S)-3-allyl-5-(3-chlorophenyl)-6-(4-chlorophenyl)-1-((3S)-4-hydroxy-6-methylheptan-3-yl)-3-methylpiperidin-2-one (Example 204, Step A) in a mixture of 1.5 mL of water, 1.0 mL of acetonitrile and 1.0 mL of $CCl_4$ was added sodium periodate (204 mg, 0.995 mmol), followed by ruthenium(III) chloride hydrate (5.38 mg, 0.024 mmol). After being stirred vigorously for 2 h, the reaction was acidified (10% citric acid) and diluted with EtOAc. The reaction mixture was filtered through Celite® (J. T. Baker, Phillipsberg, N.J., diatomaceous earth) and the filtrate was extracted with EtOAc. The combined organic layers were washed with sat. NaCl solution, dried over $Na_2SO_4$, filtered and the filtrate was concentrated under reduced pressure. The residue was purified by the flash chromatography on silica gel (eluent: 10 to 20% iPrOH/hexane, gradient elution) to provide the title compound as a white solid.

$^1$H NMR (400 MHz, CHLOROFORM-d) δ ppm 0.64 (t, J=8.0 Hz, 3 H), 0.89 (d, J=8.0 Hz, 3 H), 0.92 (d, J=8.0 Hz, 3 H), 1.21 (m, 1 H), 1.39 (s, 3H), 1.82 (m, 1 H), 210-2.45 (m, 7 H), 2.87 (dd, J=16.0, 12 Hz, 2 H), 3.09 (t, J=8.0 Hz, 1 H), 3.26 (m, 1 H), 4.44 (d, J=8.0 Hz, 1 H), 6.76 (d, J=8.0 Hz, 1 H), 6.90-7.02 (m, 3 H), 7.08 (t, J=8.0 Hz, 1 H), 7.12 (d, J=8.0 Hz, 1 H), 7.23 (d, J=8.0 Hz, 2 H); MS (ESI) 531.1 [M+H]$^+$.

Example 205

2-((3R,5R,6S)-5-(3-chlorophenyl)-6-(4-chlorophenyl)-1-((S)-1-(ethylsulfonyl)pentan-3-yl)-3-methyl-2-oxopiperidin-3-yl)acetic acid

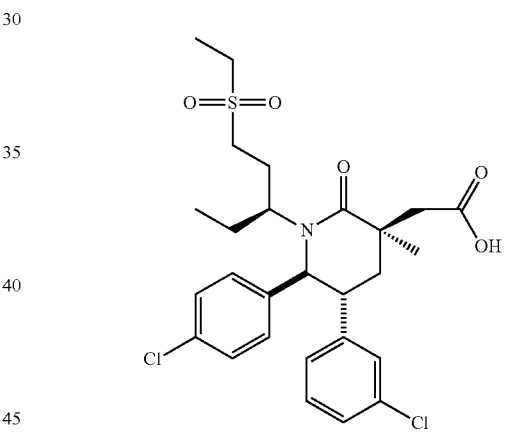

Step A. Diethyl Ethylsulfonylmethylphosphonate

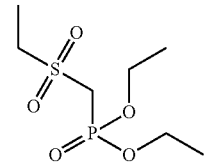

To a stirred solution of diethyl ethylthiomethylphosphonate (Aldrich, St. Louis, Mo.) (0.912 mL, 4.71 mmol) in dichloromethane (47.1 mL) at 0° C. was added meta-chloroperoxybenzoic acid (2.63 g, 15.2 mmol). The reaction mixture was stirred at 25° C. for 24 hours. The reaction solvent was removed in vacuo, the crude material was diluted with diethyl ether, and was then washed with saturated sodium bicarbonate (3×). The organic layer was dried over $Na_2SO_4$, filtered and the filtrate was concentrated under reduced pressure to provide the title compound as an off-white solid.

Step B. (3R,5R,6S)-5-(3-chlorophenyl)-6-(4-chlorophenyl)-3-((2,2-dimethyl-1,3-dioxolan-4-yl)methyl)-1-((S,E)-1-(ethylsulfonyl)pent-1-en-3-yl)-3-methylpiperidin-2-one

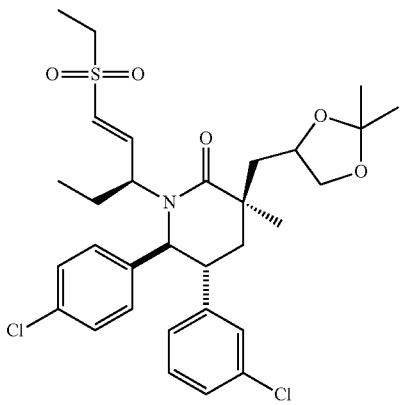

To a stirred solution of diethyl ethylsulfonylmethylphosphonate (153 mg, 0.625 mmol; Example 202, Step A) in THF (2.60 mL) at −78° C. was added butyllithium (177 µL, 0.443 mmol). After 30 minutes, a solution of (2S)-2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanal (135 mg, 0.260 mmol; Example 150, Step D) in THF (0.50 mL) was added. The reaction was stirred for 15 minutes at −78° C. and was then stirred at 25° C. for 3 hours. The reaction was partitioned between saturated ammonium chloride and EtOAc (2×), and then the combined organic layers were dried over Na$_2$SO$_4$, filtered and the filtrate was concentrated under reduced pressure. Purification of the residue by flash chromatography on silica gel (4 g column, eluent: 0 to 40% EtOAc/hexanes) provided the title compound as an off-white solid.

Step C. (3R,5R,6S)-5-(3-chlorophenyl)-6-(4-chlorophenyl)-3-((2,2-dimethyl-1,3-dioxolan-4-yl)methyl)-1-((S)-1-(ethylsulfonyl)pentan-3-yl)-3-methylpiperidin-2-one

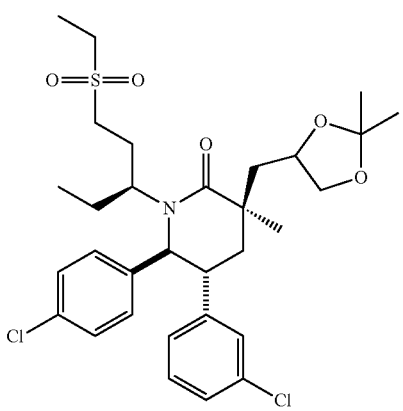

To a solution of (3R,5R,6S)-5-(3-chlorophenyl)-6-(4-chlorophenyl)-3-((2,2-dimethyl-1,3-dioxolan-4-yl)methyl)-1-((S,E)-1-(ethylsulfonyl)pent-1-en-3-yl)-3-methylpiperidin-2-one (65.0 mg, 0.107 mmol; Example 205, Step B) in 1,2-dichloroethane (1.07 mL) at 25° C. was added Crabtree's catalyst (7.74 mg, 9.61 µmol). The reaction system (a hydrogenation bomb) was flushed with hydrogen gas 3×, pressurized with hydrogen at 3447.38 kilopascal, and the reaction was stirred at 25° C. for 24 hours. The reaction mixture was filtered through celite, washed with DCM, and concentrated under reduced pressure to yield the title compound as an off-white solid.

Step D. 2-((3R,5R,6S)-5-(3-chlorophenyl)-6-(4-chlorophenyl)-1-((S)-1-(ethylsulfonyl)pentan-3-yl)-3-methyl-2-oxopiperidin-3-yl)acetic acid To a stirred solution of (3R,5R,6S)-5-(3-chlorophenyl)-6-(4-chlorophenyl)-3-((2,2-dimethyl-1,3-dioxolan-4-yl)methyl)-1-((S)-1-(ethylsulfonyl)pentan-3-yl)-3-methylpiperidin-2-one (70.0 mg, 0.115 mmol; Example 202, Step C) in THF (1.15 mL) at 25° C. was added a solution of Jones' Reagent (chromium (VI) oxide) (138 µL, 0.172 mmol) and the reaction mixture was stirred for 1 hour. The reaction mixture was partitioned between water and EtOAc (2×), and then the combined organic layers were dried over Na$_2$SO$_4$, filtered and the filtrate was concentrated under reduced pressure. Purification of the residue by reverse phase high-pressure liquid chromatography (Eclipse column (Agilient Technologies, Santa Clara, Calif.), eluent: 30-75% acetonitrile/water) provided the title compound as an off-white solid.

$^1$H NMR (500 MHz, CDCl$_3$) δ ppm 0.58 (t, J=7.34 Hz, 3 H), 1.43 (t, J=7.46 Hz, 3 H), 1.49 (s, 3 H), 1.51-1.57 (m, 1 H), 1.86 (dt, J=14.55, 7.40 Hz, 1 H), 1.98 (dd, J=12.84, 5.75 Hz, 1 H), 2.04 (dd, J=13.94, 2.45 Hz, 1 H), 2.16-2.23 (m, 2 H), 2.76 (d, J=15.16 Hz, 1 H), 2.97-3.04 (m, 5 H), 3.11-3.20 (m, 1 H), 3.24-3.38 (m, 1 H), 4.58 (d, J=10.51 Hz, 1 H), 6.75 (d, J=7.58 Hz, 1 H), 6.95 (s, 1 H), 7.05 (d, J=4.89 Hz, 2 H), 7.09-7.14 (m, 1 H), 7.14-7.18 (m, 1 H), 7.23-7.27 (m, 2 H); MS (ESI) 554.2 [M+H]$^+$.

Example 206

2-((3R,5R,6S)-5-(3-chlorophenyl)-6-(4-chlorophenyl)-1-((S)-1-(isopropylsulfonyl)pentan-3-yl)-3-methyl-2-oxopiperidin-3-yl)acetic acid

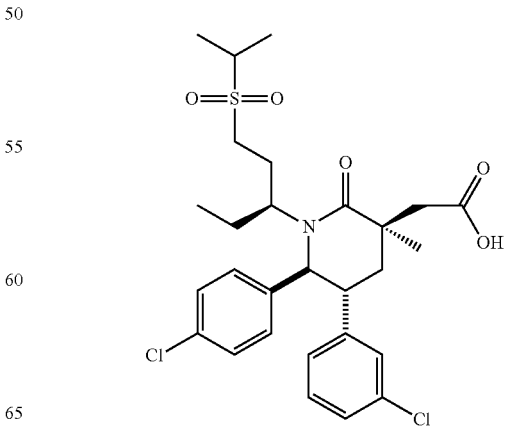

409

Step A. S-(diisopropoxyphosphoryl)methyl ethanethioate

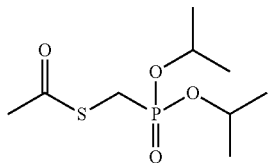

To a stirred solution of diisopropyl bromomethylphosphonate (5.00 g, 19.3 mmol) in N,N-dimethylformamide (15.4 mL) was added potassium thioacetate (3.75 g, 32.8 mmol) followed by tetrabutylammonium iodide (0.36 g, 0.97 mmol). The reaction mixture was stirred at 85° C. for 2.5 hours. The reaction mixture was cooled and partitioned between water and EtOAc (3×) and the layers were separated. The combined organic layers were dried over $Na_2SO_4$, filtered and the filtrate was concentrated under reduced pressure. Purification of the residue by flash chromatography on silica gel (24 g column, eluent: 0 to 90% EtOAc/hexanes) provided the title compound as an off-white solid.

Step B. Diisopropyl Isopropylthiomethylphosphonate

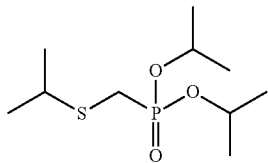

To a stirred solution of S-(diisopropoxyphosphoryl)methyl ethanethioate (1.00 g, 3.93 mmol; Example 206, Step A) in methanol (39.3 mL) at 0° C. was added sodium methoxide (7.87 mL, 3.93 mmol), followed by 2-bromopropane (0.44 mL, 4.72 mmol). The reaction was stirred at 25° C. for 16 hours. The reaction solvent was removed in vacuo and the crude material was partitioned between water and EtOAc (2×) and the layers were separated. The aqueous layer was extracted with EtOAc and the combined organic layers were dried over $Na_2SO_4$, filtered and the filtrate was concentrated under reduced pressure. Purification of the residue by flash chromatography on silica gel (40 g column, eluent: 0 to 75% DCM/hexanes) provided the title compound as an off-white solid.

Step C. Diisopropyl Isopropylsulfonylmethylphosphonate

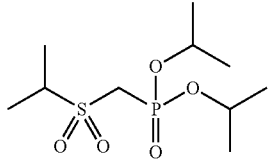 [SMILES: CC(C)OP(=O)(CS(=O)(=O)C(C)C)OC(C)C]

410

Diisopropyl isopropylthiomethylphosphonate was converted to the title compound by the procedure described in Example 205, Step A and was isolated as an off-white solid.

Step D. (3R,5R,6S)-5-(3-chlorophenyl)-6-(4-chlorophenyl)-3-((2,2-dimethyl-1,3-dioxolan-4-yl)methyl)-1-((S,E)-1-(isopropylsulfonyl)pent-1-en-3-yl)-3-methylpiperidin-2-one

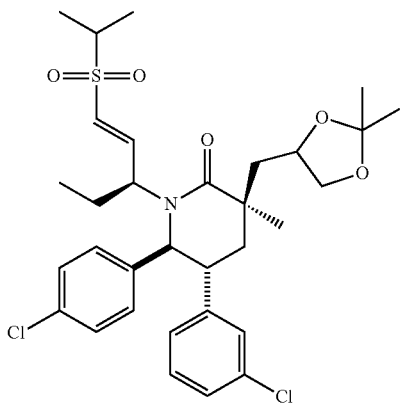

(2S)-2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanal (Example 150, Step D) was converted to the title compound as described in Example 205, Step B and was isolated as an off-white solid.

Step E. (3R,5R,6S)-5-(3-chlorophenyl)-6-(4-chlorophenyl)-3-((2,2-dimethyl-1,3-dioxolan-4-yl)methyl)-1-((S)-1-(isopropylsulfonyl)pentan-3-yl)-3-methylpiperidin-2-one

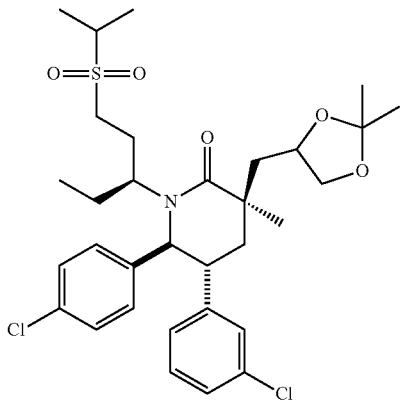

(3R,5R,6S)-5-(3-chlorophenyl)-6-(4-chlorophenyl)-3-((2,2-dimethyl-1,3-dioxolan-4-yl)methyl)-1-((S,E)-1-(isopropylsulfonyl)pent-1-en-3-yl)-3-methylpiperidin-2-one was converted to the title compound as described in Example 205, Step C and was isolated as an off-white solid.

Step F. 2-((3R,5R,6S)-5-(3-chlorophenyl)-6-(4-chlorophenyl)-1-((S)-1-(isopropylsulfonyl)pentan-3-yl)-3-methyl-2-oxopiperidin-3-yl)acetic acid (3R,5R,6S)-5-(3-chlorophenyl)-6-(4-chlorophenyl)-3-((2,2-dimethyl-1,3-dioxolan-4-yl)methyl)-1-((S)-1-(isopropyl-

Example 207

2-((3R,5R,6S)-5-(3-chlorophenyl)-6-(4-chlorophenyl)-1-((S)-1-(cyclopropylmethylsulfonyl)pentan-3-yl)-3-methyl-2-oxopiperidin-3-yl)acetic acid

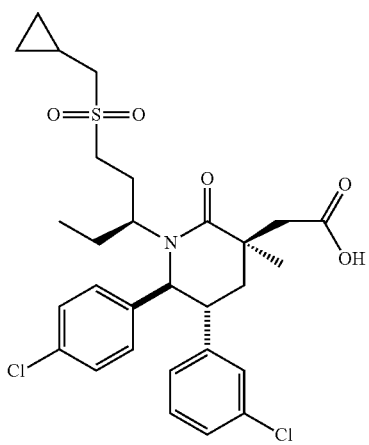

(2S)-2-((3R,5R,6S)-5-(3-chlorophenyl)-6-(4-chlorophenyl)-3-((2,2-dimethyl-1,3-dioxolan-4-yl)methyl)-3-methyl-2-oxopiperidin-1-yl)butanal (Example 150, Step D) with diisopropyl (cyclopropylmethylsulfonyl)methylphosphonate (prepared as an off-white solid in analogy to the procedure of Example 206 steps A and B) were converted to the title compound by the sequence as described in Example 205. The title compound is an off-white solid.

$^{1}$H NMR (400 MHz, CDCl$_{3}$) δ ppm 0.39-0.48 (m, 2 H), 0.56 (t, J=7.10 Hz, 3 H), 0.74-0.86 (m, 2 H), 1.13-1.25 (m, 1 H), 1.48 (br. s., 3 H), 1.51-1.59 (m, 1 H), 1.79-1.94 (m, 1 H), 1.97-2.11 (m, 2 H), 2.13-2.24 (m, 1 H), 2.24-2.42 (m, 1 H), 2.78 (d, J=14.87 Hz, 1 H), 2.92 (d, J=5.28 Hz, 2 H), 2.97-3.11 (m, 3 H), 3.16 (t, J=11.54 Hz, 1 H), 3.21-3.33 (m, 1 H), 4.62 (d, J=10.37 Hz, 1 H), 6.75 (d, J=7.04 Hz, 1 H), 6.96 (br. s., 1 H), 7.01-7.20 (m, 4 H), 7.21-7.27 (m, 2 H); MS (ESI) 580.2 [M+H]$^{+}$.

Example 208

2-((3R,5R,6S)-5-(3-chlorophenyl)-6-(4-chlorophenyl)-3-methyl-2-oxo-1-((S)-1-(2-oxopyrrolidin-1-yl)butan-2-yl)piperidin-3-yl)acetic acid

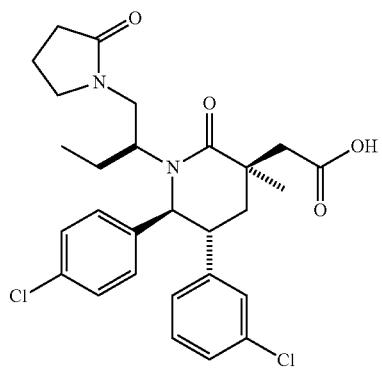 [SMILES: CC[C@@H](CN1CCCC1=O)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-3-methyl-1-((S)-1-(2-oxopyrrolidin-1-yl)butan-2-yl)piperidin-2-one

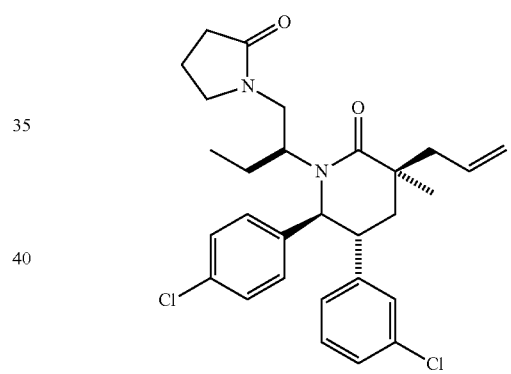

To a solution of (S)-2-((3S,5R,6S)-3-allyl-5-(3-chlorophenyl)-6-(4-chlorophenyl)-3-methyl-2-oxopiperidin-1-yl)butanal (84 mg, 0.189 mmol; Example 91, Step C), ethyl 4-aminobutyrate hydrochloride (127 mg, 0.756 mmol) and acetic acid (3 drops) in DCE/MeOH (3/1, 4.0 mL) was added sodium triacetoxyhydroborate (200 mg, 0.945 mmol) at 25° C. After being stirred at 25° C. for 18 h, the reaction was quenched by adding ice-cold saturated aqueous NaHCO$_{3}$ solution and was extracted with DCM. The combined organic layers were washed (1×sat. aq. NaCl solution) and concentrated under reduced pressure. The residue was purified by reverse phase preparatory HPLC (acetonitrile in water with 0.1% TFA, gradient elution) to give the title compound as a white solid.

Step B. 2-((3R,5R,6S)-5-(3-chlorophenyl)-6-(4-chlorophenyl)-3-methyl-2-oxo-1-((S)-1-(2-oxopyrrolidin-1-yl)butan-2-yl)piperidin-3-yl)acetic acid The title compound was obtained from ((3S,5R,6S)-3-allyl-5-(3-chlorophenyl)-6-(4-chlorophenyl)-3-methyl-1-((S)-

1-(2-oxopyrrolidin-1-yl)butan-2-yl)piperidin-2-one (Example 208, Step A) by a procedure similar to the one described in Example 71, Step F.

$^1$H NMR (400 MHz, CHLOROFORM-d) δ ppm 0.55 (t, J=8.0 Hz, 3 H), 1.52 (s, 3 H), 1.65 (m, 1 H), 1.90-2.28 (m, 5 H), 2.58 (m, 2 H), 2.75 (d, J=12.0 Hz, 1 H), 3.02 (d, J=12.0 Hz, 1 H), 3.08 (m, 3 H), 3.47 (m, 2 H), 3.99 (m, 1 H), 4.37 (d, J=12.0 Hz, 1 H), 6.72 (d, J=8.0 Hz, 1 H), 6.89-7.00 (m, 3 H), 71.0 (t, J=8.0 Hz, 1 H), 7.16 (m, 1 H), 7.26 (d, J=4.0 Hz, 2 H); MS (ESI) 531.1 [M+H]$^+$.

Example 209

2-((3R,5R,6S)-1-((S)-1-((1R,4R)-2-oxa-5-azabicyclo[2.2.1]heptan-5-yl)butan-2-yl)-5-(3-chlorophenyl)-6-(4-chlorophenyl)-3-methyl-2-oxopiperidin-3-yl)acetic acid-TFA salt

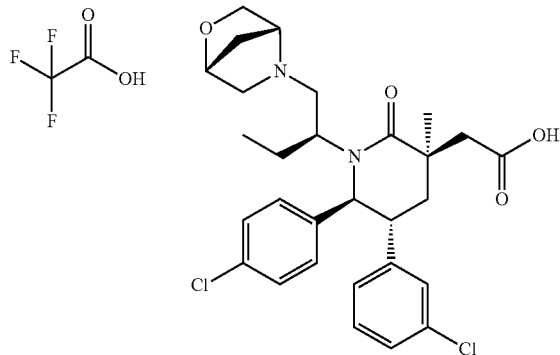 [SMILES: O=C(O)C(F)(F)F ; CC[C@@H](CN1C[C@H]2C[C@@H]1CO2)N1C(=O)[C@@](C)(CC(=O)O)C[C@H](c2cccc(Cl)c2)[C@H]1c1ccc(Cl)cc1]

Step A. (3S,5R,6S)-1-((S)-1-((1R,4R)-2-oxa-5-azabicyclo[2.2.1]heptan-5-yl)butan-2-yl)-3-allyl-5-(3-chlorophenyl)-6-(4-chlorophenyl)-3-methylpiperidin-2-one

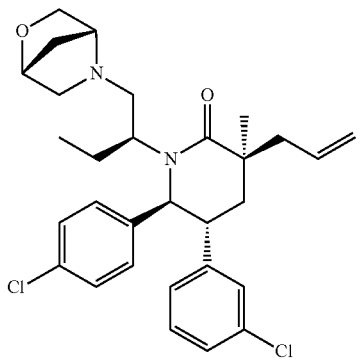 [SMILES: C=CC[C@@]1(C)C[C@H](c2cccc(Cl)c2)[C@@H](c2ccc(Cl)cc2)N([C@@H](CC)CN2C[C@H]3C[C@@H]2CO3)C1=O]

To a solution of (S)-2-((3S,5R,6S)-3-allyl-5-(3-chlorophenyl)-6-(4-chlorophenyl)-3-methyl-2-oxopiperidin-1-yl)butanal (100 mg, 0.224 mmol; Example 91, Step C) in DCE (2 mL) was added (1R,4R)-2-oxa-5-azabicyclo[2.2.1]heptane (Butora, G.; Goble, S.; Pastemak, A.; Yang, L.; Zhou, C.; Moyes, C. U.S. Patent Publication No. 2008/0081803 (50 mg, 0.504 mmol) followed by sodium triacetoxyborohydride (95 mg, 0.448 mmol) and acetic acid (1.2 µL, 0.022 mmol).

After stirring overnight, the mixture was quenched with sat. aq. NaHCO$_3$ solution. The mixture was extracted with ethyl acetate (2×). The combined organic layers were washed with sat. aq. NaCl solution, dried over Na$_2$SO$_4$, and concentrated. The residue was purified by flash chromatography on silica gel (eluent: 1 to 5% methanol/dichloromethane) to afford the title compound.

Step B. 2-((3R,5R,6S)-1-((S)-1-((1R,4R)-2-oxa-5-azabicyclo[2.2.1]heptan-5-yl)butan-2-yl)-5-(3-chlorophenyl)-6-(4-chlorophenyl)-3-methyl-2-oxopiperidin-3-yl)acetic acid-TFA salt To a solution of (3S,5R,6S)-1-((S)-1-((1R,4R)-2-Oxa-5-azabicyclo[2.2.1]heptan-5-yl)butan-2-yl)-3-allyl-5-(3-chlorophenyl)-6-(4-chlorophenyl)-3-methylpiperidin-2-one (87 mg, 0.17 mmol; Example 209, Step A) in THF (0.8 mL), water (0.4 mL), and t-butanol (0.4 mL) was added 4-methylmorpholine N-oxide (29 mg, 0.25 mmol) and 5 drops of 4% aq. OsO$_4$. After 18 hours, Jones' Reagent (0.20 mL) was added. After 24 hours, 50 mL water was added to the mixture and then the mixture was extracted with ethyl acetate (3×). The combined organic layers were washed with water, dried over Na$_2$SO$_4$ and concentrated. The residue was purified by reverse phase preparatory HPLC (column: Gemini-NX C$_{18}$ 5 um column; Phenomonex, Torrance, Calif.; eluent: 0 to 100% MeCN +0.1% TFA in water +0.1% TFA, over 20 minutes) to afford the title compound.

$^1$H NMR (400 MHz, CHLOROFORM-d) δ ppm 0.95-1.17 (m, 3 H) 1.30-1.53 (m, 5 H) 1.75-1.95 (m, 1 H) 2.03-2.17 (m, 2 H) 2.18-2.32 (m, 2 H) 2.37-2.54 (m, 1 H) 2.59-2.79 (m, 2 H) 2.80-2.94 (m, 1 H) 3.17-3.32 (m, 1 H) 3.73-3.93 (m, 2 H) 3.95-4.14 (m, 1 H) 4.40-4.55 (m, 2 H) 4.56-4.65 (m, 1 H) 4.90-5.23 (m, 1 H) 6.58-6.73 (m, 1 H) 6.93-7.02 (m, 1 H) 7.04-7.09 (m, 1 H) 7.14 (d, J=7.43 Hz, 2 H) 7.23-7.36 (m, 3 H). Mass Spectrum (ESI) m/z=545.2 (M+1).

Example 210

2-((3R,5R,6S)-5-(3-chlorophenyl)-6-(4-chlorophenyl)-3-methyl-1-((S)-1-((S)-3-methylmorpholino)butan-2-yl)-2-oxopiperidin-3-yl)acetic acid or
2-((3R,5R,6S)-5-(3-chlorophenyl)-6-(4-chlorophenyl)-3-methyl-1-((S)-1-((R)-3-methylmorpholino)butan-2-yl)-2-oxopiperidin-3-yl)acetic acid

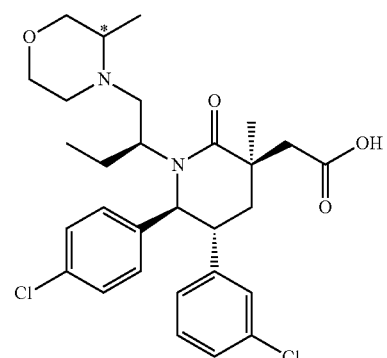

*stereochemistry not determined

Step A. 2-((3R,5R,6S)-5-(3-chlorophenyl)-6-(4-chlorophenyl)-3-methyl-2-oxo-1-((2S)-1-oxobutan-2-yl)piperidin-3-yl)acetic acid

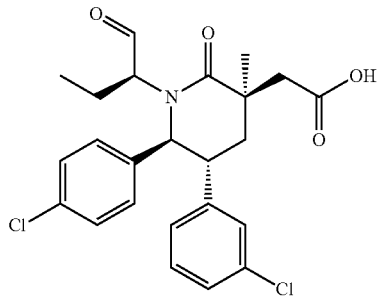 [SMILES: CC[C@@H](C=O)N1C(=O)[C@@](C)(CC(=O)O)C[C@H](c2cccc(Cl)c2)[C@H]1c1ccc(Cl)cc1]

To a −78° C. solution of oxalyl chloride (0.166 mL, 0.332 mmol) in dichloromethane (2 mL) was added dimethylsulfoxide (0.047 mL, 0.663 mmol) dropwise. After ten minutes, 2-((3R,5R,6S)-5-(3-chlorophenyl)-6-(4-chlorophenyl)-1-((S)-1-hydroxybutan-2-yl)-3-methyl-2-oxopiperidin-3-yl)acetic acid (140 mg, 0.301 mmol; Example 185) in dichloromethane (2 mL) was added dropwise. After 15 minutes, triethylamine (0.210 mL, 1.507 mmol) was added dropwise. The mixture was warmed to 0° C. for 10 minutes and then quenched with 10% aq. citric acid. The mixture was diluted with water and extracted with dichloromethane (2×). The combined organic layers were washed with sat. aq. NaCl solution, dried over anhydrous $Na_2SO_4$, and concentrated to afford the title compound.

Step B. 2-((3R,5R,6S)-5-(3-chlorophenyl)-6-(4-chlorophenyl)-3-methyl-1-((2S)-1-(3-methylmorpholino)butan-2-yl)-2-oxopiperidin-3-yl)acetic acid To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (960 mg, 2.076 mmol; Example 210, Step A) in 1,2-dichloroethane (15 mL) was added 3-methylmorpholine (Enamine Ltd, Kiev, Ukraine) (0.471 mL, 4.15 mmol) and sodium triacetoxyborohydride (880 mg, 4.15 mmol). After stirring overnight, the mixture was quenched with sat. aq. $NH_4Cl$ solution. The mixture was extracted with dichloromethane (2×). The combined organic layers were washed with sat. aq. NaCl solution, dried over anhydrous $Na_2SO_4$, and concentrated. The residue was purified by flash chromatography on silica gel (eluent: 1 to 10% methanol/dichloromethane) to afford the title compound as the major diastereomer. Stereochemistry of the 3-morpholine stereocenter is unknown.

$^1$H NMR (400 MHz, CHLOROFORM-d) δ ppm 0.50 (t, J=7.53 Hz, 3 H) 1.02 (d, J=6.26 Hz, 3 H) 1.46 (s, 3 H) 1.54-1.68 (m, 1 H) 1.85-1.98 (m, 2 H) 2.01-2.06 (m, 1 H) 2.15-2.28 (m, 2 H) 2.58-2.89 (m, 4 H) 2.97-3.13 (m, 2 H) 3.26-3.37 (m, 1 H) 3.55-3.71 (m, 2 H) 3.77-3.85 (m, 1 H) 3.90 (d, J=10.96 Hz, 1 H) 4.78 (d, J=10.17 Hz, 1 H) 6.77 (dt, J=7.48, 1.54 Hz, 1 H) 6.82-6.96 (m, 2 H) 6.97-7.02 (m, 1 H) 7.08-7.30 (m, 4 H). Mass Spectrum (ESI) m/z=547.2 (M+1).

Example 211

2-((3R,5R,6S)-5-(3-chlorophenyl)-6-(4-chlorophenyl)-1-((S)-1-(thiomorpholino-,1-dioxide)butan-2-yl)-3-methyl-2-oxopiperidin-3-yl)acetic acid

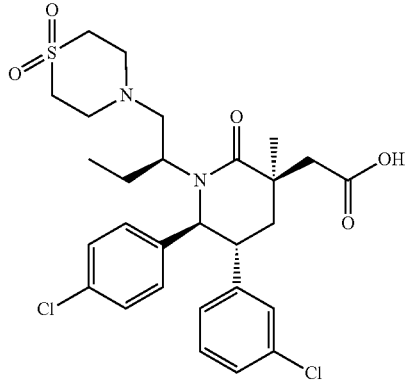 [SMILES: CC[C@@H](CN1CCS(=O)(=O)CC1)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (0.101 g, 0.219 mmol; Example 210, Step A) in 1,2-dichloroethane (3 mL) was added thiomorpholine 1,1-dioxide (0.128 g, 0.947 mmol), sodium triacetoxyborohydride (0.093 g, 0.438 mmol), and 2 drops of acetic acid. After stirring for 2 days, the mixture was quenched with water. The mixture was extracted with ethyl acetate (2×). The combined organic layers were washed with sat. aq. NaCl solution, dried over anhydrous $Na_2SO_4$, and concentrated. The colorless film was purified by reverse phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes). Fractions containing the product were transferred to a separatory funnel and sat. aq. $NaHCO_3$ solution and dichloromethane were added. The aqueous layer was back extracted with dichloromethane. The combined organic layers were washed with sat. aq. NaCl solution, dried over anhydrous $Na_2SO_4$, and concentrated to afford the title compound.

$^1$H NMR (400 MHz, CHLOROFORM-d) δ ppm 0.66 (t, J=7.14 Hz, 3 H) 1.46 (s, 4 H) 1.53-1.64 (m, 1 H) 1.78-1.91 (m, 1 H) 1.99-2.26 (m, 5 H) 2.77 (d, J=15.06 Hz, 1 H) 2.91-3.17 (m, 9 H) 4.41 (d, J=9.98 Hz, 1 H) 6.73 (d, J=7.43 Hz, 1 H) 6.90-6.91 (m 1 H) 7.09-7.22 (m, 2 H) 7.23-7.30 (m, 4 H). Mass Spectrum (ESI) m/z=581.2 (M+1).

Example 212

2-((3R,5R,6S)-5-(3-chlorophenyl)-6-(4-chlorophenyl)-1-((S)-1-(3,3-difluoroazetidin-1-yl)butan-2-yl)-3-methyl-2-oxopiperidin-3-yl)acetic acid

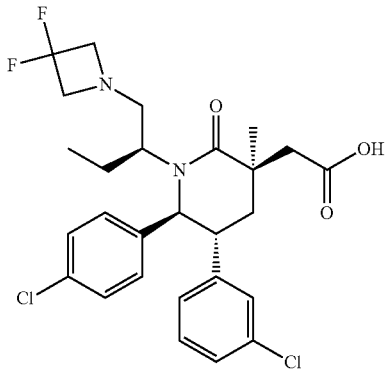 [SMILES: CC[C@@H](CN1CC(F)(F)C1)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (99 mg, 0.215 mmol; Example 210, Step A) in 1,2-dichloroethane (3 mL) was added 3,3-difluoroazetidine hydrochloride (55.7 mg, 0.430 mmol) followed by sodium triacetoxyborohydride (91 mg, 0.430 mmol). After stirring overnight, the mixture was quenched with water. The mixture was extracted with ethyl acetate (2×). The combined organic layers were washed with sat. aq. NaCl solution, dried over anhydrous $Na_2SO_4$ and concentrated. The residue was purified by reverse phase preparatory HPLC (column: Gemini-NX $C_{18}$ 5 um column; Phenomonex, Torrance, Calif.; eluent: 0 to 100% MeCN +0.1% TFA in water +0.1% TFA, over 20 minutes). Fractions containing the product were transferred to a separatory funnel and sat. aq. $NaHCO_3$ and dichloromethane were added. The aqueous layer was back extracted with dichloromethane. The combined organic layers were washed with sat. aq. NaCl solution, dried over anhydrous $Na_2SO_4$, filtered and the filtrate was concentrated to afford the title compound.

$^1$H NMR (400 MHz, ACETONITRILE-$d_3$) δ ppm 0.48 (t, J=7.53 Hz, 3 H) 1.32 (s, 3 H) 1.46-1.62 (m, 1 H) 1.68-1.82 (m, 1 H) 1.90-1.98 (m, 2 H) 2.01-2.05 (m 1 H) 2.13-2.23 (m, 1 H) 2.40 (dd, J=12.42, 4.99 Hz, 1 H) 2.67-2.78 (m, 1 H) 2.82-2.92 (m, 1 H) 3.16-3.29 (m, 1 H) 3.43-3.70 (m, 4 H) 4.55 (d, J=10.37 Hz, 1 H) 6.96 (td, J=4.35, 1.66 Hz, 1 H) 7.03-7.10 (m, 1 H) 7.12-7.21 (m, 4 H) 7.23-7.31 (m, 2 H). Mass Spectrum (ESI) m/z=539.0 (M+1).

Example 213

2-((3R,5R,6S)-1-((2S)-1-(8-oxa-3-azabicyclo[3.2.1]octan-3-yl)butan-2-yl)-5-(3-chlorophenyl)-6-(4-chlorophenyl)-3-methyl-2-oxopiperidin-3-yl)acetic acid

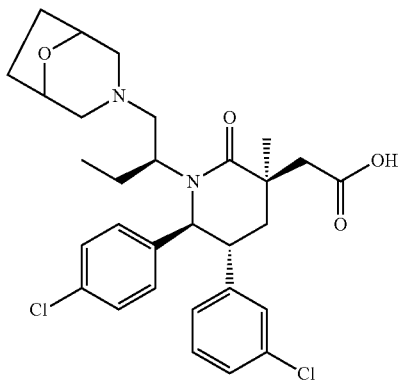 [SMILES: CC[C@@H](CN1CC2CCC(C1)O2)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (99 mg, 0.215 mmol; Example 210, Step A) in DCE (3 mL) was added 48.7 mg (0.43 mmol) of 8-oxa-3-azabicyclo[3.2.1]octane (Connolly, T.; Considine, J.; Ding, Z.; Forsatz, B.; Jennings, M.; MacEwan, M.; McCoy, K.; Place, D.; Sharma, A.; Sutherland, K. *Organic Process Research & Development.* 2010, 14(2), 459-465. Note: reference is for the HCl Salt). Sodium triacetoxyborohydride (91 mg, 0.430 mmol) was added followed by acetic acid (1.2 μL, 0.022 mmol). After stirring overnight, the mixture was partitioned between 5% aq. HCl and ethyl acetate. The organic layer was washed with sat. aq. NaCl solution, dried over $Na_2SO_4$, and concentrated. The residue was purified by reversed phase preparatory HPLC (eluent: 0-100% MeCN +0.1% TFA in water +0.1% TFA, over 20 minutes). Fractions containing the product were transferred to a separatory funnel and sat. aq. $NaHCO_3$ and dichloromethane were added. The aqueous layer was back extracted with dichloromethane. The combined organic layers were washed with sat. aq. NaCl solution, dried over anhydrous $Na_2SO_4$, filtered and the filtrate was concentrated to afford the title compound.

$^1$H NMR (400 MHz, CHLOROFORM-d) δ ppm 0.37-0.53 (m, 3 H) 1.48-1.58 (m, 4 H) 1.83-2.15 (m, 7 H) 2.18-2.31 (m, 2 H) 2.50 (s, 2 H) 2.60 (d, J=10.76 Hz, 1 H) 2.70 (d, J=15.65 Hz, 1 H) 2.96-3.17 (m, 4 H) 4.29-4.42 (m, 2 H) 4.55 (d, J=10.56 Hz, 1 H) 6.65 (dt, J=7.68, 1.44 Hz, 1 H) 6.94-7.02 (m, 1 H) 7.06-7.13 (m, 1 H) 7.14-7.21 (m, 1 H) 7.21-7.33 (m, 4 H). Mass Spectrum (ESI) m/z=559.2 (M+1).

Example 214

2-((3R,5R,6S)-5-(3-chlorophenyl)-6-(4-chlorophenyl)-1-((S)-1-(3,3-dimethylmorpholino)butan-2-yl)-3-methyl-2-oxopiperidin-3-yl)acetic acid

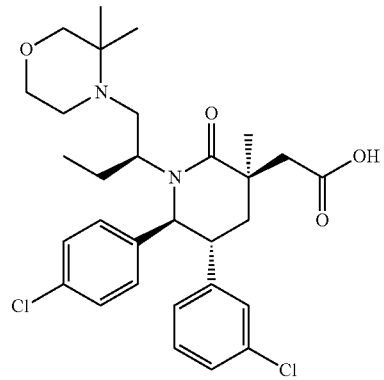 [SMILES: CC[C@@H](CN1CCOCC1(C)C)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (70 mg, 0.151 mmol; Example 210, Step A) in DCE (3 mL) was added 45.9 mg (0.303 mmol) of 3,3-dimethylmorpholine hydrochloride (Cottle, D.; Jeltsch, A.; Stoudt, T.; Walters, D. *Journal of Organic Chemistry.* 1946, 11(3), 286-91; Note: reference is for the free base) and sodium triacetoxyborohydride (64.2 mg, 0.303 mmol). After stirring overnight, the mixture was diluted with sat. aq. $NH_4Cl$ solution. The mixture was extracted with DCM (2×). The combined organic layers were washed with sat. aq. NaCl solution, dried over anhydrous $Na_2SO_4$, filtered and the filtrate was concentrated. The residue was purified by preparative thin layer chromatography on silica gel (eluent: 50% ethyl acetate/hexanes). The product containing fractions were pooled, concentrated and repurified by preparative thin layer chromatography on silica gel (eluent: 10% MeOH/DCM) to afford the title compound.

$^1$H NMR (400 MHz, CHLOROFORM-d) δ ppm 0.47-0.51 (m 3 H) 0.92-1.07 (m, 6 H) 1.26 (s, 3 H) 1.44-1.48 (m 6 H) 1.83-1.98 (m, 2 H) 1.99-2.08 (m, 1 H) 2.14-2.52 (m, 3 H) 3.34-3.37 (m 1 H) 3.42-3.52 (m, 1 H) 3.57-3.69 (m, 1 H) 3.87

(d, J=10.96 Hz, 1 H) 4.86 (d, J=11.15 Hz, 1 H) 6.77 (d, J=7.43 Hz, 1 H) 6.94-7.05 (m, 1 H) 7.08-7.30 (m, 6 H). Mass Spectrum (ESI) m/z=561.3 (M+1).

Example 215

2-((3R,5R,6S)-5-(3-chlorophenyl)-6-(4-chlorophenyl)-1-((S)-1-(3-hydroxy-3-(trifluoromethyl)azetidin-1-yl)butan-2-yl)-3-methyl-2-oxopiperidin-3-yl)acetic acid

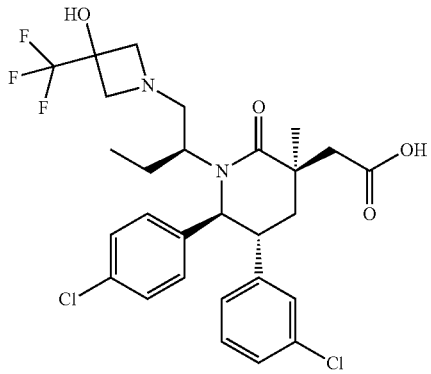 [SMILES: CC[C@@H](CN1CC(O)(C(F)(F)F)C1)N1C(=O)[C@@](C)(CC(=O)O)C[C@H](c2cccc(Cl)c2)[C@H]1c1ccc(Cl)cc1]

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (70 mg, 0.151 mmol; Example 210, Step A) in DCE (3 mL) was added 53.8 mg (0.303 mmol) of 3-(trifluoromethyl)azetidin-3-ol hydrochloride (U.S. patent application publication no 2007/0275930) and sodium triacetoxyborohydride (64.2 mg, 0.303 mmol). After stirring for 18 hours, the mixture was partitioned between water and DCM. The aqueous layer was washed with DCM. The combined organic layers were washed with sat. aq. NaCl solution, dried over anhydrous Na$_2$SO$_4$, filtered and the filtrate was concentrated. The residue was purified by preparative thin layer chromatography on silica gel (eluent: 50% ethyl acetate/hexanes) to afford the title compound.

$^1$H NMR (400 MHz, MeOH) δ ppm 0.51 (t, J=7.43 Hz, 3 H) 1.36 (s, 3 H) 1.50-1.66 (m, 1 H) 1.71-1.86 (m, 1 H) 2.09-2.26 (m, 2 H) 2.38 (dd, J=12.52, 3.91 Hz, 1 H) 2.52-2.64 (m, 1 H) 2.75 (br. s., 1 H) 2.93 (d, J=14.87 Hz, 1 H) 3.11-3.27 (m, 2 H) 3.28-3.43 (m, 3 H) 3.66-3.79 (m, 2 H) 4.62 (d, J=10.56 Hz, 1 H) 6.86-6.98 (m, 1 H) 7.03 (s, 1 H) 7.09-7.22 (m, 4 H) 7.27 (d, J=7.24 Hz, 2 H). Mass Spectrum (ESI) m/z=587.2 (M+1).

Example 216

2-((3R,5R,6S)-5-(3-chlorophenyl)-6-(4-chlorophenyl)-3-methyl-1-((S)-1-(methyl(oxetan-3-yl)amino)butan-2-yl)-2-oxopiperidin-3-yl)acetic acid

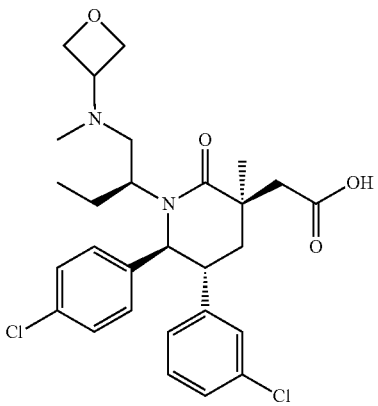 [SMILES: CC[C@@H](CN(C)C1COC1)N1C(=O)[C@@](C)(CC(=O)O)C[C@H](c2cccc(Cl)c2)[C@H]1c1ccc(Cl)cc1]

Step A. 2-((3R,5R,6S)-5-(3-chlorophenyl)-6-(4-chlorophenyl)-3-methyl-1-((S)-1-(methylamino)butan-2-yl)-2-oxopiperidin-3-yl)acetic acid-ammonium salt

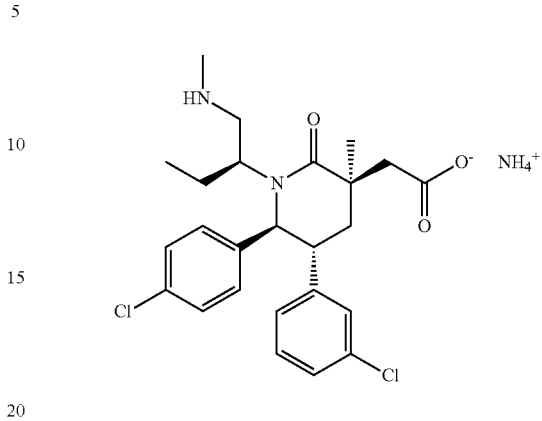

To a solution of 2-((3R,5R,6S)-5-(3-chlorophenyl)-6-(4-chlorophenyl)-3-methyl-2-oxo-1-((S)-1-oxobutan-2-yl)piperidin-3-yl)acetic acid (201 mg, 0.434 mmol; Example 210 Step A) in DCE (3 mL) was added methylamine hydrochloride (117 mg, 1.736 mmol) followed by sodium triacetoxyborohydride (184 mg, 0.868 mmol). After 4 hours, the mixture was diluted with methanol and DCM, filtered, and concentrated. The residue was purified by flash chromatography on silica gel (eluent: 20-100% ethylacetate/hexanes followed by 6:1:0.1 DCM:MeOH:NH$_4$OH) to afford the title compound.

Step B. 2-((3R,5R,6S)-5-(3-chlorophenyl)-6-(4-chlorophenyl)-3-methyl-1-((S)-1-(methyl(oxetan-3-yl)amino)butan-2-yl)-2-oxopiperidin-3-yl)acetic acid To a solution of oxetan-3-one (17.78 mg, 0.247 mmol) in DCE (3 mL) was added 2-((3R,5R,6S)-5-(3-chlorophenyl)-6-(4-chlorophenyl)-3-methyl-1-((S)-1-(methylamino)butan-2-yl)-2-oxopiperidin-3-yl)acetic acid ammonium salt (61 mg, 0.123 mmol) obtained in Step A followed by sodium triacetoxyborohydride (78 mg, 0.370 mmol) and 3 drops AcOH. After 45 minutes, 3 ml MeOH and oxetan-3-one (12 mg, 0.17 mmol) were added. After stirring overnight, oxetan-3-one (12 mg, 0.17 mol) and sodium triacetoxyborohydride (60 mg, 0.32 mmol) were added. After 24 hours, the mixture was diluted with methanol and evaporated onto silica gel. The solid was purified by flash chromatography on silica gel (eluent: 0 to 100% [6:1:0.1 DCM/MeOH/NH$_4$OH] in DCM). The product containing fractions were pooled, concentrated and repurified by preparative thin layer chromatography on silica gel (eluent: 10% MeOH/DCM) to afford the title compound.

$^1$H NMR (400 MHz, CHLOROFORM-d) δ ppm 0.51 (t, J=7.53 Hz, 3 H) 0.78-0.93 (m, 1 H) 1.14-1.32 (m, 3 H) 1.87-1.95 (m 1 H) 2.04 (d, J=13.30 Hz, 1 H) 2.12 (s, 3 H) 2.19-2.38 (m, 2 H) 2.71 (d, J=15.65 Hz, 1 H) 2.99-3.15 (m, 3 H) 3.44-3.60 (m, 1 H) 4.44-4.81 (m, 6 H) 6.81 (d, J=7.24 Hz, 1 H) 6.94-7.04 (m, 2 H) 7.09-7.21 (m, 2 H) 7.23-7.31 (m, 3 H). Mass Spectrum (ESI) m/z=533.2 (M+1).

Example 217

2-((3R,5R,6S)-5-(3-Chlorophenyl)-6-(4-chlorophenyl)-3-methyl-2-oxo-1-((S)-1-(2-oxooxazolidin-3-yl)butan-2-yl)piperidin-3-yl)acetic acid

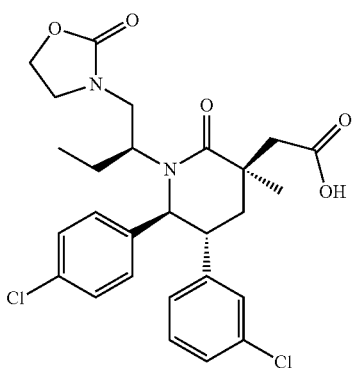 [SMILES: CC[C@@H](CN1CCOC1=O)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-1-((S)-1-((2-hydroxyethyl)amino)butan-2-yl)-3-methylpiperidin-2-one and (3S,5R,6S)-3-allyl-5-(3-chlorophenyl)-6-(4-chlorophenyl)-1-((R)-1-((2-hydroxyethyl)amino)butan-2-yl)-3-methylpiperidin-2-one

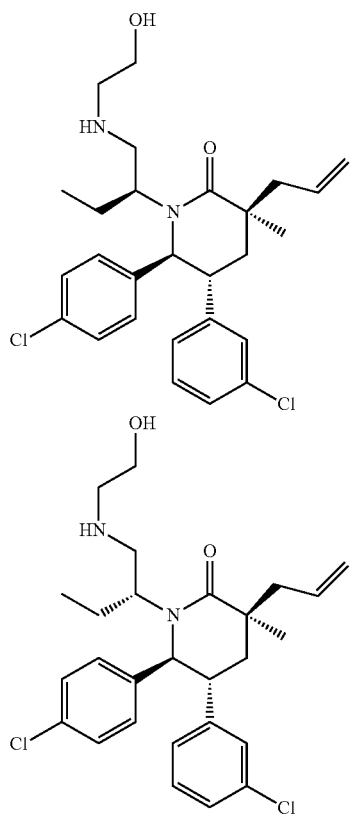

(S)-2-((3S,5R,6S)-3-Allyl-5-(3-chlorophenyl)-6-(4-chlorophenyl)-3-methyl-2-oxopiperidin-1-yl)butanal (180 mg, 0.405 mmol; Example 91, Step C) in ClCH$_2$CH$_2$Cl (1 mL) was stirred with sodium triacetoxyborohydride (172 mg, 0.81 mmol), ethanolamine (0.04 mL, 0.73 mmol) and acetic acid (0.06 mL, 1.013 mmol) at ambient temperature for 18 h, by which time analysis by LC-MS indicated the presence of the desired product. The mixture was partitioned between saturated NaHCO$_3$ and CH$_2$Cl$_2$. The organic layer was concentrated, and the residue purified by chromatography (silica gel, hexane/EtOAc, then EtOAc/MeOH, up to 15%) to afford the title compounds as a 1:1 mixture of two diastereomers. MS (ESI) m/z=489 (M+1).

Step B. 3-((S)-2-((3S,5R,6S)-3-Allyl-5-(3-chlorophenyl)-6-(4-chlorophenyl)-3-methyl-2-oxopiperidin-1-yl)butyl)oxazolidin-2-one and 3-((R)-2-((3S,5R,6S)-3-Allyl-5-(3-chlorophenyl)-6-(4-chlorophenyl)-3-methyl-2-oxopiperidin-1-yl)butyl)oxazolidin-2-one

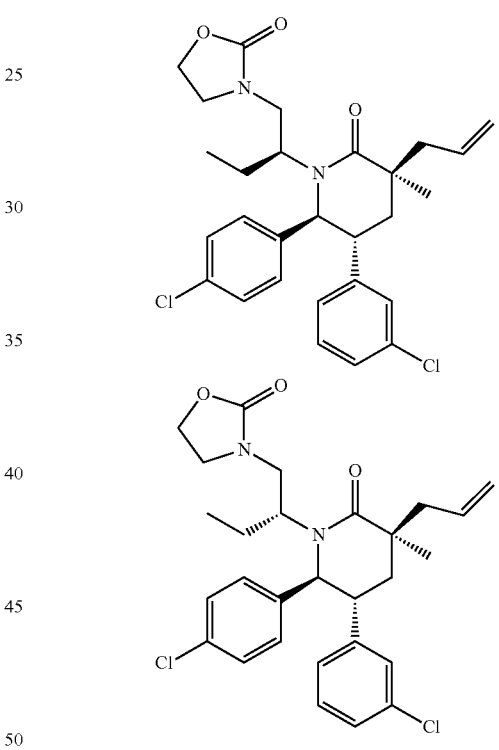

A mixture of (3S,5R,6S)-3-allyl-5-(3-chlorophenyl)-6-(4-chlorophenyl)-1-((S)-1-((2-hydroxyethyl)amino)butan-2-yl)-3-methylpiperidin-2-one and (3S,5R,6S)-3-allyl-5-(3-chlorophenyl)-6-(4-chlorophenyl)-1-((R)-1-((2-hydroxyethyl)amino)butan-2-yl)-3-methylpiperidin-2-one (60 mg, 0.123 mmol; Example 217, Step A) was mixed with 1,1'-carbonyldiimidazole (99 mg, 0.61 mmol) and 1,8-diazabicyclo[5.4.0]undec-7-ene (37 mg, 0.245 mmol) in 1,4 dioxane (1 mL). The mixture was heated to 100° C. in an oil bath for 18 h. The mixture was allowed to cool to ambient temperature, was diluted with EtOAc and washed with water three times. The crude product was then filtered through a pad comprised of silica gel and Na$_2$SO$_4$ to give the title compound, which was used without further purification. MS (ESI) m/z=515 (M+1).

Step C. 2-((3R,5R,6S)-5-(3-chlorophenyl)-6-(4-chlorophenyl)-3-methyl-1-((2S)-1-(5-methyl-2-oxooxazolidin-3-yl)butan-2-yl)-2-oxopiperidin-3-yl)acetic acid The title compound was prepared from the mixture obtained in Example 217, Step B by a procedure similar to the one described in Example 71, Step F. A mixture of two diastereomers was isolated, which was then further purified by chiral separation to afford the title compound (250×30 mm Chiralpak® IC column (Chiral Technologies, Inc., West Chester, Pa., USA) with 32 g/min MeOH (20 mM $NH_3$)).

$^1$H NMR (CDCl$_3$, 500 MHz) δ ppm 0.57 (t, 3H), 1.50 (s, 3H), 1.70 (m, 1H), 1.90 (m, 1H), 2.00 (m, 1H), 2.25 (t, 1H), 2.78 (br, 1H), 2.98 (br, 1H), 3.13 (m, 3H), 3.62 (m, 2H), 3.85 (br, 1H), 4.40 (m, 3H), 6.67 (m, 1H), 6.93 (s, 1H), 6.99 (br, 2H), 7.14 (m, 2H), 7.24 (m, 2 H). MS (ESI) m/z=533 (M+1).

Example 218

2-((3R,5R,6S)-5-(3-chlorophenyl)-6-(4-chlorophenyl)-3-methyl-2-oxo-1-((S)-1-(2-oxopyridin-1(2H)-yl)butan-2-yl)piperidin-3-yl)acetic acid

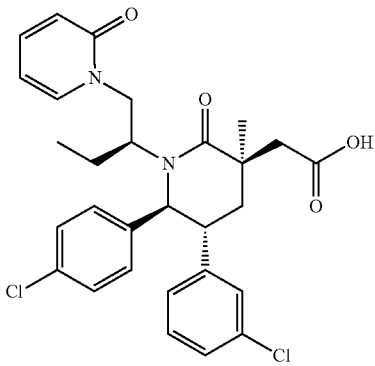 [SMILES: CC[C@@H](Cn1ccccc1=O)N1C(=O)[C@@](C)(CC(=O)O)C[C@H](c2cccc(Cl)c2)[C@H]1c1ccc(Cl)cc1]

Step A. (3S,5R,6S)-3-Allyl-5-(3-chlorophenyl)-6-(4-chlorophenyl)-1-((S)-1-hydroxybutan-2-yl)-3-methylpiperidin-2-one

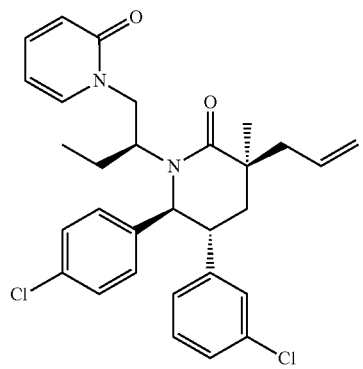 [SMILES: C=CC[C@@]1(C)C[C@H](c2cccc(Cl)c2)[C@@H](c2ccc(Cl)cc2)N([C@@H](CC)Cn2ccccc2=O)C1=O]

(3S,5R,6S)-3-Allyl-5-(3-chlorophenyl)-6-(4-chlorophenyl)-1-((S)-1-hydroxybutan-2-yl)-3-methylpiperidin-2-one (60 mg, 0.134 mmol; Example 91, Step C) was mixed with triphenylphosphine (42 mg, 0.161 mmol), 2-hydroxypyridine (14.1 mg. 0.148 mmol) and diisopropyl azodicarboxylate (0.029 mL, 0.148 mmol) in toluene in an oven-dried 3-neck roundbottom flask. The mixture was stirred at ambient temperature for 18 h under nitrogen. Solvent was evaporated. The residue was then purified by chromatography (silica gel, hexane/EtOAc, 1:0 to 2:3) to afford the title compound as a colorless oil.

Step B. 2-((3R,5R,6S)-5-(3-Chlorophenyl)-6-(4-chlorophenyl)-3-methyl-2-oxo-1-((S)-1-(2-oxopyridin-1(2H)-yl)butan-2-yl)piperidin-3-yl)acetic acid To a 25 mL roundbottom flask charged with (3S,5R,6S)-3-allyl-5-(3-chlorophenyl)-6-(4-chlorophenyl)-1-((S)-1-hydroxybutan-2-yl)-3-methylpiperidin-2-one (35 mg, 0.067 mmol; Example 218, Step A) was added THF, water (until the reaction became and remained cloudy with gentle stirring), and tBuOH (until the cloudy reaction became translucent). 4-Methylmorpholine 4-oxide monohydrate (13.6 mg, 0.10 mmol) was added followed by osmium tetroxide, 4 wt. %, in water (0.016 mL, 0.067 mmol). The reaction was allowed to stir at ambient temperature for 16 h to complete the formation of the diol. To the resulting mixture was added Jones reagent (70 µL) at ambient temperature and stirring was continued for 18 h. The reaction was quenched with water, diluted with EtOAc, and extracted with additional EtOAc (3×8 mL). The combined organic layers were washed with water, dried over MgSO$_4$, filtered and the filtrate was concentrated. The light greenish residue was purified by preparative HPLC to afford the title compound.

$^1$H NMR (CDCl$_3$, 400 MHz) δ ppm 0.53 (t, 3H), 1.43 (s, 3H), 1.68 (m, 1H), 1.85 (t, 1H), 2.03 (m, 2H), 2.65 (m, 1H), 2.91 (m, 1H), 3.30 (m, 2H), 3.72 (m, 1H), 4.25 (m, 1H), 4.42 (m, 1H), 6.71 (m, 4H), 7.70 (m, 4H), 7.26 (m, 2H), 7.51 (m, 1H), 7.77 (m, 1H). Mass spectrum (ESI) m/z=541 (M+1).

Example 219

2-((3R,5R,6S)-5-(3-Chlorophenyl)-6-(4-chlorophenyl)-3-methyl-2-oxo-1-((S)-1-(2-oxo-5-(trifluoromethyl)pyridin-1(2H)-yl)butan-2-yl)piperidin-3-yl)acetic acid

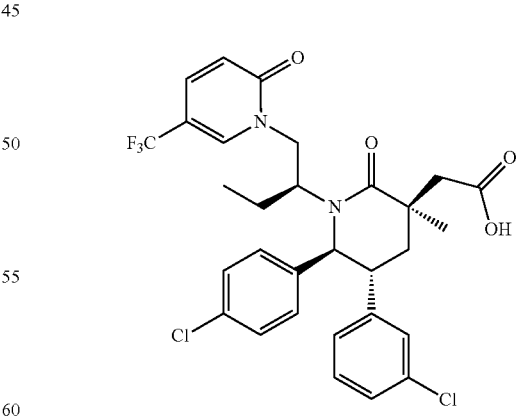

2-((3R,5R,6S)-5-(3-Chlorophenyl)-6-(4-chlorophenyl)-3-methyl-2-oxo-1-((S)-1-(2-oxo-5-(trifluoromethyl)pyridin-1(2H)-yl)butan-2-yl)piperidin-3-yl)acetic acid was prepared using the procedure described for example 218 by using 2-hydroxy-5-(trifluoromethyl)pyridine, and tri-n-butylphosphine, azodicarboxylic dipiperidine in Step A.

¹H NMR (CDCl₃, 500 MHz) δ ppm 0.54 (t, 3H), 1.42 (s, 3H), 1.60 (m, 1H), 1.78 (m, 1H), 2.01 (m, 2H), 2.77-2.93 (m, 2H), 3.13 (m, 1H), 3.42 (m, 1H), 3.81 (m, 1H), 4.32 (m, 2H), 6.50 (m, 1H), 6.71 (m, 1H), 6.77 (m, 1H), 6.91 (br, 2H), 7.03 (m, 1H), 7.11 (m, 1H), 7.23 (m, 2H), 7.69 (m, 2H).

Mass spectrum (ESI) m/z=609 (M+1).

Example 220

(3S,5R,6S)-3-allyl-5-(3-chlorophenyl)-6-(4-chlorophenyl)-3-methyl-1-((S)-1-(pyridin-3-yloxy)butan-2-yl)piperidin-2-one

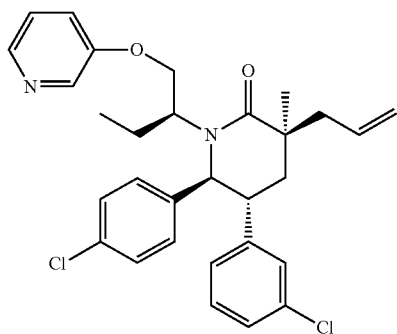 [SMILES: C=CC[C@@]1(C)C[C@H](c2cccc(Cl)c2)[C@@H](c2ccc(Cl)cc2)N([C@@H](CC)COc2cccnc2)C1=O]

(3S,5R,6S)-3-Allyl-5-(3-chlorophenyl)-6-(4-chlorophenyl)-3-methyl-1-((S)-1-(pyridin-2-yloxy)butan-2-yl)piperidin-2-one (10 mg) was prepared as described for example 218 using 3-hydroypyridine in place of 2 hydroxypyridine.

¹H NMR (MeOH-d₄, 500 MHz) δ ppm 0.62 (m, 3H), 1.27 (s, 3H), 1.70 (m, 1H), 1.97 (m, 1H), 2.18 (m, 2H), 2.59 (m, 1H), 2.96 (m, 1H), 3.44 (m, 2H), 4.11 (m, 1H), 4.58 (m, 1H), 4.70 (m, 1H), 6.97 (m, 1H), 7.06 (m, 1H), 7.15-7.28 (m, 6H), 7.81 (m, 1H), 7.98 (m, 1H), 8.37 (m, 1H), 8.56 (s, 1H). Mass spectrum (ESI) m/z=541 (M+1).

Example 221

2-((3R,5R,6S)-5-(3-chlorophenyl)-6-(4-chlorophenyl)-3-methyl-2-oxo-1-((1S)-1-(tetrahydrofuran-2-yl)propyl)piperidin-3-yl)acetic acid (Isomer 1)

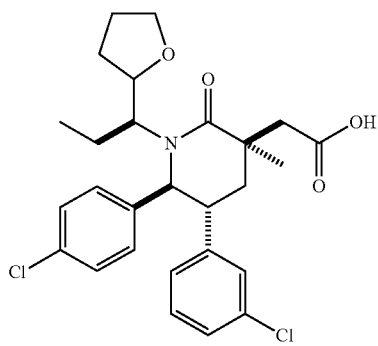

*stereochemistry not determined

Step A. (3S,5R,6S)-3-allyl-1-((3S)-7-((tert-butyldimethylsilyl)oxy)-4-hydroxyheptan-3-yl)-5-(3-chlorophenyl)-6-(4-chlorophenyl)-3-methylpiperidin-2-one

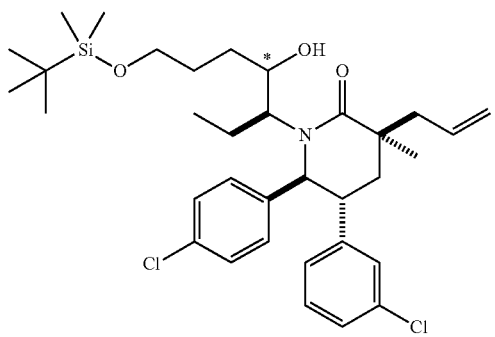

*stereochemistry not determined

The Grignard reagent derived from of (3-bromopropoxy)(tert-butyl)dimethylsilane was prepared on 1.8 mmol scale according to Minguez, et al. Biorg. Med. Chem. 11, 3335, 2003 as a gray solution in THF (~3 mL). About 1.5 mL of the Grignard regent was added slowly to a solution of (S)-2-((3S,5R,6S)-3-allyl-5-(3-chlorophenyl)-6-(4-chlorophenyl)-3-methyl-2-oxopiperidin-1-yl)butanal (100 mg, 0.22 mmol; Example 91, Step C) in THF (1 mL) at ambient temperature. After 2 h, the reaction was diluted in ethyl acetate and washed with saturated ammonium chloride solution followed by sat. aq. NaCl solution. The organic layer was dried over sodium sulfate and concentrated. Purification by silica chromatography eluting with ethyl acetate/hexane provided the title compound as a mixture of diastereomers.

¹H NMR (400 MHz, CHLOROFORM-d) representative signals:
major diastereomer δ ppm 1.17 (s, 3H), 4.25 (d J=10.6 Hz, 1H).
minor diastereomer δ ppm 1.21 (s, 3H), 4.37 (d, J=10.6 Hz, 1H).
Mass Spectrum (ESI) m/z=618.4 (M+1).

Step B. (3S,5R,6S)-3-allyl-5-(3-chlorophenyl)-6-(4-chlorophenyl)-1-((3S)-4,7-dihydroxyheptan-3-yl)-3-methylpiperidin-2-one

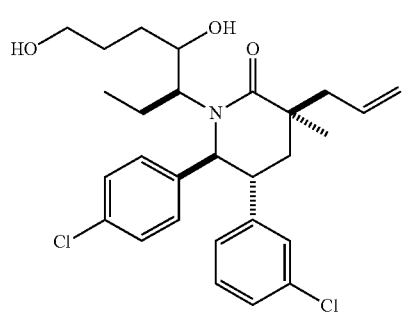 [SMILES: C=CC[C@@]1(C)C[C@H](c2cccc(Cl)c2)[C@@H](c2ccc(Cl)cc2)N([C@@H](CC)C(O)CCCO)C1=O]

A solution of (3S,5R,6S)-3-allyl-1-((3S)-7-(tert-butyldimethylsilyloxy)-4-hydroxyheptan-3-yl)-5-(3-chlorophenyl)-6-(4-chlorophenyl)-3-methylpiperidin-2-one (127 mg, 0.21 mmol; Example 221, Step A) in THF (1.5 mL) was treated with tetrabutylammonium fluoride (0.62 mL 1M in THF, 0.62 mmol) at ambient temperature for 1.5 hours. The solvent was removed under vacuum. Purification by silica chromatography eluting with ethyl acetate/hexane provided the title compound as a mixture of diastereomers.

$^1$H NMR (400 MHz, CHLOROFORM-d) representative signals:
major diastereomer δ ppm 1.15 (s, 3H), 4.26 (d J=10.6 Hz, 1H),
minor diastereomer δ ppm 1.20 (s, 3H), 4.31 (d, J=10.6 Hz, 1H).
Mass Spectrum (ESI) m/z=504.3 (M+1).

Step C. (3S,5R,6S)-3-allyl-5-(3-chlorophenyl)-6-(4-chlorophenyl)-3-methyl-1-((S)-1-((S)-tetrahydrofuran-2-yl)propyl)piperidin-2-one and (3S,5R,6S)-3-allyl-5-(3-chlorophenyl)-6-(4-chlorophenyl)-3-methyl-1-((S)-1-((R)-tetrahydrofuran-2-yl)propyl)piperidin-2-one

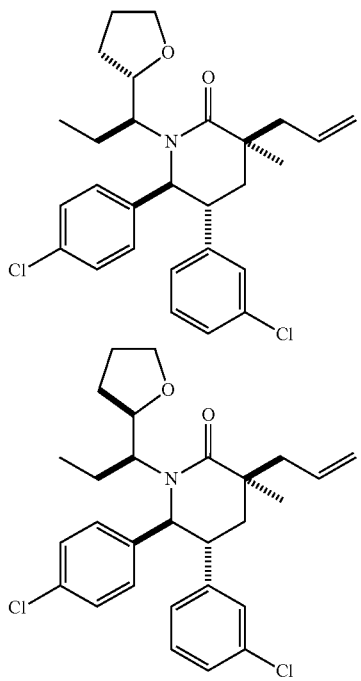

A solution of (3S,5R,6S)-3-allyl-5-(3-chlorophenyl)-6-(4-chlorophenyl)-1-((3S)-4,7-dihydroxyheptan-3-yl)-3-methylpiperidin-2-one (55 mg, 0.11 mmol; Example 221, Step B) and triphenylphosphine (57.2 mg, 0.22 mmol) in dichloromethane (2 mL) was treated with (E)-diethyl diazene-1,2-dicarboxylate (0.033 ml, 0.22 mmol) at ambient temperature for 2 hours. Purification by silica chromatography eluting with ethyl acetate/hexane provided one of the title compounds as the major diastereomer as the first eluting compound followed by the minor diastereomer.

(3S,5R,6S)-3-allyl-5-(3-chlorophenyl)-6-(4-chlorophenyl)-3-methyl-1-((1S)-1-(tetrahydrofuran-2-yl)propyl)piperidin-2-one (major diastereomer; first eluting compound)

$^1$H NMR (400 MHz, CHLOROFORM-d) δ ppm 0.65 (t, J=7.43 Hz, 3H) 1.20 (s, 3H) 1.51-1.58 (m, 3H), 1.71 (m, 3H), 1.83-1.97 (m, 4H), 2.54-2.57 (dd, J=7.53, 3.62 Hz, 2H), 3.08-3.14 (ddd, J=13.01, 10.47, 3.72 Hz, 1H), 3.53-3.58 (m, 2H), 3.73-3.77 (m, 1H), 4.30 (d, J=10.56 Hz, 1H), 5.08 (s, 1H), 5.11 (d, J=4 Hz, 1H), 5.74-5.84 (m, 1H), 6.62-6.64 (d, J=8 Hz, 1 H), 6.86 (s, 3H), 7.02 (t, J=8 Hz, 1H), 7.04-7.09 (s, 1H), 7.15 (d, J=4 Hz, 2H). Mass Spectrum (ESI) m/z=486.3 (M+1).

(3S,5R,6S)-3-allyl-5-(3-chlorophenyl)-6-(4-chlorophenyl)-3-methyl-1-((1S)-1-(tetrahydrofuran-2-yl)propyl)piperidin-2-one (minor diastereomer; second eluting compound)

$^1$H NMR (400 MHz, CHLOROFORM-d) δ ppm 0.47 (t, J=7.53 Hz, 3H), 1.10-1.21 (m, 4H), 1.36-1.46 (m, 1H), 1.51 (s, 1H), 1.73-2.06 (m, 5H), 2.45-2.59 (m, 3H), 3.07-3.14 (ddd, J=13.60, 10.56, 3.23 Hz, 1 H) 3.70-3.80 (m, 2 H) 4.37 (d, J=0.59 Hz, 1 H) 4.69 (d, J=10.76 Hz, 1 H) 5.14-5.23 (m, 2H) 5.75-5.85 (m, J=17.17, 9.83, 7.43, 7.43 Hz, 1H) 6.68 (dt, J=7.38, 1.59 Hz, 1H) 6.90-6.94 (m, 3H) 7.04 (m, 2H), 7.12 (d, J=8 Hz, 2H). Mass Spectrum (ESI) m/z=486.3 (M+1)

Step D. 2-((3R,5R,6S)-5-(3-chlorophenyl)-6-(4-chlorophenyl)-3-methyl-2-oxo-1-((1S)-1-(tetrahydrofuran-2-yl)propyl)piperidin-3-yl)acetic acid (Isomer 1)

The title compound was prepared from (3S,5R,6S)-3-allyl-5-(3-chlorophenyl)-6-(4-chlorophenyl)-3-methyl-1-((1S)-1-(tetrahydrofuran-2-yl)propyl)piperidin-2-one (major diastereomer; first eluting compound; Example 121, Step C) by a procedure similar to the one described in Example 71, Step F.

$^1$H NMR (400 MHz, CHLOROFORM-d) δ ppm 0.61 (t, J=7.63 Hz, 3 H) 1.34 (s, 3 H) 1.46-1.56 (m, 2 H) 1.72 (s, br, 3 H) 1.82-1.89 (m, 2 H) 2.00-2.14 (m, 2 H) 2.61 (d, J=13.89 Hz, 2 H) 2.76-2.84 (m, 2 H) 3.20 (dd, J=13.30, 7.24 Hz, 2 H) 3.29 (br. s., 1 H) 3.73 (td, J=7.87, 5.18 Hz, 1 H) 4.34 (d, J=10.37 Hz, 1 H) 6.68 (dd, J=7.43, 1.56 Hz, 1 H) 6.87 (s, 1 H) 7.00-7.15 (m, 4 H) 7.14 (dd, J=8.12, 0.5 Hz, 2 H). Mass Spectrum (ESI) m/z=504.3 (M+1)

Example 222

2-((3R,5R,6S)-5-(3-chlorophenyl)-6-(4-chlorophenyl)-3-methyl-2-oxo-1-((1S)-1-(tetrahydrofuran-2-yl)propyl)piperidin-3-yl)acetic acid (Isomer 2)

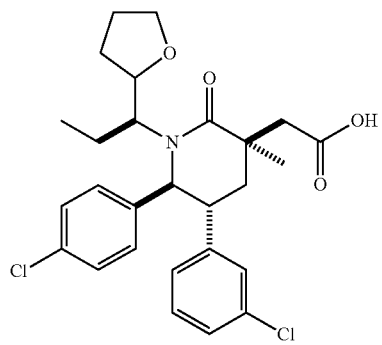

*stereochemistry not determined

The title compound was prepared from (3S,5R,6S)-3-allyl-5-(3-chlorophenyl)-6-(4-chlorophenyl)-3-methyl-1-((1S)-1-(tetrahydrofuran-2-yl)propyl)piperidin-2-one (minor diastereomer; second eluting compound; Example 121, Step C) by a procedure similar to the one described in Example 71, Step F.

¹H NMR (400 MHz, CHLOROFORM-d) δ ppm 0.46 (t, J=7.63 Hz, 3 H) 1.15-1.26 (m, 3 H) 1.36 (s, br. 3H), 1.46-1.50 (m, 1H), 1.79-1.85 (m, 4H), 2.05-2.09 (dd, J=12, 4 Hz, 1H), 2.17 (t, J=12 Hz, 1H), 2.51 (s, br, 1H), 2.66 (d, J=12 Hz, 1 H), 2.77 (d, J=12 Hz, 1 H), 3.76 (m, 2 H), 4.68 (d, J=8 nHz, 1H), 6.76 (d, J=8 Hz, 1H), 6.92-7.03 (m, 3H), 7.06 (d, J=2.2 Hz, 2H), 7.16 (d, J=8.8 Hz, 2H). Mass Spectrum (ESI) m/z=504.3 (M+1)

Example 223

2-((3R,5R,6S)-5-(3-chlorophenyl)-6-(4-chlorophenyl)-3-methyl-2-oxo-1-((1S)-1-(5-oxotetrahydrofuran-2-yl)propyl)piperidin-3-yl)acetic acid

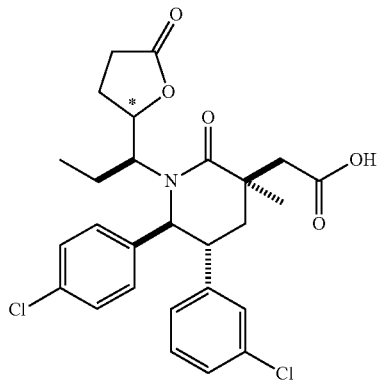

*stereochemistry not determined

The title compound was prepared using the oxidation procedure of Example 221, but using a larger excess of sodium periodate (7 eq) and reacting for a longer period of time (18 h).

¹H NMR (400 MHz, CD₃OD) δ ppm 0.7 (s, be, 3H), 1.42 (s, br, 3H), 1.68-1.75 (m, 1H), 1.96 (m, 1H), 2.21-2.24 (m, 3H), 2.33 (m, 1H), 2.49-2.67 (m, 3H), 2.97 (d, J=12 Hz, 1H), 3.37 (m, 2H), 3.51 (m, 1H), 4.60 (d, J=8 Hz, 1H), 6.96 (m, 1H), 7.10 (s, 1H) 7.13-7.19 (m, 2H), 7.31 (s, br, 4H).

Mass Spectrum (ESI) m/z=518.2 (M+1).

Example 224

2-((3R,5R,6S)-5-(3-Chlorophenyl)-6-(4-chlorophenyl)-3-methyl-2-oxo-1-((1S)-1-(tetrahydro-2H-pyran-2-yl)propyl)piperidin-3-yl)acetic acid (Isomer 1)

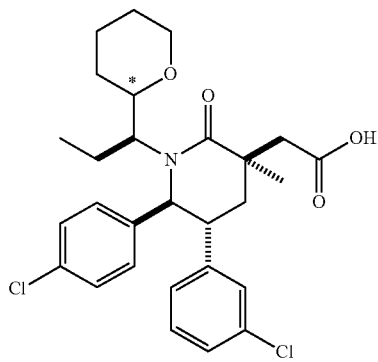

*stereochemistry not determined

Step A. (3S,5R,6S)-3-Allyl-1-((3S)-8-((tert-butyldimethylsilyl)oxy)-4-hydroxyoctan-3-yl)-5-(3-chlorophenyl)-6-(4-chlorophenyl)-3-methylpiperidin-2-one

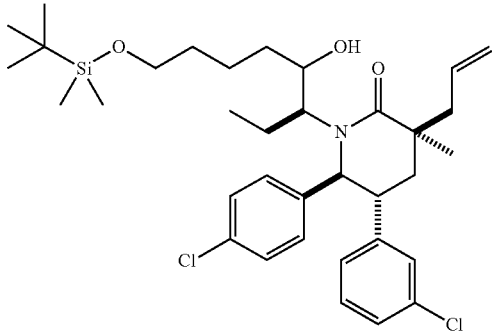 [SMILES: C=CC[C@@]1(C)C[C@H](c2cccc(Cl)c2)[C@@H](c2ccc(Cl)cc2)N([C@@H](CC)C(O)CCCCO[Si](C)(C)C(C)(C)C)C1=O]

The title compound was prepared as a mixture of diastereomers by a procedure similar to the one described in Example 221, Step A, substituting (4-chlorobutoxy)(tert-butyl)dimethylsilane for (3-bromopropoxy)(tert-butyl)dimethylsilane during the preparation of the Grignard reagent.

Mass Spectrum (ESI) m/z=632.2 (M+1).

Step B. (3S,5R,6S)-3-Allyl-5-(3-chlorophenyl)-6-(4-chlorophenyl)-1-((3S)-4,8-dihydroxyoctan-3-yl)-3-methylpiperidin-2-one

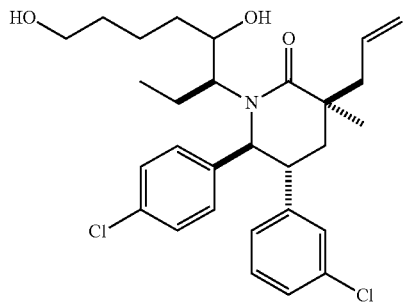 [SMILES: C=CC[C@@]1(C)C[C@H](c2cccc(Cl)c2)[C@@H](c2ccc(Cl)cc2)N([C@@H](CC)C(O)CCCCO)C1=O]

The title compound was obtained from (3S,5R,6S)-3-allyl-1-((3S)-8-((tert-butyldimethylsilyl)oxy)-4-hydroxyoctan-3-yl)-5-(3-chlorophenyl)-6-(4-chlorophenyl)-3-methylpiperidin-2-one (Example 224, Step B) by using a procedure similar to the one described in Example 221, Step B. The diastereomer ratio was observed by NMR to be about 2:1.

¹H NMR (400 MHz, d₄-methanol) representative signals:

major diastereomer δ ppm 0.45 (t, J=7.6 Hz, 3H), 4.76 (d, J=12 Hz, 1H).

minor diastereomer: δ ppm 0.54 (t, J=7.6 Hz, 3H), 4.53 (d, J=12 Hz, 1H).

m/z=518.2 (M+1).

Step C. (3S,5R,6S)-3-allyl-5-(3-chlorophenyl)-6-(4-chlorophenyl)-3-methyl-1-((1S)-1-(tetrahydro-2H-pyran-2-yl)propyl)piperidin-2-one

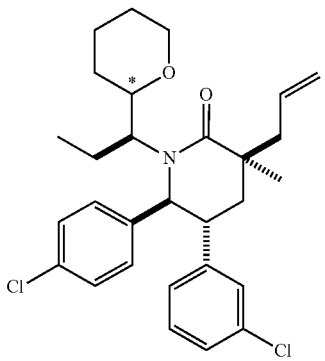

*stereochemistry not determined

A solution of (3S,5R,6S)-3-allyl-5-(3-chlorophenyl)-6-(4-chlorophenyl)-1-((3S)-4,8-dihydroxyoctan-3-yl)-3-methylpiperidin-2-one (31 mg, 0.060 mmol; diastereomeric mixture; Example 224, Step B) and triphenylphosphine (31.4 mg, 0.12 mmol) in dichloromethane (1.5 mL) was treated with (E)-diethyl diazene-1,2-dicarboxylate (0.02 ml, 0.12 mmol) at ambient temperature for 2 hours. Purification by silica chromatography eluting with ethyl acetate/hexane provided the title compound as a mixture of diastereomers.

$^1$H NMR (400 MHz, d-4-Methanol) representative signals:
major diastereomer δ ppm 0.46 (t, J=8 Hz, 3H), 4.75 (d, J=12 Hz, 1H).
minor diastereomer δ ppm 0.55 (t, J=8 Hz, 3H), 4.53 (d, J=12 Hz, 1H).
Mass Spectrum (ESI) m/z=500.2 (M+1)

Step D. (3R,5R,6S)-5-(3-chlorophenyl)-6-(4-chlorophenyl)-3-(2,3-dihydroxypropyl)-3-methyl-1-((1S)-1-(tetrahydro-2H-pyran-2-yl)propyl)piperidin-2-one

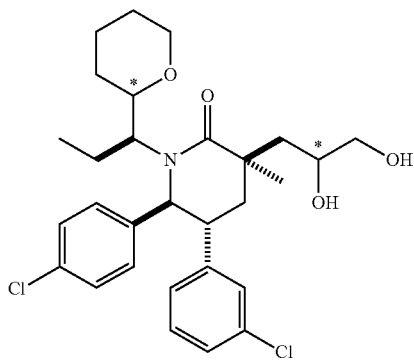

*stereochemistry not determined

A solution of (3S,5R,6S)-3-allyl-5-(3-chlorophenyl)-6-(4-chlorophenyl)-3-methyl-1-((1S)-1-(tetrahydro-2H-pyran-2-yl)propyl)piperidin-2-one (3 mg, 5.99 μmol; Example 224, Step C) in THF (37.5 μL), H$_2$O (25 μL) and t-butanol (21 μL) was treated with 4-methylmorpholine N-oxide (2.45 mg, 0.021 mmol) and 2.5% osmium tetroxide in t-BuOH (2 μL, 0.15 μmol) at ambient temperature for 18 h. The mixture was diluted with ethyl acetate, washed with water then sat. aq. NaCl solution and dried over sodium sulfate. After concentration the diastereomeric mixture was used in the next step without further purification. Mass Spectrum (ESI) m/z=534.1 (M+1)

Step E. 2-((3R,5R,6S)-5-(3-chlorophenyl)-6-(4-chlorophenyl)-3-methyl-2-oxo-1-((1S)-1-(tetrahydro-2H-pyran-2-yl)propyl)piperidin-3-yl)acetaldehyde

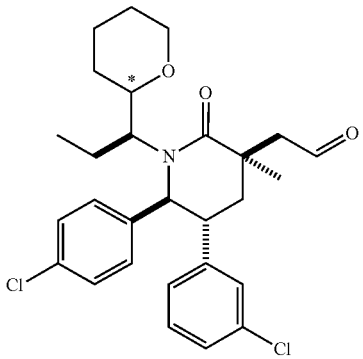

*stereochemistry not determined

A solution of (3R,5R,6S)-5-(3-chlorophenyl)-6-(4-chlorophenyl)-3-(2,3-dihydroxypropyl)-3-methyl-1-((1S)-1-(tetrahydro-2H-pyran-2-yl)propyl)piperidin-2-one (3 mg, 5.61 μmol; Example 224, Step D) in water (20.0 μL) and THF (40.0 μL) was treated with sodium periodate (3.60 mg, 0.02 mmol). After a precipitate formed, methanol (40 μL) was added to form an emulsion which was stirred at ambient temperature for 1 hour. The reaction was diluted with sat. aq. NaCl solution and extracted with ethyl acetate. The combined organic layers were dried over sodium sulfate, filtered and the filtrate was concentrated to provide a mixture of two diastereomers which was used in the next step. Mass Spectrum (ESI) m/z=502.1 (M+1)

Step F. 2-((3R,5R,6S)-5-(3-Chlorophenyl)-6-(4-chlorophenyl)-3-methyl-2-oxo-1-((1S)-1-(tetrahydro-2H-pyran-2-yl)propyl)piperidin-3-yl)acetic acid (Isomer 1)

A solution of 2-((3R,5R,6S)-5-(3-chlorophenyl)-6-(4-chlorophenyl)-3-methyl-2-oxo-1-((1S)-1-(tetrahydro-2H-pyran-2-yl)propyl)piperidin-3-yl)acetaldehyde (3 mg, 5.97 μmoL; mixture of stereoisomers, Example 224, Step E) in a solution of 1.25 M potassium phosphate monobasic in water (0.050 mL), t-butanol (0.050 mL) and 2.0 M 2-methylbut-2-ene in THF (0.15 mL, 0.30 mmol) was treated with sodium chlorite (2.16 mg, 0.024 mmol) at ambient temperature for 3 h. The reaction was quenched with 1 M sodium thiosulphate solution (0.03 mL). After 10 min, the mixture was acidified with 1M potassium bisulphate solution (0.03 mL) and extracted with ethyl acetate. The organic layers were washed with sat. aq. NaCl solution and dried over anhydrous sodium sulfate. Purification by reversed phase preparatory HPLC (eluent: 0 to 100% MeCN +0.1% TFA in water +0.1% TFA, over 20 minutes) gave the title compound as the first eluting isomer.

$^1$H NMR (400 MHz, MeOH-D4) δ ppm 0.51 (t, J=8 Hz, 3H), 1.03 (m, 1H), 1.32 (s, br, 1H), 1.39 (s, 3H), 1.50 (m, 2H), 1.67 (m, 1H), 1.85 (m, 1H), 1.96 (m, 3H), 2.19-2.22 (m, 2H), 2.60 (d, J=12 Hz, 1H), 2.99 (d, J=12 Hz, 1H), 3.16 (m, 1H), 3.44 (m, 1H), 3.51 (m. 1H), 3.85 (m, 1H), 4.57 (d, J=12 hZ, 1H), 6.97-6.99 (m, 1H), 7.06 (s, br, 1H), 7.15-7.21 (m, 3H), 7.29-7.31 (d, J=8 Hz, 2H). Mass Spectrum (ESI) m/z=518.2 (M+1).

433

Further elution provided Example 225 as the second eluting isomer.

Example 225

2-((3R,5R,6S)-5-(3-Chlorophenyl)-6-(4-chlorophenyl)-3-methyl-2-oxo-1-((1S)-1-(tetrahydro-2H-pyran-2-yl)propyl)piperidin-3-yl)acetic acid (Isomer 2)

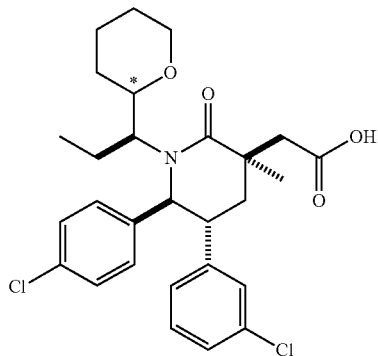

*stereochemistry not determined $^1$H NMR (400 MHz, MeOH-d4) δ ppm 0.39 (t, J=8 Hz, 3H), 1.00-1.07 (m, 1H), 1.18-1.20 (m, 1H), 1.32 (s, br, 1H), 1.37 (s, br, 3H), 1.50-1.68 (m, 4H), 1.86 (m, 2H), 2.15-2.19 (m, 2H), 2.58 (d, J=16 Hz, 1H), 2.96 (d, J=16 Hz, 1H), 3.41 (m, 1H), 3.52 (m, 1H), 3.89-3.94 (m, 1H), 4.11 (m, 1H), 3.71 (d, J=8 HZ, 1H), 6.94 (m, 1H), 7.03 (s, br, 1H), 7.14-7.20 (m, 4H), 7.28-7.30 (d, J=8 HZ, 2H). Mass Spectrum (ESI) m/z=518.2 (M+1)

Example 226

2-((3R,5R,6S)-1-((R)-1-(Benzo[d]thiazol-2-yl)propyl)-5-(3-chlorophenyl)-6-(4-chlorophenyl)-3-methyl-2-oxopiperidin-3-yl)acetic acid or 2-((3R,5R,6S)-1-((S)-1-(Benzo[d]thiazol-2-yl)propyl)-5-(3-chlorophenyl)-6-(4-chlorophenyl)-3-methyl-2-oxopiperidin-3-yl)acetic acid (Isomer 1)

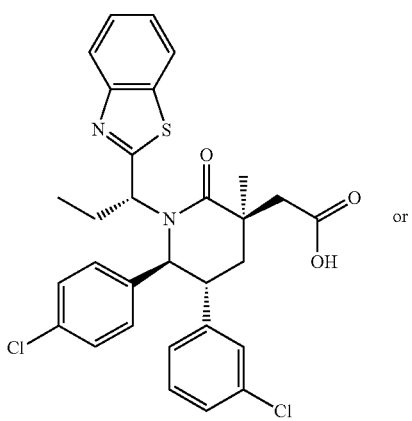

or

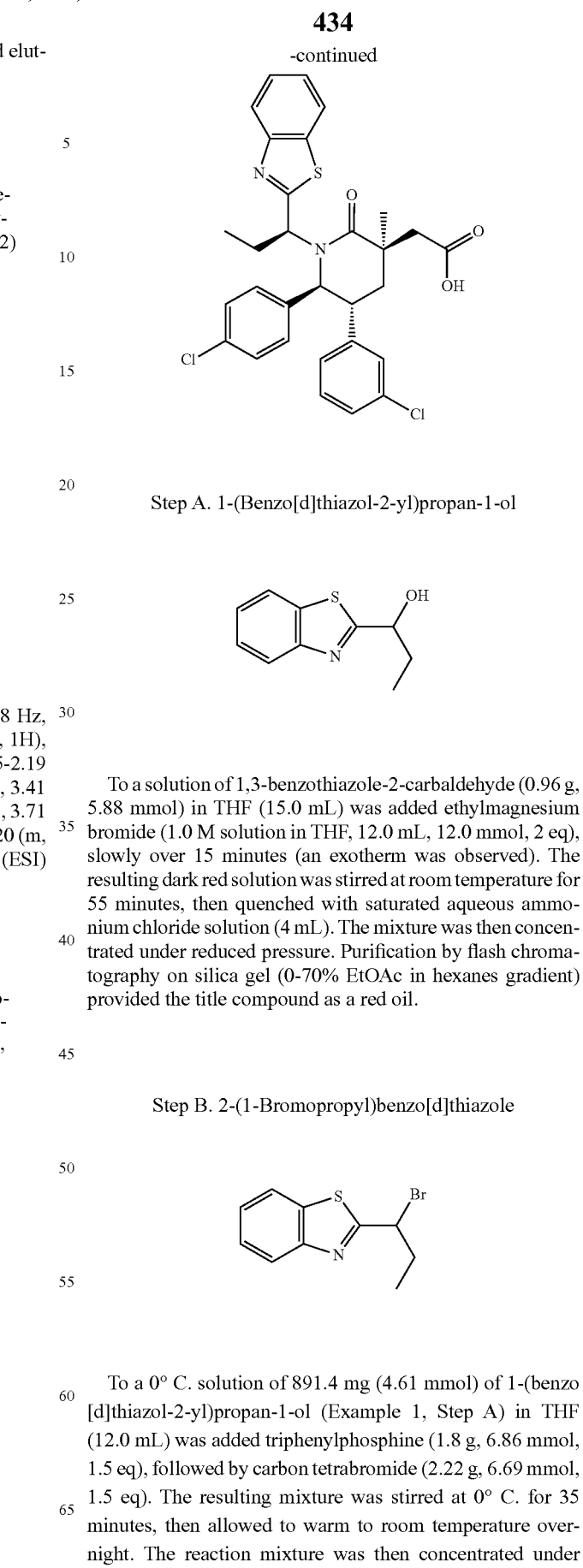

Step A. 1-(Benzo[d]thiazol-2-yl)propan-1-ol

To a solution of 1,3-benzothiazole-2-carbaldehyde (0.96 g, 5.88 mmol) in THF (15.0 mL) was added ethylmagnesium bromide (1.0 M solution in THF, 12.0 mL, 12.0 mmol, 2 eq), slowly over 15 minutes (an exotherm was observed). The resulting dark red solution was stirred at room temperature for 55 minutes, then quenched with saturated aqueous ammonium chloride solution (4 mL). The mixture was then concentrated under reduced pressure. Purification by flash chromatography on silica gel (0-70% EtOAc in hexanes gradient) provided the title compound as a red oil.

Step B. 2-(1-Bromopropyl)benzo[d]thiazole

To a 0° C. solution of 891.4 mg (4.61 mmol) of 1-(benzo[d]thiazol-2-yl)propan-1-ol (Example 1, Step A) in THF (12.0 mL) was added triphenylphosphine (1.8 g, 6.86 mmol, 1.5 eq), followed by carbon tetrabromide (2.22 g, 6.69 mmol, 1.5 eq). The resulting mixture was stirred at 0° C. for 35 minutes, then allowed to warm to room temperature overnight. The reaction mixture was then concentrated under Step C. (3S,5R,6S)-3-Allyl-1-((R)-1-(Benzo[d]thiazol-2-yl)propyl)-5-(3-chlorophenyl)-6-(4-chlorophenyl)-3-methylpiperidin-2-one and (3S,5R,6S)-3-Allyl-1-((S)-1-(benzo[d]thiazol-2-yl)propyl)-5-(3-chlorophenyl)-6-(4-chlorophenyl)-3-methylpiperidin-2-one

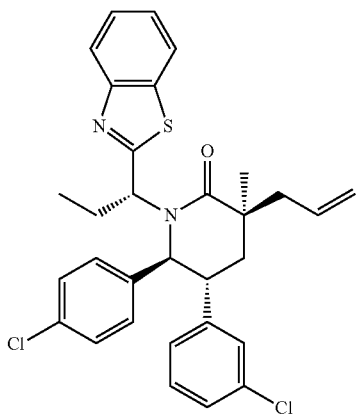

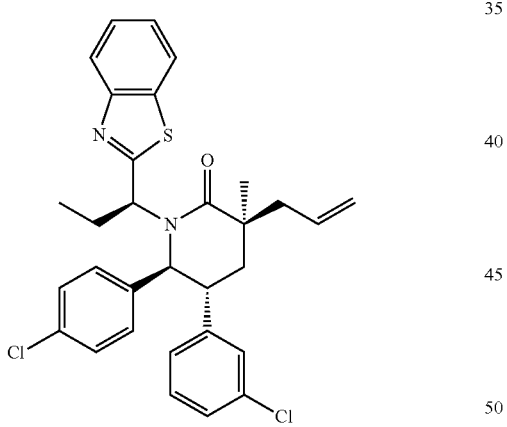

To a suspension of sodium hydride (60% dispersion in oil, 100.0 mg, 2.500 mmol, 3.1 eq) in DMF (1 mL) at 0° C. was added a solution of 300 mg (0.801 mmol) of (3S,5R,6S)-3-allyl-5-(3-chlorophenyl)-6-(4-chlorophenyl)-3-methylpiperidin-2-one (Example 71, Step D) in DMF (1 mL) over 1 minute. After 5 minutes, a solution of 576.7 mg (2.25 mmol, 2.8 eq) of 2-(1-bromopropyl)benzo[d]thiazol (Example 226, Step B) in DMF (1 mL) was added dropwise. The resulting mixture was allowed to warm to room temperature overnight. The reaction was quenched with water, and then concentrated under reduced pressure. Purification by reverse-phase preparative HPLC (Agilent Eclipse Plus C18 column (Agilent Technologies, Santa Clara, Calif.), 0.1% TFA in CH₃CN/H₂O, gradient 70% to 90% over 25 minutes) provided a mixture of the title compounds as a white solid.

Step D. 2-((3R,5R,6S)-1-((R)-1-(Benzo[d]thiazol-2-yl)propyl)-5-(3-chlorophenyl)-6-(4-chlorophenyl)-3-methyl-2-oxopiperidin-3-yl)acetic acid or 2-((3R,5R,6S)-1-((S)-1-(Benzo[d]thiazol-2-yl)propyl)-5-(3-chlorophenyl)-6-(4-chlorophenyl)-3-methyl-2-oxopiperidin-3-yl)acetic acid (Isomer 1)

To a solution of 97.5 mg (0.177 mmol) of (3S,5R,6S)-3-allyl-1-((R)-1-(benzo[d]thiazol-2-yl)propyl)-5-(3-chlorophenyl)-6-(4-chlorophenyl)-3-methylpiperidin-2-one (Example 226, Step C) in acetonitrile (1 mL), water (1.5 mL), and carbon tetrachloride (1 mL) were added sodium periodate (154.2 mg, 0.721 mmol, 4.1 eq), followed by ruthenium(III) chloride hydrate (11.0 mg, 0.049 mmol, 0.27 eq). The resulting mixture was stirred at room temperature for 2.75 hours, then passed through a 0.45 μm filter to remove residual solids, and then concentrated under reduced pressure. Purification by reverse-phase preparative HPLC (Agilent Eclipse Plus C18 column (Agilent Technologies, Santa Clara, Calif.), 0.1% TFA in CH₃CN/H₂O, gradient 40% to 80% over 25 minutes) provided one of the title compounds as the first eluting isomer as a white solid.

¹H NMR (500 MHz, CHLOROFORM-d) δ ppm 1.05 (t, J=7.46 Hz, 3 H) 1.55 (s, 3 H) 2.10-2.32 (m, 3 H) 2.41-2.54 (m, 1 H) 2.87-2.98 (m, 2 H) 3.16-3.25 (m, 1 H) 4.62 (d, J=10.27 Hz, 1 H) 4.81 (dd, J=8.56, 6.85 Hz, 1 H) 6.71 (d, J=7.58 Hz, 1 H) 6.80 (d, J=8.07 Hz, 2 H) 6.88 (d, J=8.31 Hz, 2 H) 6.96 (s, 1 H) 7.03-7.10 (m, 1 H) 7.16 (dd, J=7.95, 0.86 Hz, 1 H) 7.42-7.47 (m, 1 H) 7.48-7.54 (m, 1 H) 7.85 (t, J=8.19 Hz, 2 H). Mass Spectrum (ESI) m/z=567 (M+1).

Example 227

2-((3R,5R,6S)-1-((R)-1-(Benzo[d]thiazol-2-yl)propyl)-5-(3-chlorophenyl)-6-(4-chlorophenyl)-3-methyl-2-oxopiperidin-3-yl)acetic acid or 2-((3R,5R,6S)-1-((S)-1-(Benzo[d]thiazol-2-yl)propyl)-5-(3-chlorophenyl)-6-(4-chlorophenyl)-3-methyl-2-oxopiperidin-3-yl)acetic acid (Isomer 2)

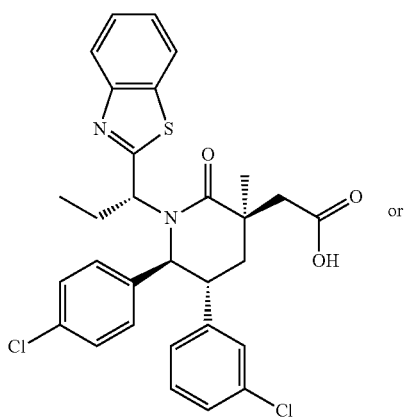

-continued

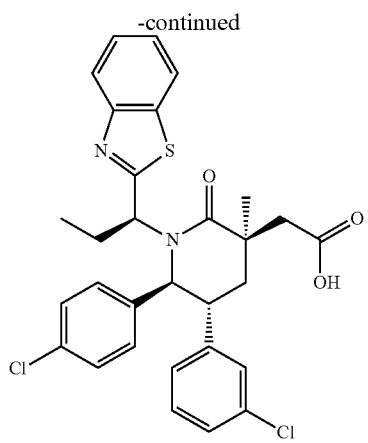

One of the title compounds (Isomer 2) was prepared from (3S,5R,6S)-3-allyl-1-((S)-1-(benzo[d]thiazol-2-yl)propyl)-5-(3-chlorophenyl)-6-(4-chlorophenyl)-3-methylpiperidin-2-one (Example 226, Step C) as the second eluting isomer as described in Example 226, Step D.

$^1$H NMR (500 MHz, CHLOROFORM-d) δ ppm 0.77 (t, J=7.34 Hz, 3 H) 1.39 (s, 3 H) 2.03-2.16 (m, 2 H) 2.16-2.24 (m, 1 H) 2.58 (dt, J=14.61, 7.49 Hz, 1 H) 2.82-2.98 (m, 2 H) 3.20-3.29 (m, 1 H) 4.75-4.84 (m, 2 H) 6.75 (d, J=7.58 Hz, 1 H) 6.94 (s, 1 H) 7.00 (d, J=8.31 Hz, 2 H) 7.05-7.11 (m, 3 H) 7.13-7.17 (m, 1 H) 7.44-7.49 (m, 1 H) 7.53 (t, J=7.46 Hz, 1 H) 7.87 (d, J=8.07 Hz, 1 H) 8.01 (d, J=8.07 Hz, 1 H). Mass Spectrum (ESI) m/z=567 (M+1).

Examples 228 to 240 were also prepared from (3S,5R,6S)-3-allyl-5-(3-chlorophenyl)-6-(4-chlorophenyl)-3-methylpiperidin-2-one (Example 71, Step D) as described in Example 226, substituting 2-(1-bromopropyl)benzo[d]thiazole in Example 226, Step C, with an equivalent amount of the appropriate alkylhalide. The required alkylhalides (reagents) are prepared as described in the individual examples.

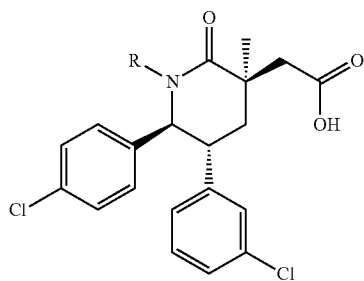

| Example | R | Reagent used |
|---------|---|--------------|
| 228 | ![structure] | 5-(1-Bromopropyl)-3-methylisoxazole |
| 229 | ![structure] | 2-(1-Bromopropyl)-6-chloropyridine |
| 230 | ![structure] | 2-(1-Bromopropyl)pyridine |
| 231 | ![structure] | 2-(1-Bromobutyl)pyridine |
| 232 | ![structure] | 2-(1-Bromo-2-cyclopropylethyl)pyridine |
| 233 | ![structure] | 3-(1-Bromopropyl)pyridine |
| 234 | ![structure] | 2-(1-Bromopropyl)pyrazine |
| 235 | ![structure] | 2-(1-Bromopropyl)pyrimidine |

| Example | R | Reagent used |
|---|---|---|
| 236 | 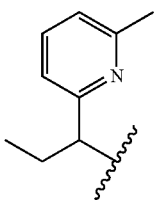 [SMILES: *C(CC)c1cccc(C)n1] | 2-(1-Bromopropyl)-6-methylpyridine |
| 237 | 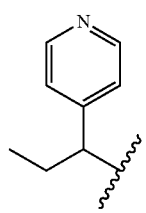 | 4-(1-Bromopropyl)pyridine |
| 238 | 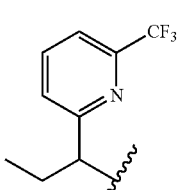 | 2-(1-Bromopropyl)-6-(trifluoromethyl)pyridine |
| 239 | 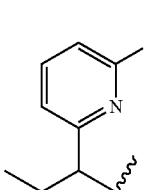 | 2-(1-Bromopropyl)-6-bromopyridine |
| 240 | 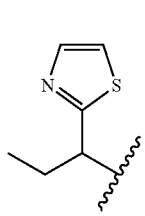 [SMILES: *C(CC)c1nccs1] | 2-(1-Bromopropyl)thiazole |

Example 228

2-((3R,5R,6S)-5-(3-chlorophenyl)-6-(4-chlorophenyl)-3-methyl-1-((S)-1-(3-methylisoxazol-5-yl)propyl)-2-oxopiperidin-3-yl)acetic acid or 2-((3R,5R,6S)-5-(3-chlorophenyl)-6-(4-chlorophenyl)-3-methyl-1-((R)-1-(3-methylisoxazol-5-yl)propyl)-2-oxopiperidin-3-yl)acetic acid $^{1}$H NMR (400 MHz, CHLOROFORM-d) δ ppm 0.74 (t, J=7.43 Hz, 3 H) 1.33 (s, 3 H) 1.90-2.11 (m, 2 H) 2.14-2.29 (m, 5 H) 2.90 (q, J=7.24 Hz, 2 H) 3.37-3.47 (m, 1 H) 4.47 (t, J=7.14 Hz, 1 H) 4.60 (d, J=10.37 Hz, 1 H) 5.70 (s, 1 H) 6.80 (dt, J=7.48, 1.54 Hz, 1 H) 6.90-7.02 (m, 3 H) 7.04-7.19 (m, 4 H). Mass Spectrum (ESI) m/z=515 (M+1).

Synthesis of 5-(1-bromopropyl)-3-methylisoxazole

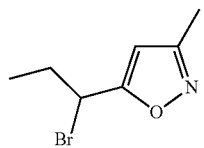

Step A. 1-(3-methylisoxazol-5-yl)propan-1-ol

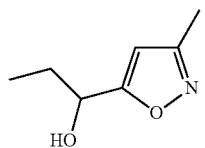

To a solution of 3-methylisoxazole-5-carbaldehyde (0.801 g, 7.21 mmol) in 10 mL of THF at −78° C. was added ethylmagnesium bromide (3.60 mL, 10.81 mmol) slowly. The reaction mixture was stirred at −78° C. for 2 h, then quenched with saturated aq. NH$_4$Cl solution, and extracted with ether (3×80 mL). The combined organic layers were dried over Na$_2$SO$_4$ filtered and the filtrate was evaporated to provide the crude product. The crude product was purified by chromatography on silica gel, eluting with 10 to 60% EtOAc/hexane to provide the title compound. Mass Spectrum (ESI) m/z=142.2 (M+1).

Step B. 5-(1-Bromopropyl)-3-methylisoxazole

To a solution of 1-(3-methylisoxazol-5-yl)propan-1-ol (0.589 g, 4.17 mmol) in 15 mL of THF was added CBr$_4$ (1.730 g, 5.22 mmol) and triphenylphosphine (1.423 g, 5.42 mmol). The reaction mixture was stirred at room temperature for 3 h. The solid was filtered off, and washed with THF. The filtrate was concentrated and residue was purified by chromatography on silica gel, eluting with 5 to 30% EtOAc/hexane to provide the title compound. Mass Spectrum (ESI) m/z=204.2 (M+1).

Example 229

2-((3R,5R,6S)-5-(3-chlorophenyl)-6-(4-chlorophenyl)-1-((S)-1-(6-chloropyridin-2-yl)propyl)-3-methyl-2-oxopiperidin-3-yl)acetic acid or 2-((3R,5R,6S)-5-(3-chlorophenyl)-6-(4-chlorophenyl)-1-((R)-1-(6-chloropyridin-2-yl)propyl)-3-methyl-2-oxopiperidin-3-yl)acetic acid $^{1}$H NMR (400 MHz, CHLOROFORM-d) δ ppm 0.77 (t, J=7.43 Hz, 3 H) 1.30 (s, 3 H) 1.99-2.13 (m, 2 H) 2.15-2.37 (m, 2 H) 2.70-2.90 (m, 2 H) 3.20 (ddd, J=12.96, 9.73, 3.33 Hz, 1 H) 4.56 (t, J=7.24 Hz, 1 H) 4.84 (d, J=9.98 Hz, 1 H) 6.82 (dt, J=7.43, 1.56 Hz, 1 H) 6.88 (d, J=8.22 Hz, 2 H) 6.99-7.24 (m, 7 H) 7.47 (t, J=7.73 Hz, 1 H). Mass Spectrum (ESI) m/z=545 (M+1).

Synthesis of 2-(1-bromopropyl)-6-chloropyridine

Step A. 1-(6-Chloropyridin-2-yl)propan-1-ol

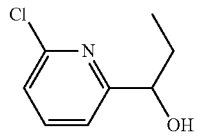

To a solution of 6-chloropicolinaldehyde (1.00 g, 7.06 mmol) in 20 mL of THF at −78° C. was added ethylmagnesium bromide, 3.0 M solution in diethyl ether (3.53 mL, 10.60 mmol) slowly. The reaction mixture was stirred at −78° C. for 2 h. The reaction mixture was quenched with sat'd $NH_4Cl$ aqueous solution, and extracted with ether (3×100 mL). The combined organic layers were dried over $Na_2SO_4$ and evaporated to provide the crude product. The crude product was purified by chromatography on silica gel, eluting with 10 to 60% EtOAc/hexane to provide the title compound. Mass Spectrum (ESI) m/z=172 (M+1).

Step B. 2-(1-bromopropyl)-6-chloropyridine

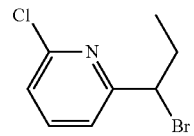

A mixture of 1-(6-chloropyridin-2-yl)propan-1-ol (0.497 g, 2.90 mmol), $CBr_4$ (1.2 g, 3.62 mmol) and triphenylphosphine (0.987 g, 3.76 mmol) in 25 mL of THF was stirred at room temperature for 2 h. The solid was filtered off and washed with THF. The filtrate was concentrated and residue was purified by chromatography on silica gel, eluting with 10 to 50% EtOAc/hexane to provide the title compound. Mass Spectrum (ESI) m/z=236 (M+1).

Example 230

2-((3R,5R,6S)-5-(3-chlorophenyl)-6-(4-chlorophenyl)-3-methyl-2-oxo-1-((S)-1-(pyridin-2-yl)propyl)piperidin-3-yl)acetic acid or 2-((3R,5R,6S)-5-(3-chlorophenyl)-6-(4-chlorophenyl)-3-methyl-2-oxo-1-((R)-1-(pyridin-2-yl)propyl)piperidin-3-yl)acetic acid $^1$H NMR (400 MHz, CHLOROFORM-d) δ ppm 0.75 (t, J=7.43 Hz, 3H), 1.21-1.31 (m, 3H), 1.93-2.10 (m, 2H), 2.10-2.23 (m, 1H), 2.50 (dt, J=14.77, 7.48 Hz, 1H), 2.75 (d, J=13.89 Hz, 1H), 2.97 (d, J=14.28 Hz, 1H), 3.09-3.25 (m, 1H), 4.65 (dd, J=8.22, 6.06 Hz, 1H), 4.95 (d, J=9.00 Hz, 1H), 6.80 (d, J=7.63 Hz, 1H), 6.89 (d, J=8.22 Hz, 2H), 7.02-7.21 (m, 6H), 7.34 (d, J=7.83 Hz, 1H), 7.54 (td, J=7.68, 1.66 Hz, 1H), 8.42 (d, J=4.30 Hz, 1H). Mass Spectrum (ESI) m/z=511.1 (M+1).

Synthesis of 2-(1-bromopropyl)pyridine

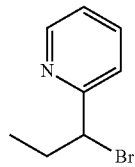

To a mixture of 2-propylpyridine (2.5 g, 20.63 mmol, purchased from Sigma-Aldrich, St. Louis, Mo.) and (E)-2,2'-(diazene-1,2-diyl)bis(2-methylpropanenitrile) (1.253 g, 7.63 mmol, purchased from Sigma-Aldrich) in $CCl_4$ (60 mL) at rt was added n-bromosuccinimide (1.93 mL, 22.7 mmol, purchased from Sigma-Aldrich). The mixture was stirred under fluorescent light at rt for 12 hr. The precipitate was removed by filtration of the mixture through a pad of Celite® (J.T. Baker, Phillipsberg, N.J., diatomaceous earth), which was washed with $CCl_4$ (10 mL). The filtrate was concentrated under reduced pressure. Purification of the residue by flash chromatography on silica gel (eluent: 20% EtOAc/hexanes) provided the title compound as a yellow liquid. Mass Spectrum (ESI) m/z=199.9 and 201.9 (M+1).

Example 231

2-((3R,5R,6S)-5-(3-chlorophenyl)-6-(4-chlorophenyl)-3-methyl-2-oxo-1-((S)-1-(pyridin-2-yl)butyl)piperidin-3-yl)acetic acid or 2-((3R,5R,6S)-5-(3-chlorophenyl)-6-(4-chlorophenyl)-3-methyl-2-oxo-1-((R)-1-(pyridin-2-yl)butyl)piperidin-3-yl)acetic acid $^1$H NMR (400 MHz, CHLOROFORM-d) δ ppm 1.04 (m, 3H), 1.41-1.71 (m, 5H), 2.03 (br. s., 1H), 2.18 (d, J=13.69 Hz, 1H), 2.30 (t, J=13.69 Hz, 1H), 2.44-2.74 (m, 2H), 3.08 (d, J=15.26 Hz, 1H), 3.47 (t, J=10.56 Hz, 1H), 4.31 (br. s., 1H), 4.59 (d, J=10.37 Hz, 1H), 6.77 (d, J=6.46 Hz, 1H), 6.89-7.20 (m, 8H), 7.79 (br. s., 1H), 8.17 (br. s., 1H), 8.72-9.01 (m, 1H), 11.51 (br. s., 1H).
Mass Spectrum (ESI) m/z=525.1 (M+1).

Synthesis of 2-(1-bromobutyl)-6-chloropyridine

Step A. 1-(Pyridin-2-yl)butan-1-ol

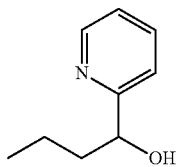

To a solution of 2-bromopyridine (1.1 g, 6.96 mmol, purchased from Sigma-Aldrich) in diethyl ether (8 mL) at −78° C. under $N_2$ was added butyllithium (3.1 mL×2.5 M) over 10 min. The reaction solution was stirred at −78° C. for 1.0 hr. To the mixture was added butyraldehyde (0.602 g, 8.35 mmol, purchased from Sigma-Aldrich) dropwise over 10 min. After stirring at −78° C. for 15 min, the mixture was allowed to warm to rt and stirred at rt for 1.5 hr. The reaction mixture was poured into saturated aqueous NH$_4$Cl solution (10 mL), diluted with water (15 mL), and extracted with EtOAc (20 mL×3). The organic layers were combined, washed with water, sat. aq. NaCl solution, and dried over MgSO$_4$. After removal of organic solvents under reduced pressure, purification of the residue by flash chromatography on silica gel with 20-80% EtOAc/Hexanes provided the title compound as a white solid. Mass Spectrum (ESI) m/z=152.1 (M+1).

Step B. 2-(1-Bromobutyl)pyridine

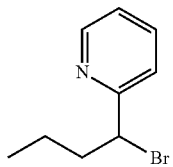

To a mixture of 1-(pyridin-2-yl)butan-1-ol (0.35 g, 2.3 mmol; Example 231, Step A) and triphenylphosphine (1.1 g, 4.2 mmol) in THF (15 mL) at 0° C. under N$_2$ atmosphere was added CBr$_4$ (1.2 g, 3.5 mmol). The mixture was stirred at 0° C. for 2 min, and then was allowed to warm to rt and stirred for 25 min. The precipitate was filtered off through a pad of Celite® (J. T. Baker, Phillipsberg, N.J., diatomaceous earth), the solid was washed with cold THF (10 mL). The filtrate was concentrated under reduced pressure. Purification of the residue by flash chromatography on silica gel with 0-5-15% EtOAc/Hexanes provided the title compound as colorless oil. Mass Spectrum (ESI) m/z=214.0 and 216.0 (M+1).

Example 232

2-((3R,5R,6S)-5-(3-chlorophenyl)-6-(4-chlorophenyl)-1-((S)-2-cyclopropyl-1-(pyridin-2-yl)ethyl)-3-methyl-2-oxopiperidin-3-yl)acetic acid or 2-((3R,5R,6S)-5-(3-chlorophenyl)-6-(4-chlorophenyl)-1-((R)-2-cyclopropyl-1-(pyridin-2-yl)ethyl)-3-methyl-2-oxopiperidin-3-yl)acetic acid $^1$H NMR (400 MHz, CHLOROFORM-d) δ ppm −0.45--0.34 (m, 1H), −0.06 (dq, J=9.19, 4.63 Hz, 1H), 0.16-0.39 (m, 2H), 0.46 (dd, J=7.43, 5.28 Hz, 1H), 1.16-1.31 (m, 3H), 1.63 (dt, J=13.60, 6.90 Hz, 1H), 2.00-2.17 (m, 2H), 2.50-2.65 (m, 1H), 2.77 (br. s., 1H), 2.88 (d, J=9.59 Hz, 1H), 3.19 (t, J=8.80 Hz, 1H), 4.84 (br. s., 1H), 4.97 (d, J=9.19 Hz, 1H), 6.78 (d, J=7.43 Hz, 1H), 6.93 (d, J=7.83 Hz, 2H), 7.00-7.17 (m, 7H), 7.34 (d, J=7.43 Hz, 1H), 7.48-7.57 (m, 1H), 8.34-8.56 (m, 1H). Mass Spectrum (ESI) m/z=537.2 (M+1).

Synthesis of
2-(1-bromo-2-cyclopropylethyl)pyridine

Step A. 2-Cyclopropyl-1-(pyridin-2-yl)ethanol

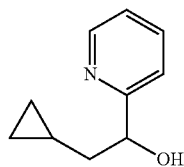 [SMILES: OC(CC1CC1)c1ccccn1]

To a solution of 2-cyclopropylacetaldehyde (1.00 g, 11.89 mmol, purchased from Beta Pharma, Inc., Branford, Conn.) in THF (15 mL) at 0° C. under N$_2$ was added 2-pyridylmagnesium bromide (47.6 mL×0.25 M, purchased from Rieke Metals, Inc., Lincoln, Nebr.) dropwise over 15 min. The mixture was stirred at 0° C. after 30 min, allowed to warm to rt and stirred at rt for 3.5 hr. To the reaction mixture was added saturated aqueous NH$_4$Cl solution (5 mL) followed by water (15 mL). The mixture was extracted with EtOAc (2×10 mL). The combined organic layers were dried over Na$_2$SO$_4$. After removal of organic solvents, purification of the residue by flash chromatography on silica gel with 40-70% EtOAc/hexanes the title compound was obtained as a white solid. Mass Spectrum (ESI) m/z=164.1 (M+1).

Step B. 2-(1-Bromo-2-cyclopropylethyl)pyridine

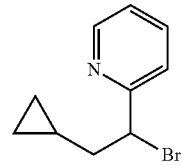

The title compound was prepared from 2-cyclopropyl-1-(pyridin-2-yl)ethanol (Example 232, Step A) using a procedure similar to the one described in Example 231, Step B. Mass Spectrum (ESI) m/z=226.0 and 228.0 (M+1).

Example 233

2-((3R,5R,6S)-5-(3-chlorophenyl)-6-(4-chlorophenyl)-3-methyl-2-oxo-1-((S)-1-(pyridin-3-yl)propyl)piperidin-3-yl)acetic acid or 2-((3R,5R,6S)-5-(3-chlorophenyl)-6-(4-chlorophenyl)-3-methyl-2-oxo-1-((R)-1-(pyridin-3-yl)propyl)piperidin-3-yl)acetic acid $^1$H NMR (400 MHz, CHLOROFORM-d) δ ppm 0.97-1.10 (d, J=8.6 Hz, 3H), 1.44 (s, 3H), 1.95-2.09 (m, 1H), 2.09-2.23 (m, 2H), 2.28 (s, 1H), 2.62 (d, J=13.89 Hz, 1H), 2.87 (d, J=13.89 Hz, 1H), 3.33 (ddd, J=13.40, 10.47, 3.13 Hz, 1H), 4.37 (d, J=10.37 Hz, 1H), 5.93 (t, J=7.92 Hz, 1H), 6.54-6.61 (m, 1H), 6.62-6.79 (m, 3H), 6.83-6.90 (m, 1H), 6.91-7.00 (m, 1H), 7.00-7.07 (m, 1H), 7.07-7.15 (m, 1H), 7.15-7.23 (m, 1H), 7.26 (dd, J=8.02, 5.67 Hz, 1H), 7.36 (d, J=8.02 Hz, 1H), 8.35 (d, J=5.48 Hz, 1H), 8.80 (s, 1 H). Mass Spectrum (ESI) m/z=511.1 (M+1).

Synthesis of 3-(1-bromopropyl)pyridine

Step A. 1-(Pyridin-3-yl)propan-1-ol

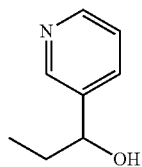

To a solution of 1-(pyridin-3-yl)propan-1-one (2.46 g, 18.20 mmol, purchased from Lancaster Synthesis Ltd.) in MeOH (15 mL) at rt under $N_2$ atmosphere was added sodium borohydride powder (0.690 g, 18.20 mmol). After stirring at rt for 1.5 hr, to the reaction solution was added water (20 ml). The resulting mixture was stirred for 4 min, extracted with EtOAc (20 mL×3). The organic layers were combined, washed with water, sat. aq. NaCl solution and dried over $MgSO_4$. Removal of the solvents provided the crude title compound as white solid. Mass Spectrum (ESI) m/z=138.0 (M+1).

Step B. 3-(1-Bromopropyl)pyridine

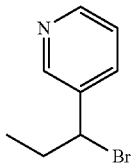

The title compound was prepared from 1-(pyridin-3-yl) propan-1-ol (Example 233, Step A) following the procedure described in Example 231, Step B. Mass Spectrum (ESI) m/z=199.9 and 201.9 (M+1).

Example 234

2-((3R,5R,6S)-5-(3-chlorophenyl)-6-(4-chlorophenyl)-3-methyl-2-oxo-1-((S)-1-(pyrazin-2-yl)propyl) piperidin-3-yl)acetic acid or 2-((3R,5R,6S)-5-(3-chlorophenyl)-6-(4-chlorophenyl)-3-methyl-2-oxo-1-((R)-1-(pyrazin-2-yl)propyl)piperidin-3-yl)acetic acid $^1$H NMR (400 MHz, CHLOROFORM-d) δ ppm 0.95 (t, J=7.14 Hz, 3H), 1.39 (s, 3H), 1.94-2.24 (m, 4H), 2.71 (s, 2H), 3.39-3.54 (m, 1H), 4.46 (d, J=9.98 Hz, 1H), 5.71 (t, J=7.43 Hz, 1H), 6.61 (d, J=7.82 Hz, 1H), 6.77 (br. s., 4H), 6.86-7.00 (m, 2H), 7.04 (d, J=8.80 Hz, 1H), 8.03-8.16 (m, 1H), 8.25 (br. s., 1H), 8.34 (s, 1H). Mass Spectrum (ESI) m/z=512.1 (M+1).

Synthesis of 2-(1-bromopropyl)pyrazine

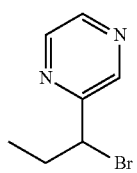

The title compound was prepared from 2-propylpyrazine (purchased from Matrix Scientific) following a procedure similar to the one described in Example 230. Mass Spectrum (ESI) m/z=200.8 and 202.9 (M+1).

Example 235

2-((3R,5R,6S)-5-(3-chlorophenyl)-6-(4-chlorophenyl)-3-methyl-2-oxo-1-((S)-1-(pyrimidin-2-yl)propyl)piperidin-3-yl)acetic acid or 2-((3R,5R,6S)-5-(3-chlorophenyl)-6-(4-chlorophenyl)-3-methyl-2-oxo-1-((R)-1-(pyrimidin-2-yl)propyl)piperidin-3-yl)acetic acid $^1$H NMR (400 MHz, CHLOROFORM-d) δ ppm 0.78 (t, J=7.43 Hz, 3H), 1.34 (s, 3H), 1.90-2.07 (m, 1H), 2.08-2.19 (m, 1H), 2.20-2.34 (m, 1H), 2.52 (dt, J=14.33, 7.21 Hz, 1H), 2.80 (br. s., 1H), 2.93 (qd, J=7.27, 2.05 Hz, 1H), 3.29-3.49 (m, 1H), 4.50 (br. s., 1H), 4.80 (d, J=10.17 Hz, 1H), 6.79 (d, J=7.63 Hz, 1H), 6.90-7.19 (m, 8H), 8.60 (d, J=4.69 Hz, 2H). Mass Spectrum (ESI) m/z=512.2 (M+1).

Synthesis of 2-(1-bromopropyl)pyrimidine

Step A. 2-Propylpyrimidine

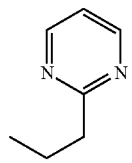

To a 0° C. solution of triphenylphosphine (2.290 g, 8.73 mmol), nickel(II) acetylacetonate (0.464 mL, 2.62 mmol) and 2-chloropyrimidine (5.00 g, 43.7 mmol, purchased from Sigma-Aldrich) in THF (45 mL) under $N_2$ atmosphere was added propylmagnesium chloride (21.83 mL, 43.7 mmol) over 5 min. The mixture was allowed to warm to rt and stirred at rt for 3 hr. To the reaction mixture was added saturated aqueous $NH_4Cl$ solution (5 mL) followed by water (12 mL). The mixture was extracted with EtOAc (2×10 mL). The combined organic layers were dried over $Na_2SO_4$.filtered and concentrated. The residue was purified by flash chromatography on silica gel (eluent: 0 to 50% EtOAc/hexanes) to provide the title compound as a colorless liquid.

Step B. 2-(1-Bromopropyl)pyrimidine

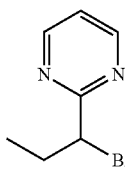

The title compound was prepared from 2-propylpyrimidine (Example 235, Step A) following a procedure similar to the one described in Example 230. Mass Spectrum (ESI) m/z=201.0 and 203.0 (M+1).

Example 236

2-((3R,5R,6S)-5-(3-chlorophenyl)-6-(4-chlorophenyl)-3-methyl-1-((S)-1-(6-methylpyridin-2-yl)propyl)-2-oxopiperidin-3-yl)acetic acid or 2-((3R,5R, 6S)-5-(3-chlorophenyl)-6-(4-chlorophenyl)-3-methyl-1-((R)-1-(6-methylpyridin-2-yl)propyl)-2-oxopiperidin-3-yl)acetic acid $^1$H NMR (400 MHz, CHLOROFORM-d) δ ppm 0.99 (br. s., 3H), 1.39 (s, 3H), 1.90-2.06 (m, 1H), 2.11 (d, J=12.72 Hz, 1H), 2.16-2.37 (m, 2H), 2.68 (d, J=15.06 Hz, 1H), 2.89 (s, 3H), 3.03 (d, J=15.06 Hz, 1H), 3.34 (t, J=10.76 Hz, 1H), 4.78 (d, J=9.59 Hz, 1H), 5.61 (br. s., 1H), 6.76 (d, J=7.04 Hz, 1H), 6.96 (br. s., 6H), 6.99-7.20 (m, 2H), 7.50 (d, J=7.43 Hz, 1H), 7.90 (t, J=7.63 Hz, 1H), 8.60 (br. s., 1 H). Mass Spectrum (ESI) m/z=525.1 (M+1).

Synthesis of 2-(1-bromopropyl)-6-methlpyridine

Step A. 1-(6-Methylpyridin-2-yl)propan-1-ol

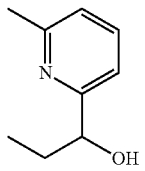

The title compound was prepared from 6-methyl-2-pyridinecarboxaldehyde (purchased from Tokyo Chemical Industry Co. Ltd.) using a procedure similar to the one described above for the synthesis of 2-cyclopropyl-1-(pyridin-2-yl)ethanol (Example 232, Step A). Mass Spectrum (ESI) m/z=151.4 (M+1).

Step B. 2-(1-Bromopropyl)-6-methylpyridine

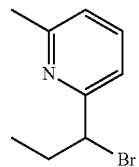

The title compound was prepared from 1-(6-methylpyridin-2-yl)propan-1-ol (Example 236, Step A) following a procedure similar to the one described in Example 231, Step B. Mass Spectrum (ESI) m/z=214.0 and 216.0 (M+1).

Example 237

2-((3R,5R,6S)-5-(3-chlorophenyl)-6-(4-chlorophenyl)-3-methyl-2-oxo-1-((S)-1-(pyridin-4-yl)propyl)piperidin-3-yl)acetic acid or 2-((3R,5R,6S)-5-(3-chlorophenyl)-6-(4-chlorophenyl)-3-methyl-2-oxo-1-((R)-1-(pyridin-4-yl)propyl)piperidin-3-yl)acetic acid $^1$H NMR (400 MHz, CHLOROFORM-d) δ ppm 1.14 (t, J=7.14 Hz, 3H), 1.48-1.54 (m, 3H), 1.94-2.09 (m, 1H), 2.09-2.32 (m, 2H), 2.64 (d, J=16.24 Hz, 1H), 2.96-3.11 (m, 1H), 3.26 (d, J=16.24 Hz, 1H), 3.52-3.69 (m, 1H), 4.39 (d, J=10.37 Hz, 1H), 6.02 (br. s., 1H), 6.61 (d, J=7.63 Hz, 3H), 6.77 (br. s., 2H), 6.89-7.09 (m, 5H), 7.13 (d, J=7.43 Hz, 1H), 8.33 (br. s., 1H). Mass Spectrum (ESI) m/z=511.1 (M+1).

Synthesis of 4-(1-bromopropyl)pyridine

Step A. 1-(Pyridin-4-yl)propan-1-ol

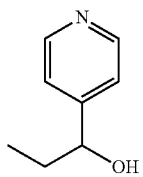

The title compound was prepared from 1-(pyridin-4-yl)propan-1-one (purchased from Waterstone Technology) following a procedure similar to the one described for the synthesis of 1-(pyridin-3-yl) propan-1-ol (Example 233, Step A). Mass Spectrum (ESI) m/z=138.0 (M+1).

Step B. 4-(1-Bromopropyl)pyridine

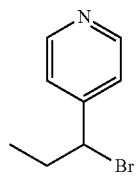

The title compound was prepared from 1-(pyridin-4-yl)propan-1-ol (Example 237, Step A) following a procedure similar to the one described in Example 231, Step B. Mass Spectrum (ESI) m/z=199.9 and 201.9 (M+1).

Example 238

2-((3R,5R,6S)-5-(3-chlorophenyl)-6-(4-chlorophenyl)-3-methyl-2-oxo-1-((S)-1-(6-(trifluoromethyl)pyridin-2-yl)propyl)piperidin-3-yl)acetic acid or 2-((3R,5R,6S)-5-(3-chlorophenyl)-6-(4-chlorophenyl)-3-methyl-2-oxo-1-((R)-1-(6-(trifluoromethyl)pyridin-2-yl)propyl)piperidin-3-yl)acetic acid $^1$H NMR (400 MHz, CHLOROFORM-d) δ ppm 0.75 (t, J=7.43 Hz, 3H), 1.21-1.30 (m, 3H), 1.98-2.19 (m, 2H), 2.29 (t, J=13.50 Hz, 1H), 2.47 (dt, J=14.62, 7.46 Hz, 1H), 2.78 (d, J=14.87 Hz, 1H), 2.98 (d, J=14.87 Hz, 1H), 3.14-3.28 (m, 1H), 4.23-4.33 (m, 1H), 5.05 (d, J=9.98 Hz, 1H), 6.84 (d, J=7.24 Hz, 1H), 6.91-7.06 (m, 3H), 7.10-7.22 (m, 4H), 7.54 (d, J=7.63 Hz, 2H), 7.80 (t, J=7.83 Hz, 1H). Mass Spectrum (ESI) m/z=579.0 (M+1).

Synthesis of 2-(1-bromopropyl)-6-(trifluoromethyl)pyridine

Step A. 1-(6-(Trifluoromethyl)pyridin-2-yl)propan-1-ol

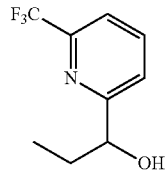

The title compound was prepared from 2-bromo-6-(trifluoromethyl)pyridine (purchased from Oakwood Products Inc., West Columbia, S.C.) and propionaldehyde following the procedure as described above for the synthesis of 1-(pyridin-2-yl)butan-1-ol (Example 231, Step A). Mass Spectrum (ESI) m/z=206.1 (M+1).

Step B.
2-(1-Bromopropyl)-6-(trifluoromethyl)pyridine

The title compound was prepared from 1-(6-(trifluoromethyl)pyridin-2-yl)propan-1-ol (Example 238, Step A) following a procedure similar to the one described for the synthesis of 2-(1-bromobutyl)pyridine (Example 231, Step B). Mass Spectrum (ESI) m/z=268.0 (M+1) and 269.9 (M+1).

Example 239

2-((3R,5R,6S)-1-((S)-1-(6-bromopyridin-2-yl)propyl)-5-(3-chlorophenyl)-6-(4-chlorophenyl)-3-methyl-2-oxopiperidin-3-yl)acetic acid or 2-((3R,5R,6S)-1-((R)-1-(6-bromopyridin-2-yl)propyl)-5-(3-chlorophenyl)-6-(4-chlorophenyl)-3-methyl-2-oxopiperidin-3-yl)acetic acid $^1$H NMR (400 MHz, CHLOROFORM-d) δ ppm 0.66 (t, J=7.43 Hz, 3H), 1.23 (s, 3H), 1.90-2.10 (m, 2H), 2.15-2.34 (m, 2H), 2.69-2.88 (m, 2H), 3.05-3.22 (m, 1H), 4.29 (t, J=7.04 Hz, 1H), 4.84 (d, J=9.78 Hz, 1H), 6.77 (d, J=7.43 Hz, 1H), 6.85 (d, J=8.02 Hz, 2H), 6.97 (s, 1H), 6.99-7.14 (m, 4H), 7.16-7.27 (m, 2H), 7.29-7.40 (m, 1H), 8.16 (br. s., 1H). Mass Spectrum (ESI) m/z=589.0, 591.0, 593.0 (M+1).

Synthesis of 2-bromo-6-(1-bromopropyl)pyridine

Step A. 1-(6-Bromopyridin-2-yl)propan-1-ol

The title compound was prepared from 2,6-dibromopyridine (purchased from Sigma-Aldrich, St. Louis, Mo.) and propionaldehyde following a procedure similar to the one described above for the synthesis of 1-(pyridin-2-yl)butan-1-ol (Example 231, step A). Mass Spectrum (ESI) m/z=219.9 and 217.9 (M+1).

Step B. 2-Bromo-6-(1-bromopropyl)pyridine

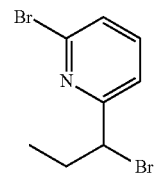

The title compound was prepared from 1-(6-bromopyridin-2-yl)propan-1-ol (example 239, Step A) following the procedure as described above for the synthesis of 2-(1-bromobutyl)pyridine (Example 231, Step B). Mass Spectrum (ESI) m/z=277.7, 279.7 and 281.7 (M+1).

Example 240

2-((3R,5R,6S)-5-(3-chlorophenyl)-6-(4-chlorophenyl)-3-methyl-2-oxo-1-((S)-1-(thiazol-2-yl)propyl)piperidin-3-yl)acetic acid or 2-((3R,5R,6S)-5-(3-chlorophenyl)-6-(4-chlorophenyl)-3-methyl-2-oxo-1-((R)-1-(thiazol-2-yl)propyl)piperidin-3-yl)acetic acid $^1$H NMR (400 MHz, CHLOROFORM-d) δ ppm 0.66 (t, J=7.43 Hz, 3H), 1.19-1.41 (m, 3H), 1.90-2.06 (m, 1H), 2.06-2.25 (m, 2H), 2.54 (dt, J=15.11, 7.60 Hz, 1H), 2.77-2.98 (m, 2H), 3.14-3.37 (m, 1H), 4.57 (dd, J=8.41, 4.70 Hz, 1H), 4.85 (d, J=9.78 Hz, 1H), 6.79 (d, J=7.43 Hz, 1H), 6.95 (s, 1H), 6.99-7.24 (m, 6H), 7.40 (d, J=3.33 Hz, 1H), 7.83 (d, J=3.13 Hz, 1H), 8.60 (br. s., 1H). Mass Spectrum (ESI) m/z=517.0 (M+1).

Synthesis of 2-(1-bromopropyl)thiazole

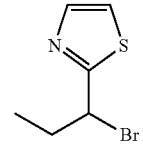

The title compound was prepared from 2-propylthiazole (purchased from Waterstone Technologies, Inc., Carmel, Ind.) following a procedure similar to the one described above for the synthesis of 2-(1-bromopropyl)pyridine (Example 230). Mass Spectrum (ESI) m/z=205.8 and 207.8 (M+1).

Example 241

2-((3R,5R,6S)-5-(3-chlorophenyl)-6-(4-chlorophenyl)-1-((S)-1-(6-(2-hydroxypropan-2-yl)pyridin-2-yl)propyl)-3-methyl-2-oxopiperidin-3-yl)acetic acid or 2-((3R,5R,6S)-5-(3-chlorophenyl)-6-(4-chlorophenyl)-1-((R)-1-(6-(2-hydroxypropan-2-yl)pyridin-2-yl)propyl)-3-methyl-2-oxopiperidin-3-yl)acetic acid

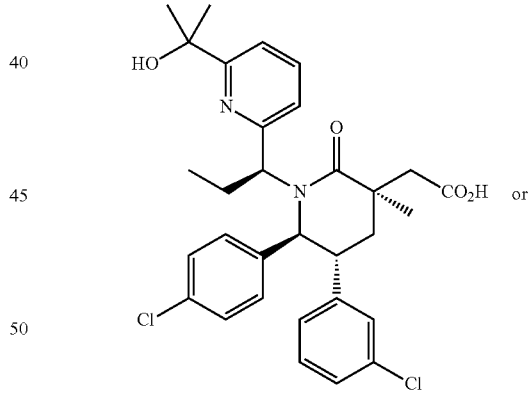

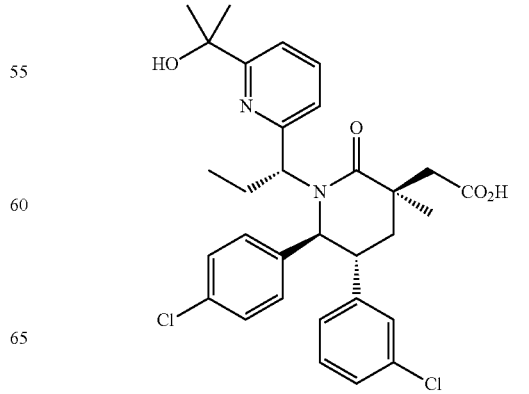

Step A. Ethyl 6-propylpicolinate

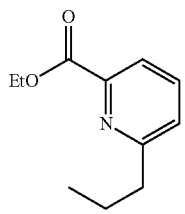

A solution of ethyl 6-bromopicolinate (8 g, 34.8 mmol, purchased from AK Scientific, Inc., Union City, Calif.) in THF (200 mL) was sparged with $N_2$ at 0° C. for 20 min. To the mixture under $N_2$ atmosphere was added $Pd(PPh_3)_4$ (3.21 g, 2.78 mmol) and a solution of propylzinc bromide (100 mL, 0.5 M in THF, 50.0 mmol) dropwise over 30 min. The mixture was removed from the ice bath and heated to reflux for 18 h. After that time the solution was cooled to rt, poured into saturated aqueous $NH_4Cl$ solution (18 mL), diluted with water (30 mL), and extracted with EtOAc (3×30 mL). The combined organic layers were washed with water and sat. aq. NaCl solution and were dried over $Na_2SO_4$. After removal of the organic solvents under reduced pressure, purification of the residue by flash chromatography on silica gel with 0 to 50% EtOAc/hexanes provided the title compound. Mass Spectrum (ESI) m/z=194.0 (M+1).

Step B. Ethyl 6-(1-bromopropyl)picolinate

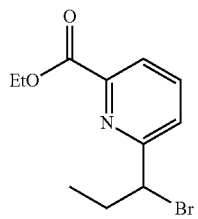

The title compound was prepared from Example 241, Step A following a procedure similar to the one described for the synthesis of 2-(1-bromopropyl)pyridine (Example 230). Mass Spectrum (ESI) m/z=272.0 and 274.0 (M+1).

Step C. Ethyl 6-((R)-1-((3S,5R,6S)-3-allyl-5-(3-chlorophenyl)-6-(4-chlorophenyl)-3-methyl-2-oxopiperidin-1-yl)propyl)picolinate and ethyl 6-((S)-1-((3S,5R,6S)-3-allyl-5-(3-chlorophenyl)-6-(4-chlorophenyl)-3-methyl-2-oxopiperidin-1-yl)propyl)picolinate

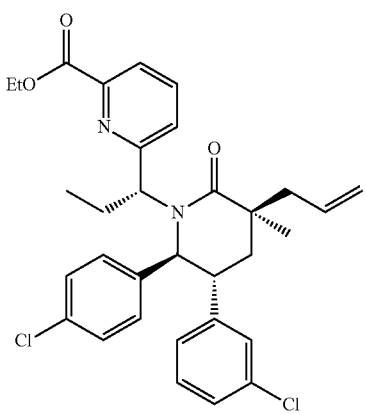

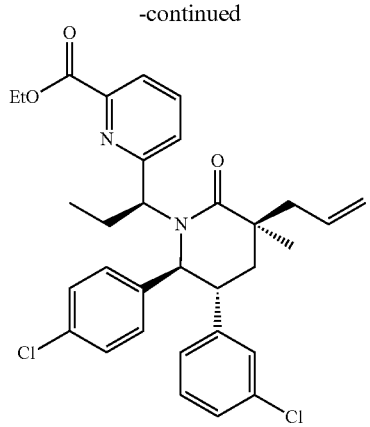

The title compounds were prepared as a mixture from ethyl 6-(1-bromopropyl)picolinate (Example 241, Step B) following a procedure similar to the one described in Example 226, Step C.

Mass Spectrum (ESI) m/z=566.2 (M+1).

Step D. (3S,5R,6S)-3-allyl-5-(3-chlorophenyl)-6-(4-chlorophenyl)-1-((R)-1-(6-(2-hydroxypropan-2-yl)pyridin-2-yl)propyl)-3-methylpiperidin-2-one and (3S,5R,6S)-3-allyl-5-(3-chlorophenyl)-6-(4-chlorophenyl)-1-((S)-1-(6-(2-hydroxypropan-2-yl)pyridin-2-yl)propyl)-3-methylpiperidin-2-one

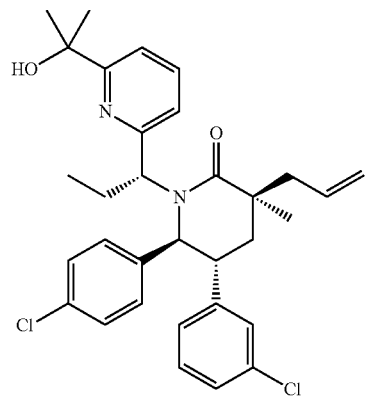

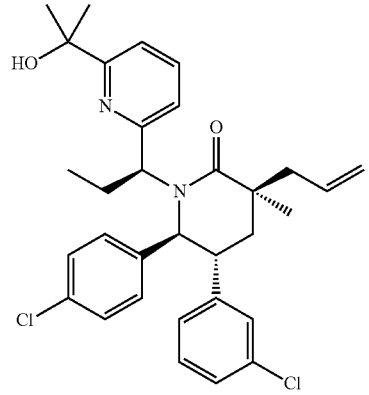

To a 0° C. solution of ethyl 6-((R)-1-((3S,5R,6S)-3-allyl-5-(3-chlorophenyl)-6-(4-chlorophenyl)-3-methyl-2-oxopiperidin-1-yl)propyl)picolinate and ethyl 6-((S)-1-((3S,5R, 6S)-3-allyl-5-(3-chlorophenyl)-6-(4-chlorophenyl)-3-methyl-2-oxopiperidin-1-yl)propyl)picolinate (160 mg, 0.283 mmol, Example 241, Step C) in THF (3 mL) under $N_2$ was added $CH_3MgBr$ (3.0 M solution in diethyl ether, 0.377 mL, 1.132 mmol). The mixture was removed from the ice bath and stirred at rt for 30 min. To the reaction mixture was added additional $CH_3MgBr$ (3.0 M solution in diethyl ether, 0.24 mL, 0.78 mmol). After stirring at rt for 2.0 hr, to the reaction mixture was added saturated aqueous $NH_4Cl$ solution (3 mL) and water (4 mL). The mixture was extracted with EtOAc (3×8 mL). The combined organic layers were washed with water, sat. aq. NaCl solution, and dried over $Na_2SO_4$. After removal of organic solvents under reduced pressure, purification of the residue by flash chromatography on silica gel with 20-80% EtOAc/hexanes provided the title compounds as a mixture of stereoisomers. Mass Spectrum (ESI) m/z=551.1 (M+1).

Step E. 2-((3R,5R,6S)-5-(3-chlorophenyl)-6-(4-chlorophenyl)-1-((S)-1-(6-(2-hydroxypropan-2-yl)pyridin-2-yl)propyl)-3-methyl-2-oxopiperidin-3-yl)acetic acid or 2-((3R,5R,6S)-5-(3-chlorophenyl)-6-(4-chlorophenyl)-1-((R)-1-(6-(2-hydroxypropan-2-yl)pyridin-2-yl)propyl)-3-methyl-2-oxopiperidin-3-yl)acetic acid The title compound was prepared from a mixture of (3S, 5R,6S)-3-allyl-5-(3-chlorophenyl)-6-(4-chlorophenyl)-1-((R)-1-(6-(2-hydroxypropan-2-yl)pyridin-2-yl)propyl)-3-methylpiperidin-2-one and (3S,5R,6S)-3-allyl-5-(3-chlorophenyl)-6-(4-chlorophenyl)-1-((S)-1-(6-(2-hydroxypropan-2-yl)pyridin-2-yl)propyl)-3-methylpiperidin-2-one (Example 241, Step D) following a procedure similar to the one described above in example 230, Step C. Purification of the crude mixture as described provided one of the title compounds as a single isomer as a white solid.
$^1$H NMR (400 MHz, CHLOROFORM-d) δ ppm 1.08-1.17 (m, 3H), 1.32-1.50 (m, 9H), 1.87-1.97 (m, 1H), 1.97-2.08 (m, 1H), 2.08-2.18 (m, 1H), 2.27-2.48 (m, 1H), 2.70 (br. s., 2H), 3.23 (br. s., 1H), 4.63-4.74 (m, 2H), 6.76 (m, 3H), 6.84 (br. s., 1H), 6.93 (d, J=5.87 Hz, 2H), 6.99-7.11 (m, 3H), 7.13-7.24 (m, 2H), 7.48 (br. s., 1H). Mass Spectrum (ESI) m/z=569.1 (M+1).

Example 242

2-((3R,5R,6S)-5-(3-chlorophenyl)-6-(4-chlorophenyl)-1-((S)-1-(6-cyclopropylpyridin-2-yl)propyl)-3-methyl-2-oxopiperidin-3-yl)acetic acid or 2-((3R,5R,6S)-5-(3-chlorophenyl)-6-(4-chlorophenyl)-1-((R)-1-(6-cyclopropylpyridin-2-yl)propyl)-3-methyl-2-oxopiperidin-3-yl)acetic acid

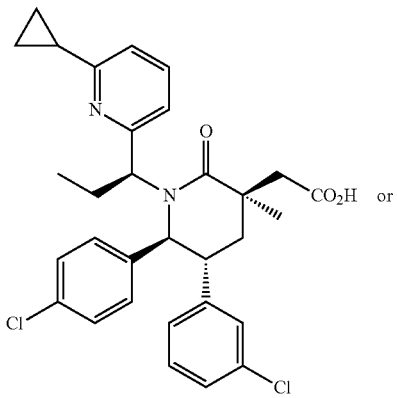

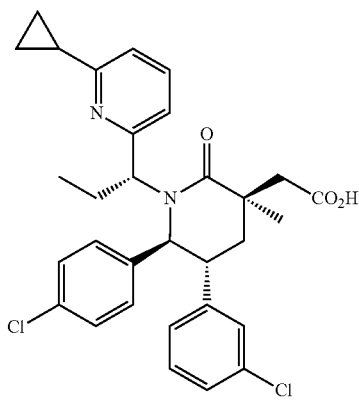

Step A. (3S,5R,6S)-3-Allyl-5-(3-chlorophenyl)-6-(4-chlorophenyl)-1-((S)-1-(6-cyclopropylpyridin-2-yl)propyl)-3-methylpiperidin-2-one or (3S,5R,6S)-3-Allyl-5-(3-chlorophenyl)-6-(4-chlorophenyl)-1-((R)-1-(6-cyclopropylpyridin-2-yl)propyl)-3-methylpiperidin-2-one

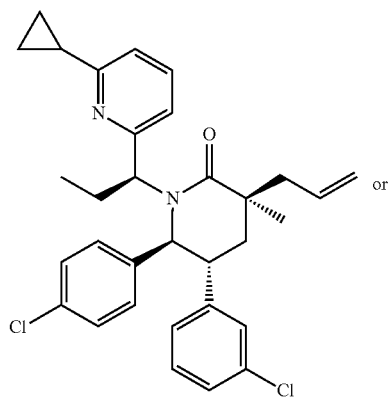

or

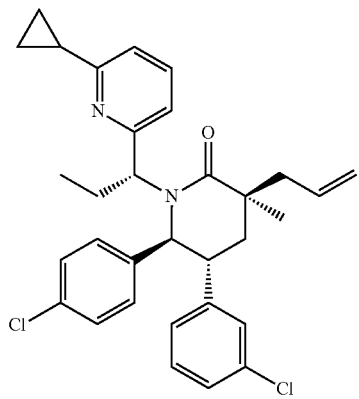

455

To a rt solution of mixture of ((3S,5R,6S)-3-allyl-1-(1-(6-bromopyridin-2-yl)propyl)-5-(3-chlorophenyl)-6-(4-chlorophenyl)-3-methylpiperidin-2-one (165 mg, 0.288 mmol; Example 239 in DMF (3 mL) was added tricyclohexylphosphine (11.32 mg, 0.04 mmol), potassium phosphate (214 mg, 1.009 mmol), cyclopropylboronic acid (49.5 mg, 0.577 mmol) and diacetoxypalladium (4.53 mg, 0.020 mmol). The mixture was sparged with $N_2$ for 5 min and then heated to 80° C. for 5 hr. The resulting solution was cooled to rt, diluted with water (6 mL), and extracted with EtOAc (8 mL×2). The organic layers were combined, washed with water, sat. aq. NaCl solution, and dried over $MgSO_4$. After removal of organic solvents under reduced pressure, purification of the residue by flash chromatography on silica gel with 0 to 70% EtOAc/hexanes provided the title compound as a colorless syrup.

Step B. 2-((3R,5R,6S)-5-(3-Chlorophenyl)-6-(4-chlorophenyl)-1-((S)-1-(6-cyclopropylpyridin-2-yl)propyl)-3-methyl-2-oxopiperidin-3-yl)acetic acid The title compound was prepared from (3S,5R,6S)-3-allyl-5-(3-chlorophenyl)-6-(4-chlorophenyl)-1-(1-(6-cyclopropylpyridin-2-yl)propyl)-3-methylpiperidin-2-one (Example 242, Step A) following a procedure similar to the one described in Example 71, Step F).

$^1$H NMR (400 MHz, CHLOROFORM-d) δ ppm 0.95-1.08 (m, 3H), 1.08-1.23 (m, 2H), 1.36-1.44 (m, 3H), 1.44-1.54 (m, 1H), 1.54-1.66 (m, 1H), 1.99-2.29 (m, 4H), 2.49-2.60 (m, 1H), 2.72 (d, J=15.26 Hz, 1H), 3.04 (d, J=15.26 Hz, 1H), 3.30-3.43 (m, 1H), 4.71 (d, J=10.17 Hz, 1H), 5.52 (br. s., 1H), 6.74 (d, J=7.63 Hz, 2H), 6.90-7.01 (m, 5H), 7.01-7.08 (m, 1H), 7.10 (d, J=8.02 Hz, 2H), 7.75 (t, J=8.02 Hz, 1H). Mass Spectrum (ESI) m/z=551.2 (M+1).

Example 243

2-((3R,5R,6S)-5-(3-Chlorophenyl)-6-(4-chlorophenyl)-3-methyl-2-oxo-1-((S)-3,3,3-trifluoro-1-(pyridin-2-yl)propyl)piperidin-3-yl)acetic acid, 2,2,2-trifluoroacetic acid salt (1:1) or 2-((3R,5R,6S)-5-(3-chlorophenyl)-6-(4-chlorophenyl)-3-methyl-2-oxo-1-((R)-3,3,3-trifluoro-1-(pyridin-2-yl)propyl)piperidin-3-yl)acetic acid, 2,2,2-trifluoroacetic acid salt (1:1)

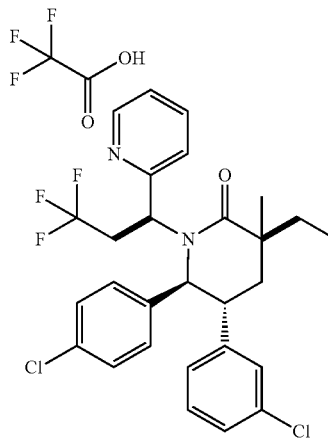

456

Step A. (3S,5R,6S)-3-Allyl-5-(3-chlorophenyl)-6-(4-chlorophenyl)-3-methyl-1-(pyridin-2-ylmethyl)piperidin-2-one

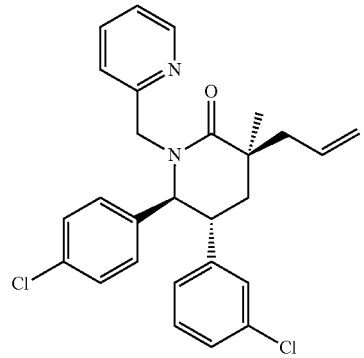 [SMILES: C=CC[C@@]1(C)C[C@H](c2cccc(Cl)c2)[C@@H](c2ccc(Cl)cc2)N(Cc2ccccn2)C1=O]

To a solution of (3S,5R,6S)-3-allyl-5-(3-chlorophenyl)-6-(4-chlorophenyl)-3-methylpiperidin-2-one (2.246 g, 6 mmol; Example 71D) in DMF (25 mL) was added sodium hydride, 60% dispersion in mineral oil (0.504 g, 12.60 mmol) and the mixture was stirred at 0° C. for 5 minutes. To this was added 2-(bromomethyl)pyridine hydrobromide (1.593 g, 6.30 mmol) at 0° C. The resulting mixture was stirred at 0° C. for 10 min and quenched with saturated $NH_4Cl$ solution, extracted with EtOAc, washed with sat. aq. NaCl solution, dried over $MgSO_4$, filtered and the filtrate was concentrated. The residue was purified by flash chromatography on silica gel (eluent: 0 to 100% EtOAc in hexanes) to give the title compound. Mass Spectrum (ESI) m/z=465 (M+1).

Step B. (3S,5R,6S)-3-Allyl-5-(3-chlorophenyl)-6-(4-chlorophenyl)-3-methyl-1-((S)-3,3,3-trifluoro-1-(pyridin-2-yl)propyl)piperidin-2-one or (3S,5R,6S)-3-Allyl-5-(3-chlorophenyl)-6-(4-chlorophenyl)-3-methyl-1-((R)-3,3,3-trifluoro-1-(pyridin-2-yl)propyl)piperidin-2-one

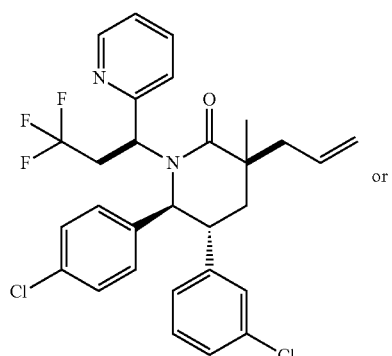

or

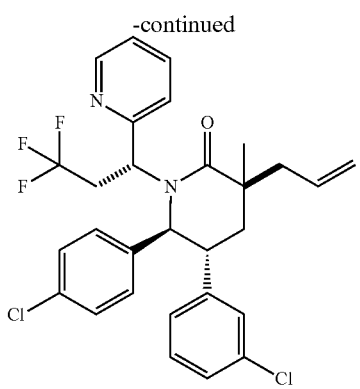

To a solution of (3S,5R,6S)-3-allyl-5-(3-chlorophenyl)-6-(4-chlorophenyl)-3-methyl-1-(pyridin-2-ylmethyl)piperidin-2-one (660 mg, 1.418 mmol; Example 243, Step A) in inhibitor free THF (7 mL) under N₂ at −78° C. was added lithium diisopropylamide (1.418 mL, 2.84 mmol) and the mixture was stirred for 30 min. 1,1,1-Trifluoro-2-iodoethane (744 mg, 3.55 mmol; Sigma, St. Louis, Mo.) was added and the orange reaction was stirred at −78° C. for 1 h. The reaction was then warmed to rt and stirred overnight. The mixture was quenched with 0.2 mL of MeOH, filtered, concentrated and the residue was purified by HPLC(C18 column, eluted with 10-95% CH₃CN in Water, with 0.1% TFA) to give the title compound as the slower eluting diasteromer.

Mass Spectrum (ESI) m/z=547 (M+1).

Step C. 2-((3R,5R,6S)-5-(3-chlorophenyl)-6-(4-chlorophenyl)-3-methyl-2-oxo-1-((S)-3,3,3-trifluoro-1-(pyridin-2-yl)propyl)piperidin-3-yl)acetic acid/2,2,2-Trifluoroacetic acid (1:1)

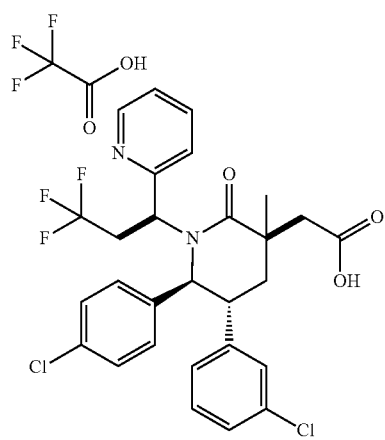

The title compound was obtained from (3S,5R,6S)-3-allyl-5-(3-chlorophenyl)-6-(4-chlorophenyl)-3-methyl-1-((S)-3,3,3-trifluoro-1-(pyridin-2-yl)propyl)piperidin-2-one (61.2 mg, 0.112 mmol; Example 243, Step B) by a procedure similar to the one described in Example 71, Step F.

¹H NMR (400 MHz, CHLOROFORM-d) δ ppm 8.96 (1 H, d, J=4.7 Hz), 8.09 (1 H, t, J=7.8 Hz), 7.86 (1 H, d, J=8.2 Hz), 7.56-7.68 (1 H, m), 7.22 (4 H, s), 7.08-7.17 (3 H, m), 6.94 (1 H, s), 6.90 (1 H, d, J=6.7 Hz), 5.27-5.38 (1 H, m), 4.95 (1 H, d, J=6.5 Hz), 3.63 (1 H, dt, J=16.1, 9.8 Hz), 3.28-3.40 (1 H, m), 2.88 (1 H, d, J=15.1 Hz), 2.74 (1 H, d, J=15.1 Hz), 2.59-2.71 (1 H, m), 2.12-2.25 (1 H, m), 1.98-2.09 (1 H, m), 1.15 (3 H, s). Mass Spectrum (ESI) m/z=565 (M+1).

Example 244

2-((3R,5R,6S)-5-(3-chlorophenyl)-6-(4-chlorophenyl)-3-methyl-2-oxo-1-((S)-3,3,3-trifluoro-1-(pyridin-2-yl)propyl)piperidin-3-yl)acetic acid, as the 2,2,2-trifluoroacetic acid (1:1) salt

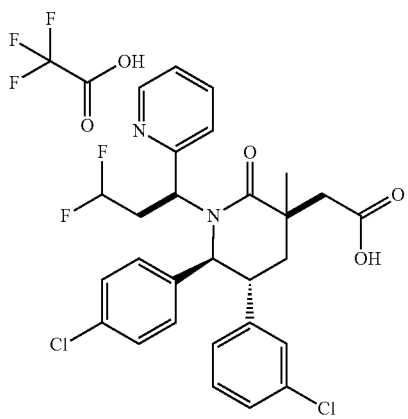

Step A. (3S,5R,6S)-3-Allyl-5-(3-chlorophenyl)-6-(4-chlorophenyl)-1-((S)-3,3-difluoro-1-(pyridin-2-yl)propyl)-3-methylpiperidin-2-one

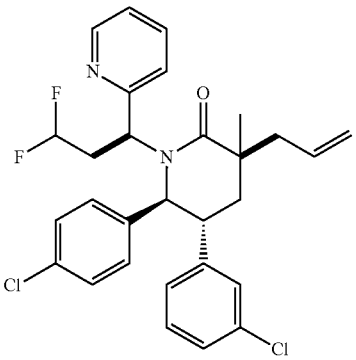 [SMILES: C=CC[C@@]1(C)C[C@H](c2cccc(Cl)c2)[C@@H](c2ccc(Cl)cc2)N([C@@H](CC(F)F)c2ccccn2)C1=O]

To a solution of (3S,5R,6S)-3-allyl-5-(3-chlorophenyl)-6-(4-chlorophenyl)-3-methyl-1-(pyridin-2-ylmethyl)piperidin-2-one (705 mg, 1.515 mmol; Example 71, Step D) in inhibitor free THF (7 mL) under N₂ at −78° C. was added lithium diisopropylamide (1.515 mL, 3.03 mmol) and the mixture was stirred for 30 min. 1,1-Difluoro-2-iodoethane (727 mg, 3.79 mmol; Oakwood) was added and the orange reaction mixture was stirred at −78° C. for 1 h. The reaction was warmed to rt overnight and quenched with 0.2 mL of MeOH, filtered and concentrated. The residue was purified by HPLC(C18 column, eluted with 10-95% CH₃CN in water, with 0.1% TFA) to give (3S,5R,6S)-3-allyl-5-(3-chlorophenyl)-6-(4-chlorophenyl)-1-((R)-3,3-difluoro-1-(pyridin-2-yl)propyl)-3-methylpiperidin-2-one (HPLC retention time 7.38 min, Agilent Eclipse Plus C18 column, 0.1% TFA in CH₃CN/H₂O, gradient 70%-90% over 25 minutes) and (3S,5R,6S)-3-allyl-5-(3-chlorophenyl)-6-(4-chlorophenyl)-1-((S)-3,3-difluoro-1-(pyridin-2-yl)propyl)-3-methylpiperidin-2-one (HPLC retention time 7.94 min, Agilent Eclipse Plus C18 column (Agilent Technologies, Santa Clara, Calif.), 0.1% TFA in CH₃CN/H₂O, gradient 70%-90% over 25 minutes). Mass Spectrum (ESI) m/z=529 (M+1).

Step B. 2-((3R,5R,6S)-5-(3-chlorophenyl)-6-(4-chlorophenyl)-3-methyl-2-oxo-1-((S)-3,3,3-trifluoro-1-(pyridin-2-yl)propyl)piperidin-3-yl)acetic acid/2,2,2-Trifluoroacetic acid (1:1)

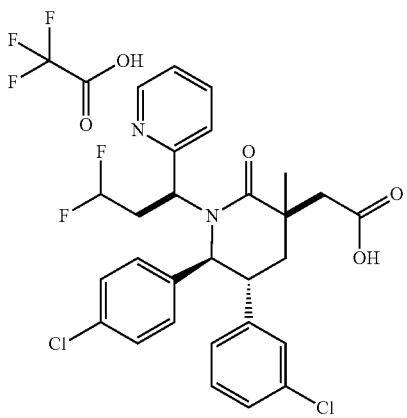

The title compound was obtained from (3S,5R,6S)-3-allyl-5-(3-chlorophenyl)-6-(4-chlorophenyl)-1-((S)-3,3-difluoro-1-(pyridin-2-yl)propyl)-3-methylpiperidin-2-one (50 mg, 0.095 mmol; Example 244, Step A;) by a procedure similar to the one described in Example 71, Step F.

¹H NMR (400 MHz, CHLOROFORM-d) δppm 9.03 (1 H, d, J=4.3 Hz), 8.17 (1 H, t, J=7.8 Hz), 7.79 (1 H, d, J=8.2 Hz), 7.72 (1 H, t, J=6.3 Hz), 7.18-7.25 (4 H, m), 7.08-7.16 (2 H, m), 6.95 (1 H, s), 6.88-6.93 (1 H, m), 5.44 (1 H, br. s.), 5.31 (2 H, d, J=10.4 Hz), 5.21 (6 H, br. s.), 5.10 (2 H, br. s.), 3.30-3.42 (1 H, m), 3.18 (1 H, br. s.), 2.90 (1 H, d, J=15.1 Hz), 2.72 (1 H, d, J=15.1 Hz), 2.44 (1 H, d, J=16.4 Hz), 2.27 (1 H, t, J=13.8 Hz), 1.98-2.08 (1 H, m), 1.21 (3 H, s).
Mass Spectrum (ESI) m/z=547 (M+1).

Example 245

2-((3R,5R,6S)-5-(3-chlorophenyl)-6-(4-chlorophenyl)-3-methyl-1-((S)-2-methyl-1-(pyridin-2-yl)propyl)-2-oxopiperidin-3-yl)acetic acid or 2-((3R,5R,6S)-5-(3-chlorophenyl)-6-(4-chlorophenyl)-3-methyl-1-((R)-2-methyl-1-(pyridin-2-yl)propyl)-2-oxopiperidin-3-yl)acetic acid

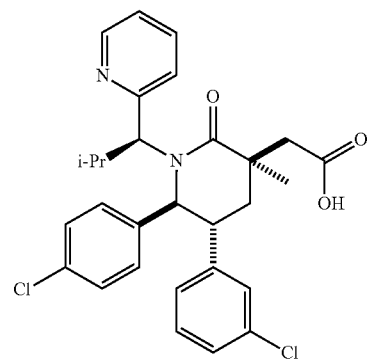

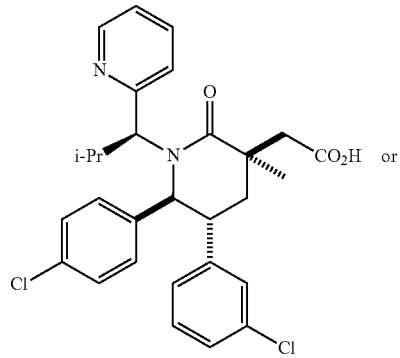

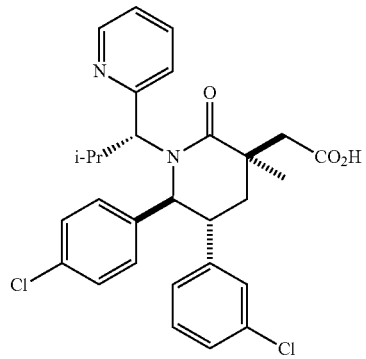

Step A: 2-(1-Bromo-2-methylpropyl)pyridine

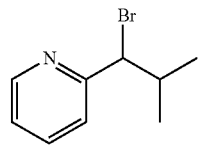

The title compound was prepared from 2-isobutylpyridine (5.17 g, 38.2 mmol; Alfa Aesar, Ward Hill, Mass.) following a procedure similar to the one described in Example 230. The reaction mixture was cooled to rt and filtered, washing the filtered cake copiously with DCM. The filtrate was concentrated in vacuo and purified by chromatography on silica gel, eluting with a 0 to 25% gradient of EtOAc in hexanes. Fractions containing the desired product were concentrated to give the title compound.

Step B. (3S,5R,6S)-3-allyl-5-(3-chlorophenyl)-6-(4-chlorophenyl)-3-methyl-1-((S)-2-methyl-1-(pyridin-2-yl)propyl)piperidin-2-one or (3S,5R,6S)-3-allyl-5-(3-chlorophenyl)-6-(4-chlorophenyl)-3-methyl-1-((S)-2-methyl-1-(pyridin-2-yl)propyl)piperidin-2-one

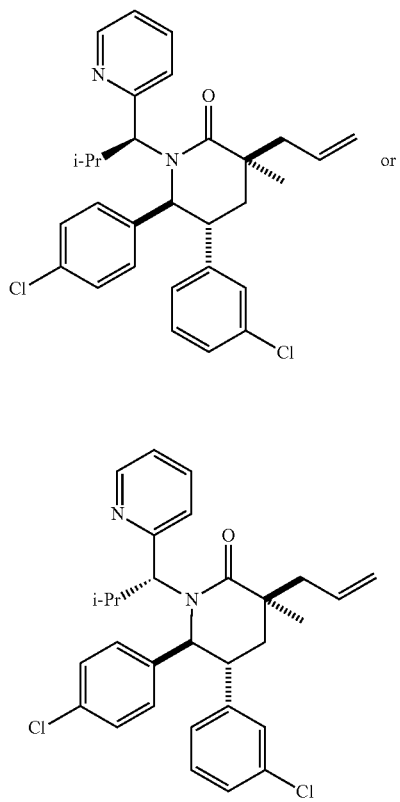 [SMILES: C=CC[C@@]1(C)C[C@H](c2cccc(Cl)c2)[C@@H](c2ccc(Cl)cc2)N([C@H](c2ccccn2)C(C)C)C1=O ; C=CC[C@@]1(C)C[C@H](c2cccc(Cl)c2)[C@@H](c2ccc(Cl)cc2)N([C@@H](c2ccccn2)C(C)C)C1=O]

2-(1-Bromo-2-methylpropyl)pyridine (Example 245, Step A) and (3S,5R,6S)-3-allyl-5-(3-chlorophenyl)-6-(4-chlorophenyl)-3-methylpiperidin-2-one (Example 71, Step D) were combined according to a procedure similar to the one described in Example 226, Step C leading after separation to the title compound as the less abundant diastereomer. MS (ESI) 507 [M+H]$^+$.

Step C 2-((3R,5R,6S)-5-(3-chlorophenyl)-6-(4-chlorophenyl)-3-methyl-1-((S)-2-methyl-1-(pyridin-2-yl)propyl)-2-oxopiperidin-3-yl)acetic acid or 2-((3R,5R,6S)-5-(3-chlorophenyl)-6-(4-chlorophenyl)-3-methyl-1-((R)-2-methyl-1-(pyridin-2-yl)propyl)-2-oxopiperidin-3-yl)acetic acid The title compound was obtained by treating the compound of Example 245, Step B by the procedure as described in Example 71, Step F.

$^1$H NMR (500 MHz, DICHLOROMETHANE-d$_2$) δ 0.87 (d, J=6.11 Hz, 3 H), 1.18 (br. s., 3 H), 1.33-1.47 (m, 3 H), 1.96-2.10 (m, 1 H), 2.10-2.27 (m, 1 H), 2.70-2.88 (m, 3 H), 3.19-3.30 (m, 1 H), 4.66 (d, J=9.54 Hz, 1 H), 6.73 (d, J=7.58 Hz, 1 H), 6.84 (br. s., 2 H), 6.97 (br. s., 3 H), 7.05-7.23 (m, 3 H), 7.55 (t, J=6.60 Hz, 1 H), 7.82 (t, J=8.31 Hz, 1 H), 8.79 (d, J=4.89 Hz, 1 H). MS (ESI) 525 [M+H]$^+$.

Example 246

(3R,5R,6S)-3-((1H-tetrazol-5-yl)methyl)-5-(3-chlorophenyl)-6-(4-chlorophenyl)-3-methyl-1-(pentan-3-yl)piperidin-2-one

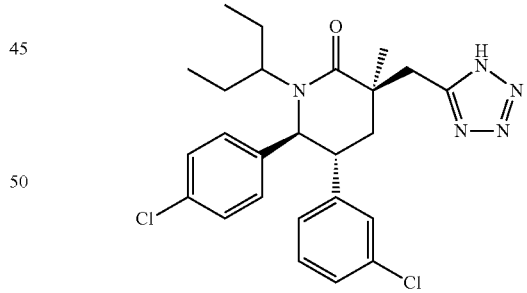

The title compound was prepared from 2-((3R,5R,6S)-5-(3-chlorophenyl)-6-(4-chlorophenyl)-3-methyl-2-oxo-1-(pentan-3-yl)piperidin-3-yl)acetic acid (Example 71) as described in Example 86.

$^1$H NMR (400 MHz, CHLOROFORM-d) δ ppm 0.49 (t, J=7.53 Hz, 3 H) 0.97 (t, J=7.43 Hz, 3 H) 1.33 (s, 3 H) 1.37-1.58 (m, 2 H) 1.84-2.05 (m, 2 H) 2.17-2.35 (m, 2 H) 2.77 (dt, J=9.00, 4.50 Hz, 1 H) 3.05-3.21 (m, 1 H) 3.42-3.64 (m, 2

H) 4.36 (d, J=10.37 Hz, 1 H) 6.71 (d, J=7.63 Hz, 1 H) 6.82 (d, J=7.63 Hz, 2 H) 6.98 (t, J=1.66 Hz, 1 H) 7.06-7.25 (m, 4 H). Mass spectrum (ESI) m/z 486.3 [M+H]+.

Example 247

(3R,5R,6S)-5-(3-chlorophenyl)-6-(4-chlorophenyl)-3-((R)-2,3-dihydroxypropyl)-1-((2S,3S)-2-hydroxypentan-3-yl)-3-methylpiperidin-2-one and (3R,5R,6S)-5-(3-chlorophenyl)-6-(4-chlorophenyl)-3-((S)-2,3-dihydroxypropyl)-1-((2S,3S)-2-hydroxypentan-3-yl)-3-methylpiperidin-2-one

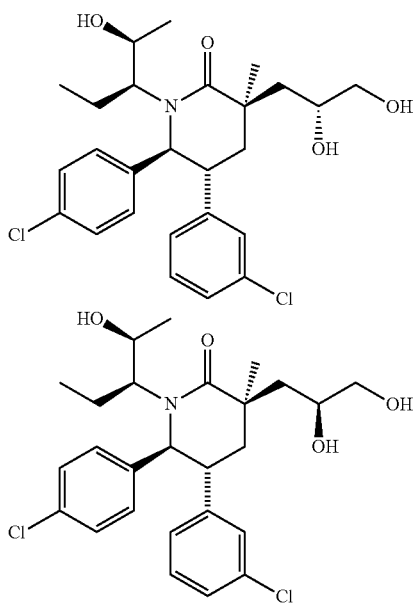

Step A. (3S,5R,6S)-3-Allyl-5-(3-chlorophenyl)-6-(4-chlorophenyl)-1-((2S,3S)-2-hydroxypentan-3-yl)-3-methylpiperidin-2-one

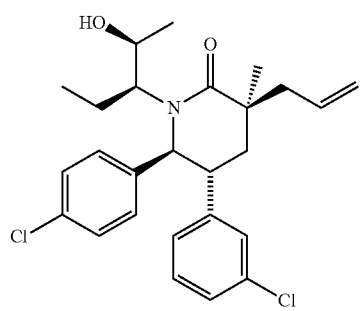 [SMILES: C=CC[C@@]1(C)C[C@H](c2cccc(Cl)c2)[C@@H](c2ccc(Cl)cc2)N([C@@H](CC)[C@H](C)O)C1=O]

To a stirred solution of (3S,5R,6S)-3-allyl-5-(3-chlorophenyl)-6-(4-chlorophenyl)-3-methyl-1-((S)-2-oxopentan-3-yl)piperidin-2-one (185 mg, 0.40 mmol; Example 149, Step B) in THF (4 mL) under a nitrogen atmosphere at −8° C. (internal temperature) was added L-Selectride® (Aldrich, St. Louis, Mo.) (0.48 mL, 0.48 mmol, 1M solution in THF) dropwise over 2 minutes (internal temperature reached −5° C.). After 10 minutes the reaction was quenched with MeOH (0.1 mL) and treated with Oxone® (2 KHSO$_5$.KHSO$_4$.K$_2$SO$_4$, DuPont, Wilmington, Del.) (992 mg, 1.61 mmol) in water (30 mL) and then it was stirred at rt for 2 hours. After this time the reaction was partitioned between EtOAc (50 mL) and Na$_2$S$_2$O$_3$ (30 mL, saturated aqueous solution). The separated organic layer was washed with brine (20 mL) and then it was dried over MgSO$_4$, filtered and evaporated in vacuo to give the title compound. Mass Spectrum (ESI) m/z=460.0 (M+1).

Step B: (3R,5R,6S)-5-(3-chlorophenyl)-6-(4-chlorophenyl)-3-((R)-2,3-dihydroxypropyl)-1-((2S,3S)-2-hydroxypentan-3-yl)-3-methylpiperidin-2-one and (3R,5R,6S)-5-(3-chlorophenyl)-6-(4-chlorophenyl)-3-((S)-2,3-dihydroxypropyl)-1-((2S,3S)-2-hydroxypentan-3-yl)-3-methylpiperidin-2-one To a stirred solution of (3S,5R,6S)-3-allyl-5-(3-chlorophenyl)-6-(4-chlorophenyl)-1-((2S,3S)-2-hydroxypentan-3-yl)-3-methylpiperidin-2-one (75 mg, 0.163 mmol, Example 247, Step A) in t-BuOH (2 mL) was added 4-methylmorpholine 4-oxide (76 mg, 0.652 mmol) and osmium tetroxide (2.1 mg, 8.14 μmol) and the reaction was stirred at rt overnight. After this time the reaction was partitioned between EtOAc (100 mL) and Na$_2$S$_2$O$_3$ (40 mL, saturated aqueous solution). The separated organic layer was washed with NaHCO$_3$ (40 mL, saturated aqueous solution), dried over MgSO$_4$, filtered and evaporated in vacuo. The resulting residue was purified by reverse phase HPLC (Sunfire™ Prep C$_{18}$ OBD 10 μm column (Waters, Milford, Mass.), gradient of elution of 20% MeCN in water to 80% MeCN in water over a 30 min period, where both solvents contain 0.1% TFA) to give the title compounds as a separable mixture of diastereomers.

1$^{st}$ eluted isomer: $^1$H NMR (400 MHz, CHLOROFORM-d) δ ppm 6.96-7.28 (8 H, m), 6.73 (1 H, dt, J=7.6, 1.6 Hz), 4.39 (1 H, d, J=10.6 Hz), 3.96-4.06 (1 H, m), 3.71 (1 H, dd, J=11.0, 3.5 Hz), 3.56 (1 H, dd, J=11.1, 7.3 Hz), 3.26-3.38 (1 H, m), 1.78-2.15 (6 H, m), 1.44 (3 H, s), 1.19-1.39 (4 H, m), 0.50-0.67 (3 H, m). Mass Spectrum (ESI) m/z=494.0 (M+1).

2$^{nd}$ eluted isomer: $^1$H NMR (400 MHz, CHLOROFORM-d) δ ppm 6.96-7.28 (8 H, m), 6.70 (1 H, dd, J=6.2, 1.5 Hz), 4.38 (1 H, d, J=10.4 Hz), 4.31 (1 H, br. s.), 3.66-3.76 (1 H, m), 3.53-3.63 (1 H, m), 3.22-3.33 (1 H, m), 1.80-2.32 (4 H, m), 1.45 (3 H, s), 1.16-1.45 (6H, m), 0.40-0.55 (3 H, br. s.). Mass Spectrum (ESI) m/z=494.0 (M+1).

Example 248

2-((3R,5R,6S)-5-(3-Chlorophenyl)-6-(4-chlorophenyl)-1-((S)-1-hydroxybutan-2-yl)-3-methyl-2-oxopiperidin-3-yl)cyclopropanecarboxylic acid

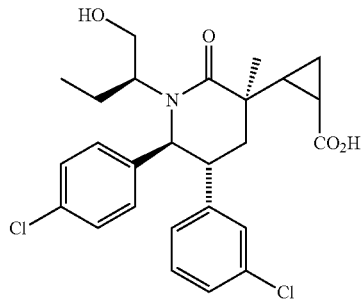 [SMILES: CC[C@@H](CO)N1C(=O)[C@@](C)(C2CC2C(=O)O)C[C@H](c2cccc(Cl)c2)[C@H]1c1ccc(Cl)cc1]

Step A. (3S,5R,6S)-Methyl 1-((S)-1-(tert-butyldiphenylsilyloxy)butan-2-yl)-5-(3-chlorophenyl)-6-(4-chlorophenyl)-3-methyl-2-oxopiperidine-3-carboxylate

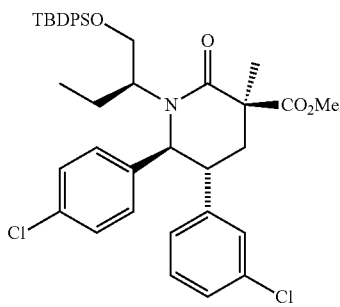

A stirred solution of (5R,6S)-1-((S)-1-(tert-butyldiphenylsilyloxy)butan-2-yl)-5-(3-chlorophenyl)-6-(4-chlorophenyl)-3-methylpiperidin-2-one (1.3 g, 2.016 mmol; Example 185, Step D) in inhibitor free THF (10 mL) was degassed for 30 minutes with argon. The reaction was transferred via cannula over 5 minutes to a freshly prepared solution of LDA at −78° C. (the LDA solution was prepared by treating N,N-diisopropylamine (0.72 mL, 5.04 mmol) in inhibitor free THF (2 mL) at −20° C. under an argon atmosphere with butyllithium (2.02 mL, 5.04 mmol, 2.5 M in hexanes) over 1 minute and stirring the mixture at −15° C. for 30 minutes). The resulting reaction mixture was stirred while warming to 0° C. over 30 minutes. The reaction was cooled to −78° C. and treated with methyl chloroformate (0.47 mL, 6.05 mmol) dropwise over 2 minutes. The reaction was stirred at −78° C. for 2 hours and 30 minutes and then quenched with 30 mL of a saturated aqueous NH₄Cl solution and allowed to warm to rt. The mixture was partitioned between ethyl acetate (150 mL) and water (50 mL). The separated organic layer was dried over MgSO₄, filtered and evaporated in vacuo. Column chromatography (SiO₂, hexanes:EtOAc, 1:0 to 4:1) gave the title compound. Mass Spectrum (ESI) m/z=702.1 (M+1).

Step B. (3R,5R,6S)-1-((S)-1-(tert-Butyldiphenylsilyloxy)butan-2-yl)-5-(3-chlorophenyl)-6-(4-chlorophenyl)-3-(hydroxymethyl)-3-methylpiperidin-2-one

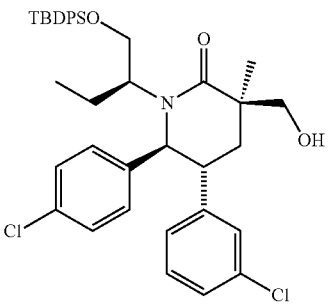

To a stirred solution of (3S,5R,6S)-methyl 1-((S)-1-(tert-butyldiphenylsilyloxy)butan-2-yl)-5-(3-chlorophenyl)-6-(4-chlorophenyl)-3-methyl-2-oxopiperidine-3-carboxylate (450 mg, 0.640 mmol; Example 248, Step A) at 0° C. in THF (4 mL) under a nitrogen atmosphere was added dropwise lithium triethylborohydride (1.60 mL, 1.60 mmol, 1M solution in THF). The reaction was stirred at 0° C. for 1 hour and then it was quenched with methanol (0.2 mL) and treated with Oxone® (2 KHSO₅.KHSO₄.K₂SO₄, DuPont, Wilmington, Del.) (1.18 g, 1.92 mmol) in water (50 mL). The mixture was stirred for 1 hour and then extracted with ethyl acetate (100 mL). The separated organic layer was washed with Na₂S₂O₃ (50 mL, saturated aqueous solution) and then dried over MgSO₄, filtered and evaporated in vacuo. Column chromatography (SiO₂, hexanes:EtOAc, 1:0 to 7:3) gave the title compound. Mass Spectrum (ESI) m/z=674.2 (M+1).

Step C. (3R,5R,6S)-1-((S)-1-(tert-Butyldiphenylsilyloxy)butan-2-yl)-5-(3-chlorophenyl)-6-(4-chlorophenyl)-3-methyl-2-oxopiperidine-3-carbaldehyde

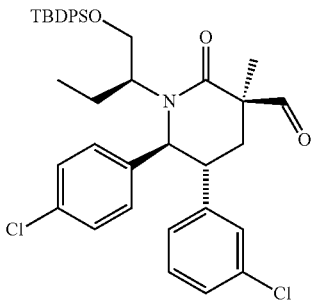

To a stirred solution of (3R,5R,6S)-1-((S)-1-(tert-butyldiphenylsilyloxy)butan-2-yl)-5-(3-chlorophenyl)-6-(4-chlorophenyl)-3-(hydroxymethyl)-3-methylpiperidin-2-one (210 mg, 0.311 mmol; Example 248, Step B) in CH₂Cl₂ (8 mL) at 0° C. was added NaHCO₃ (131 mg, 1.56 mmol) and Dess Martin periodinane (158 mg, 0.373 mmol) in one portion. The reaction was stirred at rt for 2 hours. The reaction was diluted with CH₂Cl₂ (30 mL) and treated with Na₂S₂O₃ (15 mL, saturated aqueous solution) and NaHCO₃ (15 mL, saturated aqueous solution) at rt for 2 hours. The separated aqueous layer was extracted with CH₂Cl₂ (2×50 mL) and the combined organic extracts were dried over MgSO₄, filtered and evaporated in vacuo to give the title compound.
Mass Spectrum (ESI) m/z=672.2 (M+1).

Step D. (E)-Methyl 3-((3R,5R,6S)-1-((S)-1-(tert-butyldiphenylsilyloxy)butan-2-yl)-5-(3-chlorophenyl)-6-(4-chlorophenyl)-3-methyl-2-oxopiperidin-3-yl)acrylate

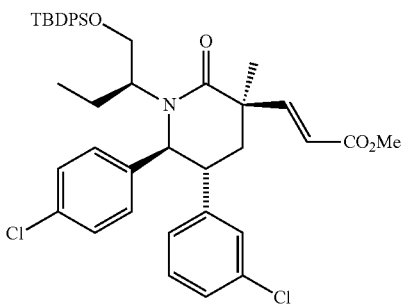

To a stirred solution of THF (4 mL) and sodium hydride (16 mg, 0.40 mmol, 60% dispersion in oil) under a nitrogen atmosphere at 0° C. was added trimethyl phosphonoacetate (61 μL, 0.43 mmol) dropwise over 30 seconds. The mixture was allowed to warm to rt for 30 minutes. A solution of (3R,5R,6S)-1-((S)-1-(tert-butyldiphenylsilyloxy)butan-2-yl)-5-(3-chlorophenyl)-6-(4-chlorophenyl)-3-methyl-2-oxopiperidine-3-carbaldehyde (205 mg, 0.305 mmol; Example 248, Step C) in THF (3 mL) was added. The resulting mixture was stirred at rt for 2 hours. The reaction was partitioned between EtOAc (80 mL) and water (40 mL). The separated organic layer was dried over MgSO$_4$, filtered and evaporated in vacuo. Column chromatography (SiO$_2$, hexanes:EtOAc, 1:0 to 8:2) gave the title compound. Mass Spectrum (ESI) m/z=728.2 (M+1).

Step E. Methyl 2-((3R,5R,6S)-1-((S)-1-((tert-butyl-diphenylsilyl)oxy)butan-2-yl)-5-(3-chlorophenyl)-6-(4-chlorophenyl)-3-methyl-2-oxopiperidin-3-yl)cyclopropanecarboxylate

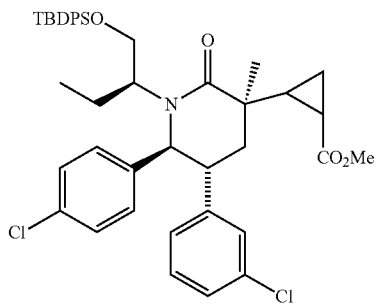

To a stirred solution of sodium hydride (12 mg, 0.30 mmol, 60% dispersion in oil) in THF (1.0 mL) under an argon atmosphere was added trimethylsulfoxonium iodide (72 mg, 0.33 mmol) portionwise over 1 minute. The reaction was stirred at rt for 1 hour. A solution of (E)-methyl 3-((3R,5R,6S)-1-((S)-1-(tert-butyldiphenylsilyloxy)butan-2-yl)-5-(3-chlorophenyl)-6-(4-chlorophenyl)-3-methyl-2-oxopiperidin-3-yl)acrylate (120 mg, 0.165 mmol; Example 248, Step D) in DMSO (1.0 mL) was added dropwise over 1 minute. The reaction was stirred at rt overnight. After this time more sulfur ylide was synthesized by suspending trimethylsulfoxonium iodide (140 mg) in DMSO (0.5 mL) under a nitrogen atmosphere and treating the mixture with NaH (24 mg, 60% dispersion in oil) and stirring for 30 minutes. The sulfur ylide was then added to the reaction and the mixture was stirred at rt for 16 hours After this time more sulfur ylide was synthesized by suspending trimesulfoxonium iodide (140 mg) in DMSO (0.5 mL) under a nitrogen atmosphere and treating the mixture with NaH (24 mg, 60% dispersion in oil) and stirring for 30 minutes. The sulfur ylide was then added to the reaction and the mixture was stirred at rt for 16 hours. The reaction was partitioned between ethyl acetate (70 mL) and NH$_4$Cl (30 mL, saturated aqueous solution). The separated organic layer was dried over MgSO$_4$, filtered and evaporated in vacuo. Purification by reverse phase HPLC (Sunfire Prep C$_{18}$ OBD 10 μm column, gradient elution of 40% MeCN in water to 100% MeCN in water over a 40 min period, where both solvents contain 0.1% TFA) gave the title compound as the first eluting and major diastereomer. Stereochemistry at the cyclopropane is a single but unassigned diastereomer. Mass Spectrum (ESI) m/z=742.2 (M+1).

Step F. 2-((3R,5R,6S)-1-((S)-1-(tert-Butyldiphenylsilyloxy)butan-2-yl)-5-(3-chlorophenyl)-6-(4-chlorophenyl)-3-methyl-2-oxopiperidin-3-yl)cyclopropanecarboxylic acid

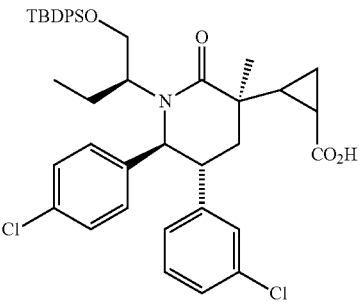

To a stirred solution of the ester from Example 248, Step E (10 mg, 0.013 mmol) in THF (1.0 mL) was added sodium hydroxide (404 μL, 0.404 mmol, 1M aqueous solution). The reaction was stirred at rt for 24 hours. After this time the reaction was partitioned between EtOAc (30 mL) and 1.0 M HCl (5 mL). The separated organic layer was dried over MgSO$_4$, filtered and evaporated in vacuo to give the title compound as a single diastereomer. Mass Spectrum (ESI) m/z=728.2 (M+1).

Step G. 2-((3R,5R,6S)-5-(3-Chlorophenyl)-6-(4-chlorophenyl)-1-((S)-1-hydroxybutan-2-yl)-3-methyl-2-oxopiperidin-3-yl)cyclopropanecarboxylic acid To a stirred solution of the acid from Example 248, Step F (10 mg, 0.014 mmol) in THF (0.2 mL) was added TBAF (0.1 mL, 1.0 M solution in THF). After 30 minutes more TBAF (0.1 mL, 1.0 M solution in THF) was added and the reaction was stirred at rt for 3 hours. After this time the reaction was partitioned between EtOAc (30 mL) and 1M aqueous HCl (5 mL). The separated organic layer was dried over MgSO$_4$, filtered and evaporated in vacuo. The resulting residue was purified by reverse phase HPLC (Sunfire Prep C$_{18}$ OBD 10 μm column, gradient elution of 20% MeCN in water to 80% MeCN in water over a 30 min period, where both solvents contain 0.1% TFA) to give the title compound.

$^1$H NMR (400 MHz, CD$_3$OD) δ ppm 7.29-7.34 (2 H, m), 7.06-7.21 (5 H, m), 6.87-6.98 (1 H, m), 4.70 (1 H, d, J=11.0 Hz), 4.06 (1 H, dd, J=11.1, 9.3 Hz), 3.45-3.56 (2 H, m), 2.89 (1 H, dt, J=8.9, 4.5 Hz), 2.48 (1 H, t, J=13.5 Hz), 1.92-2.04 (1 H, m), 1.78-1.88 (1 H, m), 1.61-1.72 (1H, m), 1.43-1.53 (2 H, m), 1.22-1.36 (6 H, m), 0.41-0.52 (3 H, m). Mass Spectrum (ESI) m/z=490.0 (M+1).

Example 249

2-((3R,5R,6S)-1-((S)-2-(tert-Butoxy)-1-cyclopropyl-2-oxoethyl)-5-(3-chlorophenyl)-6-(4-chlorophenyl)-2-oxopiperidin-3-yl)acetic acid

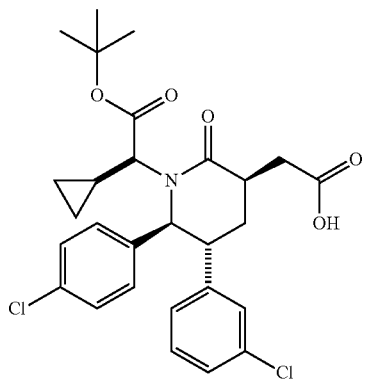 [SMILES: CC(C)(C)OC(=O)[C@H](C1CC1)N1C(=O)[C@@H](CC(=O)O)C[C@H](c2cccc(Cl)c2)[C@H]1c1ccc(Cl)cc1]

Step A. Ethyl 2-bromo-2-cyclopropylacetate

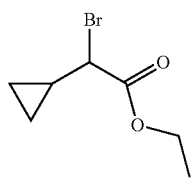

To a solution of 2-cyclopropylacetic acid (24.7 g, 247 mmol) in anhydrous DCE (250 mL) was added thionyl chloride (22 mL, 302 mmol) dropwise for 5 minutes at 25° C. After being refluxed for 2 h, the reaction was cooled to room temperature, N-bromosuccinimde (53.6 g, 301 mmol) and hydrogen bromide (48% aqueous solution) (0.195 mL, 1.727 mmol) were added successively at 25° C. The resulted mixture was heated to reflux for 96 h. After the reaction mixture was cooled to room temperature, absolute EtOH (200 mL) was added and the resulting dark brown solution was stirred at room temperature for an hour. The reaction mixture was concentrated under reduced pressure (35° C., 4.0 kilopascal) and the residue was suspended in carbon tetrachloride (300 mL) and passed through a glass filter. The filtrate was concentrated under reduced pressure (35° C., 4.0 kilopascal). Purification of the crude product by chromatography (silica gel, 330 g×2, 5% ethyl acetate/hexane) and concentration of the desired combined fractions under reduced pressure (35° C., 4.0 kilopascal) provided the title compound as a pale yellow liquid.

$^1$H NMR (400 MHz, CHLOROFORM-d) δ ppm 4.20-4.32 (2 H, m), 3.59 (1 H, d, J=10.4 Hz), 1.53-1.66 (1 H, m), 1.29-1.36 (3 H, m), 0.76-0.93 (2 H, m), 0.51-0.61 (1 H, m), 0.40-0.47 (1 H, m).

Step B. (S)-Ethyl 2-((2S,3R)-3-(3-chlorophenyl)-2-(4-chlorophenyl)-6-oxopiperidin-1-yl)-2-cyclopropylacetate

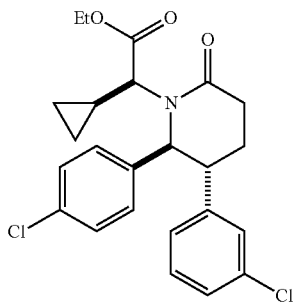 [SMILES: CCOC(=O)[C@H](C1CC1)N1C(=O)CC[C@H](c2cccc(Cl)c2)[C@H]1c1ccc(Cl)cc1]

To a solution of (3S,5R,6S)-5-(3-chlorophenyl)-6-(4-chlorophenyl)-3-piperidin-2-one (8.01 g, 25 mmol; Example 1, Step E) in DMF (60 mL) was added 60% sodium hydride in mineral oil (2.0 g, 50 mmol) at 0° C. and the mixture thus obtained was stirred at same temperature for 30 min. To the mixture was added ethyl 2-bromo-2-cyclopropylacetate (12.18 g, 50 mmol) in DMF (10 mL) dropwise and the mixture was stirred at room temperature 2 h, then the reaction was quenched with sat. ammonium chloride solution and diluted with ethyl acetate. The organic layer was washed with 10% aq. citric acid, 5% aq. NaHCO$_3$ solution, water, sat. aq. NaCl solution, then dried over MgSO$_4$. The solvent was evaporated under reduced pressure and the residue was purified by chromatography on silica gel eluting with 20% to 50% ethyl acetate in hexane to give the title compound as the first eluting diastereomer, a white solid.

$^1$H NMR (400 MHz, CHLOROFORM-d) δ ppm −0.34 (m, 1H), 0.23 (m, 1H), 0.38 (m, 1H), 0.62 (m, 1H), 1.26 (t, J=8 Hz, 3H), 1.39 (m, 1H), 2.13 (m, 2H), 2.63 (m, 2H), 3.09 (m, 1H), 3.20 (d, J=12 Hz, 1H), 4.07 (m, 2H), 4.81 (d, J=8 Hz, 1H), 6.90 (dt, J=7.1, 1.7 Hz, 1H), 7.11-7.19 (m, 5H), 7.28 (m, 2H). Mass Spectrum (ESI) m/z=446.2 (M+1).

Step C. (S)-tert-Butyl 2-((2S,3R)-3-(3-chlorophenyl)-2-(4-chlorophenyl)-6-oxopiperidin-1-yl)-2-cyclopropylacetate

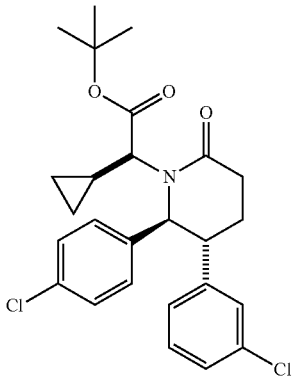 [SMILES: CC(C)(C)OC(=O)[C@H](C1CC1)N1C(=O)CC[C@H](c2cccc(Cl)c2)[C@H]1c1ccc(Cl)cc1]

To a solution of (S)-ethyl 2-((2S,3R)-3-(3-chlorophenyl)-2-(4-chlorophenyl)-6-oxopiperidin-1-yl)-2-cyclopropylacetate (500 mg, 1.12 mmol) (Example 249, Step B) in THF/MeOH/H$_2$O (5/5/5, 15 mL) was added lithium hydroxide (1.68 mL, 3.36 mmol) at rt, and then the reaction was heated to 60° C. After being stirred at 60° C. for 1.5 h, the reaction was quenched with saturated aqueous NH$_4$Cl solution and extracted (2×DCM). The combined organic layers were washed (1×sat. aq. NaCl solution), dried over Na$_2$SO$_4$, filtered and the filtrate was concentrated and concentrated under reduced pressure.

The crude acid (450 mg, 1.076 mmol) synthesized above was dissolved in DCM (10 mL) and sulfuric acid (115 uL, 2.151 mmol) was added, followed by 2-methylprop-1-ene (1.207 g, 21.51 mmol) at −78° C. The reaction vessel was sealed and the mixture was slowly warmed to ambient temperature. After being vigorously stirred for 4 days, the reaction was quenched with sat. aqueous NH$_4$Cl solution and extracted with ethyl acetate. The combined organic layers were washed with sat. aq. NaCl solution and dried over sodium sulfate, filtered and the filtrate was concentrated under reduced pressure. Purification of the residue by flash chromatography on silica gel (eluent: 40% EtOAc/hexanes) provided the title compound.

Step D. (S)-tert-Butyl 2-((3S,5R,6S)-3-allyl-5-(3-chlorophenyl)-6-(4-chlorophenyl)-2-oxopiperidin-1-yl)-2-cyclopropylacetate

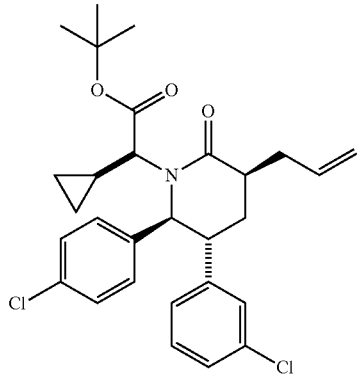 [SMILES: C=CC[C@H]1C[C@H](c2cccc(Cl)c2)[C@@H](c2ccc(Cl)cc2)N([C@H](C(=O)OC(C)(C)C)C2CC2)C1=O]

A solution of lithium bis(trimethylsilyl)amide (1M in THF, 0.165 mL, 0.165 mmol) was added dropwise at −78° C. to a solution of (S)-tert-butyl 2-((2S,3R)-3-(3-chlorophenyl)-2-(4chlorophenyl)-6-oxopiperidin-1-yl)-2-cyclopropylacetate (Example 249, Step C, 71 mg, 0.15 mmol) and allyl bromide (15.54 uL, 0.165 mmol) in 0.5 mL of THF. The reaction was allowed to warm to ambient temperature. After stirring for 2 h, the reaction was quenched with sat. aqueous ammonium chloride solution and extracted with ethyl acetate. The combined organic layers were washed with sat. aq. NaCl solution and dried over sodium sulfate, then filtered and the filtrate was concentrated under reduced pressure. Purification by flash chromatography on silica gel eluting with ethyl acetate/hexane provided the title compound.

Step E. 2-((3R,5R,6S)-5-(3-Chlorophenyl)-6-(4-chlorophenyl)-1-((S)-1-(N-cyclopropylacetamido)butan-2-yl)-3-methyl-2-oxopiperidin-3-yl)acetic acid The title compound was obtained from (S)-tert-butyl 2-((3S,5R,6S)-3-allyl-5-(3-chlorophenyl)-6-(4-chlorophenyl)-2-oxopiperidin-1-yl)-2-cyclopropylacetate (Example 249, Step D) by the procedure of example 71, step F.

¹H NMR (400 MHz, CHLOROFORM-d) δ ppm 0.08 (m, 1 H), 0.49 (m, 1 H), 0.58 (m, 1 H), 0.66 (m, 1 H), 1.02 (m, 1 H), 1.44 (s, 9 H), 1.99 (m, 1 H), 2.19 (m, 1 H), 2.58 (dd, J=16.0, 4.0 Hz, 1 H), 2.66 (m, 1 H), 2.93 (dd, J=12.0, 12.0 HZ, 1 H), 3.20 (s, 1 H), 3.34 (d, J=12 HZ, 1 H), 5.37 (s, 1 H), 7.14 (m, 1 H), 7.25-7.33 (m, 3 H), 7.37-7.45 (m, 4 H). Mass Spectrum (ESI) m/z=532.2 (M+1).

Example 250

2-((3R,5R,6S)-5-(3-Chlorophenyl)-6-(4-chlorophenyl)-1-((S)-1-cyclopropyl-2-ethoxy-2-oxoethyl)-3-methyl-2-oxopiperidin-3-yl)acetic acid

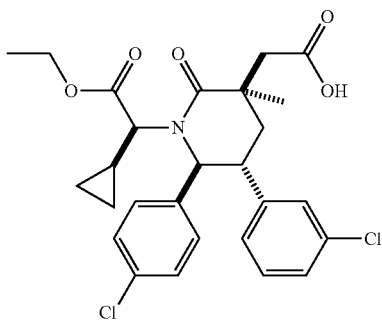

Step A. Ethyl 2-((3S,5R,6S)-3-allyl-5-(3-chlorophenyl)-6-(4-chlorophenyl)-3-methyl-2-oxopiperidin-1-yl)-2-cyclopropylacetate

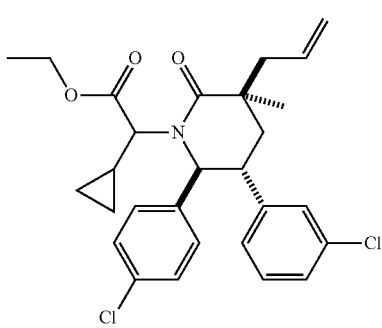

Coupling of (3S,5R,6S)-3-allyl-5-(3-chlorophenyl)-6-(4-chlorophenyl)-3-methylpiperidin-2-one (Example 71, Step D) and ethyl 2-bromo-2-cyclopropylacetate (Example 249, Step A) using the procedure as described in Example 9, step A afforded the title compound as a mixture of two diastereomers.

Step B. 2-((3R,5R,6S)-5-(3-Chlorophenyl)-6-(4-chlorophenyl)-1-((S)-1-cyclopropyl-2-ethoxy-2-oxoethyl)-3-methyl-2-oxopiperidin-3-yl)acetic acid

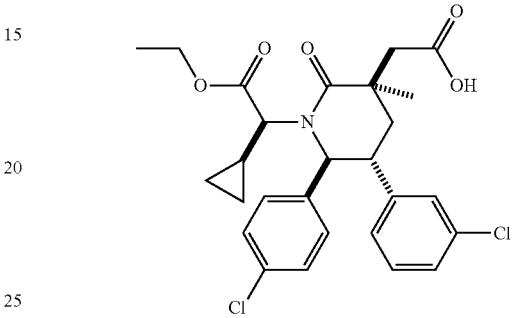

The title compound was obtained from diastereomeric ethyl 2-((3S,5R,6S)-3-allyl-5-(3-chlorophenyl)-6-(4-chlorophenyl)-3-methyl-2-oxopiperidin-1-yl)-2-cyclopropylacetate (Example 250, Step A) using the oxidation procedure described in Example 71, Step F. Individual stereoisomers were separated by chiral HPLC (150×30 mm CHIRALPAK® IC column (CHIRAL TECHNOLOGIES, INC., West Chester, Pa., USA) with 20% IPA (0.1% DEA)/CO₂, 50 mL/min, on Thar 350 SFC (Thar Technologies, Inc., Pittsburg, Pa.)) to give the title compound as the faster eluting stereoisomer.

¹H NMR (400 MHz, CHLOROFORM-d) δ ppm −0.49-−0.40 (m, 1 H) 0.12-0.21 (m, 1 H) 0.36-0.46 (m, 1 H) 0.64 (m, 1 H) 1.28 (t, J=7.14 Hz, 3 H) 1.37 (s, 3 H) 1.40-1.56 (m, 1 H) 2.14-2.27 (m, 2 H) 2.83 (d, J=14.48 Hz, 1 H) 2.95 (d, J=14.48 Hz, 1 H) 3.02 (d, J=9.78 Hz, 1 H) 3.22-3.36 (m, 1 H) 4.06-4.22 (m, 2 H) 4.75 (d, J=9.39 Hz, 1 H) 6.81 (m, 1 H) 7.00-7.21 (m, 5 H) 7.21-7.35 (m, 2 H). Mass Spectrum (ESI) m/z=518.0 (M+1).

Example 251

2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetic acid

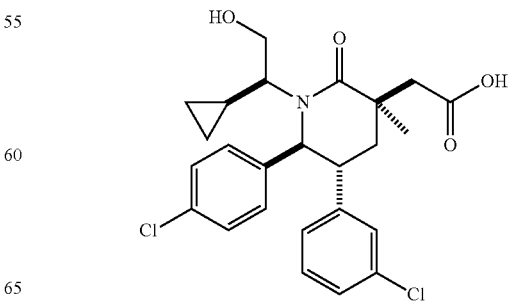

Step A. (5R,6S)-5-(3-chlorophenyl)-6-(4-chlorophenyl)-1-((S)-1-cyclopropyl-2-hydroxyethyl)piperidin-2-one

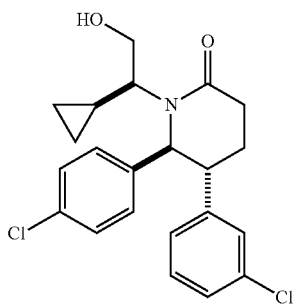

A solution of lithium borohydride (2M in THF, 15.46 mL, 30.9 mmol) was added to a solution at 0° C. of (S)-ethyl 2-((2S,3R)-3-(3-chlorophenyl)-2-(4-chlorophenyl)-6-oxopiperidin-1-yl)-2-cyclopropylacetate (Example 249, Step B, 2.3 g, 5.15 mmol) in ether (40 mL). After stirring at ambient temperature for 20 hours, the reaction was quenched with saturated aq. NH₄Cl solution and extracted into EtOAc. The organic layer was washed with sat. aq. NaCl solution, dried over sodium sulfate and concentrated to give the title compound as a solid, which was used without further purification.

¹H NMR (400 MHz, CHLOROFORM-d) δ ppm 0.00 (m, 1H), 0.23 (m, 1H), 0.48-0.57 (m, 2H), 0.85 (m, 1H), 1.99 (m, 1H), 2.07 (m, 1H), 2.61 (m, 2H), 2.64 (m, 1H), 3.22 (dd, J=11.2, 9.8 Hz, 1H), 3.42 (td, J=10.1, 4.3 Hz, 1H), 3.60 (m, 1H), 4.93 (d, J=6.5 Hz, 1H), 6.89 (m, 1H), 7.09 (m, 4H), 7.18 (m, 2H), 7.27 (m, 1H). Mass Spectrum (ESI) m/z=404.0 (M+1).

Step B. (5R,6S)-1-((S)-2-((tert-Butyldiphenylsilyl)oxy)-1-cyclopropylethyl)-5-(3-chlorophenyl)-6-(4-chlorophenyl)piperidin-2-one

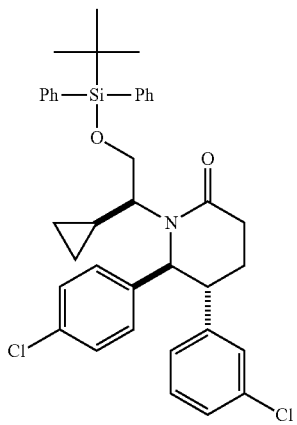

The product of example 251 step A was converted to the title compound by a procedure similar to the one described in example 185 step C.

¹H NMR (400 MHz, CHLOROFORM-d) δ ppm −0.70 (m, 1H), −0.40 (m, 1H), 0.02 (m, 1H), 0.13 (m, 1H), 0.91 (s, 9H), 1.09 (m, 1H), 1.92-1.91 (m, 2H), 2.47-2.50 (m, 2H), 2.78 (s, br, 1H), 2.80 (m, 1H), 3.31 (m, 1H), 3.98 (m, 1H), 4.62 (d, J=7.8 Hz, 1H), 6.60 (m, 1H), 6.82-6.91 (m, 4H), 6.91-7.03 (m, 3H), 7.18-7.26 (6H), 7.37-7.45 (m, 4H). Mass Spectrum (ESI) m/z=642.3 (M+1).

Step C. (5R,6S)-1-((S)-2-((tert-Butyldiphenylsilyl)oxy)-1-cyclopropylethyl)-5-(3-chlorophenyl)-6-(4-chlorophenyl)-3-methylpiperidin-2-one

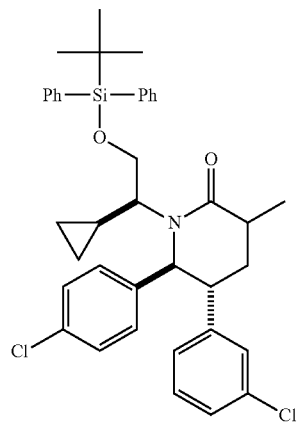

(5R,6S)-1-((S)-2-((tert-butyldiphenylsilyl)oxy)-1-cyclopropylethyl)-5-(3-chlorophenyl)-6-(4-chlorophenyl)piperidin-2-one (Example 251 Step B, 7.9 g, 12.29 mmol) was converted to the title compound, mixture of diastereomers by the method of Example 185, Step D.

¹H NMR (400 MHz, CHLOROFORM-d) δ ppm −0.15 (m, 1H), 0.00 (m, 1H), 0.41-0.52 (m, 2H), 1.26 (s, 9H), 1.41 (m, 1H), 1.62 (d, J=7.2 Hz, 3H), 2.09 (m, 1H), 2.30 (m, 1H), 2.87 (m, 1H), 3.28 (m, 2H), 3.68 (m, 1H), 4.23 (m, 1H), 5.11 (d, J=6.1 Hz, 1H), 7.16-7.34 (m, 4H), 7.37-7.46 (m, 4H), 7.51-7.65 (m, 6H), 7.74-7.78 (m, 4H).

Step D. (5R,6S)-3-Allyl-1-((S)-2-((tert-butyldiphenylsilyl)oxy)-1-cyclopropylethyl)-5-(3-chlorophenyl)-6-(4-chlorophenyl)-3-methylpiperidin-2-one

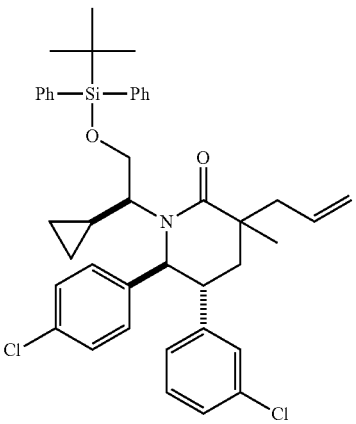

(5R,6S)-1-((S)-2-(tert-Butyldiphenylsilyloxy)-1-cyclopropylethyl)-5-(3-chlorophenyl)-6-(4-chlorophenyl)-3-methylpiperidin-2-one (5.02 g, 7.64 mmol, Example 251, Step C) was converted into the title compound by the procedure described for Example 185, Step E. After workup, the unpurified product was used as obtained.

Step E. 2-((3R,5R,6S)-1-((S)-2-((tert-Butyldiphenylsilyl)oxy)-1-cyclopropylethyl)-5-(3-chlorophenyl)-6-(4-chlorophenyl)-3-methyl-2-oxopiperidin-3-yl)acetic acid

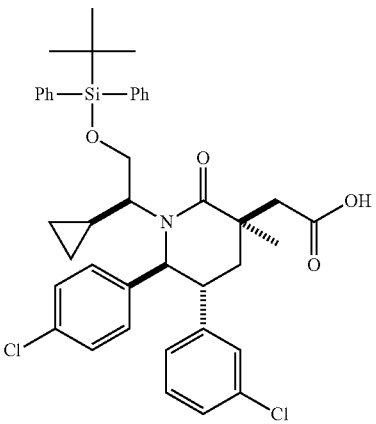

(5R,6S)-3-allyl-1-((S)-2-((tert-Butyldiphenylsilyl)oxy)-1-cyclopropylethyl)-5-(3-chlorophenyl)-6-(4-chlorophenyl)-3-methylpiperidin-2-one (Example 251, Step D, 106 mg, 0.15 mmol) was treated according to the procedure of Example 185, Step F to provide 2-((3R,5R,6S)-1-((S)-2-((tert-butyldiphenylsilyl)oxy)-1-cyclopropylethyl)-5-(3-chlorophenyl)-6-(4-chlorophenyl)-3-methyl-2-oxopiperidin-3-yl)acetic acid. Mass Spectrum (ESI) m/z=714.3 (M+1).

Step F. 2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetic acid A solution of tetrabutylammonium fluoride, (1.0 M in THF, 0.453 mL, 0.453 mmol) was added to a solution of 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)acetic acid (Example 251, Step E, 108 mg, 0.151 mmol) in THF (4 ml) and the reaction was stirred at ambient temperature for 20 hours. Analysis by LC-MS showed incomplete reaction so an extra 0.225 ml of tetrabutylammonium fluoride solution was added and the reaction was stirred for another 26 hours. The mixture was diluted in ethyl acetate then washed with water and sat. aq. NaCl solution. The organic layer was dried over sodium sulfate and concentrated. Purification by RP-HPLC (Sunfire Prep $C_{18}$ OBD 10 μm column, gradient elution of 10% MeCN in water to 80% MeCN in water over a 30 min period, where both solvents contain 0.1% TFA) afforded the title compound as a solid.

$^1$H NMR (400 MHz, CHLOROFORM-d) δppm −0.30 (s, m, 1H), 0.00 (s, m, 1H), 0.37 (m, 2H), 0.79 (m, 1H), 1.22 (s, 3H), 2.00 (m, 2H), 2.52 (d, J=14.1 Hz, 1H), 2.70 (d, J=13.9 Hz, 1H), 3.00 (m, 2H), 3.20 (s, br, 3H), 3.29 (m, 1H), 4.65 (d, J=10.0 Hz, 1H), 6.61 (m, 1H), 6.84 (s, br, 2H), 6.97 (m, 3H), 7.04 (m, 2H). Mass Spectrum (ESI) m/z=476.2 (M+1).

Example 252

2-((3R,5R,6S)-5-(3-Chlorophenyl)-6-(4-chlorophenyl)-1-((1S,2S)-1-cyclopropyl-2-hydroxybutyl)-3-methyl-2-oxopiperidin-3-yl)acetic acid or 2-((3R,5R,6S)-5-(3-Chlorophenyl)-6-(4-chlorophenyl)-1-((1S,2R)-1-cyclopropyl-2-hydroxybutyl)-3-methyl-2-oxopiperidin-3-yl)acetic acid

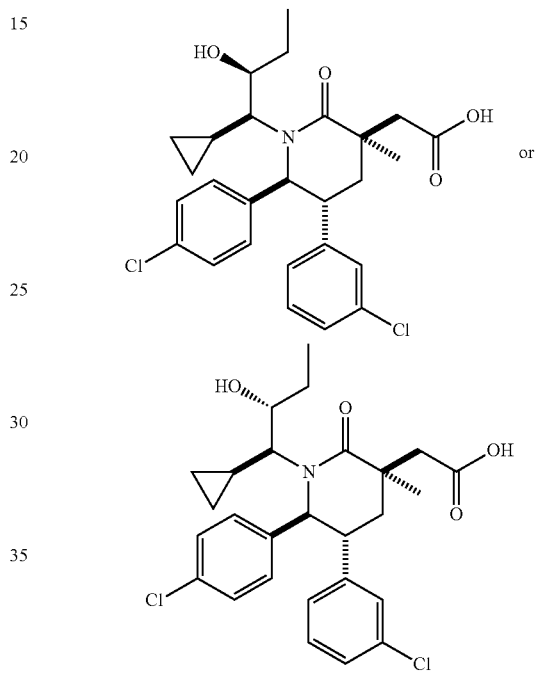

Step A. (3S,5R,6S)-3-Allyl-5-(3-chlorophenyl)-6-(4-chlorophenyl)-1-((S)-1-cyclopropyl-2-hydroxyethyl)-3-methylpiperidin-2-one

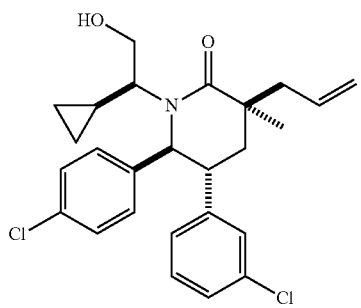

A solution of tetrabutylammonium fluoride in THF (1M, 2.10 mL, 2.10 mmol) was added to a solution of diastereomers (5R,6S)-3-allyl-1-((S)-2-(tert-butyldiphenylsilyloxy)-1-cyclopropylethyl)-5-(3-chlorophenyl)-6-(4-chlorophenyl)-3-methylpiperidin-2-one (Example 251, Step D, 488 mg, 0.700 mmol) in THF (10 ml). The reaction was stirred at ambient temperature for 2 hours. The mixture was diluted in ethyl acetate and washed with water and sat. aq. NaCl solution. The organic layer was dried over sodium sulfate. Silica gel chromatography eluting with ethyl acetate/hexane gave the title compound as a single diastereomer.

Mass Spectrum (ESI) m/z=458.0 (M+1)

Step B. (S)-2-((3S,5R,6S)-3-Allyl-5-(3-chlorophenyl)-6-(4-chlorophenyl)-3-methyl-2-oxopiperidin-1-yl)-2-cyclopropylacetaldehyde

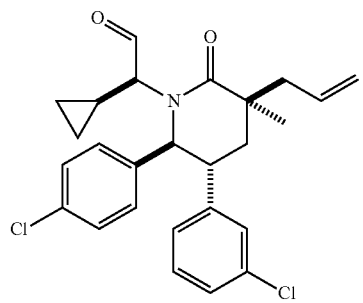

(3S,5R,6S)-3-Allyl-5-(3-chlorophenyl)-6-(4-chlorophenyl)-1-((S)-1-cyclopropyl-2-hydroxyethyl)-3-methylpiperidin-2-one (Example 252, Step A, 80 mg, 0.17 mmol) was converted to the title compound as a white foam by the procedure described in Example 91, Step C. Mass Spectrum (ESI) m/z=456.1 (M+1)

Step C. (3S,5R,6S)-3-Allyl-5-(3-chlorophenyl)-6-(4-chlorophenyl)-1-((1S,2S)-1-cyclopropyl-2-hydroxybutyl)-3-methylpiperidin-2-one or (3S,5R,6S)-3-Allyl-5-(3-chlorophenyl)-6-(4-chlorophenyl)-1-((1S,2R)-1-cyclopropyl-2-hydroxybutyl)-3-methylpiperidin-2-one

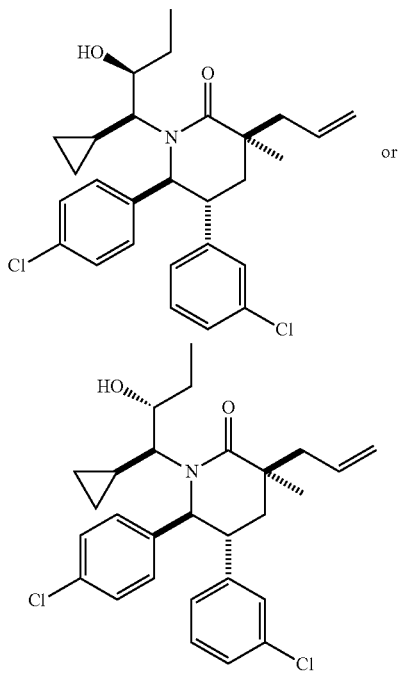

By the procedure of Example 149, Step A, substituting ethyl magnesium bromide for methyl magnesium bromide, (S)-2-((3S,5R,6S)-3-allyl-5-(3-chlorophenyl)-6-(4-chlorophenyl)-3-methyl-2-oxopiperidin-1-yl)-2-cyclopropylacetaldehyde (Example 252, Step B, 90 mg, 0.20 mmol) was converted to the title compound which was obtained as the second eluting diastereomer after chromatography.

$^1$H NMR (400 MHz, CHLOROFORM-d) δ ppm −0.43 (m, 1H), −0.16 (m, 1H), 0.32 (m, 1H), 0.51 (m, 1H), 0.78 (t, J=0.3 Hz, 3H), 1.18 (s, 3H), 1.21-1.35 (m, 1H), 2.54 (m, 2H), 1.57 (s, br, 1H), 1.87-2.0 (m, 2H), 2.21 (s, br, 1H), 2.50-2.62 (m, 2H), 3.22 (ddd, J=12.8, 10.2, 4.0 Hz, 1H), 3.68 (s, br, 1H), 4.34 (d, J=10.0 Hz, 1H), 5.12 (s, 1H), 5.14 (d, J=8 Hz, 1H), 5.79 (m, 1H), 6.65 (dt, J=7.6, 1.6 Hz, 1H), 6.87-6.91 (m, 3H), 7.01-7.07 (m, 2H), 7.16-7.18 (m, 2H). Mass Spectrum (ESI) m/z=486.3 (M+1)

Step D. 2-((3R,5R,6S)-5-(3-Chlorophenyl)-6-(4-chlorophenyl)-1-((1S,2S)-1-cyclopropyl-2-hydroxybutyl)-3-methyl-2-oxopiperidin-3-yl)acetic acid or 2-((3R,5R,6S)-5-(3-Chlorophenyl)-6-(4-chlorophenyl)-1-((1S,2R)-1-cyclopropyl-2-hydroxybutyl)-3-methyl-2-oxopiperidin-3-yl)acetic acid

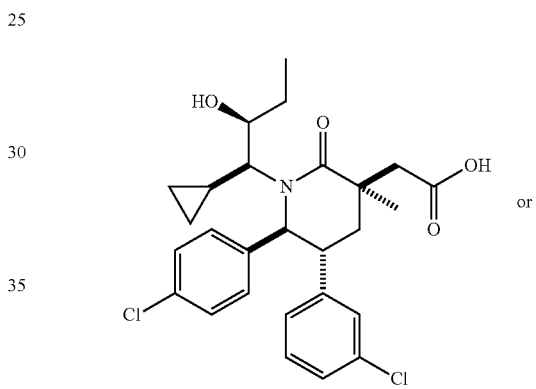

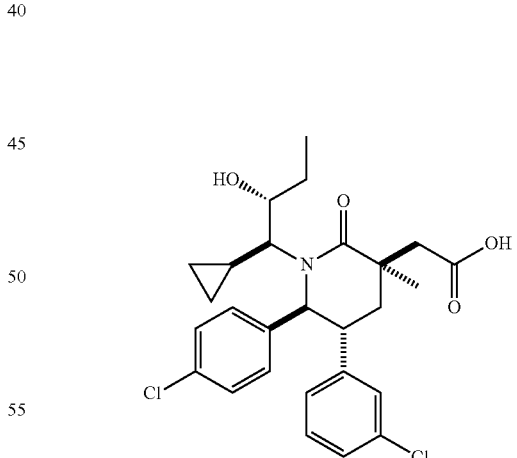

The title compound was obtained by treating the compound of Example 252, Step C by the method described in Example 71, Step F.

$^1$H NMR (400 MHz, Methanol-d4) δ ppm −0.16 (s, br, 1H), 0.26 (s, br, 1H), 0.55 (s, br, 1H), 0.67 (s, br, 1H), 0.86 (m, 3H), 1.32 (m, 4H), 1.41 (s, 3H), 1.68 (m, 1H), 1.92 (m, 2H), 2.64 (d, J=12 Hz, 1H), 2.99 (d, J=12 Hz, 1H), 3.51 (m, 1H), 4.97

(m, 1H), 6.97 (m, 1H), 7.06 (m, 1H), 7.17 (m, 4H), 7.28 (m, 2H). Mass Spectrum (ESI) m/z=504.1 (M+1).

Example 253

2-((3R,5R,6S)-5-(3-Chlorophenyl)-6-(4-chlorophenyl)-1-((S)-1-cyclopropyl-2-(N-methylcyclopropanesulfonamido)ethyl)-3-ethyl-2-oxopiperidin-3-yl)acetic acid

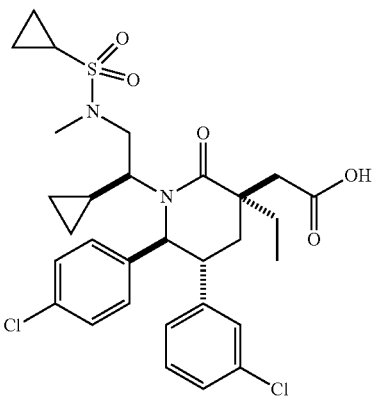

Step A. (5R,6S)-1-((S)-2-((tert-Butyldiphenylsilyl)oxy)-1-cyclopropylethyl)-5-(3-chlorophenyl)-6-(4-chlorophenyl)-3-ethylpiperidin-2-one

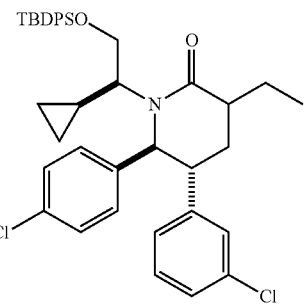

Using the procedure described for Example 185, Step D, substituting ethyl iodide for methyl iodide, (5R,6S)-1-((S)-2-(tert-butyldiphenylsilyloxy)-1-cyclopropylethyl)-5-(3-chlorophenyl)-6-(4-chlorophenyl)piperidin-2-one (Example 251, Step B, 2.6 g, 4.05 mmol) was converted to the title compound as a foam.

$^1$H NMR (400 MHz, Methanol-d4) δ ppm −0.39 (m, 1H), −0.22 (m, 1H), 0.20-0.24 (m, 1H), 0.35-0.38 (m, 1H), 1.03-1.19 (m, 14), 1.26 (t, J=4 Hz, 1H), 1.78-1.84 (m, 1H), 1.94-1.99 (m, 1H), 2.13-2.19 (m, 2H), 2.46-2.51 (m, 1H), 3.24-3.26 (m, 1H), 3.52-3.53 (m, 1H), 5.0 (d, J=8 Hz, 1H), 7.06 (m, 1H), 7.17-7.24 (m, 5H), 7.30-7.32 (m, 2H), 7.37-7.50 (m, 6H), 7.58-7.62 (m, 4H). Mass Spectrum (ESI) m/z=670.2 (M+1)

Step B. (5R,6S)-3-Allyl-1-((S)-2-((tert-butyldiphenylsilyl)oxy)-1-cyclopropylethyl)-5-(3-chlorophenyl)-6-(4-chlorophenyl)-3-ethylpiperidin-2-one

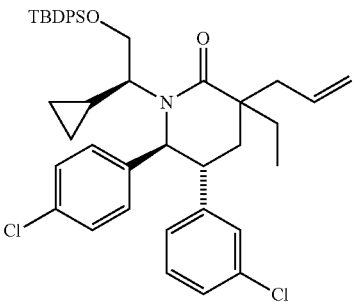

Using the procedure described for Example 185, Step E, (5R,6S)-1-((S)-2-(tert-butyldiphenylsilyloxy)-1-cyclopropylethyl)-5-(3-chlorophenyl)-6-(4-chlorophenyl)-3-methylpiperidin-2-one (Example 253, Step A, 1.6 g, 2.38 mmol) was converted to the title compound which was used without further purification.

Step C. (3S,5R,6S)-3-Allyl-5-(3-chlorophenyl)-6-(4-chlorophenyl)-1-((S)-1-cyclopropyl-2-hydroxyethyl)-3-ethylpiperidin-2-one

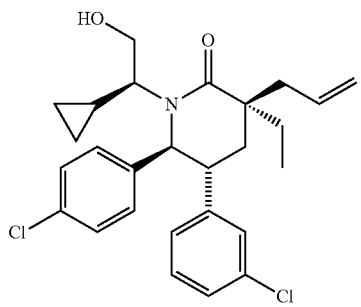 [SMILES: C=CC[C@@]1(CC)C[C@H](c2cccc(Cl)c2)[C@@H](c2ccc(Cl)cc2)N([C@H](CO)C2CC2)C1=O]

The title compound was prepared using a similar procedure as Example 202, Step A. It was isolated as the second eluting diastereomer after silica gel chromatography eluting with ethyl acetate/hexanes.

$^1$H NMR (400 MHz, Methanol-d4) δ ppm −0.48 (m, 1H), −0.01 (m, 1H), 0.40 (m, 1H), 0.48 (m, 1H), 0.97-1.01 (m, 3H), 1.37 (m, 1H), 1.49-1.58 (m, 1H), 1.75-1.78 (d, J=12 Hz, 1H), 1.97 (m, 1H), 2.38 (t, J=16 Hz, 1H), 2.65 (m, 2H), 2.76 (m, 1H), 3.94 (t, J=12 Hz, 1H), 4.79 (d, J=12 Hz, 1H), 5.20-5.28

(m, 2H), 5.94-6.03 (m, 1H), 6.96 (s, br, 1H), 7.09 (s, 2H), 3.01 (s, br, 3H), 7.29 (s, br, 2H). Mass Spectrum (ESI) m/z=472.1 (M+1).

Step D. N-((S)-2-((3S,5R,6S)-3-Allyl-5-(3-chlorophenyl)-6-(4-chlorophenyl)-3-ethyl-2-oxopiperidin-1-yl)-2-cyclopropylethyl)-N-methylcyclopropanesulfonamide

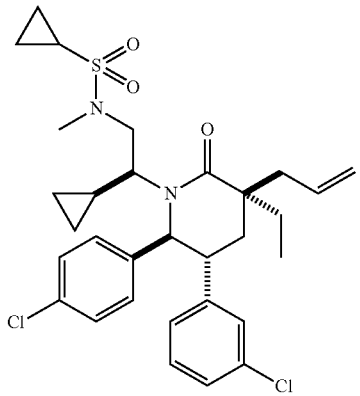 [SMILES: C=CC[C@@]1(CC)C[C@H](c2cccc(Cl)c2)[C@@H](c2ccc(Cl)cc2)N([C@H](CN(C)S(=O)(=O)C2CC2)C2CC2)C1=O]

(3S,5R,6S)-3-Allyl-5-(3-chlorophenyl)-6-(4-chlorophenyl)-1-((S)-1-cyclopropyl-2-hydroxyethyl)-3-ethylpiperidin-2-one (Example 253, Step C, 125 mg, 0.265 mmol) was converted to the title compound by the procedure described in Example 202, Step C.

¹H NMR (400 MHz, Methanol-d4) δ ppm –0.46 (s, br, 1H), –0.24 (s, br, 1H), 0.48 (s, br, 2H), 0.96 (t, J=7.5 Hz, 3H), 0.99 (m, 6H), 1.71-1.79 (m, 2H), 1.88 (m, 1H), 2.35 (t, J=16 Hz, 1H), 2.51 (s, br, 1H), 2.69 (m, 2H), 3.43 (m, 2H), 4.89 (m, 1H), 5.17-5.28 (m, 2H), 5.94-6.05 (m, 1H), 7.0 (m, 1H), 7.05 (m, 1H), 7.17-7.19 (m, 4H), 7.30 (m, 2H). Mass Spectrum (ESI) m/z=589.2 (M+1).

Step E. 2-((3R,5R,6S)-5-(3-Chlorophenyl)-6-(4-chlorophenyl)-1-((S)-1-cyclopropyl-2-(N-methylcyclopropanesulfonamido)ethyl)-3-ethyl-2-oxopiperidin-3-yl)acetic acid The title compound was obtained from N-((S)-2-((3S,5R,6S)-3-allyl-5-(3-chlorophenyl)-6-(4-chlorophenyl)-3-ethyl-2-oxopiperidin-1-yl)-2-cyclopropylethyl)-N-methylcyclopropanesulfonamide (Example 253, Step D) by the procedure described in Example 71, Step F.

¹H NMR (400 MHz, CHLOROFORM-d) δ ppm –0.71 (s, br, 1H), –0.29 (s, br, 1H), 0.31-0.41 (d, br, 2H), 0.88 (m, 6H), 1.10 (s, br, 2H), 1.19 (m, 2H), 1.82-1.87 (m, 2H), 2.20-2.27 (m, 2H), 2.69-2.73 (d, J=16 Hz, 1H), 2.82 (s, br, 4H), 2.97- 3.03 (m, 3H), 4.72 (d, J=12 Hz, 1H), 6.77 (m, 1H), 6.88 (s, br, 2H), 7.06 (m, 3H), 7.16 (s, br, 2H). Mass Spectrum (ESI) m/z=607.2 (M+1).

Example 254

2-((3R,5R,6S)-5-(3-Chlorophenyl)-6-(4-chlorophenyl)-1-((S)-2-(cyclopropanesulfonamido)-1-cyclopropylethyl)-3-ethyl-2-oxopiperidin-3-yl)acetic acid

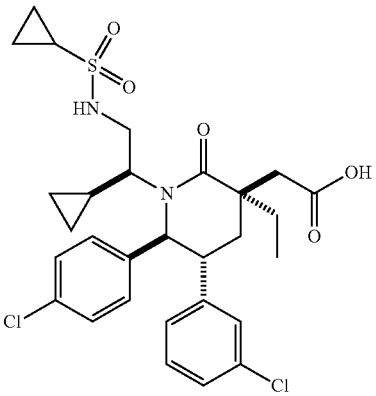 [SMILES: CC[C@]1(CC(=O)O)C[C@H](c2cccc(Cl)c2)[C@@H](c2ccc(Cl)cc2)N([C@H](CNS(=O)(=O)C2CC2)C2CC2)C1=O]

Step A. N-((S)-2-((3S,5R,6S)-3-Allyl-5-(3-chlorophenyl)-6-(4-chlorophenyl)-3-ethyl-2-oxopiperidin-1-yl)-2-cyclopropylethyl)cyclopropanesulfonamide

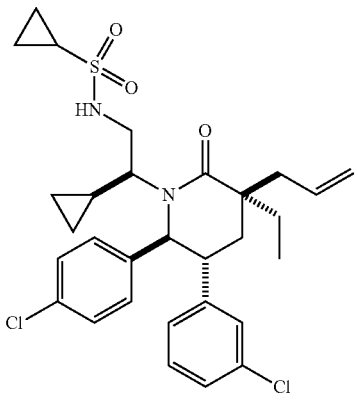 [SMILES: C=CC[C@@]1(CC)C[C@H](c2cccc(Cl)c2)[C@@H](c2ccc(Cl)cc2)N([C@H](CNS(=O)(=O)C2CC2)C2CC2)C1=O]

(3S,5R,6S)-3-Allyl-5-(3-chlorophenyl)-6-(4-chlorophenyl)-1-((S)-1-cyclopropyl-2-hydroxyethyl)-3-ethylpiperidin-2-one (Example 253, Step C,) was coupled with cyclopropanesulfonamide by the procedure described in example 202, step C to afford the title compound as a white foam.

¹H NMR (400 MHz, CHLOROFORM-d) δ ppm –0.28 (s, br, 1H), 0.00 (s, br, 1H), 0.36 (d, br, 2H), 0.66 (m, 7H), 0.89 (m, 2H), 1.50 (m, 1H), 1.53 (dd, J=13.7, 3.1 Hz, 1H), 1.98 (t, J=13.7 Hz, 1H), 2.15 (m, 1H), 2.35 (m, 1H), 2.44 (m, 1H), 2.71 (s, br, 1H), 2.85 (m, 1H), 2.97 (ddd, J=13.6, 10.6, 3.0 Hz, 1H), 3.13 (s, br, 1H), 4.54 (d, J=10.4 Hz, 1H), 4.91-4.96 (m, 2H), 5.63-5.73 (m, 1H), 6.49 (dt, J=7.5, 1.5 Hz, 1H), 6.72 (t, J=1.9 Hz, 2H), 6.85-6.91 (m, 3H), 6.94 (s, br, 2H). Mass Spectrum (ESI) m/z=575.2 (M+1).

Step B. N-((2S)-2-((3R,5R,6S)-5-(3-Chlorophenyl)-6-(4-chlorophenyl)-3-(2,3-dihydroxypropyl)-3-ethyl-2-oxopiperidin-1-yl)-2-cyclopropylethyl)cyclopropanesulfonamide

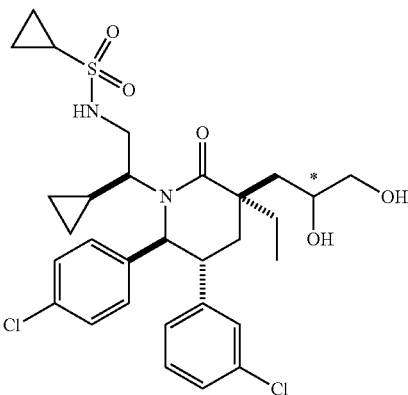 [SMILES: CC[C@]1(CC(O)CO)C[C@H](c2cccc(Cl)c2)[C@@H](c2ccc(Cl)cc2)N([C@H](CNS(=O)(=O)C2CC2)C2CC2)C1=O]

A solution of N-((S)-2-((3S,5R,6S)-3-allyl-5-(3-chlorophenyl)-6-(4-chlorophenyl)-3-ethyl-2-oxopiperidin-1-yl)-2-cyclopropylethyl)cyclopropanesulfonamide (Example 254, Step A, 80 mg, 0.139 mmol) in THF (375 µL), water (250 µL) and t-butanol (208 µL) was treated with 4-methylmorpholine N-oxide (57.0 mg, 0.486 mmol) followed by 2.5% osmium tetroxide in t-butanol (45.6 µL, 3.47 µmol). After stirring at ambient temperature for 16 h, the mixture was diluted with ethyl acetate and washed with water and sat. aq. NaCl solution. The organic layer was dried over sodium sulfate and concentrated to provide the title compound as a mixture of diastereomers (85 mg) which was used directly in the next step. Mass Spectrum (ESI) m/z=609.1 (M+1)

Step C. N-((S)-2-((3R,5R,6S)-5-(3-Chlorophenyl)-6-(4-chlorophenyl)-3-ethyl-2-oxo-3-(2-oxoethyl)piperidin-1-yl)-2-cyclopropylethyl)cyclopropanesulfonamide

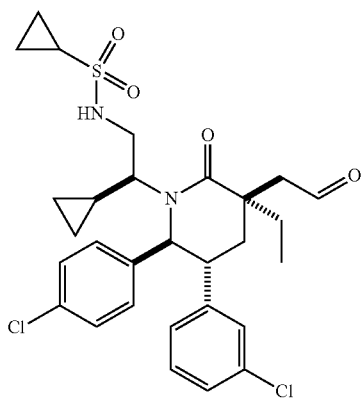 [SMILES: CC[C@]1(CC=O)C[C@H](c2cccc(Cl)c2)[C@@H](c2ccc(Cl)cc2)N([C@H](CNS(=O)(=O)C2CC2)C2CC2)C1=O]

Sodium periodate (89 mg, 0.418 mmol) was added to a clear solution of N-((2S)-2-((3R,5R,6S)-5-(3-chlorophenyl)-6-(4-chlorophenyl)-3-(2,3-dihydroxypropyl)-3-ethyl-2-oxopiperidin-1-yl)-2-cyclopropylethyl)cyclopropanesulfonamide (Example 254, Step B, 85 mg, 0.14 mmol) in water (0.5 mL) and THF (1 mL). After several minutes, a solid formed. Methanol (1 ml) was added and the resulting emulsion was stirred for 30 min. The reaction was diluted with sat. aq. NaCl solution and extracted twice with ethyl acetate. The combined organic layers were washed with sat. aq. NaCl solution, dried over sodium sulfate and concentrated under the reduced pressure to provide the title compound (94 mg) which was used without purification in the next step. Mass Spectrum (ESI) m/z=577.0 (M+1)

Step D. 2-((3R,5R,6S)-5-(3-Chlorophenyl)-6-(4-chlorophenyl)-1-((S)-2-(cyclopropanesulfonamido)-1-cyclopropylethyl)-3-ethyl-2-oxopiperidin-3-yl)acetic acid A solution of sodium chlorite (58.9 mg, 0.651 mmol) in 0.25×1.25 M potassium phosphate monobasic in water (1 mL) at 0° C. was added to a clear solution of N-((S)-2-((3R,5R,6S)-5-(3-chlorophenyl)-6-(4-chlorophenyl)-3-ethyl-2-oxo-3-(2-oxoethyl)piperidin-1-yl)-2-cyclopropylethyl)cyclopropanesulfonamide (Example 254, Step C, 94 mg, 0.163 mmol) in 1.25 M potassium phosphate monobasic in water (1 mL)+t-butanol (1 mL)+2 M 2-methylbut-2-ene in THF (4.07 mL, 8.14 mmol). After stirring at ambient temperature for 4 hours, the reaction was quenched with 0.6 mL of 1 M sodium thiosulfate solution. After stirring for 10 min at ambient temperature, the mixture was acidified with 1.2 mL of 1 M potassium bisulphate solution. The mixture was extracted with ethyl acetate. The organic layer was washed with water then sat. aq. NaCl solution and dried over sodium sulfate. Purification by reverse phase HPLC (Sunfire Prep $C_{18}$ OBD 10 µm column, gradient elution of 20% MeCN in water to 80% MeCN in water over a 30 min period, where both solvents contain 0.1% TFA) afforded the title compound.

$^1$H NMR (400 MHz, CHLOROFORM-d) δ ppm 0.00 (s, br, 1H), 0.30 (s, br, 1H), 0.64 (d, br, 2H), 0.96 (m, 7H), 1.12 (m, 3H), 1.75-1.82 (m, 1H), 1.92 (dd, J=13.8, 3.03 Hz, 1H), 2.02 (m, 1H), 2.34 (t, J=13.8 Hz, 1H), 2.47 (m, 1H), 2.84 (s, br, 3H), 3.05 (dd, J=13.0, 5.18 Hz, 1H), 3.24 (ddd, J=13.5, 10.3, 2.74 Hz, 1H), 3.53 (s, br, 1H), 4.84 (d, J=10.4 Hz, 1H), 6.78 (dt, J=7.63, 1.37 Hz, 1H) 7.02 (t, J=1.86 Hz, 2H) 7.10-7.20 (m, 5H). Mass Spectrum (ESI) m/z=593.0 (M+1).

Example 255

2-((3R,5R,6S)-5-(3-Chlorophenyl)-6-(4-chlorophenyl)-1-((S)-1-cyclopropyl-2-(ethylsulfonamido)ethyl)-3-ethyl-2-oxopiperidin-3-yl)acetic acid

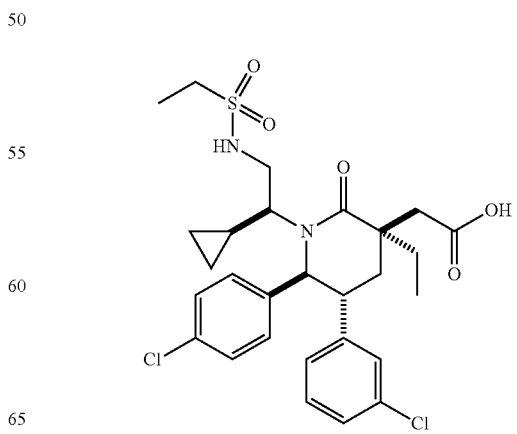

Step A. N-((S)-2-((3S,5R,6S)-3-Allyl-5-(3-chlorophenyl)-6-(4-chlorophenyl)-3-ethyl-2-oxopiperidin-1-yl)-2-cyclopropylethyl)ethanesulfonamide

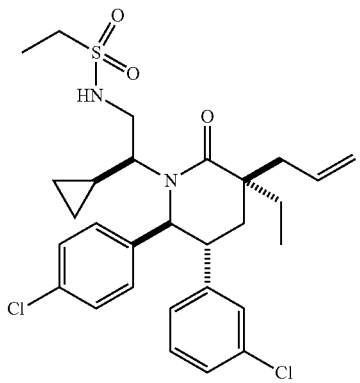 [SMILES: C=CC[C@@]1(CC)C[C@H](c2cccc(Cl)c2)[C@@H](c2ccc(Cl)cc2)N([C@H](CNS(=O)(=O)CC)C2CC2)C1=O]

Coupling of (3S,5R,6S)-3-allyl-5-(3-chlorophenyl)-6-(4-chlorophenyl)-1-((S)-1-cyclopropyl-2-hydroxyethyl)-3-ethylpiperidin-2-one (Example 253, Step C) with ethylsulfonamide according to the procedure of Example 202, Step D afforded the title compound.

$^1$H NMR (400 MHz, CHLOROFORM-d) δ ppm −0.29 (s, br, 1H), 0.00 (s, br, 1H), 0.37 (d, br, 2H), 0.69 (t, J=7.3 Hz, 3H), 1.14 (t, J=8 Hz, 3H), 1.30 (m, 1H), 1.56 (dd, J=13.7, 3.1 Hz, 1H), 1.69 (m, 1H), 2.01 (t, J=13.7 Hz, 1H), 2.38-2.40 (m, 1H), 2.44-2.48 (m, 1H), 2.77 (m, 4H), 2.99-3.12 (m, 2H), 4.58 (d, J=10.6 Hz, 1H), 4.96 (s, 1H), 4.98 (dd, J=7.0, 2.0 Hz, 1H), 5.43 (s, br, 1H), 5.67-5.76 (m, 1H), 6.54 (dt, J=7.4, 1.6 Hz, 1H), 6.75 (s, br, 2H), 63.87-6.93 (m, 3H), 6.94 (s, br, 2H). Mass Spectrum (ESI) m/z=563.2 (M+1).

Step B. N-((2S)-2-((3R,5R,6S)-5-(3-Chlorophenyl)-6-(4-chlorophenyl)-3-(2,3-dihydroxypropyl)-3-ethyl-2-oxopiperidin-1-yl)-2-cyclopropylethyl)ethanesulfonamide

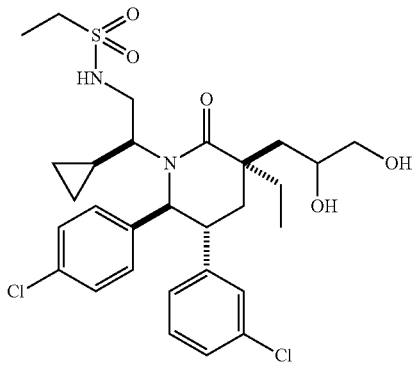 [SMILES: CC[C@]1(CC(O)CO)C[C@H](c2cccc(Cl)c2)[C@@H](c2ccc(Cl)cc2)N([C@H](CNS(=O)(=O)CC)C2CC2)C1=O]

The title compound was prepared as a mixture of diastereomers using a procedure similar to the one described in Example 254, Step B.

Step C. N-((S)-2-((3R,5R,6S)-5-(3-Chlorophenyl)-6-(4-chlorophenyl)-3-ethyl-2-oxo-3-(2-oxoethyl)piperidin-1-yl)-2-cyclopropylethyl)ethanesulfonamide

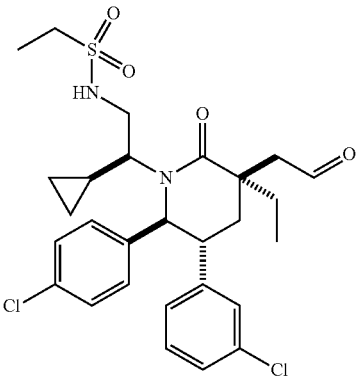 [SMILES: CC[C@]1(CC=O)C[C@H](c2cccc(Cl)c2)[C@@H](c2ccc(Cl)cc2)N([C@H](CNS(=O)(=O)CC)C2CC2)C1=O]

The title compound was prepared using a similar procedure as described for Example 254, Step C.
Mass Spectrum (ESI) m/z=565.2 (M+1).

Step D. 2-((3R,5R,6S)-5-(3-Chlorophenyl)-6-(4-chlorophenyl)-1-((S)-1-cyclopropyl-2-(ethylsulfonamido)ethyl)-3-ethyl-2-oxopiperidin-3-yl)acetic acid The title compound was obtained using a similar procedure as described for Example 254, step D.
$^1$H NMR (400 MHz, CHLOROFORM-d) δ ppm −0.51 (s, br, 1H), 0.00 (s, br, 1H), 0.39 (s, br, 1H), 0.47 (s, br, 1H), 0.97 (t, J=7.4 Hz, 4H), 1.32 (t, J=7.4 Hz, 5H), 1.74-1.81 (m, 1H), 1.93-2.02 (m, 2H), 2.37 (t, J=12 Hz, 1H), 2.64 (d, J=13.7 Hz, 1H), 2.91 (d, J=13.5 Hz, 1H), 3.04 (m, 3H), 3.40 (m, 1H), 4.90 (d, J=10.8 Hz, 1H), 6.99 (m, 1H), 7.05 (m, 2H), 7.14-7.19 (m, 5H). Mass Spectrum (ESI) m/z=581.2 (M+1).

Example 256

2-((3R,5R,6S)-5-(3-Chlorophenyl)-6-(4-chlorophenyl)-1-((S)-1-cyclopropyl-2-(N-methylcyclopropanesulfonamido)ethyl)-3-methyl-2-oxopiperidin-3-yl)acetic acid

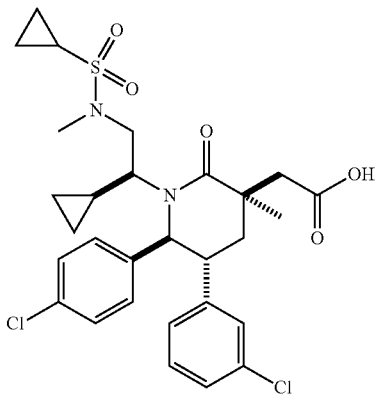 [SMILES: CN(C[C@H](C1CC1)N1C(=O)[C@@](C)(CC(=O)O)C[C@H](c2cccc(Cl)c2)[C@H]1c1ccc(Cl)cc1)S(=O)(=O)C1CC1]

487

Step A. N-((S)-2-((3S,5R,6S)-3-Allyl-5-(3-chlorophenyl)-6-(4-chlorophenyl)-3-methyl-2-oxopiperidin-1-yl)-2-cyclopropylethyl)-N-methylcyclopropanesulfonamide

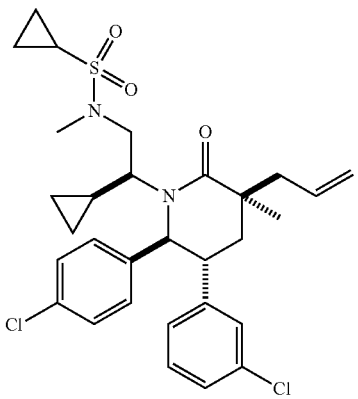 [SMILES: C=CC[C@@]1(C)C[C@H](c2cccc(Cl)c2)[C@@H](c2ccc(Cl)cc2)N([C@H](CN(C)S(=O)(=O)C2CC2)C2CC2)C1=O]

The title compound was prepared using a similar procedure as described for Example 202, Step D.

¹H NMR (400 MHz, CHLOROFORM-d) δ ppm −0.71 (s, br, 1H), −0.31 (s, br, 1H), 0.31 (s, br, 1H), 0.40 (s, br, 1H), 1.01 (m, 2H), 1.25 (m, 3H), 1.29 (s, 3H), 1.59 (s, br, 1H), 1.85-1.89 (dd, J=13.6, 3.4 Hz, 2H), 2.22 (m, 1H), 2.35 (s, br, 1H), 2.67 (d, J=8 Hz, 2H), 2.94 (s, 3H), 3.11 (m, 1H), 3.19 (m, 1H), 4.78 (d, J=8 Hz, 1H), 5.19 (m, 2H), 5.25 (s, 1H), 5.85-5.95 (m, 1H), 6.93 (m, 2H), 7.06 (m, 2H), 7.14 (m, 2H), 7.23 (m, 2H). Mass Spectrum (ESI) m/z=575.2 (M+1).

Step B. N-((2S)-2-((3R,5R,6S)-5-(3-Chlorophenyl)-6-(4-chlorophenyl)-3-(2,3-dihydroxypropyl)-3-methyl-2-oxopiperidin-1-yl)-2-cyclopropylethyl)-N-methylcyclopropanesulfonamide

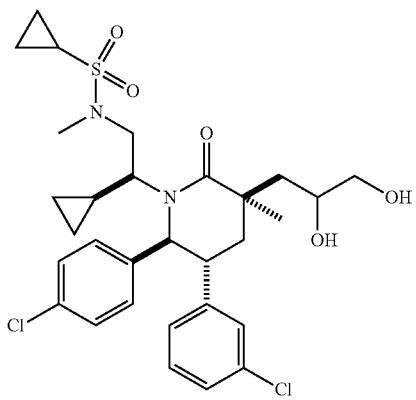 [SMILES: CN(C[C@H](C1CC1)N1C(=O)[C@@](C)(CC(O)CO)C[C@H](c2cccc(Cl)c2)[C@H]1c1ccc(Cl)cc1)S(=O)(=O)C1CC1]

488

The title compound was prepared as a mixture of diastereomers using a similar procedure to the one described in Example 254, Step B. Mass Spectrum (ESI) m/z=609.1 (M+1).

Step C. N-((S)-2-((3R,5R,6S)-5-(3-Chlorophenyl)-6-(4-chlorophenyl)-3-methyl-2-oxo-3-(2-oxoethyl)piperidin-1-yl)-2-cyclopropylethyl)-N-methylcyclopropanesulfonamide

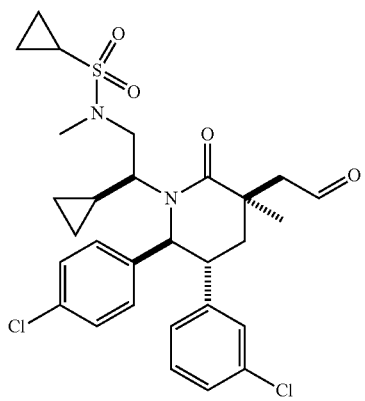

The title compound was prepared using a similar procedure as described for Example 254, Step C. Mass Spectrum (ESI) m/z=577.2 (M+1).

Step D. 2-((3R,5R,6S)-5-(3-Chlorophenyl)-6-(4-chlorophenyl)-1-((S)-1-cyclopropyl-2-(N-methylcyclopropanesulfonamido)ethyl)-3-methyl-2-oxopiperidin-3-yl)acetic acid The title compound was prepared using a similar procedure as described for Example 254, Step D.
¹H NMR (400 MHz, Methanol-d4) δ ppm −0.71 (s, br, 1H), −0.28 (s, br, 1H), 0.29 (s, br, 1H), 0.40 (s, br, 1H), 1.06 (d, br, 4H), 1.44 (s, 3H), 1.73 (s, br, 1H), 2.08 (m, 1H), 2.20 (s, br, 1H), 2.35 (t, J=8 Hz, 1H), 2.57 (s, br, 1H), 2.70 (d, J=12 Hz, 1H), 2.94 (s, 3H), 2.99 (d, J=12 Hz, 1H), 3.07 (m, 1H), 3.42 (m, 1H), 4.40 (s, br, 1H), 4.82 (d, J=8 Hz, 1H), 7.02-7.05 (m, 3H), 7.11 (m, 3H), 7.31 (s, br, 2H). Mass Spectrum (ESI) m/z=593.2 (M+1).

Example 257

2-((3R,5R,6S)-5-(3-Chlorophenyl)-6-(4-chlorophenyl)-1-((1S,2R)-1-cyclopropyl-2-hydroxypropyl)-3-methyl-2-oxopiperidin-3-yl)acetic acid

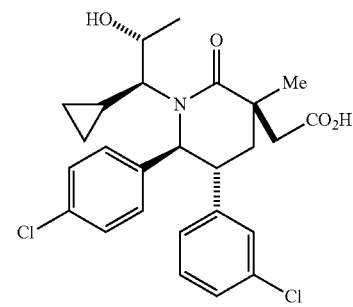 [SMILES: C[C@@H](O)[C@H](C1CC1)N1C(=O)[C@@](C)(CC(=O)O)C[C@H](c2cccc(Cl)c2)[C@H]1c1ccc(Cl)cc1]

Step A. (3S,5R,6S)-3-Allyl-1-((S)-2-(tert-butyldiphenylsilyloxy)-1-cyclopropylethyl)-5-(3-chlorophenyl)-6-(4-chlorophenyl)-3-methylpiperidin-2-one

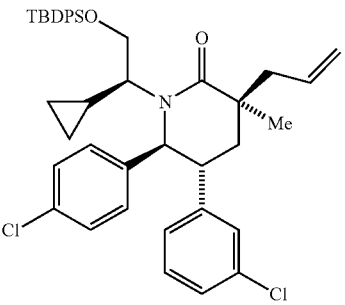

The mixture of diastereomers prepared from (5R,6S)-1-((S)-2-(tert-butyldiphenylsilyloxy)-1-cyclopropylethyl)-5-(3-chlorophenyl)-6-(4-chlorophenyl)-3-methylpiperidin-2-one (4.34 g, 6.61 mmol) by the method of Example 251, Step D was purified by silica gel chromatography, eluting with ethyl acetate/hexanes. Fractions containing the desired epimer were combined and concentrated to give (3S,5R,6S)-3-allyl-1-((S)-2-(tert-butyldiphenylsilyloxy)-1-cyclopropylethyl)-5-(3-chlorophenyl)-6-(4-chlorophenyl)-3-methylpiperidin-2-one as a white foam weighing 3.01 g (65% yield). MS (ESI) m/z=696 [M+H]+.

Step B. (3S,5R,6S)-3-Allyl-5-(3-chlorophenyl)-6-(4-chlorophenyl)-1-((S)-1-cyclopropyl-2-hydroxyethyl)-3-methylpiperidin-2-one. (see also Example 252 step A)

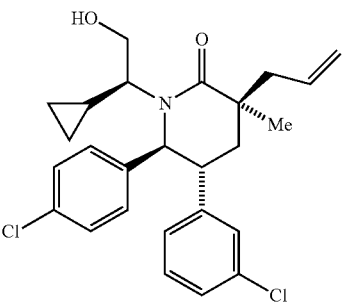 [SMILES: C=CC[C@@]1(C)C[C@H](c2cccc(Cl)c2)[C@@H](c2ccc(Cl)cc2)N([C@H](CO)C2CC2)C1=O]

Treating (3S,5R,6S)-3-allyl-1-((S)-2-(tert-butyldiphenylsilyloxy)-1-cyclopropylethyl)-5-(3-chlorophenyl)-6-(4-chlorophenyl)-3-methylpiperidin-2-one (Example 257, Step A, 3.00 g, 4.31 mmol) according to the procedure of Example 252, Step A gave (3S,5R,6S)-3-allyl-5-(3-chlorophenyl)-6-(4-chlorophenyl)-1-((S)-1-cyclopropyl-2-hydroxyethyl)-3-methylpiperidin-2-one as a white foam (1.905 g, 97%).

¹H NMR (500 MHz, CHLOROFORM-d) δ 0.00-0.15 (m, 1 H), 0.18-0.35 (m, 1 H), 0.44-0.69 (m, 2 H), 0.75-0.87 (m, 1 H), 1.28 (s, 3 H), 1.87-2.03 (m, 2 H), 2.48-2.72 (m, 2 H), 3.01-3.22 (m, 2 H), 3.41 (td, J=10.33, 4.52 Hz, 1 H), 3.60 (dd, J=11.00, 4.40 Hz, 1 H), 4.86 (d, J=10.03 Hz, 1 H), 5.06-5.24 (m, 2 H), 5.74-5.97 (m, 1 H), 6.74 (d, J=7.58 Hz, 1 H), 6.86-7.10 (m, 3 H), 7.10-7.26 (m, 4 H). MS (ESI) m/z=458 [M+H]+

Step C. (S)-2-((3S,5R,6S)-3-Allyl-5-(3-chlorophenyl)-6-(4-chlorophenyl)-3-methyl-2-oxopiperidin-1-yl)-2-cyclopropylacetaldehyde. (see also Example 252 step B)

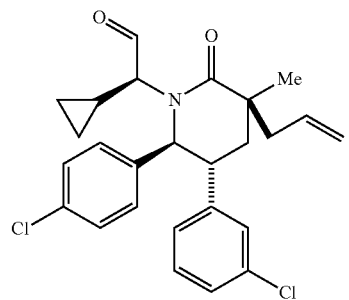 [SMILES: C=CC[C@@]1(C)C[C@H](c2cccc(Cl)c2)[C@@H](c2ccc(Cl)cc2)N([C@H](C=O)C2CC2)C1=O]

(3S,5R,6S)-3-Allyl-5-(3-chlorophenyl)-6-(4-chlorophenyl)-1-((S)-1-cyclopropyl-2-hydroxyethyl)-3-methylpiperidin-2-one (Example 257, Step B, 1.01 g, 2.2 mmol) was converted to the title compound as a white foam (866 mg, 86%) by the procedure described in Example 91, Step C. MS (ESI) m/z=456 [M+H]+.

Step D. (3S,5R,6S)-3-allyl-5-(3-chlorophenyl)-6-(4-chlorophenyl)-1-((1S,2R)-1-cyclopropyl-2-hydroxypropyl)-3-methylpiperidin-2-one and (3S,5R,6S)-3-allyl-5-(3-chlorophenyl)-6-(4-chlorophenyl)-1-((1S,2S)-1-cyclopropyl-2-hydroxypropyl)-3-methylpiperidin-2-one

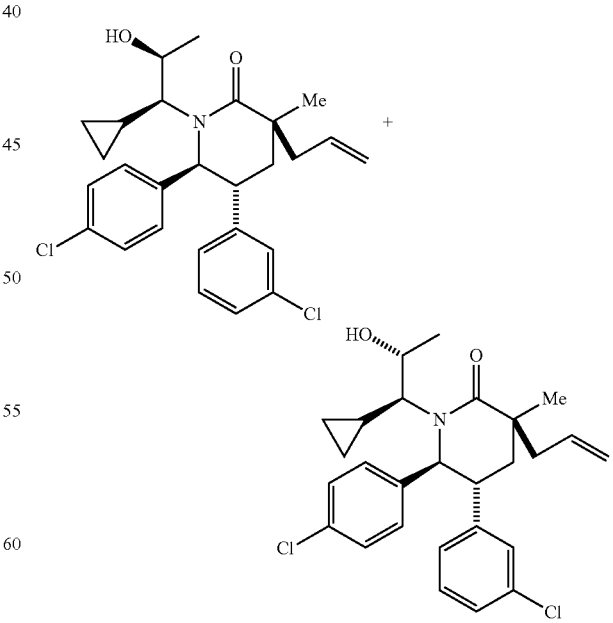

By the procedure of Example 149, Step A, (S)-2-((3S,5R,6S)-3-allyl-5-(3-chlorophenyl)-6-(4-chlorophenyl)-3-methyl-2-oxopiperidin-1-yl)-2-cyclopropylacetaldehyde (Example 257, Step C, 866 mg, 1.897 mmol) was treated with methyl magnesium bromide to give the diastereomeric alcohols (3S,5R,6S)-3-allyl-5-(3-chlorophenyl)-6-(4-chlorophenyl)-1-((1S,2R)-1-cyclopropyl-2-hydroxypropyl)-3-methylpiperidin-2-one and (3S,5R,6S)-3-allyl-5-(3-chlorophenyl)-6-(4-chlorophenyl)-1-((1S,2S)-1-cyclopropyl-2-hydroxypropyl)-3-methylpiperidin-2-one as a white foam. MS (ESI) m/z=472 [M+H]$^+$.

Step E. 2-((3R,5R,6S)-5-(3-Chlorophenyl)-6-(4-chlorophenyl)-1-((S)-1-cyclopropyl-2-oxopropyl)-3-methyl-2-oxopiperidin-3-yl)acetic acid

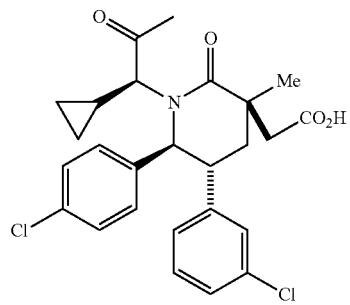 [SMILES: CC(=O)[C@H](C1CC1)N1C(=O)[C@@](C)(CC(=O)O)C[C@H](c2cccc(Cl)c2)[C@H]1c1ccc(Cl)cc1]

(3S,5R,6S)-3-Allyl-5-(3-chlorophenyl)-6-(4-chlorophenyl)-1-((S)-1-cyclopropyl-2-hydroxypropyl)-3-methylpiperidin-2-one (Example 257, Step D, 809 mg, 1.71 mmol) was treated according to the procedure described in Example 71, Step F, to afford, after SFC purification, 2-((3R,5R,6S)-5-(3-chlorophenyl)-6-(4-chlorophenyl)-1-((S)-1-cyclopropyl-2-oxopropyl)-3-methyl-2-oxopiperidin-3-yl)acetic acid as a white solid.

$^1$H NMR (500 MHz, Methanol-D4) δ −0.70−−0.47 (m, 1 H), 0.10 (dq, J=9.78, 5.05 Hz, 1 H), 0.31-0.48 (m, 1 H), 0.63 (tt, J=8.59, 5.35 Hz, 1 H), 1.34 (s, 3 H), 1.47-1.58 (m, 1 H), 2.15-2.35 (m, 6 H), 2.65 (d, J=13.69 Hz, 1 H), 2.79 (d, J=10.03 Hz, 1 H), 2.98 (d, J=13.69 Hz, 1 H), 3.48-3.57 (m, 1 H), 4.65 (d, J=10.51 Hz, 1 H), 6.94-7.01 (m, 1 H), 7.08 (s, 1 H), 7.11-7.54 (m, 6 H). MS (ESI) m/z=488 [M+H]$^+$.

Step F. 2-((3R,5R,6S)-5-(3-Chlorophenyl)-6-(4-chlorophenyl)-1-((1S,2R)-1-cyclopropyl-2-hydroxypropyl)-3-methyl-2-oxopiperidin-3-yl)acetic acid

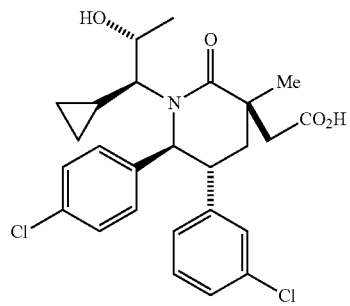 [SMILES: C[C@@H](O)[C@H](C1CC1)N1C(=O)[C@@](C)(CC(=O)O)C[C@H](c2cccc(Cl)c2)[C@H]1c1ccc(Cl)cc1]

Reduction of 2-((3R,5R,6S)-5-(3-chlorophenyl)-6-(4-chlorophenyl)-1-((S)-1-cyclopropyl-2-oxopropyl)-3-methyl-2-oxopiperidin-3-yl)acetic acid in methanol at 0° C. with sodium borohydride provided a mixture of the diastereomeric alcohols in ~2:1 ratio. The residue was purified by silica gel chromatography eluting with a gradient of isopropanol in hexanes. Fractions containing the major isomer were concentrated and then lyophilized from acetonitrile/water to provide the title compound as a fluffy white solid.

$^1$H NMR (500 MHz, Methanol-d4) δ ppm −0.29 (br s, 1 H), 0.20 (br s, 1 H), 0.46 (br s, 1 H), 0.60 (br s, 1 H), 1.19 (br s, 3 H), 1.24-1.35 (m, 1 H), 1.39 (s, 3 H), 2.10-2.29 (m, 2 H), 2.63 (d, J=13.69 Hz, 1 H), 2.82 (br s, 1 H), 2.98 (d, J=13.94 Hz, 1 H), 3.40-3.50 (m, 1 H), 3.57 (br s, 1 H), 4.82 (d, J=11.00 Hz, 1 H), 6.61-7.64 (m, 8 H). MS (ESI) m/z=490 [M+H]$^+$.

Example 258

2-((3R,5R,6S)-5-(3-Chlorophenyl)-6-(4-chlorophenyl)-1-((1S,2S)-1-cyclopropyl-2-hydroxypropyl)-3-methyl-2-oxopiperidin-3-yl)acetic acid

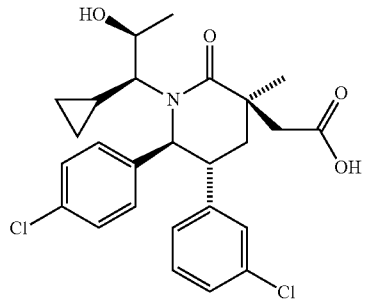 [SMILES: C[C@H](O)[C@H](C1CC1)N1C(=O)[C@@](C)(CC(=O)O)C[C@H](c2cccc(Cl)c2)[C@H]1c1ccc(Cl)cc1]

L-Selectride® (Aldrich, St. Louis, Mo.), (1M in THF, 5.0 ml, 5.00 mmol) was added dropwise over the course of 5 minutes to a solution of 2-((3R,5R,6S)-5-(3-chlorophenyl)-6-(4-chlorophenyl)-1-((S)-1-cyclopropyl-2-oxopropyl)-3-methyl-2-oxopiperidin-3-yl)acetic acid (Example 257, Step E, 1.035 g, 2.12 mmol) in THF (35 ml) at −78° C. After 90 min, the mixture was allowed to warm to 0° C. and was carefully quenched by the addition of saturated ammonium chloride. The aqueous phase was extracted three times with ethyl acetate. The combined organic layer was washed with 1 M HCl, water, sat. aq. NaCl solution and dried over sodium sulfate. After concentration in vacuo, the residue was purified by silica chromatography eluting with a gradient of isopropanol in hexanes. Fractions containing the major isomer were concentrated and then lyophilized from acetonitrile/water to provide the title compound as a white powder. Stereochemistry assigned by analogy to Example 152.

$^1$H NMR (500 MHz, DMSO-d$_6$) δ -0.69 (br s, 1 H), −0.35 (br s, 1 H), 0.17 (br s, 1 H), 0.36 (br s, 1 H), 1.07 (br s, 1 H), 1.27 (s, 4 H), 1.98-2.23 (m, 2 H), 2.53-2.58 (m, 1 H), 2.93 (d, J=13.94 Hz, 1 H), 3.36-3.49 (m, 1 H), 3.74-4.44 (m, 1 H), 4.46-5.11 (m, 2 H), 6.60-7.59 (m, 8 H). MS (ESI) m/z=490 [M+H]$^+$.

Example 259

2-((3R,5R,6S)-5-(3-Chlorophenyl)-6-(4-chlorophenyl)-1-((S)-1-cyclopropyl-2-(1-methylethylsulfonamido)ethyl)-3-methyl-2-oxopiperidin-3-yl)acetic acid

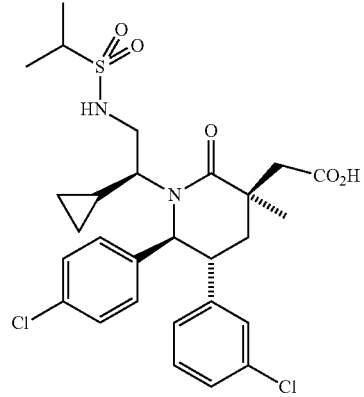 [SMILES: CC(C)S(=O)(=O)NC[C@H](C1CC1)N1C(=O)[C@@](C)(CC(=O)O)C[C@H](c2cccc(Cl)c2)[C@H]1c1ccc(Cl)cc1]

Step A: N-((S)-2-((3S,5R,6S)-3-Allyl-5-(3-chlorophenyl)-6-(4-chlorophenyl)-3-methyl-2-oxopiperidin-1-yl)-2-cyclopropylethyl)propane-2-sulfonamide

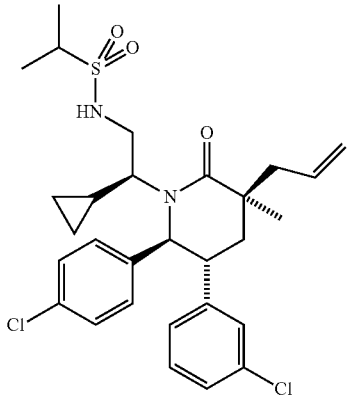 [SMILES: C=CC[C@@]1(C)C[C@H](c2cccc(Cl)c2)[C@@H](c2ccc(Cl)cc2)N([C@H](CNS(=O)(=O)C(C)C)C2CC2)C1=O]

(3S,5R,6S)-3-Allyl-5-(3-chlorophenyl)-6-(4-chlorophenyl)-1-((S)-1-cyclopropyl-2-hydroxyethyl)-3-methylpiperidin-2-one (Example 252, Step A, 59.3 mg, 0.129 mmol;) and isopropyl sulfonamide (48.7 mg, 0.395 mmol) were coupled by the procedure as described in Example 202, Step C to form the title compound isolated after silica gel chromatography as an off-white solid. MS (ESI) m/z=563 [M+H]+.

Step B: 2-((3R,5R,6S)-5-(3-Chlorophenyl)-6-(4-chlorophenyl)-1-((S)-1-cyclopropyl-2-(1-methylethylsulfonamido)ethyl)-3-methyl-2-oxopiperidin-3-yl)acetic acid The title compound was obtained from N-((S)-2-((3S,5R,6S)-3-allyl-5-(3-chlorophenyl)-6-(4-chlorophenyl)-3-methyl-2-oxopiperidin-1-yl)-2-cyclopropylethyl)propane-2-sulfonamide (Example 259, Step A) by a procedure similar to the one described in Example 71, Step F. The product was purified by reversed phase HPLC, eluting with 60 to 95% MeCN in water (0.1% TFA in both solvents). High purity fractions were combined, stripped of volatiles, and the resulting solution was frozen and lyophilized to provide the title compound as an off-white solid.

$^1$H NMR (500 MHz, CD$_3$OD) δ ppm –0.98--–0.71 (m, 1 H) –0.38--–0.16 (m, 1 H) 0.12-0.29 (m, 1 H) 0.30-0.44 (m, 1 H) 1.31-1.39 (m, 6 H) 1.41 (s, 3 H) 1.52-1.64 (m, 1 H) 2.08 (dd, J=13.69, 3.18 Hz, 1 H) 2.26 (br. s, 1 H) 2.40 (t, J=13.69 Hz, 1 H) 2.70 (d, J=13.45 Hz, 1 H) 3.00 (d, J=13.20 Hz, 1 H) 3.09 (dd, J=13.69, 3.42 Hz, 1 H) 3.25 (dt, J=13.51, 6.82 Hz, 1 H) 3.33-3.34 (m, 1 H) 3.41 (ddd, J=13.75, 10.82, 3.06 Hz, 1 H) 3.96 (br s, 1 H) 4.94 (d, J=11.00 Hz, 1 H) 6.98-7.18 (m, 5 H) 7.27 (br s, 3 H). MS (ESI) m/z=581 [M+H]+.

Example 260
2-((3R,5R,6S)-5-(3-Chlorophenyl)-6-(4-chlorophenyl)-1-((R)-1-cyclopropyl-2-(N-methylcyclopropanesulfonamido)ethyl)-3-methyl-2-oxopiperidin-3-yl)acetic acid

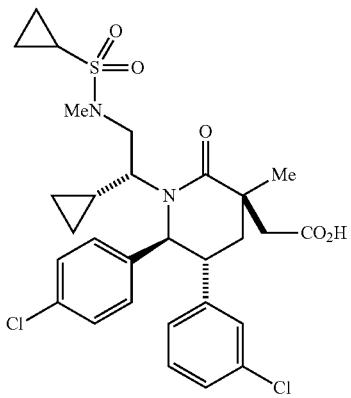 [SMILES: CN(C[C@@H](C1CC1)N1C(=O)[C@@](C)(CC(=O)O)C[C@H](c2cccc(Cl)c2)[C@H]1c1ccc(Cl)cc1)S(=O)(=O)C1CC1]

Step A: (3S,5R,6S)-3-Allyl-5-(3-chlorophenyl)-6-(4-chlorophenyl)-1-((R)-1-cyclopropyl-2-(methylamino)ethyl)-3-methylpiperidin-2-one

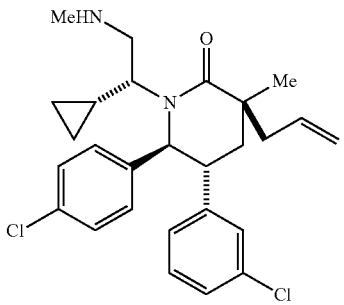 [SMILES: C=CC[C@@]1(C)C[C@H](c2cccc(Cl)c2)[C@@H](c2ccc(Cl)cc2)N([C@@H](CNC)C2CC2)C1=O]

(S)-2-((3S,5R,6S)-3-Allyl-5-(3-chlorophenyl)-6-(4-chlorophenyl)-3-methyl-2-oxopiperidin-1-yl)-2-cyclopropylacetaldehyde (Example 252, Step B, 554 mg, 1.21 mmol) was taken up in 10 mL anhydrous toluene and stripped to dryness in vacuo twice to effect azeotropic removal of trace moisture. After removal of residual solvents under high vacuum, the aldehyde was dissolved in dichloroethane (12 mL). Methylamine (2.0 M in THF, 6.1 mL, 12.20 mmol) and acetic acid (2 mL, 35.0 mmol) were added to the solution which was stirred at ambient temperature for about 30 minutes. Sodium triacetoxyborohydride (1.12 g, 5.28 mmol) was added as a solid in a single portion and the mixture was stirred at ambient temperature overnight. HPLC analysis showed that epimerization had occurred to give both diastereomers. The reaction was quenched with saturated sodium bicarbonate solution. The amine diastereomers were extracted into dichloromethane. The organic phase was washed with water, and dried over sodium sulfate. After concentration the resulting residue gave a slightly turbid solution on redissolution in ethyl acetate, and was consequently redried over magnesium sulfate. Concentration gave a mixture of diastereomers as a yellowish-white foam (577 mg). The two epimeric products were separated by SFC chromatography (250×30 mm Chiralpak® IC column (Chiral Technologies, Inc., West Chester, Pa., USA) with 42 g/min IPA and [20 mM NH$_3$] and 78 g/min CO$_2$. On concentration, the first eluting, epimer 3S,5R,6S)-3-allyl-5-(3-chlorophenyl)-6-(4-chlorophenyl)-1-((S)-1-cyclopropyl-2-(methylamino)ethyl)-3-methylpiperidin-2-one was obtained. Concentration of fractions containing the second eluting component gave the title compound. MS (ESI) m/z=471 [M+H]+.

Step B: N—((R)-2-((3S,5R,6S)-3-Allyl-5-(3-chlorophenyl)-6-(4-chlorophenyl)-3-methyl-2-oxopiperidin-1-yl)-2-cyclopropylethyl)-N-methylcyclopropanesulfonamide

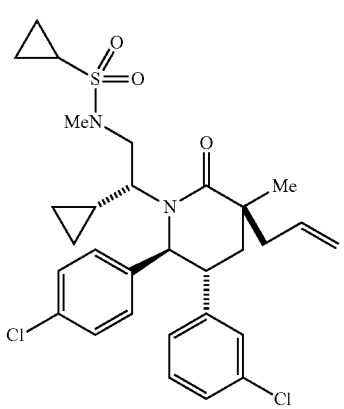 [SMILES: C=CC[C@@]1(C)C[C@H](c2cccc(Cl)c2)[C@@H](c2ccc(Cl)cc2)N([C@@H](CN(C)S(=O)(=O)C2CC2)C2CC2)C1=O]

(3S,5R,6S)-3-allyl-5-(3-chlorophenyl)-6-(4-chlorophenyl)-1-((R)-1-cyclopropyl-2-(methylamino)ethyl)-3-methylpiperidin-2-one (Example 260, Step A, 168 mg, 0.356 mmol) was transferred as a solution in 3 mL anhydrous toluene to an oven-dried 10 mL round bottom flask and the solution was stripped to dryness on a rotary evaporator. This was repeated twice to effect azeotropic removal of trace moisture. Cyclopropanesulfonyl chloride and pyridine were added to the flask. The reaction was monitored for completion by LC-MS. Ultimately 5× (0.15 ml sulfonyl chloride and 0.15 mL pyridine) were added over the course of 4 days. Dichloromethane was added when solids began to appear. The reaction mixture was diluted with ethyl acetate and citric acid solution (10%). The aqueous phase was washed twice with ethyl acetate. The combined organic layer was washed with sat. aq. NaCl solution and dried over sodium sulfate. After concentration in vacuo, the yellow residual oil was purified by chromatography on silica, eluting with a gradient of ethyl acetate in hexanes. Fractions containing the title compound were combined and concentrated to give the title compound as a white foam. MS (ESI) m/z=575 [M+H]$^+$ Step C. 2-((3R,5R,6S)-5-(3-chlorophenyl)-6-(4-chlorophenyl)-1-((R)-1-cyclopropyl-2-(N-methylcyclopropanesulfonamido)ethyl)-3-methyl-2-oxopiperidin-3-yl)acetic acid The title compound was obtained from N—((R)-2-((3S,5R,6S)-3-allyl-5-(3-chlorophenyl)-6-(4-chlorophenyl)-3-methyl-2-oxopiperidin-1-yl)-2-cyclopropylethyl)-N-methylcyclopropanesulfonamide (Example 260, Step B, 153 mg, 0.265 mmol) by a procedure similar to the one described in Example 71, Step F. The compound was purified by reverse phase HPLC on a Sunfire™ C18 column (Waters, Milford, Mass.), eluting with a gradient of 50 to 100% MeCN in water (0.1% TFA in both solvents), then further purified by SFC chromatography (250×30 mm Lux2® column (Phenomenex, Torrance, Calif. 90501, USA) with 32 g/min methanol [20 mM NH$_3$]+48 g/min CO$_2$ on Thar 80 SFC (Thar Technologies, Pittsburg, Pa.). Outlet pressure=100 bar; Temp.=23 C.; Wavelength=220 nm. Used 0.8 mL injections of 95 mg/15 mL [6.3 mg/mL sample solution in methanol, i.e. 5.1 mg/injection]. Run time=6 min, Cycle time=3.5 min). Pooled fractions were concentrated to give the title compound as a white solid.
$^1$H NMR (500 MHz, CHLOROFORM-d) δ 0.14 (d, J=3.91 Hz, 2 H), 0.51 (t, J=5.26 Hz, 2 H), 0.93-1.11 (m, 2 H), 1.14-1.23 (m, 1 H), 1.25-1.28 (m, 1 H), 1.46 (br s, 3 H), 1.52-1.76 (m, 2 H), 1.87-2.00 (m, 1 H), 2.20-2.39 (m, 2 H), 2.72 (d, J=15.41 Hz, 4 H), 2.92-3.07 (m, 3 H), 3.13 (d, J=15.41 Hz, 1 H), 3.98 (dd, J=13.82, 11.13 Hz, 1 H), 4.93 (br s, 1 H), 6.90 (d, J=5.87 Hz, 1 H), 7.00 (s, 1 H), 7.05-7.26 (m, 6 H). MS (ESI) m/z=593 [M+H]$^+$.

Example 261

2-((3R,5R,6S)-5-(3-Chlorophenyl)-6-(4-chlorophenyl)-1-((2S,3S)-2-hydroxy-4-methylpentan-3-yl)-3-methyl-2-oxopiperidin-3-yl)acetic acid

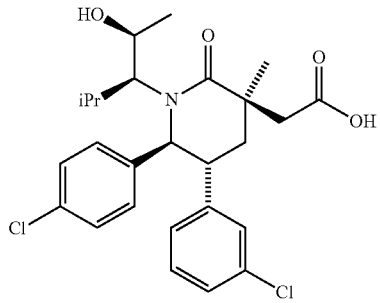 [SMILES: CC(C)[C@@H]([C@H](C)O)N1C(=O)[C@@](C)(CC(=O)O)C[C@H](c2cccc(Cl)c2)[C@H]1c1ccc(Cl)cc1]

Step A: Methyl 4-(3-chlorophenyl)-5-(4-chlorophenyl)-2-methyl-5-oxopentanoate

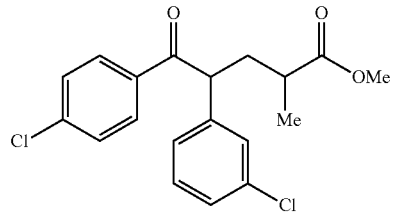 [SMILES: COC(=O)C(C)CC(C(=O)c1ccc(Cl)cc1)c1cccc(Cl)c1]

Methyl methacrylate (82 mL, 773 mmol) was added to a solution of 2-(3-chlorophenyl)-1-(4-chlorophenyl)ethanone (195.2 g, 736 mmol; Example 1, Step A) in anhydrous THF (1.5 L) under an atmosphere of nitrogen. A suspension of potassium t-butoxide (8.26 g, 73.6 mmol) in anhydrous THF (340 mL) (sonicated to break up the solids) was then prepared and cannulated into the solution containing the 2-(3-chlorophenyl)-1-(4-chlorophenyl)ethanone. The solution was cooled to ~16° C. and the orange colored solution was left to stir at ambient temperature for 2.5d. (After 2 d TLC shows the absence of the starting material). The mixture was concentrated under vacuum. The residual reddish brown oil was diluted with ethyl acetate (900 mL) and washed with water (4×190 mL) and then sat. aq. NaCl solution. The organic layer was dried over magnesium sulfate and concentrated under reduced pressure to provide the title compound as a racemic mixture of diastereomers.

$^1$H-NMR (500 MHz, CDCl$_3$) δ 7.88 (m, 4H), 7.39 (m, 2H), 7.27-7.12 (series of m, 4H), 4.62 (dd, J=9.0, 5.6 Hz, 0.5H), 4.59 (dd, J=9.3, 5.4 Hz, 0.5H), 3.69 (s, 1.5H), 3.60 (s, 1.5 H), 2.46 (m, 1H), 2.33 (m, 1H), 2.08 (ddd, J=13.9, 9.3, 5.4 Hz, 0.5H), 1.97 (ddd, J=13.7, 9.0, 4.4 Hz, 0.5H), 1.23 (d, J=6.9 Hz, 1.5 H), 1.16 (d, J=7.1 Hz, 1.5H) ppm.

Step B: Racemic mixture of (4R,5R)-methyl 4-(3-chlorophenyl)-5-(4-chlorophenyl)-5-hydroxy-2-methylpentanoate (4S,5S)-methyl 4-(3-chlorophenyl)-5-(4-chlorophenyl)-5-hydroxy-2-methylpentanoate

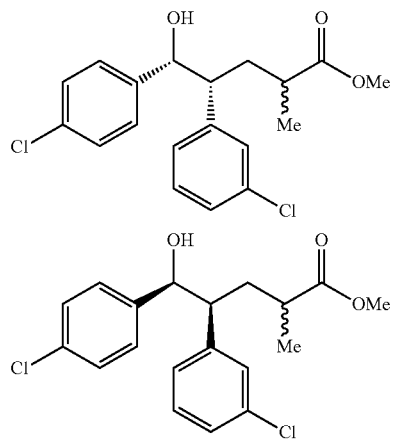

Anhydrous methanol (600 mL) was placed in a 3 L three-necked round-bottomed flask equipped with a stir bar and temperature probe under an atmosphere of $N_2$ and cooled to about −20° C. Sodium borohydride (26.2 g, 693 mmol) was added in 5 g portions. Via an addition funnel, a solution of methyl 4-(3-chlorophenyl)-5-(4-chlorophenyl)-2-methyl-5-oxopentanoate (253 g, 693 mmol; Example 261, Step A) in methanol (600 mL) was added dropwise to the reaction, maintaining a temperature between −27° C. to −30° C. The reddish solution was stirred at −30° C. for 30 minutes and then allowed to warm to −15° C. The reaction was monitored for completion by TLC. The reaction was quenched by slowly adding water (68.6 mL, 3.8 mol) through the addition funnel. The mixture was allowed to warm to ambient temperature. Solvents were removed under vacuum. The residual yellowish oil was diluted in ethyl acetate (1.2 L) and washed with water (400 mL). The organic layer was washed with sat. aq. NaCl solution (2×300 mL), forming an emulsion. After waiting for the most of the emulsion to separate, the organic layer was dried over magnesium sulfate. The solution was filtered through filter paper and concentrated under vacuum to provide a racemic mixture of diastereomers.

$^1$H-NMR (500 MHz, DMSO-d6) δ 7.33 (m, 2H), 7.27-7.17 (series of m, 5H), 7.04 (m, 1H), 5.43 (d, J=4.4 Hz, 0.5H), 5.37 (d, J=4.6 Hz, 0.5H), 4.77 (t, J=5.4 Hz, 0.5H), 4.71 (dd, J=6.6, 4.9 Hz, 0.5H), 5.33 (s, 1.5H), 3.46 (s, 1.5H), 2.87 (dt, J=10.2, 4.7 Hz, 0.5H), 2.75 (ddd, J=11.2, 6.6, 4.9 Hz, 0.5H), 2.04 (m, 1.5H), 1.71 (m, 1H), 1.46 (m, 0.5H), 0.97 (d, J=6.6 Hz, 1.5H), 0.94 (d, J=7.1 Hz, 1.5H) ppm. TLC (20% EtOAc/Hexane) $R_f$=0.34.

Step C. (4R,5R)-4-(3-Chlorophenyl)-5-(4-chlorophenyl)-5-hydroxy-2-methylpentanoic acid and (4S,5S)-4-(3-Chlorophenyl)-5-(4-chlorophenyl)-5-hydroxy-2-methylpentanoic acid

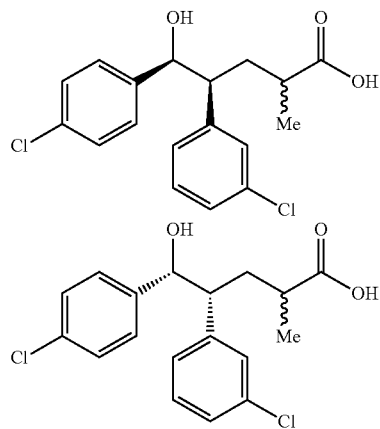

A solution of the racemic mixture of (4R,5R)-methyl 4-(3-chlorophenyl)-5-(4-chlorophenyl)-5-hydroxy-2-methylpentanoate and (4S,5S)-methyl 4-(3-chlorophenyl)-5-(4-chlorophenyl)-5-hydroxy-2-methylpentanoate (245.7 g, 669 mmol; Example 261, Step B) in THF (1.17 L) was prepared by warming to 40° C. The flask was cooled to ~14° C., internal temperature.

A solution of lithium hydroxide hydrate (42.1 g, 1.0 mol) in water (585 mL) was cautiously added to the THF solution. The mixture was left to stir at ambient temperature and monitored by LC/MS for the absence of starting material (~2.5 h). Upon completion, the solution was again cooled to a temperature of ~14° C. 2N HCl (526 mL) was added slowly. The layers were partitioned and the aqueous layer (pH ~2) was washed with ethyl acetate (1×500 mL then 1×250 mL). The combined organic layers were dried over magnesium sulfate and concentrated to afford 264 g of a racemic mixture of (4R,5R)-4-(3-chlorophenyl)-5-(4-chlorophenyl)-5-hydroxy-2-methylpentanoic acid and (4S,5S)-4-(3-chlorophenyl)-5-(4-chlorophenyl)-5-hydroxy-2-methylpentanoic acid was obtained. The crude material containing some residual solvent was used as-is in the subsequent transformation. The product (estimated after solvent correction 227 g) is a roughly 1:1 mixture of diastereomers at the 2-position.

$^1$H-NMR (500 MHz, CDCl$_3$) δ 7.31 (m, 2H), 7.25 (m, 3H), 7.17 (m, 2H), 7.05 (m, 1H) 4.74 (m, 1H), 2.99 (ddd, J=11.2, 1.7, 3.7 Hz, 0.5H), 2.90 (ddd, J=11.5, 7.3, 4.6 Hz, 1H), 2.15 (m, 1.5 H), 1.85 (m, 0.5 H), 1.67 (ddd, J=14.3, 11.5, 3.4 Hz, 0.5H), 1.52 (m, 0.5 H), 1.08 (d, J=7.1 Hz, 1.5 H), 1.05 (d, J=6.9 Hz, 1.5H) ppm.

Alternatively, (4R,5R)-4-(3-Chlorophenyl)-5-(4-chlorophenyl)-5-hydroxy-2-methylpentanoic acid, as a mixture of methyl diastereomers, can be prepared from racemic methyl 4-(3-chlorophenyl)-5-(4-chlorophenyl)-2-methyl-5-oxopentanoate.

In a three-neck flask, a solution of racemic methyl 4-(3-chlorophenyl)-5-(4-chlorophenyl)-2-methyl-5-oxopentanoate (500 g, 1.37 mol, 1 eq) in anhydrous 2-propanol (2.5 L) was charged with KO$^t$Bu (46.1 g, 0.41 mol, 0.3 eq) and stirred for 30 min until a clear yellow solution was formed. The solution was then treated with a solution of dichloro {(S)-(−)-2,2'-bis[di(3,5-xylyl)phosphino]-1,1'-binaphthyl} [(2S)-(+)-1,1-bis(4-methoxyphenyl)-3-methyl-1,2-butanediamine]ruthenium(II) (5 g, 4.1 mmol, 0.003 eq, Strem Chemicals inc., Newburyport, Mass.) in anhydrous toluene (250 mL) and stirred at RT for 2 hours (Note: Most of methyl ester was converted to isopropyl). The solution was transferred to two Parr shakers, sealed and purged with hydrogen 3 times. The reaction was shaken at RT under 414 kilopascals hydrogen pressure. After 18 hrs, the reaction was quenched with sat. NH$_4$Cl, concentrated and extracted with EtOAc (2 L×2). The combined organics was washed with brine and concentrated as a brown oil and used as such in the next step.

The crude intermediate (542 g, 1.37 mol) was dissolved in THF (3 L) and MeOH (1 L) and charged with 2 M LiOH (1 L). The solution was rotated at RT overnight, concentrated to remove most of THF and MeOH, and quenched with 1 L of 2 M HCl. After phase separation, the aqueous layer was extracted with EtOAc (1 L×2). The combined organics were washed with brine, dried over anhydrous Na$_2$SO$_4$, filtered and concentrated in vacuo. This product, (4R,5R)-4-(3-Chlorophenyl)-5-(4-chlorophenyl)-5-hydroxy-2-methylpentanoic acid, as a mixture of methyl diastereomers, was taken crude to the next step.

Step D. (5R,6R)-5-(3-chlorophenyl)-6-(4-chlorophenyl)-3-methyltetrahydro-2H-pyran-2-one and (5S,6S)-5-(3-chlorophenyl)-6-(4-chlorophenyl)-3-methyltetrahydro-2H-pyran-2-one

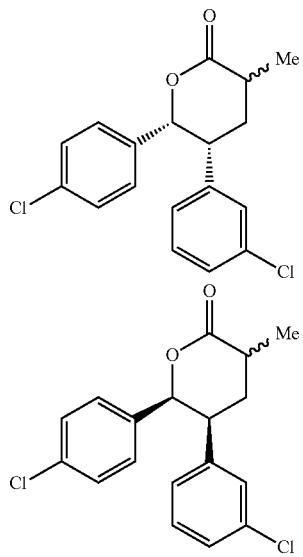

The mixture of hydroxy acid diastereomers (227 g, 643 mmol; Example 261, Step C) was lactonized under Dean-Stark conditions in toluene (1.07 L) with pyridine 4-methyl-benzenesulfonate (PPTS, 4.84 g, 19.28 mmol) under an atmosphere of nitrogen. After 2 h of vigorous reflux the solution was cooled to ambient temperature and transferred to a separatory funnel. The flask residue was rinsed in with ethyl acetate. The combined organic phase was washed in succession with water (1×250 mL), sat. sodium bicarbonate solution (1×250 mL), and sat. aq. NaCl solution (1×250 mL). After drying with magnesium sulfate, concentration under reduced pressure provides a mixture of diastereomeric lactones as a light brown solid.

$^1$H-NMR (500 MHz, CDCl$_3$) δ 7.24-6.95 (series of m, 6H), 6.91 (d, J=7.6 Hz, 0.5H), 6.82 (m, 1.5H), 6.73 (d, J=7.6 Hz, 0.5H), 5.77 (d, J=3.9 Hz, 0.5H), 5.69 (d, J=4.6 Hz, 0.5H), 3.67 (dt, J=7.6, 4.2 Hz, 0.5H), 3.55 (td, J=7.8, 4.6 Hz, 0.5H), 2.97 (m, 0.5 H), 2.81 (doublet of quintets, J=14.4, 7.1 Hz, 0.5H), 2.56 (dt, 16.1, 8.0 Hz, 0.5H), 2.32 (dt, J=13.7, 6.9 Hz, 0.5 H), 2.07 (ddd, J=13.2, 8.6, 4.4 Hz, 0.5H), 1.85 (ddd, J=14.2, 12.7, 7.6 hz, 0.5H), 1.41 (d, J=7.1 Hz, 1.5H), 1.39 (d, J=6.9 Hz, 1.5H) ppm.

Step E: (3S,5R,6R)-3-Allyl-5-(3-chlorophenyl)-6-(4-chlorophenyl)-3-methyltetrahydro-2H-pyran-2-one and (3R,5S,6S)-3-Allyl-5-(3-chlorophenyl)-6-(4-chlorophenyl)-3-methyltetrahydro-2H-pyran-2-one

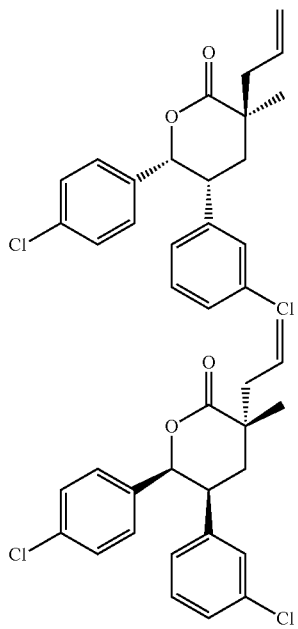

A solution of racemic lactone from the previous step (Example 261, Step D, 190.28 g, 568 mmol) in THF (946 mL) was prepared in a 1 neck round bottomed flask equipped with a Claisen adapter, 500 mL dropping funnel, and internal temperature probe under an atmosphere of nitrogen. The solution was cooled to a temperature of −35° C. Allyl bromide (120 mL, 1.42 mol) was added via the addition funnel, maintaining the temperature below −30° C. during addition. A solution of LHMDS (1M in THF, 738 mL, 738 mmol) was added dropwise to the reaction, maintaining the temperature below −30° C. The reaction was allowed to slowly warm to −5° C. over a period of 1 h. The solution was recooled to about −20° C. and added via cannula into a solution of ammonium chloride in water at about 5 C. After separation of the layers, the aqueous layers were extracted twice with ethyl acetate. The combined organic layers were washed with sat. aq. NaCl solution and dried over sodium sulfate. Concentration under vacuum provided 219 g of a light yellow solid. The solids were slurried at ambient temperature for 2 h with hexane (2 L). The solids were then collected by filtration, rinsed with hexane (2×100 mL) and dried to provide the title compounds as a racemic mixture.

$^1$H-NMR (500 MHz, CDCl$_3$) δ 7.24 (m, 1H), 7.20-7.15 (m, 3H), 6.91 (t, J=1.7 Hz, 1H), 6.77 (d, J=7.6 Hz, 1H), 6.59 (m, 2H), 5.84 (ddt, J=17.6, 10.3, 7.6 Hz, 1H), 5.71 (d, J=5.4 Hz, 1H), 5.21-5.13 (m, 2H), 3.81 (dt, J=12.0, 4.2 Hz, 1H), 2.62 (ABX J$_{AB}$=14.0, J$_{AX}$=7.8 Hz, 1H), 2.52 (ABX, J$_{AB}$=13.9, J$_{AX}$=7.3 Hz, 1H), 1.98 (dd, J=14.0, 12.0 Hz, 1H), 1.91 (ddd, J=14.0, 3.7, 1.2 Hz, 1H), 1.42 (s, 3H) ppm.

Step F: Separation of (3S,5R,6R)-3-allyl-5-(3-chlorophenyl)-6-(4-chlorophenyl)-3-methyltetrahydro-2H-pyran-2-one and (3R,5S,6S)-3-allyl-5-(3-chlorophenyl)-6-(4-chlorophenyl)-3-methyltetrahydro-2H-pyran-2-one

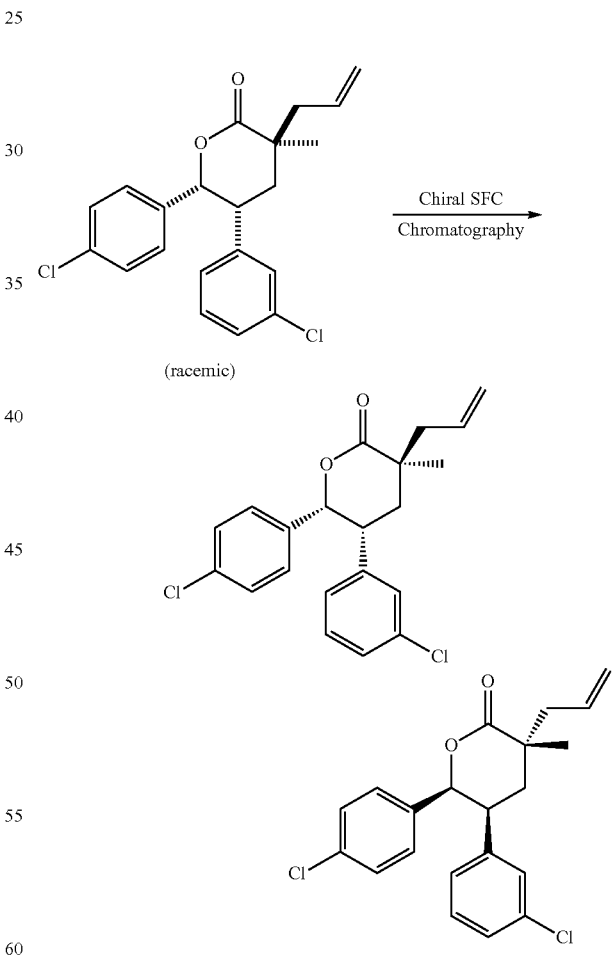

A racemic mixture of (3S,5R,6R)-3-allyl-5-(3-chlorophenyl)-6-(4-chlorophenyl)-3-methyltetrahydro-2H-pyran-2-one and (3R,5S,6S)-3-allyl-5-(3-chlorophenyl)-6-(4-chlorophenyl)-3-methyltetrahydro-2H-pyran-2-one can be separated using chiral Supercritical Fluid Chromatography (SFC) as follows: Using a 250×30 mm Lux2® column (Phenomenex, Torrance, Calif. 90501, USA) with 20 g/min methanol (20 mM NH3)+60 g/min CO$_2$ on a Thar 80 SFC. Outlet pressure=100 bar; Temp.=23 C.; Wavelength=220 nm. Used 0.3 mL injections of 5.0 g/80 mL (62.5 mg/mL sample solution in methanol/dichloromethane (75:5), i.e. 18.75 mg/injection. Run time=8 min, Cycle time=3 min.

The first peak collected was assigned as (3R,5S,6S)-3-allyl-5-(3-chlorophenyl)-6-(4-chlorophenyl)-3-methyltetrahydro-2H-pyran-2-one. The second peak collected was determined to be (3S,5R,6R)-3-allyl-5-(3-chlorophenyl)-6-(4-chlorophenyl)-3-methyltetrahydro-2H-pyran-2-one by subsequent chemical derivatization with (S)-2-amino-1-butanol and conversion to the same compound as prepared in Example 91, Step B, by the procedures described for Example 261, Steps G and H. The NMR of the separated enantiomers was consistent with the spectrum of the racemate described above.

Alternatively, (3S,5R,6R)-3-allyl-5-(3-chlorophenyl)-6-(4-chlorophenyl)-3-methyltetrahydro-2H-pyran-2-one can be prepared from racemic methyl 4-(3-chlorophenyl)-5-(4-chlorophenyl)-2-methyl-5-oxopentanoate.

In a three-neck flask, a solution of racemic methyl 4-(3-chlorophenyl)-5-(4-chlorophenyl)-2-methyl-5-oxopentanoate (500 g, 1.37 mol, 1 eq) in anhydrous 2-propanol (2.5 L) was charged with KO$^t$Bu (46.1 g, 0.41 mol, 0.3 eq) and stirred for 30 mins until a clear yellow solution was formed. The solution was then treated with a solution of Dichloro{(S)-(-)-2,2'-bis[di(3,5-xylyl)phosphino]-1,1'-binaphthyl}[(2S)-(+)-1,1-bis(4-methoxyphenyl)-3-methyl-1,2-butanediamine]ruthenium(II) (5 g, 4.1 mmol, 0.003 eq, /Strem Chemicals Inc., Newburyport, Mass.) in anhydrous toluene (250 mL) and stirred at RT for 2 hours (Note: Most of methyl ester was converted to isopropyl). The solution was transferred to two Parr shakers, sealed and purged with hydrogen 3 times. The reaction was shaken at RT under 414 kilopascals hydrogen pressure. After 18 hrs, the reaction was quenched with sat. NH$_4$Cl, concentrated and extracted with EtOAc (2 L×2). The combined organics was washed with brine and concentrated as a brown oil and used as such in the next step.

The crude intermediate (542 g, 1.37 mol) was dissolved in THF (3 L) and MeOH (1 L) and charged with 2 M LiOH (1 L). The solution was rotated at RT overnight, concentrated to remove most of THF and MeOH, and quenched with 1 L of 2 M HCl. After phase separation, the aqueous layer was extracted with EtOAc (1 L×2). The combined organics was washed with brine, dried over anhydrous Na$_2$SO$_4$, filtered and concentrated in vacuo.

Step G: (S)-2-((2R,3R)-2-(3-Chlorophenyl)-3-(4-chlorophenyl)-3-hydroxypropyl)-N-((S)-1-hydroxy-3-methylbutan-2-yl)-2-methylpent-4-enamide

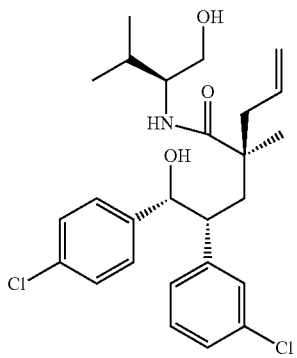 [SMILES: C=CC[C@@](C)(C[C@H](c1cccc(Cl)c1)[C@@H](O)c1ccc(Cl)cc1)C(=O)N[C@H](CO)C(C)C]

A mixture of (S)-2-amino-3-methylbutan-1-ol (550 mg, 5.33 mmol) and (3S,5R,6R)-3-allyl-5-(3-chlorophenyl)-6-(4-chlorophenyl)-3-methyltetrahydro-2H-pyran-2-one (Example 261, Step H, 2$^{nd}$ compound, 500 mg, 1.332 mmol) was heated to 100° C. for 24h. After cooling to room temperature, the residue was dissolved in ethyl acetate and washed 3× with 1N HCl (5 mL) followed by sat. aq. NaCl solution (5 mL). The organic phase was dried over MgSO$_4$, filtered, and the filtrate was concentrated to afford the title compound.

$^1$H-NMR (500 MHz, DMSO-d$_6$) δ 7.21 (m, 2H), 7.10 (m, 2H), 7.06 (br s, 1H), 6.99 (m, 2H), 6.86 (br d, J=8.8 Hz, 1H), 6.84 (br d, J=7.1 Hz, 1H), 5.53 (dddd, J=16.9, 10.3, 8.1, 6.6 Hz, 1H), 5.46 (d, J=4.4 Hz, 1H), 4.90 (m, 2H), 4.78 (t, J=4.2 Hz, 1H), 4.56 (t, J=5.1 Hz, 1H), 3.56 (m, 1H), 3.37 (m, 2H), 2.87 (dt, J=7.8, 4.2 Hz, 1H), 2.29 (dd, J=13.7, 6.4 Hz, 1H), 2.14 (dd, J=14.4, 7.8 Hz, 1H), 1.97 (dd, J=14.4, 3.9 Hz, 1H), 1.88 (dd, J=13.9, 8.1 Hz, 1H), 1.76 (octet, J=6.4 Hz, 1H), 0.97 (s, 3H), 0.81 (d, J=6.8 Hz, 3H), 0.75 (d, J=6.6 Hz, 3H) ppm.

Step H. (3S,5R,6S)-3-Allyl-5-(3-chlorophenyl)-6-(4-chlorophenyl)-1-((S)-1-hydroxy-3-methylbutan-2-yl)-3-methylpiperidin-2-one

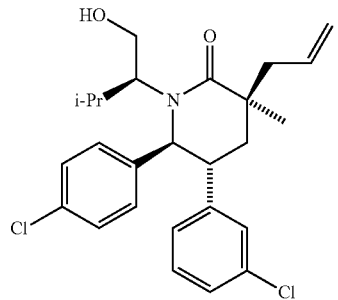 [SMILES: C=CC[C@@]1(C)C[C@H](c2cccc(Cl)c2)[C@@H](c2ccc(Cl)cc2)N([C@H](CO)C(C)C)C1=O]

(S)-2-((2R,3R)-2-(3-Chlorophenyl)-3-(4-chlorophenyl)-3-hydroxypropyl)-N-((S)-1-hydroxy-3-methylbutan-2-yl)-2-methylpent-4-enamide (example 261, step G) was transferred as a solution in anhydrous benzene to a pre-weighed, oven-dried 50 mL round bottom flask and stripped to dryness. Azeotropic distillation of benzene/water was performed twice more, and the residue was dried under high vacuum for 2 h, after which it weighed 550 mg. An oven-dried stir bar was added to the flask. The vessel was sealed and purged with nitrogen and then anhydrous dichloromethane (23 mL) was added, followed by triethylamine (1.3 mL, 9.33 mmol). The resulting stirred solution was cooled to 0° C. Methanesulfonyl chloride (0.270 mL, 3.49 mmol) was added dropwise by microsyringe. After 1 h, the reaction was quenched by addition of HCl (1.2M, 12 mL) and diluted in ethyl acetate. The organic layer was washed with 1.2 M HCl (30 mL), saturated sodium bicarbonate (2×25 mL), and sat. aq. NaCl solution. After drying over magnesium sulfate and concentration in vacuo an intermediate was obtained as an off-white foam (0.64 g,). 1,8-Bis(dimethylamino)naphthalene, 314 mg, 1.465 mmol) and water (0.104 mL, 5.75 mmol) were added to the intermediate, followed by dioxane (23 mL). The mixture was heated under nitrogen at 110° C. overnight. After cooling, the mixture was dissolved in ethyl acetate and washed with saturated ammonium chloride solution. The aqueous phase was back-extracted with ethyl acetate. The combined organic layers were washed with sat. aq. NaCl solution, dried over sodium sulfate, filtered, and concentrated in vacuo. The residue was purified by chromatography on silica, eluting with ethyl acetate in hexanes. Chromatography fractions containing predominantly the desired product were combined. The product was re-purified by chromatography on a 40 g silica column, eluting with a gradient of 0 to 50% ethyl acetate in hexanes to give the title compound.

¹H NMR (400 MHz, CHLOROFORM-d) δ 0.73 (d, J=6.46 Hz, 3 H), 0.83 (d, J=6.65 Hz, 3 H), 1.28 (s, 3 H), 1.91-2.00 (m, 1 H), 2.00-2.10 (m, 1 H), 2.26-2.45 (m, 1 H), 2.56-2.74 (m, 2 H), 3.16 (br. s., 1 H), 3.26 (ddd, J=13.50, 10.47, 3.42 Hz, 1 H), 3.43 (br. s., 1 H), 3.76 (dd, J=11.25, 3.42 Hz, 1 H), 4.49 (d, J=10.56 Hz, 1 H), 5.18 (s, 1 H), 5.21 (d, J=6.46 Hz, 1 H), 5.87 (ddt, J=16.95, 9.85, 7.53 Hz, 1 H), 6.72 (apparent d, J=7.63 Hz, 1 H), 6.95 (t, J=1.66 Hz, 1 H), 6.97-7.17 (m, 4 H), 7.23 (d, J=8.41 Hz, 2 H). MS (ESI) m/z=460 [M+H]⁺.

Step I. (S)-2-((3S,5R,6S)-3-Allyl-5-(3-chlorophenyl)-6-(4-chlorophenyl)-3-methyl-2-oxopiperidin-1-yl)-3-methylbutanal

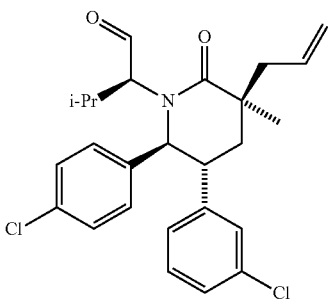 [SMILES: C=CC[C@@]1(C)C[C@H](c2cccc(Cl)c2)[C@@H](c2ccc(Cl)cc2)N([C@H](C=O)C(C)C)C1=O]

Dess-Martin periodinane (938 mg, 2.212 mmol) was added as a solid to a solution of (3S,5R,6S)-3-allyl-5-(3-chlorophenyl)-6-(4-chlorophenyl)-1-((S)-1-hydroxy-3-methylbutan-2-yl)-3-methylpiperidin-2-one (Example 261, Step H, 365.4 mg, 0.794 mmol) in dichloromethane (8 mL) and water (0.04 mL, 2.220 mmol). The resulting suspension was vigorously stirred at ambient temperature for 1.5 h. The reaction was quenched with sodium thiosulfate solution (1M aq, 6 mL). Additional sodium thiosulfate solution (1M aq, 6 mL) was added and stirred until the chalky suspension became a slightly cloudy biphasic mixture. The aqueous phase was separated and back extracted with dichloromethane. The organic layer was washed with sodium thiosulfate solution, saturated aqueous sodium bicarbonate and sat. aq. NaCl solution. After drying over sodium sulfate and concentration, the residue was purified on silica gel, eluting with a gradient of 0 to 30% ethyl acetate in hexanes. Fractions containing the desired product were pooled to give the title compound as a white foam. MS (ESI) m/z=458 [M+H]⁺.

Step J. (3S,5R,6S)-3-Allyl-5-(3-chlorophenyl)-6-(4-chlorophenyl)-1-((S)-2-hydroxy-4-methylpentan-3-yl)-3-methylpiperidin-2-one

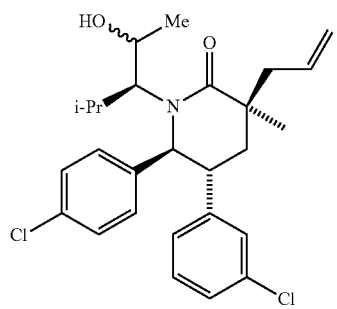 [SMILES: C=CC[C@@]1(C)C[C@H](c2cccc(Cl)c2)[C@@H](c2ccc(Cl)cc2)N([C@@H](C(C)C)C(C)O)C1=O]

Methylmagnesium bromide (1.4 mL, 1.960 mmol, 1.4 M in 1:3 THF:toluene) was added by syringe to a solution under nitrogen of pre-dried (S)-2-((3S,5R,6S)-3-allyl-5-(3-chlorophenyl)-6-(4-chlorophenyl)-3-methyl-2-oxopiperidin-1-yl)-3-methylbutanal (Example 261, Step I, 286 mg, 0.624 mmol) in THF (6.5 mL) at 0° C. The ice bath was removed. After 2 h, the solution was recooled to 0° C. and quenched by careful addition of saturated ammonium chloride solution. The resulting mixture was extracted with ethyl acetate. The organic layer was washed with sat. aq. NaCl solution, dried over sodium sulfate, filtered, and concentrated. The residue was purified by chromatography on silica, eluting with a gradient of 0 to 40% ethyl acetate in hexanes. Fractions containing the desired product were combined and re-purified to give the title compound as a mixture of diastereomeric alcohols) as a white foam. MS (ESI) m/z=474 [M+H]⁺.

Step K. 2-((3R,5R,6S)-5-(3-Chlorophenyl)-6-(4-chlorophenyl)-3-methyl-1-((S)-2-methyl-4-oxopentan-3-yl)-2-oxopiperidin-3-yl)acetic acid

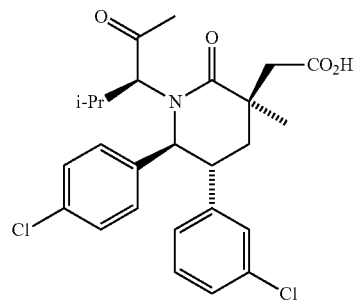 [SMILES: CC(=O)[C@H](C(C)C)N1C(=O)[C@@](C)(CC(=O)O)C[C@H](c2cccc(Cl)c2)[C@H]1c1ccc(Cl)cc1]

(3S,5R,6S)-3-Allyl-5-(3-chlorophenyl)-6-(4-chlorophenyl)-1-((S)-2-hydroxy-4-methylpentan-3-yl)-3-methylpiperidin-2-one (Example 261, Step J, 244 mg, 0.51 mmol) was converted by a procedure similar to the one described in Example 257, Step E to the title compound obtained after silica gel chromatography eluting with ethyl acetate in hexanes as a white solid. MS (ESI) 490 [M+H]⁺.

Step L. 2-((3R,5R,6S)-5-(3-Chlorophenyl)-6-(4-chlorophenyl)-1-((2S,3S)-2-hydroxy-4-methylpentan-3-yl)-3-methyl-2-oxopiperidin-3-yl)acetic acid The title compound was obtained from 2-((3R,5R,6S)-5-(3-chlorophenyl)-6-(4-chlorophenyl)-3-methyl-1-((S)-2-methyl-4-oxopentan-3-yl)-2-oxopiperidin-3-yl)acetic acid (Example 261, Step K, 79.9 mg, 0.16 mmol) by a procedure similar to the one described in Example 258. After workup, the material was purified by chromatography on a 24 g silica column, eluting with a gradient of 10 to 20% isopropanol in hexanes. The purest fractions were combined, concentrated, re-dissolved in 1:1 MeCN/water, passed through a pall microfilter, frozen, and lyophilized to give the title compound as a white solid. Stereochemistry assigned by analogy to example 152.

¹H NMR (400 MHz, Methanol-d4) δ 0.62 (d, J=7.04 Hz, 3 H), 0.67 (d, J=6.65 Hz, 3 H), 1.26 (d, J=6.46 Hz, 3 H), 1.42 (s, 3 H), 2.13-2.29 (m, 3 H), 2.49 (t, J=7.14 Hz, 1 H), 2.62 (d, J=13.69 Hz, 1 H), 3.01 (d, J=13.69 Hz, 1 H), 3.57 (td, J=10.81, 6.16 Hz, 1 H), 4.23 (t, J=6.65 Hz, 1 H), 4.70 (d, J=10.95 Hz, 1 H), 6.65-7.51 (m, 8 H). MS (ESI) m/z=492 [M+H]⁺.

Example 262

2-((3R,5R,6S)-5-(3-Chlorophenyl)-6-(4-chlorophenyl)-1-((S)-cyclopropyl(pyridin-2-yl)methyl)-3-methyl-2-oxopiperidin-3-yl)acetic acid or 2-((3R,5R,6S)-5-(3-Chlorophenyl)-6-(4-chlorophenyl)-1-((R)-cyclopropyl(pyridin-2-yl)methyl)-3-methyl-2-oxopiperidin-3-yl)acetic acid

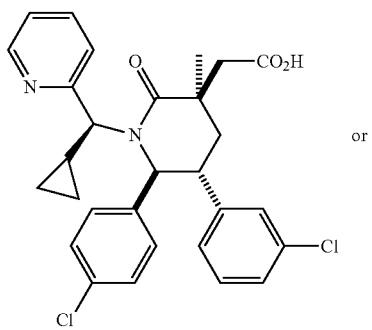

or

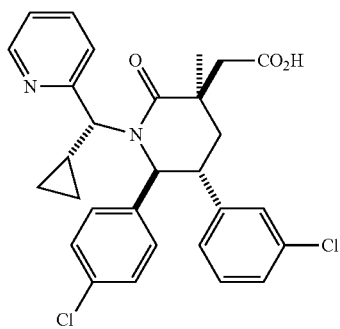

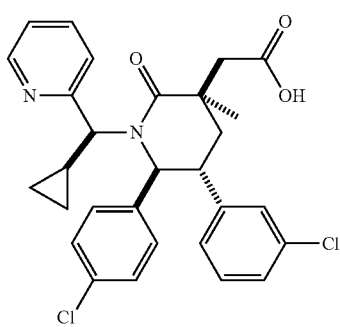

Step A. (1S,2R)-4-Carboxy-2-(3-chlorophenyl)-1-(4-chlorophenyl)butan-1-aminium chloride

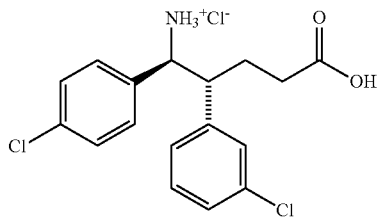

A suspension of (5R,6S)-5-(3-chlorophenyl)-6-(4-chlorophenyl)piperidin-2-one (Example 1, Step E, 29 g, 91 mmol) in 5 M hydrochloric acid (91 mL, 453 mmol) was brought to reflux. After 2 h, TLC indicated complete consumption of starting material to the ring opened product (elution with 75% ethyl acetate in hexanes; $R_f$ starting material=0.5, $R_f$ product=0.0). The reaction contents were co-distilled with toluene (4×100 mL) then brought to dryness. Solids were suspended in diethyl ether (100 mL), filtered, and washed with ether (100 mL). The white crystalline solid was brought to dryness under high vacuum to provide the title compound.

¹H NMR (500 MHz, DMSO-d₆) δ 7.31-7.39 (m, 2H), 7.24-7.30 (m, 2H), 7.10-7.23 (m, 3H), 6.90-7.01 (m, 1H), 4.65 (d, J=10.03 Hz, 1H), 3.27 (dt, J=3.67, 10.51 Hz, 1H), 2.25-2.36 (m, 1H), 1.95-2.10 (m, 1H), 1.77-1.94 (m, 2H).

Step B. (4R,5S)-4-(3-Chlorophenyl)-5-(4-chlorophenyl)-5-(cyclopropyl(pyridin-2-yl)methylamino)pentanoic acid

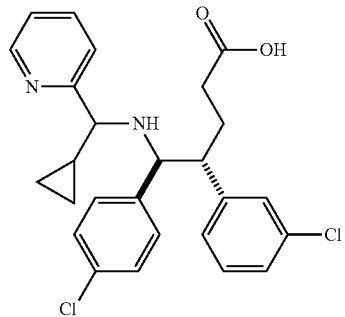 [SMILES: O=C(O)CC[C@H](c1cccc(Cl)c1)[C@H](NC(c1ccccn1)C1CC1)c1ccc(Cl)cc1]

Cyclopropyl(pyridin-2-yl)methanone (0.393 g, 2.67 mmol) [Meijer, Louis H. P. et al., Tetrahedron, 40, 5185 (1984)] was mixed with neat tetra-isopropoxy-titanium (0.782 mL, 2.67 mmol) and stirred at room temperature for 20 min. (1S,2R)-4-carboxy-2-(3-chlorophenyl)-1-(4-chlorophenyl)butan-1-aminium chloride (0.500 g, 1.334 mmol; Example 262, Step A) was added as a solid and stirred overnight. Methanol (13 mL) was added followed by careful addition of sodium borohydride (0.151 g, 4.00 mmol). The resulting solution was stirred at room temperature for 10 min. The reaction was quenched with HCl (1 N aq.), extracted with dichloromethane and washed with sat. aq. NaCl solution. The combined organic layer was dried over sodium sulfate and concentrated to provide a crude product used in the next step without further purification.

Step C. (5R,6S)-5-(3-Chlorophenyl)-6-(4-chlorophenyl)-1-((S)-cyclopropyl(pyridin-2-yl)methyl)piperidin-2-one or (5R,6S)-5-(3-Chlorophenyl)-6-(4-chlorophenyl)-1-((R)-cyclopropyl(pyridin-2-yl)methyl)piperidin-2-one

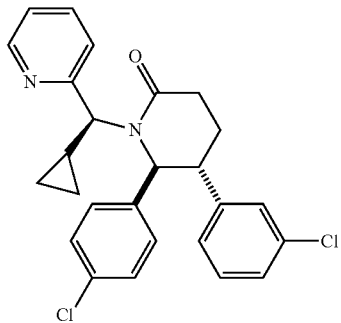

or

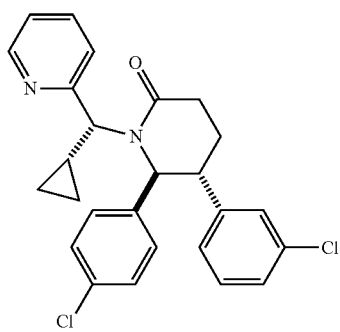

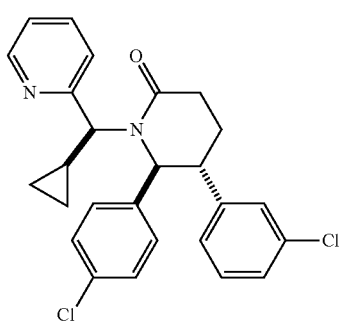

The crude product from Example 162, Step B was dissolved in dichloroethane (13 mL) in the presence of 4 Å molecular sieves (15 pieces) and heated at reflux overnight. The reaction was filtered through Celite® (J. T. Baker, Phillipsberg, N.J., diatomaceous earth), rinsed with dichloromethane and concentrated under reduced pressure. The residue was purified by reverse phase HPLC (eluent: 10 to 90% acetonitrile, water, 0.1% TFA, gradient elution) to give the title compound as the first eluting diastereomer.

Step D. (5R,6S)-5-(3-Chlorophenyl)-6-(4-chlorophenyl)-1-((S)-cyclopropyl(pyridin-2-yl)methyl)-3-methylpiperidin-2-one or (5R,6S)-5-(3-Chlorophenyl)-6-(4-chlorophenyl)-1-((R)-cyclopropyl(pyridin-2-yl)methyl)-3-methylpiperidin-2-one

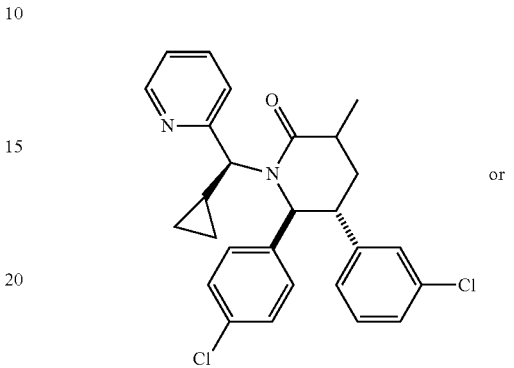

or

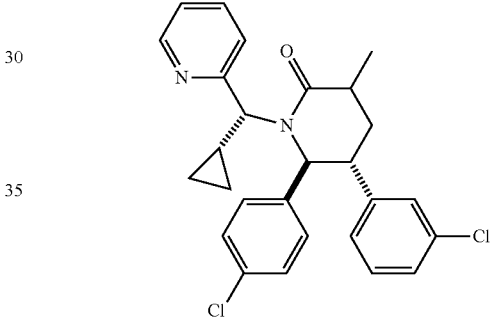

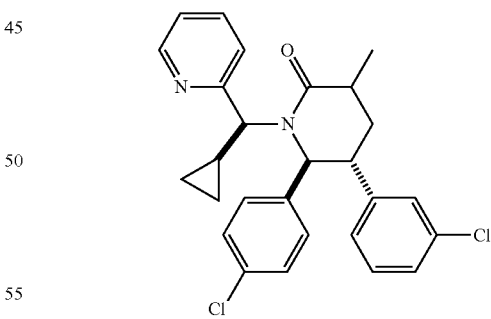

A solution of LHMDS (1M in THF, 0.585 mL, 0.585 mmol) was added to a solution of the compound from Example 262, Step C (0.220 g, 0.487 mmol) and iodomethane (0.040 mL, 0.634 mmol) in THF (5.0 mL) at −78° C. The reaction was allowed to warm to ambient temperature, then was quenched (sat. aqueous NH₄Cl solution), extracted (2×EtOAc), and washed (sat. aq. NaCl solution). The combined organic layers were dried over sodium sulfate and concentrated under reduced pressure. The crude material was absorbed onto a plug of silica gel and purified by chromatography (SiO$_2$, 40 g, eluting with 20% to 60% ethyl acetate in hexane) to provide the title compound as a mixture of diastereomers.

Step E. (5R,6S)-3-Allyl-5-(3-chlorophenyl)-6-(4-chlorophenyl)-1-((S)-cyclopropyl(pyridin-2-yl)methyl)-3-methylpiperidin-2-one or (5R,6S)-3-Allyl-5-(3-chlorophenyl)-6-(4-chlorophenyl)-1-((R)-cyclopropyl(pyridin-2-yl)methyl)-3-methylpiperidin-2-one

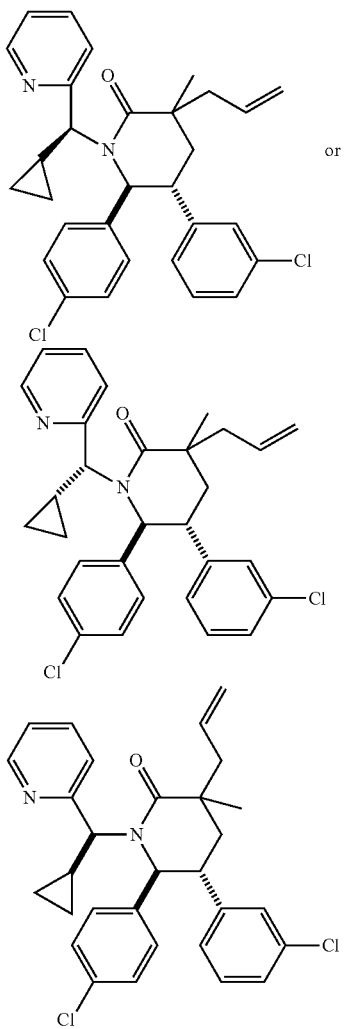

A solution of LHMDS (1.0M in THF, 0.838 mL, 0.838 mmol) was added to a solution of the diastereomeric mixture from Example 262, Step D (0.130 g, 0.279 mmol) and allyl bromide (0.095 mL, 1.117 mmol) in THF (2.80 mL). The reaction mixture was stirred at room temperature for 5 min, then heated to 50° C. for 3 h. The solution was diluted with sat. NH$_4$Cl solution, extracted (2× ethyl acetate), and washed (sat. aq. NaCl solution). The combined organic layers were dried over sodium sulfate and concentrated under reduced pressure. The crude material was absorbed onto a plug of silica gel and purified by chromatography (SiO$_2$, 40 g, eluted with a gradient of 0 to 35% EtOAc in hexane) to provide the title compound as a mixture of diastereomers as a white foam.

Step F. 2-((3R,5R,6S)-5-(3-Chlorophenyl)-6-(4-chlorophenyl)-1-((S)-cyclopropyl(pyridin-2-yl)methyl)-3-methyl-2-oxopiperidin-3-yl)acetic acid or 2-((3R,5R,6S)-5-(3-Chlorophenyl)-6-(4-chlorophenyl)-1-((R)-cyclopropyl(pyridin-2-yl)methyl)-3-methyl-2-oxopiperidin-3-yl)acetic acid The compound of Example 262, Step E (90 mg, 0.178 mmol) was treated by a procedure similar to the one described in Example 71, Step F. Separation of the diastereomers by reverse phase preparatory HPLC (eluent: 10 to 90% acetonitrile, water, 0.1% TFA, gradient elution) gave the title compound as the first eluting diastereomer.
$^1$H NMR (400 MHz, CHLOROFORM-d) δ ppm 0.09 (br s, 1 H) 0.28-0.34 (m, 1 H) 0.77-0.95 (m, 2 H) 1.37 (s, 3 H) 1.51-1.66 (m, 1 H) 2.13 (dd, J=14.09, 3.13 Hz, 1 H) 2.28 (t, J=13.69 Hz, 1 H) 2.79 (d, J=15.06 Hz, 1 H) 2.98 (d, J=15.06 Hz, 1 H) 3.29-3.41 (m, 1 H) 4.83 (d, J=9.98 Hz, 1 H) 5.08 (d, J=10.37 Hz, 1 H) 6.80 (d, J=7.63 Hz, 1 H) 6.96 (m, 5 H) 7.04-7.17 (m, 2 H) 7.63 (d, J=8.22 Hz, 1 H) 7.72 (t, J=6.65 Hz, 1 H) 8.07 (t, J=7.24 Hz, 1 H) 9.06 (d, J=4.89 Hz, 1 H). MS (ESI) m/z=523.2 (M+1).

Example 263

2-((3R,5R,6S)-5-(3-Chlorophenyl)-6-(4-chlorophenyl)-1-((S)-1-cyclopropyl-2-(thiophene-2-sulfonamido)ethyl)-3-methyl-2-oxopiperidin-3-yl)acetic acid

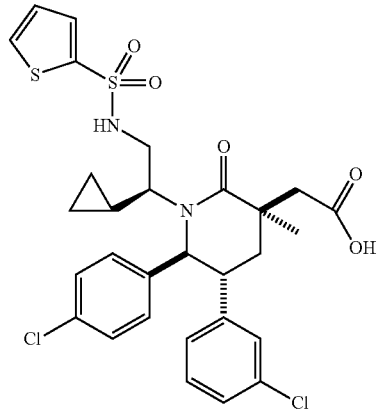 [SMILES: C[C@]1(CC(=O)O)C[C@H](c2cccc(Cl)c2)[C@@H](c2ccc(Cl)cc2)N([C@H](CNS(=O)(=O)c2cccs2)C2CC2)C1=O]

Step A. 2-((3R,5R,6S)-1-((S)-2-((tert-Butyldiphenylsilyl)oxy)-1-cyclopropylethyl)-5-(3-chlorophenyl)-6-(4-chlorophenyl)-3-methyl-2-oxopiperidin-3-yl)acetic acid

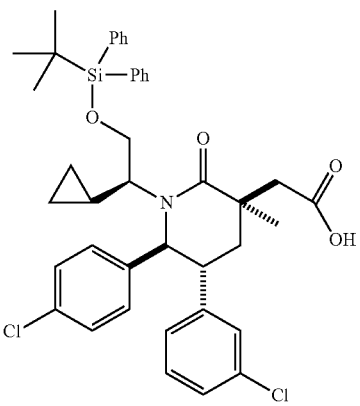 [SMILES: CC(C)(C)[Si](OC[C@H](C1CC1)N1C(=O)[C@@](C)(CC(=O)O)C[C@H](c2cccc(Cl)c2)[C@H]1c1ccc(Cl)cc1)(c1ccccc1)c1ccccc1]

To a rapidly stirring solution of (3S,5R,6S)-3-allyl-1-((S)-2-(tert-butyldiphenylsilyloxy)-1-cyclopropylethyl)-5-(3-chlorophenyl)-6-(4-chlorophenyl)-3-methylpiperidin-2-one (1450 mg, 2.08 mmol; Example 251, Step D) in a mixture of water (11 mL), acetonitrile (7.2 mL), and CCl$_4$ (7.2 mL) was added sodium periodate (1780 mg, 8.32 mmol), followed by ruthenium (III) chloride hydrate (47 mg, 0.21 mmol). After being stirred vigorously for 16 h, additional water (5.4 mL), acetonitrile (3.6 mL), and CCl$_4$ (3.6 mL) were added and to the resulting clear dark solution as was added additional sodium periodate (890 mg, 4.16 mmol) and ruthenium (III) chloride hydrate (24 mg, 0.10 mmol). After being stirred vigorously for additional 4 h, the reaction was acidified (10% citric acid) and diluted (EtOAc). The reaction mixture was filtered through pad of Celite® (J. T. Baker, Phillipsberg, N.J., diatomaceous earth) and the filtrate was extracted (2×EtOAc). The combined organic layers were washed (brine), dried (Na$_2$SO$_4$), and concentrated under the reduced pressure. Purification of the residue by chromatography on silica gel (80 g SiO$_2$, 30%, 40%, and 50% EtOAc/Hex) provided the title compound as a pale yellow foam.

Step B. Methyl 2-((3R,5R,6S)-1-((S)-2-((tert-butyldiphenylsilyl)oxy)-1-cyclopropylethyl)-5-(3-chlorophenyl)-6-(4-chlorophenyl)-3-methyl-2-oxopiperidin-3-yl)acetate

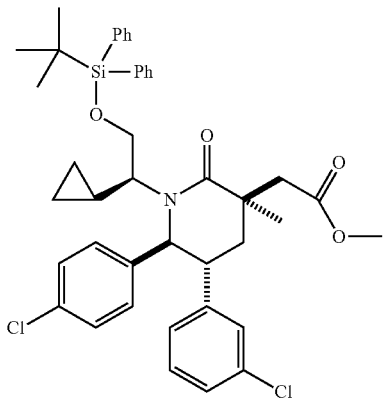 [SMILES: COC(=O)C[C@@]1(C)C[C@H](c2cccc(Cl)c2)[C@@H](c2ccc(Cl)cc2)N([C@H](CO[Si](c2ccccc2)(c2ccccc2)C(C)(C)C)C2CC2)C1=O]

To a solution of 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)acetic acid (1400 mg, 1.96 mmol; Example 263, Step A) in a mixture of MeOH (3.1 mL) and benzene (12.5 mL) was added 2.0 M (trimethylsilyl)diazomethane in hexanes (1.96 mL, 3.92 mmol) at 0° C. dropwise. After being stirred at 0° C. for 1 h, the reaction was concentrated under reduced pressure. Purification of the residue by chromatography on silica gel (40 g SiO$_2$, 10%, and 20% EtOAc/Hex) provided the title compound as a pale yellow foam.

Step C. Methyl 2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetate

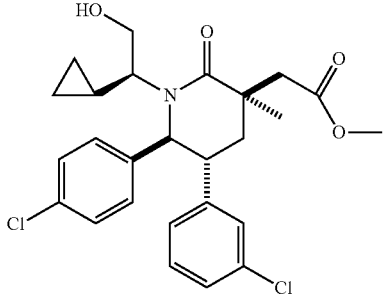 [SMILES: COC(=O)C[C@@]1(C)C[C@H](c2cccc(Cl)c2)[C@@H](c2ccc(Cl)cc2)N([C@H](CO)C2CC2)C1=O]

To a solution of methyl 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)acetate (578 mg, 0.793 mmol; Example 263, Step B) in THF (3.2 mL) was added 1 M TBAF in THF (2.38 mL, 2.38 mmol) at 0° C. and the reaction mixture was allowed to warm to rt. After being stirred at rt for 6 h, the reaction was quenched (sat. NH$_4$Cl), extracted (2×EtOAc) and washed (brine). The combined organic layers were dried (Na$_2$SO$_4$) and concentrated under the reduced pressure. Purification of the residue by chromatography on silica gel (40 g SiO$_2$, 10% and 50% EtOAc/Hex) provided the title compound as a colorless foam.

Step D. Methyl 2-((3R,5R,6S)-5-(3-chlorophenyl)-6-(4-chlorophenyl)-1-((S)-1-cyclopropyl-2-(thiophene-2-sulfonamido)ethyl)-3-methyl-2-oxopiperidin-3-yl)acetate

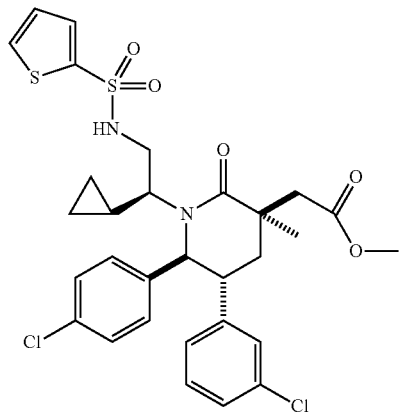 [SMILES: COC(=O)C[C@@]1(C)C[C@H](c2cccc(Cl)c2)[C@@H](c2ccc(Cl)cc2)N([C@H](CNS(=O)(=O)c2cccs2)C2CC2)C1=O]

To a solution of methyl 2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetate (100 mg, 0.184 mmol; Example 263, Step C) and cyanomethylenetributylphosphorane (177 µL, 0.734 mmol) in toluene (0.92 mL) was added thiophene-2-sulfonamide (90 mg, 0.55 mmol) and the resulting solution was stirred at 35° C. overnight. The reaction was quenched (sat. NH$_4$Cl), extracted (2×EtOAc), and washed (brine). The combined organic layers were dried (Na$_2$SO$_4$) and concentrated under the reduced pressure. Purification of the residue by chromatography on silica gel (24 g SiO$_2$, 35% EtOAc/Hex) provided the title compound as a pale yellow foam.

Step E. 2-((3R,5R,6S)-5-(3-Chlorophenyl)-6-(4-chlorophenyl)-1-((S)-1-cyclopropyl-2-(thiophene-2-sulfonamido)ethyl)-3-methyl-2-oxopiperidin-3-yl)acetic acid To a solution of methyl 2-((3R,5R,6S)-5-(3-chlorophenyl)-6-(4-chlorophenyl)-1-((S)-1-cyclopropyl-2-(thiophene-2-sulfonamido)ethyl)-3-methyl-2-oxopiperidin-3-yl)acetate (30 mg, 0.048 mmol; Example 263, Step D) in a mixture of water (0.16 mL), MeOH (0.16 mL), and THF (0.16 mL) was added 2 M aq. LiOH (48 µL, 0.095 mmol) at rt and the resulting solution was stirred at rt for 5 h. The reaction was quenched (sat. NH$_4$Cl), extracted (2×EtOAc), and washed (brine). The combined organic layers were dried (Na$_2$SO$_4$) and concentrated under the reduced pressure. Purification of the residue by chromatography on silica gel (12 g SiO$_2$, gradient elution of 50% to 100% EtOAc in Hex and 30% iPrOH/DCM) provided the title compound as a white powder.

$^1$H NMR (400 MHz, CHLOROFORM-d) δ ppm 7.50-7.66 (2H, m), 6.95-7.25 (8H, m), 6.81 (1H, d, J=7.4 Hz), 5.66 (1H, br, s), 4.87 (1H, d, J=10.0 Hz), 3.05-3.26 (3H, m), 2.87-3.02 (2H, m), 2.78-2.84 (1H, m), 2.18-2.32 (1H, m), 2.04-2.15 (1H, m), 1.47 (3H, s), 1.06-1.18 (1H, m), 0.41-0.57 (2H, m), −0.02-0.10 (1H, m), −0.35--0.20 (1H, m); MS (ESI) 621.0 [M+H]$^+$.

Example 264

2-((3R,5R,6S)-5-(3-Chlorophenyl)-6-(4-chlorophenyl)-1-((S)-1-cyclopropyl-2-(N-methylthiophene-2-sulfonamido)ethyl)-3-methyl-2-oxopiperidin-3-yl) acetic acid

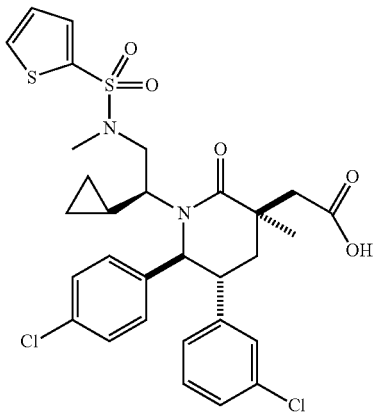 [SMILES: CN(C[C@H](C1CC1)N1C(=O)[C@@](C)(CC(=O)O)C[C@H](c2cccc(Cl)c2)[C@H]1c1ccc(Cl)cc1)S(=O)(=O)c1cccs1]

To a solution of methyl 2-((3R,5R,6S)-5-(3-chlorophenyl)-6-(4-chlorophenyl)-1-((S)-1-cyclopropyl-2-(thiophene-2-sulfonamido)ethyl)-3-methyl-2-oxopiperidin-3-yl)acetate (31 mg, 0.049 mmol; Example 263) in DMF (0.25 mL) was added sodium hydride (60% dispersion in mineral oil; 6 mg, 0.15 mmol) at rt, and the solution was stirred for 10 min. Then iodomethane (28 mg, 0.20 mmol) was added and the resulting solution was stirred at rt for 5 h. The reaction was quenched (sat. NH$_4$Cl), extracted (2×EtOAc), and washed (brine). The combined organic layers were dried (Na$_2$SO$_4$) and concentrated under the reduced pressure provided a mixture of the title compound and methyl ester.

To a solution of this crude mixture in water (0.16 mL), MeOH (0.16 mL), and THF (0.16 mL) was added lithium hydroxide (2.4 mg, 0.098 mmol) at rt and the resulting solution was stirred at RT overnight. The reaction was quenched (sat. NH$_4$Cl), extracted (2×EtOAc) and washed (brine). The combined organic layers were dried (Na$_2$SO$_4$) and concentrated under reduced pressure. Purification of the residue by chromatography on silica gel (4 g SiO$_2$, 50% and 90% EtOAc/Hex) provided the title compound as a white powder.

$^1$H NMR (400 MHz, CDCl$_3$) δ ppm 7.50-7.68 (2 H, m), 7.23-7.27 (2 H, m), 7.12-7.22 (4 H, m), 6.88-7.02 (3 H, m), 4.86 (1 H, d, J=10.0 Hz), 2.98-3.24 (2 H, m), 2.70-2.96 (3 H, m), 2.80 (3 H, s), 2.35-2.50 (2 H, m), 1.96-2.04 (1 H, m), 1.54 (3 H, br, s), 1.29-1.39 (1 H, m), 0.15-0.50 (2 H, m), −0.41--0.15 (1 H, m), −0.95--0.65 (1 H, m); MS (ESI) 635.0 [M+H]$^+$.

Example 265

2-((3R,5R,6S)-5-(3-Chlorophenyl)-6-(4-chlorophenyl)-1-((S)-2-(5-chlorothiophene-2-sulfonamido)-1-cyclopropylethyl)-3-methyl-2-oxopiperidin-3-yl) acetic acid

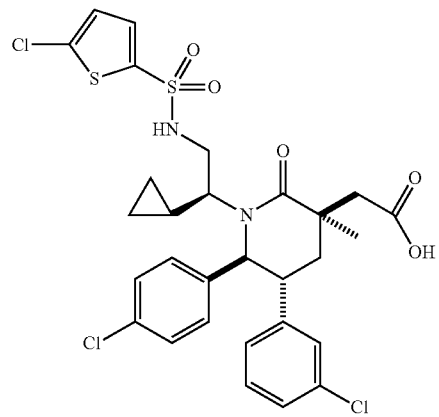 [SMILES: C[C@]1(CC(=O)O)C[C@H](c2cccc(Cl)c2)[C@@H](c2ccc(Cl)cc2)N([C@H](CNS(=O)(=O)c2ccc(Cl)s2)C2CC2)C1=O]

The title compound was prepared from methyl 2-((3R,5R,6S)-5-(3-chlorophenyl)-6-(4-chlorophenyl)-1-((S)-1-cyclopropyl-2-hydroxyethyl)-3-methyl-2-oxopiperidin-3-yl)acetate (Example 263, Step C) by procedures similar to those described in Example 263, Step D and E, substituting thiophene-2-sulfonamide in Step D with the appropriate amount of 5-chlorothiophene-2-sulfonamide.

$^1$H NMR (400 MHz, CDCl$_3$) δ ppm 7.35 (1 H, d, J=4.1 Hz), 6.97-7.25 (7 H, m), 6.94 (1 H, d, J=4.1 Hz), 6.78 (1 H, d, J=7.4 Hz), 5.82 (1 H, br, s), 4.86 (1 H, d, J=10.0 Hz), 2.87-3.20 (5 H, m), 2.78-2.85 (1 H, m), 2.19-2.27 (1 H, m), 2.07-2.16 (1 H, m), 1.46 (3 H, s), 1.01-1.13 (1 H, m), 0.50-0.60 (2 H, m), 0.06-0.17 (1 H, m), −0.25--0.10 (1 H, m);
MS (ESI) 655.0 [M+H]$^+$, 652.9 [M−H]$^−$.

Example 266

2-((3R,5R,6S)-1-((S)-2-(5-Chloro-N-methylthiophene-2-sulfonamido)-1-cyclopropylethyl)-5-(3-chlorophenyl)-6-(4-chlorophenyl)-3-methyl-2-oxopiperidin-3-yl)acetic acid

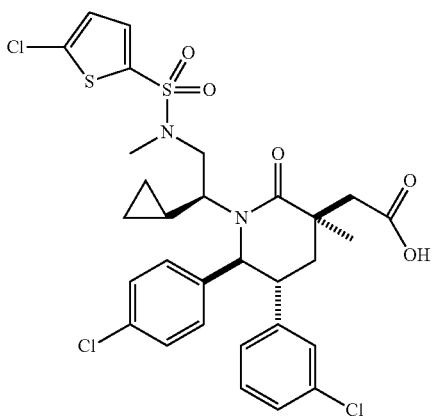 [SMILES: CN(C[C@H](C1CC1)N1C(=O)[C@@](C)(CC(=O)O)C[C@H](c2cccc(Cl)c2)[C@H]1c1ccc(Cl)cc1)S(=O)(=O)c1ccc(Cl)s1]

The title compound was prepared from the methyl ester precursor of 2-((3R,5R,6S)-5-(3-chlorophenyl)-6-(4-chlorophenyl)-1-((S)-2-(5-chlorothiophene-2-sulfonamido)-1-cyclopropylethyl)-3-methyl-2-oxopiperidin-3-yl)acetic acid (Example 265) by a procedure similar to the one described in Example 264.

¹H NMR (400 MHz, CDCl₃) δ ppm 7.28-7.40 (2 H, m), 6.83-7.18 (8 H, m), 4.75-4.88 (1 H, m), 3.00-3.21 (2 H, m), 2.74-2.86 (2 H, m), 2.81 (3H, s), 2.25-2.54 (2 H, m), 1.95-2.05 (1 H, m), 1.57-1.84 (2 H, m), 1.53 (3 H, br, s), 0.18-0.55 (2 H, m), −0.46--0.15 (1 H, m), −0.95--0.65 (1 H, m); MS (ESI) m/z=669.0 [M+H]⁺, 667.0 [M−H]⁻.

Example 267

2-((3R,5R,6S)-5-(3-Chlorophenyl)-6-(4-chlorophenyl)-1-((S)-1-cyclopropyl-2-(N-(difluoromethyl)-2-methylpropan-2-ylsulfonamido)ethyl)-3-methyl-2-oxopiperidin-3-yl)acetic acid

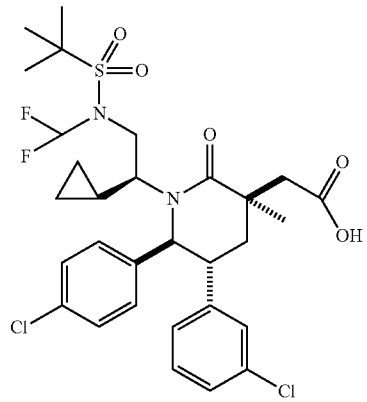 [SMILES: CC(C)(C)S(=O)(=O)N(C[C@H](C1CC1)N1C(=O)[C@@](C)(CC(=O)O)C[C@H](c2cccc(Cl)c2)[C@H]1c1ccc(Cl)cc1)C(F)F]

Step A. N-((S)-2-((3S,5R,6S)-3-Allyl-5-(3-chlorophenyl)-6-(4-chlorophenyl)-3-methyl-2-oxopiperidin-1-yl)-2-cyclopropylethyl)-2-methylpropane-2-sulfonamide

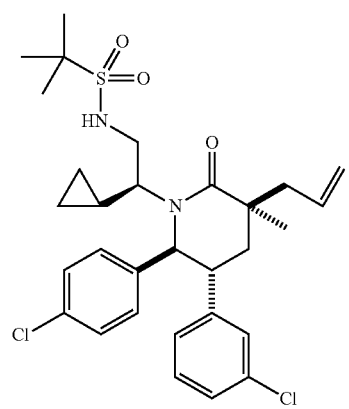 [SMILES: C=CC[C@@]1(C)C[C@H](c2cccc(Cl)c2)[C@@H](c2ccc(Cl)cc2)N([C@H](CNS(=O)(=O)C(C)(C)C)C2CC2)C1=O]

The title compound was obtained from (3S,5R,6S)-3-allyl-5-(3-chlorophenyl)-6-(4-chlorophenyl)-1-((S)-1-cyclopropyl-2-hydroxyethyl)-3-methylpiperidin-2-one (300 mg, 0.654 mmol; Example 252, Step A) and 2-methylpropane-2-sulfonamide (189 mg, 1.37 mmol) by a procedure similar to the one described in Example 127, Step F reacting for a total of 21 h. Purification of the residue by chromatography on silica gel (40 g SiO₂, 30% and 50% EtOAc/Hex) provided the title compound as a pale yellow foam.

Step B. N-((S)-2-((3S,5R,6S)-3-Allyl-5-(3-chlorophenyl)-6-(4-chlorophenyl)-3-methyl-2-oxopiperidin-1-yl)-2-cyclopropylethyl)-N-(difluoromethyl)-2-methylpropane-2-sulfonamide

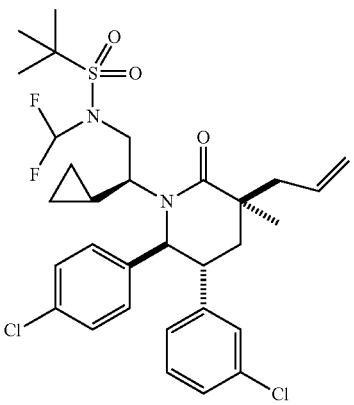 [SMILES: C=CC[C@@]1(C)C[C@H](c2cccc(Cl)c2)[C@@H](c2ccc(Cl)cc2)N([C@H](CN(C(F)F)S(=O)(=O)C(C)(C)C)C2CC2)C1=O]

To a solution of N-((S)-2-((3S,5R,6S)-3-allyl-5-(3-chlorophenyl)-6-(4-chlorophenyl)-3-methyl-2-oxopiperidin-1-yl)-2-cyclopropylethyl)-2-methylpropane-2-sulfonamide (88 mg, 0.152 mmol; Example 267, Step A) in DMF (1.0 mL) was added 60% sodium hydride in mineral oil (24 mg, 0.61 mmol) and the resulting solution was stirred at rt for 10 min. Then chlorodifluoromethane was bubbled into the reaction for 10 min while the reaction was vigorously stirred and the resulting reaction was stirred for 2 h. The reaction was quenched (sat. NH₄Cl), extracted (2×EtOAc) and washed (brine). The combined organic layers were dried (Na₂SO₄) and concentrated under the reduced pressure. Purification of the residue by chromatography on silica gel (12 g SiO₂, 20% and 30% EtOAc/Hex) provided the title compound as a colorless film.

Step C. 2-((3R,5R,6S)-5-(3-Chlorophenyl)-6-(4-chlorophenyl)-1-((S)-1-cyclopropyl-2-(N-(difluoromethyl)-2-methylpropan-2-ylsulfonamido)ethyl)-3-methyl-2-oxopiperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(difluoromethyl)-2-methylpropane-2-sulfonamide (57 mg, 0.091 mmol; Example 267, Step B) by a procedure similar to the one described in Example 71, Step F. Purification of the residue by reverse phase preparatory HPLC (Gemini™ Prep C₁₈ 5 μm column, Phenomenex, Torrance, Calif.; gradient elution of 50% to 75% MeCN in water, where both solvents contain 0.1% TFA) provided the title compound as a white foam.

¹H NMR (400 MHz, CDCl₃) δ ppm 7.08-7.27 (4 H, m), 6.93-7.00 (2 H, m), 6.65-6.87 (2 H, m), 5.50 (1 H, br, s), 4.55-4.70 (2 H, m), 3.55-3.68 (1 H, m), 3.09-3.18 (2 H, m), 2.79 (1 H, d, J=15.1 Hz), 2.35-2.69 (2 H, m), 1.74-1.94 (2 H, m), 1.53 (3 H, s), 1.47 (9 H, s.), 0.36-0.49 (1 H, m), 0.23-0.35

(1 H, m), −0.34−−0.15 (1 H, m), −0.87−−0.71 (1 H, m); MS (ESI) m/z=645.0 [M+H]⁺, 643.0 [M−H]⁻.

Examples 268 and 269 were also prepared from (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, Step A) by procedures similar to the ones described in Example 267, substituting 2-methylpropane-2-sulfonamide in step A with the appropriate amount of reagent listed in the table.

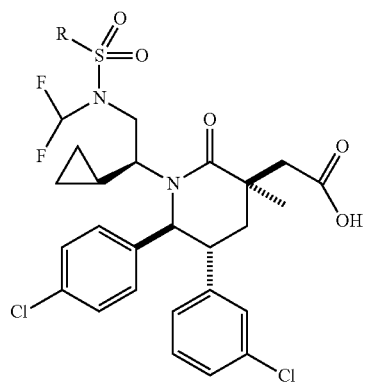

| Example | R | Reagent used |
|---|---|---|
| 268 | (ethyl) | ethanesulfonamide |
| 269 | (cyclopropyl) | cyclopropanesulfonamide |

Example 268

2-((3R,5R,6S)-5-(3-Chlorophenyl)-6-(4-chlorophenyl)-1-((S)-1-cyclopropyl-2-(N-(difluoromethyl)ethylsulfonamido)ethyl)-3-methyl-2-oxopiperidin-3-yl)acetic acid ¹H NMR (500 MHz, CHLOROFORM-d) δ ppm −0.78 (br. s., 1 H) −0.22 (br. s., 1 H) 0.31 (br. s., 1 H) 0.42 (br. s., 1 H) 1.38-1.49 (m, 3 H) 1.52 (s, 3 H) 1.57-2.11 (br. s., 2 H) 2.40-2.52 (m., 2 H) 2.78 (d, J=15.41 Hz, 1 H) 3.08-3.27 (m, 4H) 3.42-4.02 (br. s., 2 H) 4.57-4.74 (m, 2 H) 6.80 (d, J=7.34 Hz, 1 H) 6.95 (s, 1 H) 7.08-7.18 (m, 2 H) 7.27 (m., 4 H); Mass Spectrum (ESI) m/z=617 (M+1).

Example 269

2-((3R,5R,6S)-5-(3-Chlorophenyl)-6-(4-chlorophenyl)-1-((S)-1-cyclopropyl-2-(N-(difluoromethyl)cyclopropanesulfonamido)ethyl)-3-methyl-2-oxopiperidin-3-yl)acetic acid ¹H NMR (500 MHz, CHLOROFORM-d) δ ppm −0.79 (br. s., 1 H) −0.23 (br. s., 1 H) 0.31 (br. s., 1 H) 0.42 (br. s., 1 H) 1.12-1.36 (m, 3 H) 1.51 (s, 3 H) 1.59-1.95 (m, 5 H) 2.44 (br. s., 2 H) 2.77 (d, J=15.41 Hz, 1 H) 3.04-3.26 (m, 2 H) 3.53 (m, 1 H) 4.48-4.70 (m, 2 H) 6.79 (d, J=7.34 Hz, 1 H) 6.93 (s, 1 H) 7.07-7.18 (m, 2H) 7.27 (m., 4 H); Mass Spectrum (ESI) m/z=629 (M+1).

Example 270

1-((3R,5R,6S)-5-(3-Chlorophenyl)-6-(4-chlorophenyl)-1-((S)-2-(cyclopropanesulfonamido)-1-cyclopropylethyl)-3-methyl-2-oxopiperidin-3-yl)cyclopropanecarboxylic acid

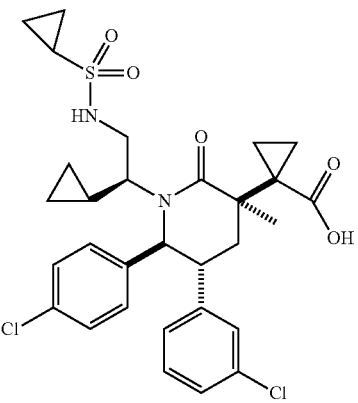 [SMILES: C[C@]1(C2(C(=O)O)CC2)C[C@H](c2cccc(Cl)c2)[C@@H](c2ccc(Cl)cc2)N([C@H](CNS(=O)(=O)C2CC2)C2CC2)C1=O]

Step A. (S)-Methyl 2-((3R,5R,6S)-1-((S)-2-((tert-butyldiphenylsilyl)oxy)-1-cyclopropylethyl)-5-(3-chlorophenyl)-6-(4-chlorophenyl)-3-methyl-2-oxopiperidin-3-yl)-3-hydroxypropanoate

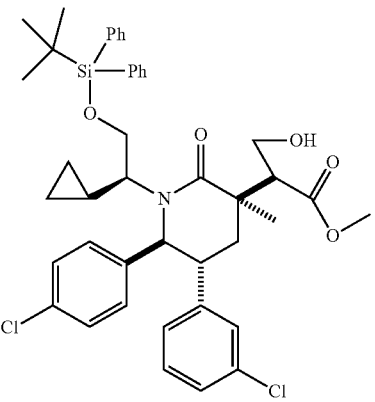 [SMILES: COC(=O)C(CO)[C@@]1(C)C[C@H](c2cccc(Cl)c2)[C@@H](c2ccc(Cl)cc2)N([C@H](CO[Si](c2ccccc2)(c2ccccc2)C(C)(C)C)C2CC2)C1=O]

To a solution of diisopropylamine (249 μL, 1.75 mmol) in THF (1.2 mL) was added 1.6 M n-BuLi in hexanes (984 μL, 1.57 mmol) slowly at −15° C. After 30 minutes, a solution of methyl 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)acetate (255 mg, 0.35 mmol; Example 263, Step B) in THF (1.2 mL) was added dropwise to the LDA solution and the resulting solution was stirred at −15° C. for 30 min (the solution turned bright yellow). Then, formaldehyde in N₂ stream was carried over the reaction surface for 5 min (formaldehyde was generated by cracking para-formaldehyde (105 mg, 3.50 mmol) with heat gun) at −15° C. After being stirred at −15° C. for 30 min, the reaction was allowed to warm to rt and stirred for 4 h. The reaction was quenched (ice cold sat. NH₄Cl), extracted (2×EtOAc) and washed (brine×3). The combined organic layers were dried (Na₂SO₄) and concentrated under the reduced pressure. Purification of the residue by chromatography on silica gel (24 g SiO₂, 20% and 50% EtOAc/Hex) provided the title compound as a colorless film.

Step B. Methyl 2-((3R,5R,6S)-1-((S)-2-((tert-butyldiphenylsilyl)oxy)-1-cyclopropylethyl)-5-(3-chlorophenyl)-6-(4-chlorophenyl)-3-methyl-2-oxopiperidin-3-yl)acrylate

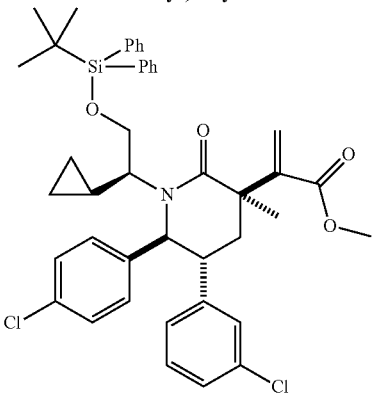

To a solution of (S)-methyl 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)-3-hydroxypropanoate (132 mg, 0.173 mmol; Example 270, Step A) and triethylamine (97 µL, 0.69 mmol) in DCM (2.2 mL) was added a solution of methanesulfonyl chloride (27 µL, 0.35 mmol) in DCM (2.2 mL) at 0° C. Then the reaction was allowed to warm to rt and stirred for 3 h. The reaction was quenched (water), extracted (2×EtOAc) and washed (brine). The combined organic layers were dried (Na₂SO₄) and concentrated under the reduced pressure to provide a crude mesylated compound, (S)-methyl 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)-3-(methylsulfonyloxy)propanoate.

To a solution of the crude mesylated compound from above in DCM (2.2 mL) was added DBU (78 µL, 0.52 mmol) and the resulting solution was stirred at rt for 1 h. The reaction was quenched (ice cold sat. NH₄Cl), extracted (2×EtOAc) and washed (brine). The combined organic layers were dried (Na₂SO₄) and concentrated under the reduced pressure. Purification of the residue by chromatography on silica gel (12 g SiO₂, 10% and 20% EtOAc/Hex) provided the title compound as a colorless film.

Step C. Methyl 1-((3R,5R,6S)-1-((S)-2-((tert-butyldiphenylsilyl)oxy)-1-cyclopropylethyl)-5-(3-chlorophenyl)-6-(4-chlorophenyl)-3-methyl-2-oxopiperidin-3-yl)cyclopropanecarboxylate

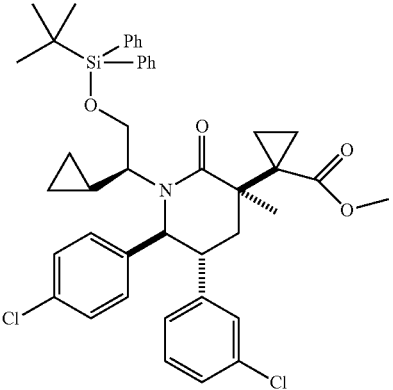 [SMILES: COC(=O)C1([C@@]2(C)C[C@H](c3cccc(Cl)c3)[C@@H](c3ccc(Cl)cc3)N([C@H](CO[Si](c3ccccc3)(c3ccccc3)C(C)(C)C)C3CC3)C2=O)CC1]

To a suspension of trimethylsulfoxonium iodide (39 mg, 0.18 mmol) in DMSO (0.71 mL) was added a suspension of 60% sodium hydride in mineral oil (7.1 mg, 0.18 mmol). After being stirred 15 min, a solution of methyl 2-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)acrylate (66 mg, 0.089 mmol; Example 270, Step B) in DMSO (0.71 mL) was added and the mixture was stirred at rt for 3 h. The reaction was quenched (ice cold sat. NH₄Cl), extracted (2×EtOAc), and washed (brine×3). The combined organic layers were dried (Na₂SO₄) and concentrated under the reduced pressure. Purification of the residue by chromatography on silica gel (4 g SiO₂, 10% and 20% EtOAc/Hex) provided the title compound as a colorless film.

Step D. Methyl 1-((3R,5R,6S)-5-(3-chlorophenyl)-6-(4-chlorophenyl)-1-((S)-1-cyclopropyl-2-hydroxyethyl)-3-methyl-2-oxopiperidin-3-yl)cyclopropanecarboxylate

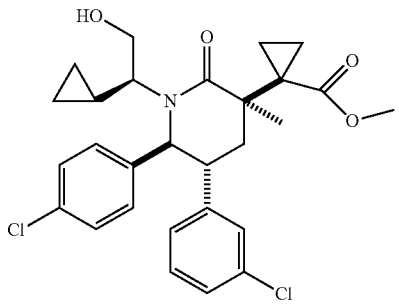 [SMILES: COC(=O)C1([C@@]2(C)C[C@H](c3cccc(Cl)c3)[C@@H](c3ccc(Cl)cc3)N([C@H](CO)C3CC3)C2=O)CC1]

To a solution of methyl 1-((3R,5R,6S)-1-((S)-2-(tert-butyldiphenylsilyloxy)-1-cyclopropylethyl)-5-(3-chlorophenyl)-6-(4-chlorophenyl)-3-methyl-2-oxopiperidin-3-yl)cyclopropanecarboxylate (53 mg, 0.070 mmol; Example 270, Step C) in THF (0.70 mL) was added 1 M TBAF in THF (0.21 mL, 0.21 mmol) and the reaction was stirred at rt overnight. The reaction was quenched (sat. NH₄Cl), extracted (2×EtOAc), and washed (brine). The combined organic layers were dried (Na₂SO₄) and concentrated under the reduced pressure. Purification of the residue by chromatography on silica gel (4 g SiO₂, 10%, 45%, and 55% EtOAc/Hex) provided the title compound as a white foam Step E. Methyl 1-((3R,5R,6S)-5-(3-chlorophenyl)-6-(4-chlorophenyl)-1-((S)-2-(cyclopropanesulfonamido)-1-cyclopropylethyl)-3-methyl-2-oxopiperidin-3-yl)cyclopropanecarboxylate

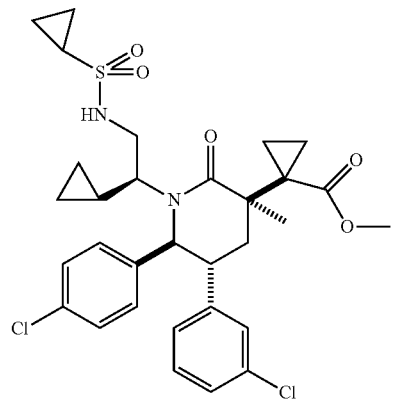 [SMILES: COC(=O)C1([C@@]2(C)C[C@H](c3cccc(Cl)c3)[C@@H](c3ccc(Cl)cc3)N([C@H](CNS(=O)(=O)C3CC3)C3CC3)C2=O)CC1]

The tile compound was prepared from methyl 1-((3R,5R,6S)-5-(3-chlorophenyl)-6-(4-chlorophenyl)-1-((S)-1-cyclopropyl-2-hydroxyethyl)-3-methyl-2-oxopiperidin-3-yl)cyclopropanecarboxylate (35 mg, 0.068 mmol; Example 270, Step D) and cyclopropanesulfonamide (25 mg, 0.20 mmol) by a procedure similar to the one described in Example 202, Step C. Purification of the residue by chromatography on silica gel (4 g SiO$_2$, 45% and 60% EtOAc/Hex) provided the title compound as a pale yellow.

Step F. 1-((3R,5R,6S)-5-(3-chlorophenyl)-6-(4-chlorophenyl)-1-((S)-2-(cyclopropanesulfonamido)-1-cyclopropylethyl)-3-methyl-2-oxopiperidin-3-yl)cyclopropanecarboxylic acid The title compound was prepared from methyl 1-((3R,5R,6S)-5-(3-chlorophenyl)-6-(4-chlorophenyl)-1-((S)-2-(cyclopropanesulfonamido)-1-cyclopropylethyl)-3-methyl-2-oxopiperidin-3-yl)cyclopropanecarboxylate (27 mg, 0.043 mmol; Example 270, Step E) by a procedure similar to the one described in Example 263, Step E. Purification of the residue by reverse phase preparatory HPLC (Gemini™ Prep C$_{18}$ 5 µm column, Phenomenex, Torrance, Calif.; gradient elution of 45% to 70% MeCN in water, where both solvents contain 0.1% TFA) provided the title compound.

$^1$H NMR (400 MHz, CHLOROFORM-d) δ ppm 7.03-7.26 (6 H, m), 6.92-6.96 (1 H, m), 6.79 (1 H, d, J=7.0 Hz), 4.79 (1 H, d, J=10.6 Hz), 3.37-3.48 (1 H, m), 3.12-3.20 (1 H, m), 2.78 (1 H, dd, J=14.0, 2.2 Hz), 2.37-2.45 (1 H, m), 2.15-2.25 (1 H, m), 1.80-1.88 (1 H, m), 1.38-1.50 (2 H, m), 1.45 (3 H, s), 1.10-1.31 (7 H, m), 0.93-1.01 (2 H, m), 0.35-0.54 (2 H, m), −0.09-0.12 (1 H, m), −0.72--0.23 (1 H, m); MS (ESI) m/z=605.0 [M+H]$^+$, 603.1 [M−H]$^-$.

Example 271

Intermediate

A: N-(2-fluorophenyl)ethanesulfonamide

To a solution of ethanesulfonyl chloride (0.368 ml, 3.89 mmol) in DCM (1 ml) and pyridine (1 ml) was added 2-fluoroaniline (0.360 ml, 3.89 mmol) at rt and the reaction was stirred at 50° C. for 5 hours. The reaction was then stirred at rt overnight. The reaction was diluted with EtOAc and washed with H$_2$O and sat. NaCl solution. The organic layer was dried over Na$_2$SO$_4$ and concentrated. Purification of the residue by flash chromatography on silica gel (eluent: 0% to 35% EtOAc/hexane) provided the title compound as a white solid.

$^1$H NMR (400 MHz, CHLOROFORM-d) δ ppm 1.42 (t, J=8 Hz, 3 H), 3.15 (q, J=8 Hz, 2 H), 6.48 (s, br, 1 H), 7.17 (m, 3 H), 7.64 (m, 1 H).

In a similar fashion the following were prepared:
B: N-(phenyl)ethanesulfonamide: $^1$H NMR (400 MHz, chloroform-d) δ ppm 1.38 (t, J=8 Hz, 3H), 3.14-3.20 (q, J=8 Hz, 2H), 7.15-7.17 (m, 1H), 7.29-7.36 (m, 4H).
C: N-(3-fluorophenyl)ethanesulfonamide: $^1$H NMR (400 MHz, chloroform-d) δ ppm 1.42 (t, J=8 Hz, 3H), 3.17-3.23 (q, J=8 Hz, 2H), 6.78 (s, br, 1H), 6.89 (m, 1H), 6.99 (m, 1H), 7.04 (m, 1H), 7.77 (m, 1H).
D: N-(pyridin-3-yl)methanesulfonamide: $^1$H NMR (400 MHz, methanol-d4) δ ppm 3.05 (s, 3H), 7.43-7.46 (dd, J=4, 8 Hz, 1H), 7.78-7.81 (dd, J=2, 4 Hz, 1H), 8.33 (d, J=4 Hz, 1H), 8.45 (s, 1H). Mass Spectrum (ESI) m/z=173.2 (M+1).
E: N-(phenyl)cyclopropanesulfonamide: $^1$H NMR (400 MHz, CHLOROFORM-d) δ ppm 0.96-1.00 (m, 2H), 1.18-1.22 (m, 2H), 2.48-2.55 (m, 1H), 7.20-7.22 (m, 1H), 7.28-7.30 (m, 2H), 7.37-7.39 (m, 2H).

F: propane-1-sulfonamide [CAS no. 24243-71-8]

A stream of anhydrous ammonia was bubbled into a solution of propane-1-sulfonyl chloride (7.3 g, 51.2 mmol) in anhydrous THF (100 ml) on ice bath. Bubbling was continued for 1 hour during which a lot of white solid precipitated. The reaction was then stirred at rt for 2 days. The reaction mixture was diluted with EtOAc, washed with H$_2$O and sat. NaCl, dried with Na$_2$SO$_4$, and then concentrated. Purification of the crude using flash chromatography on silica gel (eluted with 0% to 35% EtOAc/hexane) gave the title compound as a white solid (3.0 g, 47.6%).

$^1$H NMR (400 MHz, chloroform-d) δ ppm −1.10 (t, J=8 Hz, 3H), 1.91 (m, 2H), 3.11 (m, 2H), 4.94 (s, 2H).

G: Cyclobutanesulfonamide [CAS no. 445305-91-9]

A stream of anhydrous ammonia was bubbled for 30 min through a stirred solution of cyclobutanesulfonyl chloride (5 g, 32.3 mmol; Hande Sciences) in dry THF (100 mL) at 0° C., causing formation of a white precipitate. The suspension was warmed to ambient temperature and stirred overnight. The mixture was filtered and the filter cake was copiously washed with ethyl acetate. The filtrate was concentrated under reduced pressure, redissolved in ca. 150 mL EtOAc, and washed 3× with brine. Organics were dried over sodium sulfate, filtered, and concentrated in vacuo to give a white, partially crystalline residue that was triturated with hexanes and dried under high vacuum to give cyclobutanesulfonamide as a fluffy white solid, 1.8 g (41% yield).

$^1$H NMR (400 MHz, CHLOROFORM-d) δ 1.96-2.10 (m, 2 H), 2.30-2.43 (m, 2 H), 2.43-2.59 (m, 2 H), 3.72-4.01 (m, 1 H), 4.70 (br. s., 2 H).

Example 272

2-((3R,5R,6S)-5-(3-Chlorophenyl)-6-(4-chlorophenyl)-1-((S)-1-cyclopropyl-2-(N-(2-fluorophenyl)ethylsulfonamido)ethyl)-3-methyl-2-oxopiperidin-3-yl)acetic acid

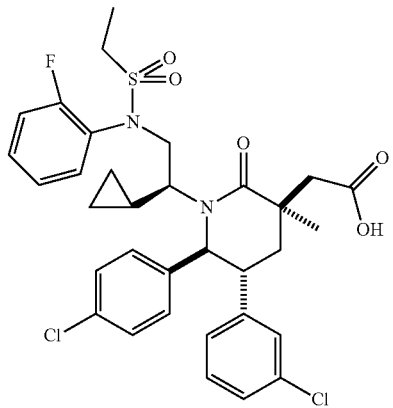 [SMILES: CCS(=O)(=O)N(C[C@H](C1CC1)N1C(=O)[C@@](C)(CC(=O)O)C[C@H](c2cccc(Cl)c2)[C@H]1c1ccc(Cl)cc1)c1ccccc1F]

Step A. N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(2-fluorophenyl)ethanesulfonamide

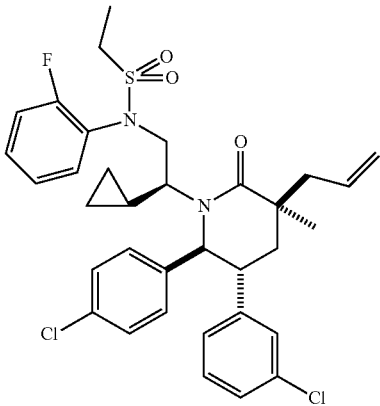 [SMILES: C=CC[C@@]1(C)C[C@H](c2cccc(Cl)c2)[C@@H](c2ccc(Cl)cc2)N([C@H](CN(c2ccccc2F)S(=O)(=O)CC)C2CC2)C1=O]

To a mixture of (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, Step A, 70 mg, 0.153 mmol) and N-(2-fluorophenyl)ethanesulfonamide (93 mg, 0.458 mmol) in toluene (1 ml) was added cyanomethylenetri-n-butylphosphorane (0.111 ml, 0.458 mmol) at rt and the mixture was flushed with $N_2$ for about 20 minutes. The reaction was sealed and heated to 70° C. overnight. The reaction mixture was purified by flash chromatography on silica gel (eluent: 0% to 35% EtOAc/hexanes) to provide the title compound as a solid.

$^1$H NMR (400 MHz, methanol-d4) ppm −1.25 (s, br, 1 H), −0.64 (s, br, 1 H), 0.00 (s, br, 1 H), 0.16 (s, br, 1 H), 0.73 (m, 1 H), 0.92 (s, 3 H), 1.19 (m, 4 H), 1.48 (m, 1 H), 1.66 (m, 1 H), 2.00 (m, 2 H), 2.24 (m, 1 H), 2.52 (m, 1 H), 2.97 (m, 2 H), 3.71 (s, br, 1 H), 4.56 (d, J=12 Hz, 1 H), 5.01 (m, 1 H), 5.05 (s, 1 H), 5.73 (m, 1 H), 6.83-6.91 (m, 3 H), 7.03-7.16 (m, 7 H), 7.28 (m, 1 H), 7.45 (m, 1 H).

Mass Spectrum (ESI) m/z=643.2 (M+1)

Step B: 2-((3R,5R,6S)-5-(3-chlorophenyl)-6-(4-chlorophenyl)-1-((S)-1-cyclopropyl-2-(N-(2-fluorophenyl)ethylsulfonamido)ethyl)-3-methyl-2-oxopiperidin-3-yl)acetic acid To a solution of N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(2-fluorophenyl)ethanesulfonamide (Example 272, Step A, 72 mg, 0.112 mmol) in THF (0.600 ml), water (0.396 ml) and BuOH (0.3 ml) was added 4-methylmorpholine 4-oxide (45.9 mg, 0.392 mmol) followed by osmium(VIII) oxide (0.037 ml, 2.80 µmol). The reaction was stirred at rt overnight. Sodium periodate (71.8 mg, 0.336 mmol) was added and the reaction was stirred at rt for 2 hours. To this reaction was added 1.25M $KH_2PO_4$ (0.80 ml), 1 M of 2-methylbut-2-ene solution in THF (2.24 ml, 4.47 mmol) and sodium chlorite (50.6 mg, 0.56 mmol) and the reaction was stirred at rt for 2 hours. Upon the end of the reaction 0.8 ml of 1 M aq. $NaS_2O_3$ aq. was added and the reaction was stirred at rt for 10 minutes followed by adding 0.8 ml of 1 M aq. $KHSO_4$.

The reaction was then diluted with EtOAc and washed with $H_2O$ and sat. NaCl. The organic layer was dried with $Na_2SO_4$ and concentrated. The product was purified by reversed phase preparatory HPLC (eluents: 40-85% of acetonitile in water with 0.1% of TFA gradient on Gemini™ Prep $C_{18}$ 5 um column, Phenomenex, Torrance, Calif.) to give the title compound as a white solid.

$^1$H NMR (400 MHz, methanol-$d_4$) ppm −1.28 (s, br, 1H), −0.63 (s, br, 1H), 0.00 (s, br, 1H), 0.17 (s, br, 1H), 1.07 (s, 3H), 1.20 (t, J=4 Hz, 3H), 1.51-1.55 (m, 1H), 1.91-1.95 (dd, J=4 Hz, 16 Hz, 1H), 2.05 (s, br, 1H), 2.11 (t, J=12 Hz, 1H), 2.49-2.53 (d, J=16 Hz, 1H), 2.79-2.83 (d, J=16 Hz, 1H), 2.98 (s, br, 2H), 3.27 (m, 1H), 3.71 (s, br, 1H), 4.62 (s, br, 2H), 6.87 (d, J=8 Hz, 2H), 6.92 (s, 1H), 7.03-7.18 (m, 7H), 7.29 (m, 1H), 7.49 (s, br, 1H).

Mass Spectrum (ESI) m/z=661.2 (M+1)

Examples 273-289, were prepared in a similar fashion to example 272. Using the corresponding sulfonamide and the alcohol of Example 252, Step A, allyl sulfonamides were formed in Step A and converted to the corresponding carboxylic acids in Step B.

| Example | Reagent used | Source or CAS# |
| --- | --- | --- |
| 272 | N-(2-fluorophenyl)ethanesulfonamide | Example 271A |
| 273 | N-(2-fluorophenyl)methanesulfonamide | [98611-90-6] |
| 274 | N-(phenyl)cyclopropanesulfonamide | Example 271E |
| 275 | N-(phenyl)ethanesulfonamide | Example 271B |
| 276 | ethanesulfonamide | [1520-70-3] |
| 277 | N-(3-fluorophenyl)ethanesulfonamide | Example 271C |
| 278 | N-(2-cyanophenyl)methanesulfonamide | [50790-29-9] |
| 279 | propane-1-sulfonamide | Example 271F |
| 280 | N-(phenyl)methanesulfonamide | [1197-22-4] |
| 281 | N-(3-cyanophenyl)methanesulfonamide | [50790-30-2] |
| 282 | N-(pyridin-3-yl)methanesulfonamide | Example 271D |
| 283 | N-(thiophen-2-ylmethyl)methanesulfonamide | BBB-SCI 3B3-026467, Libertyville, IL |
| 284 | N-(3-MeOPhenylmethyl)-methanesulfonamide | |
| 285 | alpha-toluenesulfonamide | [4563-33-1] |
| 286 | pyridin-2-ylmethanesulfonamide | Princeton PBMR006092, Monmouth Junction NJ |
| 287 | pyridin-3-ylmethanesulfonamide | Princeton PBMR006093, Monmouth Junction NJ |
| 288 | N-(pyridin-2-yl)methanesulfonamide | [74351-44-3] |
| 289 | methanesulfonamide | [3144-09-0] |

Example 273

2-((3R,5R,6S)-5-(3-chlorophenyl)-6-(4-chlorophenyl)-1-((S)-1-cyclopropyl-2-(N-(2-fluorophenyl)methylsulfonamido)ethyl)-3-methyl-2-oxopiperidin-3-yl)acetic acid

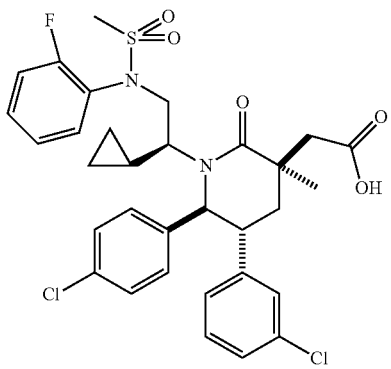 [SMILES: C[C@]1(CC(=O)O)C[C@H](c2cccc(Cl)c2)[C@@H](c2ccc(Cl)cc2)N([C@H](CN(c2ccccc2F)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(2-fluorophenyl)methanesulfonamide

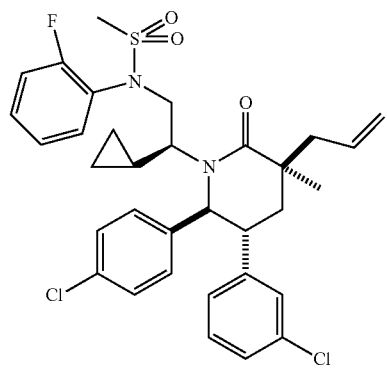 [SMILES: C=CC[C@@]1(C)C[C@H](c2cccc(Cl)c2)[C@@H](c2ccc(Cl)cc2)N([C@H](CN(c2ccccc2F)S(C)(=O)=O)C2CC2)C1=O]

$^1$H NMR (400 MHz, methanol-d4) δ ppm −1.20 (s, br, 1H), −0.63 (s, br, 1H), 0.00 (s, br, 1H), 0.13 (s, br, 1H), 0.88 (s, 3H), 1.48 (m, 1H), 1.64 (d, J=12 Hz, 1H), 1.94-1.99 (s, 2H), 2.19 (d, J=8 Hz, 2H), 2.72 (s, 3H), 2.99 (m, 1H), 3.54 (s, br, 1H), 4.50 (d, J=8 Hz, 1H), 4.59 (s, br, 1H), 4.96-5.01 (m, 2H), 5.65 (m, 1H), 6.70 (s, br, 2H), 6.80 (s, br, 2H), 6.96-7.08 (m, 6H), 7.19 (m, 1H), 7.27 (m, 1H).
Mass Spectrum (ESI) m/z=629.2 (M+1).

Step B: 2-((3R,5R,6S)-5-(3-chlorophenyl)-6-(4-chlorophenyl)-1-((S)-1-cyclopropyl-2-(N-(2-fluorophenyl)methylsulfonamido)ethyl)-3-methyl-2-oxopiperidin-3-yl)acetic acid $^1$H NMR (400 MHz, methanol-d$_4$) δ ppm −1.27 (s, br, 1H), −0.58 (s, br, 1H), 0.00 (s, br, 1H), 0.18 (s, br, 1H), 1.03 (s, 3H), 1.07-1.04 (m, 1H), 1.50 (m, 1H), 1.90-1.94 (dd, J=4, 12 Hz, 1H), 2.08 (t, J=16 Hz, 1H), 2.47 (d, J=16 Hz, 1H), 2.78 (d, J=16 Hz, 1H), 2.81 (s, 3H), 3.26 (m, 1H), 3.67 (s, br, 1H), 4.57 (d, J=12 Hz, 1H), 6.84 (d, J=8 Hz, 2H), 6.90 (s, 1H), 7.03 (m, 4H), 7.16 (m, 2H), 7.29 (m, 1H), 7.31 (m, 1H).
Mass Spectrum (ESI) m/z=647.0 (M+1).

Example 274

2-((3R,5R,6S)-5-(3-chlorophenyl)-6-(4-chlorophenyl)-1-((S)-1-cyclopropyl-2-(N-phenylcyclopropanesulfonamido)ethyl)-3-methyl-2-oxopiperidin-3-yl)acetic acid

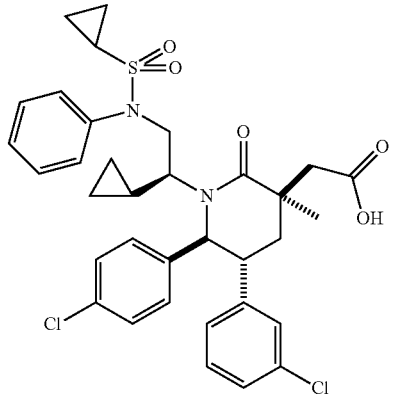 [SMILES: C[C@]1(CC(=O)O)C[C@H](c2cccc(Cl)c2)[C@@H](c2ccc(Cl)cc2)N([C@H](CN(c2ccccc2)S(=O)(=O)C2CC2)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-phenylcyclopropanesulfonamide

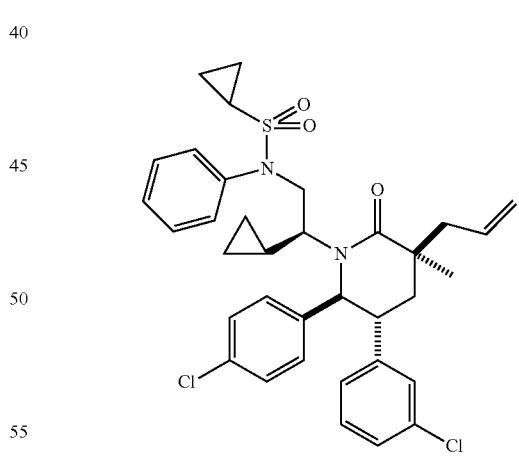

$^1$H NMR (400 MHz, methanol-d$_4$) δ ppm −1.24 (s, br, 1H), −0.56 (s, br, 1H), 0.00 (s, br, 1H) 0.20 (s, br, 1H), 0.69-0.78 (m, 4H), 0.92 (s, br, 3H), 1.55 (s, br, 1H), 1.62-1.66 (dd, J=4, 12 Hz, 1H), 1.93-2.00 (m, 2H), 2.36-2.45 (m, 2H), 2.51-2.57 (m, 1H), 3.12-3.19 (m, 1H), 3.81 (s, br, 1H), 4.42-4.45 (d, br, J=12 Hz, 1H), 4.76 (s, br, 1H), 5.00-5.05 (t, J=8 Hz, 1H), 5.09 (s, 1H), 5.70-5.79 (m, 1H), 6.79 (m, 2H), 6.92 (s, 1H), 7.04 (m, 4H), 7.18-7.30 (m, 2H), 7.72 (m, 2H), 7.44 (d, J=8 Hz).
Mass Spectrum (ESI) m/z=637.2 (M+1).

Step B: 2-((3R,5R,6S)-5-(3-chlorophenyl)-6-(4-chlorophenyl)-1-((S)-1-cyclopropyl-2-(N-phenylcyclopropanesulfonamido)ethyl)-3-methyl-2-oxopiperidin-3-yl)acetic acid $^1$H NMR (400 MHz, methanol-d$_4$) δ ppm −1.28 (s, br, 1H), −0.54 (s, br, 1H), 0.00 (s, br, 1H), 0.20 (s, br, 1H), 0.70-0.78 (m, 5H), 1.06 (s, 3H), 1.53 (s, br, 1H), 1.91-2.07 (m, 3H), 2.37 (s, br, 1H), 2.48 (d, J=12 Hz, 1H), 2.78 (d, J=12 Hz, 1H), 3.24 (m, 1H), 3.80 (s, br, 1H), 4.43 (d, J=12 Hz, 1H), 6.82 (d, J=8 Hz, 2H), 6.92 (s, 1H), 7.05 (m, 4H), 7.22 (t, J=8 Hz, 2H), 7.33 (t, J=8 Hz, 2H), 7.44 (d, J=8 Hz, 2H).
Mass Spectrum (ESI) m/z=655.2 (M+1).

Example 275

2-((3R,5R,6S)-5-(3-chlorophenyl)-6-(4-chlorophenyl)-1-((S)-1-cyclopropyl-2-(N-phenylethylsulfonamido)ethyl)-3-methyl-2-oxopiperidin-3-yl)acetic acid

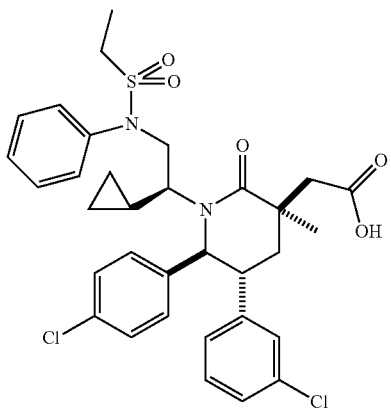 [SMILES: CCS(=O)(=O)N(C[C@H](C1CC1)N1C(=O)[C@@](C)(CC(=O)O)C[C@H](c2cccc(Cl)c2)[C@H]1c1ccc(Cl)cc1)c1ccccc1]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-phenylethanesulfonamide

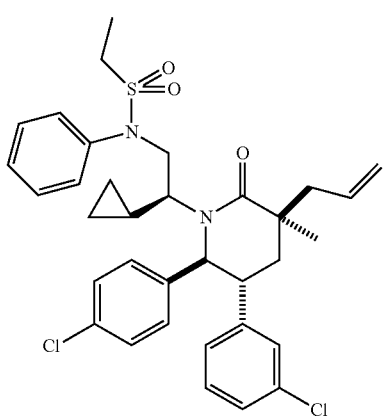 [SMILES: C=CC[C@@]1(C)C[C@H](c2cccc(Cl)c2)[C@@H](c2ccc(Cl)cc2)N([C@H](CN(c2ccccc2)S(=O)(=O)CC)C2CC2)C1=O]

$^1$H NMR (400 MHz, methanol-d$_4$) δ ppm −1.23 (s, br, 1H), −0.56 (s, br, 1H), 0.00 (s, br, 1H), 0.19 (s, br, 1H), 0.92 (s, 3H), 1.13 (t, J=8 Hz, 3H), 1.55 (s, br, 2H), 1.63 (dd, J=4, 8 Hz, 1H), 1.96 (m, 2H), 2.45 (m, 1H), 2.53 (m, 1H), 2.90 (m, 2H), 3.17 (m, 1H), 3.79 (s, br, 1H), 4.42 (d, J=12 Hz, 1H), 4.81 (s, br, 1H), 5.00 (m, 1H), 5.09 (s, 1H), 5.72 (m, 1H), 6.79 (m, 2H), 6.94 (s, 1H), 7.02 (m, 4H), 7.19 (m, 2H), 7.32 (t, J=8 Hz, 2H), 7.47 (d, J=8 Hz, 2H).
Mass Spectrum (ESI) m/z=625.2 (M+1).

Step B: 2-((3R,5R,6S)-5-(3-chlorophenyl)-6-(4-chlorophenyl)-1-((S)-1-cyclopropyl-2-(N-phenylethylsulfonamido)ethyl)-3-methyl-2-oxopiperidin-3-yl)acetic acid $^1$H NMR (400 MHz, methanol-d4) δ ppm −1.26 (s, br, 1H), −0.55 (s, br, 1H), 0.19 (s, br, 1H), 1.06 (s, 3H), 1.13 (t, J=8 Hz, 3H), 1.51 (s, br, 1H), 1.88 (dd, J=4, 8 Hz, 1H), 2.00 (s, br, 1H), 2.03 (t, J=12 Hz, 1H), 2.48 (d, J=12 Hz, 1H), 2.78 (d, J=12 Hz, 1H), 2.90 (m, 2H), 3.23 (m, 1H), 3.77 (d, J=12 Hz, 1H), 4.46 (d, J=8 Hz, 1H), 4.76 (s, br, 1H),
Mass Spectrum (ESI) m/z=643.2 (M+1).

Example 276

2-((3R,5R,6S)-5-(3-chlorophenyl)-6-(4-chlorophenyl)-1-((S)-1-cyclopropyl-2-(ethylsulfonamido)ethyl)-3-methyl-2-oxopiperidin-3-yl)acetic acid

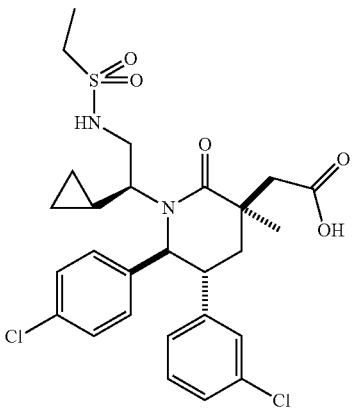 [SMILES: CCS(=O)(=O)NC[C@H](C1CC1)N1C(=O)[C@@](C)(CC(=O)O)C[C@H](c2cccc(Cl)c2)[C@H]1c1ccc(Cl)cc1]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)ethanesulfonamide

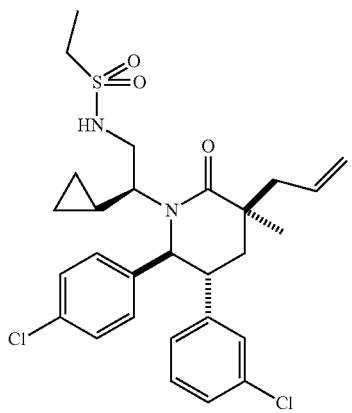 [SMILES: C=CC[C@@]1(C)C[C@H](c2cccc(Cl)c2)[C@@H](c2ccc(Cl)cc2)N([C@H](CNS(=O)(=O)CC)C2CC2)C1=O]

529

¹H NMR (400 MHz, methanol-d₄) δ ppm −1.06 (s, br, 1H), −0.98 (m, 1H), −0.02 (m, 1H), 0.14 (m, 1H), 1.08 (s, 3H), 1.14 (t, J=4 Hz, 3H), 1.39 (m, 1H), 1.59 (dd, J=4, 12 Hz, 1H), 2.05 (m, 1H), 2.10 (t, J=16 Hz, 1H), 2.42 (m, 1H), 2.50 (m, 1H), 2.89 (m, 3H), 3.12 (m, 1H), 3.74 (m, 1H), 4.68 (d, J=12 Hz, 1H), 4.96-5.06 (m, 2H), 5.71 (m, 1H), 6.79 (m, 2H), 6.87 (s, 1H), 6.93 (m, 3H), 7.06 (m, 2H).
Mass Spectrum (ESI) m/z=549.0 (M+1).

Step B: 2-((3R,5R,6S)-5-(3-chlorophenyl)-6-(4-chlorophenyl)-1-((S)-1-cyclopropyl-2-(ethylsulfonamido)ethyl)-3-methyl-2-oxopiperidin-3-yl)acetic acid ¹H NMR (400 MHz, methanol-d₄) δ ppm −1.06 (s, br, 1H), −0.47 (m, 1H), −0.02 (m, 1H), 0.14 (m, 1H), 1.13 (t, J=8 Hz, 3H), 1.22 (s, 3H), 1.06 (s, br, 1H), 1.89 (dd, J=4, 12 Hz, 1H), 2.08 (s, 1H), 2.15 (t, J=16 Hz, 1H), 2.46 (d, J=12 Hz, 1H), 2.80 (d, J=12 Hz, 1H), 3.07 (m, 3H), 3.19 (m, 1H), 3.65 (m, 1H), 4.69 (d, J=8 Hz, 1H), 6.81 (m, 2H), 6.92 (s, 1H), 6.87 (m, 3H), 7.05 (s, br, 2H).
Mass Spectrum (ESI) m/z=567.0 (M+1).

Example 277

2-((3R,5R,6S)-5-(3-chlorophenyl)-6-(4-chlorophenyl)-1-((S)-1-cyclopropyl-2-(N-(3-fluorophenyl)ethylsulfonamido)ethyl)-3-methyl-2-oxopiperidin-3-yl)acetic acid

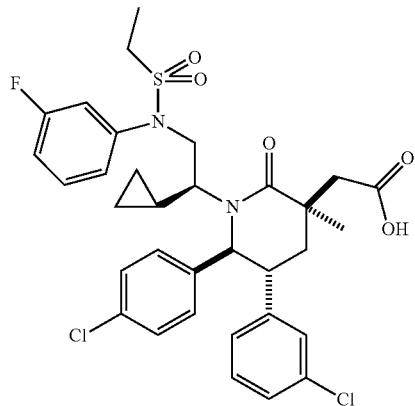 [SMILES: CCS(=O)(=O)N(C[C@H](C1CC1)N1C(=O)[C@@](C)(CC(=O)O)C[C@H](c2cccc(Cl)c2)[C@H]1c1ccc(Cl)cc1)c1cccc(F)c1]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(3-fluorophenyl)ethanesulfonamide

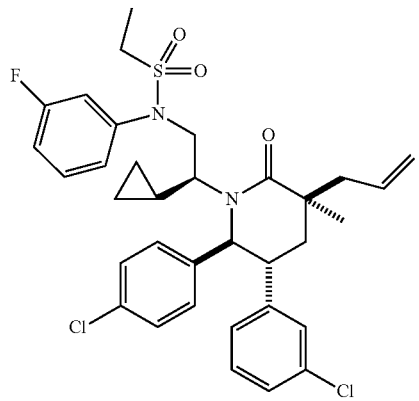 [SMILES: C=CC[C@@]1(C)C[C@H](c2cccc(Cl)c2)[C@@H](c2ccc(Cl)cc2)N([C@H](CN(c2cccc(F)c2)S(=O)(=O)CC)C2CC2)C1=O]

530

¹H NMR (400 MHz, methanol-d₄) δ ppm −1.20 (s, br, 1H), −0.56 (s, br, 1H), 0.00 (s, br, 1H), 0.19 (s, br, 1H), 0.89 (s, 3H), 1.08 (m, 3H), 1.53 (s, br, 1H), 1.62 (dd, J=4, 12 Hz, 1H), 1.90 (t, J=12 Hz, 1H), 1.95 (m, 1H), 2.38 (m, 1H), 2.52 (m, 1H), 2.86-2.96 (m, 2H), 3.11-3.17 (m, 1H), 3.76 (d, J=12 Hz, 1H), 4.77 (s, br, 1H), 5.00 (t, J=8 Hz, 1H), 5.06 (s, 1H), 5.72 (m, 1H), 6.77 (m, 2H), 6.89 (m, 3H), 7.00 (m, 4H), 7.28 (m, 3H).
Mass Spectrum (ESI) m/z=643.2 (M+1).

Step B: 2-((3R,5R,6S)-5-(3-chlorophenyl)-6-(4-chlorophenyl)-1-((S)-1-cyclopropyl-2-(N-(3-fluorophenyl)ethylsulfonamido)ethyl)-3-methyl-2-oxopiperidin-3-yl)acetic acid ¹H NMR (400 MHz, methanol-d4) δ ppm −1.06 (s, br, 1H), −0.39 (s, br, 1H), 0.16 (1H), 0.35 (s, br, 1H), 1.21 (s, br, 3H), 1.28 (t, J=4 Hz, 3H), 1.67 (s, br, 1H), 2.04-2.18 (m, 3H), 2.63 (d, J=12 Hz, 1H), 2.93 (d, J=12 Hz, 1H), 3.09 (s, br, 2H), 3.39 (m, 1H), 3.92 (m, 1H), 3.92 (s, br, 1H), 4.56 (s, br, 1H), 6.96 (m, 2H), 7.06 (m, 3H), 7.17 (m, 4H), 7.45 (m, 3H).
Mass Spectrum (ESI) m/z=661.2 (M+1)

Example 278

2-((3R,5R,6S)-5-(3-chlorophenyl)-6-(4-chlorophenyl)-1-((S)-2-(N-(2-cyanophenyl)methylsulfonamido)-1-cyclopropylethyl)-3-methyl-2-oxopiperidin-3-yl)acetic acid

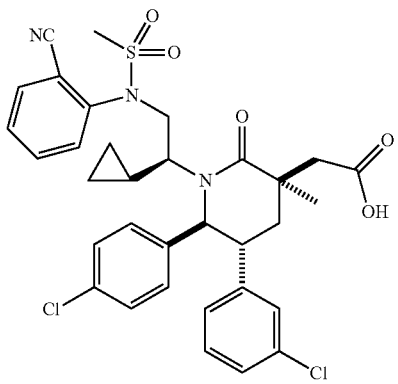 [SMILES: C[C@]1(CC(=O)O)C[C@H](c2cccc(Cl)c2)[C@@H](c2ccc(Cl)cc2)N([C@H](CN(c2ccccc2C#N)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(2-cyanophenyl)methanesulfonamide

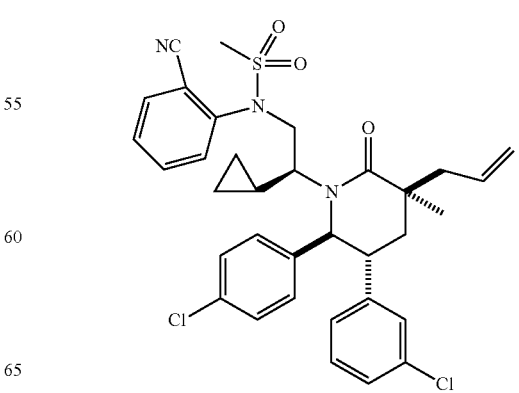

¹H NMR (400 MHz, methanol-d₄) δ ppm −1.22 (s, br, 1H), −0.47 (s, br, 1H), 0.00 (s, br, 1H), 0.19 (s, br, 1H), 0.91 (s, br, 1H), 1.45 (m, 1H), 1.67 (d, J=12 Hz, 1H), 1.97 (m, 1H), 2.10 (s, br, 1H), 2.42 (m, 1H), 2.52 (m, 1H), 2.87 (s, 3H), 3.15-3.18 (m, 2H), 3.91 (s, br, 1H), 4.47 (s, br, 1H), 4.99 (m, 1H), 5.07 (s, 1H), 5.71 (m, 1H), 6.79 (s, br, 2H), 6.89 (s, 1H), 6.96 (s, br, 3H), 7.05 (s, br, 2H), 7.40 (m, 1H), 7.62 (m, 2H), 7.72 (s, br, 1H).
Mass Spectrum (ESI) m/z=636.2 (M+1).

Step B: 2-((3R,5R,6S)-5-(3-chlorophenyl)-6-(4-chlorophenyl)-1-((S)-2-(N-(2-cyanophenyl)methylsulfonamido)-1-cyclopropylethyl)-3-methyl-2-oxopiperidin-3-yl)acetic acid ¹H NMR (400 MHz, methanol-d₄) δ ppm −1.12 (s, br, 1H), −0.31 (s, br, 1H), 0.15 (s, br, 1H), 0.35 (s, br, 1H), 1.20 (s, 3H), 1.29 (m, 1H), 1.62 (s, br, 1H), 2.06 (d, 1H), 2.24 (t, J=12 Hz, 1H), 2.27 (s, br, 1H), 2.60 (d, J=12 Hz, 1H), 2.93 (d, J=12 Hz, 1H), 3.02 (s, 3H), 3.41 (m, 1H), 4.01 (m, 1H), 4.68 (s, br, 1H), 6.98 (d, J=8 Hz, 2H), 7.06 (s, 1H), 7.12 (m, 3H), 7.21 (s, br, 2H), 7.57 (m, 1H), 7.79 (m, 2H), 7.88 (s, br, 1H).
Mass Spectrum (ESI) m/z=654.0 (M+1).

Example 279

2-((3R,5R,6S)-5-(3-chlorophenyl)-6-(4-chlorophenyl)-1-((S)-1-cyclopropyl-2-(propylsulfonamido)ethyl)-3-methyl-2-oxopiperidin-3-yl)acetic acid

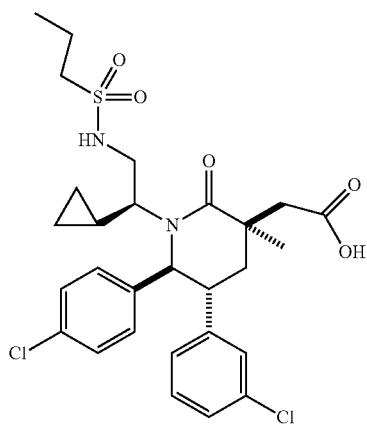 [SMILES: CCCS(=O)(=O)NC[C@H](C1CC1)N1C(=O)[C@@](C)(CC(=O)O)C[C@H](c2cccc(Cl)c2)[C@H]1c1ccc(Cl)cc1]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)propane-1-sulfonamide

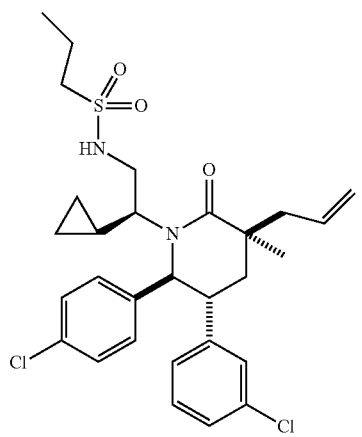 [SMILES: C=CC[C@@]1(C)C[C@H](c2cccc(Cl)c2)[C@@H](c2ccc(Cl)cc2)N([C@H](CNS(=O)(=O)CCC)C2CC2)C1=O]

Crude product used directly in Step B.
Mass Spectrum (ESI) m/z=563.2 (M+1).

Step B: 2-((3R,5R,6S)-5-(3-chlorophenyl)-6-(4-chlorophenyl)-1-((S)-1-cyclopropyl-2-(propylsulfonamido)ethyl)-3-methyl-2-oxopiperidin-3-yl)acetic acid ¹H NMR (400 MHz, methanol-d₄) δ ppm −0.85 (s, br, 1H), −0.25 (s, br, 1H), 0.22 (s, br, 1H), 0.35 (m, 1H), 1.08 (t, J=4 Hz, 3H), 1.43 (s, 3H), 1.55 (s, br, 1H), 1.84 (m, 2H), 2.10 (dd, J=4, 8 Hz, 1H), 2.30 (s, br, 1H), 2.36 (t, J=12 Hz, 1H), 2.67 (d, J=16 Hz, 1H), 2.98 (d, J=16 Hz, 1H), 3.05 (m, 3H), 3.41 (m, 1H), 3.88 (m, 1H), 4.92 (d, J=8 Hz, 1H), 7.02 (m, 2H), 7.08 (s, 1H), 7.14 (m, 3H), 7.26 (s, br, 2H).
Mass Spectrum (ESI) m/z=581.2 (M+1).

Example 280

2-((3R,5R,6S)-5-(3-chlorophenyl)-6-(4-chlorophenyl)-1-((S)-1-cyclopropyl-2-(N-phenylmethylsulfonamido)ethyl)-3-methyl-2-oxopiperidin-3-yl)acetic acid

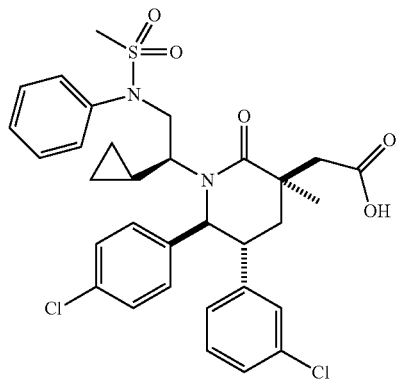 [SMILES: C[C@]1(CC(=O)O)C[C@H](c2cccc(Cl)c2)[C@@H](c2ccc(Cl)cc2)N([C@H](CN(c2ccccc2)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-phenylmethanesulfonamide

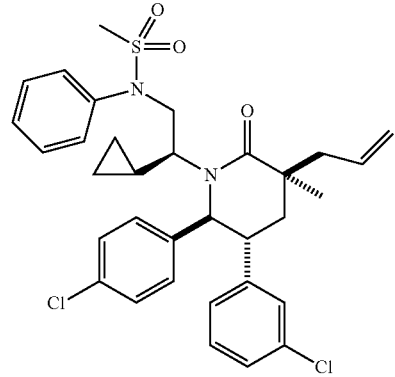 [SMILES: C=CC[C@@]1(C)C[C@H](c2cccc(Cl)c2)[C@@H](c2ccc(Cl)cc2)N([C@H](CN(c2ccccc2)S(C)(=O)=O)C2CC2)C1=O]

Mass Spectrum (ESI) m/z=611.2 (M+1).

Step B: 2-((3R,5R,6S)-5-(3-chlorophenyl)-6-(4-chlorophenyl)-1-((S)-1-cyclopropyl-2-(N-phenylmethylsulfonamido)ethyl)-3-methyl-2-oxopiperidin-3-yl)acetic acid $^1$H NMR (400 MHz, methanol-$d_4$) δ ppm −1.26 (s, br, 1H), −0.51 (s, br, 1H), 0.00 (s, br, 1H), 0.20 (s, br, 1H), 1.03 (s, 3H), 1.54 (s, br, 1H), 1.80-2.04 (m, 3H), 2.47 (d, J=16 Hz, 1H), 2.73 (s, 3H), 2.78 (d, J=16 Hz, 1H), 3.18 (m, 1H), 3.75 (s, br, 1H), 4.42 (s, J=12 Hz, 1H), 6.81 (m, 2H), 6.91 (s, 1H), 7.04 (m, 4H), 7.24 (m, 2H), 7.35 (m, 2H), 7.43 (m, 2H).
Mass Spectrum (ESI) m/z=629.0 (M+1).

Example 281

2-((3R,5R,6S)-5-(3-chlorophenyl)-6-(4-chlorophenyl)-1-((S)-2-(N-(3-cyanophenyl)methylsulfonamido)-1-cyclopropylethyl)-3-methyl-2-oxopiperidin-3-yl)acetic acid

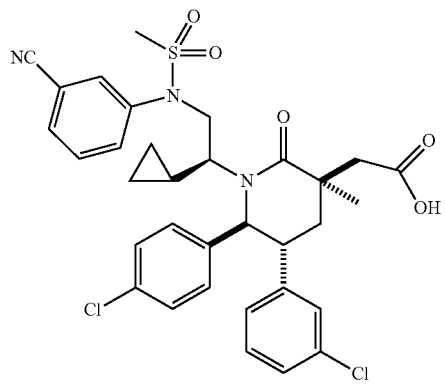 [SMILES: C[C@]1(CC(=O)O)C[C@H](c2cccc(Cl)c2)[C@@H](c2ccc(Cl)cc2)N([C@H](CN(c2cccc(C#N)c2)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(3-cyanophenyl)methanesulfonamide

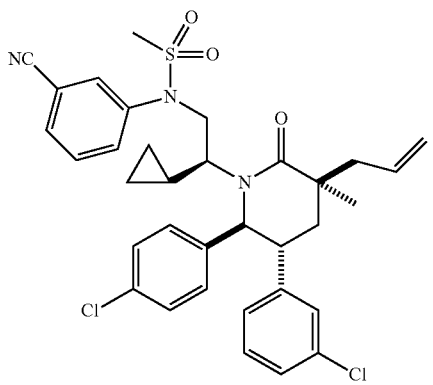 [SMILES: C=CC[C@@]1(C)C[C@H](c2cccc(Cl)c2)[C@@H](c2ccc(Cl)cc2)N([C@H](CN(c2cccc(C#N)c2)S(C)(=O)=O)C2CC2)C1=O]

$^1$H NMR (400 MHz, chloroform-$d_1$) δ ppm −1.17 (s, br, 1H), −0.59 (s, br, 1H), 0.00 (s, br, 1H), 0.12 (s, br, 1H), 0.74 (s, 3H), 1.36 (m, 1H), 1.44-1.60 (m, 2H), 1.68 (t, J=12 Hz, 1H), 2.36 (d, J=8 Hz, 2H), 2.60 (s, 3H), 2.95 (m, 1H), 4.33 (s, br, 1H), 4.70 (s, br, 1H), 4.92 (s, 1H), 4.95 (d, J=4 Hz, 1H), 5.58 (m, 1H), 6.62 (s, br, 2H), 6.69 (s, br, 2H), 6.95 (m, 4H), 7.33-7.40 (m, 2H), 7.50 (s, 1H), 7.54 (s, 1H).
Mass Spectrum (ESI) m/z=636.2 (M+1).

Step B: 2-((3R,5R,6S)-5-(3-chlorophenyl)-6-(4-chlorophenyl)-1-((S)-2-(N-(3-cyanophenyl)methylsulfonamido)-1-cyclopropylethyl)-3-methyl-2-oxopiperidin-3-yl)acetic acid $^1$H NMR (400 MHz, methanol-$d_4$) δ ppm −1.21 (s, br, 1H), −0.55 (s, br, 1H), 0.00 (s, br, 1H), 0.18 (s, br, 1H), 0.95 (s, 3H), 1.45 (s, br, 1H), 1.89 (d, J=8 Hz, 2H), 1.99 (s, br, 1H), 2.42 (d, J=12 Hz, 1H), 2.72 (s, 3H), 2.75 (d, J=12 Hz, 1H), 3.19 (m, 1H), 3.73 (s, br, 1H), 4.37 (s, br, 1H), 6.80 (s, 3H), 6.96-7.05 (m, 5H), 7.45-7.49 (m, 1H), 7.52 (d, J=8 Hz, 1H), 7.70 (s, br, 1H), 7.77 (s, br, 1H).
Mass Spectrum (ESI) m/z=654.1 (M+1).

Example 282

2-((3R,5R,6S)-5-(3-chlorophenyl)-6-(4-chlorophenyl)-1-((S)-1-cyclopropyl-2-(N-(pyridin-3-yl)methylsulfonamido)ethyl)-3-methyl-2-oxopiperidin-3-yl)acetic acid

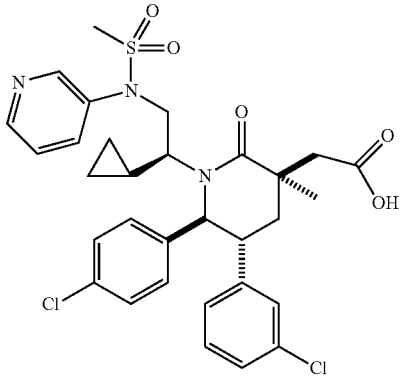 [SMILES: C[C@]1(CC(=O)O)C[C@H](c2cccc(Cl)c2)[C@@H](c2ccc(Cl)cc2)N([C@H](CN(c2cccnc2)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(pyridin-3-yl)methanesulfonamide

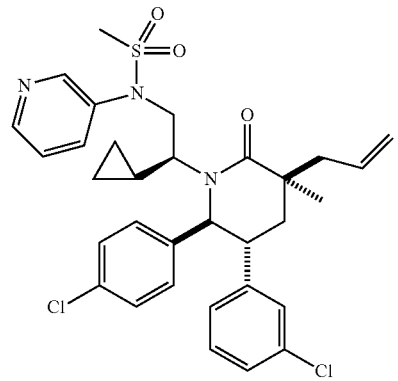 [SMILES: C=CC[C@@]1(C)C[C@H](c2cccc(Cl)c2)[C@@H](c2ccc(Cl)cc2)N([C@H](CN(c2cccnc2)S(C)(=O)=O)C2CC2)C1=O]

¹H NMR (400 MHz, methanol-d₄) δ ppm −1.18 (s, br, 1H), −0.57 (s, br, 1H), 0.00 (s, br, 1H), 0.17 (s, br, 1H), 0.78 (s, 3H), 1.45 (s, br, 1H), 1.60 (m, 1H), 1.86 (m, 1H), 2.00 (s, br, 1H), 2.38 (m, 1H), 2.47 (m, 1H), 2.74 (s, 3H), 3.14 (m, 2H), 3.76 (s, br, 1H), 4.41 (s, br, 1H), 4.95-5.00 (m, 2H), 5.67 (m, 1H), 6.78-6.82 (m, 3H), 6.97-7.04 (m, 5H), 7.36 (m, 1H), 7.84 (s, br, 1H), 8.31 (m, 1H), 8.60 (s, br, 1H).
Mass Spectrum (ESI) m/z=612.2 (M+1).

Step B: 2-((3R,5R,6S)-5-(3-chlorophenyl)-6-(4-chlorophenyl)-1-((S)-1-cyclopropyl-2-(N-(pyridin-3-yl)methylsulfonamido)ethyl)-3-methyl-2-oxopiperidin-3-yl)acetic acid ¹H NMR (400 MHz, methanol-d₄) δ ppm −1.19 (s, br, 1H), −0.55 (s, br, 1H), 0.00 (s, br, 1H), 0.16 (s, br, 1H), 0.95 (m, 4H), 1.34 (s, br, 1H), 1.90 (m, 2H), 2.42 (d, J=12 Hz, 1H), 2.72 (s, J=12 Hz, 1H), 2.75 (s, 3H), 3.20 (s, br, 1H), 3.38 (s, br, 1H), 4.43 (s, br, 2H), 6.83 (m, 3H), 6.98 (m, 5H), 7.52 (s, br, 1H), 8.04 (s, br, 1H), 8.39 (s 1H), 0.68 (s, 1H).
Mass Spectrum (ESI) m/z=630.1 (M+1).

Example 283

2-((3R,5R,6S)-5-(3-chlorophenyl)-6-(4-chlorophenyl)-1-((S)-1-cyclopropyl-2-(N-(thiophen-2-ylmethyl)methylsulfonamido)ethyl)-3-methyl-2-oxopiperidin-3-yl)acetic acid

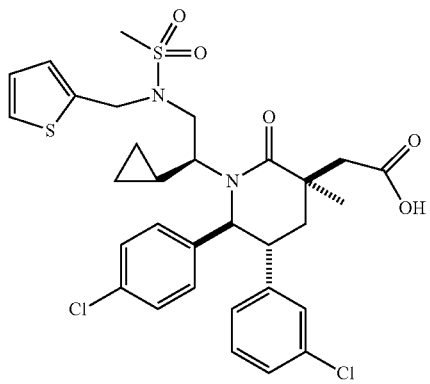 [SMILES: C[C@]1(CC(=O)O)C[C@H](c2cccc(Cl)c2)[C@@H](c2ccc(Cl)cc2)N([C@H](CN(Cc2cccs2)S(C)(=O)=O)C2CC2)C1=O]

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(thiophen-2-ylmethyl)methanesulfonamide

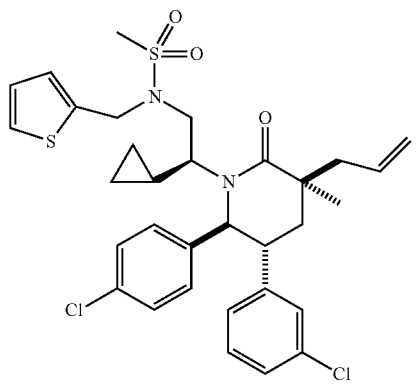 [SMILES: C=CC[C@@]1(C)C[C@H](c2cccc(Cl)c2)[C@@H](c2ccc(Cl)cc2)N([C@H](CN(Cc2cccs2)S(C)(=O)=O)C2CC2)C1=O]

¹H NMR (400 MHz, methanol-d₄) δ ppm (representative signals) 5.30-5.35 (m, 1H), 5.40 (s, 1H), 6.06 (m, 1H). Mass Spectrum (ESI) m/z=631.2 (M+1).

Step B: 2-((3R,5R,6S)-5-(3-chlorophenyl)-6-(4-chlorophenyl)-1-((S)-1-cyclopropyl-2-(N-(thiophen-2-ylmethyl)methylsulfonamido)ethyl)-3-methyl-2-oxopiperidin-3-yl)acetic acid ¹H NMR (400 MHz, methanol-d₄) δ ppm −1.12 (s, br, 1H), −0.59 (s, br, 1H), 0.00 (s, br, 1H), 0.14 (s, br, 1H), 1.21 (s, 3H), 1.49 (s, br, 1H), 1.80 (d, J=12 Hz, 1H), 1.94 (s, br, 1H), 2.19 (t, J=12 Hz, 1H), 2.47 (d, J=12 Hz, 1H), 2.58 (s, 3H), 2.73 (d, J=12 Hz, 1H), 3.01 (s, br, 1H), 3.14 (m, 2H), 2.47 (s, br, 1H), 4.53-4.47 (m, 3H), 6.76 (m, 3H), 6.85 (s, 2H), 6.95-7.02 (m, 5H), 7.11 (d, J=4 Hz, 1H).
Mass Spectrum (ESI) m/z=649.0 (M+1).

Example 284

2-((3R,5R,6S)-5-(3-chlorophenyl)-6-(4-chlorophenyl)-1-((S)-1-cyclopropyl-2-(N-(3-methoxybenzyl)methylsulfonamido)ethyl)-3-methyl-2-oxopiperidin-3-yl)acetic acid

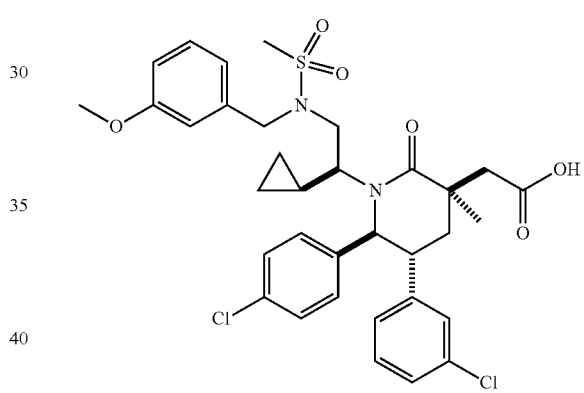

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(3-methoxybenzyl)methanesulfonamide

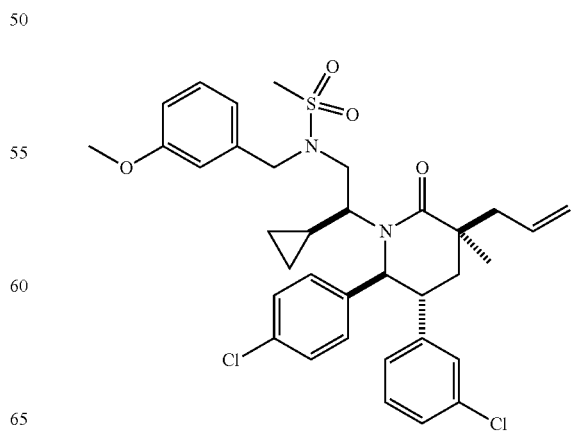

¹H NMR (400 MHz, methanol-d₄) δ ppm −1.07 (s, br, 1H), −0.43 (s, br, 1H), 0.13 (s, br, 1H), 0.28 (s, br, 1H), 1.25 (s, 3H), 1.68 (s, br, 2H), 1.90 (s, br, 1H), 2.37 (s, br, 1H), 2.62 (m, 2H), 2.83 (s, 3H), 3.19 (m, 2H), 3.78 (s, 3H), 4.21 (s, 2H), 4.50 (s, br, 2H), 5.14-5.22 (m, 2H), 5.87 (m, 1H), 6.82-6.93 (m, 3H), 6.94 (m, 4H), 7.17-7.27 (m, 5H).
Mass Spectrum (ESI) m/z=655.2 (M+1).

Step B: 2-((3R,5R,6S)-5-(3-chlorophenyl)-6-(4-chlorophenyl)-1-((S)-1-cyclopropyl-2-(N-(3-methoxybenzyl)methylsulfonamido)ethyl)-3-methyl-2-oxopiperidin-3-yl)acetic acid ¹H NMR (400 MHz, methanol-d₄) δ ppm −1.23 (s, br, 1H), −0.55 (s, br, 1H), 0.00 (s, br, 1H), 0.16 (s, br, 1H), 1.28 (s, 3H), 1.81 (m, 2H), 2.31 (m, 1H), 2.54 (d, J=12 Hz, 1H), 2.77 (m, 4H), 3.10 (s, br, 1H), 3.16 (m, 1H), 3.59 (s, 5H), 3.98 (s, br, 1H), 4.45 (s, br, 2H), 6.73-6.78 (m, 3H), 6.85 (m, 2H), 6.94 (s, 1H), 7.06 (m, 5H).
Mass Spectrum (ESI) m/z=673.0 (M+1).

Example 285

2-((3R,5R,6S)-5-(3-chlorophenyl)-6-(4-chlorophenyl)-1-((S)-1-cyclopropyl-2-(phenylmethylsulfonamido)ethyl)-3-methyl-2-oxopiperidin-3-yl)acetic acid ¹H NMR (400 MHz, chloroform-d₁) δ ppm −0.36 (s, br, 1H), 0.00 (s, br, 1H), 0.48 (s, br, 2H), 1.28 (s, br, 1H), 1.32 (s, 3H), 2.00 (m, 1H), 2.16 (m, 2H), 2.72 (m, 2H), 2.89 (s, br, 2H), 3.23 (m, 1H), 3.26 (s, 1H), 4.84 (d, J=12 Hz, 1H), 5.11 (s, br, 1H), 5.26 (s, 1H), 5.29 (d, J=4 Hz, 1H), 5.93 (m, 1H), 6.89 (d, J=8 Hz, 1H), 7.05 (s, 1H), 7.10 (s, br, 1H), 7.22 (m, 2H), 7.29 (d, J=4 Hz, 2H), 7.48 (m, 5H).
Mass Spectrum (ESI) m/z=611.2 (M+1).

Step B: 2-((3R,5R,6S)-5-(3-chlorophenyl)-6-(4-chlorophenyl)-1-((S)-1-cyclopropyl-2-(phenylmethylsulfonamido)ethyl)-3-methyl-2-oxopiperidin-3-yl)acetic acid ¹H NMR (400 MHz, chloroform-d₁) δ ppm −0.92 (s, br, 1H), −0.35 (s, br, 1H), 0.15 (s, br, 1H), 0.29 (m, 1H), 1.42 (s, 3H), 1.48 (s, 1H), 2.05 (dd, J=4, 12 Hz, 1H), 2.20 (s, 1H), 2.33 (t, J=16 Hz, 1H), 2.65 (d, J=12 Hz, 1H), 2.84 (dd, J=4, 12 Hz, 1H), 2.96 (d, J=12 Hz, 1H), 3.38 (m, 1H), 3.72 (m, 1H), 4.37 (s, 2H), 4.97 (m, 1H), 7.01 (d, J=4 Hz, 2H), 7.06 (s, 1H), 7.13 (m, 3H), 7.24 (s, br, 2H), 7.38-7.46 (m, 5H).
Mass Spectrum (ESI) m/z=629.2 (M+1).

Example 286

2-((3R,5R,6S)-5-(3-chlorophenyl)-6-(4-chlorophenyl)-1-((S)-1-cyclopropyl-2-(pyridin-2-ylmethylsulfonamido)ethyl)-3-methyl-2-oxopiperidin-3-yl)acetic acid

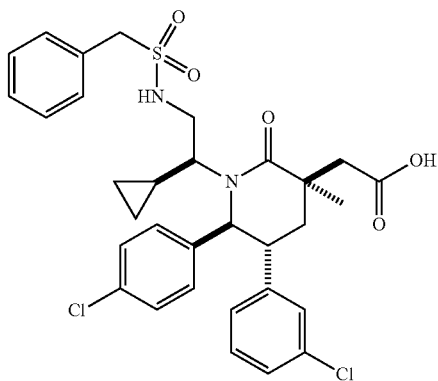

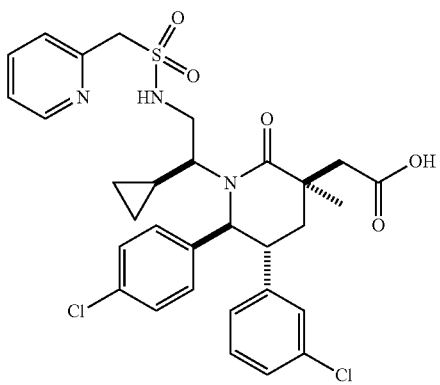

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-1-phenylmethanesulfonamide Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-1-(pyridin-2-yl)methanesulfonamide

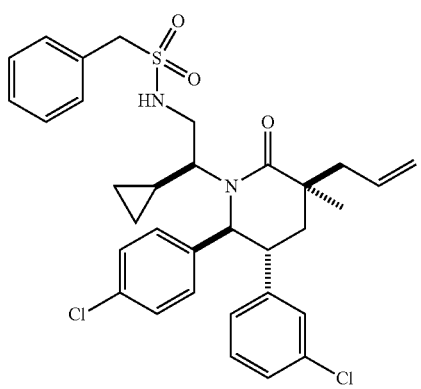

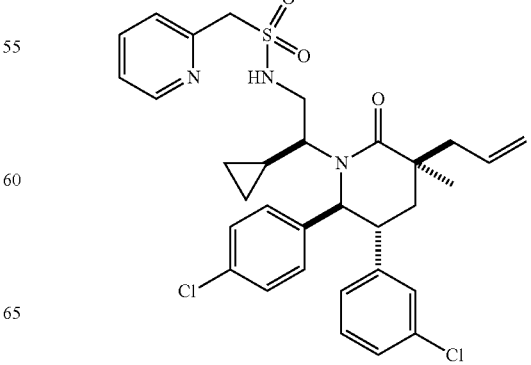

¹H NMR (400 MHz, methanol-d₄) δ ppm −1.08 (s, br, 1H), −0.49 (s, br, 1H), 0.02 (s, br, 1H), 0.12 (s, br, 1H), 1.09 (s, 3H), 1.36 (s, br, 1H), 1.63 (dd, J=4, 12 Hz, 1H), 1.93 (s, br, 1H), 2.08 (t, J=12 Hz, 1H), 2.43 (m, 1H), 2.53 (m, 1H), 2.83 (m, 1H), 3.66 (m, 1H), 4.36 (s, 2H), 4.39 (s, br, 1H), 4.64 (m, 1H), 4.98-5.07 (m, 2H), 5.72 (m, 1H), 6.79 (m, 2H), 6.87 (s, 1H), 6.94 (m, 3H), 7.10 (s, br, 2H), 7.24 (m, 1H), 7.42 (d, J=8 Hz, 1H), 7.70 (m, 1H), 8.40 (m, 1H).

Mass Spectrum (ESI) m/z=612.2 (M+1).

Step B: 2-((3R,5R,6S)-5-(3-chlorophenyl)-6-(4-chlorophenyl)-1-((S)-1-cyclopropyl-2-(pyridin-2-ylmethylsulfonamido)ethyl)-3-methyl-2-oxopiperidin-3-yl) acetic acid ¹H NMR (400 MHz, methanol-d₄) δ ppm −1.07 (s, br, 1H), −0.47 (s, br, 1H), 0.00 (s, br, 1H), 0.16 (s, br, 1H), 1.20 (s, 3H), 1.35 (s, br, 1H), 1.87 (dd, J=4, 8 Hz, 1H), 2.10 (m, 2H), 2.45 (d, J=12 Hz, 1H), 2.75 (d, J=12 Hz, 1H), 2.84 (m, 1H), 3.59 (m, 1H), 4.43 (s, 2H), 4.61 (m, 1H), 6.76 (m, 2H), 6.84 (s, 1H), 6.91 (m, 3H), 7.05 (s, br, 2H), 7.45 (m, 1H), 7.57 (d, J=8 Hz, 1H), 7.92 (t, J=8 Hz, 1H), 8.47 (m, 1H).

Mass Spectrum (ESI) m/z=630.1 (M+1).

¹H NMR (400 MHz, methanol-d₄) δ ppm −1.06 (s, br, 1H), −0.48 (s, br, 1H), 0.02 (s, br, 1H), 0.15 (s, br, 1H), 1.08 (s, 3H), 1.37 (s, br, 1H), 1.61 (dd, J=4, 8 Hz, 1H), 1.99 (s, br, 1H), 2.08 (t, J=16 Hz, 1H), 2.43 (m, 1H), 2.50 (m, 1H), 2.78 (m, 1H), 3.14 (m, 1H), 3.69 (s, br, 1H), 4.26 (s, 2H), 4.63 (m, 1H), 4.97-5.05 (m, 2H), 5.71 (m, 1H), 6.78 (m, 2H), 6.86 (s, 1H), 6.93 (m, 3H), 7.10 (s, br, 2H), 7.28 (m, 1H), 7.75 (m, 1H), 8.36 (m, 1H), 8.41 (s, 1H).

Mass Spectrum (ESI) m/z=612.2 (M+1).

Step B: 2-((3R,5R,6S)-5-(3-chlorophenyl)-6-(4-chlorophenyl)-1-((S)-1-cyclopropyl-2-(pyridin-3-ylmethylsulfonamido)ethyl)-3-methyl-2-oxopiperidin-3-yl) acetic acid ¹H NMR (400 MHz, methanol-d₄) δ ppm −0.59 (s, br, 1H), 0.00 (s, br, 1H), 0.47 (s, br, 1H), 0.61 (s, br, 1H), 1.65 (s, 3H), 1.81 (s, br, 1H), 2.33 (m, 1H), 2.55 (m, 2H), 2.91 (d, J=12 Hz, 1H), 3.21 (d, J=12 Hz, 1H), 3.32 (m, 1H), 4.13 (s, br, 1H), 4.86 (s, 2H), 5.07 (m, 1H), 7.21 (m, 2H), 7.30 (s, 1H), 7.36 (m, 3H), 7.49 (s, 2H), 8.15 (m, 1H), 8.69 (m, 1H), 9.02 (m, 1H), 9.10 (s, 1H).

Mass Spectrum (ESI) m/z=630.1 (M+1).

Example 287

2-((3R,5R,6S)-5-(3-chlorophenyl)-6-(4-chlorophenyl)-1-((S)-1-cyclopropyl-2-(pyridin-3-ylmethylsulfonamido)ethyl)-3-methyl-2-oxopiperidin-3-yl)acetic acid Example 288

2-((3R,5R,6S)-5-(3-chlorophenyl)-6-(4-chlorophenyl)-1-((S)-1-cyclopropyl-2-(N-(pyridin-2-yl)methylsulfonamido)ethyl)-3-methyl-2-oxopiperidin-3-yl) acetic acid

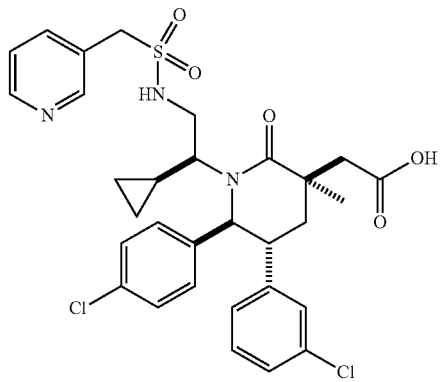

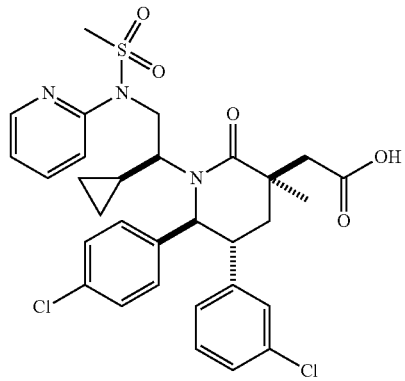

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-1-(pyridin-3-yl)methanesulfonamide Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-(pyridin-2-yl)methanesulfonamide

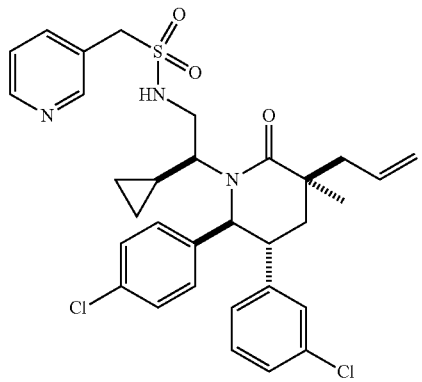

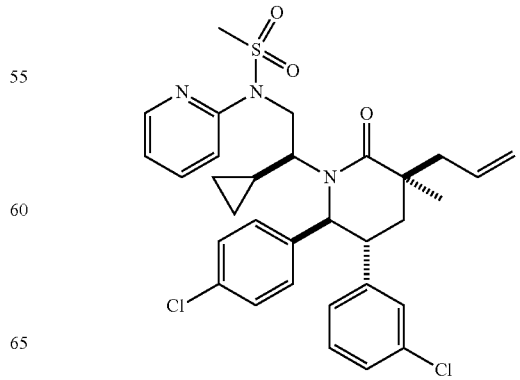

¹H NMR (400 MHz, methanol-d₄) δ ppm −0.75 (s, br, 1H), 0.00 (s, br, 1H), 0.45 (s, br, 1H), 0.60 (s, br, 1H), 1.52 (s, 3H), 1.94-2.03 (m, 3H), 2.83-2.95 (m, 2H), 3.08 (s, 3H), 3.12 (s, 1H), 3.48 (m, 1H), 3.87 (s, br, 1H), 4.78 (s, br, 1H), 4.94 (s, br, 1H), 5.39-5.50 (m, 2H), 6.11 (m, 1H), 6.83 (s, br, 1H), 6.94 (s, br, 1H), 7.14 (m, 1H), 7.32 (m, 3H), 7.39 (s, br, 1H), 7.50 (s, br, 2H), 7.85 (m, 1H), 7.99 (m, 1H), 8.14 (s, br, 1H).
Mass Spectrum (ESI) m/z=612.2 (M+1).

Step B: 2-((3R,5R,6S)-5-(3-chlorophenyl)-6-(4-chlorophenyl)-1-((S)-1-cyclopropyl-2-(N-(pyridin-2-yl)methylsulfonamido)ethyl)-3-methyl-2-oxopiperidin-3-yl)acetic acid ¹H NMR (400 MHz, methanol-d4) δ ppm −0.75 (s, br, 1H), 0.00 (s, br, 1H), 0.47 (s, br, 1H), 0.60 (s, br, 1H), 1.68 (s, 3H), 2.02 (s, br, 2H), 2.30 (m, 1H), 2.94 (d, J=12 Hz, 1H), 3.11 (s, 3H), 3.19 (d, J=12 Hz, 1H), 3.19 (s, br, 1H), 3.62 (m, 1H), 3.99 (s, br, 1H), 4.79 (s, br, 1H), 4.93 (s, br, 1H), 6.92 (s, br, 1H), 7.00 (s, br, 1H), 7.15 (s, br, 1H), 7.35 (m, 2H), 7.51 (s, br, 3H), 7.87 (s, br, 1H), 8.03 (d, J=4 Hz, 1H), 8.15 (s, br, 1H).
Mass Spectrum (ESI) m/z=630.1 (M+1).

Example 289

2-((3R,5R,6S)-5-(3-chlorophenyl)-6-(4-chlorophenyl)-1-((S)-1-cyclopropyl-2-(methylsulfonamido)ethyl)-3-methyl-2-oxopiperidin-3-yl)acetic acid

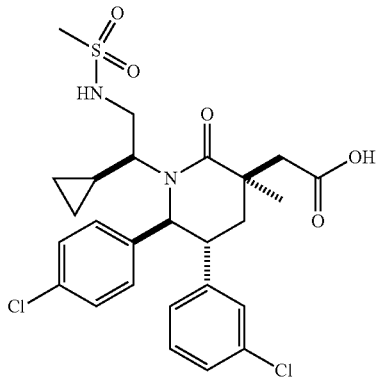

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)methanesulfonamide

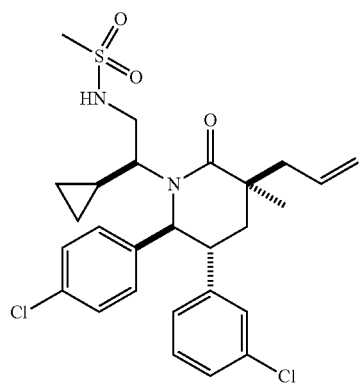

¹H NMR (400 MHz, methanol-d₄) δ ppm −0.87 (s, br, 1H), −0.24 (m, 1H), 0.22 (m, 1H), 0.38 (m, 1H), 0.90 (m, 1H), 1.28 (s, 3H), 1.58 (m, 2H), 1.84 (dd, J=4, 12 Hz, 1H), 2.13 (m, 1H), 2.27 (t, J=16 Hz, 1H), 2.63 (dd, J=8, 16 Hz, 1H), 2.70 (dd, J=8, 16 Hz, 1H), 2.97 (s, 3H), 3.13 (m, 1H), 3.90 (m, 1H), 2.42 (s, br, 1H), 5.17-5.27 (m, 2H), 5.92 (m, 1H), 6.98 (m, 2H), 7.06 (s, 1H), 7.14 (m, 3H), 7.27 (m, 2H).
Mass Spectrum (ESI) m/z=535.2 (M+1).

Step B: 2-((3R,5R,6S)-5-(3-chlorophenyl)-6-(4-chlorophenyl)-1-((S)-1-cyclopropyl-2-(methylsulfonamido)ethyl)-3-methyl-2-oxopiperidin-3-yl)acetic acid ¹H NMR (400 MHz, methanol-d₄) δ ppm −1.07 (s, br, 1H), −0.45 (s, br, 1H), 0.01 (s, br, 1H), 0.13 (m, br, 1H), 1.21 (s, 3H), 1.33 (s, br, 1H), 1.89 (dd, J=4, 12 Hz, 1H), 2.11 (t, J=12 Hz, 1H), 2.15 (s, br, 1H), 2.45 (d, J=16 Hz, 1H), 2.75 (s, 3H), 2.76 (d, J=16 Hz, 1H), 2.89 (m, 1H), 3.18 (m, 1H), 3.62 (m, 1H), 4.67 (d, 1H), 6.79 (m, 2H), 6.85 (s, 1H), 6.93 (m, 3H), 7.04 (s, br, 2H).
Mass Spectrum (ESI) m/z=553.2 (M+1).

Example 290

2-((3R,5R,6S)-5-(3-chlorophenyl)-6-(4-chlorophenyl)-1-((S)-1-cyclopropyl-2-(N-ethylmethylsulfonamido)ethyl)-3-methyl-2-oxopiperidin-3-yl)acetic acid

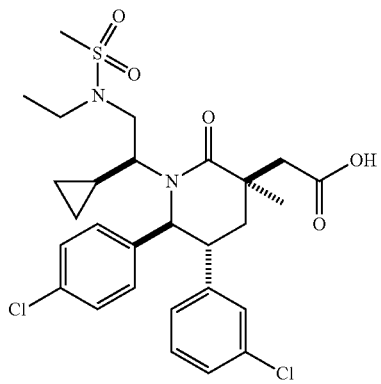

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-ethylmethanesulfonamide

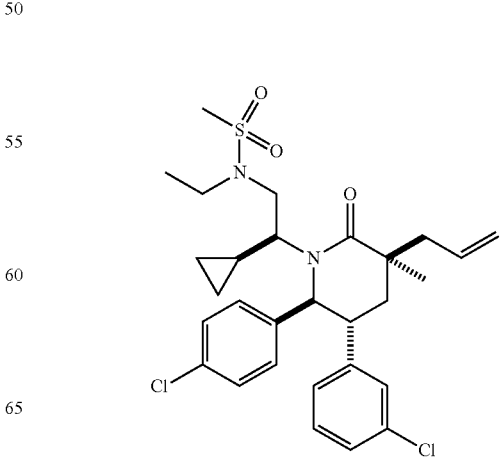

To a solution of N-((S)-2-((3S,5R,6S)-3-allyl-5-(3-chlorophenyl)-6-(4-chlorophenyl)-3-methyl-2-oxopiperidin-1-yl)-2-cyclopropylethyl)methanesulfonamide (Example 289, Step A, 86 mg, 0.161 mmol) in DMF (1.5 ml) was added sodium hydride (16.06 mg, 0.401 mmol) at rt and the reaction was stirred at rt for 30 minutes. To this reaction was added iodoethane (0.058 mL, 0.723 mmol) and the reaction was stirred at rt for 2 hours. The reaction was diluted with EtOAc, washed with water and sat. NaCl, dried with $Na_2SO_4$ and then concentrated. The crude was used on next reaction.

Mass Spectrum (ESI) m/z=563.2 (M+1).

Step B: 2-((3R,5R,6S)-5-(3-chlorophenyl)-6-(4-chlorophenyl)-1-((S)-1-cyclopropyl-2-(N-ethylmethylsulfonamido)ethyl)-3-methyl-2-oxopiperidin-3-yl)acetic acid The title compound was prepared using similar procedures as described for Example 272, Step B.

$^1$H NMR (400 MHz, methanol-$d_4$) δ ppm −0.67 (s, br, 1H), −0.27 (s, br, 1H), 0.30 (s, br, 1H), 0.40 (s, br, 1H), 1.18 (t, J=8 Hz, 3H), 1.41 (s, 3H), 1.71 (s, br, 1H), 2.07 (dd, J=4, 12 Hz, 1H), 2.24 (s, br, 1H), 2.36 (t, J=12 Hz, 1H), 2.68 (d, J=16 Hz, 1H), 2.92 (s, 3H), 2.96 (d, J=16 Hz, 1H), 3.25 (s, br, 1H), 3.27 (m, 1H), 3.37 (m, 2H), 4.28 (s, br, 1H), 4.81 (s, br, 1H), 6.98 (m, 2H), 7.04 (s, 1H), 7.14 (m, 3H), 7.27 (s, br, 2H).

Mass Spectrum (ESI) m/z=581.2 (M+1).

Example 291

2-((3R,5R,6S)-5-(3-chlorophenyl)-6-(4-chlorophenyl)-1-((S)-1-cyclopropyl-2-(N-isopropylmethylsulfonamido)ethyl)-3-methyl-2-oxopiperidin-3-yl)acetic acid

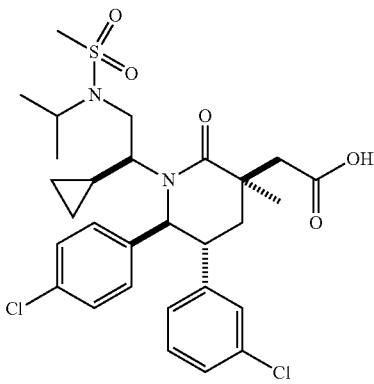

Step A: N-((S)-2-((3S,5R,6S)-3-allyl-5-(3-chlorophenyl)-6-(4-chlorophenyl)-3-methyl-2-oxopiperidin-1-yl)-2-cyclopropylethyl)-N-isopropylmethanesulfonamide

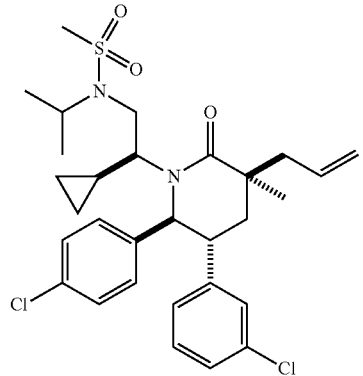

This compound was prepared using similar procedures as described for Example 290, Step A.

Mass Spectrum (ESI) m/z=577.2 (M+1).

Step B: 2-((3R,5R,6S)-5-(3-chlorophenyl)-6-(4-chlorophenyl)-1-((S)-1-cyclopropyl-2-(N-isopropylmethylsulfonamido)ethyl)-3-methyl-2-oxopiperidin-3-yl)acetic acid This compound was prepared using similar procedures as described for Example 272 Step B.

$^1$H NMR (400 MHz, methanol-$d_4$) δ ppm −0.43 (s, br, 1H), 0.00 (s, br, 1H), 0.51 (s, br, 1H), 0.62 (s, br, 1H), 1.36 (s, br, 3H), 1.45 (s, br, 3H), 1.62 (s, br, 3H), 1.97 (s, br, 1H), 2.24 (d, br, 1H), 2.54 (d, br, 2H), 2.90 (d, J=12 Hz, 1H), 3.12 (s, br, 3H), 3.16 (d, J=12 Hz, 1H), 3.42 (s, br, 1H), 3.59 (m, 1H), 4.17 (s, br, 1H), 4.42 (s, br, 1H), 7.19 (m, 2H), 7.24 (s, 1H), 7.38 (m, 3H), 7.47 (s, br, 2H).

Mass Spectrum (ESI) m/z=595.2 (M+1).

Examples 292-294 were prepared using similar procedures as described for Example 272 starting with (3S,5R,6S)-3-allyl-5-(3-chlorophenyl)-6-(4-chlorophenyl)-1-((S)-1-cyclopropyl-2-hydroxyethyl)-3-ethylpiperidin-2-one (Example 253, Step C).

| Example | Reagent Used | Source or CAS# |
|---------|--------------|----------------|
| 292 | propane-2-sulfonamide | [81363-76-0] |
| 293 | cyclobutanesulfonamide | Example 271G |
| 294 | cyclopentanesulfonamide | [73945-39-8] |

Example 292

2-((3R,5R,6S)-5-(3-chlorophenyl)-6-(4-chlorophenyl)-1-((S)-1-cyclopropyl-2-(1-methylethylsulfonamido)ethyl)-3-ethyl-2-oxopiperidin-3-yl)acetic acid

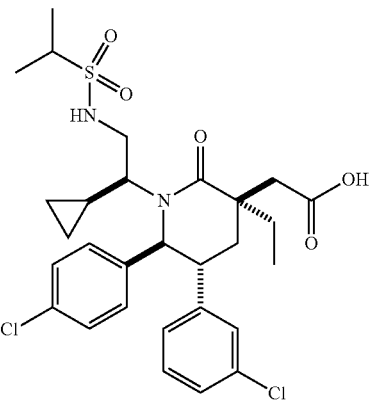

545

Step A: N-((S)-2-((3S,5R,6S)-3-allyl-5-(3-chlorophenyl)-6-(4-chlorophenyl)-3-ethyl-2-oxopiperidin-1-yl)-2-cyclopropylethyl)propane-2-sulfonamide

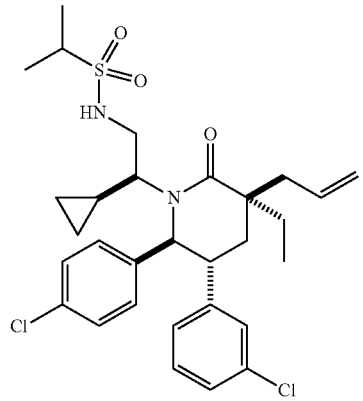 [SMILES: C=CC[C@@]1(CC)C[C@H](c2cccc(Cl)c2)[C@@H](c2ccc(Cl)cc2)N([C@H](CNS(=O)(=O)C(C)C)C2CC2)C1=O]

¹H NMR (400 MHz, methanol-d₄) δ ppm −0.32 (s, br, 1H), 0.01 (s, br, 1H), 0.36 (d, br, 2H), 0.71 (t, J=8 Hz, 3H), 0.78 (m, 1H), 1.17 (m, 6H), 1.32 (m, 1H), 1.58 (dd, J=4, 12,Hz, 1H), 1.70-1.79 (m, 1H), 2.03 (t, J=12 Hz, 1H), 2.37 (dd, J=4, 12 Hz, 1H), 2.47 (dd, J=4, 12 Hz, 1H), 2.86 (s, br, 1H), 2.93 (m, 1H), 3.02 (m, 2H), 4.59 (d, J=12 Hz, 1H), 4.98 (s, 1H), 5.00 (d, J=8 Hz, 1H), 5.27 (s, 1H), 5.72 (m, 1H), 6.56 (d, J=8 Hz, 2H), 6.77 (s, 1H), 6.89-6.97 (m, 3H), 6.98 (s, br, 2H). Mass Spectrum (ESI) m/z=577.2 (M+1).

Step B: 2-((3R,5R,6S)-5-(3-chlorophenyl)-6-(4-chlorophenyl)-1-((S)-1-cyclopropyl-2-(1-methylethylsulfonamido)ethyl)-3-ethyl-2-oxopiperidin-3-yl)acetic acid ¹H NMR (400 MHz, chloroform-d₁) δ ppm −0.47 (s, br, 1H), 0.00 (s, br, 1H), 0.41 (s, br, 1H), 0.48 (s, br, 1H), 0.97 (t, J=8 Hz, 3H), 1.32 (m, 7H), 1.80 (m, 1H), 1.94 (m, 2H), 2.38 (t, J=12 Hz, 3H), 2.64 (d, J=16 Hz, 1H), 2.70 (s, br, 1H), 2.91 (d, J=16 Hz, 1H), 3.01 (s, br, 1H), 3.19 (m, 1H), 3.40 (m, 1H), 3.53 (s, br, 1H), 4.94 (s, br, 1H), 7.00 (m, 2H), 7.06 (s, 1H), 7.17 (m, 3H), 7.25 (s, br, 2H). Mass Spectrum (ESI) m/z=595.2 (M+1).

Example 293

2-((3R,5R,6S)-5-(3-chlorophenyl)-6-(4-chlorophenyl)-1-((S)-2-(cyclobutanesulfonamido)-1-cyclopropylethyl)-3-ethyl-2-oxopiperidin-3-yl)acetic acid

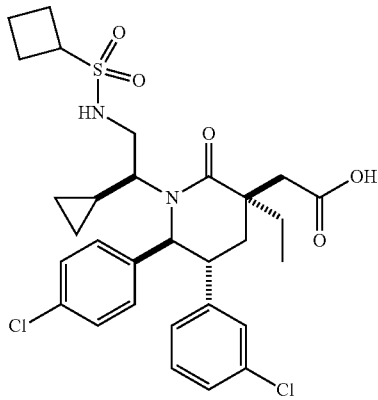 [SMILES: CC[C@]1(CC(=O)O)C[C@H](c2cccc(Cl)c2)[C@@H](c2ccc(Cl)cc2)N([C@H](CNS(=O)(=O)C2CCC2)C2CC2)C1=O]

546

Step A: N-((S)-2-((3S,5R,6S)-3-allyl-5-(3-chlorophenyl)-6-(4-chlorophenyl)-3-ethyl-2-oxopiperidin-1-yl)-2-cyclopropylethyl)cyclobutanesulfonamide

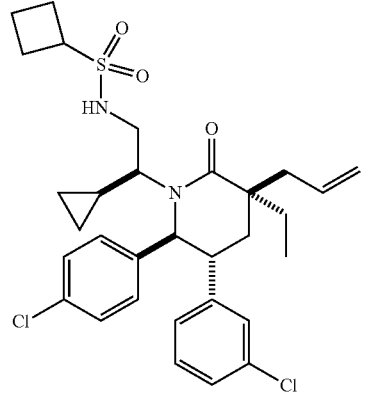 [SMILES: C=CC[C@@]1(CC)C[C@H](c2cccc(Cl)c2)[C@@H](c2ccc(Cl)cc2)N([C@H](CNS(=O)(=O)C2CCC2)C2CC2)C1=O]

Mass Spectrum (ESI) m/z=589.2 (M+1).

Step B: 2-((3R,5R,6S)-5-(3-chlorophenyl)-6-(4-chlorophenyl)-1-((S)-2-(cyclobutanesulfonamido)-1-cyclopropylethyl)-3-ethyl-2-oxopiperidin-3-yl)acetic acid ¹H NMR (400 MHz, methanol-d₄) δ ppm −0.48 (s, br, 1H), −0.01 (s, br, 1H), 0.40 (s, br, 1H), 0.48 (s, br, 1H), 0.97 (t, J=8 Hz, 3H), 1.33 (s, br, 1H), 1.81 (m, 1H), 1.94-2.05 (m, 4H), 2.34 (m, 2H), 2.37 (m, 3H), 2.64 (d, J=12 Hz, 1H), 2.72 (s, br, 1H), 2.91 (d, J=12 Hz, 1H), 3.00 (s, br, 1H), 3.39 (m, 2H), 3.90 (m, 1H), 4.92 (s, br, 1H), 6.99 (m, 2H), 7.05 (s, br, 1H), 7.15 (m, 3H), 7.25 (s, br, 2H). Mass Spectrum (ESI) m/z=607.0 (M+1).

Example 294

2-((3R,5R,6S)-5-(3-chlorophenyl)-6-(4-chlorophenyl)-1-((S)-2-(cyclopentanesulfonamido)-1-cyclopropylethyl)-3-ethyl-2-oxopiperidin-3-yl)acetic acid

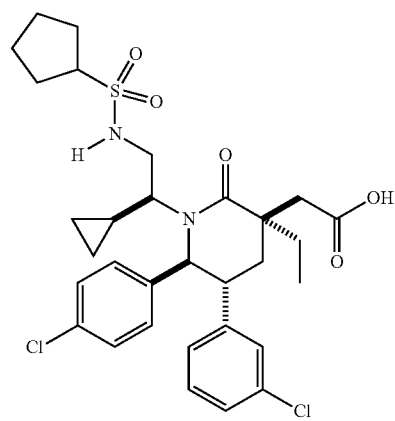 [SMILES: CC[C@]1(CC(=O)O)C[C@H](c2cccc(Cl)c2)[C@@H](c2ccc(Cl)cc2)N([C@H](CNS(=O)(=O)C2CCCC2)C2CC2)C1=O]

547

Step A: N-((S)-2-((3S,5R,6S)-3-allyl-5-(3-chlorophenyl)-6-(4-chlorophenyl)-3-ethyl-2-oxopiperidin-1-yl)-2-cyclopropylethyl)cyclopentanesulfonamide

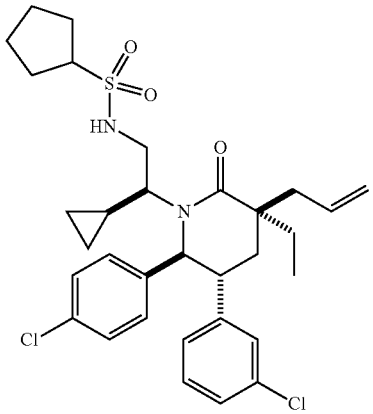 [SMILES: C=CC[C@@]1(CC)C[C@H](c2cccc(Cl)c2)[C@@H](c2ccc(Cl)cc2)N([C@H](CNS(=O)(=O)C2CCCC2)C2CC2)C1=O]

$^1$H NMR (400 MHz, methanol-$d_4$) δ ppm −0.32 (s, br, 1H), 0.00 (s, br, 1H), 0.36 (s, br, 1H), 0.38 (s, br, 1H), 0.71 (t, J=8 Hz, 3H), 0.78 (m, 1H), 1.33 (m, 1H), 1.44 (m, 2H), 1.58 (m, 3H), 1.80 (m, 6H), 2.03 (t, J=12 Hz, 1H), 2.36 (dd, J=8 Hz, 16, 1H), 2.46 (dd, J=8, 16 Hz, 1H), 2.85 (s, br, 2H), 3.01 (m, 2H), 3.24 (m, 1H), 4.59 (d, J=12 Hz, 1H), 4.97 (s, 1H), 5.00 (d, J=4 Hz, 1H), 5.32 (s, br, 1H), 5.72 (m, 1H), 6.56 (s, 1H), 6.58 (s, 1H), 6.77 (s, 1H), 6.91 (m, 3H), 6.98 (s, br, 2H). Mass Spectrum (ESI) m/z=603.3 (M+1).

Step B: 2-((3R,5R,6S)-5-(3-chlorophenyl)-6-(4-chlorophenyl)-1-((S)-2-(cyclopentanesulfonamido)-1-cyclopropylethyl)-3-ethyl-2-oxopiperidin-3-yl)acetic acid $^1$H NMR (400 MHz, chloroform-$d_1$) δ ppm −0.47 (s, br, 1H), 0.01 (s, br, 1H), 0.41 (s, br, 1H), 0.48 (s, br, 1H), 0.96 (t, J=12 Hz, 3H), 1.42 (s, br, 1H), 1.65 (m, 2H), 1.71 (m, 3H), 1.96 (m, 6H), 2.37 (t, J=12 Hz, 1H), 2.64 (d, J=16 Hz, 1H), 2.71 (s, br, 1H), 2.91 (d, J=16 Hz, 1H), 2.97 (s, br, 1H), 3.40 (m, 1H), 3.54 (m, 2H), 4.93 (s, br, 1H), 7.00 (s, 1H), 7.01 (s, 1H), 7.05 (s, 1H), 7.14 (m, 3H), 7.25 (s, br, 2H). Mass Spectrum (ESI) m/z=621.1 (M+1).

Example 295

2-((3R,5R,6S)-5-(3-chlorophenyl)-6-(4-chlorophenyl)-3-methyl-1-((S)-3-methyl-1-(N-methylcyclopropanesulfonamido)butan-2-yl)-2-oxopiperidin-3-yl)acetic acid

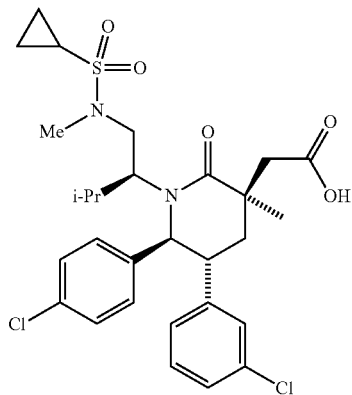 [SMILES: CC(C)[C@@H](CN(C)S(=O)(=O)C1CC1)N1C(=O)[C@@](C)(CC(=O)O)C[C@H](c2cccc(Cl)c2)[C@H]1c1ccc(Cl)cc1]

548

Step A: N-((S)-2-((3S,5R,6S)-3-allyl-5-(3-chlorophenyl)-6-(4-chlorophenyl)-3-methyl-2-oxopiperidin-1-yl)-3-methylbutyl)-N-methylcyclopropanesulfonamide

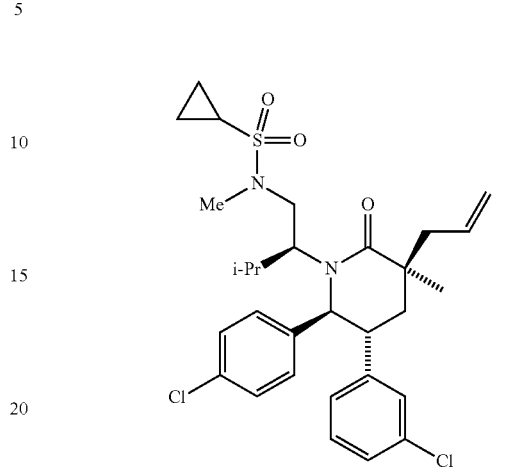

The title compound was prepared from (3S,5R,6S)-3-allyl-5-(3-chlorophenyl)-6-(4-chlorophenyl)-1-((S)-1-hydroxy-3-methylbutan-2-yl)-3-methylpiperidin-2-one (Example 261, Step H, 109 mg, 0.237 mmol) and N-methylcyclopropanesulfonamide (WO2005/108358, 120 mg, 0.888 mmol) using the general procedure described in Step A of Example 272 and was purified by silica chromatography eluting with ethyl acetate in hexanes. The product was obtained as beige foam (113.5 mg, 83%). LCMS (ESI): m/z=577.2 (M+H).

Step B: 2-((3R,5R,6S)-5-(3-chlorophenyl)-6-(4-chlorophenyl)-3-methyl-1-((S)-3-methyl-1-(N-methylcyclopropanesulfonamido)butan-2-yl)-2-oxopiperidin-3-yl)acetic acid A mixture of N-((S)-2-((3S,5R,6S)-3-allyl-5-(3-chlorophenyl)-6-(4-chlorophenyl)-3-methyl-2-oxopiperidin-1-yl)-3-methylbutyl)-N-methylcyclopropanesulfonamide (Example 295, Step A, 112.5 mg, 0.195 mmol), sodium periodate (170 mg, 0.795 mmol), and ruthenium(III) chloride hydrate (6 mg, 0.023 mmol) in acetonitrile (1.0 mL), carbon tetrachloride (1.0 mL), and water (1.5 mL) was vigorously stirred at ambient temperature overnight. The reaction mixture was acidified with aqueous citric acid (10% by weight), diluted in ethyl acetate, and filtered through a pad of Celite® (J. T. Baker, Phillipsberg, N.J., diatomaceous earth). The filtrate was partitioned between 2 M aqueous HCl and ethyl acetate. Combined organics were washed with brine, dried over sodium sulfate, filtered, and concentrated in vacuo to a residue that was purified by preparative HPLC (Sunfire™ Prep $C_{18}$ OBD 10 μm column, 30×150 mm, Waters, Milford, Mass.) eluting with a gradient of 50 to 100% acetonitrile in water (0.1% trifluoroacetic acid in both solvents). Chromatography fractions containing the product were stripped of volatiles, redissolved in minimal volumes of acetonitrile and water, frozen, and lyophilized to give the product as a white solid.

¹H NMR (500 MHz, methanol-d₄) δ ppm 0.63 (d, J=6.60 Hz, 3 H), 0.69 (s, 3 H), 0.95-1.22 (m, 4 H), 1.40 (s, 3 H), 2.07 (dd, J=13.7, 3.2 Hz, 1 H), 2.23 (dquin, J=9.5, 6.7 Hz, 1 H), 2.38 (t, J=13.7 Hz, 1 H), 2.51-2.60 (m, 1 H), 2.60-2.71 (m, 2 H), 2.87-2.96 (m, 4 H), 3.01 (d, J=13.5 Hz, 1 H), 3.48 (ddd, J=13.8, 11.0, 3.1 Hz, 1 H), 4.13-4.40 (m, 1 H), 4.97 (d, J=11.0 Hz, 1 H), 6.98-7.06 (m, 2 H), 7.07-7.16 (m, 2 H), 7.29 (br s, 4 H). LCMS (ESI): m/z=595.2 (M+H).

Example 296

2-((3R,5R,6S)-5-(3-chlorophenyl)-6-(4-chlorophenyl)-1-((S)-1-(cyclopropanesulfonamido)-3-methylbutan-2-yl)-3-methyl-2-oxopiperidin-3-yl)acetic acid

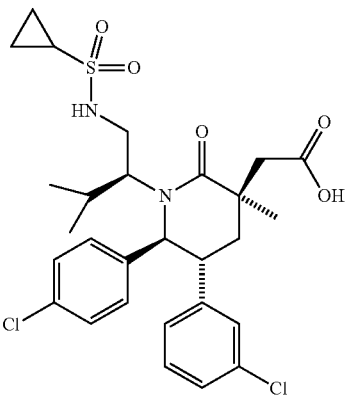 [SMILES: CC(C)[C@@H](CNS(=O)(=O)C1CC1)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)-3-methylbutyl)cyclopropanesulfonamide

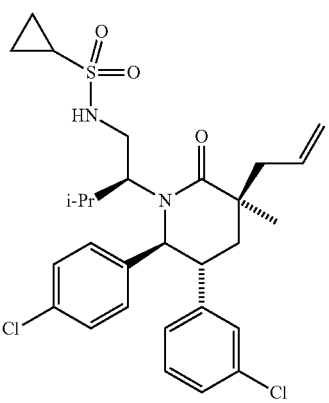 [SMILES: C=CC[C@@]1(C)C[C@H](c2cccc(Cl)c2)[C@@H](c2ccc(Cl)cc2)N([C@H](CNS(=O)(=O)C2CC2)C(C)C)C1=O]

The title compound was prepared using cyclopropanesulfonamide (101 mg, 0.834 mmol) according to the procedure described in Step A of Example 272 and purified by silica chromatography eluting with a gradient of ethyl acetate in hexanes. The product was obtained as a solid. LCMS (ESI): m/z=563.2 (M+H).

Step B. 2-((3R,5R,6S)-5-(3-chlorophenyl)-6-(4-chlorophenyl)-1-((S)-1-(cyclopropanesulfonamido)-3-methylbutan-2-yl)-3-methyl-2-oxopiperidin-3-yl)acetic acid The title compound was prepared by the general procedure described in step B of Example 295. The product was obtained as an off-white powder.
¹H NMR (500 MHz, methanol-d₄) δ ppm 0.59 (d, J=6.9 Hz, 3 H), 0.63 (d, J=6.4 Hz, 3 H), 0.95-1.10 (m, 3 H), 1.10-1.18 (m, 1 H), 1.42 (s, 3 H), 2.09 (dd, J=13.7, 3.2 Hz, 1 H), 2.14-2.24 (m, 1 H), 2.38 (t, J=13.7 Hz, 1 H), 2.52-2.61 (m, 1 H), 2.62-2.80 (m, 2 H), 3.01 (d, J=13.5 Hz, 1 H), 3.21 (dd, J=14.1, 2.1 Hz, 1 H), 3.51 (ddd, J=13.6, 11.2, 3.1 Hz, 1 H), 3.83 (br s, 1 H), 5.07 (d, J=11.25 Hz, 1 H), 7.04 (d, J=7.34 Hz, 1 H), 7.07-7.63 (m, 7 H). LCMS (ESI): m/z=581.2 (M+H).

Example 297

2-((3R,5R,6S)-5-(3-chlorophenyl)-6-(4-chlorophenyl)-1-((S)-1-(ethylsulfonamido)-3-methylbutan-2-yl)-3-methyl-2-oxopiperidin-3-yl)acetic acid

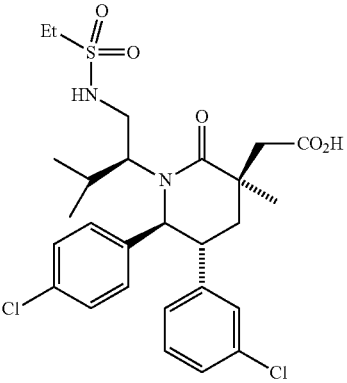 [SMILES: CCS(=O)(=O)NC[C@H](C(C)C)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)-3-methylbutyl)ethanesulfonamide

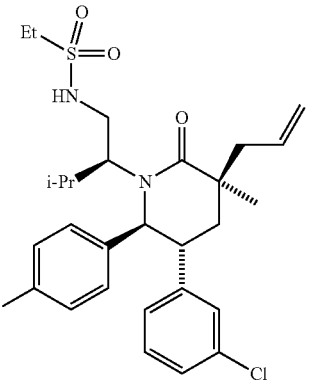

The title compound was prepared from ethanesulfonamide (76 mg, 0.696 mmol; Allichem) by the general procedure described in Step A of Example 295, and purified by silica gel chromatography eluting with a gradient of ethyl acetate in hexanes. The product was obtained in 89% yield. LCMS (ESI) m/z=551.2 (M+H).

Step B. 2-((3R,5R,6S)-5-(3-chlorophenyl)-6-(4-chlorophenyl)-1-((S)-1-(ethylsulfonamido)-3-methylbutan-2-yl)-3-methyl-2-oxopiperidin-3-yl)acetic acid The title compound was prepared using the procedure described in Step B of example 295 an obtained as a white solid (56% yield).

$^1$H NMR (500 MHz, methanol-$d_4$) δ ppm 0.59 (d, J=6.9 Hz, 3 H), 0.62 (d, J=6.6 Hz, 3 H), 1.36 (t, J=7.5 Hz, 3 H), 1.42 (s, 3 H), 2.09 (d, J=10.5 Hz, 1 H), 2.14-2.23 (m, 1 H), 2.34-2.47 (m, 1 H), 2.64 (s, 0 H), 2.70 (br. s., 1 H), 3.02 (d, J=13.2 Hz, 1 H), 3.06-3.20 (m, 3 H), 3.53 (ddd, J=13.8, 11.1, 3.1 Hz, 1 H), 3.79 (br. s., 1 H), 5.10 (d, J=11.0 Hz, 1 H), 7.03-7.08 (m, 1 H), 7.09-7.17 (m, 3 H), 7.17-7.87 (m, 4 H). LCMS (ESI): m/z=569.2 (M+H).

Example 298

2-((3R,5R,6S)-5-(3-chlorophenyl)-6-(4-chlorophenyl)-1-((S)-1-(cyclobutanesulfonamido)butan-2-yl)-3-methyl-2-oxopiperidin-3-yl)acetic acid

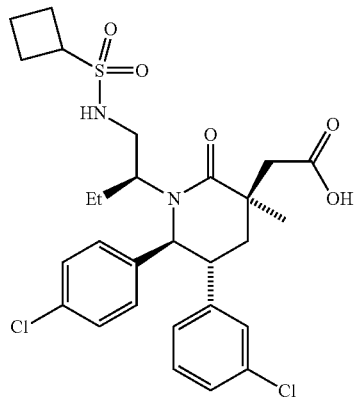 [SMILES: CC[C@@H](CNS(=O)(=O)C1CCC1)N1C(=O)[C@@](C)(CC(=O)O)C[C@H](c2cccc(Cl)c2)[C@H]1c1ccc(Cl)cc1]

Step A. N-((S)-2-((3S,5R,6S)-3-allyl-5-(3-chlorophenyl)-6-(4-chlorophenyl)-3-methyl-2-oxopiperidin-1-yl)butyl)cyclobutanesulfonamide

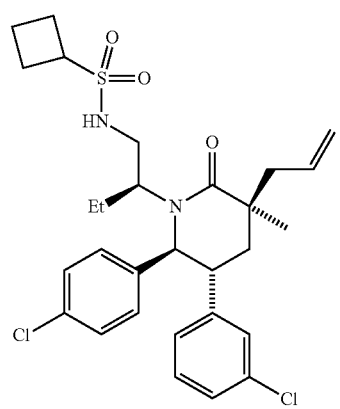 [SMILES: C=CC[C@@]1(C)C[C@H](c2cccc(Cl)c2)[C@@H](c2ccc(Cl)cc2)N([C@@H](CC)CNS(=O)(=O)C2CCC2)C1=O]

The title compound was prepared from (3S,5R,6S)-3-allyl-5-(3-chlorophenyl)-6-(4-chlorophenyl)-1-((S)-1-hydroxybutan-2-yl)-3-methylpiperidin-2-one (Example 91, Step B, 250 mg, 0.560 mmol) and cyclobutanesulfonamide (Example 271G, 256 mg, 1.894 mmol) using the general procedure described in Step A of Example 272, albeit with an oil bath heated at 40° C. The crude product was purified by silica gel chromatography eluting with a gradient of EtOAc in hexanes. The product was obtained as a white powder (220 mg, 70%). LCMS (ESI): m/z=563.2 (M+H).

Step B. 2-((3R,5R,6S)-5-(3-chlorophenyl)-6-(4-chlorophenyl)-1-((S)-1-(cyclobutanesulfonamido)butan-2-yl)-3-methyl-2-oxopiperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)butyl)cyclobutanesulfonamide (Example 298, Step A, 50 mg, 0.089 mmol) by the general procedure described in Step B of Example 295. The crude product was purified by preparative HPLC chromatography (Sunfire™ Prep $C_{18}$ OBD 10 µm column, 30×150 mm, Waters, Milford, Mass.) eluting with a 50 to 95% gradient of acetonitrile in water (0.1% trifluoroacetic acid in both solvents) to afford a white powder.

$^1$H NMR (500 MHz, methanol-$d_4$) δ ppm 0.44 (t, J=7.6 Hz, 3 H), 1.42 (s, 3 H), 1.50-1.63 (m, 1 H), 1.73-1.88 (m, 1 H), 1.94-2.14 (m, 3 H), 2.20-2.53 (m, 5 H), 2.62 (s, 1 H), 2.80 (t, J=9.2 Hz, 1 H), 2.87-3.01 (m, 2 H), 3.32-3.39 (m, 1 H), 3.80 (dd, J=13.9, 10.0 Hz, 1 H), 3.92 (quin, J=8.25 Hz, 1 H), 4.93 (d, J=11.00 Hz, 1 H), 7.03 (d, J=7.3 Hz, 1 H), 7.08 (s, 1 H), 7.11-7.22 (m, 4 H), 7.26 (d, J=7.6 Hz, 2 H). LCMS (ESI): m/z=581.2 (M+H).

Example 299

2-((3R,5R,6S)-5-(3-chlorophenyl)-6-(4-chlorophenyl)-1-((S)-1-(N-ethylcyclobutanesulfonamido)butan-2-yl)-3-methyl-2-oxopiperidin-3-yl)acetic acid

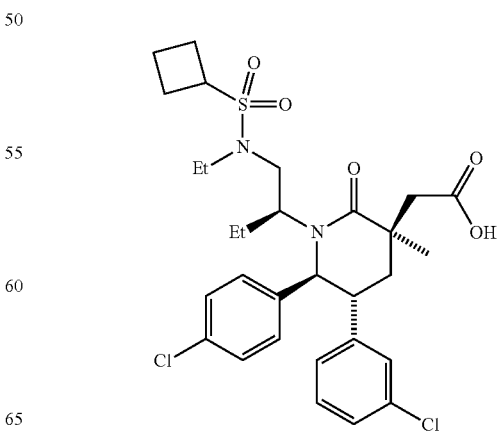

553

Step A. N-((S)-2-((3S,5R,6S)-3-allyl-5-(3-chlorophenyl)-6-(4-chlorophenyl)-3-methyl-2-oxopiperidin-1-yl)butyl)-N-ethylcyclobutanesulfonamide

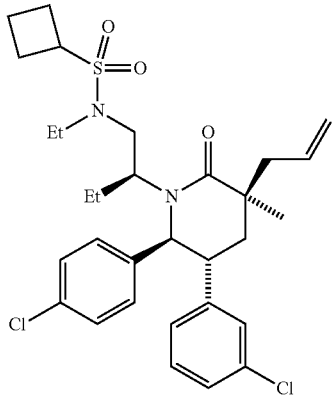 [SMILES: C=CC[C@@]1(C)C[C@H](c2cccc(Cl)c2)[C@@H](c2ccc(Cl)cc2)N([C@@H](CC)CN(CC)S(=O)(=O)C2CCC2)C1=O]

By the method of Example 290, Step A, N-((S)-2-((3S,5R,6S)-3-allyl-5-(3-chlorophenyl)-6-(4-chlorophenyl)-3-methyl-2-oxopiperidin-1-yl)butyl)cyclobutanesulfonamide (Example 298, Step A) was treated with ethyl iodide to afford the title compound as a white foam. LCMS (ESI) m/z=591.2 (M+H).

Step B. 2-((3R,5R,6S)-5-(3-chlorophenyl)-6-(4-chlorophenyl)-1-((S)-1-(N-ethylcyclobutanesulfonamido)butan-2-yl)-3-methyl-2-oxopiperidin-3-yl)acetic acid The title compound was prepared from N-((S)-2-((3S,5R,6S)-3-allyl-5-(3-chlorophenyl)-6-(4-chlorophenyl)-3-methyl-2-oxopiperidin-1-yl)butyl)-N-ethylcyclobutanesulfonamide (Example 299, Step A) by the general procedure described in Step B of Example 295 and obtained as a fluffy white solid.

$^1$H NMR (500 MHz, methanol-$d_4$) δ ppm 0.50 (t, J=7.21 Hz, 3 H), 1.05-1.13 (m, 3 H), 1.43 (s, 3 H), 1.54-1.67 (m, 1 H), 1.88 (dquin, J=15.2, 7.5 Hz, 1 H), 1.93-2.12 (m, 3 H), 2.22-2.36 (m, 2 H), 2.37-2.59 (m, 3 H), 2.64 (d, J=13.20 Hz, 1 H), 2.70-2.99 (m, 3 H), 3.17 (dq, J=14.6, 7.2 Hz, 1 H), 3.33-3.43 (m, 1 H), 3.96 (quin, J=8.4 Hz, 1 H), 4.06-4.33 (m, 1 H), 4.83 (m, 1 H), 7.02 (d, J=7.1 Hz, 1 H), 7.05 (s, 1 H), 7.08-7.21 (m, 3 H), 7.27 (br. s., 3 H). LCMS (ESI): m/z=609.2 (M+H).

Example 300

2-((3R,5R,6S)-5-(3-Chlorophenyl)-6-(4-chlorophenyl)-3-methyl-2-oxo-1-((S)-1-(phenylsulfonyl)butan-2-yl)piperidin-3-yl)acetic acid

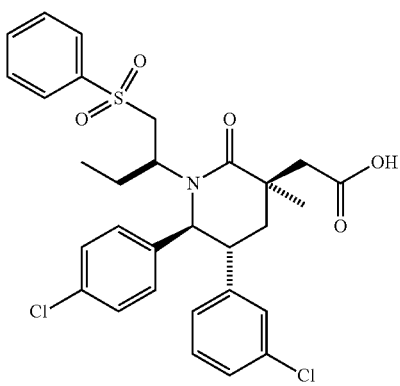 [SMILES: CC[C@@H](CS(=O)(=O)c1ccccc1)N1C(=O)[C@@](C)(CC(=O)O)C[C@H](c2cccc(Cl)c2)[C@H]1c1ccc(Cl)cc1]

554

Step A. (3S,5R,6S)-3-Allyl-5-(3-chlorophenyl)-6-(4-chlorophenyl)-3-methyl-1-((S)-1-(phenylthio)butan-2-yl)piperidin-2-one

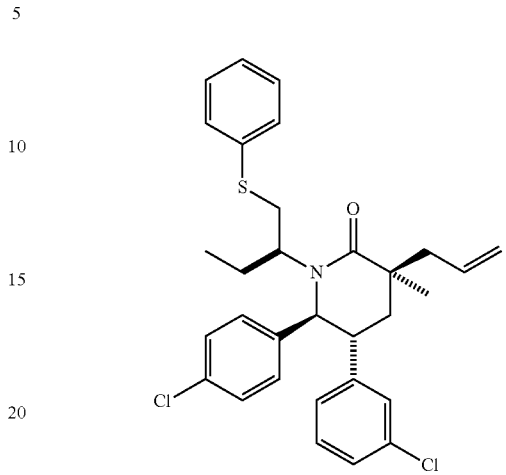

To a solution of (3S,5R,6S)-3-allyl-5-(3-chlorophenyl)-6-(4-chlorophenyl)-1-((S)-1-hydroxybutan-2-yl)-3-methylpiperidin-2-one (180 mg, 0.403 mmol; Example 91, Step B) in 2 mL of toluene was added cyanomethylenetributylphosphorane (324 uL, 1.21 mmol) and benzenethiol (121 μL 1.21 mmol) at RT. The mixture was heated to 110° C. for 2 h. The reaction was cooled down, quenched (sat. aq. NH$_4$Cl solution), extracted (2×EtOAc), and washed with brine. The combined organic layers were dried over Na$_2$SO$_4$, filtered and the filtrate was concentrated under reduced pressure. Purification of the residue by chromatography on silica gel (4 g SiO$_2$, 10, 20, 40% EtOAc/hexane) provided the title compound.

Step B. 2-((3R,5R,6S)-5-(3-Chlorophenyl)-6-(4-chlorophenyl)-3-methyl-2-oxo-1-((S)-1-(phenylsulfonyl)butan-2-yl)piperidin-3-yl)acetic acid The title compound was prepared from (3S,5R,6S)-3-allyl-5-(3-chlorophenyl)-6-(4-chlorophenyl)-3-methyl-1-((S)-1-(phenylthio)butan-2-yl)piperidin-2-one (Example 300, Step A) by a procedure similar to the one described in Example 71, Step F. The crude product was purified by reverse phase preparatory HPLC (Gemini™ Prep C$_{18}$ 5 μm column; Phenomenex, Torrance, Calif.; MeCN in water with 0.1% TFA, gradient elution) to give a white solid.

$^1$H NMR (400 MHz, CDCl$_3$) δ ppm 0.37 (t, J=8 Hz, 3 H), 1.46 (m, 1 H), 1.58 (s, 3 H), 1.94 (dd, J=12, 4 Hz, 1 H), 2.08 (m, 1 H), 2.50 (t, J=16 Hz, 1 H), 2.79 (d, J=16 Hz, 1 H), 2.88 (dd, J=16 Hz, 1 H), 3.05 (d, J=16 Hz, 1 H), 3.15 (m, 1 H), 3.41 (m, 1 H), 4.24 (dd, J=16, 12 Hz, 1 H), 5.04 (d, J=8.0 Hz, 1 H), 6.88 (d, J=8.0 Hz, 1 H), 6.99 (s, 1 H), 7.14 (m, 4 H), 7.27 (m, 2 H), 7.61 (m, 2 H), 7.71 (m, 1 H), 7.93 (d, J=8 Hz, 2 H); Mass Spectrum (ESI) 588.1 [M+H]$^+$.

Example 301

2-((3R,5R,6S)-5-(3-Chlorophenyl)-6-(4-chlorophenyl)-3-methyl-1-((S)-1-(methylsulfonyl)butan-2-yl)-2-oxopiperidin-3-yl)acetic acid

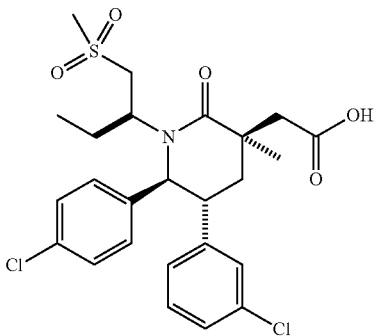 [SMILES: CC[C@@H](CS(C)(=O)=O)N1C(=O)[C@@](C)(CC(=O)O)C[C@H](c2cccc(Cl)c2)[C@H]1c1ccc(Cl)cc1]

Step A. (3S,5R,6S)-3-Allyl-5-(3-chlorophenyl)-6-(4-chlorophenyl)-3-methyl-1-((S)-1-(((trimethylsilyl)methyl)thio)butan-2-yl)piperidin-2-one

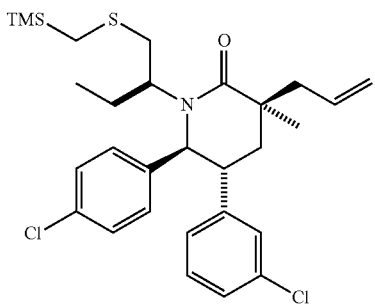 [SMILES: C=CC[C@@]1(C)C[C@H](c2cccc(Cl)c2)[C@@H](c2ccc(Cl)cc2)N([C@@H](CC)CSC[Si](C)(C)C)C1=O]

The title compound was prepared from (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) by a procedure similar to the one described in Example 300, Step A, replacing benzenethiol with the appropriate amount of (trimethylsilyl)methanethiol.

Step B. (3S,5R,6S)-3-Allyl-5-(3-chlorophenyl)-6-(4-chlorophenyl)-3-methyl-1-((S)-1-(methylthio)butan-2-yl)piperidin-2-one

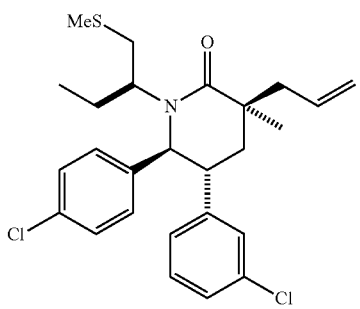 [SMILES: C=CC[C@@]1(C)C[C@H](c2cccc(Cl)c2)[C@@H](c2ccc(Cl)cc2)N([C@@H](CC)CSC)C1=O]

(3S,5R,6S)-3-allyl-5-(3-chlorophenyl)-6-(4-chlorophenyl)-3-methyl-1-((S)-1-(((trimethylsilyl)methyl)thio)butan-2-yl)piperidin-2-one (60 mg, 0.118 mmol, Example 301, Step A) was dissolved in a 1 M solution of tetrabutylammonium fluoride in tetrahydrofuran (3.5 mL, 3.5 mmol) at room temperature. The resulting solution was stirred at ambient temperature for 16 h. After that time volatiles were removed under reduced pressure, and the residue was purified by chromatography on silica gel (4 g $SiO_2$, 10, 20, 40% EtOAc/hexane) to provide the title compound.

Step C. 2-((3R,5R,6S)-5-(3-Chlorophenyl)-6-(4-chlorophenyl)-3-methyl-1-((S)-1-(methylsulfonyl)butan-2-yl)-2-oxopiperidin-3-yl)acetic acid The title compound was prepared from (3S,5R,6S)-3-allyl-5-(3-chlorophenyl)-6-(4-chlorophenyl)-3-methyl-1-((S)-1-(methylthio)butan-2-yl)piperidin-2-one (Example 301, Step B) to by a procedure similar to the one described in Example 71, Step F.

$^1$H NMR (400 MHz, $CDCl_3$) δ ppm 0.42 (t, J=8.0 Hz, 3 H), 1.45 (m, 1 H), 1.48 (s, 3 H), 1.90 (d, J=12 Hz, 1 H), 2.14 (m, 1 H), 2.37 (t, J=16.0 Hz, 1 H), 2.76 (d, J=16 Hz, 1 H), 2.90 (d, J=12 Hz, 1 H), 2.97 (m, 1 H), 2.99 (s, 3 H), 3.13 (m, 1 H), 3.37 (m, 1 H), 4.24 (m, 1 H), 4.90 (d, J=8.0 Hz, 1 H), 6.84 (d, J=8.0 Hz, 1 H), 6.95 (s, 1 H), 7.12 (m, 4 H), 7.27 (m, 2 H); Mass Spectrum (ESI) 526.0 $[M+H]^+$.

Examples 302 to 311 were also prepared from (3S,5R,6S)-3-allyl-5-(3-chlorophenyl)-6-(4-chlorophenyl)-1-((S)-1-hydroxybutan-2-yl)-3-methylpiperidin-2-one (Example 91, Step B) by procedures similar to the one described in Example 300, replacing benzenethiol with the appropriate amount of thiol. The requisite thiols are either commercially available, prepared as described in the table below or are prepared by the following general procedure from the corresponding alcohols.

General Thiol Procedure

Methanesulfonyl chloride (1 eq.) was added dropwise to a 0.5 M solution of the corresponding alcohol and triethylamine (1 eq.) in dichloromethane. The resulting mixture was stirred rt for 2 h. The reaction was then partitioned with water, washed with brine, dried over sodium sulfate, filtered and concentrated. This material was dissolved in DMF to give a 0.5M solution of the mesylate. To this sodium hydrosulfide (1.2 eq.) was added. The resulting mixture was stirred overnight at 45° C. The mixture was then partitioned with ether/water, washed with brine, dried over sodium sulfate, filtered the filtrate was concentrated under reduced pressure. The crude thiol obtained was used in the next step without further purification.

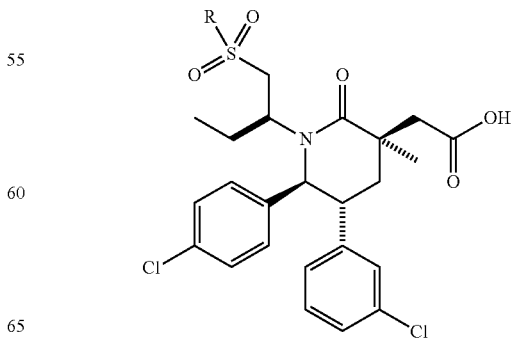

| Example | R | Reagent used |
|---|---|---|
| 302 | propyl | 1-propanethiol |
| 303 | isobutyl | 2-methyl-1-propanethiol |
| 304 | cyclopropylmethyl | cyclopropylmethanethiol; prepared from bromomethylcyclopropane by the procedure described in U.S. Pat. No. 3,975,429. |
| 305 | cyclobutylmethyl | cyclobutylmethanethiol; prepared from bromomethylcyclobutane by a procedure similar to the one described for the preparation of cyclopropylmethanethiol in U.S. Pat. No. 3,975,429. |
| 306 | cyclopentyl | cyclopentanethiol; prepared from bromocyclopentane by a procedure similar to the one described for the preparation of cyclopropylmethanethiol in U.S. Pat. No. 3,975,429. |
| 307 | oxetan-3-ylmethyl | oxetan-3-ylmethanethiol |
| 308 | (3-methyloxetan-3-yl)methyl | prepared by general procedure above |
| 309 | tetrahydropyran-4-yl | prepared by general procedure above |
| 310 | 2-hydroxy-2-methylpropyl | prepared by general procedure above |
| 311 | (R)- or (S)-butan-2-yl | butane-2-thiol |
| 312 | (R)- or (S)-butan-2-yl | butane-2-thiol |

Example 302

2-((3R,5R,6S)-5-(3-Chlorophenyl)-6-(4-chlorophenyl)-3-methyl-2-oxo-1-((S)-1-(propylsulfonyl)butan-2-yl)piperidin-3-yl)acetic acid $^1$H NMR (400 MHz, CHLOROFORM-d) δ ppm 7.23-7.27 (2 H, m), 7.01-7.21 (4 H, m), 6.93-7.00 (1 H, m), 6.84 (1 H, dt, J=7.1, 1.6 Hz), 4.93 (1 H, d, J=10.8 Hz), 4.05-4.20 (1 H, m), 3.33 (1 H, t, J=10.1 Hz), 3.12 (1 H, ddd, J=13.7, 10.9, 2.6 Hz), 2.95-3.04 (3 H, m), 2.71-2.85 (2 H, m), 2.38 (1 H, t, J=13.8 Hz), 2.14 (1 H, ddd, J=14.3, 9.9, 7.3 Hz), 1.86-1.98 (3 H, m), 1.49 (3 H, s), 1.39-1.48 (1 H, m), 1.13 (3 H, t, J=7.5 Hz), 0.41 (3 H, t, J=7.5 Hz); Mass Spectrum (ESI) 554.2 [M+H]$^+$.

Example 303

2-((3R,5R,6S)-5-(3-Chlorophenyl)-6-(4-chlorophenyl)-1-((S)-1-(isobutylsulfonyl)butan-2-yl)-3-methyl-2-oxopiperidin-3-yl)acetic acid $^1$H NMR (400 MHz, CHLOROFORM-d) δ ppm 7.27-7.24 (2 H, m), 7.02-7.20 (4 H, m), 6.93-7.00 (1 H, m), 6.84 (1 H, dt, J=7.2, 1.5 Hz), 4.93 (1 H, d, J=10.6 Hz), 4.15 (1 H, t, J=12.2 Hz), 3.33 (1 H, t, J=9.5 Hz), 3.13 (1 H, ddd, J=13.6, 10.9, 2.6

Hz), 2.84-3.03 (3 H, m), 2.66-2.83 (2 H, m), 2.33-2.47 (2 H, m), 2.12 (1 H, ddd, J=14.3, 9.9, 7.3 Hz), 1.90 (1 H, dd, J=13.7, 2.7 Hz), 1.48 (3 H, s), 1.40-1.47 (1 H, m), 1.17 (3 H, d, J=6.8 Hz), 1.15 (3 H, d, J=6.8 Hz) 0.41 (3 H, t, J=7.5 Hz); Mass Spectrum (ESI) 568.2 [M+H]$^+$.

Example 304

2-((3R,5R,6S)-5-(3-Chlorophenyl)-6-(4-chlorophenyl)-1-((S)-1-((cyclopropylmethyl)sulfonyl)butan-2-yl)-3-methyl-2-oxopiperidin-3-yl)acetic acid $^1$H NMR (400 MHz, CHLOROFORM-d) δ ppm 7.23-7.27 (2 H, m), 7.00-7.22 (4 H, m), 6.94-6.98 (1 H, m), 6.85 (1 H, dt, J=7.1, 1.5 Hz), 4.95 (1 H, d, J=10.8 Hz), 4.17 (1 H, t, J=12.1 Hz), 3.35 (1 H, t, J=9.7 Hz), 3.13 (1 H, ddd, J=13.6, 10.9, 2.7 Hz), 2.83-3.07 (4 H, m), 2.77 (1 H, d, J=14.9 Hz), 2.39 (1 H, t, J=13.8 Hz), 2.07-2.22 (1 H, m), 1.91 (1 H, dd, J=13.9, 2.7 Hz), 1.48 (3 H, s), 1.40-1.47 (1 H, m), 1.12-1.25 (1 H, m), 0.75-0.85 (2 H, m), 0.37-0.48 (5 H, m); Mass Spectrum (ESI) 566.2 [M+H]$^+$.

Example 305

2-((3R,5R,6S)-5-(3-Chlorophenyl)-6-(4-chlorophenyl)-1-((S)-1-((cyclobutylmethyl)sulfonyl)butan-2-yl)-3-methyl-2-oxopiperidin-3-yl)acetic acid $^1$H NMR (400 MHz, CHLOROFORM-d) δ ppm 7.22-7.27 (2 H, m), 6.99-7.20 (4 H, m), 6.93-6.98 (1 H, m), 6.84 (1 H, dt, J=7.2, 1.4 Hz), 4.91 (1 H, d, J=10.8 Hz), 4.09 (1 H, t, J=12.2 Hz), 3.31 (1 H, t, J=10.1 Hz), 3.05-3.18 (3 H, m), 2.84-3.02 (2 H, m), 2.67-2.82 (2 H, m), 2.36 (1 H, t, J=13.8 Hz), 2.20-2.31 (2 H, m), 2.01-2.18 (2 H, m), 1.82-1.97 (4 H, m), 1.47 (3 H, s), 1.38-1.46 (1 H, m), 0.40 (3 H, t, J=7.5 Hz); Mass Spectrum (ESI) 580.2 [M+H]$^+$.

Example 306

2-((3R,5R,6S)-5-(3-Chlorophenyl)-6-(4-chlorophenyl)-1-((S)-1-(cyclopentylsulfonyl)butan-2-yl)-3-methyl-2-oxopiperidin-3-yl)acetic acid $^1$H NMR (400 MHz, CHLOROFORM-d) δ ppm 0.40 (t, J=8.0 Hz, 3H), 1.46 (m, 1H), 1.49 (s, 3H), 1.70 (m, 2H), 1.80-1.95 (m, 3H), 2.09 (m, 5H), 2.40 (t, J=12 Hz, 1H), 2.76 (d, J=16.0 Hz, 2H), 3.00 (d, J=16 Hz, 1H), 3.12 (m, 1H), 3.36 (m, 2H), 4.10 (t, J=12 Hz, 1H), 4.97 (d, J=8.0 Hz, 1H), 6.85 (d, J=8.0 Hz, 1H), 6.96 (s, 1H), 7.12 (m, 4H), 7.25 (m, 2H); Mass Spectrum (ESI) 580.1 [M+H]$^+$.

Example 307

2-((3R,5R,6S)-5-(3-Chlorophenyl)-6-(4-chlorophenyl)-3-methyl-1-((S)-1-(oxetan-3-ylsulfonyl)butan-2-yl)-2-oxopiperidin-3-yl)acetic acid $^1$H NMR (400 MHz, CD$_3$OD) δ ppm 0.39 (t, J=7.63 Hz, 3H) 1.34-1.43 (m, 3H) 1.46-1.63 (m, 1H) 2.02-2.10 (m, 2H) 2.29 (t, J=13.69 Hz, 1H) 2.61 (d, J=13.69 Hz, 1H) 2.95 (d, J=13.69 Hz, 1H) 2.98-3.07 (m, 1H) 3.41 (ddd, J=13.60, 10.96, 2.84 Hz, 1H) 3.94-4.20 (m, 1H) 4.55-4.76 (m, 1H) 4.87-4.93 (m, 4H) 4.94-5.01 (m, 2H) 6.97 (dt, J=6.65, 1.76 Hz, 1H) 7.00-7.07 (m, 1H) 7.07-7.22 (m, 3H) 7.28 (br s, 3H); Mass Spectrum (ESI) m/z=568 (M+1).

Example 308

2-((3R,5R,6S)-5-(3-Chlorophenyl)-6-(4-chlorophenyl)-3-methyl-1-((S)-1-(((3-methyloxetan-3-yl)methyl)sulfonyl)butan-2-yl)-2-oxopiperidin-3-yl)acetic acid 1H NMR (500 MHz, CD$_3$OD) δ ppm −1.06 (br s, 1 H) −0.21 (br s, 1 H) 0.23 (br s, 1 H) 0.37 (br s, 1 H) 1.22-1.30 (m, 3 H) 1.38-1.45 (m, 3 H) 1.70-1.77 (m, 3 H) 1.99-2.09 (m, 1 H) 2.31 (t, J=13.69 Hz, 1 H) 2.65-2.73 (m, 1 H) 2.95-3.03 (m, 1 H) 3.39-3.49 (m, 1 H) 3.59-3.66 (m, 1 H) 3.66-3.73 (m, 1 H) 4.07-4.16 (m, 2 H) 4.40-4.45 (m, 2 H) 4.80 (d, J=6.11 Hz, 2 H) 4.91 (d, J=10.76 Hz, 2 H) 6.94-7.00 (m, 1 H) 7.06 (s, 1 H) 7.08-7.22 (m, 3 H) 7.32 (br s, 3 H); Mass Spectrum (ESI) m/z=608 (M+1).

Example 309

2-((3R,5R,6S)-5-(3-Chlorophenyl)-6-(4-chlorophenyl)-3-methyl-2-oxo-1-((S)-1-((tetrahydro-2H-pyran-4-yl)sulfonyl)butan-2-yl)piperidin-3-yl)acetic acid $^1$H NMR (400 MHz, CD$_3$OD) δ ppm 0.41 (t, J=7.53 Hz, 3 H) 1.26 (t, J=7.14 Hz, 2 H) 1.39 (s, 3 H) 1.87 (dd, J=12.52, 4.50 Hz, 2 H) 2.04-2.16 (m, 4H) 2.28 (t, J=13.69 Hz, 1 H) 2.61 (d, J=13.69 Hz, 1 H) 2.96 (d, J=13.69 Hz, 1 H) 3.34-3.58 (m, 4 H) 3.98-4.26 (m, 4 H) 4.98 (d, J=10.96 Hz, 1 H) 6.97 (dt, J=6.55, 1.81 Hz, 1 H) 7.04 (s, 1 H) 7.09-7.22 (m, 3 H) 7.30 (br s, 3 H); Mass Spectrum (ESI) m/z=596 (M+1).

Example 310

2-((3R,5R,6S)-5-(3-Chlorophenyl)-6-(4-chlorophenyl)-1-((S)-1-((2-hydroxy-2-methylpropyl)sulfonyl)butan-2-yl)-3-methyl-2-oxopiperidin-3-yl)acetic acid $^1$H NMR (400 MHz, CD$_3$OD) δ ppm 0.38 (t, J=7.43 Hz, 3 H) 1.17-1.27 (m, 2 H) 1.38 (s, 3 H) 1.44 (s, 6 H) 1.46-1.56 (m, 1 H) 2.01-2.12 (m, 2 H) 2.26 (t, J=13.69 Hz, 1 H) 2.50-2.66 (m, 1 H) 2.94 (d, J=13.50 Hz, 1 H) 3.33-3.46 (m, 3 H) 4.19 (dd, J=13.99, 11.05 Hz, 1 H) 4.97 (d, J=10.76 Hz, 1 H) 6.85-6.99 (m, 1 H) 7.03 (s, 1 H) 7.08-7.18 (m, 3 H) 7.26 (br s, 3 H); Mass Spectrum (ESI) m/z=584 (M+1).

Example 311

2-((3R,5R,6S)-1-((S)-1-((R)-sec-butylsulfonyl)butan-2-yl)-5-(3-chlorophenyl)-6-(4-chlorophenyl)-3-methyl-2-oxopiperidin-3-yl)acetic acid or 2-((3R,5R,6S)-1-((S)-1-((S)-sec-butylsulfonyl)butan-2-yl)-5-(3-chlorophenyl)-6-(4-chlorophenyl)-3-methyl-2-oxopiperidin-3-yl)acetic acid The crude product was purified by reversed phase preparatory HPLC (Gemini™ Prep C$_{18}$ 5 mm column; Phenomenex, Torrance, Calif.) (gradient elution of 50% to 85% MeCN in water, where both solvents contain 0.1% TFA, 27 min method) to provide the title compound as the faster eluting isomer (t$_R$=9.43 min).

$^1$H NMR (400 MHz, CHLOROFORM-d) δ ppm 7.24 (d, J=7.43 Hz, 2H), 7.04-7.15 (m, 3H), 6.96 (s, 1H), 6.85 (td, J=1.83, 6.70 Hz, 1H), 4.96 (d, J=10.56 Hz, 1H), 4.15 (ddd, J=3.13, 10.81, 13.45 Hz, 1H), 3.29 (t, J=10.17 Hz, 1H), 3.14 (ddd, J=2.93, 10.86, 13.60 Hz, 1H), 2.77-2.93 (m, 2H), 2.62-2.74 (m, 2H), 2.38 (t, J=13.79 Hz, 1H), 2.02-2.20 (m, 2H), 1.85 (dd, J=2.84, 13.79 Hz, 1H), 1.54-1.66 (m, 1H), 1.37-1.53 (m, 7H), 1.08 (dt, J=3.33, 7.43 Hz, 3H), 0.41 (t, J=7.53 Hz, 3H). Mass Spectrum (ESI) m/z=668.2 [M]⁺.

Example 312

2-((3R,5R,6S)-1-((S)-1-((R)-sec-butylsulfonyl)butan-2-yl)-5-(3-chlorophenyl)-6-(4-chlorophenyl)-3-methyl-2-oxopiperidin-3-yl)acetic acid or 2-((3R,5R,6S)-1-((S)-1-((S)-sec-butylsulfonyl)butan-2-yl)-5-(3-chlorophenyl)-6-(4-chlorophenyl)-3-methyl-2-oxopiperidin-3-yl)acetic acid The crude product was purified by reversed phase preparatory HPLC (Gemini™ Prep C18 5 μmm column; Phenomenex, Torrance, Calif.) (gradient elution of 50% to 85% MeCN in water, where both solvents contain 0.1% TFA) to provide the title compound as the slower eluting isomer (t$_R$=10.2 min).

¹H NMR (400 MHz, CHLOROFORM-d) δ ppm 9.97 (t, J=2.74 Hz, 1H), 7.24 (d, J=7.43 Hz, 2H), 7.04-7.15 (m, 3H), 6.96 (s, 1H), 6.85 (td, J=1.83, 6.70 Hz, 1H), 4.96 (d, J=10.56 Hz, 1H), 4.15 (ddd, J=3.13, 10.81, 13.45 Hz, 1H), 3.29 (t, J=10.17 Hz, 1H), 3.14 (ddd, J=2.93, 10.86, 13.60 Hz, 1H), 2.77-2.93 (m, 2H), 2.62-2.74 (m, 2H), 2.38 (t, J=13.79 Hz, 1H), 2.02-2.20 (m, 2H), 1.85 (dd, J=2.84, 13.79 Hz, 1H), 1.54-1.66 (m, 1H), 1.37-1.53 (m, 7H), 1.08 (dt, J=3.33, 7.43 Hz, 3H), 0.41 (t, J=7.53 Hz, 3H);

Mass Spectrum (ESI) m/z=668.2 [M]⁺.

Examples 313 to 323 were prepared from (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, Step A) by procedures similar to the one described in Example 300, replacing benzenethiol with the appropriate amount of thiol.

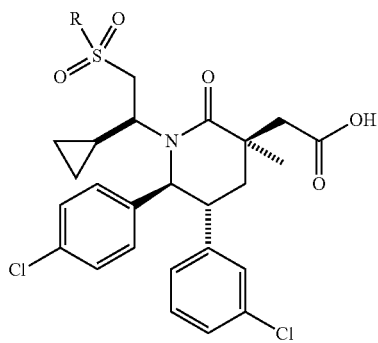

| Example | R | Reagent used |
|---------|---|--------------|
| 313 |  | cyclopentanethiol; prepared from bromocyclopentane by a procedure similar to the one described for the preparation of cyclopropylmethanethiol in U.S. Pat. No. 3,975,429. |
| 314 | | example 308 |
| 315 | | benzenethiol |
| 316 | | o-toluenethiol |
| 317 | | 2-chlorobenzenethiol |
| 318 | | 4-chlorobenzenethiol |
| 319 | | 4-fluorobenzenethiol |
| 320 | | 4-mercaptopyridine |
| 321 | | 2-chloro-4-fluorobenzenethiol (Oakwood Products, West Columbia, SC) |
| 322 | | cyclopropylmethanethiol; prepared from bromomethylcyclopropane by a procedure similar to the one described in U.S. Pat. No. 3,975,429. |
| 323 | | 2,2,2-trifluoroethanethiol |

Example 313

2-((3R,5R,6S)-5-(3-Chlorophenyl)-6-(4-chlorophenyl)-1-((S)-2-(cyclopentylsulfonyl)-1-cyclopropylethyl)-3-methyl-2-oxopiperidin-3-yl)acetic acid ¹H NMR (400 MHz, CHLOROFORM-d) δ ppm -1.08 (br. s, 1 H) -0.30 (br. s, 1 H) 0.21-0.29 (m, 1 H) 0.33-0.42 (m, 1 H) 1.51 (s, 3 H) 1.65-1.77 (m, 2 H) 1.80-1.92 (m, 4 H) 2.10 (m, 4 H) 2.48 (t, J=13.79 Hz, 1 H) 2.75 (m, 2 H) 2.89 (dd, J=13.60, 2.25 Hz, 1 H) 3.09-3.18 (m, 2 H) 3.38 (quin, J=8.02 Hz, 1 H)

4.33 (m 1 H) 4.92 (d, J=10.56 Hz, 1 H) 6.84-6.90 (m, 1 H) 6.95 (s, 1 H) 7.07-7.17 (m, 2 H) 7.37 (m., 4 H); Mass Spectrum (ESI) m/z=592 (M+1).

Example 314

2-((3R,5R,6S)-5-(3-Chlorophenyl)-6-(4-chlorophenyl)-1-((S)-1-cyclopropyl-2-(((3-methyloxetan-3-yl)methyl)sulfonyl)ethyl)-3-methyl-2-oxopiperidin-3-yl)acetic acid $^1$H NMR (500 MHz, CD$_3$OD) δ ppm −1.06 (br s, 1 H) −0.21 (br s, 1 H) 0.23 (br s, 1 H) 0.37 (br s, 1 H) 1.22-1.30 (m, 3 H) 1.38-1.45 (m, 3 H) 1.70-1.77 (m, 3 H) 1.99-2.09 (m, 1 H) 2.31 (t, J=13.69 Hz, 1 H) 2.65-2.73 (m, 1 H) 2.95-3.03 (m, 1 H) 3.39-3.49 (m, 1 H) 3.59-3.66 (m, 1 H) 3.66-3.73 (m, 1 H) 4.07-4.16 (m, 2 H) 4.40-4.45 (m, 2 H) 4.80 (d, J=6.11 Hz, 2 H) 4.91 (d, J=10.76 Hz, 2 H) 6.94-7.00 (m, 1 H) 7.06 (s, 1 H) 7.08-7.22 (m, 3 H) 7.32 (br s, 3 H); Mass Spectrum (ESI) m/z=608 (M+1).

Example 315

2-((3R,5R,6S)-5-(3-Chlorophenyl)-6-(4-chlorophenyl)-1-((S)-1-cyclopropyl-2-(phenylsulfonyl)ethyl)-3-methyl-2-oxopiperidin-3-yl)acetic acid $^1$H NMR (500 MHz, CHLOROFORM-d) δ ppm −1.12-−1.02 (m, 1 H) −0.33 (m, 1 H) 0.19-0.27 (m, 1 H) 0.29-0.35 (m, 1 H) 1.60 (s, 3 H) 1.77-1.89 (m, 1 H) 1.92 (dd, J=13.69, 2.93 Hz, 1 H) 2.57 (t, J=13.94 Hz, 1 H) 2.81 (d, J=15.16 Hz, 2 H) 3.00 (dd, J=13.94, 2.45 Hz, 1 H) 3.08-3.25 (m, 2 H) 4.47 (t, J=12.35 Hz, 1 H) 5.01 (d, J=10.51 Hz, 1 H) 6.90 (dt, J=7.03, 1.62 Hz, 1 H) 6.96-7.02 (m, 1 H) 7.07-7.19 (m, 2 H) 7.20-7.30 (m, 4 H) 7.56-7.67 (m, 2 H) 7.67-7.77 (m, 1 H) 7.87-7.98 (m, 2 H); Mass Spectrum (ESI) m/z=600 (M+1).

Example 316

2-((3R,5R,6S)-5-(3-chlorophenyl)-6-(4-chlorophenyl)-1-((S)-1-cyclopropyl-2-(o-tolylsulfonyl)ethyl)-3-methyl-2-oxopiperidin-3-yl)acetic acid $^1$H NMR (400 MHz, CHLOROFORM-d) δ ppm 8.00 (1 H, dd, J=7.9, 1.1 Hz), 7.51-7.64 (1 H, m), 7.34-7.48 (3 H, m), 7.22-7.34 (2 H, m), 7.06-7.18 (3 H, m), 6.98-7.04 (1 H, m), 6.86-6.96 (1 H, m), 5.02 (1 H, d, J=10.8 Hz), 4.60 (1 H, t, J=12.4 Hz), 3.20 (1 H, ddd, J=13.7, 10.8, 2.7 Hz), 3.09 (1 H, d, J=14.9 Hz), 2.99 (1 H, dd, J=14.0, 2.2 Hz), 2.77-2.87 (2 H, m), 2.71 (3 H, s), 2.53 (1 H, t, J=13.8 Hz), 1.94 (1 H, dd, J=13.8, 2.8 Hz), 1.78-1.86 (1 H, m), 1.56 (3 H, s), 0.17-0.40 (2 H, m), −0.40-−0.30 (1 H, m), −1.12-1-−1.00 (1 H, m); Mass Spectrum (ESI) 614.2 [M+H]$^+$.

Example 317

2-((3R,5R,6S)-5-(3-Chlorophenyl)-6-(4-chlorophenyl)-1-((S)-2-((2-chlorophenyl)sulfonyl)-1-cyclopropylethyl)-3-methyl-2-oxopiperidin-3-yl)acetic acid $^1$H NMR (500 MHz, CHLOROFORM-d) δ ppm −1.08 (br s, 1 H) −0.27 (m, 1 H) 0.20-0.29 (m, 1 H) 0.31-0.40 (m, 1 H) 1.58 (s, 3 H) 1.82-1.96 (m, 2 H) 2.53 (t, J=13.82 Hz, 1 H) 2.77-2.90 (m, 2 H) 3.11-3.22 (m, 2 H) 3.37 (dd, J=13.94, 2.45 Hz, 1 H) 4.76 (t, J=12.23 Hz, 1 H) 4.97 (d, J=10.51 Hz, 1 H) 6.89 (d, J=7.09 Hz, 1 H) 7.00 (s, 1 H) 7.09-7.19 (m, 2 H) 7.27-7.35 (m, 4 H) 7.49-7.57 (m, 1 H) 7.57-7.68 (m, 2 H) 8.15 (dd, J=7.83, 1.47 Hz, 1 H); Mass Spectrum (ESI) m/z=636 (M+1).

Example 318

2-((3R,5R,6S)-5-(3-Chlorophenyl)-6-(4-chlorophenyl)-1-((S)-2-((4-chlorophenyl)sulfonyl)-1-cyclopropylethyl)-3-methyl-2-oxopiperidin-3-yl)acetic acid $^1$H NMR (500 MHz, CHLOROFORM-d) δ ppm −0.38-−0.22 (m, 1 H) 0.26 (br s, 1 H) 0.33 (dd, J=8.93, 4.52 Hz, 2 H) 1.59 (s, 3 H) 1.83 (br s, 1 H) 1.96 (dd, J=13.82, 2.81 Hz, 1 H) 2.55 (t, J=13.94 Hz, 1 H) 2.84 (d, J=15.16 Hz, 2 H) 2.98 (dd, J=13.94, 2.45 Hz, 1 H) 3.11 (d, J=14.92 Hz, 1 H) 3.22 (ddd, J=13.69, 10.76, 2.93 Hz, 1 H) 4.99 (d, J=10.51 Hz, 1 H) 6.88-6.96 (m, 1 H) 6.98-7.03 (m, 1 H) 7.09-7.21 (m, 2 H) 7.29 (m, 4 H) 7.56-7.66 (m, 2 H) 7.83-7.94 (m, 2 H); Mass Spectrum (ESI) m/z=636 (M+1).

Example 319

2-((3R,5R,6S)-5-(3-Chlorophenyl)-6-(4-chlorophenyl)-1-((S)-1-cyclopropyl-2-((4-fluorophenyl)sulfonyl)ethyl)-3-methyl-2-oxopiperidin-3-yl)acetic acid $^1$H NMR (500 MHz, CHLOROFORM-d) δ ppm −1.05 (br s, 1 H) −0.33 (br s, 1 H) 0.17-0.38 (m, 2 H) 1.59 (s, 3 H) 1.76-1.88 (m, 1 H) 1.93 (dd, J=13.82, 2.81 Hz, 1 H) 2.55 (t, J=13.82 Hz, 1 H) 2.82 (m, 2 H) 2.98 (dd, J=13.94, 2.45 Hz, 1 H) 3.06-3.28 (m, 2 H) 4.48 (t, J=12.10 Hz, 1 H) 4.99 (d, J=10.51 Hz, 1 H) 6.89 (dt, J=7.09, 1.59 Hz, 1 H) 6.95-7.04 (m, 1 H) 7.06-7.21 (m, 2 H) 7.21-7.40 (m, 6 H) 7.86-8.01 (m, 2 H); Mass Spectrum (ESI) m/z=618 (M+1).

Example 320

2-((3R,5R,6S)-5-(3-Chlorophenyl)-6-(4-chlorophenyl)-1-((S)-1-cyclopropyl-2-(pyridin-4-ylsulfonyl)ethyl)-3-methyl-2-oxopiperidin-3-yl)acetic acid $^1$H NMR (500 MHz, CHLOROFORM-d) δ ppm −1.01 (br s, 1 H) −0.30 (br s, 1 H) 0.28 (br s, 1 H) 0.30-0.46 (m, 1 H) 1.58 (s, 3 H) 1.83 (br s, 1 H) 1.96 (dd, J=13.94, 2.93 Hz, 1 H) 2.52 (t, J=13.94 Hz, 1 H) 2.83 (m, 2 H) 3.00 (dd, J=13.94, 2.45 Hz, 1 H) 3.11 (d, J=15.16 Hz, 1 H) 3.21 (ddd, J=13.69, 10.64, 2.81 Hz, 1 H) 4.55 (br s, 1 H) 4.94 (d, J=10.51 Hz, 1 H) 6.88 (d, J=7.09 Hz, 1 H) 6.99 (s, 1 H) 7.08-7.20 (m, 2 H) 7.20-7.39 (m, 4 H) 7.77-7.83 (m, 2 H) 8.92-8.99 (m, 2 H); Mass Spectrum (ESI) m/z=601 (M+1).

Example 321

2-((3R,5R,6S)-1-((S)-2-((2-Chloro-4-fluorophenyl)sulfonyl)-1-cyclopropylethyl)-5-(3-chlorophenyl)-6-(4-chlorophenyl)-3-methyl-2-oxopiperidin-3-yl)acetic acid $^1$H NMR (400 MHz, CHLOROFORM-d) δ ppm −1.05 (br s, 1H), −0.29 (br s, 1H), 0.25 (br s, 1H), 0.29-0.44 (m, 1H), 1.56 (s, 3H), 1.84 (br s, 1H), 1.89-2.03 (m, 1H), 2.50 (t, J=13.89 Hz, 1H), 2.82 (d, J=14.87 Hz, 2H), 3.08 (d, J=14.67

Hz, 1H), 3.15-3.26 (m, 1H), 3.31 (d, J=13.69 Hz, 1H), 4.75 (br s, 1H), 4.96 (d, J=10.56 Hz, 1H), 6.89 (d, J=6.85 Hz, 1H), 7.00 (s, 1H), 7.08-7.18 (m, 3H), 7.18-7.25 (m, 2H), 7.26-7.31 (m, 1H), 7.33 (dd, J=7.92, 2.25 Hz, 2H), 8.17 (dd, J=8.80, 5.87 Hz, 1H); Mass Spectrum (ESI) m/z=652.0 and 653.9 (M+1).

Example 322

2-((3R,5R,6S)-5-(3-Chlorophenyl)-6-(4-chlorophenyl)-1-((S)-1-cyclopropyl-2-((cyclopropylmethyl)sulfonyl)ethyl)-3-methyl-2-oxopiperidin-3-yl)acetic acid ¹H NMR (400 MHz, CHLOROFORM-d) δ ppm −1.06 (m, 1 H), −0.27 (m, 1 H), 0.39 (m, 1 H), 0.43 (m, 3 H), 0.80 (m, 2 H), 1.18 (m, 1 H), 1.52 (s, 3 H), 1.85 (d, J=12 Hz, 1 H), 1.95 (m, 1 H), 2.44 (t, J=12 Hz, 1 H), 2.76 (d, J=16 Hz, 2 H), 2.90 (m, 1 H), 3.02 (m, 2 H), 3.14 (m, 2 H), 4.39 (m, 1 H), 4.92 (d, J=12 Hz, 1 H), 6.86 (d, J=8.0 Hz, 1 H), 6.96 (s, 1 H), 7.13 (m, 3 H), 7.27 (m, 3 H); Mass Spectrum (ESI) m/z=578.0 [M+H]⁺.

Example 323

2-((3R,5R,6S)-5-(3-Chlorophenyl)-6-(4-chlorophenyl)-1-((S)-1-cyclopropyl-2-((2,2,2-trifluoroethyl)sulfonyl)ethyl)-3-methyl-2-oxopiperidin-3-yl)acetic acid ¹H NMR (500 MHz, CHLOROFORM-d) δ ppm 7.08-7.17 (2 H, m), 6.95 (1 H, s), 6.83 (1 H, d, J=7.3 Hz), 4.79 (1 H, d, J=10.5 Hz), 3.80-3.93 (2 H, m), 3.11-3.23 (2 H, m), 3.04 (1 H, d, J=14.7 Hz), 2.82 (2 H, d, J=14.7 Hz), 2.37 (1 H, t, J=13.7 Hz), 1.94 (1 H, d, J=13.0 Hz), 1.49 (3 H, s), 0.43 (1 H, br. s.), 0.31 (1 H, br. s.), −0.24 (1 H, br. s.), −1.03 (1 H, br. s.); Mass Spectrum (ESI) m/z=606 (M+1).

Example 324

2-((3R,5R,6S)-5-(3-Chlorophenyl)-6-(4-chlorophenyl)-1-((S)-1-cyclopropyl-2-((trifluoromethyl)sulfonyl)ethyl)-3-methyl-2-oxopiperidin-3-yl)acetic acid

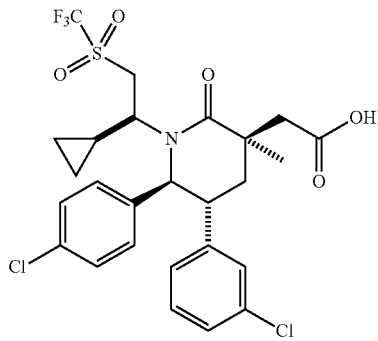 [SMILES: C[C@]1(CC(=O)O)C[C@H](c2cccc(Cl)c2)[C@@H](c2ccc(Cl)cc2)N([C@H](CS(=O)(=O)C(F)(F)F)C2CC2)C1=O]

Step A. (3S,5R,6S)-3-Allyl-5-(3-chlorophenyl)-6-(4-chlorophenyl)-1-((S)-1-cyclopropyl-2-((trifluoromethyl)thio)ethyl)-3-methylpiperidin-2-one

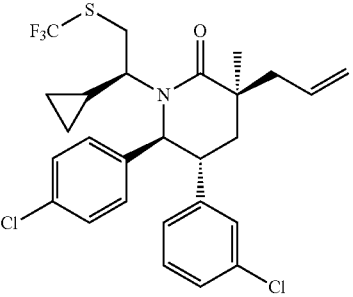 [SMILES: C=CC[C@@]1(C)C[C@H](c2cccc(Cl)c2)[C@@H](c2ccc(Cl)cc2)N([C@H](CSC(F)(F)F)C2CC2)C1=O]

A mixture of ((trifluoromethyl)thio)copper (41.3 mg, 0.251 mmol, TCI America, Portland, Oreg.), 2-(tributylphosphoranylidene)acetonitrile (194 mg, 0.803 mmol), and (3S,5R,6S)-3-allyl-5-(3-chlorophenyl)-6-(4-chlorophenyl)-1-((S)-1-cyclopropyl-2-hydroxyethyl)-3-methylpiperidin-2-one (115 mg, 0.251 mmol, Example 252, Step A) was stirred at 110° C. for 3 h. A few drops of 4N HCl in dioxane were added and the mixture stirred for 30 min. Toluene (0.15 ml) was added and stirring continued at 110° C. for 20 h. HPLC purification (Gemini™ Prep $C_{18}$ 5 µm column; Phenomenex, Torrance, Calif.; gradient elution of 10% to 95% MeCN in water with 0.1% TFA) gave the title compound.

Mass Spectrum (ESI) m/z=542 (M+1).

Step B. 2-((3R,5R,6S)-5-(3-Chlorophenyl)-6-(4-chlorophenyl)-1-((S)-1-cyclopropyl-2-((trifluoromethyl)sulfonyl)ethyl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-cyclopropyl-2-((trifluoromethyl)thio)ethyl)-3-methylpiperidin-2-one (Example 324, step A) by a procedure similar to the one described in Example 71, Step F. The crude product was purified by reverse phase preparatory HPLC (Gemini™ Prep $C_{18}$ 5 µm column; Phenomenex, Torrance, Calif.; gradient elution of 10% to 95% MeCN in water, where both solvents contain 0.1% TFA).

¹H NMR (500 MHz, CDCl₃) δ ppm 7.10-7.17 (3 H, m), 6.93 (1 H, s), 6.82-6.86 (1 H, m), 4.70 (1 H, d, J=10.5 Hz), 3.17-3.26 (2 H, m), 3.02 (1 H, d, J=14.7 Hz), 2.85 (1 H, d, J=14.9 Hz), 2.77 (1 H, br. s.), 2.35 (1 H, t, J=13.9 Hz), 1.99 (2 H, dd, J=13.9, 2.9 Hz), 1.51 (3 H, s), 1.26 (1 H, s), 0.41-0.50 (1 H, m), 0.31 (1 H, br. s.), −0.23 (1 H, br. s.), −1.01 (1 H, br. s.); Mass Spectrum (ESI) m/z=592 (M+1).

Examples 325 to 335 were prepared from (3S,5R,6S)-3-allyl-5-(3-chlorophenyl)-6-(4-chlorophenyl)-1-((S)-1-cyclopropyl-2-hydroxyethyl)-3-ethylpiperidin-2-one (Example 253, Step C) by procedures similar to the one described in Example 300, replacing benzenethiol with the appropriate amount of thiol.

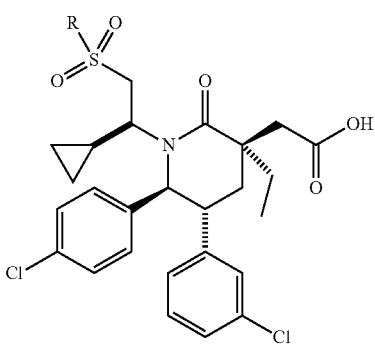

| Example | R | Reagent used |
|---|---|---|
| 325 | (phenyl) | benzenethiol |
| 326 | (2-Cl-phenyl) | 2-chlorobenzenethiol |
| 327 | (2-F-phenyl) | 2-fluorobenzenethiol |
| 328 | (3-F-phenyl) | 3-fluorobenzenethiol |
| 329 | (4-F-phenyl) | 4-fluorobenzenethiol |
| 330 | (propyl) | propanethiol |
| 331 | (butyl) | butanethiol |
| 332 | (isopentyl) | 3-methylbutanethiol |

-continued

| Example | R | Reagent used |
|---|---|---|
| 333 | (cyclopentyl) | cyclopentanethiol; prepared from bromocyclopentane by a procedure similar to the one described for the preparation of cyclopropylmethanethiol in U.S. Pat. No. 3,975,429. |
| 334 | (cyclohexyl) | cyclohexanethiol; prepared from bromocyclopentane by a procedure similar to the one described for the preparation of cyclopropylmethanethiol in U.S. Pat. No. 3,975,429. |
| 335 | Me— | trimethylsilylmethanethiol (as per Example 301) |

Example 325

2-((3R,5R,6S)-5-(3-Chlorophenyl)-6-(4-chlorophenyl)-1-((S)-1-cyclopropyl-2-(phenylsulfonyl)ethyl)-3-ethyl-2-oxopiperidin-3-yl)acetic acid $^1$H NMR (500 MHz, CHLOROFORM-d) δ ppm −1.01 (br. m., 1 H) −0.32 (br. m., 1 H) 0.19-0.37 (m, 2 H) 1.06 (t, J=7.46 Hz, 3 H) 1.87 (m, 2 H) 2.02-2.17 (m, 2 H) 2.54 (t, J=13.82 Hz, 1H) 2.83 (m, 2H) 3.03 (d, J=12.96 Hz, 1H) 3.07-3.23 (m, 2H) 4.38 (br s, 1H) 5.03 (d, J=10.51 Hz, 1H) 6.91 (d, J=7.09 Hz, 1H) 6.98-7.04 (m, 1H) 7.08-7.20 (m, 3H) 7.48 (m, 3H) 7.56-7.67 (m, 2H) 7.67-7.78 (m, 1H) 7.84-7.99 (m, 2H);
Mass Spectrum (ESI) m/z=614 (M+1).

Example 326

2-((3R,5R,6S)-5-(3-Chlorophenyl)-6-(4-chlorophenyl)-1-((S)-2-((2-chlorophenyl)sulfonyl)-1-cyclopropylethyl)-3-ethyl-2-oxopiperidin-3-yl)acetic acid $^1$H NMR (500 MHz, CHLOROFORM-d) δ ppm −1.01 (br. m., 1 H) −0.26 (br. m., 1 H) 0.28 (br. m., 1 H) 0.31-0.44 (m, 1 H) 1.02 (t, J=7.46 Hz, 3 H) 1.88 (m, 2 H) 2.02-2.16 (m, 2 H) 2.48 (t, J=13.82 Hz, 1 H) 2.83 (d, J=15.65 Hz, 1 H) 2.90 (br s, 1 H) 3.07-3.23 (m, 2 H) 3.42 (dd, J=14.06, 2.08 Hz, 1 H) 4.64 (br s, 1 H) 4.98 (d, J=10.51 Hz, 1 H) 6.89 (d, J=7.09 Hz, 1 H) 6.97-7.04 (m, 1 H) 7.09-7.22 (m, 3 H) 7.33-7.48 (m, 3 H) 7.48-7.56 (m, 1 H) 7.56-7.67 (m, 2 H) 8.14 (dd, J=7.95, 1.59 Hz, 1 H); Mass Spectrum (ESI) m/z=648 (M+1).

Example 327

2-((3R,5R,6S)-5-(3-Chlorophenyl)-6-(4-chlorophenyl)-1-((S)-1-cyclopropyl-2-((2-fluorophenyl)sulfonyl)ethyl)-3-ethyl-2-oxopiperidin-3-yl)acetic acid $^1$H NMR (400 MHz, CHLOROFORM-d) δ ppm −1.00 (br s, 1H), −0.26 (br s, 1H), 0.19-0.45 (m, 2H), 1.02 (t, J=7.43 Hz, 3H), 1.87 (dd, J=13.69, 2.93 Hz, 2H), 1.97-2.20 (m, 2H), 2.49 (t, J=13.79 Hz, 1H), 2.83 (d, J=15.26 Hz, 2H), 3.08 (d, J=15.26 Hz, 1H), 3.19 (ddd, J=13.55, 10.71, 2.74 Hz, 1H), 3.30 (d, J=13.89 Hz, 1H), 4.57 (br s, 1H), 4.95 (d, J=10.76 Hz, 1H), 6.89 (d, J=6.85 Hz, 1H), 7.02 (s, 1H), 7.08-7.23 (m, 3H), 7.23-7.35 (m, 3H), 7.35-7.52 (m, 2H), 7.67-7.81 (m, 1H), 7.91-8.05 (m, 1H); Mass Spectrum (ESI) m/z=632.0 (M+1).

Example 328

2-((3R,5R,6S)-5-(3-Chlorophenyl)-6-(4-chlorophenyl)-1-((S)-1-cyclopropyl-2-((3-fluorophenyl)sulfonyl)ethyl)-3-ethyl-2-oxopiperidin-3-yl)acetic acid $^1$H NMR (400 MHz, CHLOROFORM-d) δ ppm −0.97 (br s, 1H), −0.31 (br s, 1H), 0.18-0.48 (m, 2H), 1.05 (t, J=7.43 Hz, 3H), 1.88 (dd, J=13.79, 2.84 Hz, 2H), 1.96-2.21 (m, 2H), 2.51 (t, J=13.79 Hz, 1H), 2.84 (d, J=15.06 Hz, 2H), 2.95-3.13 (m, 2H), 3.13-3.31 (m, 1H), 4.41 (br s, 1H), 5.00 (d, J=10.56 Hz, 1H), 5.72 (br s, 2H), 6.91 (d, J=6.85 Hz, 1H), 7.01-7.04 (m, 2H), 7.09-7.18 (m, 3H), 7.36-7.45 (m, 2H), 7.57-7.66 (m, 3H), 7.70 (d, J=7.83 Hz, 1H); Mass Spectrum (ESI) m/z=632.0 (M+1).

Example 329

2-((3R,5R,6S)-5-(3-Chlorophenyl)-6-(4-chlorophenyl)-1-((S)-1-cyclopropyl-2-((4-fluorophenyl)sulfonyl)ethyl)-3-ethyl-2-oxopiperidin-3-yl)acetic acid $^1$H NMR (400 MHz, CHLOROFORM-d) δ ppm −0.97 (br s, 1H), −0.31 (br s, 1H), 0.32 (d, J=4.89 Hz, 2H), 1.05 (t, J=7.53 Hz, 3H), 1.26 (s, 1H), 1.88 (dd, J=13.69, 2.93 Hz, 2H), 1.97-2.21 (m, 2H), 2.52 (t, J=13.79 Hz, 1H), 2.83 (d, J=15.26 Hz, 1H), 2.92-3.13 (m, 2H), 3.13-3.30 (m, 1H), 4.38 (br s, 2H), 5.01 (d, J=10.56 Hz, 1H), 6.91 (d, J=6.65 Hz, 2H), 7.01 (s, 2H), 7.07-7.22 (m, 3H), 7.28-7.37 (m, 3H), 7.83-8.03 (m, 2H); Mass Spectrum (ESI) m/e=632.0 (M+1).

Example 330

2-((3R,5R,6S)-5-(3-Chlorophenyl)-6-(4-chlorophenyl)-1-((S)-1-cyclopropyl-2-(propylsulfonyl)ethyl)-3-ethyl-2-oxopiperidin-3-yl)acetic acid $^1$H NMR (400 MHz, methanol-d4) δ ppm −0.71 (s, br, 1H), 0.00 (br s, 1H), 0.51 (br s, 1H), 0.60 (br s, 1H), 1.19 (t, J=8 Hz, 3H), 1.32 (t, J=8 Hz, 3H), 1.93-2.14 (m, 5H), 2.24 (m, 1H), 2.61 (t, J=12 Hz, 1H), 2.87 (d, J=12 Hz, 1H), 2.97 (br s, 1H), 3.13 (d, J=12 Hz, 1H), 3.32 (m, 3H), 3.69 (m, 1H), 4.45 (s, br, 1H), 5.16 (d, J=12 Hz, 1H), 7.20-7.21 (d, J=4 Hz, 2H), 7.28 (s, 1H), 7.36 (m, 3H), 7.51 (br s, 2H); Mass Spectrum (ESI) m/z=580.2 (M+1).

Example 331

2-((3R,5R,6S)-1-((S)-2-(Butylsulfonyl)-1-cyclopropylethyl)-5-(3-chlorophenyl)-6-(4-chlorophenyl)-3-ethyl-2-oxopiperidin-3-yl)acetic acid $^1$H NMR (400 MHz, methanol-d4) δ ppm −0.73 (s, br, 1H), 0.00 (br s, 1H), 0.51 (br s, 1H), 0.60 (br s, 1H), 1.17-1.23 (m, 6H), 1.70-1.76 (m, 2H), 2.01 (m, 4H), 2.13 (d, J=8 Hz, 1H), 2.24 (m, 1H), 2.61 (t, J=12 Hz, 1H), 2.87 (d, J=16 Hz, 1H), 2.98 (br s, 1H), 4.14 (d, J=16 Hz, 1H), 3.31-3.42 (m, 3H), 3.69 (m, 1H), 4.48 (br s, 1H), 5.17 (d, J=16 Hz, 1H), 7.20 (m, 2H), 7.28 (s, 1H), 7.36 (m, 3H), 7.50 (br s, 2H); Mass Spectrum (ESI) m/z=594.2 (M+1).

Example 332

2-((3R,5R,6S)-5-(3-Chlorophenyl)-6-(4-chlorophenyl)-1-((S)-1-cyclopropyl-2-(isopentylsulfonyl)ethyl)-3-ethyl-2-oxopiperidin-3-yl)acetic acid $^1$H NMR (400 MHz, methanol-d4) δ ppm −0.73 (br s, 1H), 0.00 (br s, 1H), 0.50 (br s, 1H), 0.60 (br s, 1H), 1.17-1.20 (m, 9H), 1.92 (m, 5H), 2.10 (dd, J=4, 12 Hz, 1H), 2.24 (m, 1H), 2.61 (t, J=12 Hz, 1H), 2.87 (d, J=12 Hz, 1H), 2.97 (br s, 1H), 3.13 (d, J=12 Hz, 1H), 3.37 (m, 3H), 3.69 (m, 1H), 4.46 (br s, 1H), 5.16 (d, J=12 Hz, 1H), 7.20 (m, 2H), 7.27 (s, 1H), 7.36 (m, 3H), 7.50 (br s, 2H); Mass Spectrum (ESI) m/z=608.2 (M+1).

Example 333

2-((3R,5R,6S)-5-(3-Chlorophenyl)-6-(4-chlorophenyl)-1-((S)-2-(cyclopentylsulfonyl)-1-cyclopropylethyl)-3-ethyl-2-oxopiperidin-3-yl)acetic acid $^1$H NMR (400 MHz, methanol-d4) δ ppm −0.94 (br s, 1H), −0.23 (br s, 1H), 0.30 (br s, 1H), 0.39 (br s, 1H), 0.99 (t, J=4 Hz, 3H), 1.73-1.83 (m, 6H), 1.87 (m, 1H), 2.05 (m, 5H), 2.42 (t, J=12 Hz, 1H), 2.68 (d, J=12 Hz, 1H), 2.78 (br s, 1H), 2.94 (d, J=12 Hz, 1H), 3.48 (br s, 1H), 3.50 (m, 1H), 3.61 (m, 1H), 4.27 (br s, 1H), 4.98 (d, J=12 Hz, 1H), 7.02 (d, J=8 Hz, 2H), 7.08 (s, 1H), 7.17 (m, 3H), 7.31 (br s, 2H); Mass Spectrum (ESI) m/z=606.2 (M+1).

Example 334

2-((3R,5R,6S)-5-(3-Chlorophenyl)-6-(4-chlorophenyl)-1-((S)-2-(cyclohexylsulfonyl)-1-cyclopropylethyl)-3-ethyl-2-oxopiperidin-3-yl)acetic acid $^1$H NMR (400 MHz, methanol-d4) δ ppm −0.97 (s, br, 1H), −0.25 (br s, 1H), 0.29 (s, 1H), 0.39 (s, 1H), 0.99 (t, J=8 Hz, 3H), 1.24-1.52 (m, 6H), 1.75-1.78 (m, 2H), 1.91-1.96 (m, 3H), 2.05 (m, 1H), 2.18 (s, br, 2H), 2.39-2.46 (t, J=12 Hz, 1H), 2.68-2.71 (d, J=12 Hz, 1H), 2.78 (br s, 1H), 2.94-2.98 (d, J=12 Hz, 1H), 3.08 (m, 2H), 3.48-3.53 (m, 1H), 4.27 (s, br, 1H), 4.99 (d, J=12 Hz, 1H), 7.01 (d, J=8 Hz, 2H), 7.08 (s, 1H), 7.16-7.21 (m, 3H), 7.31 (s, br, 2H); Mass Spectrum (ESI) m/z=620.2 (M+1)

Example 335

2-((3R,5R,6S)-5-(3-Chlorophenyl)-6-(4-chlorophenyl)-1-((S)-1-cyclopropyl-2-(methylsulfonyl)ethyl)-3-ethyl-2-oxopiperidin-3-yl)acetic acid $^1$H NMR (400 MHz, methanol-d4) δ ppm −0.71 (s, br, 1H), 0.00 m(s, br, 1H), 0.47 (s, br, 1H), 0.55 (s, br, 1H), 1.14 (t, J=8 Hz, 3H), 1.92-1.94 (m, 2H), 2.08 (dd, J=4, 12 Hz, 1H), 2.18 (m, 1H), 2.55 (t, J=12 Hz, 1H), 2.86 (d, J=16 Hz, 1H), 3.03 (s, br, 1H), 3.12 (d, J=16 Hz, 1H), 3.43 (s, br, 1H), 3.48 (s, 3H), 3.63 (m, 1H), 4.41 (s, br, 1H), 5.09 (d, J=12 Hz, 1H), 7.14 (m, 2H), 7.30 (s, 1H), 7.32 (m, 3H), 7.46 (s, br, 2H); Mass Spectrum (ESI) m/z=552.2 (M+1).

Examples 336 to 339 were prepared from (3S,5R,6S)-3-allyl-5-(3-chlorophenyl)-6-(4-chlorophenyl)-1-((S)-1-hydroxy-3-methylbutan-2-yl)-3-methylpiperidin-2-one (Example 261, Step H) by procedures similar to the one described in Example 300, replacing benzenethiol with the designated reagent.

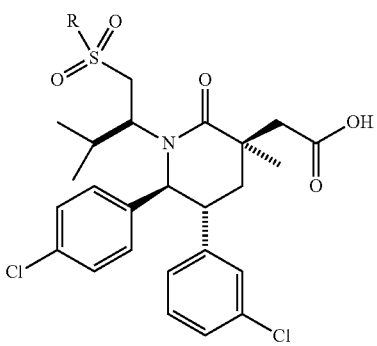

| Example | R | Reagent used |
|---|---|---|
| 336 | F₃C— (wavy bond) | 2,2,2-trifluoroethanethiol |
| 337 | ᵗBu— | 2-methylpropane-2-thiol |
| 338 | Me | trimethylsilylmethanethiol (as per Example 301) |

Example 336

2-((3R,5R,6S)-5-(3-Chlorophenyl)-6-(4-chlorophenyl)-3-methyl-1-((S)-3-methyl-1-((2,2,2-trifluoroethyl)sulfonyl)butan-2-yl)-2-oxopiperidin-3-yl)acetic acid $^1$H NMR (500 MHz, methanol-d$_4$) δ ppm 0.52 (s, 3 H), 0.67 (s, 3 H), 1.35 (br s, 3 H), 2.07 (dd, J=13.7, 2.9 Hz, 1 H), 2.19 (dq, J=14.4, 7 Hz, 1 H), 2.27 (t, J=13.7 Hz, 1 H), 2.61 (d, J=13.5 Hz, 1 H), 2.99 (d, J=13.5 Hz, 1 H), 3.26-3.30 (m, 1 H), 3.41 (dd, J=13.8, 1.6 Hz, 1 H), 3.58 (ddd, J=13.7, 11, 2.9 Hz, 1 H), 4.24 (dd, J=13.9, 10.5 Hz, 1 H), 4.36-4.60 (m, 2 H), 4.99-5.07 (m, 1 H), 6.95-7.01 (m, 1 H), 7.01-7.05 (m, 1 H), 7.08-7.16 (m, 3 H), 7.17-8.26 (m, 3 H); Mass Spectrum (ESI) m/z=608 (M+H)

Example 337

2-((3R,5R,6S)-1-((S)-1-(tert-Butylsulfonyl)-3-methylbutan-2-yl)-5-(3-chlorophenyl)-6-(4-chlorophenyl)-3-methyl-2-oxopiperidin-3-yl)acetic acid $^1$H NMR (500 MHz, methanol-d$_4$) δ ppm 0.51 (d, J=6.9 Hz, 3 H), 0.65 (d, J=6.6 Hz, 3 H), 1.37 (s, 3 H), 1.45 (s, 9 H), 2.01-2.10 (m, 1 H), 2.11-2.25 (m, 1 H), 2.30 (t, J=13.7 Hz, 1 H), 2.61 (d, J=13.5 Hz, 1 H), 2.99 (d, J=13.7 Hz, 1 H), 3.10 (dd, J=13.7, 1.71 Hz, 1 H), 3.25-3.29 (m, 1 H), 3.57 (ddd, J=13.6, 11.1, 2.9 Hz, 1 H), 3.96 (dd, J=13.8, 10.4 Hz, 1 H), 5.15 (d, J=11.3 Hz, 1 H), 6.98-7.03 (m, 1 H), 7.04-7.17 (m, 3 H), 7.18-8.01 (m, 3 H); Mass Spectrum (ESI) m/z=582.2 (M+H).

Example 338

2-((3R,5R,6S)-5-(3-Chlorophenyl)-6-(4-chlorophenyl)-3-methyl-1-((S)-3-methyl-1-(methylsulfonyl)butan-2-yl)-2-oxopiperidin-3-yl)acetic acid $^1$H NMR (500 MHz, methanol-d$_4$) δ ppm 0.50 (d, J=6.9 Hz, 3 H), 0.67 (d, J=6.6 Hz, 3 H), 1.37 (s, 3 H), 2.05 (dd, J=13.8, 3.1 Hz, 1 H), 2.18 (dq, J=14.2, 6.9 Hz, 1 H), 2.29 (t, J=13.6 Hz, 1 H), 2.62 (d, J=13.5 Hz, 1 H), 2.99 (d, J=13.5 Hz, 1 H), 3.09 (br s, 3 H), 3.20-3.29 (m, 1 H), 3.32-3.35 (m, 1 H), 3.56 (ddd, J=13.8, 10.9, 2.9 Hz, 1 H), 4.07 (dd, J=13.9, 10.5 Hz, 1 H), 5.09 (d, J=11 Hz, 1 H), 6.98 (dt, J=7.2, 1.4 Hz, 1 H), 7.03-7.08 (m, 1 H), 7.08-7.16 (m, 2 H), 7.29 (br s, 4 H); Mass Spectrum (ESI) m/z=540.2 (M+H).

Example 339

2-((3R,5R,6S)-5-(3-Chlorophenyl)-6-(4-chlorophenyl)-1-((S)-1-(ethylsulfonyl)butan-2-yl)-3-methyl-2-oxopiperidin-3-yl)acetic acid

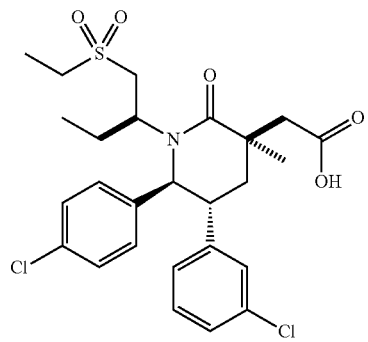 [SMILES: CC[C@@H](CS(=O)(=O)CC)N1C(=O)[C@@](C)(CC(=O)O)C[C@H](c2cccc(Cl)c2)[C@H]1c1ccc(Cl)cc1]

Step A. (3S,5S,6R,8S)-8-Allyl-6-(3-chlorophenyl)-5-(4-chlorophenyl)-3-ethyl-8-methyl-2,3,5,6,7,8-hexahydrooxazolo[3,2-a]pyridin-4-ium trifluoromethanesulfonate

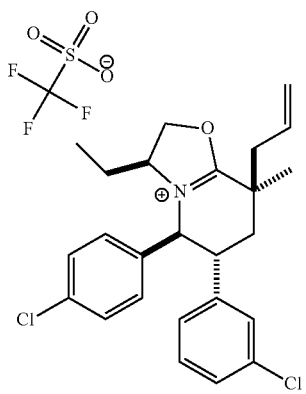

By the method of Example 361 Step A using (S)-2-aminobutanol in place of L-valinol, the title compound was obtained as the first eluting diastereomer.

$^1$H NMR (500 MHz, DMSO-d$_6$) δ ppm 7.95 (1 H, br. s), 7.34-7.60 (2 H, m), 7.18-7.34 (4 H, m), 7.13 (1 H, dt, J=7.5, 1.3 Hz), 5.88 (1 H, m), 5.37 (1 H, dd, J=16.8, 1.6 Hz), 5.28 (1 H, dd, J=10.0, 2.0 Hz), 5.16 (1 H, d, J=10.8 Hz), 5.06 (1 H, t, J=9.8 Hz), 4.78 (1 H, dd, J=9.5, 7.1 Hz), 4.45 (1 H, m, J=2.7 Hz), 3.88-3.98 (1 H, m), 2.66-2.85 (2 H, m), 2.33 (1 H, t, J=13.4 Hz), 1.99 (1 H, dd, J=13.7, 3.4 Hz), 1.32 (3 H, s), 0.94

(1 H, m), 0.59 (3 H, t, J=7.2 Hz), 0.41-0.53 (1 H, m); Mass Spectrum (ESI) m/z=428.2 (M+).

Step B. (3S,5R,6S)-3-Allyl-5-(3-chlorophenyl)-6-(4-chlorophenyl)-1-((S)-1-(ethylthio)butan-2-yl)-3-methylpiperidin-2-one

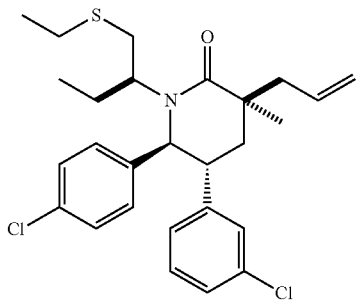 [SMILES: C=CC[C@@]1(C)C[C@H](c2cccc(Cl)c2)[C@@H](c2ccc(Cl)cc2)N([C@@H](CC)CSCC)C1=O]

To a solution of (3S,5S,6R,8S)-8-allyl-6-(3-chlorophenyl)-5-(4-chlorophenyl)-3-ethyl-8-methyl-2,3,5,6,7,8-hexahydrooxazolo[3,2-a]pyridin-4-ium trifluoromethanesulfonate (86 mg, 0.15 mmol; Example 339, Step A) in DMF (0.74 ml) was added sodium ethanethiolate (38 mg, 0.45 mmol). After being stirred at 25° C. for 1.5 h, the reaction was quenched (sat. aq. NH$_4$Cl), extracted (2×EtOAc), and washed (2× brine). The combined organic layers were dried over Na$_2$SO$_4$, filtered and the filtrate was concentrated under reduced pressure. Purification of the residue by chromatography on silica gel (12 g SiO$_2$, 10% and 20% EtOAc/hex) provided the title compound as a colorless liquid.

Step C. 2-((3R,5R,6S)-5-(3-Chlorophenyl)-6-(4-chlorophenyl)-1-((S)-1-(ethylsulfonyl)butan-2-yl)-3-methyl-2-oxopiperidin-3-yl)acetic acid To a rapidly stirring solution of (3S,5R,6S)-3-allyl-5-(3-chlorophenyl)-6-(4-chlorophenyl)-1-((S)-1-(ethylthio)butan-2-yl)-3-methylpiperidin-2-one (60 mg, 0.12 mmol; Example 339, Step B) in a mixture of water (0.66 mL), acetonitrile (0.44 mL), and CCl$_4$ (0.44 mL) was added sodium periodate (157 mg, 0.734 mmol), followed by ruthenium(III) chloride hydrate (2.8 mg, 0.012 mmol). After being vigorously stirred for 5 h, the reaction was acidified (10% citric acid) and diluted (EtOAc). The reaction mixture was filtered through a pad of Celite® (J. T. Baker, Phillipsberg, N.J., diatomaceous earth) and the filtrate was extracted (2×EtOAc). The combined organic layers were washed with brine, dried over Na$_2$SO$_4$ filtered and the filtrate was concentrated under reduced pressure. Purification of the residue by reverse phase preparatory HPLC (Gemini™ Prep C$_{18}$ 5 μm column, Phenomenex, Torrance, Calif.; gradient elution of 40% to 60% MeCN in water, where both solvents contain 0.1% TFA) provided the title compound as a white foam.

$^1$H NMR (400 MHz, CHLOROFORM-d) δ ppm 7.24-7.26 (2 H, m), 7.01-7.20 (4 H, m), 6.93-6.98 (1 H, m), 6.85 (1 H, d, J=7.0 Hz), 4.94 (1 H, d, J=10.6 Hz), 4.15 (1 H, t, J=12.1 Hz), 3.24-3.37 (1 H, m), 2.92-3.18 (4 H, m), 2.71-2.82 (2 H, m), 2.38 (1 H, t, J=13.8 Hz), 2.06-2.21 (1 H, m), 1.92 (1 H, dd, J=13.7, 2.7 Hz), 1.48 (3 H, s), 1.42-1.46 (1 H, m) 1.44 (3 H, t, J=7.5 Hz), 0.41 (3 H, t, J=7.5 Hz); Mass Spectrum (ESI) m/z=540.1 [M+H.

Example 340

2-((3R,5R,6S)-5-(3-Chlorophenyl)-6-(4-chlorophenyl)-1-((S)-1-(cyclopropylsulfonyl)butan-2-yl)-3-methyl-2-oxopiperidin-3-yl)acetic acid

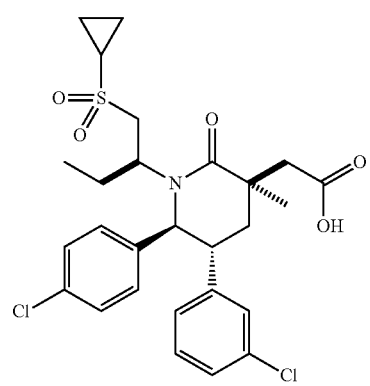 [SMILES: CC[C@@H](CS(=O)(=O)C1CC1)N1C(=O)[C@@](C)(CC(=O)O)C[C@H](c2cccc(Cl)c2)[C@H]1c1ccc(Cl)cc1]

Step A. (3S,5R,6S)-3Allyl-5-(3-chlorophenyl)-6-(4-chlorophenyl)-1-((S)-1-(cyclopropylsulfonyl)butan-2-yl)-3-methylpiperidin-2-one

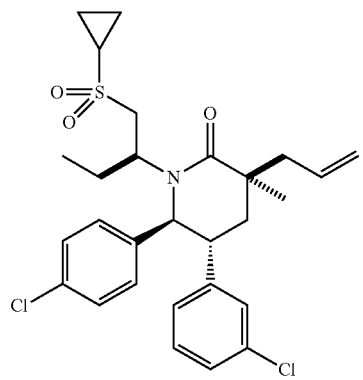

To a solution of (3S,5S,6R,8S)-8-allyl-6-(3-chlorophenyl)-5-(4-chlorophenyl)-3-ethyl-8-methyl-2,3,5,6,7,8-hexahydrooxazolo[3,2-a]pyridin-4-ium trifluoromethanesulfonate (75 mg, 0.130 mmol; Example 339, Step A) in acetonitrile (1.3 mL) was added cyclopropanesulfinic acid sodium salt (50 mg, 0.39 mmol) at 25° C. After being stirred at 90° C. for 1 day, the reaction was quenched with sat. aq. NH$_4$Cl solution, extracted (2×EtOAc) and the combined organic layers wer washed with brine (2×), dried over Na$_2$SO$_4$, filtered and the filtrate was concentrated under reduced pressure. Purification of the residue by chromatography on silica gel (12 g SiO$_2$, 35% and 45% EtOAc/hex) provided the title compound as a colorless liquid.

Step B. 2-((3R,5R,6S)-5-(3-chlorophenyl)-6-(4-chlorophenyl)-1-((S)-1-(cyclopropylsulfonyl)butan-2-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-(cyclopropylsulfonyl)butan-2-yl)-3-methylpiperidin-2-one (Example 340, Step A) by a procedure similar to the one described in Example 339 Step C.

¹H NMR (400 MHz, CHLOROFORM-d) δ ppm 7.22-7.26 (2 H, m), 6.99-7.19 (4 H, m), 6.91-6.97 (1 H, m), 6.76-6.89 (1 H, m), 4.91 (1 H, d, J=10.8 Hz), 4.21 (1 H, dd, J=13.5, 11.3 Hz), 3.31 (1 H, t, J=10.3 Hz), 3.12 (1 H, ddd, J=13.6, 10.9, 2.6 Hz), 2.88-3.02 (2 H, m), 2.76 (1 H, d, J=14.9 Hz), 2.31-2.49 (2 H, m), 2.06-2.24 (1 H, m), 1.90 (1 H, dd, J=13.7, 2.7 Hz), 1.40-1.56 (1 H, m), 1.47 (3 H, s), 1.23-1.36 (2 H, m), 1.01-1.16 (2 H, m), 0.42 (3 H, t, J=7.5 Hz); Mass Spectrum (ESI) 552.2 [M+H]⁺.

Examples 340 and 341 were prepared from (3S,5S,6R,8S)-8-allyl-6-(3-chlorophenyl)-5-(4-chlorophenyl)-3-ethyl-8-methyl-2,3,5,6,7,8-hexahydrooxazolo[3,2-a]pyridin-4-ium trifluoromethanesulfonate (Example 339, Step A) by a procedure similar to the one described in either Example 339 or Example 340, using an equivalent amount of the appropriate reagent in step B.

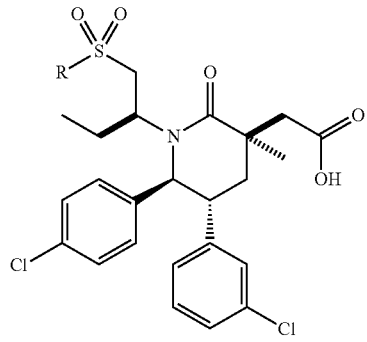

| Example | R | Method | Reagent used |
|---|---|---|---|
| 341 | *isopropyl* | Example 339 | propane-2-thiolate, prepared in situ from cesium carbonate (206 mg, 0.63 mmol) and 2-propanethiol (59 μl, 0.63 mmol) |
| 342 | *tert-butyl* | Example 339 | 2-methylpropanethiolate, prepared in situ from 2-methylpropane-2-thiol (113 μl, 1.00 mmol) and sodium carbonate (106 mg, 1.00 mmol) |
| 343 | *cyclobutyl* | Example 340 | cyclobutanesulfinic acid, sodium salt, |

Example 341

2-((3R,5R,6S)-5-(3-chlorophenyl)-6-(4-chlorophenyl)-1-((S)-1-(isopropylsulfonyl)butan-2-yl)-3-methyl-2-oxopiperidin-3-yl)acetic acid ¹H NMR (400 MHz, CHLOROFORM-d) δ ppm 7.22-7.26 (2 H, br s), 7.02-7.21 (4 H, m), 6.92-6.94 (1 H, s), 6.85 (1 H, d, J=7.0 Hz), 4.97 (1 H, d, J=10.8 Hz), 4.10 (1 H, t, J=11.7 Hz), 3.27-3.42 (1 H, m), 2.98-3.16 (3 H, m), 2.70-2.78 (2 H, m), 2.40 (1 H, t, J=13.9 Hz), 2.08-2.26 (1 H, m), 1.86-1.93 (1 H, s), 1.49 (3 H, s), 1.43 (3 H, d, J=6.8 Hz), 1.43 (3 H, d, J=6.8 Hz), 1.40-1.50 (1 H, m) 0.41 (3 H, t, J=7.5 Hz); Mass Spectrum (ESI) m/z=554.2 [M+H]⁺.

Example 342

2-((3R,5R,6S)-1-((S)-1-(tert-butylsulfonyl)butan-2-yl)-5-(3-chlorophenyl)-6-(4-chlorophenyl)-3-methyl-2-oxopiperidin-3-yl)acetic acid ¹H NMR (500 MHz, CHLOROFORM-d) δ ppm 7.21-7.26 (2 H, m), 7.01-7.20 (4 H, m), 6.92-6.94 (1 H, m), 6.85 (1 H, d, J=7.1 Hz), 4.99 (1 H, d, J=10.8 Hz), 4.04 (1 H, dd, J=13.2, 11.2 Hz), 3.33 (1 H, t, J=10.4 Hz), 3.03-3.15 (2 H, m), 2.80 (1 H, dd, J=13.2, 2.0 Hz), 2.72 (1 H, d, J=15.4 Hz), 2.43 (1 H, t, J=13.8 Hz), 2.08-2.23 (1 H, m), 1.86 (1 H, dd, J=13.7, 2.4 Hz), 1.50 (3 H, s), 1.46-1.49 (1 H, m), 1.44 (9 H, s), 0.41 (3 H, t, J=7.6 Hz); Mass Spectrum (ESI) 568.2 [M+H]⁺.

Example 343

2-((3R,5R,6S)-5-(3-Chlorophenyl)-6-(4-chlorophenyl)-1-((S)-1-(cyclobutylsulfonyl)butan-2-yl)-3-methyl-2-oxopiperidin-3-yl)acetic acid ¹H NMR (500 MHz, CHLOROFORM-d) δ ppm 7.21-7.27 (2 H, m), 7.00-7.21 (4 H, m), 6.93-6.97 (1 H, s), 6.86 (1 H, d, J=7.1 Hz), 4.97 (1 H, d, J=10.8 Hz), 3.98 (1 H, t, J=12.2 Hz), 3.76 (1 H, quin, J=8.3 Hz), 3.31 (1 H, t, J=9.9 Hz), 3.12 (1 H, ddd, J=13.6, 10.9, 2.7 Hz), 2.99 (1 H, d, J=14.9 Hz), 2.75 (1 H, d, J=14.9 Hz), 2.50-2.69 (3 H, m), 2.27-2.46 (3 H, m), 2.04-2.19 (3 H, m), 1.91 (1 H, dd, J=13.7, 2.7 Hz), 1.48-1.52 (3 H, m), 1.41-1.47 (1 H, m), 0.40 (3 H, t, J=7.6 Hz); Mass Spectrum (ESI) 566.2 [M+H]⁺.

Synthesis of Cyclobutanesulfinic Acid, Sodium Salt

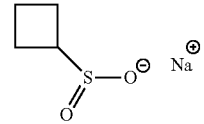

The reagent was prepared by procedures similar to the ones described in WO2007/14011 and WO2010/39982. To a suspension of magnesium (306 mg, 12.6 mmol) in ether (7.4 mL) was added a solution of bromocyclobutane (1.00 g, 7.41 mmol) in ether (7.4 mL) in several small portions at 25° C. After the initial exotherm had ceased, the mixture was further heated to reflux for 1 h. Then the suspension was added in small portions to an ice cold solution of sulfuryl dichloride (3.00 g, 22.2 mmol) in DCM (12 mL). The suspension was warmed to room temperature and the volatiles were removed under reduced pressure. The residue was dried under a vacuum, then extracted with hexane (80 mL). The hexane suspension was filtered and the filter cake was washed with hexanes. The combined filtrates were dried (Na₂SO₄) and concentrated under reduced pressure to give crude cyclobutanesulfonyl chloride. The crude cyclobutanesulfonyl chloride (1.15 g, 7.44 mmol) was added to a suspension of sodium sulfite (2.16 g, 17.1 mmol) in water (9.7 ml) and sodium carbonate (1.42 g, 13.4 mmol). The resulting solution was heated to reflux for 1 h. The reaction was cooled and lyophilized to remove water. Ethanol (50 mL) was added to the residue, and the resulting mixture was heated under reflux for 2 h. The mixture was filtered. The filtrate was concentrated under the reduced pressure to give the crude title compound which was used as is in the next step.

Example 344

2-((3R,5R,6S)-5-(3-Chlorophenyl)-6-(4-chlorophenyl)-3-ethyl-1-((S)-1-(ethylsulfonyl)butan-2-yl)-2-oxopiperidin-3-yl)acetic acid

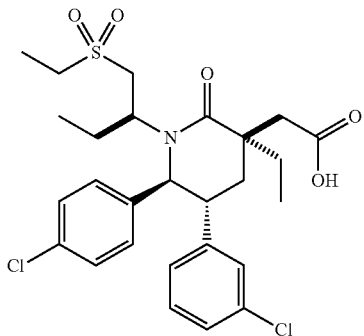

Step A. (3S,5S,6R,8S)-8-Allyl-6-(3-chlorophenyl)-5-(4-chlorophenyl)-3,8-diethyl-2,3,5,6,7,8-hexahydrooxazolo[3,2-a]pyridin-4-ium methanesulfonate

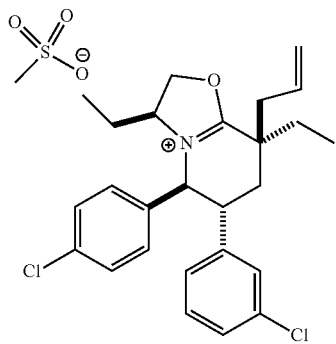

To a solution of (3S,5R,6S)-3-allyl-5-(3-chlorophenyl)-6-(4-chlorophenyl)-3-ethyl-1-((S)-1-hydroxybutan-2-yl)piperidin-2-one (300 mg, 0.652 mmol) (Example 202, Step B) in DCM (6 mL) was added triethylamine (270 µl, 1.955 mmol) and methanesulfonic anhydride (170 mg, 0.977 mmol) successively at 0° C. The reaction was allowed to warm to rt. After being stirred at rt for 2 h, the reaction was quenched with 10% aq. citric acid, extracted with DCM and the combined extracts were washed with water, dried over $Na_2SO_4$, filtered and the filtrate was and concentrated to give the title compound.

Step B. (3S,5R,6S)-3-Allyl-5-(3-chlorophenyl)-6-(4-chlorophenyl)-3-ethyl-1-((S)-1-(ethylthio)butan-2-yl)piperidin-2-one

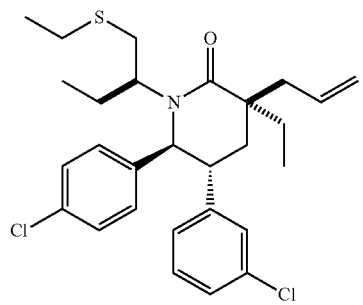

The title compound was prepared from (3S,5S,6R,8S)-8-allyl-6-(3-chlorophenyl)-5-(4-chlorophenyl)-3,8-diethyl-2,3,5,6,7,8-hexahydrooxazolo[3,2-a]pyridin-4-ium methanesulfonate (Example 344, step A) by a procedure similar to the one described in Example 339, step B.

Step C. 2-((3R,5R,6S)-5-(3-Chlorophenyl)-6-(4-chlorophenyl)-3-ethyl-1-((S)-1-(ethylsulfonyl)butan-2-yl)-2-oxopiperidin-3-yl)acetic acid The title compound was prepared from (3S,5R,6S)-3-allyl-5-(3-chlorophenyl)-6-(4-chlorophenyl)-3-ethyl-1-((S)-1-(ethylthio)butan-2-yl)piperidin-2-one (Example 344, step B) by a procedure similar to the one described in Example 339, step C.

$^1$H NMR (400 MHz, CHLOROFORM-d) δ ppm 0.41 (t, J=8.0 Hz, 3 H), 0.97 (t, J=8.0 Hz, 3 H), 1.44 (s, 3 H), 1.50 (m, 1 H), 1.86 (dd, J=12, 4 Hz, 1 H), 1.97 (m, 2 H), 2.15 (m, 1 H), 2.36 (t, J=12 Hz, 1 H), 2.79 (m, 1 H), 2.81 (d, J=16 Hz, 1 H), 2.92 (d, J=16.0 Hz, 1 H), 3.04 (m, 2 H), 3.16 (m, 1 H), 3.19 (m, 1 H), 4.11 (m, 1 H), 4.97 (d, J=12 Hz, 1 H), 6.86 (d, J=8.0 Hz, 1 H), 6.97 (s, 1 H), 7.13 (m, 3 H), 7.38 (m, 3 H); Mass Spectrum (ESI) m/z=554.0 [M+H]$^+$.

Examples 345 to 347 were prepared from (3S,5S,6R,8S)-8-allyl-6-(3-chlorophenyl)-5-(4-chlorophenyl)-3,8-diethyl-2,3,5,6,7,8-hexahydrooxazolo[3,2-a]pyridin-4-ium methanesulfonate (Example 344, Step A) by a procedure similar to the one described in either Example 339 or Example 340, using an equivalent amount of the appropriate reagent in step B.

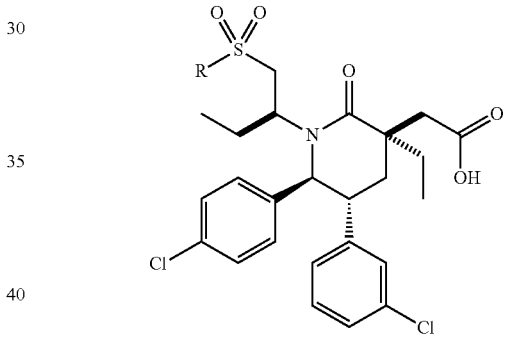

| Example | R | Method | Reagent used |
|---|---|---|---|
| 345 | isopropyl | Example 339 | propane-2-thiolate, prepared in situ from cesium carbonate (206 mg, 0.63 mmol) and 2-propanethiol (59 µl, 0.63 mmol) |
| 346 | tert-butyl | Example 339 | 2-methylpropanethiolate, prepared in situ from 2-methylpropane-2-thiol (113 µl, 1.00 mmol) and sodium carbonate (106 mg, 1.00 mmol) |
| 347 | cyclobutyl | Example 340 | cyclobutanesulfinic acid sodium salt, prepared as described in Example 343 |
| 348 | cyclopropyl | Example 340 | cyclopropanesulfinic acid sodium salt, prepared by the method as described in Example 343 |

Example 345

2-((3R,5R,6S)-5-(3-Chlorophenyl)-6-(4-chlorophenyl)-3-ethyl-1-((S)-1-(isopropylsulfonyl)butan-2-yl)-2-oxopiperidin-3-yl)acetic acid $^1$H NMR (400 MHz, CHLOROFORM-d) δ ppm 0.40 (t, J=8.0 Hz, 3 H), 0.97 (t, J=8.0 Hz, 3 H), 1.43 (d, J=4 Hz, 6 H), 1.50 (m, 1 H), 1.86 (dd, J=12, 4 Hz, 1 H), 1.98 (m, 2 H), 2.19 (m, 1 H), 2.37 (t, J=12 Hz, 1 H), 2.73 (d, J=12 Hz, 1 H), 2.79 (d, J=12.0 Hz, 1 H), 2.97 (d, J=12 Hz, 1 H), 3.10 (m, 2 H), 3.37 (m, 1 H), 4.09 (m, 1 H), 4.99 (d, J=12 Hz, 1 H), 6.86 (d, J=8.0 Hz, 1 H), 6.98 (s, 1 H), 7.12 (m, 4 H), 7.27 (m, 2 H); Mass Spectrum (ESI) m/z=568.0 [M+H]$^+$.

Example 346

2-((3R,5R,6S)-1-((S)-1-(tert-butylsulfonyl)butan-2-yl)-5-(3-chlorophenyl)-6-(4-chlorophenyl)-3-ethyl-2-oxopiperidin-3-yl)acetic acid $^1$H NMR (400 MHz, CHLOROFORM-d) δ ppm 0.39 (t, J=8.0 Hz, 3 H), 0.97 (t, J=8.0 Hz, 3 H), 1.43 (s, 9 H), 1.50 (m, 1 H), 1.85 (dd, J=12.4 Hz, 1 H), 1.97 (m, 2 H), 2.15 (m, 1 H), 2.38 (t, J=12 Hz, 1 H), 2.80 (d, J=16 Hz, 1 H), 2.96 (d, J=16.0 Hz, 1 H), 3.14 (m, 2 H), 3.35 (m, 1 H), 4.01 (m, 1 H), 5.02 (d, J=8 Hz, 1 H), 6.87 (d, J=8.0 Hz, 1 H), 6.98 (s, 1 H), 7.13 (m, 4 H), 7.38 (m, 2 H); Mass Spectrum (ESI) m/z=582.1 [M+H]$^+$.

Example 347

2-((3R,5R,6S)-5-(3-Chlorophenyl)-6-(4-chlorophenyl)-1-((S)-1-(cyclobutylsulfonyl)butan-2-yl)-3-ethyl-2-oxopiperidin-3-yl)acetic acid $^1$H NMR (400 MHz, CHLOROFORM-d) δ ppm 0.39 (t, J=8.0 Hz, 3 H), 0.98 (t, J=8.0 Hz, 3 H), 1.50 (m, 1 H), 1.84-2.45 (m, 6 H), 2.38 (m, 3 H), 2.62 (m, 3H), 2.80 (d, J=16 Hz, 1 H), 2.94 (d, J=16.0 Hz, 1 H), 3.15 (d, J=12 Hz, 1 H), 3.34 (m, 1 H), 3.76 (m, 1 H), 3.94 (m, 1 H), 5.00 (d, J=12 Hz, 1 H), 6.87 (d, J=8.0 Hz, 1H), 6.98 (s, 1 H), 7.13 (m, 3 H), 7.28 (m, 3 H); Mass Spectrum (ESI) 580.0 [M+H]$^+$.

Example 348

2-((3R,5R,6S)-5-(3-Chlorophenyl)-6-(4-chlorophenyl)-1-((S)-1-(cyclopropylsulfonyl)butan-2-yl)-3-ethyl-2-oxopiperidin-3-yl)acetic acid $^1$H NMR (400 MHz, CHLOROFORM-d) δ ppm 0.42 (t, J=8.0 Hz, 3 H), 0.97 (t, J=8.0 Hz, 3 H), 1.10 (m, 2 H), 1.26 (m, 2 H), 1.52 (m, 1 H), 1.83 (dd, J=16, 4 Hz, 1 H), 1.96 (m, 2 H), 2.14 (m, 1 H), 2.34 (d, J=16.0 Hz, 1 H), 2.42 (m, 1 H), 2.79 (d, J=12 Hz, 1 H), 2.95 (m, 1 H), 2.98 (d, J=16 Hz, 1 H), 3.12 (m, 1 H), 3.34 (m, 1 H), 4.15 (m, 1 H), 5.00 (d, J=12 Hz, 1 H), 6.84 (d, J=8.0 Hz, 1 H), 6.96 (s, 1 H), 7.12 (m, 4 H), 7.27 (m, 2 H); Mass Spectrum (ESI) m/z=566.0 [M+H]$^+$.

Example 349

2-((3R,5R,6S)-5-(3-chlorophenyl)-6-(4-chlorophenyl)-1-((S)-1-cyclopropyl-2-(ethylsulfonyl)ethyl)-3-methyl-2-oxopiperidin-3-yl)acetic acid

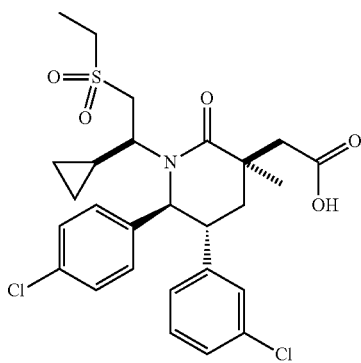 [SMILES: CCS(=O)(=O)C[C@H](C1CC1)N1C(=O)[C@@](C)(CC(=O)O)C[C@H](c2cccc(Cl)c2)[C@H]1c1ccc(Cl)cc1]

Step A. (3S,5S,6R,8S)-8-Allyl-6-(3-chlorophenyl)-5-(4-chlorophenyl)-3-cyclopropyl-8-methyl-2,3,5,6,7,8-hexahydrooxazolo[3,2-a]pyridin-4-ium methanesulfonate

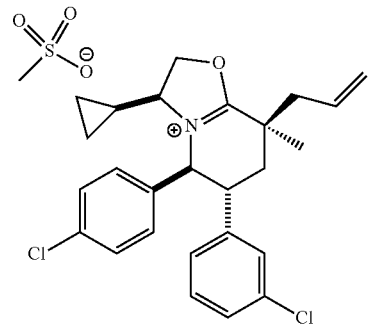

The title compound was prepared from (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, Step A) by a procedure similar to the one described in Example 344, step A.

Step B. (3S,5R,6S)-3-Allyl-5-(3-chlorophenyl)-6-(4-chlorophenyl)-1-((S)-1-cyclopropyl-2-(ethylthio)ethyl)-3-methylpiperidin-2-one

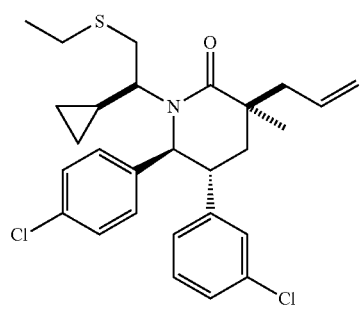

The title compound was prepared from (3S,5S,6R,8S)-8-allyl-6-(3-chlorophenyl)-5-(4-chlorophenyl)-3-cyclopropyl-8-methyl-2,3,5,6,7,8-hexahydrooxazolo[3,2-a]pyridin-4-ium methanesulfonate (Example 349, Step A) and sodium ethanethiolate as described in Example 339.

Step C. 2-((3R,5R,6S)-5-(3-Chlorophenyl)-6-(4-chlorophenyl)-1-((S)-1-cyclopropyl-2-(ethylsulfonyl)ethyl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-cyclopropyl-2-(ethylthio)ethyl)-3-methylpiperidin-2-one (Example 349, step B) by a procedure similar to the one described in Example 339, step C.

$^1$H NMR (400 MHz, CHLOROFORM-d) δ ppm 7.20-7.26 (3 H, m), 7.07-7.17 (3 H, m), 6.95-6.98 (1 H, m), 6.82-6.88 (1 H, m), 4.90 (1 H, d, J=10.6 Hz), 4.25-4.46 (1 H, m), 3.11-3.24 (1 H, m), 2.99-3.09 (3 H, m), 2.92 (1 H, d, J=12.1 Hz), 2.80 (1 H, d, J=14.7 Hz), 2.64-2.77 (1 H, m), 2.42 (1 H, t, J=13.8 Hz), 1.91 (1 H, dd, J=13.9, 2.5 Hz), 1.83 (1 H, br. s.), 1.49 (3 H, s), 1.44 (3 H, t, J=7.5 Hz), 0.32-0.42 (1 H, m), 0.18-0.27 (1 H, m), −0.35--0.24 (1 H, m), −1.15--0.95 (1 H, m); Mass Spectrum (ESI) 552.2 [M+H]$^+$.

Examples 350 to 356 were prepared from (3S,5S,6R,8S)-8-allyl-6-(3-chlorophenyl)-5-(4-chlorophenyl)-3-cyclopropyl-8-methyl-2,3,5,6,7,8-hexahydrooxazolo[3,2-a]pyridin-4-ium methanesulfonate (Example 349, Step A) by a procedure similar to the one described in either Example 339 or Example 340, using an equivalent amount of the appropriate reagent in step B.

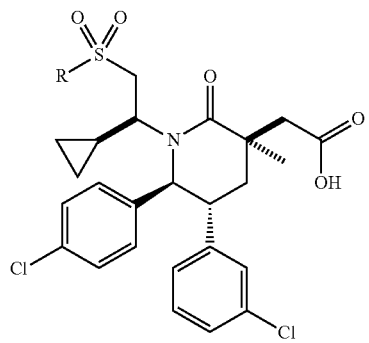

| Example | R | Method | Reagent used |
|---|---|---|---|
| 350 | | Example 339 | propane-2-thiolate, prepared in situ from 2-propanethiol and sodium carbonate |
| 351 | | Example 339 | 2-methylpropanethiolate, prepared in situ from 2-methylpropane-2-thiol and sodium carbonate |
| 352 | | Example 340 | cyclobutanesulfinic acid sodium salt, prepared as described in Example 343 |
| 353 | | Example 340 | cyclopropanesulfinic acid sodium salt, prepared by the method as described in Example 343 |
| 354 | Me | Example 340 | sodium methanesulfinate |
| 355 | | Example 339 | 2-methylbutane-2-thiolate, prepared in situ from 2-methylbutane-2-thiol and NaH |
| 356 | | Example 339 | 2,4-di-fluorobenzenethiolate prepared in situ from 2,4-di-fluorobenzenethiol and NaH |

Example 350

2-((3R,5R,6S)-5-(3-Chlorophenyl)-6-(4-chlorophenyl)-1-((S)-1-cyclopropyl-2-(isopropylsulfonyl)ethyl)-3-methyl-2-oxopiperidin-3-yl)acetic acid $^1$H NMR (400 MHz, CHLOROFORM-d) δ ppm 7.23-7.26 (3 H, m), 7.04-7.20 (3 H, m), 6.93-6.97 (1 H, m), 6.84-6.88 (1 H, m), 4.93 (1 H, d, J=10.8 Hz), 4.34 (1 H, br. s.), 3.05-3.18 (3 H, m), 2.86 (1 H, d, J=13.3 Hz), 2.77 (2 H, d, J=15.3 Hz), 2.46 (1 H, t, J=13.8 Hz), 1.86 (2 H, dd, J=13.5, 2.5 Hz), 1.51 (3 H, s), 1.44 (6 H, d, J=6.8 Hz), 0.31-0.44 (1 H, m), 0.18-2.80 (1 H, m), −0.35--0.23 (1 H, m), −1.15--1.02 (1 H, br. s.);
Mass Spectrum (ESI) 566.2 [M+H]$^+$.

Example 351

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetic acid $^1$H NMR (400 MHz, CHLOROFORM-d) δ ppm 7.20-7.26 (3 H, m), 7.03-7.17 (3 H, m), 6.93-6.97 (1 H, m), 6.82-6.92 (1 H, m), 4.95 (1 H, d, J=10.6 Hz), 4.30 (1 H, t, J=12.0 Hz), 3.14 (1 H, ddd, J=13.6, 10.8, 2.6 Hz), 3.07 (1 H, d, J=15.1 Hz), 2.92 (1 H, d, J=11.9 Hz), 2.79 (1 H, d, J=15.1 Hz), 2.72 (1 H, t, J=9.6 Hz), 2.45 (1 H, t, J=13.8 Hz), 1.88 (2 H, dd, J=13.6, 2.4 Hz), 1.50 (3 H, s), 1.44 (9 H, s), 0.30-0.44 (1 H, m), 0.17-0.30 (1 H, m), −0.37--0.26 (1 H, m), −1.15--1.05 (1 H, m); Mass Spectrum (ESI) 580.2 [M+H]$^+$.

Example 352

2-((3R,5R,6S)-5-(3-Chlorophenyl)-6-(4-chlorophenyl)-1-((S)-2-(cyclobutylsulfonyl)-1-cyclopropyl-ethyl)-3-methyl-2-oxopiperidin-3-yl)acetic acid $^1$H NMR (400 MHz, CHLOROFORM-d) δ ppm 7.20-7.27 (3 H, m), 7.07-7.15 (3 H, m), 6.94-6.98 (1 H, m), 6.84-6.93 (1 H, m), 4.93 (1 H, d, J=10.6 Hz), 4.23 (1 H, t, J=11.3 Hz), 3.77 (1 H, quin, J=8.3 Hz), 3.12-3.22 (1 H, m), 3.08 (1 H, d, J=15.1 Hz), 2.70-2.83 (3 H, m), 2.53-2.69 (2 H, m), 2.47 (1 H, t, J=13.8 Hz), 2.27-2.40 (2 H, m), 2.04-2.19 (2 H, m), 1.73-1.97

(2 H, m), 1.51 (3 H, s), 0.30-0.41 (1 H, m), 0.20-0.30 (1 H, m), -0.35--0.25 (1 H, m), -1.12--0.95 (1 H, m); Mass Spectrum (ESI) 578.1 [M+H]⁺.

Example 353

2-((3R,5R,6S)-5-(3-chlorophenyl)-6-(4-chlorophenyl)-1-((S)-1-cyclopropyl-2-(cyclopropylsulfonyl)ethyl)-3-methyl-2-oxopiperidin-3-yl)acetic acid $^1$H NMR (400 MHz, CHLOROFORM-d) δ ppm 7.18-7.26 (3 H, m), 7.06-7.15 (3 H, m), 6.92-6.97 (1 H, m), 6.82-6.88 (1 H, m), 4.87 (1 H, d, J=10.6 Hz), 4.44 (1 H, br. s.), 3.11-3.23 (1 H, m), 3.01-3.10 (2 H, m), 2.78 (1 H, d, J=15.1 Hz), 2.73 (1 H, br. s.), 2.35-2.47 (2 H, m), 1.88 (1 H, dd, J=13.8, 2.6 Hz), 1.76-1.85 (1 H, m), 1.49 (3 H, s), 1.24-1.35 (2 H, m), 1.03-1.16 (2 H, m), 0.32-0.44 (1 H, m), 0.20-0.30 (1 H, m), -0.33--0.21 (1 H, m), -1.02--0.98 (1 H, br. s.); Mass Spectrum (ESI) 564.1 [M+H]⁺.

Example 354

2-((3R,5R,6S)-5-(3-Chlorophenyl)-6-(4-chlorophenyl)-1-((S)-1-cyclopropyl-2-(methylsulfonyl)ethyl)-3-methyl-2-oxopiperidin-3-yl)acetic acid $^1$H NMR (400 MHz, CHLOROFORM-d) δ ppm -1.03 (br s, 1 H) -0.26 (br s, 1 H) 0.27 (br s, 1 H) 0.33-0.49 (m, 1 H) 1.51 (s, 3 H) 1.71-1.97 (m, 2 H) 2.43 (t, J=13.79 Hz, 1 H) 2.78 (m, 2 H) 3.00 (s, 3 H) 3.01-3.24 (m, 3 H) 4.44 (br s, 1 H) 4.87 (d, J=10.56 Hz, 1 H) 6.81-6.92 (m, 1 H) 6.96 (s, 1 H) 7.07-7.20 (m, 2 H) 7.27 (m, 4 H); Mass Spectrum (ESI) m/z=540 (M+1).

Example 355

2-((3R,5R,6S)-5-(3-Chlorophenyl)-6-(4-chlorophenyl)-1-((S)-1-cyclopropyl-2-(tert-pentylsulfonyl)ethyl)-3-methyl-2-oxopiperidin-3-yl)acetic acid $^1$H NMR (400 MHz, CHLOROFORM-d) δ ppm -1.11 (br s, 1H), -0.31 (br s, 1H), 0.23 (br s, 1H), 0.36 (br s, 1H), 1.04 (t, J=7.53 Hz, 3H), 1.28-1.44 (m, 6H), 1.50 (s, 3H), 1.73-1.95 (m, 4H), 2.48 (t, J=13.89 Hz, 1H), 2.76 (d, J=15.26 Hz, 2H), 2.91 (d, J=13.11 Hz, 1H), 3.04-3.23 (m, 2H), 4.28 (t, J=11.15 Hz, 1H), 4.90-5.07 (m, 1H), 6.84-6.93 (m, 1H), 6.94-7.03 (m, 1H), 7.05-7.37 (br s, 6H); Mass Spectrum (ESI) m/z=594.0 (M+1).

Example 356

2-((3R,5R,6S)-5-(3-Chlorophenyl)-6-(4-chlorophenyl)-1-((S)-1-cyclopropyl-2-((2,4-difluorophenyl)sulfonyl)ethyl)-3-methyl-2-oxopiperidin-3-yl)acetic acid $^1$H NMR (400 MHz, CHLOROFORM-d) δ ppm -1.06 (br s, 1H), -0.29 (br s, 1H), 0.15-0.28 (m, 1H), 0.28-0.44 (m, 1H), 1.37 (s, 1H), 1.54 (s, 3H), 1.77-1.95 (m, 2H), 2.48 (t, J=13.79 Hz, 1H), 2.67-2.85 (m, 1H), 3.07 (d, J=14.87 Hz, 1H), 3.13-3.32 (m, 2H), 4.65 (br s, 1H), 4.92 (d, J=10.56 Hz, 1H), 6.81-6.94 (m, 2H), 6.94-7.21 (m, 8H), 7.99 (td, J=8.31, 6.06 Hz, 1H); MS (ESI) m/e=636.0 (M+1).

Example 357

2-((3R,5R,6S)-5-(3-Chlorophenyl)-6-(4-chlorophenyl)-1-((S)-1-cyclopropyl-2-(ethylsulfonyl)ethyl)-3-ethyl-2-oxopiperidin-3-yl)acetic acid

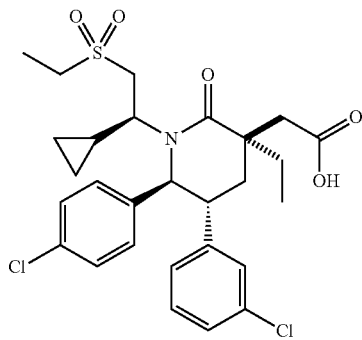 [SMILES: CC[C@]1(CC(=O)O)C[C@H](c2cccc(Cl)c2)[C@@H](c2ccc(Cl)cc2)N([C@H](CS(=O)(=O)CC)C2CC2)C1=O]

Step A. (3S,5S,6R,8S)-8-Allyl-6-(3-chlorophenyl)-5-(4-chlorophenyl)-3-cyclopropyl-8-ethyl-2,3,5,6,7,8-hexahydrooxazolo[3,2-a]pyridin-4-ium methanesulfonate

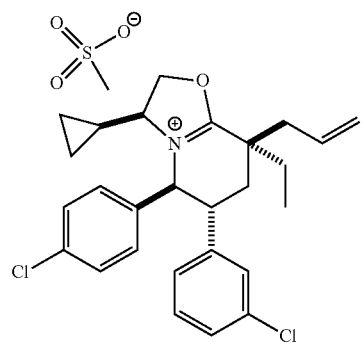

The title compound was prepared from (3S,5R,6S)-3-allyl-5-(3-chlorophenyl)-6-(4-chlorophenyl)-1-((S)-1-cyclopropyl-2-hydroxyethyl)-3-ethylpiperidin-2-one (Example 253, Step C) by a procedure similar to the one described in Example 344, step A.

Step B. (3S,5R,6S)-3-Allyl-5-(3-chlorophenyl)-6-(4-chlorophenyl)-1-((S)-1-cyclopropyl-2-(ethylthio)ethyl)-3-ethylpiperidin-2-one

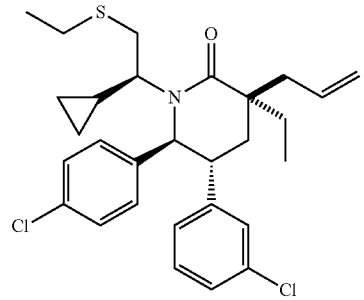 [SMILES: C=CC[C@@]1(CC)C[C@H](c2cccc(Cl)c2)[C@@H](c2ccc(Cl)cc2)N([C@H](CSCC)C2CC2)C1=O]

The title compound was prepared from (3S,5S,6R,8S)-8-Allyl-6-(3-chlorophenyl)-5-(4-chlorophenyl)-3-cyclopropyl-8-ethyl-2,3,5,6,7,8-hexahydrooxazolo[3,2-a]pyridin-4-ium methanesulfonate (Example 357, Step A) and sodium ethanethiolate by the method described in Example 339.

Step C. 2-((3R,5R,6S)-5-(3-Chlorophenyl)-6-(4-chlorophenyl)-1-((S)-1-cyclopropyl-2-(ethylsulfonyl)ethyl)-3-ethyl-2-oxopiperidin-3-yl)acetic acid The title compound was prepared from (3S,5R,6S)-3-allyl-5-(3-chlorophenyl)-6-(4-chlorophenyl)-1-((S)-1-cyclopropyl-2-(ethylthio)ethyl)-3-ethylpiperidin-2-one (Example 357, step B) by a procedure similar to the one described in Example 339, step C.

$^1$H NMR (500 MHz, CHLOROFORM-d) δ ppm −0.99 (br s, 1 H) −0.25 (br s, 1 H) 0.30 (br s, 1 H) 0.40 (br s, 1 H) 0.98 (t, J=7.46 Hz, 3 H) 1.44 (t, J=7.58 Hz, 3 H) 1.83 (m, 2 H) 1.92-2.09 (m, 2 H) 2.41 (t, J=13.69 Hz, 1 H) 2.71-2.88 (m, 2 H) 2.94 (d, J=13.45 Hz, 1 H) 3.00-3.20 (m, 4 H) 4.30 (br. s, 1 H) 4.92 (d, J=10.76 Hz, 1 H) 6.81-6.87 (m, 1 H) 6.97 (m, 1 H) 7.08-7.26 (m, 3 H); 7.30-7.50 (m, 4 H); Mass Spectrum (ESI) m/z=566 (M+1).

Examples 358 to 360 were prepared from (3S,5S,6R,8S)-8-allyl-6-(3-chlorophenyl)-5-(4-chlorophenyl)-3-cyclopropyl-8-ethyl-2,3,5,6,7,8-hexahydrooxazolo[3,2-a]pyridin-4-ium methanesulfonate (Example 357, Step A) by a procedure similar to the one described in either Example 339 or Example 340, using an equivalent amount of the appropriate reagent in step B.

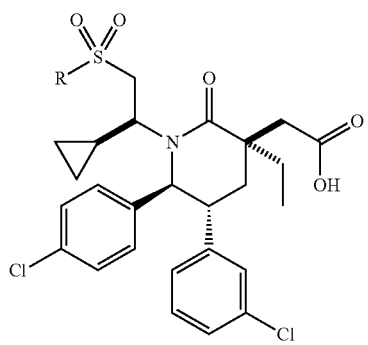

| Example | R | Method | Reagent used |
|---|---|---|---|
| 358 | isopropyl | Example 339 | propane-2-thiolate, prepared in situ from 2-propanethiol and NaH |
| 359 | tert-butyl | Example 339 | 2-methylpropanethiolate, prepared in situ from 2-methylpropane-2-thiol and NaH |
| 360 | cyclopropyl | Example 340 | cyclopropanesulfinate |

Example 358

2-((3R,5R,6S)-5-(3-Chlorophenyl)-6-(4-chlorophenyl)-1-((S)-1-cyclopropyl-2-(isopropylsulfonyl)ethyl)-3-ethyl-2-oxopiperidin-3-yl)acetic acid $^1$H NMR (400 MHz, CHLOROFORM-d) δ ppm −1.01 (br s, 1H), −0.27 (br s, 1H), 0.29 (br s, 1H), 0.39 (br s, 1H), 0.98 (t, J=7.53 Hz, 3H), 1.33-1.52 (m, 6H), 1.71-1.94 (m, 2H), 2.01 (q, J=7.43 Hz, 2H), 2.42 (t, J=13.79 Hz, 1H), 2.70-2.95 (m, 3H), 2.99-3.24 (m, 3H), 4.28 (br s, 1H), 4.95 (d, J=10.56 Hz, 1H), 6.83-6.94 (m, 2H), 6.94-7.05 (m, 2H), 7.05-7.21 (m, 4H); MS (ESI) m/z=580.0 and 581.9 (M+1).

Example 359

2-((3R,5R,6S)-1-((S)-2-(tert-Butylsulfonyl)-1-cyclopropylethyl)-5-(3-chlorophenyl)-6-(4-chlorophenyl)-3-ethyl-2-oxopiperidin-3-yl)acetic acid $^1$H NMR (500 MHz, CHLOROFORM-d) δ ppm −1.05 (br s, 1 H) −0.29 (br s, 1 H) 0.27 (br s, 1 H) 0.34-0.42 (m, 1 H) 0.98 (t, J=7.46 Hz, 3 H) 1.44 (s, 9 H) 1.81 (dd, J=13.69, 2.93 Hz, 1 H) 1.87-2.11 (m, 3 H) 2.43 (t, J=13.82 Hz, 1 H) 2.79 (d, J=15.89 Hz, 2 H) 2.95 (d, J=13.20 Hz, 1 H) 3.04-3.19 (m, 2 H) 4.21 (m, 1 H) 4.97 (d, J=10.76 Hz, 1 H) 6.75-6.92 (m, 2 H) 6.92-7.01 (m, 1 H) 7.06-7.17 (m, 3 H) 7.43 (m, 2 H); Mass Spectrum (ESI) m/z=594 (M+1).

Example 360

2-((3R,5R,6S)-5-(3-Chlorophenyl)-6-(4-chlorophenyl)-1-((S)-1-cyclopropyl-2-(cyclopropylsulfonyl)ethyl)-3-ethyl-2-oxopiperidin-3-yl)acetic acid $^1$H NMR (500 MHz, CHLOROFORM-d) δ ppm −0.99 (br s, 1 H) −0.25 (br s, 1 H) 0.29 (br s, 1 H) 0.36-0.45 (m, 1 H) 0.97 (t, J=7.46 Hz, 3 H) 1.07-1.16 (m, 2 H) 1.21-1.34 (m, 2 H) 1.82 (dd, J=13.69, 2.93 Hz, 1 H) 1.86-1.92 (m, 1 H) 1.92-2.14 (m, 2 H) 2.36-2.46 (m, 2 H) 2.80 (d, J=15.65 Hz, 1 H) 3.03-3.16 (m, 3 H) 4.34 (m, 1 H) 4.90 (d, J=10.51 Hz, 1 H) 6.80-6.89 (m, 1 H) 6.92-6.99 (m, 1 H) 7.06-7.17 (m, 3 H) 7.35-7.45 (m, 3 H);
Mass Spectrum (ESI) m/z=578 (M+1).

Example 361

2-((3R,5R,6S)-5-(3-Chlorophenyl)-6-(4-chlorophenyl)-1-((S)-1-(ethylsulfonyl)-3-methylbutan-2-yl)-3-methyl-2-oxopiperidin-3-yl)acetic acid

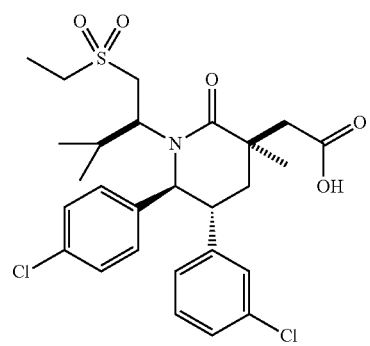 [SMILES: CCS(=O)(=O)C[C@H](C(C)C)N1C(=O)[C@@](C)(CC(=O)O)C[C@H](c2cccc(Cl)c2)[C@H]1c1ccc(Cl)cc1]

Step A. (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate

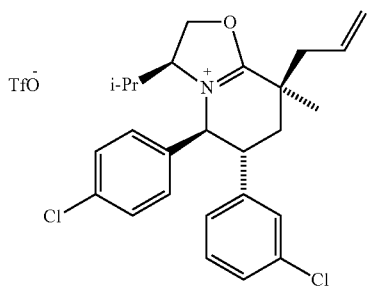

L-valinol (Sigma Aldrich, St. Louis, Mo.) (3.64 g), racemic (3S/R,5R/S,6R/S)-3-allyl-5-(3-chlorophenyl)-6-(4-chlorophenyl)-3-methyltetrahydro-2H-pyran-2-one (3.17 g; Example 261, step E) and lithium t-butoxide (0.025 g) were heated as a melt for 17 hr using an oil bath set at 135° C. After cooling, the glassy solid was dissolved in dichloromethane. The organic layer was washed with sat. ammonium chloride solution followed by 1N sodium hydroxide solution and then brine. The organic layer was dried over magnesium sulfate and concentrated to give 3.88 g of a mixture of diastereomers. A 2.61 g portion (67% of total) of the ca. 1:1 mixture obtained above was dissolved in toluene and evaporated to dryness three times to remove residual moisture. Dichloromethane (55 ml) and 2,6-dimethylpyridine (3.3 ml, 28.5 mmol) were added and the resulting stirred solution was cooled to −50° C. in a dry ice/acetonitrile bath. Trifluoromethanesulfonic anhydride (2.4 ml, 14.27 mmol) was added over the course of 10 minutes such that the internal temperature never exceeded −45° C. After 40 min, the reaction was quenched by addition of 2 M HCl. The mixture was warmed to room temperature, diluted in dichloromethane, washed with 2 N HCl, water, and finally brine. The organics were dried over magnesium sulfate, filtered, and concentrated to a yellow foam that weighed ca. 2.6 g. A portion of this material (1.92 g, 74%) was purified by medium-pressure liquid chromatography using a 120 g column, eluting with a gradient of 20 to 100% acetone in hexanes. Fractions containing the faster-eluting (less polar) diastereomer were concentrated to give the title compound as a white foam.

$^1$H NMR (400 MHz, CDCl$_3$) δ ppm 0.62 (d, J=2.4 Hz, 3 H), 0.64-0.74 (m, 4 H), 1.51 (s, 3 H), 2.04 (dd, J=14.1, 3.5 Hz, 1 H), 2.54-2.79 (m, 3 H), 3.58 (ddd, J=13.7, 10.8, 3.5 Hz, 1 H), 4.59 (dd, J=10.2, 4.7 Hz, 1 H), 4.67 (dd, J=9.2, 4.9 Hz, 1 H), 5.23-5.45 (m, 3 H), 5.71 (d, J=11 Hz, 1 H), 5.83 (ddt, J=17, 9.9, 7.4 Hz, 1 H), 7.06 (t, J=1.8 Hz, 1 H), 7.11-7.16 (m, 1 H), 7.19 (t, J=7.7 Hz, 1 H), 7.23-7.32 (m, 3 H), 7.39 (br s, 2 H); Mass Spectrum (ESI) m/z=442.2 (M$^+$).

Step B. 2-((3R,5R,6S)-5-(3-Chlorophenyl)-6-(4-chlorophenyl)-1-((S)-1-(ethylsulfonyl)-3-methylbutan-2-yl)-3-methyl-2-oxopiperidin-3-yl)acetic acid The title compound was prepared from (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (Example 361, step A) by procedures similar to the ones described in Example 339, using an equivalent amount of ethanethiol in step B.

$^1$H NMR (500 MHz, methanol-d$_4$) δ ppm 0.51 (d, J=7.1 Hz, 3 H), 0.66 (d, J=6.6 Hz, 3 H), 1.37 (s, 3 H), 1.41 (t, J=7.5 Hz, 3 H), 2.05 (dd, J=13.7, 2.9 Hz, 1 H), 2.18 (dq, J=14.2, 6.9 Hz, 1 H), 2.31 (t, J=13.7 Hz, 1 H), 2.62 (d, J=13.7 Hz, 1 H), 3.00 (d, J=13.7 Hz, 1 H), 3.14-3.24 (m, 3 H), 3.25-3.30 (m, 1 H), 3.57 (ddd, J=13.8, 10.9, 2.9 Hz, 1 H), 4.02 (dd, J=13.9, 10.5 Hz, 1 H), 5.12 (d, J=11 Hz, 1 H), 7.00 (dt, J=7.3, 1.5 Hz, 1 H), 7.04-8.17 (m, 7 H); Mass Spectrum (ESI) m/z=554.2 (M+1).

Example 362

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

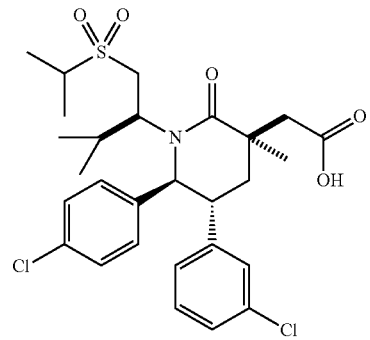 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

The title compound was prepared from (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (Example 361, step A) by procedures similar to the ones described in Example 339, using an equivalent amount of propane-2-thiol in step B.

$^1$H NMR (500 MHz, methanol-d$_4$) δ ppm 0.50 (d, J=6.9 Hz, 3 H), 0.65 (d, J=6.6 Hz, 3 H), 1.37 (s, 3 H), 1.41 (d, J=6.9 Hz, 6 H), 2.05 (dd, J=13.6, 2.8 Hz, 1 H), 2.18 (dq, J=14, 6.9 Hz, 1 H), 2.31 (t, J=13.7 Hz, 1 H), 2.61 (d, J=13.5 Hz, 1 H), 2.99 (d, J=13.7 Hz, 1 H), 3.11 (d, J=13.7 Hz, 1 H), 3.25-3.29 (m, 1 H), 3.32-3.37 (m, 1 H), 3.49-3.65 (m, 1 H), 4.01 (dd, J=13.7, 10.5 Hz, 1 H), 5.13 (d, J=11 Hz, 1 H), 6.93-7.03 (m, 1 H), 7.03-8.23 (m, 7 H); Mass Spectrum (ESI) m/z=568.0 (M+1).

Example 363

2-((3R,5R,6S)-5-(3-Chlorophenyl)-6-(4-chlorophenyl)-1-((S)-3,3-dimethyl-1-(methylsulfonyl)butan-2-yl)-3-methyl-2-oxopiperidin-3-yl)acetic acid

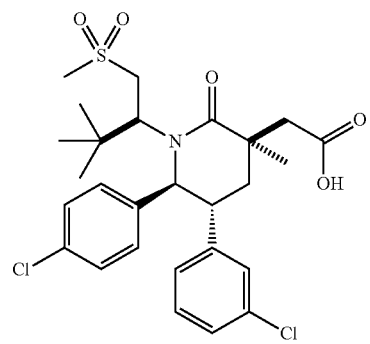 [SMILES: CC(C)(C)[C@@H](CS(C)(=O)=O)N1C(=O)[C@@](C)(CC(=O)O)C[C@H](c2cccc(Cl)c2)[C@H]1c1ccc(Cl)cc1]

Step A. (S)-2-((2R,3R)-2-(3-Chlorophenyl)-3-(4-chlorophenyl)-3-hydroxypropyl)-N-((S)-1-hydroxy-3,3-dimethylbutan-2-yl)-2-methylpent-4-enamide

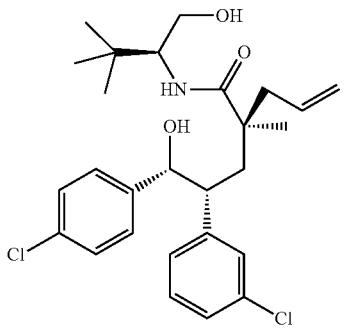 [SMILES: C=CC[C@@](C)(C[C@H](c1cccc(Cl)c1)[C@@H](O)c1ccc(Cl)cc1)C(=O)N[C@H](CO)C(C)(C)C]

(S)-tert-leucinol (0.937 g, 7.99 mmol) and (3S,5R,6R)-3-allyl-5-(3-chlorophenyl)-6-(4-chlorophenyl)-3-methyltetrahydro-2H-pyran-2-one (1 g, 2.66 mmol; Example 261, Step F) were combined in a reaction flask and heated to 100° C. After 2d, the reaction mixture was cooled to RT and dissolved in ethyl acetate. The organic phase was washed with 3×10 mL 1N HCl and 1×10 mL brine, dried over MgSO$_4$, filtered and concentrated to afford the title compound.

$^1$H-NMR (500 MHz, CDCl$_3$) δ 7.21-7.10 (series of m, 5H), 7.07 (t, J=1.7 Hz, 1H), 6.97 (m, 2H), 6.87 (br d, J=7.6 Hz, 1H), 5.91 (br d, J=8.3 Hz, 1H), 5.65 (ddt, J=17.4, 10.3, 7.3 Hz, 1H), 5.05 (dd, J=10.5, 2.0 Hz, 1H), 4.77 (d, J=4.9 Hz, 1H), 3.77 (m, 2H), 3.42 (m, 1H), 3.02 (dt, J=7.6, 5.4 Hz, 1H), 2.42 (dd, J=13.9, 7.1 Hz, 1H), 2.23 (dd, J=14.7, 5.6 Hz, 1H), 2.05 (dd J=13.7, 7.6 Hz, 1H), 1.87 (dd, J=14.4, 7.6 Hz, 1H), 1.17 (s, 3H), 0.92 (s, 9H); Mass Spectrum (ESI) m/z=492.2 (M+1).

Step B. (3S,5S,6R,8S)-8-Allyl-3-(tert-butyl)-6-(3-chlorophenyl)-5-(4-chlorophenyl)-8-methyl-2,3,5,6,7,8-hexahydrooxazolo[3,2-a]pyridin-4-ium triflate

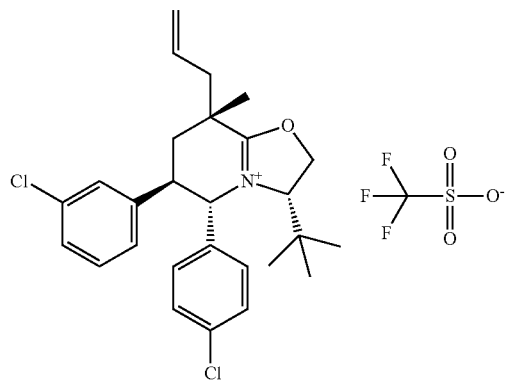 [SMILES: C=CC[C@@]1(C)C[C@H](c2cccc(Cl)c2)[C@@H](c2ccc(Cl)cc2)[N+]2=C1OC[C@@H]2C(C)(C)C ; O=S(=O)([O-])C(F)(F)F]

To a solution of (S)-2-((2R,3R)-2-(3-chlorophenyl)-3-(4-chlorophenyl)-3-hydroxypropyl)-N-((S)-1-hydroxy-3,3-dimethylbutan-2-yl)-2-methylpent-4-enamide (Example 363, step A, 950 mg, 1.929 mmol) in DCM (19 mL) at −50° C. was added 2,6-lutidine (896 μl, 7.72 mmol) followed by trifluoromethanesulfonic anhydride solution (1M DCM, 4.34 mL, 4.34 mmol). The progress of the reaction was monitored by LC/MS. An additional charge of 450 uL (2 eq) 2,6-lutidine followed by 1.12 eq triflic anhydride (2.16 mmol, 2.16 mL of 1M solution in dichloromethane). The reaction was allowed to warm to 0° C. and then poured into sat. aq. CuSO$_4$ solution. To the mixture was added 100 mL ethyl acetate. The layers were separated and the organic phase was washed with sat. aq. CuSO$_4$. The combined organic layers were concentrated and purified by column chromatography on silica gel (eluent: 20 to 50% acetone in hexanes) to afford the title compound.

$^1$H-NMR (500 MHz, DMSO-d$_6$) δ ppm 7.80-7.42 (series of m, 3H), 7.38-7.28 (series of m, 4H), 7.14 (d, J=7.6 Hz, 1H), 5.85 (ddt, J=17.2, 10.0, 7.3 Hz, 1H), 5.61 (d, J=7.1 Hz, 1H), 5.37 (dd, J=16.9, 1.7 Hz, 1H), 5.22 (dd, J=10.0, 7.0 Hz, 1H), 5.17 (t, J=9.7 Hz, 1H), 4.61 (dd, J=9.3, 6.9 Hz, 1H), 3.92 (ddd, J=9.8, 7.6, 4.2 Hz, 1H), 2.71 (m, 2H), 2.23 (dd, J=14.2, 9.5 Hz, 1H), 2.10 (dd, J=14.2, 4.4 Hz, 1H), 1.08 (s, 3H), 0.62 (s, 9H);

Mass Spectrum (ESI) m/z=474.2 (M$^+$).

Step C. 2-((3R,5R,6S)-5-(3-Chlorophenyl)-6-(4-chlorophenyl)-1-((S)-3,3-dimethyl-1-(methylsulfonyl)butan-2-yl)-3-methyl-2-oxopiperidin-3-yl)acetic acid The title compound was prepared from (3S,5S,6R,8S)-8-allyl-3-(tert-butyl)-6-(3-chlorophenyl)-5-(4-chlorophenyl)-8-methyl-2,3,5,6,7,8-hexahydrooxazolo[3,2-a]pyridin-4-ium triflate (Example 363, Step B) by procedures similar to the ones described in Example 340, using an equivalent amount of sodium methanesulfinate in step B.

Example 364

2-((3R,5R,6S)-5-(3-Chlorophenyl)-6-(4-chlorophenyl)-1-((S)-1-(ethylsulfonyl)-3,3-dimethylbutan-2-yl)-3-methyl-2-oxopiperidin-3-yl)acetic acid

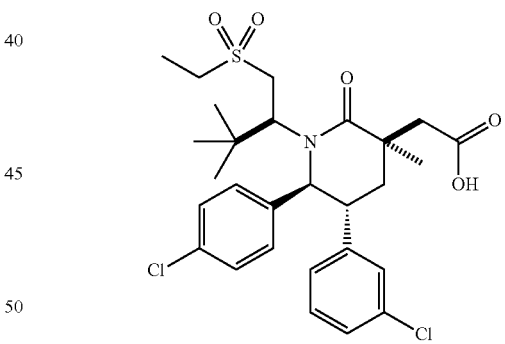

The title compound was prepared from (3S,5S,6R,8S)-8-allyl-3-(tert-butyl)-6-(3-chlorophenyl)-5-(4-chlorophenyl)-8-methyl-2,3,5,6,7,8-hexahydrooxazolo[3,2-a]pyridin-4-ium triflate (Example 363, Step B) by procedures similar to the ones described in Example 340, using an equivalent amount of sodium ethanesulfinate in step B.

$^1$H NMR (500 MHz, CHLOROFORM-d) δ ppm 7.13-7.60 (m, 4 H), 7.04-7.12 (m, 2 H), 6.94-7.00 (m, 2 H), 5.90 (ddt, J=17.2, 9.8, 7.5 Hz, 1 H), 5.17-5.29 (m, 2 H), 5.12 (d, J=11.0 Hz, 1 H), 4.27 (dd, J=13.2, 11.2 Hz, 1 H), 3.56 (dd, J=11.0, 2.2 Hz, 1 H), 3.45 (ddd, J=13.8, 10.9, 3.2 Hz, 1 H), 3.03-3.14 (m, 2 H), 2.78 (dd, J=13.2, 2.2 Hz, 1 H), 2.67 (ABX, J$_{AB}$=13.7 Hz, J$_{AX}$=8.1 Hz, 1H), 2.61 (ABX J$_{AB}$=13.7 Hz, J$_{BX}$=6.8 Hz, 1H) (m, 2 H), 2.27 (t, J=13.7 Hz, 1 H), 1.81 (dd, J=13.6, 3.3 Hz, 1

H), 1.47 (t, J=7.5 Hz, 3 H), 1.25 (s, 3 H), 0.71 (s, 9 H); Mass Spectrum (ESI) m/z=550.2 (M+1).

Example 365

2-((3R,5R,6S)-5-(3-Chlorophenyl)-6-(4-chlorophenyl)-1-((S)-1-(isopropylsulfonyl)-3,3-dimethylbutan-2-yl)-3-methyl-2-oxopiperidin-3-yl)acetic acid

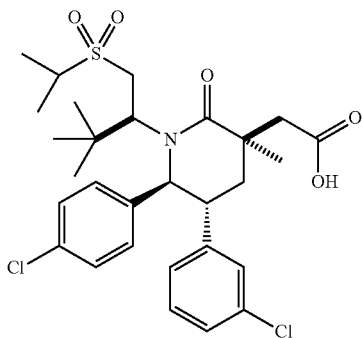 [SMILES: CC(C)S(=O)(=O)C[C@@H](N1C(=O)[C@@](C)(CC(=O)O)C[C@H](c2cccc(Cl)c2)[C@H]1c1ccc(Cl)cc1)C(C)(C)C]

Step A. (3S,5R,6S)-3-Allyl-5-(3-chlorophenyl)-6-(4-chlorophenyl)-1-((S)-1-hydroxy-3,3-dimethylbutan-2-yl)-3-methylpiperidin-2-one

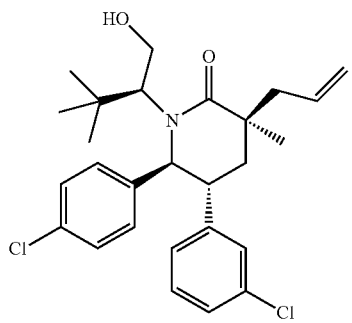 [SMILES: C=CC[C@@]1(C)C[C@H](c2cccc(Cl)c2)[C@@H](c2ccc(Cl)cc2)N([C@H](CO)C(C)(C)C)C1=O]

To a solution of (3S,5S,6R,8S)-8-allyl-3-(tert-butyl)-6-(3-chlorophenyl)-5-(4-chlorophenyl)-8-methyl-2,3,5,6,7,8-hexahydrooxazolo[3,2-a]pyridin-4-ium trifluoromethanesulfonate (290 mg, 0.478 mmol; Example 363, Step B) in 1,2-dichloroethane (4.78 mL) was added 5 mL of sat. aq. NaHCO₃ solution. The reaction mixture was heated to 50° C. for 3d. The reaction mixture was poured into a separatory funnel and the aqueous layer was extracted with dichloromethane. The combined organic layers were washed with sat. aq. NaHCO₃ solution, dried over MgSO₄, filtered and the filtrate was concentrated. Purification by column chromatography using 25-35% ethyl acetate in hexanes on a 4 g silica gel column afforded the title compound.

¹H-NMR (500 MHz, DMSO-d6) δ ppm 7.50-7.05 (series of m, 7H), 6.97 (d, J=7.3 Hz, 1H), 5.87 (dddd, J=16.9, 10.0, 8.3, 6.6 Hz, 1H), 5.26 (br d, J=16.6 Hz, 1H), 5.14 (dd, J=10.0, 2.2 Hz, 1H), 4.76 (d, J=11.0 Hz, 1H), 3.97 (td, J=10.3, 6.8 Hz, 1H), 2.51 (m, 2H), 2.76 (dd, J=9.5, 4.4 Hz), 2.65 (dd, J=13.7, 8.3 Hz, 1H), 2.50 (m, obscured by solvent), 2.07 (t, J=13.5 Hz, 1H), 1.75 (dd, J=13.2, 3.0 Hz, 1H), 1.12 (s, 3H), 0.63 (s, 9H); Mass Spectrum (ESI) m/z=474.2 (M+1).

Step B. 2-((3R,5R,6S)-5-(3-Chlorophenyl)-6-(4-chlorophenyl)-1-((S)-1-(isopropylsulfonyl)-3,3-dimethylbutan-2-yl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-hydroxy-3,3-dimethylbutan-2-yl)-3-methylpiperidin-2-one (Example 365, step A) by a procedure similar to the one described in Example 300, replacing benzenethiol with the appropriate amount of propane-2-thiol.

¹H-NMR (500 MHz, DMSO-d₆) δ ppm 12.36 (s, 1H), 7.81 (br s, 1H), 7.48 (br s, 1H), 7.25 (br s, 1H), 7.22 (t, J=7.8 Hz, 1H), 7.15 (ddd, J=7.8, 2.0, 0.7 Hz, 1H), 7.04 (t, J=1.7 Hz, 1H), 7.00 (br d, J=7.8 Hz, 1H), 5.05 (d, J=11.2 Hz, 1H), 3.90 (dd, J=13.7, 11.0, 2.6 Hz, 1H), 3.70 (ddd, J=13.7, 11.0, 2.6 Hz, 1H), 3.45 (m, 2H), 3.12 (dd, J=13.4, 2.0, 1H), 2.97 (d, J=13.9 Hz, 1H), 2.52 (m, obscured by solvent), 2.14 (t, J=13.2 Hz, 1H), 2.03 (dd, J=13.4 Hz, 1H), 1.32 (d, J=6.8 Hz, 3H), 1.31 (d, J=6.6 Hz, 3H), 1.23 (s, 3H), 0.62 (s, 9H); Mass Spectrum (ESI) m/z=582.2 (M+1).

Example 366

2-((3R,5R,6S)-5-(3-Chlorophenyl)-6-(4-chlorophenyl)-1-((S)-1-cyclopropyl-2-(pentan-3-ylsulfonyl)ethyl)-3-methyl-2-oxopiperidin-3-yl)acetic acid

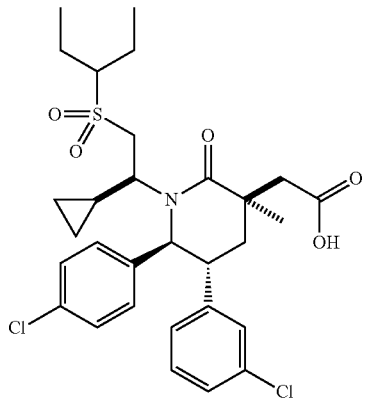 [SMILES: CCC(CC)S(=O)(=O)C[C@H](C1CC1)N1C(=O)[C@@](C)(CC(=O)O)C[C@H](c2cccc(Cl)c2)[C@H]1c1ccc(Cl)cc1]

Step A. (3S,5R,6S)-3-allyl-5-(3-chlorophenyl)-6-(4-chlorophenyl)-1-((S)-1-cyclopropyl-2-mercaptoethyl)-3-methylpiperidin-2-one

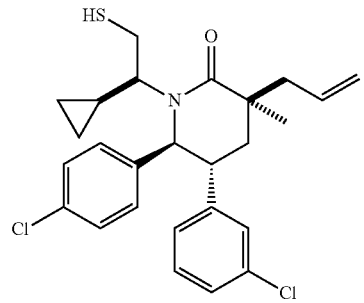 [SMILES: C=CC[C@@]1(C)C[C@H](c2cccc(Cl)c2)[C@@H](c2ccc(Cl)cc2)N([C@H](CS)C2CC2)C1=O]

To a solution of (3S,5S,6R,8S)-8-allyl-6-(3-chlorophenyl)-5-(4-chlorophenyl)-3-cyclopropyl-8-methyl-2,3,5,6,7,8-hexahydrooxazolo[3,2-a]pyridin-4-ium methanesulfonate (370 mg; Example 349, Step A) in DMF (1.6 mL) was added sodium hydrogensulfide (105 mg, 1.88 mmol). After being stirred at rt overnight, the reaction was quenched (sat. aq. NH₄Cl solution), extracted (2×EtOAc) and the combined organics were washed with brine (3×). The combined organic layers were dried (Na₂SO₄) and concentrated under the reduced pressure. Purification of the residue by chromatography on silica gel (24 g SiO₂, gradient elution of 10% to 40% EtOAc in hex) provided the title compound.

Step B. (3S,5R,6S)-3-allyl-5-(3-chlorophenyl)-6-(4-chlorophenyl)-1-((S)-1-cyclopropyl-2-(pentan-3-ylthio)ethyl)-3-methylpiperidin-2-one

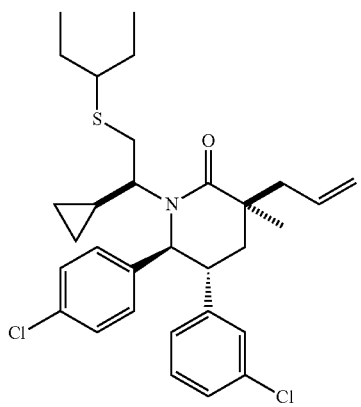 [SMILES: C=CC[C@@]1(C)C[C@H](c2cccc(Cl)c2)[C@@H](c2ccc(Cl)cc2)N([C@H](CSC(CC)CC)C2CC2)C1=O]

To a solution of (3S,5R,6S)-3-allyl-5-(3-chlorophenyl)-6-(4-chlorophenyl)-1-((S)-1-cyclopropyl-2-mercaptoethyl)-3-methylpiperidin-2-one (49 mg, 0.10 mmol; Example 366, Step A) and 3-bromopentane (51 μl, 0.41 mmol) in DMF (0.52 mL) was added 60% sodium hydride in mineral oil (17 mg, 0.41 mmol) at 25° C. The reaction was stirred at 25° C. for 1 h and then heated to 60° C. After being stirred at 60° C. overnight, the reaction was quenched (10% aq. citric acid), extracted (2×EtOAc), and washed (3× brine). The combined organic layers were dried (Na₂SO₄) and concentrated under reduced pressure. Purification of the residue by chromatography on silica gel (4 g SiO₂, 9% and 18% EtOAc/hex) provided the title compound.

Step C. 2-((3R,5R,6S)-5-(3-chlorophenyl)-6-(4-chlorophenyl)-1-((S)-1-cyclopropyl-2-(pentan-3-ylsulfonyl)ethyl)-3-methyl-2-oxopiperidin-3-yl)acetic acid The title compound was prepared from (3S,5R,6S)-3-allyl-5-(3-chlorophenyl)-6-(4-chlorophenyl)-1-((S)-1-cyclopropyl-2-(pentan-3-ylthio)ethyl)-3-methylpiperidin-2-one (Example 366, Step B) by procedures similar to the one described in Example 71, Step F.

¹H NMR (400 MHz, CHLOROFORM-d) δ ppm 7.20-7.34 (3 H, m), 7.06-7.16 (3 H, m), 6.93-6.98 (1 H, s), 6.83-6.90 (1 H, m), 4.93 (1 H, d, J=10.6 Hz), 4.35 (1 H, br, s), 3.05-3.20 (2 H, m), 2.65-2.92 (4 H, m), 2.46 (1 H, t, J=13.8 Hz), 1.92-2.11 (2 H, m), 1.75-1.91 (4 H, m), 1.50 (3 H, s), 1.06-1.19 (6 H, m), 0.32-0.42 (1 H, m), 0.18-0.28 (1 H, m), −0.35-−0.25 (1 H, m), −1.12-−1.02 (1 H, m); Mass Spectrum (ESI) m/z=594.2 [M+H]⁺.

Example 367

2-((3R,5R,6S)-5-(3-Chlorophenyl)-6-(4-chlorophenyl)-1-((S)-1-((S)-isopropylsulfinyl)butan-2-yl)-3-methyl-2-oxopiperidin-3-yl)acetic acid or 2-((3R,5R,6S)-5-(3-Chlorophenyl)-6-(4-chlorophenyl)-1-((S)-1-((R)-isopropylsulfinyl)butan-2-yl)-3-methyl-2-oxopiperidin-3-yl)acetic acid; more polar isomer

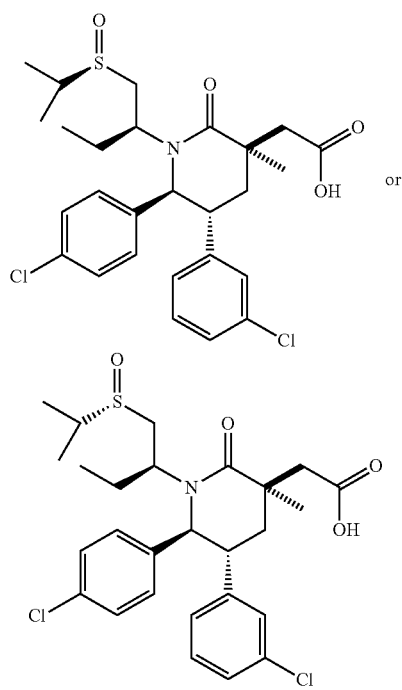

Step A. Methyl 2-((3R,5R,6S)-5-(3-chlorophenyl)-6-(4-chlorophenyl)-1-((S)-1-(isopropylthio)butan-2-yl)-3-methyl-2-oxopiperidin-3-yl)acetate

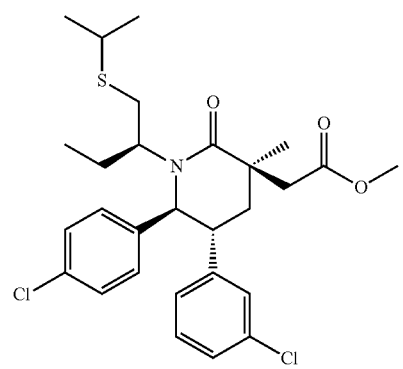 [SMILES: CC[C@@H](CSC(C)C)N1C(=O)[C@@](C)(CC(=O)OC)C[C@H](c2cccc(Cl)c2)[C@H]1c1ccc(Cl)cc1]

The above compound was obtained from methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (Example 186, Step A, 187 mg, 0.391 mmol) and propane-2-thiol (119 mg, 1.56 mmol) by a procedure similar to the one described in Example 300, Step A, using the appropriate amount of propanethiol and reacting for a total of 3 h. Purification of the residue by chromatography on silica gel (12 g, SiO$_2$, 5% to 20% EtOAc/Hex) provided the title compound as a pale yellow oil.

$^1$H NMR (400 MHz, CHLOROFORM-d) δ ppm 7.22 (d, J=8.4 Hz, 2H), 7.05-7.18 (m, 2H), 7.02 (t, J=1.7 Hz, 2H), 6.79 (td, J=1.4, 7.4 Hz, 1H), 4.66 (d, J=10.6 Hz, 1H), 3.70 (s, 3H), 3.41 (dd, J=11, 12.7 Hz, 1H), 3.16 (ddd, J=3.1, 10.6, 13.6 Hz, 1H), 2.82-2.94 (m, 2H), 2.67-2.79 (m, 2H), 2.57 (dd, J=4.1, 12.9 Hz, 1H), 2.16-2.27 (m, 1H), 1.97-2.12 (m, 2H), 1.57 (ddd, J=3.8, 7.8, 14. Hz, 1H), 1.41 (d, J=6.9 Hz, 3H), 1.29-1.34 (m, 5H), 0.49 (d, J=15.3 Hz, 3H); Mass Spectrum (ESI) m/z=558.1 [M−H]$^−$, 560.1 [M+H]$^+$.

Step B. Methyl 2-((3R,5R,6S)-5-(3-chlorophenyl)-6-(4-chlorophenyl)-1-((S)-1-((S)-isopropylsulfinyl)butan-2-yl)-3-methyl-2-oxopiperidin-3-yl)acetate and methyl 2-((3R,5R,6S)-5-(3-chlorophenyl)-6-(4-chlorophenyl)-1-((S)-1-((R)-isopropylsulfinyl)butan-2-yl)-3-methyl-2-oxopiperidin-3-yl)acetate

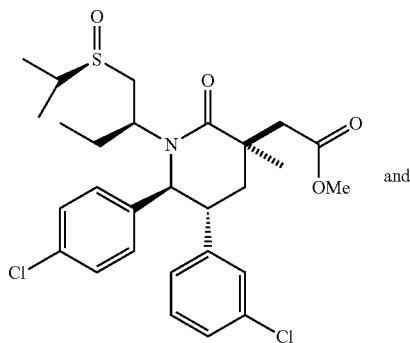

and

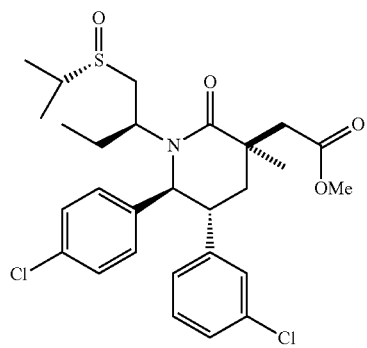

3-Chlorobenzoperoxoic acid (45.4 mg, 0.203 mmol) was added to a solution of methyl 2-((3R,5R,6S)-5-(3-chlorophenyl)-6-(4-chlorophenyl)-1-((S)-1-(isopropylthio)butan-2-yl)-3-methyl-2-oxopiperidin-3-yl)acetate (136 mg, 0.253 mmol; Example 367, Step A) in DCM (3 mL) at 0° C. After 1 h at 0° C. the reaction was monitored by LCMS (MS (ESI) 552.2 [M+H]$^+$, 554.0 [M−H]$^−$) showing 60% conversion. At this time an additional 0.2 eq. of 3-chorobenzoperoxoic acid was added. The reaction was monitored again after 2 hours showing 85% conversion and was quenched at this time with sat. aq. NaHCO$_3$ solution. The solution was extracted with EtOAc and the combined organic layers were washed with brine dried over MgSO$_4$, filtered and the filtrate was concentrated. The residue was purified by chromatography on silica gel (12 g, SiO$_2$, 10-60% EtOAc/hexane, 50 min) to give the title compounds as a 2:1 mixture of diatereomers, as a pale yellow oil.

$^1$H NMR (400 MHz, CHLOROFORM-d) δ ppm 7.20-7.29 (m, 4H), 7.20-7.26 (m, 2H), 7.19-7.20 (m, 1H), 7.04-7.20 (m, 6H), 6.95-7.02 (m, 2H), 6.82-6.95 (m, 2H), 4.75-4.90 (m, 1H), 3.62-3.74 (m, 5H), 3.37-3.48 (m, 1H), 3.07-3.32 (m, 3H), 2.59-2.95 (m, 6H), 1.93-2.33 (m, 5H), 1.47-1.74 (m, 3H), 1.22-1.42 (m, 17H), 0.79-0.95 (m, 2H), 0.37-0.56 (m, 4H); Mass Spectrum (ESI) m/z=552.2[M−H]$^−$, 554.0 [M+H]$^+$.

Step C. 2-((3R,5R,6S)-5-(3-Chlorophenyl)-6-(4-chlorophenyl)-1-((S)-1-((S)-isopropylsulfinyl)butan-2-yl)-3-methyl-2-oxopiperidin-3-yl)acetic acid or 2-((3R,5R,6S)-5-(3-Chlorophenyl)-6-(4-chlorophenyl)-1-((S)-1-((R)-isopropylsulfinyl)butan-2-yl)-3-methyl-2-oxopiperidin-3-yl)acetic acid; more polar isomer To a solution of methyl 2-((3R,5R,6S)-5-(3-chlorophenyl)-6-(4-chlorophenyl)-1-((S)-1-((S)-isopropylsulfinyl)butan-2-yl)-3-methyl-2-oxopiperidin-3-yl)acetate and methyl 2-((3R,5R,6S)-5-(3-chlorophenyl)-6-(4-chlorophenyl)-1-((S)-1-((R)-isopropylsulfinyl)butan-2-yl)-3-methyl-2-oxopiperidin-3-yl)acetate (100 mg, 0.181 mmol, as a 2:1 mixture of isomers; Example 267, Step B) in MeOH/THF/H$_2$O (1 mL/2 mL/1 mL) was added lithium hydroxide (43.3 mg, 1.810 mmol). The reaction mixture was allowed to stir for 18 h. After this period, the reaction mixture was acidified with 1N HCl and extracted with EtOAc (3×10 mL). The organics were pooled, washed with brine, dried (MgSO$_4$), filtered and concentrated in vacuo. The crude material was purified by reverse-phase preparative HPLC (Gemini™ Prep C$_{18}$ 5 mm column; Phenomenex, Torrance, Calif.; gradient elution of 25% to 55% MeCN in water, where both solvents contain 0.1% TFA, 30 min method) to provide one of the title compounds as the more polar isomer (t$_R$=21.45 min)

$^1$H NMR (400 MHz, CHLOROFORM-d) δ ppm 7.22 (d, J=8.0 Hz, 2H), 7.00-7.17 (m, 4H), 6.80-6.98 (m, 2H), 4.80 (d, J=10.8 Hz, 1H), 3.53-3.73 (m, 1H), 3.11-3.30 (m, 2H), 2.68-3.00 (m, 4H), 1.97-2.29 (m, 3H), 1.40-1.54 (m, 4H), 1.36 (d, J=6.9 Hz, 3H), 1.28 (d, J=6.9 Hz, 3H), 0.41 (t, J=7.5 Hz, 3H); Mass Spectrum (ESI) 538.2 [M−H]$^−$, 540.2 [M+H]$^+$.

Further elution from Example 367 provided the less polar isomer:

Example 368

2-((3R,5R,6S)-5-(3-Chlorophenyl)-6-(4-chlorophenyl)-1-((S)-1-((S)-isopropylsulfinyl)butan-2-yl)-3-methyl-2-oxopiperidin-3-yl)acetic acid or 2-((3R,5R,6S)-5-(3-Chlorophenyl)-6-(4-chlorophenyl)-1-((S)-1-((R)-isopropylsulfinyl)butan-2-yl)-3-methyl-2-oxopiperidin-3-yl)acetic acid;

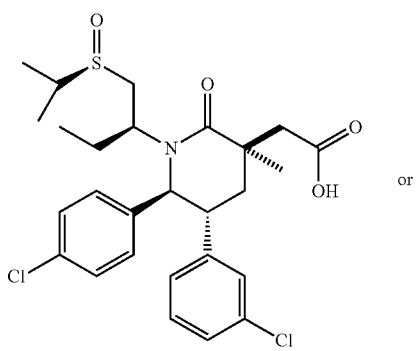

or

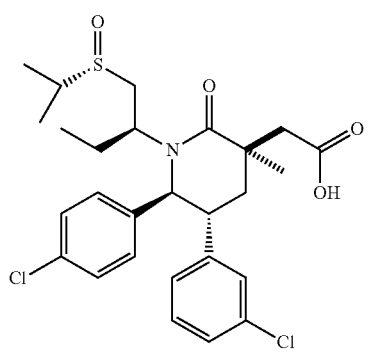

Less polar isomer ($t_R$=21.45 min).

$^1$H NMR (400 MHz, CHLOROFORM-d) δ ppm 7.23-7.27 (m, 2H), 7.10 (td, J=7.9, 15.7 Hz, 4H), 6.96 (s, 1H), 6.81 (d, J=7.4 Hz, 1H), 4.75 (s, 1H), 3.07-3.54 (m, 3H), 2.70-3.01 (m, 3H), 2.58 (d, J=10.4 Hz, 1H), 2.27-2.40 (m, 1H), 2.01-2.17 (m, 1H), 1.95 (dd, J=2.6, 13.8 Hz, 1H), 1.55-1.69 (m, 1H), 1.46 (s, 3H), 1.23-1.35 (m, 6H), 0.52 (d, J=14.3 Hz, 3H); Mass Spectrum (ESI) m/z=538.2 [M−H]⁻, 540.2 [M+H]⁺.

Example 369

2-((3R,5R,6S)-5-(3-Chlorophenyl)-6-(4-chlorophenyl)-3-methyl-1-((2S,3S)-2-(methylsulfonyl)pentan-3-yl)-2-oxopiperidin-3-yl)acetic acid or 2-((3R,5R,6S)-5-(3-Chlorophenyl)-6-(4-chlorophenyl)-3-methyl-1-((2R,3S)-2-(methylsulfonyl)pentan-3-yl)-2-oxopiperidin-3-yl)acetic acid

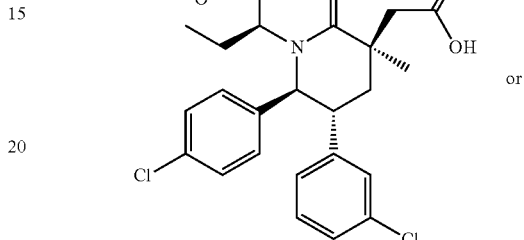

or

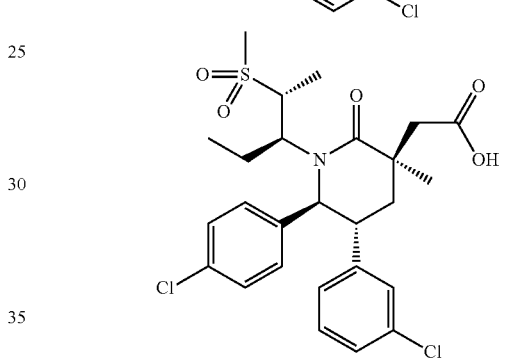

Step A. (3S,5S,6R,8S)-8-Allyl-6-(3-chlorophenyl)-5-(4-chlorophenyl)-3-ethyl-2,8-dimethyl-2,3,5,6,7,8-hexahydrooxazolo[3,2-a]pyridin-4-ium 4-methylbenzenesulfonate

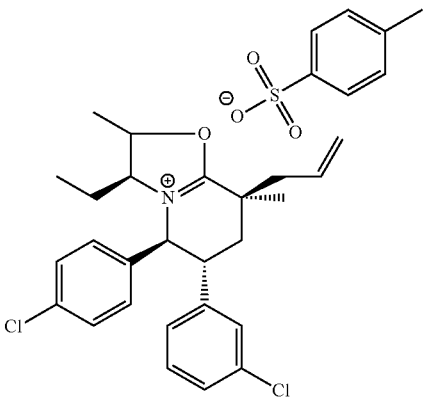 [SMILES: C=CC[C@@]1(C)C[C@H](c2cccc(Cl)c2)[C@@H](c2ccc(Cl)cc2)[N+]2=C1OC(C)[C@@H]2CC ; Cc1ccc(S(=O)(=O)[O-])cc1]

To a solution of (3S,5R,6S)-3-allyl-5-(3-chlorophenyl)-6-(4-chlorophenyl)-1-((3S)-2-hydroxypentan-3-yl)-3-methylpiperidin-2-one (2.25 g, 4.89 mmol; Example 151, Step C)

in toluene (65 mL) was added p-toluenesulfonic acid monohydrate (930 mg, 4.89 mmol). After being heated to reflux using a Dean-Stark trap for 2.5 h, the reaction was concentrated under reduced pressure to provide the title compound as a pale yellow powder.

Step B. (3S,5R,6S)-3-Allyl-5-(3-chlorophenyl)-6-(4-chlorophenyl)-3-methyl-1-((2S,3S)-2-(methylsulfonyl)pentan-3-yl)piperidin-2-one and (3S,5R,6S)-3-Allyl-5-(3-chlorophenyl)-6-(4-chlorophenyl)-3-methyl-1-((2R,3S)-2-(methylsulfonyl)pentan-3-yl)piperidin-2-one

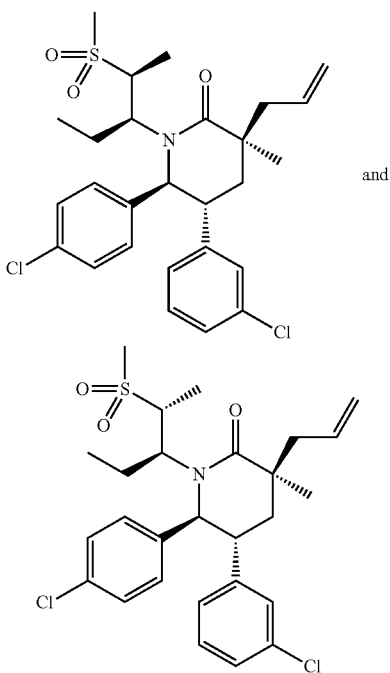

and

The reaction was set in a high pressure reaction vessel. To a solution of (3S,5S,6R,8S)-8-allyl-6-(3-chlorophenyl)-5-(4-chlorophenyl)-3-ethyl-2,8-dimethyl-2,3,5,6,7,8-hexahydrooxazolo[3,2-a]pyridin-4-ium 4-methylbenzenesulfonate (0.200 g, 0.325 mmol; Example 370, step A) in acetonitrile (2 ml) was added sodium methanesulfinate (0.166 g, 1.627 mmol) at 25° C. Then the reaction was heated to 110° C. for 24 h. The reaction was quenched with sat. aq. NH$_4$Cl solution, extracted (2×EtOAc) and washed (2× brine). The combined organic layers were dried (Na$_2$SO$_4$) and concentrated under reduced pressure. Purification by chromatography on silica gel (40 g SiO$_2$, gradient elution, 20% to 40% EtOAc in hexanes) provided the title compounds as a mixture of two stereoisomers.

Step C. 2-((3R,5R,6S)-5-(3-Chlorophenyl)-6-(4-chlorophenyl)-3-methyl-1-((2S,3S)-2-(methylsulfonyl)pentan-3-yl)-2-oxopiperidin-3-yl)acetic acid or 2-((3R,5R,6S)-5-(3-Chlorophenyl)-6-(4-chlorophenyl)-3-methyl-1-((2R,3S)-2-(methylsulfonyl)pentan-3-yl)-2-oxopiperidin-3-yl)acetic acid The title compound was obtained from a mixture of 3S,5R,6S)-3-allyl-5-(3-chlorophenyl)-6-(4-chlorophenyl)-3-methyl-1-((2S,3S)-2-(methylsulfonyl)pentan-3-yl)piperidin-2-one and (3S,5R,6S)-3-allyl-5-(3-chlorophenyl)-6-(4-chlorophenyl)-3-methyl-1-((2R,3S)-2-(methylsulfonyl)pentan-3-yl)piperidin-2-one (Example 370, Step B) by a procedure similar to the one described in Example 71, Step F. The crude product was purified by reversed phase preparatory HPLC (Gemini™ Prep C$_{18}$ 5 µm column; Phenomenex, Torrance, Calif.; eluent: 40 to 60% acetonitrile, water, 0.1% TFA, gradient elution) to provide the title compound as the first eluting isomer as a single stereoisomer.

$^1$H NMR (400 MHz, CHLOROFORM-d) δ ppm 0.46 (t, J=7.5 Hz, 3 H) 1.55 (s, 3 H) 1.60 (d, J=7.2 Hz, 3 H) 1.78-1.81 (m, 1 H) 1.84-1.93 (m, 1 H) 2.29-2.43 (m, 2 H) 2.72 (d, J=15.5 Hz, 1 H) 2.93 (s, 3 H) 2.97-3.09 (m, 2 H) 3.14 (m, 1 H) 3.53 (m, 1 H) 5.00 (d, J=10.6 Hz, 1 H) 6.82 (m, 1 H) 6.92-6.97 (m, 1 H) 7.07-7.18 (m, 2 H), 7.27 (m, 4 H);

Mass Spectrum (ESI) m/z=540 (M+1).

Example 370

2-((3R,5R,6S)-5-(3-Chlorophenyl)-6-(4-chlorophenyl)-1-((2S,3S)-2-(ethylsulfonyl)pentan-3-yl)-3-methyl-2-oxopiperidin-3-yl)acetic acid or 2-((3R,5R,6S)-5-(3-Chlorophenyl)-6-(4-chlorophenyl)-1-((2R,3S)-2-(ethylsulfonyl)pentan-3-yl)-3-methyl-2-oxopiperidin-3-yl)acetic acid; first eluting isomer

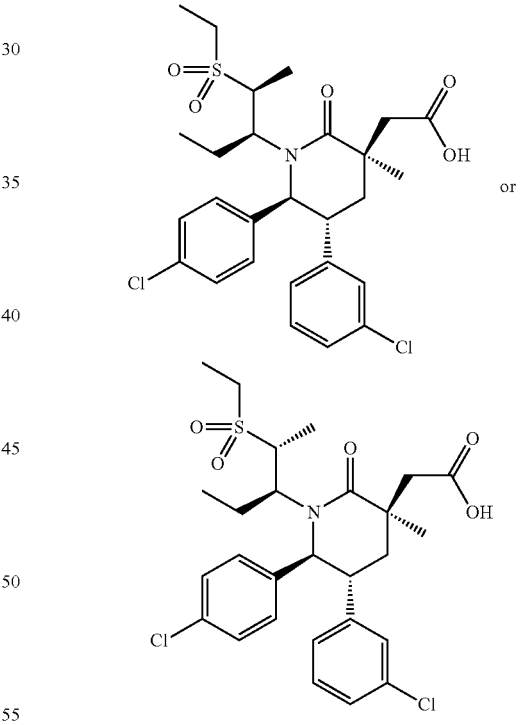

or

The title compound was prepared from (3S,5S,6R,8S)-8-allyl-6-(3-chlorophenyl)-5-(4-chlorophenyl)-3-ethyl-2,8-dimethyl-2,3,5,6,7,8-hexahydrooxazolo[3,2-a]pyridin-4-ium 4-methylbenzenesulfonate (Example 369, Step A) by a procedure similar to the one described in Example 369, replacing sodium methanesulfinate in step B with sodium ethanesulfinate. The crude product was purified by reversed phase preparatory HPLC (Gemini™ Prep C$_{18}$ 5 mm column; Phenomenex, Torrance, Calif.; eluent: 40 to 60% acetonitrile, water, 0.1% TFA, gradient elution) to provide the title compound as the first eluting isomer as a single stereoisomer.

¹H NMR (400 MHz, CHLOROFORM-d) δ ppm 0.45 (t, J=7.53 Hz, 3 H) 1.41 (t, J=7.53 Hz, 3 H) 1.48-1.62 (m, 6 H) 1.69-1.92 (m, 2 H) 2.29-2.43 (m, 2 H) 2.70 (d, J=15.45 Hz, 1 H) 2.92-3.19 (m, 5 H) 3.49-3.56 (m, 1 H) 5.02 (d, J=10.56 Hz, 1 H) 6.84 (dt, J=6.99, 1.88 Hz, 1 H) 6.95 (t, J=1.96 Hz, 1 H) 7.08-7.19 (m, 3 H) 7.25 (br s, 3 H); Mass Spectrum (ESI) m/z=554 (M+1).

Further elution provided:

Example 371

2-((3R,5R,6S)-5-(3-Chlorophenyl)-6-(4-chlorophenyl)-1-((2R,3S)-2-(ethylsulfonyl)pentan-3-yl)-3-methyl-2-oxopiperidin-3-yl)acetic acid or 2-((3R,5R,6S)-5-(3-Chlorophenyl)-6-(4-chlorophenyl)-1-((2S,3S)-2-(ethylsulfonyl)pentan-3-yl)-3-methyl-2-oxopiperidin-3-yl)acetic acid; second eluting isomer

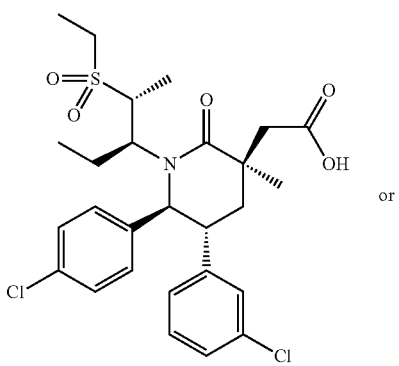

or

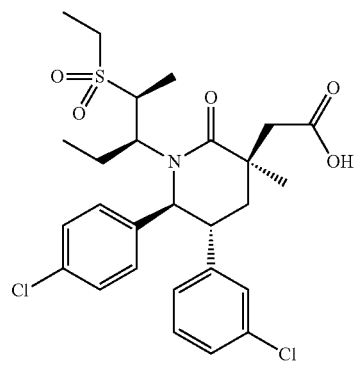

The title compound was obtained in Example 370 as the second eluting isomer.

¹H NMR (400 MHz, CHLOROFORM-d) δ ppm 0.20 (t, J=7.63 Hz, 3 H) 1.12-1.30 (m, 3 H) 1.30-1.45 (m, 6 H) 1.45-1.60 (m, 1 H) 1.71-1.80 (m, 1 H) 1.85-1.98 (m, 1 H) 2.40 (t, J=13.79 Hz, 1 H) 2.63 (d, J=15.26 Hz, 1 H) 2.86-3.09 (m, 5 H) 4.05-4.19 (m, 1 H) 4.93 (d, J=10.76 Hz, 1 H) 6.78 (dt, J=6.90, 1.93 Hz, 1 H) 6.89 (t, J=1.96 Hz, 1 H) 6.95-7.11 (m, 4 H) 7.11-7.25 (m, 2 H); Mass Spectrum (ESI) m/z=554 (M+1).

Example 372

2-((3R,5R,6S)-5-(3-Chlorophenyl)-6-(4-chlorophenyl)-3-methyl-1-((S)-1-(N-(oxetan-3-yl)sulfamoyl)butan-2-yl)-2-oxopiperidin-3-yl)acetic acid

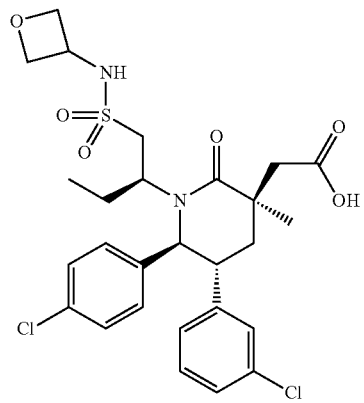 [SMILES: CC[C@@H](CS(=O)(=O)NC1COC1)N1C(=O)[C@@](C)(CC(=O)O)C[C@H](c2cccc(Cl)c2)[C@H]1c1ccc(Cl)cc1]

Step A. Methyl 2-((3R,5R,6S)-1-((S)-1-(benzylthio)butan-2-yl)-5-(3-chlorophenyl)-6-(4-chlorophenyl)-3-methyl-2-oxopiperidin-3-yl)acetate

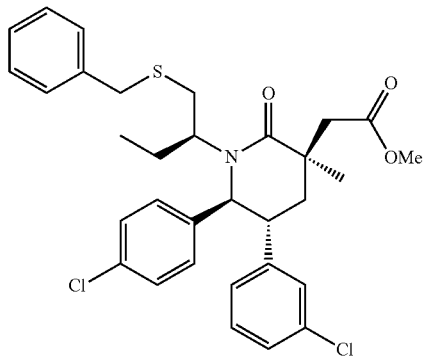 [SMILES: CC[C@@H](CSCc1ccccc1)N1C(=O)[C@@](C)(CC(=O)OC)C[C@H](c2cccc(Cl)c2)[C@H]1c1ccc(Cl)cc1]

To a solution of methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (214.4 mg, 0.448 mmol; Example 186, Step A) in toluene (2.0 mL) was added benzyl mercaptan (0.106 mL, 0.90 mmol), followed by cyanomethylenetributylphosphorane (0.235 mL, 0.896 mmol; TCI). The solution was heated at 100° C. for 3.75 hours, then concentrated in vacuo. Purification of the residue by chromatography on silica gel (12 g SiO$_2$, 0% to 50% EtOAc in hexanes) provided the title compound as colorless oil.

Step B. (S)-2-((3R,5R,6S)-5-(3-Chlorophenyl)-6-(4-chlorophenyl)-3-(2-methoxy-2-oxoethyl)-3-methyl-2-oxopiperidin-1-yl)butane-1-sulfonic acid

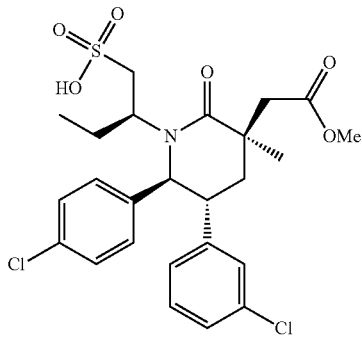 [SMILES: CC[C@@H](CS(=O)(=O)O)N1C(=O)[C@@](C)(CC(=O)OC)C[C@H](c2cccc(Cl)c2)[C@H]1c1ccc(Cl)cc1]

To a solution of methyl 2-((3R,5R,6S)-1-((S)-1-(benzylthio)butan-2-yl)-5-(3-chlorophenyl)-6-(4-chlorophenyl)-3-methyl-2-oxopiperidin-3-yl)acetate (1.31 g, 2.24 mmol; Example 372, Step A) in acetic acid (9.5 ml) and water (1.0 ml) was added hydrogen peroxide (31.3% solution in water, 0.23 ml, 2.35 mmol). The resulting solution was stirred at room temperature for 3 hours, then chlorine gas was bubbled into the reaction for one minute. After stirring at room temperature for one hour, the reaction was concentrated in vacuo, then a few mL of anhydrous benzene were added and the solvent was removed under reduced pressure on a rotary evaporator. This procedure was repeated several times to provide the title compound as a yellow solid. This crude material was used directly in the next step without purification.

Step C. Methyl 2-((3R,5R,6S)-5-(3-chlorophenyl)-6-(4-chlorophenyl)-3-methyl-1-((S)-1-(N-(oxetan-3-yl)sulfamoyl)butan-2-yl)-2-oxopiperidin-3-yl)acetate

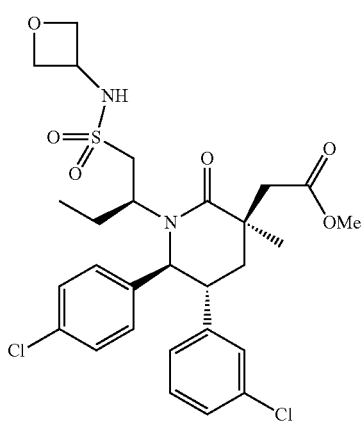 [SMILES: CC[C@@H](CS(=O)(=O)NC1COC1)N1C(=O)[C@@](C)(CC(=O)OC)C[C@H](c2cccc(Cl)c2)[C@H]1c1ccc(Cl)cc1]

To a solution of (S)-2-((3R,5R,6S)-5-(3-chlorophenyl)-6-(4-chlorophenyl)-3-(2-methoxy-2-oxoethyl)-3-methyl-2-oxopiperidin-1-yl)butane-1-sulfonic acid (189.8 mg, 0.35 mmol; Example 372, Step B) in dichloromethane (5.0 mL) was added oxalyl chloride (0.061 mL, 0.70 mmol), followed by DMF (2 drops). The reaction was stirred at room temperature for 3.5 hours, then concentrated in vacuo. The sulfonyl chloride intermediate was dissolved in dichloromethane (5.0 mL), then treated with 3-oxetanamine (50.0 mg, 0.684 mmol; Pharmablock R & D Co. Ltd., Nanjing, China) and N,N-diisopropylethylamine (0.122 mL, 0.699 mmol). After stirring at room temperature for 16 hours, the reaction was quenched with methanol (2.0 mL), then concentrated in vacuo. Purification of the residue by chromatography on silica gel (4 g SiO$_2$, 0%-50% EtOAc in hexanes) provided the title compound as a colorless oil.

Step D. 2-((3R,5R,6S)-5-(3-chlorophenyl)-6-(4-chlorophenyl)-3-methyl-1-((S)-1-(N-(oxetan-3-yl)sulfamoyl)butan-2-yl)-2-oxopiperidin-3-yl)acetic acid To a solution of methyl 2-((3R,5R,6S)-5-(3-chlorophenyl)-6-(4-chlorophenyl)-3-methyl-1-((S)-1-(N-(oxetan-3-yl)sulfamoyl)butan-2-yl)-2-oxopiperidin-3-yl)acetate (41.1 mg, 0.069 mmol; Example 372, Step C) in THF (2.0 ml) and MeOH (1.0 ml) was added 1 N lithium hydroxide (3.0 ml, 3.0 mmol). The suspension was stirred at room temperature for 15 hours, then acidified to pH 4 using 1 N HCl, and then concentrated in vacuo. Purification of the residue by chromatography on silica gel (4 g SiO$_2$, 5 to 25% gradient of a 1:6.5 MeOH/acetone mixture in hexanes) provided the title compound. The material was purified further by reversed phase preparatory HPLC (Eclipse Plus C$_1$s, 30×250 mm, 5 μm column; Agilent, Santa Clara, Calif.) (eluent: 0.1% TFA in acetonitrile/water, gradient 30% to 60% over 25 min) to provide the title compound, as a white solid.

$^1$H NMR (500 MHz, methanol-d$_4$) δ ppm 0.39 (t, J=7.5 Hz, 3 H) 1.38 (s, 3 H) 1.45-1.56 (m, 1 H) 1.91-2.01 (m, 1 H) 2.02-2.08 (m, 1 H) 2.26 (t, J=13.7 Hz, 1 H) 2.59 (d, J=13.7 Hz, 1 H) 2.88-2.99 (m, 2 H) 3.07-3.19 (m, 1 H) 3.34-3.41 (m, 2 H) 3.91-4.01 (m, 1 H) 4.55-4.66 (m, 3 H) 6.91-6.97 (m, 1 H) 7.02 (s, 1 H) 7.10-7.19 (m, 3 H) 7.28 (br s, 3 H); Mass Spectrum (ESI) m/z=583.2 [M+H]$^+$.

Examples 373 and 374 were prepared from (S)-2-((3R,5R,6S)-5-(3-chlorophenyl)-6-(4-chlorophenyl)-3-(2-methoxy-2-oxoethyl)-3-methyl-2-oxopiperidin-1-yl)butane-1-sulfonic acid (Example 372, Step B) by procedures similar to the one described in Example 372, replacing 3-oxetanamine in step B with the appropriate reagent.

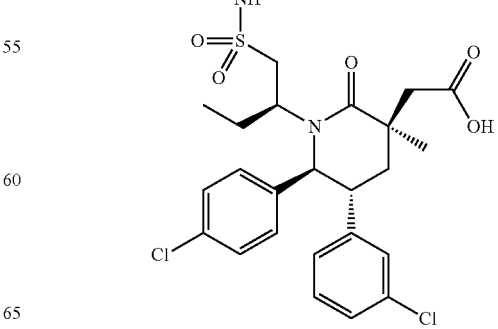

| Example | R | Reagent used |
|---------|---|--------------|
| 373 | (3-methyloxetan-3-yl group) | (3-methyloxetan-3-yl) methanamine (Pharmablock R & D Co. Ltd., Nanjing, China) |
| 374 | (oxetan-3-ylmethyl group) | oxetan-3-ylmethanamine (Pharmablock R & D Co. Ltd., Nanjing, China) |

Example 373

2-((3R,5R,6S)-5-(3-Chlorophenyl)-6-(4-chlorophenyl)-3-methyl-1-((S)-1-(N-((3-methyloxetan-3-yl)methyl)sulfamoyl)butan-2-yl)-2-oxopiperidin-3-yl) acetic acid $^1$H NMR (500 MHz, methanol-$d_4$) δ ppm 0.42 (t, J=7.58 Hz, 3 H) 1.25 (s, 2 H) 1.34 (s, 3 H) 1.39 (s, 3 H) 1.53 (ddd, J=14.24, 7.76, 3.18 Hz, 1 H) 1.97-2.08 (m, 2 H) 2.16 (s, 1 H) 2.18 (s, 1 H) 2.29 (t, J=13.69 Hz, 1 H) 2.57-2.64 (m, 1 H) 2.95 (d, J=13.45 Hz, 1 H) 3.00-3.06 (m, 1 H) 3.19 (br s, 1 H) 3.35-3.42 (m, 1 H) 4.04 (t, J=12.35 Hz, 1 H) 4.37 (d, J=6.11 Hz, 1 H) 4.54 (d, J=6.11 Hz, 1 H) 4.91 (d, J=10.76 Hz, 1 H) 6.96 (d, J=7.34 Hz, 1 H) 7.03 (s, 1 H) 7.11-7.20 (m, 3 H) 7.28 (br s, 3 H); Mass Spectrum (ESI) 611.2 [M+H]$^+$.

Example 374

2-((3R,5R,6S)-5-(3-Chlorophenyl)-6-(4-chlorophenyl)-3-methyl-1-((S)-1-(N-(oxetan-3-ylmethyl)sulfamoyl)butan-2-yl)-2-oxopiperidin-3-yl)acetic acid $^1$H NMR (500 MHz, methanol-$d_4$) δ ppm 0.41 (t, J=7.58 Hz, 3 H) 1.38 (s, 3 H) 1.46-1.59 (m, 1 H) 2.01-2.08 (m, 2 H) 2.28 (t, J=13.69 Hz, 1 H) 2.60 (d, J=13.69 Hz, 1 H) 2.94 (d, J=13.69 Hz, 1 H) 3.03 (d, J=12.47 Hz, 1 H) 3.10-3.25 (m, 3 H) 3.34-3.42 (m, 2 H) 3.95-4.07 (m, 1 H) 4.42-4.51 (m, 2 H) 4.76-4.82 (m, 2 H) 4.88-4.91 (m, 1 H) 6.95 (dt, J=7.03, 1.62 Hz, 1H) 7.00-7.04 (m, 1 H) 7.09-7.18 (m, 3 H) 7.28 (br s, 3 H); Mass Spectrum (ESI) 597.1 [M+H]$^+$.

Example 375

2-((3R,5R,6S)-1-((S)-2-(N-(tert-Butyl)sulfamoyl)-1-cyclopropylethyl)-5-(3-chlorophenyl)-6-(4-chlorophenyl)-3-methyl-2-oxopiperidin-3-yl)acetic acid

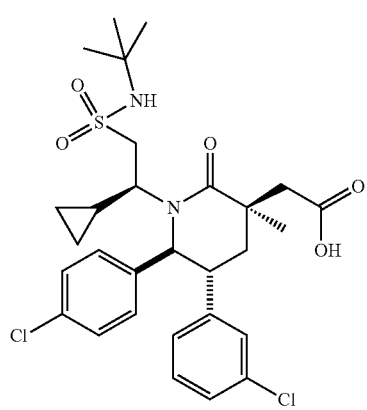

Step A. (3S,5R,6S)-3-Allyl-1-((S)-2-(benzylthio)-1-cyclopropylethyl)-5-(3-chlorophenyl)-6-(4-chlorophenyl)-3-methylpiperidin-2-one

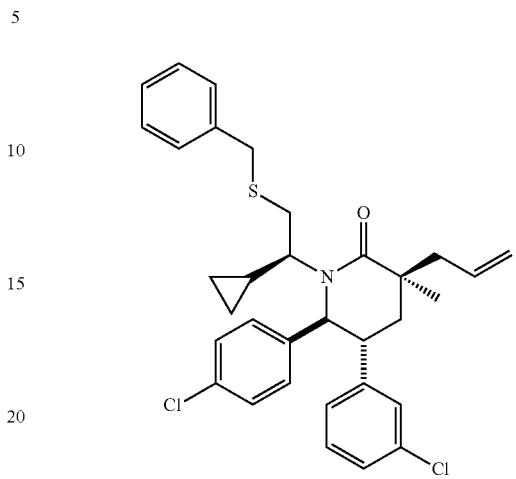

A mixture of (3S,5R,6S)-3-allyl-5-(3-chlorophenyl)-6-(4-chlorophenyl)-1-((S)-1-cyclopropyl-2-hydroxyethyl)-3-methylpiperidin-2-one (1.35 g, 2.94 mmol; Example 252, Step A), benzyl mercaptan (0.691 ml, 5.89 mmol) and 2-(tributylphosphoranylidene) in acetonitrile (1.579 ml, 5.89 mmol) was heated to 100° C. for 2 h. The reaction mixture was cooled to RT, and extracted with 80 mL of EtOAc. The combined organics were washed with sat. aq. NH$_4$Cl solution and brine, dried over Na$_2$SO$_4$, filtered and the filtrate was concentrated. The crude product was purified by chromatography on silica gel eluting with 0 to 50% EtOAc/hexane to give the title compound.

Mass Spectrum (ESI) m/z=564.1 (M+1).

Step B. 2-((3R,5R,6S)-1-((S)-2-(N-(tert-Butyl)sulfamoyl)-1-cyclopropylethyl)-5-(3-chlorophenyl)-6-(4-chlorophenyl)-3-methyl-2-oxopiperidin-3-yl)acetic acid To a solution of (3S,5R,6S)-3-allyl-1-((S)-2-(benzylthio)-1-cyclopropylethyl)-5-(3-chlorophenyl)-6-(4-chlorophenyl)-3-methylpiperidin-2-one (0.075 g, 0.133 mmol; Example 375, Step A) in 5 mL of a mixture of MeCN/HOAc/H$_2$O (40:1.5:1) at 0° C. was added portionwise 1,3-dichloro-5,5-dimethylimidazolidine-2,4-dione (0.052 g, 0.266 mmol) (Alfa Aesar, Ward Hill, Mass.). The reaction mixture was stirred at 0° C.-5° C. for 2 h. This solution was added into a mixture of tert-butylamine (97 mg, 140 µL, 5.0 eq.) and DIEA (5.0 eq.) in 2 mL of DCM at 0° C. The resulting mixture was stirred at room temperature for 3 h. The solvents were removed under reduced pressure and residue was purified by chromatography on silica gel eluting with 30 to 80% EtOAc/hexane to provide the corresponding sulfonamide. This sulfonamide was converted into the title compound by a procedure similar to the one described in Example 71, Step F. The crude product was purified by reverse phase HPLC (40 to 90% acetonitrile in water, gradient with 0.1% TFA) to give the title compound.

$^1$H NMR (400 MHz, CHLOROFORM-d) δ ppm −1.09 (br s, 1 H), −0.26 (br s, 1 H), 0.19-0.50 (m, 2 H), 1.42 (s, 9 H), 1.54 (s, 3 H), 1.88 (d, J=13.30 Hz, 2 H), 2.48 (d, J=12.32 Hz, 1 H), 2.76 (d, J=15.26 Hz, 1 H), 2.97-3.26 (m, 3 H), 4.14-4.52 (m, 2 H), 4.82 (d, J=10.76 Hz, 1 H), 6.86 (d, J=5.87 Hz, 1 H), 6.97 (s, 1 H), 7.06-7.22 (m, 3 H), 7.29 (br s, 3 H). Mass Spectrum (ESI) m/z=595.2 (M+1).

Examples 376 to 382 were prepared from (3S,5R,6S)-3-allyl-1-((S)-2-(benzylthio)-1-cyclopropylethyl)-5-(3-chlorophenyl)-6-(4-chlorophenyl)-3-methylpiperidin-2-one (Example 375, Step A) by procedures similar to the one described in Example 375, replacing tert-butylamine in step B with the appropriate reagent.

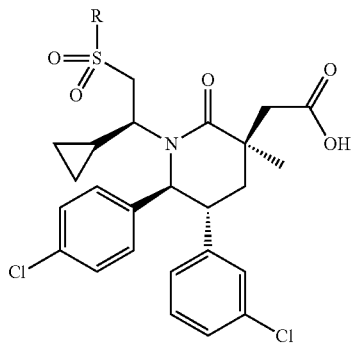

| Example | R | Reagent used |
|---|---|---|
| 376 | ⟋NH | methylamine |
| 377 | ⟋N⟍ | dimethylamine |
| 378 | (isopropyl)NH | isopropylamine |
| 379 | morpholinyl | morpholine |
| 380 | piperidinyl | piperidine |
| 381 | pyrrolidinyl | pyrrolidine |
| 382 | azetidinyl | azetidine |

Example 376

2-((3R,5R,6S)-5-(3-Chlorophenyl)-6-(4-chlorophenyl)-1-((S)-1-cyclopropyl-2-(N-methylsulfamoyl)ethyl)-3-methyl-2-oxopiperidin-3-yl)acetic acid $^1$H NMR (400 MHz, CHLOROFORM-d) δ ppm −1.13--0.88 (m, 1 H), −0.23 (br s, 1 H), 0.23-0.50 (m, 2 H), 1.51 (s, 3 H), 1.70-1.89 (m, 1 H), 2.10-2.16 (m, 1 H), 2.21-2.32 (m, 1 H), 2.40-2.51 (m, 1 H), 2.78 (d, J=15.26 Hz, 1 H), 2.84 (d, J=3.52 Hz, 3 H), 2.93-3.06 (m, 1 H), 3.07-3.23 (m, 2 H), 3.52-3.67 (m, 1 H), 4.82 (d, J=10.37 Hz, 1 H), 6.83 (d, J=7.24 Hz, 1 H), 6.96 (s, 1 H), 7.12-7.15 (m, 3 H), 7.19-7.27 (m, 3 H). Mass Spectrum (ESI) m/z=553.0. (M+1).

Example 377

2-((3R,5R,6S)-5-(3-Chlorophenyl)-6-(4-chlorophenyl)-1-((S)-1-cyclopropyl-2-(N,N-dimethylsulfamoyl)ethyl)-3-methyl-2-oxopiperidin-3-yl)acetic acid $^1$H NMR (400 MHz, CHLOROFORM-d) δ ppm −1.07 (br s, 1 H), −0.28 (br s, 1 H), 0.18-0.44 (m, 2 H), 1.53 (s, 3 H), 1.87 (dd, J=13.79, 2.84 Hz, 2H), 2.50 (t, J=13.79 Hz, 1 H), 2.60 (br s, 1H), 2.73-2.84 (m, 2 H), 2.90 (s, 6 H), 3.07-3.19 (m, 2 H), 4.19 (t, J=12.42 Hz, 1 H), 4.83 (d, J=10.56 Hz, 1 H), 6.83-6.89 (m, 1 H), 6.95 (s, 1 H), 7.07-7.16 (m, 3 H), 7.27 (br s, 3 H). Mass Spectrum (ESI) m/z=567.0 (M+1).

Example 378

2-((3R,5R,6S)-5-(3-Chlorophenyl)-6-(4-chlorophenyl)-1-((S)-1-cyclopropyl-2-(N-isopropylsulfamoyl)ethyl)-3-methyl-2-oxopiperidin-3-yl)acetic acid $^1$H NMR (400 MHz, CHLOROFORM-d) δ ppm −1.08 (br s, 1 H), −0.27 (br s, 1 H), 0.19-0.49 (m, 2 H), 1.22-1.33 (m, 6 H), 1.50 (s, 3 H), 1.67-1.99 (m, 2 H), 2.44 (br s, 1 H), 2.58 (br s, 1 H), 2.77 (d, J=14.87 Hz, 1 H), 2.98 (d, J=10.76 Hz, 1 H), 3.02-3.25 (m, 2 H), 3.64 (d, J=6.26 Hz, 1 H), 4.10-4.46 (m, 1 H), 4.81 (d, J=10.56 Hz, 1 H), 6.84 (d, J=6.46 Hz, 1 H), 6.95 (s, 1 H), 7.06-7.16 (m, 3 H), 7.27 (br s, 3 H). Mass Spectrum (ESI) m/z=581.2 (M+1).

Example 379

2-((3R,5R,6S)-5-(3-Chlorophenyl)-6-(4-chlorophenyl)-1-((S)-1-cyclopropyl-2-(morpholinosulfonyl)ethyl)-3-methyl-2-oxopiperidin-3-yl)acetic acid $^1$H NMR (400 MHz, CHLOROFORM-d) δ ppm −1.06 (br s, 1 H), −0.29 (br s, 1 H), 0.19-0.44 (m, 2 H), 1.50 (s, 3 H), 1.79-1.94 (m, 2 H), 2.47 (t, J=13.89 Hz, 1 H), 2.60 (br s, 1 H), 2.79 (d, J=15.06 Hz, 2 H), 3.08 (d, J=15.06 Hz, 1 H), 3.11-3.20 (m, 1 H), 3.24-3.30 (m, 4 H), 3.77-3.83 (m, 4 H), 4.22 (t,

Example 380

2-((3R,5R,6S)-5-(3-Chlorophenyl)-6-(4-chlorophenyl)-1-((S)-1-cyclopropyl-2-(piperidin-1-ylsulfonyl)ethyl)-3-methyl-2-oxopiperidin-3-yl)acetic acid $^1$H NMR (400 MHz, CHLOROFORM-d) δ ppm −1.09 (br s, 1 H), −0.30 (br s, 1 H), 0.20-0.43 (m, 2 H), 1.53 (s, 3 H), 1.56-1.62 (m, 2 H), 1.63-1.96 (m, 5 H), 2.00-2.13 (m, 1 H), 2.52 (t, J=13.79 Hz, 1 H), 2.60 (br s, 1 H), 2.71-2.81 (m, 2 H), 3.07-3.20 (m, 2 H), 3.24 (t, J=5.28 Hz, 4 H), 4.13 (d, J=13.11 Hz, 1 H), 4.85 (d, J=10.76 Hz, 1 H), 6.86 (d, J=7.04 Hz, 1 H), 6.94 (s, 1 H), 7.07-7.18 (m, 3 H), 7.23-7.38 (m, 3 H). Mass Spectrum (ESI) m/z=607.2 (M+1).

Example 381

2-((3R,5R,6S)-5-(3-Chlorophenyl)-6-(4-chlorophenyl)-1-((S)-1-cyclopropyl-2-(pyrrolidin-1-ylsulfonyl)ethyl)-3-methyl-2-oxopiperidin-3-yl)acetic acid $^1$H NMR (400 MHz, CHLOROFORM-d) δ ppm −1.08 (br s, 1 H), −0.28 (br s, 1 H), 0.17-0.42 (m, 2 H), 1.52 (s, 3 H), 1.81 (br s, 1 H), 1.88 (dd, J=13.79, 2.84 Hz, 1 H), 1.94-2.01 (m, 4 H), 2.50 (t, J=13.79 Hz, 1 H), 2.62 (br s, 1 H), 2.78 (d, J=15.06 Hz, 1 H), 2.86 (d, J=12.13 Hz, 1 H), 3.05-3.20 (m, 2 H), 3.28-3.45 (m, 4 H), 4.24 (br s, 1 H), 4.84 (d, J=10.56 Hz, 1 H), 6.89 (d, J=6.65 Hz, 1 H), 6.98 (s, 1 H), 7.07-7.19 (m, 3 H), 7.21-7.37 (m, 3 H). Mass Spectrum (ESI) m/z=593.0 (M+1).

Example 382

2-((3R,5R,6S)-1-((S)-2-(Azetidin-1-ylsulfonyl)-1-cyclopropylethyl)-5-(3-chlorophenyl)-6-(4-chlorophenyl)-3-methyl-2-oxopiperidin-3-yl)acetic acid $^1$H NMR (400 MHz, CHLOROFORM-d) δ ppm −1.07 (br s, 1 H), −0.28 (br s, 1 H), 0.18-0.44 (m, 2 H), 1.51 (s, 3 H), 1.80 (br s, 1 H), 1.90 (dd, J=13.79, 2.84 Hz, 1 H), 2.31 (quin, J=7.68 Hz, 2 H), 2.45 (t, J=13.79 Hz, 1 H), 2.60 (br s, 1 H), 2.74-2.82 (m, 1 H), 2.94 (d, J=13.69 Hz, 1 H), 3.07 (d, J=14.87 Hz, 1 H), 3.16 (ddd, J=13.74, 10.71, 2.74 Hz, 1 H), 3.94-4.06 (m, 4 H), 4.27 (br s, 1 H), 4.82 (d, J=10.56 Hz, 1 H), 6.81-6.88 (m, 1 H), 6.97 (m, 1 H), 7.07-7.17 (m, 3 H), 7.24-7.28 (m, 3 H). Mass Spectrum (ESI) m/z=579.0 (M+1).

Example 383

2-((3R,5R,6S)-5-(3-Chlorophenyl)-6-(4-chlorophenyl)-1-((S)-1-cyclopropyl-2-((N,N-dimethylsulfamoyl)amino)ethyl)-3-methyl-2-oxopiperidin-3-yl)acetic acid

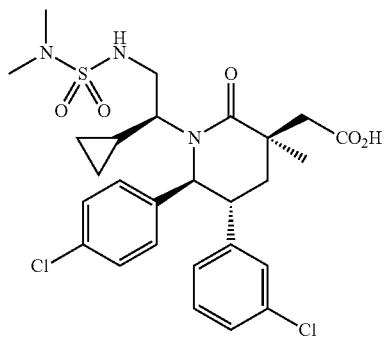 [SMILES: CN(C)S(=O)(=O)NC[C@H](C1CC1)N1C(=O)[C@@](C)(CC(=O)O)C[C@H](c2cccc(Cl)c2)[C@H]1c1ccc(Cl)cc1]

Step A. (3S,5R,6S)-5-(3-Chlorophenyl)-6-(4-chlorophenyl)-1-[(1S)-1-cyclopropyl-2-[(dimethylsulfamoyl)amino]ethyl]-3-methyl-3-(prop-2-en-1-yl)piperidin-2-one

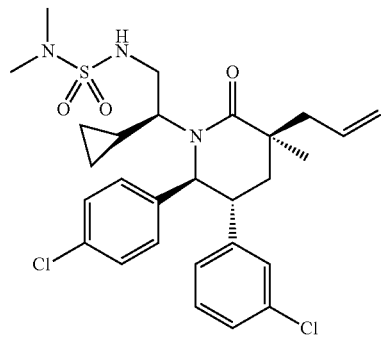 [SMILES: C=CC[C@@]1(C)C[C@H](c2cccc(Cl)c2)[C@@H](c2ccc(Cl)cc2)N([C@H](CNS(=O)(=O)N(C)C)C2CC2)C1=O]

The title compound was prepared from (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, Step A) and N,N-dimethylsulfamide (TCI America, Portland, Oreg.) following a procedure similar to the one described in Example 202, Step C.
Mass Spectrum (ESI) m/z=561.5 (M+1).

Step B. 2-((3R,5R,6S)-5-(3-Chlorophenyl)-6-(4-chlorophenyl)-1-((S)-1-cyclopropyl-2-((N,N-dimethylsulfamoyl)amino)ethyl)-3-methyl-2-oxopiperidin-3-yl)acetic acid The title compound was prepared from (3S,5R,6S)-5-(3-chlorophenyl)-6-(4-chlorophenyl)-1-[(1S)-1-cyclopropyl-2-[(dimethylsulfamoyl)amino]ethyl]-3-methyl-3-(prop-2-en-1-yl)piperidin-2-one (Example 383, Step A) following a procedure similar to the one described in Example 226, Step D.

$^1$H NMR (400 MHz, CHLOROFORM-d) δ ppm −0.34 (br s, 1H), 0.02-0.19 (m, 1H), 0.42-0.60 (m, 2H), 1.14 (br s, 1H), 1.40-1.52 (m, 4H), 2.00-2.14 (m, 1H), 2.18-2.38 (m, 1H), 2.79 (s, 6H), 2.80-2.83 (m, 1H), 2.90-3.00 (m, 1H), 3.00-3.12 (m, 1H), 3.12-3.29 (m, 2H), 3.79 (br s, 1H), 4.89 (d, J=10.2 Hz, 1H), 6.82 (d, J=7.4 Hz, 1H), 6.94-7.02 (m, 1H), 7.03-7.21 (m, 4H), 7.24-7.28 (m, 2H); Mass Spectrum (ESI) m/z=582.0 (M+1).

Example 384

2-((3R,5R,6S)-5-(3-Chlorophenyl)-6-(4-chlorophenyl)-1-((S)-1-cyclopropyl-2-((N,N-dimethylsulfamoyl)(methyl)amino)ethyl)-3-methyl-2-oxopiperidin-3-yl)acetic acid

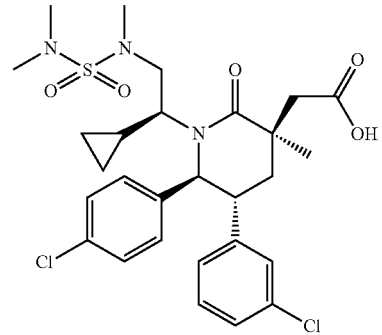 [SMILES: CN(C)S(=O)(=O)N(C)C[C@H](C1CC1)N1C(=O)[C@@](C)(CC(=O)O)C[C@H](c2cccc(Cl)c2)[C@H]1c1ccc(Cl)cc1]

Step A. (3S,5R,6S)-5-(3-Chlorophenyl)-6-(4-chlorophenyl)-1-[(1S)-1-cyclopropyl-2-[[(dimethylsulfamoyl)(methyl)amino]ethyl]-3-methyl-3-(prop-2-en-1-yl)piperidin-2-one

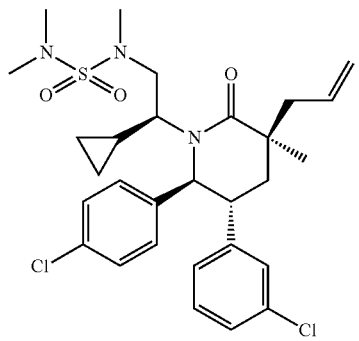 [SMILES: C=CC[C@@]1(C)C[C@H](c2cccc(Cl)c2)[C@@H](c2ccc(Cl)cc2)N([C@H](CN(C)S(=O)(=O)N(C)C)C2CC2)C1=O]

The title compound was prepared from (3S,5R,6S)-5-(3-chlorophenyl)-6-(4-chlorophenyl)-1-[(1S)-1-cyclopropyl-2-[(dimethylsulfamoyl)amino]ethyl]-3-methyl-3-(prop-2-en-1-yl)piperidin-2-one (Example 383, Step A) following a procedure similar to the one described in Example 264.

Step B. 2-((3R,5R,6S)-5-(3-Chlorophenyl)-6-(4-chlorophenyl)-1-((S)-1-cyclopropyl-2-((N,N-dimethylsulfamoyl)(methyl)amino)ethyl)-3-methyl-2-oxopiperidin-3-yl)acetic acid

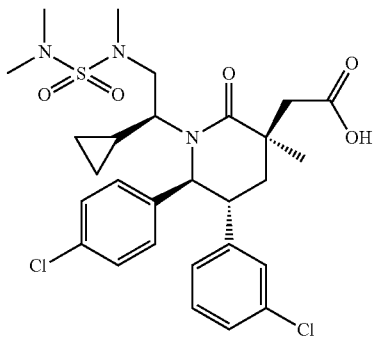 [SMILES: CN(C)S(=O)(=O)N(C)C[C@H](C1CC1)N1C(=O)[C@@](C)(CC(=O)O)C[C@H](c2cccc(Cl)c2)[C@H]1c1ccc(Cl)cc1]

The title compound was prepared from (3S,5R,6S)-5-(3-chlorophenyl)-6-(4-chlorophenyl)-1-[(1S)-1-cyclopropyl-2-[(dimethylsulfamoyl)(methyl)amino]ethyl]-3-methyl-3-(prop-2-en-1-yl)piperidin-2-one (example 384, Step A) following a procedure similar to the one described in Example 226, Step D.

¹H NMR (400 MHz, CHLOROFORM-d) δ ppm −0.76 (br s, 1H), −0.34 (br s, 1H), 0.32 (br s, 1H), 0.42 (br s, 1H), 1.43-1.61 (m, 3H), 1.62-1.84 (m, 1H), 1.94 (d, J=13.3 Hz, 2H), 2.21 (d, J=12.9 Hz, 1H), 2.44 (br s, 1H), 2.73-2.90 (m, 9H), 3.03-3.21 (m, 3H), 4.65 (br s, 6H), 4.81 (d, J=10.2 Hz, 2H), 6.83-6.96 (m, 2H), 7.00 (s, 2H), 7.08-7.18 (m, 3H), 7.25 (br s, 1H); Mass Spectrum (ESI) m/z=596.0 (M+1).

Examples 385 to 389 were prepared from (3S,5R,6S)-3-allyl-5-(3-chlorophenyl)-6-(4-chlorophenyl)-1-((S)-1-cyclopropyl-2-hydroxyethyl)-3-methylpiperidin-2-one (Example 252, step A) following procedures similar to the one described in Example 202, Step C and D, replacing N-methylcyclopropanesulfonamide in step B with the appropriate reagent.

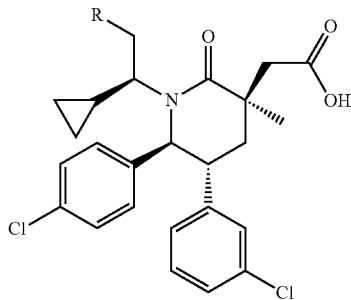

| Example | R | Reagent used |
|---|---|---|
| 385 | 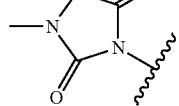 | 1-methylhydantoin (Sigma-Aldrich, St. Louis, MO) |
| 386 | 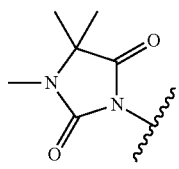 [SMILES: *N1C(=O)N(C)C(C)(C)C1=O] | 1,5,5-trimethylimidazolidine-2,4-dione (Sigma-Aldrich, St. Louis, MO)) |
| 387 | 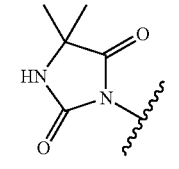 | 5,5-dimethylimidazolidine-2,4-dione (Sigma-Aldrich, St. Louis, MO) |
| 388 | 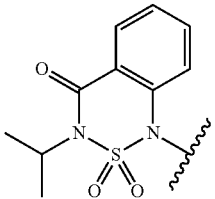 [SMILES: *N1c2ccccc2C(=O)N(C(C)C)S1(=O)=O] | bentazon (Chem Service, West Chester, PA) |
| 389 | 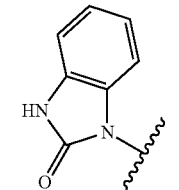 [SMILES: *n1c(=O)[nH]c2ccccc21] | 1H-benzo[d]imidazol-2(3H)-one (Sigma-Aldrich, St. Louis, MO) |

Example 385

2-((3R,5R,6S)-5-(3-Chlorophenyl)-6-(4-chlorophenyl)-1-((S)-1-cyclopropyl-2-(3-methyl-2,5-dioxoimidazolidin-1-yl)ethyl)-3-methyl-2-oxopiperidin-3-yl)acetic acid ¹H NMR (400 MHz, CHLOROFORM-d) δ ppm 0.24 (br s, 1H), 0.58 (br s, 2H), 1.12-1.36 (m, 1H), 1.36-1.55 (m, 3H), 1.99-2.11 (m, 1H), 2.11-2.26 (m, 1H), 2.71 (d, J=15.1 Hz, 1H), 3.01-3.08 (m, 4H), 3.08-3.23 (m, 2H), 3.53 (br s, 1H), 3.78-4.01 (m, 3H), 4.63 (br s, 1H), 5.58 (br s, 1H), 6.68 (d, J=7.6 Hz, 1H), 6.92-7.02 (m, 1H), 7.06-7.22 (m, 3H), (7.24-7.32 (m, 3H); Mass Spectrum (ESI) m/z=572.0 (M+1).

Example 386

2-((3R,5R,6S)-5-(3-Chlorophenyl)-6-(4-chlorophenyl)-1-((S)-1-cyclopropyl-2-(3,4,4-trimethyl-2,5-dioxoimidazolidin-1-yl)ethyl)-3-methyl-2-oxopiperidin-3-yl)acetic acid $^1$H NMR (400 MHz, CHLOROFORM-d) δ ppm 0.23 (br s, 1H), 0.56 (br s, 2H), 1.32-1.55 (m, 10H), 2.02 (dd, J=13.9, 2.7 Hz, 1H), 2.15-2.32 (m, 1H), 2.72 (d, J=15.1 Hz, 1H), 2.84-2.96 (m, 4H), 3.04-3.25 (m, 3H), 3.55 (br s, 1H), 3.87-4.10 (br s, 1H), 4.87 (br s, 1H), 6.66 (d, J=7.0 Hz, 1H), 6.99 (s, 1H), 7.08 (t, J=7.8 Hz, 2H), 7.17 (d, J=8.6 Hz, 2H), 7.28 7.32 (m, 2H); Mass Spectrum (ESI) m/z=600.0 (M+1).

Example 387

2-((3R,5R,6S)-5-(3-Chlorophenyl)-6-(4-chlorophenyl)-1-((S)-1-cyclopropyl-2-(4,4-dimethyl-2,5-dioxoimidazolidin-1-yl)ethyl)-3-methyl-2-oxopiperidin-3-yl)acetic acid $^1$H NMR (400 MHz, CHLOROFORM-d) δ ppm 0.18 (br s, 1H), 0.56 (br s, 2H), 1.37-1.52 (m, 11H), 2.05 (dd, J=13.89, 2.93 Hz, 1H), 2.20 (t, J=13.40 Hz, 1H), 2.74 (d, J=14.9 Hz, 1H), 3.05 (d, J=14.9 Hz, 1H), 3.18 (ddd, J=12.81 9.9, 3.1 Hz, 1H), 3.53 (br s, 1H), 3.99 (br s, 1H), 4.67 (br s, 1H), 5.31 (s, 1H), 5.44-5.73 (m, 5H), 6.27 (br s, 1H), 6.68 (d, J=7.4 Hz, 1H), 6.99 (s, 1H), 7.05-7.13 (m, 2H), 7.13-7.21 (m, 2H), 7.22 (br s, 1H);
Mass Spectrum (ESI) m/z=586.0 (M+1).

Example 388

2-((3R,5R,6S)-5-(3-Chlorophenyl)-6-(4-chlorophenyl)-1-((S)-1-cyclopropyl-2-(3-isopropyl-2,2-dioxido-4-oxo-3,4-dihydro-1H-benzo[c][1,2,6]thiadiazin-1-yl)ethyl)-3-methyl-2-oxopiperidin-3-yl)acetic acid $^1$H NMR (400 MHz, CHLOROFORM-d) δ ppm −0.11 (br s, 1H), 0.45 (br s, 2H), 1.22-1.34 (m, 1H), 1.43-1.66 (m, 9H), 1.95-2.14 (m, 1H), 2.21 (t, J=13.60 Hz, 1H), 2.83 (d, J=14.7 Hz, 1H), 3.07 (d, J=14.5 Hz, 1H), 3.14-3.28 (m, 1H), 3.51 (s, 3H), 3.69 (br s, 1H), 4.79 (br s, 1H), 4.95-5.12 (m, 1H), 6.78 (d, J=7.43 Hz, 1H), 6.93 (br s, 1H), 7.01 (br s, 1H), 7.04-7.20 (m, 3H), 7.28-7.31 (m, 3H), 7.39 (t, J=7.4 Hz, 1H), 7.59-7.70 (m, 1H), 8.19 (d, J=8.0 Hz, 1H); Mass Spectrum (ESI) m/z=698.0 (M+1).

Example 389

2-((3R,5R,6S)-5-(3-Chlorophenyl)-6-(4-chlorophenyl)-1-((S)-1-cyclopropyl-2-(2-oxo-2,3-dihydro-1H-benzo[d]imidazol-1-yl)ethyl)-3-methyl-2-oxopiperidin-3-yl)acetic acid $^1$H NMR (400 MHz, CHLOROFORM-d) δ ppm −0.29-−0.06 (m, 1H), 0.41 (br s, 2H), 1.32-1.43 (m, 3H), 1.43-1.60 (m, 2H), 1.64-1.94 (m, 3H), 2.75 (d, J=14.1 Hz, 1H), 2.97 (d, J=14.1 Hz, 1H), 3.11 (br s, 1H), 3.51-3.72 (m, 1H), 3.74 (m, 1H), 4.34 (s, 1H), 6.45 (br s, 1H), 6.63 (br s, 1H), 6.75 (br s, 1H), 7.01 (d, J=6.5 Hz, 2H), 7.11 (d, J=7.6 Hz, 2H), 7.15-7.27 (m, 4H), 9.55 (br s, 1H); Mass Spectrum (ESI) m/z=592.0 (M+1).

Example 390

2-((3R,5R,6S)-5-(3-Chloro-4-fluorophenyl)-6-(4-chlorophenyl)-1-isopropyl-3-methyl-2-oxopiperidin-3-yl)acetic acid

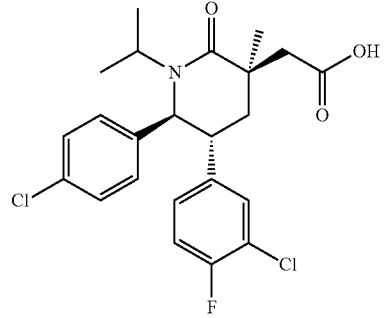 [SMILES: CC(C)N1C(=O)[C@@](C)(CC(=O)O)C[C@H](c2ccc(F)c(Cl)c2)[C@H]1c1ccc(Cl)cc1]

Step A. (5R,6S)-5-(3-Chloro-4-fluorophenyl)-6-(4-chlorophenyl)piperidin-2-one

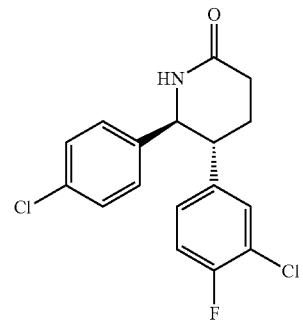 [SMILES: O=C1CC[C@H](c2ccc(F)c(Cl)c2)[C@@H](c2ccc(Cl)cc2)N1]

The title compound was prepared using 2-(3-chloro-4-fluorophenyl)acetic acid according to the procedures described in Example 1, Steps A-E. The individual enantiomers were separated by chiral HPLC (flowrate: 400 mL/min on a Varian SD-2 prep HPLC system (Wakefield, R.I.) and a MODCOL spring load column from Grace (Hesperia, Calif.) with an inner diameter of 10 cm and packed to a length of approximately 35 cm with 2.0 kg of Chiralcel® OD CSP (Chiral Technologies, Inc., West Chester, Pa., USA) using 25% isopropyl alcohol/methanol as the eluent) to give the title compound as an off-white solid. [α]$_D$=+152° (T=23° C., c=1.0, CHCl$_3$).

Step B. (4R,5S)-5-Amino-4-(3-chloro-4-fluorophenyl)-5-(4-chlorophenyl)pentanoic acid hydrochloride

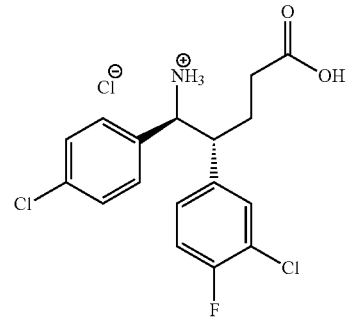 [SMILES: [NH3+][C@H](c1ccc(Cl)cc1)[C@H](CCC(=O)O)c1ccc(F)c(Cl)c1 ; [Cl-]]

A suspension of (5R,6S)-5-(3-chloro-4-fluorophenyl)-6-(4-chlorophenyl)piperidin-2-one (5.00 g, 14.78 mmol; Example 390, step A) in 5 M HCl (15 mL) was heated to reflux for seven hours. The reaction mixture was cooled to rt and diluted with toluene. The solvent was removed in vacuo and any remaining water was removed by azeotropic distillation with toluene four times to provide a white solid (5.81 g).

Step C. (5R,6S)-5-(3-Chloro-4-fluorophenyl)-6-(4-chlorophenyl)-1-isopropylpiperidin-2-one

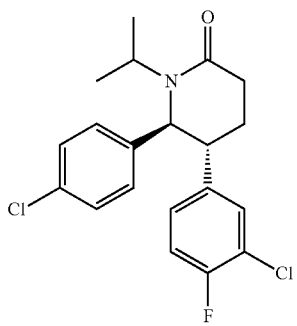 [SMILES: CC(C)N1C(=O)CC[C@H](c2ccc(F)c(Cl)c2)[C@H]1c1ccc(Cl)cc1]

Sodium triacetoxyborohydride (1.796 g, 8.48 mmol) was added to a solution of (4R,5S)-5-amino-4-(3-chloro-4-fluorophenyl)-5-(4-chlorophenyl)pentanoic acid hydrochloride (2.56 g, 6.52 mmol; Example 390, Step B) and acetone (0.491 mL, 6.68 mmol) in anhydrous DMF (6.52 mL) at rt. The reaction mixture was stirred at rt for 16 hours. Dichloroethane (25 mL) was added followed by 3 Å molecular sieves. The reaction mixture was heated to 70° C. for 22 hours, filtered and concentrated in vacuo. Purification by flash chromatography on silica gel using a 220 g column and eluting with 30 to 100% EtOAc/hexanes provided the desired product as a white solid.

Step D. (3S,5R,6S)-3-Allyl-5-(3-chloro-4-fluorophenyl)-6-(4-chlorophenyl)-1-isopropyl-3-methylpiperidin-2-one

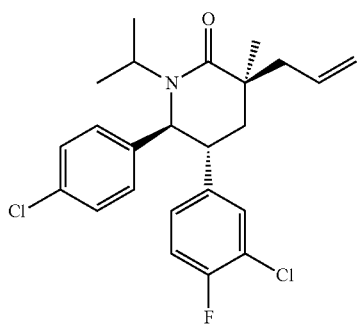 [SMILES: C=CC[C@@]1(C)C[C@H](c2ccc(F)c(Cl)c2)[C@@H](c2ccc(Cl)cc2)N(C(C)C)C1=O]

A solution of (5R,6S)-5-(3-chloro-4-fluorophenyl)-6-(4-chlorophenyl)-1-isopropylpiperidin-2-one (0.50 g, 1.32 mmol; Example 390, Step C) in anhydrous THF (3 mL) was degassed by bubbling argon through the solution for 15 minutes. LHMDS (1 M in THF that was degassed by bubbling argon through the solution for 15 minutes) (1.64 mL, 1.64 mmol) was added to the lactam solution at −15° C. dropwise while keeping the temperature below −8° C. After 15 minutes at −15° C. iodomethane (0.085 mL, 1.354 mmol) was added. Thirty five minutes later freshly prepared LDA (3.29 mmol) in THF (1 mL) was added to the reaction mixture. After 30 minutes the reaction mixture was cooled to −78° C. and allyl bromide (0.398 mL, 4.60 mmol) was added slowly while keeping the temperature at or below −68° C. The reaction mixture was allowed to warm as the cold bath warmed. After 16 hours the reaction mixture temperature was 18° C. The reaction was quenched with MeOH (0.5 mL), washed with 10 mL of 50% brine/water, brine, dried ($Na_2SO_4$), decanted and concentrated in vacuo to provide a yellow oil. Purification by flash chromatography on silica gel (eluent: 5-15% EtOAc/hexanes, gradient elution) provided the title compound.

Step E. 2-((3R,5R,6S)-5-(3-Chloro-4-fluorophenyl)-6-(4-chlorophenyl)-1-isopropyl-3-methyl-2-oxopiperidin-3-yl)acetic acid A solution of potassium permanganate (0.341 g, 2.155 mmol) in water (2 mL) was added to a solution of (3S,5R,6S)-3-allyl-5-(3-chloro-4-fluorophenyl)-6-(4-chlorophenyl)-1-isopropyl-3-methylpiperidin-2-one (0.312 g, 0.718 mmol; Example 390, step D) and tetrabutylammonium chloride hydrate (0.021 g, 0.072 mmol) in DCM (2 mL) at 0° C. After 5 minutes the reaction mixture was removed from the ice bath and stirred at rt. After 2 hours at rt the reaction mixture was diluted with aq. sodium bisulfite. This solution was filtered and then extracted with DCM three times. The combined organics were pooled, washed with 50 mL of 10% sodium bisulfite, brine, dried ($MgSO_4$), filtered and concentrated in vacuo to provide a yellow oil. Purification by flash chromatography on silica gel using a 24 g column and eluting with 0 to 50% IPA/hexanes provided fractions containing the desired product and an impurity. Upon standing over night the desired product crystallized as colorless prisms and were collected by vacuum filtration to provide the title compound.

$^1$H NMR (500 MHz, CHLOROFORM-d) δ ppm 1.25 (d, J=6.8 Hz, 3 H), 1.26 (d, J=6.8 Hz, 3 H), 1.40 (s, 3 H), 2.00 (dd, J=3.4 and 13.9 Hz, 1 H), 2.09 (dd, J=11.9 and 13.7 Hz, 1 H), 2.67 (d, J=15.4 Hz, 1 H), 3.02 (dt, J=3.2 and 9.3 Hz, 1 H), 3.03 (d, J=15.4 Hz, 1 H), 3.41 (m, 1 H), 4.41 (d, J=9.0 Hz, 1 H), 6.70-6.73 (m, 1 H), 6.95-6.99 (m, 3 H), 7.06 (dd, J=2.5 and 6.9 Hz, 1 H), 7.28 (d, J=9.5 Hz, 2 H); Mass Spectrum (ESI) m/z=452.2 [M+H]$^+$.

Example 391

2-((3R,5R,6S)-5-(3-Chloro-5-fluorophenyl)-6-(4-chlorophenyl)-1-isopropyl-3-methyl-2-oxopiperidin-3-yl)acetic acid

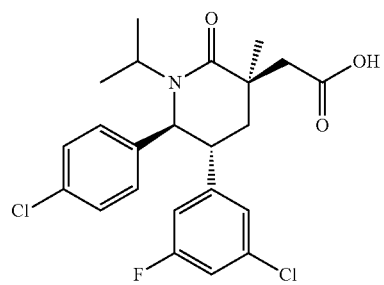 [SMILES: CC(C)N1C(=O)[C@@](C)(CC(=O)O)C[C@H](c2cc(F)cc(Cl)c2)[C@H]1c1ccc(Cl)cc1]

Step A. (5R,6S)-5-(3-Chloro-5-fluorophenyl)-6-(4-chlorophenyl)piperidin-2-one

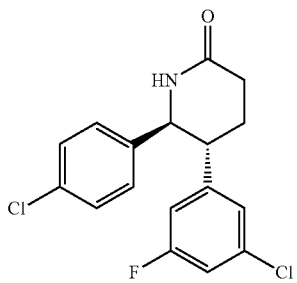 [SMILES: O=C1CC[C@H](c2cc(F)cc(Cl)c2)[C@@H](c2ccc(Cl)cc2)N1]

The title compound was prepared using 2-(3-chloro-5-fluorophenyl)acetic acid according to the procedures described in Example 1, Steps A-E. The individual enantiomers were separated by chiral HPLC (150×50 mm Chiralpak® AD-H column (Chiral Technologies, Inc., West Chester, Pa., USA) with 50 g/min methanol+(20 mM NH$_3$)+130 g/min CO$_2$ on Thar 350 SFC (Thar Technologies, Inc., Pittsburg, Pa.)). [α]$_D$=+114° (T=23° C., c=4.0, CHCl$_3$).

Step B. (4R,5S)-5-Amino-4-(3-chloro-5-fluorophenyl)-5-(4-chlorophenyl)pentanoic acid hydrochloride

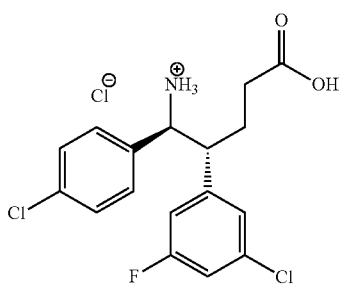 [SMILES: [NH3+][C@H](c1ccc(Cl)cc1)[C@H](CCC(=O)O)c1cc(F)cc(Cl)c1 ; [Cl-]]

The title compound was prepared from (5R,6S)-5-(3-chloro-5-fluorophenyl)-6-(4-chlorophenyl)piperidin-2-one (Example 391, Step A) using the procedure described in Example 390, Step B.

Step C. (5R,6S)-5-(3-Chloro-5-fluorophenyl)-6-(4-chlorophenyl)-1-isopropylpiperidin-2-one

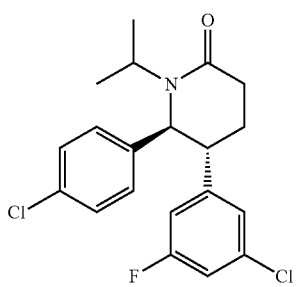 [SMILES: CC(C)N1C(=O)CC[C@H](c2cc(F)cc(Cl)c2)[C@H]1c1ccc(Cl)cc1]

The title compound was prepared from (4R,5S)-5-amino-4-(3-chloro-5-fluorophenyl)-5-(4-chlorophenyl)pentanoic acid hydrochloride (Example 391, step B) using the procedure described in Example 390, Step C.

Step D. (3S,5R,6S)-5-(3-Chloro-5-fluorophenyl)-6-(4-chlorophenyl)-1-isopropyl-3-methylpiperidin-2-one and (3R,5R,6S)-5-(3-chloro-5-fluorophenyl)-6-(4-chlorophenyl)-1-isopropyl-3-methylpiperidin-2-one

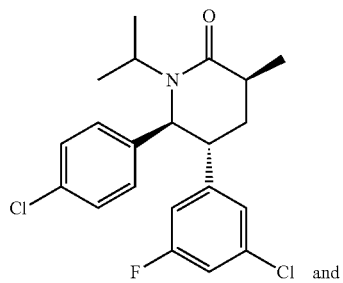

and

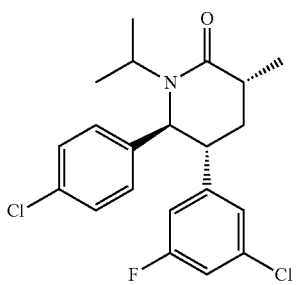

A solution of (5R,6S)-5-(3-chloro-5-fluorophenyl)-6-(4-chlorophenyl)-1-isopropylpiperidin-2-one (0.400 g, 1.052 mmol; Example 391, Step C) was dissolved in benzene and the solvent removed under a vacuum three times. The resulting oil was dissolved in anhydrous 2-methylTHF (2 mL) and was degassed by bubbling argon through the solution for 15 minutes while cooling to −15° C. LHMDS (1.0 M in THF) (1.315 ml, 1.315 mmol) was added and the solution turned yellow. After 10 minutes, iodomethane (0.069 ml, 1.104 mmol) was added dropwise while keeping the temperature below −10° C. Forty minutes later the reaction mixture was quenched with sat. aq. NH$_4$Cl and warmed to rt. The layers were separated and the aqueous layer was extracted with EtOAc twice. The organics were pooled, washed with brine, dried (Na$_2$SO$_4$), decanted and concentrated in vacuo to provide an orange oil. Purification by flash chromatography on silica gel using a 24 g column and eluting with 10 to 30% EtOAc/hexanes provided a 96:4 mixture of (3S,5R,6S)-5-(3-chloro-5-fluorophenyl)-6-(4-chlorophenyl)-1-isopropyl-3-methylpiperidin-2-one and (3R,5R,6S)-5-(3-chloro-5-fluorophenyl)-6-(4-chlorophenyl)-1-isopropyl-3-methylpiperidin-2-one as a colorless syrup.

Step E. (3S,5R,6S)-3-Allyl-5-(3-chloro-5-fluorophenyl)-6-(4-chlorophenyl)-1-isopropyl-3-methylpiperidin-2-one and (3R,5R,6S)-3-allyl-5-(3-chloro-5-fluorophenyl)-6-(4-chlorophenyl)-1-isopropyl-3-methylpiperidin-2-one

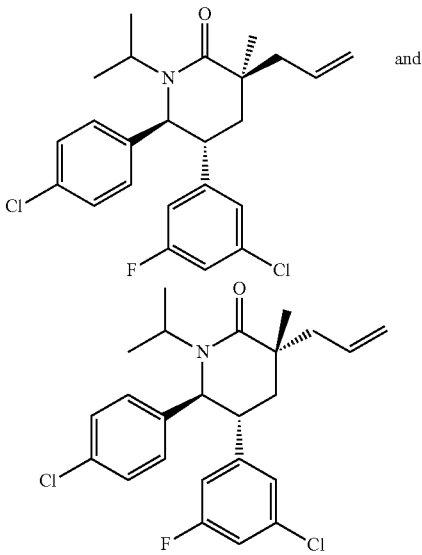

and

A solution of (3S,5R,6S)-5-(3-chloro-5-fluorophenyl)-6-(4-chlorophenyl)-1-isopropyl-3-methylpiperidin-2-one and (3R,5R,6S)-5-(3-chloro-5-fluorophenyl)-6-(4-chlorophenyl)-1-isopropyl-3-methylpiperidin-2-one (0.320 g, 0.812 mmol; Example 391, Step D) in anhydrous 2-methylTHF (1.5 mL) was degassed by bubbling argon through the solution for 15 minutes and then cooled to −15° C. Freshly prepared LDA (1.22 mmol) in 2-methyl-THF (1.5 mL) was added slowly while keeping the temperature at or below −14° C. After 30 minutes at −15° C. the reaction mixture was cooled to −74° C. and allyl bromide (0.176 ml, 2.029 mmol) was added slowly while keeping the temperature below −70° C. After 2 hours additional allyl bromide (0.176 ml, 2.029 mmol) was added and the reaction mixture was allowed to warm to rt. The reaction was quenched with sat. aq. NH₄Cl and the layers were separated. The aqueous layer was extracted with EtOAc twice and the organics were pooled, washed with brine, dried (Na₂SO₄), decanted and concentrated under a vacuum to provide a pale yellow oil. Purification by flash chromatography on silica gel using a 24 g column and eluting with 0 to 50% acetone/hexanes provided a colorless oil as a 3.3:1 mixture of (3S,5R,6S)-3-allyl-5-(3-chloro-5-fluorophenyl)-6-(4-chlorophenyl)-1-isopropyl-3-methylpiperidin-2-one and (3R,5R,6S)-3-allyl-5-(3-chloro-5-fluorophenyl)-6-(4-chlorophenyl)-1-isopropyl-3-methylpiperidin-2-one.

Step F. 2-((3R,5R,6S)-5-(3-Chloro-5-fluorophenyl)-6-(4-chlorophenyl)-1-isopropyl-3-methyl-2-oxopiperidin-3-yl)acetic acid Ruthenium(III) chloride hydrate (2.19 mg, 9.72 µmol) was added to a solution of (3S,5R,6S)-3-allyl-5-(3-chloro-5-fluorophenyl)-6-(4-chlorophenyl)-1-isopropyl-3-methylpiperidin-2-one and (3R,5R,6S)-3-allyl-5-(3-chloro-5-fluorophe-nyl)-6-(4-chlorophenyl)-1-isopropyl-3-methylpiperidin-2-one (0.192 g, 0.442 mmol; Example 391, Step E) and NaIO₄ (97 mg) in EtOAc (1 mL), ACN (1 mL) and water (2 mL) at rt. After 3 minutes NaIO₄ (97 mg) was added. The remaining two portions of NaIO₄ (97 mg each) were added after three and six minutes respectively. After 30 minutes the reaction mixture was filtered and the layers were separated. The aqueous layer was extracted with EtOAc twice and the organics were pooled, washed with 10% aq. NaHSO₃, brine, dried (Na₂SO₄), decanted and concentrated in vacuo to provide a tan oil. Purification by flash chromatography on silica gel using a 24 g column and eluting with 5 to 30% (15% MeOH/acetone)/hexanes provided a 3.3:1 mixture of 2-((3R,5R,6S)-5-(3-chloro-5-fluorophenyl)-6-(4-chlorophenyl)-1-isopropyl-3-methyl-2-oxopiperidin-3-yl)acetic acid and 2-((3S,5R,6S)-5-(3-chloro-5-fluorophenyl)-6-(4-chlorophenyl)-1-isopropyl-3-methyl-2-oxopiperidin-3-yl)acetic acid (170 mg, 85%). The individual isomers were separated by chiral HPLC (2×(250 mm×30 mm) Chiralpak® AD-H column (Chiral Technologies, Inc., West Chester, Pa., USA) with 20 g/min methanol+(20 mM NH₃)+80 g/min CO₂ on Thar 350 SFC (Thar Technologies, Inc., Pittsburg, Pa.)) to provide the title compound.

¹H NMR (400 MHz, CHLOROFORM-d) δ ppm 1.26 (d, J=6.9 Hz, 3 H), 1.27 (d, J=6.7 Hz, 3 H), 1.38 (s, 3 H), 1.99-2.11 (m, 2 H), 2.65 (d, J=15.7 Hz, 1 H), 3.02 (d, J=15.7 Hz, 1 H), 3.30 (dt, J=2.2 and 8.8 Hz, 1 H), 3.46 (m, 1 H), 4.48 (d, J=8.8 Hz, 1 H), 6.57 (dt, J=1.8 and 9.2 Hz, 1 H), 6.79 (s, 1 H), 6.97 (dt, J=2.2 and 8.4 Hz, 1 H), 6.99 (d, J=8.4 Hz, 2 H), 7.30 (d, J=8.6 Hz, 2 H); Mass Spectrum (ESI) m/z=452.2 [M+H]⁺.

Example 392

2-((3S,5R,6S)-5-(3-Chloro-5-fluorophenyl)-6-(4-chlorophenyl)-1-isopropyl-3-methyl-2-oxopiperidin-3-yl)acetic acid

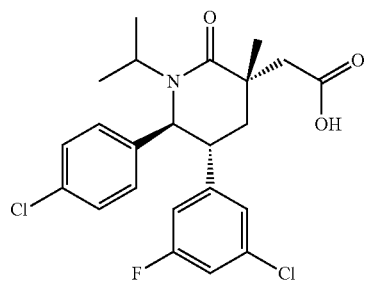 [SMILES: CC(C)N1C(=O)[C@](C)(CC(=O)O)C[C@H](c2cc(F)cc(Cl)c2)[C@H]1c1ccc(Cl)cc1]

Further elution from the HPLC column in Example 391, Step F provided the title compound (14.8 mg). ¹H NMR (400 MHz, CHLOROFORM-d) δ ppm 1.22 (d, J=6.9 Hz, 3 H), 1.27 (d, J=7.0 Hz, 3 H), 1.58 (s, 3 H), 1.72 (dd, J=3.1 and 13.3 Hz, 1 H), 2.32 (t, J=13.5 Hz, 1 H), 2.65-2.75 (m, 2 H), 3.13 (dt, J=2.9 and 10.6 Hz, 1 H), 3.26 (m, 1 H), 4.33 (d, J=10.4 Hz, 1 H), 6.53 (d, J=9.0 Hz, 1 H), 6.74 (s, 1 H), 6.91-6.97 (m, 3 H), 7.27 (d, J=8.6 Hz, 2 H); Mass Spectrum (ESI) m/z=452.2 [M+H]⁺.

Example 393

2-((3R,5R,6S)-5-(3-Chloro-5-fluorophenyl)-6-(4-chlorophenyl)-1-((S)-1-(ethylsulfonamido)butan-2-yl)-3-methyl-2-oxopiperidin-3-yl)acetic acid

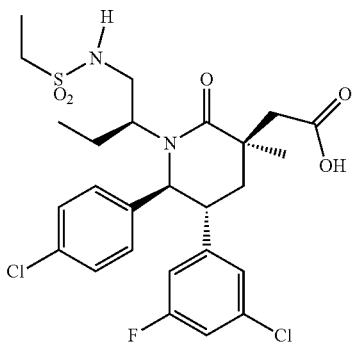 [SMILES: CC[C@@H](CNS(=O)(=O)CC)N1C(=O)[C@@](C)(CC(=O)O)C[C@H](c2cc(F)cc(Cl)c2)[C@H]1c1ccc(Cl)cc1]

Step A. (3S,5R,6S)-3-Allyl-1-((S)-1-((tert-butyldiphenylsilyl)oxy)butan-2-yl)-5-(3-chloro-5-fluorophenyl)-6-(4-chlorophenyl)-3-methylpiperidin-2-one

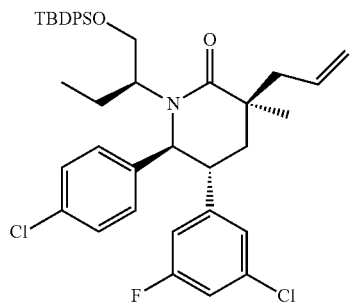

The title compound was prepared as described in Example 185, Step E replacing 2-(3-chlorophenyl acetyic acid with 2-(3-chloro-5-fluorophenyl)acetic acid in Example 1, Step A.

Step B. (3S,5R,6S)-3-Allyl-5-(3-chloro-5-fluorophenyl)-6-(4-chlorophenyl)-1-((S)-1-hydroxybutan-2-yl)-3-methylpiperidin-2-one

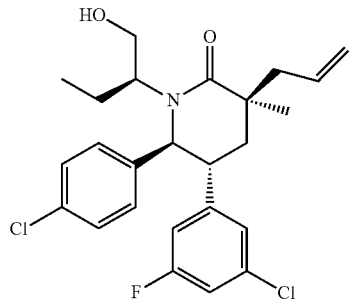 [SMILES: C=CC[C@@]1(C)C[C@H](c2cc(F)cc(Cl)c2)[C@@H](c2ccc(Cl)cc2)N([C@@H](CC)CO)C1=O]

To a solution of (3S,5R,6S)-3-allyl-1-((S)-1-((tert-butyldiphenylsilyl)oxy)butan-2-yl)-5-(3-chloro-5-fluorophenyl)-6-(4-chlorophenyl)-3-methylpiperidin-2-one (2.15 g, 3.06 mmol; Example 393, Step A) in THF (30.6 ml) at rt was added TBAF (1.0 M in THF) (6.12 ml, 6.12 mmol). The light yellow mixture was stirred at rt overnight. The mixture was diluted with water and EtOAc. The organic layer was washed with brine, dried over Na$_2$SO$_4$, filtered and the filtrate was concentrated. The residue was purified by flash chromatography on silica gel (40 g column; eluent: 0 to 50% EtOAc in hexanes) to give the title compound.

Step C. N-((S)-2-((3S,5R,6S)-3-Allyl-5-(3-chloro-5-fluorophenyl)-6-(4-chlorophenyl)-3-methyl-2-oxopiperidin-1-yl)butyl)ethanesulfonamide

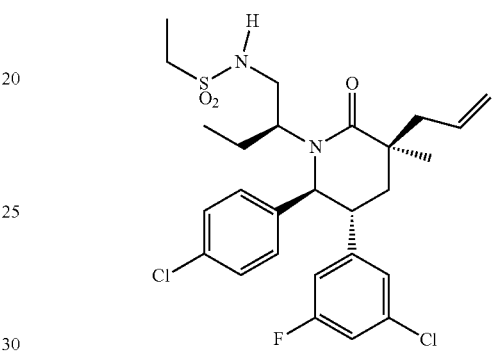

(3S,5R,6S)-3-allyl-5-(3-chloro-5-fluorophenyl)-6-(4-chlorophenyl)-1-((S)-1-hydroxybutan-2-yl)-3-methylpiperidin-2-one (100 mg, 0.215 mmol; Example 393, Step B) and ethanesulfonamide (70.5 mg, 0.646 mmol) were coupled by the procedure as described in Example 202, Step C to form the title compound, isolated after silica gel chromatography (4 g column; eluent 0 to 50% EtOAC/hexanes) as an off-white solid.

Step D. 2-((3R,5R,6S)-5-(3-Chloro-5-fluorophenyl)-6-(4-chlorophenyl)-1-((S)-1-(ethylsulfonamido)butan-2-yl)-3-methyl-2-oxopiperidin-3-yl)acetic acid To a solution of N-((S)-2-((3S,5R,6S)-3-allyl-5-(3-chloro-5-fluorophenyl)-6-(4-chlorophenyl)-3-methyl-2-oxopiperidin-1-yl)butyl)ethanesulfonamide (Example 393, Step C, 120 mg, 0.216 mmol) in EtOAc:MeCN:water (1.450 mL) (2/2/3) at rt was added sodium periodate (185 mg, 0.864 mmol) slowly. Then ruthenium chloride hydrate (1.071 mg, 4.75 μmol) was added. The mixture was stirred vigourously at rt for 2 h. Then the mixture was filtered and the solid was washed with EtOAc. The filtrate was extracted with EtOAc 2×. The combined organic layers were dried over Na$_2$SO$_4$, filtered and the filtrate was concentrated under reduced pressure. The residue was purified by reverse phase preparatory HPLC (column: Gemini™ Prep C$_{18}$ 5 um column; Phenomenex, Torrance, Calif.; eluent: 0 to 100% MeCN +0.1% TFA in water +0.1% TFA, over 20 minutes) to give the title compound.

$^1$H NMR (400 MHz, CHLOROFORM-d) δ ppm 0.53 (t, J=7.6 Hz, 3 H) 1.40 (t, J=7.3 Hz, 3 H) 1.46-1.56 (m, 4 H) 1.80-1.94 (m, 1 H) 1.96-2.00 (m, 2 H) 2.36 (t, J=13.9 Hz, 1 H) 2.77 (d, J=14.9 Hz, 1 H) 2.97 (d, J=14.9 Hz, 1 H) 3.02-3.21 (m, 5 H) 4.61 (br s, 1 H) 4.81 (d, J=10.6 Hz, 1 H) 6.62-6.69 (m, 1 H) 6.79 (t, J=1.8 Hz, 1 H) 6.90 (dt, J=8.3, 2.1 Hz, 1 H) 7.07 (br s, 2 H) 7.24-7.30 (m, 2 H); Mass Spectrum (ESI) m/z=573 (M+1).

Example 394

2-((3R,5R,6S)-5-(3-Chloro-5-fluorophenyl)-6-(4-chlorophenyl)-3-methyl-1-((S)-1-(N-methylethylsulfonamido)butan-2-yl)-2-oxopiperidin-3-yl)acetic acid

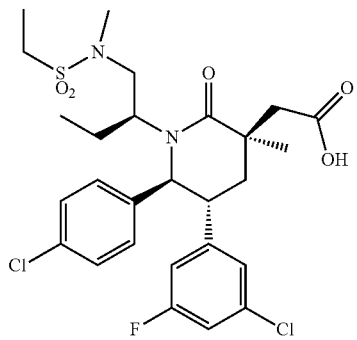 [SMILES: CC[C@@H](CN(C)S(=O)(=O)CC)N1C(=O)[C@@](C)(CC(=O)O)C[C@H](c2cc(F)cc(Cl)c2)[C@H]1c1ccc(Cl)cc1]

To a solution of 2-((3R,5R,6S)-5-(3-chloro-5-fluorophenyl)-6-(4-chlorophenyl)-1-((S)-1-(ethylsulfonamido)butan-2-yl)-3-methyl-2-oxopiperidin-3-yl)acetic acid (Example 393, Step D, 26.6 mg, 0.046 mmol) in DMF (464 μl) at rt was added a dispersion of 60% sodium hydride in mineral oil (5.57 mg, 0.139 mmol). The grey slurry was stirred at rt for 30 min then iodomethane (5.80 μl, 0.093 mmol) was added. The mixture was stirred at rt for 1 h. The mixture was quenched with 1 M HCl and diluted with EtOAc. The aqueous layer was extracted with EtOAc 2×. The organic layer was dried over $Na_2SO_4$, filtered and the filtrate was concentrated. The residue was purified by reverse phase preparatory HPLC (column: Gemini™ Prep $C_{18}$ 10 um column; Phenomenex, Torrance, Calif.; eluent: 0 to 100% MeCN +0.1% TFA in water +0.1% TFA, over 20 minutes) to give the title compound.
$^1$H NMR (400 MHz, CHLOROFORM-d) δ ppm 0.50 (t, J=7.5 Hz, 3 H) 1.38 (t, J=7.4 Hz, 3 H) 1.52 (s, 3 H) 1.57-1.63 (m, 1 H) 1.85-2.00 (m, 2 H) 2.46 (t, J=13.9 Hz, 1 H) 2.66-2.89 (m, 6 H) 2.94-3.16 (m, 4 H) 4.31 (dd, J=13.7, 10.8 Hz, 1 H) 4.81 (d, J=10.8 Hz, 1 H) 6.59 (br s, 1 H) 6.69 (dt, J=9.1, 2.1 Hz, 1 H) 6.80 (t, J=1.8 Hz, 1 H) 6.91 (dt, J=8.3, 2.0 Hz, 1 H) 7.01 (br s, 1 H) 7.29 (br s, 2 H); Mass Spectrum (ESI) m/z=587 (M+1).

Example 395

2-((3R,5R,6S)-5-(3-Chloro-5-fluorophenyl)-6-(4-chlorophenyl)-3-methyl-1-((S)-1-(methylsulfonyl)butan-2-yl)-2-oxopiperidin-3-yl)acetic acid

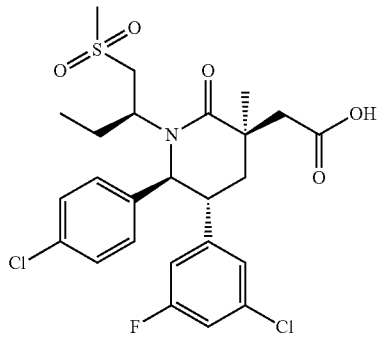 [SMILES: CC[C@@H](CS(C)(=O)=O)N1C(=O)[C@@](C)(CC(=O)O)C[C@H](c2cc(F)cc(Cl)c2)[C@H]1c1ccc(Cl)cc1]

Step A. (3S,5S,6R,8S)-8-Allyl-6-(3-chloro-5-fluorophenyl)-5-(4-chlorophenyl)-3-ethyl-8-methyl-2,3,5,6,7,8-hexahydrooxazolo[3,2-a]pyridin-4-ium methanesulfonate

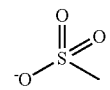
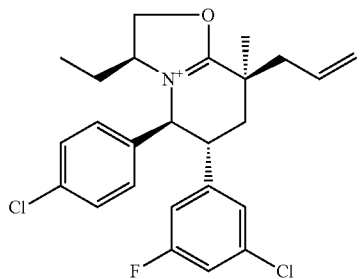

The title compound was prepared from (3S,5R,6S)-3-allyl-5-(3-chloro-5-fluorophenyl)-6-(4-chlorophenyl)-1-((S)-1-hydroxybutan-2-yl)-3-methylpiperidin-2-one (Example 393, Step B) by a procedure similar to the one described in Example 344, Step A.

Step B. (3S,5R,6S)-3-Allyl-5-(3-chloro-5-fluorophenyl)-6-(4-chlorophenyl)-3-methyl-1-((S)-1-(methylsulfonyl)butan-2-yl)piperidin-2-one

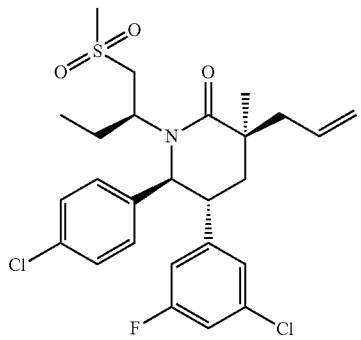 [SMILES: C=CC[C@@]1(C)C[C@H](c2cc(F)cc(Cl)c2)[C@@H](c2ccc(Cl)cc2)N([C@@H](CC)CS(C)(=O)=O)C1=O]

To a solution of (3S,5S,6R,8S)-8-allyl-6-(3-chloro-5-fluorophenyl)-5-(4-chlorophenyl)-3-ethyl-8-methyl-2,3,5,6,7,8-hexahydrooxazolo[3,2-a]pyridin-4-ium methanesulfonate (Example 395, step A, 100 mg, 0.184 mmol) in MeCN (1.8 mL) was added methanesulfinic acid, sodium salt (56.5 mg, 0.553 mmol). The mixture was heated to 114° C. After heating for 24 hours, the mixture was cooled to room temperature and stirred for 2 days. The mixture was partitioned between EtOAc and aq. $NH_4Cl$. The organic layer was washed with brine, dried over $Na_2SO_4$, filtered and the filtrate was concentrated. The residue was purified by flash chromatography on silica gel (eluent: 20 to 60% EtOAc/hexanes, gradient elution) to afford the title compound.

Step C. 2-((3R,5R,6S)-5-(3-Chloro-5-fluorophenyl)-6-(4-chlorophenyl)-3-methyl-1-((S)-1-(methylsulfonyl)butan-2-yl)-2-oxopiperidin-3-yl)acetic acid To a solution of (3S,5R,6S)-3-allyl-5-(3-chloro-5-fluorophenyl)-6-(4-chlorophenyl)-3-methyl-1-((S)-1-(methylsulfonyl)butan-2-yl)piperidin-2-one (Example 395, Step B, 58 mg, 0.110 mmol) in acetonitrile (1.0 mL), EtOAc (1.0 mL), and water (1.5 mL) was added ruthenium(III) chloride hydrate (0.55 mg, 2.42 µmol) and sodium periodate (144 mg, 0.672 mmol). After 2 hours, the mixture was partitioned between water and EtOAc. The organic layer was washed with brine, dried over $Na_2SO_4$, filtered and the filtrate was concentrated. The residue was purified by preparative thin layer chromatography on silica gel (eluent: 10% MeOH/DCM) to provide the title compound.

$^1$H NMR (400 MHz, CHLOROFORM-d) δ ppm 0.43 (t, J=7.5 Hz, 3 H) 1.48 (s, 3 H) 1.64 (br s, 1 H) 1.91 (dd, J=13.7, 2.4 Hz, 1 H) 2.06-2.22 (m, 1 H) 2.33 (t, J=13.8 Hz, 1 H) 2.76 (d, J=15.1 Hz, 1 H) 2.90 (d, J=12.1 Hz, 1 H) 2.94-3.03 (m, 4 H) 3.13 (t, J=11 Hz, 1 H) 3.33 (t, J=9.7 Hz, 1 H) 4.22 (t, J=12.3 Hz, 1 H) 4.88 (d, J=10.8 Hz, 1H) 6.61 (d, J=9.2 Hz, 1 H) 6.75 (s, 1 H) 6.89 (dt, J=8.3, 1.9 Hz, 1 H) 7.12 (br s, 2 H) 7.21-7.35 (m, 2 H). Mass Spectrum (ESI) m/z=544.0 (M+1).

Examples 396 to 398 were prepared from (3S,5S,6R,8S)-8-allyl-6-(3-chloro-5-fluorophenyl)-5-(4-chlorophenyl)-3-ethyl-8-methyl-2,3,5,6,7,8-hexahydrooxazolo[3,2-a]pyridin-4-ium methanesulfonate (Example 395, Step A) by a procedure similar to those described in either Example 339 or Example 395, using an equivalent amount of the appropriate reagent in Step B. Example 399 was prepared from (3S,5R,6S)-3-allyl-5-(3-chloro-5-fluorophenyl)-6-(4-chlorophenyl)-1-((S)-1-hydroxybutan-2-yl)-3-methylpiperidin-2-one (Example 393, step B) by a procedure similar to the one described in Example 300, using an equivalent amount of the appropriate thiol in Step A.

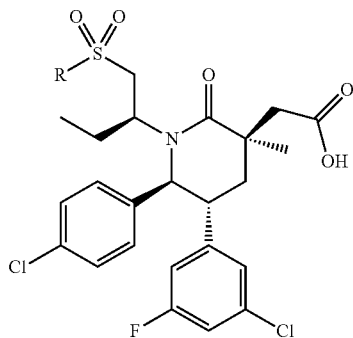

| Example | R | Method | Reagent used |
|---|---|---|---|
| 396 | Ethyl | Example 395 | ethanesulfinic acid, sodium salt |
| 397 | cyclopropyl | Example 395 | cyclopropanesulfinic acid, sodium salt |
| 398 | tert-butyl | Example 339 | 2-methylpropanethiolate, prepared in situ from 2-methylpropane-2-thiol and sodium hydride |
| 399 | isopropyl | Example 300 | 2-propanethiol |

Example 396

2-((3R,5R,6S)-5-(3-Chloro-5-fluorophenyl)-6-(4-chlorophenyl)-1-((S)-1-(ethylsulfonyl)butan-2-yl)-3-methyl-2-oxopiperidin-3-yl)acetic acid $^1$H NMR (400 MHz, CHLOROFORM-d) δ ppm 0.42 (t, J=7.5 Hz, 3 H) 1.45 (t, J=7.5 Hz, 3 H) 1.49 (s, 3 H) 1.65 (br s, 1 H) 1.90 (dd, J=13.7, 2.4 Hz, 1 H) 2.06-2.21 (m, 1 H) 2.35 (t, J=13.8 Hz, 1 H) 2.73-2.82 (m, 2 H) 2.98 (d, J=15.1 Hz, 1 H) 3.01-3.08 (m, 2 H) 3.13 (t, J=11.0 Hz, 1 H) 3.34 (t, J=10.2 Hz, 1 H) 4.13 (t, J=12.1 Hz, 1 H) 4.92 (d, J=10.8 Hz, 1 H) 6.62 (d, J=9.2 Hz, 1 H) 6.75 (s, 1 H) 6.89 (dt, J=8.4, 2.0 Hz, 1 H) 7.12 (br s, 2 H) 7.21-7.34 (m, 2 H). Mass Spectrum (ESI) m/z=558.0 (M+1).

Example 397

2-((3R,5R,6S)-5-(3-Chloro-5-fluorophenyl)-6-(4-chlorophenyl)-1-((S)-1-(cyclopropylsulfonyl)butan-2-yl)-3-methyl-2-oxopiperidin-3-yl)acetic acid $^1$H NMR (400 MHz, CHLOROFORM-d) δ ppm 0.43 (t, J=7.6 Hz, 3 H) 1.05-1.15 (m, 2 H) 1.25-1.33 (m, 2 H) 1.38-1.54 (m, 4 H) 1.90 (dd, J=13.8, 2.8 Hz, 1 H) 2.07-2.21 (m, 1 H) 2.34 (t, J=13.8 Hz, 1 H) 2.42 (tt, J=8.0, 4.8 Hz, 1 H) 2.76 (d, J=15.1 Hz, 1 H) 2.88-3.01 (m, 2 H) 3.13 (ddd, J=13.4, 10.8, 2.5 Hz, 1 H) 3.31 (t, J=10.4 Hz, 1 H) 4.20 (dd, J=13.5, 11.2 Hz, 1 H) 4.90 (d, J=10.8 Hz, 1 H) 6.61 (dt, J=9.0, 2.0 Hz, 1 H) 6.74 (s, 1 H) 6.88 (dt, J=8.4, 2.1 Hz, 1 H) 7.11 (br s, 2 H) 7.21-7.34 (m, 2 H). Mass Spectrum (ESI) m/z=570.0 (M+1).

Example 398

2-((3R,5R,6S)-1-((S)-1-(tert-Butylsulfonyl)butan-2-yl)-5-(3-chloro-5-fluorophenyl)-6-(4-chlorophenyl)-3-methyl-2-oxopiperidin-3-yl)acetic acid The crude product was purified by SFC 20 mL/min; 30×250 mm Chiralpak® IC column (Chiral Technologies, Inc., West Chester, Pa., USA) using methanol (20 mM $NH_3$)/$CO_2$ as the eluent on Thor SFC (Thor Technologies, Inc. Pittsburg, Pa.) to provide the title compound.

$^1$H NMR (400 MHz, CHLOROFORM-d) δ ppm 0.41 (t, J=7.5 Hz, 3 H) 1.38-1.68 (m, 13 H) 1.88 (dd, J=13.7, 2.5 Hz, 1 H) 2.06-2.26 (m, 1 H) 2.38 (t, J=13.8 Hz, 1 H) 2.73 (d, J=15.5 Hz, 1 H) 2.80 (d, J=13.5 Hz, 1 H) 3.01 (d, J=15.3 Hz, 1 H) 3.11 (t, J=11.8 Hz, 1 H) 3.33 (t, J=10.4 Hz, 1 H) 4.03 (dd, J=13.0, 11.3 Hz, 1 H) 4.97 (d, J=10.8 Hz, 1 H) 6.63 (d, J=9.2 Hz, 1 H) 6.75 (s, 1 H) 6.89 (d, J=8.4 Hz, 1 H) 7.14 (br s, 2 H) 7.25-7.36 (m, 2 H). Mass Spectrum (ESI) m/z=586.0 (M+1).

Example 399

2-((3R,5R,6S)-5-(3-Chloro-5-fluorophenyl)-6-(4-chlorophenyl)-1-((S)-1-(isopropylsulfonyl)butan-2-yl)-3-methyl-2-oxopiperidin-3-yl)acetic acid The crude product was purified by preparative thin layer chromatography on silica gel (eluent: 10% MeOH/DCM) followed by purification by reverse phase preparatory HPLC (column: Gemini™ Prep $C_{18}$ 10 um column; Phenomenex, Torrance, Calif.; eluent: 0 to 100% MeCN +0.1% TFA in water +0.1% TFA, over 20 minutes) to give the title compound.

$^1$H NMR (400 MHz, CHLOROFORM-d) δ ppm 0.41 (t, J=7.5 Hz, 3 H) 1.34-1.55 (m, 10 H) 1.88 (dd, J=13.8, 2.6 Hz, 1 H) 2.07-2.24 (m, 1 H) 2.38 (t, J=13.8 Hz, 1 H) 2.68-2.81 (m, 2 H) 3.01 (d, J=15.5 Hz, 1 H) 3.06-3.18 (m, 2 H) 3.35 (t, J=10.2 Hz, 1 H) 4.08 (dd, J=13.1, 11.5 Hz, 1 H) 4.95 (d, J=10.8 Hz, 1 H) 6.63 (d, J=9.0 Hz, 1 H) 6.75 (s, 1 H) 6.89 (dt, J=8.2, 2.0 Hz, 1 H) 7.14 (br s, 2 H) 7.24-7.37 (m, 2 H). Mass Spectrum (ESI) m/z=572.0 (M+1).

Example 400

2-((3R,5R,6S)-6-(4-Chlorophenyl)-5-(5-chloropyridin-3-yl)-1-((S)-1-(cyclopropylsulfonyl)butan-2-yl)-3-methyl-2-oxopiperidin-3-yl)acetic acid

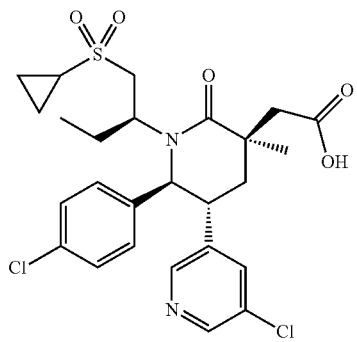 [SMILES: CC[C@@H](CS(=O)(=O)C1CC1)N1C(=O)[C@@](C)(CC(=O)O)C[C@H](c2cncc(Cl)c2)[C@H]1c1ccc(Cl)cc1]

Step A. 1-(4-Chlorophenyl)-2-(5-chloropyridin-3-yl)ethanone

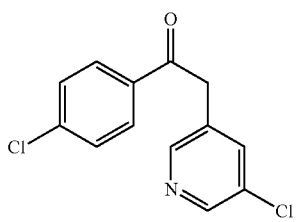 [SMILES: O=C(Cc1cncc(Cl)c1)c1ccc(Cl)cc1]

1-(4-chlorophenyl)ethanone (17.22 ml, 133 mmol) was added to an ice cold solution of 3-bromo-5-chloropyridine (24.3 g, 126 mmol) and sodium 2-methylpropan-2-olate (30.3 g, 316 mmol) in THF (158 ml) under an argon atmosphere. (9,9-dimethyl-9H-xanthene-4,5-diyl)bis(diphenylphosphine) (0.731 g, 1.263 mmol) and diacetoxypalladium (0.283 g, 1.263 mmol) were then added and the solution was heated to 70° C. for 1.5 hours. The solution was cooled to rt and diluted with ice, 2N HCl (95 mL) followed by EtOAc (300 ml). The layers were partitioned and the aqueous layer was washed with EtOAc (2×100 ml). The organics were washed with brine, dried over $Na_2SO_4$, filtered, and concentrated. The residue obtained was enriched on a silica gel column. The fractions containing the product were combined and concentrated. To the residue obtained was added 130 ml of $Et_2O$ and the suspension was heated to a reflux in a water bath. The suspension was then cooled in an ice bath. The solids were collected by filtration to provide the title compound.

$^1$H NMR (500 MHz, DMSO-$d_6$) δ ppm 8.53 (1 H, d, J=2.4 Hz), 8.43 (1 H, d, J=1.7 Hz), 8.05-8.11 (2 H, m), 7.85 (1 H, t, J=2.1 Hz), 7.63-7.68 (2 H, m), 4.55 (2 H, s).

Step B. 1-Methyl 5-(4-chlorophenyl)-4-(5-chloropyridin-3-yl)-2-methyl-5-oxopentanoate

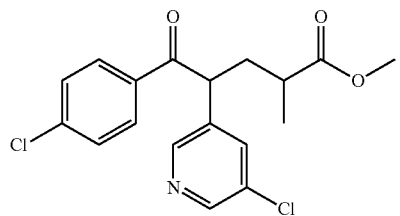 [SMILES: COC(=O)C(C)CC(C(=O)c1ccc(Cl)cc1)c1cncc(Cl)c1]

The title compound was obtained from 1-(4-chlorophenyl)-2-(5-chloropyridin-3-yl)ethanone (Example 400, Step A, 25.3 g, 95 mmol) by a procedure similar to the one described in Example 261, Step A. Racemic product is a 1:1 mixture of diastereomers.

$^1$H NMR (500 MHz, DMSO-$d_6$) δ ppm 8.57 (1 H, d, J=2.0 Hz), 8.54 (1 H, d, J=1.7 Hz), 8.50 (2 H, dd, J=4.4, 2.4 Hz), 8.05-8.09 (4 H, m), 7.90 (2 H, t, J=2.1 Hz), 7.57-7.64 (4H, m), 4.93-5.04 (2 H, m), 3.54 (3 H, s), 3.45 (3 H, s), 2.34-2.42 (1 H, m), 2.24-2.33 (2 H, m), 2.19 (1 H, dt, J=13.7, 6.8 Hz), 2.05-2.13 (1 H, m), 1.88-1.96 (1 H, m), 1.13 (3 H, d, J=7.1 Hz), 1.08 (3 H, d, J=7.1 Hz); Mass Spectrum (ESI) m/z=366.1 [M+H]$^+$.

Step C. Racemic mixture of (4R,5R)-methyl 5-(4-chlorophenyl)-4-(5-chloropyridin-3-yl)-5-hydroxy-2-methylpentanoate and (4S,5S)-methyl 5-(4-chlorophenyl)-4-(5-chloropyridin-3-yl)-5-hydroxy-2-methylpentanoate

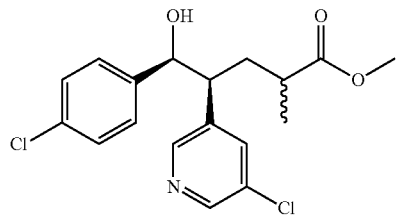

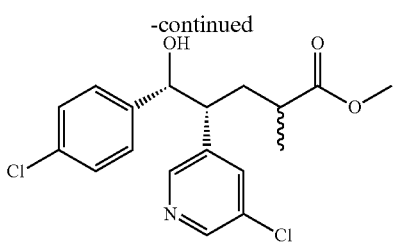

1-Methyl 5-(4-chlorophenyl)-4-(5-chloropyridin-3-yl)-2-methyl-5-oxopentanoate (Example 400, Step B, 31 g, 85 mmol) was converted to the title compounds by a procedure similar to the one described in Example 261, Step B. Product is a 1:1 mixture of diastereomers at the 2 position.

$^1$H NMR (500 MHz, CHLOROFORM-d) δ ppm 8.43 (2 H, s), 8.13 (2 H, d, J=11.7 Hz), 7.59 (2 H, dt, J=6.8, 2.0 Hz), 7.24-7.30 (4 H, m), 7.03-7.10 (4 H, m), 4.88 (1 H, d, J=5.6 Hz), 4.84 (1 H, d, J=5.6 Hz), 3.64 (3 H, s), 3.56 (3 H, s), 2.91 (2 H, tt, J=10.7, 5.3 Hz), 2.22-2.29 (1 H, m), 2.13-2.22 (4 H, m), 2.00-2.10 (1 H, m), 1.72-1.87 (2 H, m), 1.11 (3 H, d, J=7.1 Hz), 1.09 (3 H, d, J=6.8 Hz); Mass Spectrum (ESI) m/z=368.0 [M+H]$^+$.

Step D. (4R,5R)-5-(4-Chlorophenyl)-4-(5-chloropyridin-3-yl)-5-hydroxy-2-methylpentanoic acid and (4S,5S)-5-(4-chlorophenyl)-4-(5-chloropyridin-3-yl)-5-hydroxy-2-methylpentanoic acid

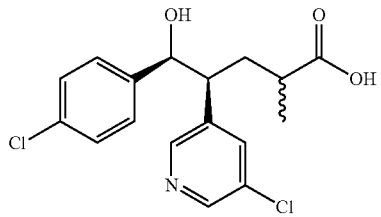

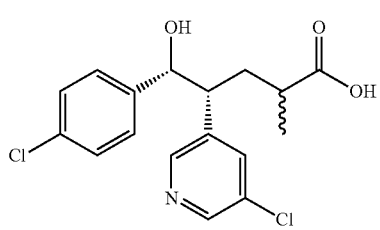

The racemic mixture of (4R,5R)-methyl 5-(4-chlorophenyl)-4-(5-chloropyridin-3-yl)-5-hydroxy-2-methylpentanoate and (4S,5S)-methyl 5-(4-chlorophenyl)-4-(5-chloropyridin-3-yl)-5-hydroxy-2-methylpentanoate (Example 400, Step C, 16.5 g, 43.4 mmol) was converted to the title compounds by the procedure described in Example 261, Step C. Mass Spectrum (ESI) m/z=354.1 [M+H]$^+$.

Step E. (5R,6R)-6-(4-Chlorophenyl)-5-(5-chloropyridin-3-yl)-3-methyltetrahydro-2H-pyran-2-one and (5S,6S)-6-(4-chlorophenyl)-5-(5-chloropyridin-3-yl)-3-methyltetrahydro-2H-pyran-2-one

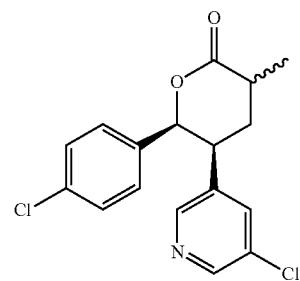

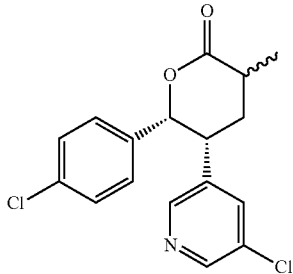

The diastereomeric mixture of (4R,5R)-5-(4-chlorophenyl)-4-(5-chloropyridin-3-yl)-5-hydroxy-2-methylpentanoic acid and (4S,5S)-5-(4-chlorophenyl)-4-(5-chloropyridin-3-yl)-5-hydroxy-2-methylpentanoic acid (Example 400, Step D, 15.39 g, 43.4 mmol) was converted to the title compounds by the procedure described in Example 261, Step D. The product is a 3:2 mixture of diastereomers at the 2 position.

$^1$H NMR (500 MHz, CHLOROFORM-d) δ ppm 8.42 (0.6 H, d, J=2.4 Hz), 8.37 (1 H, d, J=2.2 Hz), 8.22 (0.6 H, d, J=2.0 Hz), 7.91 (1 H, d, J=2.0 Hz), 7.35 (0.6H, t, J=2.1 Hz), 7.23-7.27 (1.3 H, m), 7.16-7.23 (3 H, m), 7.08 (1.3 H, d, J=8.6 Hz), 6.90 (2 H, d, J=8.6 Hz), 5.80 (0.6H, d, J=3.9 Hz), 5.74 (1 H, d, J=4.4 Hz), 3.67-3.73 (0.6 H, m), 3.60 (1 H, ddd, J=9.3, 6.4, 4.6 Hz), 2.96-3.10 (1 H, m), 2.74-2.84 (0.6H, m), 2.69 (1 H, ddd, J=14.4, 9.0, 8.1 Hz), 2.30-2.39 (0.6 H, m), 2.18 (0.6H, ddd, J=13.8, 9.2, 4.4 Hz), 1.76-1.86 (1 H, m), 1.44 (1.8 H, d, J=7.1 Hz), 1.42 (3 H, d, J=6.6 Hz).

Step F. (3S,5R,6R)-3-Allyl-6-(4-chlorophenyl)-5-(5-chloropyridin-3-yl)-3-methyltetrahydro-2H-pyran-2-one and (3R,5S,6S)-3-allyl-6-(4-chlorophenyl)-5-(5-chloropyridin-3-yl)-3-methyltetrahydro-2H-pyran-2-one

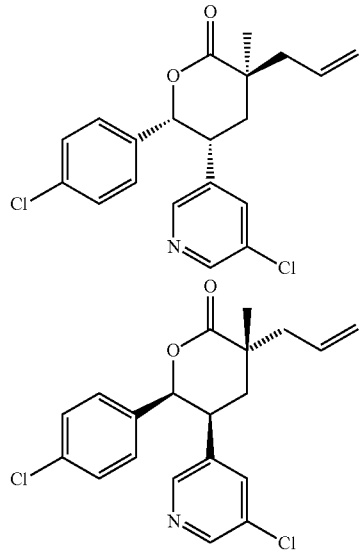

The mixture of diastereomers of (5R,6R)-6-(4-chlorophenyl)-5-(5-chloropyridin-3-yl)-3-methyltetrahydro-2H-pyran-2-one and (5S,6S)-6-(4-chlorophenyl)-5-(5-chloropyridin-3-yl)-3-methyltetrahydro-2H-pyran-2-one (Example 400, Step E, 12.2 g, 36.28 mmol) was converted to the title compounds by the procedure described in Example 261, Step E.

$^1$H NMR (500 MHz, CHLOROFORM-d) δ ppm 8.44 (1 H, d, J=2.2 Hz), 8.11 (1 H, d, J=2.0 Hz), 7.18-7.24 (2 H, m), 7.07 (1 H, t, J=2.1 Hz), 6.62-6.67 (2 H, m), 5.82 (1 H, ddt, J=17.1, 9.9, 7.4 Hz), 5.71 (1 H, d, J=5.1 Hz), 5.13-5.23 (2 H, m), 3.85 (1 H, dt, J=11.7, 4.7 Hz), 2.48-2.66 (2 H, m), 1.93-2.07 (2 H, m), 1.42 (3 H, s).

Step G. (S)-2-((2R,3R)-3-(4-Chlorophenyl)-2-(5-chloropyridin-3-yl)-3-hydroxypropyl)-N-((S)-1-hydroxybutan-2-yl)-2-methylpent-4-enamide and (R)-2-((2S,3S)-3-(4-chlorophenyl)-2-(5-chloropyridin-3-yl)-3-hydroxypropyl)-N-((S)-1-hydroxybutan-2-yl)-2-methylpent-4-enamide

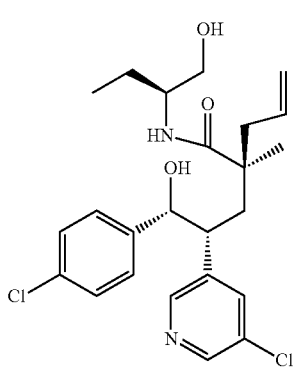

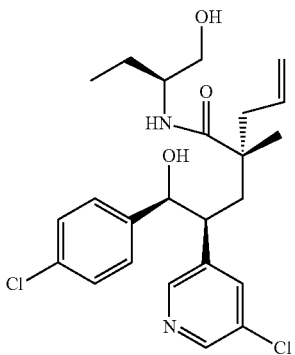

The racemic mixture of (3S,5R,6R)-3-allyl-6-(4-chlorophenyl)-5-(5-chloropyridin-3-yl)-3-methyltetrahydro-2H-pyran-2-one and (3R,5S,6S)-3-allyl-6-(4-chlorophenyl)-5-(5-chloropyridin-3-yl)-3-methyltetrahydro-2H-pyran-2-one (Example 400, Step F, 12.4 g, 33.0 mmol;) was converted to the title compounds by the procedure described in Example 261, Step G.

Mass Spectrum (ESI) m/z=465.2 [M+H]$^+$.

Step H. (3S,5R,6S)-3-Allyl-6-(4-chlorophenyl)-5-(5-chloropyridin-3-yl)-1-((S)-1-hydroxybutan-2-yl)-3-methylpiperidin-2-one

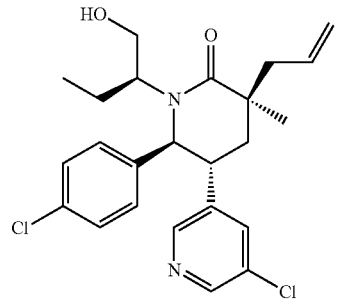 [SMILES: C=CC[C@@]1(C)C[C@H](c2cncc(Cl)c2)[C@@H](c2ccc(Cl)cc2)N([C@@H](CC)CO)C1=O]

The mixture of diastereomers of (S)-2-((2R,3R)-3-(4-chlorophenyl)-2-(5-chloropyridin-3-yl)-3-hydroxypropyl)-N-((S)-1-hydroxybutan-2-yl)-2-methylpent-4-enamide and (R)-2-((2S,3S)-3-(4-chlorophenyl)-2-(5-chloropyridin-3-yl)-3-hydroxypropyl)-N-((S)-1-hydroxybutan-2-yl)-2-methylpent-4-enamide (Example 400, Step G, 6.34 g,) was combined in DCM (68 ml) and triethylamine (13.3 ml, 95 mmol). After cooling in an ice bath, trimethylamine hydrochloride (1.953 g, 20.43 mmol) was added. 4-Methylbenzenesulfonic anhydride (17.78 g, 54.5 mmol) was added slowly as a solid, keeping the temperature below 10° C. The brownish colored solution was allowed to slowly warm to room temperature, and then stirred over night. The next day more trimethyl amine hydrochloride (0.271 mg, 2.91 mmol) was added and the solution was stirred for another day. The reaction was quenched with ice water. The layers were partitioned and the aqueous layer was washed with DCM. The combined organics were dried over MgSO$_4$, filtered, and concentrated to provide a brown oil. The oil was dissolved in MeCN (100 ml) and then heated to 60° C. for 4 hours. The solution was concentrated and the residue dissolved in 100 ml of DCM. To this was added 100 ml of sat. NaHCO$_3$ and the biphasic solution was stirred at rt. for 5 days. The solution was partitioned and the aqueous layer was washed with DCM. The organics were dried over MgSO$_4$, filtered and concentrated. The product was purified by silica gel chromatography to give (3S,5R,6S)-3-allyl-6-(4-chlorophenyl)-5-(5-chloropyridin-3-yl)-1-((S)-1-hydroxybutan-2-yl)-3-methylpiperidin-2-one as the second eluting diastereomer.

d, J=2.0 Hz), 7.91 (1 H, d, J=1.5 Hz), 7.35 (1 H, t, J=1.8 Hz), 7.26 (1 H, br s), 7.00 (2 H, br d, J=6.8 Hz), 5.78-5.94 (1 H, m), 5.15-5.24 (2 H, m), 4.45 (1 H, d, J=10.3 Hz), 3.59-3.73 (2 H, m), 3.13-3.27 (3 H, m), 2.62 (2 H, d, J=7.6 Hz), 2.02-2.11 (1 H, m), 1.85-2.00 (2 H, m), 1.40-1.52 (1 H, m), 1.30 (3 H, s), 0.66 (3 H, t, J=7.5 Hz). Mass Spectrum (ESI) m/z=447.2 [M+H]$^+$.

Step I. (3S,5S,6R,8 S)-8-allyl-5-(4-chlorophenyl)-6-(5-chloropyridin-3-yl)-3-ethyl-8-methyl-2,3,5,6,7,8-hexahydrooxazolo[3,2-a]pyridin-4-ium methanesulfonate

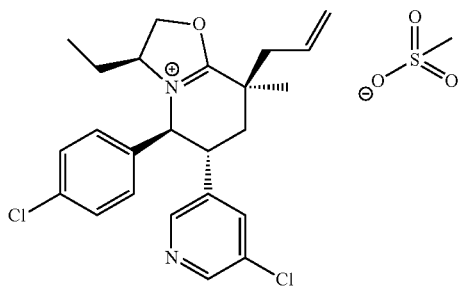

The title compound was prepared from (3S,5R,6S)-3-allyl-6-(4-chlorophenyl)-5-(5-chloropyridin-3-yl)-1-((S)-1-hydroxybutan-2-yl)-3-methylpiperidin-2-one (Example 400, Step H) by a procedure similar to the one described in Example 344, Step A.

Mass Spectrum (ESI) m/z=429.2 [M]$^+$.

Step J. (3S,5R,6S)-3-Allyl-6-(4-chlorophenyl)-5-(5-chloropyridin-3-yl)-1-((S)-1-(cyclopropylsulfonyl)butan-2-yl)-3-methylpiperidin-2-one

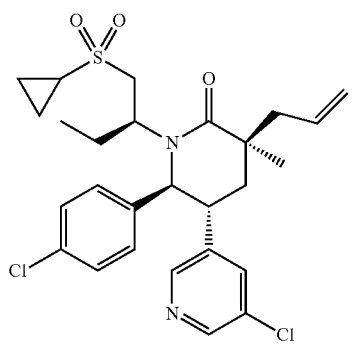 [SMILES: C=CC[C@@]1(C)C[C@H](c2cncc(Cl)c2)[C@@H](c2ccc(Cl)cc2)N([C@@H](CC)CS(=O)(=O)C2CC2)C1=O]

(3S,5S,6R,8S)-8-allyl-5-(4-chlorophenyl)-6-(5-chloropyridin-3-yl)-3-ethyl-8-methyl-2,3,5,6,7,8-hexahydrooxazolo[3,2-a]pyridin-4-ium methanesulfonate (Example 400, Step I, 0.188 g, 0.358 mmol) was converted to the title compound by a procedure similar to the one described in Example 340 using cyclopropane sulfinic acid, sodium salt (Oakwood Products, West Columbia, S.C.).

MS (ESI) m/z=535.1 [M+H]$^+$.

Step K. 2-((3R,5R,6S)-6-(4-Chlorophenyl)-5-(5-chloropyridin-3-yl)-1-((S)-1-(cyclopropylsulfonyl)butan-2-yl)-3-methyl-2-oxopiperidin-3-yl)acetic acid To a solution of (3S,5R,6S)-3-allyl-6-(4-chlorophenyl)-5-(5-chloropyridin-3-yl)-1-((S)-1-(cyclopropylsulfonyl)butan-2-yl)-3-methylpiperidin-2-one (Example 400, Step J, 0.06 g, 0.112 mmol) in DCM (2.241 ml) was added acetic acid (0.160 ml, 2.80 mmol) and tetrabutylammonium chloride hydrate (3.32 mg, 0.011 mmol). The solution was cooled in an ice bath. A solution of potassium permanganate (0.053 g, 0.336 mmol) in 1 ml of water was prepared and added dropwise to the above solution (rinsed with 1 ml of water). The purple solution was stirred in the ice bath for 30 minutes and then allowed to warm to room temperature and left overnight. The next day a solution of sodium bisulfite (10% in water) was added. The pH of the aq. layer was adjusted to 2 with 30% $H_2SO_4$ in water. The layers were partitioned and then the aqueous was washed with DCM followed by 10% iPrOH/DCM. The combined organics were concentrated under vacuum. The product was purified by silica gel chromatography to provide the title compound as a white solid.

$^1$H NMR (500 MHz, CHLOROFORM-d) δ ppm 8.38 (1 H, d, J=2.2 Hz), 8.00 (1 H, d, J=1.7 Hz), 7.67 (1 H, t, J=2.0 Hz), 7.26 (2 H, br s, overlaps with solvent), 7.17 (2 H, br s), 4.99 (1 H, d, J=11.0 Hz), 4.28 (1 H, dd, J=13.4, 11.2 Hz), 3.51 (1 H, ddd, J=13.6, 11.1, 2.4 Hz), 3.30 (1 H, t, J=10.0 Hz), 2.89-2.97 (2 H, m), 2.78 (1 H, d, J=13.7 Hz), 2.38-2.46 (1 H, m), 2.19-2.26 (1 H, m), 2.03-2.14 (1 H, m), 1.85-1.93 (1 H, m), 1.46-1.53 (1 H, m), 1.44 (3 H, s), 1.27 (2 H, m, J=5.6 Hz), 1.07-1.11 (2 H, m), 0.43 (3 H, t, J=7.6 Hz) Mass Spectrum (ESI) m/z=553.0 [M+H]$^+$.

Example 401

2-((3R,5R,6S)-1-((S)-1-(tert-Butylsulfonyl)butan-2-yl)-6-(4-chlorophenyl)-5-(5-chloropyridin-3-yl)-3-methyl-2-oxopiperidin-3-yl)acetic acid

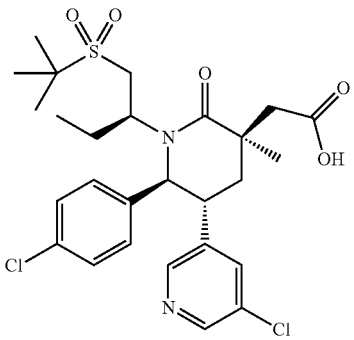 [SMILES: CC[C@@H](CS(=O)(=O)C(C)(C)C)N1C(=O)[C@@](C)(CC(=O)O)C[C@H](c2cncc(Cl)c2)[C@H]1c1ccc(Cl)cc1]

Step A. 2-(3S,5R,6S)-3-Allyl-1-((S)-1-(tert-butylthio)butan-2-yl)-6-(4-chlorophenyl)-5-(5-chloropyridin-3-yl)-3-methylpiperidin-2-one

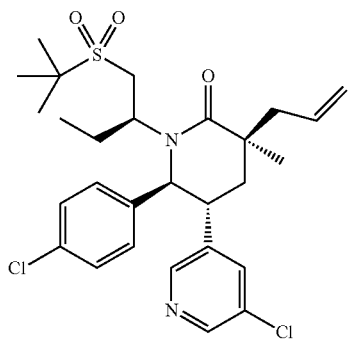 [SMILES: C=CC[C@@]1(C)C[C@H](c2cncc(Cl)c2)[C@@H](c2ccc(Cl)cc2)N([C@@H](CC)CS(=O)(=O)C(C)(C)C)C1=O]

(3S,5R,6S)-3-Allyl-6-(4-chlorophenyl)-5-(5-chloropyridin-3-yl)-1-((S)-1-hydroxybutan-2-yl)-3-methylpiperidin-2-one (Example 400, Step H, 0.2 g, 0.447 mmol) was converted to the title compounds as a clear film (0.145 g, 62%) by the procedure described in Example 339, Step B using an equivalent of 2-methylpropanethiol.

$^1$H NMR (500 MHz, CHLOROFORM-d) δ ppm 8.40 (1 H, d, J=2.2 Hz), 7.98 (1 H, d, J=1.7 Hz), 7.41 (1 H, t, J=2.1 Hz), 7.24 (2 H, br d, J=8.3 Hz), 6.99 (2 H, br d, J=6.6 Hz), 5.87 (1 H, m), 5.13-5.23 (2 H, m), 4.65 (1 H, d, J=10.8 Hz), 3.51 (1 H, t, J=11.4 Hz), 3.19 (1 H, ddd, J=13.7, 10.8, 2.9 Hz), 2.63-2.74 (1 H, m), 2.53-2.62 (3 H, m), 2.16 (1 H, t, J=13.6 Hz), 2.08 (1 H, m, J=14.2, 8.8, 7.3 Hz), 1.88 (1 H, dd, J=13.4, 3.2 Hz), 1.51-1.60 (1 H, m), 1.36 (9 H, br s), 1.31 (3 H, br s), 0.49 (3 H, t, J=7.6 Hz). Mass Spectrum (ESI) m/z=519.2 [M+H]$^+$.

Step B. 2-((3R,5R,6S)-1-((S)-1-(tert-Butylsulfonyl)butan-2-yl)-6-(4-chlorophenyl)-5-(5-chloropyridin-3-yl)-3-methyl-2-oxopiperidin-3-yl)acetic acid A solution of (3S,5R,6S)-3-allyl-1-((S)-1-(tert-butylthio)butan-2-yl)-6-(4-chlorophenyl)-5-(5-chloropyridin-3-yl)-3-methylpiperidin-2-one (Example 401, Step A, 0.147 g, 0.283 mmol;) with acetic acid (0.972 mL, 16.98 mmol) and tetrabutylammonium chloride hydrate (8.37 mg, 0.028 mmol) in 4 ml of DCM was cooled in an ice bath. A solution of potassium permanganate (0.268 g, 1.698 mmol) in 3 mL of water was added. The purple solution was stirred while cooling with an ice bath and allowed to warm to room temperature over 2 hours. Aq. NaS$_2$O$_3$ solution was added along with additional DCM. After filtering the solution through filter paper the filtrate was partitioned and then the aq. layer was washed with DCM. The combined organics were dried over Na$_2$SO$_4$ and concentrated. The product was purified by silica gel chromatography followed by preparatory HPLC (Agilent column, EXTEND C$_{18}$ PrepHT, 5 μM, 30×250 mm) eluting with a gradient of 20% MeCN/H$_2$O/0.1% TFA to 80% MeCN/H$_2$O/0.1% TFA over 25 minutes. The fractions containing the product were combined, frozen in a acetone/dry ice bath and the solvents were removed on a lyophilizer to provide the title compound as an off-white solid.

$^1$H NMR (500 MHz, DMSO-d$_6$) δ ppm 12.38 (1 H, br s), 8.42 (1 H, d, J=2.2 Hz), 8.02 (1 H, d, J=1.7 Hz), 7.57 (1 H, t, J=2.0 Hz), 7.11-7.47 (4 H, m), 4.83 (1 H, d, J=11.0 Hz), 3.84 (1 H, dd, J=13.0, 10.5 Hz), 3.47-3.57 (1 H, m), 3.13 (1 H, br s), 3.05 (1 H, d, J=12.5 Hz), 2.91 (1 H, d, J=13.9 Hz), 2.13-2.23 (1 H, m), 2.03-2.13 (2 H, m), 1.81-1.97 (1 H, m), 1.43-1.53 (1 H, m), 1.33 (9 H, s), 1.26 (3 H, s), 0.33 (3 H, t, J=7.6 Hz).

Mass Spectrum (ESI) m/z=569.2 [M+H]$^+$.

Example 402

2-((3R,5R,6S)-6-(4-Chlorophenyl)-5-(5-chloropyridin-3-yl)-1-((S)-1-(cyclopropanesulfonamido)butan-2-yl)-3-methyl-2-oxopiperidin-3-yl)acetic acid

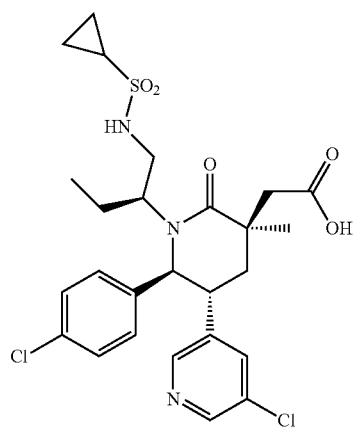 [SMILES: CC[C@@H](CNS(=O)(=O)C1CC1)N1C(=O)[C@@](C)(CC(=O)O)C[C@H](c2cncc(Cl)c2)[C@H]1c1ccc(Cl)cc1]

Step A. N-((S)-2-((3S,5R,6S)-3-Allyl-6-(4-chlorophenyl)-5-(5-chloropyridin-3-yl)-3-methyl-2-oxopiperidin-1-yl)butyl)cyclopropanesulfonamide

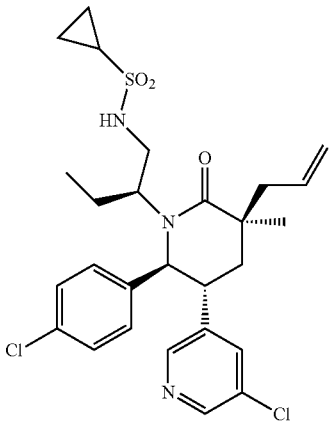 [SMILES: C=CC[C@@]1(C)C[C@H](c2cncc(Cl)c2)[C@@H](c2ccc(Cl)cc2)N([C@@H](CC)CNS(=O)(=O)C2CC2)C1=O]

(3S,5R,6S)-3-allyl-6-(4-chlorophenyl)-5-(5-chloropyridin-3-yl)-1-((S)-1-hydroxybutan-2-yl)-3-methylpiperidin-2-one (Example 400, Step H, 0.076 g, 0.170 mmol) was converted to the title compound by a procedure similar to the one described in Example 272, Step A, using cyclopropanesulfonamide.

MS (ESI) m/z=550.2 [M+H]$^+$.

Step B. 2-((3R,5R,6S)-6-(4-Chlorophenyl)-5-(5-chloropyridin-3-yl)-1-((S)-1-(cyclopropanesulfonamido)butan-2-yl)-3-methyl-2-oxopiperidin-3-yl)acetic acid N-((S)-2-((3S,5R,6S)-3-allyl-6-(4-chlorophenyl)-5-(5-chloropyridin-3-yl)-3-methyl-2-oxopiperidin-1-yl)butyl)cyclopropanesulfonamide (Example 402, Step A, 0.073 g, 0.133 mmol) was converted to the title compound by a procedure similar to the one described in Example 400, Step K.

$^1$H NMR (500 MHz, CHLOROFORM-d) δ ppm 8.46 (1 H, d, J=1.7 Hz), 8.17 (1 H, br s), 7.75 (1 H, s), 7.25 (2 H, br s, overlaps with solvent), 7.02-7.18 (2 H, m), 5.08 (1 H, br s), 4.92 (1 H, d, J=11.0 Hz), 3.78 (1 H, br s), 3.46-3.56 (1 H, m), 3.14 (1 H, dt, J=14.2, 4.5 Hz), 3.02 (1 H, br s), 2.77-2.95 (2 H, m), 2.43-2.50 (1 H, m), 2.36 (1 H, t, J=13.8 Hz), 2.00 (1 H, dd, J=13.7, 2.7 Hz), 1.79-1.89 (1 H, m), 1.50-1.59 (1 H, m), 1.48 (3 H, s), 1.15-1.20 (2 H, m), 0.98-1.05 (2 H, m), 0.51 (3 H, t, J=7.6 Hz). Mass Spectrum (ESI) m/z=568.2 [M+H]$^+$.

Example 403

2-((3R,5R,6S)-6-(4-Chlorophenyl)-5-(5-chloropyridin-3-yl)-3-methyl-1-((S)-1-(N-methylcyclopropanesulfonamido)butan-2-yl)-2-oxopiperidin-3-yl)acetic acid

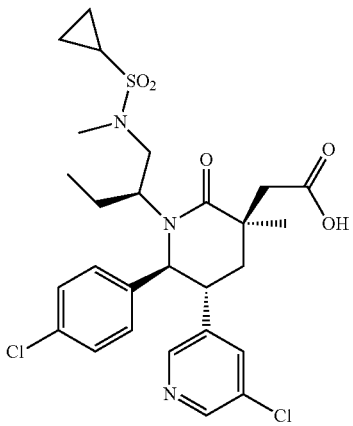 [SMILES: CC[C@@H](CN(C)S(=O)(=O)C1CC1)N1C(=O)[C@@](C)(CC(=O)O)C[C@H](c2cncc(Cl)c2)[C@H]1c1ccc(Cl)cc1]

Step A: N-((S)-2-((3S,5R,6S)-3-Allyl-6-(4-chlorophenyl)-5-(5-chloropyridin-3-yl)-3-methyl-2-oxopiperidin-1-yl)butyl)-N-methylcyclopropanesulfonamide

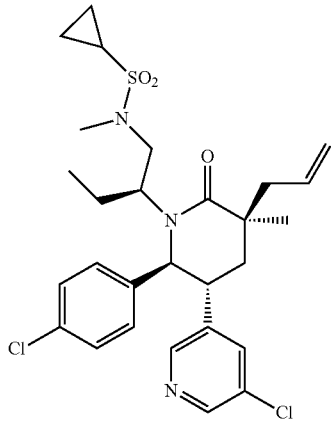 [SMILES: C=CC[C@@]1(C)C[C@H](c2cncc(Cl)c2)[C@@H](c2ccc(Cl)cc2)N([C@@H](CC)CN(C)S(=O)(=O)C2CC2)C1=O]

(3S,5R,6S)-3-Allyl-6-(4-chlorophenyl)-5-(5-chloropyridin-3-yl)-1-((S)-1-hydroxybutan-2-yl)-3-methylpiperidin-2-one (Example 400, Step H, 0.1 g, 0.224 mmol) was converted to the title compound by a procedure similar to the one described in Example 272, Step A using N-methylcyclopropanesulfonamide.

MS (ESI) m/z=564.2 [M+H]$^+$.

Step B. 2-((3R,5R,6S)-6-(4-Chlorophenyl)-5-(5-chloropyridin-3-yl)-3-methyl-1-((S)-1-(N-methylcyclopropanesulfonamido)butan-2-yl)-2-oxopiperidin-3-yl)acetic acid N-((S)-2-((3S,5R,6S)-3-allyl-6-(4-chlorophenyl)-5-(5-chloropyridin-3-yl)-3-methyl-2-oxopiperidin-1-yl)butyl)-N-methylcyclopropanesulfonamide (Example 403, Step A, 0.090 g, 0.159 mmol) was converted to the title compound by a procedure similar to the one described in Example 400, Step K.

$^1$H NMR (500 MHz, Acetone-d$_6$) δ ppm 8.38 (1 H, d, J=1.7 Hz), 8.11 (1 H, s), 7.68 (1 H, t, J=2.0 Hz), 7.21-7.43 (4 H, m), 4.92 (1 H, d, J=10.8 Hz), 4.02-4.21 (1 H, m), 3.57 (1 H, ddd, J=13.8, 10.9, 2.9 Hz), 2.99 (1 H, d, J=14.2 Hz), 2.91-2.96 (5 H, m), 2.76 (1 H, d, J=14.2 Hz), 2.53-2.62 (1 H, m), 2.39 (1 H, t, J=13.7 Hz), 2.19 (1 H, dd, J=13.4, 2.9 Hz), 1.75-1.86 (1 H, m), 1.66-1.74 (1 H, m), 1.42 (3 H, s), 0.96-1.12 (4 H, m), 0.52 (3 H, t, J=7.6 Hz). Mass Spectrum (ESI) m/z=582.0 [M+H]$^+$.

Example 404

2-((3R,5R,6S)-5-(3-Chlorophenyl)-6-(5-chloropyridin-2-yl)-1-((S)-1-(ethylsulfonyl)butan-2-yl)-3-methyl-2-oxopiperidin-3-yl)acetic acid

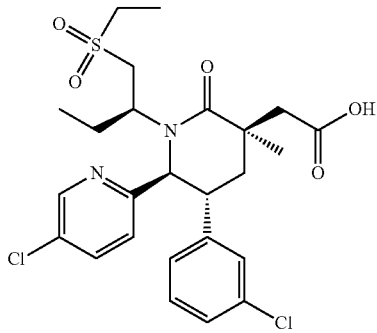 [SMILES: CC[C@@H](CS(=O)(=O)CC)N1C(=O)[C@@](C)(CC(=O)O)C[C@H](c2cccc(Cl)c2)[C@H]1c1ccc(Cl)cn1]

Step A. (3S,5R,6S)-3-Allyl-5-(3-chlorophenyl)-6-(5-chloropyridin-2-yl)-1-((S)-1-(ethylthio)butan-2-yl)-3-methylpiperidin-2-one

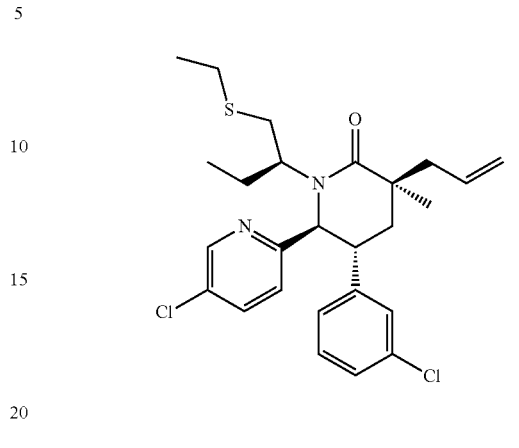

(3S,5R,6S)-3-allyl-5-(3-chlorophenyl)-6-(5-chloropyridin-2-yl)-1-((S)-1-hydroxybutan-2-yl)-3-methylpiperidin-2-one (Example 121, Step L, 100 mg, 0.224 mmol) was azeotroped three times in benzene on a rotary evaporator. The residue was dissolved in toluene and transferred to a reaction vessel. The vessel was flushed with argon. Ethanethiol (33.1 µl, 0.447 mmol) was added followed by cyanomethylenetributylphosphorane (216 µl, 0.894 mmol). The vessel was sealed and the solution was heated to 100° C. for 4 h. The reaction mixture was diluted with DCM (10 ml) and Si-maleimide (Silicycle, 2.1 g; 0.66 mmol/g; 40-63 microns) was added to scavenge excess thiol. After stirring for about 1 h, the mixture was filtered and the silica gel was rinsed with DCM. The filtrate was concentrated on a rotary evaporator. The residue was dissolved in DCM and loaded directly onto a dry 12 g gold-capped Redisep® column (Teledyne Isco, Lincoln, Nebr.). The column was eluted with a gradient of 0 to 5% MeOH:DCM. The fractions containing the desired product were combined and concentrated to afford the title compound as a colorless film.

Step B. 2-((3R,5R,6S)-5-(3-Chlorophenyl)-6-(5-chloropyridin-2-yl)-1-((S)-1-(ethylsulfonyl)butan-2-yl)-3-methyl-2-oxopiperidin-3-yl)acetic acid (3S,5R,6S)-3-Allyl-5-(3-chlorophenyl)-6-(5-chloropyridin-2-yl)-1-((S)-1-(ethylthio)butan-2-yl)-3-methylpiperidin-2-one (Example 404, step A) was converted to the title compound by a procedure similar to the one described in Example 395, Step C.

$^1$H NMR (400 MHz, CDCl$_3$) δ ppm 8.65 (d, J=2.3 Hz, 1 H), 7.48 (dd, J=2.4, 8.1 Hz, 1 H), 7.16-7.07 (m, 2 H), 6.98 (s, 1 H), 6.92-6.86 (m, 2 H), 5.00 (d, J=10.2 Hz, 1 H), 4.25-4.16 (m, 1 H), 3.57-3.46 (m, 1 H), 3.26 (br s, 1 H), 3.15 (d, J=15.3 Hz, 1 H), 3.10-3.01 (m, 2 H), 2.91 (d, J=15.5 Hz, 1 H), 2.80 (d, J=11.7 Hz, 1 H), 2.36 (t, J=13.9 Hz, 1 H), 2.04-1.90 (m, 2 H), 1.50-1.40 (m, 7 H), 0.38 (t, J=7.0 Hz, 3 H); Mass Spectrum (ESI) m/z=541.2 [M+H]$^+$.

Example 405

2-((3R,5R,6S)-5-(3-Chlorophenyl)-6-(4-chlorophenyl)-3-methyl-1-((S)-1-((S)-morpholin-2-yl)propyl)-2-oxopiperidin-3-yl)acetic acid, TFA salt or 2-((3R,5R,6S)-5-(3-chlorophenyl)-6-(4-chlorophenyl)-3-methyl-1-((S)-1-((R)-morpholin-2-yl)propyl)-2-oxopiperidin-3-yl)acetic acid, TFA salt

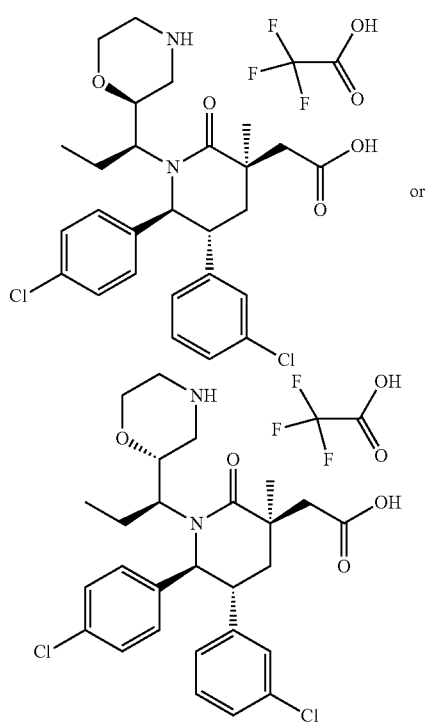

Step A. (S)-tert-Butyl 2-((S)-1-hydroxypropyl)morpholine-4-carboxylate and (R)-tert-Butyl 2-((S)-1-hydroxypropyl)morpholine-4-carboxylate and (S)-tert-Butyl 2-((R)-1-hydroxypropyl)morpholine-4-carboxylate and (R)-tert-Butyl 2-((R)-1-hydroxypropyl)morpholine-4-carboxylate

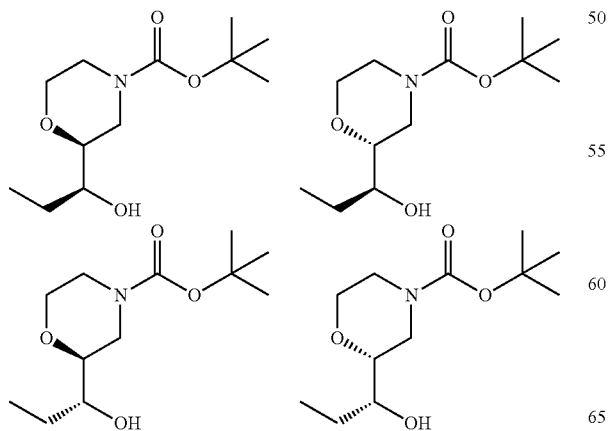

To a solution of (rac)-tert-butyl 2-formylmorpholine-4-carboxylate (0.996 g, 4.63 mmol) (Tyger Scientific Inc., Ewing, N.J., USA) in THF (25 mL) at RT was added a solution of 3.0 M ethylmagnesium bromide in diethyl ether (1.851 mL, 5.55 mmol) dropwise. After 4 h, the mixture was quenched with sat. aq. NH$_4$Cl solution. The mixture was extracted with EtOAc. The organic layers were washed with brine, dried over Na$_2$SO$_4$, filtered and the filtrate was concentrated to afford a mixture of the title compounds.

Step B. (S)-tert-butyl 2-((S)-1-(((4-bromophenyl)sulfonyl)oxy)propyl)morpholine-4-carboxylate and (R)-tert-butyl 2-((S)-1-(((4-bromophenyl)sulfonyl)oxy)propyl)morpholine-4-carboxylate and (S)-tert-butyl 2-((R)-1-(((4-bromophenyl)sulfonyl)oxy)propyl)morpholine-4-carboxylate and (R)-tert-butyl 2-((R)-1-(((4-bromophenyl)sulfonyl)oxy)propyl)morpholine-4-carboxylate

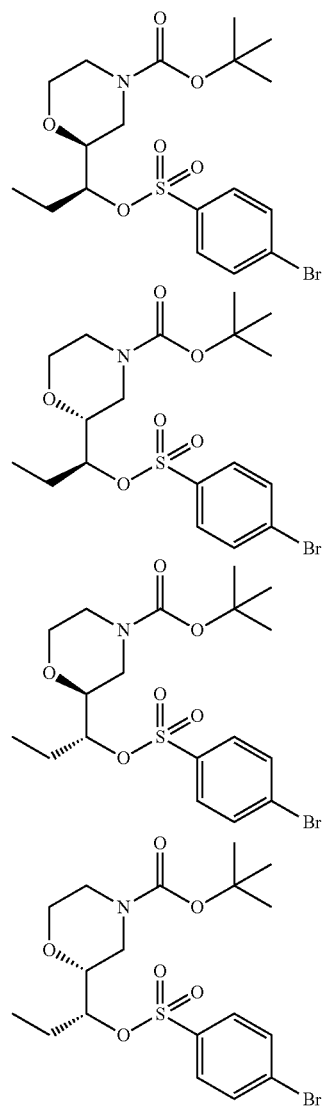

To a solution of the mixture of diastereomers from Example 405, step A (509 mg, 2.075 mmol;) in DCM (6.9 mL) was added DMAP (558 mg, 4.56 mmol) and 4-bromobenzenesulfonyl chloride (795 mg, 3.11 mmol). After stirring for 18 h, the mixture was partitioned between EtOAc and water. The organic layer was washed with brine, dried over Na$_2$SO$_4$, filtered and the filtrate was concentrated. The residue was purified by flash chromatography on silica gel (40 g column, eluent: 5 to 30% EtOAc/hexanes) to afford a mixture of the title compounds.

Step C. (S)-tert-butyl 2-((S)-1-((3S,5R,6S)-3-allyl-5-(3-chlorophenyl)-6-(4-chlorophenyl)-3-methyl-2-oxopiperidin-1-yl)propyl)morpholine-4-carboxylate and (R)-tert-butyl 2-((S)-1-((3S,5R,6S)-3-allyl-5-(3-chlorophenyl)-6-(4-chlorophenyl)-3-methyl-2-oxopiperidin-1-yl)propyl)morpholine-4-carboxylate and (S)-tert-butyl 2-((R)-1-((3S,5R,6S)-3-allyl-5-(3-chlorophenyl)-6-(4-chlorophenyl)-3-methyl-2-oxopiperidin-1-yl)propyl)morpholine-4-carboxylate and (R)-tert-butyl 2-((R)-1-((3S,5R,6S)-3-allyl-5-(3-chlorophenyl)-6-(4-chlorophenyl)-3-methyl-2-oxopiperidin-1-yl)propyl)morpholine-4-carboxylate

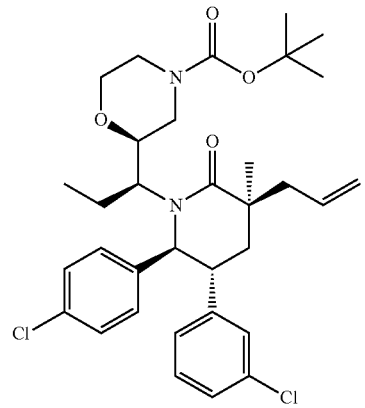

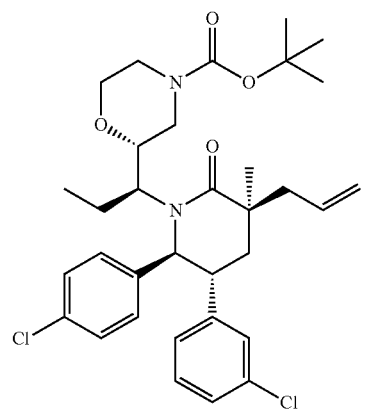

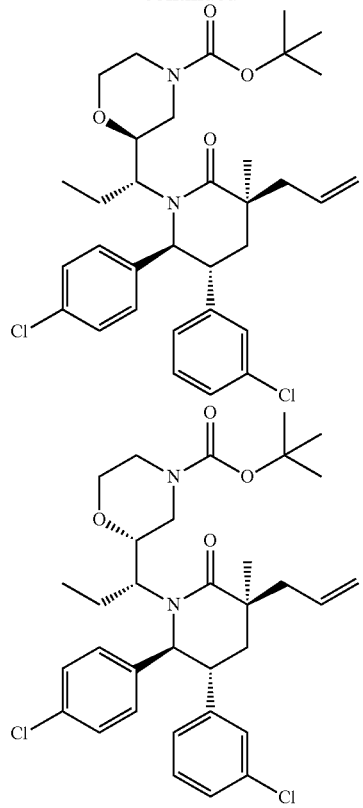

The diastereomeric brosylates (Example 404, Step B, 124 mg, 0.267 mmol) were dissolved in toluene and concentrated in vacuo twice. Dioxane (1 mL) was added followed by sodium tert-butoxide (25.7 mg, 0.267 mmol). The mixture was heated at 85° C. for 2 days. The mixture was partitioned between EtOAc and dilute aq. NH$_4$Cl solution. The organic layer was washed with brine, dried over Na$_2$SO$_4$, filtered and the filtrate was concentrated. The residue was purified by flash chromatography on silica gel (4 g column, eluent: 5 to 35% EtOAc/hexanes) to afford a mixture of the title compounds.

Step D. 2-((3R,5R,6S)-5-(3-chlorophenyl)-6-(4-chlorophenyl)-3-methyl-1-((S)-1-((S)-morpholin-2-yl)propyl)-2-oxopiperidin-3-yl)acetic acid, TFA salt or 2-((3R,5R,6S)-5-(3-chlorophenyl)-6-(4-chlorophenyl)-3-methyl-1-((S)-1-((R)-morpholin-2-yl)propyl)-2-oxopiperidin-3-yl)acetic acid, TFA salt The mixture of diastereomers obtained in Example 404, Step C (100 mg, 0.166 mmol) was dissolved in THF (1 mL). Water (about 0.5 mL) was added until the solution became cloudy. t-BuOH was added until the solution became clear. NMO (29.2 mg, 0.249 mmol) was added followed by 4% aq. osmium tetroxide solution (5.28 µl, 0.831 µmol). After stirring for 18 h, another 3 drops of 4% aq. Os O$_4$ solution was added. After stirring for 4 h, 0.20 mL of Jones Reagent was added. After 2 days, the mixture was partitioned between aq. NaHCO$_3$ and DCM. The aqueous layer was extracted with DCM and EtOAc. The combined organic layers were washed with brine, dried over Na$_2$SO$_4$, filtered and the filtrate was concentrated. The mixture was stirred in DCM (3 mL) and TFA (1 mL, 12.98 mmol) for 25 minutes and was concentrated. The residue was purified by reversed phase preparative HPLC (column: Gemini-NX C$_{18}$ 5 um column; Phenomonex, Torrance, Calif.; eluent: 30 to 50% MeCN +0.1% TFA in water +0.1% TFA over 20 minutes) to provide three of the four possible diasteromers of the title compound. The first eluting of these diastereomers is Example 405:

$^{1}$H NMR (400 MHz, CHLOROFORM-d) δ ppm 0.33 (t, J=7.5 Hz, 3 H) 1.30-1.42 (m, 1 H) 1.47 (s, 3 H) 1.68-1.82 (m, 1 H) 1.82-1.91 (m, 1 H) 2.19-2.26 (m, 2 H) 2.56-2.64 (m, 3 H) 2.68-2.87 (m, 1 H) 3.03 (d, J=12.3 Hz, 1 H) 3.07-3.33 (m, 2 H) 3.54-3.76 (m, 1 H) 3.76-3.99 (m, 1 H) 4.25-4.36 (m, 1 H) 4.51 (d, J=10.6 Hz, 1 H) 4.57-4.71 (m, 1 H) 6.70 (d, J=7.8 Hz, 1 H) 7.00 (t, J=1.9 Hz, 1 H) 7.14 (t J=7.6 Hz, 1 H) 7.21 (d, J=8.0 Hz, 1 H) 7.28-7.32 (m, 4 H) 8.13 (br s, 1 H) 11.54 (br s, 1 H). Mass Spectrum (ESI) m/z=519.1 (M+1).

Example 406

2-((3R,5R,6S)-5-(3-chlorophenyl)-6-(4-chlorophenyl)-3-methyl-1-((R)-1-((S)-morpholin-2-yl)propyl)-2-oxopiperidin-3-yl)acetic acid, TFA salt or 2-((3R, 5R,6S)-5-(3-chlorophenyl)-6-(4-chlorophenyl)-3-methyl-1-((R)-1-((R)-morpholin-2-yl)propyl)-2-oxopiperidin-3-yl)acetic acid, TFA salt

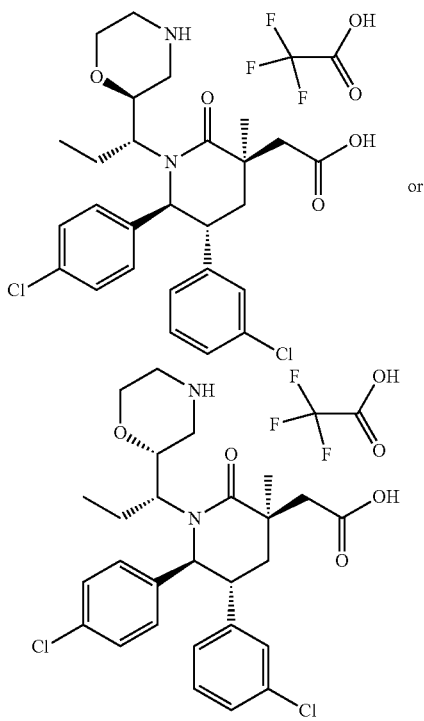

Further elution of the HPLC column in Example 405, Step D provided one of the title compounds as the second eluting isomer.

$^{1}$H NMR (400 MHz, CHLOROFORM-d) δ ppm 0.93-1.11 (m, 3 H) 1.39-1.58 (m, 3 H) 1.62-1.78 (m, 1 H) 1.79-1.92 (m, 1 H) 1.93-2.02 (m, 1 H) 2.16-2.29 (m, 1 H) 2.55-2.70 (m, 2 H) 2.73-3.00 (m, 2 H) 3.03-3.24 (m, 2 H) 3.26-3.44 (m, 2 H) 3.45-3.54 (m, 1 H) 3.60-3.67 (m, 1 H) 3.75-3.97 (m, 1 H) 4.30-4.47 (m, 2H) 6.73 (d, J=7.4 Hz, 1 H) 6.98 (br s, 1 H) 7.11 (t, J=8.0 Hz, 1 H) 7.17 (d, J=8.0 Hz, 1 H) 7.23-7.33 (m, 4 H) 8.99 (br s, 1 H) 9.96 (br s, 1 H). Mass Spectrum (ESI) m/z=519.1 (M+1).

Example 407

2-((3R,5R,6S)-5-(3-chlorophenyl)-6-(4-chlorophenyl)-3-methyl-1-((R)-1-((R)-morpholin-2-yl)propyl)-2-oxopiperidin-3-yl)acetic acid, TFA salt or 2-((3R, 5R,6S)-5-(3-chlorophenyl)-6-(4-chlorophenyl)-3-methyl-1-((R)-1-((S)-morpholin-2-yl)propyl)-2-oxopiperidin-3-yl)acetic acid, TFA salt

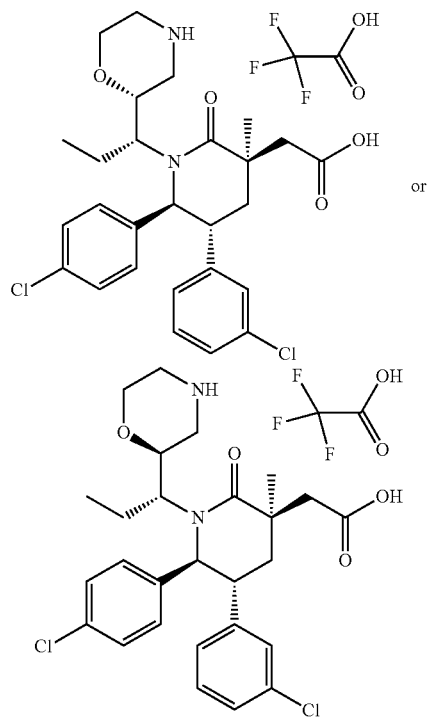

Further elution from the HPLC column in Example 405 provided the other (relative to Example 406) of the title compounds as the third eluting isomer.

$^{1}$H NMR (400 MHz, CHLOROFORM-d) δ ppm 1.10 (t, J=7.5 Hz, 3 H) 1.47 (s, 3 H) 1.83-1.93 (m, 1 H) 1.98-2.09 (m, 2 H) 2.15-2.32 (m, 2 H) 2.59-2.64 (m, 1 H) 2.66-2.72 (m, 2 H) 2.73-2.85 (m, 2 H) 3.23 (d, J=13.3 Hz, 1 H) 3.43 (t, J=12.2 Hz, 1 H) 3.66 (t, J=11.7 Hz, 1 H) 3.77-3.92 (m, 2 H) 4.34 (t, J=8.1 Hz 1 H) 4.41 (d, J=10.6 Hz, 1 H) 6.73 (d, J=7.6 Hz 1 H) 6.96 (br s, 1 H) 7.08 (t, J=8.0 Hz, 1 H) 7.13 (d, J=8.0 Hz, 1 H) 7.25-7.42 (m, 4 H) 9.16 (br s, 1 H) 9.43 (br s, 1 H). Mass Spectrum (ESI) m/z=519.1 (M+1).

Example 408

2-((3S,5R,6S)-5-(3-Chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetic acid

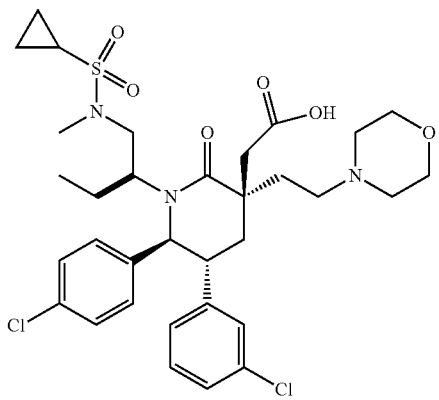 [SMILES: CC[C@@H](CN(C)S(=O)(=O)C1CC1)N1C(=O)[C@@](CCN2CCOCC2)(CC(=O)O)C[C@H](c2cccc(Cl)c2)[C@H]1c1ccc(Cl)cc1]

Step A. (3R,5R,6S)-3-Allyl-1-((S)-1-((tert-butyl-diphenylsilyl)oxy)butan-2-yl)-5-(3-chlorophenyl)-6-(4-chlorophenyl)-3-(2-((4-methoxybenzyl)oxy)ethyl)piperidin-2-one and (3S,5R,6S)-3-Allyl-1-((S)-1-((tert-butyldiphenylsilyl)oxy)butan-2-yl)-5-(3-chlorophenyl)-6-(4-chlorophenyl)-3-(2-((4-methoxybenzyl)oxy)ethyl)piperidin-2-one

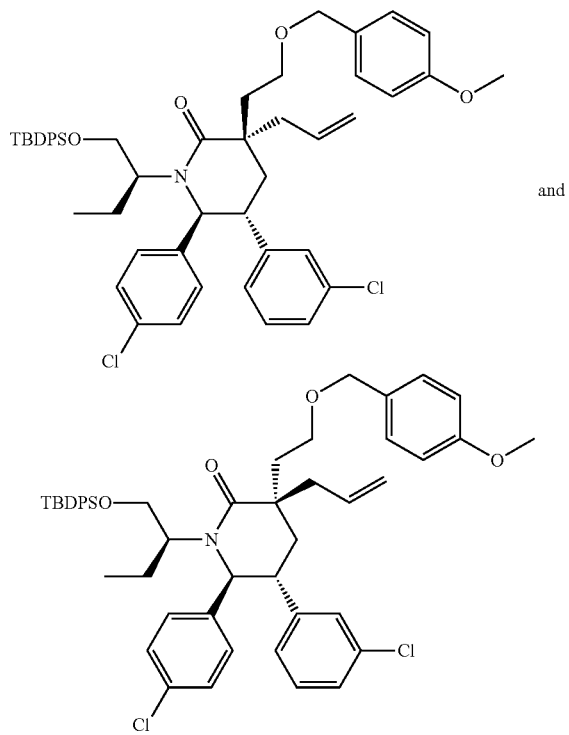

and

The title compound was obtained from (3R,5R,6S)-1-((S)-1-((tert-butyldiphenylsilyl)oxy)butan-2-yl)-5-(3-chlorophenyl)-6-(4-chlorophenyl)piperidin-2-one (Example 127, Step A) and 1-((2-iodoethoxy)methyl)-4-methoxybenzene [J. Am. Chem. Soc., 124, 8206-8219, (2002)] by a procedure similar to the one described in Example 69, Step A. Purification of the residue by flash chromatography on silica gel (eluent: 0 to 20% EtOAc/hexane, gradient elution over 30 min) provided the desired products as a mixture of C3 epimers.

Mass Spectrum (ESI) m/z=834.4 (M+1) and 856.4 (M+Na).

Step B. (3R,5R,6S)-3-Allyl-5-(3-chlorophenyl)-6-(4-chlorophenyl)-1-((S)-1-hydroxybutan-2-yl)-3-(2-((4-methoxybenzyl)oxy)ethyl)piperidin-2-one

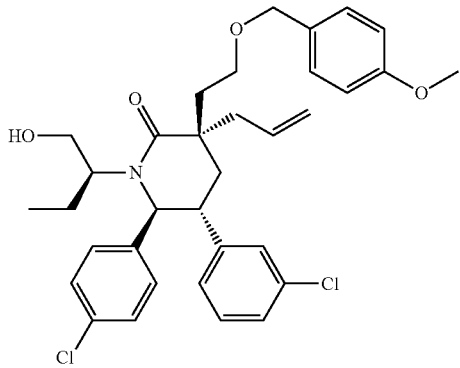 [SMILES: C=CC[C@]1(CCOCc2ccc(OC)cc2)C[C@H](c2cccc(Cl)c2)[C@@H](c2ccc(Cl)cc2)N([C@@H](CC)CO)C1=O]

To a solution of a mixture of (3R,5R,6S)-3-allyl-1-((S)-1-((tert-butyldiphenylsilyl)oxy)butan-2-yl)-5-(3-chlorophenyl)-6-(4-chlorophenyl)-3-(2-((4-methoxybenzyl)oxy)ethyl)piperidin-2-one and (3S,5R,6S)-3-allyl-1-((S)-1-((tert-butyldiphenylsilyl)oxy)butan-2-yl)-5-(3-chlorophenyl)-6-(4-chlorophenyl)-3-(2-((4-methoxybenzyl)oxy)ethyl)piperidin-2-one (19.23 g, 23.03 mmol; Example 408, Step A) in THF (92 ml) at rt was slowly added a solution of TBAF (1.0M in THF, 34.5 ml, 34.5 mmol). The reaction was monitored by LCMS, and when judged complete was concentrated under reduced pressure (no heat), then diluted in 400 mL of EtOAc. HCl (1N, 150 ml) was added. The layers were separated and the aqueous layer was extracted with EtOAc. The combined organics were washed several times with water, dried over MgSO$_4$, filtered, and the filtrate was concentrated. Purification by chromatography on silica gel (eluent: 10 to 20% EtOAc/hexane, gradient elution over 30 min) provided the title compound along with its C3 epimer as a clear, colorless foam. Individual steroisomers were separated by chiral HPLC (flowrate: 120 ml/min, 1 g per injection, on a Chiralcel® OD-H 5 cm I.D.×50 cm, 20 μm column; Daicel Chemical Industries LTD, using 6% isopropyl alcohol/hexane as the eluent) to give the title compound as the first eluting isomer ($t_R$=11-23 min) as a clear, viscous oil.

$^1$H NMR (500 MHz, CHLOROFORM-d) δ ppm 0.61 (t, J=7.5 Hz, 3 H) 1.33 (ddd, J=13.9, 7.8, 5.8 Hz, 1 H) 1.79 (dd, J=13.7, 2.9 Hz, 1 H) 1.94 (dt, J=14.8, 7.5 Hz, 1 H) 2.02 (s, 1 H) 2.11-2.21 (m, 3 H) 2.26 (t, J=13.6 Hz, 1 H) 2.77 (dd, J=13.3, 6 Hz, 1 H) 3.12 (br s, 1 H) 3.22 (ddd, J=13.5, 10.6, 2.8 Hz, 1 H) 3.58 (d, J=3.7 Hz, 2 H) 3.70 (t, J=6.4 Hz, 2 H) 3.81 (s, 3 H) 4.35 (d, J=10.5 Hz, 1 H) 4.37-4.50 (m, 2 H) 5.12-5.22 (m, 2 H) 5.75-5.86 (m, 1 H) 6.64 (d, J=7.8 Hz, 1 H) 6.85 (m, 2 H) 6.92 (s, 2 H) 7.06 (t, J=7.8 Hz, 1 H) 7.10-7.19 (m, 3 H) 7.21 (m, J=8.6 Hz, 2 H). Mass Spectrum (ESI) m/z=596.2 (M+H) and 618.2 (M+Na).

Step C. N-((S)-2-((3R,5R,6S)-3-Allyl-5-(3-chlorophenyl)-6-(4-chlorophenyl)-3-(2-(4-methoxybenzyloxy)ethyl)-2-oxopiperidin-1-yl)butyl)-N-methyl-cyclopropanesulfonamide

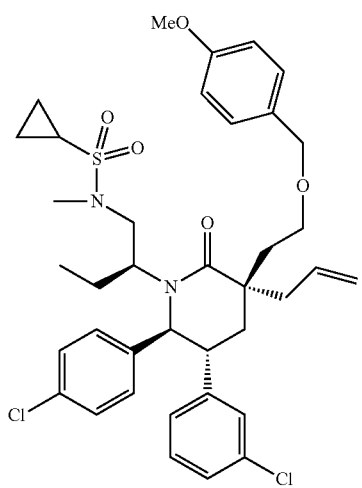 [SMILES: C=CC[C@]1(CCOCc2ccc(OC)cc2)C[C@H](c2cccc(Cl)c2)[C@@H](c2ccc(Cl)cc2)N([C@@H](CC)CN(C)S(=O)(=O)C2CC2)C1=O]

The title compound was prepared from (3R,5R,6S)-3-allyl-5-(3-chlorophenyl)-6-(4-chlorophenyl)-1-((S)-1-hydroxybutan-2-yl)-3-(2-(4-methoxybenzyloxy)ethyl)piperidin-2-one (Example 408, Step B) and N-methylcyclopropanesulfonamide by a procedure similar to the one described in Example 201, Step A.

¹H NMR (500 MHz, CHLOROFORM-d) δ ppm 0.55 (br s, 3 H) 0.87-0.99 (m, 2 H) 1.19 (td, J=5.4, 1.6 Hz, 1 H) 1.48-1.65 (m, 4 H) 1.75 (dd, J=13.7, 3.2 Hz, 1 H) 1.85 (dquin, J=14.7, 7.5 Hz, 1 H) 2.02 (s, 1 H) 2.06-2.11 (m, 1 H) 2.16-2.30 (m, 3 H) 2.52 (br s, 2 H) 2.87 (s, 1 H) 2.89 (s, 3 H) 3.20 (ddd, J=13.6, 10.7, 3.1 Hz, 1 H) 3.71 (t, J=7 Hz, 2 H) 3.81 (s, 3 H) 4.41-4.50 (m, 2 H) 4.66 (br s, 1 H) 5.04-5.12 (m, 2 H) 5.76-5.88 (m, 1 H) 6.83 (d, J=6.9 Hz, 1 H) 6.85-6.90 (m, 2 H) 6.91 (s, 1 H) 7.08-7.20 (m, 4 H) 7.25 (s, 1 H). Mass Spectrum (ESI) m/z=713.2 (M+1) and 735.2 (M+Na).

Step D. N-((S)-2-((3R,5R,6S)-3-Allyl-5-(3-chlorophenyl)-6-(4-chlorophenyl)-3-(2-hydroxyethyl)-2-oxopiperidin-1-yl)butyl)-N-methylcyclopropanesulfonamide

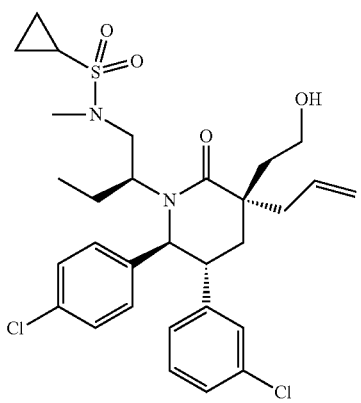 [SMILES: C=CC[C@]1(CCO)C[C@H](c2cccc(Cl)c2)[C@@H](c2ccc(Cl)cc2)N([C@@H](CC)CN(C)S(=O)(=O)C2CC2)C1=O]

To a solution of 3.09 g (4.33 mmol) N-((S)-2-((3R,5R,6S)-3-allyl-5-(3-chlorophenyl)-6-(4-chlorophenyl)-3-(2-(4-methoxybenzyloxy)ethyl)-2-oxopiperidin-1-yl)butyl)-N-methylcyclopropanesulfonamide (Example 408, step C) in a mixture of DCM (82 mL) and water (4.56 mL) [18:1] was added 2,6-di-tert-butylpyridine (2.93 mL, 12.99 mmol) followed by DDQ (3.93 g, 17.32 mmol). The reaction mixture was stirred vigorously at ambient temperature for 15 min. The reaction mixture was diluted with 150 mL sat. NaHCO₃/brine solution and extracted into 600 mL of ethyl acetate, then 200 mL of EtOAc×2 (precipitate was removed by filtration). The combined organic layers were dried over MgSO₄, filtered and the filtrate was evaporated. Purification by chromatography on silica gel (eluent: 50-100%% EtOAc/hexane, gradient elution) provided the desired product as a foam.

¹H NMR (500 MHz, CHLOROFORM-d) δ ppm 0.54 (br s, 3 H) 0.92-1.06 (m, 2 H) 1.20 (dd, J=4.8, 2.1 Hz, 2 H) 1.27 (t, J=7.2 Hz, 1 H) 1.53-1.66 (m, 1 H) 1.66-1.76 (m, 2 H) 1.95 (dt, J=14.9, 7.6 Hz, 1 H) 2.23-2.39 (m, 3 H) 2.59 (br s, 1 H) 2.87 (s, 1 H) 2.90 (s, 3 H) 3.17 (ddd, J=13.8, 10.6, 3.1 Hz, 1 H) 3.77 (dt, J=12.0, 4.6 Hz, 1 H) 4.10-4.20 (m, 1 H) 4.71 (br s, 1 H) 5.07-5.21 (m, 2 H) 5.65-5.80 (m, 1 H) 6.90 (br s, 1 H) 6.96 (s, 1 H) 7.11-7.16 (m, 2 H) 7.22 (br s, 1 H) 7.26 (br s, 2 H). Mass Spectrum (ESI) m/z=593.2 (M+1) and 615.2 (M+Na).

Step E. N-((S)-2-((3R,5R,6S)-3-Allyl-5-(3-chlorophenyl)-6-(4-chlorophenyl)-2-oxo-3-(2-((triisopropylsilyl)oxy)ethyl)piperidin-1-yl)butyl)-N-methylcyclopropanesulfonamide

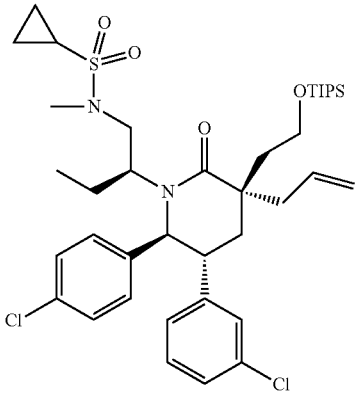

To a solution of 2.52 g (4.25 mmol) N-((S)-2-((3R,5R,6S)-3-allyl-5-(3-chlorophenyl)-6-(4-chlorophenyl)-3-(2-hydroxyethyl)-2-oxopiperidin-1-yl)butyl)-N-methylcyclopropanesulfonamide (Example 408, Step D), DMAP (0.026 g, 0.212 mmol), and imidazole (0.723 g, 10.61 mmol) in DCM (16.98 mL) at 0° C. was added slowly by syringe TIPS-Cl (1.17 mL, 5.52 mmol). The reaction was stirred at ambient temperature, with addition of reagents until reaction was judged complete by LCMS and TLC. The reaction mixture was quenched by addition of 6 mL of MeOH, then extracted with DCM (70 mls×2). The combined organics were washed with water (30 mL), satd. aq. NH₄Cl solution (20 mL), dried over Na₂SO₄, filtered and the filtrate was concentrated. Purification by chromatography on silica gel (eluent: 0 to 40% EtOAc/DCM, gradient elution) provided the title compound as a clear, colorless oil.

Mass Spectrum (ESI) m/z=749.4 (M+1).

Step F. N-((S)-2-((3R,5R,6S)-5-(3-Chlorophenyl)-6-(4-chlorophenyl)-2-oxo-3-(2-oxoethyl)-3-(2-(triisopropylsilyloxy)ethyl)piperidin-1-yl)butyl)-N-methylcyclopropanesulfonamide

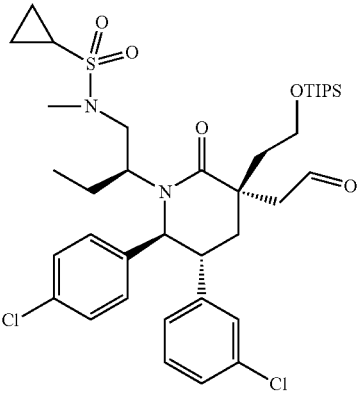

N-((S)-2-((3R,5R,6S)-3-allyl-5-(3-chlorophenyl)-6-(4-chlorophenyl)-2-oxo-3-(2-(triisopropylsilyloxy)ethyl)piperidin-1-yl)butyl)-N-methylcyclopropanesulfonamide (Example 408, Step E) was treated by a procedure similar to the one described in Example 91, Step E. Purification by chromatography on silica gel (12 g SiO₂, eluent: 0 to 30% EtOAc/hexane, gradient elution) provided the title compound as a clear oil.

Mass Spectrum (ESI) m/z=751.2 (M+1)

Step G. N-((S)-2-((3S,5R,6S)-5-(3-Chlorophenyl)-6-(4-chlorophenyl)-3-(2-morpholinoethyl)-2-oxo-3-(2-(triisopropylsilyloxy)ethyl)piperidin-1-yl)butyl)-N-methylcyclopropanesulfonamide

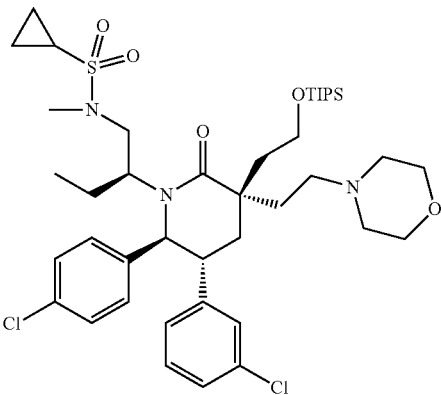

N-((S)-2-((3R,5R,6S)-5-(3-chlorophenyl)-6-(4-chlorophenyl)-2-oxo-3-(2-oxoethyl)-3-(2-((triisopropylsilyl)oxy)ethyl)piperidin-1-yl)butyl)-N-methylcyclopropanesulfonamide (Example 408, Step F) and morpholine were combined according to a procedure similar to the one described in Example 91, Step F. Purification by chromatography on silica gel (eluent: 50 to 100% EtOAc/DCM, gradient elution over 15 min) provided the title compound as a clear, colorless glass.
Mass Spectrum (ESI) m/z=822.4 (M+1)

Step H. N-((S)-2-((3S,5R,6S)-5-(3-chlorophenyl)-6-(4-chlorophenyl)-3-(2-hydroxyethyl)-3-(2-morpholinoethyl)-2-oxopiperidin-1-yl)butyl)-N-methylcyclopropanesulfonamide

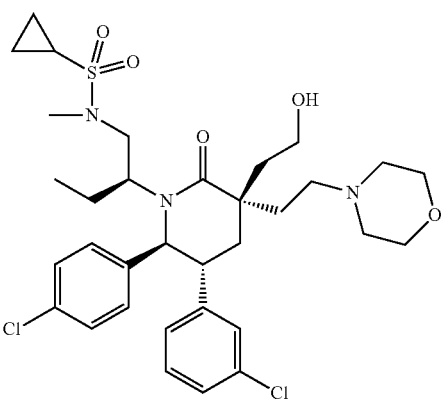 [SMILES: CC[C@@H](CN(C)S(=O)(=O)C1CC1)N1C(=O)[C@](CCO)(CCN2CCOCC2)C[C@H](c2cccc(Cl)c2)[C@H]1c1ccc(Cl)cc1]

N-((S)-2-((3S,5R,6S)-5-(3-chlorophenyl)-6-(4-chlorophenyl)-3-(2-morpholinoethyl)-2-oxo-3-(2-(triisopropylsilyloxy)ethyl)piperidin-1-yl)butyl)-N-methylcyclopropanesulfonamide (Example 408, Step G) was treated according to a procedure similar to the one described in Example 69, step D to afford the title compound.
$^1$H NMR (500 MHz, CHLOROFORM-d) δ ppm 0.53 (t, J=7.6 Hz, 3 H) 1.02-1.06 (m, 1 H) 1.06-1.14 (m, 1 H) 1.14-1.22 (m, 1 H) 1.22-1.31 (m, 1 H) 1.49 (d, J=7.1 Hz, 1 H) 1.64 (ddd, J=14.2, 7.8, 3.7 Hz, 3 H) 1.77-1.98 (m, 4 H) 1.98-2.02 (m, 1 H) 2.02-2.06 (m, 3 H) 2.25-2.43 (m, 4 H) 2.44-2.50 (m, 1 H) 2.61 (dd, J=13.8, 1.8 Hz, 1 H) 2.79-2.89 (m, 3 H) 2.89-3.06 (m, 2 H) 3.12-3.26 (m, 1 H) 3.39-3.50 (m, 2 H) 3.50-3.56 (m, 1 H) 3.61 (d, J=12.7 Hz, 1 H) 3.75-3.90 (m, 1 H) 3.92-4.09 (m, 3 H) 4.14-4.38 (m, 2 H) 4.48 (br s, 1 H) 4.68 (d, J=10.5 Hz, 1 H) 6.82-6.93 (m, 1 H) 6.98 (s, 2 H) 7.08-7.21 (m, 2 H) 12.31 (br s, 1 H).
Mass Spectrum (ESI) m/z=666.2 (M+1)

Step I. 2-((3S,5R,6S)-5-(3-Chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetic acid N-((S)-2-((3S,5R,6S)-5-(3-chlorophenyl)-6-(4-chlorophenyl)-3-(2-hydroxyethyl)-3-(2-morpholinoethyl)-2-oxopiperidin-1-yl)butyl)-N-methylcyclopropanesulfonamide (Example 408, Step H) was treated according to a procedure similar to the one described in Example 69, step E. The reaction (using 4 eq. of Jones Reagent) went to completion in less than 2 minutes at 0° C., after which it was quenched with MeOH (10 eq) and diluted in EtOAc. The solution was decanted from insoluble material, washed with aq. NaHCO$_3$ solution, dried over MgSO$_4$, filtered and concentrated under reduced pressure. Purification by reversed phase prep. HPLC (Sunfire Prep C$_{18}$ OBD 10 μm column (Waters, Milford, Mass.), gradient elution of 40% MeCN in water to 75% MeCN in water over a 30 min period, where both solvents contain 0.1% TFA) provided the title compound as the TFA salt.
$^1$H NMR (500 MHz, CHLOROFORM-d) δ ppm 0.49 (t, J=7.5 Hz, 3 H) 0.96-1.16 (m, 3 H) 1.17-1.28 (m, 1 H) 1.56-1.67 (m, 1 H) 1.85 (dt, J=15.2, 7.7 Hz, 1 H) 2.00 (dd, J=13.6, 3.1 Hz, 1 H) 2.06-2.16 (m, 1 H) 2.22-2.41 (m, 3 H) 2.57-2.66 (m, 1 H) 2.71 (br s, 1 H) 2.85 (s, 3 H) 2.87-2.96 (m, 3 H) 2.99 (br s, 1 H) 3.03 (br s, 1 H) 3.16-3.27 (m, 1 H) 3.34 (br s, 1 H) 3.52-3.66 (m, 2 H) 3.70 (d, J=12 Hz, 1 H) 3.79-3.96 (m, 2 H) 4.03 (d, J=11 Hz, 2 H) 4.38 (br s, 1 H) 4.68 (d, J=10.5 Hz, 1 H) 6.84-6.94 (m, 2 H) 6.98 (s, 2 H) 7.10-7.17 (m, 2 H) 7.22-7.27 (m, 1 H) 8.42 (br s, 3 H) 11.01 (br s, 1 H). Mass Spectrum (ESI) m/z=680.2 (M+1).

Examples 409-411 were prepared from N-((S)-2-((3R,5R,6S)-5-(3-chlorophenyl)-6-(4-chlorophenyl)-2-oxo-3-(2-oxoethyl)-3-(2-(triisopropylsilyloxy)ethyl)piperidin-1-yl)butyl)-N-methylcyclopropanesulfonamide (Example 408, Step F) by procedures similar to those described in Example 408, substituting morpholine in step G with the appropriate amine.

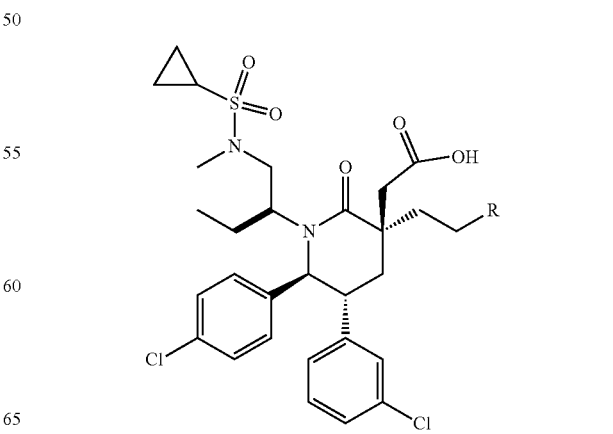

| Example | R = |
|---|---|
| 409 | 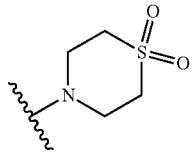 [SMILES: *N1CCS(=O)(=O)CC1] |
| 410 | 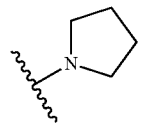 [SMILES: *N1CCCC1] |
| 411 | 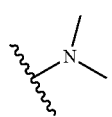 |

Example 409

2-((3S,5R,6S)-5-(3-Chlorophenyl)-6-(4-chlorophenyl)-3-(2-(1,1-dioxidothiomorpholino)ethyl)-1-((S)-1-(N-methylcyclopropanesulfonamido)butan-2-yl)-2-oxopiperidin-3-yl)acetic acid, TFA salt $^1$H NMR (500 MHz, CD$_3$OD) δ ppm 0.51 (t, J=7.5 Hz, 3 H) 1.00-1.07 (m, 1 H) 1.07-1.19 (m, 2 H) 1.21-1.30 (m, 2 H) 1.54-1.68 (m, 1 H) 1.79-1.91 (m, 1 H) 1.95 (dd, J=13.7, 2.7 Hz, 1 H) 2.26 (t, J=13.5 Hz, 2 H) 2.29-2.39 (m, 2 H) 2.61 (d, J=13 Hz, 1 H) 2.73 (br s, 1 H) 2.79 (d, J=13.7 Hz, 1 H) 2.84 (s, 3 H) 2.88-2.96 (m, 1 H) 3.20 (ddd, J=13.4, 10.7, 3.1 Hz, 1 H) 3.52 (br s, 3 H) 3.57 (d, J=8.3 Hz, 3 H) 3.86 (br s, 4 H) 4.43 (t, J=12.1 Hz, 1 H) 4.70 (d, J=10.8 Hz, 1 H) 6.87 (d, J=7.1 Hz, 1 H) 6.99 (s, 3 H) 7.12-7.21 (m, 2 H) 7.27 (br s, 1 H). Mass Spectrum (ESI) m/z=728.2 (M+1).

Example 410

2-((3S,5R,6S)-5-(3-Chlorophenyl)-6-(4-chlorophenyl)-1-((S)-1-(N-methylcyclopropanesulfonamido)butan-2-yl)-2-oxo-3-(2-(pyrrolidin-1-yl)ethyl)piperidin-3-yl)acetic acid, HCl salt $^1$H NMR (500 MHz, CD$_3$OD) δ ppm 0.52 (t, J=7.6 Hz, 3 H) 0.98-1.21 (m, 4 H) 1.69 (ddd, J=14.2, 7.6, 4.9 Hz, 1 H) 1.77-1.92 (m, 1 H) 1.92-2.10 (m, 3 H) 2.10-2.24 (m, 3 H) 2.27-2.42 (m, 2 H) 2.54-2.62 (m, 1 H) 2.76 (dd, J=14.2, 2 Hz, 1 H) 2.79-2.87 (m, 1 H) 2.88 (s, 3 H) 2.91-3.03 (m, 1 H) 3.12 (dtd, J=11.3, 8.0, 3.2 Hz, 2 H) 3.33-3.46 (m, 2 H) 3.63 (ddd, J=12.9, 8.9, 7.1 Hz, 1 H) 3.66-3.77 (m, 2 H) 4.39 (t, J=10.9 Hz, 1 H) 4.81 (d, J=11 Hz, 1 H) 6.94-7.02 (m, 1 H) 7.08 (s, 1 H) 7.12-7.24 (m, 3 H) 7.32 (d, J=7.8 Hz, 2 H). Mass Spectrum (ESI) m/z=728.2 (M+1).

Example 411

2-((3S,5R,6S)-5-(3-Chlorophenyl)-6-(4-chlorophenyl)-3-(2-(dimethylamino)ethyl)-1-((S)-1-(N-methylcyclopropanesulfonamido)butan-2-yl)-2-oxopiperidin-3-yl)acetic acid, HCl salt $^1$H NMR (500 MHz, CD$_3$OD) δ ppm 0.52 (t, J=7.6 Hz, 3 H) 0.98-1.21 (m, 4 H) 1.69 (ddd, J=14.3, 7.7, 4.2 Hz, 1 H) 1.76-1.93 (m, 1 H) 1.98 (dd, J=13.7, 3.2 Hz, 1 H) 2.12 (ddd, J=14.5, 7.6, 5 Hz, 1 H) 2.29-2.44 (m, 2 H) 2.55-2.66 (m, 1 H) 2.76 (dd, J=14.2, 2 Hz, 1 H) 2.80-2.88 (m, 1 H) 2.88-3.06 (m, 11 H) 3.24-3.37 (m, 2 H) 3.42 (ddd, J=13.6, 10.8, 3.1 Hz, 1 H) 3.61 (dt, J=13.3, 7.8 Hz, 1 H) 4.42 (t, J=11.3 Hz, 1 H) 4.81 (d, J=11 Hz, 1 H) 6.93-7.04 (m, 1 H) 7.09 (s, 1 H) 7.12-7.26 (m, 3 H) 7.32 (d, J=7.6 Hz, 2 H). Mass Spectrum (ESI) m/z=638.2 (M+1).

Example 412

2-((3S,5R,6S)-5-(3-Chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetamide, HCl salt

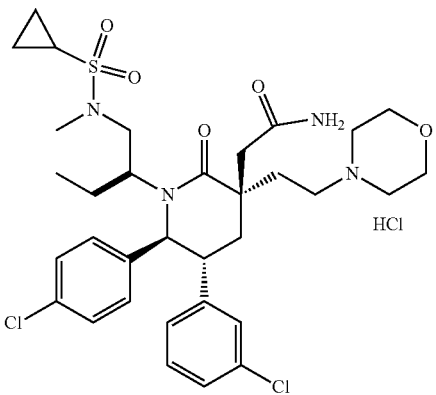

HATU (119 mg, 0.313 mmol) was added to a solution of 83 mg (0.522 mmol) of the TFA salt of 2-((3S,5R,6S)-5-(3-chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetic acid (Example 408, step I) and TEA (72.8 μL, 0.522 mmol) in DMF (2.09 mL). The mixture was stirred for 3 min at ambient temperature, then a solution of NH$_3$ (7M in MeOH, 0.45 mL, 3.13 mmol) was added. The starting material was consumed within minutes. The mixture was concentrated under reduced pressure and purified by reversed phase prep. HPLC (Sunfire Prep C$_{18}$ OBD 10 μm column (Waters, Milford, Mass.), gradient elution of 40% MeCN in water to 75% MeCN in water over a 30 min period, where both solvents contain 0.1% TFA). A few drops of HCl were added prior to lyophilization, so that the title compound was generated as the HCl salt.

$^1$ H NMR (500 MHz, CHLOROFORM-d) δ ppm 0.55 (t, J=7.6 Hz, 3 H) 0.98-1.09 (m, 2 H) 1.09-1.24 (m, 2 H) 1.61-1.78 (m, 1 H) 1.83-1.99 (m, 1 H) 2.08-2.17 (m, 1 H) 2.33 (t, J=13.7 Hz, 1 H) 2.46 (ddd, J=15, 8.1, 7.2 Hz, 1 H) 2.56-2.64 (m, 1 H) 2.73-2.83 (m, 2 H) 2.83-2.93 (m, 4 H) 2.99 (d, J=14.4 Hz, 1 H) 3.11 (td, J=12.1, 3.4 Hz, 1 H) 3.16-3.27 (m, 1 H) 3.36-3.51 (m, 2 H) 3.51-3.67 (m, 2 H) 3.67-3.73 (m, 1 H) 3.74-3.88 (m, 2 H) 4.13 (t, J=9.8 Hz, 2 H) 4.39 (t, J=12.4 Hz, 1 H) 4.81 (d, J=111 Hz, 1 H) 6.89-7.05 (m, 1 H) 7.08 (s, 1 H) 7.11-7.27 (m, 3 H) 7.34 (d, J=7.1 Hz, 2 H). Mass Spectrum (ESI) m/z=679.2 (M+1).

Example 413

2-((3S,5R,6S)-5-(3-chlorophenyl)-6-(4-chlorophenyl)-1-((S)-1-(N-methylcyclopropanesulfonamido)butan-2-yl)-3-(2-morpholinoethyl)-2-oxopiperidin-3-yl)acetamide, HCl salt

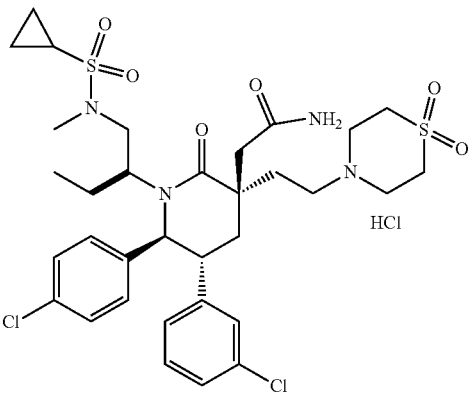

2-((3S,5R,6S)-5-(3-chlorophenyl)-6-(4-chlorophenyl)-3-(2-(1,1-dioxidothiomorpholino)ethyl)-1-((S)-1-(N-methylcyclopropanesulfonamido)butan-2-yl)-2-oxopiperidin-3-yl)acetic acid (Example 409) was treated according to a procedure similar to the one described in Example 412 to afford the title compound.

$^1$H NMR (500 MHz, CD$_3$OD) δ ppm 0.53 (t, J=7.6 Hz, 3 H) 0.98-1.07 (m, 2 H) 1.07-1.16 (m, 1 H) 1.20 (td, J=8.6, 4.4 Hz, 1 H) 1.70 (ddd, J=14.2, 7.8, 3.9 Hz, 1 H) 1.91 (dt, J=15, 7.6 Hz, 1 H) 2.01 (dd, J=13.5, 2.9 Hz, 1 H) 2.12 (dt, J=14.8, 5.3 Hz, 1 H) 2.32 (t, J=13.7 Hz, 1 H) 2.39-2.51 (m, 1 H) 2.59 (dt, J=12.6, 6.4 Hz, 1 H) 2.75-2.87 (m, 3 H) 2.89 (s, 3 H) 2.98 (d, J=14.7 Hz, 1 H) 3.37-3.49 (m, 1 H) 3.50-3.65 (m, 5 H) 3.65-3.75 (m, 1 H) 3.95 (br s, 4 H) 4.38 (t, J=12 Hz, 1 H) 4.79 (d, J=10.8 Hz, 1 H) 7.01 (dd, J=6.5, 2.1 Hz, 1 H) 7.07 (s, 1 H) 7.10-7.26 (m, 3 H) 7.32 (d, J=7.1 Hz, 2 H). Mass Spectrum (ESI) m/z=727.2 (M+1).

Example 414

(1R,3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid and (3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid

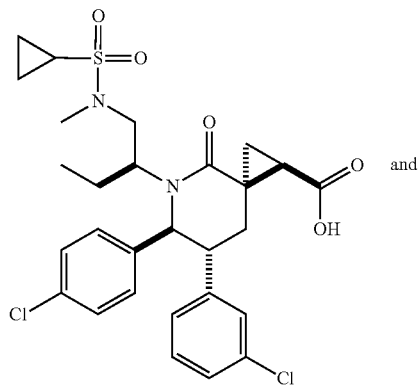

and

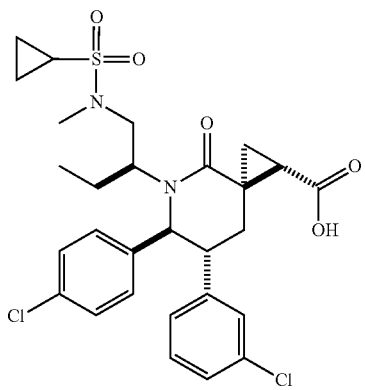

Step A. (3R,5R,6S)-3-Allyl-1-((S)-1-(tert-butyldiphenylsilyloxy)butan-2-yl)-5-(3-chlorophenyl)-6-(4-chlorophenyl)-3-((2-(trimethylsilyl)ethoxy)methyl)piperidin-2-one

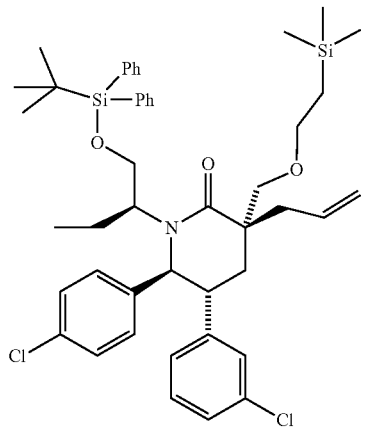 [SMILES: C=CC[C@@]1(COCC[Si](C)(C)C)C[C@H](c2cccc(Cl)c2)[C@@H](c2ccc(Cl)cc2)N([C@@H](CC)CO[Si](c2ccccc2)(c2ccccc2)C(C)(C)C)C1=O]

Lithium bis(trimethylsilyl)amide, (1M solution in toluene, 4.76 mL, 4.76 mmol) was added to a solution of (5R,6S)-1-((S)-1-(tert-butyldiphenylsilyloxy)butan-2-yl)-5-(3-chlorophenyl)-6-(4-chlorophenyl)piperidin-2-one (Example 185, Step C, 2.0 g, 3.17 mmol) and 3-bromopropene (0.274 mL, 3.17 mmol) in THF at −78° C. The reaction was warmed to 0° C. and stirred for 2 hours. After recooling to −78° C., a solution of LDA (7.93 mmol in THF) followed by 2-(chloromethoxy)ethyltrimethylsilane (0.842 mL, 4.76 mmol) was added. The reaction was warmed to 50° C. and stirred for 1.5 hours. The reaction mixture was diluted with EtOAc and washed with HCl (1N). The organic extract was washed with satd NaCl and dried over Na$_2$SO$_4$. The solution was filtered and concentrated in vacuo. The crude material was purified by chromatography on silica gel, eluting with a gradient of 0% to 20% EtOAc in hexane, to provide (3S,5R,6S)-3-allyl-1-((S)-1-(tert-butyldiphenylsilyloxy)butan-2-yl)-5-(3-chlorophenyl)-6-(4-chlorophenyl)-3-((2-(trimethylsilyl)ethoxy)methyl)piperidin-2-one as the first eluting diastereomer and the title compound as the second diastereomer as an oil.

¹H NMR (400 MHz, CHLOROFORM-d) δ ppm −0.07-0.05 (m, 9 H) 0.37 (t, J=7.6 Hz, 3 H) 0.91-1.05 (m, 3 H) 1.28-1.46 (m, 2 H) 1.79 (dd, J=13.6, 2.8 Hz, 1 H) 1.86 (ddd, J=14.1, 9.3, 7.2 Hz, 1 H) 2.35 (dd, J=13.8, 7.9 Hz, 1 H) 2.49-2.65 (m, 2 H) 2.68-2.83 (m, 1 H) 3.02-3.17 (m, 2 H) 3.39-3.53 (m, 2 H) 3.59 (td, J=10, 7.0 Hz, 2 H) 3.84 (d, J=7.8 Hz, 1 H) 4.08 (t, J=10 Hz, 1 H) 4.42 (d, J=10.6 Hz, 1 H) 5.03-5.19 (m, 2 H) 5.76-5.95 (m, 1 H) 6.66 (d, J=7.6 Hz, 1 H) 6.92 (t, J=1.8 Hz, 2 H) 6.97-7.10 (m, 3 H) 7.15 (d, J=7.4 Hz, 2 H).

Step B. (3S,5R,6S)-3-Allyl-5-(3-chlorophenyl)-6-(4-chlorophenyl)-1-((S)-1-hydroxybutan-2-yl)-3-((2-(trimethylsilyl)ethoxy)methyl)piperidin-2-one

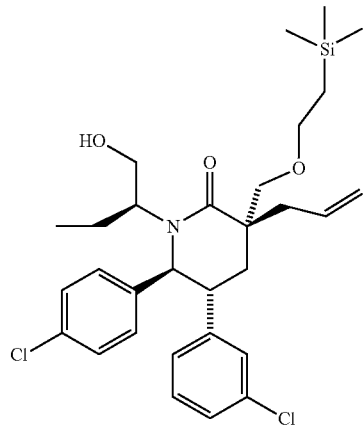 [SMILES: C=CC[C@@]1(COCC[Si](C)(C)C)C[C@H](c2cccc(Cl)c2)[C@@H](c2ccc(Cl)cc2)N([C@@H](CC)CO)C1=O]

A 1M solution of TBAF in THF (2.15 mL, 2.15 mmol) was added to a solution of (3S,5R,6S)-3-allyl-1-((S)-1-(tert-butyldiphenylsilyloxy)butan-2-yl)-5-(3-chlorophenyl)-6-(4-chlorophenyl)-3-((2-(trimethylsilyl)ethoxy)methyl)piperidin-2-one (Example 414, Step A; 860 mg, 1.074 mmol) in THF. The reaction was heated to reflux for 3 hours. After cooling, it was diluted with EtOAc and washed with HCl (1N in water). The organic extract was washed with satd NaCl and dried over Na₂SO₄. The solution was filtered and concentrated to give the crude material as a glass which was purified by chromatography on silica eluting with 20% EtOAc in hexane, to provide the title compound as a solid.

Step C. N-((S)-2-((3S,5R,6S)-3-Allyl-5-(3-chlorophenyl)-6-(4-chlorophenyl)-2-oxo-3-((2-(trimethylsilyl)ethoxy)methyl)piperidin-1-yl)butyl)cyclopropanesulfonamide

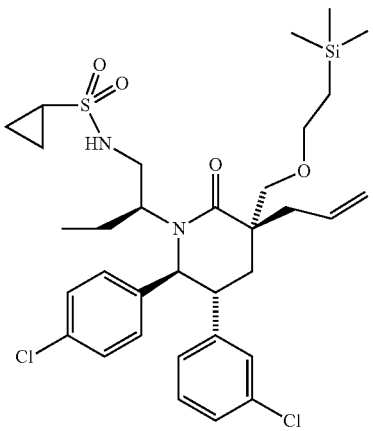 [SMILES: C=CC[C@@]1(COCC[Si](C)(C)C)C[C@H](c2cccc(Cl)c2)[C@@H](c2ccc(Cl)cc2)N([C@@H](CC)CNS(=O)(=O)C2CC2)C1=O]

The title compound was prepared from (3S,5R,6S)-3-allyl-5-(3-chlorophenyl)-6-(4-chlorophenyl)-1-((S)-1-hydroxybutan-2-yl)-3-((2-(trimethylsilyl)ethoxy)methyl)piperidin-2-one (Example 414, Step B) and N-methylcyclopropanesulfonamide by a procedure similar to the one described in Example 201, Step A. The product was purified by chromatography through a RediSep® pre-packed silica gel column (Teledyne Isco, Lincoln, Nebr.) (12 g), eluting with a gradient of 0% to 80% EtOAc in hexane, to provide the title compound as an oil.

Mass Spectrum (ESI) m/z=665.2 (M+1).

Step D. N-((S)-2-((3S,5R,6S)-3-Allyl-5-(3-chlorophenyl)-6-(4-chlorophenyl)-2-oxo-3-((2-(trimethylsilyl)ethoxy)methyl)piperidin-1-yl)butyl)-N-methylcyclopropanesulfonamide

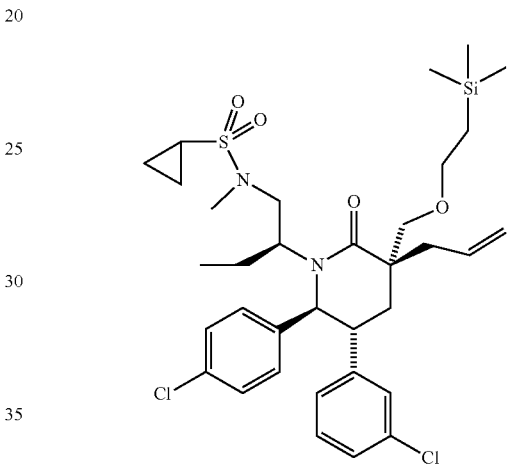

A solution of N-((S)-2-((3S,5R,6S)-3-allyl-5-(3-chlorophenyl)-6-(4-chlorophenyl)-2-oxo-3-((2-(trimethylsilyl)ethoxy)methyl)piperidin-1-yl)butyl)cyclopropanesulfonamide (Example 414, Step C, 1.5 g, 2.253 mmol) in THF was treated with sodium hydride (60% dispersion in mineral oil, 6.76 mmol) and iodomethane (0.280 ml, 4.51 mmol) at room temperature for 3 hours. The reaction mixture was quenched with HCl (1N) and diluted with DCM. The organic extract was washed with satd NaCl and dried over Na₂SO₄. The solution was filtered and concentrated in vacuo to give the crude material as an oil. The product was purified by chromatography through a RediSep® pre-packed silica gel column (Teledyne Isco, Lincoln, Nebr.) (4 g), eluting with a gradient of 0% to 80% EtOAc in hexane, to provide the title compound as an oil.

¹H NMR (400 MHz, CHLOROFORM-d) δ ppm −0.06-0.03 (m, 9 H) 0.54 (t, J=6.9 Hz, 3 H) 0.80-1.03 (m, 5 H) 1.13 (d, J=8.8 Hz, 1 H) 1.14-1.23 (m, 2 H) 1.56-1.65 (m, 2 H) 1.75-1.93 (m, 2 H) 2.28 (t, J=4.5 Hz, 1 H) 2.51 (t, J=13.8 Hz, 1 H) 2.60 (d, J=7.4 Hz, 2 H) 3.01 (s, 3 H) 3.20 (ddd, J=13.9, 10.8, 3.1 Hz, 1 H) 3.31-3.40 (m, 1 H) 3.40-3.49 (m, 1 H) 3.49-3.60 (m, 1 H) 3.79 (d, J=8.6 Hz, 1 H) 4.71 (d, J=10.8 Hz, 1 H) 5.11-5.24 (m, 2 H) 5.83-6.00 (m, 1 H) 6.84-6.91 (m, 1 H) 6.94 (s, 1 H) 7.01 (d, J=7.8 Hz, 2 H) 7.07-7.16 (m, 2 H) 7.21 (d, J=8.2 Hz, 2 H).

Step E. ((3S,5R,6S)-3-Allyl-5-(3-chlorophenyl)-6-(4-chlorophenyl)-1-((S)-1-(N-methylcyclopropanesulfonamido)butan-2-yl)-2-oxopiperidin-3-yl)methyl methanesulfonate

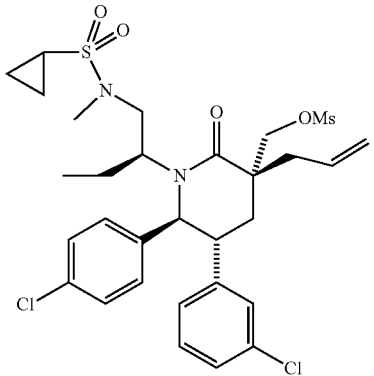 [SMILES: C=CC[C@@]1(COS(C)(=O)=O)C[C@H](c2cccc(Cl)c2)[C@@H](c2ccc(Cl)cc2)N([C@@H](CC)CN(C)S(=O)(=O)C2CC2)C1=O]

A solution of N-((S)-2-((3S,5R,6S)-3-allyl-5-(3-chlorophenyl)-6-(4-chlorophenyl)-2-oxo-3-((2-(trimethylsilyl)ethoxy)methyl)piperidin-1-yl)butyl)-N-methylcyclopropanesulfonamide (Example 414, Step D, 1.85 g, 2.72 mmol) in DCM was treated with boron trifluoride (diethyl etherate, purified, redistilled, 0.672 ml, 5.44 mmol) for 2 hours. The reaction mixture was diluted with DCM and washed with satd NaCl. The organic extract was dried over $Na_2SO_4$, filtered and concentrated in vacuo to give the crude material as an oil. The product was purified by chromatography on a RediSep® pre-packed silica gel column (Teledyne Isco, Lincoln, Nebr.) (12 g), eluting with a gradient of 0% to 80% EtOAc in hexane, to provide the intermediate N-((S)-2-((3S,5R,6S)-3-allyl-5-(3-chlorophenyl)-6-(4-chlorophenyl)-3-(hydroxymethyl)-2-oxopiperidin-1-yl)butyl)-N-methylcyclopropanesulfonamide (1.55 g, 2.67 mmol, 98% yield) as an oil which was used directly in the next reaction.

Methanesulfonyl chloride (0.200 ml, 2.59 mmol) was added to a solution of N-((S)-2-((3S,5R,6S)-3-allyl-5-(3-chlorophenyl)-6-(4-chlorophenyl)-3-(hydroxymethyl)-2-oxopiperidin-1-yl)butyl)-N-methylcyclopropanesulfonamide (1.0 g, 1.725 mmol) and triethylamine (0.480 ml, 3.45 mmol) in DCM. The reaction was stirred for 2 hours. The reaction mixture was diluted with DCM and washed with HCl (1N) and satd NaCl and dried over $Na_2SO_4$. The solution was filtered and concentrated in vacuo to give the crude material as an oil. The product was purified by chromatography through a RediSep® pre-packed silica gel column (Teledyne Isco, Lincoln, Nebr.) (12 g), eluting with a gradient of 0% to 80% EtOAc in hexane, to provide the title compound as an oil. Mass Spectrum (ESI) m/z=657.2 (M+1).

Step F. ((3R,5R,6S)-5-(3-Chlorophenyl)-6-(4-chlorophenyl)-1-((S)-1-(N-methylcyclopropanesulfonamido)butan-2-yl)-2-oxo-3-(2-oxoethyl)piperidin-3-yl)methyl methanesulfonate

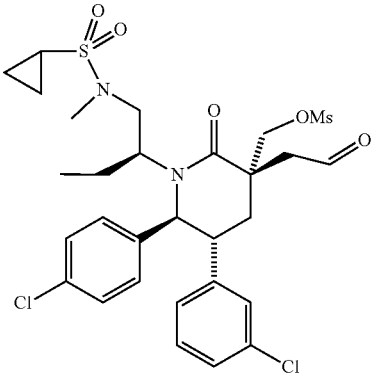 [SMILES: CC[C@@H](CN(C)S(=O)(=O)C1CC1)N1C(=O)[C@](CC=O)(COS(C)(=O)=O)C[C@H](c2cccc(Cl)c2)[C@H]1c1ccc(Cl)cc1]

Ozone was bubbled through a solution of ((3S,5R,6S)-3-allyl-5-(3-chlorophenyl)-6-(4-chlorophenyl)-1-((S)-1-(N-methylcyclopropanesulfonamido)butan-2-yl)-2-oxopiperidin-3-yl)methyl methanesulfonate (Example 414, Step E, 1.12 g, 1.703 mmol) in 10% MeOH-DCM at −78° C. until a blue color developed. The reaction was purged with nitrogen gas followed by addition of dimethyl sulfide (1.251 ml, 17.03 mmol). The reaction was warmed to room temperature. The crude material was purified by chromatography on a RediSep® pre-packed silica gel column (Teledyne Isco, Lincoln, Nebr.) (12 g), eluting with a gradient of 0% to 80% EtOAc in hexane, to provide the title compound as an oil.

$^1$H NMR (400 MHz, CHLOROFORM-d) δ ppm 0.35-0.59 (m, 3 H) 0.95 (dt, J=5.0, 2.5 Hz, 2 H) 1.05-1.17 (m, 2 H) 1.43-1.69 (m, 1 H) 1.69-1.90 (m, 2 H) 2.04-2.18 (m, 1 H) 2.17-2.32 (m, 2 H) 2.32-2.53 (m, 1 H) 2.58-2.94 (m, 5 H) 2.94-3.11 (m, 4 H) 3.49 (s, 1 H) 3.53-3.72 (m, 2 H) 4.34-4.82 (m, 3 H) 5.02-5.52 (m, 1 H) 7.01-7.15 (m, 2 H) 7.15-7.23 (m, 2 H), 9.89 (s, 1 H).

Step G: Methyl 2-((3R,5R,6S)-5-(3-chlorophenyl)-6-(4-chlorophenyl)-1-((S)-1-(N-methylcyclopropanesulfonamido)butan-2-yl)-3-(((methylsulfonyl)oxy)methyl)-2-oxopiperidin-3-yl)acetate

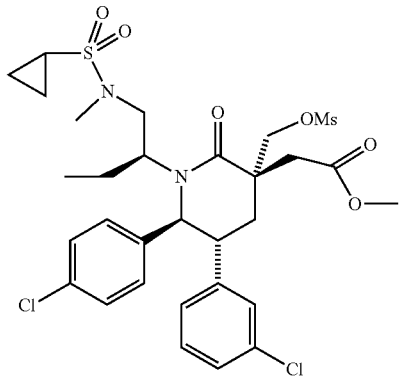 [SMILES: CC[C@@H](CN(C)S(=O)(=O)C1CC1)N1C(=O)[C@@](COS(C)(=O)=O)(CC(=O)OC)C[C@H](c2cccc(Cl)c2)[C@H]1c1ccc(Cl)cc1]

A solution of ((3R,5R,6S)-5-(3-chlorophenyl)-6-(4-chlorophenyl)-1-((S)-1-(N-methylcyclopropanesulfonamido)butan-2-yl)-2-oxo-3-(2-oxoethyl)piperidin-3-yl)methyl methanesulfonate (Example 414, Step F, 1.0 g, 1.516 mmol) in MeOH was treated with Oxone (0.932 g, 1.516 mmol) over a weekend. The reaction mixture was diluted with DCM and water. The organic extract was washed with satd NaCl and dried over $Na_2SO_4$. The solution was filtered and concentrated in vacuo to give the crude material as a white solid. The product was purified by chromatography through a RediSep® pre-packed silica gel column (Teledyne Isco, Lincoln, Nebr.) (12 g), eluting with a gradient of 0% to 80% EtOAc in hexane, to provide the title compound as an oil.

$^1$H NMR (400 MHz, CHLOROFORM-d) δ ppm 0.46-0.63 (m, 5 H) 1.01 (dd, J=7.7, 2.3 Hz, 4 H) 1.15-1.26 (m, 4 H) 1.79-1.98 (m, 2 H) 2.05 (dd, J=13.9, 3.1 Hz, 1 H) 2.19 (dd, J=13.5, 5.1 Hz, 1 H) 2.28-2.40 (m, 2 H) 2.47-2.61 (m, 1 H) 2.76-2.91 (m, 5 H) 2.91-3.02 (m, 6 H) 3.03-3.12 (m, 5 H) 3.12-3.26 (m, 2 H) 3.42 (d, J=0.8 Hz, 2 H) 3.75 (s, 3 H) 4.05-4.28 (m, 1 H) 4.50-4.62 (m, 2 H) 4.64-4.75 (m, 2 H) 4.81 (d, J=10.6 Hz, 1 H) 6.87-7.01 (m, 3 H) 7.01-7.12 (m, 2 H) 7.13-7.21 (m, 3 H) 7.27 (d, J=7.6 Hz, 2 H).

Step H. (1S,3S,6S,7R)-Methyl 7-(3-chlorophenyl)-6-(4-chlorophenyl)-5-((S)-1-(N-methylcyclopropanesulfonamido)butan-2-yl)-4-oxo-5-azaspiro[2.5]octane-1-carboxylate and (1R,3S,6S,7R)-methyl 7-(3-chlorophenyl)-6-(4-chlorophenyl)-5-((S)-1-(N-methylcyclopropanesulfonamido)butan-2-yl)-4-oxo-5-azaspiro[2.5]octane-1-carboxylate

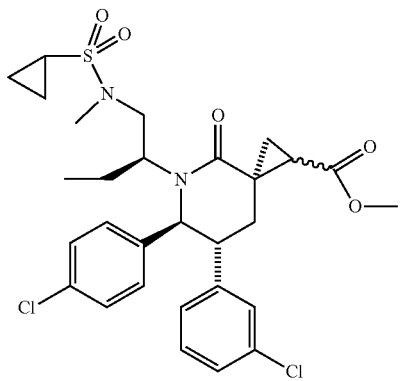

A solution of lithium bis(trimethylsilyl)amide, (1.0M in toluene, 290 μl, 0.290 mmol) was added to a solution of methyl 2-((3R,5R,6S)-5-(3-chlorophenyl)-6-(4-chlorophenyl)-1-((S)-1-(N-methylcyclopropanesulfonamido)butan-2-yl)-3-(((methylsulfonyl)oxy)methyl)-2-oxopiperidin-3-yl)acetate (Example 414, Step G, 200 mg, 0.290 mmol) in THF at 0° C. over 10 mins. The reaction mixture was quencged with 1N HCl and extracted with DCM. The organic extract was washed with sat. aq. $Na_2CO_3$ solution and dried over $Na_2SO_4$. The solution was filtered and concentrated in vacuo to give the crude material as a white glass. The product was purified by chromatography on a Redi-Sep pre-packed silica gel column (4 g), eluting with a gradient of 0% to 80% EtOAc in hexane, to provide the title compounds as a mixture of diastereomers.

$^1$H NMR (400 MHz, CHLOROFORM-d) δ ppm 0.40 (t, J=7.5 Hz, 3 H) 0.69-0.86 (m, 3 H) 0.86-0.95 (m, 2 H) 1.01-1.14 (m, 3 H) 1.14-1.23 (m, 2 H) 1.25 (dd, J=6.5, 4.3 Hz, 2 H) 1.43 (br. s., 3 H) 1.77 (dt, J=14.7, 7.4 Hz, 1 H) 1.89-2.02 (m, 2 H) 2.14-2.26 (m, 2 H) 2.51 (t, J=11.7 Hz, 1 H) 2.70-2.82 (m, 2 H) 2.84 (s, 3 H) 3.57-3.73 (m, 3 H) 4.67 (d, J=9.6 Hz, 1 H) 6.74-6.88 (m, 2 H) 6.98 (d, J=8.0 Hz, 2 H) 7.06 (d, J=5.1 Hz, 2 H) 7.17 (s, 2 H). Mass Spectrum (ESI) m/z=593.2 (M+H$^+$).

Step I: (1R,3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid and (1S,3S,6S,7R)-7-(3-Chlorophenyl)-6-(4-chlorophenyl)-5-((S)-1-(N-methylcyclopropanesulfonamido)butan-2-yl)-4-oxo-5-azaspiro[2.5]octane-1-carboxylic acid The mixture of diastereomeric esters from Example 414, Step H was treated with NaOH (3N in MeOH) overnight at room temperature. The reaction mixture was acidified with 1N HCl (1N) and extracted into DCM. The organic extract was washed with satd NaCl and dried over $Na_2SO_4$. The product was purified by chromatography on silica, eluting with a gradient of 40% EtOAc in hexane, to provide the title compounds as a mixture of diastereomers as a white glass.

$^1$H NMR (400 MHz, CHLOROFORM-d) δ ppm 0.39 (t, J=7.5 Hz, 3 H) 0.81 (s, 1 H) 0.89-1.02 (m, 2 H) 1.16-1.21 (m, 2 H) 1.21-1.30 (m, 1 H) 1.37 (dd, J=9.2, 5.7 Hz, 1 H) 1.47 (ddd, J=14.5, 7.6, 4.1 Hz, 1 H) 1.84 (ddd, J=14.5, 8.7, 7.3 Hz, 1 H) 1.95-2.05 (m, 1 H) 2.18 (dd, J=7.0, 5.7 Hz, 1 H) 2.22-2.32 (m, 1 H) 2.66-2.85 (m, 3 H) 2.87 (s, 3 H) 3.11 (ddd, J=13.1, 10.4, 2.9 Hz, 1 H) 3.42 (s, 1 H) 4.05 (d, J=7.0 Hz, 1 H) 4.71 (d, J=10.4 Hz, 1 H) 6.74 (dt, J=6.9, 1.6 Hz, 1 H) 6.82-6.95 (m, 3 H) 6.98-7.11 (m, 2 H) 7.18 (d, J=8.4 Hz, 2 H); Mass Spectrum (ESI) m/z=579.1 (M+H$^+$).

Example 415

2-((3R,5R,6S)-5-(3-Chlorophenyl)-6-(4-chlorophenyl)-1-((2S,3S)-1,2-dihydroxypentan-3-yl)-3-methyl-2-oxopiperidin-3-yl)acetic acid or 2-((3R,5R,6S)-5-(3-Chlorophenyl)-6-(4-chlorophenyl)-1-((2R,3S)-1,2-dihydroxypentan-3-yl)-3-methyl-2-oxopiperidin-3-yl)acetic acid

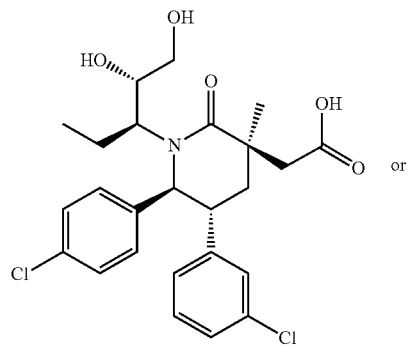 or

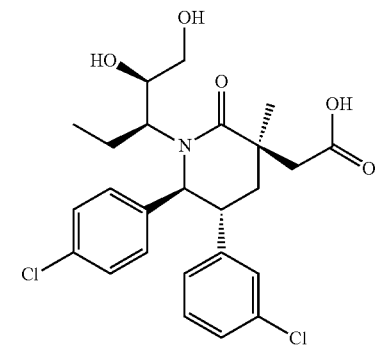

Step A. Methyl 2-((3R,5R,6S)-5-(3-chlorophenyl)-6-(4-chlorophenyl)-3-methyl-2-oxo-1-((S)-1-oxobutan-2-yl)piperidin-3-yl)acetate

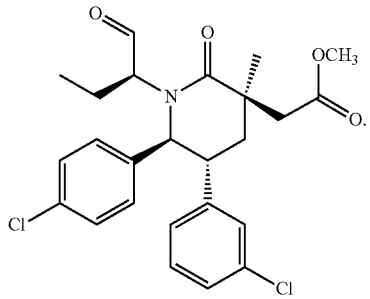 [SMILES: CC[C@@H](C=O)N1C(=O)[C@@](C)(CC(=O)OC)C[C@H](c2cccc(Cl)c2)[C@H]1c1ccc(Cl)cc1]

To a stirred solution of methyl 2-((3R,5R,6S)-5-(3-chlorophenyl)-6-(4-chlorophenyl)-1-((S)-1-hydroxybutan-2-yl)-3-methyl-2-oxopiperidin-3-yl)acetate (Example 186, Step A, 360 mg, 0.752 mmol) in DCM (3.76 mL) was added Dess-Martin periodinane (383 mg, 0.903 mmol) and the reaction was stirred at rt for 20 minutes. After this time the reaction was treated with $Na_2S_2O_3$ (30 mL, saturated aqueous solution) and DCM (40 mL) and stirred at rt for 10 minutes. The organic layer was separated and washed with $Na_2S_2O_3$ (20 mL, saturated aqueous solution) and $NaHCO_3$ (20 mL, saturated aqueous solution), dried over $MgSO_4$, filtered and concentrated to give the title compound. MS (ESI) m/z=476.0 (M+1).

Step B. Methyl 2-((3R,5R,6S)-5-(3-chlorophenyl)-6-(4-chlorophenyl)-3-methyl-2-oxo-1-((S)-pent-1-en-3-yl)piperidin-3-yl)acetate

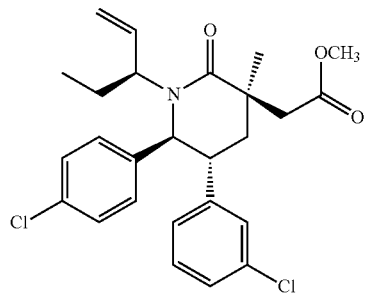 [SMILES: C=C[C@H](CC)N1C(=O)[C@@](C)(CC(=O)OC)C[C@H](c2cccc(Cl)c2)[C@H]1c1ccc(Cl)cc1]

Tebbe reagent (Bis(cyclopentadienyl)-μ-chloro(dimethylaluminum)-μ-methylenetitanium, 0.5 M solution in toluene, 1.7 mL, 0.85 mmol) was added dropwise over 5 minutes to a stirred solution of methyl 2-((3R,5R,6S)-5-(3-chlorophenyl)-6-(4-chlorophenyl)-3-methyl-2-oxo-1-((S)-1-oxobutan-2-yl)piperidin-3-yl)acetate (Example 415, Step A, 360 mg, 0.756 mmol) in toluene (4.7 mL) at 0° C. The reaction was stirred at 0° C. for 20 minutes and at rt for 30 minutes. The reaction was recooled to 0° C. and an additional portion of Tebbe reagent (0.5 M solution in toluene, 1 mL, 0.5 mmol) was added. The reaction was allowed to warm to rt for 20 minutes. The reaction was recooled to 0° C. and treated with sat. aq. $NaHCO_3$ solution (40 mL) and EtOAc (100 mL). The separated aqueous layer was extracted with EtOAc (2×60 mL) and the combined organic extracts were washed with brine (80 ml), dried over $MgSO_4$, filtered and the filtrate was concentrated under reduced pressure. Column chromatography on silica gel (24 g, $SiO_2$, eluent: hexanes:EtOAc, 1:0 to 3:1, gradient elution) gave the title compound.
MS (ESI) m/z=474.0 (M+1).

Step C. Methyl 2-((3R,5R,6S)-5-(3-chlorophenyl)-6-(4-chlorophenyl)-1-((3S)-1,2-dihydroxypentan-3-yl)-3-methyl-2-oxopiperidin-3-yl)acetate

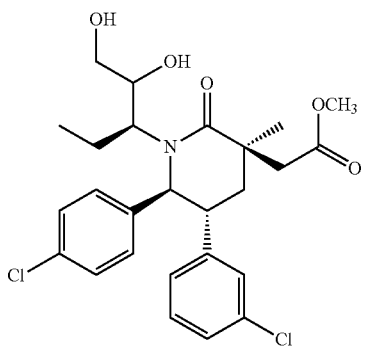 [SMILES: CC[C@@H](C(O)CO)N1C(=O)[C@@](C)(CC(=O)OC)C[C@H](c2cccc(Cl)c2)[C@H]1c1ccc(Cl)cc1]

To a stirred solution of methyl 2-((3R,5R,6S)-5-(3-chlorophenyl)-6-(4-chlorophenyl)-3-methyl-2-oxo-1-((S)-pent-1-en-3-yl)piperidin-3-yl)acetate (Example 415, Step B, 85 mg, 0.18 mmol) in THF (1 mL), t-butanol (1 mL) and water (1.5 mL) was added 4-methylmorpholine 4-oxide (63.0 mg, 0.54 mmol) and $OsO_4$ (1.1 mg, 4.5 μmol). The reaction was stirred at rt overnight. The reaction was diluted with EtOAc (40 mL) and $Na_2S_2O_3$ (20 mL, saturated aqueous solution). The separated aqueous layer was extracted with EtOAc (20 mL) and the combined organic extracts were washed with brine (20 mL), dried over $MgSO_4$, filtered and evaporated in vacuo to give the title compound as a 5:1 mixture of diastereomers.
Mass Spectrum (ESI) m/e=508.0 (M+1).

Step D. 2-((3R,5R,6S)-5-(3-chlorophenyl)-6-(4-chlorophenyl)-1-((2S,3S)-1,2-dihydroxypentan-3-yl)-3-methyl-2-oxopiperidin-3-yl)acetic acid or 2-((3R,5R,6S)-5-(3-chlorophenyl)-6-(4-chlorophenyl)-1-((2R,3S)-1,2-dihydroxypentan-3-yl)-3-methyl-2-oxopiperidin-3-yl)acetic acid A solution of LiOH in water (1M, 502 μl, 0.502 mmol) was added to a stirred solution of methyl 2-((3R,5R,6S)-5-(3-chlorophenyl)-6-(4-chlorophenyl)-1-((3S)-1,2-dihydroxypentan-3-yl)-3-methyl-2-oxopiperidin-3-yl)acetate (Example 415, Step C; 85 mg, 0.167 mmol) in EtOH (1.67 mL). The reaction was stirred at rt for 4 hours. After this time the reaction was quenched with sat. aq. $NH_4Cl$ solution (20 mL) and treated with EtOAc (40 mL). The separated aqueous layer was extracted with EtOAc (2×20 mL) and the combined organic extracts were dried over $MgSO_4$, filtered and the filtrate was concentrated under reduced pressure. The product was purified by reverse phase preparatory HPLC (Gemini™ Prep $C_{18}$ 10 μm column; Phenomenex, Torrance, Calif., using 25 to 75% acetonitrile in water with 0.1% TFA as eluent) to give one of the title compounds as the minor diastereomer, as the first eluting component.

$^1$H NMR (400 MHz, methanol-$d_4$) δ ppm 7.26 (4 H, br s), 7.11-7.17 (2 H, m), 7.07 (1 H, s), 6.93-6.98 (1 H, m), 4.75 (1 H, d, J=10.8 Hz), 3.78 (1 H, br s), 3.56-3.66 (2 H, m), 3.43 (1 H, td, J=11.3, 4.8 Hz), 2.92-3.01 (2 H, m), 2.60 (1 H, d, J=13.7

Hz), 2.14-2.22 (2 H, m), 1.94-2.05 (1 H, m), 1.72 (1 H, ddd, J=14.6, 7.6, 5.2 Hz), 1.38 (3 H, s), 0.51 (3 H, t, J=7.5 Hz); Mass Spectrum (ESI) m/z=494.0 (M+1).

Example 416

2-((3R,5R,6S)-5-(3-Chlorophenyl)-6-(4-chlorophenyl)-1-((2R,3S)-1,2-dihydroxypentan-3-yl)-3-methyl-2-oxopiperidin-3-yl)acetic acid or 2-((3R,5R,6S)-5-(3-Chlorophenyl)-6-(4-chlorophenyl)-1-((2S,3S)-1,2-dihydroxypentan-3-yl)-3-methyl-2-oxopiperidin-3-yl)acetic acid

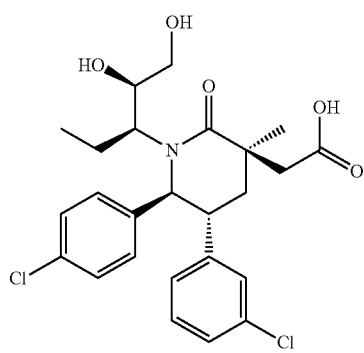

or

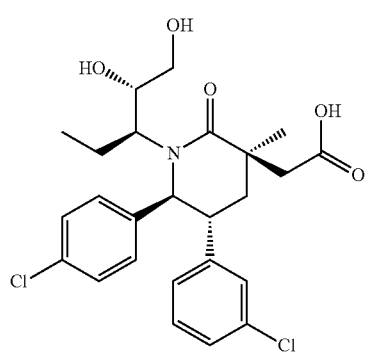

In the purification described in Example 415, Step D, the other of the title compounds was isolated as the major diastereomer, as the second eluting component.

¹H NMR (500 MHz, methanol-$d_4$) δ ppm 7.18-7.25 (3 H, br s), 7.05-7.17 (4 H, m), 6.88-6.98 (1 H, m), 4.83 (1 H, d, J=10.8 Hz), 3.96 (1 H, br s), 3.59 (1 H, dd, J=11.2, 5.4 Hz), 3.51 (1 H, dd, J=11.2, 5.1 Hz), 3.39-3.46 (1 H, m), 2.81-2.99 (2 H, m), 2.61 (1 H, d, J=13.7 Hz), 2.12-2.27 (2 H, m), 1.84-1.96 (1 H, m), 1.60 (1 H, ddd, J=14.2, 7.8, 4.6 Hz), 1.41 (3 H, m), 0.43 (3 H, t, J=7.3 Hz); Mass Spectrum (ESI) m/z=494.0 (M+1).

Example 417

2-((3R,5R,6S)-5-(3-Chlorophenyl)-6-(4-chlorophenyl)-1-((1S,2S)-1-cyclopropyl-1-hydroxybutan-2-yl)-3-methyl-2-oxopiperidin-3-yl)acetic acid or 2-((3R,5R,6S)-5-(3-Chlorophenyl)-6-(4-chlorophenyl)-1-((1R,2S)-1-cyclopropyl-1-hydroxybutan-2-yl)-3-methyl-2-oxopiperidin-3-yl)acetic acid

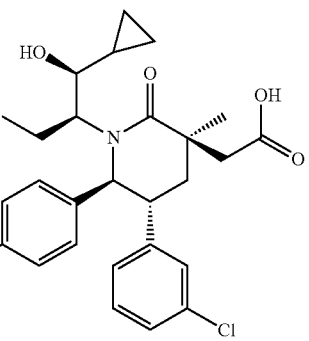

or

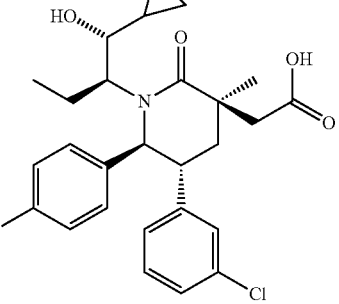

Step A. (3S,5R,6S)-3-Allyl-5-(3-chlorophenyl)-6-(4-chlorophenyl)-1-((2S)-1-cyclopropyl-1-hydroxybutan-2-yl)-3-methylpiperidin-2-one

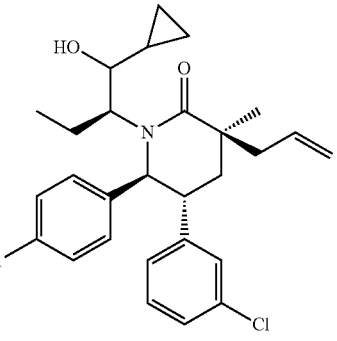

Cyclopropylmagnesium bromide (0.5 M solution in THF, 2.0 mL, 1.013 mmol) was added dropwise via syringe over a period of 1 min to a stirred solution of (S)-2-((3S,5R,6S)-3-allyl-5-(3-chlorophenyl)-6-(4-chlorophenyl)-3-methyl-2- oxopiperidin-1-yl)butanal (Example 91, Step C, 150 mg, 0.338 mmol) in THF (1.7 mL) at rt. The reaction mixture was stirred at rt for 20 minutes and then quenched with NH₄Cl (30 mL, saturated aqueous solution) and diluted with EtOAc (50 mL). The organic layer was dried over MgSO₄, filtered and evaporated in vacuo. Purification by column chromatography (24 g SiO₂, Hexanes:EtOAc, 1:0 to 4:1) gave the title compound as a mixture of diastereomers.

MS (ESI) m/z=486.2 (M+1).

Step B. 2-((3R,5R,6S)-5-(3-Chlorophenyl)-6-(4-chlorophenyl)-1-((S)-1-cyclopropyl-1-oxobutan-2-yl)-3-methyl-2-oxopiperidin-3-yl)acetic acid

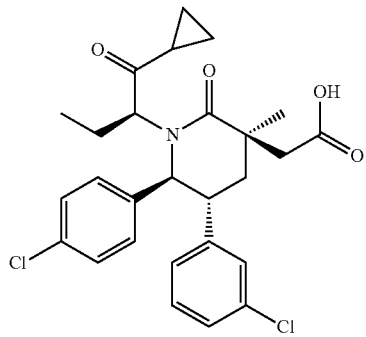 [SMILES: CC[C@@H](C(=O)C1CC1)N1C(=O)[C@@](C)(CC(=O)O)C[C@H](c2cccc(Cl)c2)[C@H]1c1ccc(Cl)cc1]

To a stirred solution of (3S,5R,6S)-3-allyl-5-(3-chlorophenyl)-6-(4-chlorophenyl)-1-((2S)-1-cyclopropyl-1-hydroxybutan-2-yl)-3-methylpiperidin-2-one (Example 417, Step A; 60 mg, 0.123 mmol) in EtOAc (1 mL), acetonitrile (1 mL) and water (1.5 mL) was added ruthenium chloride hydrate (2.8 mg, 0.012 mmol) and sodium meta-periodate (6.83 µl, 0.123 mmol) (portionwise over 5 minutes). The reaction was stirred at rt for 20 minutes and then partitioned between EtOAc (60 mL) and water (20 mL). The separated aqueous layer was extracted with EtOAc (2×20 mL) and the combined organic extracts were dried over MgSO₄, filtered and evaporated in vacuo. Purification by column chromatography (12 g, SiO₂, hexanes/IPA, 1:0 to 9:1) gave the title compound.

MS (ESI) m/z=502.1 (M+1).

Step C. 2-((3R,5R,6S)-5-(3-Chlorophenyl)-6-(4-chlorophenyl)-1-((1S,2S)-1-cyclopropyl-1-hydroxybutan-2-yl)-3-methyl-2-oxopiperidin-3-yl)acetic acid or 2-((3R,5R,6S)-5-(3-Chlorophenyl)-6-(4-chlorophenyl)-1-((1R,2S)-1-cyclopropyl-1-hydroxybutan-2-yl)-3-methyl-2-oxopiperidin-3-yl)acetic acid To a stirred solution of 2-((3R,5R,6S)-5-(3-chlorophenyl)-6-(4-chlorophenyl)-1-((S)-1-cyclopropyl-1-oxobutan-2-yl)-3-methyl-2-oxopiperidin-3-yl)acetic acid (Example 417, Step B, 33 mg, 0.066 mmol) in THF (657 µl) at −78° C. was added dropwise a solution of L-selectride (144 µl, 0.144 mmol). The reaction mixture was stirred at −78° C. for 20 minutes and then it was allowed to warm to rt for 30 minutes. After this time the reaction was quenched with a solution of oxone (121 mg, 0.197 mmol) in water (3 mL). The reaction was diluted with EtOAc (30 mL) and the separated aqueous layer was extracted with EtOAc (2×10 mL), dried over MgSO₄, filtered and evaporated in vacuo. Column chromatography (4 g, SiO₂, hexanes:IPA, 1:0 to 4:1) gave the title compound as a single stereoisomer.

¹H NMR (400 MHz, CDCl₃) δ ppm 6.95-7.27 (7 H, m), 6.72 (1 H, dt, J=7.6, 1.6 Hz), 4.58-4.70 (1 H, m), 3.07-3.34 (1 H, m), 2.80-2.93 (2 H, m), 2.09-2.25 (4 H, m), 1.47 (3 H, s), 0.28-1.47 (10 H, m); Mass Spectrum (ESI) m/z=504.0 (M+1).

Example 418

2-((3S,5R,6S)-5-(3-Chlorophenyl)-6-(4-chlorophenyl)-1-isopropyl-6-methyl-2-oxopiperidin-3-yl)acetic acid

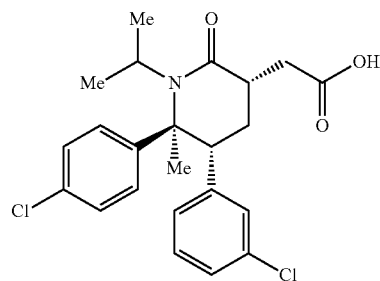 [SMILES: CC(C)N1C(=O)[C@H](CC(=O)O)C[C@H](c2cccc(Cl)c2)[C@@]1(C)c1ccc(Cl)cc1]

Step A. (S)-2-(3-Chlorophenyl)-1-(4-chlorophenyl)pent-4-en-1-one and (R)-2-(3-chlorophenyl)-1-(4-chlorophenyl)pent-4-en-1-one

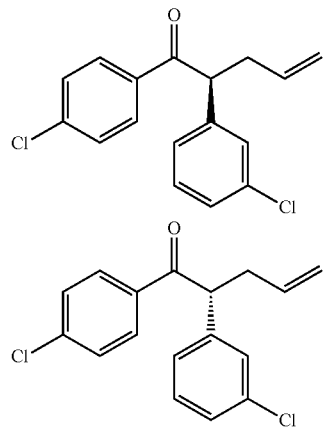

To a solution of KOH (57.1 g, 1.02 mol) in water (113 mL) was added N-benzyl-N,N-diethylethanaminium chloride (1.289 g, 5.66 mmol). A solution of 2-(3-chlorophenyl)-1-(4-chlorophenyl)ethanone (Example 1, Step A) (30 g, 113 mmol) in toluene (113 mL) was added followed by 3-bromoprop-1-ene (10.77 mL, 124 mmol). The resulting biphase was vigorously stirred at ambient temperature for twenty-one hours, then separated. The organic layer was washed with aqueous citric acid solution followed by brine then dried over anhydrous MgSO₄ and concentrated to afford the title compounds as a pale yellow oil.

¹H NMR (400 MHz, CHLOROFORM-d) δ ppm 2.49-2.67 (m, 1 H) 2.86-3.04 (m, 1 H) 4.57 (t, J=7.3 Hz, 1 H) 4.95-5.15

(m, 2 H) 5.75 (ddt, J=17.1, 10.2, 6.9 Hz, 1 H) 7.14-7.35 (m, 4 H) 7.36-7.47 (m, 2 H) 7.83-7.98 (m, 2 H).

Step B. (R)—N—((R)-2-(3-Chlorophenyl)-1-(4-chlorophenyl)pent-4-en-1-ylidene)-2-methylpropane-2-sulfinamide

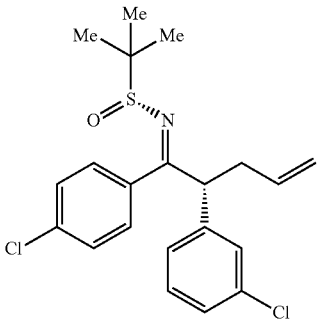 [SMILES: C=CC[C@@H](/C(=N/[S@](=O)C(C)(C)C)c1ccc(Cl)cc1)c1cccc(Cl)c1]

2-(3-Chlorophenyl)-1-(4-chlorophenyl)pent-4-en-1-one (Example 418, Step A, 48 g, 157 mmol), titanium(IV) ethoxide, technical grade (65.9 mL, 315 mmol) and (R)-(+)-2-methyl-2-propanesulfinamide (Combi-Blocks, San Diego, Calif., 33.1 g, 267 mmol) were dissolved in 400 mL of THF. The mixture was heated with stirring under reflux for eighteen hours. The reaction was cooled and poured into brine. The resulting white solid was removed by filtration, rinsing with ethyl acetate. Ethyl acetate was added to the biphasic filtrate and the layers separated. The organic layer was washed with brine, then dried with anhydrous magnesium sulfate and concentrated. The crude product was purified by three chromatographies (330 g RediSep® pre-packed silica gel column (Teledyne Isco, Lincoln, Nebr.), eluting with hexane:ethyl acetate, 95:5 to 85:5) to afford the title compound eluting second on silica gel TLC in hexane/ethyl acetate, the diastereomer (R)—N-((S)-2-(3-chlorophenyl)-1-(4-chlorophenyl)pent-4-en-1-ylidene)-2-methylpropane-2-sulfinamide eluting third on silica gel TLC in hexane/ethyl acetate, and some starting ketone eluting first on silica gel TLC in hexane/ethyl acetate.

$^1$H NMR (400 MHz, CHLOROFORM-d) δ ppm 1.28 (s, 9 H) 2.58-2.75 (m, 1 H) 2.85-3.02 (m, 1 H) 3.80-4.12 (m, 1 H) 5.01-5.16 (m, 2 H) 5.76 (ddt, J=17.0, 10.2, 6.8 Hz, 1 H) 6.94-7.11 (m, 2 H) 7.11-7.20 (m, 1 H) 7.20-7.38 (m, 5 H).

Step C. (R)—N-((2S,3R)-3-(3-Chlorophenyl)-2-(4-chlorophenyl)hex-5-en-2-yl)-2-methylpropane-2-sulfinamide

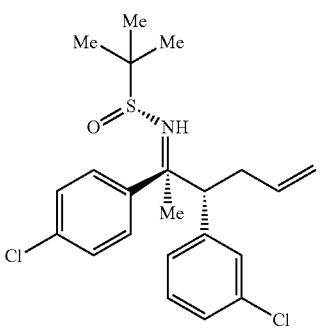

A solution of (R)—N—((R)-2-(3-chlorophenyl)-1-(4-chlorophenyl)pent-4-enylidene)-2-methylpropane-2-sulfinamide (Example 418, Step B, 9.97 g, 24.41 mmol) in THF (98 ml) was cooled to −78° C. Methyllithium (1.6M in ether, 16.78 ml, 26.9 mmol) was added over a period of six min. The reaction was removed from the cold bath and diluted with 500 mL ether and quenched with 150 mL of saturated aqueous ammonium chloride solution. The organic layer was separated and washed with brine, then dried with anhydrous magnesium sulfate and concentrated to afford a colorless oil. The crude material was adsorbed onto a plug of silica gel and purified by chromatography through (3×80 g) RediSep® pre-packed silica gel column (Teledyne Isco, Lincoln, Nebr.), eluting with 30% ethyl acetate in hexane. Fractions containing the desired product, eluting as the bottom spot on silica gel TLC in hexane/ethyl acetate, were combined and concentrated under reduced pressure to provide the title compound as a glass.

$^1$H NMR (400 MHz, DMSO-$d_6$) δ ppm 1.06 (s, 9 H) 1.80 (s, 3 H) 2.23 (td, J=13.3, 7.5 Hz, 1 H) 2.62-2.76 (m, 1 H) 3.30 (d, J=3.3 Hz, 1 H) 4.81 (d, J=10.4 Hz, 1 H) 4.85-4.97 (m, 1 H) 5.10 (s, 1 H) 5.31-5.52 (m, 1 H) 6.79 (d, J=7.2 Hz, 1 H) 6.97 (s, 1 H) 7.05-7.23 (m, 4 H) 7.28 (d, J=8.8 Hz, 2 H).

Step D. (2S,3R)-3-(3-Chlorophenyl)-2-(4-chlorophenyl)hex-5-en-2-amine

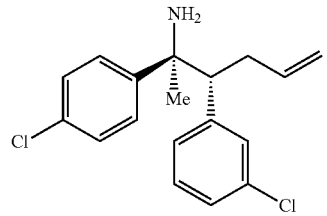 [SMILES: C=CC[C@H](c1cccc(Cl)c1)[C@](C)(N)c1ccc(Cl)cc1]

A solution of (R)—N-((2S,3R)-3-(3-chlorophenyl)-2-(4-chlorophenyl)hex-5-en-2-yl)-2-methylpropane-2-sulfinamide (Example 418, Step C, 5.96 g, 14.04 mmol) in THF (56.2 ml) was treated with. hydrochloric acid in water (36-38% wt, 6.40 ml, 211 mmol) for three hours. The reaction was diluted with 300 mL ether and the acidic aqueous layer made alkaline with sat. aq. NaHCO$_3$ solution. The organic layer was washed with sat. aq. NaHCO$_3$ solution, dried over MgSO$_4$ and concentrated to provide the title compound as a colorless glass.

$^1$H NMR (400 MHz, CHLOROFORM-d) δ ppm 1.29 (s, 3 H) 1.46 (br s, 2 H) 2.09-2.25 (m, 1 H) 2.41 (ddd, J=13.6, 12.7, 6.9 Hz, 1 H) 2.99 (dd, J=11.9, 3.3 Hz, 1 H) 4.71-4.88 (m, 2 H) 5.39 (ddt, J=17.0, 10.2, 6.8 Hz, 1 H) 6.99-7.13 (m, 1 H) 7.17-7.31 (m, 3 H) 7.31-7.38 (m, 2 H) 7.38-7.48 (m, 2 H).

Step E. (2S,3R)-3-(3-Chlorophenyl)-2-(4-chlorophenyl)-N-isopropylhex-5-en-2-amine

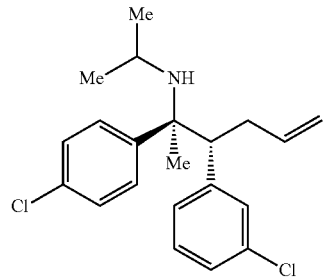 [SMILES: C=CC[C@H](c1cccc(Cl)c1)[C@](C)(NC(C)C)c1ccc(Cl)cc1]

A mixture of (2S,3R)-3-(3-chlorophenyl)-2-(4-chlorophenyl)hex-5-en-2-amine (Example 418, Step D) (270 mg, 0.843 mmol), acetic acid (0.243 mL, 4.22 mmol), acetone (3.10 mL, 42.2 mmol) and sodium cyanoborohydride (0.442 mL, 8.43 mmol) in methanol (4 mL) was heated to 65° C. overnight. After sixteen hours, an additional ten equivalents of sodium cyanoborohydride were added and heating continued for another five hours then equilibrated to room temperature and concentrated under reduced pressure. The concentrate was partitioned between aqueous sodium hydroxide solution and ethyl acetate. The aqueous layer was extracted again with ethyl acetate. The combined organic layers were washed with brine, dried over $MgSO_4$ and concentrated to afford a yellow oil. The crude product was adsorbed onto silica and purified by chromatography (24 g RediSep® pre-packed silica gel column (Teledyne Isco, Lincoln, Nebr.)) eluting with 30 to 100% ethyl acetate gradient in hexane. Fractions containing product were combined and concentrated to afford the title compound as a colorless glass.

$^1$H NMR (400 MHz, CHLOROFORM-d) δ ppm 0.95 (d, J=6.1 Hz, 3 H) 1.09 (d, J=6.1 Hz, 3 H) 1.38 (br s, 1 H) 1.51 (s, 3 H) 2.32-2.50 (m, 1 H) 2.59-2.81 (m, 3 H) 4.78-4.86 (m, 1 H) 4.86-4.98 (m, 1 H) 5.46 (ddt, J=17, 10.2, 6.7 Hz, 1 H) 6.78 (d, J=7.6 Hz, 1 H) 6.96 (t, J=1.8 Hz, 1 H) 7.03-7.11 (m, 1 H) 7.11-7.21 (m, 3 H) 7.21-7.29 (m, 2 H).

Step F. (4R,5S)-4-(3-Chlorophenyl)-5-(4-chlorophenyl)-5-(isopropylamino)hexan-1-ol

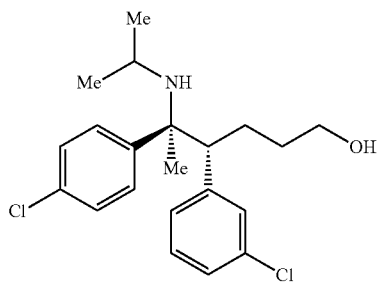 [SMILES: CC(C)N[C@](C)(c1ccc(Cl)cc1)[C@H](CCCO)c1cccc(Cl)c1]

To a solution of (2S,3R)-3-(3-chlorophenyl)-2-(4-chlorophenyl)-N-isopropylhex-5-en-2-amine (Example 418, Step E, 160 mg, 0.442 mmol) in THF (4 mL) cooled by an ice-water bath was added borane-tetrahydrofuran complex, (1.0M in THF, 2.21 mL, 2.21 mmol). After 90 minutes, an additional 5 equivalents of borane-THF were added and the cold bath removed. After 30 minutes the reaction was cooled in an ice-water bath and quenched by addition of 0.5 mL water followed by 4N aqueous sodium hydroxide (1.1 mL, 4.42 mmol) and aqueous hydrogen peroxide solution, (30% (w/w), 0.45 mL, 4.42 mmol). The biphasic mixture was stirred rapidly at 0-5° C. for 15 minutes then partitioned between water and ethyl acetate. The aqueous layer was extracted again with ethyl acetate. The combined organic layers were washed with brine then dried with anhydrous magnesium sulfate and concentrated to afford a colorless oil. The product was isolated by chromatography on silica (24 g RediSep® pre-packed silica gel column (Teledyne Isco, Lincoln, Nebr.)) eluting with 50 to 100% ethyl acetate gradient in hexane to afford the title compound as a colorless oil.

$^1$H NMR (400 MHz, CHLOROFORM-d) δ ppm 0.91 (d, J=6.3 Hz, 3 H) 1.06 (d, J=6.3 Hz, 3 H) 1.13-1.37 (m, 2 H) 1.48 (s, 3 H) 1.56-1.86 (m, 3 H) 1.89-2.04 (m, 1 H) 2.50-2.75 (m, 2 H) 3.52 (t, J=6.4 Hz, 2 H) 6.76 (d, J=7.6 Hz, 1 H) 6.89-6.98 (m, 1 H) 7.01-7.08 (m, 1 H) 7.08-7.17 (m, 3 H) 7.17-7.26 (m, 2 H).

Step G. (4R,5S)-4-(3-Chlorophenyl)-5-(4-chlorophenyl)-5-(isopropylamino)hexanoic acid

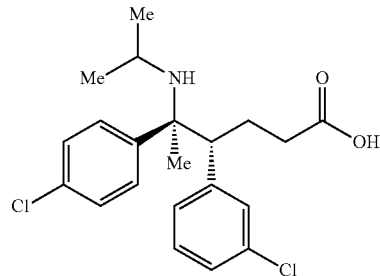 [SMILES: CC(C)N[C@](C)(c1ccc(Cl)cc1)[C@H](CCC(=O)O)c1cccc(Cl)c1]

To a solution of (4R,5S)-4-(3-chlorophenyl)-5-(4-chlorophenyl)-5-(isopropylamino)hexan-1-ol (Example 418, Step F, 185 mg, 0.486 mmol) in wet acetonitrile (0.75% water v/v) (3 mL) at ambient temperature was added over three minutes a solution of periodic acid (0.44M in acetonitrile (0.75% water v/v), 2.76 mL, 1.216 mmol) with chromium trioxide (2.43 mg, 0.024 mmol). The reaction was stirred for fifteen minutes. To the reaction was added a solution of 0.6 g disodium hydrogen phosphate in 10 mL water. The aqueous mixture was extracted with toluene. The organic layer was washed with water/brine then with a solution of 0.2 g sodium hydrogen sulfite in 5 mL water. The organic layer was then dried with anhydrous magnesium sulfate and concentrated to afford a peach-colored foamy solid. The product was isolated by chromatography on silica (24 g RediSep® pre-packed silica gel column (Teledyne Isco, Lincoln, Nebr.)) eluting with 50-100% ethyl acetate gradient in hexane to afford the title compound as a colorless foam.

$^1$H NMR (400 MHz, CHLOROFORM-d) δ ppm 1.16 (d, J=6.7 Hz, 4 H) 1.32 (d, J=6.7 Hz, 4 H) 1.43 (s, 3 H) 1.76-1.88 (m, 1 H) 2.22-2.38 (m, 1 H) 2.55-2.67 (m, 2 H) 2.79 (quin, J=6.65 Hz, 1 H) 3.11 (dd, J=13.1, 2.4 Hz, 1 H) 6.21 (d, J=7.8 Hz, 1 H) 6.49 (s, 1 H) 6.91 (dd, J=7.9, 7.9 Hz, 1 H) 6.96-7.17 (m, 3 H) 7.23 (d, J=8.2 Hz, 2 H).

Step H. (5R,6S)-5-(3-chlorophenyl)-6-(4-chlorophenyl)-1-isopropyl-6-methylpiperidin-2-one

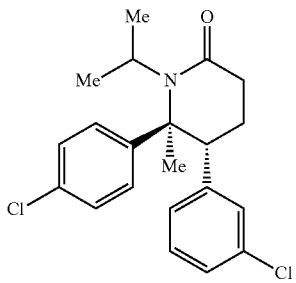 [SMILES: CC(C)N1C(=O)CC[C@H](c2cccc(Cl)c2)[C@@]1(C)c1ccc(Cl)cc1]

Oxalyl chloride (~0.38 M in benzene, 0.617 mL, 0.234 mmol) was added to a room temperature solution of (4R,5S)-4-(3-chlorophenyl)-5-(4-chlorophenyl)-5-(isopropylamino) hexanoic acid (Example 418, Step G, 84 mg, 0.213 mmol) in benzene (3 mL) followed by a drop of DMF. The reaction solution was stirred at room temperature for 25 minutes then heated to 80° C. After 3.5 hours the reaction was removed from heat and saturated aqueous sodium bicarbonate solution was added. The organic phase was diluted with ethyl acetate. The aqueous layer was extracted again with ethyl acetate. The combined organic layers were washed with brine, then dried with anhydrous magnesium sulfate and concentrated to afford a red-orange oil. The product was isolated by chromatography on silica (12 g RediSep Rf cartridge) eluting with 20-40% ethyl acetate gradient in hexane to afford the title compound as a pale yellow film. $[\alpha]_D$=+ 89.33° (T=24.0° C.; c=1, CHCl$_3$)

$^1$H NMR (400 MHz, CHLOROFORM-d) δ ppm 1.25 (d, J=6.7 Hz, 3 H) 1.41 (d, J=6.7 Hz, 3 H) 1.52 (s, 3 H) 1.84-1.98 (m, 1 H) 2.30-2.50 (m, 1H) 2.64-2.75 (m, 2 H) 2.88 (quin, J=6.7 Hz, 1 H) 3.20 (dd, J=13.2, 2.5 Hz, 1 H) 6.31 (d, J=7.6 Hz, 1 H) 6.58 (dd, J=1.8, 1.8 Hz, 1 H) 7.00 (dd, J=7.9, 7.9 Hz, 1 H) 7.05-7.27 (m, 3 H) 7.27-7.42 (m, 2 H); Mass Spectrum (ESI) m/z=376.1 [M+H]$^+$.

Step I. (3R,5R,6S)-3-Allyl-5-(3-chlorophenyl)-6-(4-chlorophenyl)-1-isopropyl-6-methylpiperidin-2-one and (3S,5R,6S)-3-Allyl-5-(3-chlorophenyl)-6-(4-chlorophenyl)-1-isopropyl-6-methylpiperidin-2-one

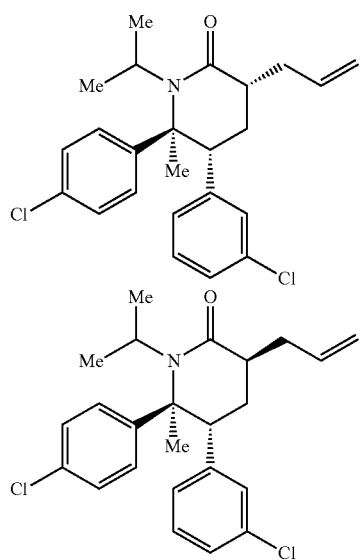

sec-Butyllithium (0.8N in cyclohexane, 0.274 mL, 0.219 mmol) was added over a period of one minute to a degassed (Argon bubbled through solution for 10 minutes at RT) solution of (5R,6S)-5-(3-chlorophenyl)-6-(4-chlorophenyl)-1-isopropyl-6-methylpiperidin-2-one (Example 418, Step H, 75 mg, 0.199 mmol) in THF (6 mL) cooled by an acetone-dry ice bath. The cold bath was removed and the reaction equilibrated to room temperature over fifteen minutes. The reaction was stirred at room temperature for 30 minutes. Allyl bromide (1M in THF, 0.219 mL, 0.219 mmol) was added over one minute at room temperature. After two hours the reaction was quenched by addition of saturated aqueous ammonium chloride solution. The organic layer was diluted with ethyl acetate and separated. The aqueous layer was extracted again with ethyl acetate. The combined organic layers were then dried with anhydrous magnesium sulfate and concentrated to afford a faintly orange glass. The diastereomeric products were isolated by chromatography on silica gel (12 g RediSep® pre-packed silica gel column (Teledyne Isco, Lincoln, Nebr.)) eluting with 20 to 80% ethyl acetate gradient in hexane to afford 25 mg of (3R,5R,6S)-3-allyl-5-(3-chlorophenyl)-6-(4-chlorophenyl)-1-isopropyl-6-methylpiperidin-2-one as the product eluting first on silica gel TLC plate (R$_f$=0.52 in 3:1 hexane:ethyl acetate eluent) and 25 mg of (3S,5R,6S)-3-allyl-5-(3-chlorophenyl)-6-(4-chlorophenyl)-1-isopropyl-6-methylpiperidin-2-one as the product eluting second on silica gel TLC plate (R$_f$=0.28 in 3:1 hexane:ethyl acetate eluent).

Diastereomer 1: (3R,5R,6S)-3-allyl-5-(3-chlorophenyl)-6-(4-chlorophenyl)-1-isopropyl-6-methylpiperidin-2-one $^1$H NMR (400 MHz, CHLOROFORM-d) δ ppm 1.17 (d, J=6.7 Hz, 3 H) 1.31 (d, J=6.7 Hz, 3 H) 1.41 (s, 3 H) 1.84 (ddd, J=13.3, 5.8, 2.5 Hz, 1 H) 2.03-2.21 (m, 1 H) 2.41-2.54 (m, 1 H) 2.54-2.69 (m, 2 H) 2.78 (quin, J=6.7 Hz, 1 H) 3.18 (dd, J=13.4, 2.3 Hz, 1 H) 4.92-5.18 (m, 2 H) 5.56-5.84 (m, 1 H) 6.20 (d, J=7.8 Hz, 1 H) 6.50 (s, 1 H) 6.90 (dd, J=7.8, 7.8 Hz, 1 H) 7.00-7.08 (m, 1 H) 7.08-7.37 (m, 4 H); MS (ESI) 416.2 [M+H]

Diastereomer 2: (3S,5R,6S)-3-allyl-5-(3-chlorophenyl)-6-(4-chlorophenyl)-1-isopropyl-6-methylpiperidin-2-one $^1$H NMR (400 MHz, CHLOROFORM-d) δ ppm 1.16 (d, J=6.7 Hz, 3 H) 1.35 (d, J=6.7 Hz, 3 H) 1.43 (s, 3 H) 1.75-1.80 (m, 1 H) 2.25-2.48 (m, 2 H) 2.56-2.68 (m, 1 H) 2.69-2.89 (m, 2 H) 3.23 (dd, J=13.6, 2.6 Hz, 1 H) 4.91-5.06 (m, 2 H) 5.76 (dddd, J=17.6, 9.5, 8.3, 5.9 Hz, 1 H) 6.25 (d, J=7.8 Hz, 1 H) 6.51 (dd, J=1.8, 1.8 Hz, 1 H) 6.87-6.97 (m, 1 H) 6.97-7.12 (m, 3 H) 7.19-7.32 (m, 2 H); MS (ESI) 416.2 [M+H]$^+$ Step J. 2-((3S,5R,6S)-5-(3-chlorophenyl)-6-(4-chlorophenyl)-1-isopropyl-6-methyl-2-oxopiperidin-3-yl)acetic acid The title compound was prepared from (3R,5R,6S)-3-allyl-5-(3-chlorophenyl)-6-(4-chlorophenyl)-1-isopropyl-6-methylpiperidin-2-one (Example 418, Step I, diastereomer 1) by a procedure similar to the one described in Example 1, Step H.

$^1$H NMR (400 MHz, CHLOROFORM-d) δ ppm 1.16 (d, J=6.7 Hz, 3 H) 1.33 (d, J=6.7 Hz, 3 H) 1.46 (s, 3 H) 1.87-2.01 (m, 1 H) 2.27 (q, J=13 Hz, 1 H) 2.62 (dd, J=15.8, 3.2 Hz, 1 H) 2.76-3.06 (m, 3 H) 3.24 (dd, J=13.3, 2.2 Hz, 1 H) 6.19 (d, J=7.8 Hz, 1 H) 6.40-6.52 (m, 1 H) 6.92 (dd, J=7.9, 7.9 Hz, 1 H) 7.07 (ddd, J=8.0, 2, 0.98 Hz, 1 H) 7.10-7.40 (m, 4 H); MS (ESI) 432.0 [M−H]$^-$.

Example 419

2-((3R,5R,6S)-5-(3-Chlorophenyl)-6-(4-chlorophenyl)-1-isopropyl-6-methyl-2-oxopiperidin-3-yl)acetic acid

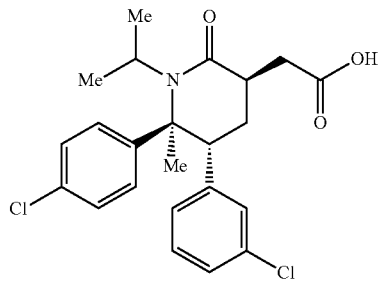 [SMILES: CC(C)N1C(=O)[C@@H](CC(=O)O)C[C@H](c2cccc(Cl)c2)[C@@]1(C)c1ccc(Cl)cc1]

The title compound was prepared from (3S,5R,6S)-3-allyl-5-(3-chlorophenyl)-6-(4-chlorophenyl)-1-isopropyl-6-methylpiperidin-2-one (Example 418, Step I, diastereomer 2) by a procedure similar to the one described in Example 1, Step H.

¹H NMR (400 MHz, CHLOROFORM-d) δ ppm 1.18 (d, J=6.7 Hz, 3 H) 1.34 (d, J=6.7 Hz, 3 H) 1.47 (s, 3 H) 1.75 (d, J=13.9 Hz, 1 H) 2.46-2.65 (m, 2 H) 2.92 (quin, J=6.7 Hz, 1 H) 2.99-3.22 (m, 3 H) 6.26 (d, J=7.8 Hz, 1 H) 6.51 (s, 1 H) 6.94 (dd, J=7.9, 7.9 Hz, 1 H) 6.98-7.12 (m, 3 H) 7.28 (d, J=8.6 Hz, 2 H); Mass Spectrum (ESI) m/z=432.0 [M−H]⁻.

Example 420

(3S,5R,6S)-5-(3-chlorophenyl)-6-(4-chlorophenyl)-1-((S)-1-(1,1-dioxidoisothiazolidin-2-yl)butan-2-yl)-3-((6-methoxypyridin-2-yl)methyl)piperidin-2-one

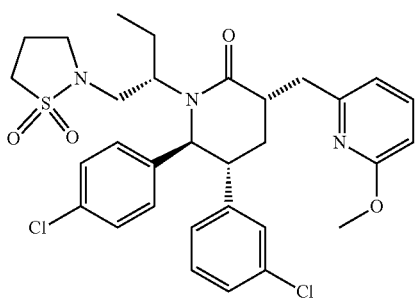 [SMILES: CC[C@@H](CN1CCCS1(=O)=O)N1C(=O)[C@H](Cc2cccc(OC)n2)C[C@H](c2cccc(Cl)c2)[C@H]1c1ccc(Cl)cc1]

Step A: (5R,6S)-5-(3-chlorophenyl)-6-(4-chlorophenyl)-1-((S)-1-(1,1-dioxidoisothiazolidin-2-yl)butan-2-yl)piperidin-2-one

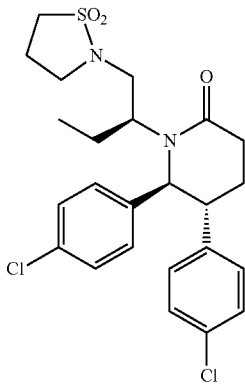 [SMILES: CC[C@@H](CN1CCCS1(=O)=O)N1C(=O)CC[C@H](c2ccc(Cl)cc2)[C@H]1c1ccc(Cl)cc1]

This compound was made according to the procedure of Example 174, Step A, utilizing propanesulfatam (*J. Org. Chem.*, 1963, 28 3537, 4.63 g, 38.2 mmol) and (5R,6S)-5-(3-chlorophenyl)-6-(4-chlorophenyl)-1-((S)-1-hydroxybutan-2-yl)piperidin-2-one (Example 185, Step B, 6.0 g, 15.29 mmol). The title compound was crystallized from ethyl acetate and hexanes.

¹H NMR (500 MHz, CHLOROFORM-d) δ ppm 7.24 (d, J=8.1 Hz, 2H), 7.10-7.20 (m, 2H), 6.99-7.09 (m, 3H), 6.86 (d, J=7.1 Hz, 1H), 4.74 (d, J=9.3 Hz, 1H), 3.36-3.46 (m, 1H), 2.96-3.33 (m, 5H), 2.93 (ddd, J=3.2, 9.3, 12 Hz, 1H), 2.63-2.71 (m, 2H), 2.32-2.50 (m, 2H), 2.12-2.26 (m, 1H), 1.97-2.04 (m, 1H), 1.91 (quind, J=7.5, 14.8 Hz, 1H), 1.44-1.61 (m, 1H), 0.53 (t, J=7.5 Hz, 3H). Mass Spectrum (ESI) m/z=495.1 (M+1).

Step B. 2-(iodomethyl)-6-methoxypyridine

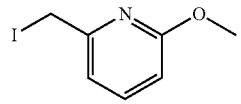

To a 0° C. solution of iodine (1.094 g, 4.31 mmol) and imidazole (0.294 g, 4.31 mmol) in dichloromethane (10.27 ml) was added portionwise triphenylphosphine (1.131 g, 4.31 mmol). After 20 min of stirring, (6-methoxypyridin-2-yl)methanol (Adesis, New Castle, Del., 0.5 g, 3.59 mmol) was added to the solution. The reaction was allowed to stir for 1 h at 0° C., quenched with water (50 mL) and extracted with Et₂O. The combined organics were dried over MgSO₄, and concentrated in vacuo. Silica gel chromatography (gradient elution 1 to 5% Et₂O in pentane) afforded 2-(iodomethyl)-6-methoxypyridine. ¹H NMR (500 MHz, CHLOROFORM-d) δ ppm 7.49 (dd, J=7.3, 8.3 Hz, 1H), 6.96 (d, J=7.1 Hz, 1H), 6.61 (d, J=8.1 Hz, 1H), 4.44 (s, 2H), 3.94 (s, 3H). Mass Spectrum (ESI) m/z=249.9 (M+1).

Step C. (3S,5R,6S)-5-(3-chlorophenyl)-6-(4-chlorophenyl)-1-((S)-1-((1,1-dioxidoisothiazolidin-2-yl)butan-2-yl)-3-((6-methoxypyridin-2-yl)methyl)piperidin-2-one To a solution of (5R,6S)-5-(3-chlorophenyl)-6-(4-chlorophenyl)-1-((S)-1-(1,1-dioxidoisothiazolidin-2-yl)butan-2-yl)piperidin-2-one (Example 420, Step A, 0.7 g, 1.413 mmol) in THF (5.65 ml) at −78° C. was added dropwise sec-butyllithium, (1.4 M in cyclohexane, 1.06 ml, 1.483 mmol). The reaction was warmed to −10° C. After about 5 minutes, the reaction was returned to a −78° C. bath. A solution of 2-(iodomethyl)-6-methoxypyridine (Example 420, Step B, 0.387 g, 1.554 mmol) in THF (1 mL) was added dropwise to the cooled reaction mixture. The reaction was allowed to warm to room temperature and stirred for 1 h. The reaction contents were poured into saturated sodium bicarbonate and the aqueous layer was extracted with dichloromethane (3×50 mL). The combined organics were dried with sodium sulfate and concentrated in vacuo. Silica gel chromatography (step gradient elution 5 to 50% diethyl ether in dichloromethane) afforded the title compound as the more polar diastereomer.

¹H NMR (500 MHz, CHLOROFORM-d) δ ppm 7.50 (t, J=7.8 Hz, 1H), 7.25 (d, J=8.6 Hz, 2H), 7.09-7.18 (m, 3H), 7.03 (d, J=8.3 Hz, 2H), 6.92-6.99 (m, 1H), 6.82 (d, J=7.3 Hz, 1H), 6.58 (d, J=8.1 Hz, 1H), 4.87 (d, J=7.6 Hz, 1H), 3.80 (s, 3H), 3.36-3.46 (m, 2H), 2.99-3.32 (m, 7H), 2.26-2.50 (m, 2H), 2.03-2.15 (m, 1H), 1.90-2.03 (m, 2H), 1.43-1.73 (m, 2H), 0.56 (t, J=7.6 Hz, 3H). Mass Spectrum (ESI) m/z=616.1 (M+1).

Example 421

(3R,5R,6S)-5-(3-Chlorophenyl)-6-(4-chlorophenyl)-1-((S)-1-((1,1-dioxidoisothiazolidin-2-yl)butan-2-yl)-3-((6-methoxypyridin-2-yl)methyl)piperidin-2-one

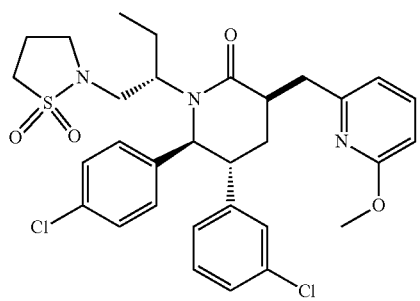 [SMILES: CC[C@@H](CN1CCCS1(=O)=O)N1C(=O)[C@@H](Cc2cccc(OC)n2)C[C@H](c2cccc(Cl)c2)[C@H]1c1ccc(Cl)cc1]

From the purification described in Example 420, Step C, (3R,5R,6S)-5-(3-chlorophenyl)-6-(4-chlorophenyl)-1-((S)-1-(1,1-dioxidoisothiazolidin-2-yl)butan-2-yl)-3-((6-methoxypyridin-2-yl)methyl)piperidin-2-one was isolated as the less polar diastereomer.

$^1$H NMR (500 MHz, CHLOROFORM-d) δ ppm 7.46 (t, J=7.8 Hz, 1H), 7.22 (d, J=8.31 Hz, 2H), 7.10-7.17 (m, 1H), 7.05-7.10 (m, 1H), 6.98-7.03 (m, 3H), 6.79 (d, J=7.1 Hz, 1H), 6.75 (d, J=7.3 Hz, 1H), 6.54 (d, J=8.3 Hz, 1H), 4.68 (d, J=10.3 Hz, 1H), 3.91 (s, 3H), 3.72 (dd, J=3.8, 14.1 Hz, 1H), 3.30 (t, J=6.7 Hz, 2H), 3.09-3.26 (m, 4H), 3.00-3.08 (m, J=14.4 Hz, 1H), 2.95 (ddd, J=3.2, 10.2, 13.0 Hz, 2H), 2.68 (dd, J=10.0, 14.2 Hz, 1H), 2.30-2.53 (m, 2H), 2.10 (q, J=12.9 Hz, 1H), 1.85-2.01 (m, 2H), 1.57-1.63 (m, J=2.2, 7.1 Hz, 1H), 0.53 (t, J=7.6 Hz, 3H). Mass Spectrum (ESI) m/z=616.1 (M+1).

Example 422

(3S,5R,6S)-5-(3-Chlorophenyl)-6-(4-chlorophenyl)-1-((S)-1-((1,1-dioxidoisothiazolidin-2-yl)butan-2-yl)-3-((6-hydroxypyridin-2-yl)methyl)piperidin-2-one

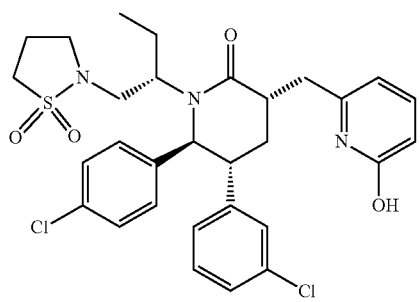 [SMILES: CC[C@@H](CN1CCCS1(=O)=O)N1C(=O)[C@H](Cc2cccc(O)n2)C[C@H](c2cccc(Cl)c2)[C@H]1c1ccc(Cl)cc1]

To the product of Example 420, Step C (0.05 g, 0.081 mmol) in chloroform (1.622 ml) was added iodotrimethylsilane (0.046 ml, 0.324 mmol). The reaction was warmed to 50° C. After 4 hours, the reaction was quenched with saturated bicarbonate (10 mL) and extracted with dichloromethane (2×15 mL) and 5% MeOH in CH$_2$Cl$_2$ (1×15 mL). The combined organics were dried with sodium sulfate and concentrated in vacuo. Silica gel chromatography (0.5 to 7.5% MeOH in dichloromethane) afforded the title compound.

$^1$H NMR (500 MHz, CHLOROFORM-d) δ 7.36 (dd, J=6.7, 9.2 Hz, 2H), 7.28 (br s, 1H), 7.26 (s, 1H), 7.12-7.20 (m, J=7.1 Hz, 3H), 7.05 (d, J=7.1 Hz, 1H), 7.00 (d, J=8.3 Hz, 2H), 6.46 (d, J=9.1 Hz, 1H), 6.03 (d, J=6.6 Hz, 1H), 5.01 (d, J=4.9 Hz, 1H), 3.64-4.03 (m, 1H), 3.40-3.57 (m, 1H), 2.85-3.34 (m, 8H), 2.74 (quin, J=6.4 Hz, 1H), 2.25-2.50 (m, 2H), 1.91-2.17 (m, J=6.8 Hz, 3H), 1.39-1.55 (m, 1H), 0.61 (t, J=7.5 Hz, 3H). Mass Spectrum (ESI) m/z=602.2 (M+1).

Example 423

(3R,5R,6S)-5-(3-Chlorophenyl)-6-(4-chlorophenyl)-1-((S)-1-((1,1-dioxidoisothiazolidin-2-yl)butan-2-yl)-3-((6-hydroxypyridin-2-yl)methyl)piperidin-2-one

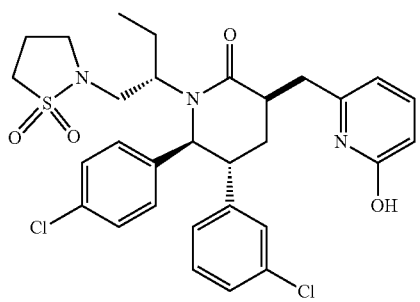 [SMILES: CC[C@@H](CN1CCCS1(=O)=O)N1C(=O)[C@@H](Cc2cccc(O)n2)C[C@H](c2cccc(Cl)c2)[C@H]1c1ccc(Cl)cc1]

Following the procedure of Example 422 using the product of Example 421, (3R,5R,6S)-5-(3-chlorophenyl)-6-(4-chlorophenyl)-1-((S)-1-(1,1-dioxidoisothiazolidin-2-yl)butan-2-yl)-3-((6-hydroxypyridin-2-yl)methyl)piperidin-2-one was obtained.

$^1$H NMR (500 MHz, CHLOROFORM-d) δ ppm 7.22 (dd, J=6.6, 9.3 Hz, 1H), 7.16 (d, J=8.3 Hz, 2H), 7.07-7.11 (m, 1H), 7.00-7.06 (m, 1H), 6.95 (s, 1H), 6.90 (d, J=8.07 Hz, 2H), 6.70 (d, J=7.6 Hz, 1H), 6.36 (d, J=9.1 Hz, 1H), 5.87 (d, J=6.6 Hz, 1H), 4.65 (d, J=10.5 Hz, 1H), 3.29 (td, J=6.7, 9.60 Hz, 1H), 3.18 (td, J=6.7, 9.6 Hz, 1H), 3.11 (t, J=7.5 Hz, 2H), 2.87-3.04 (m, 3H), 2.76-2.86 (m, 1H), 2.71 (dd, J=2.7, 14.4 Hz, 1H), 2.32 (quin, J=7.0 Hz, 2H), 2.17 (q, J=13 Hz, 1H), 1.84-1.99 (m, 2H), 1.37-1.58 (m, 2H), 0.43 (t, J=7.6 Hz, 3H).

Example 424

(3S,5R,6S)-5-(3-Chlorophenyl)-6-(4-chlorophenyl)-1-((S)-1-(1,1-dioxidoisothiazolidin-2-yl)butan-2-yl)-3-((6-methoxypyridin-2-yl)methyl)-3-methylpiperidin-2-one

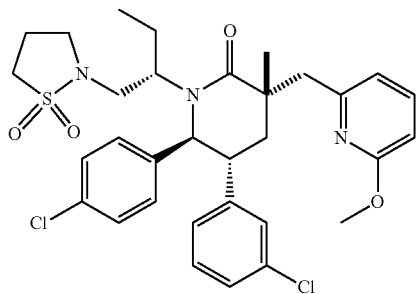 [SMILES: CC[C@@H](CN1CCCS1(=O)=O)N1C(=O)[C@](C)(Cc2cccc(OC)n2)C[C@H](c2cccc(Cl)c2)[C@H]1c1ccc(Cl)cc1]

sec-Butyllithium (1.4 M in cyclohexane, 0.59 ml, 0.824 mmol) was added to a solution of (3S,5R,6S)-5-(3-chlorophenyl)-6-(4-chlorophenyl)-1-((S)-1-(1,1-dioxidoisothiazolidin-2-yl)butan-2-yl)-3-((6-methoxypyridin-2-yl)methyl)piperidin-2-one (Example 420, Step C, 0.484 g, 0.785 mmol) in THF (3.92 ml) at −78° C. After 15 minutes iodomethane (0.098 ml, 1.57 mmol) was added and the reaction was allowed to warm to room temperature. The reaction contents were poured into saturated sodium bicarbonate (20 mL) and extracted with dichloromethane (3×30 mL). The combined organics were dried with sodium sulfate and concentrated in vacuo. Silica gel chromatography (10% step gradient elution 30 to 90% EtOAc in hexanes) afforded the title compound as the first eluting diastereomer.

$^1$H NMR (500 MHz, CHLOROFORM-d) δ 7.48 (t, J=7.6 Hz, 1H), 7.21 (d, J=8.1 Hz, 2H), 6.92-7.15 (m, 5H), 6.88 (d, J=7.1 Hz, 1H), 6.74 (d, J=7.6 Hz, 1H), 6.57 (d, J=8.3 Hz, 1H), 4.64 (d, J=10.5 Hz, 1H), 3.04-3.25 (m, 7H), 2.98 (d, J=14.7 Hz, 2H), 2.69 (t, J=13.8 Hz, 1H), 2.21-2.44 (m, 2H), 1.89 (td, J=7.4, 14.6 Hz, 1H), 1.75 (dd, J=2.8, 13.6 Hz, 1H), 0.50 (t, J=7.6 Hz, 3H). Mass Spectrum (ESI) m/z=630.2 (M+1).

Example 425

(3R,5R,6S)-5-(3-Chlorophenyl)-6-(4-chlorophenyl)-1-((S)-1-((1,1-dioxidoisothiazolidin-2-yl)butan-2-yl)-3-((6-methoxypyridin-2-yl)methyl)-3-methylpiperidin-2-one

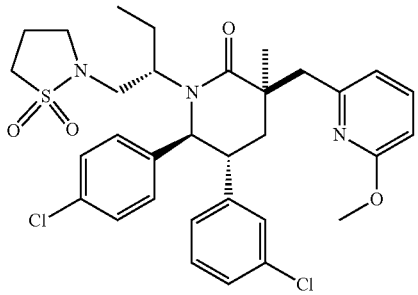 [SMILES: CC[C@@H](CN1CCCS1(=O)=O)N1C(=O)[C@@](C)(Cc2cccc(OC)n2)C[C@H](c2cccc(Cl)c2)[C@H]1c1ccc(Cl)cc1]

The title compound is the second eluting diastereomer from the purification described in Example 424.

$^1$H NMR (500 MHz, CHLOROFORM-d) δ ppm 7.53 (t, J=7.7 Hz, 1H), 7.19 (d, J=8.1 Hz, 2H), 7.03-7.13 (m, 2H), 6.87-7.03 (m, 3H), 6.84 (d, J=7.3 Hz, 1H), 6.76 (d, J=7.3 Hz, 1H), 6.62 (d, J=8.3 Hz, 1H), 4.72 (d, J=10.8 Hz, 1H), 3.86-4.00 (m, 1H), 3.69 (s, 3H), 3.43 (d, J=12.7 Hz, 1H), 3.26-3.39 (m, 2H), 3.14-3.26 (m, 3H), 2.96-3.05 (m, 2H), 2.91 (br. s., 1H), 2.31-2.51 (m, 2H), 2.14-2.23 (m, 1H), 2.02-2.12 (m, 1H), 1.95 (quind, J=7.6, 14.8 Hz, 1H), 1.39-1.64 (m, 2H), 1.29 (s, 3H), 0.51 (t, J=7.6 Hz, 3H). Mass Spectrum (ESI) m/z=630.2 (M+1).

Example 426

(3S,5R,6S)-5-(3-Chlorophenyl)-6-(4-chlorophenyl)-1-((S)-1-(1,1-dioxidoisothiazolidin-2-yl)butan-2-yl)-3-((6-hydroxypyridin-2-yl)methyl)-3-methylpiperidin-2-one

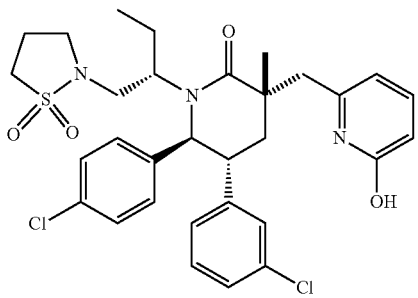 [SMILES: CC[C@@H](CN1CCCS1(=O)=O)N1C(=O)[C@](C)(Cc2cccc(O)n2)C[C@H](c2cccc(Cl)c2)[C@H]1c1ccc(Cl)cc1]

Following the procedure of Example 422 using the product of Example 424, (3S,5R,6S)-5-(3-chlorophenyl)-6-(4-chlorophenyl)-1-((S)-1-(1,1-dioxidoisothiazolidin-2-yl)butan-2-yl)-3-((6-hydroxypyridin-2-yl)methyl)-3-methylpiperidin-2-one was obtained.

$^1$H NMR (500 MHz, CHLOROFORM-d) δ ppm 7.33 (dd, J=6.7, 9.2 Hz, 1H), 7.23 (d, J=8.1 Hz, 2H), 7.08-7.19 (m, 2H), 6.87-7.05 (m, 4H), 6.81 (d, J=7.6 Hz, 1H), 6.49 (d, J=9.1 Hz, 1H), 5.95 (d, J=6.6 Hz, 1H), 4.74 (d, J=10.3 Hz, 1H), 3.75-4.14 (m, 1H), 3.30-3.42 (m, 1H), 3.10-3.28 (m, 4H), 2.68-3.09 (m, J=4.2 Hz, 4H), 2.26-2.50 (m, 3H), 1.89-2.06 (m, 1H), 1.53-1.70 (m, J=3.2, 13.2 Hz, 2H), 1.49 (s, 3H), 0.52 (t, J=7.5 Hz, 3H). Mass Spectrum (ESI) m/z=616.1 (M+1).

Example 427

(3R,5R,6S)-5-(3-Chlorophenyl)-6-(4-chlorophenyl)-1-((S)-1-(1,1-dioxidoisothiazolidin-2-yl)butan-2-yl)-3-((6-hydroxypyridin-2-yl)methyl)-3-methylpiperidin-2-one

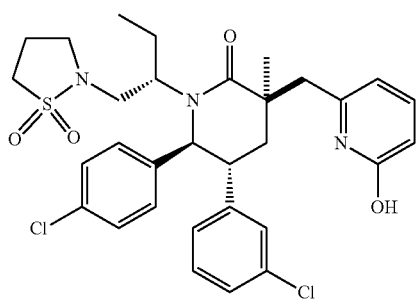 [SMILES: CC[C@@H](CN1CCCS1(=O)=O)N1C(=O)[C@@](C)(Cc2cccc(O)n2)C[C@H](c2cccc(Cl)c2)[C@H]1c1ccc(Cl)cc1]

Following the procedure of Example 422 using the product of Example 425, (3R,5R,6S)-5-(3-chlorophenyl)-6-(4-chlorophenyl)-1-((S)-1-(1,1-dioxidoisothiazolidin-2-yl)butan-2-yl)-3-((6-hydroxypyridin-2-yl)methyl)-3-methylpiperidin-2-one was obtained.

$^1$H NMR (500 MHz, CHLOROFORM-d) δ ppm 7.36-7.44 (m, 1H), 7.10-7.23 (m, 2H), 6.77-7.07 (m, 5H), 6.66 (d, J=7.8 Hz, 1H), 6.48 (d, J=9.1 Hz, 1H), 6.11 (d, J=6.6 Hz, 1H), 4.74 (d, J=10.5 Hz, 1H), 3.93 (dd, J=9.8, 13.9 Hz, 1H), 3.29 (t, J=6.6 Hz, 2H), 3.20 (dt, J=0.9, 7.5 Hz, 2H), 3.15 (d, J=13.9 Hz, 1H), 2.75-2.99 (m, 4H), 2.32-2.48 (m, 1H), 2.24 (t, J=13.8 Hz, 1H), 1.98-2.10 (m, 1H), 1.88-1.96 (m, J=2.9 Hz, 1H), 1.44-1.59 (m, 1H), 1.39 (s, 3H), 0.48 (t, J=7.6 Hz, 3H). Mass Spectrum (ESI) m/z=616.1 (M+1).

Example 428

(3R,5R,6S)-5-(3-Chlorophenyl)-6-(4-chlorophenyl)-1-((S)-1-cyclopropyl-2-(ethylsulfonyl)ethyl)-3-(3-hydroxy-2-oxopropyl)-3-methylpiperidin-2-one

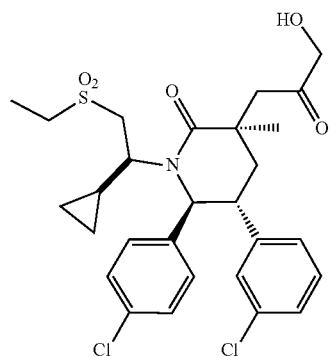 [SMILES: CCS(=O)(=O)C[C@H](C1CC1)N1C(=O)[C@@](C)(CC(=O)CO)C[C@H](c2cccc(Cl)c2)[C@H]1c1ccc(Cl)cc1]

Oxalyl chloride (0.063 ml, 0.715 mmol) was added to a solution of 2-((3R,5R,6S)-5-(3-chlorophenyl)-6-(4-chlorophenyl)-1-((S)-1-cyclopropyl-2-(ethylsulfonyl)ethyl)-3-methyl-2-oxopiperidin-3-yl)acetic acid (Example 349, 0.316 g, 0.572 mmol) in dichloromethane (1.9 ml). The reaction was stirred for 3 h at room temperature. The solvents were removed in vacuo. To the solids was added tris(trimethylsiloxy)ethylene (0.42 ml, 1.26 mmol) and the reaction was stirred at 90° C. After 2 h, the reaction was cooled, charged with THF (1 mL) and HCl (1.4 M, 0.982 ml, 1.375 mmol), and brought to reflux for 30 min. After cooling, the reaction was poured into water (20 mL) and extracted with dichloromethane (3×20 mL). The combined organics were dried over sodium sulfate and concentrated in vacuo. Silica gel chromatography (step gradient elution 1 to 5% 2 M ammonia in MeOH in dichloromethane) afforded the title compound.

$^1$H NMR (500 MHz, CHLOROFORM-d) δ 7.11-7.30 (m, 3H), 6.96-7.10 (m, 3H), 6.89 (s, 1H), 6.70-6.85 (m, 1H), 4.82 (d, J=10.8 Hz, 1H), 4.13-4.45 (m, J=1.7 Hz, 3H), 3.15 (ddd, J=2.9, 10.6, 13.6 Hz, 1H), 2.74-3.10 (m, 6H), 2.60 (br s, 1H), 2.28 (t, J=13.8 Hz, 1H), 1.96 (dd, J=3.1, 13.8 Hz, 1H), 1.77 (br s, 1H), 1.27-1.42 (m, 6H), 0.10-0.41 (m, 2H), −0.33 (br s, 1H), −1.01 (br s, 1H). Mass Spectrum (ESI) m/z=566.2 (M+1).

Example 429

2-((3R,5R,6S)-5-(3-Chlorophenyl)-6-(4-chlorophenyl)-1-(diethylamino)-3-methyl-2-oxopiperidin-3-yl)acetic acid

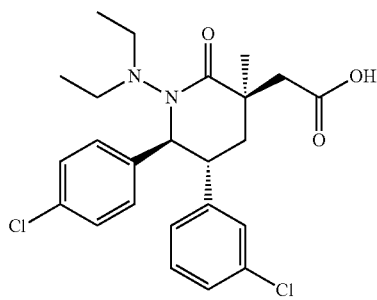 [SMILES: CCN(CC)N1C(=O)[C@@](C)(CC(=O)O)C[C@H](c2cccc(Cl)c2)[C@H]1c1ccc(Cl)cc1]

Step A. Methyl 2-((3R,5R,6S)-5-(3-chlorophenyl)-6-(4-chlorophenyl)-3-methyl-2-oxopiperidin-3-yl)acetate

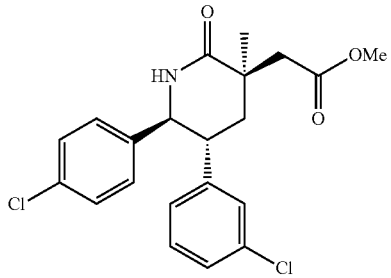 [SMILES: COC(=O)C[C@@]1(C)C[C@H](c2cccc(Cl)c2)[C@@H](c2ccc(Cl)cc2)NC1=O]

Sodium periodate (21.03 g, 98 mmol) was added slowly to a solution containing ruthenium(III) chloride hydrate (0.277 g, 1.229 mmol) and (3S,5R,6S)-3-allyl-5-(3-chlorophenyl)-6-(4-chlorophenyl)-3-methylpiperidin-2-one (4.6 g, 12.29 mmol; Example 71, step D) in acetonitrile (35.1 mL), ethyl acetate (35.1 mL) and water (52.7 mL) while maintaining a temperature below 20° C. The resulting mixture was then stirred for 2 h at room temperature. Next, the reaction was filtered and concentrated, and the resulting residue was further processed by dissolving in ethyl acetate. The organics were washed with water and brine, dried over MgSO$_4$, filtered and concentrated. Next, the residue was dissolved in a small amount of a mixture of ether and methanol (1:1) and a 2M solution of (trimethylsilyl)diazomethane in diethyl ether (12.29 ml, 24.58 mmol) was added. This solution was then allowed to stir at ambient temperature overnight. The solution was concentrated and the resulting residue was purified on silica gel (eluent: hexane/ethyl acetate 0 to 100%, gradient elution) to give the title compound.

Mass Spectrum (ESI) m/z=406 (M+1).

Step B. Methyl 2-((3R,5R,6S)-1-amino-5-(3-chlorophenyl)-6-(4-chlorophenyl)-3-methyl-2-oxopiperidin-3-yl)acetate

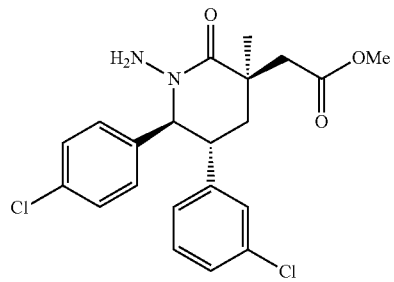 [SMILES: COC(=O)C[C@@]1(C)C[C@H](c2cccc(Cl)c2)[C@@H](c2ccc(Cl)cc2)N(N)C1=O]

A suspension of 60% sodium hydride in mineral oil (0.953 g, 23.82 mmol) was added to solution of methyl 2-((3R,5R,6S)-5-(3-chlorophenyl)-6-(4-chlorophenyl)-3-methyl-2-oxopiperidin-3-yl)acetate (Example 429, step A, 4.84 g, 11.9 mmol) in DMF (25 mL). The resulting mixture was stirred for 15 min at 23° C. O-(2,4-dinitrophenyl)hydroxylamine (4.74 g, 23.82 mmol) was added at room temperature. The solution was stirred for 1 h at room temperature then quenched with MeOH (1 mL). Excess solvent was removed under reduced pressure and the residue was purified by chromatography on silica (eluent: 0 to 5% MeOH in DCM; stepwise gradient) to give the title compound.

Mass Spectrum (ESI) m/z=421 (M+1), 443 (M+23).

Step C. Methyl 2-((3R,5R,6S)-5-(3-chlorophenyl)-6-(4-chlorophenyl)-1-(diethylamino)-3-methyl-2-oxopiperidin-3-yl)acetate

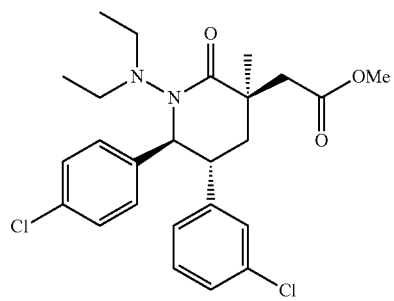 [SMILES: CCN(CC)N1C(=O)[C@@](C)(CC(=O)OC)C[C@H](c2cccc(Cl)c2)[C@H]1c1ccc(Cl)cc1]

Ethyl iodide (67.1 μL, 0.831 mmol) was added to a solution of methyl 2-((3R,5R,6S)-1-amino-5-(3-chlorophenyl)-6-(4-chlorophenyl)-3-methyl-2-oxopiperidin-3-yl)acetate (Example 429, step B, 35 mg, 0.083 mmol) and DIEA (145 μL, 0.831 mmol) in DMF. The resulting mixture was stirred at 80° C. for 12 h. The mixture was concentrated and purified by reversed phase HPLC (Sunfire™ Prep C$_{18}$ OBD 10 μm column; Waters, Milford, Mass.; 40-90% water/acetonitrile gradient with 0.1% TFA). Desired fractions were pooled and concentrated to give the title compound.

Mass Spectrum (ESI) m/z=477 (M+1).

Step D. 2-((3R,5R,6S)-5-(3-Chlorophenyl)-6-(4-chlorophenyl)-1-(diethylamino)-3-methyl-2-oxopiperidin-3-yl)acetic acid A solution of methyl 2-((3R,5R,6S)-5-(3-chlorophenyl)-6-(4-chlorophenyl)-1-(diethylamino)-3-methyl-2-oxopiperidin-3-yl)acetate (Example 429, step C) in water/methanol (1:1) was treated with lithium hydroxide (1N, 5 eq) at room temperature for 15 h. The mixture was concentrated and purified by reversed phase HPLC (Sunfire™ Prep C$_{18}$ OBD 10 µm column; Waters, Milford, Mass.; 40-90% water/acetonitrile gradient with 0.1% TFA). Desired fractions were then pooled and concentrated to give the title compound.

$^1$H NMR (500 MHz, Methanol-d$_4$) δ ppm 0.222 (t, J=7 Hz, 3 H) 1.179 (t, J=7 Hz, 3 H) 1.389 (s, 3 H) 2.143 (dd, J=14, 3.5 Hz, 1H) 2.200 (t, J=13.5 Hz, 1H) 2.570 (d, J=13.5 Hz, 1H) 2.713 (m, 1 H) 2.967 (d, J=13.5 Hz, 1 H) 3.116 (m, 1 H) 3.251 (m, 1 H) 3.519 (ddd, J=13, 11, 3.5 Hz, 1 H) 4.598 (d, J=11 Hz, 1 H) 6.972 (d, J=7 Hz, 1 H) 7.070 (m, 1 H) 7.099-7.16 (m, 2 H) 7.229 (m, 4 H); Mass Spectrum (ESI) m/z=463 (M+1), 485 (M+23).

Example 430

2-((3R,5R,6S)-5-(3-Chlorophenyl)-6-(4-chlorophenyl)-1-(dimethylamino)-3-methyl-2-oxopiperidin-3-yl)acetic acid

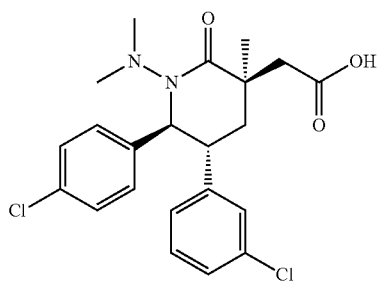 [SMILES: CN(C)N1C(=O)[C@@](C)(CC(=O)O)C[C@H](c2cccc(Cl)c2)[C@H]1c1ccc(Cl)cc1]

Methyl 2-((3R,5R,6S)-1-amino-5-(3-chlorophenyl)-6-(4-chlorophenyl)-3-methyl-2-oxopiperidin-3-yl)acetate (Example 429 step C) was treated by a procedure similar to the one described in Example 429, using methyl iodide instead of ethyl iodide in Step C.

$^1$H NMR (500 MHz, Methanol-d$_4$) δ ppm 1.356 (s, 3 H) 2.088 (dd, J=14, 3.5 Hz, 1H) 2.166 (t, J=13.5 Hz, 1H) 2.599 (br s, 6H) 2.601 (d, J=13.5, 1H) (m, 7 H) 2.933 (d, J=13.5 Hz, 1 H) 3.429 (ddd, J=13, 10.5, 3.5 Hz, 1 H) 4.672 (d, J=10.5 Hz, 1 H) 6.965 (m, 1 H) 7.10-7.16 (m, 5 H) 7.206 (d, J=8.5 Hz, 2 H); Mass Spectrum (ESI) m/z=435 (M+1).

Example 431

(2S,3S,5S,6R,7aR,10aS)-6-(3-Chlorophenyl)-5-(4-chlorophenyl)-3-ethyl-2,7a-dimethylhexahydrofuro[2,3-b]oxazolo[3,2-a]pyridin-9(5H)-one

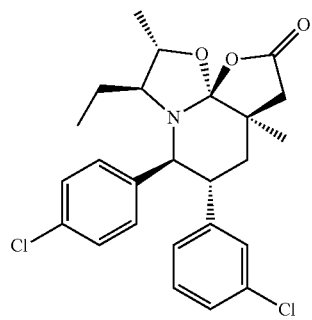 [SMILES: CC[C@H]1[C@H](C)O[C@]23OC(=O)C[C@@]2(C)C[C@H](c2cccc(Cl)c2)[C@@H](c2ccc(Cl)cc2)N13]

Step A: (3S,5R,6S)-3-Allyl-5-(3-chlorophenyl)-6-(4-chlorophenyl)-1-((2S,3S)-2-hydroxypentan-3-yl)-3-methylpiperidin-2-one

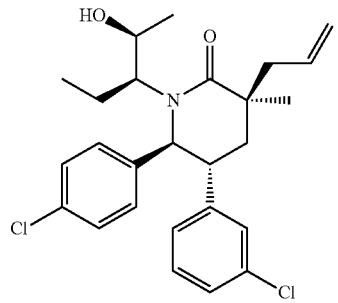 [SMILES: C=CC[C@@]1(C)C[C@H](c2cccc(Cl)c2)[C@@H](c2ccc(Cl)cc2)N([C@@H](CC)[C@H](C)O)C1=O]

L-Selectride™ (1M in THF, 5.24 ml, 5.24 mmol) was added to a solution at −10° C. of (3S,5R,6S)-3-allyl-5-(3-chlorophenyl)-6-(4-chlorophenyl)-3-methyl-1-((S)-2-oxopentan-3-yl)piperidin-2-one (Example 149, step A, 2 g, 4.36 mmol) in THF (29.1 ml) being careful to maintain the temperature below −7° C. The reaction was stirred for 40 min then quenched into an aqueous solution of Oxone™ (10.73 g, 17.45 mmol) in 60 mL water. It was noted that the temperature spiked up to 40° C. during the addition. The reaction was cooled to RT using a water/ice bath and stirred at RT for 1 h, then diluted with ethyl acetate. The layers were separated and the aq layer was extracted with ethyl acetate. The combined organics were washed with brine and dried over MgSO$_4$, filtered and concentrated. The crude material was dried under high vacuum overnight. Purification by column chromatography using 10-20% acetone in hexanes afforded the title compound.

$^1$H NMR (400 MHz, CHLOROFORM-d) δ ppm 7.21-7.27 (m, 2 H), 7.16 (ddd, J=8, 2, 1.2 Hz, 1 H), 7.10 (t, J=7.7 Hz, 1 H), 6.95-7.07 (m, 2 H), 6.93 (t, J=1.8 Hz, 1 H), 6.70 (dt, J=7.5, 1.2 Hz, 1 H), 5.80-5.92 (m, 1 H), 5.13-5.25 (m, 2 H), 4.66 (br s, 1 H), 4.37 (d, J=10.6 Hz, 1 H), 3.52-4.11 (m, 1 H), 3.20 (ddd, J=13.4, 10.5, 3.2 Hz, 1 H), 2.61 (d, J=7.4 Hz, 3 H), 2.11-2.30 (m, 1 H), 2.06 (t, J=13.7 Hz, 1 H), 1.95 (dd, J=13.7, 3.3 Hz, 1 H), 1.32-1.42 (m, 1 H), 1.22 (d, J=6.3 Hz, 3 H), 0.59 (br s, 3 H). LC/MS (M+H) m/z=460.2.

Step B: (2S,3S,5S,6R,8S)-8-Allyl-6-(3-chlorophenyl)-5-(4-chlorophenyl)-3-ethyl-2,8-dimethyl-2,3,5,6,7,8-hexahydrooxazolo[3,2-a]pyridin-4-ium 4-methylbenzenesulfonate

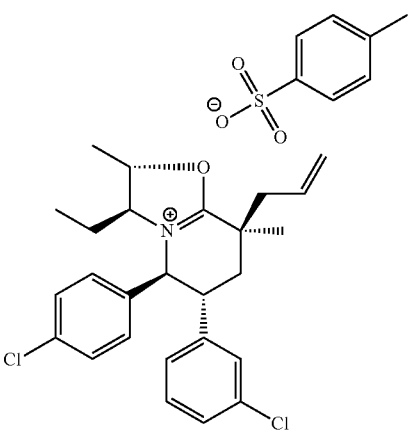 [SMILES: Cc1ccc(S(=O)(=O)[O-])cc1 ; C=CC[C@@]1(C)C[C@H](c2cccc(Cl)c2)[C@@H](c2ccc(Cl)cc2)[N+]2=C1O[C@@H](C)[C@@H]2CC]

A solution of (3S,5R,6S)-3-allyl-5-(3-chlorophenyl)-6-(4-chlorophenyl)-1-((2S,3S)-2-hydroxypentan-3-yl)-3-methylpiperidin-2-one (Example 431, Step A, 600 mg, 1.303 mmol) in toluene (43 mL) with pyridinium p-toluenesulfonate (PPTS, 327 mg, 1.30 mmol) was treated for 1 h under Dean-Stark conditions. When monitoring by NMR indicated about 95 to 97% completion, the reaction was treated with an additional 3% (10 mg) PPTS and returned to reflux for 30 min. The reaction mixture was concentrated under high vacuum and used as is for subsequent reactions.

$^1$H NMR (500 MHz, DMSO-$d_6$) δ ppm 8.15-7.10 (series of m, 12H), 5.89 (ddt, J=17.4, 10.3, 7.3, Hz, 1 H), 5.38 (d, J=11.0 Hz, 1 H), 5.36 (dd, J=16.9, 1.7 Hz, 1 H), 5.27 (dd, J=10.1, 2.1 Hz, 1 H), 5.17 (quin, J=6.3 Hz, 1 H), 4.12 (td, J=6.5, 2.6 Hz, 1 H), 3.97 (ddd, J=13.7, 11.0, 3.4 Hz, 1 H), 2.81 (A̲BX, $J_{AB}$=13.7 Hz, $J_{AX}$=7.1 Hz, 1H), 2.72 (AB̲X, $J_{AB}$=13.7 Hz, $J_{BX}$=7.8 Hz, 1H), 2.43 (t, J=13.2 Hz, 1 H), 2.29 (s, 3 H), 1.99 (dd, J=13.3, 3.3 Hz, 1 H), 1.57 (d, J=6.1 Hz, 3 H), 1.32 (s, 3 H), 0.95 (dqd, J=14.7, 7.3, 3.4 Hz, 1 H), 0.58 (t, J=7.2 Hz, 3 H), 0.45 (dquin, J=14.7, 7.2, Hz, 1 H). LC/MS m/z=442.2 (M+).

Step C: (2S,3S,5S,6R,7aR,10aS)-6-(3-Chlorophenyl)-5-(4-chlorophenyl)-3-ethyl-2,7a-dimethyl-hexahydrofuro[2,3-b]oxazolo[3,2-a]pyridin-9(5H)-one A solution of (2S,3S,5S,6R,8 S)-8-allyl-6-(3-chlorophenyl)-5-(4-chlorophenyl)-3-ethyl-2,8-dimethyl-2,3,5,6,7,8-hexahydrooxazolo[3,2-a]pyridin-4-ium 4-methylbenzenesulfonate (Example 431, Step B, 775 mg, 1.261 mmol) in dichloromethane (12 mL) at 0° C. with acetic acid (2.89 mL, 50.4 mmol) and tetra-n-butylammonium chloride (35.0 mg, 0.126 mmol) was treated by adding KMnO$_4$ (797 mg, 5.04 mmol) as a solution in water (12 mL), followed by a water rinse (12 mL).

After 20 min at 0° C., the reaction was quenched by addition of 15 mL sat. Na$_2$S$_2$O$_3$. The reaction was diluted with 150 mL of ethyl acetate and the layers were separated. The organic phase was washed with water and brine., dried over MgSO$_4$, filtered through Celite® (J. T. Baker, Phillipsberg, N.J., diatomaceous earth), and concentrated. The sample was placed under high vacuum overnight to afford product with entrained acetic acid (about 4 eq). An aliquot was purified using 60-80% ethyl acetate in hexanes to afford the title compound.

$^1$H NMR (400 MHz, DMSO-$d_6$) δ ppm 7.18-7.26 (m, 5 H), 7.07-7.16 (m, 2 H), 7.05 (dt, J=7.0, 1.7 Hz, 1 H), 3.92 (quin, J=6.1 Hz, 1 H), 3.84 (d, J=10.8 Hz, 1 H), 3.48 (d, J=17.4 Hz, 1 H), 3.34-3.42 (m, 1 H), 2.52-2.56 (m, 1 H), 2.34 (d, J=17.6 Hz, 1 H), 1.92 (A̲BX, $J_{AB}$=13.9 Hz, $J_{AX}$=13.2 Hz, 1 H), 1.82 (AB̲X, $J_{AB}$=13.9 Hz, $J_{BX}$=2.9 Hz, 1 H), 1.43 (d, J=6.3 Hz, 3 H), 1.22 (s, 5 H), 0.41 (t, J=7.5 Hz, 3 H). LC/MS (M+H) m/z=460.2.

Compounds of the present invention display inhibition of the interaction between HDM2 and p53 in the following assays.

Homogenous Time-Resolved Fluorescence Assay (HTRF1 Assay)

The standard assay conditions for the in vitro HTRF assay consisted of a 50 ul total reaction volume in black 384-well Costar polypropylene plates in 1×PBS buffer pH 7.4, 1 mM DTT, 0.1% BSA, 2.5 nM GST-hMDM2 (aa 1-188), 5 nM biotinylated-p53 (aa 1-83), 1.8 nM SA-XLent (Cisbio; Bedford, Mass.), 0.6 nM anti-GST cryptate monoclonal antibody (Cisbio; Bedford, Mass.) and 200 mM KF. Amino acid residues 1-188 of human MDM2 were expressed as an amino-terminal glutathione-5-transferase (GST) fusion protein (GST-hMDM2) in *Escherichia coli*. Residues 1-83 of human p53 were expressed as an amino-terminal AviTag™-TrxA-6× His fusion protein (biotinylated p53) in *E. coli*. Each protein was purified from cell paste by affinity chromatography.

Specifically, 10 uL of GST-hMDM2 was incubated with 10 ul of diluted compound (various concentrations, serially diluted) in 10% DMSO for 20 minutes at room temperature. 20 uL of biotinylated-p53 was added to the GST-hMDM2+ compound mixture, and then incubated at room temperature for 60 min. 10 uL of detection buffer consisting of SA-XLent, anti-GST cryptate antibody and KF was added to GST-hMDM2, biotinylated-p53 and compound reaction and left at room temperature to reach equilibrium for >4 hrs. The final concentration of DMSO in the reaction was 2%. Time-resolved fluorescence readings were measured on a microplate multilabel reader. Percentage of inhibition was calculated relative to nutlin-3.

As the potencies of the HDM2 inhibitors increased, an improved HTRF assay (HTRF2 assay) was developed. All assay conditions remained the same as described above, with the exception of the following changes in reagent concentrations: 0.2 nM GST-hMDM2 (1-188), 0.5 nM biotinylated-p53 (1-83), 0.18 nM SA-XLent, and 100 mM KF.

Results are provided in the table below.

TABLE 1

| Example | HTRF1 IC$_{50}$ (μM) | HTRF2 IC$_{50}$ (μM) |
|---|---|---|
| 1 | 0.04 | 0.004 |
| 2 | 0.20 | |
| 3 | 0.06 | 0.01 |
| 4 | 0.19 | |
| 5 | 0.27 | |
| 6 | 0.04 | |
| 7 | 0.05 | |
| 8 | 0.04 | |
| 9 | 0.03 | |
| 10 | 0.07 | |
| 11 | 0.09 | |
| 12 | 0.04 | |
| 13 | 0.11 | |
| 14 | 0.29 | |
| 15 | 0.24 | |
| 16 | 0.07 | |
| 17 | 0.24 | |
| 18 | 0.11 | |
| 19 | 0.01 | |
| 20 | 0.07 | |
| 21 | 0.07 | |
| 22 | 0.49 | |
| 23 | 0.17 | |
| 24 | 0.57 | |
| 25 | 0.14 | |
| 26 | 0.13 | |
| 27 | 0.10 | |
| 28 | 0.18 | |
| 29 | 0.03 | |
| 30 | 0.03 | 0.004 |
| 31 | 0.05 | |
| 32 | 0.09 | |
| 33 | 0.41 | |
| 34 | 0.71 | |
| 35 | 0.15 | 0.03 |
| 36 | 4.3 | |
| 37 | 0.06 | |
| 38 | 0.19 | |
| 39 | 0.30 | |
| 40 | 0.17 | |
| 41 | 0.32 | |
| 42 | 0.41 | |
| 43 | 1.97 | |
| 44 | 0.45 | |
| 45 | 0.55 | |

TABLE 1-continued

| Example | HTRF1 IC$_{50}$ (μM) | HTRF2 IC$_{50}$ (μM) |
|---|---|---|
| 46 | 0.27 | |
| 47 | 3.63 | |
| 48 | 1.37 | |
| 49 | 2.38 | |
| 50 | 0.83 | |
| 51 | 3.06 | |
| 52 | 1.70 | |
| 53 | 0.13 | |
| 54 | 2.09 | |
| 55 | 0.09 | |
| 56 | 1.89 | |
| 57 | 1.60 | |
| 58 | 0.70 | |
| 59 | 0.87 | |
| 60 | 0.16 | |
| 61 | 0.31 | |
| 62 | 0.09 | |
| 63 | 0.43 | |
| 64 | 0.22 | |
| 65 | 0.02 | 0.003 |
| 66 | 0.31 | |
| 67 | 0.02 | 0.002 |
| 68 | 0.03 | 0.002 |
| 69 | 0.06 | |
| 70 | 0.13 | |
| 71 | 0.02 | 0.003 |
| 72 | 0.06 | |
| 73 | 0.03 | 0.006 |
| 74 | 0.07 | |
| 75 | 0.03 | 0.005 |
| 76 | 0.22 | |
| 77 | 0.26 | |
| 78 | 0.53 | |
| 79 | 0.58 | |
| 80 | 0.08 | |
| 81 | 0.49 | |
| 82 | 0.02 | |
| 83 | 0.03 | |
| 84 | 1.76 | |
| 85 | 1.98 | |
| 86 | 0.01 | |
| 87 | 0.02 | |
| 88 | 0.84 | |
| 89 | 0.08 | |
| 90 | 0.04 | |
| 91 | 0.01 | 0.004 |
| 92 | 0.04 | |
| 93 | 0.01 | 0.003 |
| 94 | 0.01 | |
| 95 | 0.03 | 0.009 |
| 96 | 0.02 | 0.008 |
| 97 | 0.01 | 0.002 |
| 98 | 0.01 | 0.004 |
| 99 | 0.01 | 0.002 |
| 100 | 0.02 | |
| 101 | 0.02 | 0.006 |
| 102 | 0.05 | |
| 103 | 0.28 | |
| 104 | 0.04 | |
| 105 | 1.09 | |
| 106 | 0.19 | |
| 107 | 0.21 | |
| 108 | 0.11 | |
| 109 | 0.30 | |
| 110 | 0.34 | |
| 111 | 0.61 | |
| 112 | 0.23 | |
| 113 | 0.03 | |
| 114 | 0.03 | |
| 115 | <0.01 | 0.001 |
| 116 | 0.39 | |
| 117 | 0.71 | |
| 118 | 0.65 | |
| 119 | 0.12 | |
| 120 | 0.56 | |
| 121 | 0.05 | |
| 122 | 0.05 | 0.011 |
| 123 | 0.92 | |
| 124 | 0.02 | |
| 125 | 0.02 | 0.005 |

TABLE 2

| Example | HTRF1 IC$_{50}$ (μM) | HTRF2 IC$_{50}$ (μM) |
|---|---|---|
| 126 | | 0.012 |
| 127 | | 0.02 |
| 128 | 0.01 | 0.001 |
| 129 | 0.01 | 0.001 |
| 130 | 0.01 | 0.003 |
| 131 | 0.07 | |
| 132 | 0.12 | 0.070 |
| 133 | 0.01 | 0.002 |
| 134 | 0.01 | 0.002 |
| 135 | 0.01 | |
| 136 | 0.01 | 0.001 |
| 137 | 0.01 | 0.002 |
| 138 | 0.01 | 0.002 |
| 139 | <0.01 | 0.001 |
| 140 | 0.01 | 0.004 |
| 141 | <0.01 | 0.001 |
| 142 | 0.01 | 0.001 |
| 143 | 0.03 | 0.019 |
| 144 | 0.04 | 0.014 |
| 145 | 0.01 | 0.004 |
| 146 | 0.01 | 0.004 |
| 147 | 0.01 | 0.002 |
| 148 | <0.01 | 0.001 |
| 149 | 0.04 | 0.006 |
| 150 | 0.01 | 0.002 |
| 151 | 0.02 | 0.006 |
| 152 | 0.01 | 0.001 |
| 153 | | 0.002 |
| 154 | 0.01 | 0.002 |
| 155 | | 0.011 |
| 156 | | |
| 157 | 0.01 | 0.002 |
| 158 | 0.01 | |
| 159 | 0.01 | 0.002 |
| 160 | 0.01 | |
| 161 | 0.10 | |
| 162 | | 0.006 |
| 163 | | 0.053 |
| 164 | | 0.049 |
| 165 | | 0.026 |
| 166 | | 0.044 |
| 167 | | 0.064 |
| 168 | | 0.058 |
| 169 | | 0.002 |
| 170 | | 0.106 |
| 171 | | 0.028 |
| 172 | | 0.001 |
| 173 | | 0.015 |
| 174 | | 0.002 |
| 175 | | 0.001 |
| 176 | | 0.003 |
| 177 | | 0.053 |
| 178 | 0.02 | 0.006 |
| 179 | 0.04 | |
| 180 | 0.03 | 0.008 |
| 181 | | 0.002 |
| 182 | | 0.004 |
| 183 | | 0.003 |
| 184 | | 0.013 |
| 185 | 0.02 | 0.002 |
| 186 | | 0.007 |
| 187 | | 0.003 |
| 188 | | 0.001 |
| 189 | | 0.003 |
| 190 | | 0.005 |
| 191 | | 0.001 |
| 192 | | 0.001 |
| 193 | | 0.001 |

TABLE 2-continued

| Example | HTRF1 IC$_{50}$ (μM) | HTRF2 IC$_{50}$ (μM) |
|---|---|---|
| 194 | | 0.005 |
| 195 | | 0.002 |
| 196 | | <0.001 |
| 197 | | <0.001 |
| 198 | | <0.001 |
| 199 | | 0.001 |
| 200 | | 0.001 |
| 201 | | 0.044 |
| 202 | | 0.002 |
| 203 | | 0.001 |
| 204 | | 0.002 |
| 205 | 0.01 | 0.001 |
| 206 | 0.01 | 0.003 |
| 207 | 0.04 | 0.009 |
| 208 | 0.02 | 0.007 |
| 209 | 0.07 | 0.009 |
| 210 | 0.01 | 0.002 |
| 211 | 0.02 | 0.004 |
| 212 | 0.03 | 0.005 |
| 213 | 0.03 | |
| 214 | 0.02 | 0.003 |
| 215 | 0.04 | 0.006 |
| 216 | 0.03 | 0.003 |
| 217 | 0.03 | 0.005 |
| 218 | 0.08 | 0.019 |
| 219 | 0.03 | 0.012 |
| 220 | 0.03 | |
| 221 | 0.02 | 0.003 |
| 222 | 0.01 | 0.001 |
| 223 | 0.02 | 0.004 |
| 224 | | 0.001 |
| 225 | | 0.002 |
| 226 | 0.09 | |
| 227 | 0.07 | |
| 228 | 0.04 | |
| 229 | | 0.001 |
| 230 | 0.03 | 0.010 |
| 231 | 0.08 | |
| 232 | 0.08 | |
| 233 | 0.08 | |
| 234 | 0.05 | 0.011 |
| 235 | 0.06 | |
| 236 | 0.01 | |
| 237 | 0.04 | 0.009 |
| 238 | | 0.001 |
| 239 | | |
| 240 | 0.05 | |
| 241 | 0.02 | 0.003 |
| 242 | 0.03 | |
| 243 | 0.03 | |
| 244 | 0.04 | |
| 245 | 0.03 | 0.009 |
| 246 | 0.02 | 0.003 |
| 247-A | | 0.100 |
| 247-B | | 0.371 |
| 248 | | 0.100 |
| 249 | 0.03 | 0.006 |
| 250 | 0.01 | 0.001 |
| 251 | 0.01 | 0.001 |
| 252 | 0.06 | |
| 253 | | 0.001 |
| 254 | | <0.001 |
| 255 | | <0.001 |
| 256 | <0.01 | <0.001 |
| 257 | | 0.001 |
| 258 | 0.08 | 0.002 |
| 259 | | 0.002 |
| 260 | | 0.007 |
| 261 | | 0.001 |
| 262 | 0.02 | 0.003 |

TABLE 3

| Example | HTRF1 IC$_{50}$ (μM) | HTRF2 IC$_{50}$ (μM) |
|---|---|---|
| 263 | | 0.0002 |
| 264 | | 0.0003 |
| 265 | | 0.0005 |
| 266 | | 0.0005 |
| 267 | | 0.0003 |
| 268 | | 0.0001 |
| 269 | | 0.0001 |
| 270 | | 0.0055 |
| 272 | | 0.0001 |
| 273 | | 0.0002 |
| 274 | | 0.0002 |
| 275 | | 0.0003 |
| 276 | | 0.0005 |
| 277 | | 0.0002 |
| 278 | | 0.0002 |
| 279 | | 0.0005 |
| 280 | | 0.0006 |
| 281 | | 0.0003 |
| 282 | | 0.0002 |
| 283 | | 0.0007 |
| 284 | | 0.0015 |
| 285 | | 0.0008 |
| 286 | | 0.0006 |
| 287 | | 0.0003 |
| 288 | | 0.0135 |
| 289 | | 0.0003 |
| 290 | | |
| 291 | | |
| 292 | | 0.0009 |
| 293 | | 0.0008 |
| 294 | | 0.0007 |
| 295 | | 0.0018 |
| 296 | | 0.0044 |
| 297 | | 0.0161 |
| 298 | | 0.0013 |
| 299 | | 0.0100 |
| 300 | | |
| 301 | | 0.0003 |
| 302 | | 0.0004 |
| 303 | | 0.0005 |
| 304 | | 0.0003 |
| 305 | | 0.0005 |
| 306 | | 0.0003 |
| 307 | | 0.0003 |
| 308 | | 0.0001 |
| 309 | | 0.0002 |
| 310 | | 0.0002 |
| 311 | | 0.0001 |
| 312 | | 0.0112 |
| 313 | | 0.0002 |
| 314 | | 0.0001 |
| 315 | | 0.0014 |
| 316 | | 0.0029 |
| 317 | | 0.0012 |
| 318 | | 0.0029 |
| 319 | | 0.0024 |
| 320 | | 0.0005 |
| 321 | | 0.0013 |
| 322 | | 0.0001 |
| 323 | | 0.0002 |
| 324 | | 0.0003 |
| 325 | | 0.0016 |
| 326 | | 0.0004 |
| 327 | | 0.0004 |
| 328 | | 0.0014 |
| 329 | | 0.0016 |
| 330 | | 0.0002 |
| 331 | | 0.0002 |
| 332 | | 0.0003 |
| 333 | | 0.0002 |
| 334 | | 0.0001 |
| 335 | | 0.0003 |
| 336 | | 0.0018 |
| 337 | | 0.0006 |
| 338 | | 0.0003 |
| 339 | | 0.0003 |
| 340 | | 0.0002 |
| 341 | | 0.0002 |

TABLE 3-continued

| Example | HTRF1 IC$_{50}$ (µM) | HTRF2 IC$_{50}$ (µM) |
|---|---|---|
| 342 | | 0.0001 |
| 343 | | 0.0002 |
| 344 | | 0.0004 |
| 345 | | 0.0002 |
| 346 | | 0.0001 |
| 347 | | 0.0003 |
| 348 | | 0.0003 |
| 349 | | 0.0001 |
| 350 | | 0.0001 |
| 351 | | 0.0001 |
| 352 | | 0.0002 |
| 353 | | 0.0001 |
| 354 | | 0.0001 |
| 355 | | 0.0006 |
| 356 | | 0.0009 |
| 357 | | 0.0002 |
| 358 | | 0.0001 |
| 359 | | 0.0002 |
| 360 | | 0.0003 |
| 361 | | 0.0005 |
| 362 | | 0.0010 |
| 363 | | 0.0002 |
| 364 | | 0.0003 |
| 365 | | 0.0008 |
| 366 | | 0.0001 |
| 367 | | 0.0026 |
| 368 | | 0.0019 |
| 369 | | 0.0006 |
| 370 | | 0.0004 |
| 371 | | 0.0001 |
| 372 | | 0.0002 |
| 373 | | 0.0002 |
| 374 | | 0.0002 |
| 375 | | 0.0001 |
| 376 | | 0.0010 |
| 377 | | 0.0002 |
| 378 | | 0.0001 |
| 379 | | 0.0001 |
| 380 | | 0.0006 |
| 381 | | 0.0001 |
| 382 | | 0.0002 |
| 383 | | 0.0005 |
| 384 | | 0.0005 |
| 385 | | |
| 386 | | 0.0018 |
| 387 | | 0.0070 |
| 388 | | |
| 389 | | 0.0014 |
| 390 | | |
| 391 | | 0.0050 |
| 392 | | 0.1230 |
| 393 | | 0.0007 |
| 394 | | 0.0004 |
| 395 | | 0.0005 |
| 396 | | 0.0002 |
| 397 | | 0.0002 |
| 398 | | 0.0001 |
| 399 | | 0.0001 |
| 400 | | 0.0038 |
| 401 | | 0.0015 |
| 402 | | 0.0046 |
| 403 | | 0.0040 |
| 404 | | 0.0009 |
| 405 | | |
| 406 | | |
| 407 | | |
| 408 | | 0.0035 |
| 409 | | |
| 410 | | 0.0026 |
| 411 | | |
| 412 | | |
| 413 | | 0.0010 |
| 414 | | 0.0238 |
| 415 | | 0.0010 |
| 416 | | 0.0027 |
| 417 | | 0.0013 |
| 418 | | 0.0183 |
| 419 | | 0.0034 |
| 420 | | 0.1230 |
| 421 | | 0.1940 |
| 422 | | 0.1040 |
| 423 | | 0.0231 |
| 424 | | 0.1300 |
| 425 | | 0.2750 |
| 426 | | 0.0526 |
| 427 | | 0.1190 |
| 428 | | 0.0041 |
| 429 | 0.01 | 0.0024 |
| 430 | 0.02 | |
| 431 | | 0.0018 |

Compounds in the present invention display activation of cyclin-dependent kinase inhibitor p21$^{WAF1/CIP1}$.

p21 TaqMan® Assay

Inhibition of the interaction between hMDM2 and p53 results in activation of the p53 pathway via stabilization and accumulation of p53. p53 activates the transcription of many genes, one of which is p21$^{WAF1/CIP1}$. In order to assess the potency of hMDM2 inhibitors, quantitative reverse transcription polymerase chain reaction (qRT-PCR or TaqMan®) was used to measure the levels of p21 transcript in compound-treated cells relative to dimethyl sulfoxide (DMSO)-treated control cells.

On Day 1, SJSA-1 cells were plated at a density of 3×10$^4$ cells/well in 96-well cell culture plates in 100 ul of growth medium (RPMI 1640; 10 mM HEPES; 1 mM sodium pyruvate; 1X Penicillin-Streptomycin-Glutamine (PSQ); and 10% fetal bovine serum (all reagents from Invitrogen; Carlsbad, Calif.)). The cells were cultured overnight at 37° C. and 5% CO$_2$.

On Day 2, hMDM2 inhibitors were serially diluted in DMSO (Sigma-Aldrich; St. Louis, Mo.). 5 ul of each compound dilution was added to 245 ul of filtered assay medium (RPMI 1640, mM HEPES, 1 mM sodium pyruvate, and 1X PSQ), containing 10% FBS. Alternatively, the assay was also run in the presence of 10% human serum or 10% mouse serum, or in the absence of any serum. The growth medium was removed from the plated SJSA-1 cells and replaced with 100 ul/well of assay medium. Then 100 ul of medium containing diluted inhibitor was added to each well, to a final volume of 200 ul. The compound dose titration yielded final concentrations ranging from 0.049 uM-50 uM, plus a DMSO control. The cells were incubated in the presence of inhibitor at 37° C. and 5% CO$_2$ for 7 hours. At the end of the incubation period, the medium was removed from the cells, and the plates were stored at −80° C.

On Day 3, total RNA was purified from the inhibitor- and DMSO-treated SJSA-1 cells using the Qiagen BioRobot Universal workstation following the RNeasy 96 BioRobot 8000 kit protocol from the manufacturer (Qiagen; Valencia, Calif.), with the following exceptions: the protocol began with RLT lysis buffer addition, omitted DNase treatment, omitted addition of Top Elute fluid, and changed the final elution volume to 120 ul. After the BioRobot Universal finished the RNA extraction procedure, the collection plate containing total RNA from each well was briefly centrifuged to collect the eluate at the bottom of the tubes.

To measure the levels of p21 transcript present, qRT-PCR was used. The levels of both p21 and the housekeeping gene, glyceraldehyde 3-phosphate dehydrogenase (GAPDH) were assayed from total RNA from each inhibitor- or DMSO-treated well in technical duplicates. Each qRT-PCR assay well contained the following components from the TaqMan®

One-Step RT-PCR Master Mix Reagents Kit (Invitrogen): 10 ul of 2X TaqMan® Universal PCR Master Mix, 0.5 ul of 40X Multiscribe™ Reverse Transcriptase/RNase Inhibitor Mix, 1 ul of either p21 20X TaqMan® Gene Expression Assay (Invitrogen) or 1 ul of GAPDH 20X TaqMan® Gene Expression Assay (Invitrogen), plus 5 ul of total RNA and 3.5 ul of DEPC-$H_2O$ (EMD Chemicals; Gibbstown, N.J.). The qRT-PCR reactions were assayed on the Applied Biosystems Prism 7900HT instrument, using the relative quantification (delta delta Ct) method with the following cycling conditions: 30 minutes at 48° C., followed by 10 minutes at 95° C., then 40 cycles of 15 seconds at 95° C. and 1 minute at 60° C. The data were analyzed with Applied Biosystems SDS2.2 software, using GAPDH as the endogenous control and DMSO-treated samples as the calibrator. The SDS2.2 software calculated relative quantification (RQ) or fold increase of p21 levels relative to DMSO control for each treated sample. Maximum (100%) p21 fold induction was defined by the maximum of a fitted curve of a reference compound. The p21 fold induction at each inhibitor dose tested was converted to a value representing percentage of maximum. Dose-response curves were generated using XLFit software (ID Business Solutions, Alameda, Calif.) to calculate $IC_{50}$ transit values for each inhibitor tested.

What is claimed is:

1. A compound of Formula I:

or a pharmaceutically acceptable salt thereof, wherein:

Q is a bond or optionally can be selected from O, $NR^7$ or $S(O)_v$, when n* is an integer from 1 to 6;

Z is $S(=O)_2$;

$R^a$ at each occurrence is independently selected from H, $(C_1-C_3)$alkyl, (halo)$(C_1-C_3)$alkyl, (hydroxy)$(C_1-C_3)$alkyl, (alkoxy)$(C_1-C_3)$alkyl, or cyano;

$R^b$ is H, halo, $(C_1-C_3)$alkyl, (halo)$(C_1-C_3)$alkyl, (hydroxy)$(C_1-C_3)$alkyl, (alkoxy)$(C_1-C_3)$alkyl, or cyano;

$R^c$ and $R^d$ are independently selected from H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, or (hydroxy)$(C_1-C_3)$alkyl, or $R^c$ and $R^d$ may optionally combine to form a spirocycloalkyl or heterocyclo ring system;

$R^e$ is (a) H or halo; or (b) $(C_1-C_8)$alkyl, $(C_3-C_8)$cycloalkyl, $(C_3-C_8)$heterocyclo, cyano, halogen, hydroxyl, —$OR^5$, $NR^7R^8$, or heterocycloalkyl, any of which may be optionally substituted with 1 or more $R^x$ groups as allowed by valence;

R' and R" at each occurrence, respectively, are independently H, halo, $(C_1-C_3)$alkyl, $(C_1-C_3)$alkoxy, (halo)$(C_1-C_3)$alkyl, (halo)$(C_1-C_3)$alkoxy, (alkoxy)$(C_1-C_3)$alkyl, (hydroxy)$(C_1-C_3)$alkyl, —S—$(C_1-C_3)$alkyl, $C(O)(C_1-C_3)$alkyl, —$NR^7R^8$, or hydroxyl, or R' and R" bound to the same carbon atom may optionally combine to form =O;

$R^1$ is (a) —COOH, —$C(O)OR^{10}$, —$C(O)NHOH$, —$C(O)NH-NH_2$, —$C(O)NHS(O)_2R^{10}$, —$S(O)_2NHC(O)R^{10}$, —$S(O)_2NR^7R^8$, —$NR^7C(O)R^{10}$, —$NR^7C(O)OR^5$, —$C(O)NR^7R^8$, —$NR^7S(O)_2R^{10}$, —$NR^7C(O)NR^7R^8$, —$S(O)_vR^{10}$, hydroxylalkyl, -cyclopropyl-COOH, or CN; or (b) heteroaryl or heterocyclo, either of which may be optionally independently substituted with one or more $R^x$ groups as allowed by valence;

$R^2$ is (a) —$NR^7R^8$, $NR^7C(O)OR^{10}$, $NR^7C(O)NR^7R^{10}$, or —$C(R^a)R^5R^6$; or (b) aryl, heteroaryl, cycloalkyl, or heterocyclo, any of which may be optionally independently substituted with one or more $R^x$ groups as allowed by valence;

$R^3$ and $R^4$ are independently aryl or heteroaryl, either of which may be optionally independently substituted with one or more $R^x$ groups as allowed by valence;

$R^5$ and $R^6$ at each occurrence, respectively, are independently selected from (a) H or CN;

(b) -(alkylene)$_t$-OH, -(alkylene)$_t$-$OR^9$, -(alkylene)$_t$-$SR^9$, -(alkylene)$_t$-$NR^{10}R^{11}$, -(alkylene)$_t$-$C(O)R^9$, -(alkylene)$_t$-$C(O)OR^9$, -(alkylene)$_t$-$OC(O)R^9$, -(alkylene)$_t$-$S(O)_vR^9$, -(alkylene)$_t$-$NHS(O)_2R^{10}$, -(alkylene)$_t$-$N(R^{11})S(O)_2R^{10}$, -(alkylene)$_t$-$S(O)_2NR^{10}R^{11}$, -(alkylene)$_t$-$N(R^{11})S(O)_2NR^{10}R^{11}$, —$NR^{10}C(O)R^9$, —$C(O)NR^{10}R^{11}$, —$NR^{10}S(O)_2R^9$, $S(O)_2NR^{10}$, or $NR^{10}C(O)NR^{10}R^{11}$; or (c) haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, aryl($C_{1-3}$-alkyl), heteroaryl, heteroaryl($C_{1-3}$-alkyl), heterocyclo or heterocyclo($C_{1-3}$-alkyl), any of which may be optionally independently substituted with one or more $R^x$ groups as allowed by valence;

$R^7$ and $R^8$ at each occurrence, respectively, are independently selected from H, cyano, —$OC_{1-6}$-alkyl, $C_{1-6}$-alkyl, halo($C_{1-6}$)-alkyl, cycloalkyl, $C_{2-6}$-alkenyl, $C_{2-6}$-alkynyl, aryl, heteroaryl, heterocyclo, arylalkyl, heteroarylalkyl, heterocyclo($C_{1-10}$alkyl), or ($C_{3-8}$-cycloalkyl)($C_{1-3}$alkyl), any of which may be optionally substituted as allowed by valence with one or more $R^x$, or $R^7$ and $R^8$ may combine to form a $C_4-C_8$-heterocyclo ring optionally substituted with one or more $R^x$;

$R^9$ is haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, heteroaryl, heterocyclo, or heterocycloalkyl, any of which may be optionally independently substituted with one or more $R^x$ groups as allowed by valence;

$R^{10}$ and $R^{11}$ at each occurrence, respectively, are independently selected from H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, any of which may be optionally substituted as allowed by valence with one or more $R^x$, or $R^{10}$ and $R^{11}$ may combine to form a heterocyclo ring optionally substituted with one or more $R^x$;

$R^x$ at each occurrence is independently, deuterium, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more halo, cyano, oxo, -(alkylene)$_t$-OR*, -(alkylene)$_t$-S(O)$_v$R*, -(alkylene)$_t$-NR$^+$R$^{++}$, -(alkylene)$_t$-C(=O)R*, -(alkylene)$_t$-C(=S)R*, -(alkylene)$_t$-C(=O)OR*, -(alkylene)$_t$-OC(=O)R*, -(alkylene)$_t$-C(=S)OR*, -(alkylene)$_t$-C(=O)NR$^+$R$^{++}$, -(alkylene)$_t$-C(=S)NR$^+$R$^{++}$, -(alkylene)$_t$-N(R$^+$)C(=O)NR$^+$R$^{++}$, -(alkylene)$_t$-N(R$^+$)C(=S)NR$^+$R$^{++}$, -(alkylene)$_t$-N(R$^+$)C(=O)R*, -(alkylene)$_t$-N(R$^+$)C(=S)R*, -(alkylene)$_t$-OC(=O)NR$^+$R$^{++}$, -(alkylene)$_t$-OC(=S)NR$^+$R$^{++}$, -(alkylene)$_t$-SO$_2$NR$^+$R$^{++}$, -(alkylene)$_t$-N(R$^+$)SO$_2$R*, -(alkylene)$_t$-N(R$^+$)SO$_2$NR$^+$R$^{++}$, -(alkylene)$_t$-N(R$^+$)C(=O)OR*, -(alkylene)$_t$-N(R$^+$)C(=S)OR*, or -(alkylene)$_t$-N(R$^+$)SO$_2$R*;

R* is H, haloalkyl, haloalkoxy, $C_{1-6}$-alkyl, $C_{2-6}$-alkenyl, $C_{2-6}$-alkynyl, $C_{3-8}$-cycloalkyl, $C_{4-8}$-cycloalkenyl, aryl, heteroaryl, or heterocyclo;

R$^+$ and R$^{++}$ are independently H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, or R$^+$ and R$^{++}$ bound to the same nitrogen atom may optionally combine to form a heterocyclo ring system;

n and n* are each independently selected from 0 or an integer from 1 to 6;

t at each occurrence is independently 0 or an integer from 1 to 6; and v at each occurrence is independently 0, 1 or 2.

2. The compound of claim 1, or a pharmaceutically acceptable salt thereof, wherein R$^2$ is —C(H)R$^5$R$^6$, —NR$^7$R$^8$, phenyl or pyridine, wherein the phenyl or the pyridyl is substituted with one or more R$^x$ as allowed by valence.

3. The compound of claim 1, or a pharmaceutically acceptable salt thereof, wherein R$^2$ is selected from

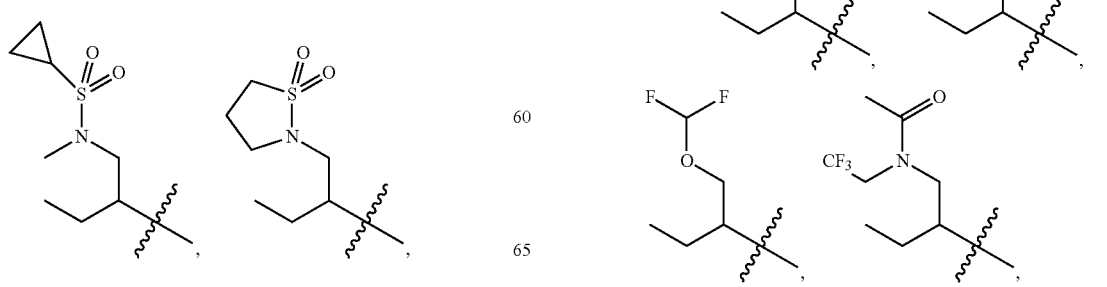

-continued
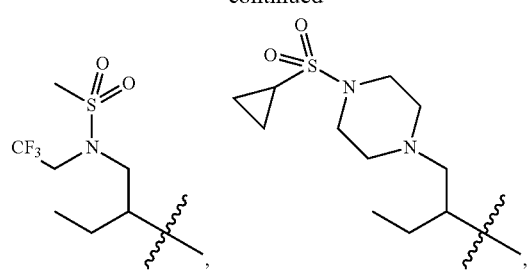
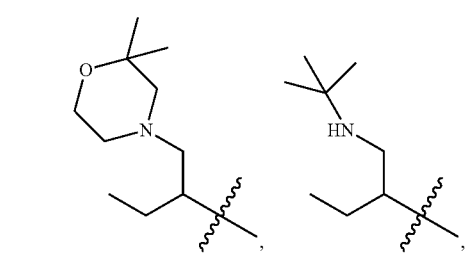
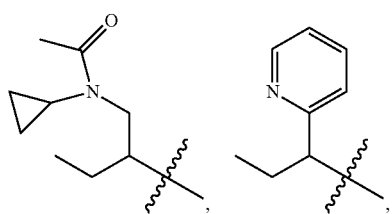
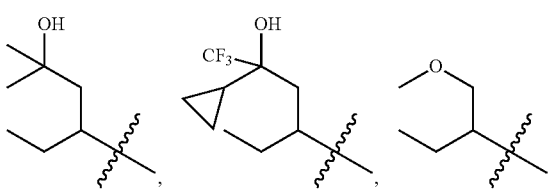
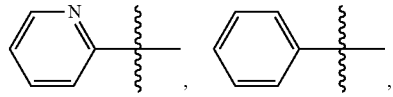
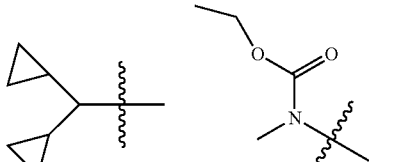
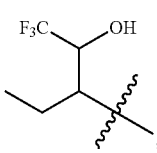
any of which may be optionally substituted with one or more $R^x$ groups as allowed by valence.
4. The compound of claim 1, or a pharmaceutically acceptable salt thereof, wherein $R^2$ is selected from
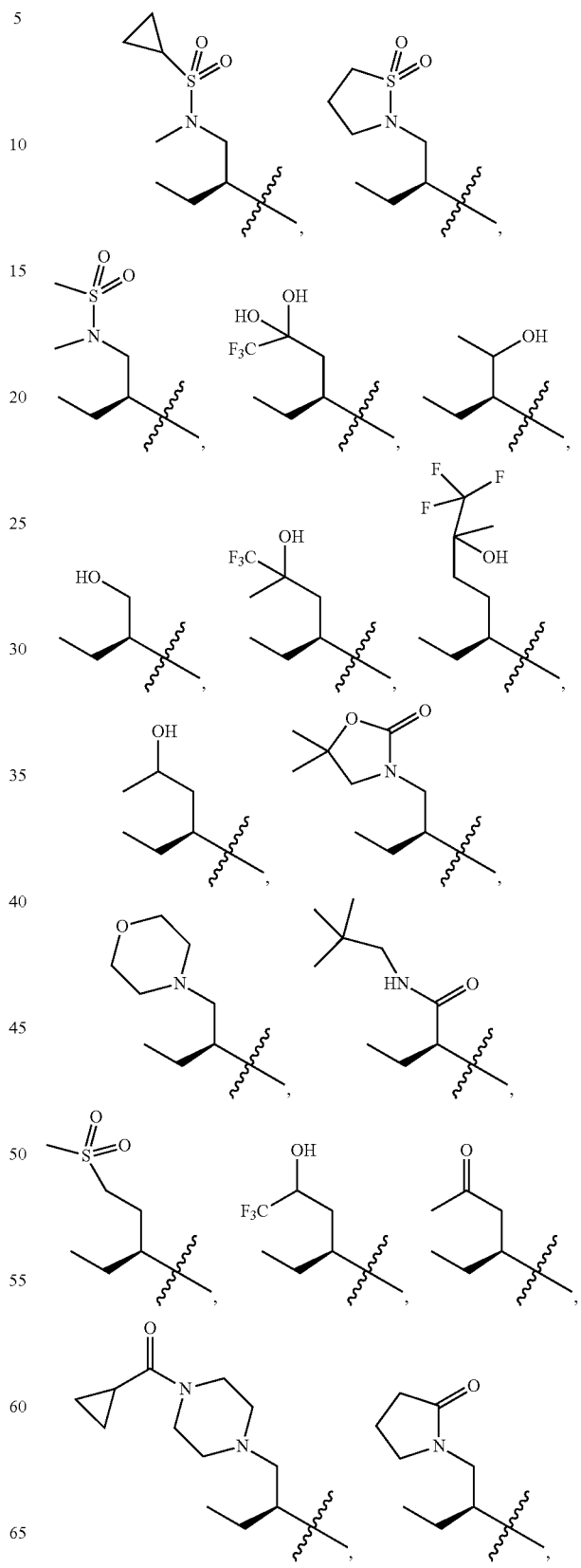

-continued
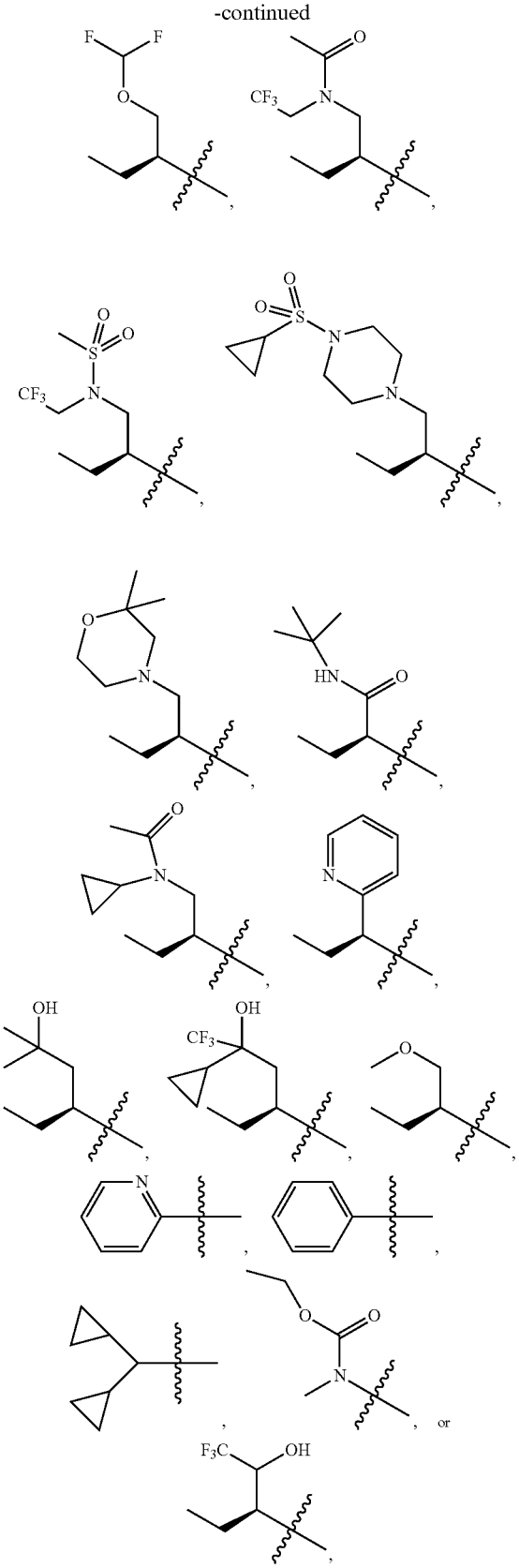
any of which may be optionally substituted with one or more $R^x$ groups as allowed by valence.
5. The compound of claim 1, or a pharmaceutically acceptable salt thereof, wherein
$R^2$ is selected from
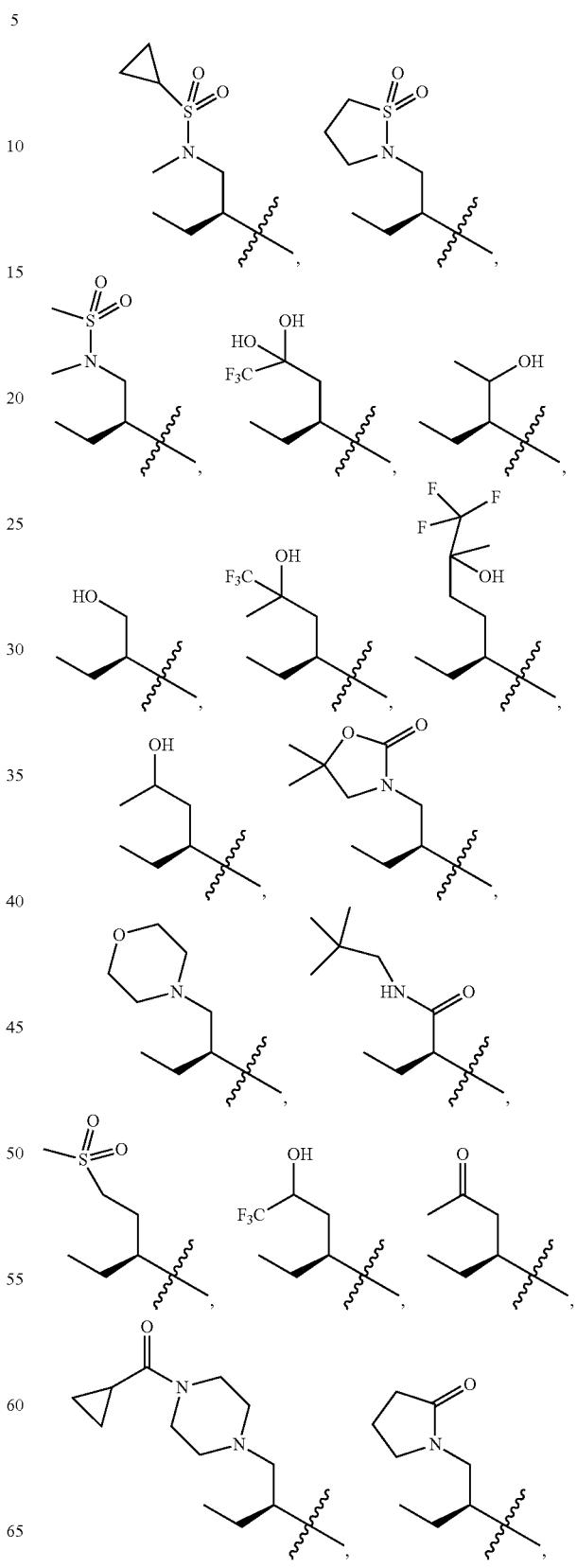

-continued
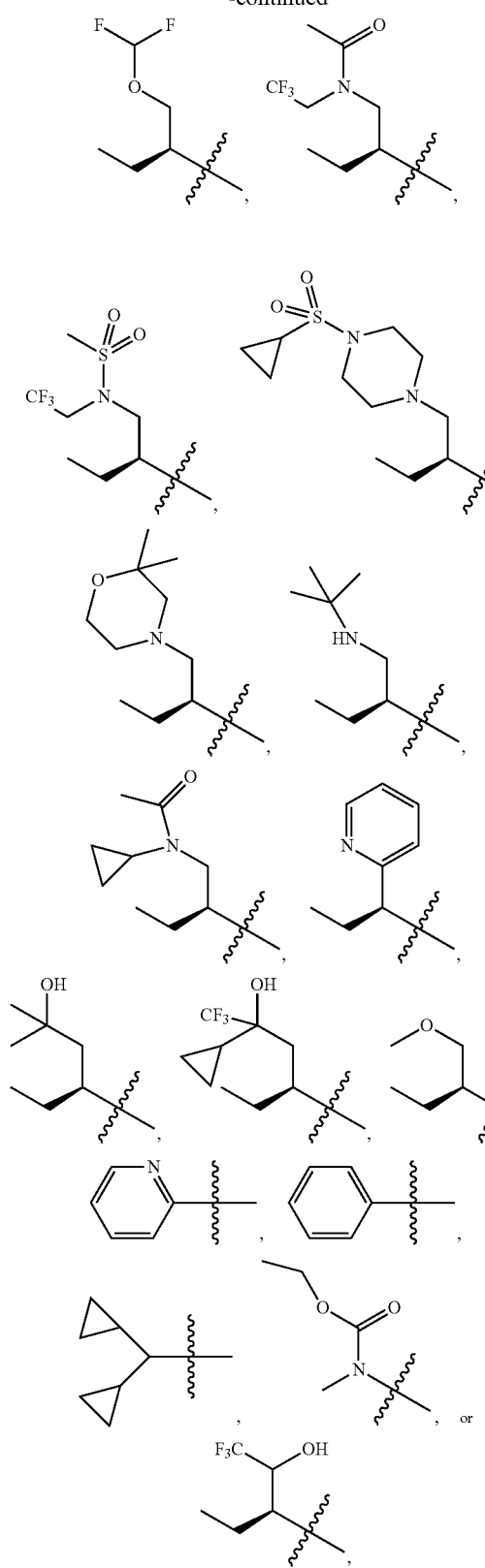
any of which may be optionally substituted with one or more R$^x$ groups as allowed by valence;
and R$^1$ is
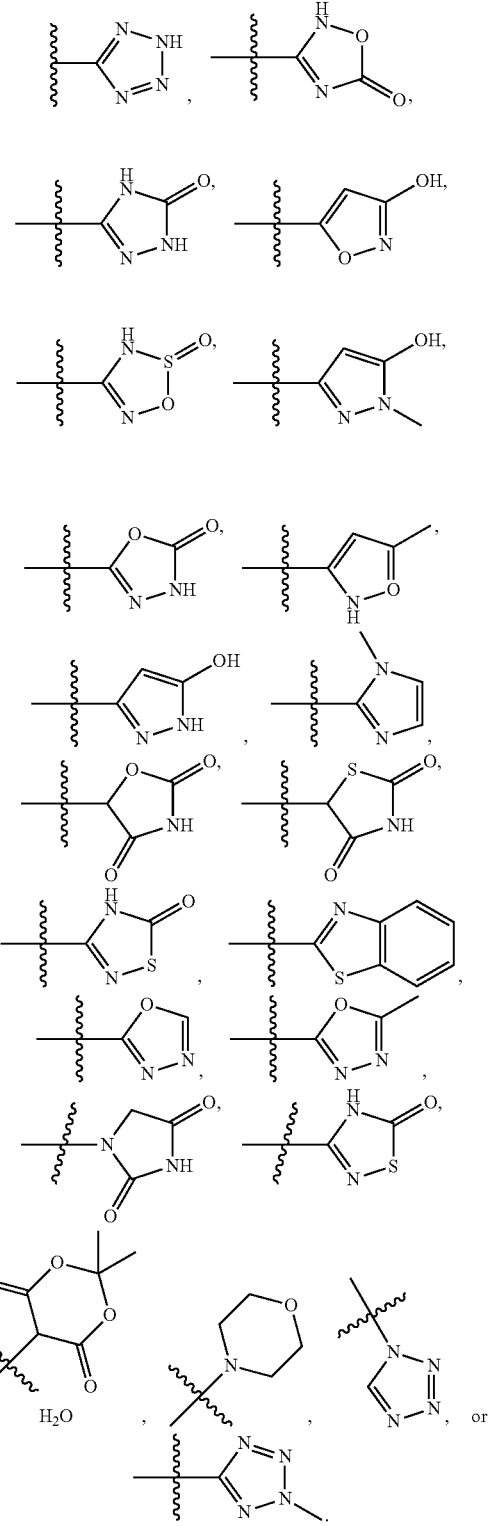
or a heteroaryl or heterocycle selected from 6. The compound of claim 1, or a pharmaceutically acceptable salt thereof, wherein
R² is selected from
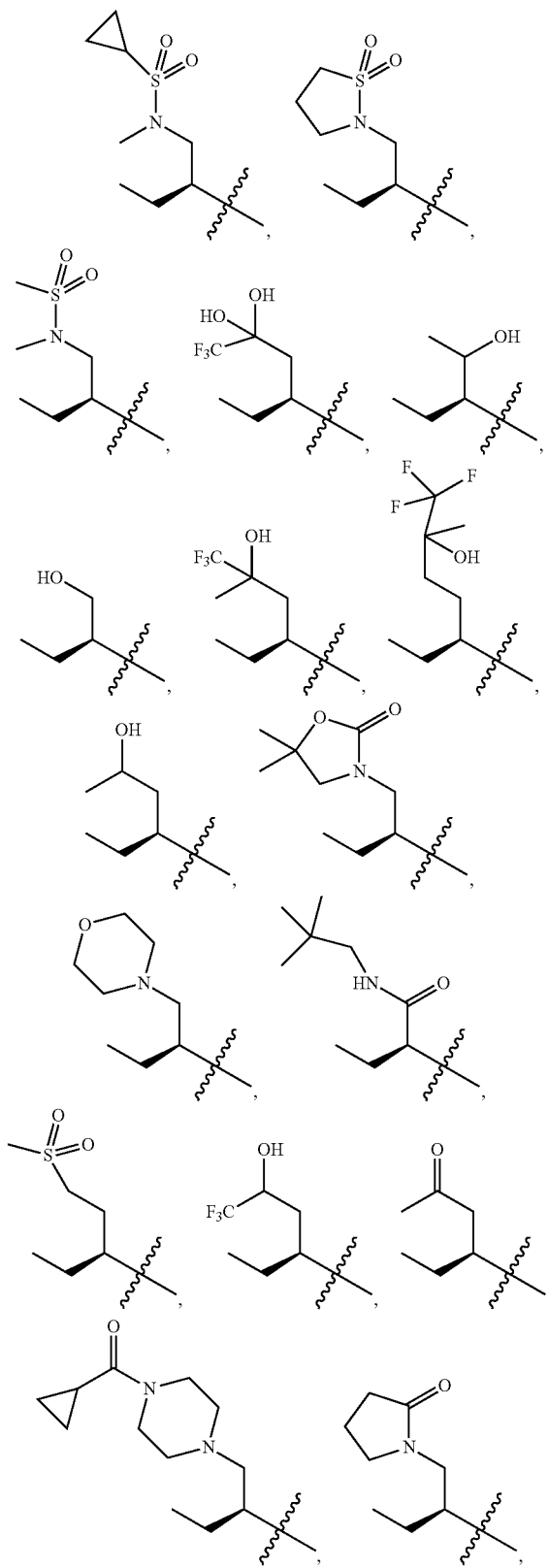
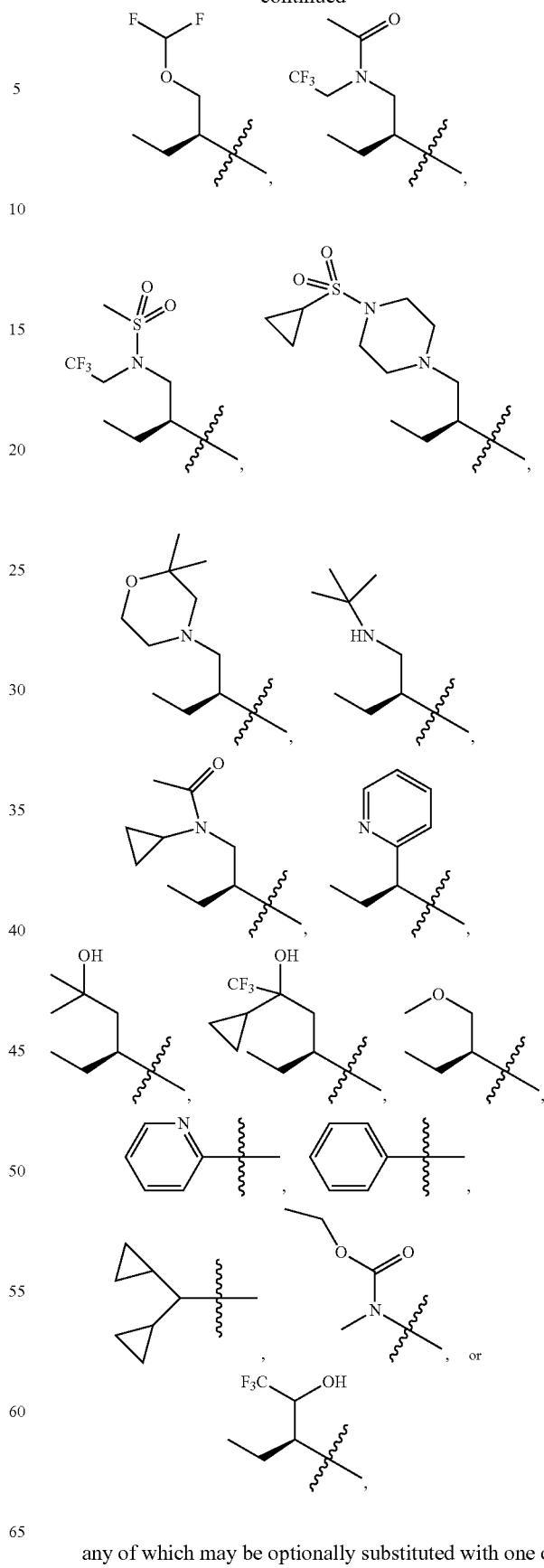
any of which may be optionally substituted with one or more Rˣ groups as allowed by valence; and $R^1$ is

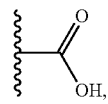 [SMILES: *C(=O)O]

or a heteroaryl or heterocycle selected from

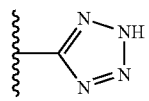 or 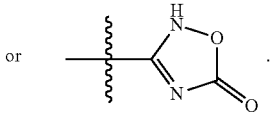 .

7. The compound of claim 1, or a pharmaceutically acceptable salt thereof, wherein $R^e$ is H or methyl or ethyl.

8. The compound of claim 1, or a pharmaceutically acceptable salt thereof, wherein $R^1$ is

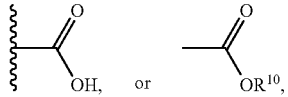

or a heteroaryl or heterocycle selected from

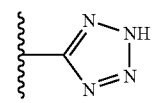 or 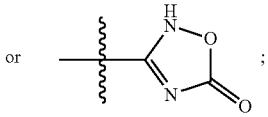 ;

$R^2$ is

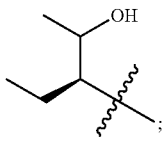 [SMILES: *[C@@H](CC)C(C)O] ;

and $R^e$ is methyl.

9. The compound of claim 1, or a pharmaceutically acceptable salt thereof, wherein:

$R^2$ is

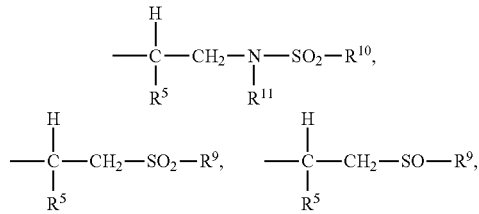

-continued

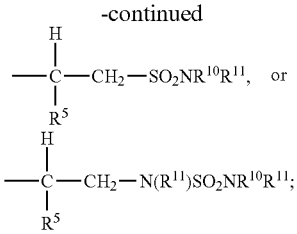

$R^5$ is cyclopropyl, or $C_{1-6}$alkyl;

$R^9$ is haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, heteroaryl, or heterocycloalkyl, or $R^9$ is haloalkyl, haloalkoxy, $C_{1-6}$-alkyl, $C_{2-6}$alkenyl, $C_{2-6}$-alkynyl, $C_{3-8}$-cycloalkyl, ($C_{3-8}$-cycloalkyl)($C_{1-3}$alkyl), $C_{4-8}$-cycloalkenyl, aryl, heteroaryl, or heterocyclo, any of which may be optionally independently substituted with one or more $R^x$ groups as allowed by valence; and $R^{10}$ and $R^{11}$ at each occurrence, respectively, are independently selected from H, alkyl, haloalkyl, cycloalkyl, alkenyl, alkynyl, aryl, heteroaryl, heterocyclo, arylalkyl, heteroarylalkyl, heterocycloalkyl, or cycloalkylalkyl, any of which may be optionally substituted as allowed by valence with one or more $R^x$, or $R^{10}$ and $R^{11}$ may combine to form a heterocyclo ring optionally substituted with one or more $R^x$.

10. The compound of claim 1, or a pharmaceutically acceptable salt thereof, wherein:

$R^1$ is

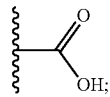 [SMILES: *C(=O)O] ;

$R^2$ is

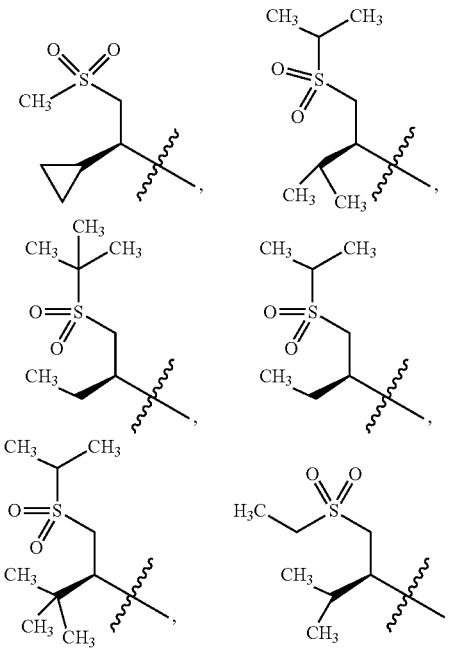

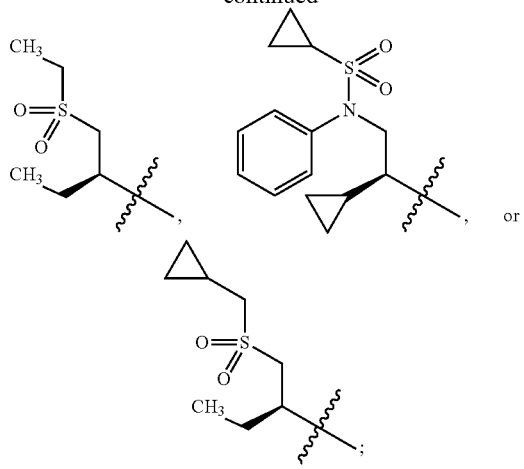

and $R^e$ is methyl.

11. A compound, or a pharmaceutically acceptable salt thereof, selected from:
- ((3S,4R,6R)-4-(3-chlorophenyl)-3-(4-chlorophenyl)-1,1-dioxido-2-(2-propanyl)-1,2-thiazinan-6-yl)acetic acid;
- ((3S,4R,6S)-4-(3-chlorophenyl)-3-(4-chlorophenyl)-1,1-dioxido-2-(2-propanyl)-1,2-thiazinan-6-yl)acetic acid;
- ((3S,4R,6R)-4-(3-chlorophenyl)-3-(4-chlorophenyl)-6-methyl-1,1-dioxido-2-(2-propanyl)-1,2-thiazinan-6-yl)acetic acid; or
- ((3S,4R,6S)-4-(3-chlorophenyl)-3-(4-chlorophenyl)-6-methyl-1,1-dioxido-2-(2-propanyl)-1,2-thiazinan-6-yl)acetic acid.

12. A pharmaceutical composition comprising a compound of claim 1, or a pharmaceutically acceptable salt thereof, together with a pharmaceutically acceptable excipient, diluent or carrier.

13. A method of treating cancer in a subject in need of said treatment, the method comprising administering to the subject an effective dosage amount of a compound of claim 1, or a pharmaceutically acceptable salt thereof, wherein the cancer is selected from
- (a) Carcinomas, which comprise cancer of the bladder, breast, colon, rectum, kidney, liver, lung, esophagus, gall-bladder, ovary, pancreas, stomach, cervix, thyroid, prostate, and skin;
- (b) hematopoietic tumors of lymphoid lineage, which comprise leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma;
- (c) hematopoietic tumors of myeloid lineage, which comprise acute and chronic myelogenous leukemias, myelodysplastic syndrome and promyelocytic leukemia;
- (d) tumors of mesenchymal origin, which comprise fibrosarcoma and rhabdomyosarcoma, and other sarcomas, which comprise soft tissue sarcomas and bone sarcomas;
- (e) tumors of the central and peripheral nervous system, which comprise astrocytoma, neuroblastoma, glioma and schwannomas; or
- (f) other tumors, which comprise melanoma, seminoma, teratocarcinoma, osteosarcoma, xenoderoma pigmentosum, keratoctanthoma, thyroid follicular cancer, Kaposi's sarcoma, endometrial cancer, head and neck cancer, glioblastoma, malignant ascites, and hematopoietic cancers.

* * * * *